(12) United States Patent
Allen et al.

(10) Patent No.: US 11,090,304 B2
(45) Date of Patent: *Aug. 17, 2021

(54) KRAS G12C INHIBITORS AND METHODS OF USING THE SAME

(71) Applicant: Amgen Inc., Thousand Oaks, CA (US)

(72) Inventors: John Gordon Allen, Newbury Park, CA (US); Jennifer Rebecca Allen, Newbury Park, CA (US); Ana Elena Minatti, Los Angeles, CA (US); Qiufen Xue, Thousand Oaks, CA (US); Ryan Paul Wurz, Newbury Park, CA (US); Christopher M. Tegley, Daly City, CA (US); Alexander J. Pickrell, Westlake Village, CA (US); Thomas T. Nguyen, Newbury Park, CA (US); Vu Van Ma, Oak Park, CA (US); Patricia Lopez, Woodland Hills, PA (US); Longbin Liu, Thousand Oaks, CA (US); David John Kopecky, Washington, DC (US); Michael J. Frohn, Thousand Oaks, CA (US); Ning Chen, Thousand Oaks, CA (US); Jian Jeffrey Chen, Camarillo, CA (US); Aaron C. Siegmund, Ventura, CA (US); Albert Amegadzie, Moorpark, CA (US); Nuria A. Tamayo, Newbury Park, CA (US); Shon Booker, Sherman Oaks, CA (US); Clifford Goodman, Thousand Oaks, CA (US); Mary Walton, Burlingame, CA (US); Nobuko Nishimura, West Hills, CA (US); Youngsook Shin, Thousand Oaks, CA (US); Jonathan D. Low, Reseda, CA (US); Victor J. Cee, Thousand Oaks, CA (US); Anthony B. Reed, Newbury Park, CA (US); Hui-Ling Wang, Thousand Oaks, CA (US); Brian Alan Lanman, Woodland Hills, CA (US)

(73) Assignee: Amgen Inc., Thousand Oaks, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/402,538

(22) Filed: May 3, 2019

(65) Prior Publication Data

US 2019/0343838 A1 Nov. 14, 2019

Related U.S. Application Data

(60) Provisional application No. 62/667,282, filed on May 4, 2018.

(51) Int. Cl.
| | | |
|---|---|---|
| *A61K 31/517* | (2006.01) | |
| *A61P 35/00* | (2006.01) | |
| *A61K 31/4985* | (2006.01) | |
| *A61K 39/395* | (2006.01) | |
| *C07D 403/04* | (2006.01) | |
| *C07D 471/04* | (2006.01) | |

(52) U.S. Cl.
CPC ........ *A61K 31/517* (2013.01); *A61K 31/4985* (2013.01); *A61K 39/39558* (2013.01); *A61P 35/00* (2018.01); *C07D 403/04* (2013.01); *C07D 471/04* (2013.01)

(58) Field of Classification Search
CPC .. C07D 403/04; C07D 471/04; A61K 31/395; A61K 31/4985; A61K 31/517
See application file for complete search history.

(56) References Cited

U.S. PATENT DOCUMENTS

| | | | |
|---|---|---|---|
| 4,232,027 | A | 11/1980 | Turk et al. |
| 5,100,883 | A | 3/1992 | Schiehser |
| 5,118,677 | A | 6/1992 | Caufield |
| 5,118,678 | A | 6/1992 | Kao et al. |
| 5,120,842 | A | 6/1992 | Failli et al. |
| 5,151,413 | A | 9/1992 | Caufield et al. |
| 5,256,790 | A | 10/1993 | Nelson |
| 5,258,389 | A | 11/1993 | Goulet et al. |
| 5,521,184 | A | 5/1996 | Zimmerman |
| 5,650,415 | A | 7/1997 | Tang et al. |
| 5,656,643 | A | 8/1997 | Spada et al. |
| 5,712,291 | A | 1/1998 | D'Amato |
| 5,728,813 | A | 3/1998 | Lyman et al. |
| 5,747,498 | A | 5/1998 | Schnur et al. |

(Continued)

FOREIGN PATENT DOCUMENTS

| | | | |
|---|---|---|---|
| DE | 19629652 | A1 | 1/1998 |
| EP | 0090505 | A2 | 10/1983 |
| EP | 0520722 | A1 | 12/1992 |
| EP | 0566226 | A1 | 10/1993 |

(Continued)

OTHER PUBLICATIONS

"A Phase 1, Study Evaluating the Safety, Tolerability, PK, and Efficacy of AMG 510 in Subjects With Solid Tumors With a S Mutation." NCT03600883, comparison of version published Jul. 17, 2018 and Apr. 3, 2019, https://www.clinicaltrials.gov/ct2/history/NCT03600883 (last accessed Apr. 25, 2020), pp. 1-7.

(Continued)

*Primary Examiner* — Timothy P Thomas
*Assistant Examiner* — George W Kosturko
(74) *Attorney, Agent, or Firm* — Markus Bergauer

(57) ABSTRACT

Provided herein are KRAS G12C inhibitors, composition of the same, and methods of using the same. These inhibitors are useful for treating a number of disorders, including pancreatic, colorectal, and lung cancers.

3 Claims, No Drawings

(56) References Cited

U.S. PATENT DOCUMENTS

| | | | |
|---|---|---|---|
| 5,770,599 A | 6/1998 | Gibson | |
| 5,789,427 A | 8/1998 | Chen et al. | |
| 5,792,783 A | 8/1998 | Tang et al. | |
| 5,861,510 A | 1/1999 | Piscopio et al. | |
| 5,863,949 A | 1/1999 | Robinson et al. | |
| 5,892,112 A | 4/1999 | Levy et al. | |
| 5,969,110 A | 10/1999 | Beckmann et al. | |
| 5,981,245 A | 11/1999 | Fox et al. | |
| 5,990,141 A | 11/1999 | Hirth et al. | |
| 6,057,124 A | 5/2000 | Bartley et al. | |
| 6,111,090 A | 8/2000 | Gorman et al. | |
| 6,232,447 B1 | 5/2001 | Cerretti | |
| 6,235,764 B1 | 5/2001 | Larson et al. | |
| 6,258,812 B1 | 7/2001 | Bold et al. | |
| 6,413,932 B1 | 7/2002 | Cerretti et al. | |
| 6,515,004 B1 | 2/2003 | Misra et al. | |
| 6,596,852 B2 | 7/2003 | Cerretti et al. | |
| 6,630,500 B2 | 10/2003 | Gingrich et al. | |
| 6,656,963 B2 | 12/2003 | Firestone et al. | |
| 6,713,485 B2 | 3/2004 | Carter et al. | |
| 6,727,225 B2 | 4/2004 | Wiley | |
| 7,025,962 B1 | 4/2006 | Gorman et al. | |
| 7,361,760 B2 | 4/2008 | Sircar et al. | |
| 7,618,632 B2 | 11/2009 | Collins et al. | |
| 7,812,135 B2 | 10/2010 | Smith et al. | |
| 8,388,967 B2 | 3/2013 | Smith et al. | |
| 8,586,023 B2 | 11/2013 | Shiku et al. | |
| 8,591,886 B2 | 11/2013 | Ponath et al. | |
| 10,519,146 B2 * | 12/2019 | Lanman ............... | A61K 31/416 |
| 10,532,042 B2 * | 1/2020 | Lanman ............... | C07D 487/10 |
| 10,640,504 B2 * | 5/2020 | Lanman ............... | A61K 31/519 |
| 10,640,540 B2 | 5/2020 | Lanman et al. | |
| 10,988,485 B2 | 4/2021 | Minatti et al. | |
| 2002/0042368 A1 | 4/2002 | Fanslow, III et al. | |
| 2003/0105091 A1 | 6/2003 | Riedl et al. | |
| 2003/0162712 A1 | 8/2003 | Cerretti et al. | |
| 2009/0012085 A1 | 1/2009 | Baum et al. | |
| 2014/0288045 A1 | 9/2014 | Ren et al. | |
| 2015/0239900 A1 | 8/2015 | Li et al. | |
| 2016/0159738 A1 | 6/2016 | Ren et al. | |
| 2016/0166571 A1 | 6/2016 | Janes et al. | |
| 2016/0297774 A1 | 10/2016 | Li et al. | |
| 2018/0015087 A1 | 1/2018 | Liu et al. | |
| 2018/0072723 A1 | 3/2018 | Blake et al. | |
| 2018/0177767 A1 * | 6/2018 | Lanman ............... | C07D 471/08 |
| 2018/0334454 A1 * | 11/2018 | Lanman ............... | C07D 417/04 |
| 2019/0077801 A1 * | 3/2019 | Lanman ............... | A61P 35/00 |
| 2019/0336514 A1 | 11/2019 | Wurz et al. | |
| 2019/0345169 A1 | 11/2019 | Minatti et al. | |
| 2019/0374542 A1 | 12/2019 | Allen et al. | |
| 2019/0375749 A1 | 12/2019 | Chen et al. | |
| 2020/0030324 A1 | 1/2020 | Booker et al. | |
| 2020/0055845 A1 | 2/2020 | Lanman et al. | |
| 2020/0069657 A1 | 5/2020 | Lanman et al. | |
| 2020/0165231 A1 | 5/2020 | Shin et al. | |
| 2020/0207766 A1 | 7/2020 | Lanman et al. | |
| 2020/0216446 A1 | 7/2020 | Parsons et al. | |
| 2020/0222407 A1 | 7/2020 | Lipford et al. | |
| 2020/0360374 A1 | 11/2020 | Henary et al. | |
| 2020/0369662 A1 | 11/2020 | Chaves et al. | |
| 2021/0009577 A1 | 1/2021 | Lanman et al. | |

FOREIGN PATENT DOCUMENTS

| | | | |
|---|---|---|---|
| EP | 0606046 A1 | 7/1994 | |
| EP | 0682027 A1 | 11/1995 | |
| EP | 0407122 A1 | 10/1996 | |
| EP | 0770622 A2 | 5/1997 | |
| EP | 0780386 A1 | 6/1997 | |
| EP | 0787772 A2 | 8/1997 | |
| EP | 0818442 A2 | 1/1998 | |
| EP | 0837063 A1 | 4/1998 | |
| EP | 0931788 A2 | 7/1999 | |
| EP | 0970070 B1 | 1/2000 | |
| EP | 1004578 A2 | 5/2000 | |
| EP | 1181017 B1 | 2/2002 | |
| EP | 1786785 B9 | 5/2007 | |
| EP | 1866339 B1 | 12/2007 | |
| EP | 1947183 A1 | 7/2008 | |
| EP | 3401314 A1 | 11/2019 | |
| EP | 3055290 B1 | 12/2019 | |
| JP | 02233610 A | 9/1990 | |
| WO | 1990005719 A1 | 5/1990 | |
| WO | 1992005179 A1 | 4/1992 | |
| WO | 1992020642 A1 | 11/1992 | |
| WO | 1993011130 A1 | 6/1993 | |
| WO | 1994002136 A1 | 2/1994 | |
| WO | 1994002485 A1 | 2/1994 | |
| WO | 1994009010 A1 | 4/1994 | |
| WO | 1995009847 A1 | 4/1995 | |
| WO | 1995014023 A1 | 5/1995 | |
| WO | 1995016691 A1 | 6/1995 | |
| WO | 1995019774 A1 | 7/1995 | |
| WO | 1995019970 A1 | 7/1995 | |
| WO | 1996027583 A1 | 9/1996 | |
| WO | 1996030347 A1 | 10/1996 | |
| WO | 1996031510 A1 | 10/1996 | |
| WO | 1996033172 A1 | 10/1996 | |
| WO | 1996033980 A1 | 10/1996 | |
| WO | 1996041807 A1 | 12/1996 | |
| WO | 1997002266 A1 | 1/1997 | |
| WO | 1997013771 A1 | 4/1997 | |
| WO | 1997019065 A1 | 5/1997 | |
| WO | 1997027199 A1 | 7/1997 | |
| WO | 1997030034 A1 | 8/1997 | |
| WO | 1997030044 A1 | 8/1997 | |
| WO | 1997032880 A1 | 9/1997 | |
| WO | 1997032881 A1 | 9/1997 | |
| WO | 1997034895 A1 | 9/1997 | |
| WO | 1997038983 A1 | 10/1997 | |
| WO | 1997038994 A1 | 10/1997 | |
| WO | 1997049688 A1 | 12/1997 | |
| WO | 1998002434 A1 | 1/1998 | |
| WO | 1998002437 A1 | 1/1998 | |
| WO | 1998002438 A1 | 1/1998 | |
| WO | 1998002441 A2 | 1/1998 | |
| WO | 1998003516 A1 | 1/1998 | |
| WO | 1998007697 A1 | 2/1998 | |
| WO | 1998007726 A1 | 2/1998 | |
| WO | 1998014449 A1 | 4/1998 | |
| WO | 1998014450 A1 | 4/1998 | |
| WO | 1998014451 A1 | 4/1998 | |
| WO | 1998017662 A1 | 4/1998 | |
| WO | 1998030566 A1 | 7/1998 | |
| WO | 1998033768 A1 | 8/1998 | |
| WO | 1998033798 A1 | 8/1998 | |
| WO | 1998034915 A1 | 8/1998 | |
| WO | 1998034918 A1 | 8/1998 | |
| WO | 1999007675 A1 | 2/1999 | |
| WO | 1999007701 A1 | 2/1999 | |
| WO | 1999020758 A1 | 4/1999 | |
| WO | 1999029667 A1 | 6/1999 | |
| WO | 1999035132 A1 | 7/1999 | |
| WO | 1999035146 A1 | 7/1999 | |
| WO | 1999040196 A1 | 8/1999 | |
| WO | 1999045009 A1 | 9/1999 | |
| WO | 1999052889 A1 | 10/1999 | |
| WO | 1999052910 A1 | 10/1999 | |
| WO | 1999061422 A1 | 12/1999 | |
| WO | 2000002871 A1 | 1/2000 | |
| WO | 2000012089 A1 | 3/2000 | |
| WO | 2000059509 A1 | 10/2000 | |
| WO | 2001003720 A2 | 1/2001 | |
| WO | 2001014387 A1 | 3/2001 | |
| WO | 2001032651 A1 | 5/2001 | |
| WO | 2001037820 A2 | 5/2001 | |
| WO | 2002055501 A2 | 7/2002 | |
| WO | 2002059110 A1 | 8/2002 | |
| WO | 2002066470 A1 | 8/2002 | |
| WO | 2002068406 A2 | 9/2002 | |
| WO | 2004005279 A2 | 1/2004 | |
| WO | 2004007458 A1 | 1/2004 | |
| WO | 2004007481 A2 | 1/2004 | |
| WO | 2004009784 A2 | 1/2004 | |

(56) References Cited

FOREIGN PATENT DOCUMENTS

| | | |
|---|---|---|
| WO | 2005005434 A1 | 1/2005 |
| WO | 2005007190 A1 | 1/2005 |
| WO | 2005011700 A1 | 2/2005 |
| WO | 2005016252 A2 | 2/2005 |
| WO | 2005021546 A1 | 3/2005 |
| WO | 2005055808 A2 | 6/2005 |
| WO | 2005115451 A2 | 12/2005 |
| WO | 2006044453 A1 | 4/2006 |
| WO | 2006083289 A2 | 8/2006 |
| WO | 2006121168 A1 | 11/2006 |
| WO | 2006122806 A2 | 11/2006 |
| WO | 2007133822 A1 | 11/2007 |
| WO | 2008070740 A1 | 6/2008 |
| WO | 2009036082 A2 | 3/2009 |
| WO | 2009055730 A1 | 4/2009 |
| WO | 2010003118 A1 | 1/2010 |
| WO | 2011028683 A1 | 3/2011 |
| WO | 2011051726 A2 | 5/2011 |
| WO | 2011090754 A1 | 7/2011 |
| WO | 2012142498 A2 | 10/2012 |
| WO | 2013039954 A1 | 3/2013 |
| WO | 2013155223 A1 | 10/2013 |
| WO | 2014143659 A1 | 9/2014 |
| WO | 2014152588 A1 | 9/2014 |
| WO | 2015001076 A1 | 1/2015 |
| WO | 2015054572 A1 | 4/2015 |
| WO | 2015075483 A1 | 5/2015 |
| WO | 2016044772 A1 | 3/2016 |
| WO | 2016049524 A1 | 3/2016 |
| WO | 2016049565 A1 | 3/2016 |
| WO | 2016049568 A1 | 3/2016 |
| WO | 2016164675 A1 | 10/2016 |
| WO | 2016168540 A1 | 10/2016 |
| WO | 2017015562 A1 | 1/2017 |
| WO | 2017058728 A1 | 4/2017 |
| WO | 2017058768 A1 | 4/2017 |
| WO | 2017058792 A1 | 4/2017 |
| WO | 2017058805 A1 | 4/2017 |
| WO | 2017058807 A1 | 4/2017 |
| WO | 2017058902 A1 | 4/2017 |
| WO | 2017058915 A1 | 4/2017 |
| WO | 2017087528 A1 | 5/2017 |
| WO | 2017100546 A1 | 6/2017 |
| WO | 2017172979 A1 | 10/2017 |
| WO | 2017201161 A1 | 11/2017 |
| WO | 2018064510 A1 | 4/2018 |
| WO | 2018068017 A1 | 4/2018 |
| WO | 2018119183 A3 | 6/2018 |
| WO | 2018140598 A1 | 8/2018 |
| WO | 2018217651 A1 | 11/2018 |
| WO | 2018218069 A1 | 11/2018 |
| WO | 2019051291 A1 | 3/2019 |
| WO | 2019213516 A1 | 11/2019 |
| WO | 2019213526 A1 | 11/2019 |
| WO | 2019217691 A1 | 11/2019 |
| WO | 2019232419 A1 | 12/2019 |
| WO | 2019241157 A1 | 12/2019 |
| WO | 2019243533 A1 | 12/2019 |
| WO | 2019243535 A1 | 12/2019 |
| WO | 2020050890 A2 | 3/2020 |
| WO | 2020/102730 A1 | 5/2020 |
| WO | 2020106640 A1 | 5/2020 |
| WO | 2020156285 A1 | 8/2020 |
| WO | 202036947 A1 | 11/2020 |
| WO | 2020232130 A1 | 11/2020 |
| WO | 2020236948 A1 | 11/2020 |
| WO | 2021081212 A1 | 4/2021 |
| WO | 2021126816 A1 | 6/2021 |

OTHER PUBLICATIONS

"Acute Leukemia," *The Merck Manual* (Online Edition), pp. 1-6 (2013).

Ahmadian, et al., "Guanosine triphosphatase stimulation of oncogenic Ras mutants," *PNAS*, 96: 7065-7070, 1999.

Airoldi, et al., "Glucose-Derived Ras Pathway Inhibitors: Evidence of Ras-Ligand Binding and Ras-GEF (Cdc25) Interaction Inhibition," *ChemBioChem*, 8: 1376-1379 (2007).

The ASCO Post Staff, "AACR-NCI-EORTC: Investigational KRAS G12C Inhibitor for KRAS-Mutant Solid Tumors," The ASCO Post (2019).

ATTC "Organism: *Mus musculus* (B cell); *Mus musculus* (myeloma), mouse (B cell); mouse (myeloma)," Accession No. HB-8508, retrieved from https://www.atcc.org/~/media/0DF7351153724BD6A3E7D78D5BA2F933.ashx, on Nov. 29, 2018.

Barnett, et al., "Identification and characterization of pleckstrin-holomogy-domain-dependent and isoenzyme specific Akt inhibitors," *Biochem. J.*,385 (2): 399-408 (2005).

Bull, et al., "Isoquino[2,1-c][1,3,2] Benzodiazaphosphorine Derivatives: New Potential Agents for Cancer Chemotherapy," *Phosphorus, Sulfur, and Silicon*, 162:231-243 (2000).

Campillo, et al., "Novel Bronchodilators: Synthesis, Transamination Reactions, and Pharmacology of a Series of Pyrazino[2,3-c][1,2,6]thiadiazine 2,2-Dioxides," *J. Med. Chem.*, 43: 4219-4227 (2000).

Canon, et al., "The clinical KRAS(G12C) inhibitor AMG 510 drives anti-tumour immunity," *Nature*, 575(7781): 217-223 (2019).

*Cecil Textbook of Medicine*, edited by Bennett, J.C., and Plum, F., 20$^{th}$ edition, vol. 1:1004-1010 (1996).

Cohen, "The development and therapeutic potential of protein kinase inhibitors," *Current Opinion in Chemical Biology*, 3:459-465 (1999).

Cowen Slide deck—Warp Drive Bio, slides 1-32, "Corporate Overview Exploiting the Molecules and Mechanisms of Nature to Create Transformative Medicines" http://www.warpdrivebio.com/news/cowen%202016.pdf (last visited Apr. 2016).

Dasmahapatra, et al., "In vitro Combination Treatment with Perifosine and UCN-01 Demonstrates Synergism Against Prostate (PC-3) and Lung (A549) Epithelial Adenocarcinoma Cell Lines," *Clin. Cancer Res.* 10(15): 5242-5252 (2004).

Dermer, et al., "Another Anniversary for the War on Cancer," *Bio/Technology*, 12: 320 (1994).

Douelle, et al., "Highly Diastereoselective Synthesis of vicinal Quaternary and Tertiary Stereocenters Using the Iodo-aldol Cyclization," *Org. Lett.*, 9 (10): 1931-1934 (2007).

Erkkilä, et al., "Mild Organocatalytic α-Methylenation of Aldehydes," *J. Org. Chem.*,71 (6), 2538-2541 (2006).

Fakih, et al., "Phase 1 study evaluating the safety, tolerability, pharmacokinetics (PK), and efficacy of AMG 510, a novel small molecule KRASG12C inhibitor, in advanced solid tumors," *Journal of Clinical Oncology*, 37(15 suppl) (May 20, 2019) 3003, published online May 26, 2019.

Final Office Action for U.S. Appl. No. 15/984,855, dated Mar. 28, 2019, 7 pages.

Final Office Action for U.S. Appl. No. 16/661,907, dated Mar. 27, 2020, 29 pages.

Freshney, et al., Culture of Animal Cells, *A Manual of Basic Technique*, Alan R. Liss, Inc, New York, p4 (1983).

Gentile, et al., "Discovery and Structural Investigation of Novel Binders to the Ras Switch II Pocket," NCI Initiative Symposium Poster (2015).

Gills and Dennis, "The development of phosphatidylinositol ether lipid analogues as inhibitors of the serine/threonine kinase, Akt," *Expert. Opin. Investig. Drugs*, 13: 787-797 (2004).

Goldberg, et al., "Role of PD-1 and its ligand, B7-H1, in early fate decisions of CD8 T cells," *Blood*,110(1): 186-192 (2007).

Goldstein, et al., "Biological Efficacy of a Chimeric Antibody to the Epidermal Growth Factor Receptor in a Human Tumor Xenograft Model," *Clin. Cancer Res.*, 1: 1311-1318 (1995).

Golub, et al., "Molecular Classification of Cancer: Class Discovery and Class Prediction by Gene Expression Monitoring," *Science*, 286: 531-537(1999).

Govindan, et al., "Phase 1 Study of AMG 510, a Novel KRAS G12C Inhibitor, in Advanced Solid Tumors with KRAS p.G12C Mutation," Poster, ESMO Congress, Barcelona, Spain, Sep. 27, 2019-Oct. 1, 2019.

(56) References Cited

OTHER PUBLICATIONS

Gura, "Cancer Models: Systems for Identifying New Drugs Are Often Faulty," *Science*, 278(5340):1041-1042 (1997).
Hallin, et al., "The KRAS$^{G12C}$ Inhibitor MRTX849 Provides Insight toward Therapeutic Susceptibility of KRAS-Mutant Cancers in Mouse Models and Patients," *Cancer Discov.*, 10: 54-71 (2020).
Hansen, et al., "Abstract 686: Drugging an undruggable pocket: the biochemical mechanism of covalent KRAS$^{G12C}$ inhibitors," Proceedings of the American Association for Cancer Research Annual Meeting 2018; Apr. 14-18, 2018; Chicago, IL; AACR; *Cancer Res.*, 78(13 Suppl): Abstract 686 (2018).
Hichri, et al., CAPLUS Abstract, 162:245378 (2015).
Hichri, et al., "A Convenient Synthesis of 1,3,2-Benzodiazaphophorine-2-Oxide," *Phosphorus, Sulfur, and Silicon*, 190: 29-35 (2015).
Hocker, et al., "Andrographolide derivatives inhibit guanine nucleotide exchange and abrogate oncogenic Ras function," *PNAS*, 110(25): 10201-10206 (2013).
Huang, et al., "Epidermal Growth Factor Receptor Blockade with C225 Modulates Proliferation, Apoptosis, and Radiosensitivity in Squamous Cell Carcinomas of the Head and Neck," *Cancer Res.*, 59(8): 1935-1940 (1999).
International Search Report for PCT/US2017/067801, dated Jul. 25, 2018, 6 pages.
International Search Report for PCT/US2018/033714, dated Jul. 17, 2018, 3 pages.
International Search Report for PCT/US2018/050044, dated Oct. 30, 2018, 7 pages.
International Search Report for PCT/US2019/030593, dated Aug. 6, 2019, 4 pages.
International Search Report for PCT/US2019/030606, dated Jul. 23, 2019, 5 pages.
International Search Report for PCT/US2019/031535, dated Jul. 25, 2019, 7 pages.
International Search Report for PCT/US2019/034974, dated Aug. 9, 2019, 5 pages.
International Search Report for PCT/US2019/036397, dated Aug. 26, 2019, 5 pages.
International Search Report for PCT/US2019/061815, dated Mar. 5, 2020, 6 pages.
Janes, et al., "Targeting KRAS Mutant Cancers with a Covalent G12C-Specific Inhibitor," *Cell*, 172: 578-589 (2018).
Jarvis, "Notorious KRAS: Taking down cancer researchers' biggest foe," *Chemical & Engineering News*, 97(37), 9 pages. (2019).
Jin, et al., "Inhibition of AKT survival pathway by a small molecule inhibitor in human endometrial cancer cells," *Br. J. Cancer*, 91: 1808-1812 (2004).
Johnson, et al., "Relationships between drug activity in NCI preclinical in vitro and in vivo models and early clinical trials," *Br. J. Cancer*, 84(10): 1424-1431 (2001).
Lanman, et al., "Discovery of a Covalent Inhibitor of KRAS$^{G12C}$ (AMG 510) for the Treatment of Solid Tumors," *J. Med. Chem.*, 63: 52-65 (2020).
"KRASG12C Inhibitor," Mirati Therapeutics, retrieved on Nov. 27, 2018, from https://www.mirati.com/mrtx849/, 5 pages.
Li, et al., "Targeting Protein-Protein Interaction with Covalent Small-Molecule Inhibitors," *Current Topics in Medicinal Chemistry*, 19(21): 1872-1876 (2019).
Lim, et al., "Therapeutic Targeting of Oncogenic K-Ras by a Covalent Catalytic Site Inhibitor," *Angew. Chem. Int. Ed*, 53: 199-204 (2014).
Liu, Y., "Session SY28—Transformative Small Molecule Therapies—Targeting KRAS mutant cancers with a covalent G12C—specific inhibitor," Presentation on Apr. 4, 2017, AACR Annual Meeting Presentation, Apr. 1-5, 2017, Washington, D.C. (2017).
Lu, et al., "KRAS G12C Drug Development: Discrimination between Switch II Pocket Configurations Using Hydrogen/Deuterium-Exchange Mass Spectrometry," *Structure*, 25: 1-7 (2017).
Maurer, et al., "Small-molecule ligands bind to a distinct pocket in Rad and inhibit SOS-mediated nucleotide exchange activity," *PNAS*, 109(14): 5299-5304 (2012).
McGregor, et al., "Expanding the Scope of Electrophiles Capable of Targeting K-Ras Oncogenes," *ACS Bio. Chem.*, 56: 3179-3183 (2017).
Mirati Therapeutics, "Corporate Presentation Nov. 2017," Slides 1-41 (2017).
Modjtahedi, et al., "The human EGF receptor as a target for cancer therapy: six new rat mAbs AGainst the receptor on the breast carcinoma MDA-MB 468," *Br. J. Cancer*, 67(2): 247-253 (1993).
National Cancer Institute identifier: NSC 154020, retrieved on Nov. 29, 2018, from https://cactus.nci.nih.gov/ncidb2.2/.
NCBI Reference Sequence, "GTPase KRas isoform a [*Homo sapiens*]," GenBank Accession No. NM_203524.1, Retrieved on Nov. 29, 2018 from https://www.ncbi.nlm.nih.gov/protein/15718763?sat=4&satkey=234448549, 4 pages.
Non-Final Office Action for U.S. Appl. No. 15/984,855, dated Sep. 27, 2018, 25 pages.
Non-Final Office Action for U.S. Appl. No. 15/849,905, dated Mar. 20, 2019, 18 pages.
Non-Final Office Action for U.S. Appl. No. 16/125,359, dated Apr. 5, 2019, 13 pages.
Non-Final Office Action (Corrected) for U.S. Appl. No. 16/125,359, dated Apr. 8, 2019, 13 pages.
Non-Final Office Action for U.S. Appl. No. 16/661,907, dated Nov. 18, 2019, 20 pages.
Non-Final Office Action for U.S. Appl. No. 16/438,349, dated Dec. 13, 2019, 15 pages.
Non-Final Office Action for U.S. Appl. No. 16/402,589, dated Mar. 6, 2020, 17 pages.
Ostrem, et al., "Development of mutant-specific small molecule inhibitors of K-Ras," Poster, AACR 104th Annual Meeting 2013; Apr. 6-10, 2013; Washington, D.C. (2013).
Ostrem, et al., "K-Ras(G12C) inhibitors allosterically control GTP affinity and effector interactions," *Nature*, 503: 548-551 (2013).
Paez, et al., "EGFR Mutations in Lung Cancer Correlation with Clinical Response to Gefitinib Therapy," *Science*, 304(5676): 1497-500 (2004).
Palmioli, et al., "First experimental identification of Ras-inhibitor binding interface using a water-soluble Ras ligand," *Bioorg. Med. Chem. Lett.*, 19: 4217-4222 (2009).
Patricelli, et al., "Selective Inhibition of Oncogenic KRAS Output with Small Molecules Targeting the Inactive State," *Cancer Discov*, 6 (3): 316-329 (2016).
Pearce, et al., "Failure modes in anticancer drug discovery and development," *Cancer Drug Design and Discovery*, Edited by Stephen Neidle, Chapter 18, pp. 424-435 (2008).
Peri, et al., "Design, Synthesis and Biological Evaluation of Sugar-Derived Ras Inhibitors," *ChemBioChem*, 6: 1839-1848 (2005).
Peri, et al., "Sugar-Derived Ras Inhibitors: Group Epitope Mapping by NMR Spectroscopy and Biological Evaluation," *Eur. J. Org. Chem.*, 16: 3707-3720 (2006).
Peters, et al., "Selective inhibition of K-Ras G12C through allosteric control of GTP affinity and effector interactions," EORTC Poster (2013).
Remington's Pharmaceutical Sciences, 1435-1712 (18th ed., Mack Publishing Co, Easton, Pennsylvania, 1990 (Table of Contents Only).
Rex et al., "KRAS—AACR 2018," Amgen Collection of Information published at Proceedings of the American Association for Cancer Research Annual Meeting 2018; Apr. 14-18, 2018; Chicago, IL; AACR; slides 1-24 (2018).
Sarkar, et al., "Indole-3-Carbinol and Prostate Cancer," *J. Nutr.*, 134(12 Suppl): 3493S-3498S (2004).
Shima, et al., "In silico discovery of small-molecule Ras inhibitors that display antitumor activity by blocking the Ras-effector interaction," *PNAS*, 110(20): 8182-8187 (2013).
Simone, "Part XIV Oncology: Introduction," *Cecil Textbook of Medicine*, 20$^{th}$ Edition, 1:1004-1010 (1996).
Singh, et al., "Improving Prospects for Targeting RAS," *J. Clinc. Oncl*, 33(31): 3650-3660 (2015).
Statsyuk, "Let K-Ras activate its own inhibitor," *Nature Structural & Molecular Biology*, 25:435-439 (2018).

(56) References Cited

OTHER PUBLICATIONS

Sun, et al., "Discovery of Small Molecules that Bind to K-Ras and Inhibit Sos-Mediated Activation," *Angew. Chem. Int. Ed.*, 51: 6140-6143 (2012).

Taveras, et al., "Ras Oncoprotein Inhibitors: The Discovery of Potent, Ras Nucleotide Exchange Inhibitors and the Structural Determination of a Drug-Protein Complex," *Biorg. Med. Chem. Lett.*,, 5(1): 125-133 (1997).

Teramoto, et al., "Inhibitory Effect of Anti-Epidermal Growth Factor Receptor Antibody on a Human Gastric Cancer," Cancer, 77(8 Suppl): 1639-1645 (1996).

Thompson, et al., "PD-1 Is Expressed by Tumor-Infiltrating Immune Cells and Is Associated with Poor Outcome for Patients with Renal Cell Carcinoma," *Clin. Cancer Res.*, 13(6): 1757-1761 (2007).

Traxler, "Tyrosine kinase inhibitors in cancer treatment (Part II)," *Exp. Opin. Ther. Patents*, 8(12): 1599-1625 (1998).

U.S. Appl. No. 60/528,340, filed Dec. 9, 2003.

Wang, et al., "Ras inhibition via direct Ras binding—is there a path forward?," *Bioorg. Med. Chem. Lett.*, 22: 5766-5776 (2012).

Written Opinion for PCT/US2017/067801, dated Jul. 25, 2018, 10 pages.

Written Opinion for PCT/US2018/033714, dated Jul. 17, 2018, 5 pages.

Written Opinion for PCT/US2018/050044, dated Oct. 30, 2018, 7 pages.

Written Opinion for PCT/US2019/030593, dated Aug. 6, 2019, 5 pages.

Written Opinion for PCT/US2019/030606, dated Jul. 23, 2019, 6 pages.

Written Opinion for PCT/US2019/031535, dated Jul. 25, 2019, 7 pages.

Written Opinion for PCT/US2019/034974, dated Aug. 9, 2019, 5 pages.

Written Opinion for PCT/US2019/036397, dated Aug. 26, 2019, 5 pages.

Written Opinion for PCT/US2019/061815, dated Mar. 5, 2020, 4 pages.

Xiong, et al., "Covalent Guanosine Mimetic Inhibitors of G12C KRAS," *ACS Med. Chem. Lett.*, 8: 61-66 (2017).

Yan, et al., "Pharmacogenetics and pharmacogenomics in oncology therapeutic antibody development," *BioTechniques*, 29(4): 565-568 (2005).

Yang, et al., "Akt/Protein Kinase B Signaling Inhibitor-2, a Selective Small Molecule Inhibitor of Akt Signaling with Antitumor Activity in Cancer Cells Overexpressing Akt," *Cancer Res.*, 64, 4394-4399 (2004).

Yang, et al., "Eradication of Established Tumors by a Fully Human Monoclonal Antibody to the Epidermal Growth Factor Receptor without Concomitant Chemotherapy," *Cancer Res.*, 59: 1236-1243 (1999).

Zeng, et al., "Potent and Selective Covalent Quinazoline Inhibitors of KRAS G12C," *Cell Chemical Biology*, 24: 1-12 (2017).

Zimmerman, et al., "Small molecule inhibition of the KRAS-PDEδ interaction impairs oncogenic KRAS signaling," *Nature*, 497: 638-642 (2013).

International Search Report for PCT/US2020/033831, dated Jul. 9, 2020, 6 pages.

International Search Report for PCT/US2020/033832, dated Jul. 8, 2020, 4 pages.

Non-Final Office Action for U.S. Appl. No. 16/407,889, dated Jul. 1, 2020, 6 pages.

Written Opinion for PCT/US2020/033831, dated Jul. 9, 2020, 7 pages.

Written Opinion for PCT/US2020/033832, dated Jul. 8, 2020, 6 pages.

Cee, et al., "Discovery of AMG 510, a first-in-humancovalent inhibitor of KRAS$^{G12C}$ for the treatment of solid tumors," Abstract and Presentation, ACS Spring Meeting, Orlando, FL, USA, Mar. 31-Apr. 4, 2019.

Extended European Search Report for European Patent Application No. 19208193.2, dated Jun. 3, 2020, pp. 1-8.

Fakih, et al., "Phase 1 study evaluating the safety, tolerability, pharmacokinetics (PK), and efficacy of AMG 510, a novel small molecule KRASG12C inhibitor, in advanced solid tumors," Presentation, ASCO, Chicago, IL, USA, May 31-Jun. 4, 2019.

Govindan, et al., "Safety, Efficacy, and Pharmacokinetics of AMG 510, a Novel KRASG12C Inhibitor, in Patients with Non-Small Cell Lung Cancer," Abstract and Presentation, North American Conference on Lung Cancer (NACLC), Chicago, IL, USA, Oct. 10-12, 2019.

Govindan, et al., "Phase 1 Study of AMG 510, a Novel KRAS G12C Inhibitor, in Advanced Solid Tumors with KRAS p.G12C Mutation," Abstract, ESMO Congress, Barcelona, Spain, Sep. 27-Oct. 1, 2019.

Govindan, et al., "Phase 1 Study of Safety, Tolerability, Pharmacokinetics, and Efficacy of AMG510, a Novel KRASG12C Inhibitor, in Non-Small Cell Lung Cancer," Abstract and Presentation, World Conference on Lung Cancer (WCLC), Barcelona, Spain, Sep. 7-10, 2019.

Halford, "Amgen unveils its Kras covalent inhibitor AMG 510," *Chemical & Engineering News* 97(14):4 (2019).

International Search Report for PCT/US2019/036626, dated Jun. 2, 2020, 5 pages (pending processing).

International Search Report for PCT/US2019/062051, dated Mar. 2, 2020, 3 pages.

Lanman, et al., "Abstract 4455: Discovery of AMG 510, a first-in-human covalent inhibitor of KRAS$^{G12C}$ for the treatment of solid tumors," Presentation, American Association for Cancer Research (AACR) Annual Meeting, Atlanta, GA, USA, Mar. 29-Apr. 3, 2019.

Lanman, et al., "Abstract 4455: Discovery of AMG 510, a first-in-human covalent inhibitor of KRAS$^{G12C}$ for the treatment of solid tumors," Proceedings of the American Association for Cancer Research Annual Meeting 2019; Mar. 29-Apr. 3, 2019; Atlanta, GA. Philadelphia (PA), AACR, *Cancer Res.* 79(13 Suppl): Abstract nr 4455 (2019).

Lipford, et al., "Pre-Clinical Development of AMG 510: The First Inhibitor of KRAS$^{G12C}$ in Clinical Testing," Presentation, American Association for Cancer Research (AACR) Annual Meeting, Atlanta, GA, USA, Mar. 29-Apr. 3, 2019.

Lopez, et al., "Optimization of quinazolinone-based covalent inhibitors of KRAS$^{G12C}$ in the discovery of AMG 510," Abstract and Poster, ACS Fall Meeting, San Diego, CA, USA, Aug. 25-29, 2019.

Morrissey, et al., "Immunotherapy and Novel Combinations in Oncology: Current Landscape, Challenges, and Opportunities," *Clin. Transl. Sci.*, 9(2):89-104 (2016).

Rex, et al., "Abstract 3090: In vivo characterization of AMG 510—a potent and selective KRAS$G12C$ covalent small molecule inhibitor in preclinical KRAS$^{G12C}$ cancer models," Poster, American Association for Cancer Research (AACR) Annual Meeting, Atlanta, GA, USA, Mar. 29-Apr. 3, 2019.

Rex, et al., "Abstract 3090: In vivo characterization of AMG 510—a potent and selective KRAS$^{G12C}$ covalent small molecule inhibitor in preclinical KRAS$^{G12C}$ cancer models," Proceedings of the American Association for Cancer Research Annual Meeting 2019; Mar. 29-Apr. 3, 2019; Atlanta, GA. Philadelphia (PA), AACR, *Cancer Res.* 79(13 Suppl): Abstract nr 3090 (2019).

Saiki, et al., "Abstract 4484: Discovery and in vitro characterization of AMG 510—a potent and selective covalent small-molecule inhibitor of KRAS$^{G12C}$," Presentation, American Association for Cancer Research (AACR) Annual Meeting, Atlanta, GA, USA, Mar. 29-Apr. 3, 2019.

Saiki, et al., "Abstract 4484: Discovery and in vitro characterization of AMG 510—a potent and selective covalent small-molecule inhibitor of KRAS$^{G12C}$," Proceedings of the American Association for Cancer Research Annual Meeting 2019; Mar. 29-Apr. 3, 2019; Atlanta, GA. Philadelphia (PA), AACR, *Cancer Res.* 79(13 Suppl): Abstract nr 4484 (2019).

Written Opinion for PCT/US2019/036626, dated Jun. 2, 2020, 12 pages.

Written Opinion for PCT/US2019/062051, dated Mar. 2, 2020, 5 pages.

(56) References Cited

OTHER PUBLICATIONS

Non-Final Office Action for U.S. Appl. No. 16/436,647, dated Aug. 7, 2020, 19 pages.
Bhatia, et al., "A Review on Bioisosterism: A Rational Approach for Drug Design and Molecular Modification," *Pharmacologyonline*, 1:272-299 (2011).
Written Opinion for PCT/US2020/032686, dated Aug. 14, 2020, 6 pages.
International Search Report for PCT/US2020/032686, dated Aug. 14, 2020, 4 pages.
Notice of Allowance dated Sep. 9, 2020 for U.S. Appl. No. 16/438,349, 9 pages.
Notice of Allowance dated Sep. 16, 2020 for U.S. Appl. No. 16/402,589, 5 pages.
Non-Final Office Action for U.S. Appl. No. 16/428,163, dated Sep. 15, 2020, 6 pages.
AMG-510; CS-0081316; Source: AbaChemScene (CS-0081316); Deposit Date: May 13, 2019 Available Date: May 13, 2019; SID: 384060804[CID: 137278711] (available at https://pubchem.ncbi.nlm.nih.gov/substance/384060804/).
AMG-510; HY-114277; Source: MedChemexpress MCE (HY-114277); Deposit Date: May 13, 2019 Available Date: May 13, 2019; SID: 384060569[CID:137278711] (available at https://pubchem.ncbi.nlm.nih.gov/substance/384060569).
Canon, et al., "The clinical KRAS(G12C) inhibitor AMG 510 drives anti-tumour immunity," *Nature*, 575(7781):217-223 (2019) (Supplementary Material, pages 1-55).
Database Registry [Online], Chemical Abstracts Service, Columbus, Ohio, US; Jul. 31, 2017 (Jul. 31, 2017), XP002801805, retrieved from STN Database accession No. 2105944-09-8.
International Search Report for PCT/US2019/62064, dated Oct. 29, 2020, 9 pages.
Meanwell, "Synopsis of Some Recent Tactical Application of Biososteres in Drug Design," *J. Med. Chem.* 54:2529-2591 (2011).
Non-Final Office Action for U.S. Appl. No. 16/675,121, dated Feb. 2, 2021, 10 pages.
Notice of Allowance dated Jan. 14, 2021 for U.S. Appl. No. 16/402,589, 5 pages.
Notice of Allowance, dated Dec. 21, 2020, for U.S. Appl. No. 16/407,889, 5 pages.
Notice of Allowance, dated Jan. 26, 2021, for U.S. Appl. No. 16/438,349, 9 pages.
Notice of Allowance, dated Jan. 27, 2021, for U.S. Appl. No. 16/428,163, 9 pages.
Shibata et al., "A Convenient Sythesis of 3-Cyano-2-methylpyridines under Ultrasonic Irradiation," *Bull. Chem. Soc. Jpn.*, 61:2199-2200 (1988).
Stanetty et al., "Synthesis of Aza Analogs of the Herbicide Sindone B," *Monatshefte Fuer Chemie*, 130:441-450 (1999).
Third Party Observation filed for PCT/US2020/033831, submitted Jan. 15, 2021, 2 pages.
Written Opinion for PCT/US2019/62064, dated Oct. 29, 2020, 14 pages.
Final Office Action for U.S. Appl. No. 16/436,647, dated Mar. 24, 2021, 7 pages.
Notice of Allowance, dated Feb. 18, 2021, for U.S. Appl. No. 16/687,546, 9 pages.
Non-Final Office Action for U.S. Appl. No. 16/817,109, dated Mar. 3, 2021, 12 pages.
Notice of Allowance, dated Apr. 19, 2021, for U.S. Appl. No. 16/428,163, 9 pages.

\* cited by examiner

KRAS G12C INHIBITORS AND METHODS OF USING THE SAME

CROSS REFERENCE TO RELATED APPLICATIONS

This application claims priority to U.S. Provisional Application No. 62/667,282, filed on May 4, 2018, which specification is hereby incorporated herein by reference in its entirety.

FIELD OF THE INVENTION

The present invention relates to compounds that inhibit the KRAS G12C protein; methods of treating diseases or conditions, such as cancer, using the compounds; and pharmaceutical compositions containing the compounds.

BACKGROUND

KRAS gene mutations are common in pancreatic cancer, lung adenocarcinoma, colorectal cancer, gall bladder cancer, thyroid cancer, and bile duct cancer. KRAS mutations are also observed in about 25% of patients with NSCLC, and some studies have indicated that KRAS mutations are a negative prognostic factor in patients with NSCLC. Recently, V-Ki-ras2 Kirsten rat sarcoma viral oncogene homolog (KRAS) mutations have been found to confer resistance to epidermal growth factor receptor (EGFR) targeted therapies in colorectal cancer; accordingly, the mutational status of KRAS can provide important information prior to the prescription of TKI therapy. Taken together, there is a need for new medical treatments for patients with pancreatic cancer, lung adenocarcinoma, or colorectal cancer, especially those who have been diagnosed to have such cancers characterized by a KRAS mutation, and including those who have progressed after chemotherapy.

The compounds disclosed herein can be in the form of a pharmaceutically acceptable salt. The compounds provided can be formulated into a pharmaceutical formulation comprising a compound disclosed herein and a pharmaceutically acceptable excipient.

Also provided is a method of inhibiting KRAS G12C in a cell, comprising contacting the cell with a compound or composition disclosed herein. Further provided is a method of treating cancer in a subject comprising administering to the subject a therapeutically effective amount of a compound or composition disclosed herein. In some embodiments, the cancer is lung cancer, pancreatic cancer, or colorectal cancer.

SUMMARY

One aspect of the present invention provides various compounds, stereoisomers, atropisomers, pharmaceutically acceptable salts, pharmaceutically acceptable salts of the stereoisomers, and pharmaceutically acceptable salts of the atropisomers as described in the embodiments set forth below.

Another aspect of the present invention provides a pharmaceutical composition that includes the compound of any of the embodiments or the pharmaceutically acceptable salt thereof, and a pharmaceutically acceptable carrier or diluent.

Another aspect of the present invention provides a method of treating cancer. Such methods include: administering to a patient in need thereof a therapeutically effective amount of the compound of any of the embodiments or a pharmaceutically acceptable salt thereof. In some such methods, the cancer is a hematologic malignancy. In some such methods, the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia. In some other such methods, the cancer is multiple myeloma. In some other such methods, the cancer is acute myelogenous leukemia. In some other such methods, the cancer is non-Hodgkin's lymphoma. In another aspect, the method further includes administering to a patient in need thereof a therapeutically effective amount of an additional pharmaceutically active compound. For example, in some such methods the additional pharmaceutically active compound is carfilzomib. In others, the additional pharmaceutically active compound is venetoclax. In still other such methods, the additional pharmaceutically active compound is cytarabine. In still other such methods, the additional pharmaceutically active compound is daratumumab. In still other such methods, the additional pharmaceutically active compound is an MCl-1 inhibitor. In still other such methods, the MCl-1 inhibitor is AMG-176. In still other such methods, the additional pharmaceutically active compound is an imid.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the Claims.

DETAILED DESCRIPTION

Definitions

Abbreviations: The following abbreviations may be used herein:

| | |
|---|---|
| AcOH | acetic acid |
| aq or aq. | aqueous |
| BOC or Boc | tert-butyloxycarbonyl |
| CPhos | 2-dicyclohexylphosphino-2',6'-bis(N,N-dimethylamino)biphenyl |
| cpme | cyclopentyl methyl ether |
| DCE | 1,2-dichloroethane |
| DABCO | 1,4-diazabicyclo[2.2.2]octane |
| DCM | dichloromethane |

| Abbreviations: The following abbreviations may be used herein: | |
|---|---|
| DMA | N,N-dimethylacetamide |
| DMAP | 4-dimethylaminopyridine |
| DME | 1,2-dimethoxyethane |
| DMF | N,N-dimethylformamide |
| DMSO | dimethyl sulfoxide |
| Dppf, DPPF or dppf | 1,1'-bis(diphenylphosphino)ferrocene |
| eq or eq. or equiv. | equivalent |
| ESI or ES | electrospray ionization |
| Et | ethyl |
| $Et_2O$ | diethyl ether |
| EtOAc | ethyl acetate |
| g | gram(s) |
| h | hour(s) |
| HBTU | N,N,N',N'-tetramethyl-O-(1H-benzotriazol-1-yl)uronium hexafluorophosphate, O-(benzotriazol-1-yl)-N,N,N',N'-tetramethyluronium hexafluorophosphate |
| HPLC | high pressure liquid chromatography |
| iPr | isopropyl |
| $iPr_2NEt$ or DIPEA | N-ethyl diisopropylamine (Hünig's base) |
| KHMDS | potassium hexamethyldisilazide |
| KOAc | potassium acetate |
| Lawesson's reagent | 2,4-bis(4-methoxyphenyl)-2,4-dithioxo-1,3,2,4-dithiadiphosphetane, 2,4-bis-(4-methoxyphenyl)-1,3-dithia-2,4-diphosphetane 2,4-disulfide |
| LC MS, LCMS, LC-MS or LC/MS | liquid chromatography mass spectroscopy |
| LG | leaving group (e.g., halogen, mesylate, triflate) |
| LHMDS or LiHMDS | lithium hexamethyldisilazide |
| m/z | mass divided by charge |
| Me | methyl |
| MeCN | acetonitrile |
| MeOH | methanol |
| Met | metal species for cross-coupling (e.g., MgX, ZnX, $SnR_3$, $SiR_3$, $B(OR)_2$) |
| mg | milligrams |
| min | minutes |
| mL | milliliters |
| MS | mass spectra |
| NaHMDS | sodium hexamethyldisilazide |
| NBS | N-bromosuccinimide |
| n-BuLi | n-butyllithium |
| NCS | N-chlorosuccinimide |
| NMR | nuclear magnetic resonance |
| $Pd_2(dba)_3$ | tris(dibenzylideneacetone)dipalladium(0) |
| $Pd(dppf)Cl_2 \cdot DCM$, $Pd(dppf)Cl_2$ | [1,1'-bis(diphenylphosphino)ferrocene]dichloropalladium(II), complex with dichloromethane |
| $Pd(PPh_3)_4$ | tetrakis(triphenylphosphine)palladium(0) |
| Ph | phenyl |
| PR or PG or Prot. group | protecting group |
| rbf | round-bottomed flask |
| RP-HPLC | reverse phase high pressure liquid chromatography |
| RT or rt or r.t. | room temperature |
| sat. or satd. | saturated |
| SFC | supercritical fluid chromatography |
| SPhos Pd G3 or SPhos G3 | (2-dicyclohexylphosphino-2',6'-dimethoxybiphenyl) [2-(2'-amino-1,1'-biphenyl)]palladium(II) methanesulfonate |
| TBAF | tetra-n-butylammonium fluoride |
| TBTU | N,N,N',N'-tetramethyl-O-(benzotriazol-1-yl)uronium tetrafluoroborate |
| t-BuOH | tert-butanol |
| TEA or $Et_3N$ | trimethylamine |
| TFA | trifluoroacetic acid |
| THF | tetrahydrofuran |
| UV | ultraviolet |

The use of the terms "a," "an," "the," and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

As used herein, the term "alkyl" refers to straight chained and branched C1-$C_8$ hydrocarbon groups, including but not limited to, methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethybutyl. The term $C_{m-n}$ means the alkyl group has 'm' to 'n' carbon atoms. The term "alkylene" refers to an alkyl group having a substituent. An alkyl (e.g., methyl), or alkylene (e.g., —$CH_2$—), group can be substituted with one or more, and typically one to three, of independently selected, for example, halo, trifluoromethyl, trifluoromethoxy, hydroxy, alkoxy, nitro, cyano, alkylamino, $C_{1-6}$alkyl. $C_{2-6}$alkenyl, $C_{2-6}$ alkynyl, —NC, amino, —$CO_2H$, —$CO_2C_1$-$C_6$alkyl, —$OCOC_1$-$C_6$alkyl, $C_3$-$C_{10}$ cycloalkyl, $C_3$-$C_{10}$ heterocycloalkyl, $C_5$-$C_{10}$aryl, and $C_5$-$C_{10}$ heteroaryl. The term "haloalkyl" specifically refers to an alkyl group wherein at least one, e.g., one to six, or all of the hydrogens of the alkyl group are substituted with halo atoms.

The terms "alkenyl" and "alkynyl" indicate an alkyl group that further includes a double bond or a triple bond, respectively.

As used herein, the term "halo" refers to fluoro, chloro, bromo, and iodo. The term "alkoxy" is defined as —OR, wherein R is alkyl.

As used herein, the term "amino" or "amine" interchangeably refers to a —$NR_2$ group, wherein each R is, e.g., H or a substituent. In some embodiments, the amino group is further substituted to form an ammonium ion, e.g., $NR_3^+$. Ammonium moieties are specifically included in the definition of "amino" or "amine." Substituents can be, for example, an alkyl, alkoxy, cycloalkyl, heterocycloalkyl, amide, or carboxylate. An R group may be further substituted, for example, with one or more, e.g., one to four, groups selected from halo, cyano, alkenyl, alkynyl, alkyl, cycloalkyl, heterocycloalkyl, aryl, heteroaryl, urea, carbonyl, carboxy late, amine, and amide. An "amide" or "amido" group interchangeably refers to a group similar to an amine or amino group but further including a C(O), e.g., —C(O)$NR_2$. Some contemplated amino or amido groups (some with optional alkylene groups, e.g., alkylene-amino, or alkylene-amido) include $CH_2NH_2$, $CH(CH_3)NH_2$, $CH(CH_3)_2NH_2$, $CH_2CH_2NH_2$, $CH_2CH_2N(CH_3)_2$, $CH_2NHCH_3$, $C(O)NHCH_3$, $C(O)N(CH_3)_2$, $CH_2C(O)NHphenyl$, $CH_2NHC(O)CH_3$, $CH_2NHCH_2CH_2OH$, $CH_2NHCH_2CO_2H$, $CH_2NH(CH_3)CH_2CO_2CH_3$, $CH_2NHCH_2CH_2OCH_3$, $CH_2NH(CH_3)CH_2CH_2OCH_3$, $CH_2NH(CH_3)CH_2C(O)N(CH_3)_2$, $CH_2NH(CH_3)CH_2C(O)NHCH_3$, $CH_2CH_2CCH$, $CH_2NMe_2$, $CH_2NH(CH_3)CH_2CH_2OH$, $CH_2NH(CH_3)CH_2CH_2F$, $CH_2N^+(CH_3)_3$, $CH_2NHCH_2CHF_2$, $CH_2NHCH_2CH_3$,

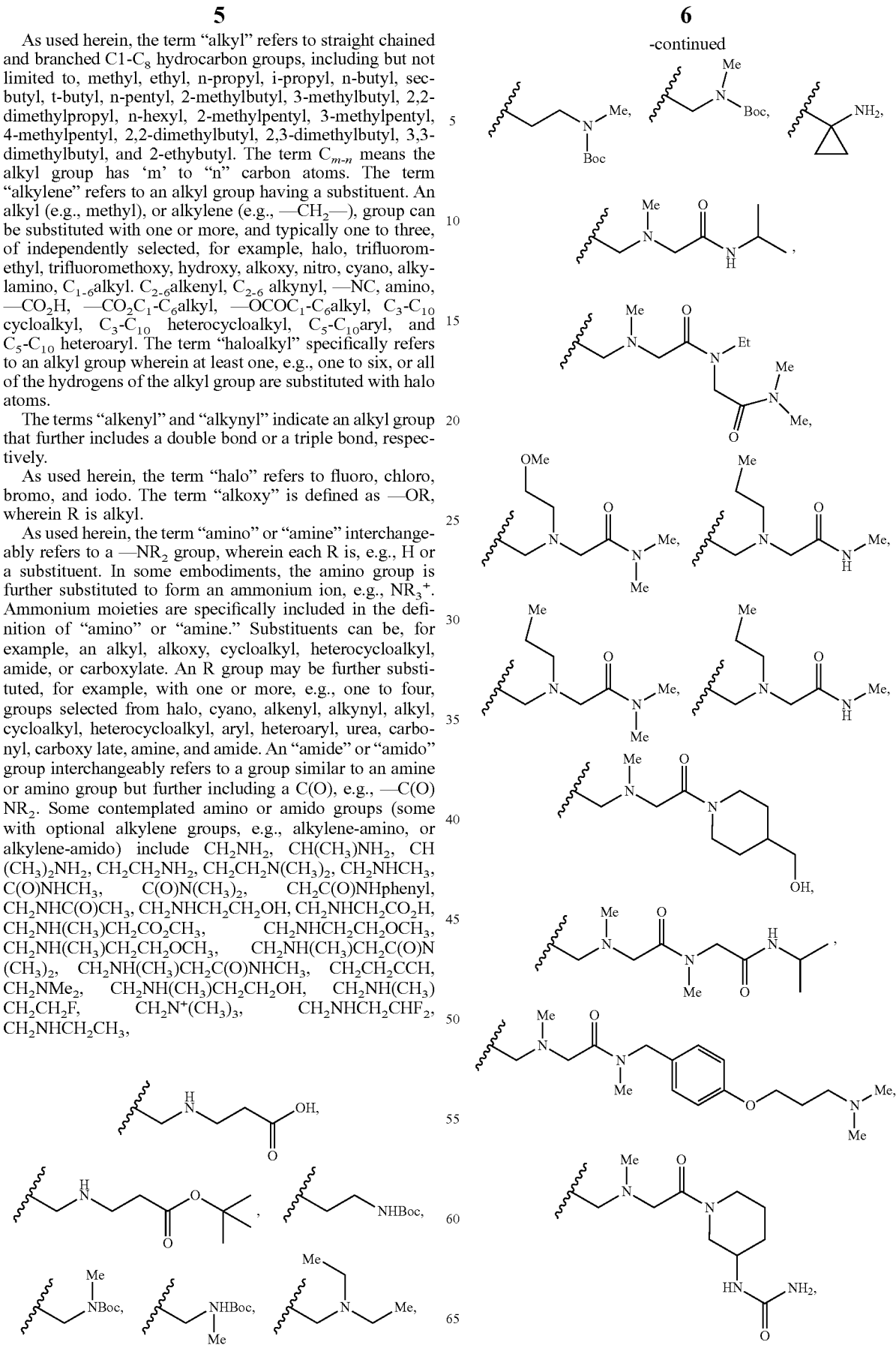

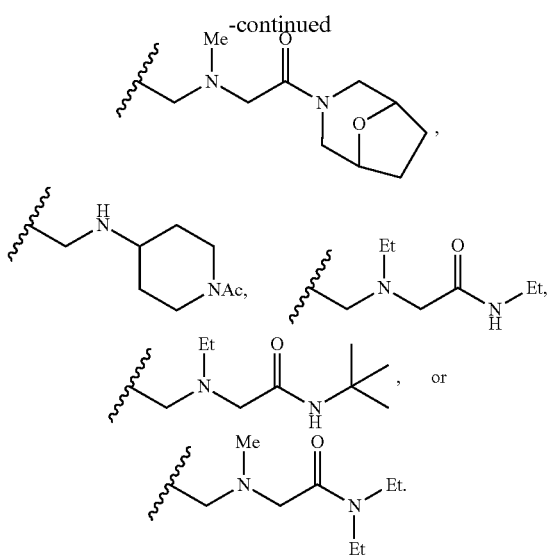

As used herein, the term "aryl" refers to a $C_{6-14}$ monocyclic or polycyclic aromatic group, preferably a $C_{6-10}$ monocyclic or bicyclic aromatic group, or $C_{10-14}$ polycyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to $C_{10-14}$ bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, groups independently selected from, for example, halo, $C_{1-6}$alkyl, $C_{2-6}$-alkenyl, $C_{2-6}$alkynyl, —$CF_3$, —$OCF_3$, —$NO_2$, —CN, —NC, —OH, alkoxy, amino, —$CO_2H$, —$CO_2C_{1-6}$alkyl, —$OCOC_{1-6}$alkyl, $C_3$-$C_{10}$ cycloalkyl, $C_3$-$C_{10}$ heterocycloalkyl, $C_5$-$C_{10}$aryl, and $C_5$-$C_{10}$ heteroaryl.

As used herein, the term "cycloalkyl" refers to a monocyclic or polycyclic non-aromatic carbocyclic ring, where the polycyclic ring can be fused, bridged, or spiro. The carbocyclic ring can have 3 to 10 carbon ring atoms. Contemplated carbocyclic rings include, but are not limited to, cyclopropyl, cyclobutyl, cyclopentyl, cyclohexyl, cycloheptyl, cyclooctyl, and cyclononyl.

As used herein, the term "heterocycloalkyl" means a monocyclic or polycyclic (e.g., bicyclic), saturated or partially unsaturated, ring system containing 3 or more (e.g., 3 to 12, 4 to 10, 4 to 8, or 5 to 7) total atoms, of which one to five (e.g., 1, 2, 3, 4, or 5) of the atoms are independently selected from nitrogen, oxygen, and sulfur. Nonlimiting examples of heterocycloalkyl groups include azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, and diazacycloheptyl.

Unless otherwise indicated, a cycloalkyl or heterocycloalkyl group can be unsubstituted or substituted with one or more, and in particular one to four, groups. Some contemplated substituents include halo, $C_{1-6}$alkyl, $C_{2-6}$alkenyl, $C_{2-6}$alkynyl, —$OCF_3$, —$NO_2$, —CN, —NC, —OH, alkoxy, amino, —$CO_2H$, —$CO_2C_{1-6}$alkyl, —$OCOC_{1-6}$alkyl, $C_3$-$C_{10}$ cycloalkyl, $C_3$-$C_{10}$ heterocycloalkyl, $C_5$-$C_{10}$aryl, and $C_5$-$C_{10}$ heteroaryl.

As used herein, the term "heteroaryl" refers to a monocyclic or polycyclic ring system (for example, bicyclic) containing one to three aromatic rings and containing one to four (e.g., 1, 2, 3, or 4) heteroatoms selected from nitrogen, oxygen, and sulfur in an aromatic ring. In certain embodiments, the heteroaryl group has from 5 to 20, from 5 to 15, from 5 to 10 ring, or from 5 to 7 atoms. Heteroaryl also refers to $C_{10-14}$ bicyclic and tricyclic rings, where one ring is aromatic and the others are saturated, partially unsaturated, or aromatic. Examples of heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, triazolyl, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four or one or two, substituents. Contemplated substituents include halo, $C_{1-6}$alkyl, $C_{2-6}$-alkenyl, $C_{2-6}$alkynyl, —$OCF_3$, —$NO_2$, —CN, —NC, —OH, alkoxy, amino, —$CO_2H$, —$CO_2C_{1-6}$alkyl, —$OCOC_1$-$C_8$alkyl, $C_3$-$C_{10}$ cycloalkyl, $C_3$-$C_{10}$ heterocycloalkyl, $C_5$-$C_{10}$aryl, and $C_5$-$C_{10}$ heteroaryl.

As used herein, the term Boc refers to the structure

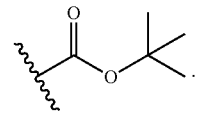 [SMILES: *C(=O)OC(C)(C)C]

As used herein, the term Cbz refers to the structure

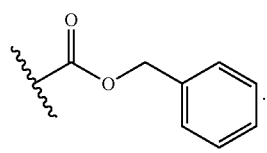 [SMILES: *C(=O)OCc1ccccc1]

As used herein, the term Bn refers to the structure

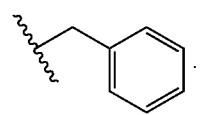

As used herein, the term trifluoroacetamide refers to the structure

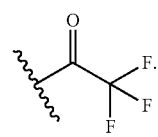 [SMILES: *C(=O)C(F)(F)F]

As used herein, the term trityl refers to the structure

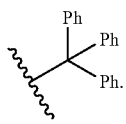

As used herein, the term tosyl refers to the structure

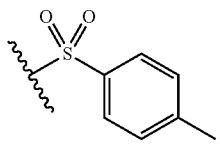

As used herein, the term Troc refers to the structure

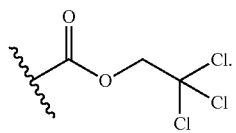 [SMILES: *C(=O)OCC(Cl)(Cl)Cl]

As used herein, the term Teoc refers to the structure

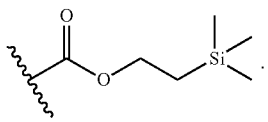 [SMILES: *C(=O)OCC[Si](C)(C)C]

As used herein, the term Alloc refers to the structure

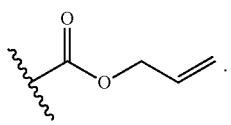 [SMILES: *C(=O)OCC=C]

As used herein, the term Fmoc refers to the structure

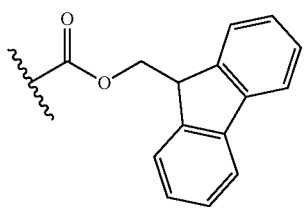

Compounds of the Disclosure

The compounds disclosed herein include all pharmaceutically acceptable isotopically-labeled compounds wherein one or more atoms of the compounds disclosed herein are replaced by atoms having the same atomic number, but an atomic mass or mass number different from the atomic mass or mass number usually found in nature. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{1}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labeled compounds of the disclosure, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready-means of detection.

Substitution with heavier isotopes such as deuterium, i.e. $^2H$, may afford certain therapeutic advantages resulting from greater metabolic stability, for example, increased in vivo half-life or reduced dosage requirements, and hence are preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Isotopically-labeled compounds as disclosed herein can generally be prepared by conventional techniques known to those skilled in the art or by processes analogous to those described in the accompanying examples and schemes using an appropriate isotopically-labeled reagent in place of the non-labeled reagent previously employed.

Certain of the compounds as disclosed herein may exist as stereoisomers (i.e., isomers that differ only in the spatial arrangement of atoms) including optical isomers and conformational isomers (or conformers). The compounds disclosed herein include all stereoisomers, both as pure individual stereoisomer preparations and enriched preparations of each, and both the racemic mixtures of such stereoisomers as well as the individual diastereomers and enantiomers that may be separated according to methods that are known to those skilled in the art. Additionally, the compounds disclosed herein include all tautomeric forms of the compounds.

Certain of the compounds disclosed herein may exist as atropisomers, which are conformational stereoisomers that occur when rotation about a single bond in the molecule is prevented, or greatly slowed, as a result of steric interactions with other parts of the molecule. The compounds disclosed herein include all atropisomers, both as pure individual atropisomer preparations, enriched preparations of each, or a non-specific mixture of each. Where the rotational barrier about the single bond is high enough, and interconversion between conformations is slow enough, separation and isolation of the isomeric species may be permitted. For example, groups such as, but not limited to, the following $R^{10}$ groups,

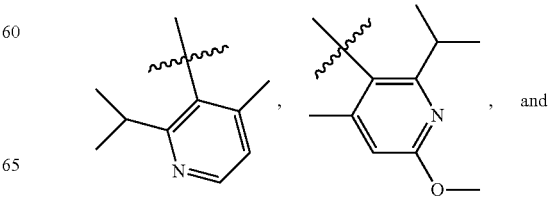

and

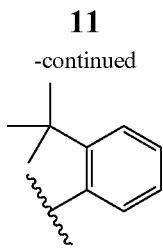

may exhibit restricted rotation.

Synthesis of Disclosed Compounds

Compounds as disclosed herein can be synthesized via a number of specific methods. The examples which outline specific synthetic routes, and the generic schemes below are meant to provide guidance to the ordinarily skilled synthetic chemist, who will readily appreciate that the solvent, concentration, reagent, protecting group, order of synthetic steps, time, temperature, and the like can be modified as necessary, well within the skill and judgment of the ordinarily skilled artisan.

EMBODIMENTS

Embodiment 1

In one embodiment of the present invention, the present invention comprises a compound having a structure selected from:

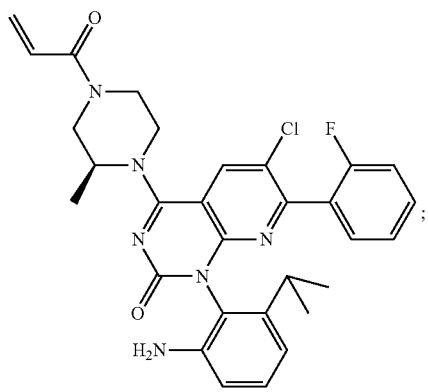

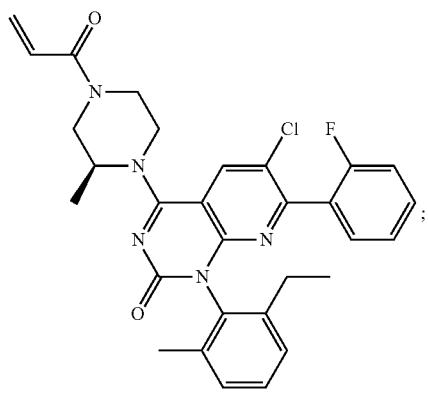

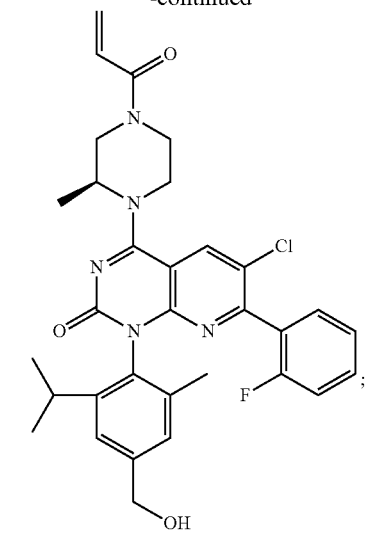

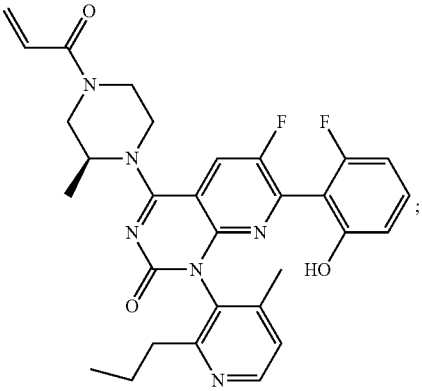

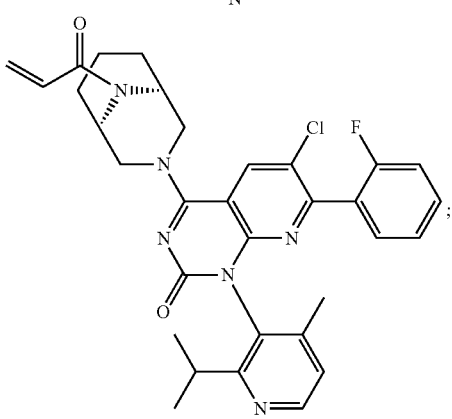

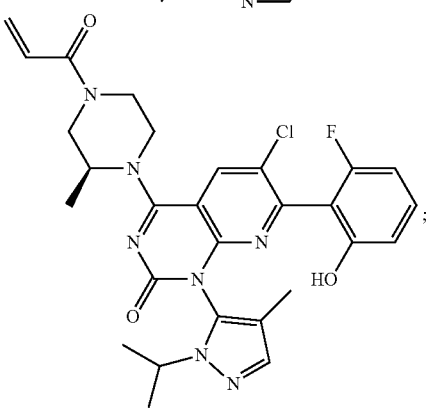

13
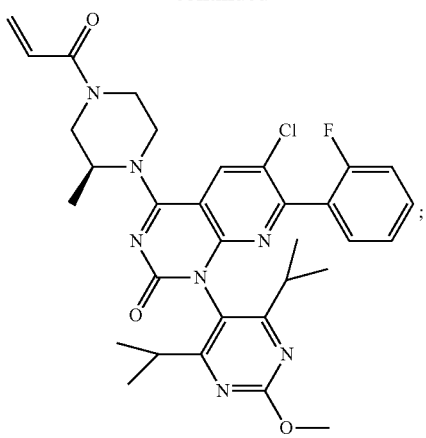
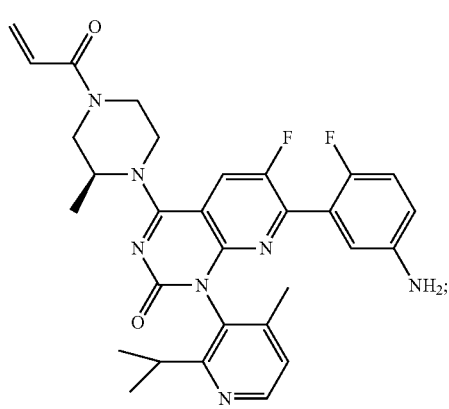
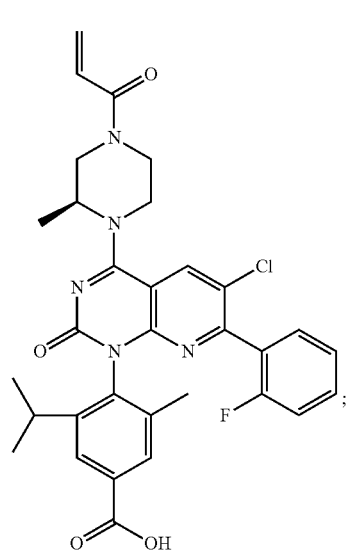
14
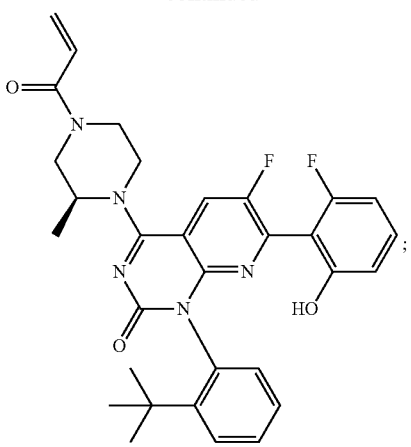
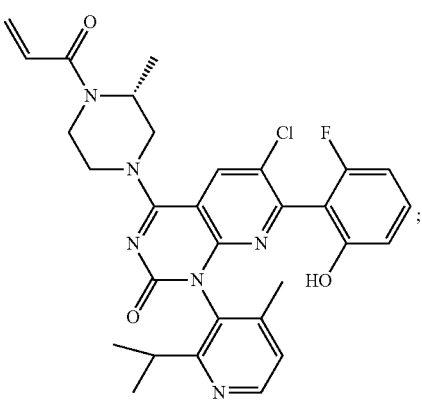
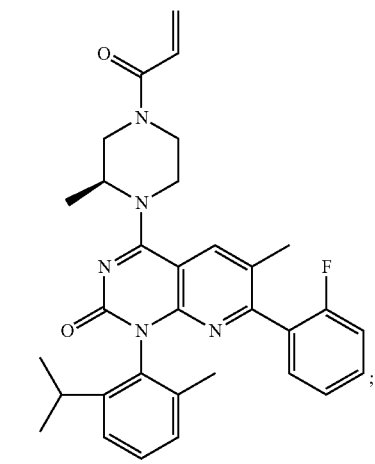

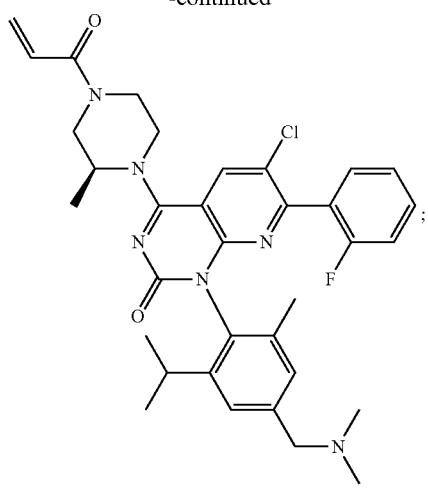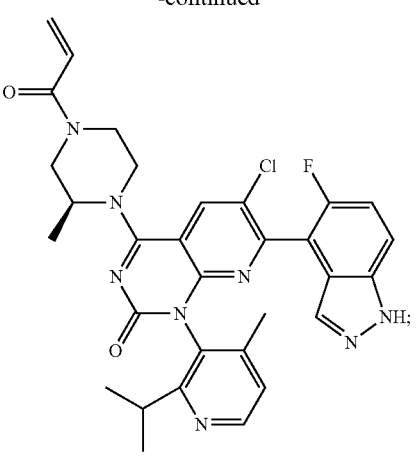

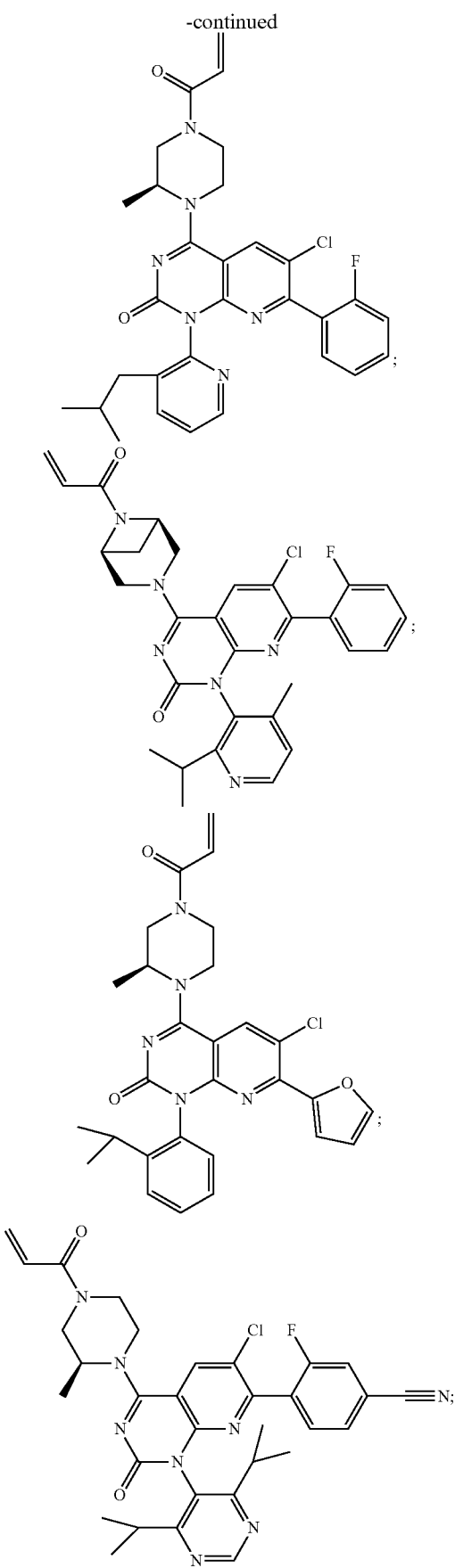
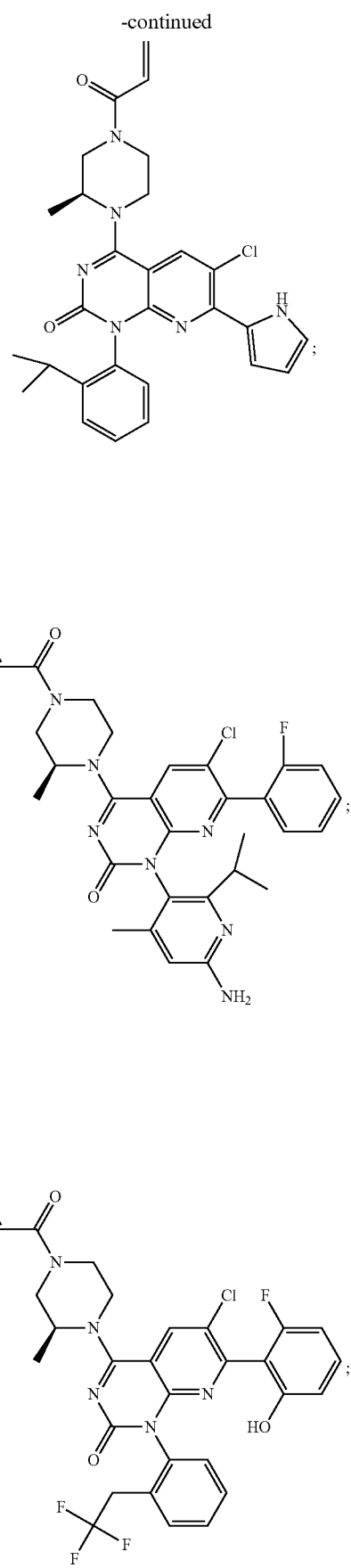

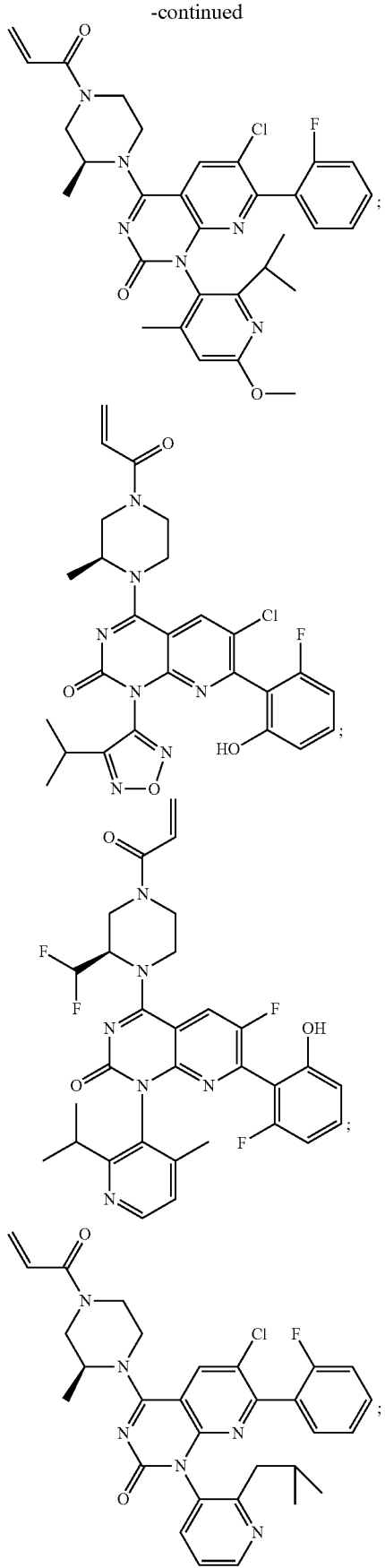
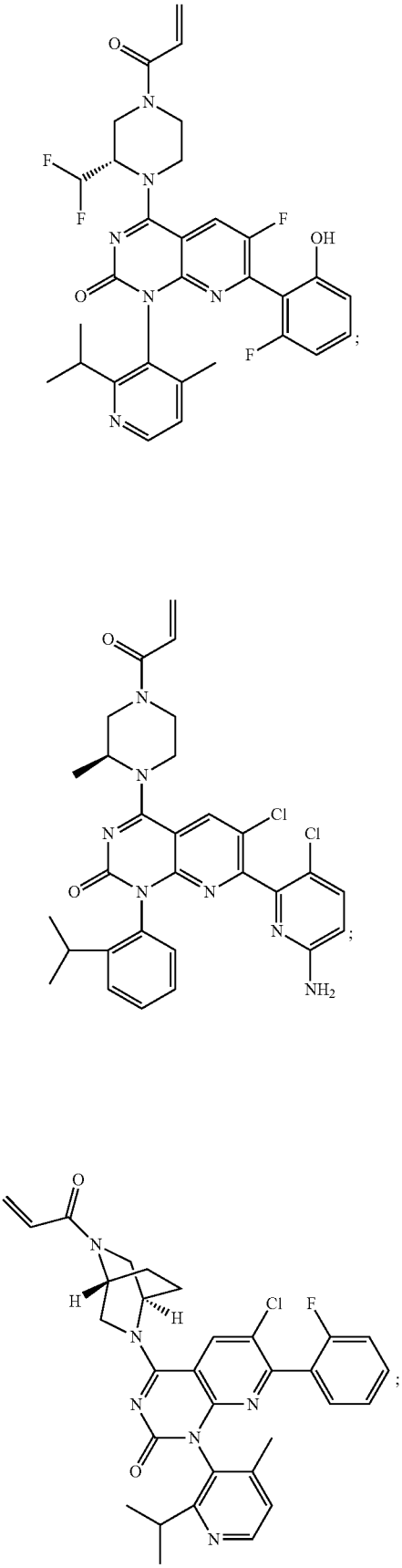

21
-continued
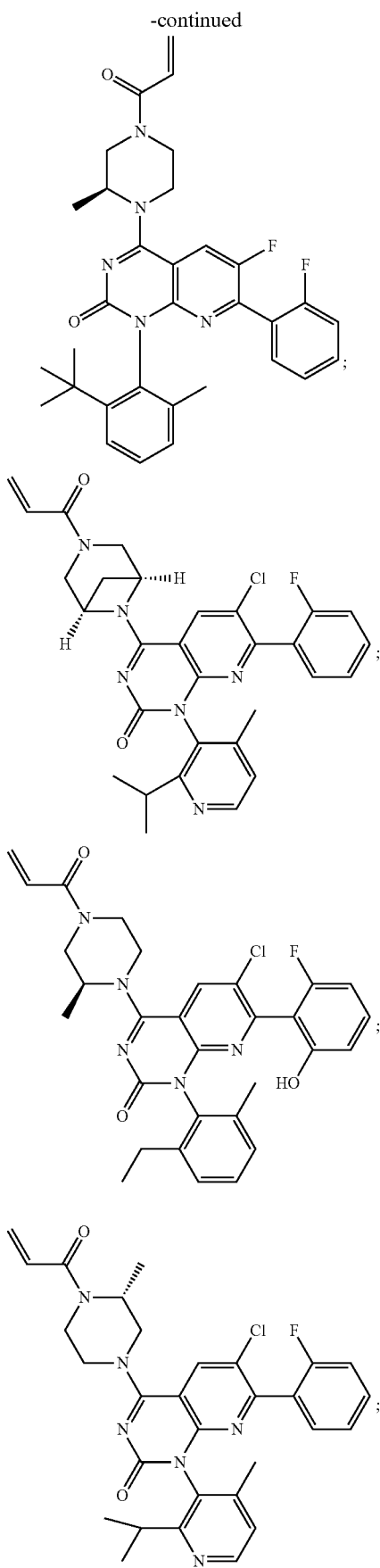
22
-continued
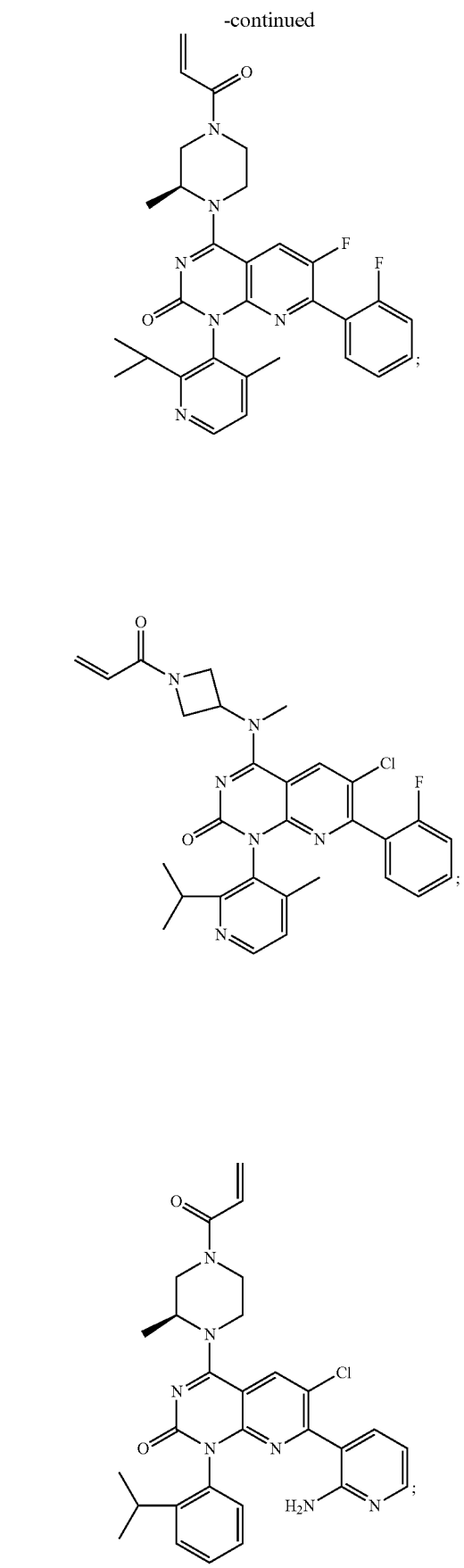

23
-continued
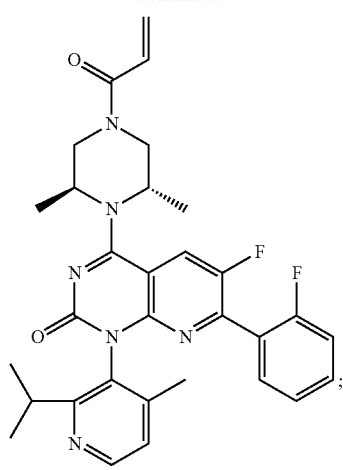
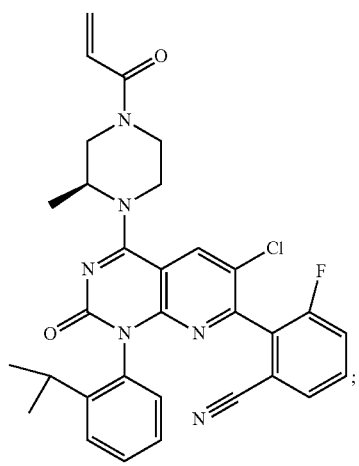
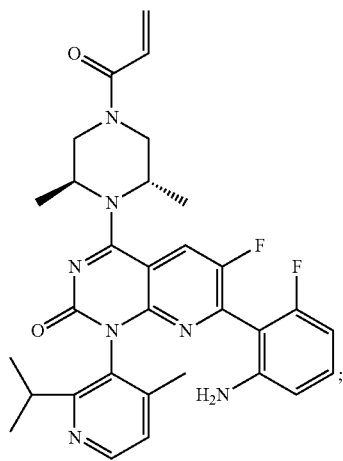
24
-continued
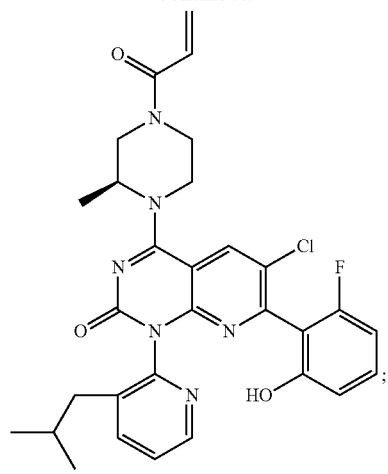
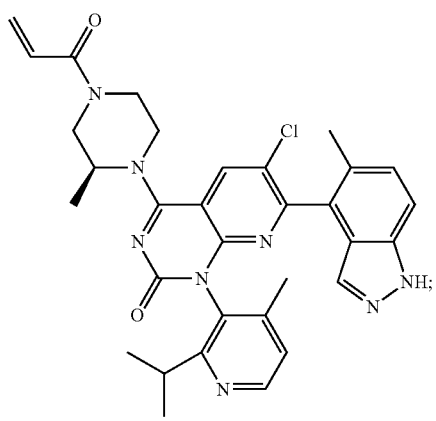
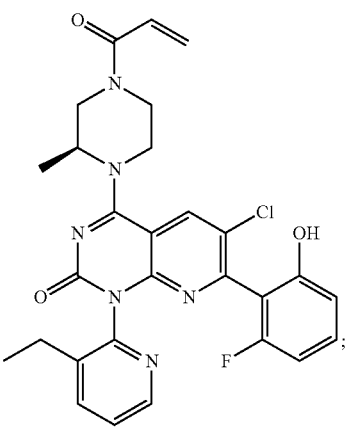

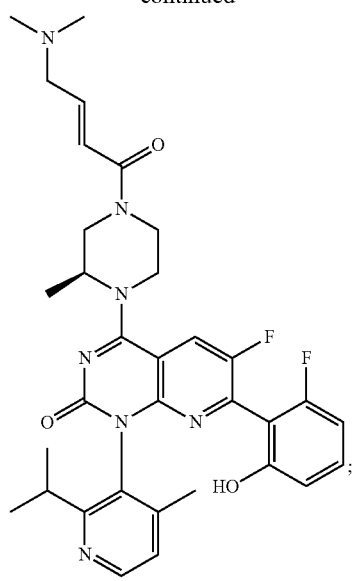
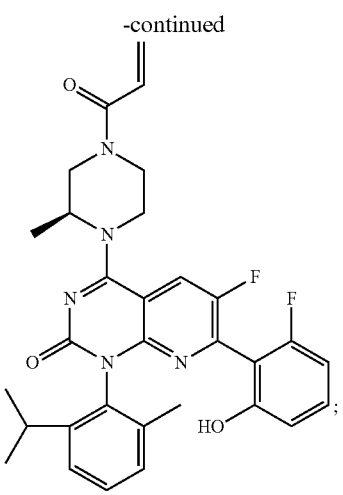

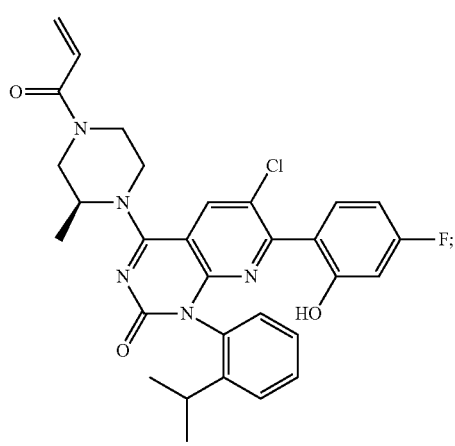
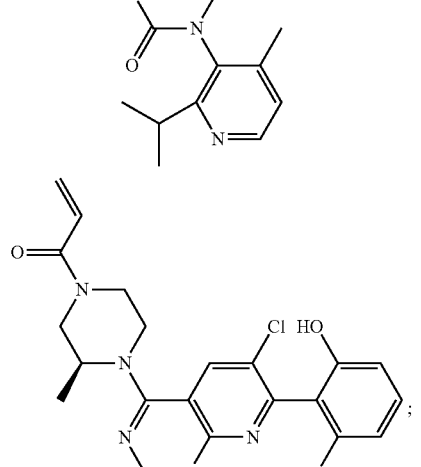
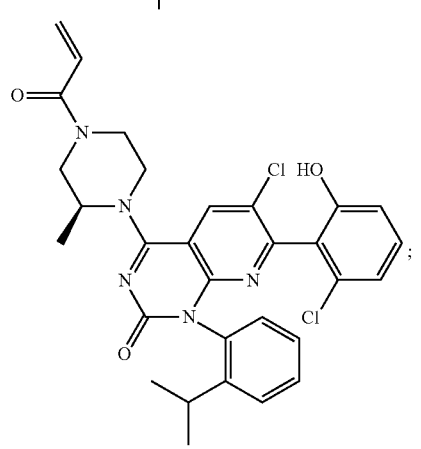
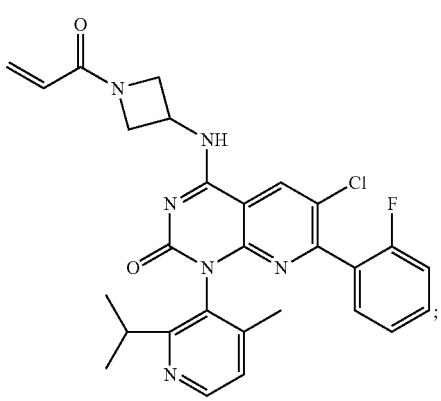

27
-continued
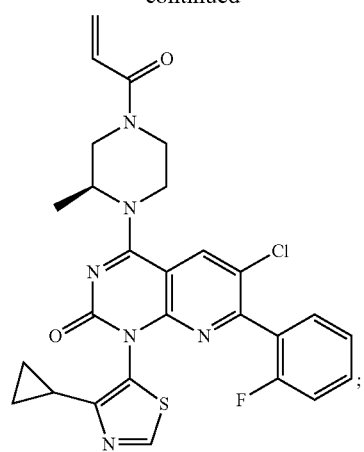
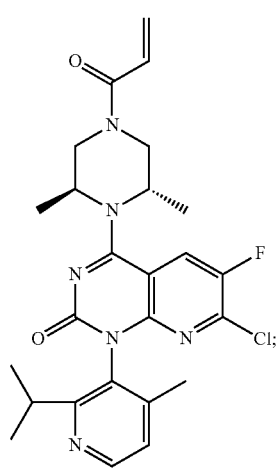
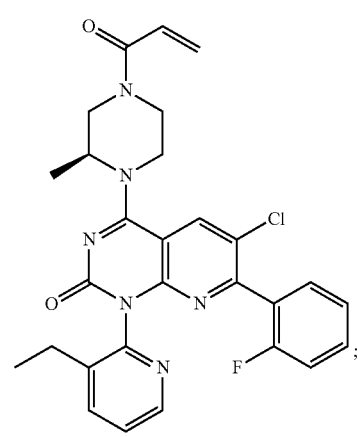
28
-continued
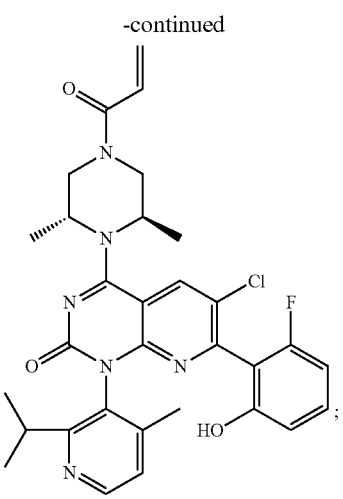
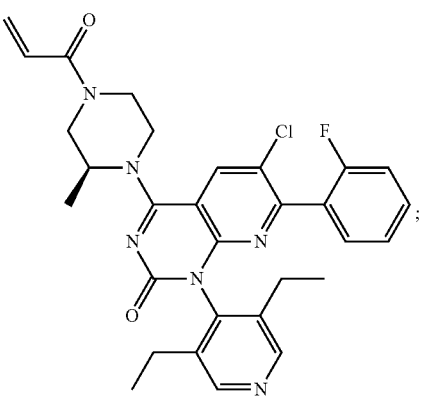
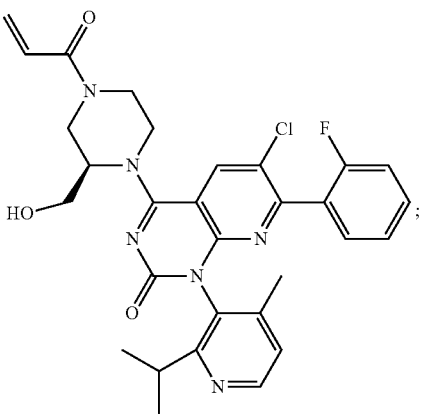
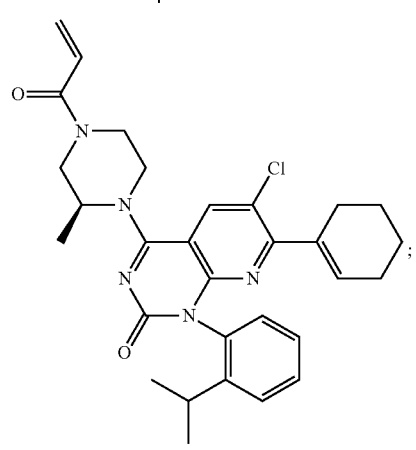

-continued
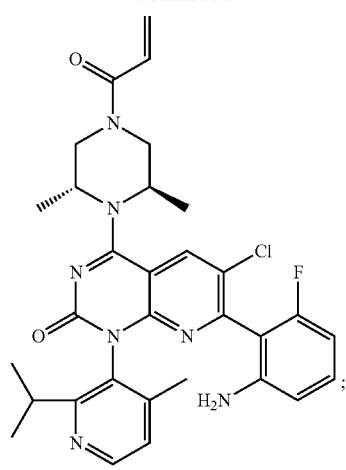
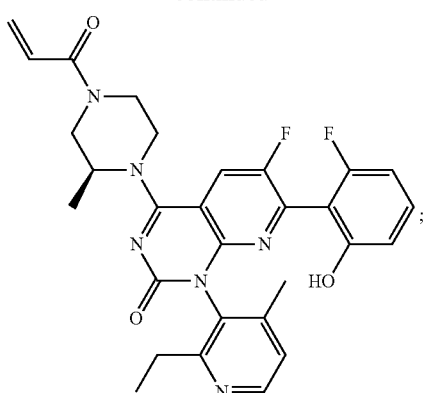
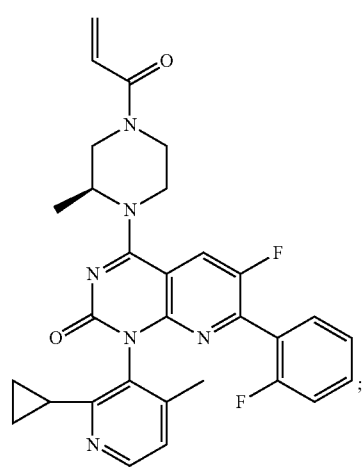
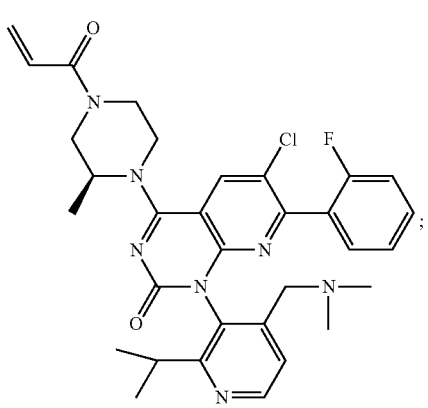
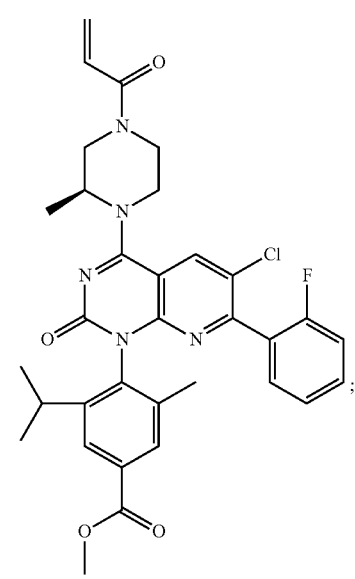
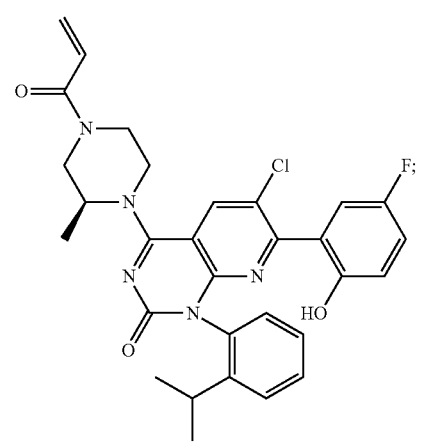
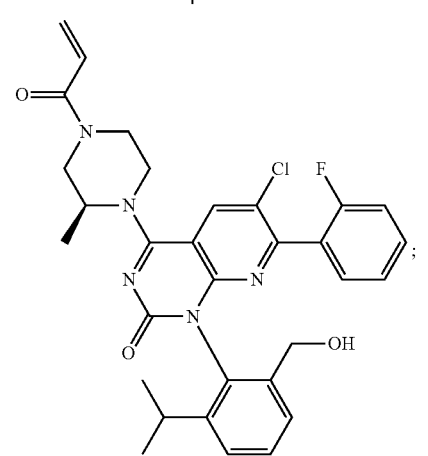

31
-continued
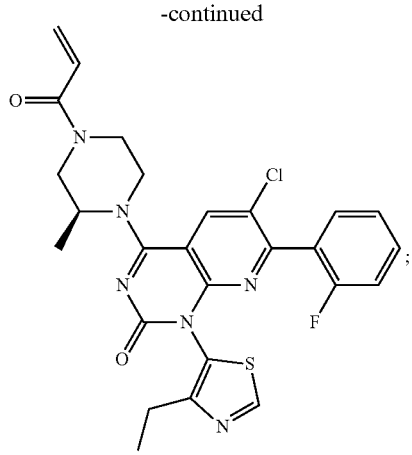
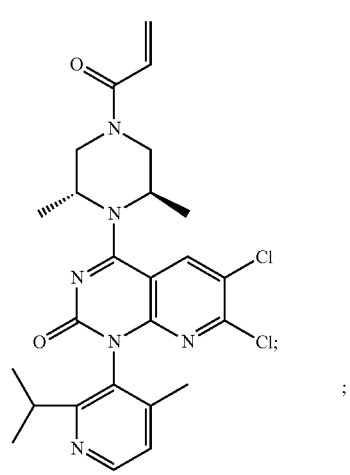
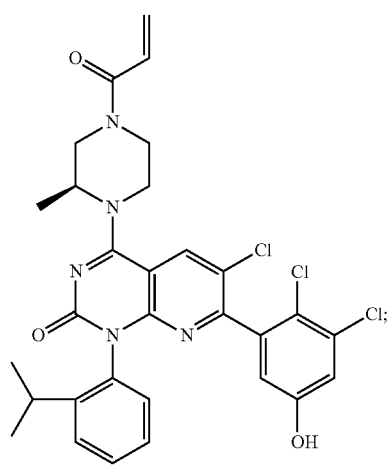
32
-continued
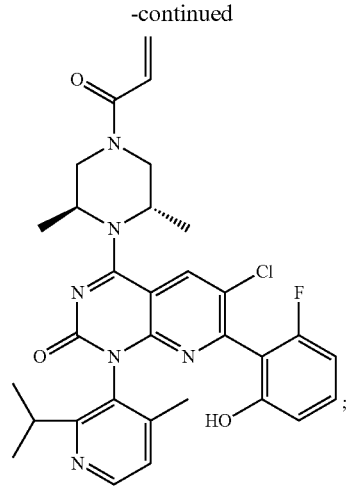
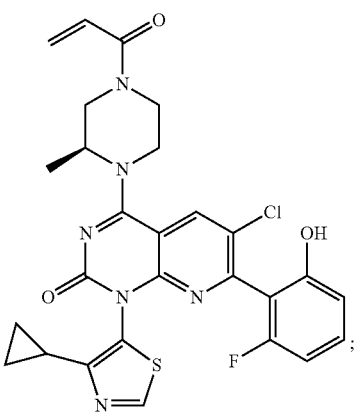
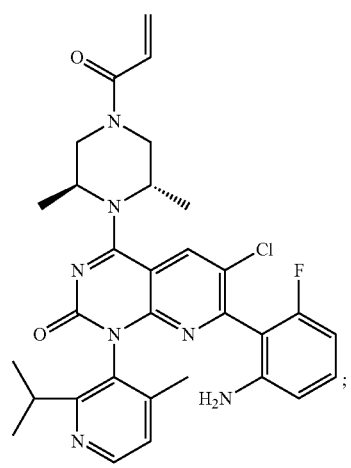

33
-continued
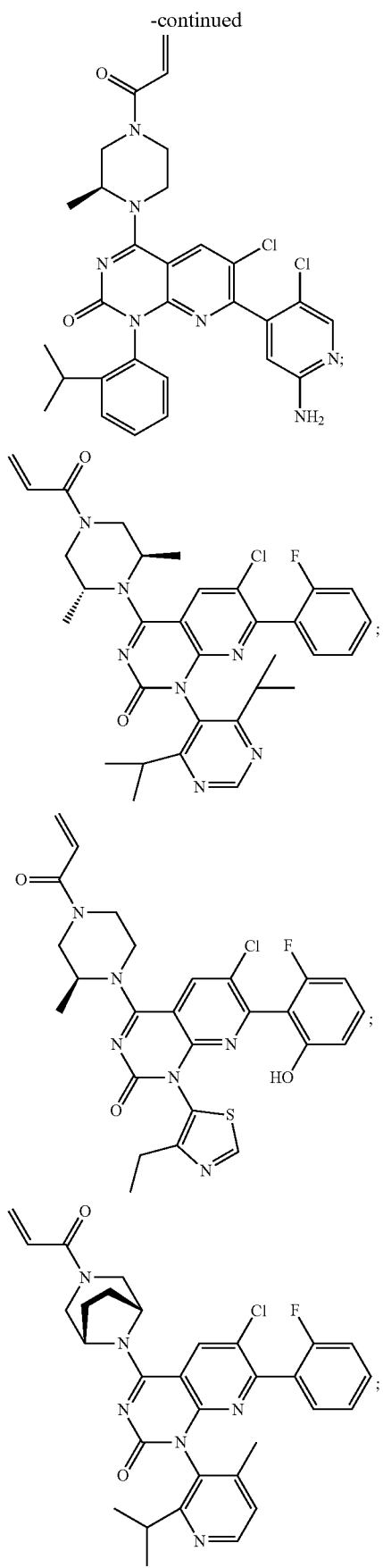
34
-continued
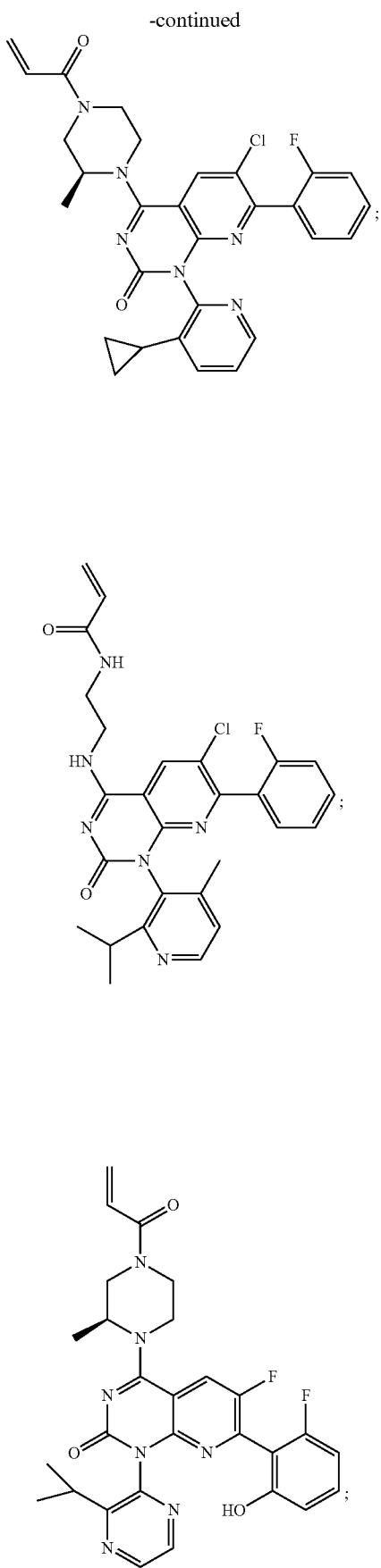

35
-continued
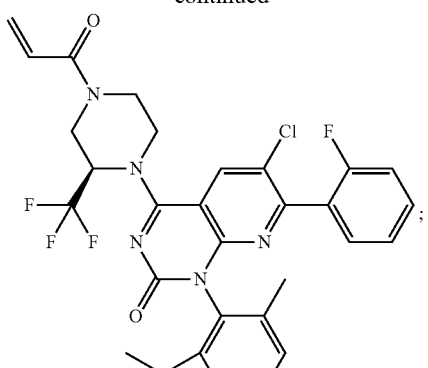
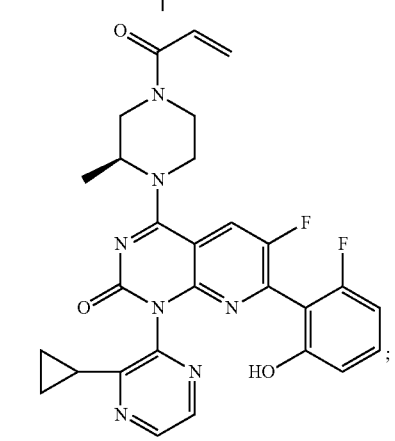
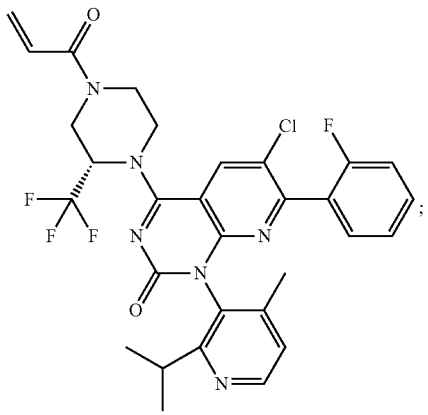
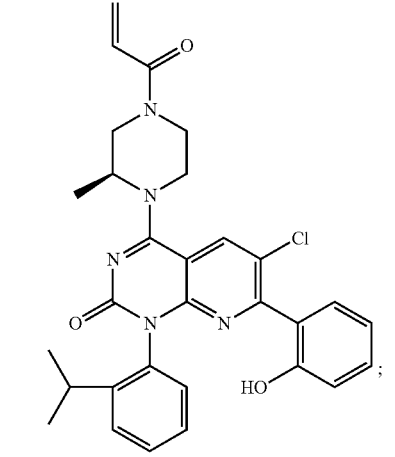
36
-continued
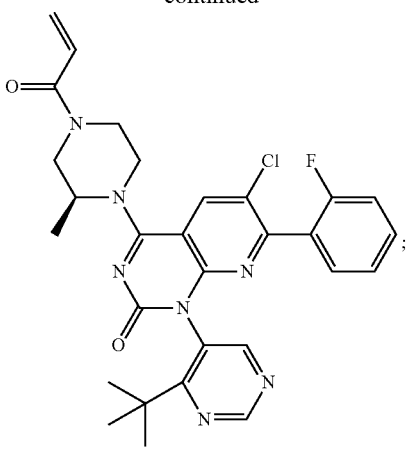
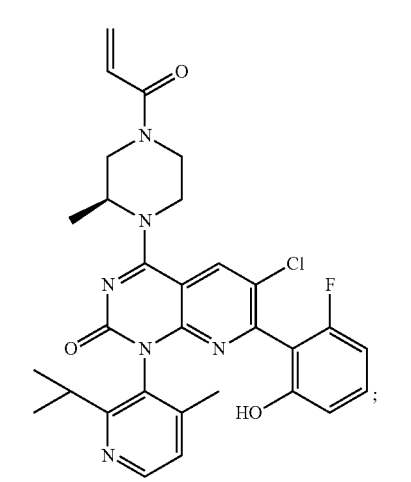
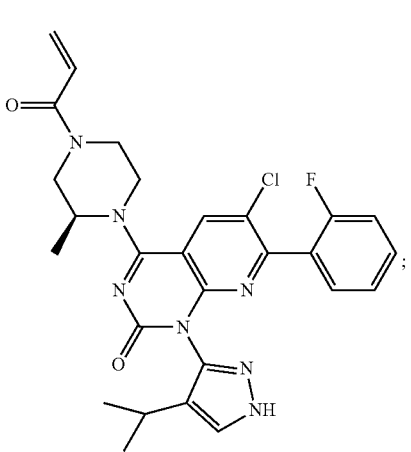

37
-continued
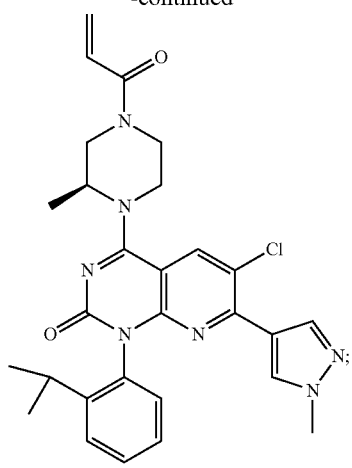
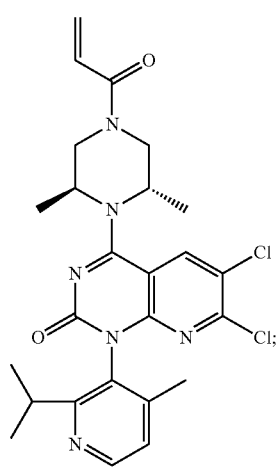
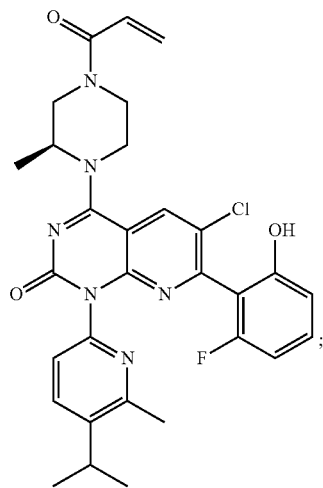
38
-continued
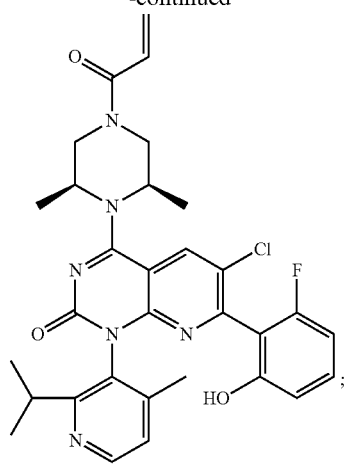
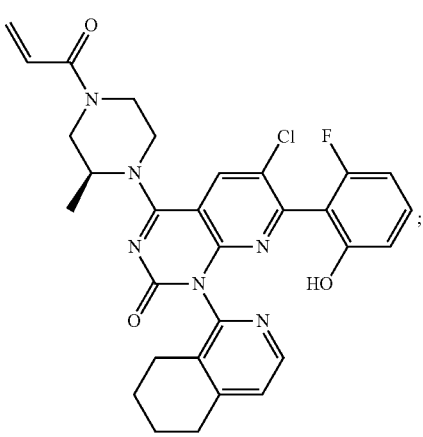
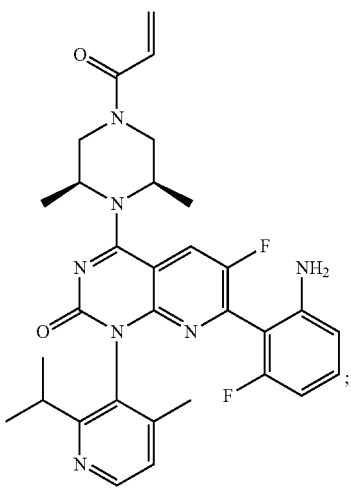

39
-continued
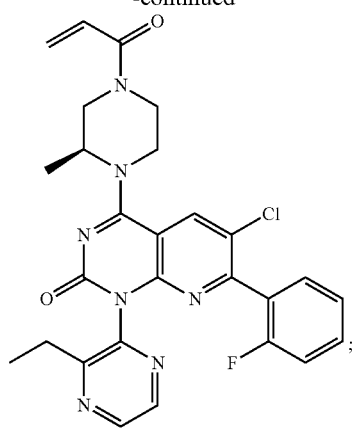
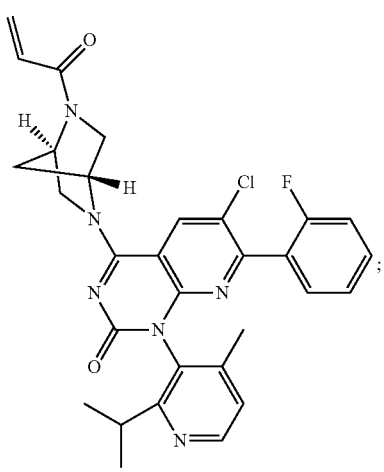
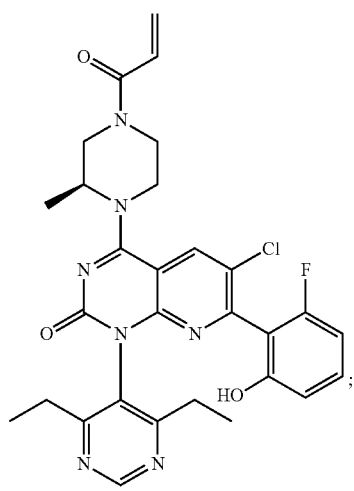
40
-continued
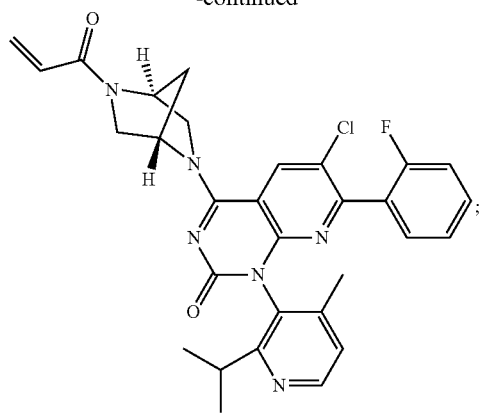
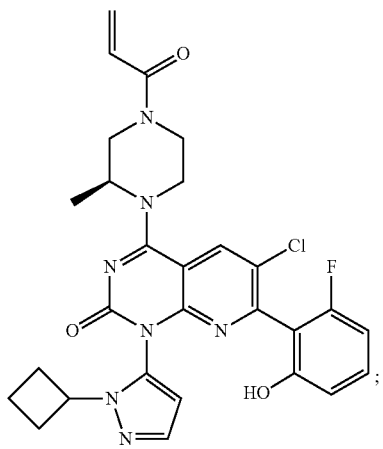
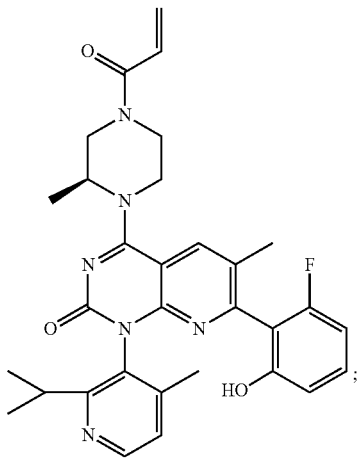

41
-continued
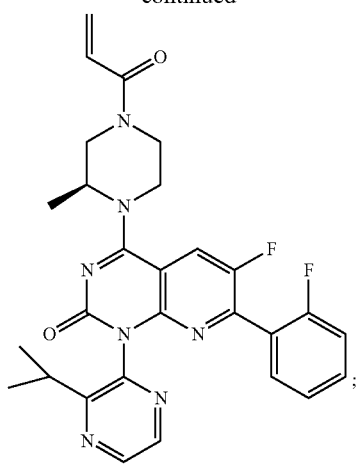
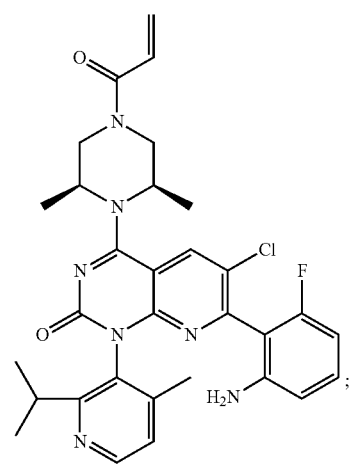
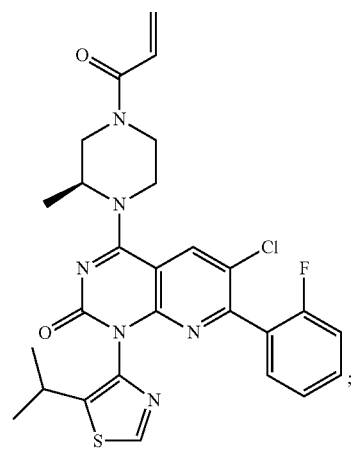
42
-continued
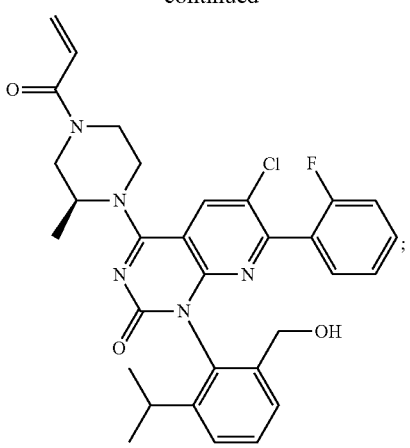
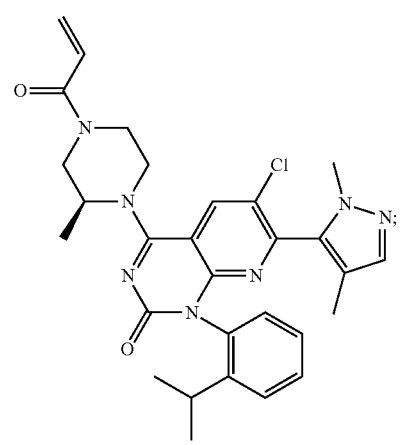
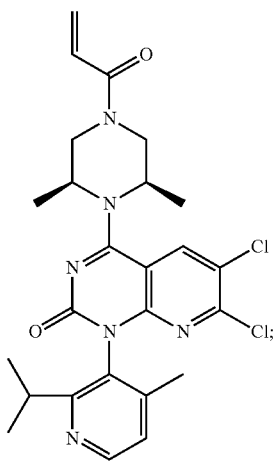

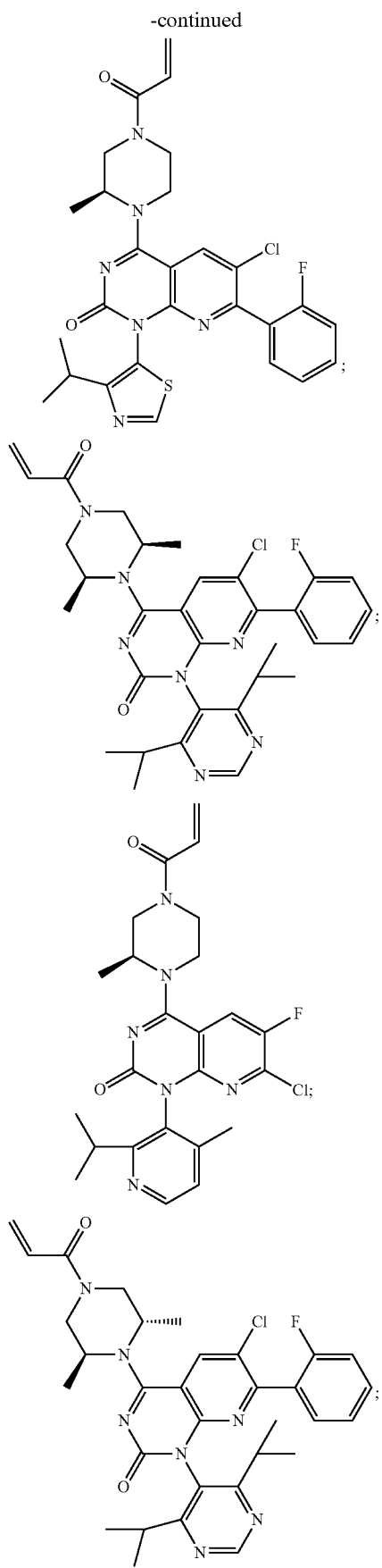
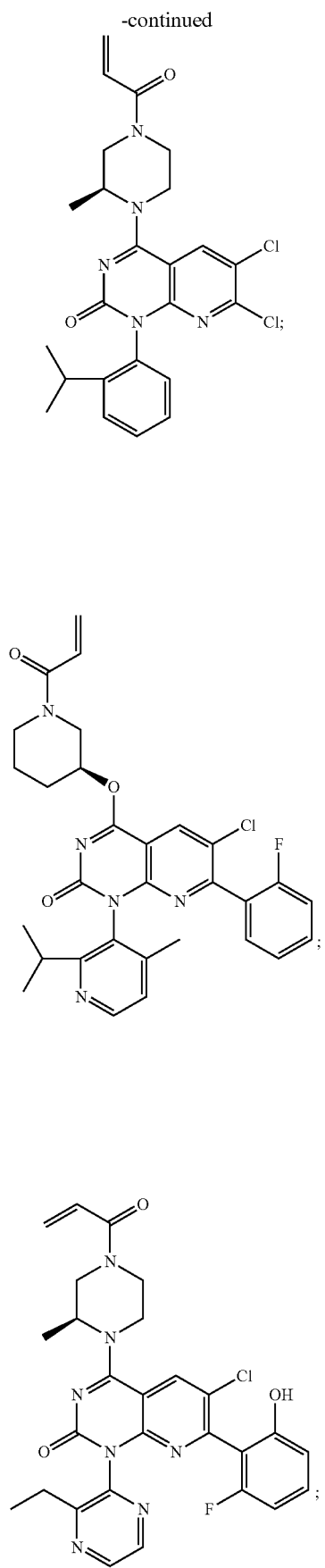

45
-continued
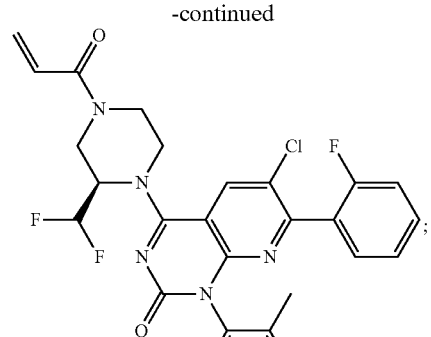
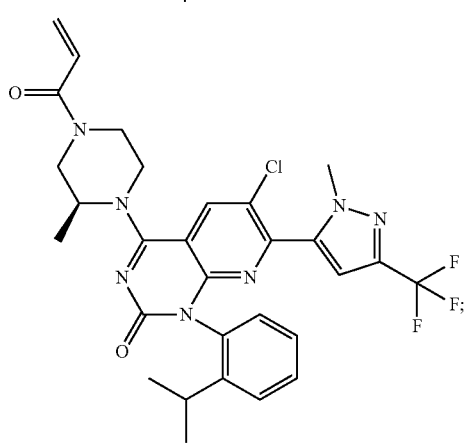
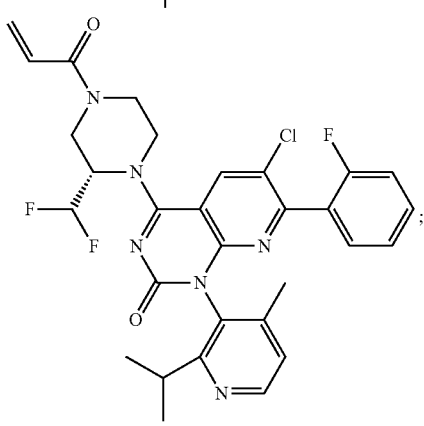
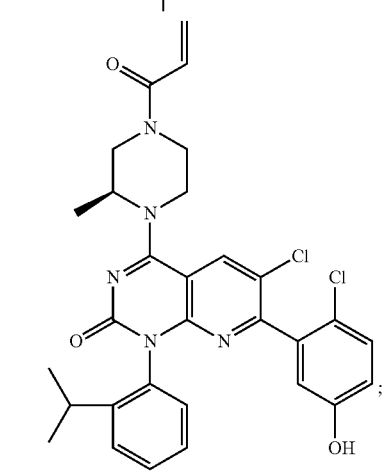
46
-continued
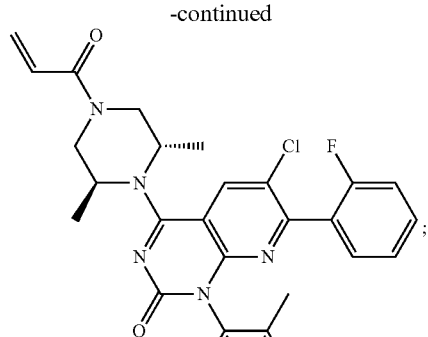
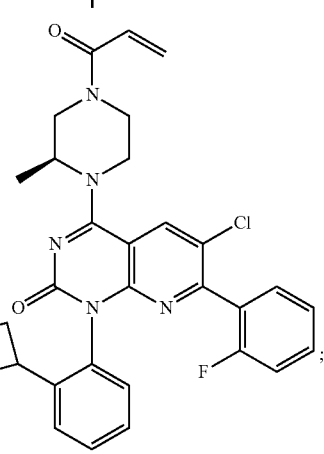
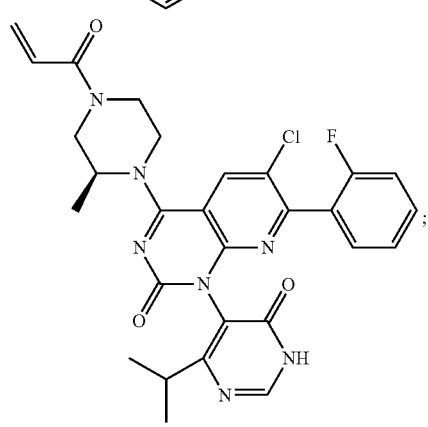
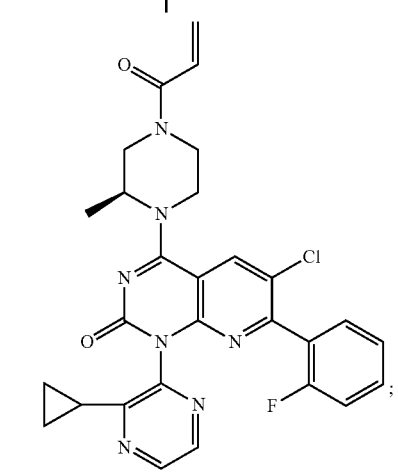

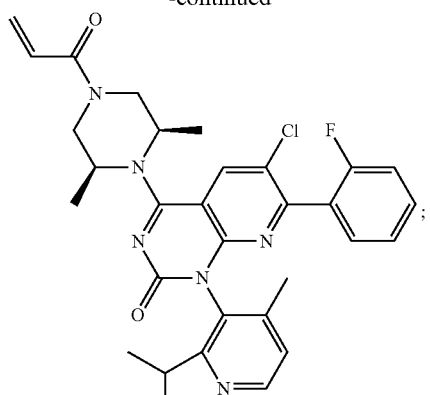
;
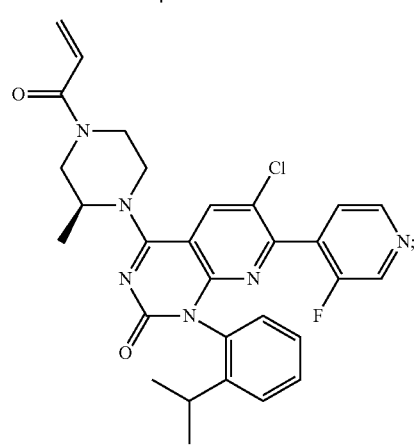
;
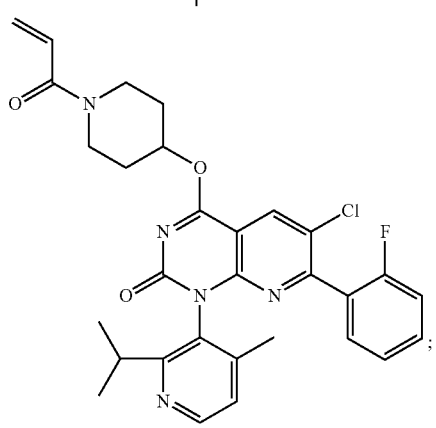
;
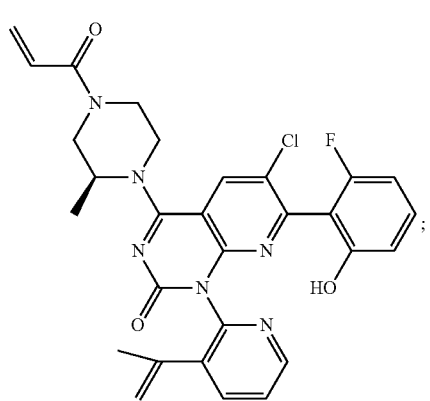
;
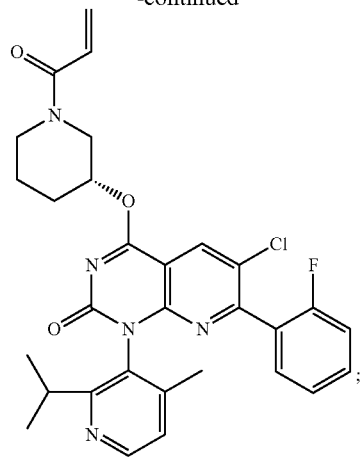
;
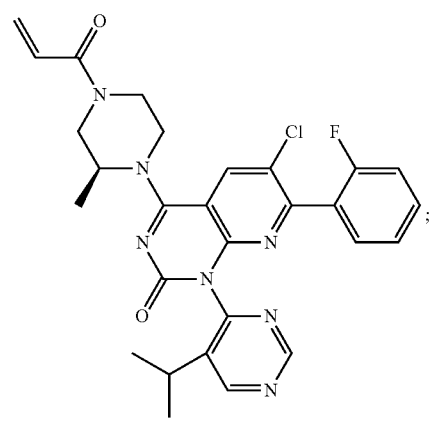
;
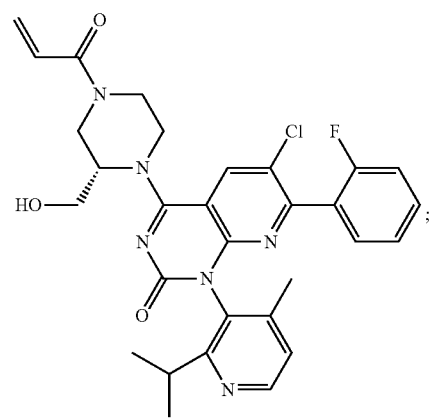
;

49
-continued
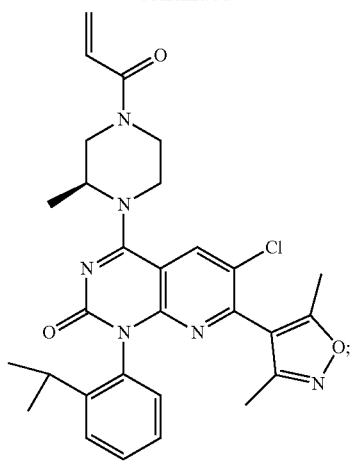
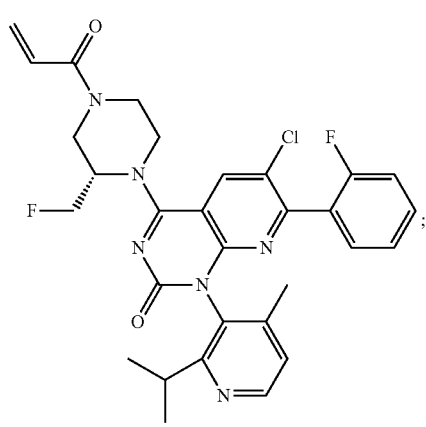
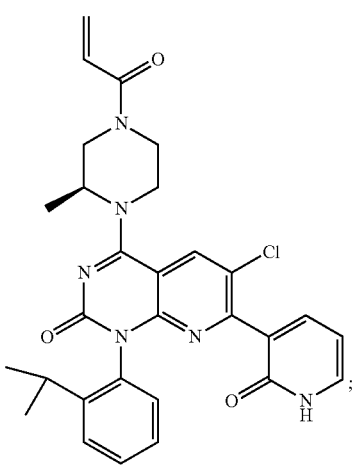
50
-continued
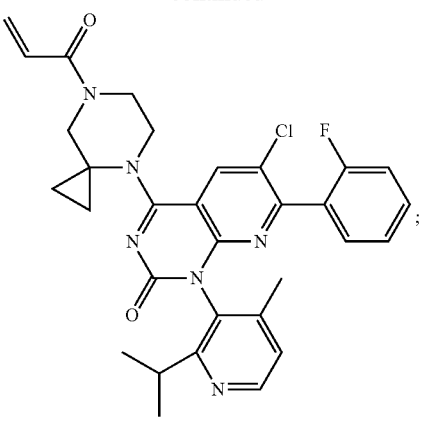
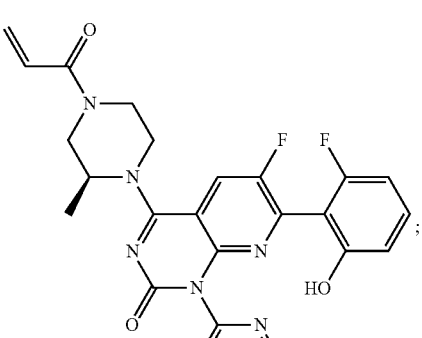
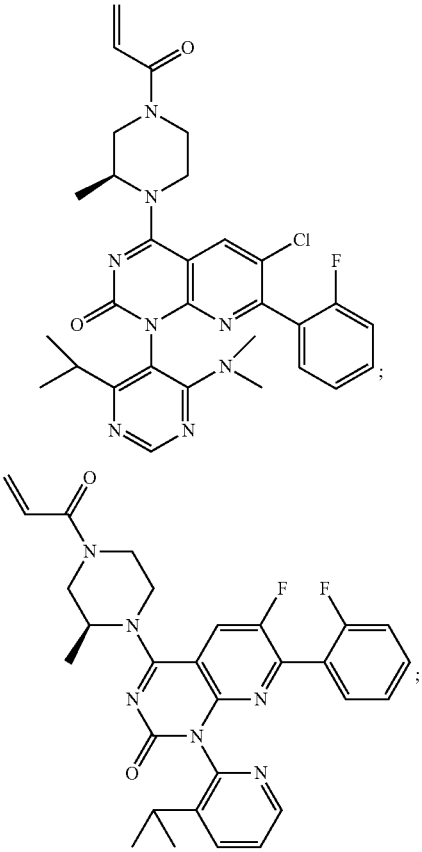

51
-continued
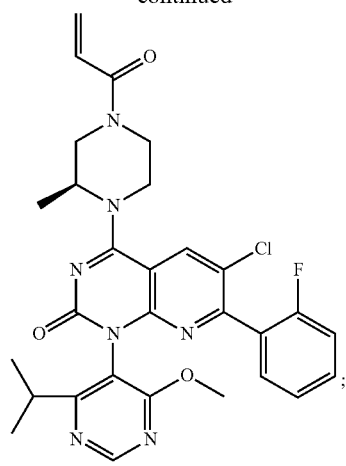
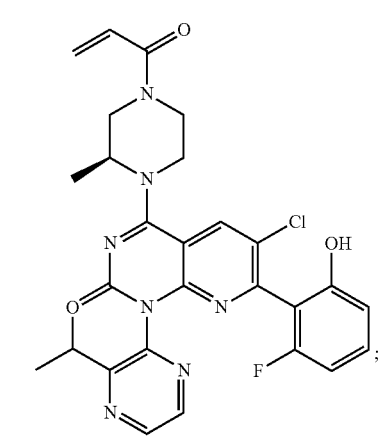
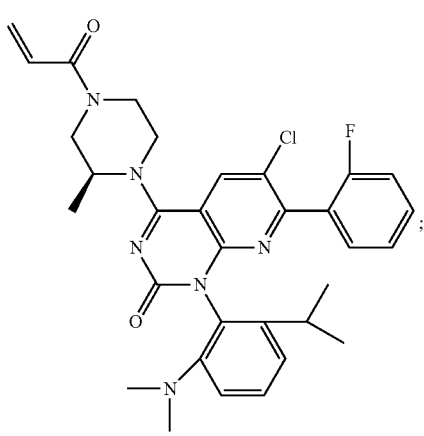
52
-continued
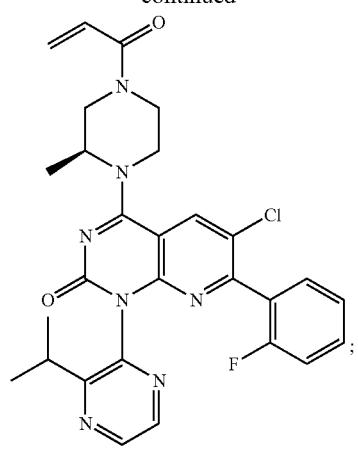
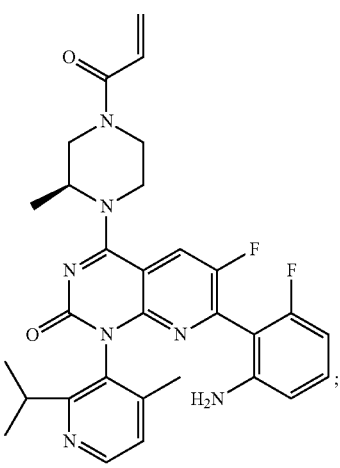
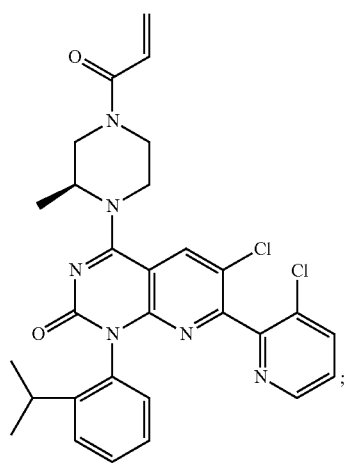

53
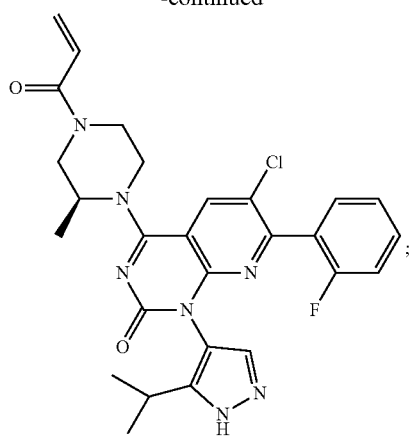
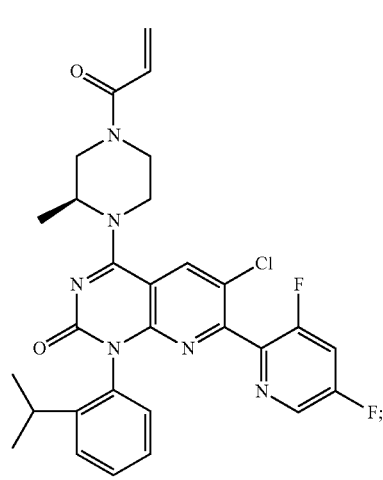
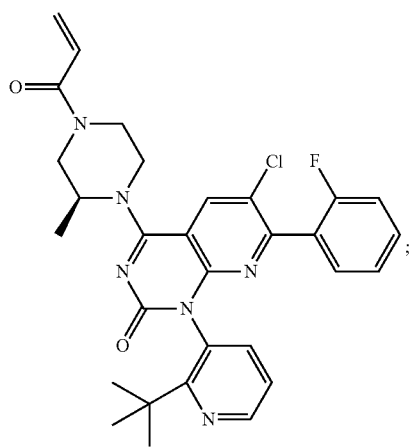
54
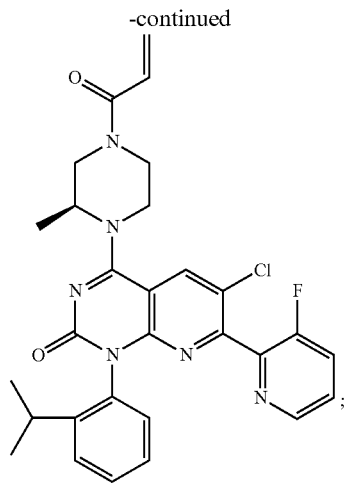
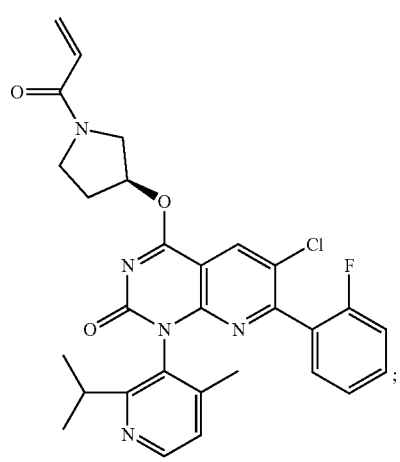
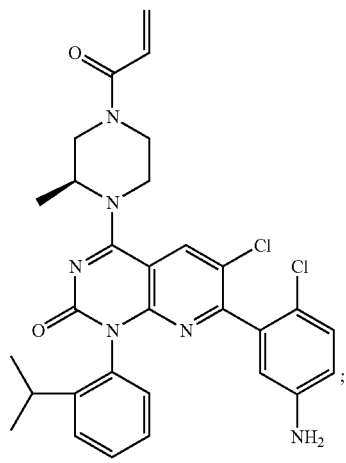

55
-continued
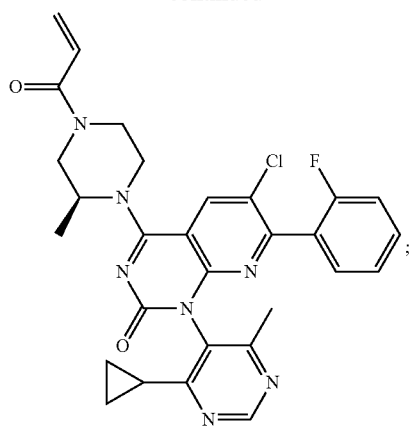
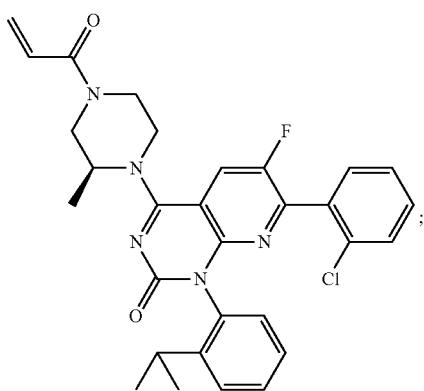
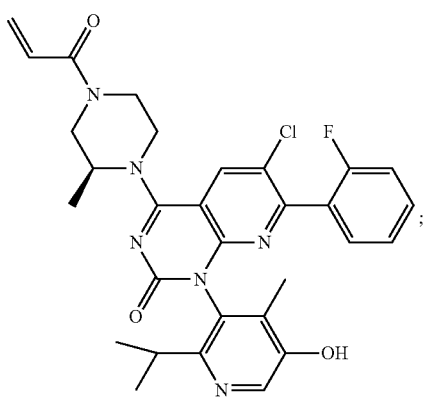
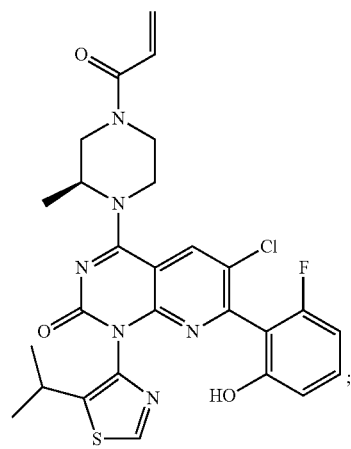
56
-continued
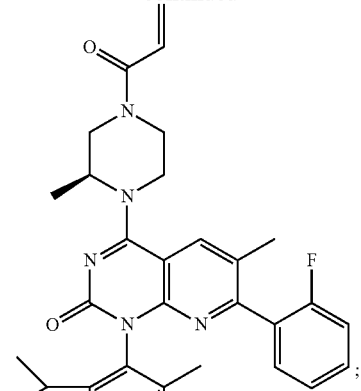
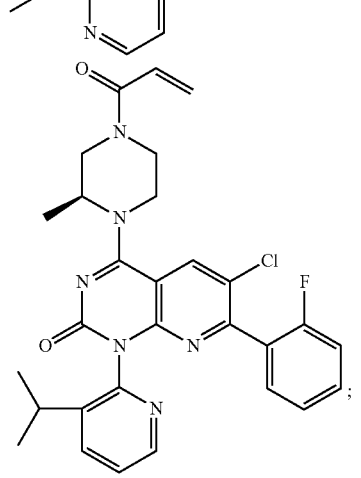
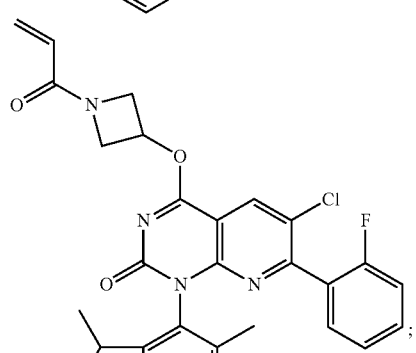
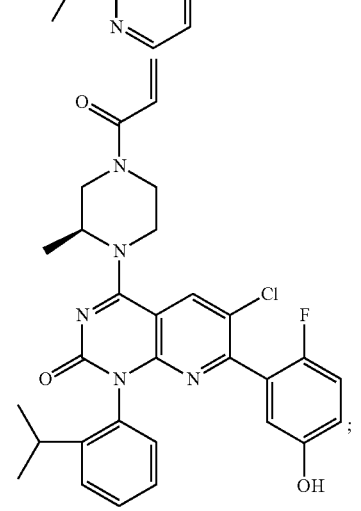

57
-continued
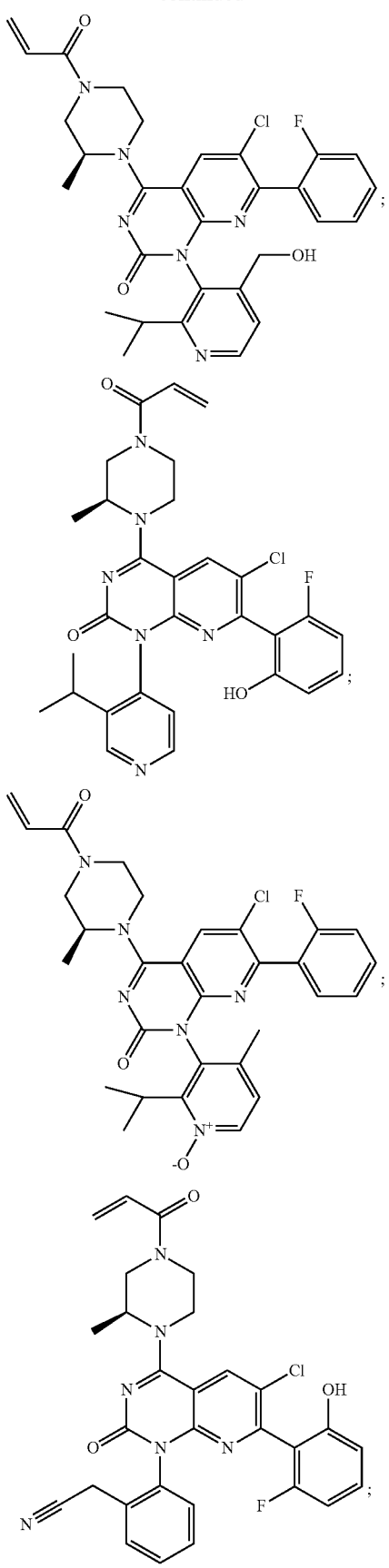
58
-continued
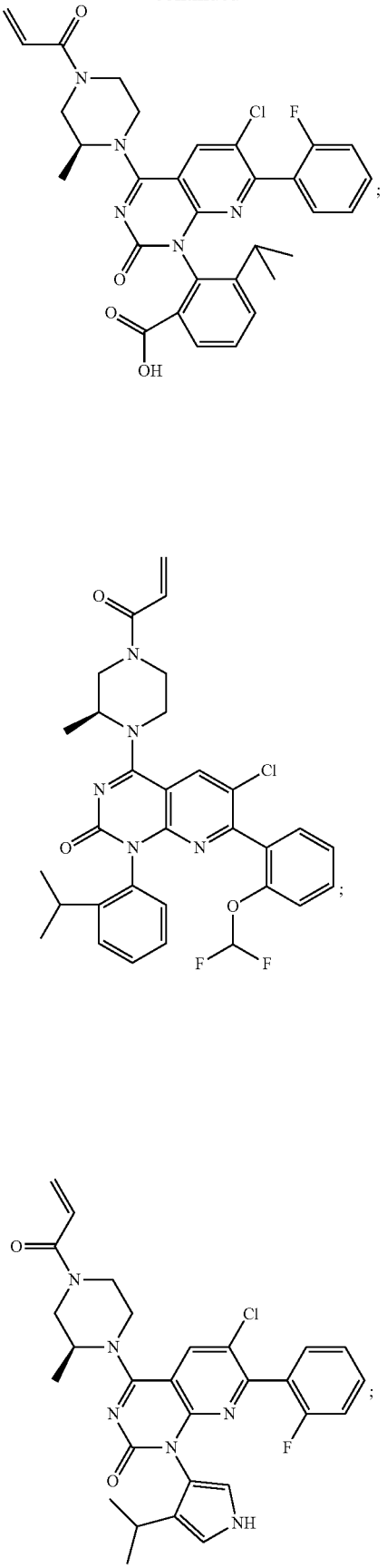

59
-continued
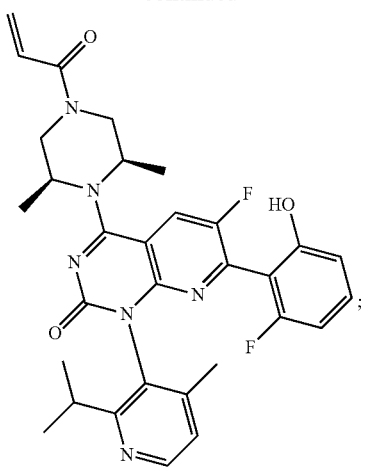
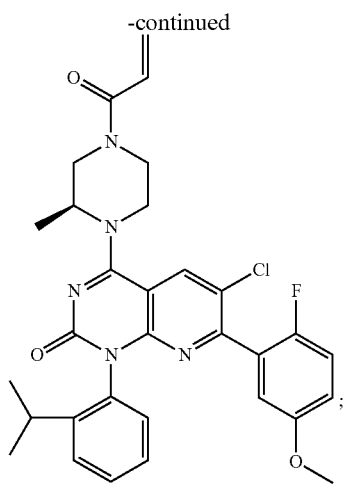
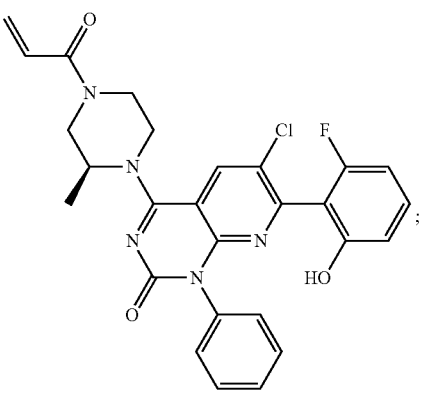
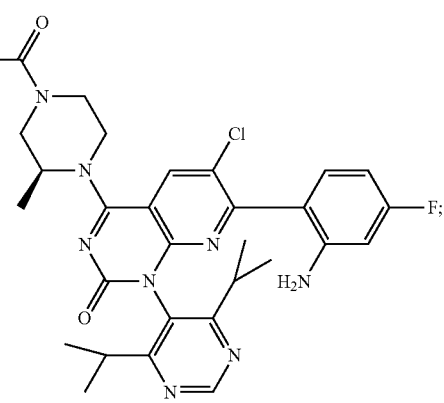
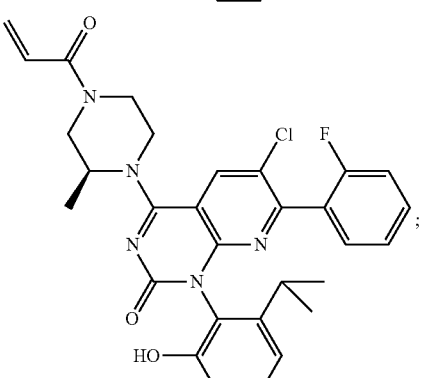
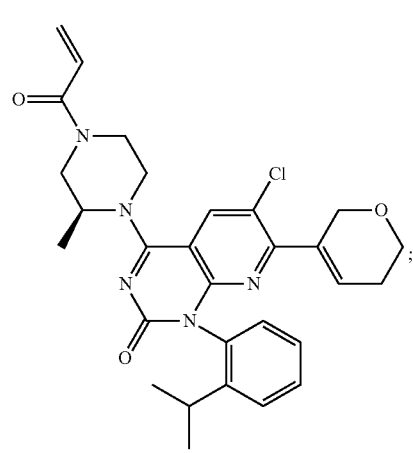
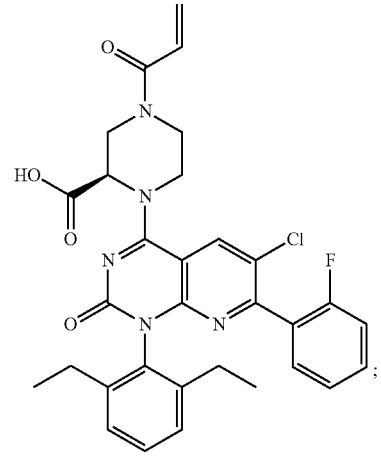
60
-continued

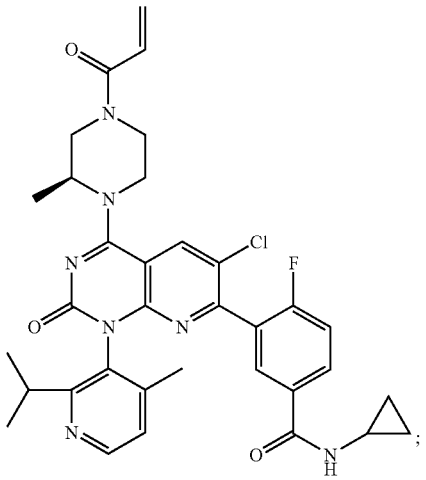
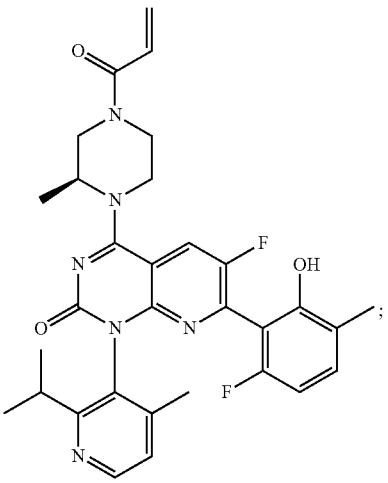
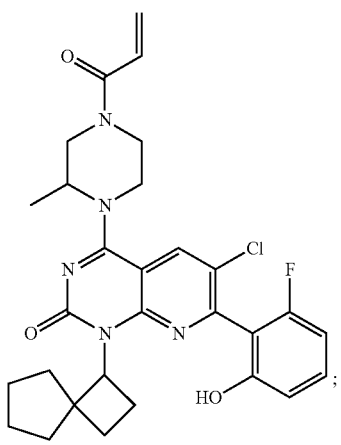
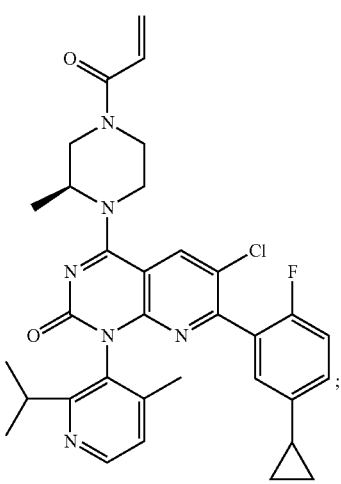

63
-continued
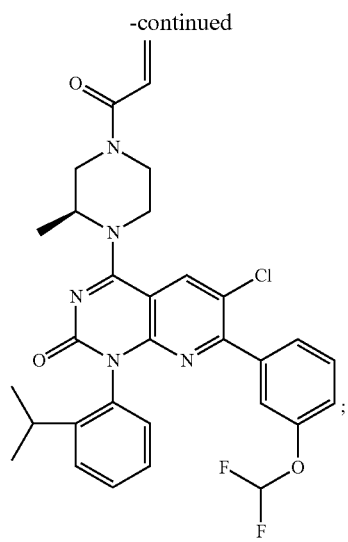
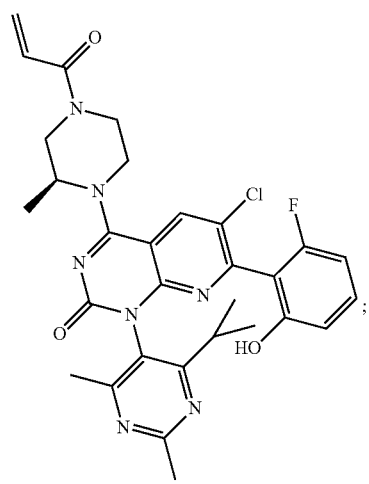
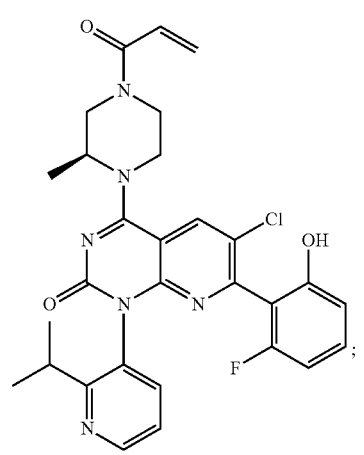
64
-continued
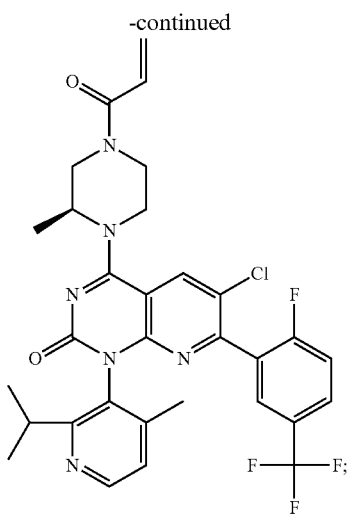
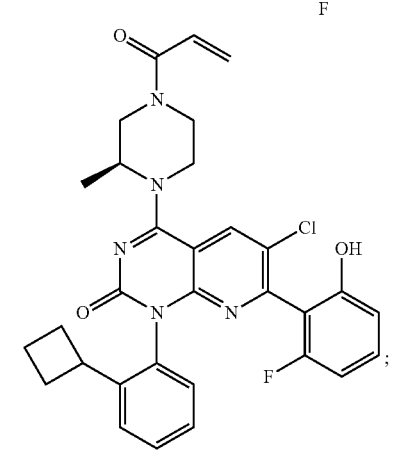
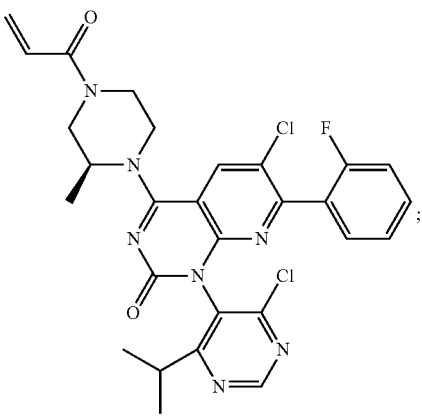
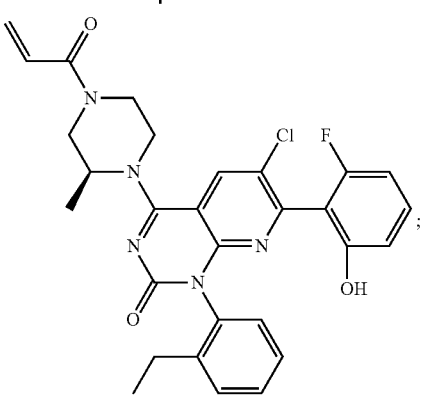

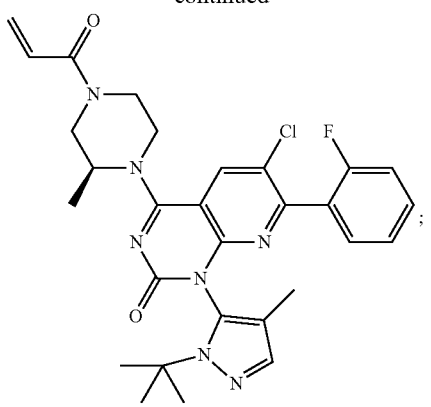
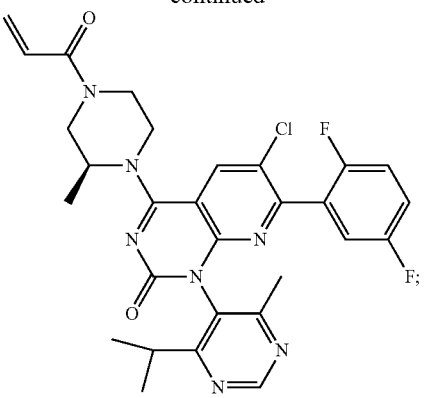
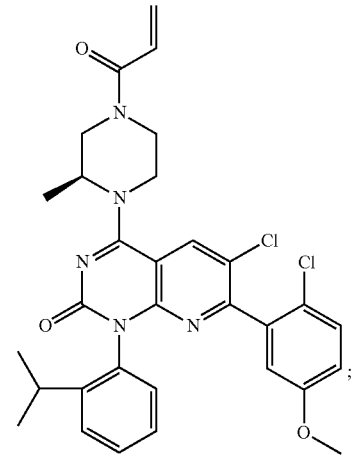
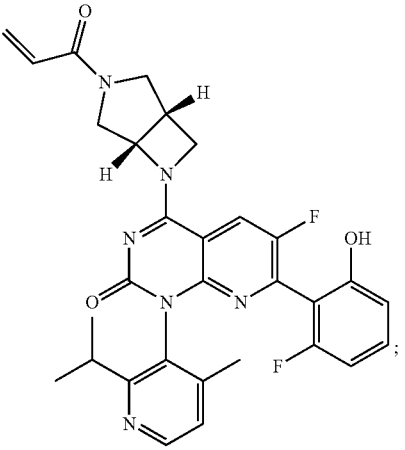

-continued
67
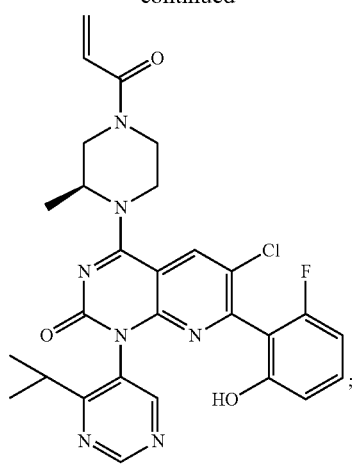
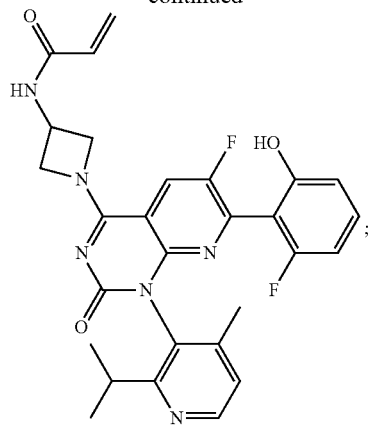
68
-continued
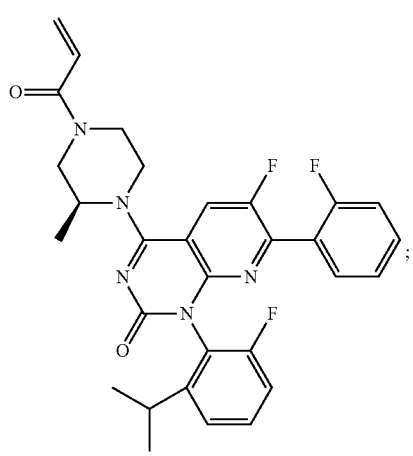
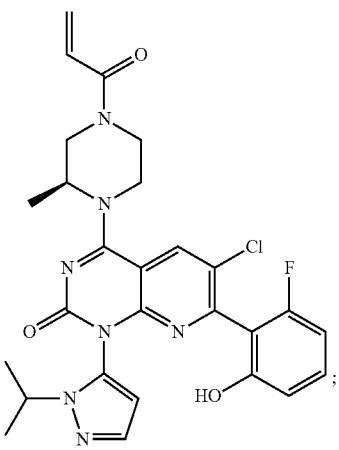
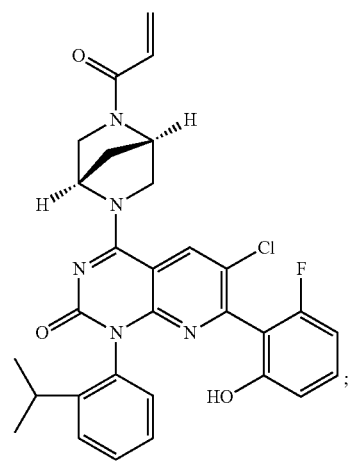
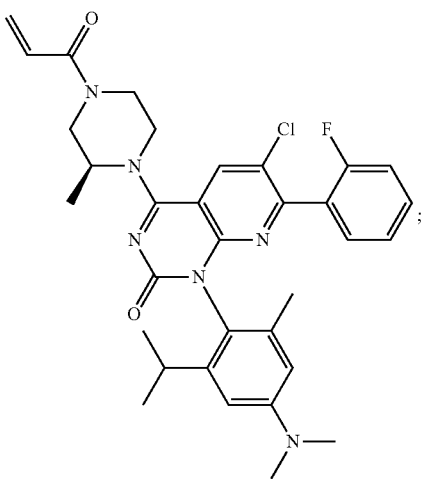

69
-continued
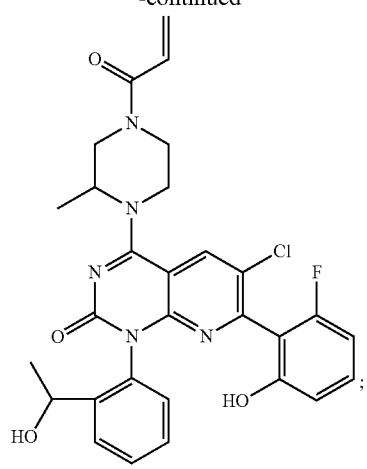
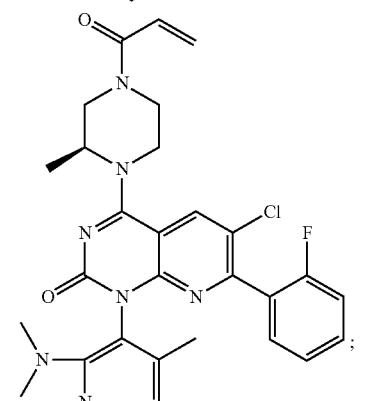
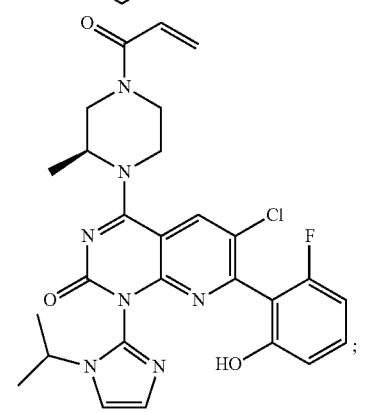

70
-continued
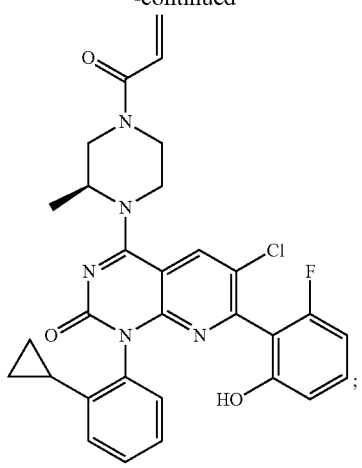
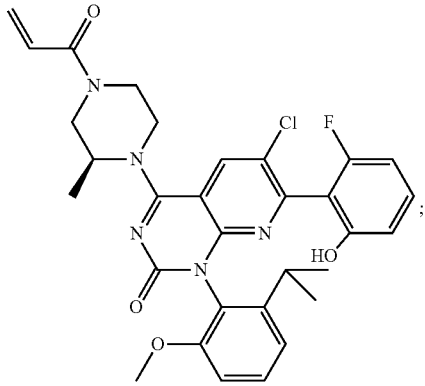
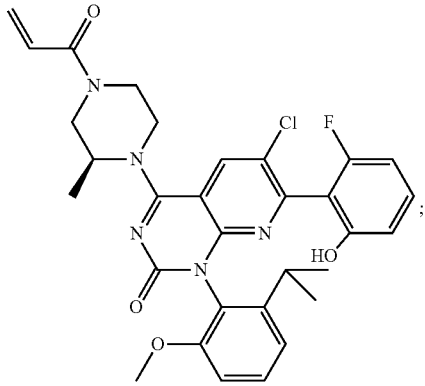
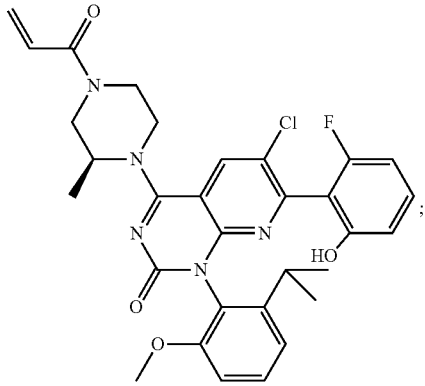

-continued
71
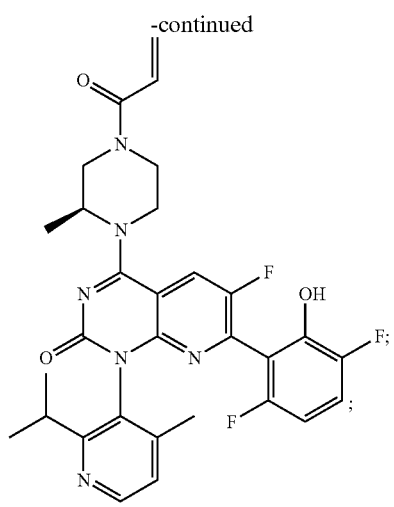
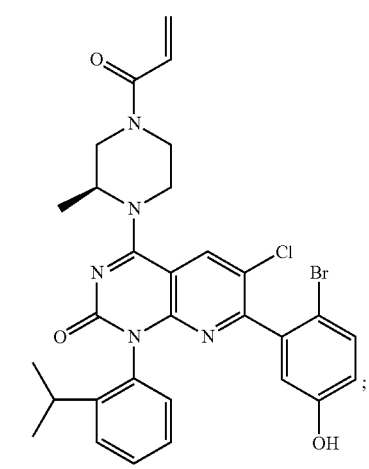
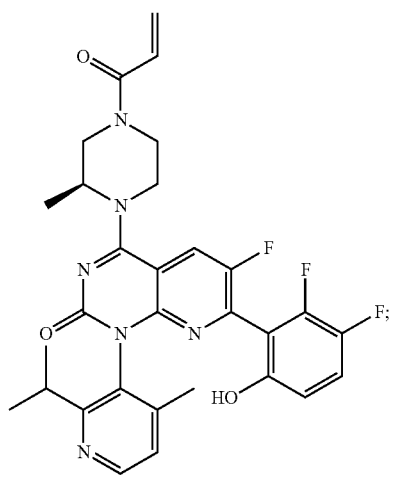
72
-continued
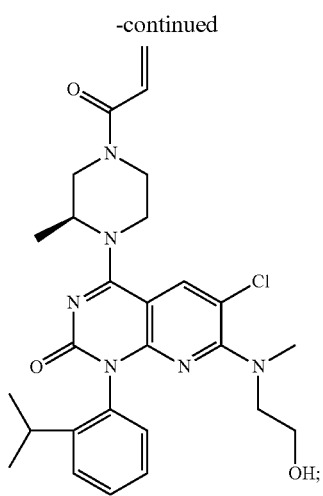
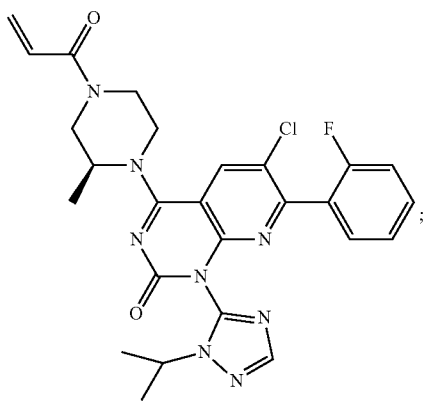
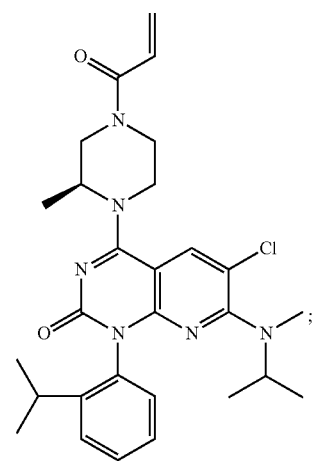

73
-continued
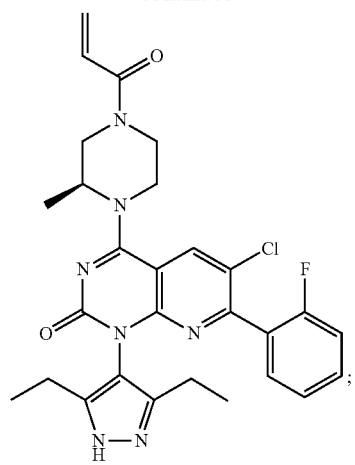
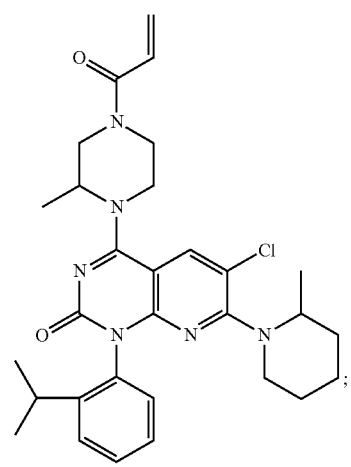
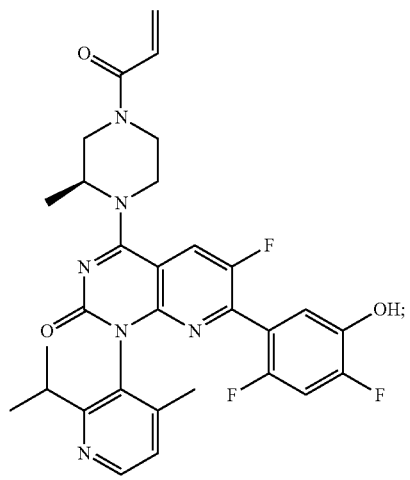
74
-continued
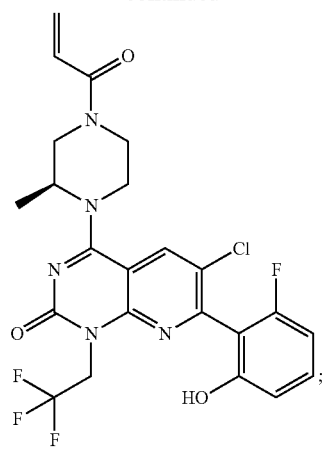
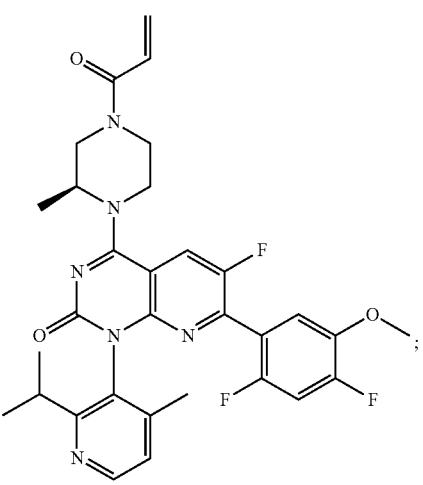
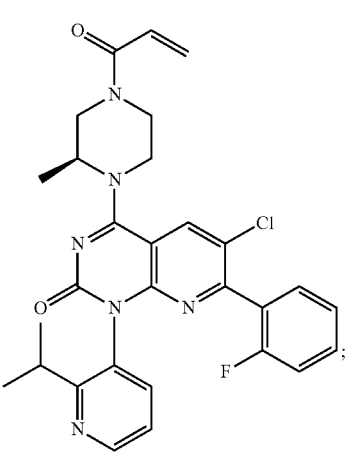

75
-continued
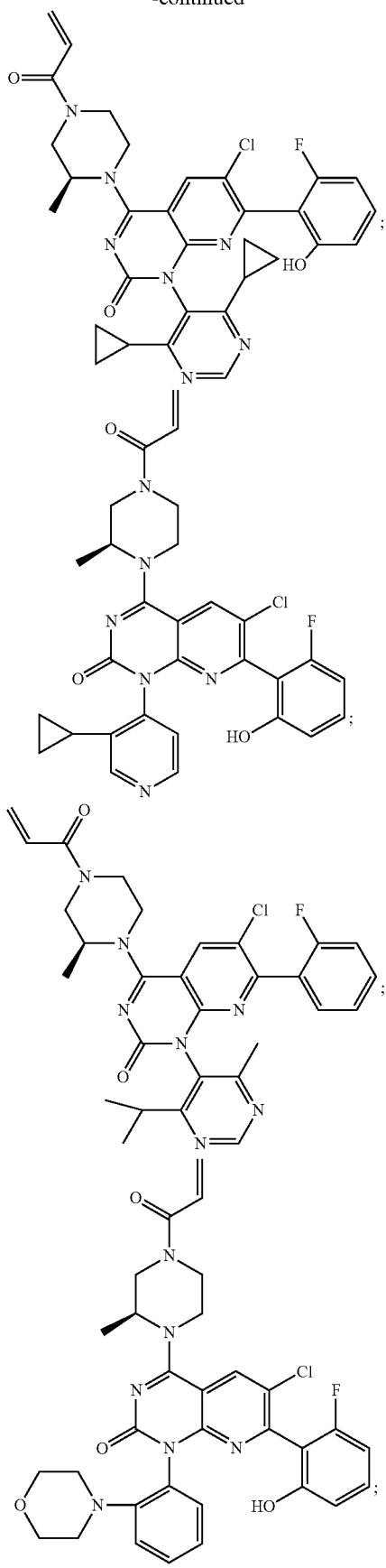
76
-continued
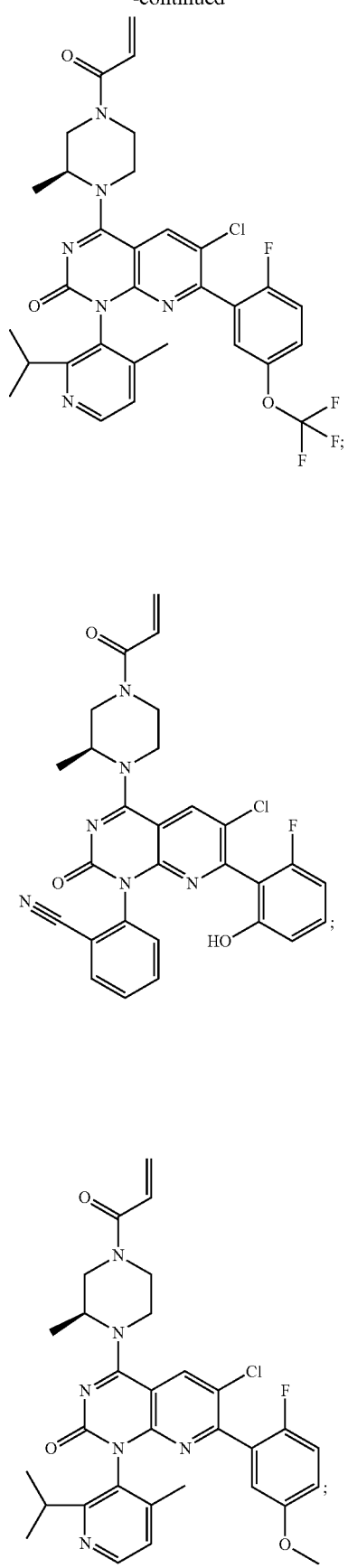

77
-continued
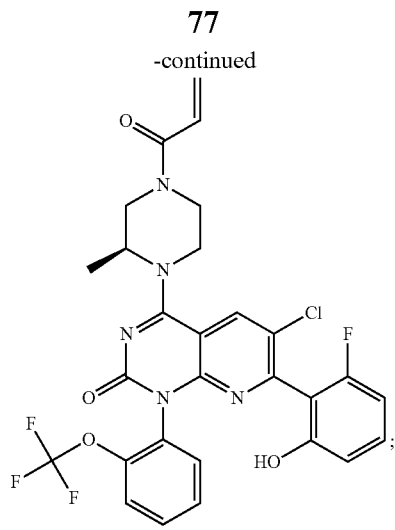
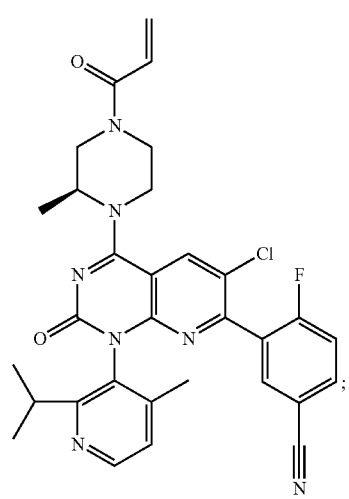
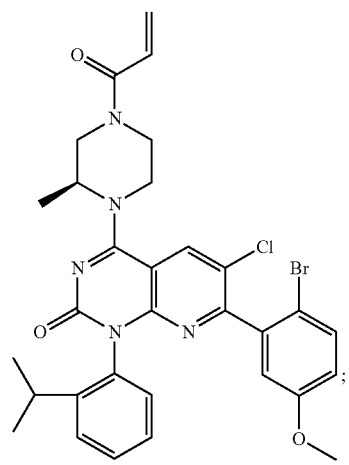
78
-continued
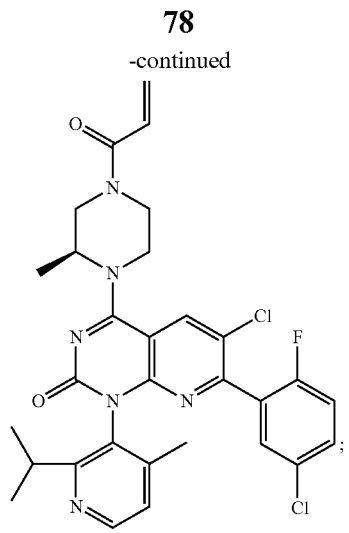
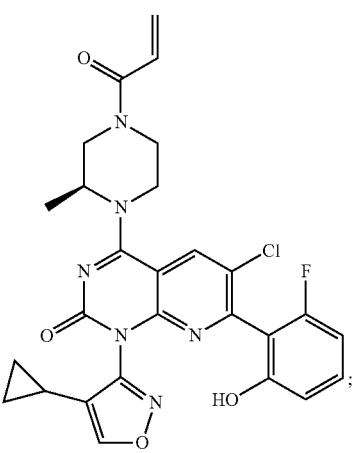
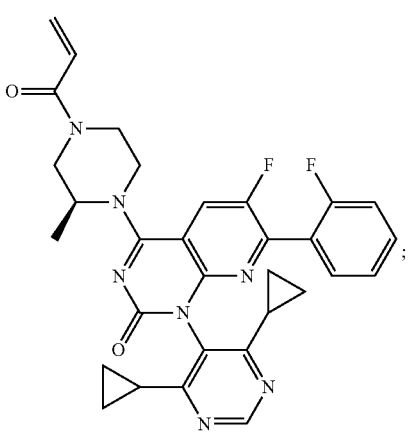

79
-continued
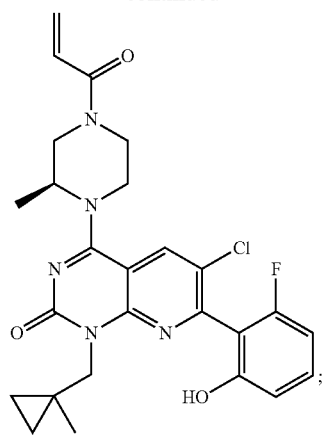
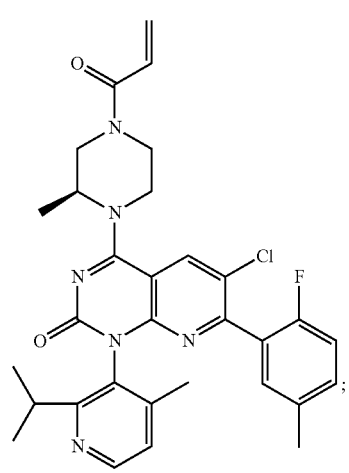
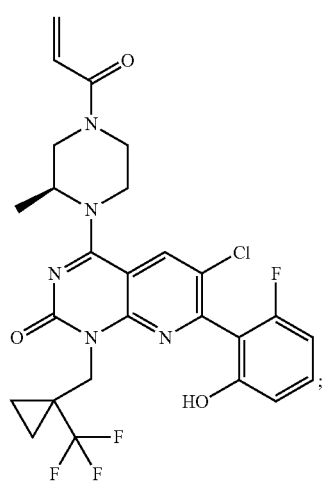
80
-continued
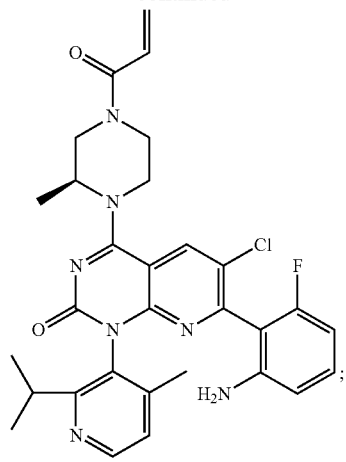
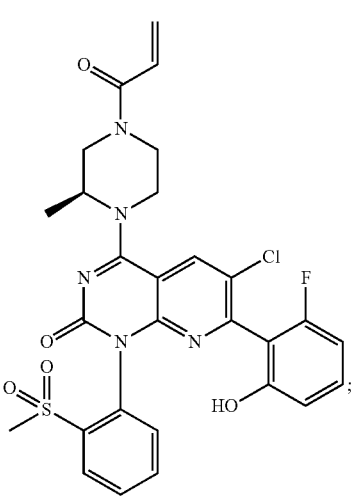
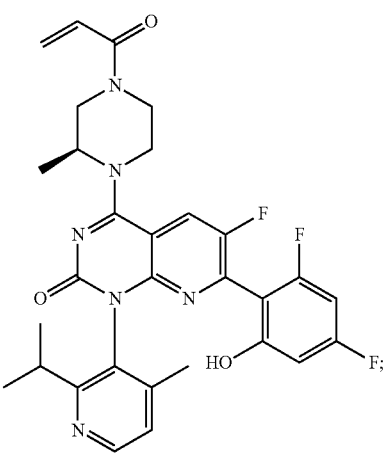

81
-continued
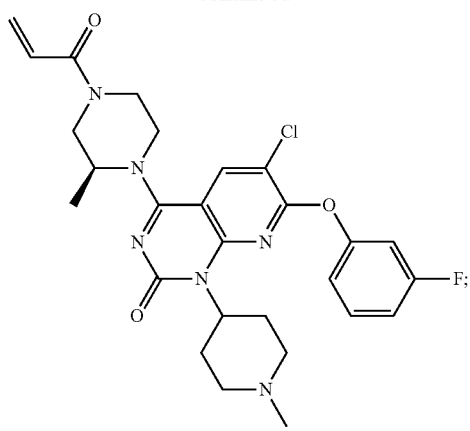
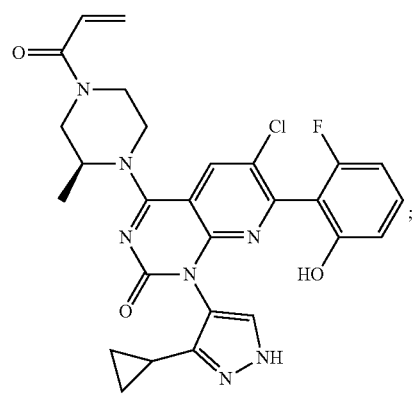
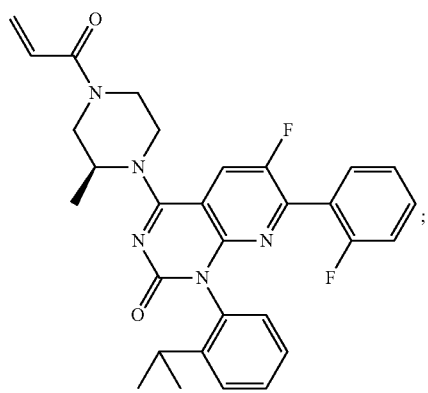
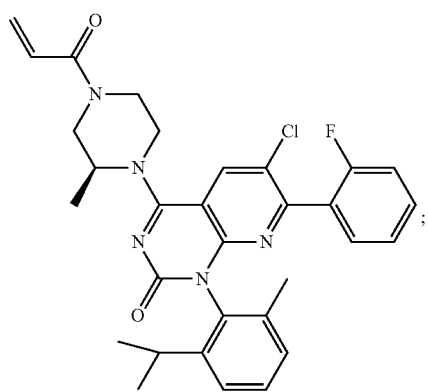
82
-continued
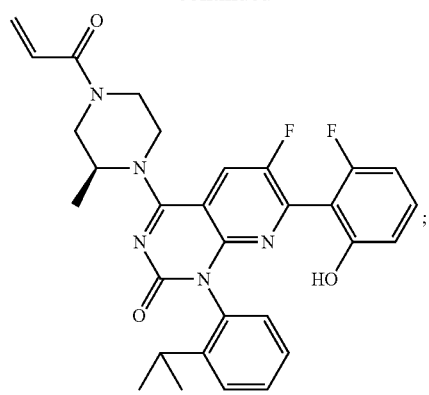
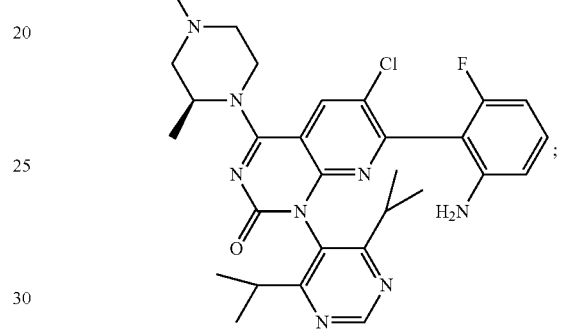
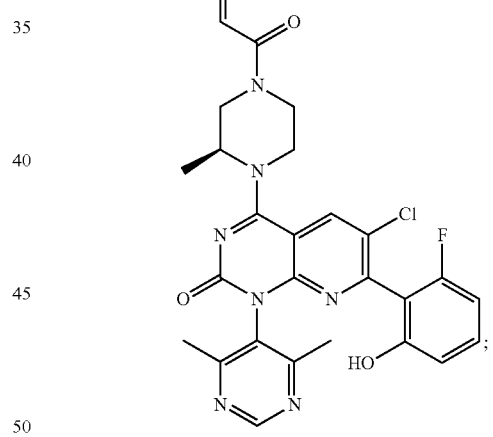
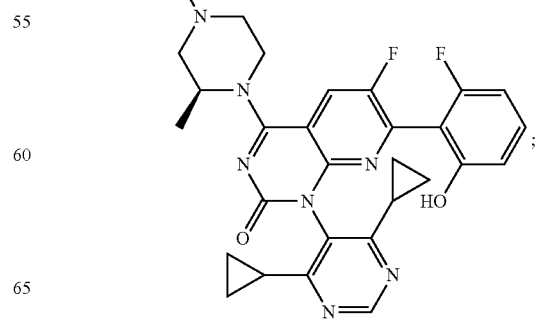

83
-continued
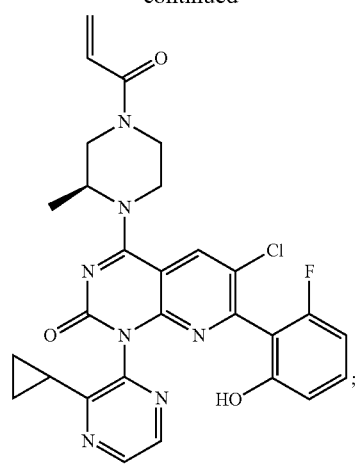
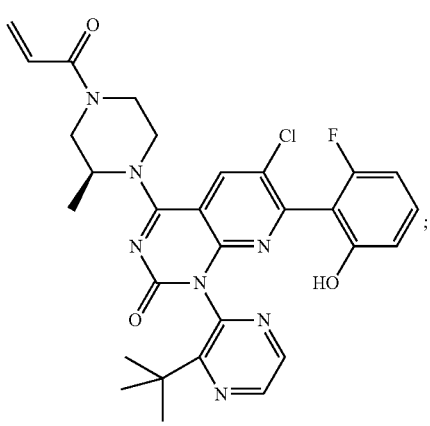
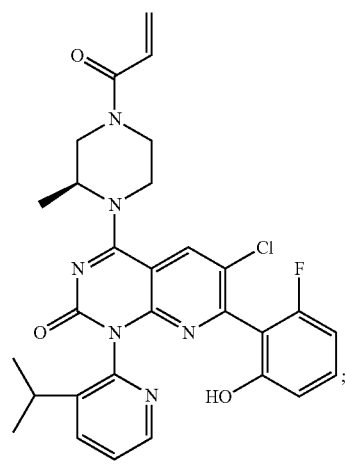
84
-continued
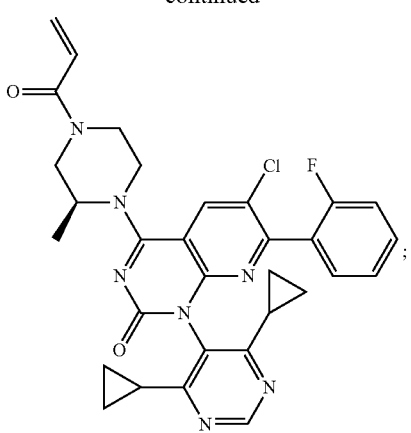
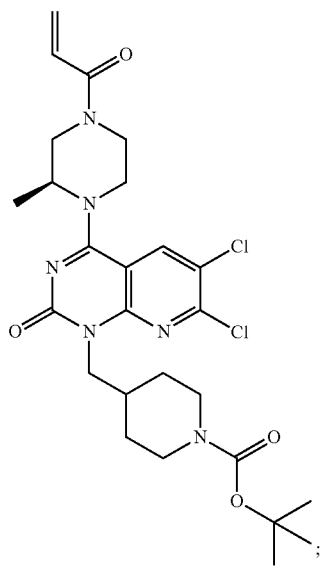
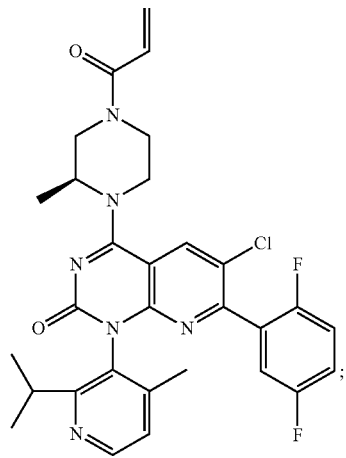

85
-continued
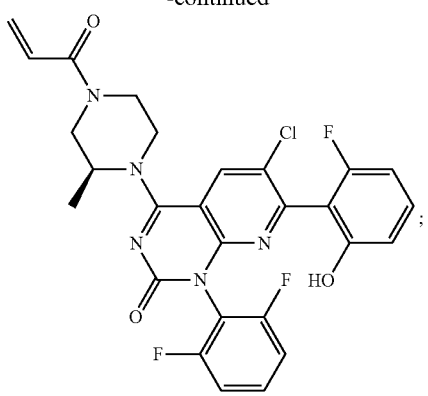
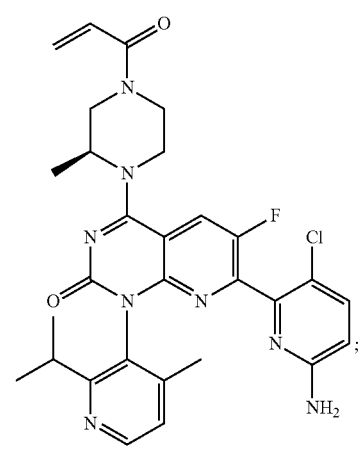
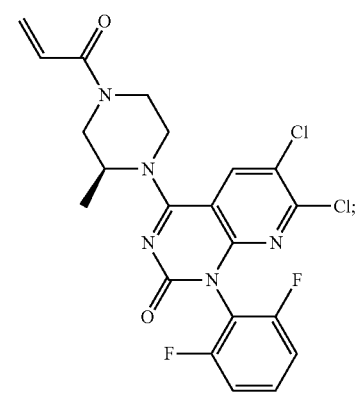
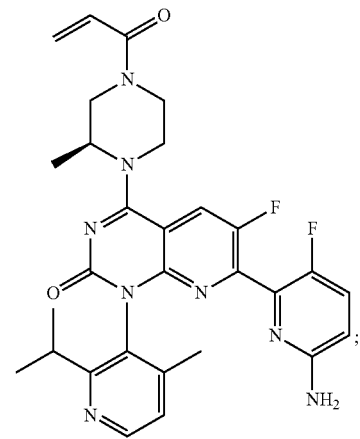
86
-continued
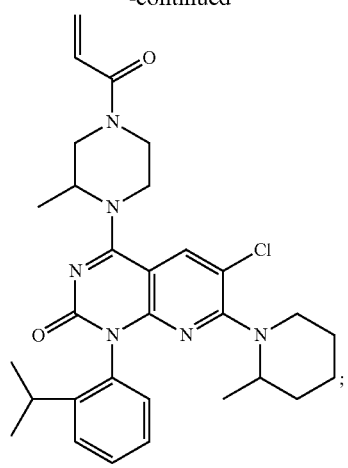
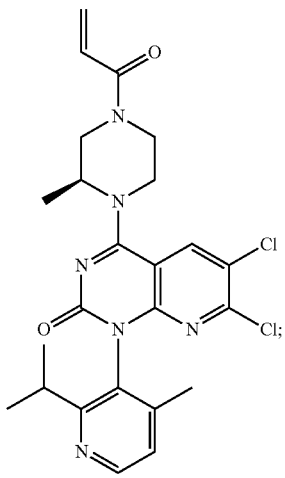
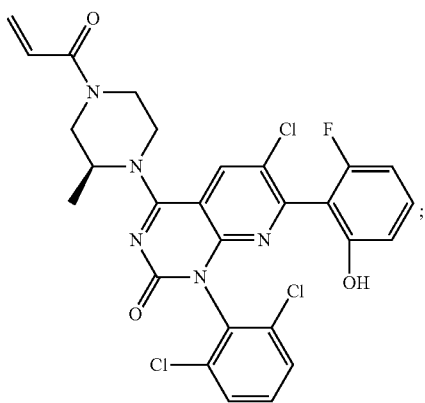

87
-continued
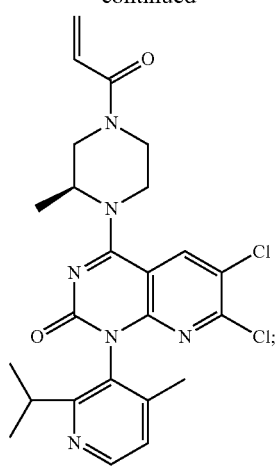
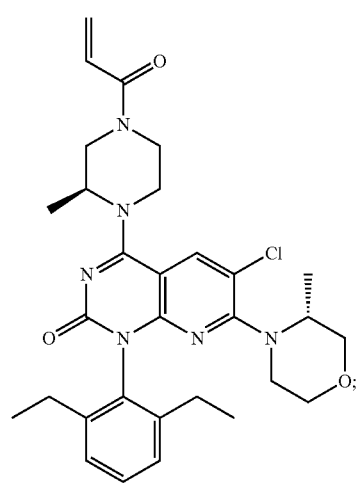
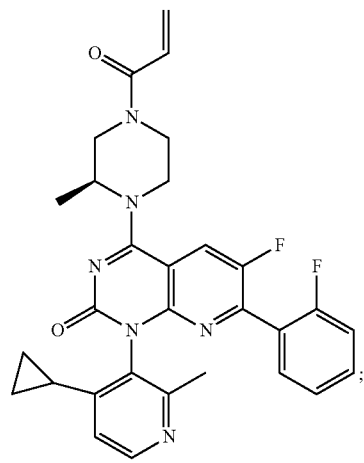
88
-continued
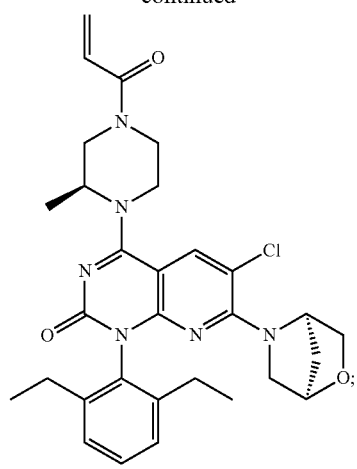
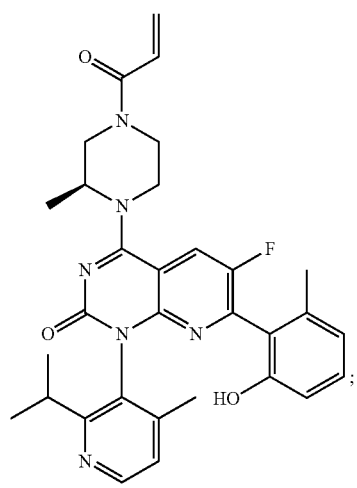
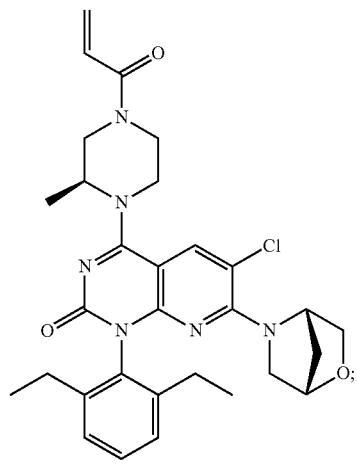

89
-continued
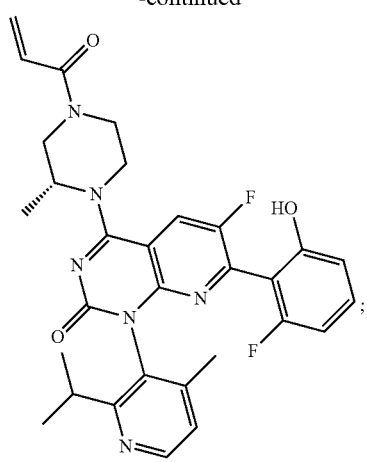
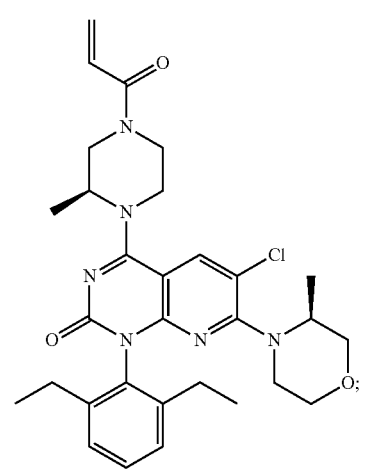
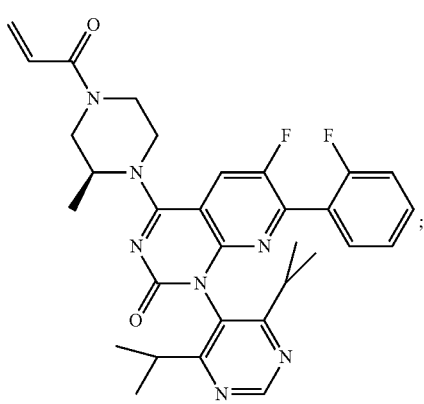
90
-continued
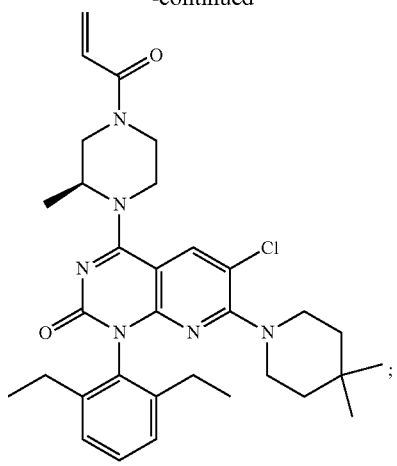
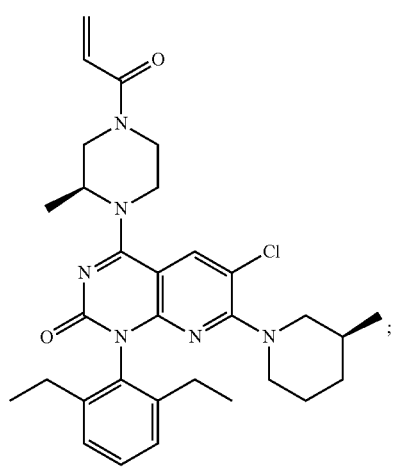

91
-continued
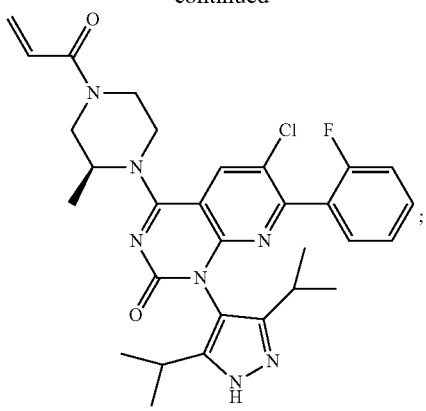
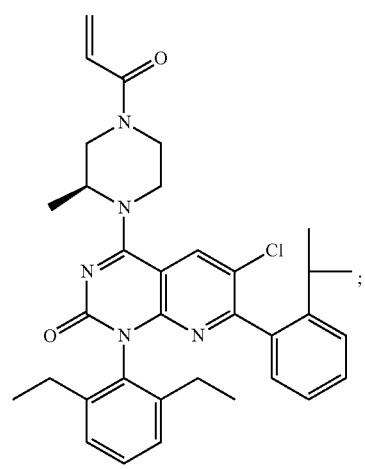
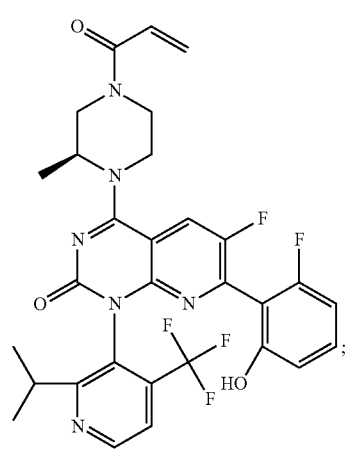
92
-continued
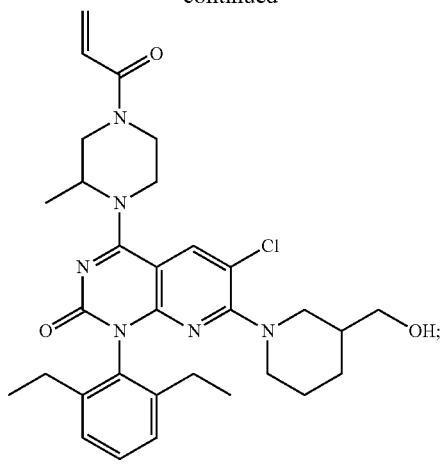
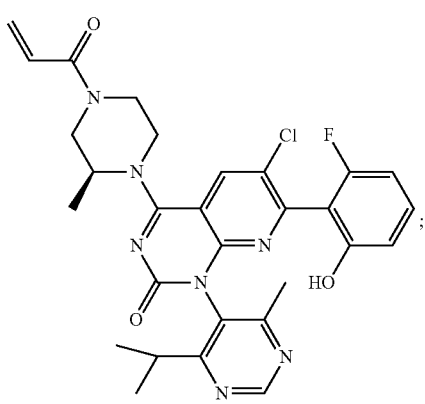
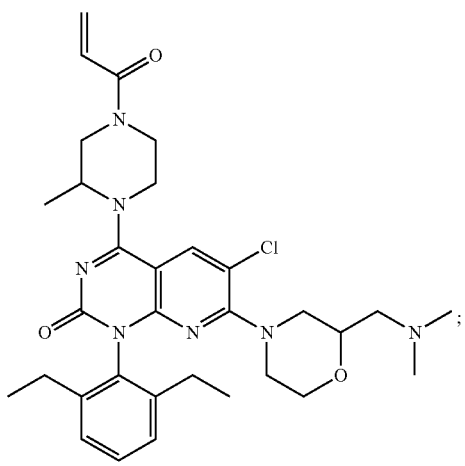

93
-continued
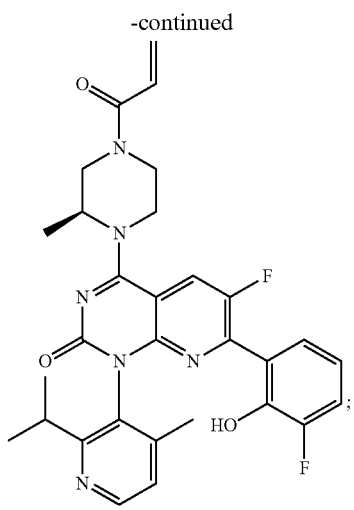
94
-continued
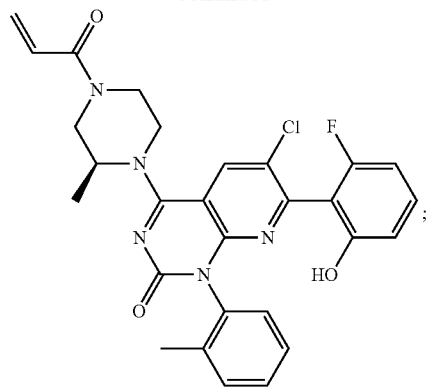
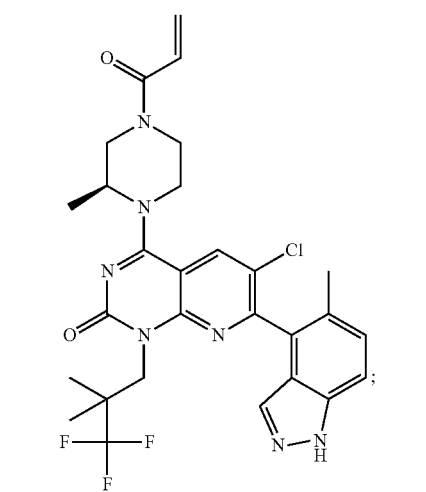
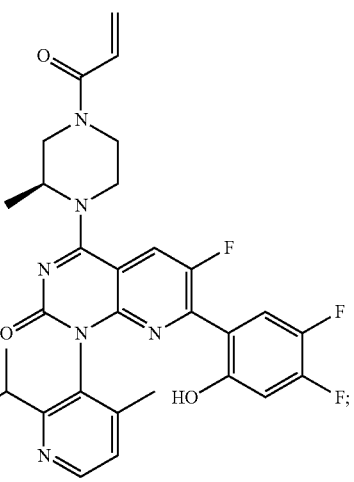
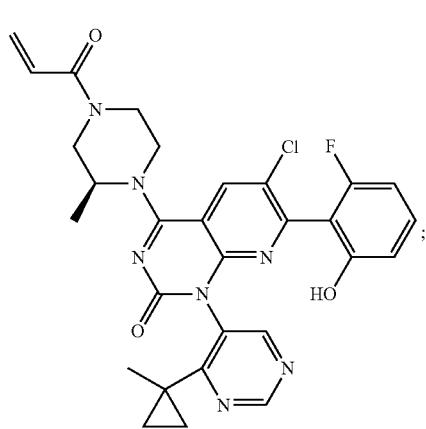
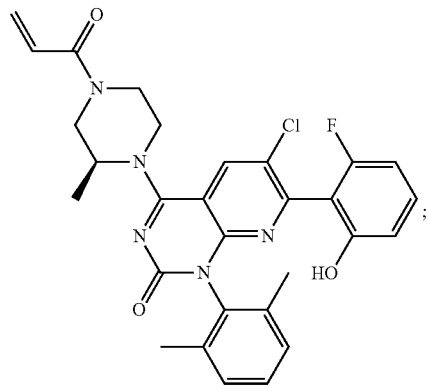

95
-continued
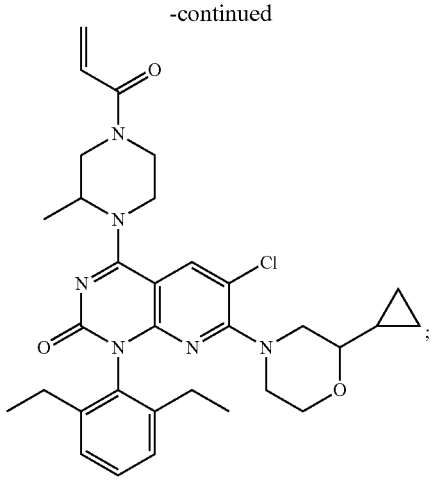
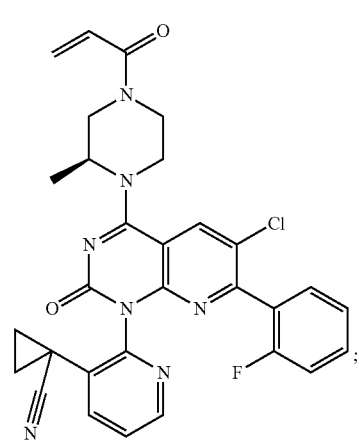
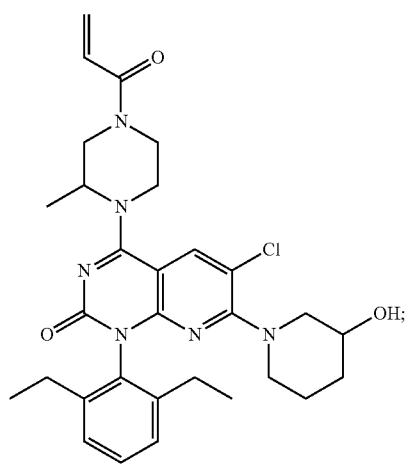
96
-continued
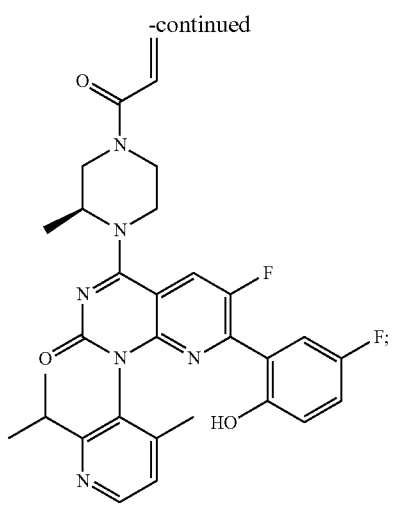
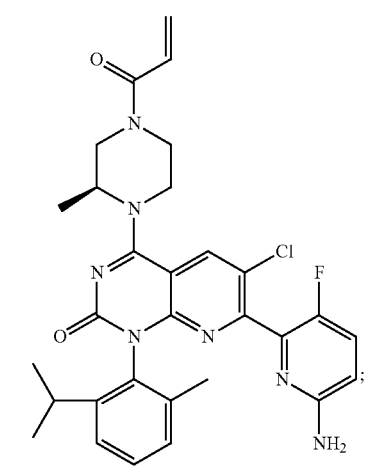

97
-continued
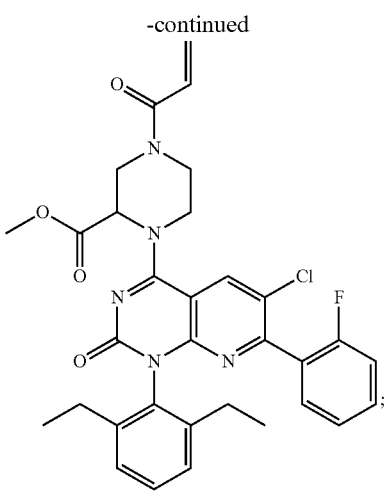
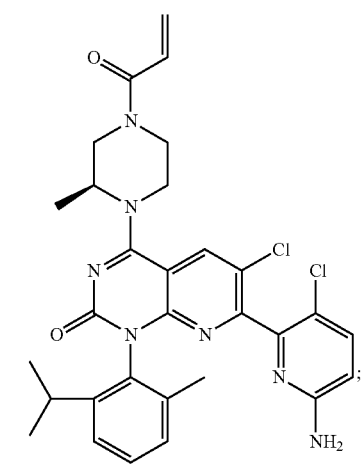
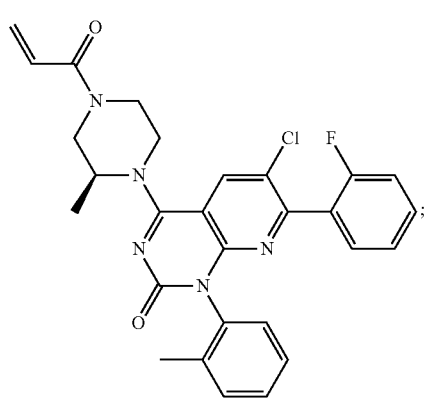
98
-continued
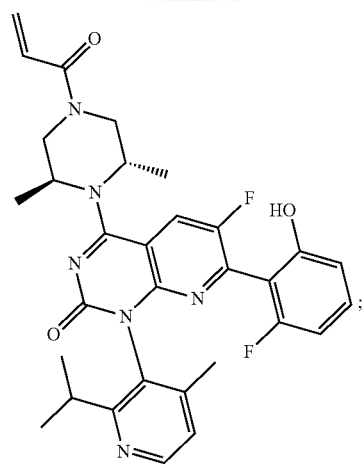
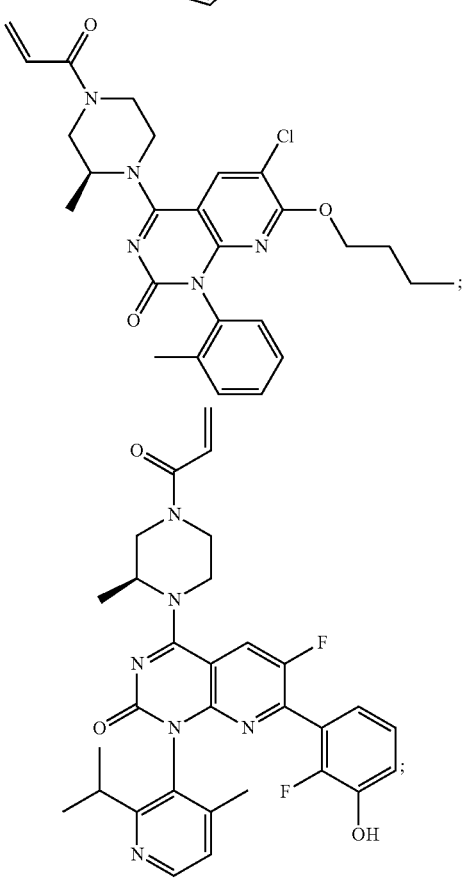

99
-continued
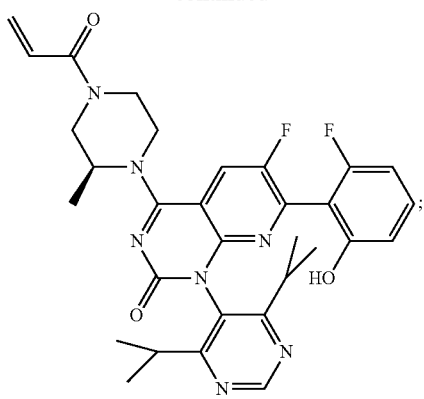
100
-continued
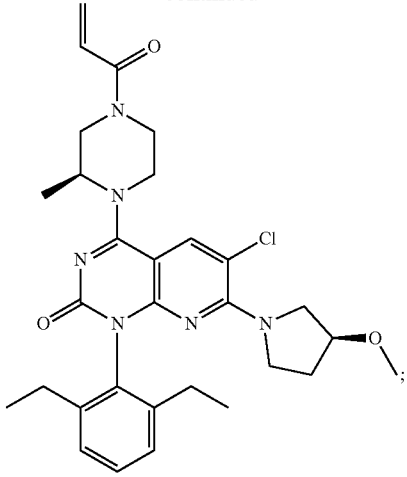
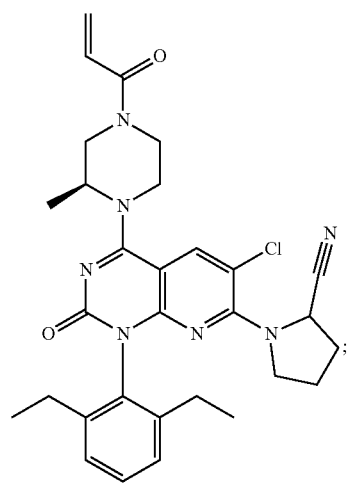
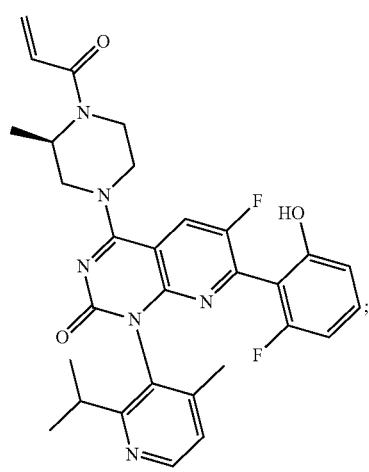
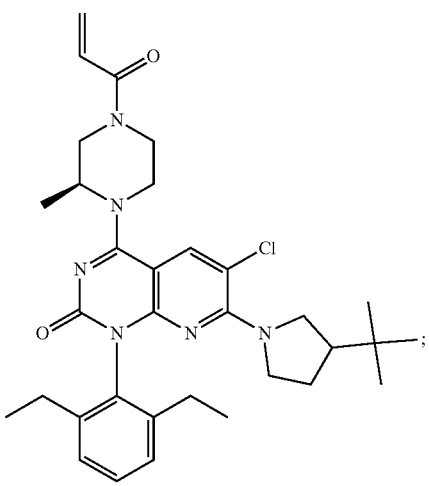

101
-continued
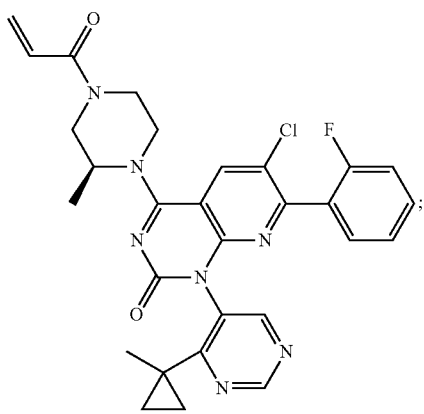
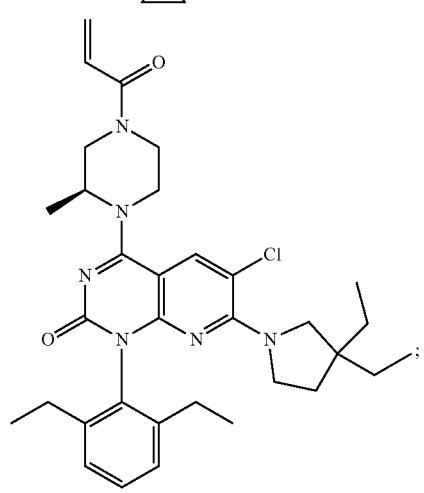
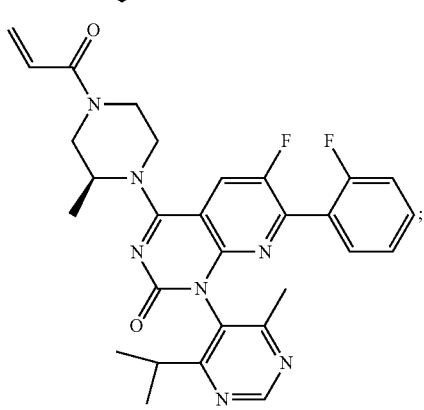
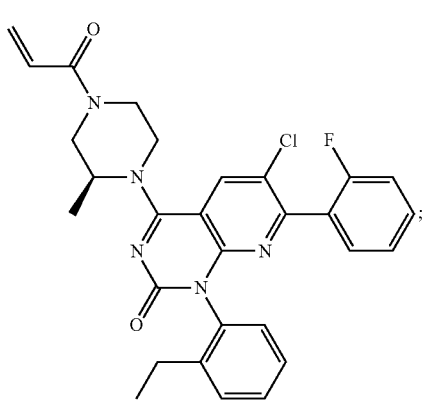
102
-continued
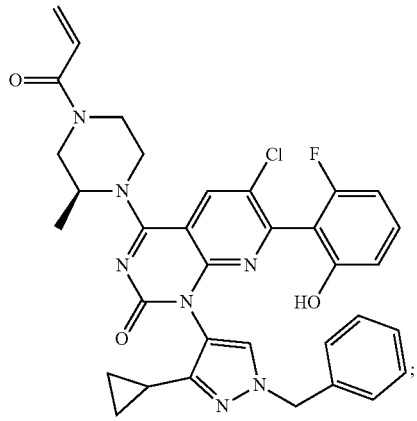
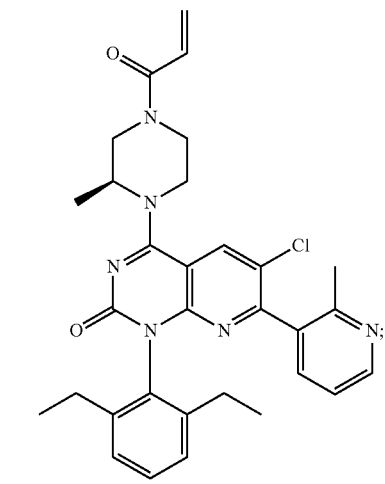
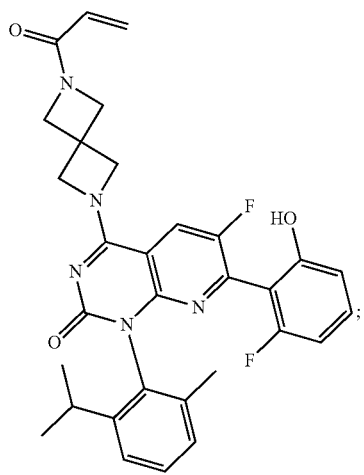

103
-continued
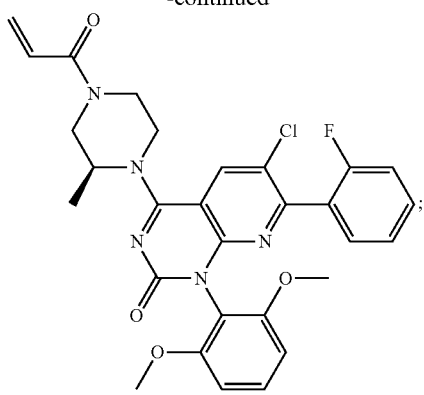
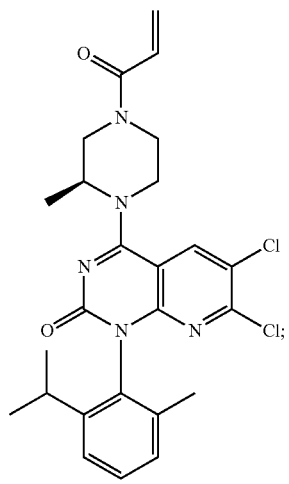
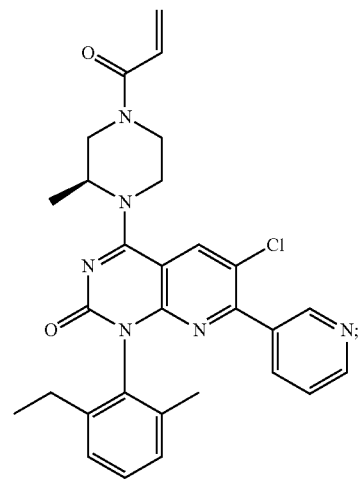
104
-continued
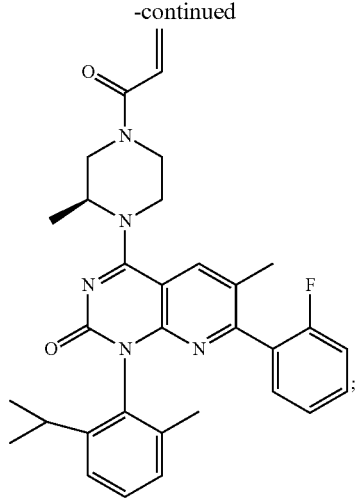
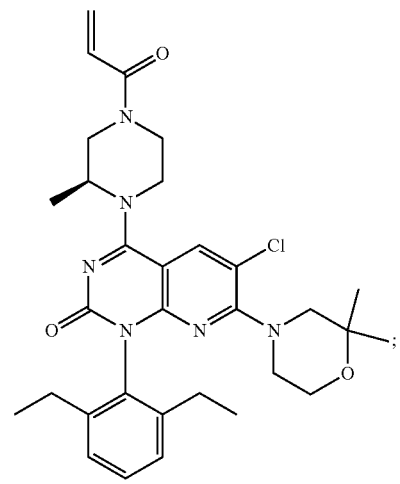
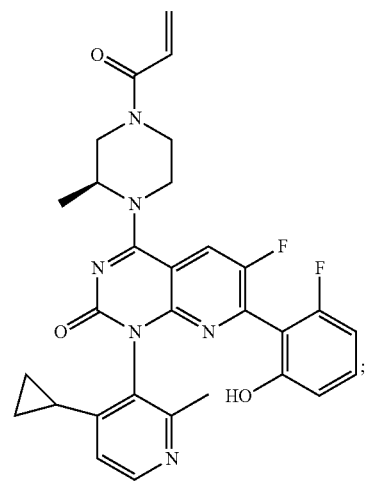

105
-continued
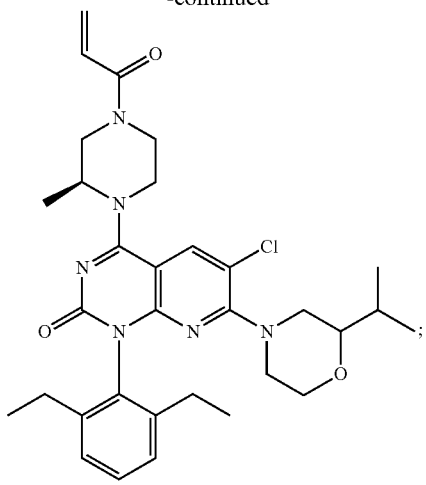
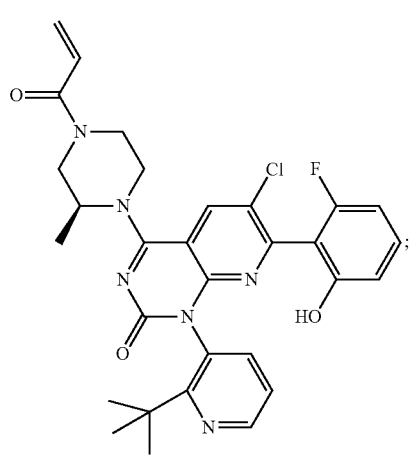
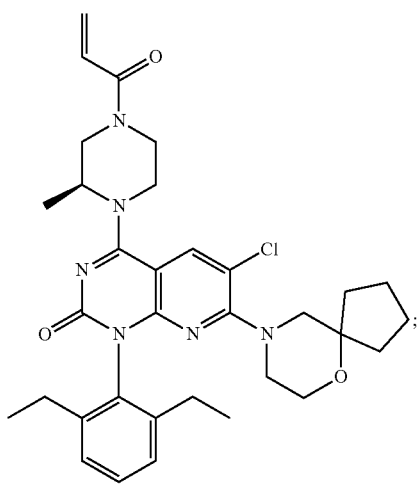
106
-continued
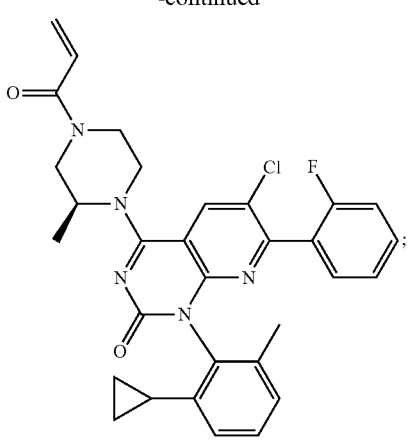
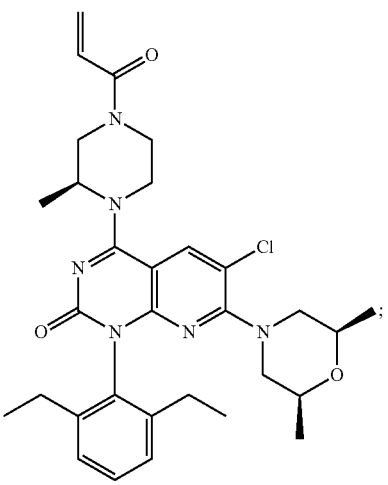
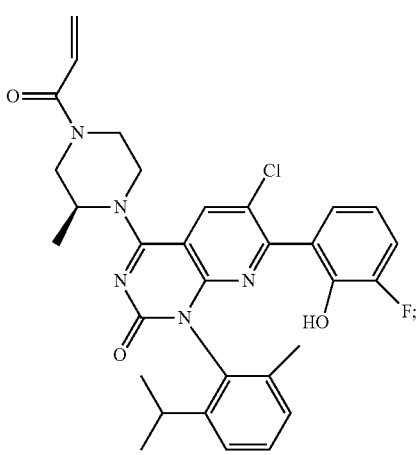

107
-continued
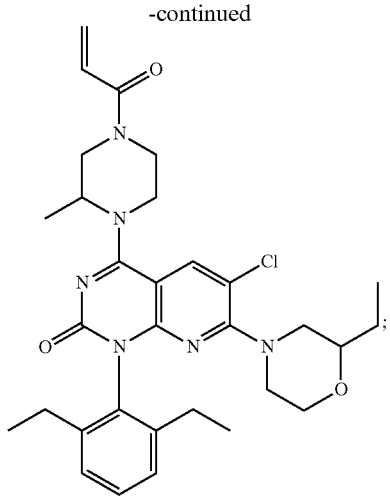
108
-continued
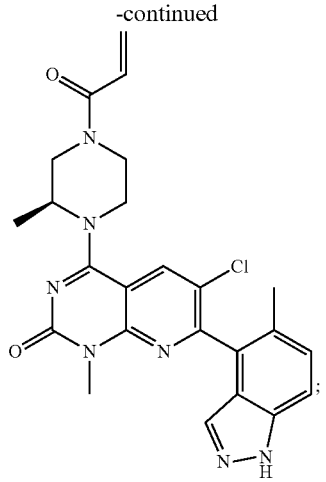
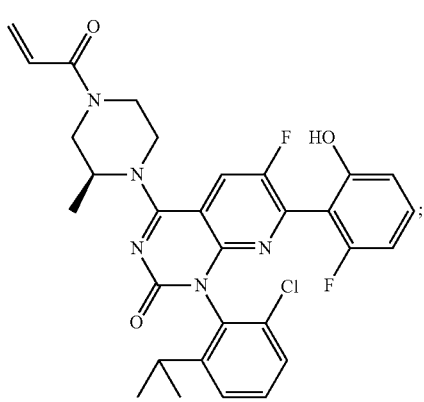
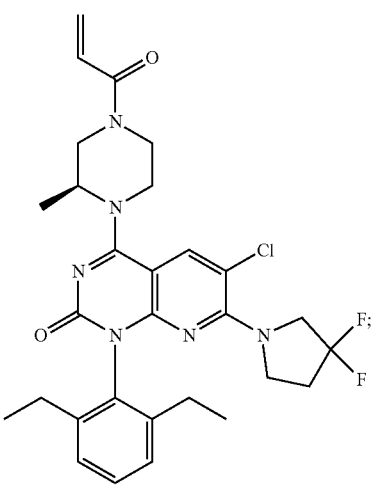
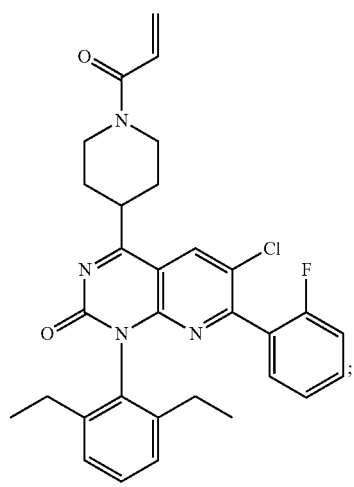
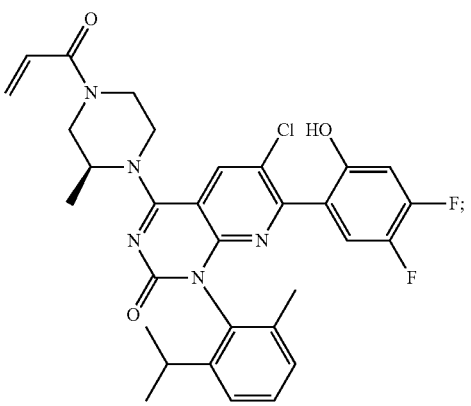

109
-continued
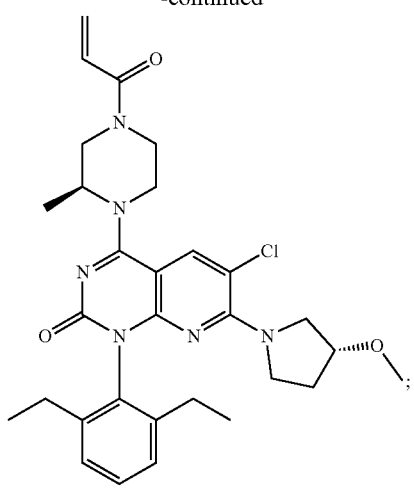
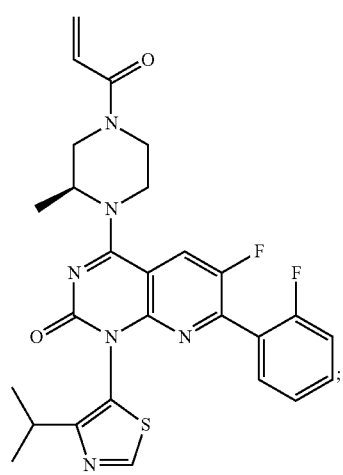
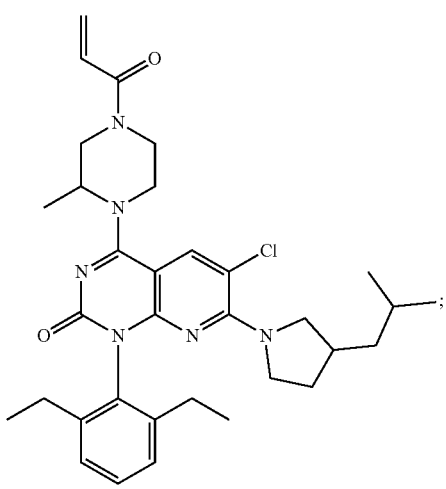
110
-continued
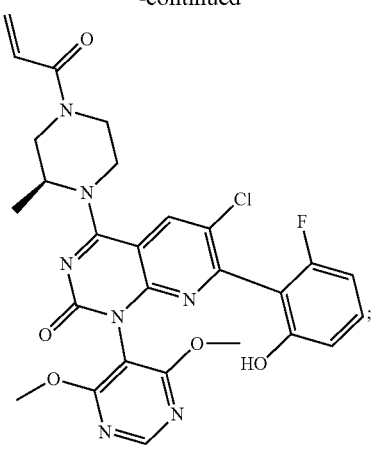
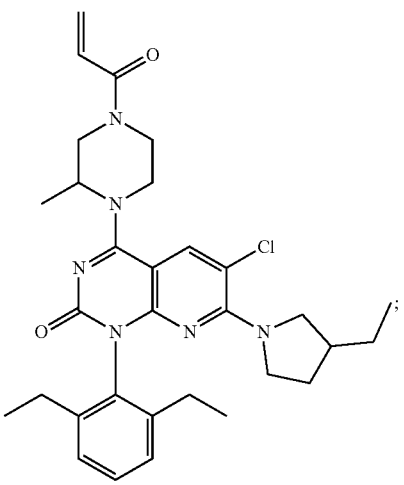
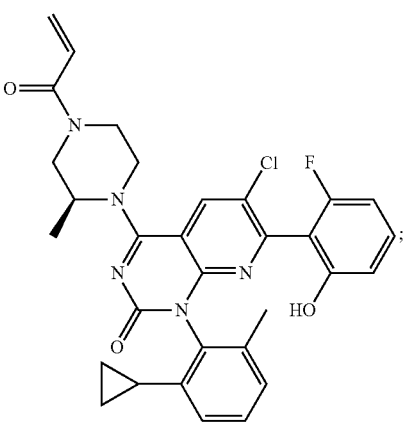

111
-continued
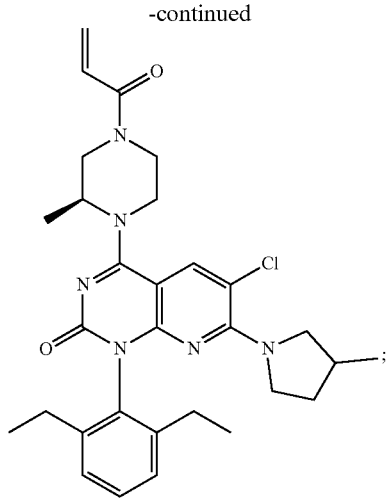
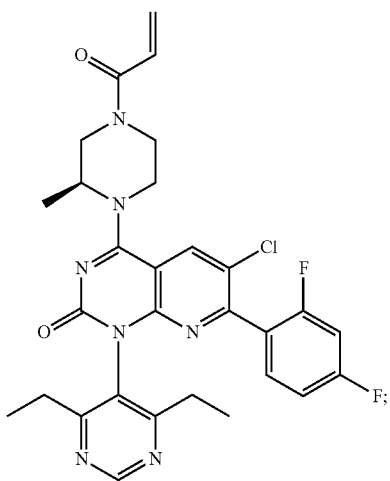
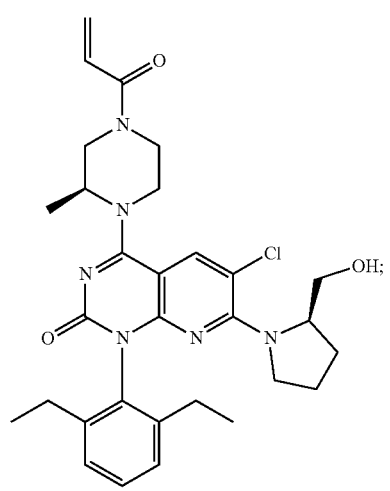
112
-continued
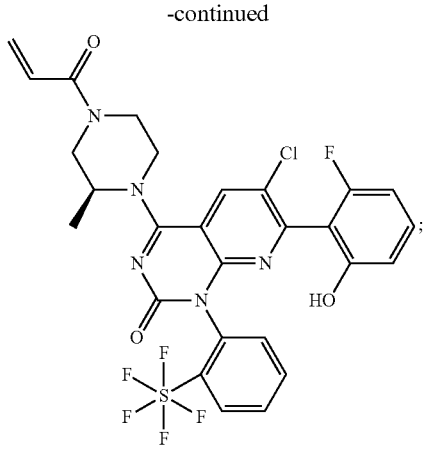
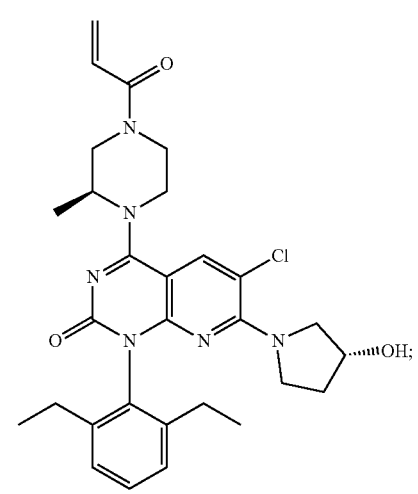
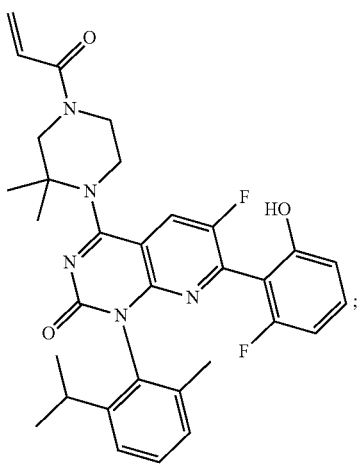

113
-continued
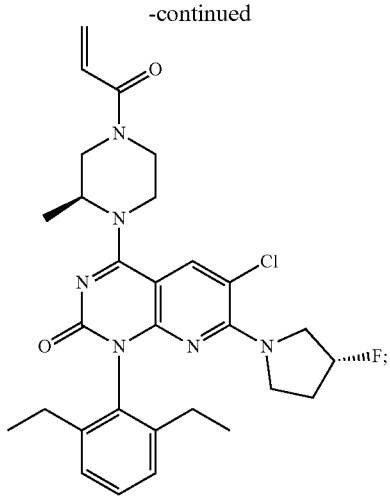
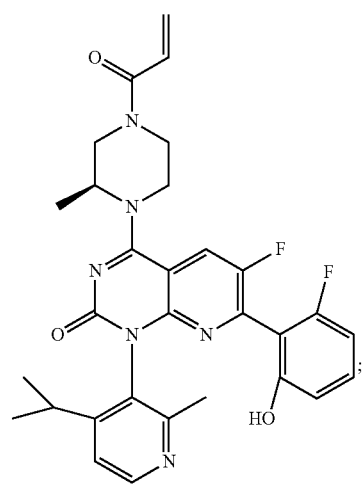
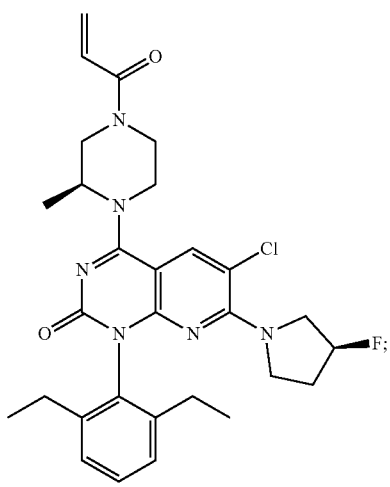
114
-continued
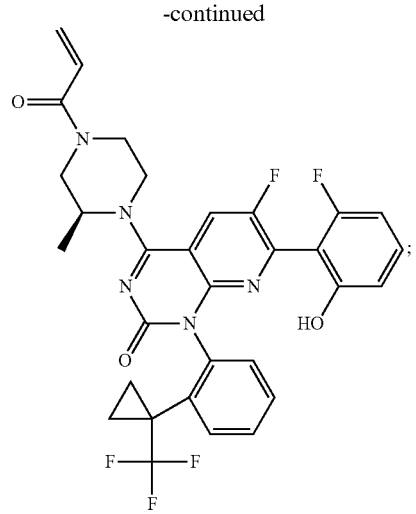
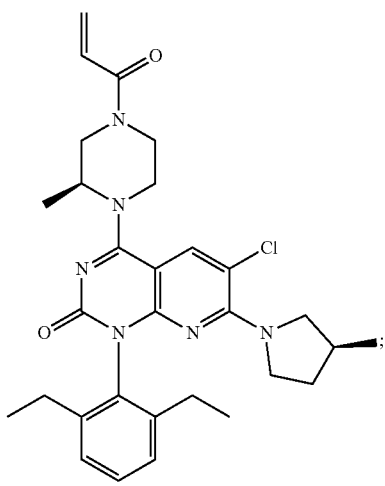
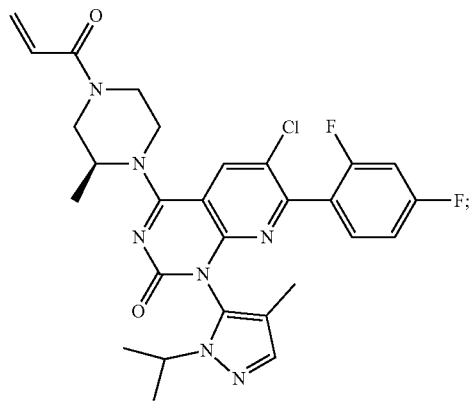

115
-continued
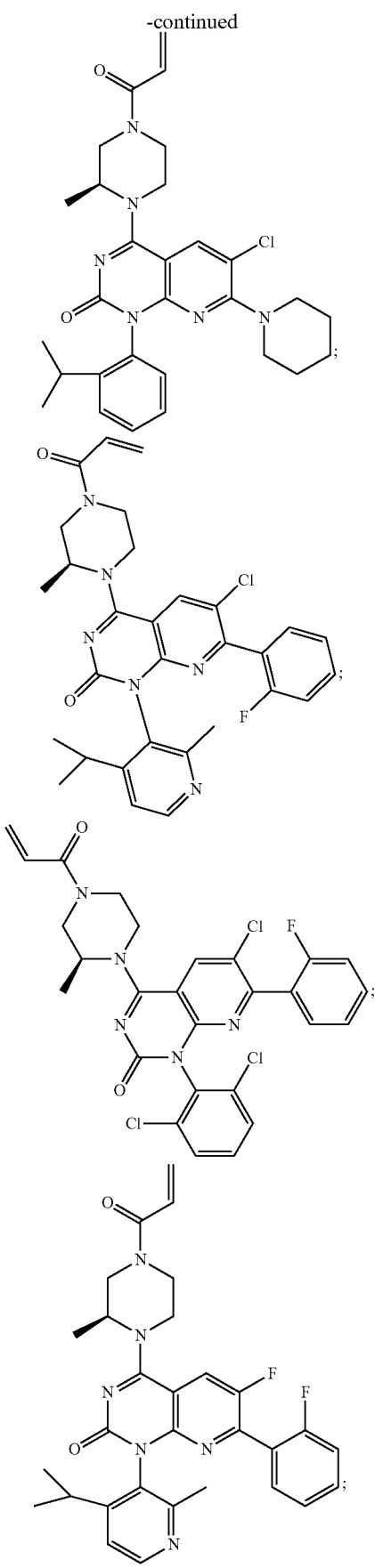
116
-continued
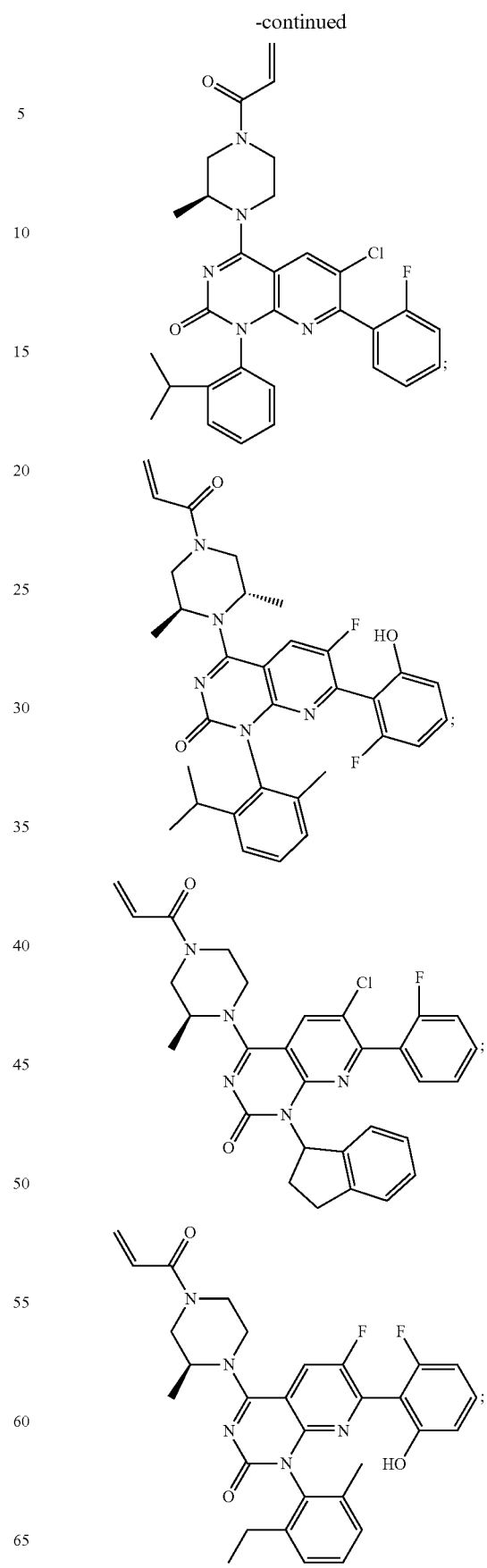

117
-continued
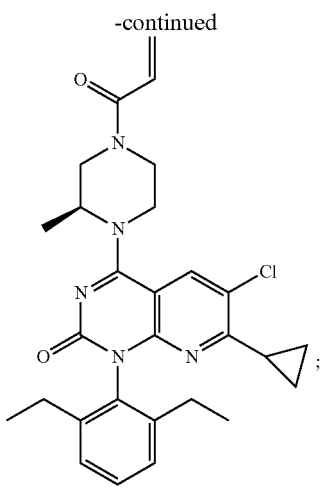
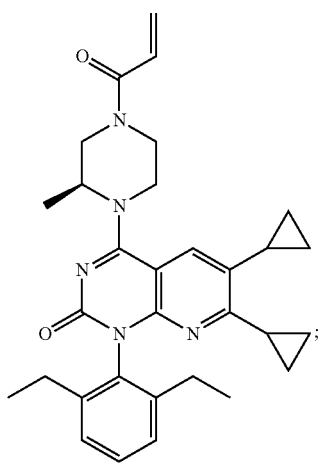
118
-continued
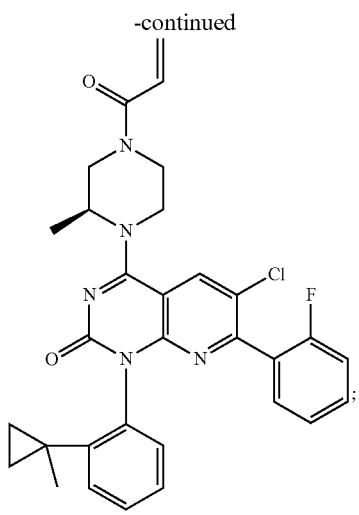
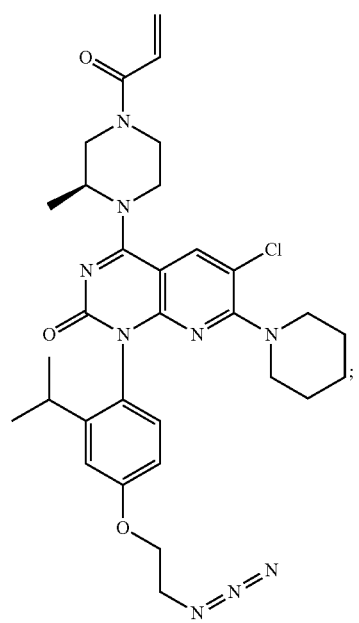
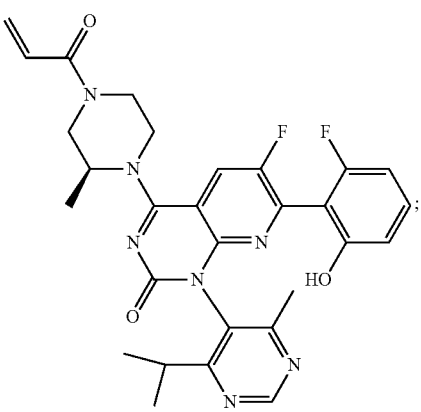

119
-continued
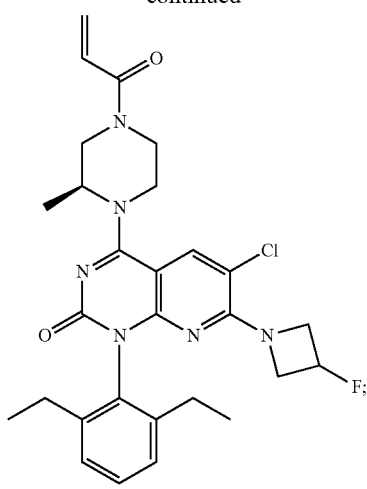
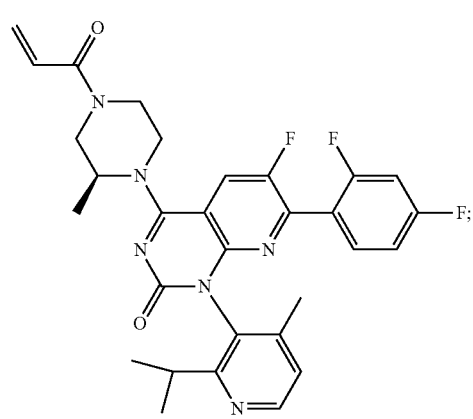
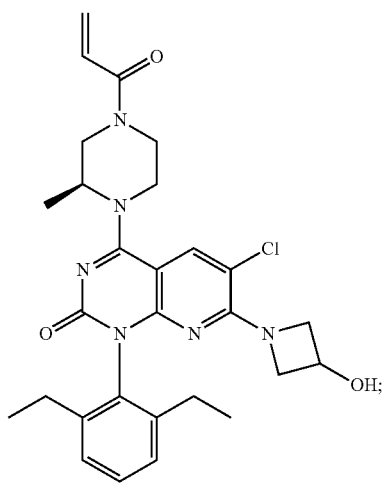
120
-continued
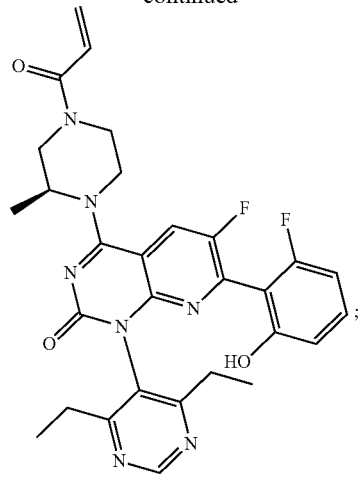
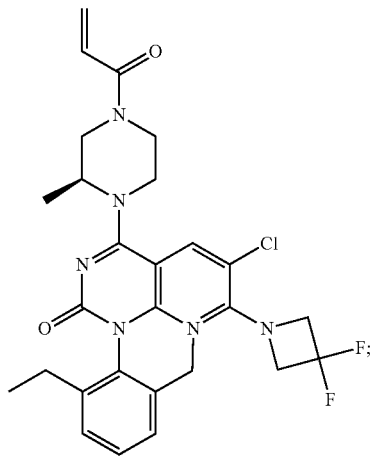
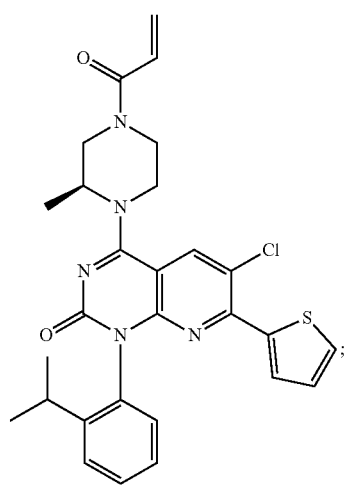

121
-continued
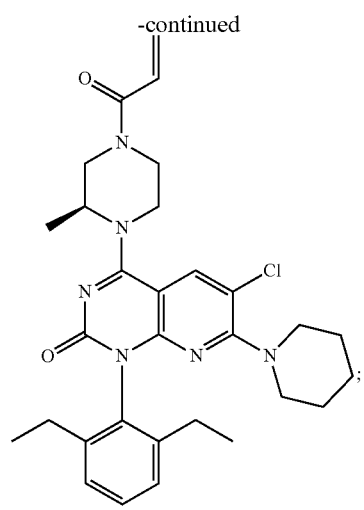
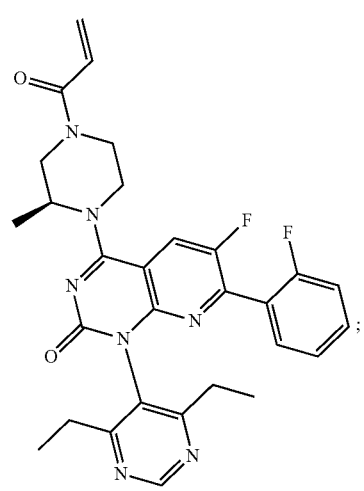
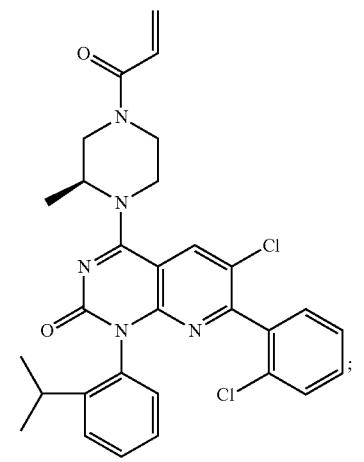
122
-continued
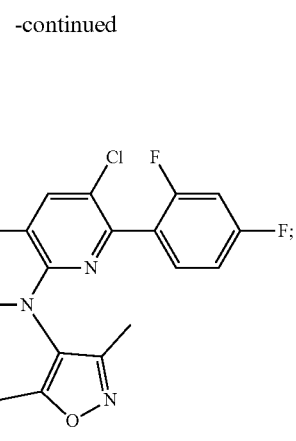
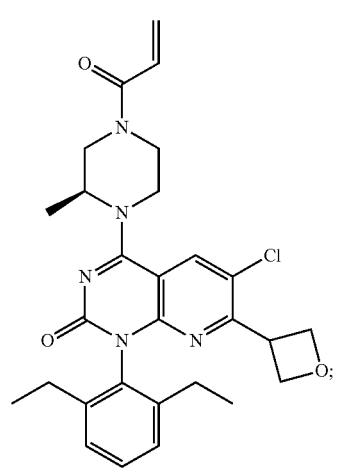
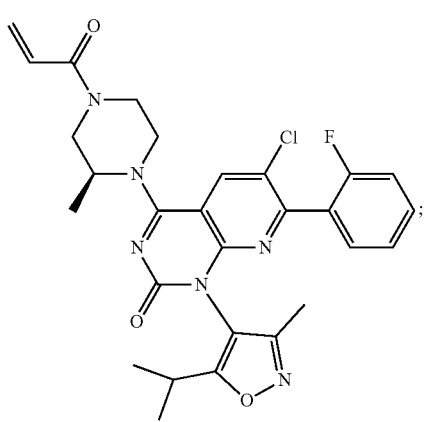

123
-continued
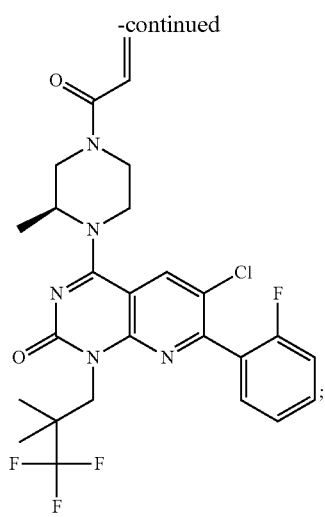
124
-continued
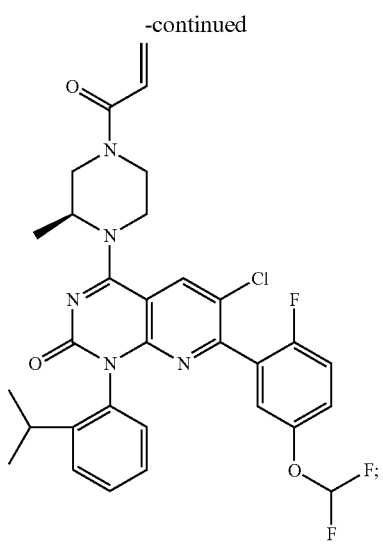
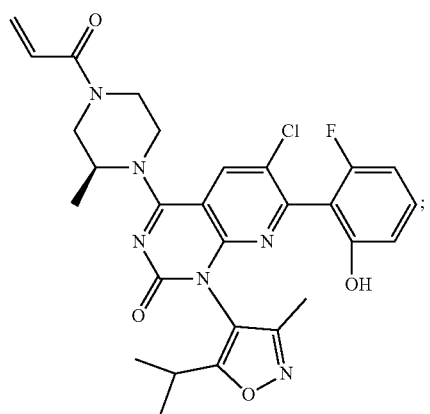
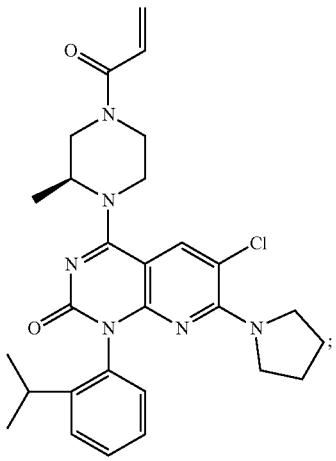
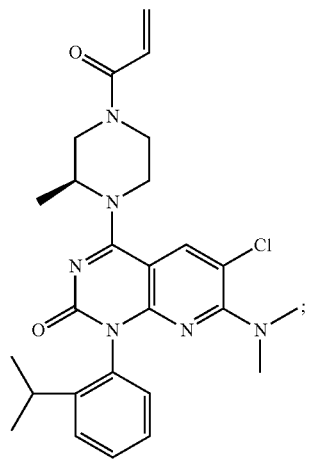
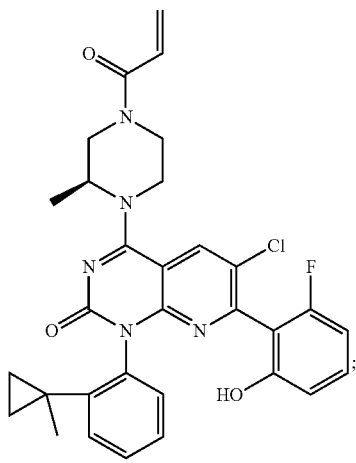

125
-continued
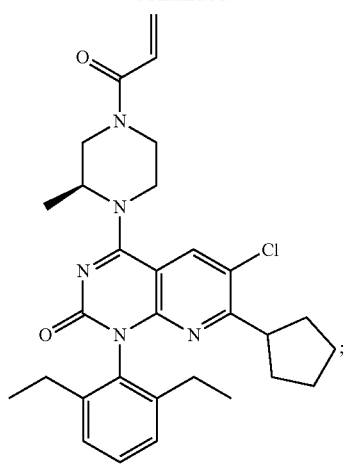
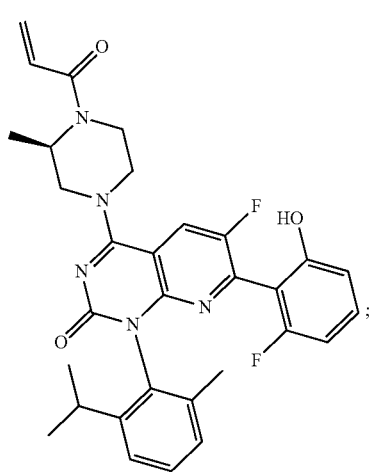
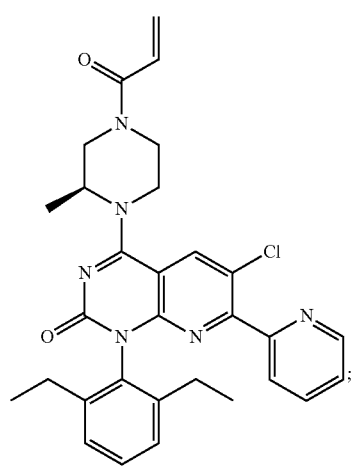
126
-continued
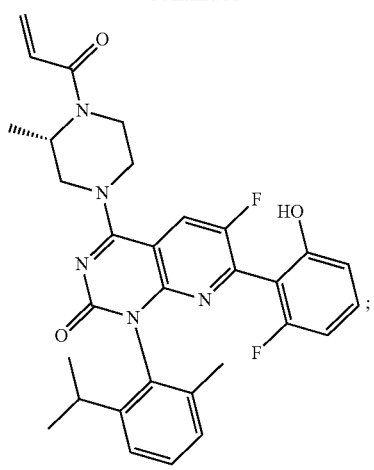
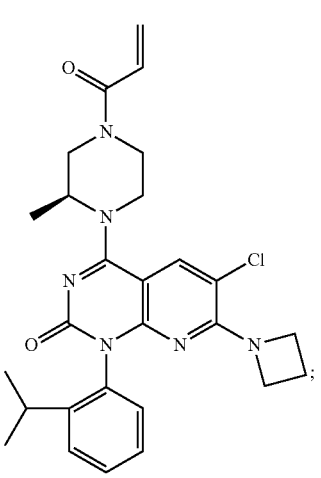
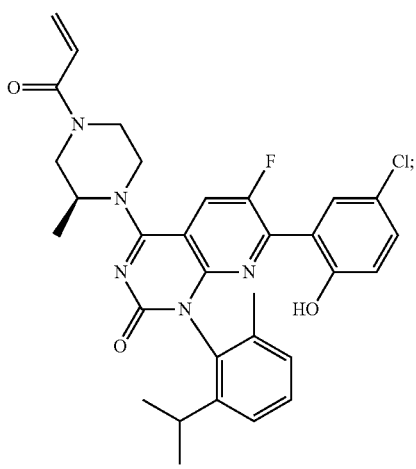

127
-continued
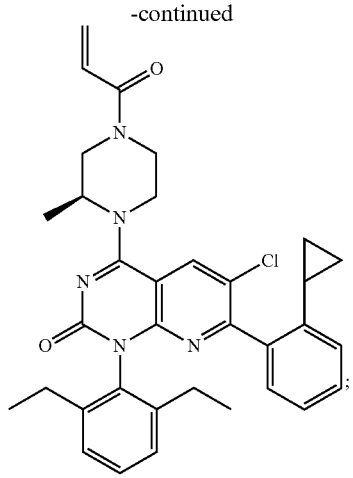
128
-continued
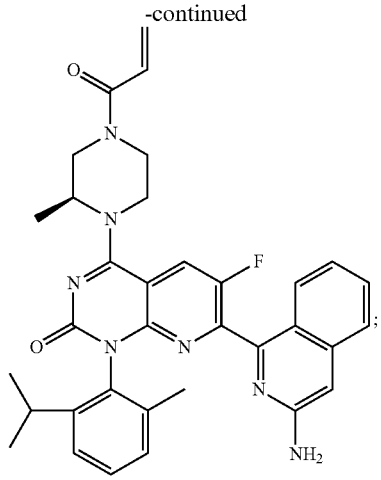
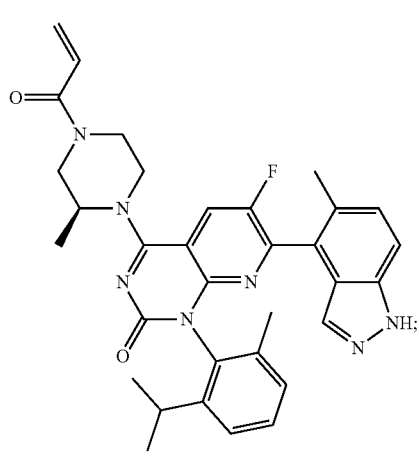
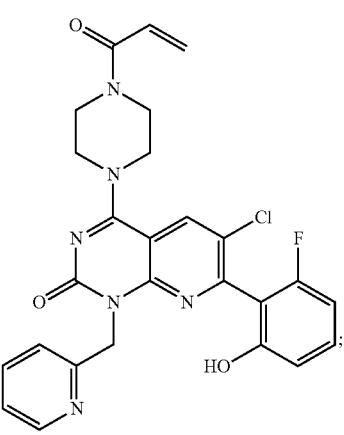
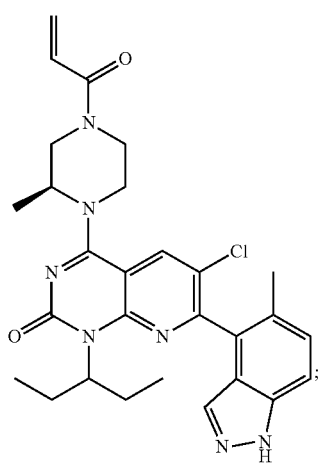
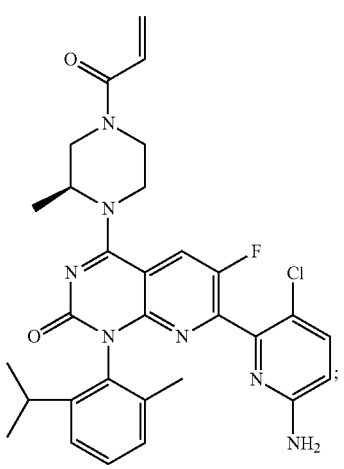

129
-continued
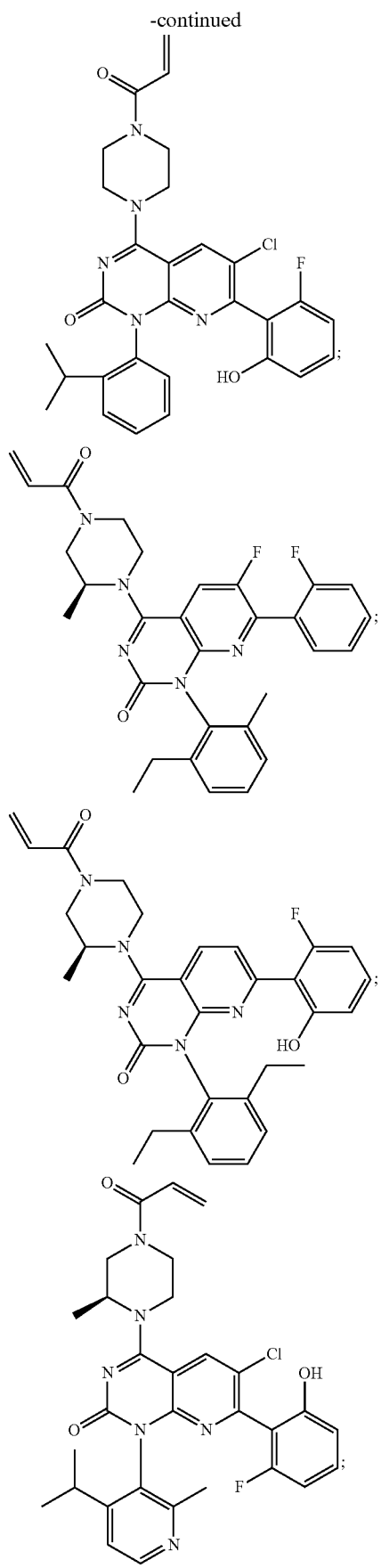
130
-continued
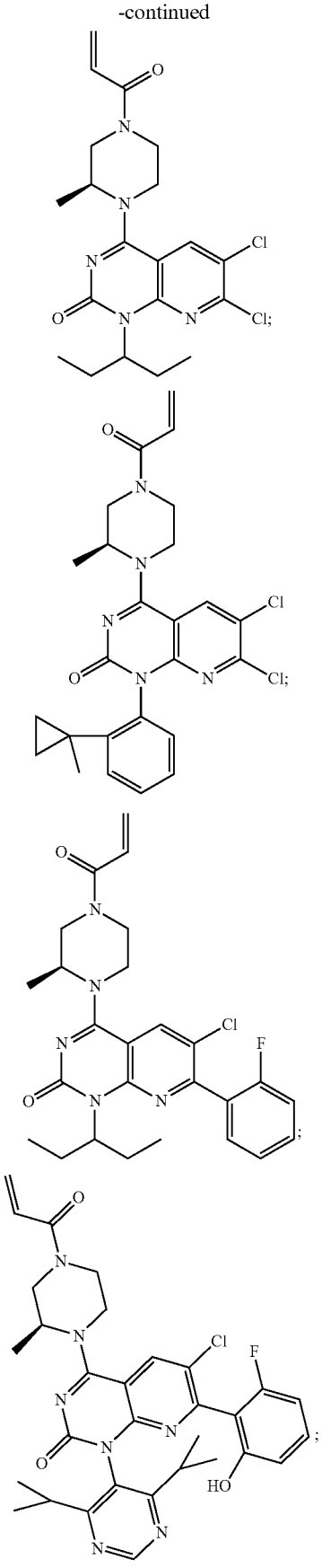

131
-continued
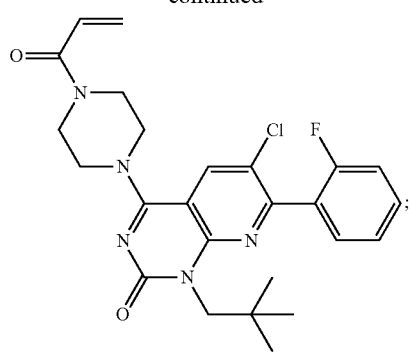
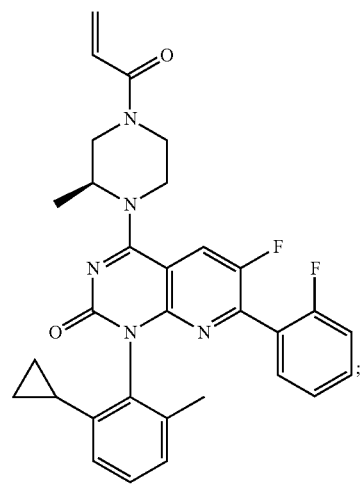
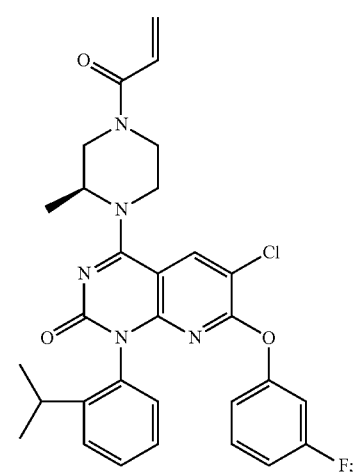
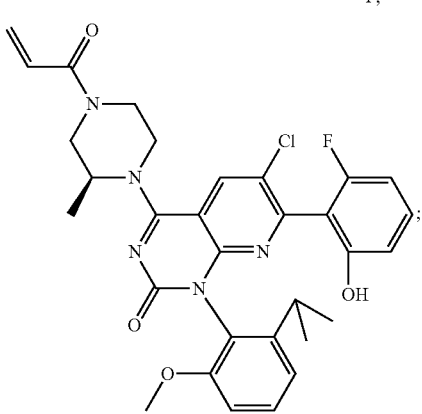
132
-continued
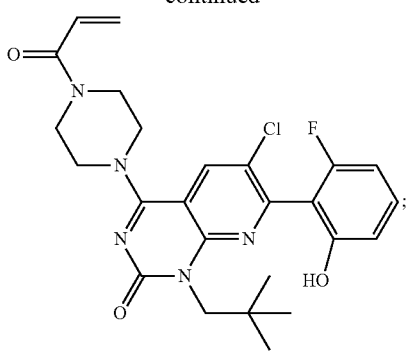
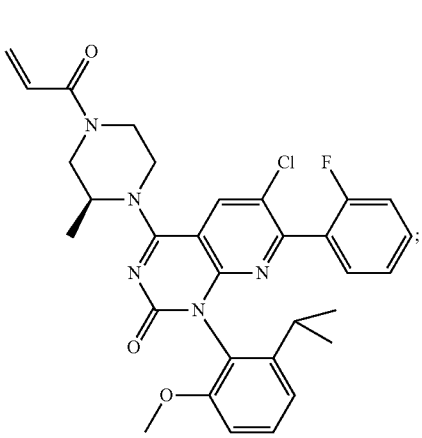
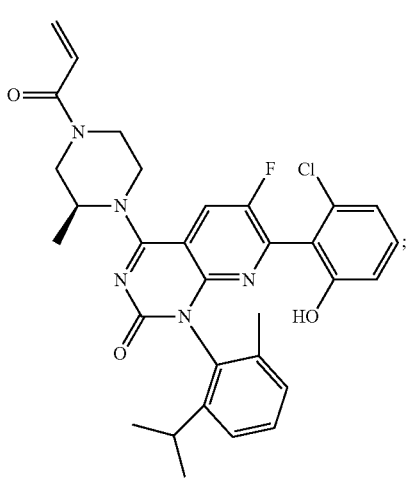

133
-continued
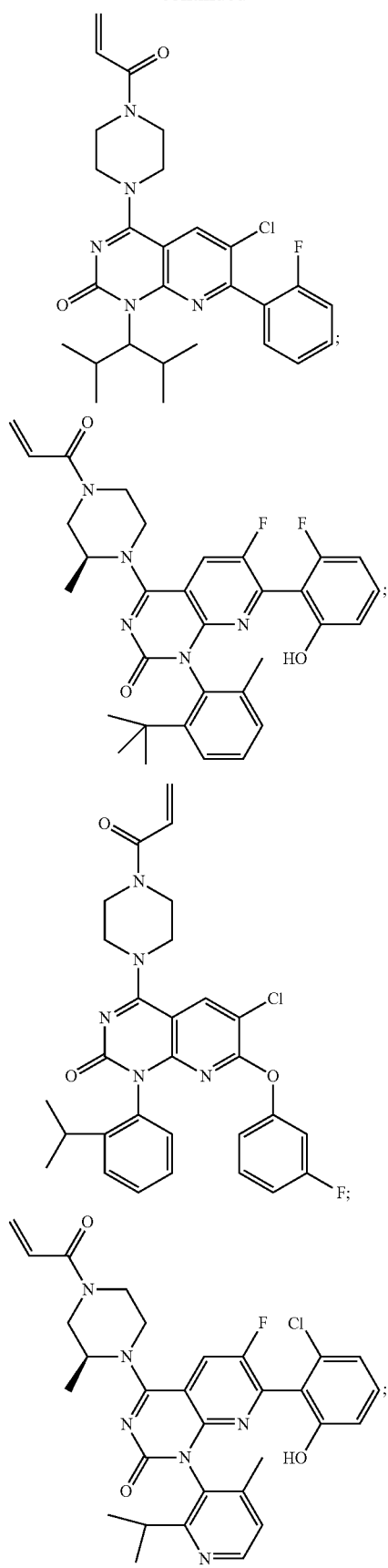
134
-continued
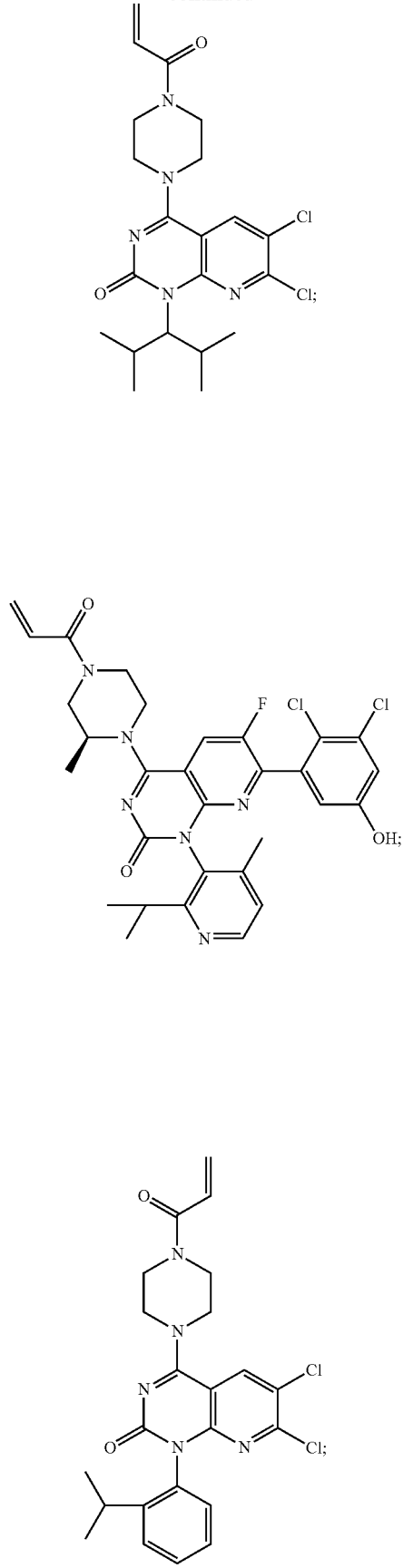

135
-continued
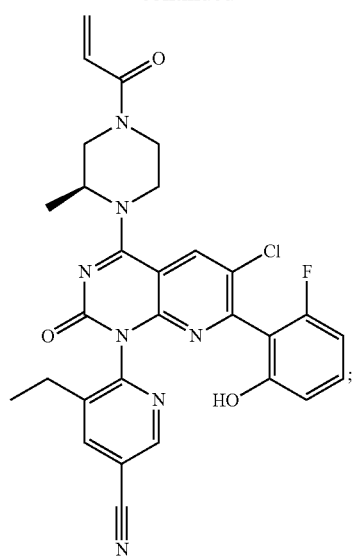
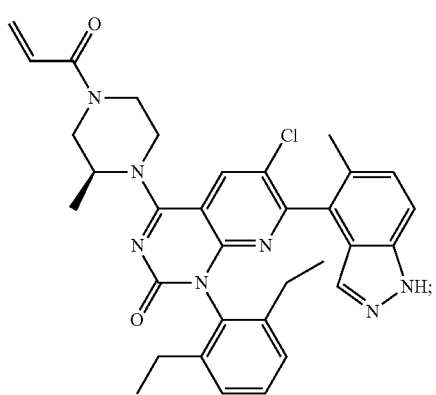
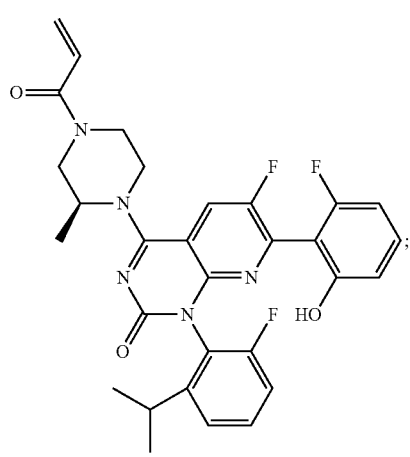
136
-continued
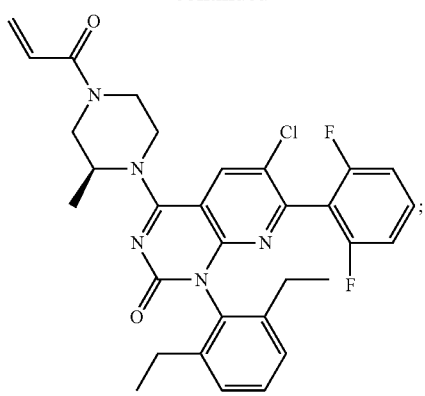
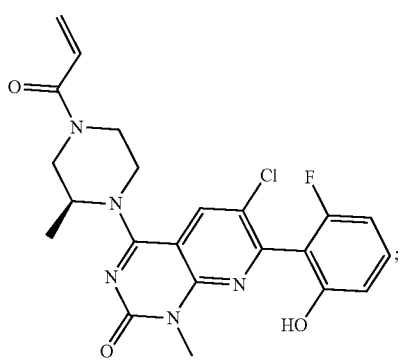
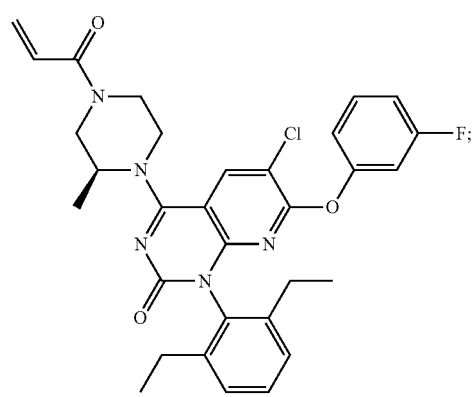
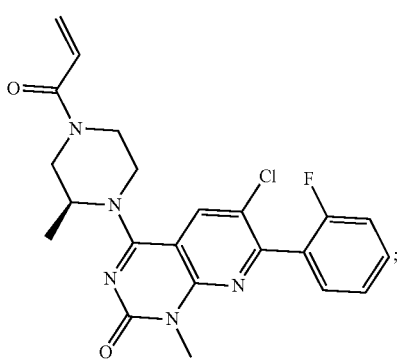

137
-continued
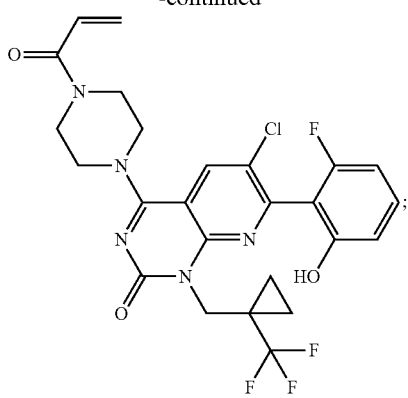
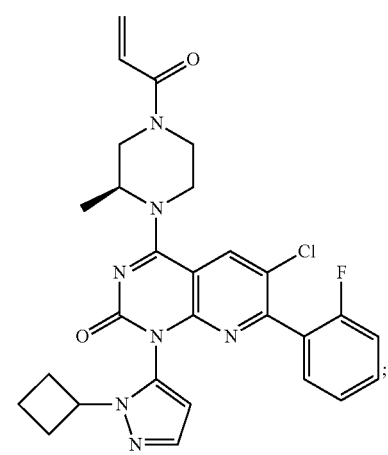
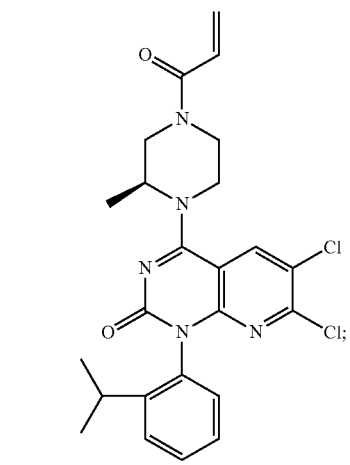
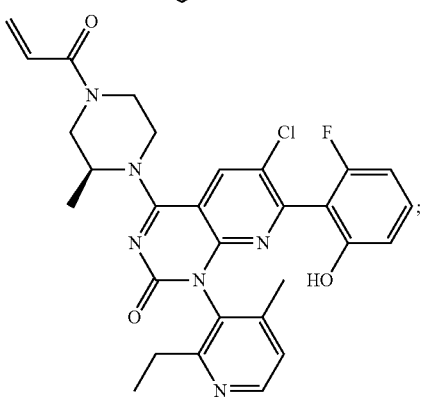
138
-continued
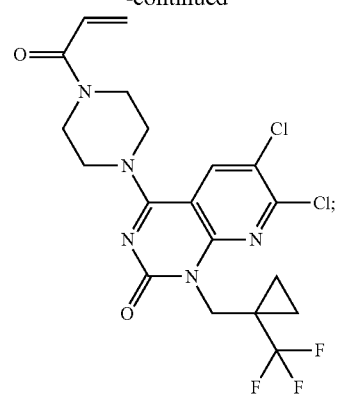
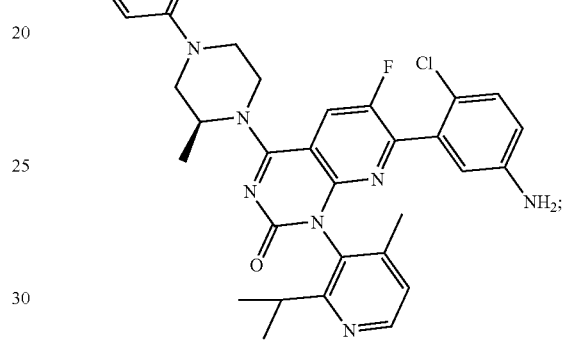
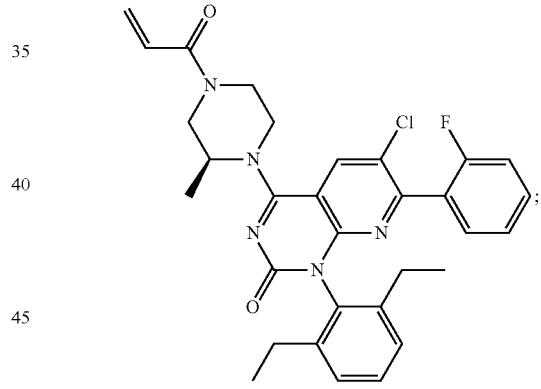
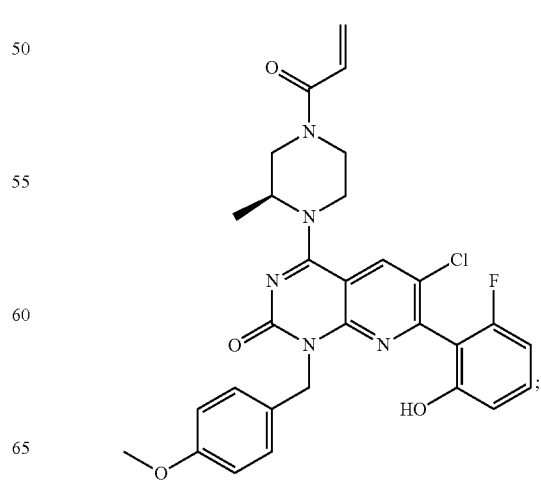

139
-continued

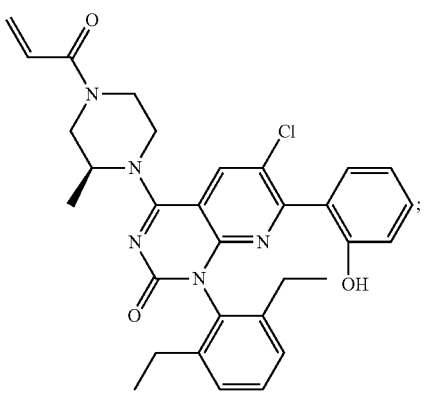

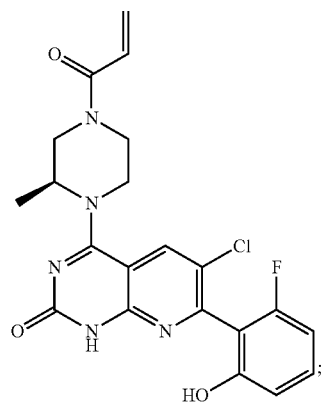

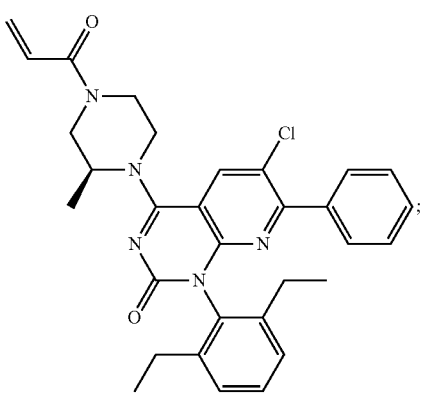

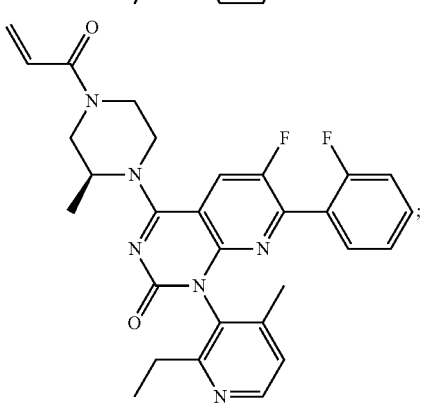

140
-continued

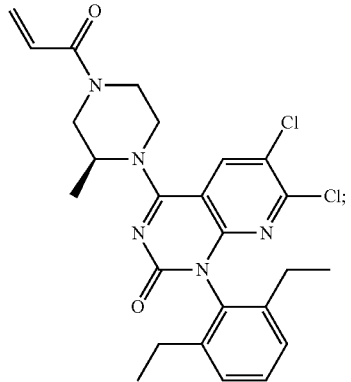

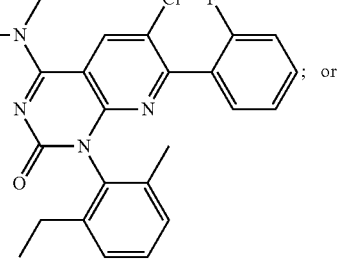

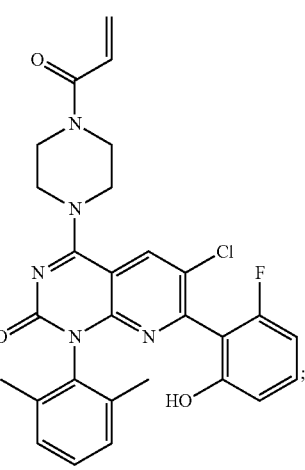

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 2

In another embodiment of the present invention, the present invention comprises a compound having a structure selected from:

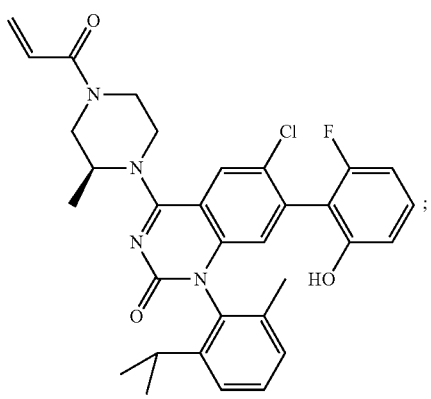
;
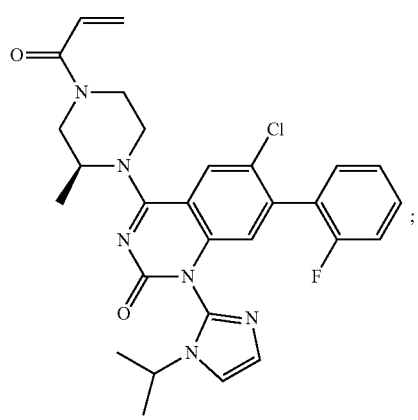
;
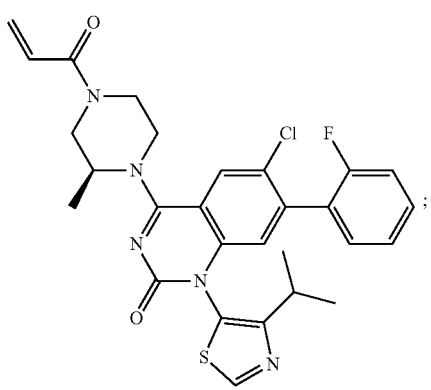
;
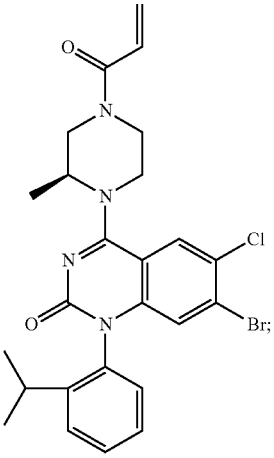
;
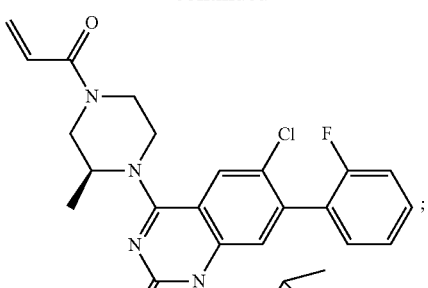
;
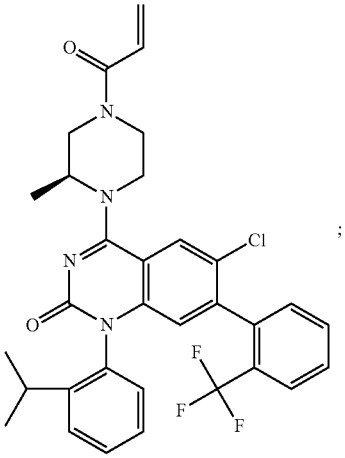
;
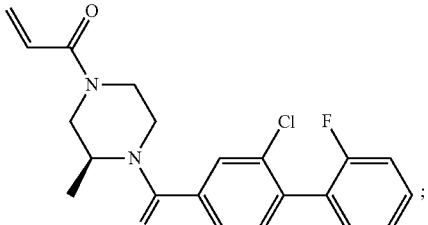
;
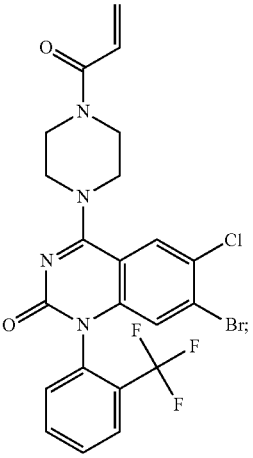

143
-continued
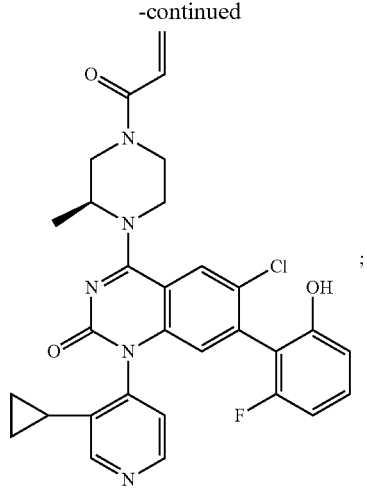
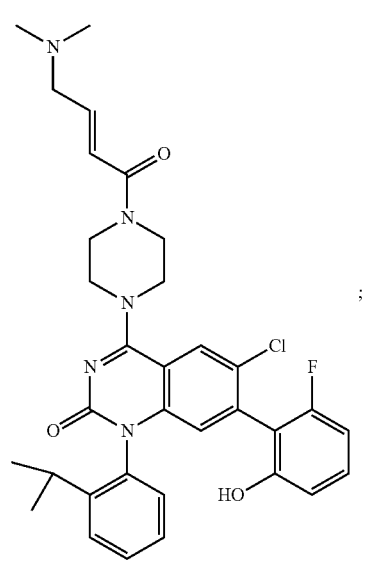
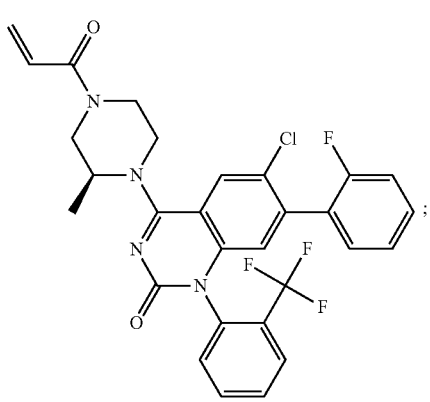
144
-continued
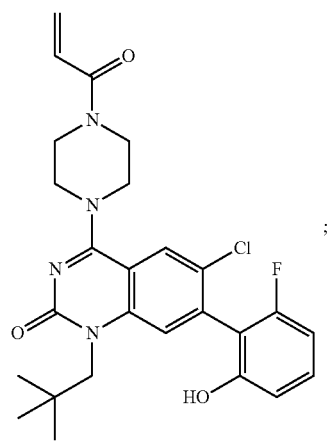
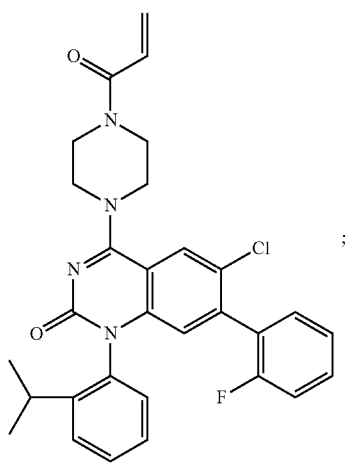
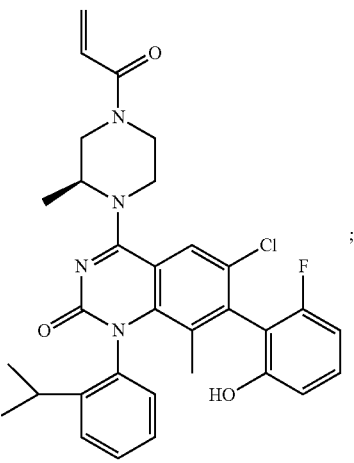

-continued

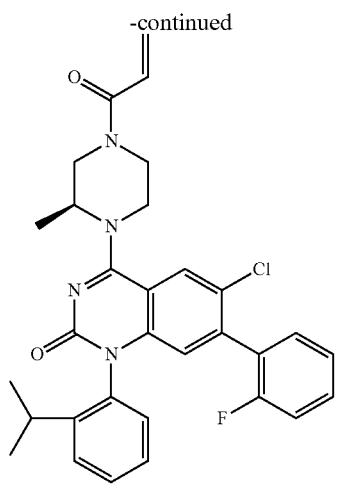

;

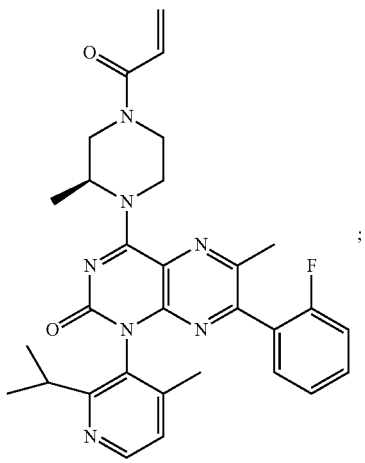

;

or a stereoisomer thereof, an atropisomer thereof, a pharmaceutically acceptable salt thereof, a pharmaceutically acceptable salt of the stereoisomer thereof, or a pharmaceutically acceptable salt of die atropisomer thereof.

Embodiment 3

In another embodiment of the present invention, the present invention comprises a compound having a structure selected from:

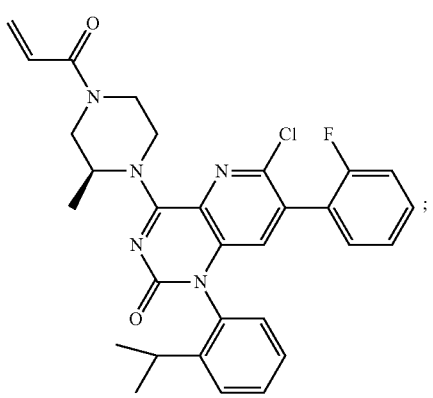 [SMILES: C=CC(=O)N1CCN(c2nc(=O)n(-c3ccccc3C(C)C)c3cc(-c4ccccc4F)c(Cl)nc23)[C@@H](C)C1]

;

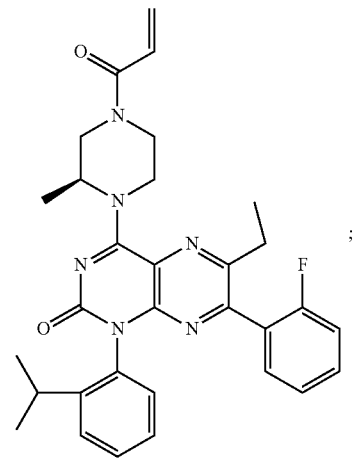 [SMILES: C=CC(=O)N1CCN(c2nc(=O)n(-c3ccccc3C(C)C)c3nc(-c4ccccc4F)c(OC)nc23)[C@@H](C)C1]

;

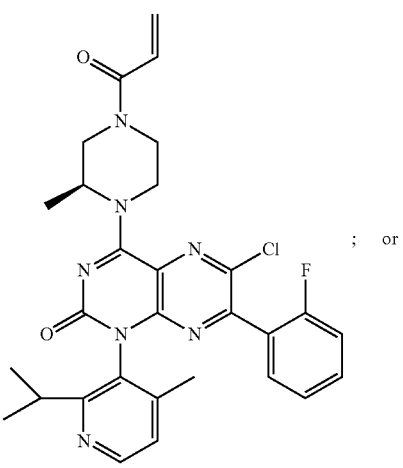

; or or a stereoisomer thereof, an atropisomer thereof, a pharmaceutically acceptable salt thereof, a pharmaceutically acceptable salt of the stereoisomer thereof, or a pharmaceutically acceptable salt of die atropisomer thereof.

Embodiment 4

In another embodiment of the present invention, the present invention comprises a compound having a structure selected from:

-continued

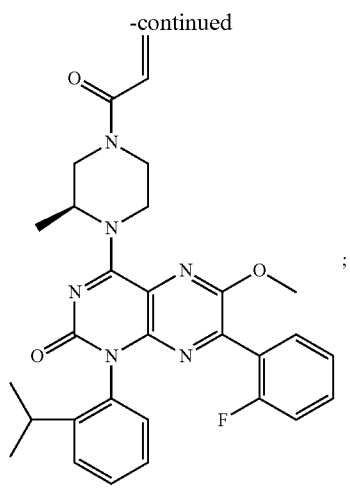

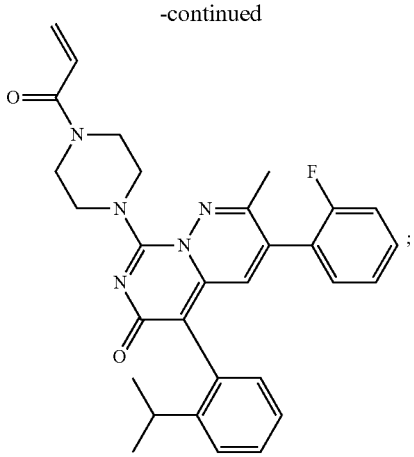

or a stereoisomer thereof, an atropisomer thereof a pharmaceutically acceptable salt thereof a pharmaceutically acceptable salt of the stereoisomer thereof a pharmaceutically acceptable salt of the atropisomer thereof.

Embodiment 5

In another embodiment of the present invention, the present invention comprises a compound having a structure selected from:

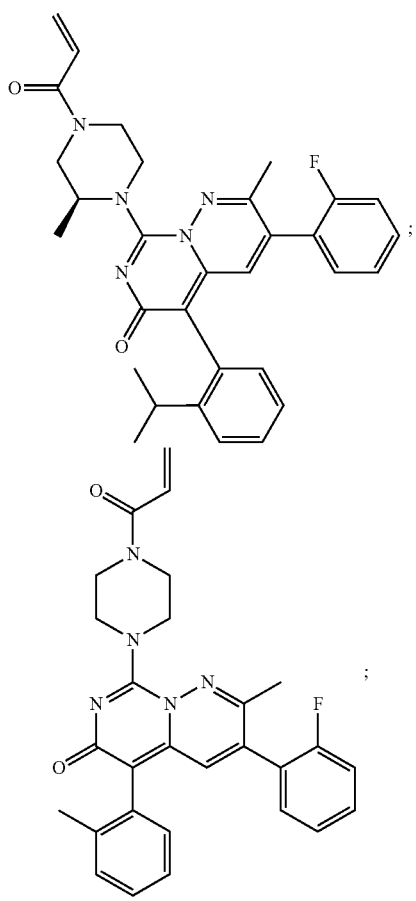

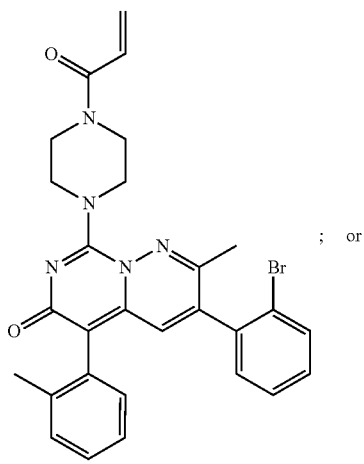

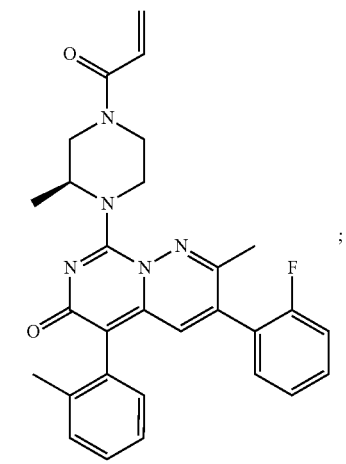

or a stereoisomer thereof, an atropisomer thereof, a pharmaceutically acceptable salt thereof, a pharmaceutically acceptable salt of the stereoisomer thereof, a pharmaceutically acceptable salt of the atropisomer thereof.

Embodiment 6

In another embodiment of the present invention, the present invention comprises a compound having a structure selected from:

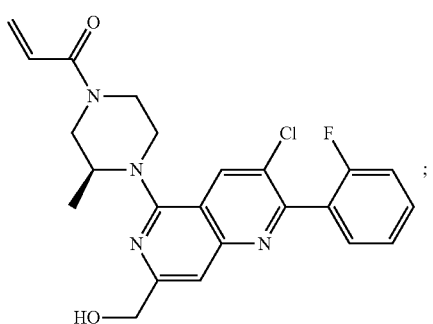
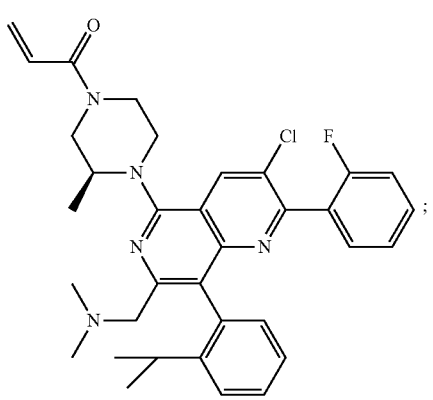
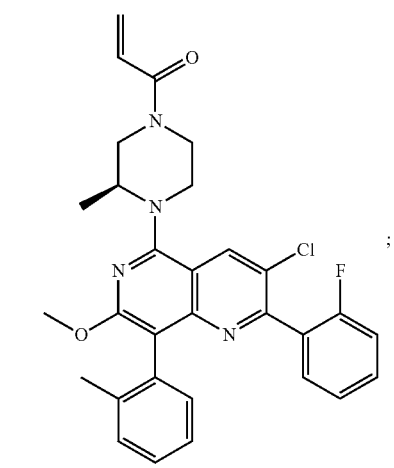
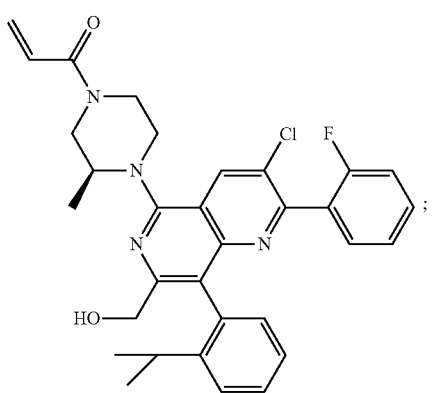
-continued
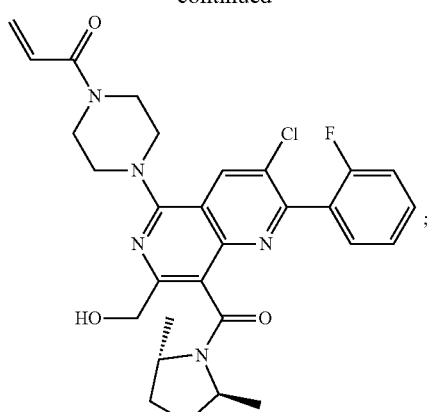
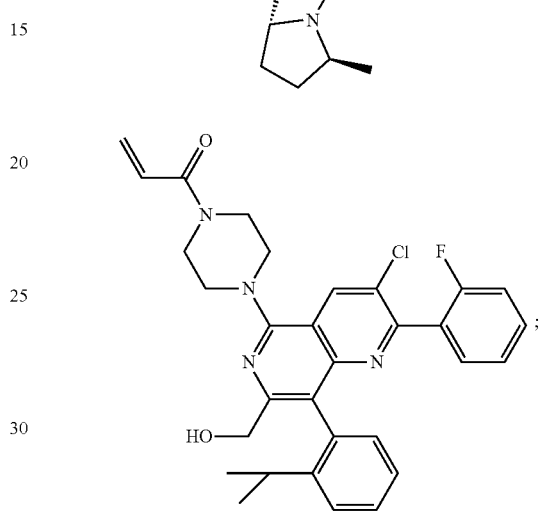
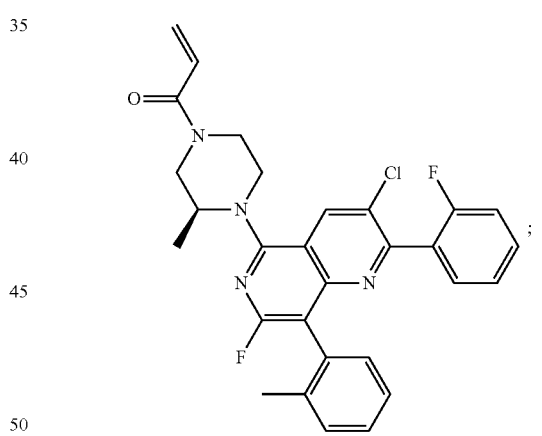
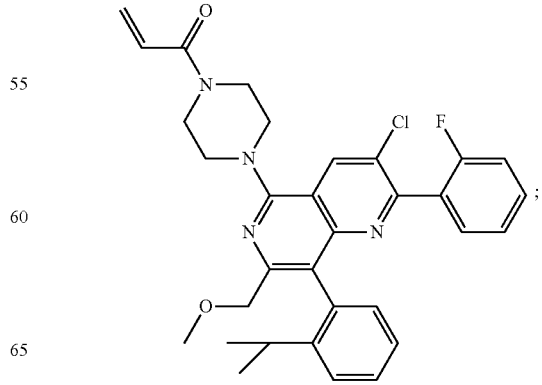

151
-continued
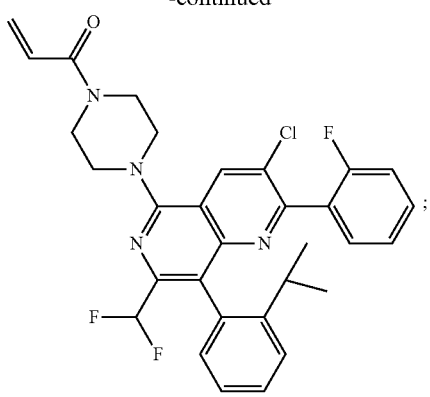
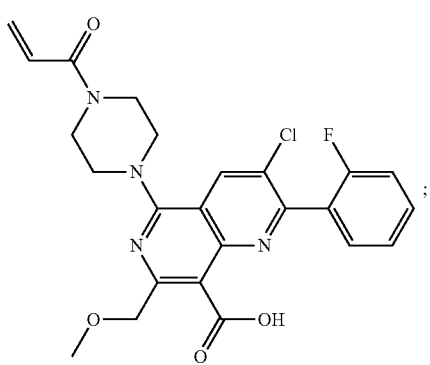
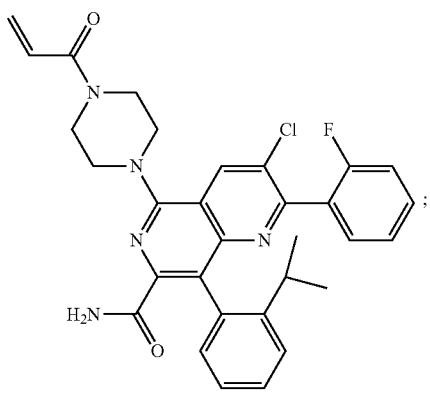
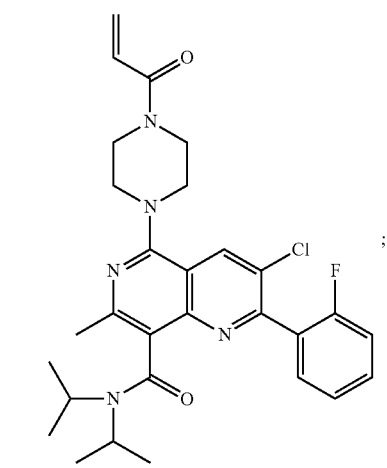
152
-continued
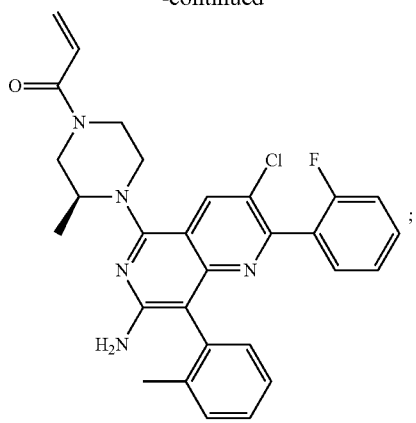
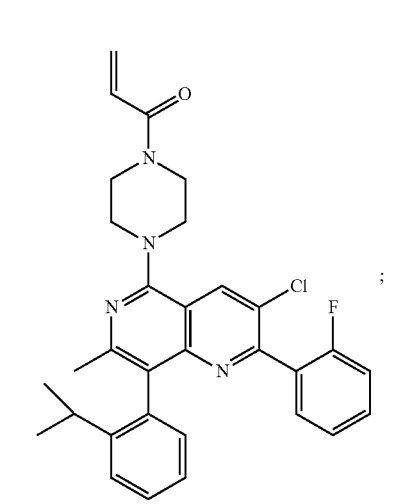
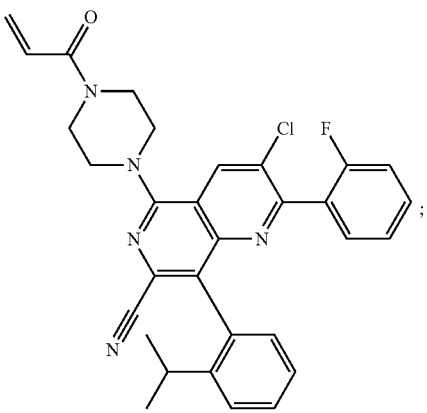

153
-continued

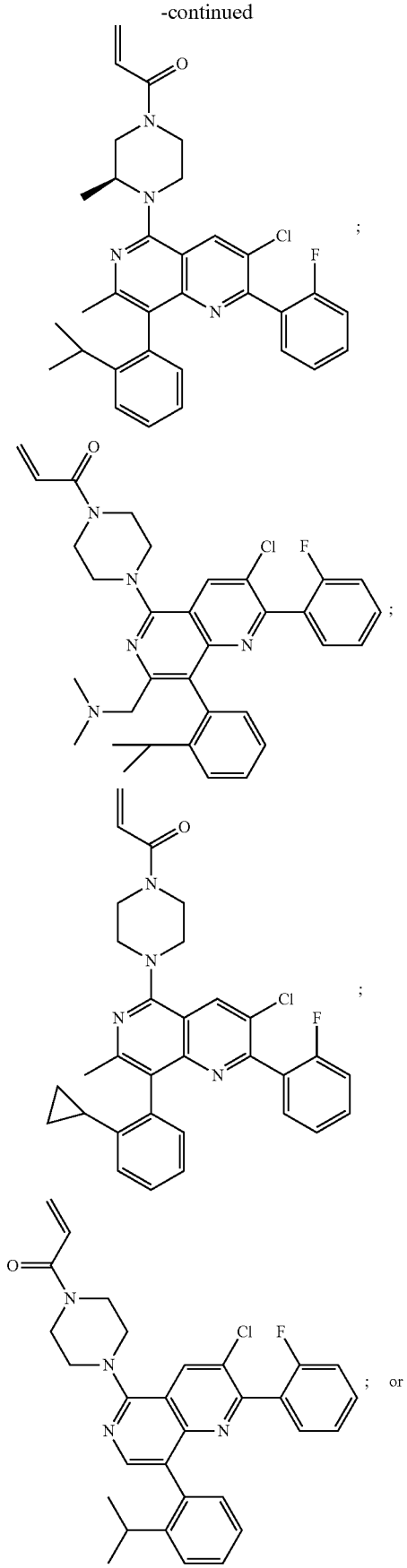

154
-continued

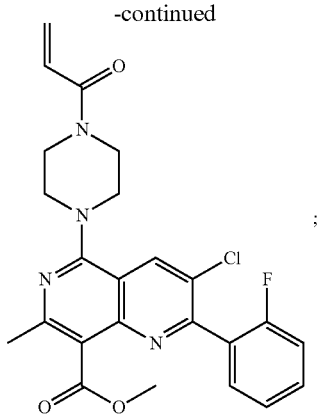

or a stereoisomer thereof, an atropisomer thereof, a pharmaceutically acceptable salt thereof, a pharmaceutically acceptable salt of the stereoisomer thereof, or a pharmaceutically acceptable salt of die atropisomer thereof.

Embodiment 7

In another embodiment of the present invention, the present invention comprises a compound having a structure selected from:

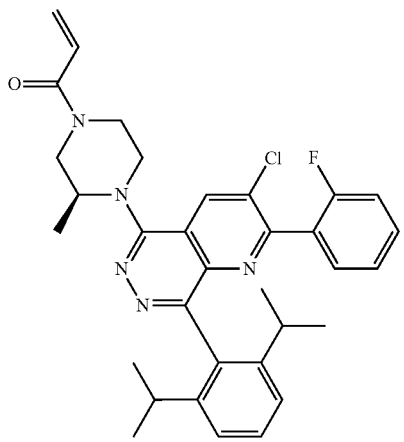 [SMILES: C=CC(=O)N1CCN(c2nnc(-c3c(C(C)C)cccc3C(C)C)c3nc(-c4ccccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 8

In another embodiment of the present invention, the present invention comprises a compound having a structure selected from:

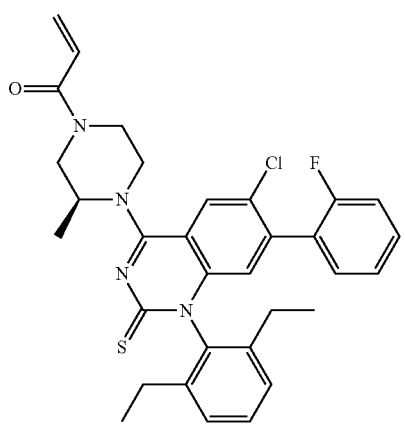 [SMILES: C=CC(=O)N1CCN(c2nc(=S)n(-c3c(CC)cccc3CC)c3cc(-c4ccccc4F)c(Cl)cc23)[C@@H](C)C1]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 9

In another embodiment of the present invention, the present invention comprises a compound having a structure selected from:

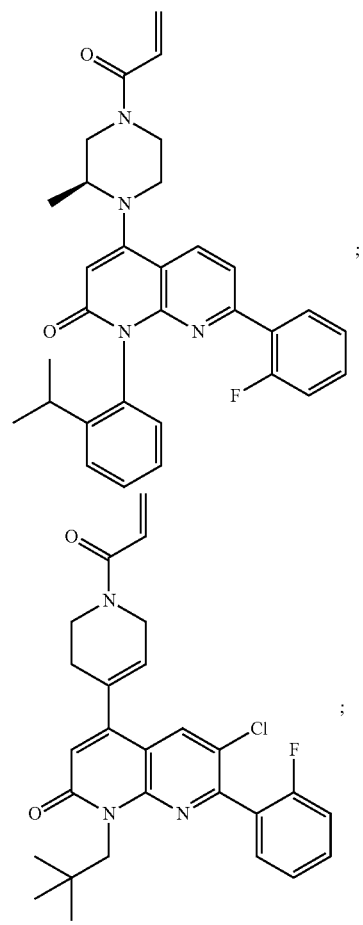

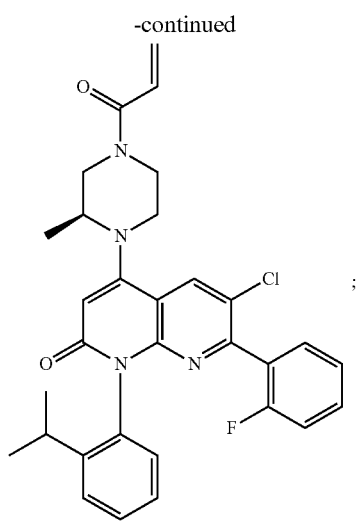

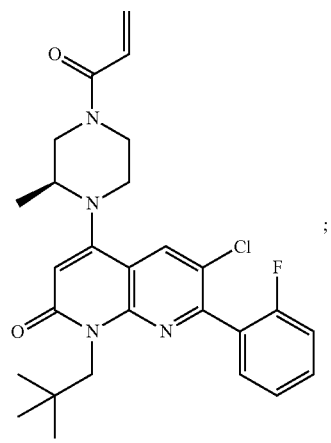

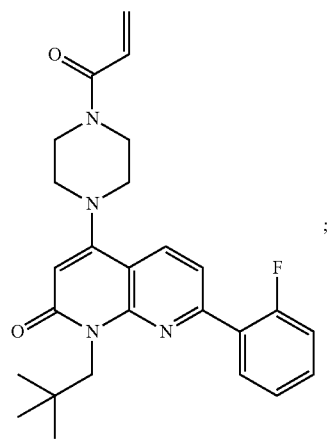

-continued

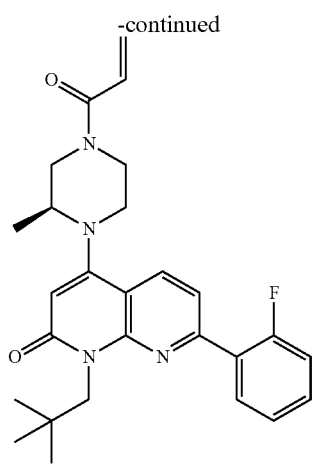

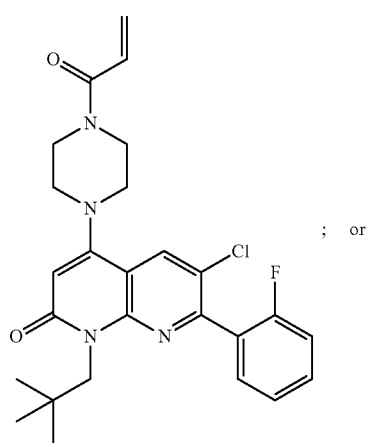

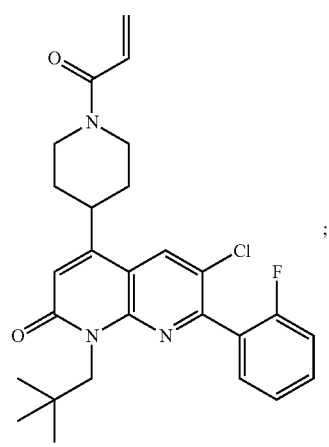

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 10

In another embodiment of the present invention, the present invention comprises a compound having a structure selected from:

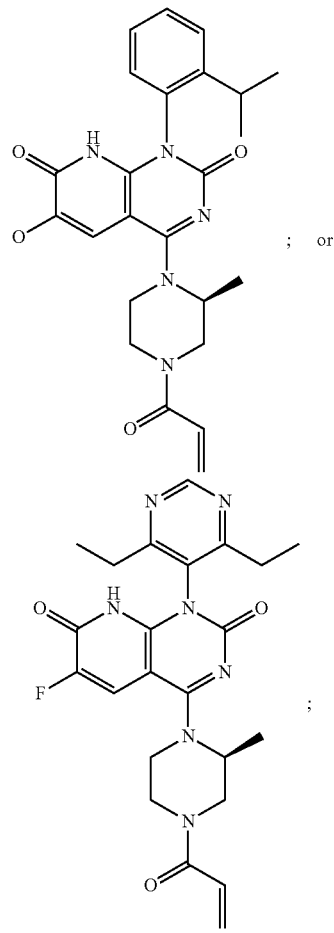

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 11

In another embodiment of the present invention, the present invention comprises a compound having a structure from.

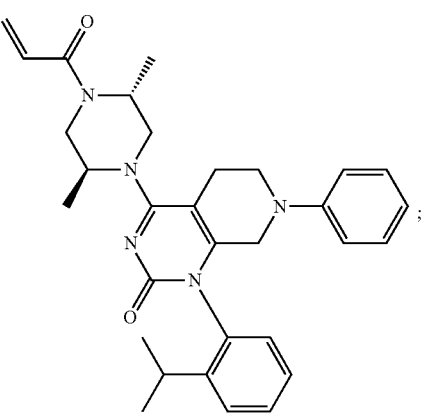 [SMILES: C=CC(=O)N1C[C@H](C)N(c2nc(=O)n(-c3ccccc3C(C)C)c3c2CCN(c2ccccc2)C3)C[C@H]1C]

or a stereoisomer thereof, an atropisomer thereof, a pharmaceutically acceptable salt thereof, a pharmaceutically acceptable salt of the stereoisomer thereof, or a pharmaceutically acceptable salt of the atropisomer thereof.

Embodiment 12

In another embodiment of the present invention, the present invention comprises the compound of any one of embodiments 1-11 in the form of a pharmaceutically acceptable salt.

Embodiment 13

In another embodiment of the present invention, the present invention comprises a pharmaceutical formulation comprising the compound of any one of the embodiments 1-12 and a pharmaceutically acceptable excipient.

Embodiment 14

In another embodiment of the present invention, the present invention comprises a method of inhibiting KRAS G12C in a cell, comprising contacting the cell with the compound of any one of the embodiments 1-13.

Embodiment 15

In another embodiment of the present invention, the present invention comprises a method of treating cancer in a subject comprising administering to the subject a therapeutically effective amount of the compound or formulation of any one of the embodiments 1-13.

Embodiment 16

In another embodiment of the present invention, the present invention comprises a method of the embodiment 15, wherein the cancer is lung cancer, pancreatic cancer, or colorectal cancer.

Embodiment 17

In another embodiment of the present invention, the cancer is lung cancer.

Embodiment 18

In another embodiment of the present invention, die cancer is pancreatic cancer.

Embodiment 19

In another embodiment of the present invention, die cancer is colorectal cancer.

Embodiment 20

In another embodiment of the present invention, the present invention comprises administering to the patient in need thereof a therapeutically effective amount of an additional pharmaceutically active compound.

Embodiment 21

In another embodiment of the present invention, the additional pharmaceutically active compound is nivolumab.

Embodiment 22

In another embodiment of the present invention, the additional pharmaceutically active compound is pembrolizumab.

Embodiment 23

In another embodiment of the present invention, the additional pharmaceutically active compound is AMG 404.

Embodiment 24

In another embodiment of the present invention, the additional pharmaceutically active compound is an anti PD-1 antagonist.

Embodiment 25

In another embodiment of the present invention, the additional pharmaceutically active compound is AMG 176.

Embodiment 26

In another embodiment of the present invention, the additional pharmaceutically active compound is daratumumab.

Embodiment 27

In another embodiment of the present invention, the present invention comprises the use of a compound or formulation according to any one of the embodiments 1-26 for treating cancer in a subject.

Embodiment 28

In another embodiment of the present invention, the present invention comprises a compound or formulation according to any one of the embodiments 1-27 in the preparation of a medicament for treating cancer.

Embodiment 29

In another embodiment of the present invention, the cancer is non small cell lung cancer.

Contemplated halogenating agents include, but are not limited to, chlorine, bromine, N-chlorosuccinimide, and N-bromosuccinimide, optionally in the presence of a catalyst, e.g., iron or aluminum. The ordinarily skilled synthetic chemist will readily understand that other halogenating agents and catalysts can be used.

Contemplated amidating agents include, but are not limited to, N,N'-diisopropylcarbodiimide, N-(3-dimethylaminopropyl)-N'-ethylcarbodiimide, benzotriazol-1-yl-oxytripyrrolidinophosphonium hexafluorophosphate, O-(benzotriazol-1-yl)-N,N,N',N'-tetramethyluronium hexafluorophosphate, thionyl chloride, isobutyl chloroformate, diethyl cyanophosphonate, carbonyl diimidazole, and polyphosphonic anhydride. The ordinarily skilled synthetic chemist will readily understand that other amidating agents can be used.

Contemplated sulfurizing agents include, but are not limited to, sulfur, phosphorus pentasulfide, and Lawesson's reagent. The ordinarily skilled synthetic chemist will readily understand that other sulfurizing agents can be used.

Contemplated oxidants include, but are not limited to, hydrogen peroxide, iodobenzene diacetate, t-butyl hydroperoxide, N-bromosuccinimide, and ammonium peroxodisulfate. The ordinarily skilled synthetic chemist will readily understand that other oxidants can be used.

Contemplated metalating agents include, but are not limited to, bis(pinacolato)diboron, magnesium, zinc, hexamethyldistannane, and n-butyllithium. The ordinarily skilled synthetic chemist will readily understand that other metalating agents and catalysts can be used.

Contemplated activating agents include, but are not limited to, sodium nitrite and t-butyl nitrite. The ordinarily skilled synthetic chemist will readily understand that other activating agents can be used.

Contemplated cross-coupling reactions include, but are not limited to, Suzuki coupling, Negishi coupling, Hiyama coupling, Kumada coupling, and Stifle coupling. The ordinarily skilled chemist will readily understand that couplings as shown in the following Methods can be performed under a number of conditions.

Pharmaceutical Compositions, Dosing, and Routes of Administration

Also provided herein are pharmaceutical compositions that includes a compound as disclosed herein, together with a pharmaceutically acceptable excipient, such as, for example, a diluent or carrier. Compounds and pharmaceutical compositions suitable for use in the present invention include those wherein the compound can be administered in an effective amount to achieve its intended purpose. Administration of the compound described in more detail below.

Suitable pharmaceutical formulations can be determined by the skilled artisan depending on the route of administration and the desired dosage. See. e.g., Remington's Pharmaceutical Sciences, 1435-712 (18th ed., Mack Publishing Co, Easton, Pa., 1990). Formulations may influence the physical state, stability, rate of in vivo release and rate of in vivo clearance of the administered agents. Depending on the route of administration, a suitable dose may be calculated according to body w eight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data obtainable through animal or human clinical trials.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable excipients" includes any and all solvents, dispersion media, coatings, antibacterial and antifungal agents, isotonic and absorption delaying agents and the like. The use of such excipients for pharmaceutically active substances is well known in the art. Except insofar as any conventional media or agent is incompatible with the therapeutic compositions, its use in therapeutic compositions is contemplated. Supplementary active ingredients also can be incorporated into the compositions. In exemplary embodiments, the formulation may comprise corn syrup solids, high-oleic safflower oil, coconut oil, soy oil, L-leucine, calcium phosphate tribasic, L-tyrosine, L-proline, L-lysine acetate, DATEM (an emulsifier), L-glutamine, L-valine, potassium phosphate dibasic, L-isoleucine, L-arginine, L-alanine, glycine, L-asparagine monohydrate, L-serine, potassium citrate, L-threonine, sodium citrate, magnesium chloride, L-histidine, L-methionine, ascorbic acid, calcium carbonate, L-glutamic acid, L-cystine dihydrochloride, L-tryptophan, L-aspartic acid, choline chloride, taurine, m-inositol, ferrous sulfate, ascorbyl palmitate, zinc sulfate, L-carnitine, alpha-tocopheryl acetate, sodium chloride, niacinamide, mixed tocopherols, calcium pantothenate, cupric sulfate, thiamine chloride hydrochloride, vitamin A palmitate, manganese sulfate, riboflavin, pyridoxine hydrochloride, folic acid, beta-carotene, potassium iodide, phylloquinone, biotin, sodium selenate, chromium chloride, sodium molybdate, vitamin D3 and cyanocobalamin.

The compound can be present in a pharmaceutical composition as a pharmaceutically acceptable salt. As used herein, "pharmaceutically acceptable salts" include, for example base addition salts and acid addition salts.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Pharmaceutically acceptable acid addition salts include inorganic or organic acid salts. Examples of suitable acid salts include the hydrochlorides, formates, acetates, citrates, salicylates, nitrates, phosphates. Other suitable pharmaceutically acceptable salts are well known to those skilled in the art and include, for example, formic, acetic, citric, oxalic, tartaric, or mandelic acids, hydrochloric acid, hydrobromic acid, sulfuric acid or phosphoric acid; with organic carboxylic, sulfonic, sulfo or phospho acids or N-substituted sulfamic acids, for example acetic acid, trifluoroacetic acid (TFA), propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane 1,2-disulfonic acid, benzenesulfonic acid, 4-methylbenzenesulfonic acid, naphthalene 2-sulfonic acid, naphthalene 1,5-disulfonic acid, 2- or 3-phosphoglycerate, glucose 6-phosphate, N-cyclohexylsulfamic acid (with the formation of cyclamates), or with other acid organic compounds, such as ascorbic acid.

Pharmaceutical compositions containing the compounds disclosed herein can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen.

For oral administration, suitable compositions can be formulated readily by combining a compound disclosed herein with pharmaceutically acceptable excipients such as carriers well known in the art. Such excipients and carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound as disclosed herein with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added. Pharmaceutically acceptable ingredients are well known for the various types of formulation and may be for example binders (e.g., natural or synthetic polymers), lubricants, surfactants, sweetening and flavoring agents, coating materials, preservatives, dyes, thickeners, adjuvants, antimicrobial agents, antioxidants and carriers for the various formulation types.

When a therapeutically effective amount of a compound disclosed herein is administered orally, the composition typically is in the form of a solid (e.g., tablet, capsule, pill, powder, or troche) or a liquid formulation (e.g., aqueous suspension, solution, elixir, or syrup).

When administered in tablet form, the composition can additionally contain a functional solid and/or solid carrier, such as a gelatin or an adjuvant. The tablet, capsule, and powder can contain about 1 to about 95% compound, and preferably from about 15 to about 90% compound.

When administered in liquid or suspension form, a functional liquid and/or a liquid carrier such as water, petroleum, or oils of animal or plant origin can be added. The liquid form of the composition can further contain physiological saline solution, sugar alcohol solutions, dextrose or other saccharide solutions, or glycols. When administered in liquid or suspension form, the composition can contain about 0.5 to about 90% by weight of a compound disclosed herein, and preferably about 1 to about 50% of a compound disclosed herein. In one embodiment contemplated, the liquid carrier is non-aqueous or substantially non-aqueous. For administration in liquid form, die composition may be supplied as a rapidly-dissolving solid formulation for dissolution or suspension immediately prior to administration.

When a therapeutically effective amount of a compound disclosed herein is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in die art A preferred composition for intravenous, cutaneous, or subcutaneous injection typically contains, in addition to a compound disclosed herein, an isotonic vehicle. Such compositions may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations can optionally contain a preservative to prevent the growth of microorganisms.

Injectable compositions can include sterile aqueous solutions, suspensions, or dispersions and sterile powders for the extemporaneous preparation of sterile injectable solutions, suspensions, or dispersions. In all embodiments the form must be sterile and must be fluid to the extent that easy syringability exists. It must be stable under the conditions of manufacture and storage and must resist the contaminating action of microorganisms, such as bacteria and fungi, by optional inclusion of a preservative. The carrier can be a solvent or dispersion medium containing, for example, water, ethanol, polyol (e.g., glycerol, propylene glycol, and liquid polyethylene glycol, and the like), suitable mixtures thereof, and vegetable oils. In one embodiment contemplated, the carrier is non-aqueous or substantially non-aqueous. The proper fluidity can be maintained, for example, by the use of a coating, such as lecithin, by the maintenance of the required particle size of the compound in the embodiment of dispersion and by the use of surfactants. The prevention of the action of microorganisms can be brought about by various antibacterial and antifungal agents, for example, parabens, chlorobutanol, phenol, sorbic acid, thimerosal, and the like. In many embodiments, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in die required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from diose enumerated above. In the embodiment of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Slow release or sustained release formulations may also be prepared in order to achieve a controlled release of the active compound in contact with the body fluids in the GI tract, and to provide a substantially constant and effective level of tire active compound in the blood plasma. For example, release can be controlled by one or more of dissolution, diffusion, and ion-exchange. In addition, the slow release approach may enhance absorption via saturable or limiting pathway s within the GI tract. For example, the compound may be embedded for this purpose in a poly mer matrix of a biological degradable poly mer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

For administration by inhalation, compounds of the present invention are conveniently delivered in the form of an aerosol spray presentation from pressurized packs or a nebulizer, with the use of a suitable propellant. In the embodiment of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds disclosed herein can be formulated for parenteral administration by injection (e.g., by bolus injection or continuous infusion). Formulations for injection can be presented in unit dosage form (e.g., in ampules or in multidose containers), with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the compounds in water-soluble form. Additionally, suspensions of the compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle (e.g., sterile pyrogen-free water) before use.

Compounds disclosed herein also can be formulated in rectal compositions, such as suppositories or retention enemas (e.g., containing conventional suppository bases). In addition to the formulations described previously, the compounds also can be formulated as a depot preparation. Such long-acting formulations can be administered by implantation (e.g., subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In particular, a compound disclosed herein can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronary. For parenteral administration, the compound is best used in the form of a sterile aqueous solution which can contain other substances, for example, salts, or sugar alcohols, such as mannitol, or glucose, to make the solution isotonic with blood.

For veterinary use, a compound disclosed herein is administered as a suitably acceptable formulation in accordance with normal veterinary practice. The veterinarian can readily determine the dosing regimen and route of administration that is most appropriate for a particular animal.

In some embodiments, all the necessary components for the treatment of KRAS-related disorder using a compound as disclosed herein either alone or in combination with another agent or intervention traditionally used for the treatment of such disease may be packaged into a kit. Specifically, the present invention provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound disclosed herein, and/or instructions for the treatment of the disease packaged with die medicaments. The instructions may be fixed in any tangible medium, such as printed paper, or a computer readable magnetic or optical medium, or instructions to reference a remote computer data source such as a world wide web page accessible via the internet.

A "therapeutically effective amount" means an amount effective to treat or to prevent development of, or to alleviate the existing symptoms of, the subject being treated. Determination of the effective amounts is well within the capability of those skilled in the art, especially in light of the detailed disclosure provided herein. Generally, a "therapeutically effective dose" refers to that amount of the compound that results in achieving the desired effect. For example, in one preferred embodiment, a therapeutically effective amount of a compound disclosed herein decreases KRAS activity by at least 5%, compared to control, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90%.

The amount of compound administered can be dependent on the subject being treated, on the subject's age, health, sex, and weight, the kind of concurrent treatment (if any), severity of the affliction, the nature of the effect desired, the manner and frequency of treatment, and the judgment of the prescribing physician. The frequency of dosing also can be dependent on pharmacodynamic effects on arterial oxygen pressures. However, the most preferred dosage can be tailored to the individual subject, as is understood and determinable by one of skill in the art, without undue experimentation. This typically involves adjustment of a standard dose (e.g., reduction of the dose if the patient has a low body weight).

While individual needs vary, determination of optimal ranges of effective amounts of the compound is within the skill of the art. For administration to a human in the curative or prophylactic treatment of the conditions and disorders identified herein, for example, typical dosages of the compounds of the present invention can be about 0.05 mg/kg/day to about 50 mg/kg/day, for example at least 0.05 mg/kg, at least 0.08 mg/kg, at least 0.1 mg/kg, at least 0.2 mg/kg, at least 0.3 mg/kg, at least 0.4 mg/kg, or at least 0.5 mg/kg, and preferably 50 mg/kg or less, 40 mg/kg or less, 30 mg/kg or less, 20 mg/kg or less, or 10 mg/kg or less, which can be about 2.5 mg/day (0.5 mg/kg×5 kg) to about 5000 mg/day (50 mg/kg×100 kg), for example. For example, dosages of the compounds can be about 0.1 mg/kg/day to about 50 mg/kg/day, about 0.05 mg/kg/day to about 10 mg/kg/day, about 0.05 mg/kg/day to about 5 mg/kg/day, about 0.05 mg/kg/day to about 3 mg/kg/day, about 0.07 mg/kg/day to about 3 mg/kg/day, about 0.09 mg/kg/day to about 3 mg/kg/day, about 0.05 mg/kg/day to about 0.1 mg/kg/day, about 0.1 mg/kg/day to about 1 mg/kg/day, about 1 mg/kg/day to about 10 mg/kg/day, about 1 mg/kg/day to about 5 mg/kg/day, about 1 mg/kg/day to about 3 mg/kg/day, about 3 mg/day to about 1000 mg/day, about 5 mg/day to about 500 mg/day, about 10 mg/day to about 200 mg/day, about 3 mg/day to about 100 mg/day, or about 100 mg/day to about 250 mg/day. Such doses may be administered in a single dose or it may be divided into multiple doses.

Methods of Using KRAS G12C Inhibitors

The present disclosure provides a method of inhibiting RAS-mediated cell signaling comprising contacting a cell with an effective amount of one or more compounds disclosed herein. Inhibition of RAS-mediated signal transduction can be assessed and demonstrated by a wide variety of ways known in the art. Non-limiting examples include a showing of (a) a decrease in GTPase activity of RAS; (b) a decrease in GTP binding affinity or an increase in GDP binding affinity; (c) an increase in K off of GTP or a decrease in K off of GDP; (d) a decrease in the levels of signaling transduction molecules downstream in the RAS pathway, such as a decrease in pMEK, pERK, or pAKT levels; and/or (e) a decrease in binding of RAS complex to downstream signaling molecules including but not limited to Raf. Kits and commercially available assays can be utilized for determining one or more of the above.

The disclosure also provides methods of using the compounds or pharmaceutical compositions of the present disclosure to treat disease conditions, including but not limited to conditions implicated by G12C KRAS, HRAS or NRAS mutation (e.g., cancer).

In some embodiments, a method for treatment of cancer is provided, the method comprising administering an effective amount of any of the foregoing pharmaceutical compositions comprising a compound as disclosed herein to a subject in need thereof. In some embodiments, the cancer is mediated by a KRAS, HRAS or NRAS G12C mutation. In various embodiments, the cancer is pancreatic cancer, colorectal cancer or lung cancer. In some embodiments, the cancer is gall bladder cancer, thyroid cancer, and bile duct cancer.

In some embodiments the disclosure provides method of treating a disorder in a subject in need thereof, wherein the said method comprises determining if the subject has a KRAS, HRAS or NRAS G12C mutation and if the subject is determined to have the KRAS, HRAS or NRAS G12C mutation, then administering to the subject a therapeutically effective dose of at least one compound as disclosed herein or a pharmaceutically acceptable salt thereof.

The disclosed compounds inhibit anchorage-independent cell growth and therefore have the potential to inhibit tumor metastasis. Accordingly, another embodiment the disclosure provides a method for inhibiting tumor metastasis, the method comprising administering an effective amount a compound disclosed herein.

KRAS, HRAS or NRAS G12C mutations have also been identified in hematological malignancies (e.g., cancers that affect blood, bone marrow and/or lymph nodes). Accordingly, certain embodiments are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other embodiments, the compounds are useful for treatment of lymphomas such as all subtypes of Hodgkins lymphoma or non-Hodgkins lymphoma. In various embodiments, the compounds are useful for treatment of plasma cell malignancies such as multiple myeloma, mantle cell lymphoma, and Waldenstrom's macroglubunemia.

Determining whether a tumor or cancer comprises a G12C KRAS, HRAS or NRAS mutation can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequence of wild-type human KRAS, HRAS or NRAS is known in the art, (e.g. Accession No. NP203524).

Methods for detecting a mutation in a KRAS, HRAS or NRAS nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C KRAS, HRAS or NRAS mutations by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS G12C mutation is identified using a direct sequencing method of specific regions (e.g., exon 2 and/or exon 3) in the KRAS, HRAS or NRAS gene. This technique will identify all possible mutations in the region sequenced.

Methods for detecting a mutation in a KRAS, HRAS or NRAS protein are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

Methods for determining whether a tumor or cancer comprises a G12C KRAS, HRAS or NRAS mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a circulating tumor cell (CTC) sample. In some embodiments, the sample is processed to a cell lysate. In some embodiments, the sample is processed to DNA or RNA.

The disclosure also relates to a method of treating a hyperproliferative disorder in a mammal that comprises administering to said mammal a therapeutically effective amount of a compound as disclosed herein, or a pharmaceutically acceptable salt thereof. In some embodiments, said method relates to the treatment of a subject who suffers from a cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, Burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

In some embodiments, the methods for treatment are directed to treating lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In some embodiments, the lung cancer is a small cell lung carcinoma. Other lung cancers treatable with the disclosed compounds include, but are not limited to, glandular tumors, carcinoid tumors and undifferentiated carcinomas.

The disclosure further provides methods of modulating a G12C Mutant KRAS, HRAS or NRAS protein activity by contacting the protein with an effective amount of a compound of the disclosure. Modulation can be inhibiting or activating protein activity. In some embodiments, the disclosure provides methods of inhibiting protein activity by contacting the G12C Mutant KRAS, HRAS or NRAS protein with an effective amount of a compound of the disclosure in solution. In some embodiments, the disclosure provides methods of inhibiting the G12C Mutant KRAS, HRAS or NRAS protein activity by contacting a cell, tissue, or organ that expresses the protein of interest. In some embodiments, the disclosure provides methods of inhibiting protein activity in subject including but not limited to rodents and mammal (e.g., human) by administering into the subject an effective amount of a compound of the disclosure. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the disclosure provides methods of inhibiting KRAS, HRAS or NRAS G12C activity in a cell by contacting said cell with an amount of a compound of the disclosure sufficient to inhibit the activity of KRAS, HRAS or NRAS G12C in said cell. In some embodiments, the disclosure provides methods of inhibiting KRAS, HRAS or NRAS G12C activity in a tissue by contacting said tissue with an amount of a compound of the disclosure sufficient to inhibit the activity of KRAS, HRAS or NRAS G12C in said tissue. In some embodiments, the disclosure provides methods of inhibiting KRAS, HRAS or NRAS G12C activity in an organism by contacting said organism with an amount of a compound of the disclosure sufficient to inhibit the activity of KRAS, HRAS or NRAS G12C in said organism. In some embodiments, the disclosure provides methods of inhibiting KRAS, HRAS or NRAS G12C activity in an animal by contacting said animal with an amount of a compound of the disclosure sufficient to inhibit the activity of KRAS, HRAS or NRAS G12C in said animal. In some embodiments, the disclosure provides methods of inhibiting KRAS, HRAS or NRAS G12C activity in a mammal by contacting said mammal with an amount of a compound of the disclosure sufficient to inhibit the activity of KRAS, HRAS or NRAS G12C in said mammal. In some embodiments, the disclosure provides methods of inhibiting KRAS, HRAS or NRAS G12C activity in a human by contacting said human with an amount of a compound of the disclosure sufficient to inhibit the activity of KRAS, HRAS or NRAS G12C in said human. The present disclosure provides methods of treating a disease mediated by KRAS, HRAS or NRAS G12C activity in a subject in need of such treatment.

Combination Therapy:

The present disclosure also provides methods for combination therapies in which an agent known to modulate other pathways, or other components of the same pathway, or even overlapping sets of target enzymes are used in combination with a compound of the present disclosure, or a pharmaceutically acceptable salt thereof. In one aspect, such therapy includes but is not limited to the combination of one or more compounds of the disclosure with chemotherapeutic agents, therapeutic antibodies, and radiation treatment, to provide a synergistic or additive therapeutic effect.

Many chemotherapeutics are presently known in the art and can be used in combination with the compounds of the disclosure. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Kyprofis® (carfilzomib), Velcade® (bortezomib), Casodex (bicalutamide), Iressa® (gefitinib), venetoclax, and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodepa, carboquone, meturedepa, and uredepa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L- norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxy uridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2'2"-trichlorotriethylamine; urethan; Vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel; retinoic acid; esperamicins; capecitabine; and pharmaceutically acceptable salts, acids or derivatives of any of the above.

Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO).

Where desired, the compounds or pharmaceutical composition of the present disclosure can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1. Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This disclosure further relates to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the disclosure in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186. Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, tire radionuclide(s) can be embodied in a gel or radioactive micro spheres.

The compounds or pharmaceutical compositions of the disclosure can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metal oprotienase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO 96/33172 WO 96/27583 European Patent Publication EP0818442, European Patent Publication EP1004578, WO 98/07697, WO 98/03516, WO 98/34918, WO 98/34915, WO 98/33768, WO 98/30566, European Patent Publication 606046, European Patent Publication 931788, WO 90/05719. WO 99/52910, WO 99/52889, WO 99/29667, WO 99/007675, European Patent Publication EPI786785, European Patent Publication No. EPI 181017, United States Publication US20090012085, U.S. Pat. No. 5,863,949, United States Publication U.S. Pat. No. 5,861,510, and European Patent Publication EP0780386, all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, and MMP-13). Some specific examples of MMP inhibitors useful in the disclosure are AG-3340, RO 32-3555, and RS 13-0830.

The present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANGER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-$_{n3}$, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764. WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02'59110. WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-angiogenic agents include ERBITUX™ (IMC-C225), KBR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include. SD-7784 (Pfizer, USA); cilengitide (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital. USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca. UK); AZD 2171, (AstraZeneca, UK); vatalanib (pINN), (Novartis, Switzerland and Schering AG, Germany); tissue factor pathway inhibitors, (EntreMed, USA); pegaptanib (Finn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin. (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 8685%, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sima, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia. USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

Additional pharmaceutically active compounds/agents that can be used in the treatment of cancers and that can be used in combination with one or more compound of the present invention include: epoetin alfa; darbepoetin alfa; panitumumab, pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

In certain embodiments, a composition provided herein is conjointly administered with a chemotherapeutic agent. Suitable chemotherapeutic agents may include, natural products such as vinca alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DT1C), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNTO328), telomerase inhibitors (e.g., GRN 163L), aurora kinase inhibitors (e.g., MLN8237), cell surface monoclonal antibodies (e.g., anti-CD38 (HUMAX-CD38), anti-CS1 (e.g., elotuzumab), HSP90 inhibitors (e.g., 17 AAG and KOS 953), PI3K/Akt inhibitors (e.g., perifosine), Akt inhibitor (e.g., GSK-2141795), PKC inhibitors (e.g., enzastaurin), FTIs (e.g., Zarnestra™), anti-CD138 (e.g., BT062), Torc1/2 specific kinase inhibitor (e.g., INK128), kinase inhibitor (e.g., GS-1101), ER/UPR targeting agent (e.g., MKC-3946), cFMS inhibitor (e.g., ARRY-382), JAK1/2 inhibitor (e.g., CYT387), PARP inhibitor (e.g., olaparib and veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art.

In certain embodiments, a pharmaceutical composition provided herein is conjointly administered with a steroid. Suitable steroids may include, but are not limited to, 21-acetoxy pregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular embodiment, the compounds of the present invention can also be used in combination with additional pharmaceutically active agents that treat nausea. Examples of agents that can be used to treat nausea include, dronabinol; granisetron; metoclopramide; ondansetron; and prochlorperazine; or a pharmaceutically acceptable salt thereof.

The compounds of the present invention may also be used in combination with an additional pharmaceutically active compound that disrupts or inhibits RAS-RAF-ERK or P13K-AKT-TOR signaling pathways. In other such combinations, the additional pharmaceutically active compound is a PD-1 and PD-L1 antagonist. The compounds or pharmaceutical compositions of the disclosure can also be used in combination with an amount of one or more substances selected from EGFR inhibitors, MEK inhibitors, P13K inhibitors, AKT inhibitors, TOR inhibitors, Mcl-1 inhibitors, BCL-2 inhibitors, SHP2 inhibitors, proteasome inhibitors, and immune therapies, including monoclonal antibodies, immunomodulatory imides (IMiDs), anti-PD-1, anti-PDL-1, anti-CTLA4, anti-LAG1, and anti-OX40 agents, GITR agonists, CAR-T cells, and BiTEs.

EGFR inhibitors include, but are not limited to, small molecule antagonists, antibody inhibitors, or specific antisense nucleotide or siRNA. Useful antibody inhibitors of EGFR include cetuximab (Erbitux), panitumumab (Vectibix), zalutumumab, nimotuzumab, and matuzumab. Small molecule antagonists of EGFR include gefitinib, erlotinib (Tarceva), and most recently, lapatinib (TykerB). See e.g., Yan L, et. al., *Pharmacogenetics and Pharmacogenomics In Oncology Therapeutic Antibody Development*, BioTechniques 2005; 39(4): 565-8, and Paez J G, et. al., *EGFR Mutations In Lung Cancer Correlation With Clinical Response To Gefitinib Therapy*, Science 2004; 304(5676): 1497-500.

Non-limiting examples of small molecule EGFR inhibitors include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCT International Publication WO 97/30034, published Aug. 21, 1997; PCT International Publication WO 97/30044, published Aug. 21, 1997; PCT International Publication WO 97/38994, published Oct. 23, 1997; PCT International Publication WO 97/49688, published Dec. 31, 1997; European Patent Application EP 837063, published Apr. 22, 1998; PCT International Publication WO 98/02434, published Jan. 22, 1998; PCT International Publication WO 97/38983, published Oct. 23, 1997; PCT International Publication WO 95/19774, published Jul. 27, 1995; PCT International Publication WO 95/19970, published Jul. 27, 1995; PCT International Publication WO 97/13771, published Apr. 17, 1997; PCT International Publication WO 98/02437, published Jan. 22, 1998; PCT International Publication WO 98/02438, published Jan. 22, 1998; PCT International Publication WO 97/32881, published Sep. 12, 1997; German Application DE 19629652, published Jan. 29, 1998; PCT International Publication WO 98/33798, published Aug. 6, 1998; PCT International Publication WO 97/32880, published Sep. 12, 1997; PCT International Publication WO 97/32880 published Sep. 12, 1997; European Patent Application EP 682027, published Nov. 15, 1995; PCT International Publication WO 97/02266, published Jan. 23, 1997; PCT International Publication WO 97/27199, published Jul. 31, 1997; PCT International Publication WO 98/07726, published Feb. 26, 1998; PCT International Publication WO 97/34895, published Sep. 25, 1997; PCT International Publication WO 96/31510', published Oct. 10, 1996; PCT International Publication WO 98/14449, published Apr. 9, 1998; PCT International Publication WO 98/14450, published Apr. 9, 1998; PCT International Publication WO 98/14451, published Apr. 9, 1998; PCT International Publication WO 95/09847, published Apr. 13, 1995; PCT International Publication WO 97/19065, published May 29, 1997; PCT International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCT International Publication WO 99/35146, published Jul. 15, 1999; PCT International Publication WO 99/35132, published Jul. 15, 1999; PCT International Publication WO 99/07701, published Feb. 18, 1999; and PCT International Publication WO 92/20642 published Nov. 26, 1992. Additional non-limiting examples of small molecule EGFR inhibitors include any of the EGFR inhibitors described in Traxler, P., 1998, Exp. Opin. Ther. Patents 8(12): 1599-1625.

Antibody-based EGFR inhibitors include any anti-EGFR antibody or antibody fragment that can partially or completely block EGFR activation by its natural ligand. Non-limiting examples of antibody-based EGFR inhibitors include those described in Modjtahedi, H., et al., 1993, Br. J. Cancer 67:247-253; Teramoto, T., et al., 19%, Cancer 77:639-645; Goldstein et al., 1995, Clin. Cancer Res. 1:1311-1318; Huang, S. M., et al., 1999. Cancer Res. 15:59(8): 1935-40; and Yang, X., et al., 1999, Cancer Res. 59:1236-1243. Thus, the EGFR inhibitor can be monoclonal antibody Mab E7.6.3 (Yang, 1999 supra), or Mab C225 (ATCC Accession No. HB-8508), or an antibody or antibody fragment having the binding specificity thereof.

MEK inhibitors include, but are not limited to, tremetinib (Mekinist®), CI-1040, AZD6244, PD318088, PD98059, PD334581, RDEA119, ARRY-142886, ARRY-438162, and PD-325901.

PI3K inhibitors include, but are not limited to, wortmannin, 17-hydroxywortmannin analogs described in WO 06/044453, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806), (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in PCT Publication No. WO 2008/070740), LY294002 (2-(4-Morpholinyl)-8-phenyl-4H-1-benzopyran-4-one available from Axon Medchem), PI 103 hydrochloride (3-[4-(4-morpholinylpyrido-[3',2':4,5]furo[3,2-d]pyrimidin-2-yl]phenol hydrochloride available from Axon Medchem), PIK 75 (N'-[(1E)-(6-bromoimidazo[1,2-a]pyridin-3-yl)methylene]-N,2-dimethyl-5-nitrobenzenesulfono-hydrazide hydrochloride available from Axon Medchem), PIK 90 (N-(7,8-dimethoxy-2,3-dihydroimidazo[1,2-c]quinazolin-5-yl)-nicotinamide available from Axon Medchem), GDC-0941 bismesylate (2-(1H-Indazol-4-yl)-6-(4-methanesulfonyl-piperazin-1-ylmethyl)-4-morpholin-4-yl-thieno[3,2-d]pyrimidine bismesylate available from Axon Medchem), AS-252424 (5-[1-[5-(4-Fluoro-2-hydroxy-phenyl)-furan-2-yl]-meth-(Z)-ylidene]-thiazolidine-2,4-dione available from Axon Medchem), and TGX-221 (7-Methyl-2-(4-morpholinyl)-9-[1-(phenylamino)ethyl]-4H-pyrido-[1,2-a]pyrimidin-4-one available from Axon Medchem), XL-765, and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TG100-115, CAL263, PI-103, GNE-477, CUDC-907, and AEZS-136.

AKT inhibitors include, but are not limited to, Akt-1-1 (inhibits Akt1) (Barnett et al. (2005) Biochem. J. 385 (Pt. 2), 399-408); Akt-1-1,2 (inhibits Ak1 and 2) (Barnett et al. (2005) Biochem. J. 385 (Pt. 2), 399-408); API-59CJ-Ome (e.g., Jin et al. (2004) Br. J. Cancer 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and Li (2004) J Nutr. 134(12 Suppl), 3493S-3498S); perifosine (e.g., interferes with Akt membrane localization; Dasmahapatra et al. (2004) Clin. Cancer Res. 10(15), 5242-52, 2004); phosphatidylinositol ether lipid analogues (e.g., Gills and Dennis (2004) Expert. Opin. Investig. Drugs 13, 787-97); and triciribine (TCN or API-2 or NCI identifier: NSC 154020; Yang et al. (2004) Cancer Res. 64, 4394-9).

TOR inhibitors include, but are not limited to, inhibitors include AP-23573, CCI-779, everolimus, RAD-001, rapamycin, temsirolimus, ATP-competitive TORC1/TORC2 inhibitors, including Pl-103, PP242, PP30 and Torin 1. Other TOR inhibitors in FKBP12 enhancer; rapamycins and derivatives thereof, including: CCI-779 (temsirolimus), RAD001 (Everolimus; WO 9409010) and AP23573; rapalogs, e.g. as disclosed in WO 98/02441 and WO 01/14387, e.g. AP23573, AP23464, or AP23841; 40-(2-hydroxyethyl) rapamycin, 40-[3-hydroxy(hydroxymethyl)methylpropanoate]-rapamycin (also called CC1779), 40-epi-(tetrazolyt)-rapamycin (also called ABT578), 32-deoxorapamycin, 16-pentynyloxy-32(S)-dihydrorapanycin, and other derivatives disclosed in WO 05005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; phosphorus-containing rapamycin derivatives (e.g., WO 05016252); 4H-1-benzopyran-4-one derivatives (e.g., U.S. Provisional Application No. 60/528,340).

MCl-1 inhibitors include, but are not limited to, AMG-176, MIK665, and S63845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

SHP inhibitors include, but are not limited to, SHP099.

Proteasome inhibitors include, but are not limited to, Kyprolis® (carfilzomib), Velcade® (bortezomib), and oprozomib.

Immune therapies include, but are not limited to, anti-PD-1 agents, anti-PDL-1 agents, anti-CTLA-4 agents, anti-LAG1 agents, and anti-OX40 agents.

Monoclonal antibodies include, but are not limited to, Darzalex® (daratumumab), Herceptin® (trastuzumab), Avastin® (bevacizumab), Rituxan® (rituximab), Lucentis® (ranibizumab), and Eylea® (aflibercept).

Immunomodulatory imide drugs (IMiDs) are a class of immunomodulatory drugs (drugs that adjust immune responses) containing an imide group. The IMiD class includes thalidomide and its analogues (lenalidomide, pomalidomide, and apremilast).

Exemplary anti-PD-1 antibodies and methods for their use are described by Goldberg et al., *Blood* 110(1):186-192 (2007), Thompson et al., *Clin. Cancer Res.* 13(6): 1757-1761 (2007), and Kerman et al., International Application No. PCT/JP2006/309606 (publication no. WO 2006/121168 A1), each of which are expressly incorporated by reference herein, include, pembrolizumab (Keytruda®), nivolumab (Opdivo®), Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG 404, AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuxumab (to CD40), Muromonab-CD3 (to CD3), Ipilumumab (to CTLA-4). Immune therapies also include genetically engineered T-cells (e.g., CAR-T cells) and bispecific antibodies (e.g., BiTEs).

GITR agonists include, but are not limited to, GITR fusion proteins and anti-GITR antibodies (e.g., bivalent anti-GITR antibodies), such as, a GITR fusion protein described in U.S. Pat. No. 6,111,090 box.c, European Patent No.: 090505B1, U.S. Pat. No. 8,586,023. PCT Publication Nos.: WO 2010/003118 and 2011/090754, or an anti-GITR antibody described, e.g., in U.S. Pat. No. 7,025,962, European Patent No.: 1947183B1, U.S. Pat. Nos. 7,812,135, 8,388,967, 8,591,886, European Patent No.: EP 1866339, PCT Publication No.: WO 2011/028683, PCT Publication No.: WO 2013/039954, PCT Publication No.: WO2005/007190, PCT Publication No.: WO 2007/133822, PCT Publication No.: WO2005/055808, PCT Publication No.: WO 99/40196, PCT Publication No.: WO 2001/03720, PCT Publication No.: WO99/20758, PCT Publication No.: WO2006/083289, PCT Publication No.: WO 2005/115451, U.S. Pat. No. 7,618,632, and PCT Publication No.: WO 2011/051726.

The compounds described herein can be used in combination with the agents disclosed herein or other suitable agents, depending on the condition being treated. Hence, in some embodiments the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some embodiments of the separate administration protocol, a compound of the disclosure and any of the agents described above are administered a few minutes apart, or a few hours apart, or a few day s apart.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

Method 8

Example 8-1: 6-Chloro-7-(2-fluoro-6-hydroxyphenyl)-1-(2-(2-propanyl)phenyl)-4-(4-(2-propenoyl)-1-piperazinyl)-2(1H)-quinazolinone

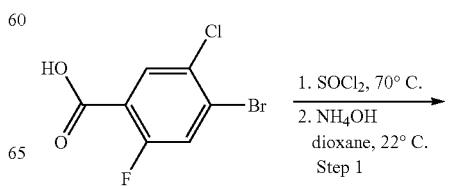

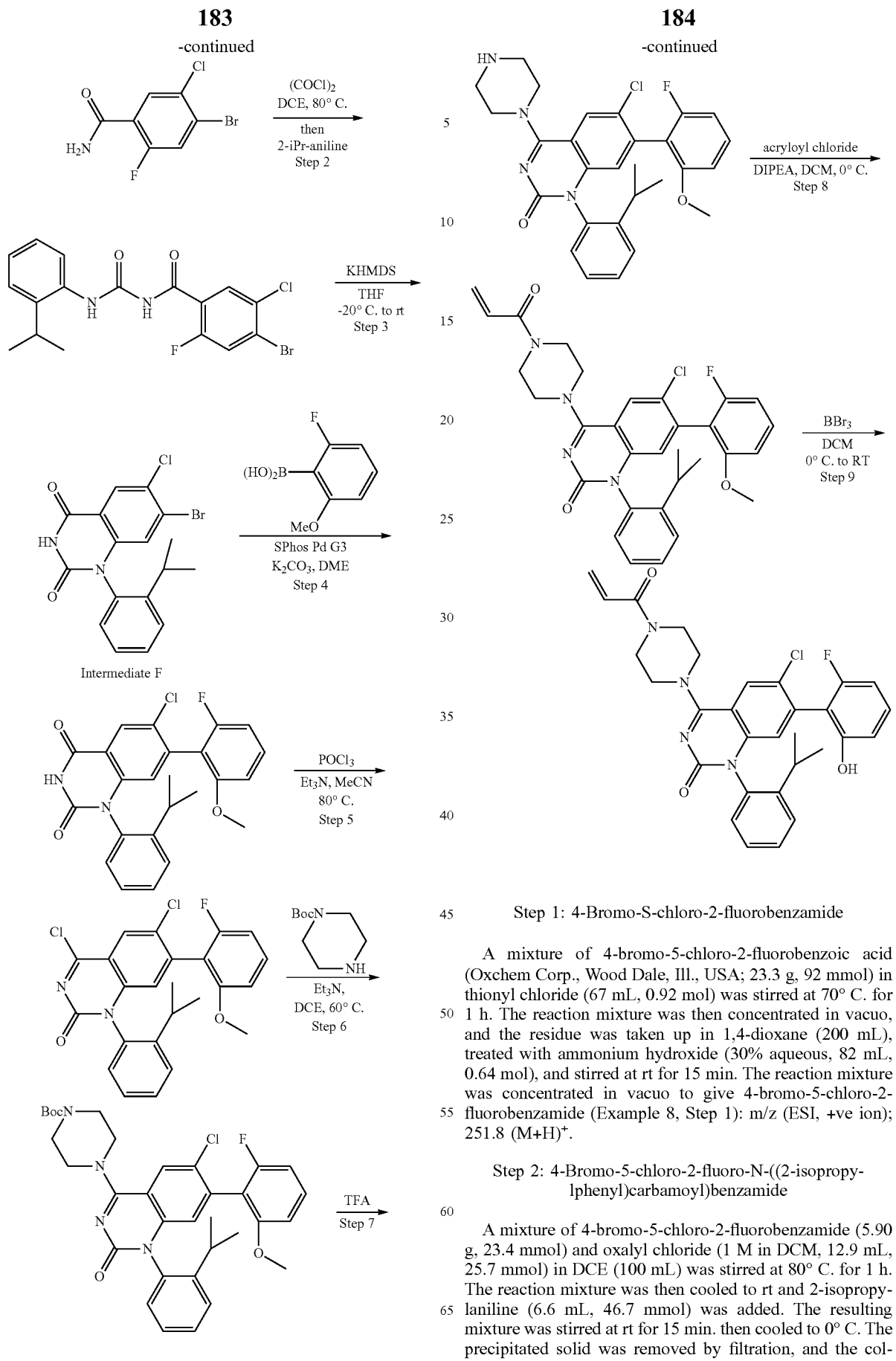

Step 1: 4-Bromo-5-chloro-2-fluorobenzamide

A mixture of 4-bromo-5-chloro-2-fluorobenzoic acid (Oxchem Corp., Wood Dale, Ill., USA; 23.3 g, 92 mmol) in thionyl chloride (67 mL, 0.92 mol) was stirred at 70° C. for 1 h. The reaction mixture was then concentrated in vacuo, and the residue was taken up in 1,4-dioxane (200 mL), treated with ammonium hydroxide (30% aqueous, 82 mL, 0.64 mol), and stirred at rt for 15 min. The reaction mixture was concentrated in vacuo to give 4-bromo-5-chloro-2-fluorobenzamide (Example 8, Step 1): m/z (ESI, +ve ion); 251.8 (M+H)$^+$.

Step 2: 4-Bromo-5-chloro-2-fluoro-N-((2-isopropylphenyl)carbamoyl)benzamide

A mixture of 4-bromo-5-chloro-2-fluorobenzamide (5.90 g, 23.4 mmol) and oxalyl chloride (1 M in DCM, 12.9 mL, 25.7 mmol) in DCE (100 mL) was stirred at 80° C. for 1 h. The reaction mixture was then cooled to rt and 2-isopropylaniline (6.6 mL, 46.7 mmol) was added. The resulting mixture was stirred at rt for 15 min. then cooled to 0° C. The precipitated solid was removed by filtration, and the collected filtrate was concentrated in vacuo to give 4-bromo-5-chloro-2-fluoro-N-((2-isopropylphenyl)carbamoyl)benzamide; $^1$H NMR (400 MHz, DMSO-$d_6$) δ 11.06 (br. s., 1H) 10.31 (s, 1H) 7.97-8.05 (m, 2H) 7.82 (d, J=7.2 Hz, 1H) 7.32-7.38 (m, 1H) 7.14-7.25 (m, 2H) 3.11 (spt, J=6.8 Hz, 1H) 1.24 (d, J=6.8 Hz, 6H). $^{19}$F NMR (376 MHz, DMSO-$d_6$) δ −113.6 (s, 1F) m/z (ESI, +ve ion): 412.7 and 414.6 (M+H)$^+$.

Step 3: 7-Bromo-6-chloro-1-(2-isopropylphenyl)quinazoline-2,4(1H,3H)-dione (Intermediate F)

1 M KHMDS in THF (8.3 mL, 8.3 mmol) was added to a mixture of 4-bromo-5-chloro-2-fluoro-N-((2-isopropylphenyl)carbamoyl)benzamide (1.56 g, 3.77 mmol) in THF (19 mL) at −20° C., and the resulting mixture was allowed to warm to rt over 1 h. The reaction mixture was then diluted with EtOAc (150 mL) and washed with saturated aqueous ammonium chloride (2×100 mL). The organic layer was dried over $Na_2SO_4$, filtered, and concentrated in vacuo. The residue was suspended in DCM (5 mL), sonicated, collected by filtration, and dried in vacuo to give 7-bromo-6-chloro-1-(2-isopropylphenyl)quinazoline-2,4(1H,3H)-dione (Intermediate F): $^1$H NMR (400 MHz, $CDCl_2$) δ 9.43 (br. s., 1H) 8.29 (s, 1H) 7.55-7.59 (m, 2H) 7.39-7.44 (m, 1H) 7.16 (d, J=7.8 Hz, 1H) 6.75 (s, 1H) 2.59-2.77 (m, 1H) 1.17-1.24 (m, 3H) 1.11 (d, J=6.8 Hz, 3H). m/z (ESI, +ve ion): 392.9 and 395.0 (M+H)$^+$.

Step 4: 6-Chloro-7-(2-fluoro-6-methoxyphenyl)-1-(2-isopropylphenyl)quinazoline-2,4(1H,3H)-dione A mixture of 7-bromo-6-chloro-1-(2-isopropylphenyl)quinazoline-2,4(1H,3H)-dione (Intermediate F, 1.17 g, 2.96 mmol), (2-fluoro-6-methoxyphenyl)boronic acid (2.02 g, 11.9 mmol), SPhos Pd G3 (0.128 g, 0.148 mmol), and potassium carbonate (2 M in water, 4.45 mL, 8.90 mmol) in DME (30 mL) was stirred at 85° C. for 16 h. The reaction mixture was then diluted with EtOAc (150 mL) and washed with saturated aqueous $NaHCO_3$ (3×100 mL). The organic layer was dried over $Na_2SO_4$, filtered, and concentrated in vacuo. The crude product was purified by silica gel chromatography (eluent: 0-50% EtOAc/heptane) to provide 6-chloro-7-(2-fluoro-6-methoxyphenyl)-1-(2-isopropylphenyl)quinazoline-2,4(1H,3H)-dione: $^1$H NMR (400 MHz, DMSO-$d_6$) δ 11.90 (d, J=1.2 Hz, 1H) 8.11 (d, J=3.3 Hz, 1H) 7.53-7.59 (m, 1H) 7.48 (tt, J=7.0, 2.2 Hz, 1H) 7.38-7.44 (m, 1H) 7.32-7.37 (m, 2H) 6.93 (dd, J=8.4, 4.3 Hz, 1H) 6.86 (t, J=8.7 Hz, 1H) 6.15 (s, 1H) 3.66 (d, J=30 Hz, 3H) 2.73 (dq, J=14.2, 7.0 Hz, 1H) 1.11 (t, J=7.1 Hz, 3H) 1.03 (dd, J=12.7, 6.8 Hz, 3H). $^{19}$F NMR (376 MHz, DMSO-$d_6$) δ −113.8 (s, 1F) −115.2 (s, 1F), m/z (ESI, +ve ion): 439.1 (M+H)$^+$.

Step 5: 4,6-Dichloro-7-(2-fluoro-6-methoxyphenyl)-1-(2-isopropylphenyl)quinazolin-2(1H)-one To a solution of 6-chloro-7-(2-fluoro-6-methoxyphenyl)-1-(2-isopropylphenyl)quinazoline-2,4(1H,3H)-dione (0.395 g, 0.9 mmol) and $Et_3N$ (0.75 mL, 5.4 mmol) in acetonitrile (9 mL) was added phosphorus oxy chloride (0.5 mL, 5.4 mmol), and the resulting solution was stirred at 80° C. for 1.5 h. The reaction mixture was concentrated in vacuo to give 4,6-dichloro-7-(2-fluoro-6-methoxyphenyl)-1-(2-isopropylphenyl)quinazolin-2(1H)-one: m/z (ESI, +ve) 457.1 (M+H)$^+$.

Alternative procedure for Step 5 (used as noted in the table below): To a stirred mixture of the product from Step 4 (1.0 equiv), triethylamine (18.0 equiv), and 1H-benzo[d][1,2,3]triazole (12 equiv.) in acetonitrile (0.07 M) was added phosphorus oxychloride (6.0 equiv.), and the resulting reaction mixture was stirred at 80° C. for 3.5 h. The reaction mixture was then poured slowly into rapidly stirred water (100 mL) at 10° C. The aqueous suspension was stirred for 15 min before extraction with EtOAc (100 mL). The organic layer was washed with brine (100 mL), dried over $MgSO_4$, filtered, and concentrated in vacuo to give a benzotriazole adduct intermediate that was used directly in Step 6.

Step 6: tert-Butyl 4-(6-chloro-7-(2-fluoro-6-methoxyphenyl)-1-(2-isopropylphenyl)-2-oxo-1,2-dihydroquinazolin-4-yl)piperazine-1-carboxylate A solution of 4,6-dichloro-7-(2-fluoro-6-methoxyphenyl)-1-(2-isopropylphenyl)quinazolin-2(1H)-one (obtained from Method 8, Step 5), tert-butyl piperazine-1-carboxylate (0.335 g, 1.80 mmol), and $Et_3N$ (0.75 mL, 5.4 mmol) in DCE (9 mL) was stirred at 60° C. for 20 min. The reaction mixture was diluted with EtOAc (100 mL) and washed with saturated aqueous $NaHCO_3$ (3×75 mL). The organic layer was dried over $Na_2SO_4$ and concentrated in vacuo. The crude product was purified by silica gel chromatography (eluent: 0-60% EtOAc-EtOH (3:1)/heptane) to provide tert-butyl 4-(6-chloro-7-(2-fluoro-6-methoxyphenyl)-1-(2-isopropylphenyl)-2-oxo-1,2-dihydroquinazolin-4-ylpiperazine-1-carboxylate, m/z (ESI, +ve ion): 607.3 (M+H)$^+$.

Note: When (S)-1-(3-methylpiperazin-1-yl)prop-2-en-1-one 2,2,2-trifluoroacetate (Example 8-1, Step 6b) was used, it was synthesized as follows:

(S)-1-(3-Methylpiperazin-1-ylprop-2-en-1-one 2,2,2-trifluoroacetate (Example 8-1, Step 6b)

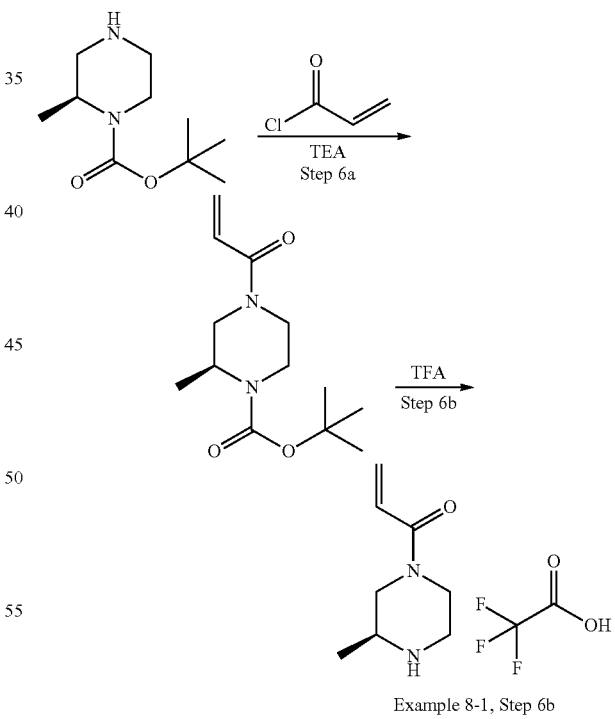

Example 8-1, Step 6b

Step 6a: (S)-tert-Butyl 4-acryloyl-2-methylpiperazine-1-carboxylate

Acryloyl chloride (1.3 mL, 16.5 mmol) was added to a solution of (S)-1-Boc-2-methyl-piperazine (3.00 g, 15.0 mmol, Boc Sciences, Shirley, N.Y.) in THF (30 mL) at −10°

C., and the resulting mixture was stirred at −10° C. for 5 min. Triethylamine (6.3 mL, 44.9 mmol) was then slowly added, and the resulting mixture was stirred at −10° C. for 15 min, then allowed to warm to rt. The reaction mixture was partitioned between EtOAc and saturated aqueous NaHCO$_3$. The aqueous layer was extracted with EtOAc, and tire organic layers were then combined, dried over MgSO$_4$, filtered, and concentrated in vacuo. The crude product was purified by silica gel chromatography (eluent: 0-100% EtOAc/heptane) to provide (S)-tert-butyl 4-acryloyl-2-methylpiperazine-1-carboxylate: $^1$H NMR (400 MHz, DMSO-d$_6$) δ 6.72-6.85 (m, 1H) 6.10-6.18 (m, 1H) 5.68-5.76 (m, 1H) 4.08-4.32 (m, 2H) 3.68-4.03 (m, 2H) 2.86-3.14 (m, 2H) 2.66-2.80 (m, 1H) 1.38-1.43 (s, 9H) 0.96-1.04 (m, 3H). m/z (ESI, +ve ion): 277.3 (M+Na)$^+$.

Step 6b: (S)-1-(3-Methylpiperazin-1-yl)prop-2-en-1-one 2,2,2-trifluoroacetate (Example 8-1, Step 6b)

A mixture of (S)-tert-butyl 4-acryloyl-2-methylpiperazine-1-carboxylate (3.21 g, 12.6 mmol) and TFA (4.7 mL, 63.1 mmol) in DCM (16 mL) was stirred at rt for 24 h. The reaction mixture was then concentrated in vacuo to give (S)-1-(3-methylpiperazin-1-yl)prop-2-en-1-one 2,2,2-trifluoroacetate (Example 8-1, Step 6b): $^1$H NMR (400 MHz, DMSO-d$_6$) δ 8.70-8.99 (m, 1H) 6.74-6.91 (m, 1H) 6.12-6.26 (m, 1H) 5.70-5.84 (m, 1H) 4.25-4.44 (m, 1H) 4.07-4.25 (m, 1H) 3.49-3.53 (m, 1H) 3.22-3.32 (m, 2H) 2.92-3.08 (m, 2H) 1.14-1.29 (m, 3H). m/z (ESI, +ve ion): 155.1 (M+H)$^+$.

Step 7: 6-Chloro-7-(2-fluoro-6-methoxyphenyl)-1-(2-isopropylphenyl)-4-(piperazin-1-yl)quinazolin-2(1H)-one A solution of tert-butyl 4-(6-chloro-7-(2-fluoro-6-methoxyphenyl)-1-(2-isopropylphenyl)-2-oxo-1,2-dihydroquinazolin-4-yl)piperazine-1-carboxylate (0.594 g, 0.978 mmol) in TFA (4 mL) was stirred at rt for 30 min. The reaction mixture was concentrated in vacuo to give 6-chloro-7-(2-fluoro-6-methoxyphenyl)-1-(2-isopropylphenyl)-4-(piperazin-1-yl)quinazolin-2(1H)-one: m/z (ESI, +ve ion): 507.2 (M+H)$^+$.

Step 8: 4-(4-Acryloylpiperazin-1-yl)-6-chloro-7-(2-fluoro-6-methoxyphenyl)-1-(2-isopropylphenyl)quinazolin-2(1H)-one To an ice-cooled solution of 6-chloro-7-(2-fluoro-6-methoxyphenyl)-1-(2-isopropylphenyl)-4-(piperazin-1-yl)quinazolin-2(1H)-one and DIPEA (0.85 mL, 4.9 mmol) in DCM (10 mL) at 0° C. was added acryloyl chloride (0.079 mL, 0.98 mmol), and the resulting mixture was stirred at 0° C. for 30 min. The reaction mixture was then diluted with EtOAc (100 mL) and washed with saturated aqueous NaHCO$_3$ (3×75 mL). The organic layer was dried over Na$_2$SO$_4$, filtered, and concentrated in vacuo. The crude product was purified by silica gel chromatography (eluent: 0-100% EtOAc-EtOH (3:1)/heptane) to provide 4-(4-acryloylpiperazin-1-yl)-6-chloro-7-(2-fluoro-6-methoxyphenyl)-1-(2-isopropylphenyl)quinazolin-2(1H)-one: $^1$H NMR (400 MHz, CDCl$_3$) δ 7.86 (d, J=1.2 Hz, 1H) 7.41-7.54 (m, 2H) 7.29-7.37 (m, 2H) 7.14 (dt, J=7.8, 1.7 Hz, 1H) 6.70-6.79 (m, 2H) 6.58-6.68 (m, 1H) 6.50 (d, J=7.4 Hz, 1H) 6.39 (dd, J=16.8, 1.8 Hz, 1H) 5.75-5.84 (m, 1H) 3.79-4.06 (m, 8H) 3.75 (s, 2H) 3.66 (s, 1H) 2.69 (tt, J=13.4, 6.8 Hz, 1H) 1.20-1.24 (m, 3H) 1.07 (dd, J=6.8, 3.9 Hz, 3H). $^{19}$F NMR (377 MHz, CDCl$_3$) δ −113.05 (s, 1F) −113.55 (s, 1F). m/z (ESI, +ve ion): 561.2 (M+H)$^+$.

Step 9: 6-Chloro-7-(2-fluoro-6-hydroxyphenyl)-1-(2-(2-propanyl)phenyl)-4-(4-(2-propenoyl)-1-piperazinyl)-2(1H)-quinazolinone BBr$_3$ (1 M in DCE, 3.3 mL, 3.3 mmol) was added to an ice-cooled solution of 4-(4-acryloylpiperazin-1-yl)-6-chloro-7-(2-fluoro-6-methoxyphenyl)-1-(2-isopropylphenyl)quinazolin-2(1H)-one (0.372 g, 0.663 mmol) in DCE (1.7 mL), and the resulting mixture was stirred at 0° C. for 20 min, then allowed to warm to rt and stir for 2 h. Saturated aqueous NaHCO$_3$ was added to the reaction mixture, followed by EtOAc (150 mL). The organic layer was separated and washed with saturated aqueous NaHCO$_3$ (3×100 mL). The organic layer was then dried over Na$_2$SO$_4$, filtered, and concentrated in vacuo. The crude product was purified by silica gel chromatography (eluent: 0-100% EtOAc-EtOH (3:1)/heptane) to provide 6-chloro-7-(2-fluoro-6-hydroxyphenyl)-1-(2-(2-propanyl)phenyl)-4-(4-(2-propenoyl)-1-piperazinyl)-2(1H)-quinazolinone: $^1$H NMR (400 MHz, DMSO-d$_6$) δ 10.06 (br. d., J=15.1 Hz, 1H) 8.03 (d, J=1.2 Hz, 1H) 7.51-7.56 (m, 1H) 7.45 (t, J=7.6 Hz, 1H) 7.33 (tdd, J=7.5, 7.5, 3.8, 1.4 Hz, 1H) 7.14-7.25 (m, 2H) 6.84 (dd, J=16.8, 10.4 Hz, 1H) 6.62-6.74 (m, 2H) 6.14-6.26 (m, 2H) 5.71-5.78 (m, 1H) 3.71-3.99 (m, 8H) 2.52-2.59 (m, 1H) 1.02-1.12 (m, 6H). $^{19}$F NMR (377 MHz, DMSO-d$_6$) δ −113.6 (s, 1F) −114.8 (s, 1F). m/z (ESI, +ve ion): 547.1 (M+H)$^+$.

TABLE 8

Compound 8-8 was prepared following the procedure described in Method 8, Steps 1-9, above as follows:

| Ex. # | Chemical Structure | Name | Reagents |
|---|---|---|---|
| 8-8 | (structure shown) | 6-chloro-1-(2,6-dimethylphenyl)-7-(2-fluoro-6-hydroxyphenyl)-4-(4-(2-propenoyl)-1-piperazinyl)pyrido[2,3-d]pyrimidin-2(1H)-one | Step-2: 2,6-dimethylaniline (Sigma-Aldrich, St. Louis, MO), Step 4: (2-fluoro-6-methoxyphenyl)boronic acid (Sigma-Aldrich Corporation) |

Method 9

Example 9-1: 6-Chloro-7-(2,3-dichloro-5-hydroxyphenyl)-4-((2S)-2-methyl-4-(2-propenoyl)-1-piperazinyl)-1-(2-(2-propanyl)phenyl)-2(1H)-quinazolinone

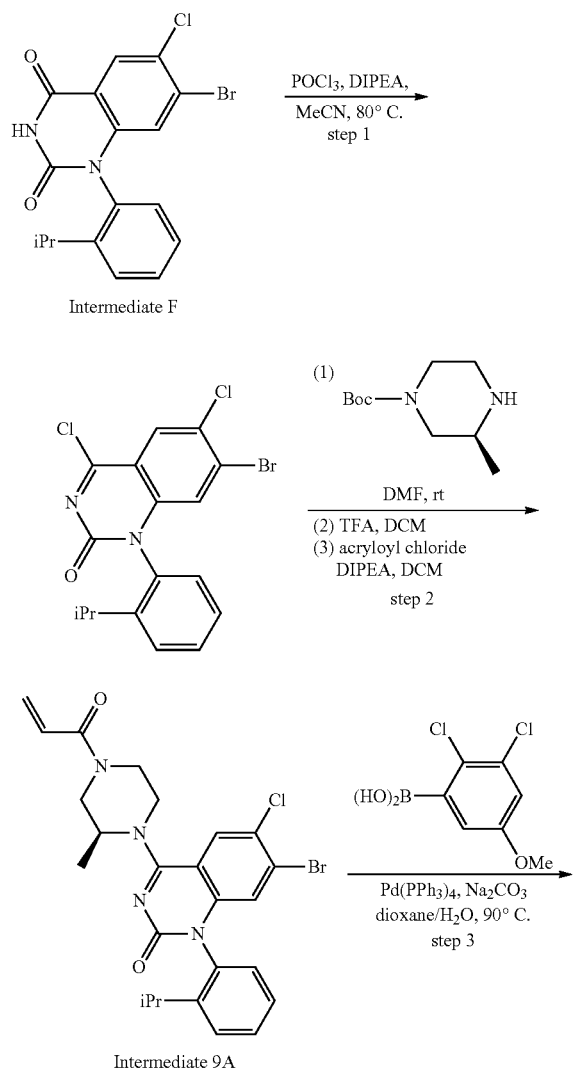

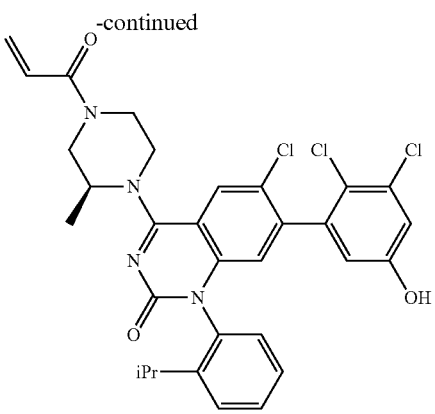

Step 1: 7-Bromo-4,6-dichloro-1-(2-isopropylphenyl)quinazolin-2(1H)-one

To a mixture of 7-bromo-6-chloro-1-(2-isopropylphenyl)quinazoline-2,4(1H,3H)-dione (Intermediate F, 470 mg, 1.19 mmol) and DIPEA (0.62 mL, 3.6 mmol) in acetonitrile (11.4 mL) was added phosphorus oxychloride (0.92 mL, 6.0 mmol). The resulting mixture was heated at 80° C. for 2 h, then cooled to rt and concentrated in vacuo to give 7-bromo-4,6-dichloro-1-(2-isopropylphenyl)quinazolin-2(1H)-one. m/z (ESI, +ve ion): 413.0 (M+H)$^+$.

Step 2: (S)-4-(4-Acryloyl-2-methylpiperazin-1-yl)-7-bromo-6-chloro-1-(2-isopropylphenyl)quinazolin-2(1H)-one (Intermediate 9A)

A mixture of 7-bromo-4,6-dichloro-1-(2-isopropylphenyl)quinazolin-2(1H)-one (492 mg, 1.19 mmol), (S)-4-N-Boc-2-methyl piperazine (478 mg, 2.39 mmol), and DIPEA (0.62 mL, 3.6 mmol) in DMF (2.3 mL) was stirred at rt for 10 min. Ice water (10 mL) was then added, and the mixture stirred for 15 min. The precipitated solid was collected by filtration, washed with water, and dried to give (S)-tert-butyl 4-(7-bromo-6-chloro-1-(2-isopropylphenyl)-2-oxo-1,2-dihydroquinazolin-4-yl)-3-methylpiperazine-1-carboxylate (Example 9, Step 2). m/z (ESI, +ve ion): 577.1 (M+H)$^+$.

TFA (2.0 mL, 26.8 mmol) was added to a solution of (S)-tert-butyl 4-(7-bromo-6-chloro-1-(2-isopropylphenyl)-2-oxo-1,2-dihydroquinazolin-4-yl)-3-methylpiperazine-1-carboxylate (297 mg, 0.516 mmol) in DCM (2 mL), and the mixture was stirred at rt for 15 min. Concentration of the resulting mixture in vacuo provided (S)-7-bromo-6-chloro-1-(2-isopropylphenyl)-4-(2-methylpiperazin-1-yl)quinazolin-2(1H)-one. m/z (ESI, +ve ion): 477.0 (M+H)$^+$.

Acryloyl chloride (0.258 M in DCM, 4.0 mL, 1.03 mmol) was added to an ice-cooled mixture of (S)-7-bromo-6-chloro-1-(2-isopropylphenyl)-4-(2-methylpiperazin-1-yl)quinazolin-2(1H)-one and DIPEA (0.27 mL, 1.5 mmol) in DCM (2.0 mL), and the resulting mixture was stirred at 0° C. for 20 min. Saturated aqueous NaHCO$_3$ was added to the reaction mixture, followed by EtOAc (50 mL). The organic layer was separated and washed with saturated aqueous NaHCO$_3$ (3×130 mL). The organic layer was then dried over Na$_2$SO$_4$, filtered, and concentrated in vacuo. The crude product was purified by silica gel chromatography (eluent: 0-100% EtOAc-EtOH (3:1)/heptane) to provide (S)-4-(4-acryloyl-2-methylpiperazin-1-yl)-7-bromo-6-chloro-1-(2-isopropylphenyl)quinazolin-2(1H)-one (Intermediate 9A):

¹H NMR (400 MHz, DMSO-d₆) δ 7.91-8.08 (m, 1H), 7.49-7.67 (m, 2H), 7.41 (br d, J=5.8 Hz, 1H), 7.21 (br s, 1H), 6.76-6.98 (m, 1H), 6.52-6.67 (m, 1H), 6.09-6.29 (m, 1H), 5.75 (br s, 1H), 4.61-4.96 (m, 1H), 4.23-4.48 (m, 1H), 3.93-4.21 (m, 2H), 3.50-3.77 (m, 1H), 3.33-3.49 (m, 1H), 3.23-3.28 (m, 1H), 2.94-3.24 (m, 1H), 1.27 (br d, J=9.3 Hz, 6H), 1.09 (br s, 3H). m/z (ESI, +ve ion): 531.1 (M+H)⁺.

Step 3: (S)-4-(4-Acryloyl-2-methylpiperazin-1-yl)-6-chloro-7-(2,3-dichloro-5-methoxyphenyl)-1-(2-isopropylphenyl)quinazolin-2(1H)-one A mixture of (S)-4-(4-acryloyl-2-methylpiperazin-1-yl)-7-bromo-6-chloro-1-(2-isopropylphenyl)quinazolin-2(1H)-one (Intermediate 9A, 120 mg, 0.226 mmol), 2-(2,3-dichloro-5-methoxyphenyl)-4,4,5,5-tetramethyl-1,3,2-dioxaborolane (82 mg, 0.27 mmol), Na₂CO₃ (96 mg, 0.91 mmol), and Pd(PPh₃)₄ (26 mg, 0.023 mmol) in 1,4-dioxane (1.6 mL) and water (0.4 mL) was heated at 90° C. for 17 h. The reaction mixture was then concentrated in vacuo and purified by silica gel chromatography (eluent: 0-100% EtOAc-EtOH (3:1)/heptane) to provide (S)-4-(4-acryloyl-2-methylpiperazin-1-yl)-6-chloro-7-(2,3-dichloro-5-methoxyphenyl)-1-(2-isopropylphenyl)quinazolin-2(1H)-one. m/z (ESI, +ve ion): 627.0 (M+H)⁺.

Step 4: 6-Chloro-7-(2,3-dichloro-5-hydroxyphenyl)-4-((2S)-2-methyl-4-(2-propenoyl)-1-piperazinyl)-1-(2-(2-propanyl)phenyl)-2(1H)-quinazolinone BBr₃ (1 M in hexanes, 0.32 mL, 0.32 mmol) was added to an ice-cooled mixture of (S)-4-(4-acryloyl-2-methylpiperazin-1-yl)-6-chloro-7-(2,3-dichloro-5-methoxyphenyl)-1-(2-isopropylphenyl)quinazolin-2(1H)-one (40 mg, 0.064 mmol) and DCE (1.0 mL), and the mixture was stirred at 0° C. for 30 min. Saturated aqueous NaHCO₃ (2.0 mL) was added, and the mixture was extracted with DCM-MeOH (2:1, 5 mL). The organic extract was dried over Na₂SO₄, filtered, and concentrated in vacuo. The crude product was purified by silica gel chromatography (eluent: 0-10% MeOH/DCM) to provide 6-chloro-7-(2,3-dichloro-5-hydroxyphenyl)-4-((2S)-2-methyl-4-(2-propenoyl)-1-piperazinyl)-1-(2-(2-propanyl)phenyl)-2(1H)-quinazolinone: ¹H NMR (400 MHz, DMSO-d₆) δ 10.42 (br d, J=17.0 Hz, 1H), 7.86-8.11 (m, 1H), 7.50-7.63 (m, 1H), 7.47 (br t, J=6.0 Hz, 1H), 7.36 (t, J=7.5 Hz, 1H), 7.15-7.26 (m, 1H), 7.05 (d, J=2.3 Hz, 1H), 6.78-6.96 (m, 1H), 6.44-6.58 (m, 1H), 6.11-6.29 (m, 2H), 5.71-5.82 (m, 1H), 4.68-4.98 (m, 1H), 3.96-4.52 (m, 3H), 3.52-3.85 (m, 2H), 3.34-3.51 (m, 1H), 2.95-3.26 (m, 1H), 1.27-1.41 (m, 3H), 0.95-1.13 (m, 6H). m/z (ESI, +ve ion): 611.0 (M+H)⁺.

TABLE 9

Compound 9-17 was prepared following the procedure described in Method 9, Steps 1-4, above as follows:

| Ex.# | Chemical Structure | Name | Method changes |
|---|---|---|---|
| 9-17 | (structure shown) | 4-((2S)-4-acetyl-2-methyl-1-piperazinyl)-7-bromo-6-chloro-1-(2-(2-propanyl)phenyl)-2(1H)-quinazolinone | Omit Step 3 and Step 4 |

Method 54

Example 54-1: 6-Chloro-7-(2-fluoro-6-hydroxyphenyl)-4-((2S)-2-methyl-4-(2-propenoyl)-1-piperazinyl)-1-(2-(methylsulfonyl)phenyl)pyrido[2,3-d]pyrimidin-2(1H)-one

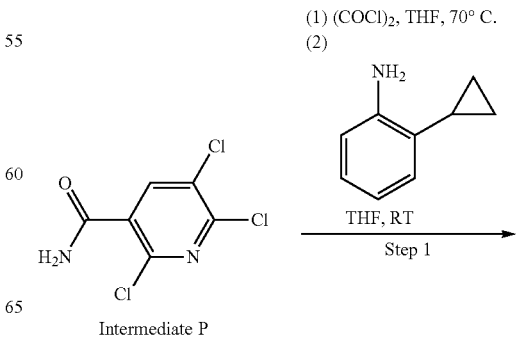

Intermediate P

-continued

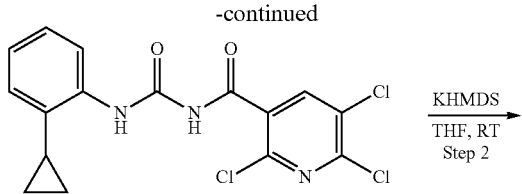

KHMDS
THF, RT
Step 2

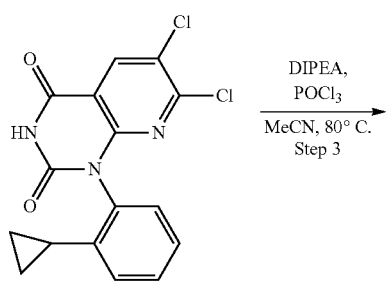

DIPEA,
POCl₃
MeCN, 80° C.
Step 3

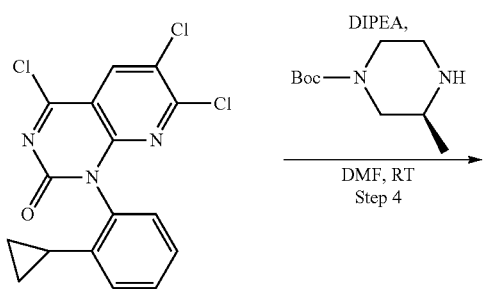

DIPEA,

Boc—N⌐⌐NH

DMF, RT
Step 4

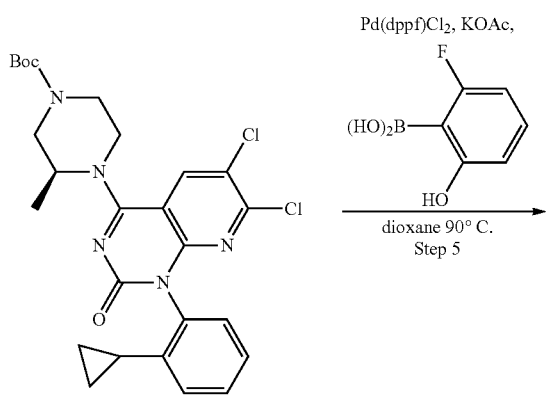

Pd(dppf)Cl₂, KOAc, (HO)₂B—⌐F⌐
        HO dioxane 90° C.
Step 5

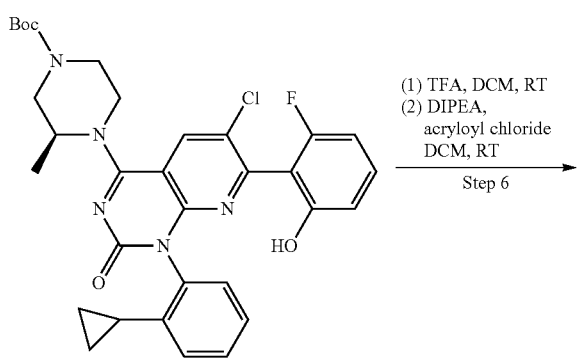

(1) TFA, DCM, RT
(2) DIPEA,
acryloyl chloride
DCM, RT
Step 6

-continued

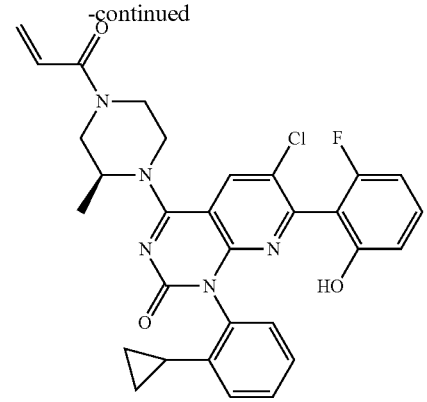

Step 1: 2,5,6-Trichloro-N-((2-cyclopropylphenyl)carbamoyl)nicotinamide

To a solution of 2,5,6-trichloronicotinamide (Intermediate P, 1.0 g, 4.5 mmol) in THF (200 mL) was added oxalyl chloride (2 M in DCM, 2.5 mL, 5.0 mmol). The mixture was stirred at 70° C. for 30 min and then allowed to cool to rt. 2-Cyclopropylaniline (0.6 mL, 4.6 mmol, ChemBridge Corporation, San Diego, Calif., USA) was added and the solution was stirred for 10 min at rt. The reaction was concentrated in vacuo and the residue was suspended in MeOH and filtered to provide 2,5,6-trichloro-N-((2-cyclopropylphenyl)carbamoyl)nicotinamide. m/z (ESI, +ve ion): 406.0 (M+Na)⁺.

Step 2: 6,7-Dichloro-1-(2-cyclopropylphenyl)pyrido[2,3-d]pyrimidine-2,4(1H,3H)-dione To an ice-cooled solution of 2,5,6-trichloro-N-((2-cyclopropylphenyl)carbamoyl)nicotinamide (1.4 g, 3.6 mmol) in THF (20 mL) was added 1 M KHMDS in THF (7.6 mL, 7.6 mmol). The mixture was warmed to rt and stirred for 5 min. then quenched with saturated aqueous ammonium chloride and extracted with EtOAc (2×50 mL). The combined organic extracts were washed with water (60 mL), dried by elution through a Chem Elut extraction cartridge (Agilent Technologies, Santa Clara, Calif., USA) and concentrated in vacuo. The residue was suspended in MeOH and filtered to provide 6,7-dichloro-1-(2-cyclopropylphenyl)pyrido[2,3-d]pyrimidine-2,4(1H,3H)-dione. This material was used without further purification in the following step. m/z (ESI, +ve ion): 348.0 (M+H)⁺.

Step 3: 4,6,7-Trichloro-1-(2-cyclopropylphenyl)pyrido[2,3-d]pyrimidin-2(1H)-one To a solution of 6,7-dichloro-1-(2-cyclopropylphenyl)pyrido[2,3-d]pyrimidine-2,4(1H,3H)-dione (1.0 g, 2.9 mmol) in acetonitrile (20 mL) was added DIPEA (1.5 mL, 8.6 mmol) followed by phosphorus oxychloride (0.54 mL, 5.7 mmol). The resulting mixture was heated to 80° C. for 25 min and then concentrated in vacuo. The residue was used without further purification in the following step.

Step 4: (S)-tert-Butyl 4-(6,7-dichloro-1-(2-cyclopropylphenyl)-2-oxo-1,2-dihydropyrido[2,3-d]pyrimidin-4-yl)-3-methylpiperazine-1-carboxylate (S)-4-N-Boc-2-methyl piperazine (0.60 g, 3.0 mmol, Sigma-Aldrich, St. Louis, Mo., USA) was added to a solution of 4,6,7-trichloro-1-(2-cyclopropylphenyl)pyrido[2,3-d]pyrimidin-2(1H)-one (1.05 g, 2.9 mmol) and DIPEA (2.5 mL, 14.3 mmol) in DMF (15 mL). The mixture was stirred at rt for 5 min, then ice-water (100 mL) was added and the mixture was stirred for an additional 15 min until a solid precipitate had formed. The reaction was filtered, and the filtered solids were dissolved in EtOAc, dried by elution through a Chem Elut extraction cartridge (Agilent Technologies, Santa Clara, Calif., USA) and concentrated. The crude product was purified by silica gel chromatography (eluent: 40-100% EtOAc/heptane) to provide (S)-tert-butyl 4-(6,7-dichloro-1-(2-cyclopropylphenyl)-2-oxo-1,2-dihydropyrido[2,3-d]pyrimidin-4-yl)-3-methylpiperazine-1-carboxylate. m/z (ESI, +ve ion): 530.2 (M+H)+.

Step 5: (3S)-tert-Butyl 4-(6-chloro-1-(2-cyclopropylphenyl)-7-(2-fluoro-6-hydroxyphenyl)-2-oxo-1,2-dihydropyrido[2,3-d]pyrimidin-4-yl)-3-methylpiperazine-1-carboxylate A mixture of (S)-tert-butyl-4-(6,7-dichloro-1-(2-cyclopropylphenyl)-2-oxo-1,2-dihydropyrido[2,3-d]pyrimidin-4-yl)-3-methylpiperazine-1-carboxylate (0.98 g, 1.9 mmol), 1,1'-bis(diphenylphosphino)ferrocene dichloropalladium (II), complex with DCM (0.14 g, 0.19 mmol), potassium acetate (0.93 g, 9.5 mmol) and (2-fluoro-6-hydroxyphenyl) boronic acid (0.39 g, 2.5 mmol, Combi-Blocks, San Diego, Calif., USA) in 1,4-dioxane (20 mL) and water (0.1 mL) were degassed with argon for 5 min. The resulting mixture was stirred at 90° C. for 90 min, then partitioned between water (40) mL) and EtOAc (2×40 mL). The combined organic layers were washed with water (40 mL), dried by elution through a Chem Elut extraction cartridge (Agilent Technologies, Santa Clara, Calif., USA) and concentrated. The crude product was purified by silica gel chromatography (eluent: 50-100% EtOAc/heptane) to provide (3S)-tert-butyl-4-(6-chloro-1-(2-cyclopropylphenyl)-7-(2-fluoro-6-hydroxyphenyl)-2-oxo-1,2-dihydropyrido[2,3-d]pyrimidin-4-yl)-3-methylpiperazine-1-carboxylate. m/z (ESI, +ve ion): 606.2 (M+H)+.

Step 6: 6-Chloro-7-(2-fluoro-1-hydroxyphenyl)-4-((2S)-2-methyl-4-(2-propenoyl)-1-piperazinyl)-1-(2-(methylsulfonyl)phenyl)pyrido[2,3-d]pyrimidin-2(1H)-one TFA (5.0 mL, 65 mmol) was added to a solution of (3S)-tert-butyl 4-(6-chloro-1-(2-cyclopropylphenyl)-7-(2-fluoro-6-hydroxyphenyl)-2-oxo-1,2-dihydropyrido[2,3-d]pyrimidin-4-yl)-3-methylpiperazine-1-carboxylate (0.80 g, 1.3 mmol) in DCM (10 mL). The resulting mixture was stirred for 1 h at rt and then concentrated in vacuo. The residue was suspended in DCM (10 mL), cooled to 0° C., and treated with DIPEA (1.2 mL, 6.6 mmol) followed by acryloyl chloride (0.26 M solution in DCM, 4.1 mL, 1.1 mmol). The reaction was warmed to rt and stirred for 10 min, then more acryloyl chloride (0.26 M solution in DCM, 1.0 mL, 0.26 mmol) was added. After stirring for an additional 10 min at rt, the reaction was concentrated in vacuo. The crude product was purified by silica gel chromatography (eluent 40-100% EtOAc/heptane) and the purified product was suspended in MeOH and filtered to afford 6-chloro-7-(2-fluoro-6-hydroxyphenyl)-4-((2S)-2-methyl-4-(2-propenoyl)-1-piperazinyl)-1-(2-(methylsulfonyl)phenyl)pyrido[2,3-d]pyrimidin-2(1H)-one: $^1$H NMR (400 MHz, DMSO-d$_6$) δ ppm 10.07 (s, 1H), 8.29-8.42 (m, 1H), 7.19-7.29 (m, 3H), 7.14 (br d, J=16.2 Hz, 1H), 7.06 (br d, J=5.4 Hz, 1H), 6.79-6.93 (m, 1H), 6.61-6.74 (m, 2H), 6.20 (br d, J=16.2 Hz, 1H), 5.71-5.80 (m, 1H), 4.73-5.04 (m, 1H), 3.96-4.49 (m, 3H), 3.42-3.91 (m, 2H), 3.20-3.27 (m, 1H), 1.41-1.63 (m, 1H), 1.28-1.40 (m, 3H), 0.47-0.67 (m, 3H), 0.41 (br s, 1H). $^{19}$F NMR (376 MHz, DMSO-d$_6$) δ −115.37 (s, 1F). m/z (ESI, +ve ion): 560.2 (M+H)+.

TABLE 54

Compounds 54-2 to 54-115 were prepared following the procedure described in Method 54, Steps 1-6, above as follows:

| Ex.# | Chemical Structure | Name | Method Changes | Reagent |
| --- | --- | --- | --- | --- |
| 54-2 | | 6-chloro-7-(2-fluorophenyl)-4-((2S)-2-methyl-4-(2-propenoyl)-1-piperazinyl)-1-(3-pentanyl)pyrido[2,3-d]pyrimidin-2(1H)-one | Step 1: 1-ethylpropyl-amine (Alfa Aesar, Avocado, Lancaster), Step 5: 2-fluorophenyl-boronic acid (Combi-Blocks Inc.) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-3 | 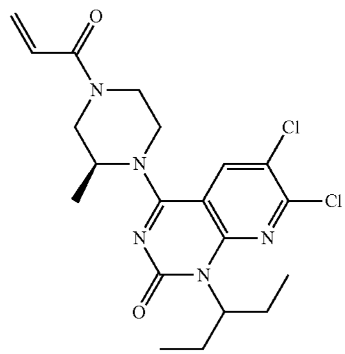 [SMILES: C=CC(=O)N1CCN(c2nc(=O)n(C(CC)CC)c3nc(Cl)c(Cl)cc23)[C@@H](C)C1] | 6,7-dichloro-4-((2S)-2-methyl-4-(2-propenoyl)-1-piperazinyl)-1-(3-pentanyl)pyrido[2,3-d]pyrimidin-2(1H)-one | Omit Step 5 | Step 1: 1-ethylpropyl-amine (Alfa Aesar, Avocado, Lancaster) |
| 54-4 | 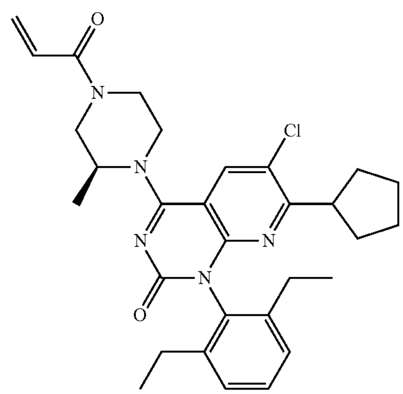 [SMILES: C=CC(=O)N1CCN(c2nc(=O)n(-c3c(CC)cccc3CC)c3nc(C4CCCC4)c(Cl)cc23)[C@@H](C)C1] | 6-chloro-7-cyclopentyl-1-(2,6-diethylphenyl)-4-((2S)-2-methyl-4-(2-propenoyl)-1-piperazinyl)pyrido[2,3-d]pyrimidin-2(1H)-one | | Step 1: 2,6-diethylaniline (Sigma-Aldrich Corporation), Step 5: cyclopentylzinc bromide and tetrakis(triphenylphosphine)palladium (o) |
| 54-5 | 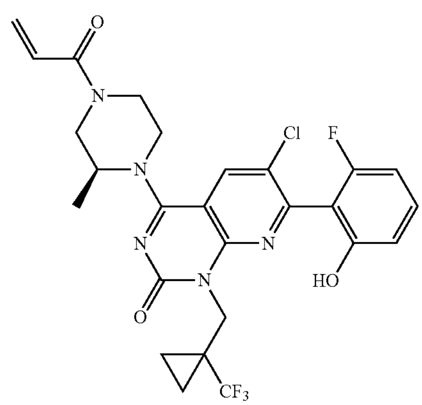 [SMILES: C=CC(=O)N1CCN(c2nc(=O)n(CC3(C(F)(F)F)CC3)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-((1-(trifluoromethyl)cyclopropyl)methyl)pyrido[2,3-d]pyrimidin-2(1H)-one | | Step 1: (1-(trifluoromethyl)cyclopropyl)methanamine (Sigma-Aldrich Corporation), Step 5: (2-fluoro-6-hydroxyphenyl)boronic acid (Wuxi) |
| 54-6 | 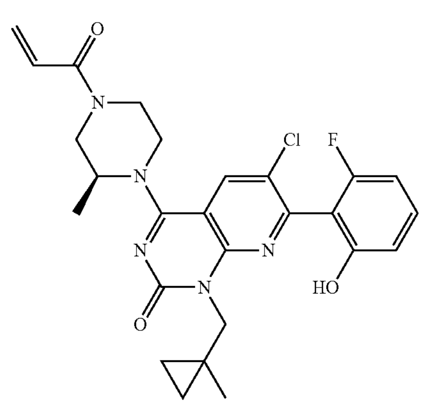 [SMILES: C=CC(=O)N1CCN(c2nc(=O)n(CC3(C)CC3)c3nc(-c4c(O)cccc4F)c(Cl)cc23)[C@@H](C)C1] | 6-chloro-7-(2-fluoro-6-hydroxyphenyl)-1-((1-methylcyclopropyl)methyl)-4-((2S)-2-methyl-4-(2-propenoyl)-1-piperazinyl)pyrido[2,3-d]pyrimidin-2(1H)-one | | Step 1: (1-methylcyclopropyl)methanamine hydrochloride (Princeton BioMolecular Research, Inc.), Step 5: (2-fluoro-6-hydroxyphenyl)boronic acid (Wuxi) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-7 | 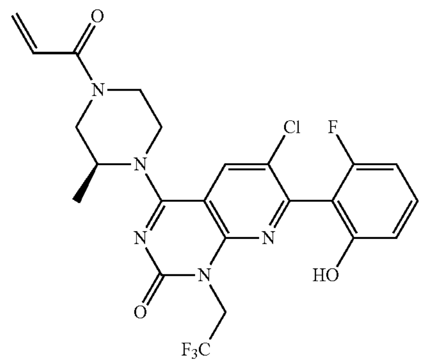 [SMILES: C=CC(=O)N1CCN(c2nc(=O)n(CC(F)(F)F)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(2,2,2-trifluoroethyl) pyrido[2,3-d]pyrimidin-2(1H)-one | | Step 1: 2,2,2-trifluoroethan-1-amine (Sigma-Aldrich Corporation), Step 5: (2-fluoro-6-hydroxyphenyl) boronic acid (Wuxi) |
| 54-8 | 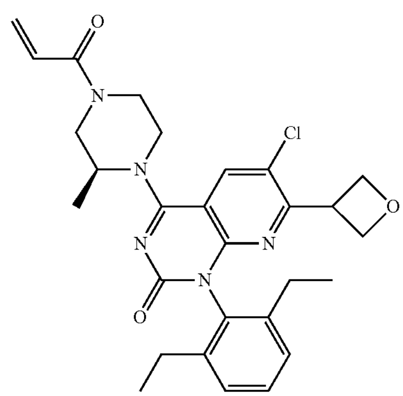 [SMILES: C=CC(=O)N1CCN(c2nc(=O)n(-c3c(CC)cccc3CC)c3nc(C4COC4)c(Cl)cc23)[C@@H](C)C1] | 6-chloro-1-(2,6-diethylphenyl)-4-((2S)-2-methyl-4-(2-propenoyl)-1-piperazinyl)-7-(3-oxetanyl) pyrido[2,3-d]pyrimidin-2(1H)-one | | Step 1: 2,6-diethylanaline (Sigma-Aldrich Corporation), Step 5: 4,4,5,5-tetramethyl-2-(oxetan-3-yl)-1,3,2-dioxaborolane (AstaTech, Inc.) |
| 54-9 | 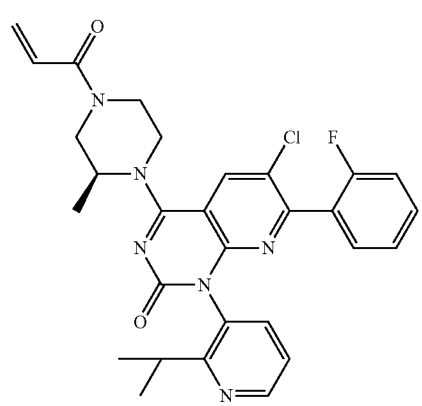 [SMILES: C=CC(=O)N1CCN(c2nc(=O)n(-c3cccnc3C(C)C)c3nc(-c4ccccc4F)c(Cl)cc23)[C@@H](C)C1] | 6-chloro-7-(2-fluorophenyl)-4-((2S)-2-methyl-4-(2-propenoyl)-1-piperazinyl)-1-(2-(2-propanyl)-3-pyridinyl) pyrido[2,3-d]pyrimidin-2(1H)-one | | Step 1: 2-isopropyl-pyridin-3-amine (HDH pharma), Step 5: 2-fluorophenyl-boronic acid (Combi-Blocks Inc.) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-10 | 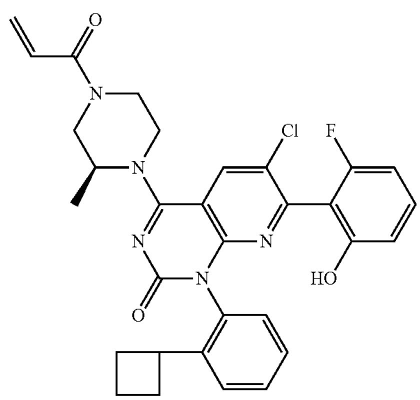 [SMILES: C=CC(=O)N1CCN(c2nc(=O)n(-c3ccccc3C3CCC3)c3nc(-c4c(O)cccc4F)c(Cl)cc23)[C@@H](C)C1] | 6-chloro-1-(2-cyclobutylphenyl)-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 2-cyclobutyl-aniline (HDH Pharma), Step 5: (2-fluoro-6-hydroxyphenyl) boronic acid (Wuxi) |
| 54-11 | 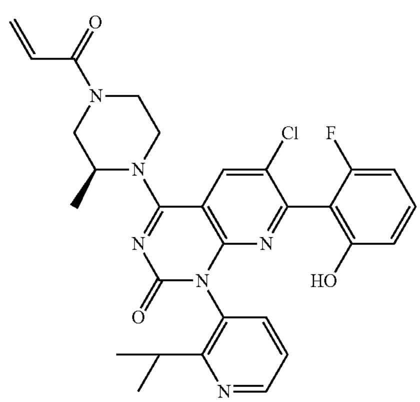 [SMILES: C=CC(=O)N1CCN(c2nc(=O)n(-c3cccnc3C(C)C)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(2-(2-propanyl)-3-pyridinyl)pyrido[2,3-d]pyrimidin-2(1H)-one | | Step 1: 2-isopropyl-pyridin-3-amine (HDH pharma), Step 5: (2-fluoro-6-hydroxyphenyl) boronic acid (Wuxi) |
| 54-12 | 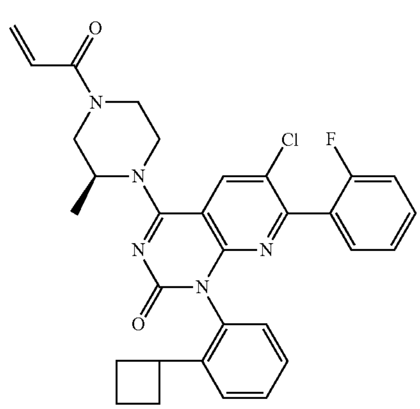 [SMILES: C=CC(=O)N1CCN(c2nc(=O)n(-c3ccccc3C3CCC3)c3nc(-c4ccccc4F)c(Cl)cc23)[C@@H](C)C1] | 6-chloro-1-(2-cyclobutyl-phenyl)-7-(2-fluorophenyl)-4-((2S)-2-methyl-4-(2-propenoyl)-1-piperazinyl)pyrido[2,3-d]pyrimidin-2(1H)-one | | Step 1: 2-cyclobutyl-aniline (HDH Pharma), Step 5: 2-fluorophenyl-boronic acid (Combi-Blocks Inc.) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-13 | 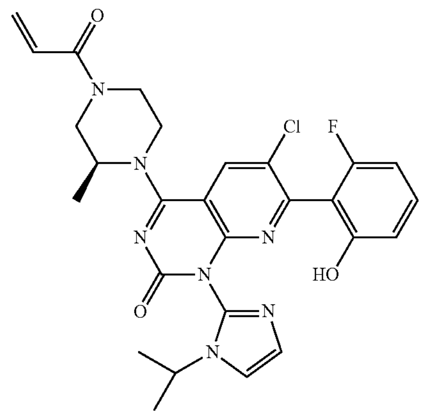 [SMILES: C=CC(=O)N1CCN(c2nc(=O)n(-c3nccn3C(C)C)c3nc(-c4c(O)cccc4F)c(Cl)cc23)[C@@H](C)C1] | 6-chloro-7-(2-fluoro-6-hydroxy-phenyl)-4-((2S)-2-methyl-4-(2-propenoyl)-1-piperazinyl)-1-(1-(2-propanyl)-1H-imidazol-2-yl)pyrido[2,3-d]pyrimidin-2(1H)-one | | Step 1: 1-(1-methylethyl)-1H-imidazol-2-amine (Oakwood Products., Inc.), Step 5: (2-fluoro-6-hydroxyphenyl) boronic acid (Wuxi) |
| 54-14 | 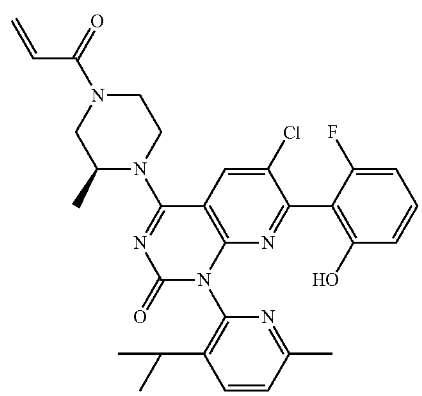 [SMILES: C=CC(=O)N1CCN(c2nc(=O)n(-c3nc(C)ccc3C(C)C)c3nc(-c4c(O)cccc4F)c(Cl)cc23)[C@@H](C)C1] | 6-chloro-7-(2-fluoro-6-hydroxyphenyl)-1-(6-methyl-3-(2-propanyl)-2-pyridinyl)-4-((2S)-2-methyl-4-(2-propenoyl)-1-piperazinyl) pyrido[2,3-d]pyrimidin-2(1H)-one | | Step 1: 3-isopropyl-6-methylpyridin-2-amine (Intermediate I-17), Step 5: (2-fluoro-6-hydroxyphenyl) boronic acid (Wuxi) |
| 54-15 | 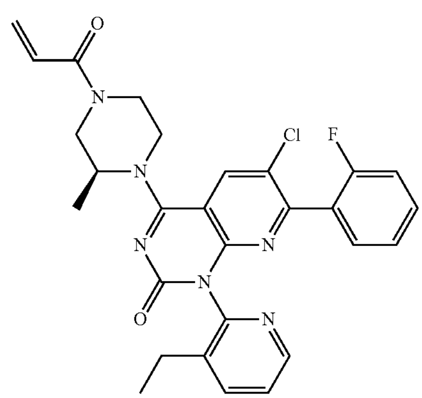 [SMILES: C=CC(=O)N1CCN(c2nc(=O)n(-c3ncccc3CC)c3nc(-c4ccccc4F)c(Cl)cc23)[C@@H](C)C1] | 6-chloro-1-(3-ethyl-2-pyridinyl)-7-(2-fluorophenyl)-4-((2S)-2-methyl-4-(2-propenoyl)-1-piperazinyl) pyrido[2,3-d]pyrimidin-2(1H)-one | | Step 1: 3-ethylpyridin-2-amine (Enamine. Monmouth Junction, NJ, USA), Step 5: 2-fluorophenyl-boronic acid (Combi-Blocks Inc.) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-16 | 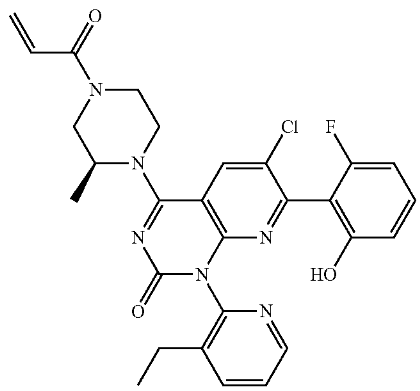 [SMILES: C=CC(=O)N1CCN(c2nc(=O)n(-c3ncccc3CC)c3nc(-c4c(O)cccc4F)c(Cl)cc23)[C@@H](C)C1] | 6-chloro-1-(3-ethyl-2-pyridinyl)-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 3-ethylpyridin-2-amine (Enamine. Monmouth Junction, NJ, USA), Step 5: (2-fluoro-6-hydroxyphenyl) boronic acid (Wuxi) |
| 54-17 | 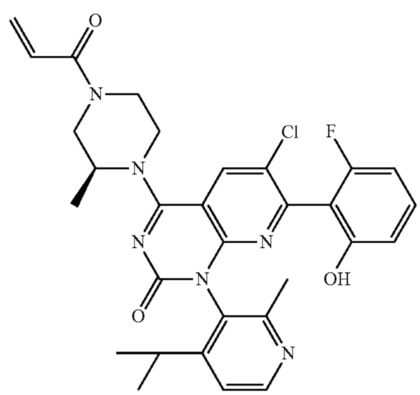 | 6-chloro-7-(2-fluoro-6-hydroxyphenyl)-1-(2-methyl-4-(2-propanyl)-3-pyridinyl)-4-((2S)-2-methyl-4-(2-propenoyl)-1-piperazinyl)pyrido[2,3-d]pyrimidin-2(1H)-one | | Step 4: 4-isopropyl-2-methylpyridin-3-amine (Intermediate I-16), Step 5: (2-fluoro-6-hydroxyphenyl) boronic acid (Wuxi) |
| 54-18 | 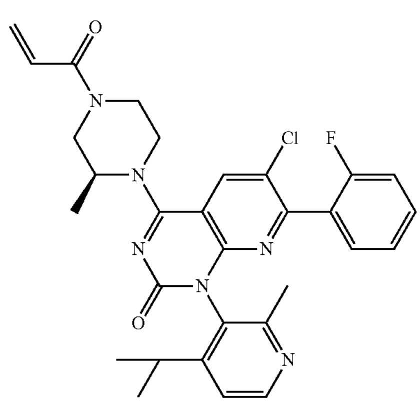 [SMILES: C=CC(=O)N1CCN(c2nc(=O)n(-c3c(C(C)C)ccnc3C)c3nc(-c4ccccc4F)c(Cl)cc23)[C@@H](C)C1] | 6-chloro-7-(2-fluorophenyl)-1-(2-methyl-4-(2-propanyl)-3-pyridinyl)-4-((2S)-2-methyl-4-(2-propenoyl)-1-piperazinyl)pyrido[2,3-d]pyrimidin-2(1H)-one | | Step 1: 4-isopropyl-2-methylpyridin-3-amine (Intermediate I-16), Step 5: 2-fluorophenyl-boronic acid (Combi-Blocks. San Diego, CA, USA) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-19 | 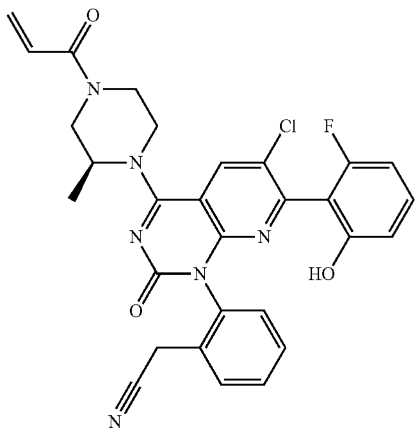 [SMILES: C=CC(=O)N1CCN(c2nc(=O)n(-c3ccccc3CC#N)c3nc(-c4c(O)cccc4F)c(Cl)cc23)[C@@H](C)C1] | (2-(6-chloro-7-(2-fluoro-6-hydroxyphenyl)-4-((2S)-2-methyl-4-(2-propenoyl)-1-piperazinyl)-2-oxopyrido[2,3-d]pyrimidin-1(2H)-yl)phenyl)acetonitrile | Step 4: THF, rt | Step 1: 2-Aminophenyl-acetonitrile (Combi-Blocks, San Diego, CA), Step 5: (2-fluoro-6-hydroxyphenyl)boronic acid (Wuxi) |
| 54-20 | 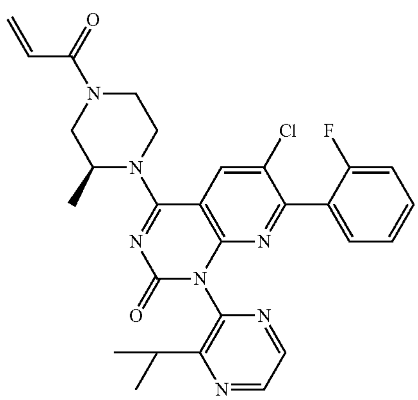 | (2-(6-chloro-7-(2-fluoro-6-hydroxyphenyl)-4-((2S)-2-methyl-4-(2-propenoyl)-1-piperazinyl)-2-oxopyrido[2,3-d]pyrimidin-1(2H)-yl)phenyl)acetonitrile | Step 3: Toluene, 50° C. Step 4: THF, rt | Step 1: 3-isopropyl-pyrazin-2-amine (Intermediate I-27), Step 5: 2-fluorophenyl-boronic acid (Combi-Blocks Inc.) |
| 54-21 | 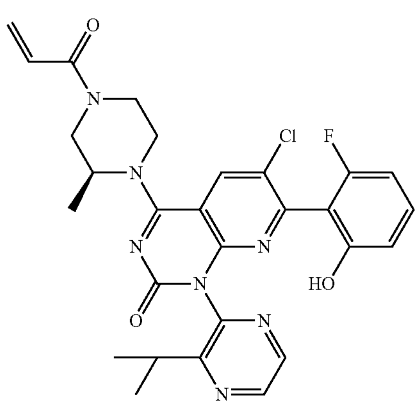 | 6-chloro-7-(2-fluoro-6-hydroxyphenyl)-4-((2S)-2-methyl-4-(2-propenoyl)-1-piperazinyl)-1-(3-(2-propanyl)-2-pyrazinyl)pyrido[2,3-d]pyrimidin-2(1H)-one | Step 3: Toluene, 50° C. Step 4: THF, rt | Step 1: 3-isopropyl-pyrazin-2-amine (Intermediate I-27), Step 5: (2-fluoro-6-hydroxyphenyl)boronic add (Wuxi) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-22 | 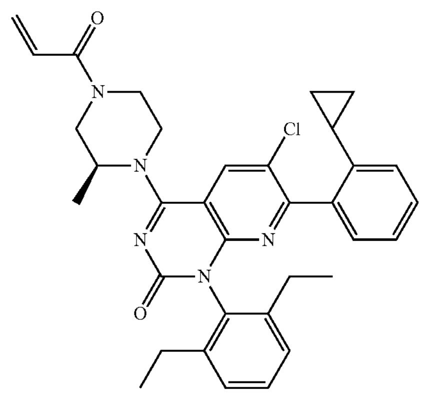 [SMILES: C=CC(=O)N1CCN(c2nc(=O)n(-c3c(CC)cccc3CC)c3nc(-c4ccccc4C4CC4)c(Cl)cc23)[C@@H](C)C1] | 6-chloro-7-(2-cyclopropyl-phenyl)-1-(2,6-diethyl-phenyl)-4-((2S)-2-methyl-4-(2-propenoyl)-1-piperazinyl)pyrido[2,3-d]pyrimidin-2(1H)-one | Step 5: SPhos Pd $G_3$, $K_2CO_3$, dioxane/water, 80° C. | Step 1: 2,6-diethylaniline (Sigma-Aldrich Corporation), Step 5: 2-cyclopropyl-phenylboronic acid (CombiPhos, Princeton, NJ, USA |
| 54-23 | 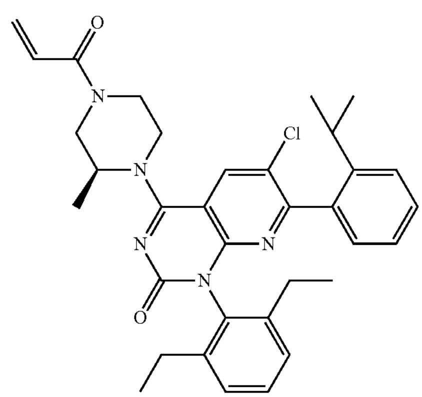 [SMILES: C=CC(=O)N1CCN(c2nc(=O)n(-c3c(CC)cccc3CC)c3nc(-c4ccccc4C(C)C)c(Cl)cc23)[C@@H](C)C1] | 6-chloro-1-(2,6-diethylphenyl)-4-((2S)-2-methyl-4-(2-propenoyl)-1-piperazinyl)-7-(2-(2-propanyl)phenyl)pyrido[2,3-d]pyrimidin-2(1H)-one | Step 5: Pd(PPh$_3$)$_4$, Na$_2$CO$_3$, dioxane/water, 80° C. | Step 1: 2,6-diethylaniline (Sigma-Aldrich Corporation), Step 5: 2-isopropylphenyl-boronic acid (Combi-Blocks, San Diego, CA, USA) |
| 54-24 | 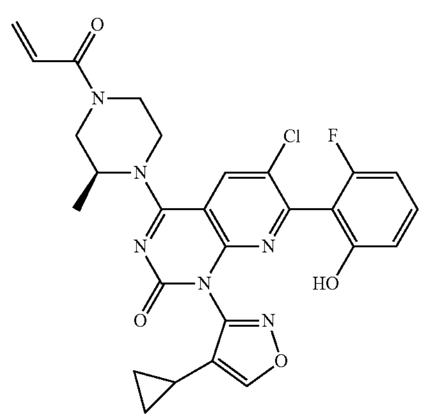 [SMILES: C=CC(=O)N1CCN(c2nc(=O)n(-c3nocc3C3CC3)c3nc(-c4c(O)cccc4F)c(Cl)cc23)[C@@H](C)C1] | 6-chloro-1-(4-cyclopropyl-1,2-oxazol-3-yl)-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 4-cyclopropyl-1,2-oxazol-3-amine (Enamine), Step 5: (2-fluoro-6-hydroxyphenyl)boronic acid (Wuxi) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-25 | 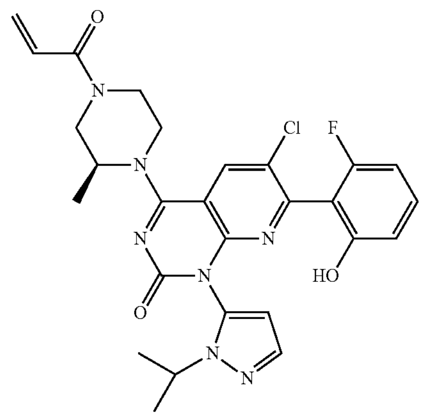 [SMILES: C=CC(=O)N1CCN(c2nc(=O)n(-c3ccnn3C(C)C)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(1-(2-propanyl)-1H-pyrazol-5-yl)pyrido[2,3-d]pyrimidin-2(1H)-one | | Step 1: 1-isopropyl-1H-pyrazol-5-amine (Enamine), Step 5: (2-fluoro-6-hydroxyphenyl)boronic acid (Wuxi) |
| 54-26 | 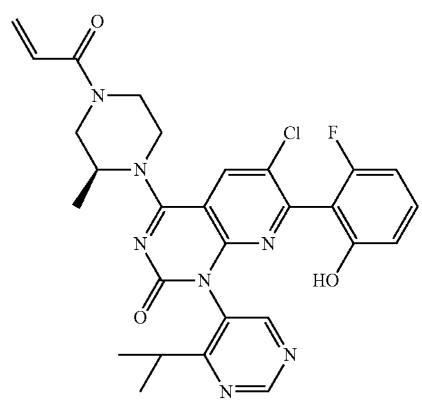 [SMILES: C=CC(=O)N1CCN(c2nc(=O)n(-c3cncnc3C(C)C)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(4-(2-propanyl)-5-pyrimidinyl)pyrido[2,3-d]pyrimidin-2(1H)-one | | Step 1: 4-isopropylpyrimidin-5-amine (ChemShuttle, Inc.), Step 5: (2-fluoro-6-hydroxyphenyl)boronic acid (Wuxi) |
| 54-27 | 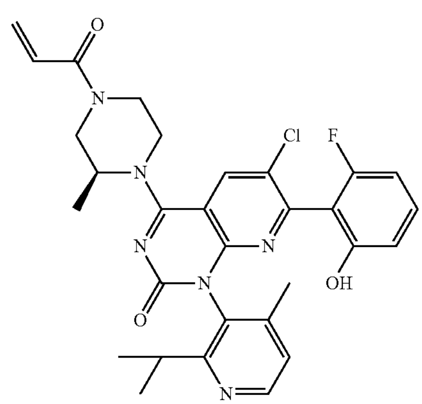 | 6-chloro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 1: 2-isopropyl-4-methylpyridin-3-amine (Intermediate R), Step 5: (2-fluoro-6-hydroxyphenyl)boronic acid (Wuxi) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-28 | 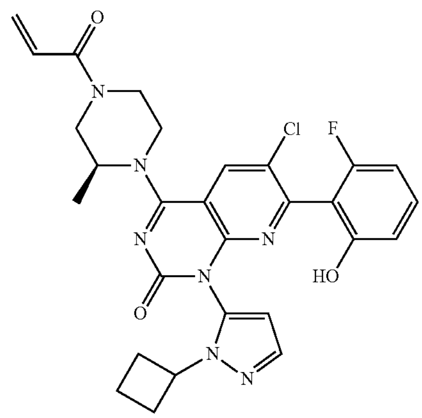 [SMILES: C=CC(=O)N1CCN(c2nc(=O)n(-c3ccnn3C3CCC3)c3nc(-c4c(O)cccc4F)c(Cl)cc23)[C@@H](C)C1] | 6-chloro-1-(1-cyclobutyl-1H-pyrazol-5-yl)-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 1-cyclobutyl-1H-pyrazol-5-amine (Oakwood Products, Inc.), Step 5: (2-fluoro-6-hydroxyphenyl)boronic acid (Wuxi) |
| 54-29 | 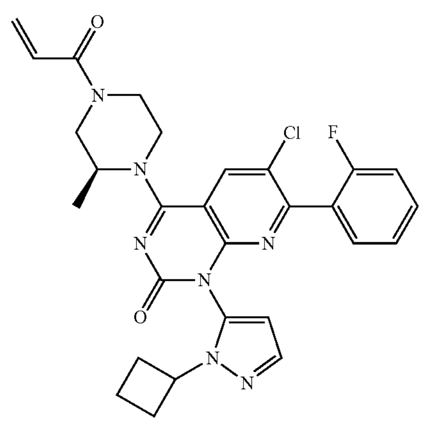 [SMILES: C=CC(=O)N1CCN(c2nc(=O)n(-c3ccnn3C3CCC3)c3nc(-c4ccccc4F)c(Cl)cc23)[C@@H](C)C1] | 6-chloro-1-(1-cyclobutyl-1H-pyrazol-5-yl)-7-(2-fluorophenyl)-4-((2S)-2-methyl-4-(2-propenoyl)-1-piperazinyl)pyrido[2,3-d]pyrimidin-2(1H)-one | | Step 1: 1-cyclobutyl-1H-pyrazol-5-amine (Oakwood Products, Inc.), Step 5: 2-fluorophenyl-boronic acid (Combi-Blocks Inc.) |
| 54-30 | 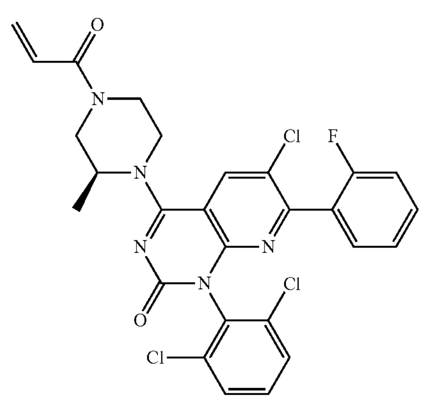 [SMILES: C=CC(=O)N1CCN(c2nc(=O)n(-c3c(Cl)cccc3Cl)c3nc(-c4ccccc4F)c(Cl)cc23)[C@@H](C)C1] | 6-chloro-1-(2,6-dichlorophenyl)-7-(2-fluorophenyl)-4-((2S)-2-methyl-4-(2-propenoyl)-1-piperazinyl)pyrido[2,3-d]pyrimidin-2(1H)-one | Step 5 using tetrakis and potassium carbonate at 80° C. | Step 1: 2,6-dichloroaniline (Sigma-Aldrich Corporation), Step 5: 2-fluorophenyl)boronic acid (Combi-Blocks) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-31 | 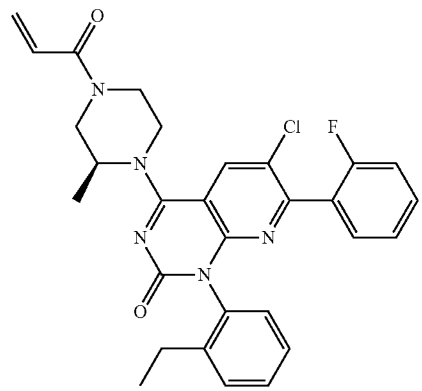 [SMILES: C=CC(=O)N1CCN(c2nc(=O)n(-c3ccccc3CC)c3nc(-c4ccccc4F)c(Cl)cc23)[C@@H](C)C1] | 6-chloro-1-(2-ethylphenyl)-7-(2-fluorophenyl)-4-((2S)-2-methyl-4-(2-propenoyl)-1-piperazinyl)pyrido[2,3-d]pyrimidin-2(1H)-one | Step 5 using tetrakis and potassium carbonate at 80° C. | Step 1: 1-amino-2-ethylbenzene (Sigma-Aldrich Corporation), Step fluorophenyl) boronic acid (Combi-Blocks) |
| 54-32 | 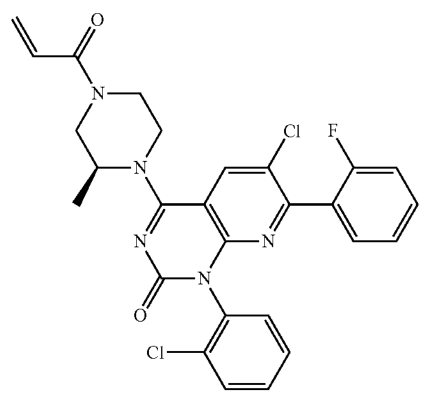 [SMILES: C=CC(=O)N1CCN(c2nc(=O)n(-c3ccccc3Cl)c3nc(-c4ccccc4F)c(Cl)cc23)[C@@H](C)C1] | 6-chloro-1-(2-chlorophenyl)-7-(2-fluorophenyl)-4-((2S)-2-methyl-4-(2-propenoyl)-1-piperazinyl)pyrido[2,3-d]pyrimidin-2(1H)-one | Step 5: using tetrakis and potassium carbonate | Step 1: 1-amino-2-chlorobenzene (Sigma-Aldrich Corporation), Step 5: 2-fluorophenyl) boronic acid (Combi-Blocks) |
| 54-33 | 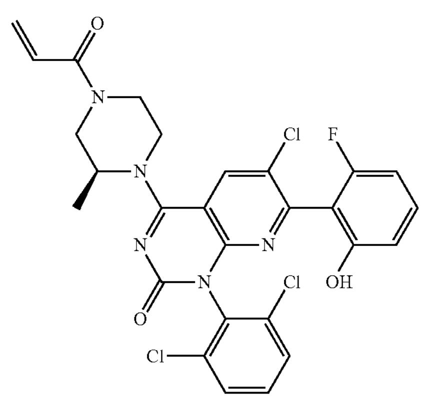 [SMILES: C=CC(=O)N1CCN(c2nc(=O)n(-c3c(Cl)cccc3Cl)c3nc(-c4c(O)cccc4F)c(Cl)cc23)[C@@H](C)C1] | 6-chloro-1-(2,6-dichlorophenyl)-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 2,6-dichloraniline (Sigma-Aldrich Corporation), Step 5: 2-fluoro-6-hydroxyphenyl boronic acid (Combi-Blocks Inc.) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-34 | 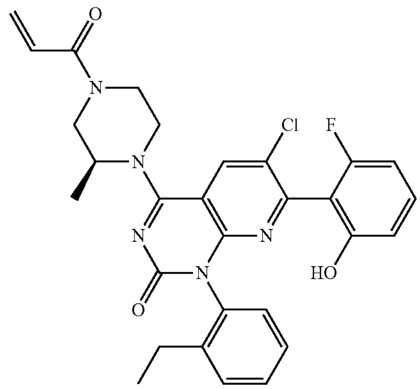 [SMILES: C=CC(=O)N1CCN(c2nc(=O)n(-c3ccccc3CC)c3nc(-c4c(O)cccc4F)c(Cl)cc23)[C@@H](C)C1] | 6-chloro-1-(2-ethylphenyl)-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 1-amino-2-ethylbenzene (Sigma-Aldrich Corporation), Step 5: 2-fluoro-6-hydroxyphenyl-boronic acid (Combi-Blocks Inc.) |
| 54-35 | 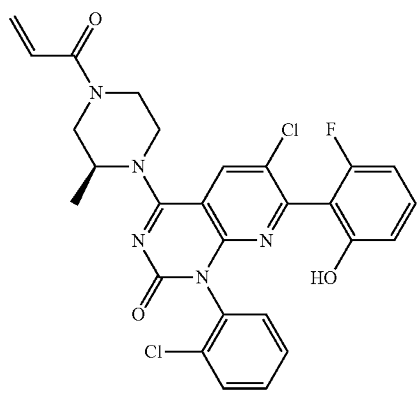 | 6-chloro-1-(2-chlorophenyl)-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 1-amino-2-chlorobenzene (Sigma-Aldrich Corporation), Step 5: 2-fluoro-6-hydroxyphenyl-boronic acid (Combi-Blocks Inc.) |
| 54-36 | 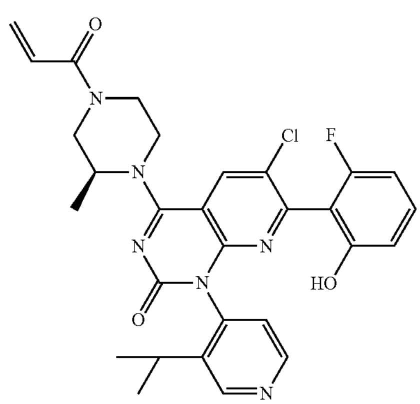 | 6-chloro-7-(2-fluoro-6-hydroxy-phenyl)-4-((2S)-2-methyl-4-(2-propenoyl)-1-piperazinyl)-1-(3-(2-propanyl)-4-pyridinyl)pyrido[2,3-d]pyrimidin-2(1H)-one | Step 3: performed in toluene at 50° C. | Step 1: 3-isopropyl-pyridin-4-amine (HDH Pharma) Step 5: (2-fluoro-6-hydroxyphenyl)boronic acid (Wuxi) |

TABLE 54-continued

Compounds 54-2 to 54-115 were prepared following the procedure described
in Method 54, Steps 1-6, above as follows:

| Ex.# | Chemical Structure | Name | Method Changes | Reagent |
|---|---|---|---|---|
| 54-37 | 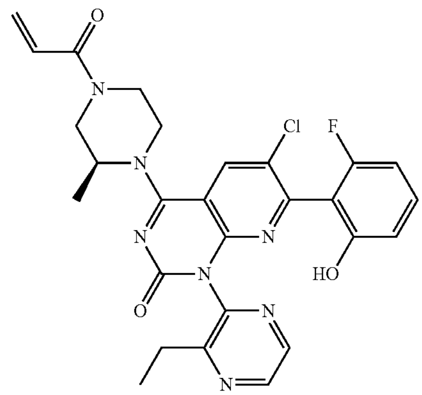 [SMILES: C=CC(=O)N1CCN(c2nc(=O)n(-c3nccnc3CC)c3nc(-c4c(O)cccc4F)c(Cl)cc23)[C@@H](C)C1] | 6-chloro-1-(3-ethyl-2-pyrazinyl)-7-(2-fluoro-6-hydroxy-phenyl)-4-((2S)-2-methyl-4-(2-propenoyl)-1-piperazinyl)pyrido[2,3-d]pyrimidin-2(1H)-one | Step 3: performed in toluene at 50° C. | Step 1: 3-ethylpyrazin-2-amine (Intermediate I-19), Step 5: (2-fluoro-6-hydroxyphenyl)boronic acid (Wuxi) |
| 54-38 | 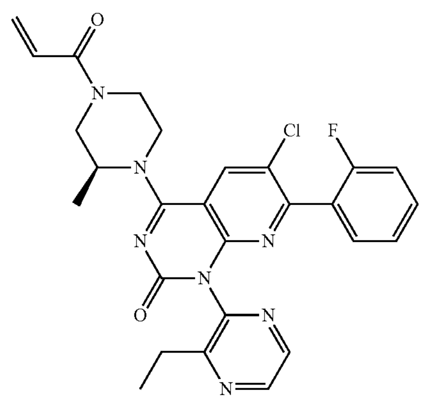 [SMILES: C=CC(=O)N1CCN(c2nc(=O)n(-c3nccnc3CC)c3nc(-c4ccccc4F)c(Cl)cc23)[C@@H](C)C1] | 6-chloro-1-(3-ethyl-2-pyrazinyl)-7-(2-fluorophenyl)-4-((2S)-2-methyl-4-(2-propenoyl)-1-piperazinyl)pyrido[2,3-d]pyrimidin-2(1H)-one | Step 3: performed in toluene at 50° C. | Step 1: 3-ethylpyrazin-2-amine (Intermediate I-19), Step 5: (2-fluorophenyl)boronic acid (Combi-Blocks Inc.) |
| 54-39 | 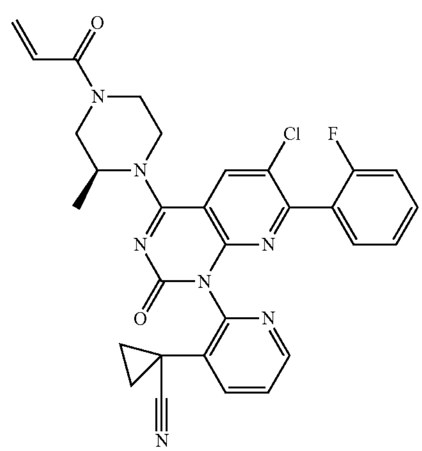 [SMILES: C=CC(=O)N1CCN(c2nc(=O)n(-c3ncccc3C3(C#N)CC3)c3nc(-c4ccccc4F)c(Cl)cc23)[C@@H](C)C1] | 1-(2-(6-chloro-7-(2-fluorophenyl)-4-((2S)-2-methyl-4-(2-propenoyl)-1-piperazinyl)-2-oxopyrido[2,3-d]pyrimidin-1(2H)-yl)-3-pyridinyl)cyclopropane carbonitrile | Step 2: performed with NaOt-Bu in THF Step 3: performed in toluene at 50° C. | Step 1: 1-(2-aminopyridin-3-yl)cyclopropane-1-carbonitrile (Intermediate I-20), Step 5: (2-fluorophenyl)boronic acid (Combi-Blocks Inc.) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-40 | 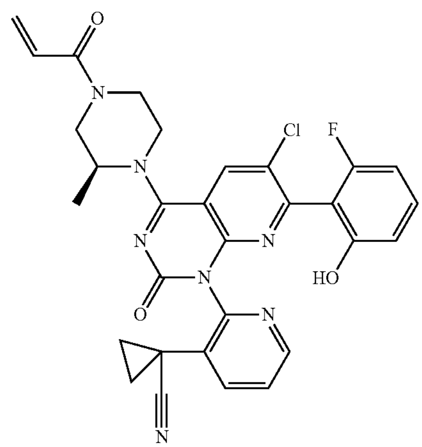 [SMILES: C=CC(=O)N1CCN(c2nc(=O)n(-c3ncccc3C3(C#N)CC3)c3nc(-c4c(O)cccc4F)c(Cl)cc23)[C@@H](C)C1] | 1-(2-(6-chloro-7-(2-fluoro-6-hydroxyphenyl)-4-((2S)-2-methyl-4-(2-propenoyl)-1-piperazinyl)-2-oxopyrido[2,3-d]pyrimidin-1(2H)-yl)-3-pyridinyl) cyclopropane carbonitrile | Step 2: performed with NaOt-Bu in THF Step 3: 81 performed in toluene at 50° C. | Step 1: 1-(2-aminopyridin-3-yl) cyclopropane-1-carbonitrile (Intermediate I-20), Step 5: (2-fluoro-6-hydroxyphenyl) boronic acid (Wuxi) |
| 54-41 | 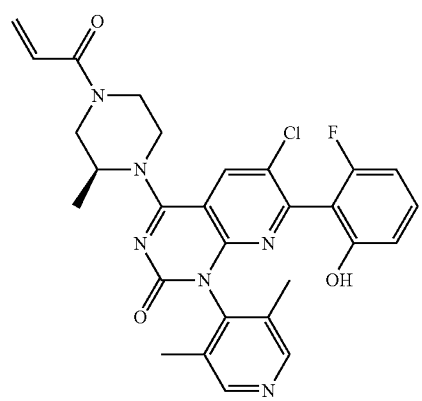 [SMILES: C=CC(=O)N1CCN(c2nc(=O)n(-c3c(C)cncc3C)c3nc(-c4c(O)cccc4F)c(Cl)cc23)[C@@H](C)C1] | 6-chloro-1-(3,5-dimethyl-4-pyridinyl)-7-(2-fluoro-6-hydroxyphenyl)-4-((2S)-2-methyl-4-(2-propenoyl)-1-piperazinyl) pyrido[2,3-d]pyrimidin-2(1H)-one | Step 2: at 0° C. | Step 1: 3,5-dimethylpyridin-4-amine (FSSI), Step 5: (2-fluoro-6-hydroxyphenyl) boronic acid (Wuxi) |
| 54-42 | 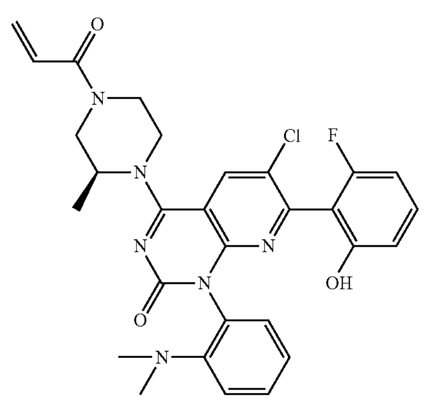 [SMILES: C=CC(=O)N1CCN(c2nc(=O)n(-c3ccccc3N(C)C)c3nc(-c4c(O)cccc4F)c(Cl)cc23)[C@@H](C)C1] | 6-chloro-1-(2-(dimethylamino) phenyl)-7-(2-fluoro-6-hydroxyphenyl)-4-((2S)-2-methyl-4-(2-propenoyl)-1-piperazinyl) pyrido[2,3-d]pyrimidin-2(1H)-one | Step 1: in DCE | Step 1: (2-aminophenyl) dimethylamine (Enamine), Step 5: (2-fluoro-6-hydroxyphenyl) boronic acid (Wuxi) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-43 | 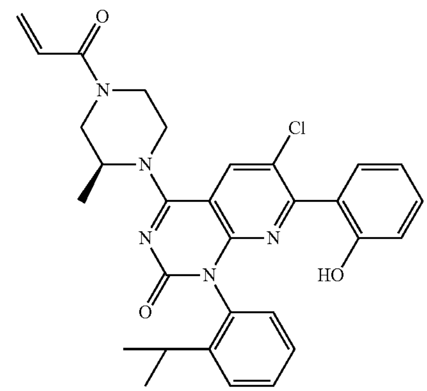 | 6-chloro-7-(2-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | | Step 1: 2-isopropylaniline (Sigma-Aldrich Corporation), Step 5: 2-hydroxybenzeneboronic acid (Frontier Scientific, Inc.) |
| 54-44 | 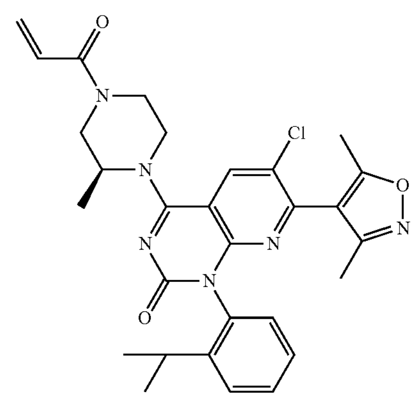 [SMILES: C=CC(=O)N1CCN(c2nc(=O)n(-c3ccccc3C(C)C)c3nc(-c4c(C)noc4C)c(Cl)cc23)[C@@H](C)C1] | 6-chloro-7-(3,5-dimethyl-1,2-oxazol-4-yl)-4-((2S)-2-methyl-4-(2-propenoyl)-1-piperazinyl)-1-(2-(2-propanyl)phenyl)pyrido[2,3-d]pyrimidin-2(1H)-one | | Step 1: 2-isopropylaniline (Sigma-Aldrich Corporation), Step 5; (3,5-dimethyl-isoxazol-4-yl)boronic acid (FSSI) |
| 54-45 | 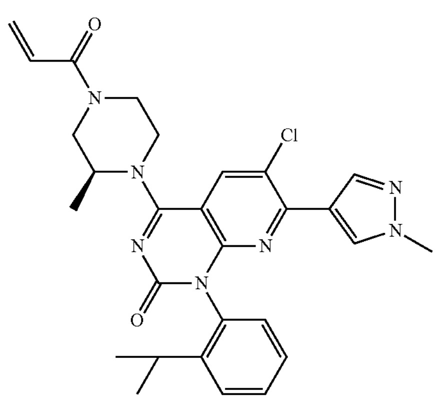 [SMILES: C=CC(=O)N1CCN(c2nc(=O)n(-c3ccccc3C(C)C)c3nc(-c4cnn(C)c4)c(Cl)cc23)[C@@H](C)C1] | 6-chloro-4-((2S)-2-methyl-4-(2-propenoyl)-1-piperazinyl)-7-(1-methyl-1H-pyrazol-4-yl)-1-(2-(2-propanyl)phenyl)pyrido[2,3-d]pyrimidin-2(1H)-one | | Step 1: 2-isopropylaniline (Sigma-Aldrich Corporation), Step 5: (1-methyl-1H-pyrazol-4-yl)boronic acid (FSSI) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-46 | 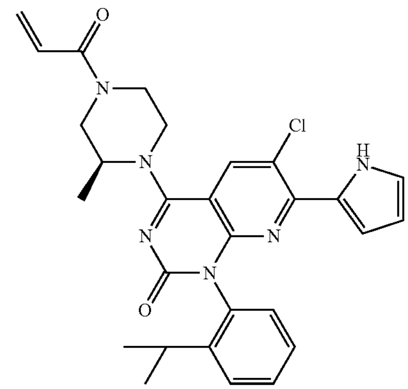 [SMILES: C=CC(=O)N1CCN(c2nc(=O)n(-c3ccccc3C(C)C)c3nc(-c4ccc[nH]4)c(Cl)cc23)[C@@H](C)C1] | 6-chloro-4-((2S)-2-methyl-4-(2-propenoyl)-1-piperazinyl)-1-(2-(2-propanyl)phenyl)-7-(1H-pyrrol-2-yl)pyrido[2,3-d]pyrimidin-2(1H)-one | | Step 1: 2-isopropylaniline (Sigma-Aldrich Corporation), Step 5: 1-N-Boc-pyrrole-2-boronic acid (Frontier Scientific, Inc.) |
| 54-47 | 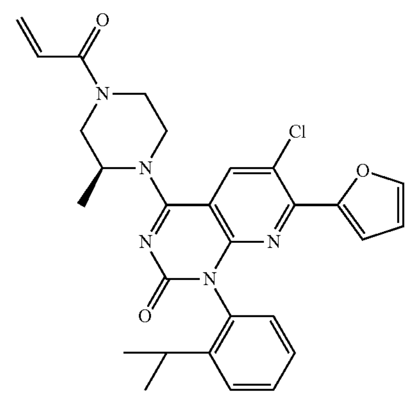 [SMILES: C=CC(=O)N1CCN(c2nc(=O)n(-c3ccccc3C(C)C)c3nc(-c4ccco4)c(Cl)cc23)[C@@H](C)C1] | 6-chloro-7-(2-furanyl)-4-((2S)-2-methyl-4-(2-propenoyl)-1-piperazinyl)-1-(2-(2-propanyl)phenyl)pyrido[2,3-d]pyrimidin-2(1H)-one | | Step 1: 2-isopropylaniline (Sigma-Aldrich Corporation), Step 5: (5-furanyl)boronic acid (Combi-Blocks Inc.) |
| 54-48 | 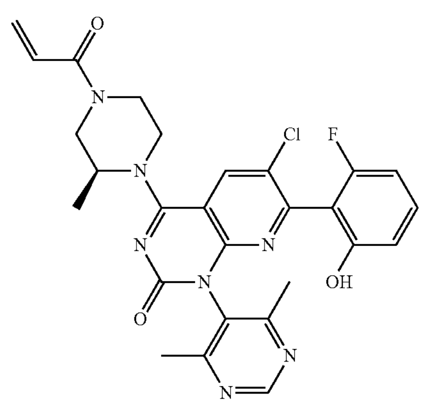 [SMILES: C=CC(=O)N1CCN(c2nc(=O)n(-c3c(C)ncnc3C)c3nc(-c4c(O)cccc4F)c(Cl)cc23)[C@@H](C)C1] | 6-chloro-1-(4,6-dimethyl-5-pyrimidinyl)-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 4,6-dimethyl-5-pyridinamine (Ark Pharm), Step 5: (2-fluoro-6-hydroxyphenyl)boronic acid (Wuxi) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-49 | 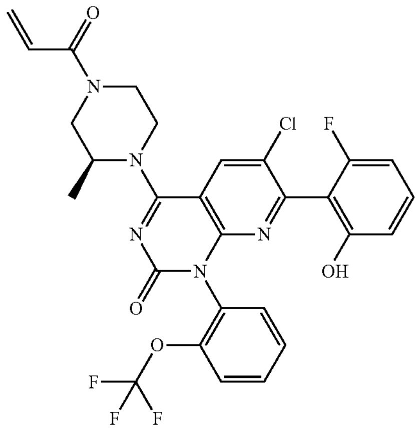 [SMILES: C=CC(=O)N1CCN(c2nc(=O)n(-c3ccccc3OC(F)(F)F)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(2-(trifluoromethoxy)phenyl)pyrido[2,3-d]pyrimidin-2(1H)-one | | Step 1: 2-trifluoromethoxy)aniline (Apollo), Step 5: (2-fluoro-6-hydroxyphenyl)boronic add (Wuxi) |
| 54-50 | 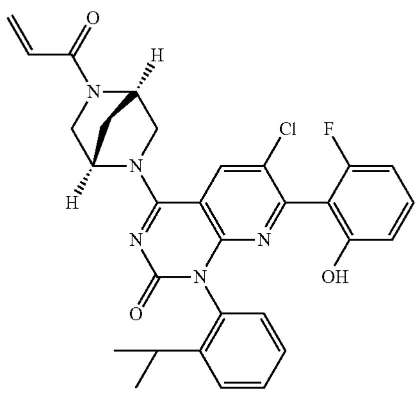 | 4-((1S,4S)-5-acryloyl-2,5-diazabicyclo[2.2.1]heptan-2-yl)-6-chloro-7-(2-fluoro-6-hydroxyphenyl)-1-(2-isopropylphenyl)pyrido[2,3-d]pyrimidin-2(1H)-one | | Step 1: 2-isopropylaniline (Sigma-Aldrich Corporation), Step 4: (1S, 4S) 2-Boc-2,5-diazobicyclo[2.2.1]heptane (Sigma-Aldrich Corporation), Step 5: (2-fluoro-6-hydroxyphenyl)boronic acid (Wuxi) |
| 54-51 | 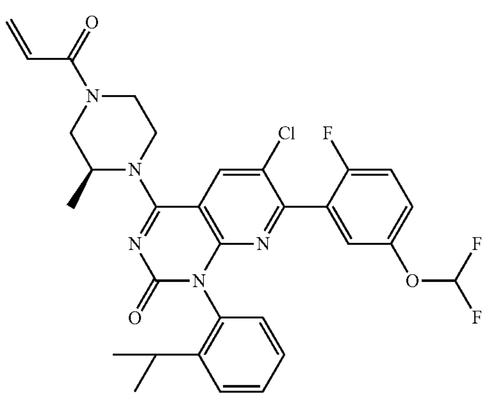 [SMILES: C=CC(=O)N1CCN(c2nc(=O)n(-c3ccccc3C(C)C)c3nc(-c4cc(OC(F)F)ccc4F)c(Cl)cc23)[C@@H](C)C1] | 6-chloro-7-(5-(difluoromethoxy)-2-fluorophenyl)-4-((2S)-2-methyl-4-(2-propenoyl)-1-piperazinyl)-1-(2-(2-propanyl)phenyl)pyrido[2,3-d]pyrimidin-2(1H)-one | Step 5: Pd(PPh$_3$)$_4$ and sodium carbonate | Step 1: 2-isopropylaniline (Sigma-Aldrich Corporation), Step 5: 2-(5-(difluoromethoxy)-2-fluorophenyl)-4,4,5,5-tetramethyl-1,3,2-dioxaborolane (Intermediate I-24) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-52 | 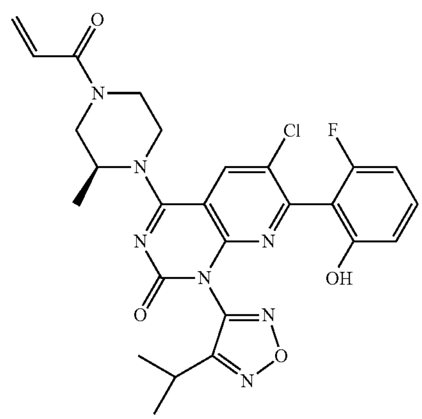 [SMILES: C=CC(=O)N1CCN(c2nc(=O)n(-c3nonc3C(C)C)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(4-(2-propanyl)-1,2,5-oxadiazol-3-yl)pyrido[2,3-d]pyrimidin-2(1H)-one | | Step 1: 4-isopropyl-1,2,5-oxadiazol-3-amine (Enamine), Step 5: (2-fluoro-6-hydroxyphenyl) boronic acid (Wuxi) |
| 54-53 | 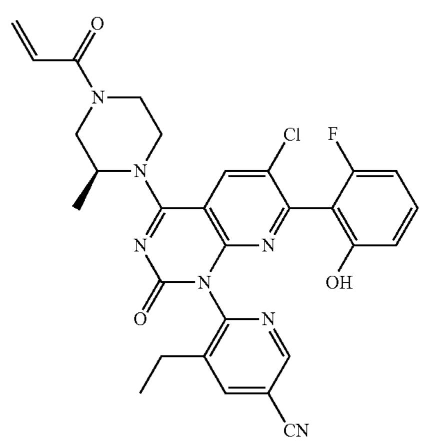 [SMILES: C=CC(=O)N1CCN(c2nc(=O)n(-c3ncc(C#N)cc3CC)c3nc(-c4c(O)cccc4F)c(Cl)cc23)[C@@H](C)C1] | 6-(6-chloro-7-(2-fluoro-6-hydroxyphenyl)-4-((2S)-2-methyl-4-(2-propenoyl)-1-piperazinyl)-2-oxopyrido[2,3-d]pyrimidin-1(2H)-yl)-5-ethyl-3-pyridinecarbonitrile | | Step 1: 6-amino-5-ethylnicotinonitrile (Intermediate I-15), Step 5: (2-fluoro-6-hydroxyphenyl) boronic acid (Wuxi) |
| 54-54 | 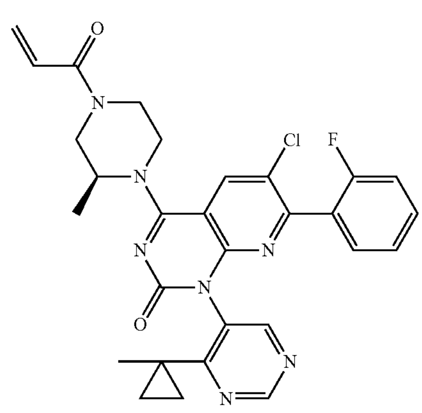 [SMILES: C=CC(=O)N1CCN(c2nc(=O)n(-c3cncnc3C3(C)CC3)c3nc(-c4ccccc4F)c(Cl)cc23)[C@@H](C)C1] | 6-chloro-7-(2-fluorophenyl)-1-(4-(1-methylcyclopropyl)-5-pyrimidinyl)-4-((2S)-2-methyl-4-(2-propenoyl)-1-piperazinyl)pyrido[2,3-d]pyrimidin-2(1H)-one | | Step 1: 4-(1-methylcyclopropyl)pyrimidin-5-amine (Intermediate I-4), Step 5: (2-fluorophenyl) boronic acid (Combi-Blocks Inc.) |

TABLE 54-continued

Compounds 54-2 to 54-115 were prepared following the procedure described
in Method 54, Steps 1-6, above as follows:

| Ex.# | Chemical Structure | Name | Method Changes | Reagent |
|---|---|---|---|---|
| 54-55 | 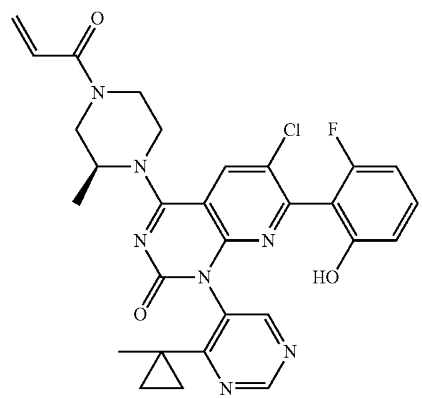 [SMILES: C=CC(=O)N1CCN(c2nc(=O)n(-c3cncnc3C3(C)CC3)c3nc(-c4c(O)cccc4F)c(Cl)cc23)[C@@H](C)C1] | 6-chloro-7-(2-fluoro-6-hydroxyphenyl)-1-(4-(1-methyl-cyclopropyl)-5-pyrimidinyl)-4-((2S)-2-methyl-4-(2-propenoyl)-1-piperazinyl)pyrido[2,3-d]pyrimidin-2(1H)-one | | Step 1: 4-(1-methylcyclo-propyl)pyrimidin-5-amine (Intermediate I-4), Step 5: (2-fluoro-6-hydroxyphenyl)boronic acid (Wuxi) |
| 54-56 | 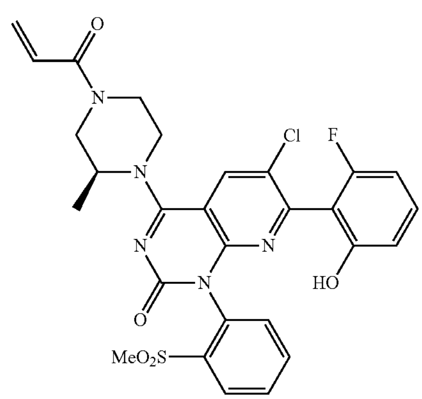 [SMILES: C=CC(=O)N1CCN(c2nc(=O)n(-c3ccccc3S(C)(=O)=O)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(2-(methylsulfonyl)phenyl)pyrido[2,3-d]pyrimidin-2(1H)-one | Step 3: DMF instead of MeCN | Step 1: 2-methanesul-fonylaniline (Enamine), Step 5: (2-fluoro-6-hydroxyphenyl)boronic acid (Wuxi) |
| 54-57 | 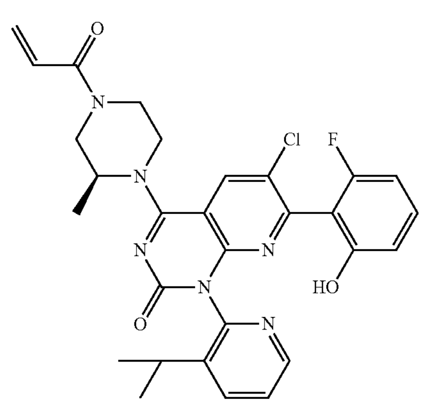 [SMILES: C=CC(=O)N1CCN(c2nc(=O)n(-c3ncccc3C(C)C)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(3-(2-propanyl)-2-pyridinyl)pyrido[2,3-d]pyrimidin-2(1H)-one | Step 3: DMF instead of MeCN | Step 1: 3-(propan-2-yl)pyridin-2-amine (Enamine), Step 3: (2-fluoro-6-hydroxyphenyl)boronic acid (Wuxi) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-58 | 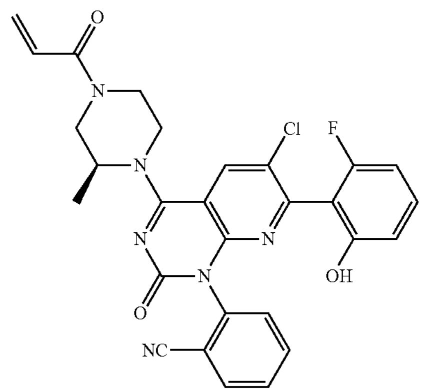 [SMILES: C=CC(=O)N1CCN(c2nc(=O)n(-c3ccccc3C#N)c3nc(-c4c(O)cccc4F)c(Cl)cc23)[C@@H](C)C1] | 2-(6-chloro-7-(2-fluoro-6-hydroxyphenyl)-4-((2S)-2-methyl-4-(2-propenoyl)-1-piperazinyl)-2-oxopyrido[2,3-d]pyrimidin-1(2H)-yl)benzonitrile | Step 3: DMF instead of MeCN | Step 1: 1-amino-2-cyanobenzene (Combi-Blocks, Inc.), Step 5: (2-fluoro-6-hydroxyphenyl) boronic acid (Wuxi) |
| 54-59 | 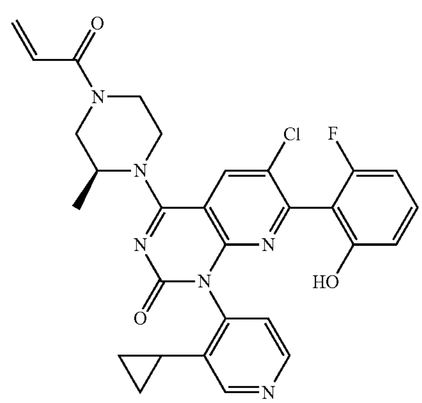 [SMILES: C=CC(=O)N1CCN(c2nc(=O)n(-c3ccncc3C3CC3)c3nc(-c4c(O)cccc4F)c(Cl)cc23)[C@@H](C)C1] | 6-chloro-1-(3-cyclopropyl-4-pyridinyl)-7-(2-fluoro-6-hydroxyphenyl)-4-((2S)-2-methyl-4-(2-propenoyl)-1-piperazinyl) pyrido[2,3-d]pyrimidin-2(1H)-one | Step 1: THF removed in vacuo and run in ACN at 80° C. Step 2: −10° C., Step 5: Pd(PPh$_3$)$_4$ and 2 M aqueous Na$_2$CO$_3$ | Step 1: 3-cyclopropyl-pyridin-4-amine (CombiPhos Catalysts, Inc.), Step 5: (2-fluoro-6-hydroxyphenyl) boronic acid (Wuxi) |
| 54-60 | 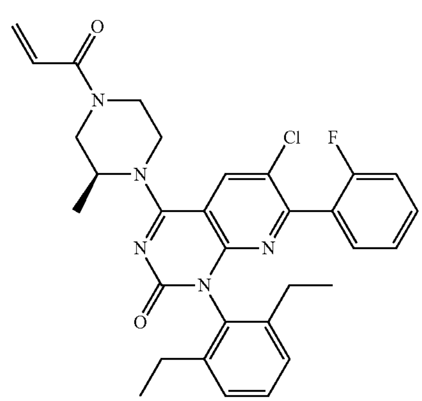 [SMILES: C=CC(=O)N1CCN(c2nc(=O)n(-c3c(CC)cccc3CC)c3nc(-c4ccccc4F)c(Cl)cc23)[C@@H](C)C1] | 6-chloro-1-(2,6-diethylphenyl)-7-(2-fluorophenyl)-4-((2S)-2-methyl-4-(2-propenoyl)-1-piperazinyl) pyrido[2,3-d]pyrimidin-2(1H)-one | Step 1: 60° C.; step 3: add DMF (2 drops), Step 4: replace DMF with THF, Step 5: tetrakis, potassium carbonate, 80° C., Step 6: exclude DCM, Step 6: 0° C. | Step 1: 2,6-diethylaniline (Sigma-Aldrich, St. Louis, MO); Step 5: (2-fluorophenyl) boronic acid (TCI America, Portland, OR) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-61 | 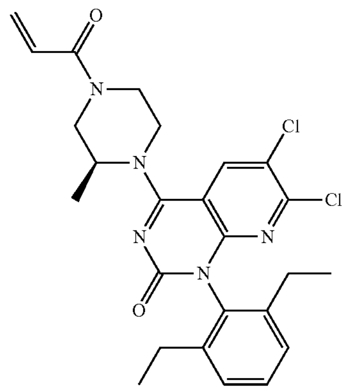 [SMILES: C=CC(=O)N1CCN(c2nc(=O)n(-c3c(CC)cccc3CC)c3nc(Cl)c(Cl)cc23)[C@@H](C)C1] | 6,7-dichloro-1-(2,6-diethylphenyl)-4-((2S)-2-methyl-4-(2-propenoyl)-1-piperazinyl)pyrido[2,3-d]pyrimidin-2(1H)-one | Step 1: 80° C., DCE, exclude TEA. Step 1: DCE, Omit Steps 5 & 6, Step 4: (S)-1-(3-methyl-piperazin-1-yl)prop-2-en-1-one | Step 1: 2,6-diethylaniline (Sigma-Aldrich, St, Louis, MO) |
| 54-62 | 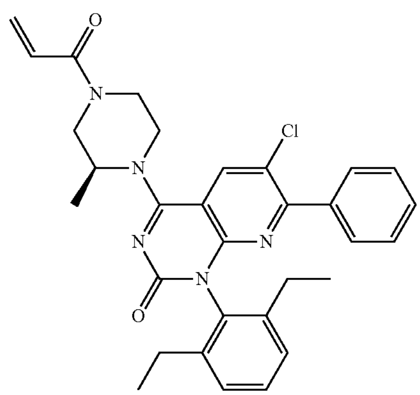 [SMILES: C=CC(=O)N1CCN(c2nc(=O)n(-c3c(CC)cccc3CC)c3nc(-c4ccccc4)c(Cl)cc23)[C@@H](C)C1] | 6-chloro-1-(2,6-diethylphenyl)-4-((2S)-2-methyl-4-(2-propenoyl)-1-piperazinyl)-7-phenyl-pyrido[2,3-d]pyrimidin-2(1H)-one | Step 1: 80° C., DCE, exclude TEA, Step 1: DCE, Omit Step 6, Step 4: (S)-1-(3-methyl-piperazin-1-yl)prop-2-en-1-one, Step 5: tetrakis, potassium carbonate, 80° C. | Step 1: 2,6-diethylaniline (Sigma-Aldrich, St. Louis, MO); Step 5: phenylboronic acid (Combi-Blocks, San Diego, CA) |
| 54-63 | 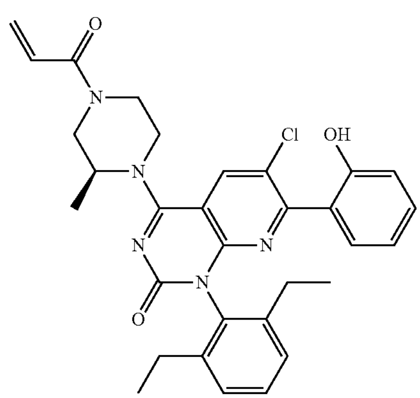 [SMILES: C=CC(=O)N1CCN(c2nc(=O)n(-c3c(CC)cccc3CC)c3nc(-c4ccccc4O)c(Cl)cc23)[C@@H](C)C1] | 6-chloro-1-(2,6-diethylphenyl)-7-(2-hydroxyphenyl)-4-((2S)-2-methyl-4-(2-propenoyl)-1-piperazinyl)pyrido[2,3-d]pyrimidin-2(1H)-one | Step 1: 80° C., DCE, exclude TEA, Step 1: DCE, Omit Step 6, Step 4: (S)-1-(3-methyl-piperazin-1-yl)prop-2-en-1-one; Step 5: tetrakis, potassium carbonate, 80° C. | Step 1: 2,6-diethylaniline (Sigma-Aldrich, St. Louis, MO); Step 5: (2-hydroxyphenyl)boronic acid (Frontier Scientific, Logan, UT) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-64 | 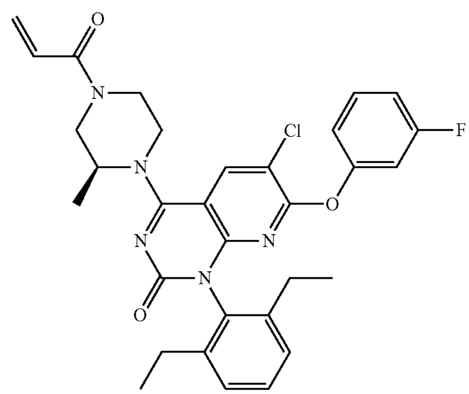 [SMILES: C=CC(=O)N1CCN(c2nc(=O)n(-c3c(CC)cccc3CC)c3nc(Oc4cccc(F)c4)c(Cl)cc23)[C@@H](C)C1] | 6-chloro-1-(2,6-diethylphenyl)-7-(3-fluorophenoxy)-4-((2S)-2-methyl-4-(2-propenoyl)-1-piperazinyl)pyrido[2,3-d]pyrimidin-2(1H)-one | Step 1: 80° C., DCE, exclude TEA; Step 1: DCE, Omit Step 6, Step 4: (S)-1-(3-methyl-piperazin-1-yl)prop-2-en-1-one; Step 5: tetrakis, potassium carbonate, 80° C. | Step 1: 2,6-diethylaniline (Sigma-Aldrich, St. Louis, MO); Step 5: (2-fluoro-6-hydroxyphenyl)boronic acid (Combi-Blocks, San Diego, CA) |
| 54-65 | 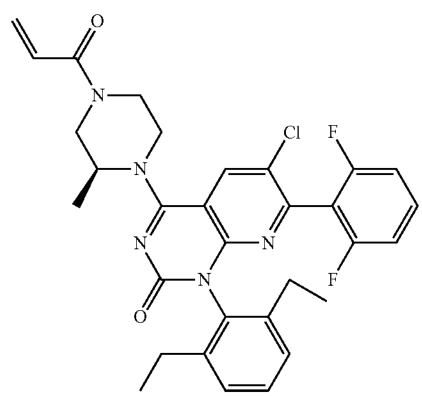 [SMILES: C=CC(=O)N1CCN(c2nc(=O)n(-c3c(CC)cccc3CC)c3nc(-c4c(F)cccc4F)c(Cl)cc23)[C@@H](C)C1] | 6-chloro-1-(2,6-diethylphenyl)-7-(2,6-difluorophenyl)-4-((2S)-2-methyl-4-(2-propenoyl)-1-piperazinyl)pyrido[2,3-d]pyrimidin-2(1H)-one | Step 1: 80° C., DCE, exclude TEA, Step 1: DCE, Omit Step 6, Step 4: (S)-1-(3-methyl-piperazin-1-yl)prop-2-en-1-one; step 5: tetrakis, dibasic potassium phosphate, 80° C. | Step 1: 2,6-diethylaniline (Sigma-Aidrich, St. Louis, MO); Step 5: 2-(2,6-difluorophenyl)-4,4,5,5-tetramethyl-1,3,2-dioxaborolane (Combi-Blocks, San Diego, CA) |
| 54-66 | 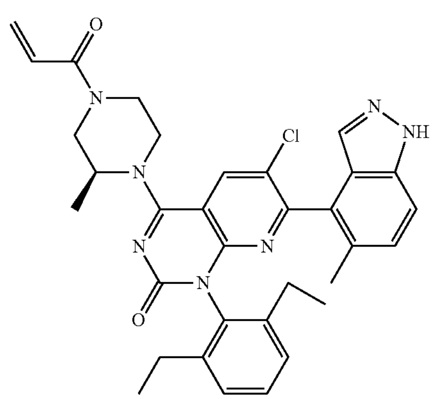 [SMILES: C=CC(=O)N1CCN(c2nc(=O)n(-c3c(CC)cccc3CC)c3nc(-c4c(C)ccc5[nH]ncc45)c(Cl)cc23)[C@@H](C)C1] | 6-chloro-1-(2,6-diethylphenyl)-7-(5-methyl-1H-indazol-4-yl)-4-((2S)-2-methyl-4-(2-propenoyl)-1-piperazinyl)pyrido[2,3-d]pyrimidin-2(1H)-one | Step 1: 80° C., DCE, exclude TEA, Step 1: DCE, Omit Step 6, Step 4: (S)-1-(3-methyl-piperazin-1-yl)prop-2-en-1-one; Step 5: SPhos Pd G₃, dibasic potassium phosphate, 80° C. | Step 1: 2,6-diethylaniline (Sigma-Aidrich, St. Louis, MO); Step 5: (5-methyl-1H-indazol-4-yl)boronic acid (Combi-Blocks, San Diego, CA) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-67 | 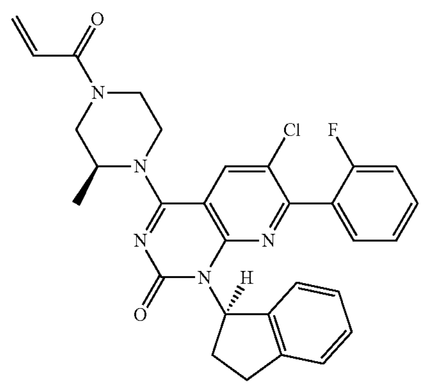 [SMILES: C=CC(=O)N1CCN(c2nc(=O)n([C@@H]3CCc4ccccc43)c3nc(-c4ccccc4F)c(Cl)cc23)[C@@H](C)C1] | 6-chloro-1-((1R)-2,3-dihydro-1H-inden-1-yl)-7-(2-fluorophenyl)-4-((2S)-2-methyl-4-(2-propenoyl)-1-piperazinyl)pyrido[2,3-d]pyrimidin-2(1H)-one | Step 1: 65° C., Step 5: tetrakis, potassium carbonate, 80° C. | Step 1: (R)-(-)-1-aminoindane HCl (AstaTech, Inc., Bristol, PA); Step 5: (2-fluorophenyl)boronic acid (TCI America, Portland, OR) |
| 54-68 | 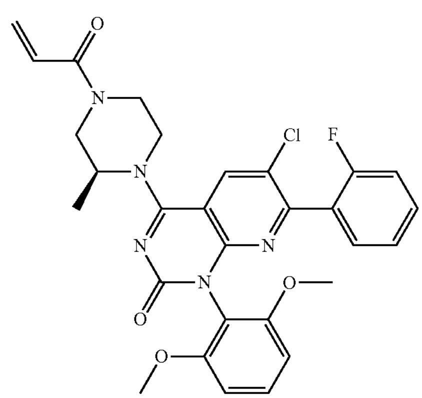 [SMILES: C=CC(=O)N1CCN(c2nc(=O)n(-c3c(OC)cccc3OC)c3nc(-c4ccccc4F)c(Cl)cc23)[C@@H](C)C1] | 6-chloro-1-(2,6-dimethoxyphenyl)-7-(2-fluorophenyl)-4-((2S)-2-methyl-4-(2-propenoyl)-1-piperazinyl)pyrido[2,3-d]pyrimidin-2(1H)-one | Step 1: 65° C., Step 5: tetrakis, potassium carbonate, 80° C. | Step 1: 2,6-dimethoxyaniline (Combi-Blocks, San Diego, CA); Step 5: (2-fluorophenyl)boronic acid (TCI America, Portland, OR) |
| 54-69 | 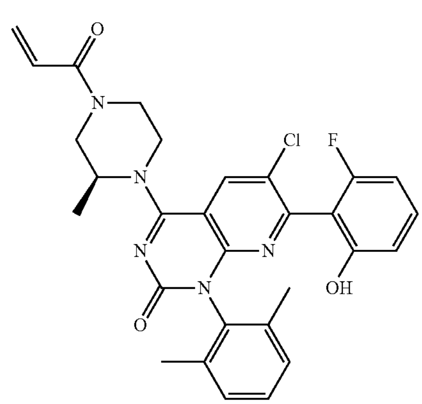 [SMILES: C=CC(=O)N1CCN(c2nc(=O)n(-c3c(C)cccc3C)c3nc(-c4c(O)cccc4F)c(Cl)cc23)[C@@H](C)C1] | 6-chloro-1-(2,6-dimethylphenyl)-7-(2-fluoro-6-hydroxyphenyl)-4-((2S)-2-methyl-4-(2-propenoyl)-1-piperazinyl)pyrido[2,3-d]pyrimidin-2(1H)-one | Step 1: 80° C., DCE, Step5: SPhos Pd G3, potassium carbonate, 80° C. | Step 1: 2,6-dimethylaniline (Sigma-Aldrich, St. Louis, MO); Step 5: (2-fluoro-6-hydroxyphenyl)boronic acid (Combi-Blocks, San Diego, CA) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-70 | 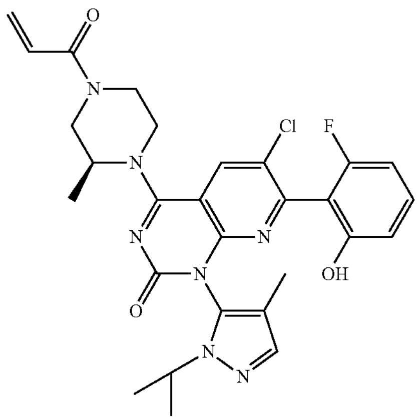 [SMILES: C=CC(=O)N1CCN(c2nc(=O)n(-c3c(C)cnn3C(C)C)c3nc(-c4c(O)cccc4F)c(Cl)cc23)[C@@H](C)C1] | 6-chloro-7-(2-fluoro-6-hydroxyphenyl)-1-(4-methyl-1-(2-propanyl)-1H-pyrazol-5-yl)-4-((2S)-2-methyl-4-(2-propenoyl)-1-piperazinyl)pyrido[2,3-d]pyrimidin-2(1H)-one | | Step 1: 1-isopropyl-4-methyl-1H-pyrazol-5-amine (ChemBridge Corporation), Step 5: (2-fluoro-6-hydroxyphenyl)boronic acid (Wuxi) |
| 54-71 | 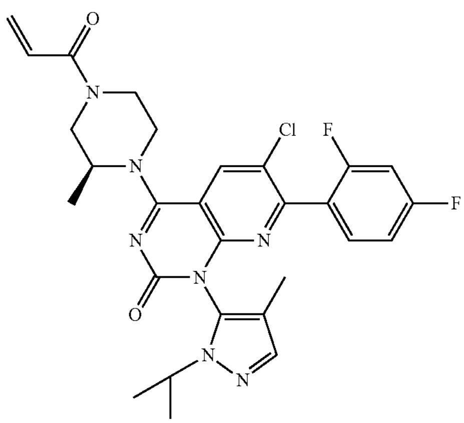 [SMILES: C=CC(=O)N1CCN(c2nc(=O)n(-c3c(C)cnn3C(C)C)c3nc(-c4ccc(F)cc4F)c(Cl)cc23)[C@@H](C)C1] | 6-chloro-7-(2,4-difluorophenyl)-1-(4-methyl-1-(2-propanyl)-1H-pyrazol-5-yl)-4-((2S)-2-methyl-4-(2-propenoyl)-1-piperazinyl)pyrido[2,3-d]pyrimidin-2(1H)-one | | Step 1: 1-isopropyl-4-methyl-1H-pyrazol-5-amine (ChemBridge Corporation), Step 5: 2,4-difluorobenzeneboronic acid (Sigma-Aldrich Corporation) |
| 54-72 | 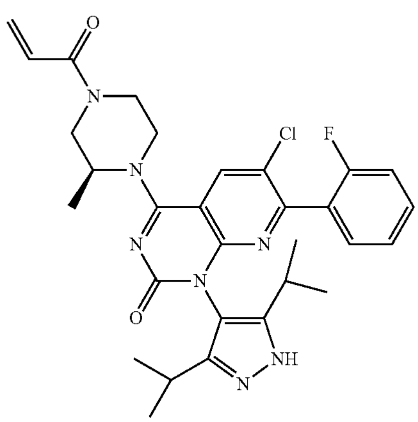 [SMILES: C=CC(=O)N1CCN(c2nc(=O)n(-c3c(C(C)C)n[nH]c3C(C)C)c3nc(-c4ccccc4F)c(Cl)cc23)[C@@H](C)C1] | 6-chloro-1-(3,5-di(2-propanyl)-1H-pyrazol-4-yl)-7-(2-fluorophenyl)-4-((2S)-2-methyl-4-(2-propenoyl)-1-piperazinyl)pyrido[2,3-d]pyrimidin-2(1H)-one | | Step 1: 3,5-diisopropyl-1H-pyrazol-4-amine (Intermediate I-11), Step 5: 2-fluorophenylboronic acid (Combi-Blocks Inc.) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-73 | 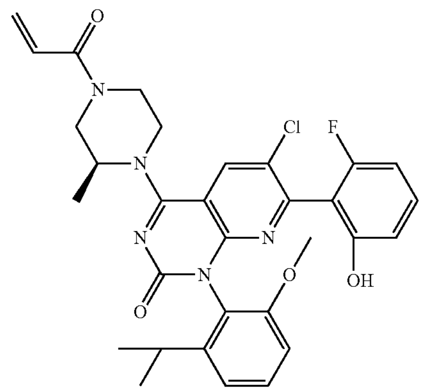 [SMILES: C=CC(=O)N1CCN(c2nc(=O)n(-c3c(OC)cccc3C(C)C)c3nc(-c4c(O)cccc4F)c(Cl)cc23)[C@@H](C)C1] | 6-chloro-7-(2-fluoro-6-hydroxyphenyl)-1-(2-methoxy-6-(2-propanyl)phenyl)-4-((2S)-2-methyl-4-(2-propenoyl)-1-piperazinyl)pyrido[2,3-d]pyrimidin-2(1H)-one | Step 2: NaOt-Bu/ toluene, 20° C. | Step 1: 2-isopropyl-6-methoxyaniline (HDH Pharma), Step 5: (2-fluoro-6-hydroxyphenyl) boronic acid (WuXi) |
| 54-74 | 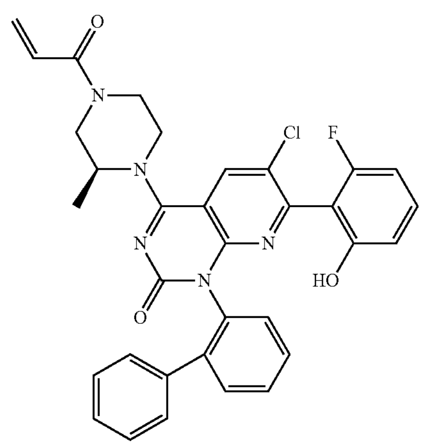 [SMILES: C=CC(=O)N1CCN(c2nc(=O)n(-c3ccccc3-c3ccccc3)c3nc(-c4c(O)cccc4F)c(Cl)cc23)[C@@H](C)C1] | 1-([biphenyl]-2-yl)-6-chloro-7-(2-fluoro-6-hydroxyphenyl)-4-((2S)-2-methyl-4-(2-propenoyl)-1-piperazinyl)pyrido[2,3-d]pyrimidin-2(1H)-one | Step 1: DCE at 80° C. | Step 1: 2-Aminobiphenyl (Acros Organics), Step 5: (2-fluoro-6-hydroxyphenyl) boronic acid (WuXi) |
| 54-75 | 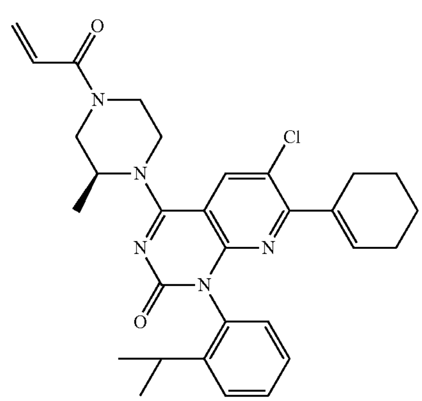 [SMILES: C=CC(=O)N1CCN(c2nc(=O)n(-c3ccccc3C(C)C)c3nc(C4=CCCCC4)c(Cl)cc23)[C@@H](C)C1] | 6-chloro-7-(1-cyclohexen-1-yl)-4-((2S)-2-methyl-4-(2-propenoyl)-1-piperazinyl)-1-(2-(2-propanyl)phenyl)pyrido[2,3-d]pyrimidin-2(1H)-one | Step 1: 60° C., 50 min. Triturated with MTBE Step 3: Et$_3$N as base, 60° C. for 20 min, Step 4: Et$_3$N base, THF solvent | Step 1: 2-isopropylaniline (Sigma-Aldrich Corporation), Step 5: 1-cyclohexen-1-yl-boronic acid (Combi-Blocks, San Diego, CA, USA) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-76 | 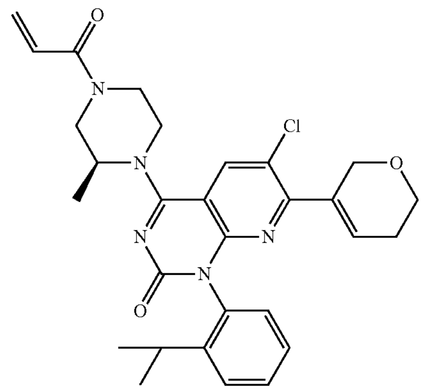 [SMILES: C=CC(=O)N1CCN(c2nc(=O)n(-c3ccccc3C(C)C)c3nc(C4=CCCOC4)c(Cl)cc23)[C@@H](C)C1] | 6-chloro-7-(5,6-dihydro-2H-pyran-3-yl)-4-((2S)-2-methyl-4-(2-propenoyl)-1-piperazinyl)-1-(2-(2-propanyl)phenyl)pyrido[2,3-d]pyrimidin-2(1H)-one | Step 1: 60° C., 50 min. Step 3: Et$_3$N as base, 60° C. for 20 min, Step 4: Et$_3$N base, THF solvent | Step 1: 2-isopropylaniline (Sigma-Akirich Corporation), Step 5: 2-(5,6-dihydro-2H-pyran-3-yl)-4,4,5,5-tetramethyl-1,3,2-dioxaborolane (Matrix Scientific) |
| 54-77 | 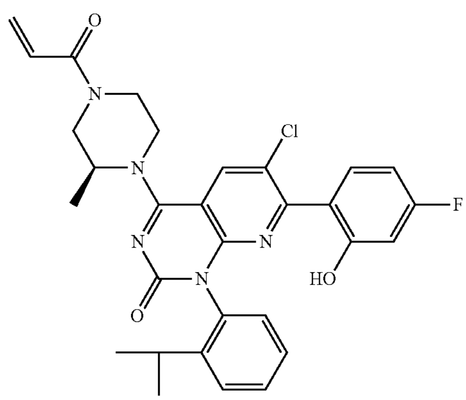 [SMILES: C=CC(=O)N1CCN(c2nc(=O)n(-c3ccccc3C(C)C)c3nc(-c4ccc(F)cc4O)c(Cl)cc23)[C@@H](C)C1] | 6-chloro-7-(4-fluoro-2-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | Step 1: 60° C., Step 2: 0° C. to rt, Step 3: 60° C. Step 4: THF, rt. | Step 1: 2-isopropylaniline (Sigma-Aldrich Corporation), Step 5: (4-fluoro-2-hydroxyphenyl)boronic acid (Combi-Blocks, San Diego, CA) |
| 54-78 | 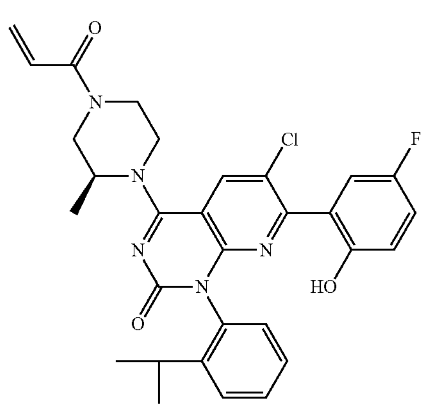 [SMILES: C=CC(=O)N1CCN(c2nc(=O)n(-c3ccccc3C(C)C)c3nc(-c4cc(F)ccc4O)c(Cl)cc23)[C@@H](C)C1] | 6-chloro-7-(5-fluoro-2-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | Step 1: 60° C., Step 2: 0° C. to rt, Step 3; 60° C., Step 4: THF, rt. | Step 1: 2-isopropylaniline (Sigma-Aldrich Corporation), Step 5: (5-fluoro-2-hydroxy)phenyl-boronic acid (Combi-Blocks, San Diego, CA) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-79 | 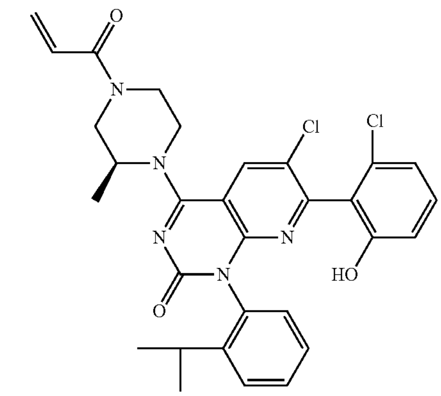 [SMILES: C=CC(=O)N1CCN(c2nc(=O)n(-c3ccccc3C(C)C)c3nc(-c4c(O)cccc4Cl)c(Cl)cc23)[C@@H](C)C1] | 6-chloro-7-(2-chloro-6-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | Step 1: 60° C., Step 2: 0° C. to rt, Step 3: 60° C., Step 4: THF, rt. | Step 1: 2-isopropylaniline (Sigma-Aldrich Corporation), Step 5: (2-chloro-6-hydroxyphenyl)boronic acid (Combi-Blocks, San Diego, CA) |
| 54-80 | 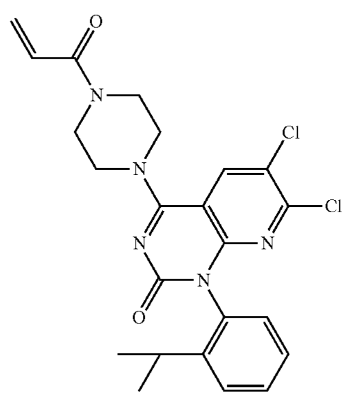 [SMILES: C=CC(=O)N1CCN(c2nc(=O)n(-c3ccccc3C(C)C)c3nc(Cl)c(Cl)cc23)CC1] | 6,7-dichloro-1-(2-(2-propanyl)phenyl)-4-(4-(2-propenoyl)-1-piperazinyl)pyrido[2,3-d]pyrimidin-2(1H)-one | Omit Step 5 | Step 1: 2-isopropylaniline (Sigma-Aldrich Corporation) |
| 54-82 | 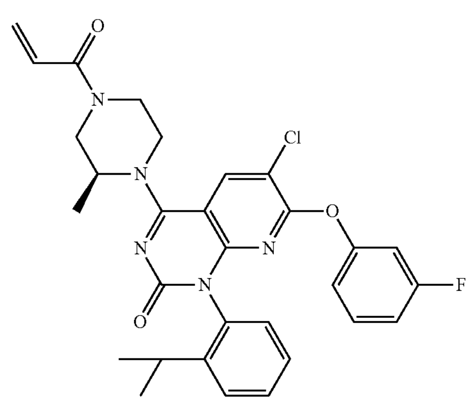 [SMILES: C=CC(=O)N1CCN(c2nc(=O)n(-c3ccccc3C(C)C)c3nc(Oc4cccc(F)c4)c(Cl)cc23)[C@@H](C)C1] | 6-chloro-7-(3-fluorophenoxy)-4-((2S)-2-methyl-4-(2-propenoyl)-1-piperazinyl)-1-(2-(2-propanyl)phenyl)pyrido[2,3-d]pyrimidin-2(1H)-one | Step 5: using tetrakis(triphenylphosphine) palladium and sodium carbonate | Step 1: 2-isopropylaniline (Sigma-Aldrich Corporation), Step 5: (2-fluoro-6-hydroxyphenyl)boronic acid (WuXi) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-84 | 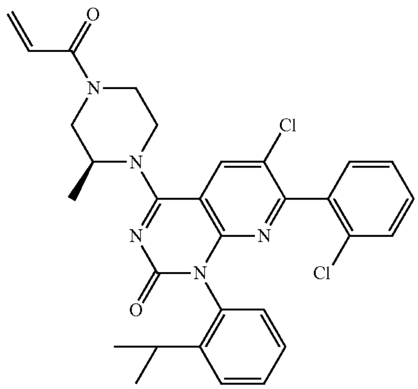 [SMILES: C=CC(=O)N1CCN(c2nc(=O)n(-c3ccccc3C(C)C)c3nc(-c4ccccc4Cl)c(Cl)cc23)[C@@H](C)C1] | 6-chloro-7-(2-chlorophenyl)-4-((2S)-2-methyl-4-(2-propenoyl)-1-piperazinyl)-1-(2-(2-propanyl)phenyl)pyrido[2,3-d]pyrimidin-2(1H)-one | Step 5: using tetrakis (triphenylphosphine) palladium and sodium carbonate | Step 5: 2-chlorobenzene boronic acid (Alfa Aesar, Avocado, Lancaster) |
| 54-85 | 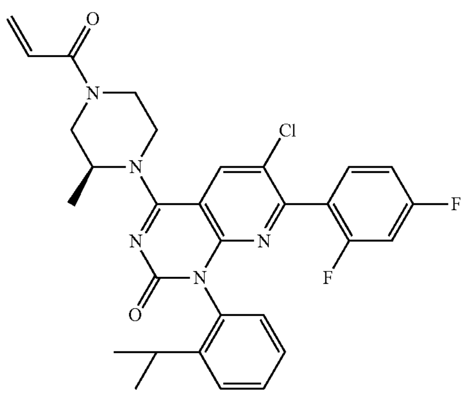 [SMILES: C=CC(=O)N1CCN(c2nc(=O)n(-c3ccccc3C(C)C)c3nc(-c4ccc(F)cc4F)c(Cl)cc23)[C@@H](C)C1] | 6-chloro-7-(2,4-difluorophenyl)-4-((2S)-2-methyl-4-(2-propenoyl)-1-piperazinyl)-1-(2-(2-propanyl)phenyl)pyrido[2,3-d]pyrimidin-2(1H)-one | Step 5: using tetrakis (triphenylphosphine) palladium and sodium carbonate | Step 1: 2-isopropylaniline (Sigma-Aldrich Corporation), Step 5: (2,4-difluorophenyl) boronic acid (Combi-Blocks Inc.) |
| 54-86 | 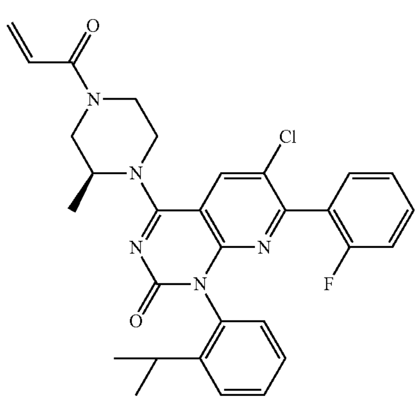 [SMILES: C=CC(=O)N1CCN(c2nc(=O)n(-c3ccccc3C(C)C)c3nc(-c4ccccc4F)c(Cl)cc23)[C@@H](C)C1] | 6-chloro-7-(2-fluorophenyl)-4-((2S)-2-methyl-4-(2-propenoyl)-1-piperazinyl)-1-(2-(2-propanyl)phenyl)pyrido[2,3-d]pyrimidin-2(1H)-one | Step 5: using tetrakis (triphenylphosphine) palladium and sodium carbonate | Step 1: 2-isopropylaniline (Sigma-Aldrich Corporation), Step 5: 2-fluorobenzene boronic acid (TCI America) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-87 | 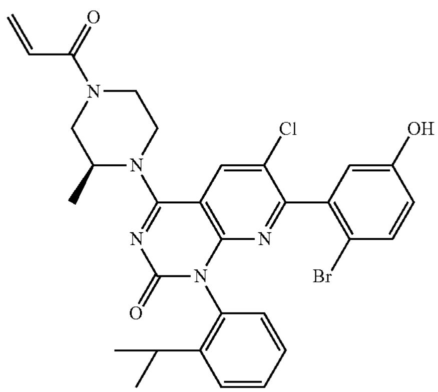 | 7-(2-bromo-5-hydroxyphenyl)-6-chloro-4-((2S)-2-methyl-4-(2-propenoyl)-1-piperazinyl)-1-(2-(2-propanyl)phenyl)pyrido[2,3-d]pyrimidin-2(1H)-one | | Step 1: 2-isopropylaniline (Sigma-Aldrich Corporation), Step 5: 2-bromo-5-methoxybenzene boronic acid (Combi-Blocks Inc.) |
| 54-88 | 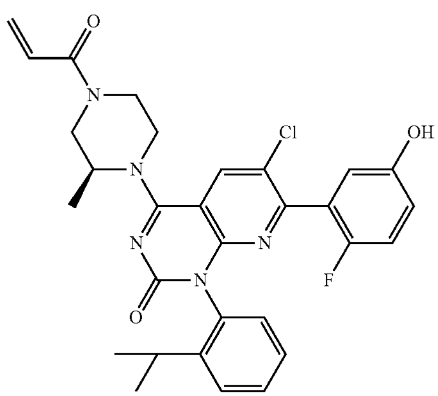 [SMILES: C=CC(=O)N1CCN(c2nc(=O)n(-c3ccccc3C(C)C)c3nc(-c4cc(O)ccc4F)c(Cl)cc23)[C@@H](C)C1] | 6-chloro-7-(2-fluoro-5-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | | Step 1: 2-isopropylaniline (Sigraa-Aldrich Corporation), Step 5: 2-fluoro-5-hydroxyphenyl-boronic acid (Combi-Blocks Inc.) |
| 54-89 | 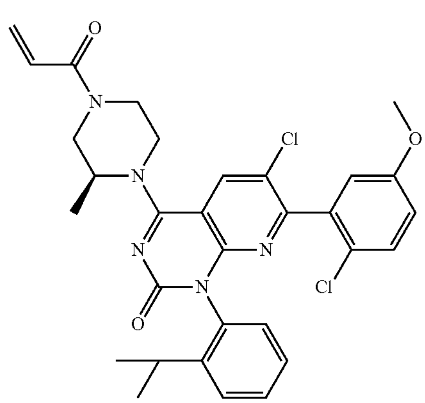 [SMILES: C=CC(=O)N1CCN(c2nc(=O)n(-c3ccccc3C(C)C)c3nc(-c4cc(OC)ccc4Cl)c(Cl)cc23)[C@@H](C)C1] | 6-chloro-7-(2-chloro-5-methoxy-phenyl)-4-((2S)-2-methyl-4-(2-propenoyl)-1-piperazinyl)-1-(2-(2-propanyl)phenyl)pyrido[2,3-d]pyrimidin-2(1H)-one | | Step 1: 2-isopropylaniline (Sigma-Aldrich Corporation), Step 5: 2-chloro-5-methoxyphenyl boronic acid (Combi-Blocks Inc.) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-90 | 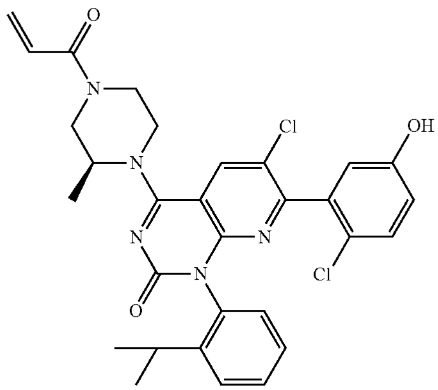 | 6-chloro-7-(2-chloro-5-hydroxy-phenyl)-4-((2S)-2-methyl-4-(2-propenoyl)-1-piperazinyl)-1-(2-(2-propanyl)phenyl)pyrido[2,3-d]pyrimidin-2(1H)-one | | Step 1: 2-isopropylaniline (Sigma-Aldrich Corporation), Step 5: 2-chloro-5-methoxyphenyl boronic acid (Combi-Blocks Inc.) |
| 54-91 | 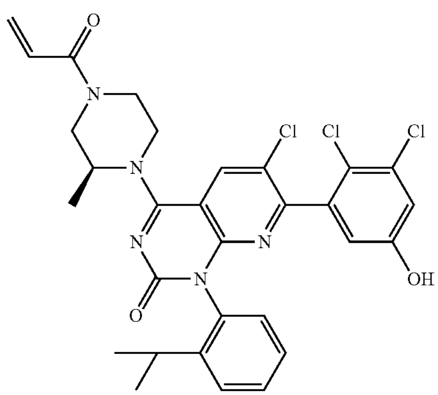 [SMILES: C=CC(=O)N1CCN(c2nc(=O)n(-c3ccccc3C(C)C)c3nc(-c4cc(O)cc(Cl)c4Cl)c(Cl)cc23)[C@@H](C)C1] | 6-chloro-7-(2,3-dichloro-5-hydroxy-phenyl)-4-((2S)-2-methyl-4-(2-propenoyl)-1-piperazinyl)-1-(2-(2-propanyl)phenyl)pyrido[2,3-d]pyrimidin-2(1H)-one | | Step 1: 2-isopropylaniline (Sigma-Aldrich Corporation), Step 5: 2-(2,3-dichloro-5-methoxyphenyl)-4,4,5,5-tetramethyl-1,3,2-dioxaborolane (ACS Scientific Inc.) |
| 54-92 | 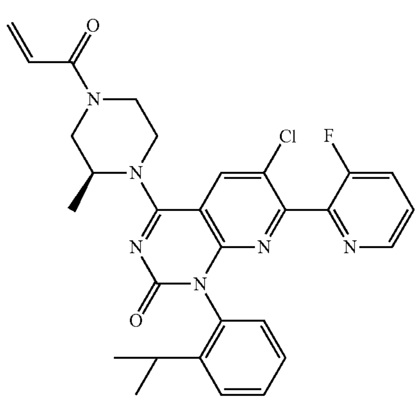 | 6-chloro-7-(3-fluoro-2-pyridinyl)-4-((2S)-2-methyl-4-(2-propenoyl)-1-piperazinyl)-1-(2-(2-propanyl)phenyl)pyrido[2,3-d]pyrimidin-2(1H)-one | Step 5: using Pd(PPh$_3$)$_4$ and CuI, microwave at 150° C. | Step 1: 2-isopropylaniline (Sigma-Aldrich Corporation), Step 3-fluoro-2-(tributylstannyl)pyridine (Indofine Chemical Company, Inc.) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-93 | 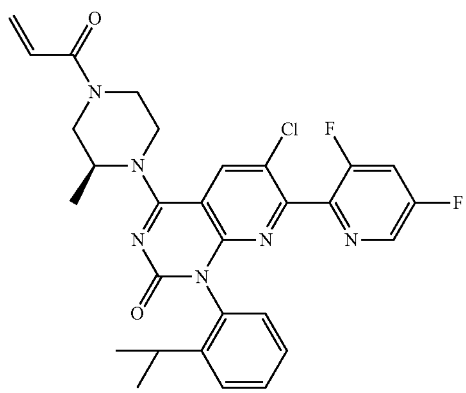 | 6-chloro-7-(3,5-difluoro-2-pyridinyl)-4-((2S)-2-methyl-4-(2-propenoyl)-1-piperazinyl)-1-(2-(2-propanyl)phenyl)pyrido[2,3-d]pyrimidin-2(1H)-one | Step 5: using Pd(PPh$_3$)$_4$ and CuI, microwave at 150° C. | Step 1: 2-isopropylaniline (Sigma-Aldrich Corporation), Step 5: 3,5-difluoro-2-tributylstannyl pyridin (Synthonix Inc.) |
| 54-94 | 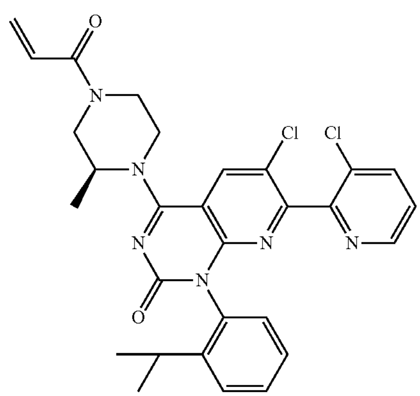 [SMILES: C=CC(=O)N1CCN(c2nc(=O)n(-c3ccccc3C(C)C)c3nc(-c4ncccc4F)c(Cl)cc23)[C@@H](C)C1] | 6-chloro-7-(3-chloro-2-pyridinyl)-4-((2S)-2-methyl-4-(2-propenoyl)-1-piperazinyl)-1-(2-(2-propanyl)phenyl)pyrido[2,3-d]pyrimidin-2(1H)-one | Step 5: using Pd(PPh$_3$)$_4$ and CuI, microwave at 150° C. | Step 1: 2-isopropylaniline (Sigma-Aldrich Corporation), Step 5: 3-chloro-2-(tributylstannyl)pyridine (Synthonix Inc.) |
| 54-95 | 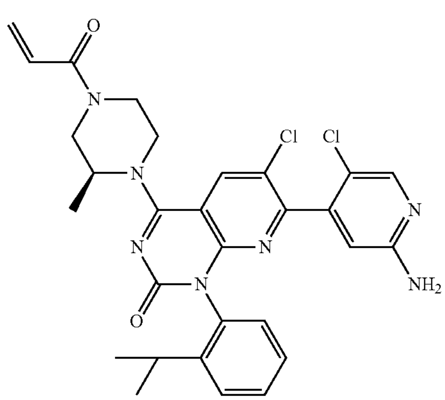 [SMILES: C=CC(=O)N1CCN(c2nc(=O)n(-c3ccccc3C(C)C)c3nc(-c4cc(N)ncc4Cl)c(Cl)cc23)[C@@H](C)C1] | 7-(2-amino-5-chloro-4-pyridinyl)-6-chloro-4-((2S)-2-methyl-4-(2-propenoyl)-1-piperazinyl)-1-(2-(2-propanyl)phenyl)pyrido[2,3-d]pyrimidin-2(1H)-one | | Step 1: 2-isopropylaniline (Sigma-Aldrich Corporation), Step 5: 2-(tert-butoxycarbonylamino)-5-chloropyridin-4-ylboronic acid (Anichem Inc.) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-96 | 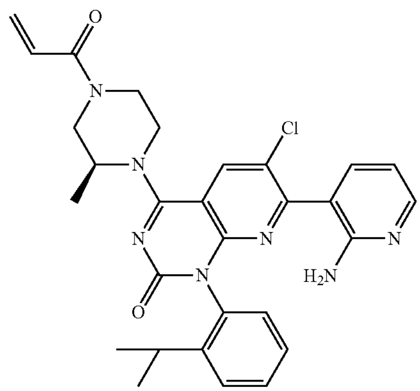 [SMILES: C=CC(=O)N1CCN(c2nc(=O)n(-c3ccccc3C(C)C)c3nc(-c4cccnc4N)c(Cl)cc23)[C@@H](C)C1] | 7-(2-amino-3-pyridinyl)-6-chloro-4-((2S)-2-methyl-4-(2-propenoyl)-1-piperazinyl)-1-(2-(2-propanyl)phenyl)pyrido[2,3-d]pyrimidin-2(1H)-one | | Step 1: 2-isopropylaniline (Sigma-Aldrich Corporation), Step 5: (2-(Boc-amino)-pyridin-3-yl)boronic acid (Combi-Blocks Inc.) |
| 54-97 | 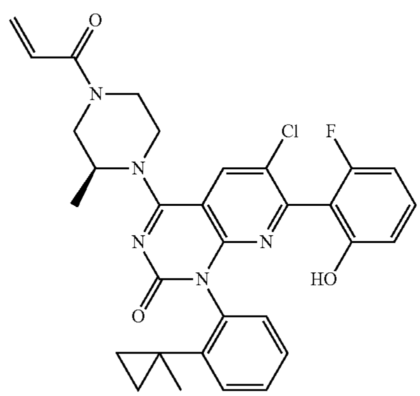 [SMILES: C=CC(=O)N1CCN(c2nc(=O)n(-c3ccccc3C3(C)CC3)c3nc(-c4c(O)cccc4F)c(Cl)cc23)[C@@H](C)C1] | 6-chloro-7-(2-fluoro-6-hydroxyphenyl)-1-(2-(1-methylcyclopropyl)phenyl)-4-((2S)-2-methyl-4-(2-propenoyl)-1-piperazinyl)pyrido[2,3-d]pyrimidin-2(1H)-one | | Step 1: 2-(1-methylcyclopropyl)aniline (ACS Scientific Inc.), Step 5: (2-fluoro-6-hydroxyphenyl)boronic acid (Wuxi) |
| 54-98 | 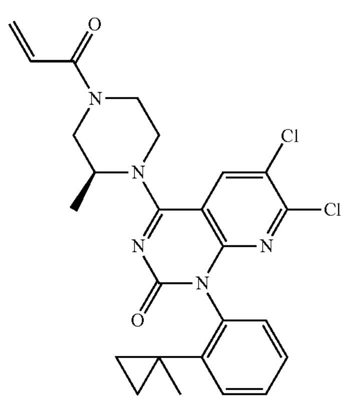 [SMILES: C=CC(=O)N1CCN(c2nc(=O)n(-c3ccccc3C3(C)CC3)c3nc(Cl)c(Cl)cc23)[C@@H](C)C1] | 6,7-dichloro-1-(2-(1-methylcyclopropyl)phenyl)-4-((2S)-2-methyl-4-(2-propenoyl)-1-piperazinyl)pyrido[2,3-d]pyrimidin-2(1H)-one | Omit Step 5 | Step 1: 2-(1-methylcyclopropyl)aniline (ACS Scientific Inc.) |

TABLE 54-continued

Compounds 54-2 to 54-115 were prepared following the procedure described in Method 54, Steps 1-6, above as follows:

| Ex.# | Chemical Structure | Name | Method Changes | Reagent |
|------|--------------------|------|----------------|---------|
| 54-99 | 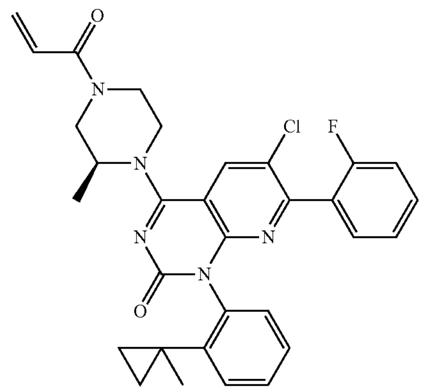 [SMILES: C=CC(=O)N1CCN(c2nc(=O)n(-c3ccccc3C3(C)CC3)c3nc(-c4ccccc4F)c(Cl)cc23)[C@@H](C)C1] | 6-chloro-7-(2-fluorophenyl)-1-(2-(1-methylcyclopropyl)phenyl)-4-((2S)-2-methyl-4-(2-propenoyl)-1-piperazinyl)pyrido[2,3-d]pyrimidin-2(1H)-one | | Step 1: 2-(1-methylcyclopropyl)aniline (ACS Scientific Inc.); Step 5: (2-fluorophenyl)boronic acid (Combi-Blocks) |
| 54-100 | 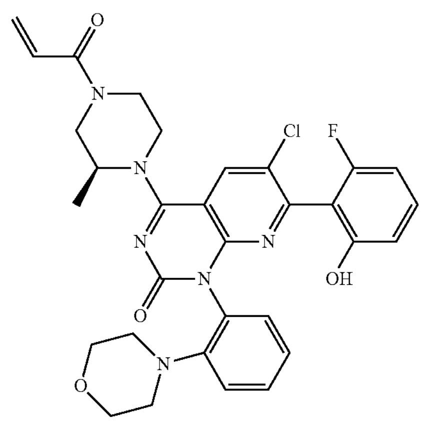 [SMILES: C=CC(=O)N1CCN(c2nc(=O)n(-c3ccccc3N3CCOCC3)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(2-(4-morpholinyl)phenyl)pyrido[2,3-d]pyrimidin-2(1H)-one | | Step 1: 2-(4-morpholino)aniline (Alfa Aesar, Avocado, Lancaster), Step 5: (2-fluoro-6-hydroxyphenyl)boronic acid (Wuxi) |
| 54-101 | 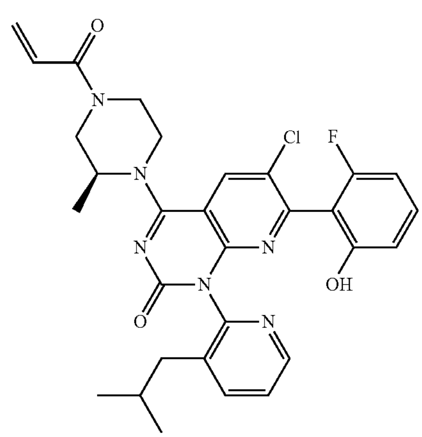 [SMILES: C=CC(=O)N1CCN(c2nc(=O)n(-c3ncccc3CC(C)C)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(3-(2-methylpropyl)-2-pyridinyl)pyrido[2,3-d]pyrimidin-2(1H)-one | | Step 1: 3-(iso-butyl)pyridin-2-amine (CombiPhos), Step 5: (2-fluoro-6-hydroxyphenyl)boronic acid (Wuxi) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-102 | 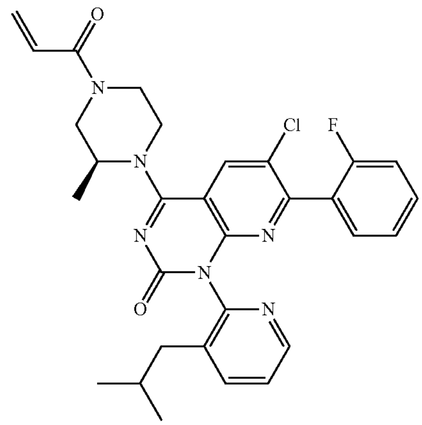 [SMILES: C=CC(=O)N1CCN(c2nc(=O)n(-c3ncccc3CC(C)C)c3nc(-c4ccccc4F)c(Cl)cc23)[C@@H](C)C1] | 6-chloro-7-(2-fluorophenyl)-4-((2S)-2-methyl-4-(2-propenoyl)-1-piperazinyl)-1-(3-(2-methylpropyl)-2-pyridinyl)pyrido[2,3-d]pyrimidin-2(1H)-one | | Step 1: 3-(isobutyl)pyridin-2-amine (ChembiPhos), Step 5: 2-fluorophenylboronic acid (Combi-Blocks Inc.) |
| 54-103 | 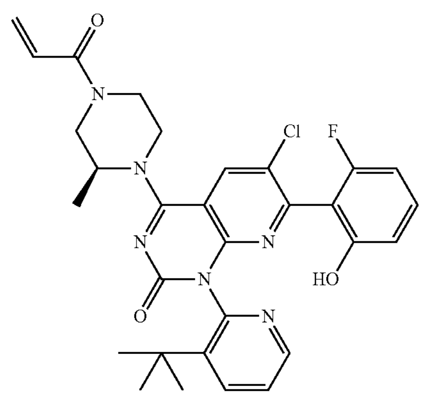 [SMILES: C=CC(=O)N1CCN(c2nc(=O)n(-c3ncccc3C(C)(C)C)c3nc(-c4c(O)cccc4F)c(Cl)cc23)[C@@H](C)C1] | 6-chloro-7-(2-fluoro-6-hydroxyphenyl)-1-(2-(2-methyl-2-propanyl)-3-pyridinyl)-4-((2S)-2-methyl-4-(2-propenoyl)-1-piperazinyl)pyrido[2,3-d]pyrimidin-2(1H)-one | | Step 1: 2-(tert-butyl)pyridin-3-amine (Intermediate I-23), Step 5: (2-fluoro-6-hydroxyphenyl)boronic acid (Wuxi) |
| 54-104 | 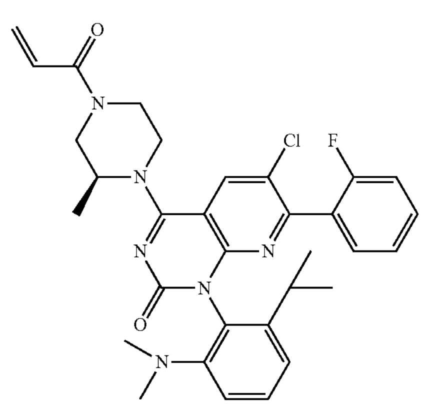 [SMILES: C=CC(=O)N1CCN(c2nc(=O)n(-c3c(C(C)C)cccc3N(C)C)c3nc(-c4ccccc4F)c(Cl)cc23)[C@@H](C)C1] | 6-chloro-1-(2-(dimethylamino)-6-(2-propanyl)phenyl)-7-(2-fluorophenyl)-4-((2S)-2-methyl-4-(2-propenoyl)-1-piperazinyl)pyrido[2,3-d]pyrimidin-2(1H)-one | | Step 1: 3-Isopropyl-N',N'-dimethylbenzene-1,2-diamine (Intermediate I-31), Step 5: 2-fluorophenyl boronic acid (Combi-Blocks Inc.) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-105 | 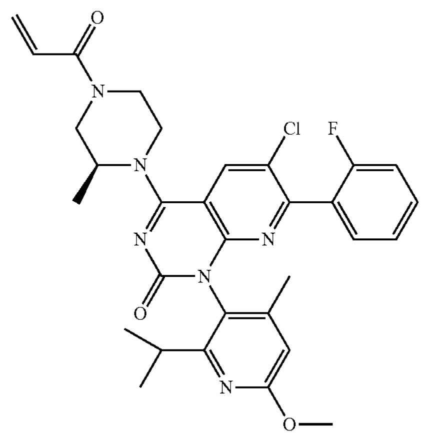 [SMILES: C=CC(=O)N1CCN(c2nc(=O)n(-c3c(C)cc(OC)nc3C(C)C)c3nc(-c4ccccc4F)c(Cl)cc23)[C@@H](C)C1] | 6-chloro-7-(2-fluorophenyl)-1-(6-methoxy-4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 1: 2-isopropyl-6-methoxy-4-methylpyridin-3-amine (Intermediate I-32), Step 5: 2-fluorophenyl boronic acid (Combi-Blocks Inc.) |
| 54-106 | 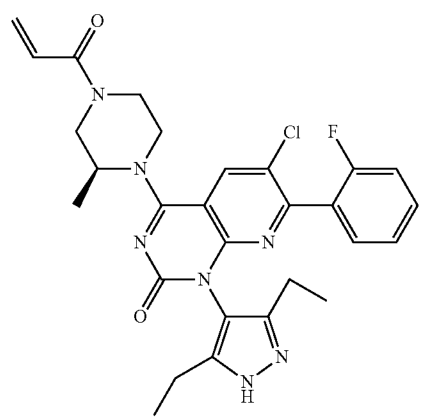 [SMILES: C=CC(=O)N1CCN(c2nc(=O)n(-c3c(CC)n[nH]c3CC)c3nc(-c4ccccc4F)c(Cl)cc23)[C@@H](C)C1] | 6-chloro-1-(3,5-diethyl-1H-pyrazol-4-yl)-7-(2-fluorophenyl)-4-((2S)-2-methy)-4-(2-propenoyl)-1-piperazinyl)pyrido[2,3-d]pyrimidin-2(1H)-one | | Step 1: 3,5-diethyl-1H-pyrazol-4-amine (Aurora Building Blocks Inc.), Step 5: 2-fluorophenyl boronic acid (Combi-Blocks Inc.) |
| 54-107 | 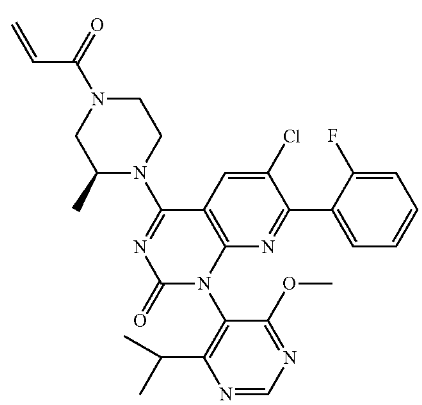 [SMILES: C=CC(=O)N1CCN(c2nc(=O)n(-c3c(OC)ncnc3C(C)C)c3nc(-c4ccccc4F)c(Cl)cc23)[C@@H](C)C1] | 6-chloro-7-(2-fluorophenyl)-1-(4-methoxy-6-(2-propanyl)-5-pyrimidinyl)-4-((2S)-2-methyl-4-(2-propenoyl)-1-piperazinyl)pyrido[2,3-d]pyrimidin-2(1H)-one | | Step 1: 4-isopropyl-6-methoxypyrimidin-5-amine (Intermediate I-39), Step 5: 2-fluorophenyl boronic acid (Combi-Blocks Inc.) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-108 | 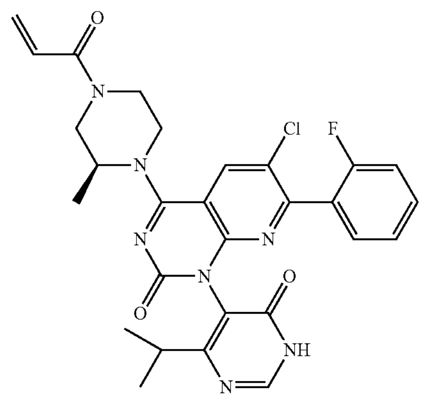 [SMILES: C=CC(=O)N1CCN(c2nc(=O)n(-c3c(C(C)C)nc[nH]c3=O)c3nc(-c4ccccc4F)c(Cl)cc23)[C@@H](C)C1] | 6-chloro-7-(2-fluorophenyl)-4-((2S)-2-methyl-4-(2-propenoyl)-1-piperazinyl)-1-(6-oxo-4-(2-propanyl)-1,6-dihydro-5-pyrimidinyl)pyrido[2,3-d]pyrimidin-2(1H)-one | Add Step 7: de-methyl-ation using BBr₃ | Step 1: 4-isopropyl-6-methoxypyrimidin-5-amine (Intermediate I-39), Step 5: 2-fluorophenyl boronic acid (Combi-Blocks Inc.) |
| 54-109 | 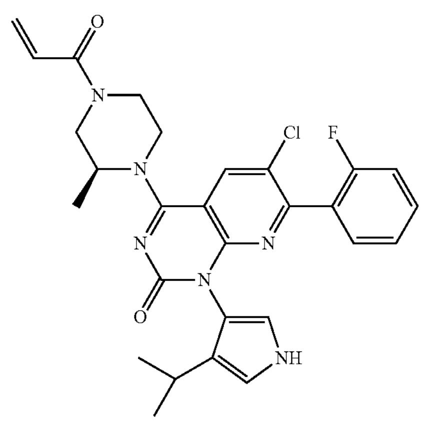 [SMILES: C=CC(=O)N1CCN(c2nc(=O)n(-c3c[nH]cc3C(C)C)c3nc(-c4ccccc4F)c(Cl)cc23)[C@@H](C)C1] | 6-chloro-7-(2-fluorophenyl)-4-((2S)-2-methyl-4-(2-propenoyl)-1-piperazinyl)-1-(4-(2-propanyl)-1H-pyrrol-3-yl)pyrido[2,3-d]pyrimidin-2(1H)-one | Add one step before Step 5 for protection of pyrrole using (Boc)₂O and DMAP | Step 1: 4-isopropyl-1H-pyrrol-3-amine (Intermediate I-41) Step 5: 2-fluorophenyl boronic acid (Combi-Blocks Inc.) |
| 54-110 | 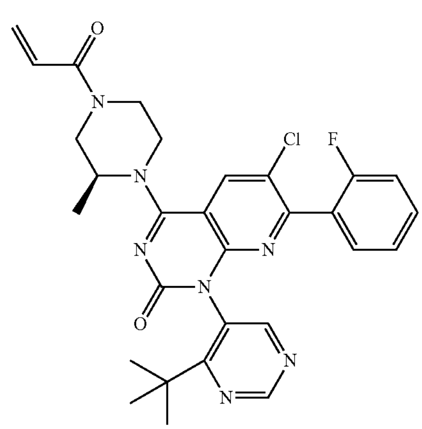 [SMILES: C=CC(=O)N1CCN(c2nc(=O)n(-c3cncnc3C(C)(C)C)c3nc(-c4ccccc4F)c(Cl)cc23)[C@@H](C)C1] | 6-chloro-7-(2-fluorophenyl)-1-(4-(2-methyl-2-propanyl)-5-pyrimidinyl)-4-((2S)-2-methyl-4-(2-propenoyl)-1-piperazinyl)pyrido[2,3-d]pyrimidin-2(1H)-one | | Step 1: 4-(tert-butyl)pyrimidin-5-amine hydrochloride (ChemShuttle), Step 5: 2-fluorophenyl boronic acid (Combi-Blocks Inc.) |

TABLE 54-continued

Compounds 54-2 to 54-115 were prepared following the procedure described in Method 54, Steps 1-6, above as follows:

| Ex.# | Chemical Structure | Name | Method Changes | Reagent |
|---|---|---|---|---|
| 54-111 | 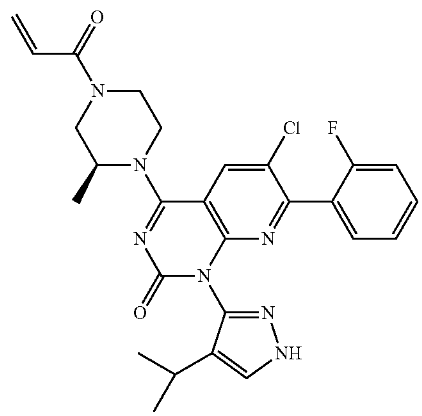 [SMILES: C=CC(=O)N1CCN(c2nc(=O)n(-c3n[nH]cc3C(C)C)c3nc(-c4ccccc4F)c(Cl)cc23)[C@@H](C)C1] | 6-chloro-7-(2-fluorophenyl)-4-((2S)-2-methyl-4-(2-propenoyl)-1-piperazinyl)-1-(4-(2-propanyl)-1H-pyrazol-3-yl)pyrido[2,3-d]pyrimidin-2(1H)-one | | Step 1: 4-(1-methylethyl)-1H-pyrazol-3-amine (Aurum Pharmatech LLC), Step 5: 2-fluorophenyl boronic acid (Combi-Blocks Inc.) |
| 54-112 | 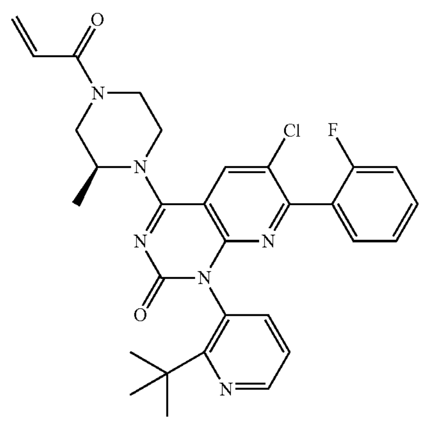 [SMILES: C=CC(=O)N1CCN(c2nc(=O)n(-c3cccnc3C(C)(C)C)c3nc(-c4ccccc4F)c(Cl)cc23)[C@@H](C)C1] | 6-chloro-7-(2-fluorophenyl)-1-(2-(2-methyl-2-propanyl)-3-pyridinyl)-4-((2S)-2-methyl-4-(2-propenoyl)-1-piperazinyl)pyrido[2,3-d]pyrimidin-2(1H)-one | | Step 1: 2-(tert-butyl)pyridin-3-amine (Intermediate I-23), Step 5: 2-fluorophenyl boronic acid (Combi-Blocks Inc.) |

Method 55

Example 55-1: 6-Chloro-7-(2-fluoro-6-hydroxyphenyl)-1-(3-methyl-5-(2-propanyl)-1,2-oxazol-4-yl)-4-((2S)-2-methyl-4-(2-propenoyl)-1-piperazinyl)pyrido[2,3-d]pyrimidin-2(1H)-one

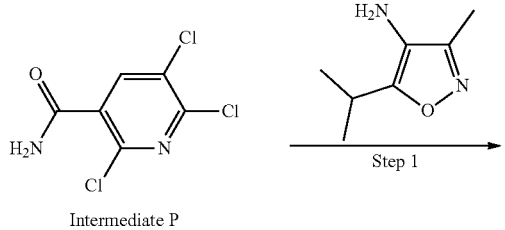

Intermediate P

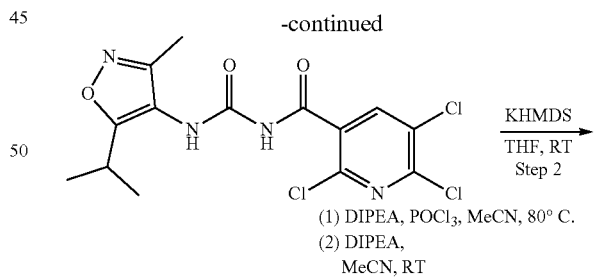

(1) DIPEA, POCl$_3$, MeCN, 80° C.
(2) DIPEA, MeCN, RT

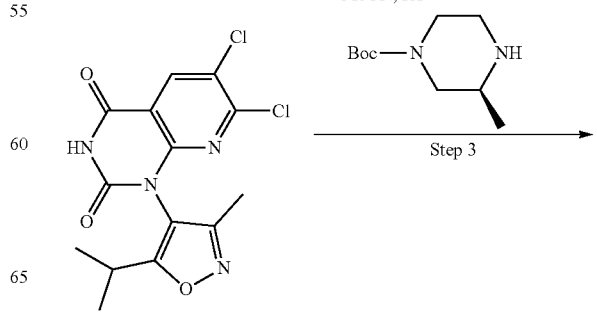

-continued

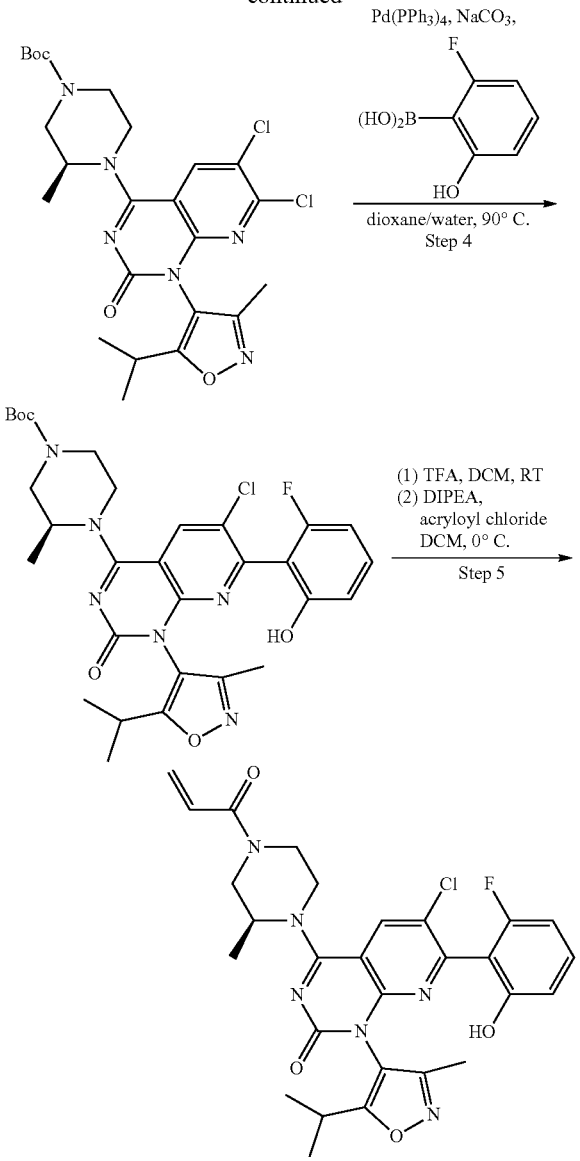

Step 1: 2,5,6-Trichloro-N-((5-isopropyl-3-methyl-isoxazol-4-yl)carbamoyl)nicotinamide To a grey heterogeneous mixture of 2,5,6-trichloronicotinamide (Intermediate P, 2.5 g, 11 mmol) in THF (22 mL) was added oxalyl chloride, 2 M solution in DCM (5.8 mL, 11.6 mmol) at rt. The resulting yellow heterogeneous mixture was stirred and heated at 65° C. After 4 h, the mixture was cooled to 0° C. and treated with a white suspension of 5-isopropyl-3-methylisoxazol-4-amine hydrochloride (1.96 g, 11.08 mmol, Enamine, Monmouth Junction, N.J., USA) and DIPEA (3.9 mL, 22.2 mmol) in THF (5 mL) and the mixture was stirred at 0° C. After 5 min, the cooling bath was removed and the mixture was stirred at rt for 2 h. The mixture was concentrated in vacuo to give the crude product as yellow syrup. The residue was partitioned between EtOAc (100 mL) and saturated NaHCO$_3$ (100 mL) and the organic extract was washed with brine (1×100 mL) and dried over Na$_2$SO$_4$. The solution was filtered and concentrated in vacuo and the resulting residue was suspended in acetonitrile (20 mL), filtered and the solid was washed with acetonitrile (20 mL), and dried to give 2,5,6-trichloro-N-((5-isopropyl-3-methylisoxazol-4-yl)carbamoyl)nicotinamide (2.84 g, 7.26 mmol, 65.5% yield) as an off-white solid. $^1$H NMR (400 MHz, DMSO-d$_6$) δ ppm 11.31 (br s, 1H), 9.22 (br s, 1H), 8.62 (s, 1H), 3.02-3.16 (m, 1H), 2.11 (s, 3H), 1.23 (d, J=7.0 Hz, 6H). m/z (ESI, +ve ion): 390.8 (M+H)$^+$.

Step 2: 6,7-Dichloro-1-(5-isopropyl-3-methylisoxazol-4-yl)pyrido[2,3-d]pyrimidine-2,4(1H,3H)-dione To a cooled mixture of 2,5,6-trichloro-N-((5-isopropyl-3-methylisoxazol-4-yl)carbamoyl)nicotinamide (2.84 g, 7.24 mmol) in THF (24 mL) at 0° C. was added dropwise KHMDS, 1 M solution in THF (14.5 mL, 14.5 mmol) and the mixture was stirred at 0° C. After 30 min, the cooling bath was removed and the reddish brown homogeneous mixture was stirred at rt for 1 h. The mixture was quenched with satd. ammonium chloride (50 mL) and brine (50 mL) and extracted with EtOAc (2×50 mL). The organic extract was dried over Na$_2$SO$_4$ and the solution was filtered and concentrated in vacuo. The crude product was purified by silica gel chromatography (eluent: 0-50% EtOAc/heptane) to provide 6,7-dichloro-1-(5-isopropyl-3-methylisoxazol-4-yl)pyrido[2,3-d]pyrimidine-2,4(1H,3H)-dione (1.68 g, 66% yield). This material was used without further purification in the following step. $^1$H NMR (400 MHz, DMSO-d$_6$) δ ppm 12.24 (s, 1H), 8.56 (s, 1H), 3.00-3.13 (m, 1H), 2.04 (s, 3H), 1.15 (dd, J=6.9, 4.3 Hz, 6H). m/z (ESI, +ve ion): 355.0 (M+H)$^+$.

Step 3: tert-Butyl (S)-4-(6,7-dichloro-1-(5-isopropyl-3-methylisoxazol-4-yl)-2-oxo-1,2-dihydropyrido[2,3-d]pyrimidin-4-yl)-3-methylpiperazine-1-carboxylate A solution of 6,7-dichloro-1-(5-isopropyl-3-methylisoxazol-4-yl)pyrido[2,3-d]pyrimidine-2,4(1H,3H)-dione (1.69 g, 4.74 mmol), DIPEA (1.1 mL, 6.2 mmol), and phosphoryl trichloride (0.53 ml, 5.7 mmol) in acetonitrile (2 ml) was stirred at 80° C. for 1 h. The reaction mixture cooled to rt, DIPEA (3.4 mL, 19.4 mmol) and tert-butyl (S)-3-methylpiperazine-1-carboxylate (1.04 g, 5.21 mmol) were added and the reaction was stirred at rt for 30 min. The mixture was poured into cold, satd. NaHCO$_3$ (5 mL) and stirred vigorously for 10 min. The mixture was partitioned between EtOAc (100 mL), and satd. NaHCO$_3$ (75 mL), the organic layer was washed with satd. NaHCO$_3$ (75 mL). The organic extract was dried over Na$_2$SO$_4$, filtered and concentrated in vacuo. The crude product was purified by silica gel chromatography (eluent: 0-5% MeOH-DCM) to provide tert-butyl (S)-4-(6,7-dichloro-1-(5-isopropyl-3-methylisoxazol-4-yl)-2-oxo-1,2-dihydropyrido[2,3-d]pyrimidin-4-yl)-3-methylpiperazine-1-carboxylate (2.5 g, 98% yield). m/z (ESI, +ve ion): 537.0 (M+H)$^+$.

Step 4: tert-Butyl (3S)-4-(6-chloro-7-(2-fluoro-6-hydroxyphenyl)-1-(5-isopropyl-3-methylisoxazol-4-yl)-2-oxo-1,2-dihydropyrido[2,3-d]pyrimidin-4-yl)-3-methylpiperazine-1-carboxylate A mixture of tert-butyl (S)-4-(6,7-dichloro-1-(5-isopropyl-3-methylisoxazol-4-yl)-2-oxo-1,2-dihydropyrido[2,3-d]pyrimidin-4-yl)-3-methylpiperazine-1-carboxylate (0.6 g, 1.1 mmol), (2-fluoro-5-hydroxyphenyl)boronic acid (261 mg, 1.68 mmol), Pd(PPh$_3$)$_4$ (0.13 g, 0.11 mmol) and sodium carbonate (0.355 g, 3.35 mmol) was purged with N2 followed by the addition of 1,4-dioxane (12 mL) and water (3 mL). The mixture was heated at 80° C. for 1 h then quenched with sat. NaHCO$_3$, extracted with EtOAc, dried over Na$_2$SO$_4$, filtered and concentrated in vacuo. The crude product was purified by silica gel chromatography (eluent: 0-5% MeOH/DCM) to provide tert-butyl (3S)-4-(6-chloro-7-(2-fluoro-6-hydroxyphenyl)-1-(5-isopropyl-3-methylisoxazol-4-yl)-2-oxo-1,2-dihydropyrido[2,3-d]pyrimidin-4-yl)-3-methylpiperazine-1-carboxylate (0.22 g, 0.37 mmol, 33% yield) with some traces of ether byproduct. m/z (ESI, +ve ion): 613.0 (M+H)$^+$.

Step 5: 6-Chloro-7-(2-fluoro-6-hydroxyphenyl)-1-(3-methyl-5-(2-propanyl)-1,2-oxazol-4-yl)-4-((2S)-2-methyl-4-(2-propenoyl)-1-piperazinyl)pyrido[2,3-d]pyrimidin-2(1H)-one To a solution of tert-butyl (3S)-4-(6-chloro-7-(2-fluoro-6-hydroxyphenyl)-1-(5-isopropyl-3-methylisoxazol-4-yl)-2-oxo-1,2-dihydropyrido[2,3-d]pyrimidin-4-yl)-3-methylpiperazine-1-carboxylate (0.224 g, 0.365 mmol) in DCM (5 mL) at rt was added TFA (5 mL, 64.9 mmol) and the mixture was stirred at rt for 30 min. The mixture was concentrated in vacuo to afford 6-chloro-7-(2-fluoro-6-hydroxyphenyl)-1-(5-isopropyl-3-methylisoxazol-4-yl)-4-((S)-2-methylpiperazin-1-yl)pyrido[2,3-d]pyrimidin-2(1H)-one. The crude product was dissolved in DCM (15 mL), treated with DIPEA (0.26 mL, 1.5 mmol) and a solution of acryloyl chloride (0.021 mL, 0.26 mmol) in DCM (1 mL) in small portions. After 30 min, the mixture was diluted with DCM, washed with satd. NaHCO$_3$, with satd. ammonium chloride. The organic extract was dried over Na$_2$SO$_4$, filtered and concentrated in vacuo. The crude product was purified by silica gel chromatography (eluent: 0-5% MeOH/DCM) to provide 6-chloro-7-(2-fluoro-6-hydroxyphenyl)-1-(3-methyl-5-(2-propanyl)-1,2-oxazol-4-yl)-4-((2S)-2-methyl-4-(2-propenoyl)-1-piperazinyl)pyrido[2,3-d]pyrimidin-2(1H)-one (0.155 g, 0.137 mmol, 37.4% yield). $^1$H NMR (400 MHz, DMSO-d$_6$) δ ppm 10.18 (br s, 1H), 8.40 (br d, J=13.1 Hz, 1H), 7.25-7.32 (m, 1H), 6.79-6.91 (m, 1H), 6.68-6.79 (m, 2H), 6.20 (br d, J=16.6 Hz, 1H), 5.74-5.79 (m, 1H), 4.93 (br d, J=27.8 Hz, 1H), 3.97-4.46 (m, 3H), 3.36-3.88 (m, 2H), 2.98-3.28 (m, 1H), 2.85-2.97 (m, 1H), 1.92 (br d, J=6.0 Hz, 3H), 1.33 (dd, J=12.6, 6.6 Hz, 3H), 1.10 (d, J=6.8 Hz, 3H), 1.05 (dd, J=6.9, 2.6 Hz, 3H). $^{19}$F NMR (376 MHz, DMSO-d$_6$) δ ppm −115.73 (br dd, J=82.4, 10.4 Hz, 1F). m/z (ESI, +ve ion): 567.2 (M+H)$^+$.

TABLE 55

Compounds 55-2 to 55-43 were prepared following the procedure described in Method 55, Steps 1-5, above as follows:

| Ex. # | Chemical Structure | Name | Method Changes | Reagent |
|---|---|---|---|---|
| 55-2 | 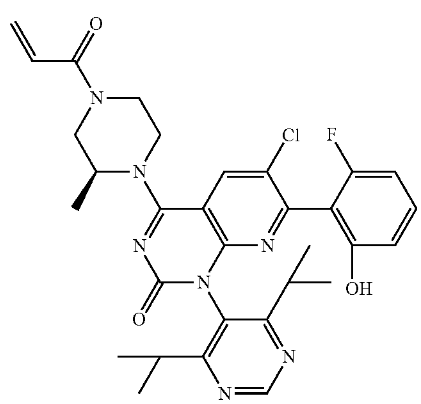 [SMILES: C=CC(=O)N1CCN(c2nc(=O)n(-c3c(C(C)C)ncnc3C(C)C)c3nc(-c4c(O)cccc4F)c(Cl)cc23)[C@@H](C)C1] | 6-chloro-1-(4,6-di(2-propanyl)-5-pyrimidinyl)-7-(2-fluoro-6-hydroxyphenyl-4-((2S)-2-methyl-4-(2-propenoyl)-1-piperazinyl)pyrido[2,3-d]pyrimidin-2(1H)-one | Step 2: −20 °C., Step 4: KOAc | Step 1: 4,6-diisopropylpyrimidin-5-amine (Intermediate U), Step 4: 2-fluoro-6-hydroxyphenyl boronic acid (Wuxi) |
| 55-3 | 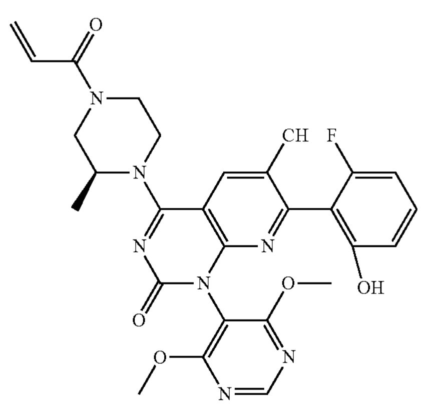 [SMILES: C=CC(=O)N1CCN(c2nc(=O)n(-c3c(OC)ncnc3OC)c3nc(-c4c(O)cccc4F)c(C)cc23)[C@@H](C)C1] | 6-chloro-1-(4,6-dimethoxy-5-pyrimidinyl)-7-(2-fluoro-6-hydroxyphenyl)-4-((2S)-methyl-4-(2-propenoyl)-1-piperazinyl)pyrido[2,3-d]pyrimidin-2(1H)-one | Step 2: −20° C., Step 4: KOAc | Step 1: 4,6-dimethoxypyrimidin-5-amine (Ark Pharm, Inc.), Step 4: 2-fluoro-6-hydroxyphenyl boronic acid (Wuxi) |

TABLE 55-continued

Compounds 55-2 to 55-43 were prepared following the procedure described in Method 55, Steps 1-5, above as follows:

| Ex. # | Chemical Structure | Name | Method Changes | Reagent |
|---|---|---|---|---|
| 55-4 | 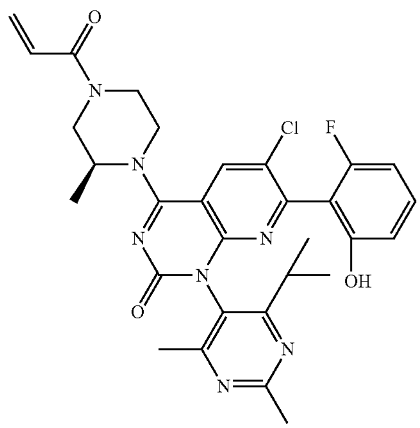 [SMILES: C=CC(=O)N1CCN(c2nc(=O)n(-c3c(C)nc(C)nc3C(C)C)c3nc(-c4c(O)cccc4F)c(Cl)cc23)[C@@H](C)C1] | 6-chloro-1-(2,4-dimethyl-6-(2-propanyl)-5-pyrimidinyl)-7-(2-fluoro-6-hydroxyphenyl)-4-((2S)-2-methyl-4-(2-propenoyl)-1-piperazinyl)pyrido[2,3-d]pyrimidin-2(1H)-one | Step 2: −20° C., Step 4: KOAc | Step 1: 4-isopropyl-2,6-dimethylpyrimidin-5-amine (Intermediate I-28), Step 4: 2-fluoro-6-hydroxyphenyl boronic acid (Wuxi) |
| 55-5 | 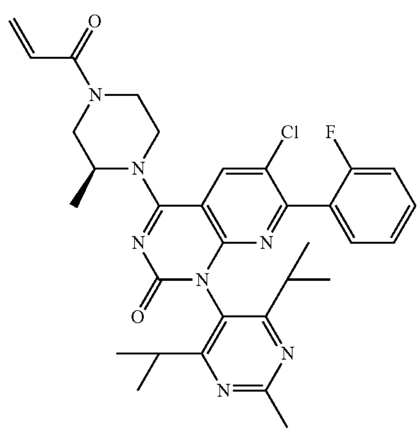 [SMILES: C=CC(=O)N1CCN(c2nc(=O)n(-c3c(C(C)C)nc(C)nc3C(C)C)c3nc(-c4ccccc4F)c(Cl)cc23)[C@@H](C)C1] | 6-chloro-7-(2-fluorophenyl)-1-(2-methyl-4,6-di(2-propanyl)-5-pyrimidinyl)-4-((2S)-2-methyl-4-(2-propenoyl)-1-piperazinyl)pyrido[2,3-d]pyrimidin-2(1H)-one | Step 2: −20° C., Step 4: KOAc | Step 1: 4,6-diisopropyl-2-methylpyrimidin-5-amine (Intermediate I-29), Step 4: (2-fluoroethyl)boronic acid (Combi-Blocks) |
| 55-6 | 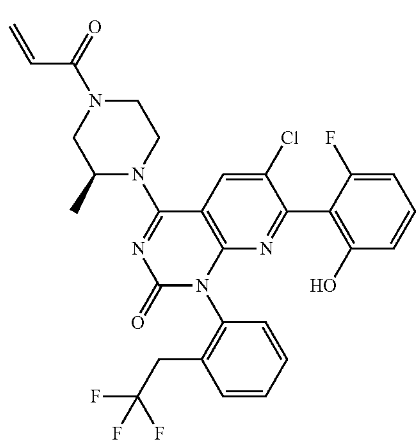 [SMILES: C=CC(=O)N1CCN(c2nc(=O)n(-c3ccccc3CC(F)(F)F)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(2-(2,2,2-trifluoroethyl)phenyl)pyrido[2,3-d]pyrimidin-2(1H)-one | Step 4: Pd(dppf)Cl₂ and K₂CO₃ | Step 1: 2-(2,2,2-trifluoroethyl)aniline (Enamine), Step 4: (2-fluoro-6-hydroxyphenyl) boronic acid (Wuxi) |

TABLE 55-continued

Compounds 55-2 to 55-43 were prepared following the procedure described in Method 55, Steps 1-5, above as follows:

| Ex. # | Chemical Structure | Name | Method Changes | Reagent |
|---|---|---|---|---|
| 55-7 | 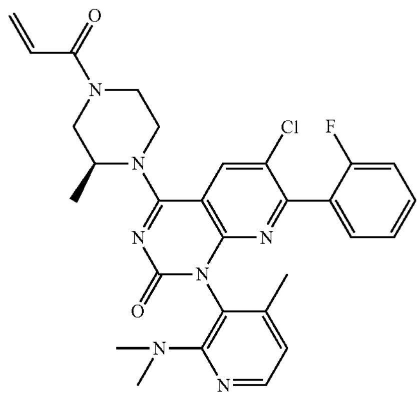 | 6-chloro-1-(2-(dimethylamino)-4-methyl)-3-pyridinyl)-7-(2-fluorophenyl)-4-((2S)-2-methyl-4-(2-propenoyl)-1-piperazinyl)pyrido[2,3-d]pyrimidin-2(1H)-one | Step 2: KOt-Bu, Step 4: Pd(dppf)Cl$_2$ and K$_2$CO$_3$ | Step 1: N,N-4-trimethylpyridine-2,3-diamine (Intermediate I-14) Step 4: (2-fluorophenyl)boronic acid (Combi-Blocks Inc.) |
| 55-8 | 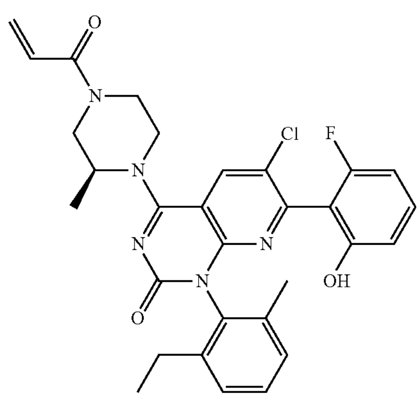 [SMILES: C=CC(=O)N1CCN(c2nc(=O)n(-c3c(C)cccc3CC)c3nc(-c4c(O)cccc4F)c(Cl)cc23)[C@@H](C)C1] | 6-chloro-1-(2-ethyl-6-methylphenyl)-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 2-amino-3-ethyltoluene (Sigma-Aldrich Corporation), Step 4: 2-fluoro-6-hydroxyphenyl boronic acid Combi-Blocks Inc.) |
| 55-9 | 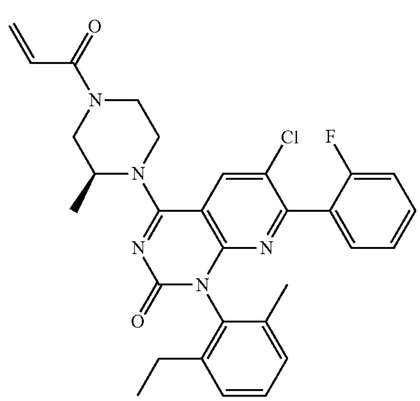 | 6-chloro-1-(2-ethyl-6-methylphenyl)-7-(2-fluorophenyl)-4-((2S)-2-methyl-4-(2-propenoyl)-1-piperazinyl)pyrido[2,3-d]pyrimidin-2(1H)-one | | Step 1: 2-amino-3-ethyltoluene (Sigma-Aldrich Corporation), Step 4: (2-fluorophenyl)boronic acid (Combi-Blocks Inc.) |

TABLE 55-continued

Compounds 55-2 to 55-43 were prepared following the procedure described in Method 55, Steps 1-5, above as follows:

| Ex. # | Chemical Structure | Name | Method Changes | Reagent |
|---|---|---|---|---|
| 55-10 | 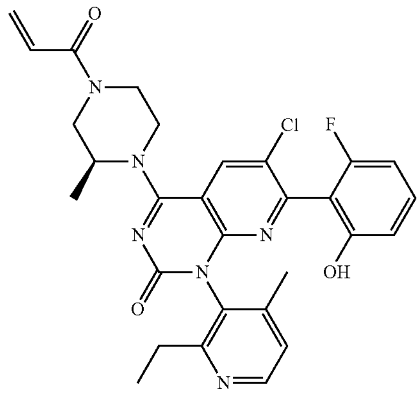 | 6-chloro-1-(2-ethyl-4-methyl-3-pyridinyl)-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 2-ethyl-4-methylpyridin-3-amine (Intermediate W), Step 4: (2-fluoro-6-hydroxyphenyl) boronic acid (Wuxi) |
| 55-11 | 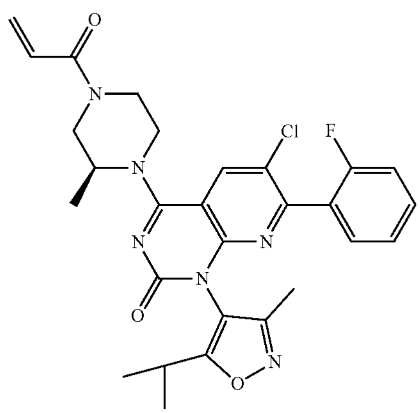 [SMILES: C=CC(=O)N1CCN(c2nc(=O)n(-c3c(C)noc3C(C)C)c3nc(-c4ccccc4F)c(Cl)cc23)[C@@H](C)C1] | 6-chloro-7-(2-fluoropheny)-1-(3-methyl-5-(2-propanyl)-1,2-oxazol-4-yl)-4-((2S)-2-methyl-4-(2-propenoyl)-1-piperazinyl)pyrido[2,3-d]pyrimidin-2(1H)-one | | Step 1: 5-isopropyl-3-methylisoxazol-4-amine hydrochloride (Enamine), Step 4: (2-fluorophenyl)boronic acid (Combi-Blocks Inc.) |
| 55-12 | 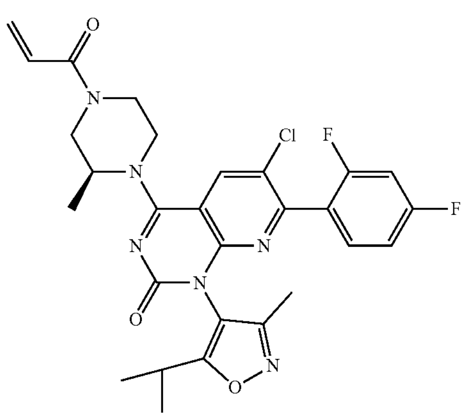 [SMILES: C=CC(=O)N1CCN(c2nc(=O)n(-c3c(C)noc3C(C)C)c3nc(-c4ccc(F)cc4F)c(Cl)cc23)[C@@H](C)C1] | 6-chloro-7-(2,4-difuorophenyl)-1-(3-methyl-5-(2-propanyl)-1,2-oxazol-4-yl)-4-((2S)-2-methyl-4-(2-propenoyl)-1-piperazinyl)pyrido[2,3-d]pyrimidin-2(1H)-one | | Step 1: 5-isopropyl-3-meythylisoxazol-4-amine hydrochloride (Enamine), Step 4: 2,4-difluorobenzeneboronic acid (Sigma-Aldrich Corporation) |

TABLE 55-continued

Compounds 55-2 to 55-43 were prepared following the procedure described in Method 55, Steps 1-5, above as follows:

| Ex. # | Chemical Structure | Name | Method Changes | Reagent |
|---|---|---|---|---|
| 55-13 | 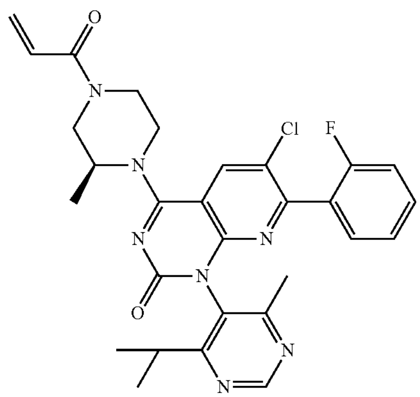 | 6-chloro-7-(2-fluorophenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | | Step 1: 4-isopropyl-6-methylpyrimidin-5-amine (Intermediate I-5). Step 4: (2-fluorophenyl)boronic acid Combi-Blocks Inc.) |
| 55-14 | 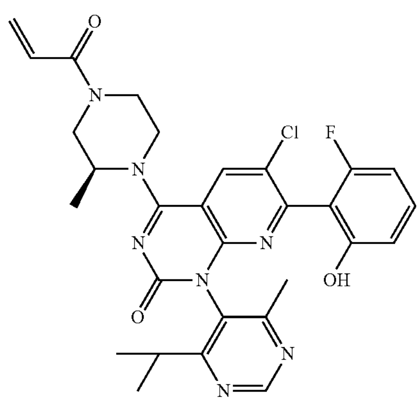 | 6-chloro-7-(2-fluoro-6-hydroxyphenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | | Step 1: 4-isopropyl-6-methylpyrimidin-5-amine (Intermediate I-5), Step 4: (2-fluoro-6-hydroxyphenyl) boronic acid (Wuxi) |
| 55-15 | 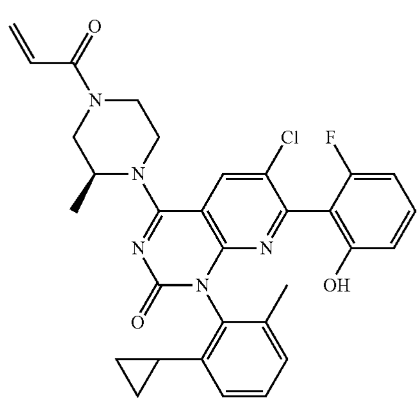 | 6-chloro-1-(2-cyclopropyl-6-methylphenyl)-7-(2-fluoro-6-hydroxyphenyl)-4-((2S)-2-methyl-4-(2-propenoyl)-1-piperazinyl)pyrido[2,3-d]pyrimidin-2(1H)-one | Step 1: 65° C., aniline in MeCN, Step 2: 0° C., Step 3: 70° C., then 0° C. | Step 1: 2-cyclopropyl-6-methylaniline (Intermediate I-9), Step 4: (2-fluoro-6-hydroxyphenyl) boronic acid (Wuxi) |

TABLE 55-continued

Compounds 55-2 to 55-43 were prepared following the procedure described in Method 55, Steps 1-5, above as follows:

| Ex. # | Chemical Structure | Name | Method Changes | Reagent |
|---|---|---|---|---|
| 55-16 | 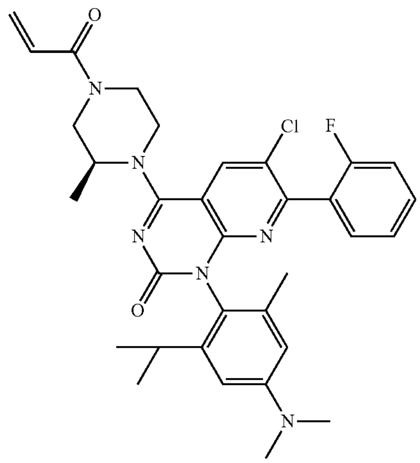 [SMILES: C=CC(=O)N1CCN(c2nc(=O)n(-c3c(C)cc(N(C)C)cc3C(C)C)c3nc(-c4ccccc4F)c(Cl)cc23)[C@@H](C)C1] | 6-chloro-1-(4-(dimethylamino)-2-methyl-6-(2-propanyl)phenyl)-7-(2-fluorophenyl)-4-((2S)-2-methyl-4-(2-propenoyl)-1-piperazinyl)pyrido[2,3-d]pyrimidin-2(1H)-one | | Step 1: 3-isopropyl-N',N'-5-trimethylbenzene-1,4-diamine (Intermediate I-8), Step 4: (2-fluorophenyl)boronic acid (Combi-Blocks Inc.) |
| 55-17 | 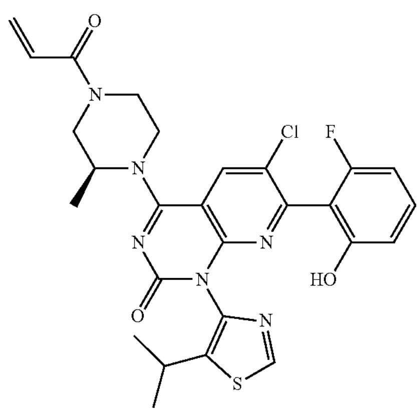 [SMILES: C=CC(=O)N1CCN(c2nc(=O)n(-c3ncsc3C(C)C)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(5-(2-propanyl)-1,3-thiazol-4-yl)pyrido[2,3-d]pyrimidin-2(1H)-one | Step 1: DIPEA instead of TEA; Step 3: 0° C. instead of rt; Step 4: Pd(dppf)Cl$_2$ and KOAc instead of Pd(PPh$_3$)$_4$ and Na$_2$CO$_3$ | Step 1: 4-amino-5-(iso-propyl)thiazole hydrochloride (Enamine), Step 4: (2-fluoro-6-hydroxyphenyl) boronic acid (Wuxi) |
| 55-18 | 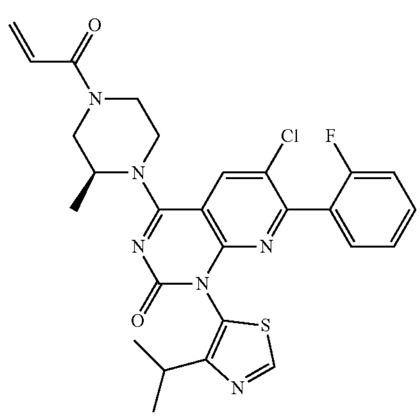 [SMILES: C=CC(=O)N1CCN(c2nc(=O)n(-c3scnc3C(C)C)c3nc(-c4ccccc4F)c(Cl)cc23)[C@@H](C)C1] | 6-chloro-7-(2-fluorophenyl)-4-((2S)-2-methyl-4-(2-propenoyl)-1-piperazinyl)-1-(4-(2-propanyl)-1,3-thiazol-5-yl)pyrido[2,3-d]pyrimidin-2(1H)-one | Step 1: without TEA; Step 3-2: 0° C. instead of rt; Step 4: Pd(dppf)Cl$_2$ and KOAc instead of Pd(PPh$_3$)$_4$ and Na$_2$CO$_3$ | Step 1: 4-(propan-2-yl)-1,3-thiazol-5-amine (Enamine), Step 4: (2-fluorophenyl)boronic acid (Combi-Blocks Inc.) |

TABLE 55-continued

Compounds 55-2 to 55-43 were prepared following the procedure described in
Method 55, Steps 1-5, above as follows:

| Ex. # | Chemical Structure | Name | Method Changes | Reagent |
|---|---|---|---|---|
| 55-19 | 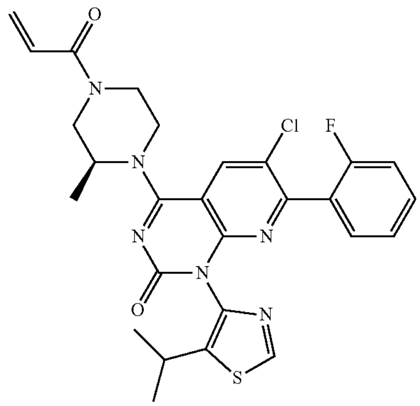 [SMILES: C=CC(=O)N1CCN(c2nc(=O)n(-c3ncsc3C(C)C)c3nc(-c4ccccc4F)c(Cl)cc23)[C@@H](C)C1] | 6-chloro-7-(2-fluorophenyl)-4-((2S)-2-methyl-4-(2-propenoyl)-1-piperazinyl)-1-(5-(2-propanyl)-1,3-thiazol-4-yl)pyrido[2,3-d]pyrimidin-2(1H)-one | Step 1: DIPEA instead of TEA; Step 3-2: 0° C. instead of rt, Step 4: Pd(dppf)Cl$_2$ and KOAc instead of Pd(PPh$_3$)$_4$ and Na$_2$CO$_3$ | Step 1: 4-amino-5-(iso-propyl)thiazole hydrochloride (Enamine), Step 4: (2-fluorophenyl)boronic acid (Combi-Blocks Inc.) |
| 55-20 | 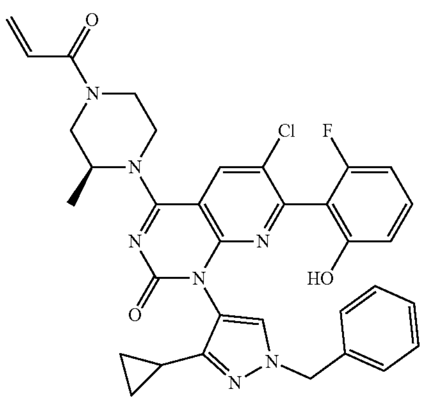 [SMILES: C=CC(=O)N1CCN(c2nc(=O)n(-c3cn(Cc4ccccc4)nc3C3CC3)c3nc(-c4c(O)cccc4F)c(Cl)cc23)[C@@H](C)C1] | 1-(1-benzyl-3-cyclopropyl-1H-pyrazol-4-yl)-6-chloro-7-(2-fluoro-6-hydroxyphenyl)-4-((2S)-2-methyl-4-(2-propenoyl)-1-piperazinyl)pyrido[2,3-d]pyrimidin-2(1H)-one | Step 1: without TEA, Step 3-2: 0° C. instead of rt; Step 4: Pd(dppf)Cl$_2$ and KOAc instead of Pd(PPh$_3$)$_4$ and Na$_2$CO$_3$ | Step1: 1-benzyl-3-cyclopropyl-1H-pyrazol-4-amine (Intermediate I-7), Step 4: (2-fluoro-6-hydroxyphenyl) boronic acid (Wuxi) |
| 55-21 | 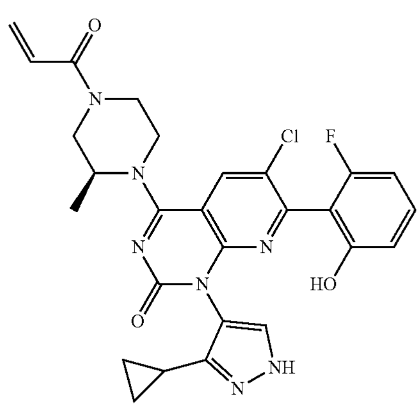 [SMILES: C=CC(=O)N1CCN(c2nc(=O)n(-c3c[nH]nc3C3CC3)c3nc(-c4c(O)cccc4F)c(Cl)cc23)[C@@H](C)C1] | 6-chloro-1-(3-cyclopropyl-1H-pyrazol-4-yl)-7-(2-fluoro-6-hydroxyphenyl)-4-((2S)-2-methyl-4-(2-propenoyl)-1-piperazinyl)pyrido[2,3-d]pyrimidin-2(1H)-one | Step 1: without TEA, Step 3: 0 °C. instead of rt; Step 4: Pd(dppf)Cl$_2$ and KOAc instead of Pd(PPh$_3$)$_4$ and Na$_2$CO$_3$; Step 5: (1) H$_2$, Pd(OH)$_2$/C MeOH, HCl, 80 bar, 50° C. (H-Cube); (2) DIPEA, acryloyl chloride DCM, 0 °C. | Step 1: 1-benzyl-3-cyclopropyl-1H-pyrazol-4-amine (Intermediate I-7), Step 4: (2-fluoro-6-hydroxyphenyl) boronic acid (Wuxi) |

TABLE 55-continued

Compounds 55-2 to 55-43 were prepared following the procedure described in Method 55, Steps 1-5, above as follows:

| Ex. # | Chemical Structure | Name | Method Changes | Reagent |
|---|---|---|---|---|
| 55-22 | 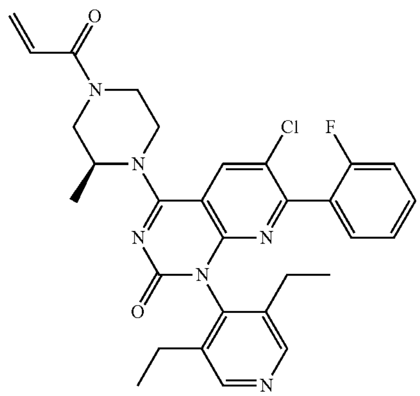 [SMILES: C=CC(=O)N1CCN(c2nc(=O)n(-c3c(CC)cncc3CC)c3nc(-c4ccccc4F)c(Cl)cc23)[C@@H](C)C1] | 6-chloro-1-(3,5-diethyl-4-pyridinyl)-7-(2-fluorophenyl)-4-((2S)-2-methyl-4-(2-propenoyl)-1-piperazinyl)pyrido[2,3-d]pyrimidin-2(1H)-one | Step 1: 65° C., Step 1: omit TEA, Step 4: 100° C., Step 5: omit DCM; Step 5: rt | Step 1: 3,5-diethylpyridin-4-amine (Enamine); Step 4: (2-fluorophenyl)boronic acid (TCI America) |
| 55-23 | 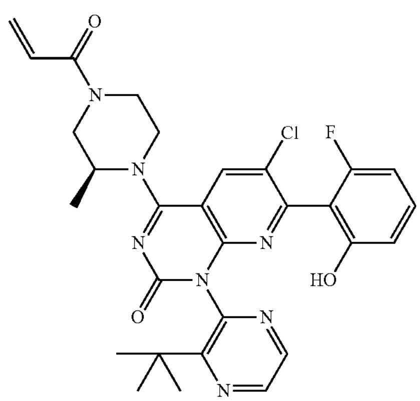 [SMILES: C=CC(=O)N1CCN(c2nc(=O)n(-c3nccnc3C(C)(C)C)c3nc(-c4c(O)cccc4F)c(Cl)cc23)[C@@H](C)C1] | 6-chloro-7-(2-fluoro-6-hydroxyphenyl)-1-(3-(2-methyl-2-propanyl)-2-pyrazinyl)-4-((2S)-2-methyl-4-(2-propenoyl)-1-piperazinyl)pyrido[2,3-d]pyrimidin-2(1H)-one | Step 1: 65° C.; step 1: omit TEA, Step 5: omit DCM, Step 5: rt | Step 1: 3-(tert-butyl)pyrazin-2-amine (Intermediate I-6), Step 4: potassium trifluoro(2-fluoro-6-hydroxyphenyl)borate (Intermediate Q) |
| 55-24 | 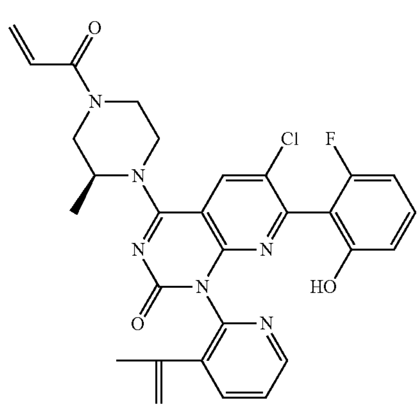 [SMILES: C=CC(=O)N1CCN(c2nc(=O)n(-c3ncccc3C(=C)C)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(3-(1-propen-2-yl)-2-pyridinyl)pyrido[2,3-d]pyrimidin-2(1H)-one | Step 4: Pd(dppf)Cl$_2$ and potassium acetate | Step 1: 3-(prop-1-en-2-yl)pyridin-2-amine (Intermediate I-10), Step 4: (2-fluoro-6-hydroxyphenyl)boronic acid (Wuxi) |

TABLE 55-continued

Compounds 55-2 to 55-43 were prepared following the procedure described in Method 55, Steps 1-5, above as follows:

| Ex. # | Chemical Structure | Name | Method Changes | Reagent |
|---|---|---|---|---|
| 55-25 | 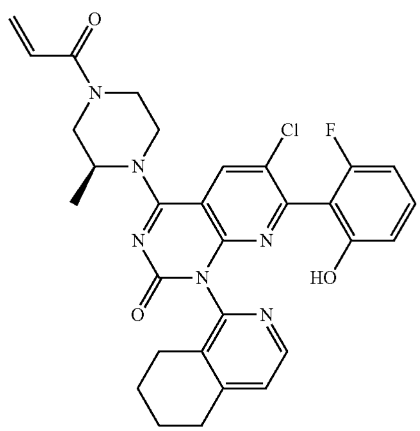 [SMILES: C=CC(=O)N1CCN(c2nc(=O)n(-c3nccc4c3CCCC4)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(5,6,7,8-tetrahydro-1-isoquinolinyl)pyrido[2,3-d]pyrimidin-2(1H)-one | Step 4: Pd(dppf)Cl$_2$ and KOAc | Step 1: 5,6,7,8-tetrahydro-isoquinolin-1-ylamine (J & W Pharmlab, LLC), Step 4: (2-fluoro-6-hydroxyphenyl) boronic acid (Wuxi) |
| 55-26 | 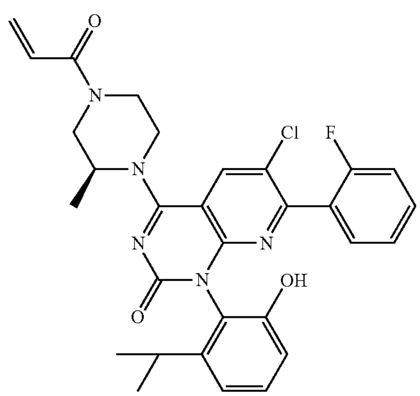 | 6-chloro-7-(2-fluorophenyl)-1-(2-hydroxy-6-(2-propanyl)phenyl)-4-((2S)-2-methyl-4-(2-propenoyl)-1-piperazinyl)pyrido[2,3-d]pyrimidin-2(1H)-one | Step 2: NaOt-Bu, toluene, 60° C., Step 5: (1) BBr$_3$, DCM, rt; 2) DIPEA, acryloyl chloride DCM, 0 °C. | Step 1: 2-isopropyl-6-methoxyaniline (HDH Pharma) Step 4: (2-fluoro-6-hydroxyphenyl) boronic acid (Wuxi) |
| 55-27 | 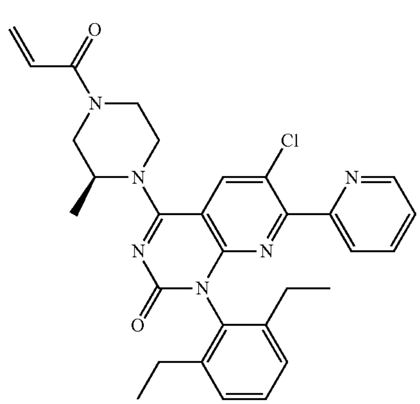 | 6-chloro-1-(2,6-diethylphenyl)-4-((2S)-2-methyl-4-(2-propenoyl)-1-piperazinyl)-7-(2-pyridinyl)pyrido[2,3-d]pyrimidin-2(1H)-one | Step 4: Pd(PPh$_3$)$_2$Cl$_2$ in DMF (no base) | Step 1: 2,6-diethylaniline (Sigma-Aldrich Corporation), Step 4: 2-(tributylstannyl) pyridine (Sigma-Aldrich Corporation) |

TABLE 55-continued

Compounds 55-2 to 55-43 were prepared following the procedure described in
Method 55, Steps 1-5, above as follows:

| Ex. # | Chemical Structure | Name | Method Changes | Reagent |
|---|---|---|---|---|
| 55-28 | 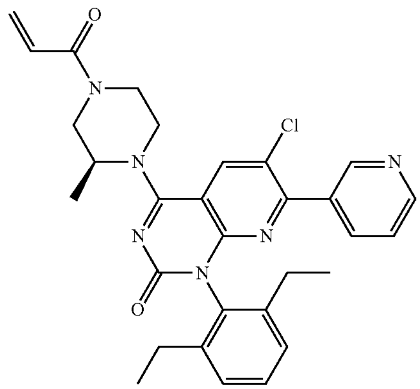 | 6-chloro-1-(2,6-diethylphenyl)-4-((2S)-2-methyl-4-(2-propenoyl)-1-piperazinyl)-7-(3-pyridinyl)pyrido[2,3-d]pyrimidin-2(1H)-one | Step 4: bis-(di-tert-butyl(4-dimethylaminophenyl)phosphine)dichloropalladium(II) | Step 1: 2,6-diethylaniline (Sigma-Aldrich Corporation), Step 4: pyridine-3-boronic acid (Matrix Scientific) |
| 55-29 | 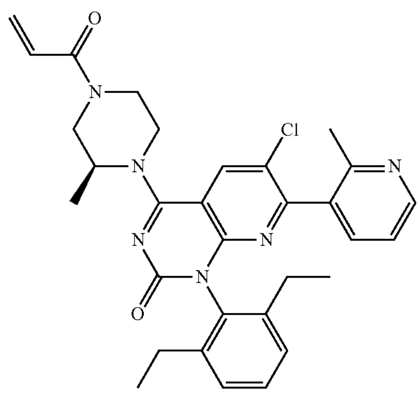 | 6-chloro-1-(2,6-diethylphenyl)-4-((2S)-2-methyl-4-(2-propenoyl)-1-piperazinyl)-7-(2-methyl-3-pyridinyl)pyrido[2,3-d]pyrimidin-2(1H)-one | Step 4: bis-(di-tert-butyl(4-dimethylaminophenyl)phosphine)dichloropalladium(II) | Step 1: 2,6-diethylaniline (Sigma-Aldrich Corporation), Step 4: (2-methylpyridin-3-yl)boronic acid (Combi Blocks Inc.) |
| 55-30 | 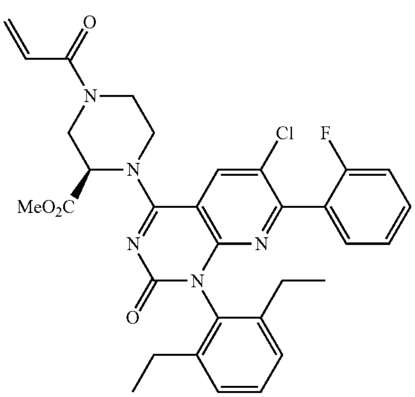 [SMILES: C=CC(=O)N1CCN(c2nc(=O)n(-c3c(CC)cccc3CC)c3nc(-c4ccccc4F)c(Cl)cc23)[C@@H](C(=O)OC)C1] | methyl (2R)-1-(6-chloro-1-(2,6-diethylphenyl)-7-(2-fluorophenyl)-2-oxo-1,2-dihydropyrido[2,3-d]pyrimidin-4-yl)-4-(2-propenoyl)-2-piperazinecarboxylate | Step 4: tetrakis(triphenylphosphine)palladium(II), sodium carbonate | Step 1: 2,6-diethylaniline (Sigma-Aldrich Corporation), Step 3: (3R)-1,3-piperazinedicarboxylic acid, 1-(1,1-dimethylethyl) 3-methyl ester (Combi Blocks Inc.), Step 4: (2-fluorophenyl)boronic acid (TCI America) |

TABLE 55-continued

Compounds 55-2 to 55-43 were prepared following the procedure described in
Method 55, Steps 1-5, above as follows:

| Ex. # | Chemical Structure | Name | Method Changes | Reagent |
|---|---|---|---|---|
| 55-31 | 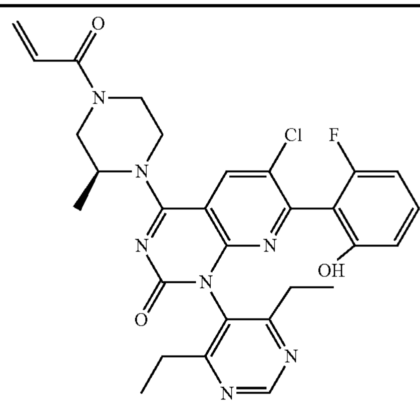 | 6-chloro-1-(4,6-diethyl-5-pyrimidinyl)-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 4,6-diethylpyrimidin-5-amine (Intermediate X), Step 4: (2-fluoro-6-hydroxyphenyl) boronic acid (Wuxi) |
| 55-32 | 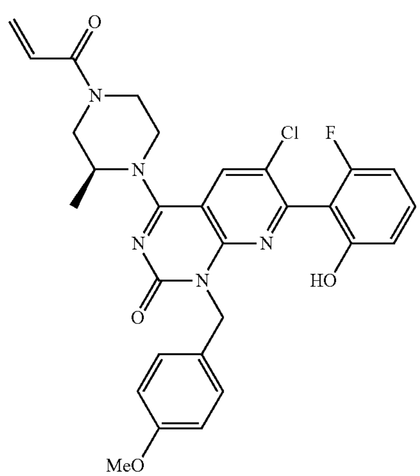 [SMILES: C=CC(=O)N1CCN(c2nc(=O)n(Cc3ccc(OC)cc3)c3nc(-c4c(O)cccc4F)c(Cl)cc23)[C@@H](C)C1] | 6-chloro-7-(2-fluoro-6-hydroxyphenyl)-1-(4-methoxybenzyl)-4-((2S)-2-methyl-4-(2-propenoyl)-1-piperazinyl)pyrido[2,3-d]pyrimidin-2(1H)-one | | Step 1: 4-methoxybenzylamine (Sigma-Aldrich Corporation), Step 4: (2-fluoro-6-hydroxyphenyl) boronic acid (Wuxi) |
| 55-33 | 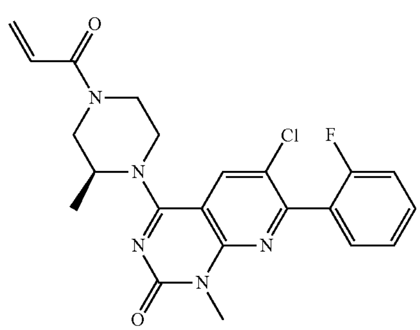 [SMILES: C=CC(=O)N1CCN(c2nc(=O)n(C)c3nc(-c4ccccc4F)c(Cl)cc23)[C@@H](C)C1] | 6-chloro-7-(2-fluorophenyl)-1-methyl-4-((2S)-2-methyl-4-(2-propenoyl)-1-piperazinyl)pyrido[2,3-d]pyrimidin-2(1H)-one | | Step 1: methylamine (Sigma-Aldrich Corporation), Step 4: (2-fluorophenyl)boronic acid (TCI America) |
| 55-34 | 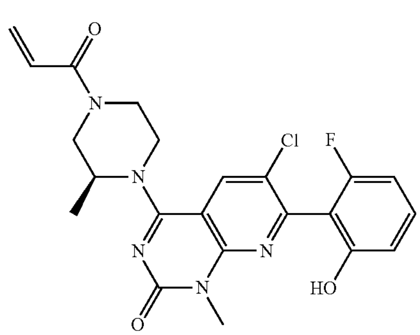 [SMILES: C=CC(=O)N1CCN(c2nc(=O)n(C)c3nc(-c4c(O)cccc4F)c(Cl)cc23)[C@@H](C)C1] | 6-chloro-7-(2-fluoro-6-hydroxyphenyl)-1-methyl-4-((2S)-2-methyl-4-(2-propenoyl)-1-piperazinyl)pyrido[2,3-d]pyrimidin-2(1H)-one | | Step 1: methylamine (Sigma-Aldrich Corporation), Step 4: (2-fluoro-6-hydroxyphenyl) boronic acid (Wuxi) |

TABLE 55-continued

Compounds 55-2 to 55-43 were prepared following the procedure described in Method 55, Steps 1-5, above as follows:

| Ex. # | Chemical Structure | Name | Method Changes | Reagent |
|---|---|---|---|---|
| 55-35 | 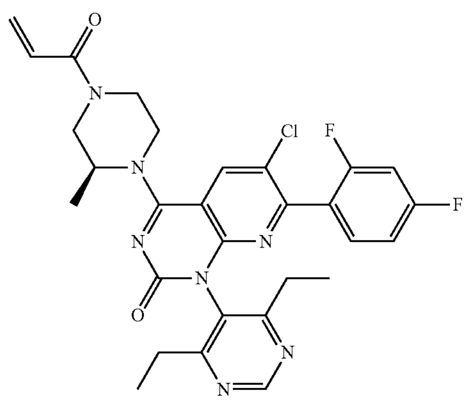 [SMILES: C=CC(=O)N1CCN(c2nc(=O)n(-c3c(CC)ncnc3CC)c3nc(-c4ccc(F)cc4F)c(Cl)cc23)[C@@H](C)C1] | 6-chloro-1-(4,6-diethyl-5-pyrimidinyl)-7-(2,4-difluorophenyl)-4-((2S)-2-methyl-4-(2-propenoyl)-1-piperazinyl)pyrido[2,3-d]pyrimidin-2(1H)-one | | Step 1: 4,6-diethylpyrimidin-5-amine (Intermediate X), Step 4: (2,4-difluorophenyl) boronic acid (Sigma-Aldrich Corporation) |
| 55-36 | 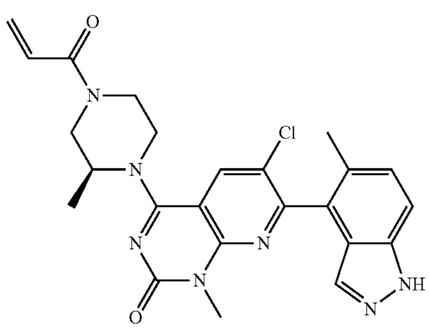 [SMILES: C=CC(=O)N1CCN(c2nc(=O)n(C)c3nc(-c4c(C)ccc5[nH]ncc45)c(Cl)cc23)[C@@H](C)C1] | 6-chloro-1-methyl-7-(5-methyl-1H-indazol-4-yl)-4-((2S)-2-methyl-4-(2-propenoyl)-1-piperazinyl)pyrido[2,3-d]pyrimidin-2(1H)-one | | Step 1: methylamine (Sigma-Aldrich Corporation), Step 4: 5-methyl-1H-indazol-4-yl boronic acid (Combi Blocks Inc.,) |
| 55-37 | 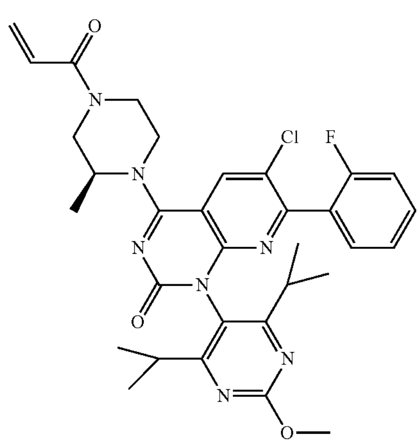 [SMILES: C=CC(=O)N1CCN(c2nc(=O)n(-c3c(C(C)C)nc(OC)nc3C(C)C)c3nc(-c4ccccc4F)c(Cl)cc23)[C@@H](C)C1] | 6-chloro-7-(2-fluorophenyl)-1-(2-methoxy-4,6-di(2-propanyl)-5-pyrimidinyl)-4-((2S)-2-methyl-4-(2-propenoyl)-1-piperazinyl)pyrido[2,3-d]pyrimidin-2(1H)-one | | Step 1: 4,6-di-isopropyl-2-methoxypyrimidin-5-amine (Intermediate I-36), Step 4: (2-fluorophenyl)boronic acid (Combi-Blocks Inc.) |

TABLE 55-continued

Compounds 55-2 to 55-43 were prepared following the procedure described in Method 55, Steps 1-5, above as follows:

| Ex. # | Chemical Structure | Name | Method Changes | Reagent |
|---|---|---|---|---|
| 55-38 | 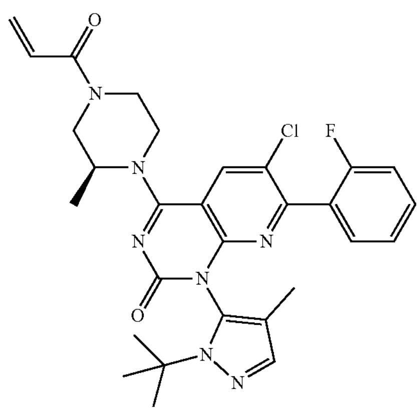 [SMILES: C=CC(=O)N1CCN(c2nc(=O)n(-c3c(C)cnn3C(C)(C)C)c3nc(-c4ccccc4F)c(Cl)cc23)[C@@H](C)C1] | 6-chloro-7-(2-fluorophenyl)-1-(4-methyl-1-(2-methyl-2-propanyl)-1H-pyrazol-5-yl)-4-((2S)-2-methyl-4-(2-propenoyl)-1-piperazinyl)pyrido[2,3-d]pyrimidin-2(1H)-one | | Step 1: 1-(tert-butyl)-4-methyl-1H-pyrazol-5-amine (Intermediate I-22), Step 4: 2-fluorophenylboronic acid (Combi-Blocks Inc.) |
| 55-39 | 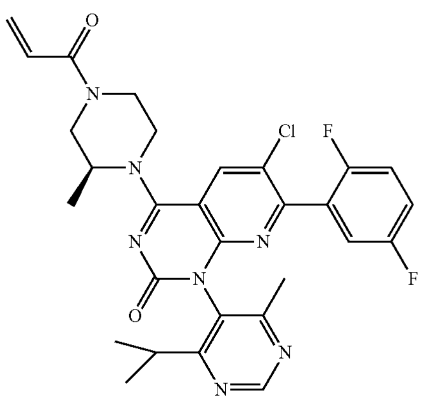 [SMILES: C=CC(=O)N1CCN(c2nc(=O)n(-c3c(C)ncnc3C(C)C)c3nc(-c4cc(F)ccc4F)c(Cl)cc23)[C@@H](C)C1] | 6-chloro-7-(2,5-difluorophenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | | Step 1: 4-isopropyl-6-methylpyrimidin-5-amine (Intermediate I-5) Step 4: (2,5-difluorophenyl)boronic acid (Combi-Blocks Inc.) |
| 55-40 | 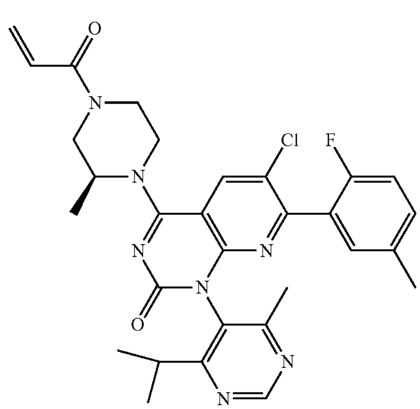 [SMILES: C=CC(=O)N1CCN(c2nc(=O)n(-c3c(C)ncnc3C(C)C)c3nc(-c4cc(C)ccc4F)c(Cl)cc23)[C@@H](C)C1] | 6-chloro-7-(2-fluoro-5-methylphenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | | Step 1: 4-isopropyl-6-methylpyrimidin-5-amine (Intermediate I-5) Step 4: (2-fluoro-5-methylphenyl)boronic acid (Sigma-Aldrich Corporation) |

TABLE 55-continued

Compounds 55-2 to 55-43 were prepared following the procedure described in Method 55, Steps 1-5, above as follows:

| Ex. # | Chemical Structure | Name | Method Changes | Reagent |
|---|---|---|---|---|
| 55-41 | 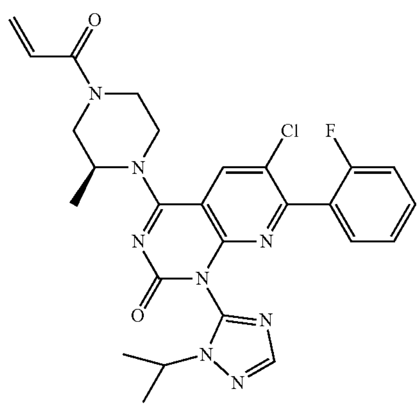 [SMILES: C=CC(=O)N1CCN(c2nc(=O)n(-c3ncnn3C(C)C)c3nc(-c4ccccc4F)c(Cl)cc23)[C@@H](C)C1] | 6-chloro-7-(2-fluorophenyl)-4-((2S)-2-methyl-4-(2-propenoyl)-1-piperazinyl)-1-(1-(2-propanyl)-1H-1,2,4-triazol-5-yl)pyrido[2,3-d]pyrimidin-2(1H)-one | | Step 1: 1-(propan-2-yl)-1h-1,2,4-triazol-5-amine (Aurum Pharmatech LLC), Step 4: (2-fluorophenyl)boronic acid (Combi-Blocks Inc.) |
| 55-42 | 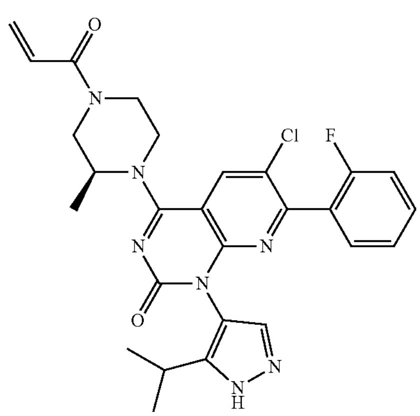 [SMILES: C=CC(=O)N1CCN(c2nc(=O)n(-c3cn[nH]c3C(C)C)c3nc(-c4ccccc4F)c(Cl)cc23)[C@@H](C)C1] | 6-chloro-7-(2-fluorophenyl)-4-((2S)-2-methyl-4-(2-propenoyl)-1-piperazinyl)-1-(5-(2-propanyl)-1H-pyrazol-4-yl)pyrido[2,3-d]pyrimidin-2(1H)-one | Add one step before Step 3: for protection of pyrazole using (Boc)$_2$O and DMAP, Step 4: Pd(dppf)Cl$_2$ and KOAc | Step 1: 3-(propan-2-yl)-1H-pyrazol-4-amine dihydrochloride (Enamine) Step 4: 2-fluorophenyl boronic acid (Combi-Blocks Inc.) |
| 55-43 | 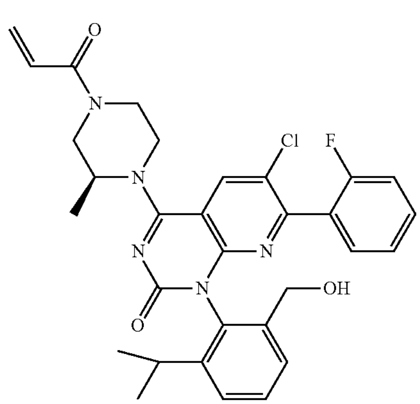 | 6-chloro-7-(2-fluorophenyl)-1-(2-(hydroxymethyl)-6-(2-propanyl)phenyl)-4-((2S)-2-methyl-4-(2-propenoyl)-1-piperazinyl)pyrido[2,3-d]pyrimidin-2(1H)-one | Step 4: Pd(dppf)Cl$_2$ and KOAc, add one step after Step 5: for deprotection of TBDPS using TBAF | Step 1: 2-(((tert-butyldiphenylsilyl)oxy)methyl)-6-isopropylaniline (Intermediate I-40) Step 4: 2-fluorophenyl boronic acid (Combi-Blocks Inc.) |

Method 56

Example 56-1: 6-Chloro-7-(2-fluoro-6-hydroxyphenyl)-4-[(2S)-2-methyl-4-prop-2-enoyl-piperazin-1-yl]-1-[2-(pentafluoro-λ⁶-sulfanyl)phenyl]pyrido[2,3-d]pyrimidin-2-one

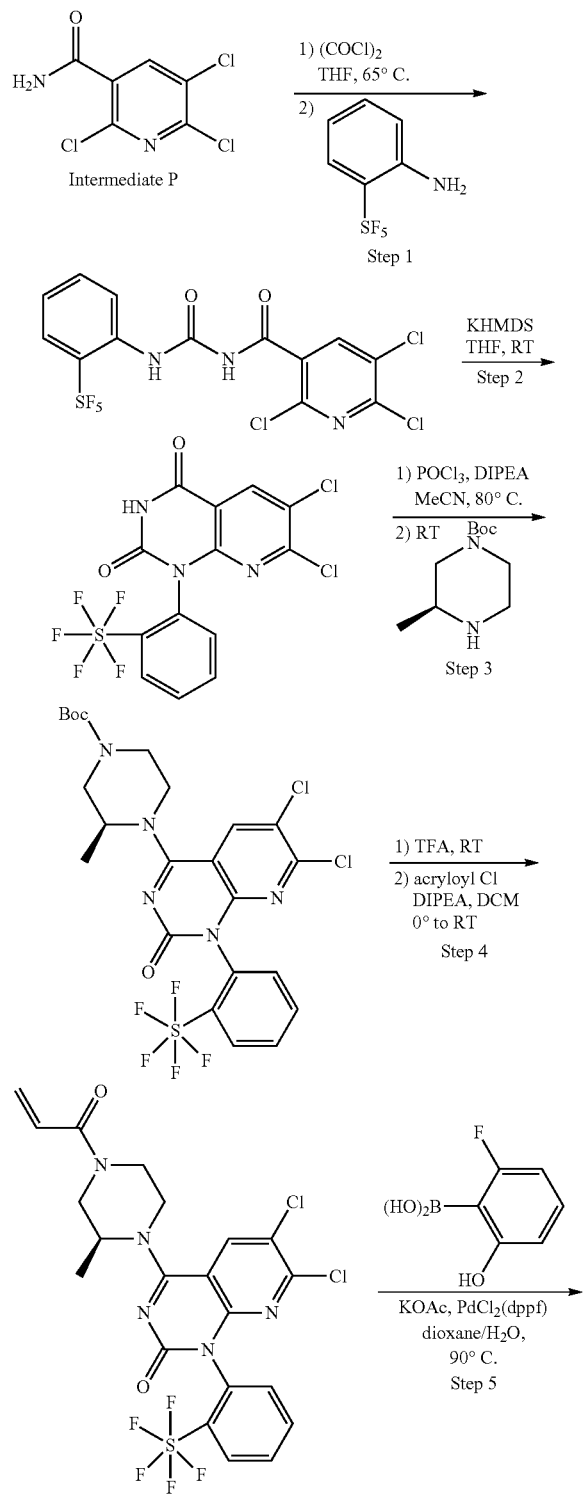

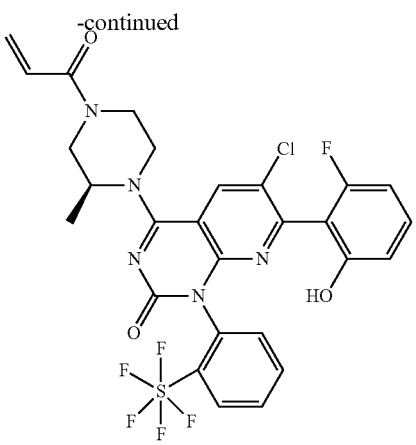

Step 1: 2,5,6-Trichloro-N-[[2-(pentafluoro-λ⁶-sulfanyl)phenyl]carbamoyl]pyridine-3-carboxamide A mixture of 2,5,6-trichloronicotinamide (Intermediate P, 1.03 g, 4.56 mmol) and oxalylchloride, 2 M in DCM (2.5 mL, 5.0 mmol) in THF (23 mL) was stirred at 65° C. for 1 h. The reaction mixture was cooled to rt, and 2-(pentafluoro-λ⁶-sulfanyl)aniline (1.0 mL, 4.6 mmol; Oakwood Products, Inc., Estill, S.C., USA) was added, the reaction mixture was stirred at rt for 10 min. The reaction mixture was diluted with EtOAc (150 mL) and washed with satd. NaHCO₃ (2×75 mL). The organic layer separated, dried over anhydrous Na₂SO₄, and concentrated in vacuo to give 2,5,6-trichloro-N-[[2-(pentafluoro-λ⁶-sulfanyl)phenyl]carbamoyl]pyridine-3-carboxamide as a white solid. m/z (ESI, +ve ion): 469.7/471.8 (M+H)⁺.

Step 2: 6,7-Dichloro-1-[2-(pentafluoro-λ⁶-sulfanyl)phenyl]pyrido[2,3-d]pyrimidine-2,4-dione 1 M KHMDS in THF (9.1 mL, 9.1 mmol) was added to a solution of 2,5,6-trichloro-N-[[2-(pentafluoro-λ⁶-sulfanyl)phenyl]carbamoyl]pyridine-3-carboxamide (2.15 g, 4.56 mmol) in THF (23 mL) at rt and the brown solution was stirred at rt for 15 min. The reaction mixture was diluted with EtOAc (150 mL) and washed with saturated, aqueous ammonium chloride (2×75 mL). The organic layer was dried over anhydrous Na₂SO₄ and concentrated in vacuo to give 6,7-dichloro-1-[2-(pentafluoro-λ⁶-sulfanyl)phenyl]pyrido[2,3-d]pyrimidine-2,4-dione (1.82 g, 4.19 mmol, 92% yield). m/z (ESI, +ve ion): 433.9 (M+H)⁺.

Step 3: tert-Butyl (3S)-4-[6,7-dichloro-2-oxo-1-[2-(pentafluoro-λ⁶-sulfanyl)phenyl]pyrido[2,3-d]pyrimidin-4-yl]-3-methyl-piperazine-1-carboxylate A solution of 6,7-dichloro-1-[2-(pentafluoro-λ⁶-sulfanyl)phenyl]pyrido[2,3-d]pyrimidine-2,4-dione (1.82 g, 4.19 mmol), DIPEA (1.5 mL, 8.4 mmol), and phosphoryl trichloride (0.47 mL, 5.0 mmol) in acetonitrile (10.5 mL) was stirred at 80° C. for 1 h. The reaction mixture was cooled to rt, DIPEA (1.5 mL, 8.4 mmol) and tert-butyl (S)-3-methylpiperazine-1-carboxylate (1.01 g, 5.03 mmol) were added, and the reaction was stirred at rt for 10 min. The mixture was poured into cold satd. NaHCO$_3$ (5 mL), stirred vigorously for 10 min, then partitioned between EtOAc (100 mL), and satd. NaHCO$_3$ (75 mL), the organic layer was washed with satd. NaHCO$_3$ (75 mL), dried over anhydrous Na$_2$SO$_4$, and concentrated in vacuo. The crude product was purified by silica gel chromatography (eluent: 0-70% EtOAc-EtOH (3:1)/heptane) to provide tert-butyl (3S)-4-[6,7-dichloro-2-oxo-1-[2-(pentafluoro-$\lambda^6$-sulfanyl)phenyl]pyrido[2,3-d]pyrimidin-4-yl]-3-methyl-piperazine-1-carboxylate (1.25 g, 2.03 mmol, 48% yield). m/z (ESI, +ve ion): 616.0 (M+H)$^+$.

Step 4: 6,7-Dichloro-4-[(2S)-2-methyl-4-prop-2-enoyl-piperazin-1-yl]-1-[2-(pentafluoro-$\lambda^6$-sulfanyl) phenyl]pyrido[2,3-d]pyrimidin-2-one A solution of tert-butyl (3S)-4-[6,7-dichloro-2-oxo-1-[2-(pentafluoro-$\lambda^6$-sulfanyl)phenyl]pyrido[2,3-d]pyrimidin-4-yl]-3-methyl-piperazine-1-carboxylate (1.25 g, 2.03 mmol) in TFA (8 mL) was stirred at rt for 15 min then concentrated in vacuo. The resulting oil was re-dissolved in DCM (10 mL) and cooled to 0° C., DIPEA (1.1 mL, 6.1 mmol) was added followed by acryloyl chloride (0.17 mL, 2.0 mmol). The reaction mixture was stirred at rt for 30 min then partitioned between EtOAc (100 mL) and satd. NaHCO$_3$ (75 mL), the organic layer was separated, dried over anhydrous Na$_2$SO$_4$, and concentrated in vacuo. The crude product was purified by silica gel chromatography (eluent: 0-100% EtOAc-EtOH (3:1)/heptane) to provide 6,7-dichloro-4-[(2S)-2-methyl-4-prop-2-enoyl-piperazin-1-yl]-1-[2-(pentafluoro-$\lambda^6$-sulfanyl)phenyl]pyrido[2,3-d]pyrimidin-2-one (611 mg, 53% yield) as an amber solid. m/z (ESI, +ve ion): 569.9 (M+H)$^+$.

Step 5: 6-Chloro-7-(2-fluoro-6-hydroxy-phenyl)-4-[(2S)-2-methyl-4-prop-2-enoyl-piperazin-1-yl]-1-[2-(pentafluoro-$\lambda^6$-sulfanyl)phenyl]pyrido[2,3-d]pyrimidin-2-one A mixture of 6,7-dichloro-4-[(2S)-2-methyl-4-prop-2-enoyl-piperazin-1-yl]-1-[2-(pentafluoro-$\lambda^6$-sulfanyl)phenyl]pyrido[2,3-d]pyrimidin-2-one (611 mg, 1.07 mmol), potassium acetate (315 mg, 3.21 mmol), (2-fluoro-6-hydroxyphenyl)boronic acid (333 mg, 2.14 mmol, Wuxi Chemical Industry Group Co., Ltd., China), and 1,1'-bis (diphenylphosphino)ferrocene dichloropalladium(II) (78 mg, 0.11 mmol) in 1,4-dioxane (2.4 mL) and water (0.24 mL) was sparged with N$_2$ for 3 min then heated to 90° C. for 2 h. The reaction mixture was cooled to rt, partitioned between EtOAc (100 mL), and satd. NaHCO$_3$ (75 mL); the organic layer was separated, dried over anhydrous Na$_2$SO$_4$, and concentrated in vacuo. The crude product was purified by silica gel chromatography (eluent: 0-100% EtOAc-EtOH (3:1)/heptane, then 3% 2 M NH$_3$ in MeOH]/DCM) to provide 6-chloro-7-(2-fluoro-6-hydroxy-phenyl)-4-[(2S)-2-methyl-4-prop-2-enoyl-piperazin-1-yl]-1-[2-(pentafluoro-$\lambda^6$-sulfanyl)phenyl]pyrido[2,3-d]pyrimidin-2-one: $^1$H NMR (400 MHz, CDCl$_3$) δ 8.27 (br s, 1H) 8.09 (br d, J=13.1 Hz, 1H) 8.03 (br d, J=8.1 Hz, 1H) 7.69-7.80 (m, 1H) 7.57-7.69 (m, 1H) 7.20-7.34 (m, 1H) 6.64-6.74 (m, 2H) 6.49-6.64 (m, 1H) 6.34-6.43 (m, 1H) 5.81 (br d, J=10.6 Hz, 1H) 4.16-5.41 (m, 3H) 2.78-4.07 (m, 4H) 1.49-1.68 (m, 3H). $^{19}$F NMR (377 MHz, CDCl$_3$) δ 66.87 (br d, J=150.9 Hz, 1F) −106.06--104.79 (m, 1F). m/z (ESI, +ve ion): 646.0 (M+H)$^+$.

TABLE 56

Compounds 56-2 to 56-10 were prepared following the procedure described in Method 56, Steps 1-5, above as follows:

| Ex. # | Chemical Structure | Name | Method Changes | Reagent |
|---|---|---|---|---|
| 56-2 | 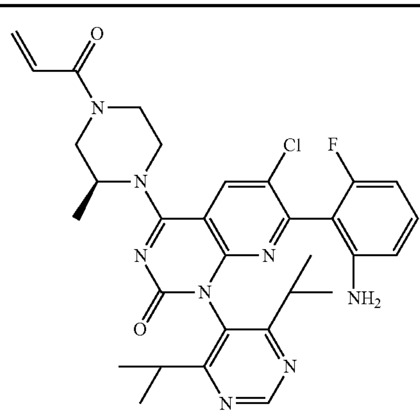 | 7-(2-amino-6-fluorophenyl)-6-chloro-1-(4,6-di(2-propanyl)-5-pyrimidinyl)-4-((2S)-2-methyl-4-(2-propenoyl)-1-piperazinyl)pyrido[2,3-d]pyrimidin-2(1H)-one | Step 2: −20° C., Step 3: 80° C., then −10° C. | Step 1: 4,6-diisopropylpyrimidin-5-amine. Step 5: 3-fluoro-2-(4,4,5,5-tetramethyl-1,3,2-dioxaborolan-2-yl)aniline (Combiphos Catalysts, Inc.) |

TABLE 56-continued

Compounds 56-2 to 56-10 were prepared following the procedure described in
Method 56, Steps 1-5, above as follows:

| Ex. # | Chemical Structure | Name | Method Changes | Reagent |
|---|---|---|---|---|
| 56-3 | 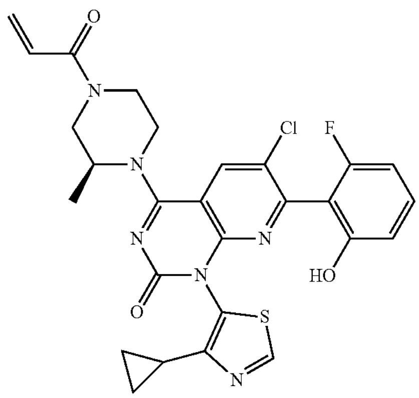 [SMILES: C=CC(=O)N1CCN(c2nc(=O)n(-c3scnc3C3CC3)c3nc(-c4c(O)cccc4F)c(Cl)cc23)[C@@H](C)C1] | 6-chloro-1-(4-cyclopropyl-1,3-thiazol-5-yl)-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 4-cyclopropylthiazol-5-amine (Enamine) Step 5: (2-fluoro-6-hydroxyphenyl)boronic acid (Wuxi) |
| 56-4 | 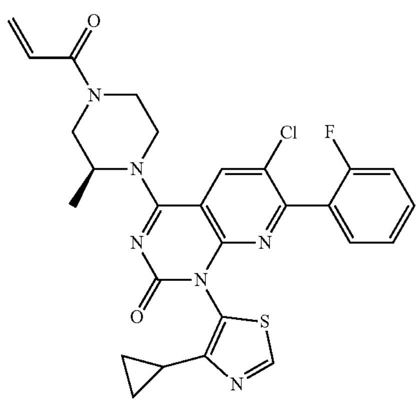 [SMILES: C=CC(=O)N1CCN(c2nc(=O)n(-c3scnc3C3CC3)c3nc(-c4ccccc4F)c(Cl)cc23)[C@@H](C)C1] | 6-chloro-1-(4-cyclopropyl-1,3-thiazol-5-yl)-7-(2-fluorophenyl)-4-((2S)-2-methyl-4-(2-propenoyl)-1-piperazinyl)pyrido[2,3-d]pyrimidin-2(1H)-one | | Step 1: 4-cyclopropylthiazol-5-amine (Enamine), Step 5: (2-fluorophenyl)boronic acid (Combi-Blocks Inc.) |
| 56-5 | 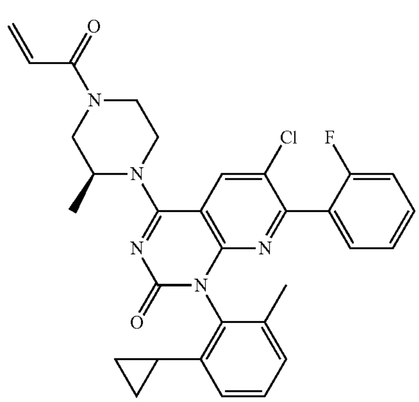 | 6-chloro-1-(2-cyclopropyl-6-methylphenyl)-7-(2-fluorophenyl)-4-((2S)-2-methyl-4-(2-propenoyl)-1-piperazinyl)pyrido[2,3-d]pyrimidin-2(1H)-one | Step 1: 65 °C., aniline in MeCN, Step 2: 0 °C., Step 3: 70 °C., then 0 °C. | Step 1: 2-cyclopropyl-6-methylaniline (Intermediate I-9), Step 5: (2-fluorophenyl)boronic acid (Combi-Blocks Inc.) |

TABLE 56-continued

Compounds 56-2 to 56-10 were prepared following the procedure described in Method 56, Steps 1-5, above as follows:

| Ex. # | Chemical Structure | Name | Method Changes | Reagent |
|---|---|---|---|---|
| 56-6 | 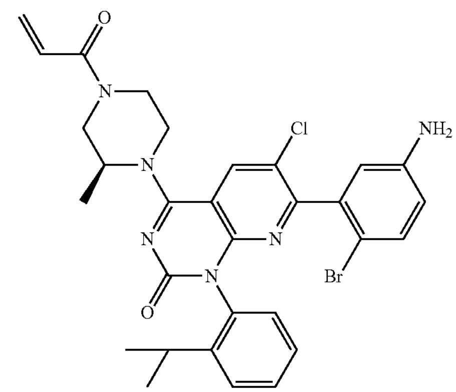 | 7-(5-amino-2-bromophenyl)-6-chloro-4-((2S)-2-methyl-4-(2-propenoyl)-1-piperazinyl)-1-(2-(2-propanyl)phenyl)pyrido[2,3-d]pyrimidin-2(1H)-one | Step 5: Pd(PPh$_3$)$_4$ and Na$_2$CO$_3$ | Step 1: 2-isopropylaniline (Sigma-Aldrich Corporation), Step 5: 2-bromo-5-aminophenylboronic acid pinacol ester (CombiPhos Catalysts, Inc.) |
| 56-7 | 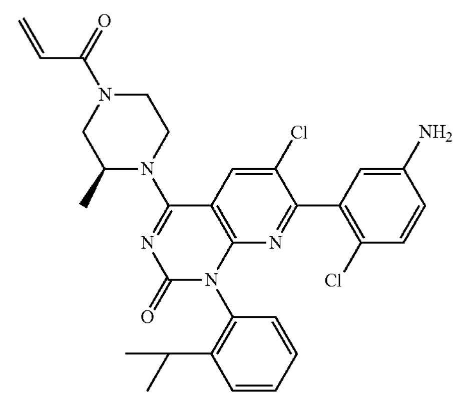 [SMILES: C=CC(=O)N1CCN(c2nc(=O)n(-c3ccccc3C(C)C)c3nc(-c4cc(N)ccc4Cl)c(Cl)cc23)[C@@H](C)C1] | 7-(5-amino-2-chlorophenyl)-6-chloro-4-((2S)-2-methyl-4-(2-propenoyl)-1-piperazinyl)-1-(2-(2-propanyl)phenyl)pyrido[2,3-d]pyrimidin-2(1H)-one | Step 5: Pd(PPh$_3$)$_4$ and Na$_2$CO$_3$ | Step 1: 2-isopropylaniline (Sigma-Aldrich Corporation), Step 5: (5-amino-2-chlorophenyl)boronic acid hydrochloride (Combi-Biocks Inc.) |
| 56-8 | 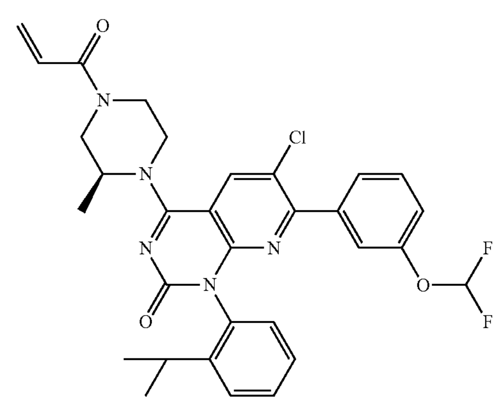 [SMILES: C=CC(=O)N1CCN(c2nc(=O)n(-c3ccccc3C(C)C)c3nc(-c4cccc(OC(F)F)c4)c(Cl)cc23)[C@@H](C)C1] | 6-chloro-7-(3-(difluoromethoxy)phenyl)-4-((2S)-2-methyl-4-(2-propenoyl)-1-piperazinyl)-1-(2-(2-propanyl)phenyl)pyrido[2,3-d]pyrimidin-2(1H)-one | Step 5: Pd(PPh$_3$)$_4$ and Na$_2$CO$_3$ | Step 1: 2-isopropylaniline (Sigma-Aldrich Corporation), Step 5: 3-(difluoromethoxy)phenylboronic acid (Combi-Biocks Inc.) |

TABLE 56-continued

Compounds 56-2 to 56-10 were prepared following the procedure described in
Method 56, Steps 1-5, above as follows:

| Ex. # | Chemical Structure | Name | Method Changes | Reagent |
|---|---|---|---|---|
| 56-9 | 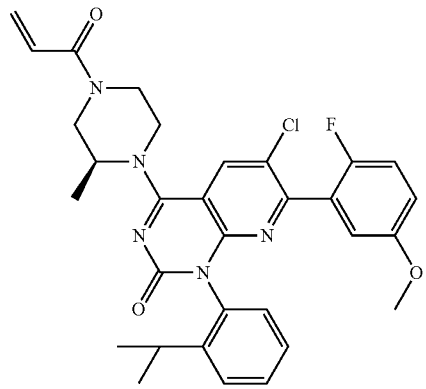 [SMILES: C=CC(=O)N1CCN(c2nc(=O)n(-c3ccccc3C(C)C)c3nc(-c4cc(OC)ccc4F)c(Cl)cc23)[C@@H](C)C1] | 6-chloro-7-(2-fluoro-5-methoxyphenyl)-4-((2S)-2-methyl-4-(2-propenoyl)-1-piperazinyl)-1-(2-(2-propanyl)phenyl)pyrido[2,3-d]pyrimidin-2(1H)-one | | Step 1: 2-isopropylaniline (Sigma-Aldrich Corporation), Step 5: 2-fluoro-5-methoxybenzeneboronic acid (Combi-Blocks Inc.) |
| 56-10 | 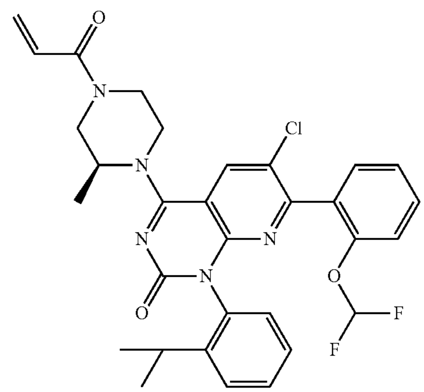 [SMILES: C=CC(=O)N1CCN(c2nc(=O)n(-c3ccccc3C(C)C)c3nc(-c4ccccc4OC(F)F)c(Cl)cc23)[C@@H](C)C1] | 6-chloro-7-(2-(difluoromethoxy)phenyl)-4-((2S)-2-methyl-4-(2-propenoyl)-1-piperazinyl)-1-(2-(2-propanyl)phenyl)pyrido[2,3-d]pyrimidin-2(1H)-one | Step 5: Pd(PPh$_3$)$_4$ and Na$_2$CO$_3$ | Step 1: 2-isopropylaniline (Sigma-Aldrich Corporation); Step 5: 2-fluoro-5-methoxybenzeneboronic acid (Combi-Blocks Inc.) |

Method 57

Example 57-1: 1-(2-Ethyl-4-methyl-3-pyridinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one

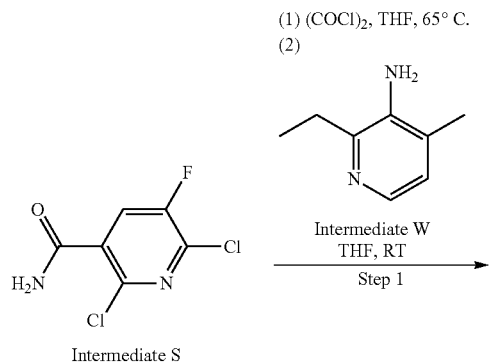

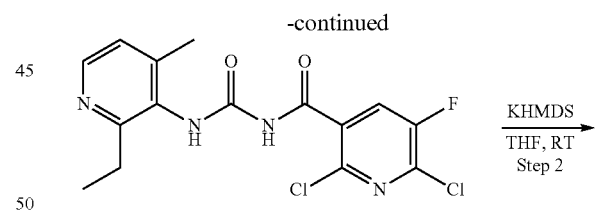

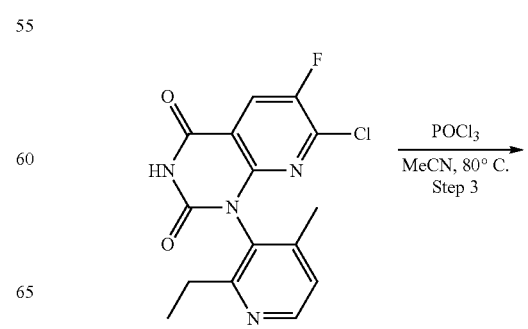

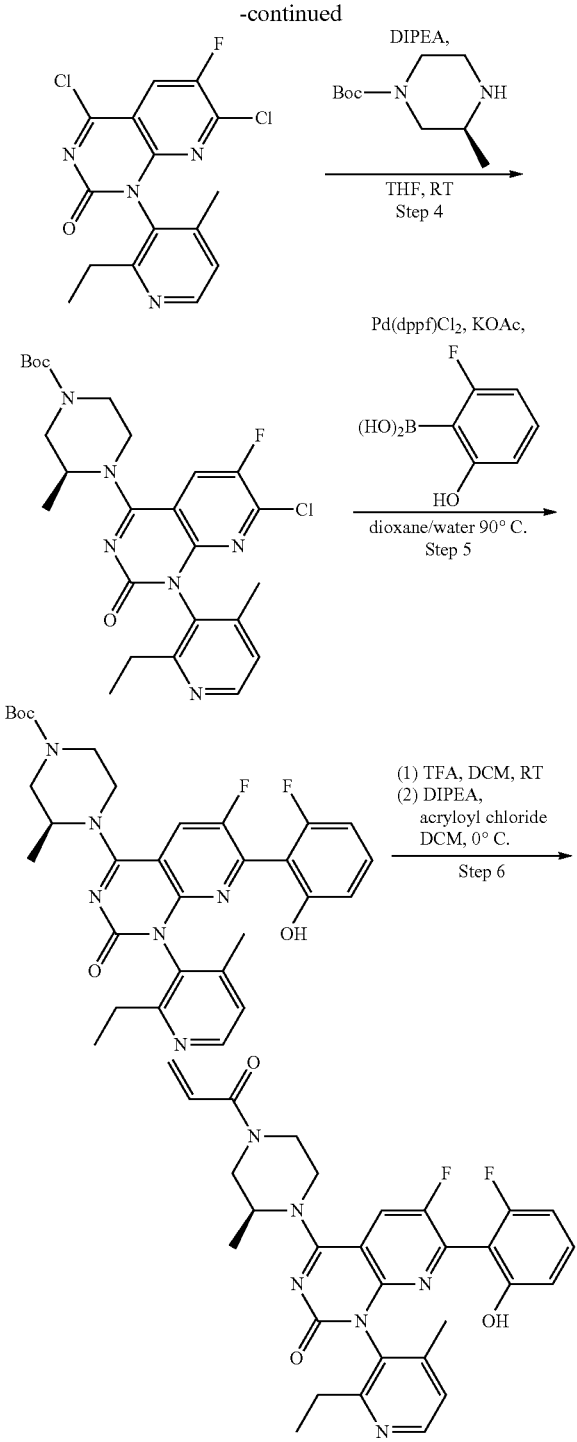

Step 1: 2,6-Dichloro-N-((2-ethyl-4-methylpyridin-3-yl)carbamoyl-5-fluoronicotinamide To a mixture of 2,6-dichloro-5-fluoronicotinamide (Intermediate S, 2.58 g, 12.4 mmol) in THF (25 mL) was added a solution of oxalyl chloride, 2 M solution in DCM (6.5 mL, 13 mmol). The mixture was heated at 65° C. (with a Finncondenser) for 2 h under nitrogen. The mixture was allowed to cool to rt and then a solution of 2-ethyl-4-methylpyridin-3-amine (Intermediate W, 1.68 g, 12.4 mmol) in THF (10 mL) was added to the reaction mixture. After 1 h, the precipitate was collected by filtration, washed with acetonitrile (20 mL) and dried to provide 2,6-dichloro-N-((2-ethyl-4-methylpyridin-3-yl)carbamoyl)-5-fluoronicotinamide. (4.08 g, 11 mmol, 89% yield) as white solid, that was used without further purification. $^1$H NMR (400 MHz, DMSO-$d_6$) δ ppm 11.60 (s, 1H), 9.99 (s, 1H), 8.61 (d, J=5.8 Hz, 1H), 8.51 (d, J=7.9 Hz, 1H), 7.79 (d, J=5.8 Hz, 1H), 2.97 (q, J=7.6 Hz, 2H), 2.44 (s, 3H), 1.25 (t, J=7.6 Hz, 3H). $^{19}$F NMR (376 MHz, DMSO-$d_6$) δ ppm −121.80 (br s, 1F). m/z (ESI, +ve ion): 371.0 (M+H)$^+$.

Step 2: 7-Chloro-1-(2-ethyl-4-methylpyridin-3-yl)-6-fluoropyrido[2,3-d]pyrimidine-2,4(1H,3H)-dione To a cooled mixture of 2,6-dichloro-N-((2-ethyl-4-methylpyridin-3-yl)carbamoyl)-5-fluoronicotinamide (4.08 g, 11 mmol) in THF (55 mL) at 0° C. was added dropwise KHMDS, 1 M solution in THF (24.3 mL, 24.3 mmol) and the mixture was allowed to warm to rt. After 4 h, the mixture was quenched with satd. ammonium chloride (50 mL) and extracted with EtOAc (2×50 mL). The organic extract was washed with brine (1×50 mL), dried over Na$_2$SO$_4$, filtered and concentrated in vacuo to give an orange syrupy solid. The crude product was purified by silica gel chromatography (eluent: 0-50% 3:1 EtOAc-EtOH/heptane) to provide 7-chloro-1-(2-ethyl-4-methylpyridin-3-yl)-6-fluoropyrido[2,3-d]pyrimidine-2,4(1H,3H)-dione (1.09 g, 3.26 mmol, 29.6% yield) as a light-yellow solid. $^1$H NMR (400 MHz, DMSO-$d_6$) δ ppm 12.28 (br s, 1H), 8.46-8.51 (m, 2H), 7.30 (d, J=5.0 Hz, 1H), 2.39-2.49 (m, 2H), 2.04 (s, 3H), 1.07 (t, J=7.5 Hz, 3H). $^{19}$F NMR (376 MHz, DMSO-$d_6$) δ ppm −126.84 (s, 1F). m/z (ESI, +ve ion): 335.0 (M+H)$^+$.

Step 3: 4,7-Dichloro-1-(2-ethyl-4-methylpyridin-3-yl)-6-fluoropyrido[2,3-d]pyrimidin-2(1H)-one To a mixture of 7-chloro-1-(2-ethyl-4-methylpyridin-3-yl)-6-fluoropyrido[2,3-d]pyrimidine-2,4(1H,3H)-dione (1.09 g, 3.25 mmol) and DIPEA (2.3 mL, 13 mmol) in acetonitrile (22 mL) was added phosphorus oxychloride (0.9 mL, 9.7 mmol) at rt and the mixture was stirred and heated at 80° C. After 1 h, the mixture was concentrated in vacuo, co-evaporated with toluene twice to give 4,7-dichloro-1-(2-ethyl-4-methylpyridin-3-yl)-6-fluoropyrido[2,3-d]pyrimidin-2(1H)-one (1.15 g, 3.25 mmol, 100% yield) as dark red syrup. m/z (ESI +ve ion): 349.0 (M+H)$^+$ (detected as OMe adduct in MeOH).

Step 4: (S)-tert-Butyl 4-(7-chloro-1-(2-ethyl-4-methylpyridin-3-yl)-6-fluoro-2-oxo-1,2-dihydropyrido[2,3-d]pyrimidin-4-yl)-3-methylpiperazine-1-carboxylate To a mixture of 4,7-dichloro-1-(2-ethyl-4-methylpyridin-3-yl)-6-fluoropyrido[2,3-d]pyrimidin-2(1H)-one (1.15 g, 3.25 mmol) in THF (16 mL) was added DIPEA (1.7 mL, 9.7 mmol) followed by (S)-4-Boc-2-methylpiperazine (0.98 g, 4.87 mmol, Combi-Blocks Inc.) and the mixture was stirred at rt. After 30 min, the reaction mixture was poured into ice-cold satd. NaHCO$_3$ (100 mL) and extracted with EtOAc (2×50 mL). The organic extract was dried over Na$_2$SO$_4$, filtered and concentrated in vacuo to give a dark red syrup. The crude product was purified by silica gel chromatography (eluent: 0-50% 3:1 EtOAc-EtOH/heptane) to provide (S)-tert-butyl 4-(7-chloro-1-(2-ethyl-4-methylpyridin-3-yl)-6-fluoro-2-oxo-1,2-dihydropyrido[2,3-d]pyrimidin-4-yl)-3- methylpiperazine-1-carboxylate (0.95 g, 1.8 mmol, 56% yield) as an orange solid. $^1$H NMR (400 MHz, DMSO-d$_6$) δ ppm 8.44 (d, J=5.0 Hz, 1H), 8.37 (t, J=8.4 Hz, 1H), 7.27 (d, J=5.0 Hz, 1H), 4.82 (br d, J=2.5 Hz, 1H), 4.10-4.22 (m, 1 H), 3.88-4.03 (m, 1H), 3.82 (br d, J=13.3 Hz, 1H), 3.58-3.72 (m, 1H), 2.98-3.29 (m, 2H), 2.27-2.45 (m, 2H), 1.93 (d, J=2.5 Hz, 3H), 1.45 (s, 9H), 1.31 (t, J=6.5 Hz, 3H), 1.05 (td, J=7.5, 2.6 Hz, 3H). $^{19}$F NMR (376 MHz, DMSO-d$_6$) δ ppm −128.31 (br d, J=8.7 Hz, 1F). m/z (ESI, +ve ion): 517.0 (M+H)$^+$.

Step 5: (3S)-tert-Butyl 4-(1-(2-ethyl-4-methylpyridin-3-yl)-6-fluoro-7-(2-fluoro-6-hydroxyphenyl)-2-oxo-1,2-dihydropyrido[2,3-d]pyrimidin-4-yl)-3-methylpiperazine-1-carboxylate A mixture of (S)-tert-butyl 4-(7-chloro-1-(2-ethyl-4-methylpyridin-3-yl)-6-fluoro-2-oxo-1,2-dihydropyrido[2,3-d]pyrimidin-4-yl)-3-methylpiperazine-1-carboxylate (0.503 g, 0.974 mmol), 2-fluoro-6-hydroxyphenylboronic acid (0.304 g, 1.95 mmol), potassium acetate (0.478 g, 4.87 mmol), and 1,4-dioxane (9.74 mL) was degassed with nitrogen for 5 min. To the mixture was added (1,1'-bis(diphenylphosphino)ferrocene)dichloropalladium-DCM (1:1) (0.04 g, 0.049 mmol) and 4 drops of water. The mixture was degassed with nitrogen for 2 min and stirred and heated at 90° C. After 4 h, the crude product was purified by silica gel chromatography (eluent: 0-50% DCM-MeOH (4:1)/DCM) to provide (3S)-tert-butyl 4-(1-(2-ethyl-4-methylpyridin-3-yl)-6-fluoro-7-(2-fluoro-6-hydroxyphenyl)-2-oxo-1,2-dihydropyrido[2,3-d]pyrimidin-4-yl)-3-methylpiperazine-1-carboxylate (0.411 g, 0.694 mmol, 71.3% yield) as a yellow solid. $^1$H NMR (400 MHz, DMSO-d$_6$) δ ppm 10.24 (br s, 1H), 8.35 (d, J=4.8 Hz, 1H), 8.26 (t, J=9.6 Hz, 1H), 7.23-7.31 (m, 1H), 7.20 (d, J=5.0 Hz, 1H), 6.73 (d, J=8.3 Hz, 1H), 6.68 (t, J=8.9 Hz, 1H), 4.87 (br s, 1H), 4.23 (br t, J=14.1 Hz, 1H), 3.91-4.05 (m, 1H), 3.84 (br d, J=12.6 Hz, 1H), 3.58-3.74 (m, 1H), 3.02-3.29 (m, 2H), 2.30-2.43 (m, 2H), 1.92 (d, J=4.1 Hz, 3H), 1.45 (s, 9H), 1.35 (dd, J=8.9, 6.8 Hz, 3H), 1.03 (td, J=7.5, 2.9 Hz, 3H). $^{19}$F NMR (376 MHz, DMSO-d$_6$) δ ppm −115.67 (br d, J=6.1 Hz, 1F), −128.39 (br d, J=6.1 Hz, 1F). m/z (ESI, +ve ion): 593.0 (M+H)$^+$.

Step 6: 1-(2-Ethyl-4-methyl-3-pyridinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one To a solution of (3S)-tert-butyl 4-(1-(2-ethyl-4-methylpyridin-3-yl)-6-fluoro-7-(2-fluoro-6-hydroxyphenyl)-2-oxo-1,2-dihydropyrido[2,3-d]pyrimidin-4-yl)-3-methylpiperazine-1-carboxylate (0.407 g, 0.687 mmol) in DCM (7 mL) was added TFA (6.9 mL) and the mixture was stirred at rt. After 10 min, the mixture was concentrated in vacuo to give 1-(2-ethyl-4-methylpyridin-3-yl)-6-fluoro-7-(2-fluoro-6-hydroxyphenyl)-4-((S)-2-methylpiperazin-1-yl)pyrido[2,3-d]pyrimidin-2(1H)-one as a yellow syrup. m/z (ESI, +ve ion): 493.0 (M+H)$^+$.

The yellow syrup was dissolved in DCM (6.9 mL) and the mixture was cooled to 0° C. To the cooled mixture was added DIPEA (1.2 mL, 6.87 mmol) followed by acryloyl chloride, 0.2 M solution in DCM (3.4 mL, 0.68 mmol) and the mixture was stirred at 0° C. After 20 min, the reaction was quenched with satd. NaHCO$_3$ (50 mL) and extracted with DCM (2×50 mL). The organic extract was dried over Na$_2$SO$_4$, filtered and concentrated in vacuo to give a yellow solid. The crude product was purified by silica gel chromatography (eluent: 0-50% DCM-MeOH (4:1)/DCM) to provide 1-(2-ethyl-4-methyl-3-pyridinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one (0.352 g, 0.644 mmol, 94% yield) as a yellow solid. $^1$H NMR (400 MHz, DMSO-d$_6$) δ ppm 10.23 (d, J=1.2 Hz, 1H), 8.37 (d, J=5.0 Hz, 1H), 8.24-8.34 (m, 1H), 7.19-7.32 (m, 2H), 6.79-6.93 (m, 1H), 6.74 (d, J=8.3 Hz, 1H), 6.69 (t, J=8.9 Hz, 1H), 6.21 (br d, J=17.2 Hz, 1H), 5.73-5.79 (m, 1H), 4.84-5.00 (m, 1H), 3.95-4.47 (m, 3H), 3.02-3.82 (m, 3H), 2.35-2.45 (m, 2H), 1.93 (s, 3H), 1.33 (dd, J=9.4, 6.7 Hz, 3H), 1.03 (td, J=7.5, 1.6 Hz, 3H). $^{19}$F NMR (377 MHz, DMSO-d$_6$) δ ppm −115.66 (d, J=6.1 Hz, 1F), −128.33 (br s, 1F). m/z (ESI, +ve ion): 547.0 (M+H)$^+$.

TABLE 57

Compounds 57-2 to 57-18 were prepared following the procedure described in Method 57, Steps 1-6, above as follows:

| Ex. # | Chemical Structure | Name | Method Changes | Reagent |
|---|---|---|---|---|
| 57-2 | (structure) | 6-fluoro-7-(2-fluorophenyl)-4-((2S)-2-methyl-4-(2-propenoyl)-1-piperazinyl)-1-(3-(2-propanyl)-2-pyrazinyl)pyrido[2,3-d]pyrimidin-2(1H)-one | Step 2: −20° C. Omit Steps 3 & 4, Used Step 3 from Method 55 instead | Step 1: 3-isopropylpyrazin-2-amine (Intermediate I-27), Step 5: (2-fluorophenyl)boronic acid (Combi-Blocks Inc.) |

TABLE 57-continued

Compounds 57-2 to 57-18 were prepared following the procedure described in Method 57, Steps 1-6, above as follows:

| Ex. # | Chemical Structure | Name | Method Changes | Reagent |
|---|---|---|---|---|
| 57-3 | 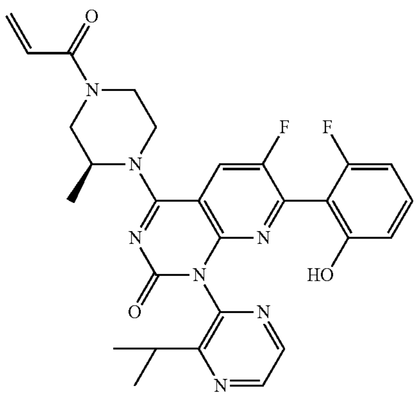 | 6-fluoro-7-(2-fluoro-6-hydroxyphenyl)-4-((2S)-2-methyl-4-(2-propenoyl)-piperazinyl)-1-(3-(2-propanyl)-2-pyrazinyl)pyrido[2,3-d]pyrimidin-2(1H)-one | Step 2: −20° C. Omit Steps 3 & 4, Used Step 3 from Method 55 instead | Step 1: 3-isopropylpyrazin-2-amine (Intermediate I-27), Step 5: (2-fluoro-6-hydroxyphenyl)boronic acid (Wuxi) |
| 57-4 | 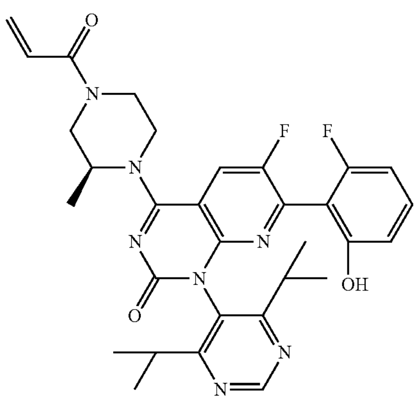 [SMILES: C=CC(=O)N1CCN(c2nc(=O)n(-c3c(C(C)C)ncnc3C(C)C)c3nc(-c4c(O)cccc4F)c(F)cc23)[C@@H](C)C1] | 1-(4,6-di(2-propanyl)-5-pyrimidinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | Step 2: −20° C., Omit Steps 3 & 4, Used Step 3 from Method 55 instead | Step 1: 4,6-diisopropylpyrimidin-5-amine (Intermediate U), Step 5: (2-fluoro-6-hydroxyphenyl)boronic acid (Wuxi) |
| 57-5 | 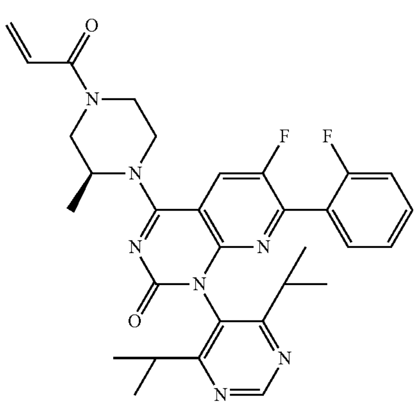 [SMILES: C=CC(=O)N1CCN(c2nc(=O)n(-c3c(C(C)C)ncnc3C(C)C)c3nc(-c4ccccc4F)c(F)cc23)[C@@H](C)C1] | 1-(4,6-di(2-propanyl)-5-pyrimidinyl)-6-fluoro-7-(2-fluorophenyl)-4-((2S)-2-methyl-4-(2-propenoyl)-1-piperazinyl)pyrido[2,3-d]pyrimidin-2(1H)-one | Step 2: −20° C., Omit Steps 3 & 4, Used Step 3 from Method 55 instead | Step 1: 4,6-diisopropylpyrimidin-5-amine (Intermediate U), Step 5: (2-fluorophenyl)boronic acid (Combi-Blocks). |

TABLE 57-continued

Compounds 57-2 to 57-18 were prepared following the procedure described in Method 57, Steps 1-6, above as follows:

| Ex. # | Chemical Structure | Name | Method Changes | Reagent |
|---|---|---|---|---|
| 57-6 | 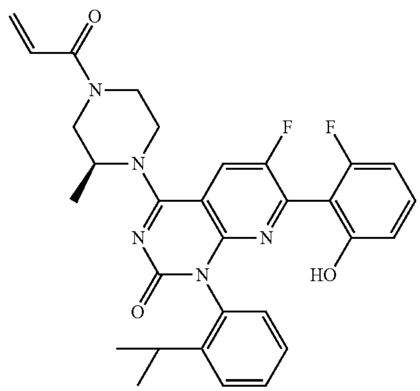 [SMILES: C=CC(=O)N1CCN(c2nc(=O)n(-c3ccccc3C(C)C)c3nc(-c4c(O)cccc4F)c(F)cc23)[C@@H](C)C1] | 6-fluoro-7-(2-fluoro-6-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | Step 5: Use Pd(PPh$_3$)$_4$ and Na$_2$CO$_3$ | Step 1: 2-isopropylaniline (Sigma-Aldrich Corporation), Step 5: (2-fluoro-6-hydroxyphenyl)boronic acid (Wuxi) |
| 57-7 | 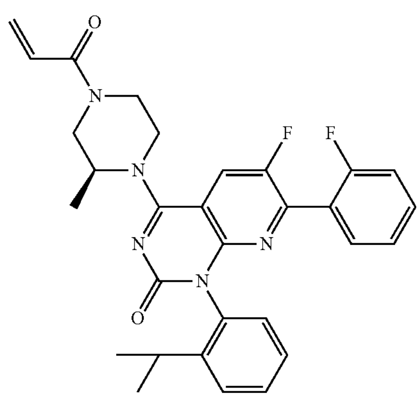 | 6-fluoro-7-(2-fluorophenyl)-4-((2S)-2-methyl-4-(2-propenoyl)-1-piperazinyl)-1-(2-(2-propanyl)phenyl)pyrido[2,3-d]pyrimidin-2(1H)-one | Step 5: Use Pd(PPh$_3$)$_4$ and Na$_2$CO$_3$ | Step 1: 2-isopropylaniline (Sigma-Aldrich Corporation), Step 5: (2-fluorophenyl)boronic acid (Combi-Blocks Inc.). |
| 57-8-1 | 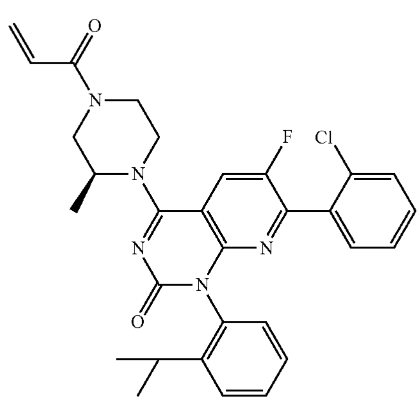 | -7-(2-chlorophenyl)-6-fluoro-4-((2S)-2-methyl-4-(2-propenoyl)-1-piperazinyl)-1-(2-(2-propanyl)phenyl)pyrido[2,3-d]pyrimidin-2(1H)-one, first eluting isomer | Step 5: Use Pd(PPh$_3$)$_4$ and K$_2$CO$_3$ | Step 1: 2-isopropylphenylamine (Sigma-Aldrich Corporation), Step 5: (2-chlorophenyl)boronic acid (Matrix Scientific) |

TABLE 57-continued

Compounds 57-2 to 57-18 were prepared following the procedure described in Method 57, Steps 1-6, above as follows:

| Ex. # | Chemical Structure | Name | Method Changes | Reagent |
|---|---|---|---|---|
| 57-8-2 | 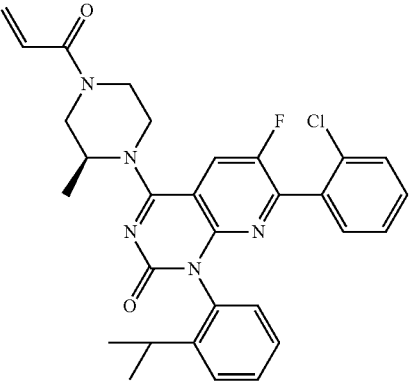 [SMILES: C=CC(=O)N1CCN(c2nc(=O)n(-c3ccccc3C(C)C)c3nc(-c4ccccc4Cl)c(F)cc23)[C@@H](C)C1] | 7-(2-chlorophenyl)-6-fluoro-4-((2S)-2-methyl-4-(2-propenoyl)-1-piperazinyl)-1-(2-(2-propanyl)phenyl)pyrido[2,3-d]pyrimidin-2(1H)-one, second eluting isomer | Step 5: Use Pd(PPh$_3$)$_4$ and K$_2$CO$_3$ | Step 1: 2-isopropylphenylamine (Sigma-Aldrich Corporation), Step 5: (2-chlorophenyl)boronic acid (Matrix Scientific) |
| 57-9 | 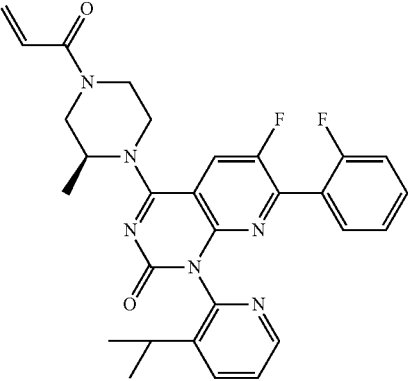 | 6-fluoro-7-(2-fluorophenyl)-4-((2S)-2-methyl-4-(2-propenoyl)-1-piperazinyl)-1-(3-(2-propanyl)-2-pyridinyl)pyrido[2,3-d]pyrimidin-2(1H)-one | Step 5: Use Pd(PPh$_3$)$_4$ and K$_2$CO$_3$ | Step 1: 3-isopropylpyridin-2-amine (Enamine), Step 5: (2-fluorophenyl)boronic acid (Combi-Blocks Inc.). |
| 57-10 | 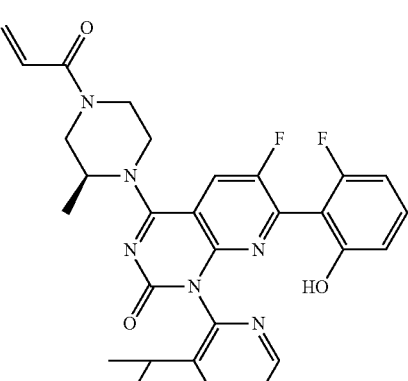 | 6-fluoro-7-(2-fluoro-6-hydroxyphenyl)-4-((2S)-2-methyl-4-(2-propenoyl)-1-piperazinyl)-1-(3-(2-propanyl)-2-pyridinyl)pyrido[2,3-d]pyrimidin-2(1H)-one | Step 5: use K$_2$CO$_3$ | Step 1: 3-isopropylpyridin-2-amine (Enamine), Step 5: (2-fluoro-6-hydroxyphenyl)boronic acid (Wuxi) |

TABLE 57-continued

Compounds 57-2 to 57-18 were prepared following the procedure described in Method 57, Steps 1-6, above as follows:

| Ex. # | Chemical Structure | Name | Method Changes | Reagent |
|---|---|---|---|---|
| 57-11 | 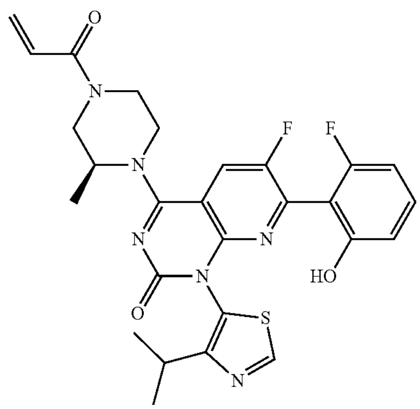 [SMILES: C=CC(=O)N1CCN(c2nc(=O)n(-c3scnc3C(C)C)c3nc(-c4c(O)cccc4F)c(F)cc23)[C@@H](C)C1] | 6-fluoro-7-(2-fluoro-6-hydroxyphenyl)-4-((2S)-2-methyl-4-(2-propenoyl)-1-piperazinyl)-1-(4-(2-propanyl)-1,3-thiazol-5-yl)pyrido[2,3-d]pyrimidin-2(1H)-one | | Step 1: 4-(propan-2-yl)-1,3-thiazol-5-amine (Enamine), Step 5: (2-fluoro-6-hydroxyphenyl)boronic acid (Wuxi) |
| 57-12 | 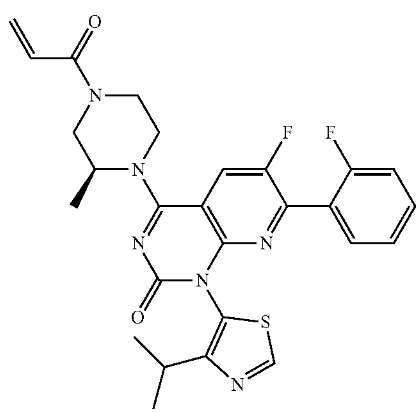 [SMILES: C=CC(=O)N1CCN(c2nc(=O)n(-c3scnc3C(C)C)c3nc(-c4ccccc4F)c(F)cc23)[C@@H](C)C1] | 6-fluoro-7-(2-fluorophenyl)-4-((2S)-2-methyl-4-(2-propenoyl)-1-piperazinyl)-1-(4-(2-propanyl)-1,3-thiazol-5-yl)pyrido[2,3-d]pyrimidin-2(1H)-one | | Step 1: 4-(propan-2-yl)-1,3-thiazol-5-amine (Enamine), Step 5: (2-fluorophenyl)boronic acid (Combi-Blocks Inc.) |
| 57-13-1 | 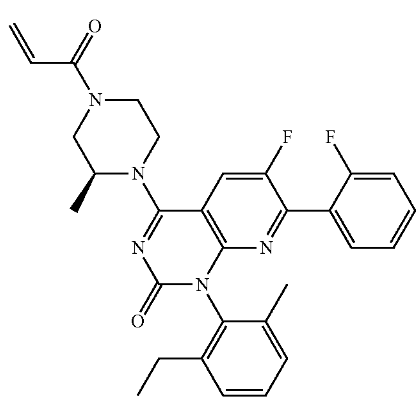 [SMILES: C=CC(=O)N1CCN(c2nc(=O)n(-c3c(C)cccc3CC)c3nc(-c4ccccc4F)c(F)cc23)[C@@H](C)C1] | 1-(2-ethyl-6-methylphenyl)-6-fluoro-7-(2-fluorophenyl)-4-((2S)-2-methyl-4-(2-propenoyl)-1-piperazinyl)pyrido[2,3-d]pyrimidin-2(1H)-one, first eluting isomer | | Step 1: 2-amino-3-ethyltoluene (Sigma-Aldrich Corporation), Step 5: (2-fluorophenyl)boronic acid (Combi-Blocks Inc.) |

TABLE 57-continued

Compounds 57-2 to 57-18 were prepared following the procedure described in Method 57, Steps 1-6, above as follows:

| Ex. # | Chemical Structure | Name | Method Changes | Reagent |
|---|---|---|---|---|
| 57-13-2 | 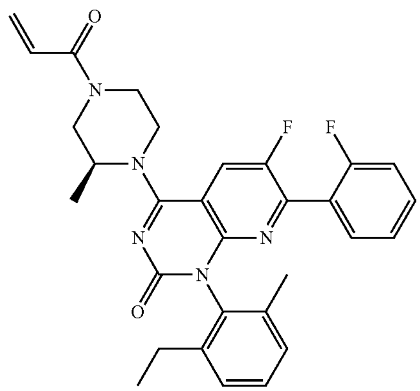 [SMILES: C=CC(=O)N1CCN(c2nc(=O)n(-c3c(C)cccc3CC)c3nc(-c4ccccc4F)c(F)cc23)[C@@H](C)C1] | 1-(2-ethyl-6-methylphenyl)-6-fluoro-7-(2-fluorophenyl)-4-((2S)-2-methyl-4-(2-propenoyl)-1-piperazinyl)pyrido[2,3-d]pyrimidin-2(1H)-one, second eluting isomer | | Step 1: 2-amino-3-ethyltoluene (Sigma-Aldrich Corporation), Step 5: (2-fluorophenyl)boronic acid (Combi-Blocks Inc.) |
| 57-14-1 | 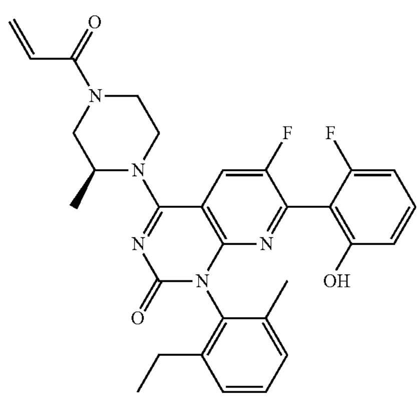 | 1-(2-ethyl-6-methylphenyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one, first eluting isomer | | Step 1: 2-amino-3-ethyltoluene (Sigma-Aldrich Corporation), Step 5: (2-fluoro-6-hydroxyphenyl)boronic acid (Wuxi) |
| 57-14-2 | 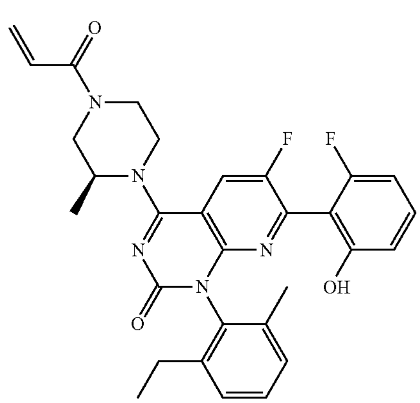 | 1-(2-ethyl-6-methylphenyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 2-amino-3-ethyltoluene (Sigma-Aldrich Corporation), Step 5: (2-fluoro-6-hydroxyphenyl)boronic acid (Wuxi) |

TABLE 57-continued

Compounds 57-2 to 57-18 were prepared following the procedure described in
Method 57, Steps 1-6, above as follows:

| Ex. # | Chemical Structure | Name | Method Changes | Reagent |
|---|---|---|---|---|
| 57-15-1 | 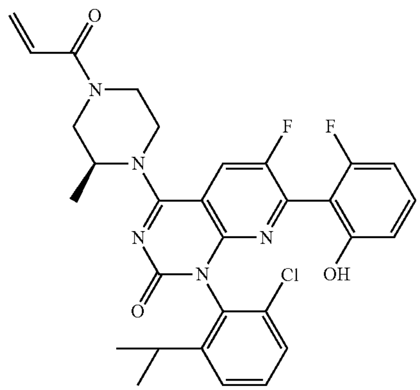 | 1-(2-chloro-6-(2-propanyl)phenyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 2-chloro-6-(1-methylethyl)benzenamine (HDH Pharma, Inc.), Step 5: (2-fluoro-6-hydroxyphenyl)boronic acid (Wuxi) |
| 57-15-2 | 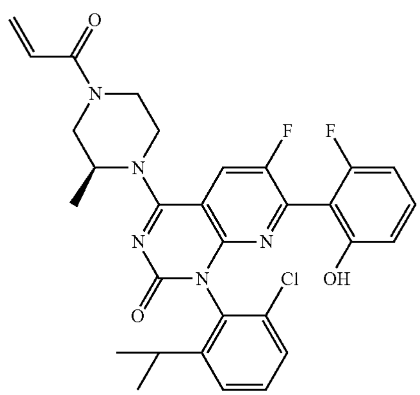 | 1-(2-chloro-6-(2-propanyl)phenyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 2-chloro-6-(1-methylethyl)benzenamine (HDH Pharma, Inc.), Step 5: (2-fluoro-6-hydroxyphenyl)boronic acid (Wuxi) |
| 57-16 | 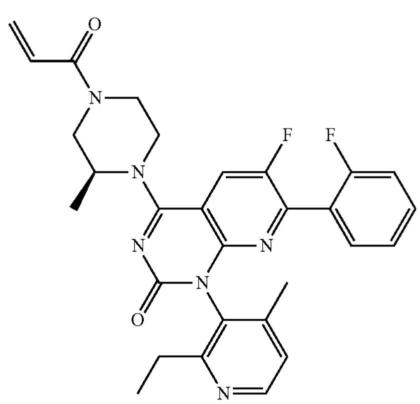 | 1-(2-ethyl-4-methyl-3-pyridinyl)-6-fluoro-7-(2-fluorophenyl)-4-((2S)-2-methyl-4-(2-propenoyl)-1-piperazinyl)pyrido[2,3-d]pyrimidin-2(1H)-one | Step 5: Use Pd(PPh$_3$)$_4$ and Na$_2$CO$_3$ | Step 1: 2-ethyl-4-methylpyridin-3-amine (Intermediate Z), Step 5: 2-fluorophenylboronic acid (Combi-Blocks Inc.) |

TABLE 57-continued

Compounds 57-2 to 57-18 were prepared following the procedure described in
Method 57, Steps 1-6, above as follows:

| Ex. # | Chemical Structure | Name | Method Changes | Reagent |
|---|---|---|---|---|
| 57-17 | 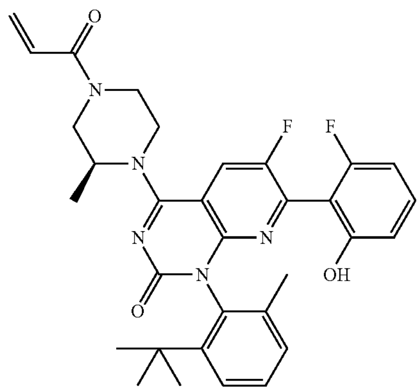 [SMILES: C=CC(=O)N1CCN(c2nc(=O)n(-c3c(C)cccc3C(C)(C)C)c3nc(-c4c(O)cccc4F)c(F)cc23)[C@@H](C)C1] | 6-fluoro-7-(2-fluoro-6-hydroxyphenyl)-1-(2-methyl-6-(2-methyl-2-propanyl)phenyl)-4-((2S)-2-methyl-4-(2-propenoyl)-1-piperazinyl)pyrido[2,3-d]pyrimidin-2(1H)-one | | Step 1: 2-methyl-6-tert-butyl aniline (Aurum Pharmatech LLC), Step 5: (2-fluoro-6-hydroxyphenyl)boronic acid (Wuxi) |
| 57-18 | 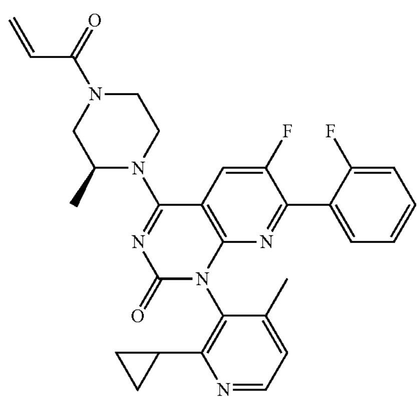 [SMILES: C=CC(=O)N1CCN(c2nc(=O)n(-c3c(C)ccnc3C3CC3)c3nc(-c4ccccc4F)c(F)cc23)[C@@H](C)C1] | 1-(2-cyclopropyl-4-methyl-3-pyridinyl)-6-fluoro-7-(2-fluorophenyl)-4-((2S)-2-methyl-4-(2-propenoyl)-1-piperazinyl)pyrido[2,3-d]pyrimidin-2(1H)-one | | Step 1: 2-cyclopropyl-4-methylpyridin-3-amine (Intermediate T), Step 5: 2-fluorophenylboronic acid (Combi-Blocks Inc.) |

Method 58

Example 58-1: 6-Fluoro-7-(2-fluoro-6-hydroxyphenyl)-1-(2-(2-methyl-2-propanyl)phenyl)-4-((2S)-2-methyl-4-(2-propenoyl)-1-piperazinyl)pyrido[2,3-d]pyrimidin-2(1H)-one

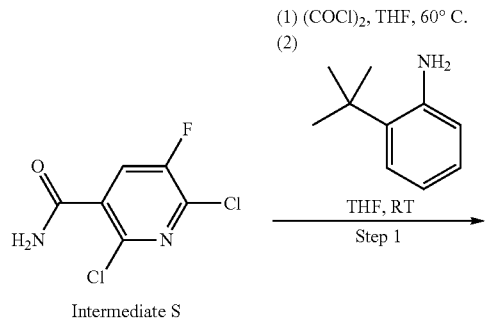

Intermediate S

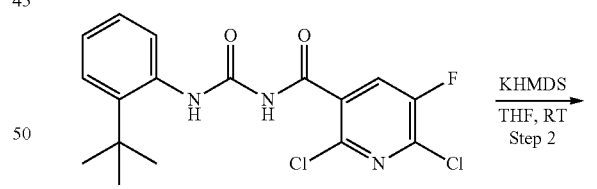

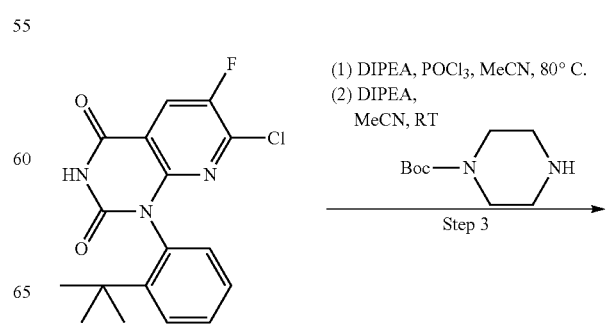

-continued

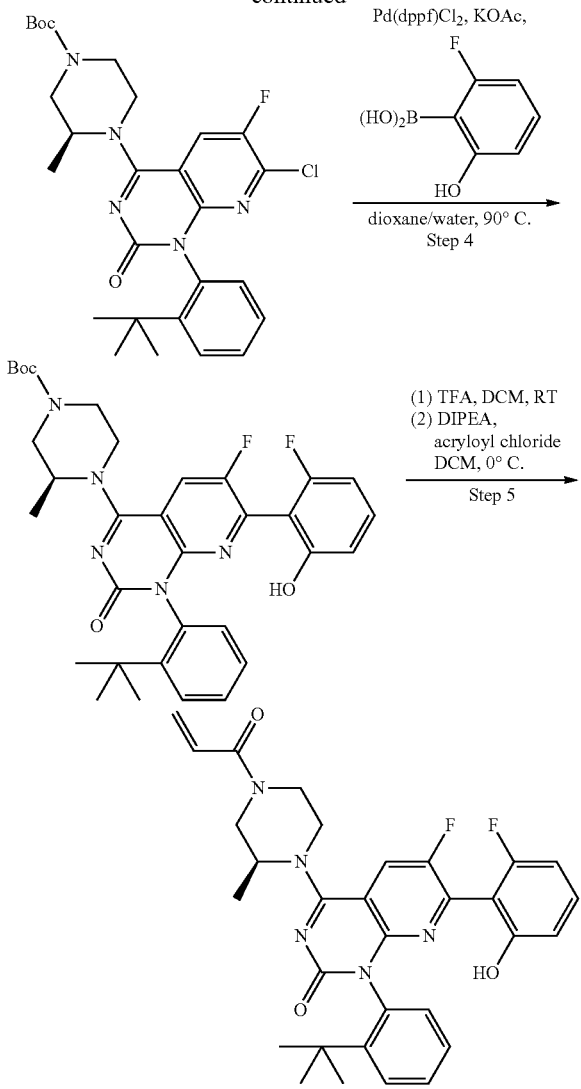

Step 1: N-((2-(tert-Butyl)phenyl)carbamoyl)-2,6-dichloro-5-fluoronicotinamide To a mixture of 2,6-dichloro-5-fluoronicotinamide (Intermediate S, 2 g, 9.56 mmol) in THF (40 mL) was added a solution of oxalyl chloride, 2 M solution in DCM (5.3 mL, 10.6 mmol). The mixture was heated at 70° C. (with a Finncondenser) for 50 min under nitrogen. The mixture was allowed to cool to rt and concentrated in vacuo. THF (40 mL) was added along with 2-(tert-butyl)aniline (1.5 mL, 9.56 mmol, Ark Pharma, Arlington Heights, Ill., USA). After 10 min, the solvent was removed in vacuo and the residue was suspended in MeOH and sonicated. The resulting white solid was collected and air-dried to give N-((2-(tert-butyl)phenyl)carbamoyl)-2,6-dichloro-5-fluoronicotinamide (4.13 g, 8.15 mmol, 85% yield) as a white solid, that was used without further purification. $^1$H NMR (400 MHz, DMSO-$d_6$) δ ppm 11.46 (1H, br s), 9.55-10.36 (1H, m), 8.52 (1H, br d, J=7.7 Hz), 7.49 (1H, br d, J=7.0 Hz), 7.43 (1H, dd, J=7.8, 1.6 Hz), 7.23 (2H, dtd, J=19.7, 7.4, 7.4, 1.6 Hz), 1.40 (9H, s). $^{19}$F NMR (376 MHz, DMSO-$d_6$) δ ppm −121.74 (br s, 1F). m/z (ESI, +ve ion): 406.0 (M+Na)$^+$.

Step 2: 1-(2-(tert-Butyl)phenyl)-7-chloro-6-fluoropyrido[2,3-d]pyrimidine-2,4(1H,3H)-dione To a cooled mixture of N-((2-(tert-butyl)phenyl)carbamoyl)-2,6-dichloro-5-fluoronicotinamide (3.13 g, 8.15 mmol) in THF (40 mL) at 0° C. was added dropwise KHMDS, 1 M solution in THF (17.1 mL, 17.1 mmol). The cold bath was removed and the mixture was stirred at rt. After 10 min, the mixture was quenched with satd. ammonium chloride (60 mL) and extracted with EtOAc (2×50 mL). The organic extract was washed with water (60 mL) and dried via ChemElute extraction cartridge. The eluent was concentrated and suspended in MeOH. The resulting solid was collected by filtration to afford 1.5 g of an off-white solid. The filtrate was purified by silica gel chromatography (eluent: 0-60% EtOAc/heptane) to provide 0.15 g of additional product. The products were combined and further triturated with DCM to give 1-(2-(tert-butyl)phenyl)-7-chloro-6-fluoropyrido[2,3-d]pyrimidine-2,4(1H,3H)-dione (1.6 g, 4.6 mmol, 56.5% yield) as a light-yellow solid. $^1$H NMR (400 MHz, DMSO-$d_6$) δ ppm 12.17 (1H, s), 8.45 (1H, d, J=7.5 Hz), 7.65 (1H, dd, J=8.3, 1.2 Hz), 7.41-7.46 (1H, m), 7.32 (1H, td, J=7.5, 1.5 Hz), 7.20 (1H, dd, J=7.9, 1.5 Hz), 1.17 (9H, s). $^{19}$F NMR (376 MHz, DMSO-$d_6$) δ ppm −127.49 (s, 1F). m/z (ESI, +ve ion): 348.0 (M+H)$^+$.

Step 3: (S)-tert-Butyl 4-(1-(2-(tert-butyl)phenyl)-7-chloro-6-fluoro-2-oxo-1,2-dihydropyrido[2,3-d]pyrimidin-4-yl)-3-methylpiperazine-1-carboxylate To a stirring solution of 1-(2-(tert-butyl)phenyl)-7-chloro-6-fluoropyrido[2,3-d]pyrimidine-2,4-(1H,3H)-dione (1.59 g, 4.57 mmol) in acetonitrile (30 mL) was added DIPEA (1.0 mL, 5.9 mmol) followed by phosphorus oxychloride (0.51 mL, 5.5 mmol). The mixture was then heated to 80° C. and stirred for 1 h. The mixture was cooled to 0° C. and additional DIPEA (2.4 mL, 13.7 mmol) was added at followed by (S)-4-N-Boc-2-methyl piperazine (1.02 g, 5.12 mmol). The reaction mixture was stirred warming to rt for 20 min then poured into cold satd. NaHCO$_3$ (70 mL) and stirred for 10 min. The aqueous phase was extracted with EtOAc (2×30 mL) and the combined organic phases were dried by passing through a Chem Elut extraction cartridge. The crude product was purified by silica gel chromatography (eluent 30-80% EtOAc/heptane) to provide (S)-tert-butyl 4-(I-(2-(tert-butyl)phenyl)-7-chloro-6-fluoro-2-oxo-1,2-dihydropyrido[2,3-d]pyrimidin-4-yl)-3-methylpiperazine-1-carboxylate (2.24 g, 4.22 mmol, 92% yield). $^1$H NMR (400 MHz, DMSO-$d_6$) δ ppm 8.24-8.40 (1H, m), 7.61 (1H, d, J=8.1 Hz), 7.36-7.42 (1H, m), 7.26-7.33 (1H, m), 6.99 (1H, d, J=7.7 Hz), 4.64-4.89 (1H, m), 4.03-4.24 (1H, m), 3.89-4.01 (1H, m), 3.80 (1H, br d, J=12.6 Hz), 3.46-3.69 (1H, m), 2.88-3.26 (2H, m), 1.44 (9H, s), 1.21-1.34 (3H, m), 1.12 (9H, s). $^{19}$F NMR (376 MHz, DMSO-$d_6$) δ ppm −129.14 (s, 1F). m/z (ESI, +ve ion): 530.2 (M+H)$^+$.

Step 4: (3S)-tert-Butyl 4-(1-(2-(tert-butyl)phenyl)-6-fluoro-7-(2-fluoro-6-hydroxyphenyl)-2-oxo-1,2-dihydropyrido[2,3-d]pyrimidin-4-yl)-3-methylpiperazine-1-carboxylate A 250 mL round-bottomed flask was charged with (S)-tert-butyl 4-(1-(2-(tert-butyl)phenyl)-7-chloro-6-fluoro-2-oxo-1,2-dihydropyrido[2,3-d]pyrimidin-4-yl)-3-methylpiperazine-1-carboxylate (1.20 g, 2.26 mmol), 2-fluoro-6-hydroxyphenylboronic acid (0.395 g, 2.53 mmol), potassium acetate (1.17 g, 5.25 mmol), (1,1'-bis(diphenylphosphino)ferrocene)dichloropalladium-DCM (1:1) (0.169 g, 0.231 mmol), and 1,4-dioxane (20 mL) and the mixture was degassed with argon for 5 min. To the mixture a drop of water was added and it was stirred for 30 min at 90° C. The reaction mixture was cooled to rt and partitioned between water (40 mL) and EtOAc (40 mL). The aqueous phase was extracted with EtOAc (40 mL) and the organic phase was washed with water (40 mL). The organic phase was dried by passing through a Chem Elut extraction cartridge, concentrated and the crude product was purified by silica gel chromatography (eluent: 40-100% EtOAc/heptane) to provide (3S)-tert-butyl 4-(1-(2-(tert-butyl)phenyl)-6-fluoro-7-(2-fluoro-6-hydroxyphenyl)-2-oxo-1,2-dihydropyrido[2,3-d]pyrimidin-4-yl)-3-methylpiperazine-1-carboxylate (1.39 g, 2.3 mmol, 100% yield) as a yellow solid. $^1$H NMR (400 MHz, DMSO-$d_6$) δ ppm 10.14 (1H, br s), 8.15-8.27 (1H, m), 7.55 (1H, d, J=8.1 Hz), 7.19-7.33 (3H, m), 6.94 (1H, dd, J=7.8, 1.3 Hz), 6.63-6.75 (2H, m), 4.79 (1H, br d, J=1.9 Hz), 4.06-4.25 (1H, m), 3.89-3.99 (1H, min), 3.83 (1H, br d, J=13.5 Hz), 3.58 (1H, br t, J=12.4 Hz), 2.82-3.25 (2H, m), 1.45 (9H, s), 1.26-1.36 (3H, m), 1.09-1.15 (9H, m). $^{19}$F NMR (376 MHz, DMSO-$d_6$) δ ppm −114.91 (br d, J=12.0 Hz, 1F), −129.18 (m, 1F). m/z (ESI, +ve ion): 606.2 (M+H)$^+$.

Step 5: 4-((S)-4-Acryloyl-2-methylpiperazin-1-yl)-1-(2-(tert-butyl)phenyl)-6-fluoro-7-(2-fluoro-6-hydroxyphenyl)pyrido[2,3-d]pyrimidin-2(1H)-one To a yellow clear solution of (3S)-tert-butyl 4-(1-(2-ethyl-4-methylpyridin-3-yl)-6-fluoro-7-(2-fluoro-6-hydroxyphenyl)-2-oxo-1,2-dihydropyrido[2,3-d]pyrimidin-4-yl)-3-methylpiperazine-1-carboxylate (1.38 g, 2.28 mmol) in DCM (10 mL) was added TFA (5 mL) and the mixture was stirred at rt. After 50 min. the mixture was concentrated in vacuo and the residue was dissolved in DCM (10 mL) cooled to 0° C. DIPEA (2 mL, 11.4 mmol) was then added followed by acryloyl chloride, 0.25 M solution in DCM (8.3 mL, 2.1 mmol). The cold bath was removed and the mixture was stirred at rt. After 10 min, the reaction was concentrated in vacuo and the crude product was purified by silica gel chromatography (eluent: 0-50%/EtOAc-EtOH (3:1)/heptane) to provide 4-((S)-4-acryloyl-2-methylpiperazin-1-yl)-1-(2-(tert-butyl)phenyl)-6-fluoro-7-(2-fluoro-6-hydroxyphenyl)pyrido[2,3-d]pyrimidin-2(1H)-one (1.02 g, 1.82 mmol, 80% yield) as a yellow solid. $^1$H NMR (400 MHz, DMSO-$d_6$) δ ppm 10.13 (br d, J=2.07 Hz, 1H), 8.16-8.29 (m, 1H), 7.55 (d, J=7.67 Hz, 1H), 7.18-7.34 (m, 3H), 6.95 (d, J=7.67 Hz, 1H), 6.78-6.91 (m, 1H), 6.63-6.76 (m, 2H), 6.14-6.25 (m, 1H), 5.76 (dd, J=2.07, 10.37 Hz, 1H), 4.75-4.89 (m, 1H), 3.92-4.53 (m, 3H), 3.45-3.74 (m, 2H), 2.90-3.24 (m, 1H), 1.22-1.36 (m, 3H), 1.12 (s, 9H). $^{19}$F NMR (377 MHz, DMSO-$d_6$) δ ppm −114.88 (br d, J=8.0 Hz, 1F), −129.19 (m, 1F). m/z (ESI, +ve ion): 560.2 (M+H)$^+$.

TABLE 58

Compounds 58-2 to 58-23 were prepared following the procedure described in Method 58, Steps 1-5, above as follows:

| Ex. # | Chemical Structure | Name | Method Changes | Reagent |
|---|---|---|---|---|
| 58-2 | 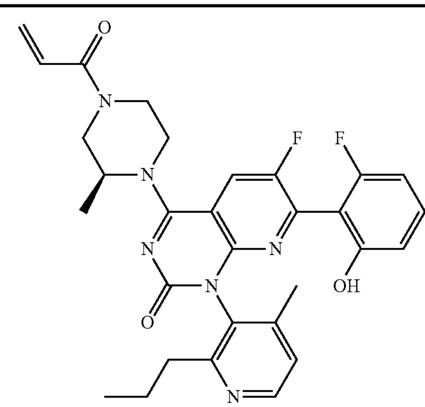 | 6-fluoro-7-(2-fluoro-6-hydroxyphenyl)-4-((2S)-2-methyl-4-(2-propenoyl)-1-piperazinyl)-1-(4-methyl-2-propyl-3-pyridinyl)pyrido[2,3-d]pyrimidin-2(1H)-one | | Step 1: 1. 4-methyl-3-propylpyridin-2-amine (Intermediate I-12); Step 4: (2-fluoro-6-hydroxyphenyl) boronic acid (Wuxi) |
| 58-3 | 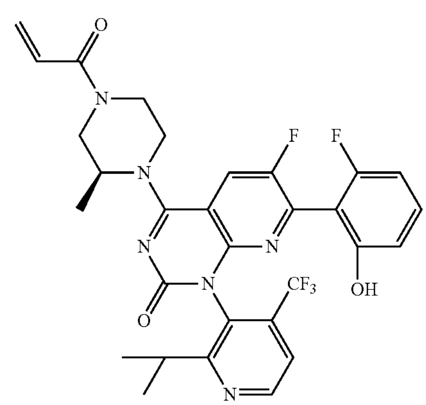 [SMILES: C=CC(=O)N1CCN(c2nc(=O)n(-c3c(C(F)(F)F)ccnc3C(C)C)c3nc(-c4c(O)cccc4F)c(F)cc23)[C@@H](C)C1] | 6-fluoro-7-(2-fluoro-6-hydroxyphenyl)-4-((2S)-2-methyl-4-(2-propenoyl)-1-piperazinyl)-1-(2-(2-propanyl)-4-(trifluoromethyl)-3-pyridinyl)pyrido[2,3-d]pyrimidin-2(1H)-one | | Step 1: 2-Isopropyl-4-(trifluoromethyl)pyridin-3-amine (Intermediate I-13), Step 4: (2-fluoro-6-hydroxyphenyl) boronic acid (Wuxi) |

TABLE 58-continued

Compounds 58-2 to 58-23 were prepared following the procedure described in Method 58, Steps 1-5, above as follows:

| Ex. # | Chemical Structure | Name | Method Changes | Reagent |
|---|---|---|---|---|
| 58-4 | 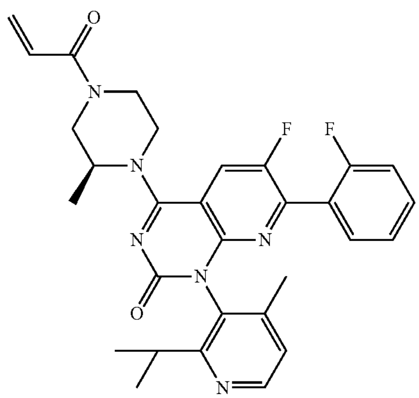 | 6-fluoro-7-(2-fluorophenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | Step 4: Use $Pd(PPh_3)_4$ and $Na_2CO_3$ | Step 1: 2-isopropyl-4-methylpyridin-3-amine (Intermediate R), Step 4: 2-fluorophenylboronic acid (Combi-Blocks Inc.) |
| 58-5 | 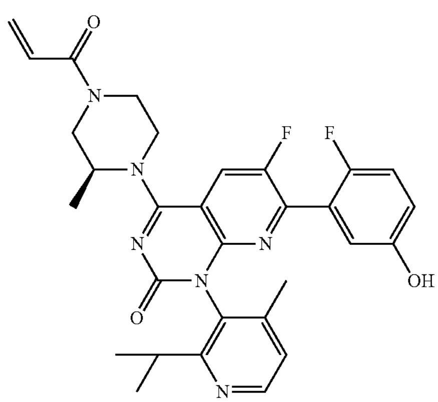 [SMILES: C=CC(=O)N1CCN(c2nc(=O)n(-c3c(C)ccnc3C(C)C)c3nc(-c4cc(O)ccc4F)c(F)cc23)[C@@H](C)C1] | 6-fluoro-7-(2-fluoro-5-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | Step 4: Use $Pd(PPh_3)_4$ and $Na_2CO_3$ | Step 1: 2-isopropyl-4-methylpyridin-3-amine (Intermediate R), Step 4: (2-fluoro-5-hydroxyphenyl)boronic acid (Ark Pharm, Inc.) |
| 58-6 | 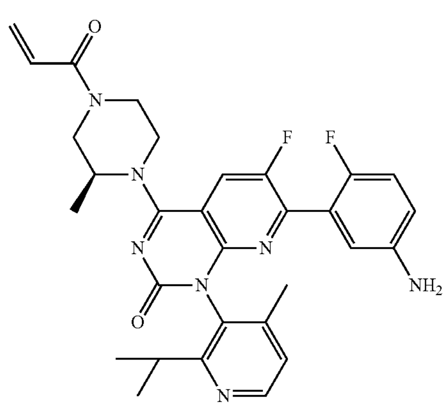 [SMILES: C=CC(=O)N1CCN(c2nc(=O)n(-c3c(C)ccnc3C(C)C)c3nc(-c4cc(N)ccc4F)c(F)cc23)[C@@H](C)C1] | 7-(5-amino-2-fluorophenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | Step 4: Use $Pd(PPh_3)_4$ and $Na_2CO_3$ | Step 1: 2-isopropyl-4-methylpyridin-3-amine (Intermediate R), Step 4: 2-fluoro-5-aminophenyl boronic acid (Combi-Blocks Inc.) |

TABLE 58-continued

Compounds 58-2 to 58-23 were prepared following the procedure described in Method 58, Steps 1-5, above as follows:

| Ex. # | Chemical Structure | Name | Method Changes | Reagent |
|---|---|---|---|---|
| 58-7 | 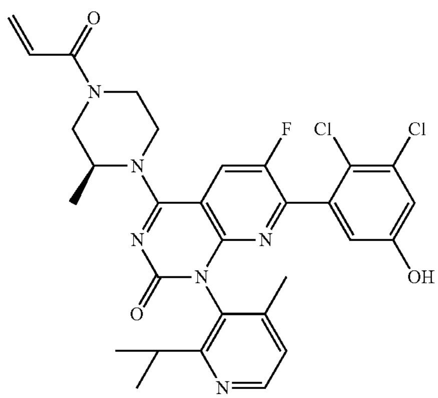 [SMILES: C=CC(=O)N1CCN(c2nc(=O)n(-c3c(C)ccnc3C(C)C)c3nc(-c4cc(O)cc(Cl)c4Cl)c(F)cc23)[C@@H](C)C1] | 7-(2,3-dichloro-5-hydroxyphenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | Step 4: Use Pd(PPh$_3$)$_4$ and Na$_2$CO$_3$; Add one step before Step 5: for demethylation using BBr$_3$ and DCE at 0° C. | Step 1: 2-isopropyl-4-methylpyridin-3-amine (Intermediate R), Step 4: 2-(2,3-dichloro-5-methoxyphenyl)-4,4,5,5-tetramethyl-1,3,2-dioxaborolane (ACS Scientific Inc.) |
| 58-8 | 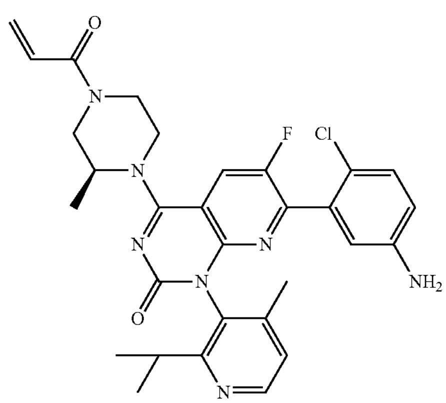 | 7-(5-amino-2-chlorophenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | Step 4: Use Pd(PPh$_3$)$_4$ and Na$_2$CO$_3$ | Step 1: 2-isopropyl-4-methylpyridin-3-amine (Intermediate R), Step 4: (5-amino-2-chlorophenyl) boronic acid (Matrix Scientific) |
| 58-9 | 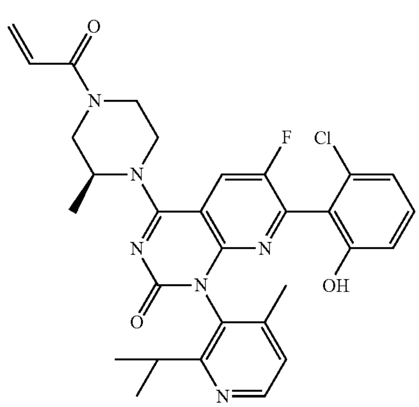 [SMILES: C=CC(=O)N1CCN(c2nc(=O)n(-c3c(C)ccnc3C(C)C)c3nc(-c4c(O)cccc4Cl)c(F)cc23)[C@@H](C)C1] | 7-(2-chloro-6-hydroxyphenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | Step 4: Use Pd(PPh$_3$)$_4$ and Na$_2$CO$_3$ | Step 1: 2-isopropyl-4-methylpyridin-3-amine (Intermediate R) Step 4: (2-chloro-6-hydroxyphenyl) boronic acid (Aurum Pharmatech LLC) |

TABLE 58-continued

Compounds 58-2 to 58-23 were prepared following the procedure described in Method 58, Steps 1-5, above as follows:

| Ex. # | Chemical Structure | Name | Method Changes | Reagent |
|---|---|---|---|---|
| 58-10 | 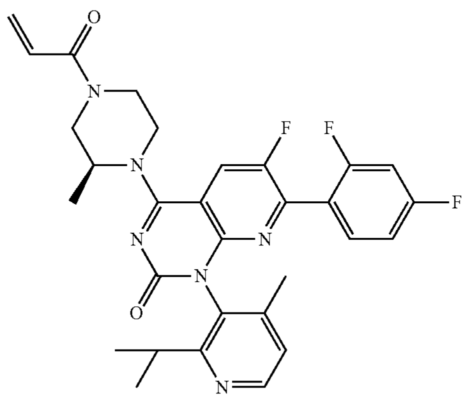 [SMILES: C=CC(=O)N1CCN(c2nc(=O)n(-c3c(C)ccnc3C(C)C)c3nc(-c4ccc(F)cc4F)c(F)cc23)[C@@H](C)C1] | 7-(2,4-difluorophenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | Step 4: Use Pd(PPh$_3$)$_4$ and Na$_2$CO$_3$ | 2 Step 1: 2-isopropyl-4-methylpyridin-3-amine (Intermediate R), Step 4: 2,4-difluorobenzeneboronic acid (Sigma-Aldrich Corporation) |
| 58-11 | 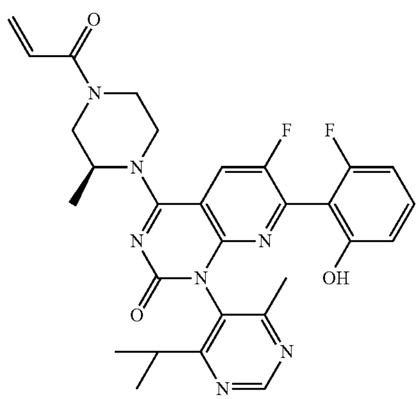 [SMILES: C=CC(=O)N1CCN(c2nc(=O)n(-c3c(C)ncnc3C(C)C)c3nc(-c4c(O)cccc4F)c(F)cc23)[C@@H](C)C1] | 6-fluoro-7-(2-fluoro-6-hydroxyphenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | Step 4: Use Pd(PPh$_3$)$_4$ and Na$_2$CO$_3$ | Step 1: 4-isopropyl-6-methylpyrimidin-5-amine (Intermediate I-5), Step 4: (2-fluoro-6-hydroxyphenyl)boronic acid (Wuxi) |
| 58-12 | 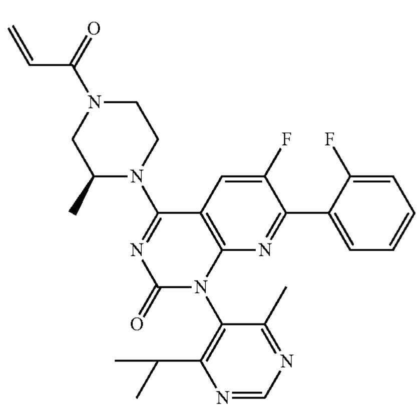 [SMILES: C=CC(=O)N1CCN(c2nc(=O)n(-c3c(C)ncnc3C(C)C)c3nc(-c4ccccc4F)c(F)cc23)[C@@H](C)C1] | 6-fluoro-7-(2-fluorophenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | Step 4: Use Pd(PPh$_3$)$_4$ and Na$_2$CO$_3$ | Step 1: 4-isopropyl-6-methylpyrimidin-5-amine (Intermediate I-5), Step 4: 2-fluorophenylboronic acid (Combi-Blocks Inc.) |

TABLE 58-continued

Compounds 58-2 to 58-23 were prepared following the procedure described in Method 58, Steps 1-5, above as follows:

| Ex. # | Chemical Structure | Name | Method Changes | Reagent |
|---|---|---|---|---|
| 58-13 | 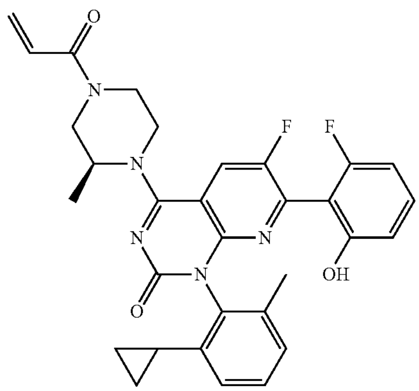 [SMILES: C=CC(=O)N1CCN(c2nc(=O)n(-c3c(C)cccc3C3CC3)c3nc(-c4c(O)cccc4F)c(F)cc23)[C@@H](C)C1] | 1-(2-cyclopropyl-6-methylphenyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 2-cyclopropyl-6-methylaniline (Intermediate I-9), Step 4: (2-fluoro-6-hydroxyphenyl)boronic acid (Wuxi) |
| 58-14 | 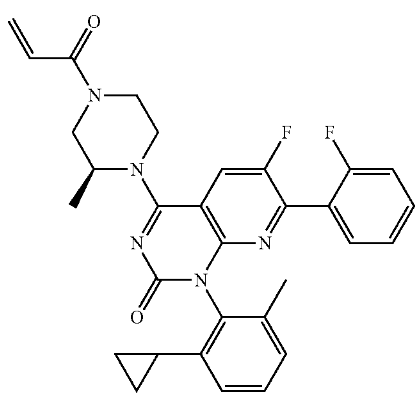 | 1-(2-cyclopropyl-6-methylphenyl)-6-fluoro-7-(2-fluorophenyl)-4-((2S)-2-methyl-4-(2-propenoyl)-1-piperazinyl)pyrido[2,3-d]pyrimidin-2(1H)-one | | Step 1: 2-cyclopropyl-6-methylaniline (Intermediate I-9), Step 4: 2-fluorophenylboronic acid (Combi-Blocks Inc.) |
| 58-15 | 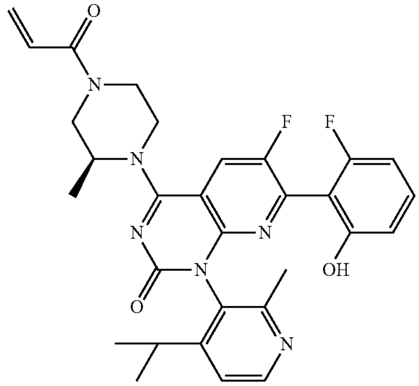 | 6-fluoro-7-(2-fluoro-6-hydroxyphenyl)-1-(2-methyl-4-(2-propanyl)-3-pyridinyl)-4-((2S)-2-methyl-4-(2-propenoyl)-1-piperazinyl)pyrido[2,3-d]pyrimidin-2(1H)-one | | Step 1: 4-isopropyl-2-methylpyridin-3-amine (Intermediate I-16), Step 4: (2-fluoro-6-hydroxyphenyl)boronic acid (Wuxi) |

TABLE 58-continued

Compounds 58-2 to 58-23 were prepared following the procedure described in Method 58, Steps 1-5, above as follows:

| Ex. # | Chemical Structure | Name | Method Changes | Reagent |
|---|---|---|---|---|
| 58-16 | 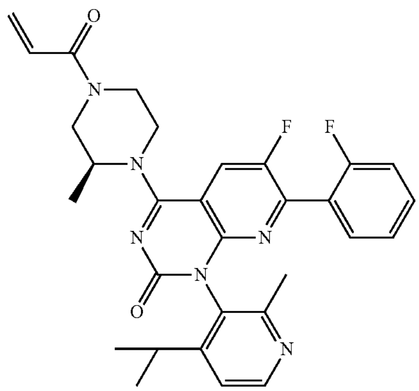 [SMILES: C=CC(=O)N1CCN(c2nc(=O)n(-c3c(C(C)C)ccnc3C)c3nc(-c4ccccc4F)c(F)cc23)[C@@H](C)C1] | 6-fluoro-7-(2-fluorophenyl)-1-(2-methyl-4-(2-propanyl)-3-pyridinyl)-4-((2S)-2-methyl-4-(2-propenoyl)-1-piperazinyl)pyrido[2,3-d]pyrimidin-2(1H)-one | | Step 1: 4-isopropyl-2-methylpyridin-3-amine (Intermediate I-16), Step 4: 2-fluorophenylboronic acid (Combi-Blocks Inc.) |
| 58-17 | 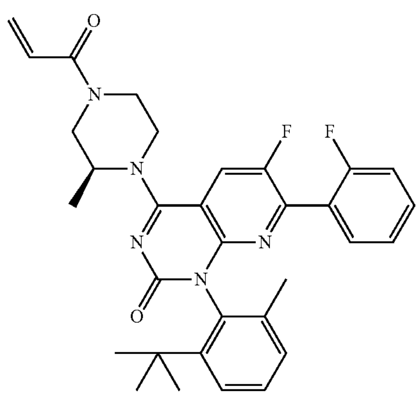 [SMILES: C=CC(=O)N1CCN(c2nc(=O)n(-c3c(C)cccc3C(C)(C)C)c3nc(-c4ccccc4F)c(F)cc23)[C@@H](C)C1] | 6-fluoro-7-(2-fluorophenyl)-1-(2-(2-methyl-2-propanyl)phenyl)-4-((2S)-2-methyl-4-(2-propenoyl)-1-piperazinyl)pyrido[2,3-d]pyrimidin-2(1H)-one | | Step 1: 2-(tert-butyl)aniline (Ark Pharm, Inc.), Step 4: (2-fluorophenyl)boronic acid (Combi-Blocks Inc.) |
| 58-18 | 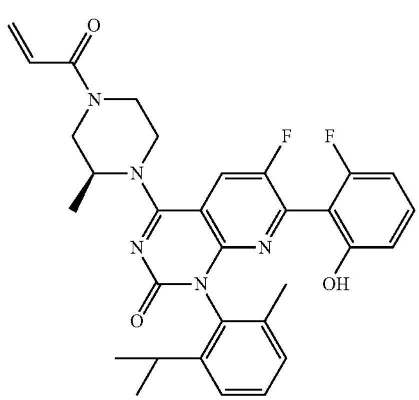 [SMILES: C=CC(=O)N1CCN(c2nc(=O)n(-c3c(C)cccc3C(C)C)c3nc(-c4c(O)cccc4F)c(F)cc23)[C@@H](C)C1] | 6-fluoro-7-(2-fluoro-6-hydroxyphenyl)-1-(2-methyl-6-(2-propanyl)phenyl)-4-((2S)-2-methyl-4-(2-propenoyl)-1-piperazinyl)pyrido[2,3-d]pyrimidin-2(1H)-one | Step 5: Aqueous work up performed after part 1, part 2 in DMA without DIEA | Step 1: 2-isopropyl-6-methylaniline (Enamine), Step 4: (2-fluoro-6-hydroxyphenyl) boronic acid (Wuxi) |

TABLE 58-continued

Compounds 58-2 to 58-23 were prepared following the procedure described in Method 58, Steps 1-5, above as follows:

| Ex. # | Chemical Structure | Name | Method Changes | Reagent |
|---|---|---|---|---|
| 58-19 | 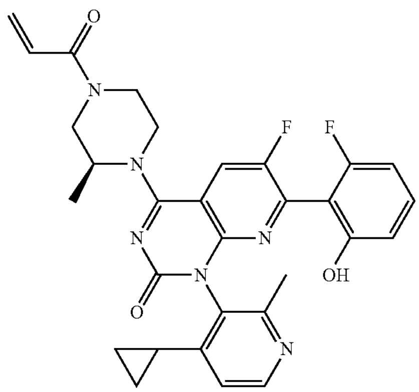 [SMILES: C=CC(=O)N1CCN(c2nc(=O)n(-c3c(C4CC4)ccnc3C)c3nc(-c4c(O)cccc4F)c(F)cc23)[C@@H](C)C1] | 1-(4-cyclopropyl-2-methyl-3-pyridinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 4-cyclopropyl-2-methyl-pyridin-3-amine (Intermediate I-21) Step 4: (2-fluoro-6-hydroxyphenyl) boronic acid (Wuxi) |
| 58-20 | 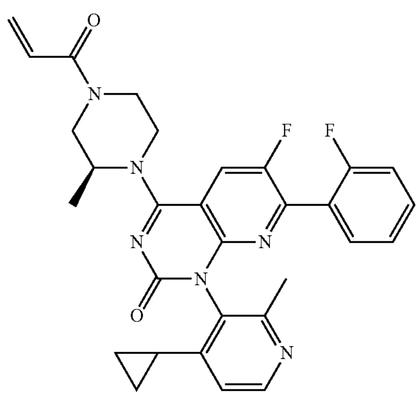 [SMILES: C=CC(=O)N1CCN(c2nc(=O)n(-c3c(C4CC4)ccnc3C)c3nc(-c4ccccc4F)c(F)cc23)[C@@H](C)C1] | 1-(4-cyclopropyl-2-methyl-3-pyridinyl)-6-fluoro-7-(2-fluorophenyl)-4-((2S)-2-methyl-4-(2-propenoyl)-1-piperazinyl)pyrido[2,3-d]pyrimidin-2(1H)-one | | Step 1: 4-cyclopropyl-2-methyl-pyridin-3-amine (Intermediate I-21), Step 4: 2-fluorophenyl boronic acid (Combi-Blocks, Inc.) |
| 58-21 | 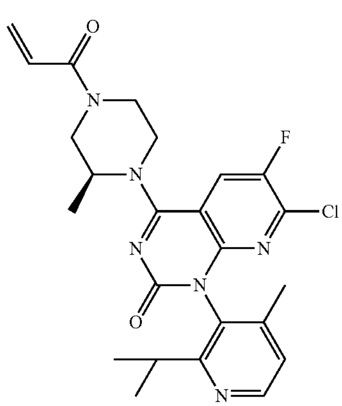 [SMILES: C=CC(=O)N1CCN(c2nc(=O)n(-c3c(C)ccnc3C(C)C)c3nc(Cl)c(F)cc23)[C@@H](C)C1] | 7-chloro-6-fluoro-1-(4-methyl-2-(2-propanyl)-3-pyridinyl)-4-((2S)-2-methyl-4-(2-propenoyl)-4-piperazinyl)pyrido[2,3-d]pyrimidin-2(1H)-one | Omit Step 4 | Step 1: 2-isopropyl-4-methylpyridin-3-amine (Intermediate R) |

TABLE 58-continued

Compounds 58-2 to 58-23 were prepared following the procedure described in
Method 58, Steps 1-5, above as follows:

| Ex. # | Chemical Structure | Name | Method Changes | Reagent |
|---|---|---|---|---|
| 58-22 | | 1-(4,6-diethyl-5-pyrimidinyl)-6-fluoro-7-(2-fluorophenyl)-4-((2S)-2-methyl-4-(2-propenoyl)-1-piperazinyl)pyrido[2,3-d]pyrimidin-2(1H)-one | Step 1: 4,6-diethylpyrimidin-5-amine (Intermediate X), Step 4: (2-fluorophenyl) boronic acid (TCI America) |
| 58-23 | | 1-(4,6-diethyl-5-pyrimidinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | Step 1: 4,6-diethylpyrimidin-5-amine (Intermediate X), Step 4: (2-fluoro-6-hydroxyphenyl) boronic acid (Wuxi) |

Method 59

Example 59-1: 6-Fluoro-7-(2-fluoro-6-hydroxyphenyl)-4-((2S)-2-methyl-4-(2-propenoyl)-1-piperazinyl)-1-(2-(1-(trifluoromethyl)cyclopropyl)phenyl)pyrido[2,3-d]pyrimidin-2(1H)-one

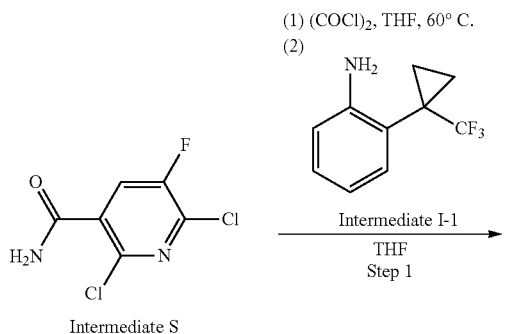
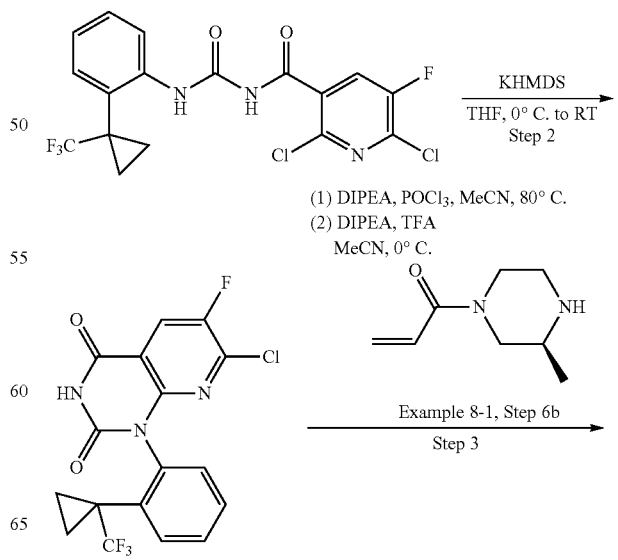

-continued

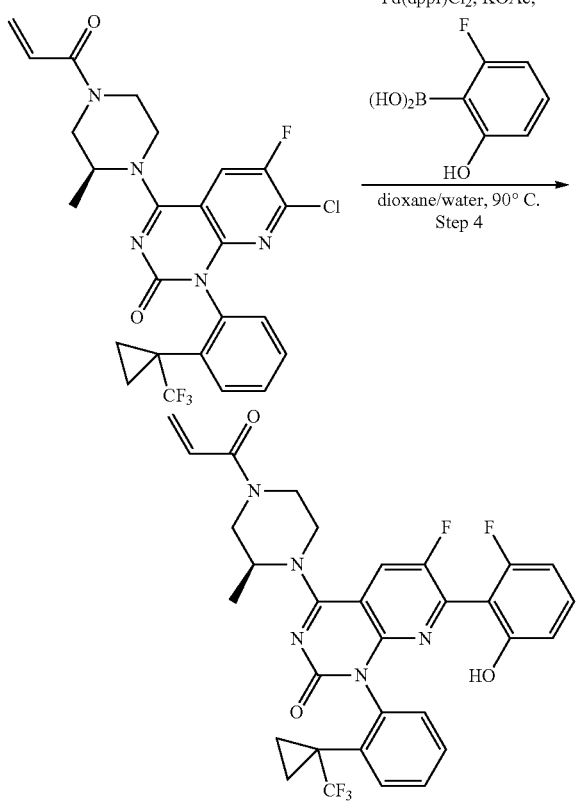

Step 1: 2,6-Dichloro-5-fluoro-N-((2-(1-(trifluoromethyl)cyclopropyl)phenyl)carbamoyl)nicotinamide Oxalyl chloride 2.0 M in DCM (4.38 mL, 8.77 mmol) was added to a mixture of 2,6-dichloro-5-fluoronicotinamide (Intermediate S, 1.75 g, 8.35 mmol) in THF (35 mL). The reaction mixture was stirred at 60° C. for 20 min before being cooled to 0° C. 2-(1-(Trifluoromethyl)cyclopropyl) aniline (Intermediate I-1, 1.68 g, 8.35 mmol) was added, and the reaction mixture was stirred at 0° C. for 45 min. The reaction mixture was partitioned between satd. NaHCO$_3$ (100 mL) and EtOAc (100 mL). The organic layer was separated, washed with brine (100 mL), dried over MgSO$_4$, filtered, and concentrated in vacuo to give 2,6-dichloro-5-fluoro-N-((2-(1-(trifluoromethyl)cyclopropyl)phenyl)carbamoyl)nicotinamide as an orange solid (3.59 g, 8.23 mmol, 99% yield). m/z (ESI, +ve ion): 435.8 (M+H)$^+$.

Step 2: 7-Chloro-6-fluoro-1-(2-(1-(trifluoromethyl) cyclopropyl)phenyl)pyrido[2,3-d]pyrimidine-2,4(1H, 3H)-dione 1 M KHMDS in THF (16.46 mL, 16.46 mmol) was added to a stirred solution of 2,6-dichloro-5-fluoro-N-((2-(1-(trifluoromethyl)cyclopropyl)phenyl)carbamoyl)nicotinamide (3.59 g, 8.23 mmol) in THF (80 mL) at 0° C. The reaction mixture was stirred at 0° C. for 2 h and then rt for another 20 h. The reaction mixture was quenched with satd. ammonium chloride (100 mL) and extracted with EtOAc (150 mL). The organic layer was separated, washed with brine (100 mL), dried over MgSO$_4$, filtered, and concentrated in vacuo. The resulting crude solid was slurried in DCM (20 mL) and filtered to give 7-chloro-6-fluoro-1-(2-(1-(trifluoromethyl)cyclopropyl)phenyl)pyrido[2,3-d]pyrimidine-2,4 (1H,3H)-dione as a tan solid (1.6 g, 4 mmol, 48.6% yield). $^1$H NMR (400 MHz, DMSO-d$_6$) δ ppm 12.24 (1H, br s) 8.47 (1H, br d, J=7.26 Hz) 7.63-7.71 (1H, m) 7.52-7.61 (2H, m) 7.42-7.47 (1H, m) 1.15-1.26 (3H, m) 0.88-0.97 (1H, m). m/z (ESI, +ve ion): 400.0 (M+H)$^+$.

Step 3: (S)-4-(4-Acryloyl-2-methylpiperazin-1-yl)-7-chloro-6-fluoro-1-(2-(1-(trifluoromethyl)cyclopropyl)phenyl)pyrido[2,3-d]pyrimidin-2(1H)-one Phosphorus oxychloride (0.45 mL, 4.77 mmol) was added to a stirred mixture of 7-chloro-6-fluoro-1-(2-(1-(trifluoromethyl)cyclopropyl)phenyl)pyrido[2,3-d]pyrimidine-2,4(1H, 3H)-dione (1.59 g, 3.98 mmol) and DIPEA (0.9 mL, 5.2 mmol) in acetonitrile (15 mL). The reaction mixture was heated to 80° C. and stirred for 30 min. The reaction mixture was cooled to 0° C. followed by a second addition of DIPEA (4.5 mL, 25.9 mmol) and addition of (S)-1-(3-methylpiperazin-1-yl)prop-2-en-1-one 2,2,2-trifluoroacetate (Example 8-1, Step 6b) 2.39 g, 3.98 mmol). The reaction mixture was stirred at 0° C. for 20 min then water (100 mL) was added, and the aqueous suspension was extracted with EtOAc (100 mL). The organic layer was separated, washed with brine (75 mL), dried over MgSO$_4$, filtered, and concentrated in vacuo. The crude product was purified by silica gel chromatography (eluent: 0-50% EtOAc-EtOH (3:1)/heptane) to provide (S)-4-(4-acryloyl-2-methylpiperazin-1-yl)-7-chloro-6-fluoro-1-(2-(1-(trifluoromethyl)cyclopropyl)phenyl)pyrido[2,3-d]pyrimidin-2(1H)-one as an off-white solid (874 mg, 1.63 mmol, 41% yield). $^1$H NMR (400 MHz, CDCl$_3$) δ ppm 7.63-7.77 (2H, m) 7.46-7.55 (2H, m) 7.15 (1H, br d, J=7.05 Hz) 6.50-6.68 (1H, m) 6.40 (1H, br d, J=16.60 Hz) 5.80 (1H, br d, J=10.37 Hz) 2.76-5.20 (7H, m) 1.45-1.64 (3H, m) 1.23-1.37 (2H, m) 0.97-1.08 (2H, m). m/z (ESI, +ve ion): 536.2 (M+H)$^+$.

Step 4: 6-Fluoro-7-(2-fluoro-6-hydroxyphenyl)-4-((2S)-2-methyl-4-(2-propenoyl)-1-piperazinyl)-1-(2-(1-(trifluoromethyl)cyclopropyl)phenyl)pyrido[2,3-d]pyrimidin-2(1H)-one (S)-4-(4-Acryloyl-2-methylpiperazin-1-yl)-7-chloro-6-fluoro-1-(2-(1-(trifluoromethyl)cyclopropyl)phenyl)pyrido [2,3-d]pyrimidin-2(1H)-one (437 mg, 0.815 mmol), (1,1'-bis(diphenylphosphino) ferrocene) dichloropalladium (60 mg, 0.082 mmol), and potassium acetate (336 mg, 3.42 mmol) were mixed in 1,4-dioxane (3 mL) under an argon atmosphere. The mixture was heated to 90° C. and 2-fluoro-6-hydroxyphenylboronic acid (191 mg, 1.22 mmol, Combi Blocks, San Diego, Calif., USA) and water (0.3 mL) were added. The reaction mixture was stirred at 90° C. for 30 min then cooled to rt. diluted with EtOAc (150 mL), and washed with water (100 mL). The organic layer was separated, washed with brine (75 mL), dried over MgSO$_4$, filtered, and concentrated in vacuo. The crude product was purified by silica gel chromatography (eluent: 0-75% EtOAc-EtOH (3:1)/heptane) to provide 6-fluoro-7-(2-fluoro-6-hydroxyphenyl)-4-((2S)-2-methyl-4-(2-propenoyl)-1-piperazinyl)-1-(2-(1-(trifluoromethyl)cyclopropyl)phenyl)pyrido[2,3-d] pyrimidin-2(1H)-one as a light yellow solid (340 mg, 0.278 mmol, 68.2% yield). $^1$H NMR (400 MHz, CDCl$_3$) δ ppm 9.35-9.39 (m, 1H), 7.79-7.89 (m, 1H), 7.72 (br d, J=7.3 Hz, 1H), 7.53-7.64 (m, 2H), 7.19-7.31 (m, 2H), 6.55-6.73 (m, 3H), 6.39-6.45 (m, 1H), 5.83 (br d, J=10.4 Hz, 1H), 2.85-5.31 (m, 7H), 1.51-1.68 (m, 3H), 1.23-1.33 (m, 1H), 1.06-1.14 (m, 1H), 0.99-1.06 (m, 1H), 0.86-0.93 (m, 1H). m/z (ESI, +ve ion): 612.1 (M+H)$^+$.

TABLE 59

Compounds 59-2 to 59-6 were prepared following the procedure described in Method 59, Steps 1-4, above as follows:

| Ex. # | Chemical Structure | Name | Method Changes | Reagent |
|---|---|---|---|---|
| 59-2 | 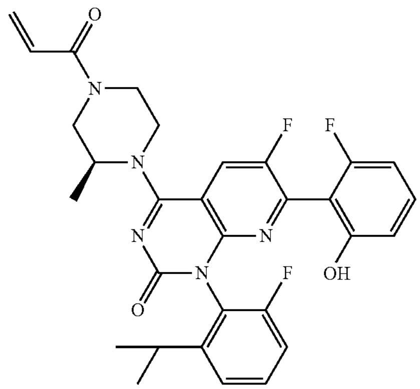 [SMILES: C=CC(=O)N1CCN(c2nc(=O)n(-c3c(F)cccc3C(C)C)c3nc(-c4c(O)cccc4F)c(F)cc23)[C@@H](C)C1] | 6-fluoro-7-(2-fluoro-6-hydroxyphenyl)-1-(2-fluoro-6-(2-propanyl)phenyl)-4-((2S)-2-methyl-4-(2-propenoyl)-1-piperazinyl)pyrido[2,3-d]pyrimidin-2(1H)-one | | Step 1: 2-fluoro-6-isopropylaniline (Intermediate I-26), Step 4: (2-fluoro-6-hydroxyphenyl) boronic acid (Wuxi) |
| 59-3 | 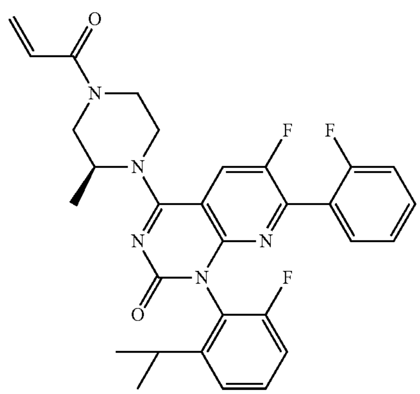 | 6-fluoro-7-(2-fluorophenyl)-1-(2-fluoro-6-(2-propanyl)phenyl)-4-((2S)-2-methyl-4-(2-propenoyl)-1-piperazinyl)pyrido[2,3-d]pyrimidin-2(1H)-one | | Step 1: 2-fluoro-6-isopropylaniline (Intermediate I-26), Step 4: 2-fluorophenylboronic acid (Combi-Blocks Inc.) |
| 59-4 | 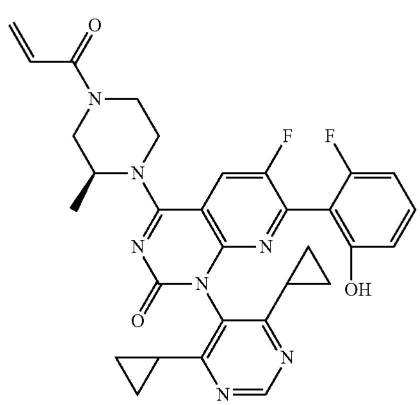 [SMILES: C=CC(=O)N1CCN(c2nc(=O)n(-c3c(C4CC4)ncnc3C3CC3)c3nc(-c4c(O)cccc4F)c(F)cc23)[C@@H](C)C1] | 1-(4,6-dicyclopropyl-5-pyrimidinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 4,6-dicyclopropyl-pyrimidin-5-amine (Intermediate I-25), Step 4: (2-fluoro-6-hydroxyphenyl) boronic acid (Wuxi) |

TABLE 59-continued

Compounds 59-2 to 59-6 were prepared following the procedure described in
Method 59, Steps 1-4, above as follows:

| Ex. # | Chemical Structure | Name | Method Changes | Reagent |
|---|---|---|---|---|
| 59-5 | 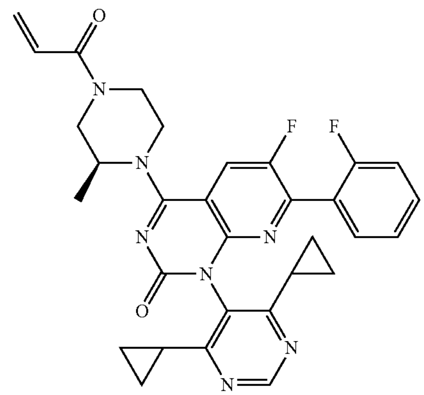 | 1-(4,6-dicyclopropyl-5-pyrimidinyl)-6-fluoro-7-(2-fluorophenyl)-4-((2S)-2-methyl-4-(2-propenoyl)-1-piperazinyl)pyrido[2,3-d]pyrimidin-2(1H)-one | | Step 1: 4,6-dicyclopropyl-pyrimidin-5-amine (I-25), Step 4: 2-fluorophenylboronic acid (Combi-Blocks Inc.) |
| 59-6 | 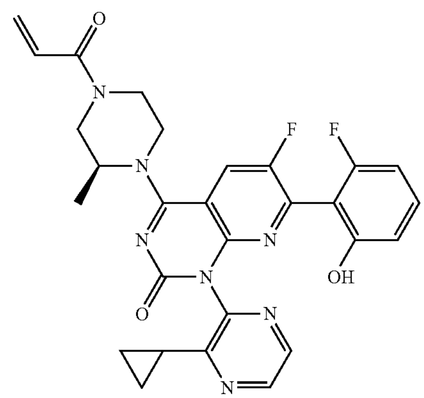 [SMILES: C=CC(=O)N1CCN(c2nc(=O)n(-c3nccnc3C3CC3)c3nc(-c4c(O)cccc4F)c(F)cc23)[C@@H](C)C1] | 1-(3-cyclopropyl-2-pyrazinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 3-cyclopropylpyrazin-2-amine (Aurum Pharmatech LLC), Step 4: (2-fluoro-6-hydroxyphenyl)boronic acid (Wuxi) |

Method 60

Example 60-1: 6-Chloro-1-(3-cyclopropyl-2-pyridinyl)-7-(2-fluorophenyl)-4-((2S)-2-methyl-4-(2-propenoyl)-1-piperazinyl)pyrido[2,3-d]pyrimidin-2(1H)-one

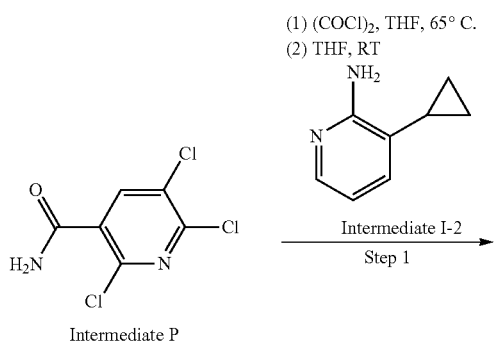

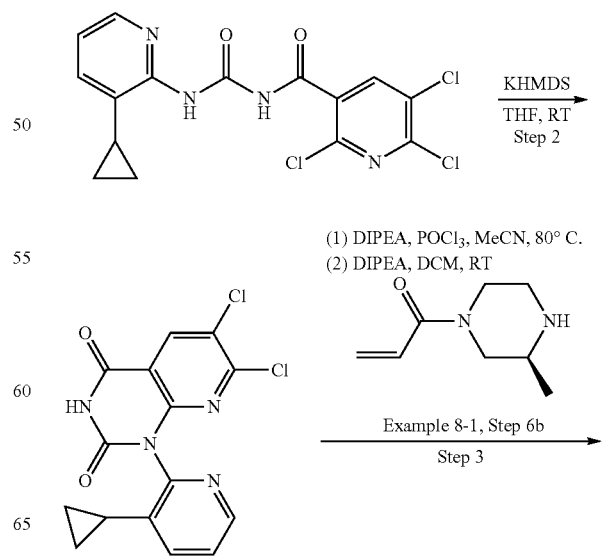

-continued

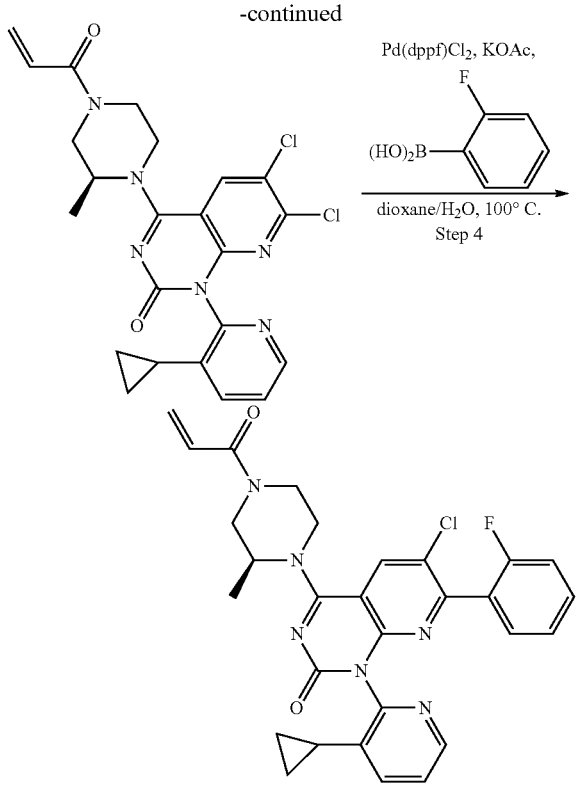

Step 1: 2,5,6-Trichloro-N-((3-cyclopropylpyridin-2-yl)carbamoyl)nicotinamide A mixture of 2,5,6-trichloronicotinamide (Intermediate P, 4.46 g, 19.8 mmol) and oxalylchloride, 1.0 M solution in DCM (21.8 mL, 21.8 mmol) in THF (99 mL) was stirred at 65° C. for 1 h. The reaction mixture was cooled to rt, and a solution of 3-cyclopropylpyridin-2-amine (Intermediate I-2, 2.66 g, 19.8 mmol) in THF (6 mL) was added over 1 min. The reaction mixture was stirred at rt for 30 min then the suspension was filtered. The filtrate was diluted with EtOAc (150 mL), added to a separatory funnel, and washed with satd. NaHCO$_3$ (3×100 mL), the organic layer was separated, dried over anhydrous Na$_2$SO$_4$, and concentrated in vacuo to give 2,5,6-trichloro-N-((3-cyclopropylpyridin-2-yl)carbamoyl)nicotinamide (5.27 g, 13.7 mmol, 69% yield) which was used without further purification. m/z (ESI, +ve ion): 384.8 (M+H)$^+$.

Step 2: 6,7-Dichloro-1-(o-tolyl)pyrido[2,3-d]pyrimidine-2,4(1H,3H)-dione

1 M KHMDS in THF (27.3 mL, 27.3 mmol) was added to a solution of 2,5,6-trichloro-N-((3-cyclopropylpyridin-2-yl)carbamoyl)nicotinamide (5.27 g, 13.7 mmol) in THF (100 mL) at rt; the solution was stirred at rt for 30 min. The reaction mixture was diluted with EtOAc (200 mL), added to a separatory funnel, and washed with saturated, aqueous ammonium chloride (3×100 mL); the organic layer was separated, dried over anhydrous Na$_2$SO$_4$, and concentrated in vacuo. The crude product was purified by silica gel chromatography (eluent: 0-60% EtOAc-EtOH (3:1)/heptane) to provide 6,7-dichloro-1-(3-cyclopropylpyridin-2-yl)pyrido[2,3-d]pyrimidine-2,4(1H,3H)-dione (1.42 g, 4.07 mmol, 30% yield). m/z (ESI, +ve ion): 348.8 (M+H)$^+$.

Step 3: 6,7-Dichloro-1-(3-cyclopropylpyridin-2-yl)pyrido[2,3-d]pyrimidine-2,4(1H,3H)-dione A solution of 6,7-dichloro-1-(3-cyclopropylpyridin-2-yl)pyrido[2,3-d]pyrimidine-2,4(1H,3H)-dione (1.00 g, 2.86 mmol), phosphoryl trichloride (0.53 mL, 5.7 mmol), and DIPEA (2.0 mL, 11.5 mmol) in acetonitrile (7 mL) was stirred at 80° C. for 30 min. The reaction mixture was concentrated and used as is. A solution of the resulting oil, (S)-1-(3-methylpiperazin-1-yl)prop-2-en-1-one TFA salt (Example 8-1, Step 6b, 1.94 g, 3.44 mmol), and DIPEA (2.5 mL, 14.3 mmol) in DCM (14 mL) was stirred at rt for 15 min. The reaction mixture was diluted with EtOAc (100 mL), added to a separatory funnel, and washed with satd. NaHCO$_3$ (2×75 mL), the organic layer was separated, dried over anhydrous Na$_2$SO$_4$, and concentrated in vacuo. The crude product was purified by silica gel chromatography (eluent: 0-70% EtOAc-EtOH (3:1)/heptane) to provide (S)-4-(4-acryloyl-2-methylpiperazin-1-yl)-6,7-dichloro-1-(3-cyclopropylpyridin-2-yl)pyrido[2,3-d]pyrimidin-2(1H)-one (290 mg, 0.597 mmol, 21% yield). m/z (ESI, +ve ion): 484.9 (M+H)$^+$.

Step 4: 6-Chloro-1-(3-cyclopropyl-2-pyridinyl)-7-(2-fluorophenyl)-4-((2S)-2-methyl-4-(2-propenoyl)-1-piperazinyl)pyrido[2,3-d]pyrimidin-2(1H)-one A mixture of (S)-4-(4-acryloyl-2-methylpiperazin-1-yl)-6,7-dichloro-1-(3-cyclopropylpyridin-2-yl)pyrido[2,3-d]pyrimidin-2(1H)-one (0.233 g, 0.48 mmol), (2-fluorophenyl)boronic acid (0.134 g, 0.96 mmol, TCI America. Portland, Oreg., USA), PdCl$_2$(dppf) (0.035 g, 0.048 mmol), and potassium acetate (0.141 g, 1.44 mmol) in 1,4-dioxane (1.1 mL)/water (0.11 mL) was sparged with nitrogen then stirred at 100° C. for 30 min. The reaction mixture was diluted with EtOAc (100 mL), added to a separatory funnel, and washed with satd. NaHCO$_3$ (2×75 mL), the organic layer was separated, dried over anhydrous Na$_2$SO$_4$, and concentrated in vacuo. The crude product was purified by silica gel chromatography (eluent: 0-100% EtOAc-EtOH (3:1)/heptane then 0-60% 2 M NH$_3$ in MeOH]/DCM) to provide (S)-4-(4-acryloyl-2-methylpiperazin-1-yl)-6-chloro-1-(3-cyclopropylpyridin-2-yl)-7-(2-fluorophenyl)pyrido[2,3-d]pyrimidin-2(1H)-one (58 mg, 0.11 mmol, 22% yield) as a yellow solid. $^1$H NMR (400 MHz, CDCl$_3$) 8.42 (dd, J=4.6, 1.5 Hz, 1H) 8.04 (d, J=1.7 Hz, 1H) 7.46 (ddd, J=7.6, 4.2, 1.5 Hz, 1H) 7.35-7.43 (m, 1H) 7.28 (dd, J=7.7, 4.8 Hz, 1H) 7.19-7.25 (m, 1H) 7.12-7.17 (m, 1H) 7.09 (t, J=9.2 Hz, 1H) 6.51-6.72 (m, 1H) 6.35-6.45 (m, 1H) 5.80 (dd, J=10.6, 1.7 Hz, 1H) 4.17-5.25 (m, 3H) 3.49-4.09 (m, 3H) 2.91-3.34 (m, 1H) 1.40-1.60 (m, 3H) 1.29-1.35 (m, 1H) 0.75-0.85 (m, 2H) 0.64-0.74 (m, 1H) 0.46-0.55 (m, 1H). $^{19}$F NMR (377 MHz, CDCl$_3$) δ −111.91 (s, 1F). m/z (ESI, +ve ion): 544.8 (M+H)$^+$.

TABLE 60

Compounds 60-2 to 60-30 were prepared following the procedure described in Method 60, Steps 1-4, above as follows:

| Ex. # | Chemical Structure | Name | Method Changes | Reagent |
|---|---|---|---|---|
| 60-2 | 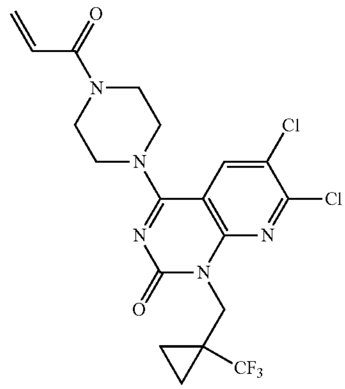 [SMILES: C=CC(=O)N1CCN(c2nc(=O)n(CC3(C(F)(F)F)CC3)c3nc(Cl)c(Cl)cc23)CC1] | 6,7-dichloro-4-(4-(2-propenoyl)-1-piperazinyl)-1-((1-(trifluoromethyl)cyclopropyl)methyl)pyrido[2,3-d]pyrimidin-2(1H)-one | Omit Step 4 | Step 1: (1-(trifluoromethyl)cyclopropyl)methanamine (Sigma-Aldrich Corporation), Step 3: 1-(piperazin-1-yl)prop-2-en-1-one TFA salt |
| 60-3 | 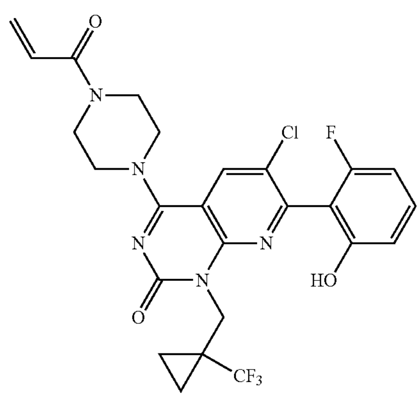 [SMILES: C=CC(=O)N1CCN(c2nc(=O)n(CC3(C(F)(F)F)CC3)c3nc(-c4c(O)cccc4F)c(Cl)cc23)CC1] | 6-chloro-7-(2-fluoro-6-hydroxyphenyl)-4-(4-(2-propenoyl)-1-piperazinyl)-1-((1-(trifluoromethyl)cyclopropyl)methyl)pyrido[2,3-d]pyrimidin-2(1H)-one | Step 3: Used no methyl group on the N-acryloyl piperazine piece | Step 1: (1-(trifluoromethyl)cyclopropyl)methanamine (Sigma-Aldrich Corporation), Step 3: 1-(piperazin-1-yl)prop-2-en-1-one TFA salt, Step 4: (2-fluoro-6-hydroxyphenyl)boronic acid (Wuxi) |
| 60-4 | 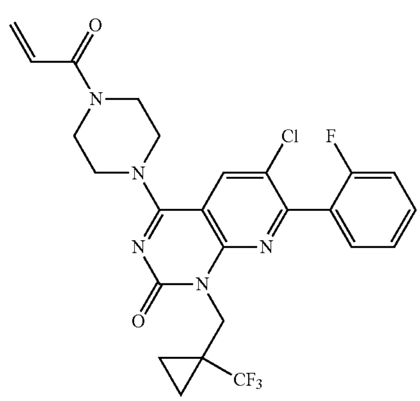 [SMILES: C=CC(=O)N1CCN(c2nc(=O)n(CC3(C(F)(F)F)CC3)c3nc(-c4ccccc4F)c(Cl)cc23)CC1] | 6-chloro-7-(2-fluorophenyl)-4-(4-(2-propenoyl)-1-piperazinyl)-1-((1-(trifluoromethyl)cyclopropyl)methyl)pyrido[2,3-d]pyrimidin-2(1H)-one | Step 3: Used no methyl group on the N-acryloyl piperazine piece | Step 1: (1-(trifluoromethyl)cyclopropyl)methanamine (Sigma-Aldrich Corporation) Step 3: 1-(piperazin-1-yl)prop-2-en-1-one TFA salt, Step 4: 2-fluorobenzene boronic acid (TCI America) |

TABLE 60-continued

Compounds 60-2 to 60-30 were prepared following the procedure described in Method 60, Steps 1-4, above as follows:

| Ex. # | Chemical Structure | Name | Method Changes | Reagent |
|---|---|---|---|---|
| 60-5 | 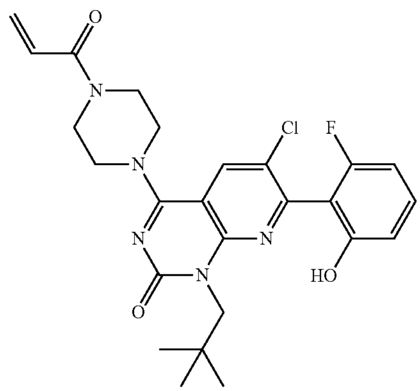 [SMILES: C=CC(=O)N1CCN(c2nc(=O)n(CC(C)(C)C)c3nc(-c4c(O)cccc4F)c(Cl)cc23)CC1] | 6-chloro-1-(2,2-dimethylpropyl)-7-(2-fluoro-6-hydroxyphenyl)-4-(4-(2-propenoyl)-1-piperazinyl)pyrido[2,3-d]pyrimidin-2(1H)-one | Step 3: Used no methyl group on the N-acryloyl piperazine piece | Step 1: neopentylamine (TCI America), Step 3: 1-(piperazin-1-yl)prop-2-en-1-one TFA salt, Step 4: (2-fluoro-6-hydroxyphenyl) boronic acid (Wuxi) |
| 60-6 | 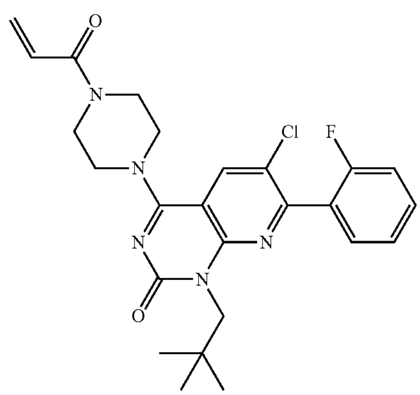 [SMILES: C=CC(=O)N1CCN(c2nc(=O)n(CC(C)(C)C)c3nc(-c4ccccc4F)c(Cl)cc23)CC1] | 6-chloro-4-(2,2-dimethylpropyl)-7-(2-fluorophenyl)-4-(4-(2-propenoyl)-1-piperazinyl)pyrido[2,3-d]pyrimidin-2(1H)-one | Step 3: Used no methyl group on the N-acryloyl piperazine piece | Step 1: neopentylamine (TCI America), Step 3: 1-(piperazin-1-yl)prop-2-en-1-one TFA salt Step 4: 2-fluorobenzene boronic acid (TCI America) |
| 60-7 | 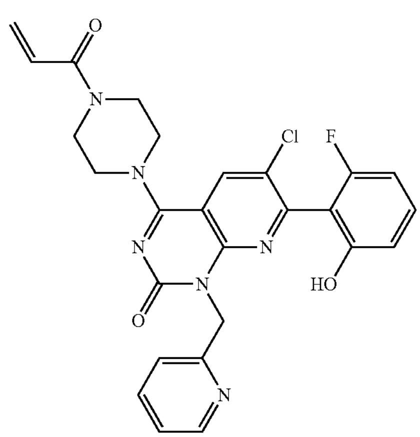 [SMILES: C=CC(=O)N1CCN(c2nc(=O)n(Cc3ccccn3)c3nc(-c4c(O)cccc4F)c(Cl)cc23)CC1] | 6-chloro-1-(2,6-diethylphenyl)-4-((2S)-2-methyl-4-(2-propenoyl)-1-piperazinyl)-7-(3-oxetanyl)pyrido[2,3-d]pyrimidin-2(1H)-one | Step 3: Used no methyl group on the N-acryloyl piperazine piece | Step 1: 2-(aminomethyl) pyridine (Sigma-Aldrich Corporation), Step 3: 1-(piperazin-1-yl)prop-2-en-1-one TFA salt, Step 4: (2-fluoro-6-hydroxyphenyl) boronic acid (Wuxi) |

TABLE 60-continued

Compounds 60-2 to 60-30 were prepared following the procedure described in Method 60, Steps 1-4, above as follows:

| Ex. # | Chemical Structure | Name | Method Changes | Reagent |
|---|---|---|---|---|
| 60-8 | 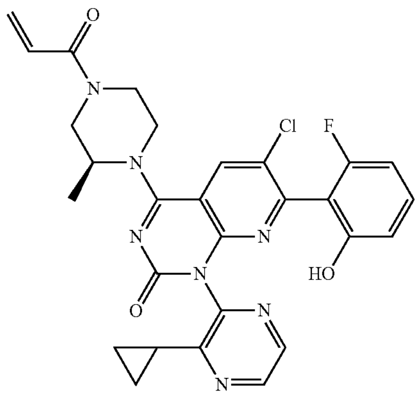 [SMILES: C=CC(=O)N1CCN(c2nc(=O)n(-c3nccnc3C3CC3)c3nc(-c4c(O)cccc4F)c(Cl)cc23)[C@@H](C)C1] | 6-chloro-1-(3-cyclopropyl-2-pyrazinyl)-7-(2-fluoro-6-hydroxyphenyl)-4-((2S)-2-methyl-4-(2-propenoyl)-1-piperazinyl)pyrido[2,3-d]pyrimidin-2(1H)-one | Step 1: 0° C., omit TEA, Step 2: 0° C., Step 3: 0° C. | Step 1: 3-cyclopropylpyrazin-2-amine (Aurum Pharmatech, LLC; Franklin Park, NJ), Step 4: 2-fluoro-6-hydroxyphenylboronic acid (Combi-Blocks Inc.) |
| 60-9 | 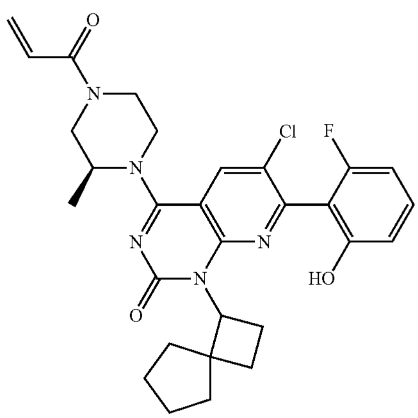 [SMILES: C=CC(=O)N1CCN(c2nc(=O)n(C3CCC34CCCC4)c3nc(-c4c(O)cccc4F)c(Cl)cc23)[C@@H](C)C1] | 6-chloro-7-(2-fluoro-6-hydroxyphenyl)-4-((2S)-2-methyl-4-(2-propenoyl)-1-piperazinyl)-1-(spiro[3.4]octan-1-yl)pyrido[2,3-d]pyrimidin-2(1H)-one | Omit Step 3, followed the procedure from Method 59 Step 3 | Step 1: spiro[3.4]octan-1-amine hydrochloride (Enamine), Step 4: 2-fluoro-6-hydroxyphenylboronic acid (Combi-Blocks Inc.) |
| 60-10 | 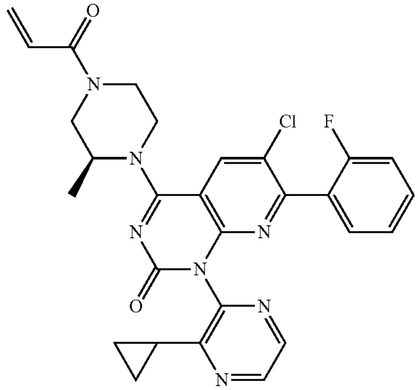 [SMILES: C=CC(=O)N1CCN(c2nc(=O)n(-c3nccnc3C3CC3)c3nc(-c4ccccc4F)c(Cl)cc23)[C@@H](C)C1] | 6-chloro-1-(3-cyclopropyl-2-pyrazinyl)-7-(2-fluorophenyl)-4-((2S)-2-methyl-4-(2-propenoyl)-1-piperazinyl)pyrido[2,3-d]pyrimidin-2(1H)-one | Omit Step 4, followed the procedure from Method 59 Step 3, Step 4: Use Pd(PPh$_3$)$_4$ and Na$_2$CO$_3$ | Step 1: 3-cyclopropylpyrazin-2-am(Aurumine Phamtatech, LLC; Franklin Park, NJ), Step 4: 2-fluorophenylboronic acid (Combi-Blocks Inc.) |

TABLE 60-continued

Compounds 60-2 to 60-30 were prepared following the procedure described in Method 60, Steps 1-4, above as follows:

| Ex. # | Chemical Structure | Name | Method Changes | Reagent |
|---|---|---|---|---|
| 60-11 | 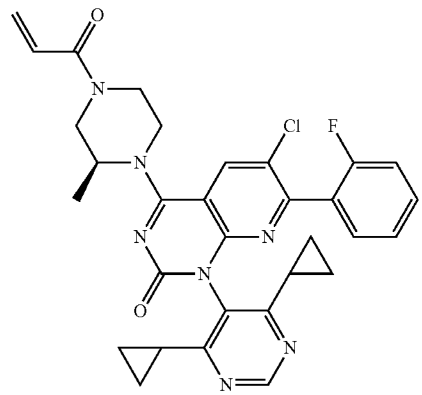 [SMILES: C=CC(=O)N1CCN(c2nc(=O)n(-c3c(C4CC4)ncnc3C3CC3)c3nc(-c4ccccc4F)c(Cl)cc23)[C@@H](C)C1] | 6-chloro-1-(4,6-dicyclopropyl-5-pyrimidinyl)-7-(2-fluorophenyl)-4-((2S)-2-methyl-4-(2-propenoyl)-1-piperazinyl)pyrido[2,3-d]pyrimidin-2(1H)-one | Omit Step 3, followed the procedure from Method 59 Step 3 | Step 1: 4,6-dicyclopropyl-pyrimidin-5-amine (Intermediate I-25), Step 4: 2-fluorophenylboronic acid (Combi-Blocks Inc.) |
| 60-12 | 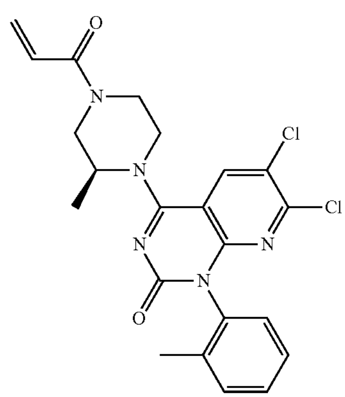 [SMILES: C=CC(=O)N1CCN(c2nc(=O)n(-c3ccccc3C)c3nc(Cl)c(Cl)cc23)[C@@H](C)C1] | 6,7-dichloro-1-(2-methylphenyl)-4-((2S)-2-methyl-4-(2-propenoyl)-1-piperazinyl)pyrido[2,3-d]pyrimidin-2(1H)-one | Omit Step 4 | Step 1: o-toluidine (Sigma-Aldrich Corporation) |
| 60-13 | 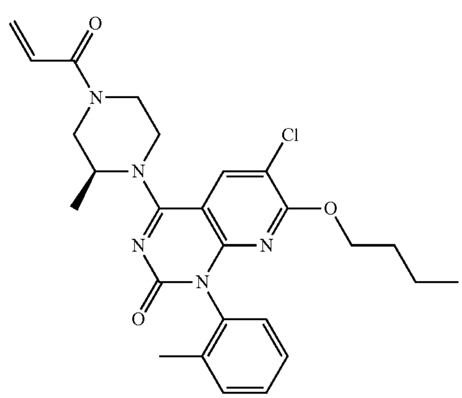 [SMILES: C=CC(=O)N1CCN(c2nc(=O)n(-c3ccccc3C)c3nc(OCCCC)c(Cl)cc23)[C@@H](C)C1] | 7-butoxy-6-chloro-1-(2-methylphenyl)-4-((2S)-2-methyl-4-(2-propenoyl)-1-piperazinyl)pyrido[2,3-d]pyrimidin-2(1H)-one | Step 4: Use X-Phos, Pd(OAc)$_2$, CsOH, 1-BuOH | Step 1: o-toluidine (Sigma-Aldrich Corporation) |

TABLE 60-continued

Compounds 60-2 to 60-30 were prepared following the procedure described in Method 60, Steps 1-4, above as follows:

| Ex. # | Chemical Structure | Name | Method Changes | Reagent |
|---|---|---|---|---|
| 60-14 | 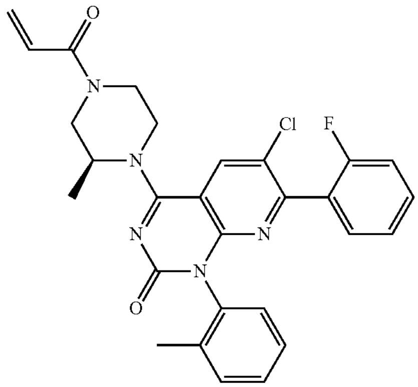 | 6-chloro-7-(2-fluorophenyl)-1-(2-methylphenyl)-4-((2S)-2-methyl-4-(2-propenoyl)-1-piperazinyl)pyrido[2,3-d]pyrimidin-2(1H)-one | Step 4: Use Pd(PPh$_3$)$_4$ and Na$_2$CO$_3$ | Step 1: o-toluidine (Sigma-Aldrich Corporation), Step 4: (2-fluorophenyl) boronic acid (TCI America) |
| 60-15 | 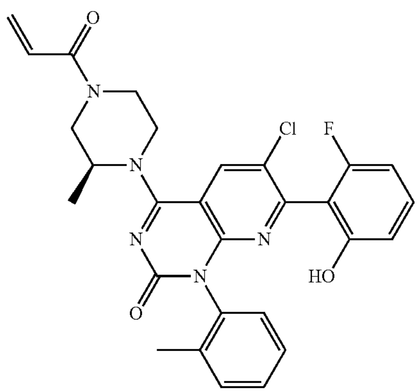 [SMILES: C=CC(=O)N1CCN(c2nc(=O)n(-c3ccccc3C)c3nc(-c4c(O)cccc4F)c(Cl)cc23)[C@@H](C)C1] | 6-chloro-7-(2-fluoro-6-hydroxyphenyl)-1-(2-methylphenyl)-4-((2S)-2-methyl-4-(2-propenoyl)-1-piperazinyl)pyrido[2,3-d]pyrimidin-2(1H)-one | Step 4: Use Pd(PPh$_3$)$_4$ and Na$_2$CO$_3$ | Step 1: o-toluidine (Sigma-Aldrich Corporation), Step 4: (2-fluoro-6-hydroxyphenyl) boronic acid (Wuxi) |
| 60-16 | 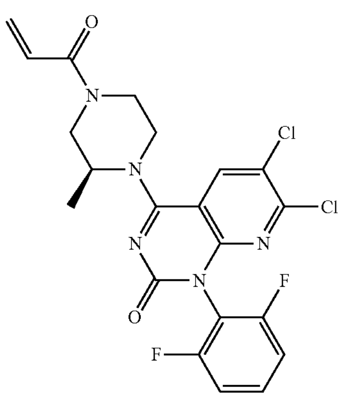 [SMILES: C=CC(=O)N1CCN(c2nc(=O)n(-c3c(F)cccc3F)c3nc(Cl)c(Cl)cc23)[C@@H](C)C1] | 6,7-dichloro-1-(2,6-difluorophenyl)-4-((2S)-2-Methyl-4-(2-propenoyl)-1-piperazinyl)pyrido[2,3-d]pyrimidin-2(1H)-one | Omit Step 4 | Step 1: 2,6-difluoroaniline (Sigma-Aldrich Corporation) |

TABLE 60-continued

Compounds 60-2 to 60-30 were prepared following the procedure described in
Method 60, Steps 1-4, above as follows:

| Ex. # | Chemical Structure | Name | Method Changes | Reagent |
|---|---|---|---|---|
| 60-17 | 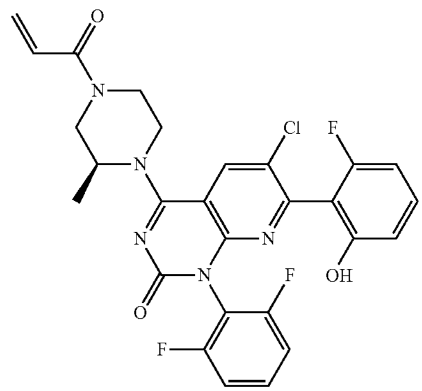 | 6-chloro-1-(2,6-difluorophenyl)-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 2,6-difluoroaniline (Sigma-Aldrich Corporation), Step 4: (2-fluoro-6-hydroxyphenyl) boronic acid (Wuxi) |
| 60-18 | 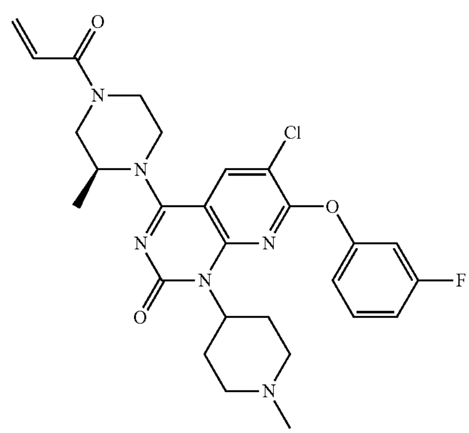 [SMILES: C=CC(=O)N1CCN(c2nc(=O)n(C3CCN(C)CC3)c3nc(Oc4cccc(F)c4)c(Cl)cc23)[C@@H](C)C1] | 6-chloro-7-(3-fluorophenoxy)-1-(1-methyl-4-piperidinyl)-4-((2S)-2-methyl-4-(2-propenoyl)-1-piperazinyl)pyrido[2,3-d]pyrimidin-2(1H)-one | Step 4: Use Pd(PPh$_3$)$_4$ and Na$_2$CO$_3$ | Step 2: 1-methylpiperidin-4-amine (Enamine), Step 4: (2-fluoro-6-hydroxyphenyl) boronic acid (Wuxi) |
| 60-19 | 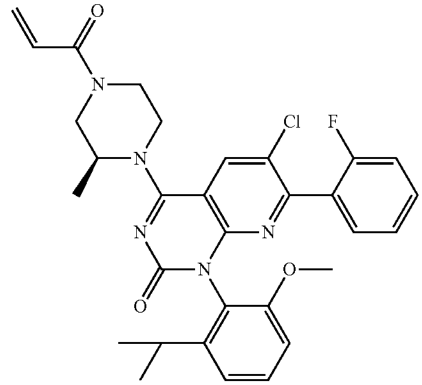 [SMILES: C=CC(=O)N1CCN(c2nc(=O)n(-c3c(OC)cccc3C(C)C)c3nc(-c4ccccc4F)c(Cl)cc23)[C@@H](C)C1] | 6-chloro-7-(2-fluorophenyl)-1-(2-methoxy-6-(2-propanyl)phenyl)-4-((2S)-2-methyl-4-(2-propenoyl)-1-piperazinyl)pyrido[2,3-d]pyrimidin-2(1H)-one | Step 2: NaOt-Bu/toluene, 20° C. | Step 2: 2-isopropyl-6-methoxyaniline (HDH Pharma), Step 5: (2-fluorophenyl) boronic acid (TCI America) |

TABLE 60-continued

Compounds 60-2 to 60-30 were prepared following the procedure described in
Method 60, Steps 1-4, above as follows:

| Ex. # | Chemical Structure | Name | Method Changes | Reagent |
|---|---|---|---|---|
| 60-20 | 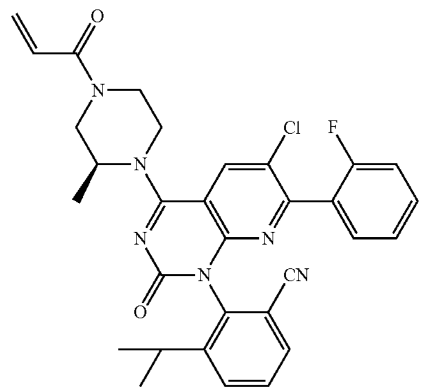 | 2-(6-chloro-7-(2-fluorophenyl)-4-((2S)-2-methyl-4-(2-propenoyl)-1-piperazinyl)-2-oxopyrido[2,3-d]pyrimidin-1(2H)-yl)-3-(2-propanyl)benzonitrile | Step 2: NaOt-Bu/toluene 20° C. | Step 1: 2-amino-3-isopropylbenzonitrile (Enamine). Step 4: (2-fluorophenyl)boronic acid (TCI America) |
| 60-21 | 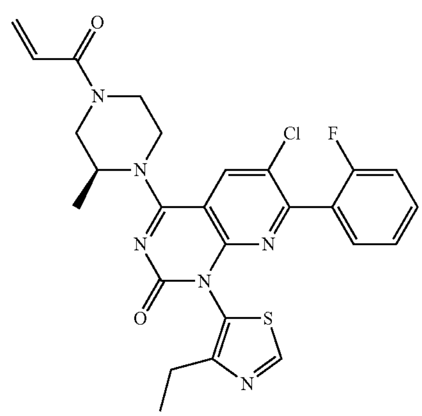 [SMILES: C=CC(=O)N1CCN(c2nc(=O)n(-c3scnc3CC)c3nc(-c4ccccc4F)c(Cl)cc23)[C@@H](C)C1] | 6-chloro-1-(4-ethyl-1,3-thiazol-5-yl)-7-(2-fluorophenyl)-4-((2S)-2-methyl-4-(2-propenoyl)-1-piperazinyl)pyrido[2,3-d]pyrimidin-2(1H)-one | | Step 1: 4-ethylthiazol-5-amine (Enamine ILC), Step 4: 2-fluorophenylboronic acid (Combi-Blocks, Inc.) |
| 60-22 | 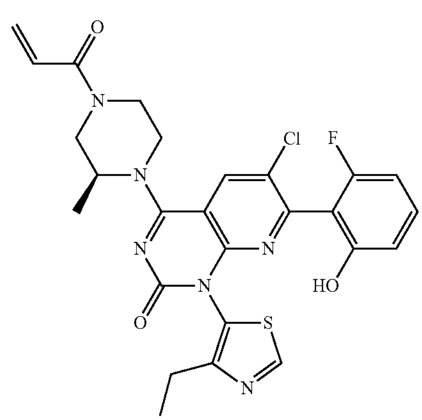 [SMILES: C=CC(=O)N1CCN(c2nc(=O)n(-c3scnc3CC)c3nc(-c4c(O)cccc4F)c(Cl)cc23)[C@@H](C)C1] | 6-chloro-1-(4-ethyl-1,3-thiazol-5-yl)-7-(2-fluoro-6-hydroxyphenyl)-4-((2S)-2-methyl-4-(2-propenoyl)-1-piperazinyl)pyrido[2,3-d]pyrimidin-2(1H)-one | | Step 1: 4-ethylthiazol-5-amine (Enamine LLC), Step 4: 2-fluoro-6-hydroxyphenylboronic acid (Wuxi) |

TABLE 60-continued

Compounds 60-2 to 60-30 were prepared following the procedure described in Method 60, Steps 1-4, above as follows:

| Ex. # | Chemical Structure | Name | Method Changes | Reagent |
|---|---|---|---|---|
| 60-23 | 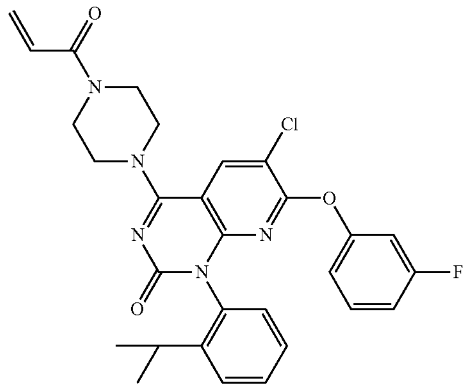 [SMILES: C=CC(=O)N1CCN(c2nc(=O)n(-c3ccccc3C(C)C)c3nc(Oc4cccc(F)c4)c(Cl)cc23)CC1] | 6-chloro-7-(3-fluorophenoxy)-1-(2-(2-propanyl)phenyl)-4-(4-(2-propenoyl)-1-piperazinyl)pyrido[2,3-d]pyrimidin-2(1H)-one | Step 4: Use Pd(PPh$_3$)$_4$ and Na$_2$CO$_3$ | Step 1: 2-isopropylaniline (Sigma-Aldrich), Step 3: 1-(piperazin-1-yl)prop-2-en-1-one TFA salt |
| 60-25 | 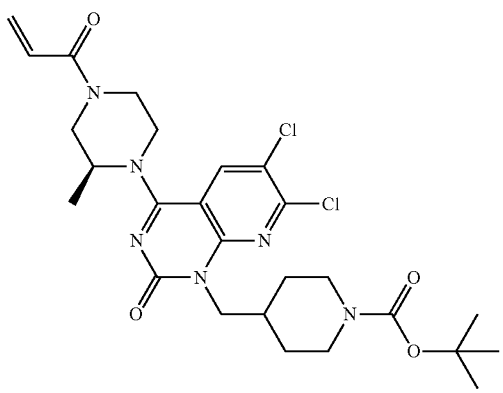 [SMILES: C=CC(=O)N1CCN(c2nc(=O)n(CC3CCN(C(=O)OC(C)(C)C)CC3)c3nc(Cl)c(Cl)cc23)[C@@H](C)C1] | 2-methyl-2-propanyl 4-((6,7-dichloro-4-((2S)-2-methyl-4-(2-propenoyl)-1-piperazinyl)-2-oxopyrido[2,3-d]pyrimidin-1(2H)-yl)methyl)-1-piperidinecarboxylate | Omit Step 4 | Step 1: 1 Boc-4-(aminomethyl)piperidine (Alfa Aesar) |
| 60-26 | 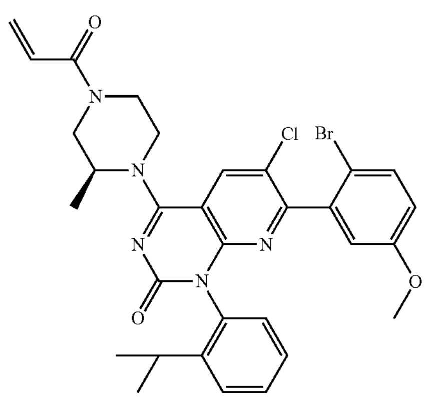 [SMILES: C=CC(=O)N1CCN(c2nc(=O)n(-c3ccccc3C(C)C)c3nc(-c4cc(OC)ccc4Br)c(Cl)cc23)[C@@H](C)C1] | 7-(2-bromo-5-methoxyphenyl)-6-chloro-4-((2S)-2-methyl-4-(2-propenoyl)-1-piperazinyl)-1-(2-(2-propanyl)phenyl)pyrido[2,3-d]pyrimidin-2(1H)-one | Step 4: Use Pd(PPh$_3$)$_4$ and Na$_2$CO$_3$ | Step 1: 2-isopropylaniline (Sigma-Aldrich); Step 4: 2-bromo-5-methoxybenzene boronic acid (Combi-Blocks Inc.) |

TABLE 60-continued

Compounds 60-2 to 60-30 were prepared following the procedure described in Method 60, Steps 1-4, above as follows:

| Ex. # | Chemical Structure | Name | Method Changes | Reagent |
|---|---|---|---|---|
| 60-27 | | 6-chloro-7-(2-fluoro-6-hydroxyphenyl)-1-(2-((1R)-1-hydroxyethyl)phenyl)-4-((2S)-2-methyl-4-(2-propenoyl)-1-piperazinyl)pyrido[2,3-d]pyrimidin-2(1H)-one \| 6-chloro-7-(2-fluoro-6-hydroxyphenyl)-1-(2-((1S)-1-hydroxyethyl)phenyl)-4-((2S)-2-methyl-4-(2-propenoyl)-1-piperazinyl)pyrido[2,3-d]pyrimidin-2(1H)-one | Add O-TBDPS deprotection using TBAF after Step 4 | Step 1: 2-(1-((tert-butyldiphenylsilyl)oxy)ethyl)aniline prepared from 1-(2-aminophenyl)ethan-1-ol (Enamine), Step 4: 2-fluoro-6-hydroxyphenylboronic acid (Wuxi) |
| 60-28 | 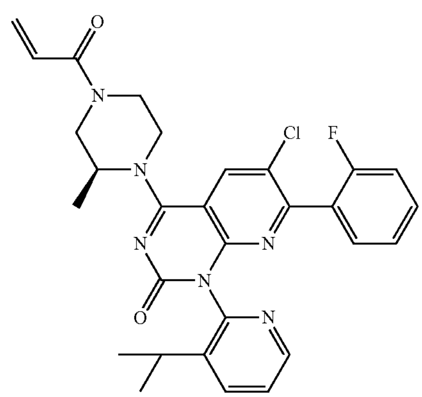 [SMILES: C=CC(=O)N1CCN(c2nc(=O)n(-c3ncccc3C(C)C)c3nc(-c4ccccc4F)c(Cl)cc23)[C@@H](C)C1] | 6-chloro-7-(2-fluorophenyl)-4-((2S)-2-methyl-4-(2-propenoyl)-1-piperazinyl)-1-(3-(2-propanyl)-2-pyridinyl)pyrido[2,3-d]pyrimidin-2(1H)-one | | Step 1: 3-isopropylpyridin-2-amine (Enamine), Step 4: 2-fluorophenylboronic acid (Combi-Blocks, Inc.) |
| 60-29 | 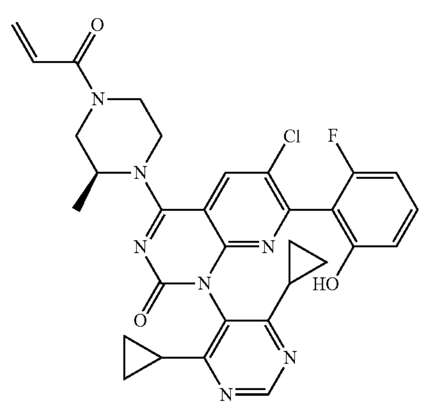 [SMILES: C=CC(=O)N1CCN(c2nc(=O)n(-c3c(C4CC4)ncnc3C3CC3)c3nc(-c4c(O)cccc4F)c(Cl)cc23)[C@@H](C)C1] | 6-chloro-1-(4,6-dicyclopropyl-5-pyrimidinyl)-7-(2-fluoro-6-hydroxyphenyl)-4-((2S)-2-methyl-4-(2-propenoyl)-1-piperazinyl)pyrido[2,3-d]pyrimidin-2(1H)-one | Step 3: followed Method 59, Step 3 | Step 1: 4,6-dicyclopropyl-pyrimidin-5-amine (Intermediate I-25) Step 4: (2-fluoro-6-hydroxyphenyl)boronic acid (WuXi) |

TABLE 60-continued

Compounds 60-2 to 60-30 were prepared following the procedure described in
Method 60, Steps 1-4, above as follows:

| Ex. # | Chemical Structure | Name | Method Changes | Reagent |
|---|---|---|---|---|
| 60-30 | 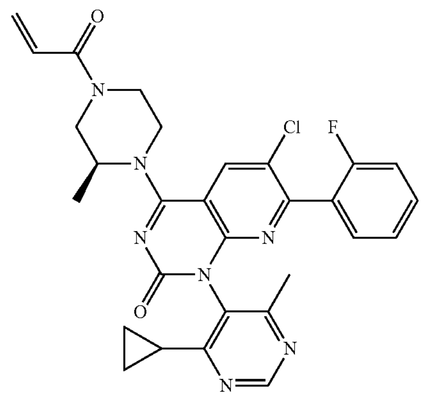 [SMILES: C=CC(=O)N1CCN(c2nc(=O)n(-c3c(C)ncnc3C3CC3)c3nc(-c4ccccc4F)c(Cl)cc23)[C@@H](C)C1] | 6-chloro-1-(4-cyclopropyl-6-methyl-5-pyrimidinyl)-7-(2-fluorophenyl)-4-((2S)-2-methyl-4-(2-propenoyl)-1-piperazinyl)pyrido[2,3-d]pyrimidin-2(1H)-one | Step 3: followed Method 59, Step 3 | Step 1: 4-cyclopropyl-6-methylpyrimidin-5-amine (Intermediate I-34) Step 4: 2-fluorophenylboronic acid (Combi-Blocks Inc.) |
| 60-31 | 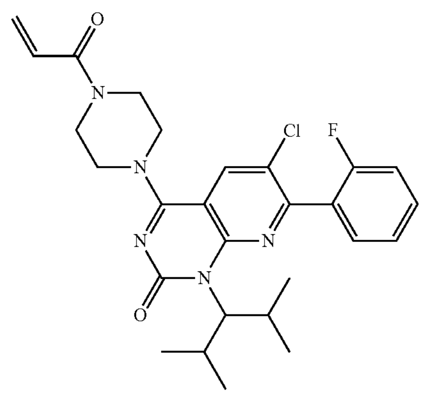 [SMILES: C=CC(=O)N1CCN(c2nc(=O)n(C(C(C)C)C(C)C)c3nc(-c4ccccc4F)c(Cl)cc23)CC1] | 6-chloro-1-(2,4-dimethyl-3-pentanyl)-7-(2-fluorophenyl)-4-(4-(2-propenoyl)-1-piperazinyl)pyrido[2,3-d]pyrimidin-2(1H)-one | Step 6: $Pd(PPh_3)_4$ and $Na_2CO_3$ | Step 1: (1-isopropyl-2-methylpropyl)amine (ChemBridge Corporation), Step 6: 2-fluorophenylboronic acid (Combi-Blocks Inc.) |
| 60-32 | 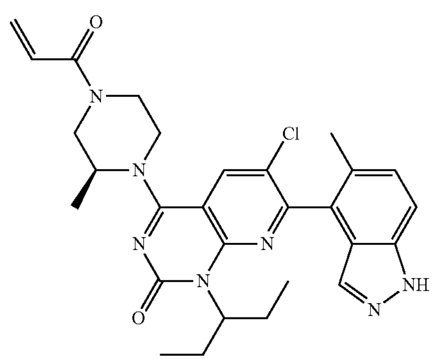 [SMILES: C=CC(=O)N1CCN(c2nc(=O)n(C(CC)CC)c3nc(-c4c(C)ccc5[nH]ncc45)c(Cl)cc23)[C@@H](C)C1] | 6-chloro-7-(5-methyl-1H-indazol-4-yl)-4-((2S)-2-methyl-4-(2-propenoyl)-1-piperazinyl)-1-(3-pentanyl)pyrido[2,3-d]pyrimidin-2(1H)-one | Step 6: $Pd(PPh_3)_4$ and $Na_2CO_3$ | Step 1: (1-ethylpropylamine (Alfa Aesar), Step 6: 5-methyl-1H-indazol-4-yl boronic acid (Combi-Blocks Inc.) |
| 60-33 | 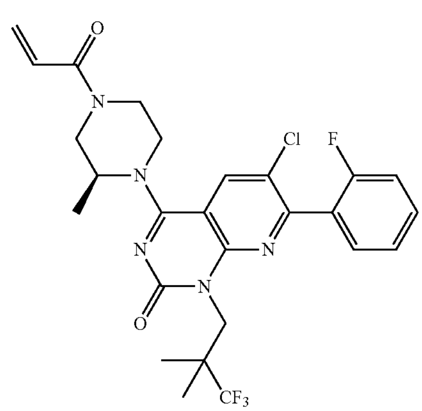 [SMILES: C=CC(=O)N1CCN(c2nc(=O)n(CC(C)(C)C(F)(F)F)c3nc(-c4ccccc4F)c(Cl)cc23)[C@@H](C)C1] | 6-chloro-7-(2-fluorophenyl)-4-((2S)-2-methyl-4-(2-propenoyl)-1-piperazinyl)-1-(3,3,3-trifluoro-2,2-dimethylpropyl)pyrido[2,3-d]pyrimidin-2(1H)-one | Step 6: $Pd(PPh_3)_4$ and $Na_2CO_3$ | Step 1: 3,3,3-trifluoro-2,2-dimethylpropan-1-amine hydrochloride (Enamine), Step 6: 2-fluorophenylboronic acid (Combi-Blocks Inc.) |

US 11,090,304 B2

373                                                                           374

TABLE 60-continued

Compounds 60-2 to 60-30 were prepared following the procedure described in
Method 60, Steps 1-4, above as follows:

| Ex. # | Chemical Structure | Name | Method Changes | Reagent |
|---|---|---|---|---|
| 60-34 | 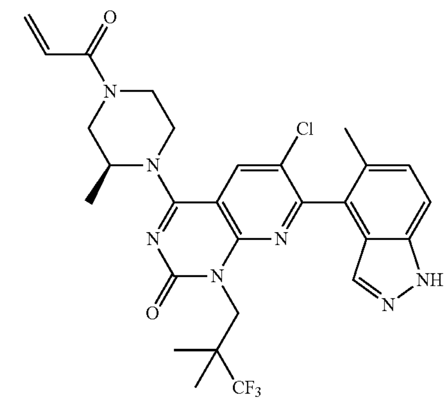 [SMILES: C=CC(=O)N1CCN(c2nc(=O)n(CC(C)(C)C(F)(F)F)c3nc(-c4c(C)ccc5[nH]ncc45)c(Cl)cc23)[C@@H](C)C1] | 6-chloro-7-(5-methyl-1H-indazol-4-yl)-4-((2S)-2-methyl-4-(2-propenoyl)-1-piperazinyl)-1-(3,3,3-trifluoro-2,2-dimethylpropyl)pyrido[2,3-d]pyrimidin-2(1H)-one | Step 6: $Pd(PPh_3)_4$ and $Na_2CO_3$ | Step 1: 3,3,3-trifluoro-2,2-dimethylpropan-1-amine hydrochloride (Enamine), Step 6: 5-methyl-1H-indazol-4-yl boronic acid (Combi-Blocks Inc.) |
| 60-35 | 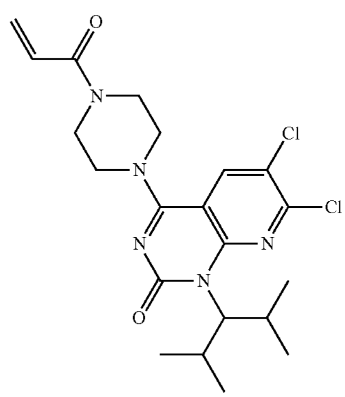 [SMILES: C=CC(=O)N1CCN(c2nc(=O)n(C(C(C)C)C(C)C)c3nc(Cl)c(Cl)cc23)CC1] | 6,7-dichloro-1-(2,4-dimethyl-3-pentanyl)-4-(4-(2-propenoyl)-1-piperazinyl)pyrido[2,3-d]pyrimidin-2(1H)-one | Omit Step 6 | Step 1: (1-isopropyl-2-methylpropyl)amine (Chembridge Corp.) |

Method 61

Example 61-1: 6,7-Dichloro-4-((2S)-2-methyl-4-(2-propenoyl)-1-piperazinyl)-1-(2-(2-propanyl)phenyl)pyrido[2,3-d]pyrimidin-2(1H)-one

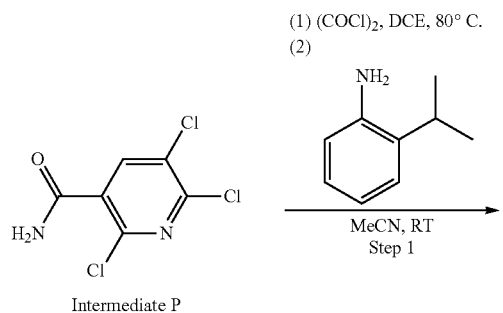

Intermediate P

-continued

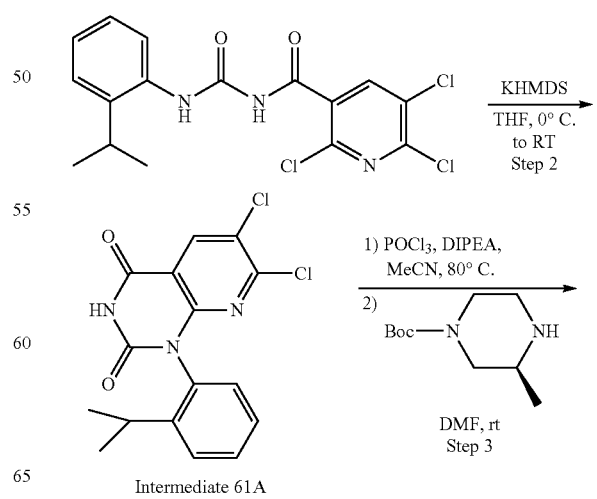

Intermediate 61A

-continued

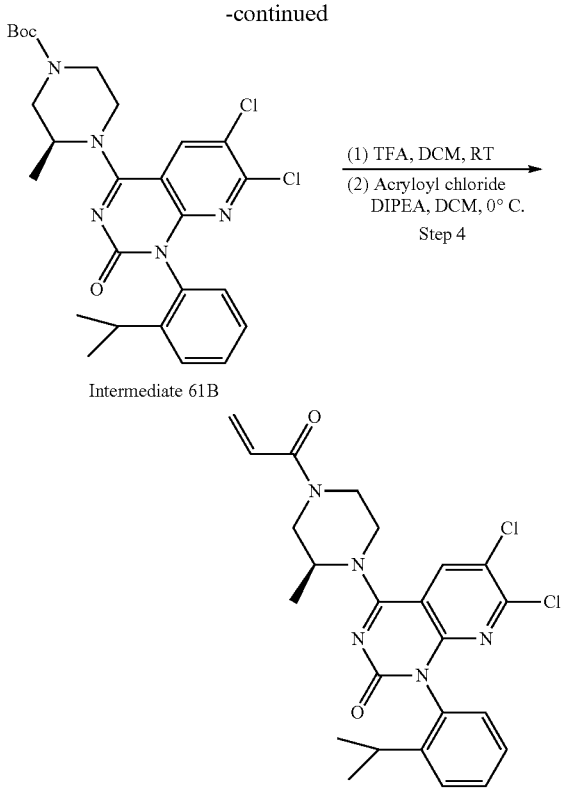

Intermediate 61B

Step 1: 2,5,6-Trichloro-N-((2-isopropylphenyl)carbamoyl)nicotinamide

A suspension mixture of 2,5,6-trichloronicotinamide (Intermediate P, 6.7 g, 29.7 mmol) in 1,2-dichloroethane (100 mL) was treated with oxalyl chloride (3.0 mL, 35.7 mmol) at rt. The resulting reaction mixture was stirred at 80° C. for 30 min then the white suspension was evaporated to give a slurry. The slurry was treated with acetonitrile (100 mL) and then with 2-isopropylaniline (4.6 mL, 32.7 mmol, Sigma-Aldrich Corporation, St. Louis, Mo., USA) at rt. The mixture was stirred for 15 min and the white solid was collected by filtration, washed with acetonitrile and dried to give pure 2,5,6-trichloro-N-((2-isopropylphenyl)carbamoyl)nicotinamide (8.55 g, 22.1 mmol, 74.4% yield) as a white solid. m/z (ESI, +ve ion): 386.0 (M+H)$^+$.

Step 2: 6,7-Dichloro-1-(2-isopropylphenyl)pyrido[2,3-d]pyrimidine-2,4(1H,3H)-dione (Intermediate 61A)

A mixture of 2,5,6-trichloro-N-((2-isopropylphenyl)carbamoyl)nicotinamide (8.55 g, 22.1 mmol) in THF (74 mL) at 0° C. was treated with KHDMS (IM solution in THF, 44.3 mL, 44.3 mmol). The mixture was stirred at 0° C. for 10 min and at rt for 30 min. The reaction mixture was quenched with satd. ammonium chloride (100 mL) and extracted with EtOAc (200 mL). The organic layer was separated, washed with brine (150 mL), dried over Na$_2$SO$_4$, filtered, and concentrated in vacuo. The resulting crude product was sonicated in MeOH (20 mL), filtered, and washed with MeOH and dried to give pure 6,7-dichloro-1-(2-isopropylphenyl)pyrido[2,3-d]pyrimidine-2,4(1H,3H)-dione (Intermediate 61A, 7.17 g, 20.5 mmol, 92% yield) as a tan solid.

$^1$H NMR (400 MHz, DMSO-d$_6$) δ ppm 12.10 (s, 1H), 8.52 (s, 1H), 7.38-7.60 (m, 2H), 7.12-7.38 (m, 2H), 2.74 (dt, J=13.5, 6.8 Hz, 1H), 1.08 (d, J=6.8 Hz, 3H), 1.03 (d, J=6.8 Hz, 3H)). m/z (ESI, +ve ion): 350.0 (M+H)$^+$.

Step 3: (S)-tert-Butyl 4-(6,7-dichloro-1-(2-isopropylphenyl)-2-oxo-1,2-dihydropyrido[2,3-d]pyrimidin-4-yl)-3-methylpiperazine-1-carboxylate (Intermediate 61B)

To a mixture of 6,7-dichloro-1-(2-isopropylphenyl)pyrido[2,3-d]pyrimidine-2,4(1H,3H)-dione (Intermediate 61A, 1.03 g, 2.94 mmol) and DIPEA (1.5 mL, 8.82 mmol) in acetonitrile (19.6 mL) was added phosphorus oxychloride (1.4 mL, 8.82 mmol) at rt and heated at 80° C. for 30 min. The mixture was concentrated in vacuo to give the crude 4,6,7-trichloro-1-(2-isopropylphenyl)pyrido[2,3-d]pyrimidin-2(1H)-one as a brown solid. m/z (ESI, +ve ion): 368.0 (M+H)$^-$. The crude material was used in next step without purification.

To a mixture of the above 4,6,7-trichloro-1-(2-isopropylphenyl)pyrido[2,3-d]pyrimidin-2(1H)-one (1.08 g, 2.94 mmol) and DIPEA (1.5 mL, 8.82 mmol) in DMF (14.7 mL) was added (S)-4-N-Boc-2-methyl piperazine (0.88 g, 4.41 mmol) and stirred at rt for 10 min. Ice water (10 mL) was added and stirred for 15 min. The resulting precipitate was collected by filtration, washed with water, and dried to give (S)-tert-butyl 4-(6,7-dichloro-1-(2-isopropylphenyl)-2-oxo-1,2-dihydropyrido[2,3-d]pyrimidin-4-yl)-3-methylpiperazine-1-carboxylate (Intermediate 61B, 1.52 g, 2.85 mmol, 97% yield) as a yellow solid. m/z (ESI, +ve ion): 532.0 (M+H)$^+$.

Step 4: 6,7-Dichloro-4-((2S)-2-methyl-4-(2-propenoyl)-1-piperazinyl)-1-(2-(2-propanyl)phenyl)pyrido[2,3-d]pyrimidin-2(1H)-one To a solution of (S)-tert-butyl 4-(6,7-dichloro-1-(2-isopropylphenyl)-2-oxo-1,2-dihydropyrido[2,3-d]pyrimidin-4-yl)-3-methylpiperazine-1-carboxylate (Intermediate 61B, 1.52 g, 2.85 mmol) in DCM (10 mL) was treated with TFA (5 mL, 67.1 mmol) at rt and stirred for 30 min. The reaction went to completion and was concentrated to afford (S)-6,7-dichloro-1-(2-isopropylphenyl)-4-(2-methylpiperazin-1-yl)pyrido[2,3-d]pyrimidin-2(1H)-one. m/z (ESI, +ve ion): 432.2 (M+H)$^+$.

A mixture of the above (S)-6,7-dichloro-1-(2-isopropylphenyl)-4-(2-methylpiperazin-1-yl)pyrido[2,3-d]pyrimidin-2(1H)-one, and DIPEA (1.5 mL, 8.55 mmol) in DCM (10 mL) was added acryloyl chloride (0.2 mL, 2.85 mmol) at 0° C. and stirred for 1 h at 0° C. The mixture was concentrated in vacuo and the crude product was purified by silica gel chromatography (eluent: 0-50%/c EtOAc/EtOH (3:1)/heptane) to provide (S)-4-(4-acryloyl-2-methylpiperazin-1-yl)-6,7-dichloro-1-(2-isopropylphenyl)pyrido[2,3-d]pyrimidin-2(1H)-one (1.21 g, 2.49 mmol, 87.5% yield) as a light yellow solid. $^1$H NMR (400 MHz, DMSO-d$_6$) δ ppm 8.33-8.55 (m, 1H), 7.37-7.59 (m, 2H), 7.30 (t, J=7.6 Hz, 1H), 7.13 (dd, J=7.6, 3.2 Hz, 1H), 6.75-6.97 (m, 1H), 6.21 (br d, J=16.8 Hz, 1H), 5.76 (dd, J=10.3, 2.2 Hz, 1H), 4.74-5.05 (m, 1H), 3.92-4.45 (m, 3H), 3.28-3.87 (m, 3H), 2.92-3.26 (m, 1H), 1.22-1.30 (m, 3H), 1.08 (br d, J=6.8 Hz, 3H), 1.03 (br d, J=6.8 Hz, 3H). m/z (ESI, +ve ion): 486.2 (M+H)$^+$.

Example 61-1-1 and 61-1-2: (M)-6,7-Dichloro-4-((2S)-2-methyl-4-(2-propenoyl)-1-piperazinyl)-1-(2-(2-propanyl)phenyl)pyrido[2,3-d]pyrimidin-2(1H)-one (1st Eluting Isomer) and (P)-6,7-dichloro-4-((2S)-2-methyl-4-(2-propenoyl)-1-piperazinyl)-1-(2-(2-propanyl)phenyl)pyrido[2,3-d]pyrimidin-2(1H)-one (2nd Eluting Isomer)

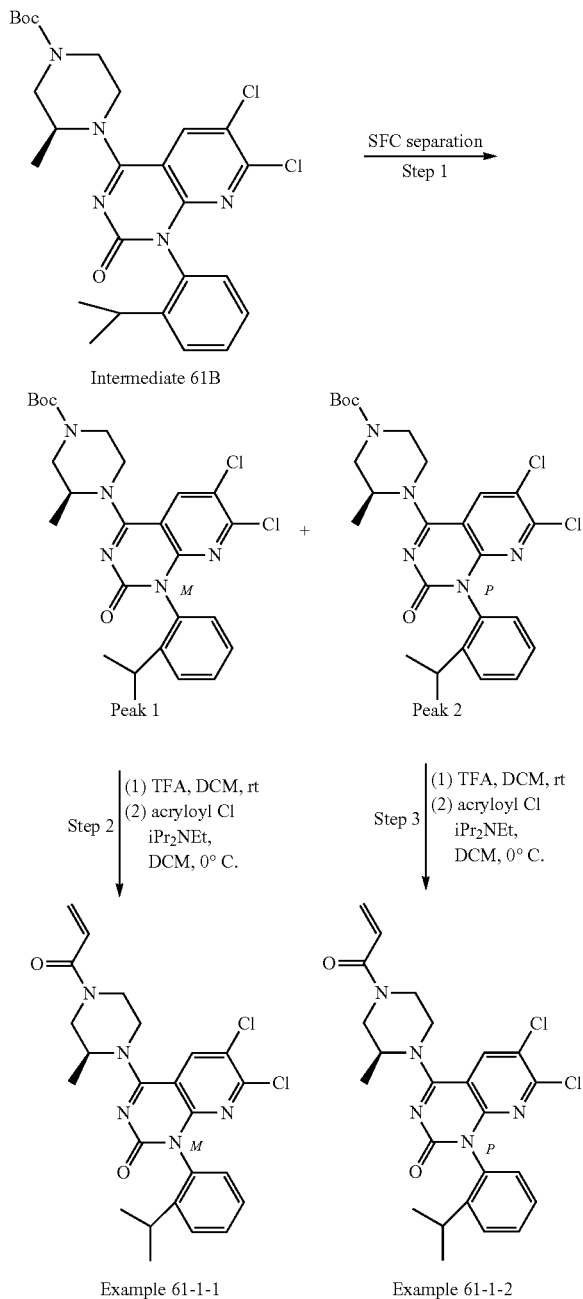

Step 1: (S)-tert-Butyl 4-(6,7-dichloro-1-(2-isopropylphenyl)-2-oxo-1,2-dihydropyrido[2,3-d]pyrimidin-4-yl)-3-methylpiperazine-1-carboxylate (Two Separate Isomers)

A mixture of atropisomers Intermediate 61B (1.87 g) was purified with ID column (250×21 mm, 5 µm) using methanol containing 20 mM NH$_3$ in supercritical CO$_2$ as a mobile phase to obtain two peaks: Peak 1 (isomer 1, 720 mg, 97.5% ee). $^1$H NMR (400 MHz, DMSO-d$_6$) δ ppm 8.41 (s, 1H), 7.46-7.51 (m, 1H), 7.39-7.45 (m, 1H), 7.29 (td, J=7.5, 1.6 Hz, 1H), 7.12 (dd, J=7.7, 1.0 Hz, 1H), 4.88 (br s, 1H), 4.06 (br d, J=13.3 Hz, 1H), 3.88-4.00 (m, 1H), 3.83 (br d, J=13.3 Hz, 1H), 3.72 (br t, J=10.9 Hz, 1H), 2.92-3.14 (m, 1H), 2.39-2.48 (m, 2H), 1.45 (s, 9H), 1.30 (d, J=6.6 Hz, 3H), 1.07 (d, J=6.8 Hz, 3H), 1.01 (d, J=6.8 Hz, 3H). m/z (ESI, +ve ion): 532.3 (M+H)$^+$.

Peak 2 (isomer 2, 698 mg, 98.0% ee). $^1$H NMR (400 MHz, DMSO-d$_6$) δ ppm 8.37 (s, 1H), 7.47-7.52 (m, 1H), 7.40-7.46 (m, 1H), 7.30 (td, J=7.5, 1.5 Hz, 1H), 7.12 (dd, J=7.8, 0.9 Hz, 1H), 4.77 (br s, 1H), 4.19 (br d, J=13.5 Hz, 1H), 3.90-4.05 (m, 1H), 3.82 (br d, J=13.5 Hz, 1H), 3.62 (br t, J=1.4 Hz, 1H), 3.02-3.18 (m, 1H), 2.41-2.50 (m, 2H), 1.45 (s, 9H), 1.34 (d, J=6.6 Hz, 3H), 1.08 (d, J=6.8 Hz, 3H), 1.02 (d, J=6.6 Hz, 3H). m/z (ESI, +ve ion): 532.3 (M+H)$^+$.

Step 2: 6,7-Dichloro-4-((2S)-2-methyl-4-(2-propenoyl)-1-piperazinyl)-1-(2-(2-propanyl)phenyl)pyrido[2,3-d]pyrimidin-2(1H)-one. (1st Isomer)

To a solution of (S)-tert-butyl 4-(6,7-dichloro-1-(2-isopropylphenyl)-2-oxo-1,2-dihydropyrido[2,3-d]pyrimidin-4-yl)-3-methylpiperazine-1-carboxylate (Peak 1, M-isomer, 391 mg, 0.74 mmol) in DCM (3.0 mL) was treated with TFA (1.0 mL) at rt and stirred for 15 min. The reaction went to completion and was concentrated in vacuo to afford (S)-6,7-dichloro-1-(2-isopropylphenyl)-4-(2-methylpiperazin-1-yl)pyrido[2,3-d]pyrimidin-2(1H)-one. m/z (ESI, +ve ion): 432.0 (M+H)$^+$.

A mixture of the above (S)-6,7-dichloro-1-(2-isopropylphenyl)-4-(2-methylpiperazin-1-yl)pyrido[2,3-d]pyrimidin-2(1H)-one and DIPEA (0.6 mL, 3.67 mmol) in DCM (3.0 mL) was treated with acryloyl chloride (0.06 mL, 0.74 mmol) at 0° C. and stirred for 10 min at 0° C. The resulting mixture was concentrated in vacuo and the crude product was purified by of silica gel chromatography (eluent: 0-50% EtOAc-EtOH (3:1)/heptane) to provide pure 6,7-dichloro-4-((2S)-2-methyl-4-(2-propenoyl)-1-piperazinyl)-1-(2-(2-propanyl)phenyl)pyrido[2,3-d]pyrimidin-2(1H)-one (302 mg, 0.62 mmol, 85% yield) as a light-yellow solid. $^1$H NMR (400 MHz, DMSO-d$_6$) δ ppm 8.45 (br s, 1H), 7.46-7.52 (m, 1H), 7.39-7.45 (m, 1H), 7.30 (td, J=7.5, 1.6 Hz, 1H), 7.12 (d, J=7.0 Hz, 1H), 6.75-6.93 (m, 1H), 6.20 (br d, J=16.8 Hz, 1H), 5.70-5.80 (m, 1H), 4.93 (br s, 1H), 3.97-4.42 (m, 3H), 3.53-3.84 (m, 2H), 2.92-3.26 (m, 1H), 2.41-2.49 (m, 1H), 1.28 (br d, J=6.6 Hz, 3H), 1.07 (d, J=6.8 Hz, 3H), 1.01 (d, J=6.8 Hz, 3H). m/z (ESI, +ve ion): 486.2 (M+H)$^+$.

Step 3: 6,7-Dichloro-4-((2S)-2-methyl-4-(2-propenoyl)-1-piperazinyl)-1-(2-(2-propanyl)phenyl)pyrido[2,3-d]pyrimidin-2(1H)-one. (2nd Isomer)

Preparation analogous to step 2 above. To a solution of (S)-tert-butyl 4-(6,7-dichloro-1-(2-isopropylphenyl)-2-oxo-1,2-dihydropyrido[2,3-d]pyrimidin-4-yl)-3-methylpiperazine-1-carboxylate (Peak 2, P-isomer, 292 mg, 0.55 mmol) in DCM (2.0 mL) was treated with TFA (1.0 mL) at rt and stirred for 2 h. The reaction went to completion and was concentrated to afford (S)-6,7-dichloro-1-(2-isopropylphenyl)-4-(2-methylpiperazin-1-yl)pyrido[2,3-d]pyrimidin-2(1H)-one. m/z (ESI, +ve) 432.2 (M+H).

A mixture of the above (S)-6,7-dichloro-1-(2-isopropylphenyl)-4-(2-methylpiperazin-1-yl)pyrido[2,3-d]pyrimidin-2(1H)-one and DIPEA (0.5 mL, 2.74 mmol) in DCM (2.0 mL) was treated with acryloyl chloride (0.05 mL, 0.55 mmol) at 0° C. and stirred for 10 min at 0° C. The resulting mixture was concentrated in vacuo. The crude product was purified by silica gel chromatography (eluent: 0-50% EtOAc-EtOH (3:1)/heptane) to provide pure 6,7-dichloro-4-((2S)-2-methyl-4-(2-propenoyl)-1-piperazinyl)-1-(2-(2-propanyl)phenyl)pyrido[2,3-d]pyrimidin-2(1H)-one (253 mg, 0.52 mmol, 95% yield) as a light-yellow solid. $^1$H NMR (400 MHz, DMSO-d$_6$) δ ppm 8.40 (br d, J=6.0 Hz, 1H), 7.46-7.52 (m, 1H), 7.38-7.46 (m, 1H), 7.29 (td, J=7.5, 1.5 Hz, 1H), 7.08-7.15 (m, 1H), 6.77-6.93 (m, 1H), 6.20 (br d, J=17.0 Hz, 1H), 5.70-5.81 (m, 1H), 4.82 (br s, 1H), 4.20-4.42 (m, 2H), 3.94-4.17 (m, 1H), 3.45-3.75 (m, 2H), 3.01-3.24 (m, 1H), 2.52 (br s, 1H), 1.31 (d, J=6.6 Hz, 3H), 1.05-1.10 (m, 3H), 0.99-1.05 (m, 3H). m/z (ESI, +ve ion): 486.2 (M+H)$^+$.

TABLE 61

Compounds 61-24 to 61-2-2 were prepared following the procedure described in Method 61, Steps 1-3, above as follows:

| Ex. # | Chemical Structure | Name |
|---|---|---|
| 61-2-1 | 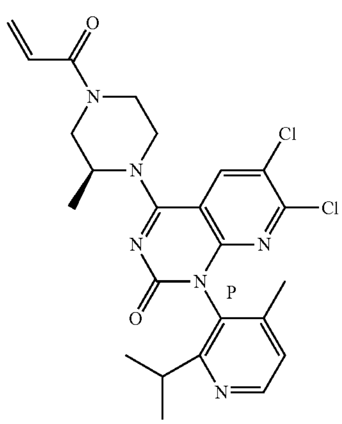 | (P)-6,7-dichloro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one |
| 61-2-2 | 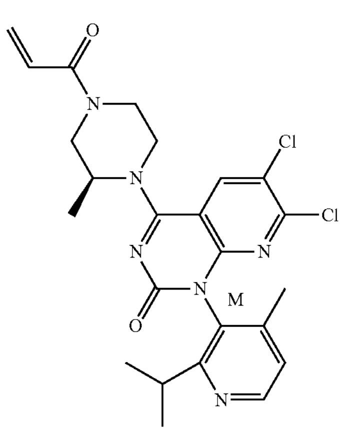 | (M)-6,7-dichloro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one |

Method 62

Example 62-1: 6-Chloro-7-(2-fluorophenyl)-4-((2S)-2-methyl-4-(2-propenoyl)-1-piperazinyl)-1-(2-(2-propanyl)phenyl)-2(1H)-quinazolinone

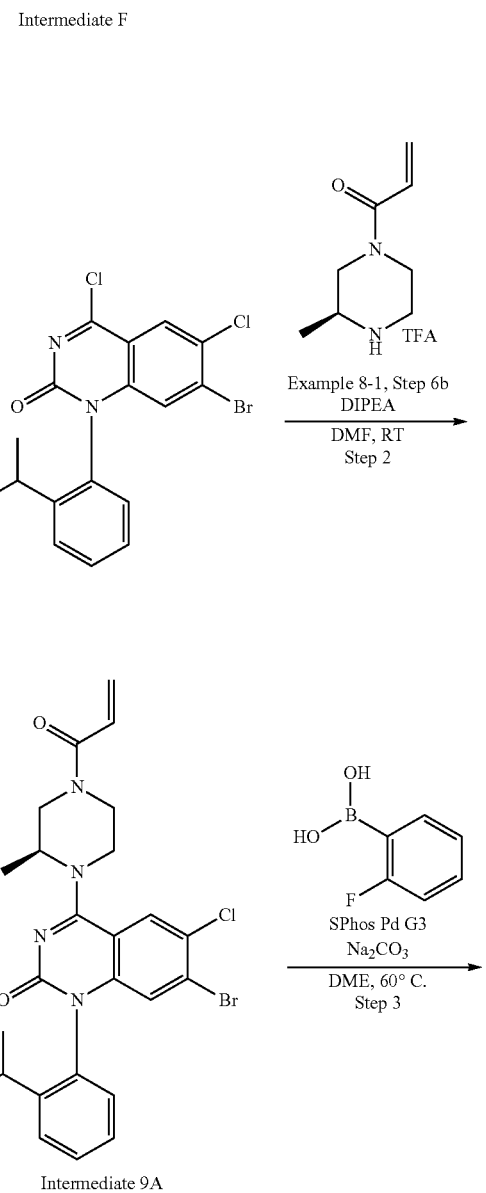

-continued

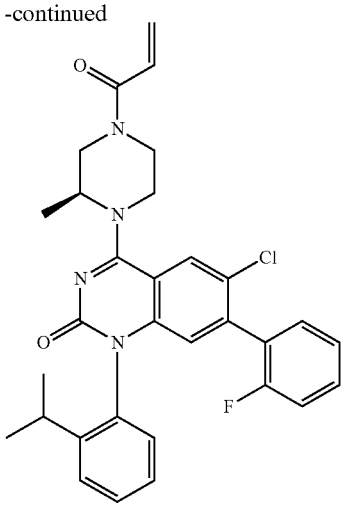

Step 1: 7-Bromo-4,6-dichloro-1-(2-isopropylphenyl)quinazolin-2(1H)-one

Phosphorus oxychloride (4.31 mL, 46.2 mmol) was added to a stirred mixture of 7-bromo-6-chloro-1-(2-isopropylphenyl)quinazoline-2,4(1H,3H)-dione (Intermediate F, 3.64 g, 9.25 mmol) and DIPEA (4.8 mL, 27.7 mmol) in acetonitrile (60 mL). The reaction mixture was heated to 80° C. and stirred for 1.5 h. The reaction mixture was concentrated in vacuo to give crude 7-bromo-4,6-dichloro-1-(2-isopropylphenyl)quinazolin-2(1H)-one which was used in the next step without purification.

Step 2: (S)-4-(4-Acryloyl-2-methylpiperazin-1-yl)-7-bromo-6-chloro-1-(2-isopropylphenyl)quinazolin-2(1H)-one DIPEA (8.1 mL, 46.2 mmol) was added to a stirred mixture of crude 7-bromo-4,6-dichloro-1-(2-isopropylphenyl)quinazolin-2(1H)-one (3.81 g, 9.25 mmol) and (S)-1-(3-methylpiperazin-1-yl)prop-2-en-1-one 2,2,2-trifluoroacetate (Example 8-1, Step 6b, 4.96 g, 18.5 mmol) in DMF (30 mL). The reaction mixture was stirred at rt for 1.5 h. Water (150 mL) was added, and the resulting precipitate was filtered. The crude product was purified by silica gel chromatography (eluent: 0-75% EtOAc-EtOH (3:1)/heptane) to provide (S)-4-(4-acryloyl-2-methylpiperazin-1-yl)-7-bromo-6-chloro-1-(2-isopropylphenyl)quinazolin-2(1H)-one as a tan solid (Intermediate 9A, 1.29 g, 2.44 mmol, 26.3% yield). m/z (ESI, +ve ion): 529.1 (M+H)$^+$.

Step 3: 6-Chloro-7-(2-fluorophenyl)-4-((2S)-2-methyl-4-(2-propenoyl)-1-piperazinyl)-1-(2-(2-propanyl)phenyl)-2(1H)-quinazolinone (S)-4-(4-acryloyl-2-methylpiperazin-1-yl)-7-bromo-6-chloro-1-(2-isopropylphenyl)quinazolin-2(1H)-one (Intermediate 9A, 372 mg, 0.702 mmol), 2-fluorobenzeneboronic acid (98 mg, 0.702 mmol), (2-dicyclohexylphosphino-2',6'-dimethoxybiphenyl) [2-(2'-amino-1,1'-biphenyl)]palladium (1H) methanesulfonate (55 mg, 0.07 mmol), and sodium carbonate (2 M aqueous, 1.4 mL, 2.8 mmol) were combined in 1,2-dimethoxyethane (5 mL) in a sealed vial under an argon atmosphere. The reaction mixture was stirred at 60° C. for 16 h then diluted with water (50 mL) and extracted with EtOAc (75 mL). The combined organic layers were washed with brine (100 mL), dried over MgSO$_4$, filtered, and concentrated in vacuo. The crude product was purified by silica gel chromatography (eluent: o-75% EtOAc-EtOH (3:1)/heptane) to provide (S)-4-(4-acryloyl-2-methylpiperazin-1-yl)-6-chloro-7-(2-fluorophenyl)-1-(2-isopropylphenyl)quinazolin-2(1H)-one as a white solid (236 mg, 0.216 mmol, 61.7% yield). $^1$H NMR (400 MHz, CDCl$_3$) δ ppm 7.84 (1H, s) 7.34-7.57 (4H, m) 7.12-7.25 (4H, m) 6.58-6.75 (1H, m) 6.55 (1H, s) 6.43 (1H, dd, J=16.79, 1.24 Hz) 5.83 (1H, dd, J=10.47, 0.94 Hz) 2.61-5.22 (9H, m) 1.43-1.61 (3H, m) 1.26 (3H, d, J=6.63 Hz) 1.11 (3H, d, J=6.84 Hz). m/z (ESI, +ve ion): 544.8 (M+H)$^+$.

TABLE 62

Compounds 62-2 to 62-3 were prepared following the procedure described in Method 62, Steps 1-3, above as follows:

| Ex. # | Chemical Structure | Name | Method Changes | Reagent |
|---|---|---|---|---|
| 62-2 | 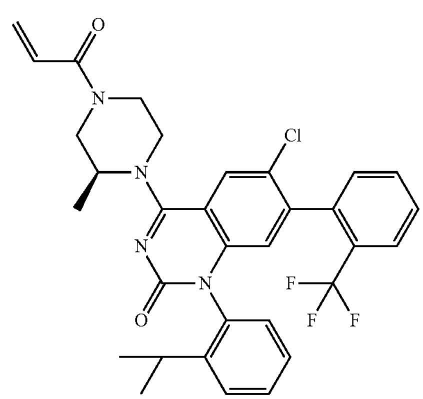 [SMILES: C=CC(=O)N1CCN(c2nc(=O)n(-c3ccccc3C(C)C)c3cc(-c4ccccc4C(F)(F)F)c(Cl)cc23)[C@@H](C)C1] | 6-chloro-4-((2S)-2-methyl-4-(2-propenoyl)-1-piperazinyl)-1-(2-(2-propanyl)phenyl)-7-(2-(trifluoromethyl)phenyl)-2(1H)-quinazolinone | | Step 1: 2-isopropylaniline (Sigma-Aldrich Corporation, Step 3: 2-(trifluoromethyl)phenylboronic acid (Combi-Blocks Inc.) |

TABLE 62-continued

Compounds 62-2 to 62-3 were prepared following the procedure described in Method 62, Steps 1-3, above as follows:

| Ex. # | Chemical Structure | Name | Method Changes | Reagent |
|---|---|---|---|---|
| 62-3 | 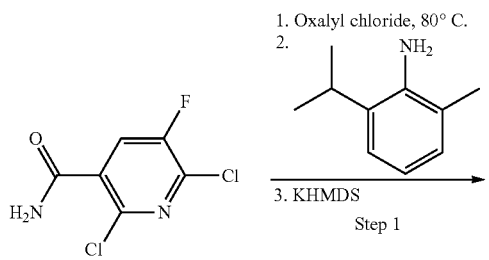 | 6-chloro-1-(3-cyclopropyl-4-pyridinyl)-7-(2-fluoro-6-hydroxyphenyl)-4-((2S)-2-methyl-4-(2-propenoyl)-1-piperazinyl)-2(1H)-quinazolinone | | Step 1: 3-cyclopropylpyridin-4-amine (CombiPhos Catalysts, Inc.), Step 3: 2-fluoro-6-hydroxyphenylboronic acid (Combi-Blocks Inc.) |

Method 63

Example 63-1: 6-Fluoro-7-(2-fluoro-6-hydroxyphenyl)-1-(2-methyl-6-(2-propanyl)phenyl)-4-((3S)-3-methyl-4-(2-propenoyl)-1-piperazinyl)pyrido[2,3-d]pyrimidin-2(1H)-one

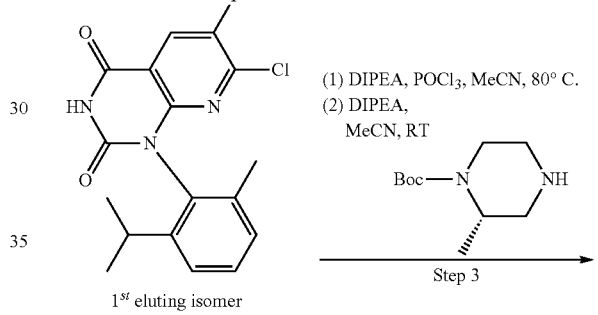

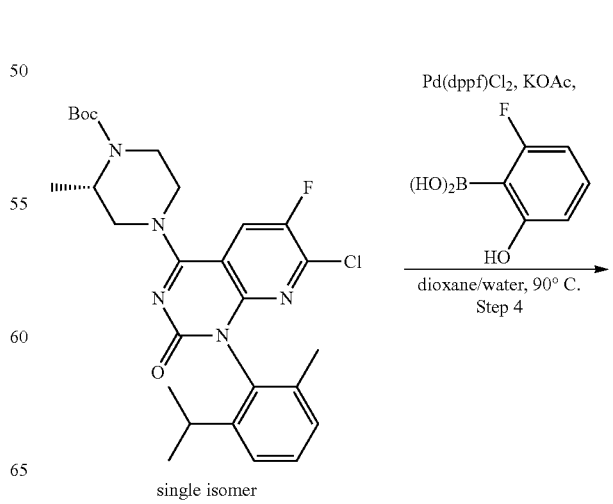

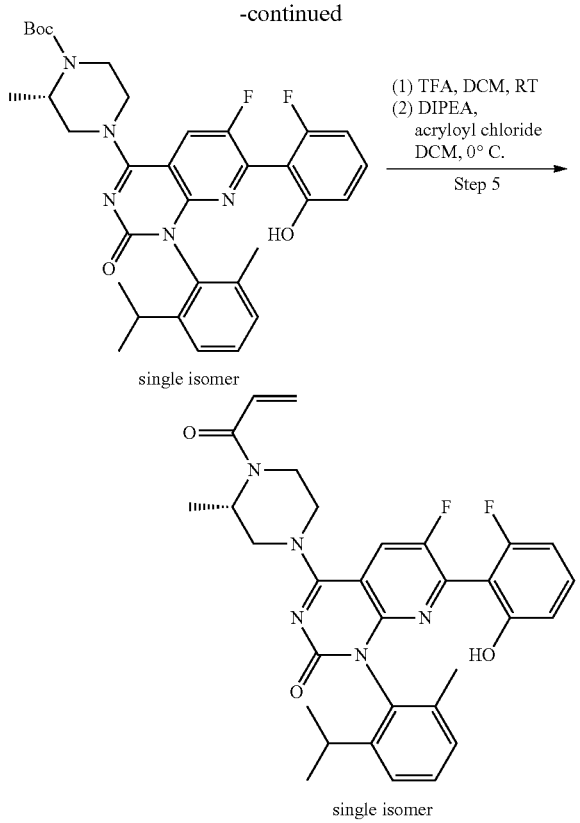

Step 1: 7-Chloro-6-fluoro-1-(2-isopropyl-6-methylphenyl)pyrido[2,3-d]pyrimidine-2,4(1H,3H)-dione (Intermediate 63A)

To a solution of 2,6-dichloro-5-fluoronicotinamide (Intermediate S, 13.0 g, 62.2 mmol) in THF (100 mL) was added oxalyl chloride, 2 M solution in DCM (37.3 mL, 74.6 mmol). The reaction mixture was stirred at 80° C. for 30 min before being cooled to 0° C. 2-(1-Methylethyl)-6-methylaniline (10.7 mL, 71.5 mmol, Enamine, Monmouth Junction, N.J., USA) was added, and the reaction mixture was stirred at 0° C. for 30 min before warming to rt. After stirring at rt for 1 h, the reaction mixture was partially concentrated and partitioned between satd. NaHCO$_3$ (200 mL) and EtOAc (300 mL). The organic layer was separated, washed with brine (150 mL), dried over MgSO$_4$, filtered, and concentrated in vacuo to give crude 2,6-dichloro-5-fluoro-N-((2-isopropyl-6-methylphenyl)carbamoyl)nicotinamide. The crude material was dissolved in THF (40 mL) and 1 M KHMDS in THF (131 mL, 131 mmol) was added at 0° C. The reaction mixture was stirred and warmed to rt for 1 h. The reaction mixture was quenched with satd. ammonium chloride (300 mL) and extracted with EtOAc (400 mL). The organic layer was separated, washed with brine (300 mL), dried over MgSO$_4$, filtered, and concentrated in vacuo. The crude product was purified by silica gel chromatography (eluent: 0-60%/EtOAc/heptane) to give 7-chloro-6-fluoro-1-(2-isopropyl-6-methylphenyl)pyrido[2,3-d]pyrimidine-2,4(1H,3H)-dione (Intermediate 63A, 16.3 g, 46.8 mmol, 75% yield) as a mixture of atropisomers. m/z (ESI, +ve ion): 348.1 (M+H)$^+$.

Step 2: 7-Chloro-6-fluoro-1-(2-isopropyl-6-methylphenyl)pyrido[2,3-d]pyrimidine-2,4(1H,3H)-dione (1$^{st}$ Eluting Isomer)

The mixture of atropisomers (Intermediate 63A) was purified by SFC (OJ-H, 150×30 mm, 5 μm), 10% MeOH/CO$_2$, 140 g/min, 100 bar) to obtain two peaks: Peak 1 (6.66 g, >99% ee) and Peak 2 (6.74 g, >99% ee). m/z (ESI, +ve ion): 348.1 (M+H)$^+$.

Step 3: tert-Butyl (S)-4-(7-chloro-6-fluoro-1-(2-isopropyl-6-methylphenyl)-2-oxo-1,2-dihydropyrido[2,3-d]pyrimidin-4-yl)-2-methylpiperazine-1-carboxylate Phosphorous oxychloride (0.072 mL, 0.776 mmol) was added dropwise to a solution of 7-chloro-6-fluoro-1-(2-isopropyl-6-methylphenyl)pyrido[2,3-d]pyrimidine-2,4(1H,3H)-dione (Peak 1, 180 mg, 0.518 mmol) and DIPEA (0.15 mL, 0.828 mmol) in acetonitrile (2 mL) under argon. The mixture was heated to 80° C. for 3 h, then cooled to 10° C. and DIPEA (0.27 mL, 1.55 mmol) was added followed by (S)-1-N-Boc-2-methylpiperazine (114 mg, 0.569 mmol). This mixture was stirred with warming to rt over 1 h. The mixture was poured into cooled satd. NaHCO$_3$ solution and stirred vigorously for 10 min. EtOAc was added and the resulting biphasic mixture was separated. The organic extracts were dried over Na$_2$SO$_4$, filtered, and concentrated in vacuo to give a yellow oil [m/z (ESI, +ve ion): 530.2 (M+H)$^+$.] which was used directly in the following step.

Step 4: tert-Butyl (2S)-4-(6-fluoro-7-(2-fluoro-6-hydroxyphenyl)-1-(2-isopropyl-6-methylphenyl)-2-oxo-1,2-dihydropyrido[2,3-d]pyrimidin-4-yl)-2-methylpiperazine-1-carboxylate A 150-mL RBF was charged with tert-butyl (S)-4-(7-chloro-6-fluoro-1-(2-isopropyl-6-methylphenyl)-2-oxo-1,2-dihydropyrido[2,3-d]pyrimidin-4-yl)-2-methylpiperazine-1-carboxylate (264 mg, 0.498 mmol). (2-fluoro-6-hydroxyphenyl)boronic acid (93 mg, 0.598 mmol), dichloro[1,1'-bis(diphenylphosphino)ferrocene]palladium (II) DCM adduct (36 mg, 0.05 mmol), potassium acetate (244 mg, 2.49 mmol), and 1,4-dioxane (5 mL). The mixture was degassed by bubbling nitrogen through the reaction mixture. A drop of water was added and the mixture was stirred at 90° C. for 3 h. The reaction mixture was cooled to rt, partitioned between EtOAc and brine. The aqueous layer was back extracted with EtOAc and the combined EtOAc layers were dried over Na$_2$SO$_4$ and concentrated in vacuo. The crude product was purified by silica gel chromatography (eluent: 0-25% EtOAc-EtOH (3:1)/heptane) to provide tert-butyl (2S)-4-(6-fluoro-7-(2-fluoro-6-hydroxyphenyl)-1-(2-isopropyl-6-methylphenyl)-2-oxo-1,2-dihydropyrido[2,3-d]pyrimidin-4-yl)-2-methylpiperazine-1-carboxylate (200 mg, 0.33 mmol, 66.3% yield) as a light-yellow solid. m/z (ESI, +ve ion): 606.2 (M+H)$^+$.

Step 5: 4-((S)-4-Acryloyl-3-methylpiperazin-1-yl)-6-fluoro-7-fluoro-7-(2-fluoro-6-hydroxyphenyl)-1-(2-isopropyl-6-methylphenyl)pyrido[2,3-d]pyrimidin-2(1H)-one To a solution of tert-Butyl (2S)-4-(6-fluoro-7-(2-fluoro-6-hydroxyphenyl)-1-(2-isopropyl-6-methylphenyl)-2-oxo-1,2-dihydropyrido[2,3-d]pyrimidin-4-yl)-2-methylpiperazine-1-carboxylate (200 mg, 0.33 mmol) in DCM (2.2 mL)

was added TFA (0.74 ml, 9.91 mmol) dropwise. The reaction mixture was stirred at rt for 30 min. The solvent was concentrated in vacuo to give crude product which was used directly in the following step.

A mixture of 6-fluoro-7-(2-fluoro-6-hydroxyphenyl)-1-(2-isopropyl-6-methylphenyl)-4-((S)-3-methylpiperazin-1-yl)pyrido[2,3-d]pyrimidin-2(1H)-one and N,N'-diisopropylethylamine (0.26 mL, 1.49 mmol) in DCM (2.2 mL) was added acryloyl chloride (27 µL, 0.33 mmol) at 0° C. and stirred for 30 min. The crude product was purified by silica gel chromatography (eluent: 0-45%/o EtOAc-EtOH (3:1)/heptane) to provide 6-fluoro-7-(2-fluoro-6-hydroxyphenyl)-1-(2-methyl-6-(2-propanyl)phenyl)-4-((3S)-3-methyl-4-(2-propenoyl)-1-piperazinyl)pyrido[2,3-d]pyrimidin-2(1H)-one as an off-white solid. $^1$H NMR (400 MHz, DMSO-$d_6$) δ 10.16 (s, 1H), 8.40 (d, J=9.33 Hz, 1H), 7.18-7.32 (m, 3H), 7.10 (dd, J=2.18, 6.53 Hz, 1H), 6.63-6.87 (m, 3H), 6.18 (br d, J=17.21 Hz, 1H), 5.70-5.76 (m, 1H), 4.47-4.77 (m, 1H), 4.33-4.45 (m, 1H), 3.96-4.21 (m, 2H), 3.58-3.89 (m, 3H), 2.66-2.68 (m, 1H), 1.82 (s, 3H), 1.06 (d, J=6.84 Hz, 3H), 0.92 (d, J=6.84 Hz, 3H), 0.83-0.89 (m, 3H). $^{19}$F NMR (376 MHz, DMSO-$d_6$) δ −115.53 (br d, J=6.07 Hz, 1F), −128.92 (br d, J=5.20 Hz, 1F). m/z (ESI, +ve ion): 560.3 (M+H)$^+$.

TABLE 63

Compounds 63-2 to 63-5 were prepared following the procedure described in Method 63, Steps 1-5, above as follows:

| Ex. # | Chemical Structure | Name | Method. Changes | Reagent |
|---|---|---|---|---|
| 63-2 | single isomer | 6-fluoro-7-(2-fluoro-6-hydroxyphenyl)-1-(2-methyl-6-(2-propanyl)phenyl)-4-((3R)-3-methyl-4-(2-propenoyl)-1-piperazinyl)pyrido[2,3-d]pyrimidin-2(1H)-one | | Step 1: 2-isopropyl-6-methylaniline (Enamine), Step 3: (R)-1-Boc-2-methyl-piperazine J & W Pharmlab, LLC), Step 4: (2-fluoro-6-hydroxyphenyl)boronic acid (Wuxi) |
| 63-3 | single isomer | 4-((2S,6S)-2,6-dimethyl-4-(2-propenoyl)-1-piperazinyl)-6-fluoro-7-(2-fluoro-6-hydroxyphenyl)-1-(2-methyl-6-(2-propanyl)phenyl)yl)pyrido[2,3-d]pyrimidin-2(1H)-one | | Step 1: 2-isopropyl-6-methylaniline (Enamine) Step 3: tert-butyl (3s,5s)-3,5-dimethylpiperazine-1-carboxylate (eNovation Chemicals LLC), Step 4: (2-fluoro-6-hydroxyphenyl)boronic acid (Wuxi) |

TABLE 63-continued

Compounds 63-2 to 63-5 were prepared following the procedure described in Method 63, Steps 1-5, above as follows:

| Ex. # | Chemical Structure | Name | Method. Changes | Reagent |
|---|---|---|---|---|
| 63-4 | Single isomer | 4-(2,2-dimethyl-4-(2-propenoyl)-1-piperazinyl)-6-fluoro-7-(2-fluoro-6-hydroxyphenyl)-1-(2-methyl-6-(2-propanyl)phenyl pyrido[2,3-d]pyrimidin-2(1H)-one | | Step 1: 2-isopropyl-6-methylaniline (Enamine), Step 3: 1-Boc-3,3-dimethylpiperazine (Synthonix Inc.), Step 4: (2-fluoro-6-hydroxyphenyl) boronic acid (Wuxi) |
| 63-5 | single isomer | 6-fluoro-7-(2-fluoro-6-hydroxyphenyl)-1-(2-methyl-6-(2-proyanyl)phenyl)-4-(6-(2-propenoyl)-2,6-diazaspiro[3.3]heptan-2-yl)pyrido[2,3-d]pyrimidin-2(1H)-one | | Step 1: 2-isopropyl-6-methylaniline (Enamine), Step 3: 2-Boc-2,6-diazaspiro[3.3]heptane (AstaTech, Inc.), Step 4: (2-fluoro-6-hydroxyphenyl) boronic acid (Wuxi) |

Method 64

Example 64-1: (M)-6-Chloro-7-(2-fluorophenyl)-1-(2-methyl-6-(2-propanyl)phenyl)-4-((2S)-2-methyl-4-(2-propenoyl)-1-piperazinyl)pyrido[2,3-d]pyrimidin-2(1H)-one

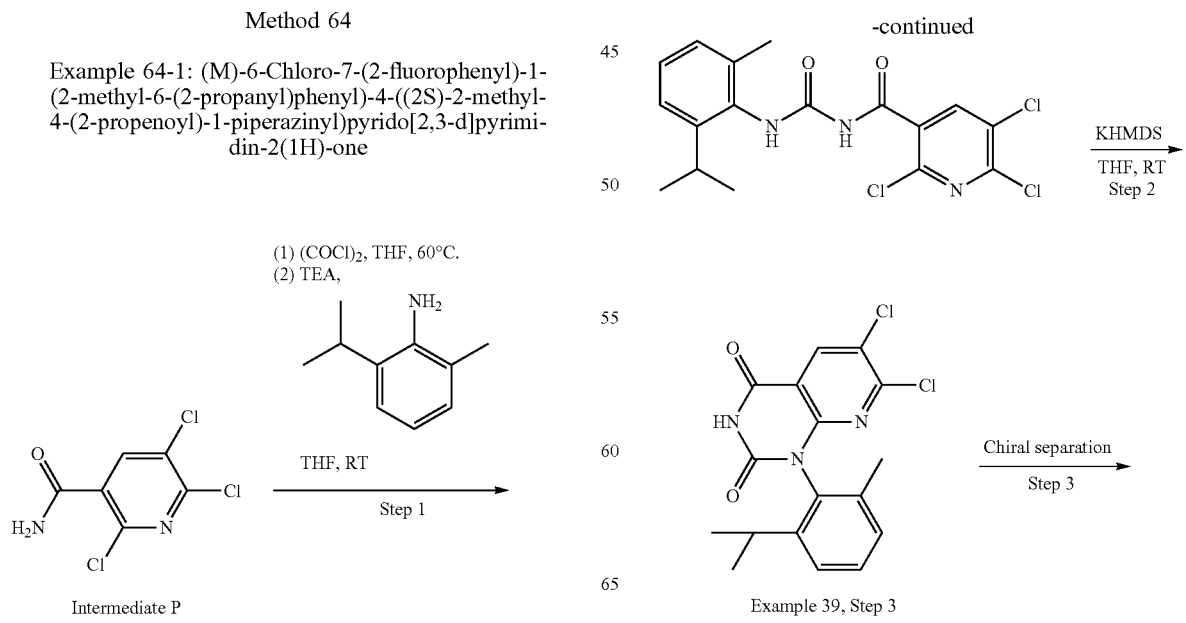

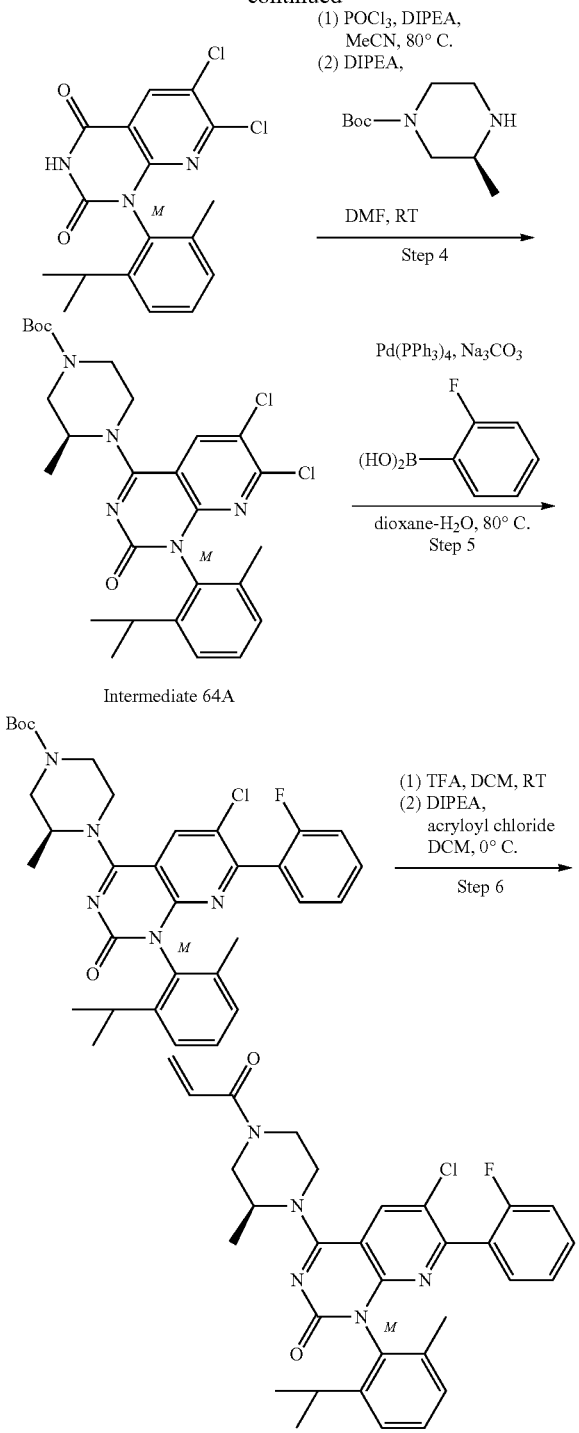

Step 1: 2,5,6-Trichloro-N-((2-isoproropyl-6-methylphenyl)carbamoyl) nicotinamide To a mixture of 2,5,6-trichloronicotinamide (Intermediate P, 1.13 g, 5.0 mmol) in THF (30 mL) was added a oxalyl chloride (2 M solution in DCM, 2.7 mL, 5.4 mmol). The resulting slurry was heated at 65° C. for 40 min, then heating was stopped and the reaction was allowed to cool to rt. 2-Isopropyl-6-methylaniline (0.8 mL, 5.36 mmol, Enamine, Monmouth Junction, N.J., USA) was added and the reaction was stirred at rt for 14 h. The reaction was concentrated in vacuo and the residue was partitioned between EtOAc (50 mL) and satd. NaHCO₃ (10 mL). The organic layer was washed with brine (10 mL), dried over anhydrous Na₂SO₄ and concentrated in vacuo. The residue was suspended in heptane-EtOAc (5:1, 10 mL) and filtered to provide 2,5,6-trichloro-N-((2-isopropyl-6-methylphenyl)carbamoyl)nicotinamide (1.45 g, 72% yield). $^1$H NMR (400 MHz, CDCl₃) ppm 9.63 (s, 1H), 9.35 (br s, 1H), 8.25 (s, 1H), 7.19-7.26 (m, 2H), 7.13 (d, J=7.3 Hz, 1H), 3.14 (quin, J=6.9 Hz, 1H), 2.29 (s, 3H), 1.23 (d, J=6.8 Hz, 6H). m/z (ESI, +ve ion): 400.0 (M+H)⁺.

Step 2: 6,7-Dichloro-1-(2-isopropyl-6-methylphenyl)pyrido[2,3-d]pyrimidine-2,4(1H,3H)-dione (Example 39, Step 3)

To a mixture of 2,5,6-trichloro-N-((2-isopropyl-6-methylphenyl)carbamoyl)nicotinamide (1.45 g, 3.6 mmol) in THF (20 mL) was added KHMDS (1 M in THF, 7.5 mL, 7.5 mmol). After stirring for 30 min at rt, the reaction was concentrated to 1/3 volume and quenched with satd. ammonium chloride (10 mL). The mixture was extracted with EtOAc (40 mL). The organic layer was washed with brine (10 mL), dried over anhydrous Na₂SO₄ and concentrated in vacuo to provide 6,7-dichloro-1-(2-isopropyl-6-methylphenyl)pyrido[2,3-d]pyrimidine-2,4(1H,3H)-dione (Example 39, Step 3). m/z (ESI, +ve ion): 364.0 (M+H)⁺.

Step 3: (M)-6,7-Dichloro-1-(2-isopropyl-6-methylphenyl)pyrido[2,3-d]pyrimidine-2,4(1H,3H)-dione 6,7-Dichloro-1-(2-isopropyl-6-methylphenyl)pyrido[2,3-d]pyrimidine-2,4(1H,3H)-dione (Example 39, Step 3) was purified by SFC to give (M)-6,7-dichloro-1-(2-isopropyl-6-methylphenyl)pyrido[2,3-d]pyrimidine-2,4(1H,3H)-dione. 2$^{nd}$-eluting isomer, SFC (Chiralpak IC, 30×250 mm, 50% MeOH/CO₂, 100 mL/min, 100 bar. m/z (ESI, +ve ion): 364.0 (M+H)⁺.

Step 4: (M)-(S)-tert-Butyl 4-(6,7-dichloro-1-(2-isopropyl-6-methylphenyl)-2-oxo-1,2-dihydropyrido[2,3-d]pyrimidin-4-yl)-3-methylpiperazine-1-carboxylate (Intermediate 64A). To a mixture of crude 6,7-dichloro-1-(2-isopropyl-6-methylphenyl)pyrido[2,3-d]pyrimidine-2,4(1H,3H)-dione (1.3 g, 3.6 mmol) in acetonitrile (10 mL) was added DIPEA (1.5 mL, 8.6 mmol) followed by phosphorus oxychloride (0.5 mL, 5.3 mmol). The resulting mixture was heated at 80° C. for 1 h, then was cooled to rt and concentrated in vacuo. The residue was dissolved in DMF (15 mL) and treated with DIPEA (1.5 mL, 8.6 mmol), followed by (S)-4-N-Boc-2-methyl piperazine (900 mg, 4.5 mmol, ArkPharm Inc., Arlington Heights, Ill., USA). The resulting solution was stirred at rt for 14 h and then was diluted with EtOAc (30 mL). The mixture was washed with water (10 mL) and brine (10 mL), and the organic layer was dried over anhydrous MgSO₄ and concentrated in vacuo. The crude product was purified by silica gel chromatography (eluent: 10-50% EtOAc-EtOH (3:1)/heptane) to provide (M)-(S)-tert-butyl 4-(6,7-dichloro-1-(2-isopropyl-6-methylphenyl)-2-oxo-1,2-dihydropyrido[2,3-d]pyrimidin-4-yl)-3-methylpiperazine-1-carboxylate (Intermediate 64A, 1.4 g, 71% yield). $^1$H NMR (400 MHz, MeOH-d₄) δ ppm 8.45 (s, 1H), 7.34-7.43 (m, 2H), 7.23 (d, J=7.3 Hz, 1H), 4.97 (br s, 1H), 4.34 (br d, J=13.3 Hz, 1H), 4.15 (br d, J=12.0 Hz, 1H), 4.01 (br d, J=13.7 Hz, 1H), 3.80 (br s, 1H), 3.09-3.32 (m, 2H), 2.49-2.59 (m, 1H), 1.99 (d, J=3.7 Hz, 3H), 1.55 (s, 9H), 1.50 (dd, J=1.7, 6.6 Hz, 3H), 1.18 (dd, J=6.7, 1.8 Hz, 3H), 1.09 (dd, J=6.8, 2.3 Hz, 3H). m/z (ESI, +ve ion): 546.1 (M+H)$^+$.

Step 5: (M)-tert-Butyl (S)-4-(6-chloro-7-(2-fluorophenyl)-1-(2-isopropyl-6-methylphenyl)-2-oxo-1,2-dihydropyrido[2,3-d]pyrimidin-4-yl)-3-methylpiperazine-1-carboxylate A round-bottomed flask was charged with tert-butyl (S)-4-(6,7-dichloro-1-(2-isopropyl-6-methylphenyl)-2-oxo-1,2-dihydropyrido[2,3-d]pyrimidin-4-yl)-3-methylpiperazine-1-carboxylate (Intermediate 64A, 0.127 g, 0.232 mmol), 2-fluorophenylboronic acid (0.058 g, 0.417 mmol), sodium carbonate, anhydrous, powder (0.074 g, 0.695 mmol), tetrakis(triphenylphosphine)palladium(0) (0.027 g, 0.023 mmol) in 1,4-dioxane (0.9 mL) and water (0.2 mL) and the yellow heterogeneous mixture was stirred and heated at 80° C. After 4 h, the crude product was purified by silica gel chromatography (eluent: 0-100% EtOAc/heptane) to provide tert-butyl (S)-4-(6-chloro-7-(2-fluorophenyl)-1-(2-isopropyl-6-methylphenyl)-2-oxo-1,2-dihydropyrido[2,3-d]pyrimidin-4-yl)-3-methylpiperazine-1-carboxylate (0.11 g, 0.181 mmol, 78% yield) as a white solid: $^1$H NMR (400 MHz, DMSO-d$_6$) δ ppm 8.41 (s, 1H), 7.46-7.55 (m, 1H), 7.07-7.35 (m, 6H), 4.88 (br s, 1H), 4.22 (br d, J=13.1 Hz, 1H), 3.90-4.09 (m, 1H), 3.84 (br d, J=13.1 Hz, 1H), 3.70 (br t, J=11.1 Hz, 1H), 3.38 (br s, 1H), 3.13 (br s, 1H), 2.53-2.59 (m, 1H), 1.88 (s, 3H), 1.45 (s, 9H), 1.35 (br d, J=6.4 Hz, 3H), 1.05 (br d, J=6.8 Hz, 3H), 0.94 (br d, J=6.8 Hz, 3H). $^{19}$F NMR (376 MHz, DMSO-d$_6$) δ ppm −113.98 (s, 1F). m/z (ESI, +ion): 606.0 (M+H)$^+$.

Step 6: (M)-6-Chloro-7-(2-fluorophenyl)-1-(2-methyl-6-(2-propanyl)phenyl)-4-((2S)-2-methyl-4-(2-propenoyl)-1-piperazinyl)pyrido[2,3-d]pyrimidin-2(1H)-one To a solution of tert-butyl (S)-4-(6-chloro-7-(2-fluorophenyl)-1-(2-isopropyl-6-methylphenyl)-2-oxo-1,2-dihydropyrido[2,3-d]pyrimidin-4-yl)-3-methylpiperazine-1-carboxylate (0.106 g, 0.174 mmol) in DCM (1.7 mL) was added TFA (1.7 mL) and the mixture was stirred at rt. After 1 h, the mixture was concentrated in vacuo to give (S)-6-chloro-7-(2-fluorophenyl)-1-(2-isopropyl-6-methylphenyl)-4-(2-methylpiperazin-1-yl)pyrido[2,3-d]pyrimidin-2(1H)-one as a yellow syrup. The yellow syrup was dissolved in DCM (1.7 mL), cooled to 0° C., and treated with DIPEA (0.46 mL, 2.61 mmol) followed by acryloyl chloride, 0.2 M solution in DCM (0.9 mL, 0.18 mmol) dropwise. After 20 min, the reaction was quenched with satd. NaHCO$_3$ (50 mL) and the mixture was extracted with DCM (2×50 mL). The organic extract was washed with brine (1×100 mL) and dried over Na$_2$SO$_4$. The solution was filtered and concentrated in vacuo to give the crude material as a white syrupy solid. The crude product was purified by silica gel chromatography (eluent: 0-60% DCM-MeOH (4:1)/DCM) to provide (M)-6-chloro-7-(2-fluorophenyl)-1-(2-methyl-6-(2-propanyl)phenyl)-4-((2S)-2-methyl-4-(2-propenoyl)-1-piperazinyl)pyrido[2,3-d]pyrimidin-2(1H)-one (83.7 mg, 0.149 mmol, 86% yield) as a white solid. $^1$H NMR (400 MHz, DMSO-d$_6$) δ ppm 8.44 (br s, 1H), 7.46-7.55 (m, 1H), 7.07-7.35 (m, 6H), 6.86 (dt, J=16.1, 10.7 Hz, 1H), 6.21 (br d, J=16.6 Hz, 1H), 5.72-5.81 (m, 1H), 4.93 (brs, 1H), 3.95-4.47 (m, 3H), 3.40-3.84 (m, 2H), 3.02-3.30 (m, 1H), 2.52-2.59 (m, 1H), 1.89 (s, 3H), 1.33 (d, J=6.6 Hz, 3H), 1.06 (d, J=6.8 Hz, 3H), 0.94 (d, J=6.8 Hz, 3H). $^{19}$F NMR (376 MHz, DMSO-d$_6$) δ ppm −113.97 (s, 1F). m/z (ESI, +ion): 560.0 (M+H)$^+$.

TABLE 64

Compounds 64-2 to 64-3 were prepared following the procedure described in Method 64, Steps 1-6, above as follows:

| Ex. # | Chemical Structure | Name | Method Changes | Reagent |
|---|---|---|---|---|
| 64-2 | 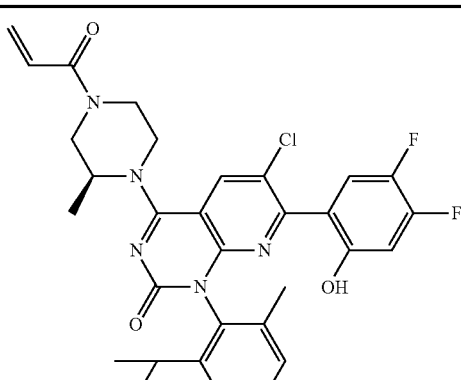<br>single isomer<br>(M) | (M)-6-chloro-7-(4,5-difluoro-2-hydroxyphenyl)-1-(2-methyl-6-(2-propanyl)phenyl)-4-((2S)-2-methyl-4-(2-propenoyl)-1-piperazinyl)pyrido[2,3-d]pyrimidin-2(1H)-one, single isomer | Step 5: KOAc in place of Na$_2$CO$_3$ | Step 1: 2-isopropyl-6-methylaniline (Enamine), Step 5: 4,5-difluoro-2-hydroxyphenylboronic acid (Combi-Blocks Inc. |

TABLE 64-continued

Compounds 64-2 to 64-3 were prepared following the procedure described in Method 64, Steps 1-6, above as follows:

| Ex. # | Chemical Structure | Name | Method Changes | Reagent |
|---|---|---|---|---|
| 64-3 | 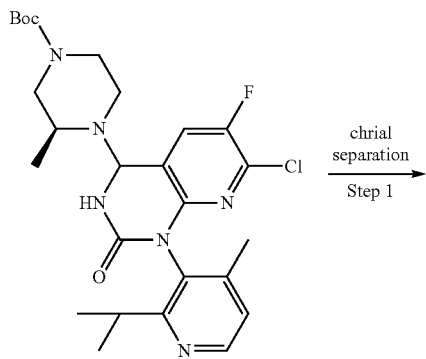 single isomer (M) | (M)-6-chloro-7-(3-fluoro-2-hydroxyphenyl)-1-(2-methyl-6-(2-propanyl)phenyl)-4-((2S)-2-methyl-4-(2-propenoyl)-1-piperazinyl)pyrrido[2,3-d]pyrimidin-2(1H)-one | | Step 1: 2-isopropyl-6-methylaniline (Enamine), Step 5: 3-fluoro-2-hydroxyphenylboronic acid (Frontier Scientific Services, Inc.) |

Method 65

Example 65-1: (M)-7-(6-Amino-3-chloro-2-pyridinyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one

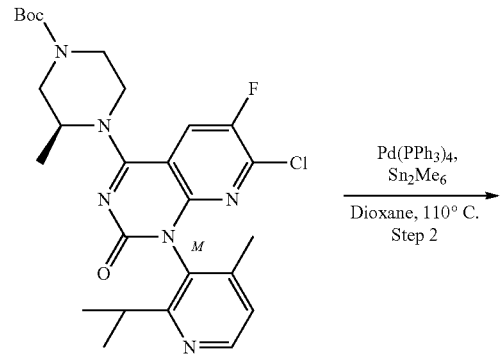

Example 41, Step 5

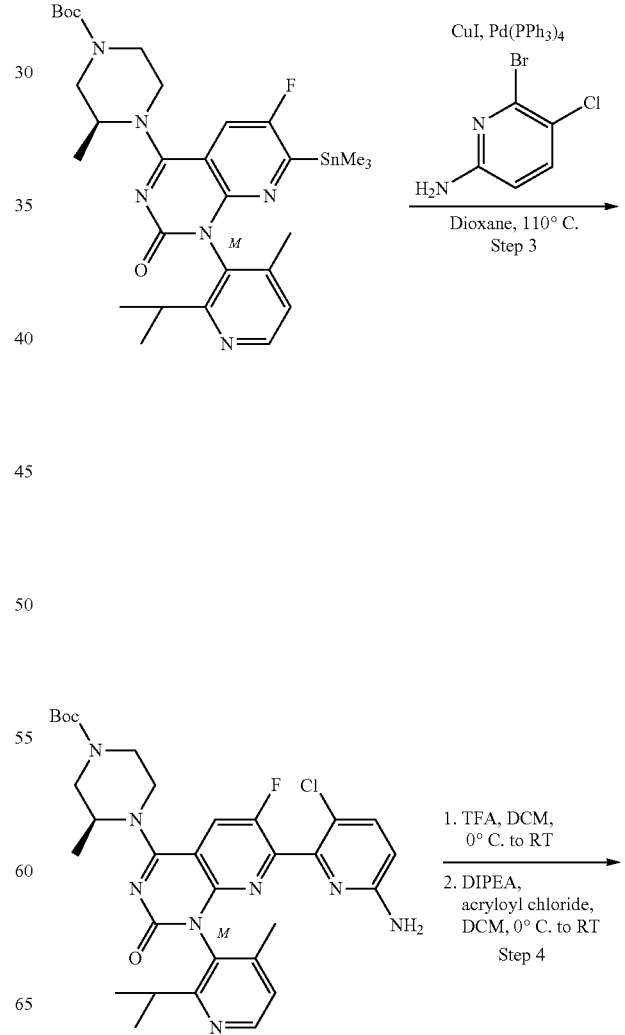

Intermediate 65A

-continued

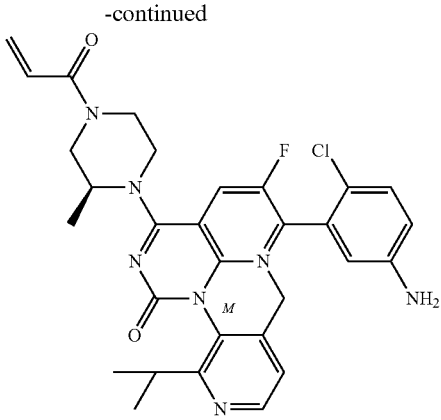

Step 1: (M)-tert-Butyl (S)-4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (Intermediate 65A)

A mix of atropisomers (Example 41, Step 5) was separated into isomerically pure material using preparative normal phase HPLC (ChiralPak IC; eluent 20% MeOH-EtOH (1:1)/heptane) to provide isomerically pure tert-butyl (M)-(S)-4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate as a white solid (Intermediate 65A, $1^{st}$-eluting atropisomer.)

Step 2: (M)-tert-Butyl (S)-4-(6-fluoro-1-(2-isopropyl-4-methylpyridin-3-yl)-2-oxo-7-(trimethylstannyl)-1,2-dihydropyrido[2,3-d]pyrimidin-4-yl)-3-methylpiperazine-1-carboxylate To a vial was added tetrakis(triphenylphosphine)palladium (0) (0.13 g, 0.11 mmol) and tert-butyl (M)-(S)-4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (Intermediate 65A, 0.6 g, 1.13 mmol). The reaction vessel was evacuated and refilled with $N_2$ followed by addition of 1,4-dioxane (3.2 mL) and hexamethylditin (0.52 mL, 2.49 mmol, Fisher Scientific, Hampton, N.H., USA). The mixture was heated to 110° C. for 1 h then cooled to rt. The crude product was purified by silica gel chromatography (eluent: 30-50% EtOAc-EtOH (3:1)/heptane) to provide (M)-tert-butyl (S)-4-(6-fluoro-1-(2-isopropyl-4-methylpyridin-3-yl)-2-oxo-7-(trimethylstannyl)-1,2-dihydropyrido[2,3-d]pyrimidin-4-yl)-3-methylpiperazine-1-carboxylate (550 mg, 73.8% yield) as a white solid. m/z (ESI, +ve ion): 661.0 (M+H)+.

Step 3: (M)-tert-Butyl (S)-4-(7-(6-amino-3-chloropyridin-2-yl)-6-fluoro-1-(2-isopropyl-4-methylpyridin-3-yl)-2-oxo-1,2-dihydropyrido[2,3-d]pyrimidin-4-yl)-3-methylpiperazine-1-carboxylate To a vial was added tert-butyl (M)-(S)-4-(6-fluoro-1-(2-isopropyl-4-methylpyridin-3-yl)-2-oxo-7-(trimethylstannyl)-1,2-dihydropyrido[2,3-d]pyrimidin-4-yl)-3-methylpiperazine-1-carboxylate (0.18 g, 0.28 mmol), copper(I) iodide, (5.3 mg, 0.028 mmol, Strem Chemicals, Newburyport, Mass., USA) and tetrakis(triphenylphosphine)palladium (0) (0.016 g, 0.014 mmol). The atmosphere was evacuated and backfilled with $N_2$ followed by addition of 1,4-dioxane (2.8 mL) and 2-amino-6-bromo-5-chloropyridine (0.06 mL, 0.28 mmol, CombiBlocks, San Diego, Calif., USA). The reaction mixture was heated to 150° C. (using a Biotage Initiation+ microwave) for 1 h, cooled to rt, and purified by silica gel chromatography eluent of 0-50% DCM-MeOH (4:1)/DCM] to provide (M)-tert-butyl (S)-4-(7-(6-amino-3-chloropyridin-2-yl)-6-fluoro-1-(2-isopropyl-4-methylpyridin-3-yl)-2-oxo-1,2-dihydropyrido[2,3-d]pyrimidin-4-yl)-3-methylpiperazine-1-carboxylate (0.12 g, 70.5% yield) as a yellow solid. m/z (ESI, +ve ion): 623.0 (M+H)+.

Step 4: (M)-(S)-4-(4-Acryloyl-2-methylpiperazin-1-yl)-7-(6-amino-3-chloropyridin-2-yl)-6-fluoro-1-(2-isopropyl-4-methylpyridin-3-yl)pyrido[2,3-d]pyrimidin-2(1H)-one To a solution of tert-butyl (M)-(S)-4-(7-(6-amino-3-chloropyridin-2-yl)-6-fluoro-1-(2-isopropyl-4-methylpyridin-3-yl)-2-oxo-1,2-dihydropyrido[2,3-d]pyrimidin-4-yl)-3-methylpiperazine-1-carboxylate (0.12 g, 0.20 mmol) and DCM (2 mL) at 0° C. was added TFA (0.3 mL, 3.92 mmol). The reaction was warmed slowly to rt and stirred for 2 h then partitioned between EtOAc and satd. NaHCO₃, back-extracted with EtOAc-EtOH (5:1), dried over MgSO₄, filtered, and concentrated in vacuo. The crude was re-dissolved in DCM (1.96 mL). This mixture was cooled to 0° C. followed by addition of DIPEA (0.07 mL, 0.39 mmol) and dropwise addition of an acryloyl chloride solution (1.1 M in DCM, 0.19 mL, 0.21 mmol). The reaction was warmed to rt, stirred for 10 min, then partitioned between EtOAc and said. NaHCO₃, back-extracted with EtOAc (3×), dried over MgSO4, filtered, and concentrated in vacuo. The crude product was purified by silica gel chromatography (eluent: 0-20% MeOH/DCM) to provide (M)-4-((2S)-4-acryloyl-2-methylpiperazin-1-yl)-7-(6-amino-3-chloropyridin-2-yl)-6-fluoro-1-(2-isopropyl-4-methylpyridin-3-yl)pyrido[2,3-d]pyrimidin-2(1H)-one (0.074 g, 65.5% yield) as a yellow solid. $^1$H NMR (400 MHz DMSO-$d_6$) δ ppm 8.29-8.42 (m, 2H), 7.49 (m, 1H), 7.20 (m, 1H), 6.79-6.92 (m, 1H), 6.53 (m, 1H), 6.31 (m, 2H), 6.20 (m, 1H), 5.76-4.89 (br s, 1H), 4.30 (m, 2H), 3.93-4.19 (m, 1H), 3.44-3.76 (m, 2H), 3.17 (m, 1H), 2.68-2.73 (m, 1H), 1.85-1.93 (m, 3H), 1.34 (br d, J=6.4 Hz, 3H), 1.06 (br d, J=6.2 Hz, 3H), 0.95 ppm (m, 3H). $^{19}$F NMR (377 MHz, DMSO-$d_6$): δ −131.55 ppm (s, 1F). m/z (ESI, +ve ion): 577.0 (M+H)+.

TABLE 65

Compounds 65-2 to 65-3 were prepared following the procedure described in Method 65, Steps 1-4, above as follows:

| Ex. # | Chemical Structure | Name | Method Changes | Reagent |
|---|---|---|---|---|
| 65-2 | 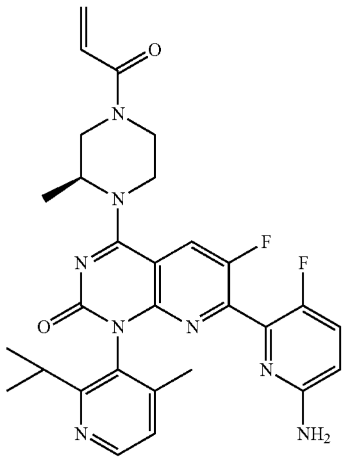 [SMILES: C=CC(=O)N1CCN(c2nc(=O)n(-c3c(C)ccnc3C(C)C)c3nc(-c4nc(N)ccc4F)c(F)cc23)[C@@H](C)C1] | (M)-7-(6-amino-3-fluoro-2-pyridinyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 3: tert-butyl (6-bromo-5-fluoropyridin-2-yl)carbamate (Strem) |
| 65-3 | 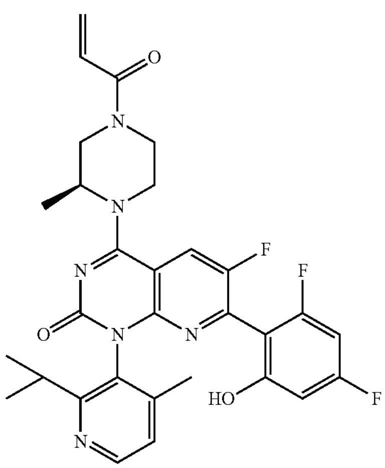 [SMILES: C=CC(=O)N1CCN(c2nc(=O)n(-c3c(C)ccnc3C(C)C)c3nc(-c4c(O)cc(F)cc4F)c(F)cc23)[C@@H](C)C1] | (M)-7-(2,4-difluoro-6-hydroxyphenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | Step 4: purified using preparative HPLC | Step 3: 2-bromo-3,5-difluorophenol (ArkPharm) |

Method 66

Example 66-1: 6-Chloro-1-(2,6-diethylphenyl)-4-((2S)-2-methyl-4-(2-propenoyl)-1-piperazinyl)-7-(1-piperidinyl)pyrido[2,3-d]pyrimidin-2(1H)-one

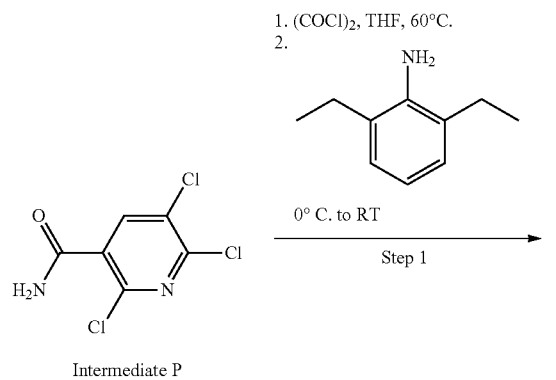

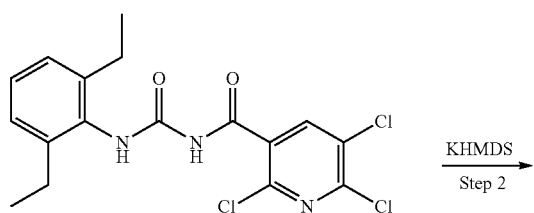

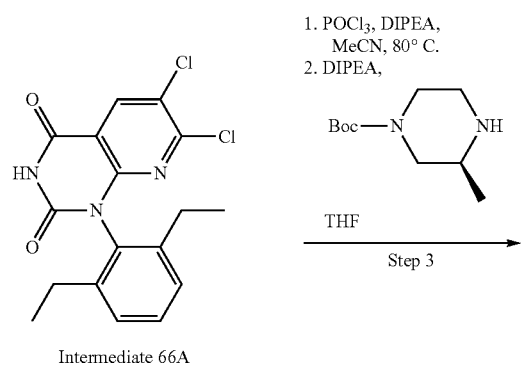

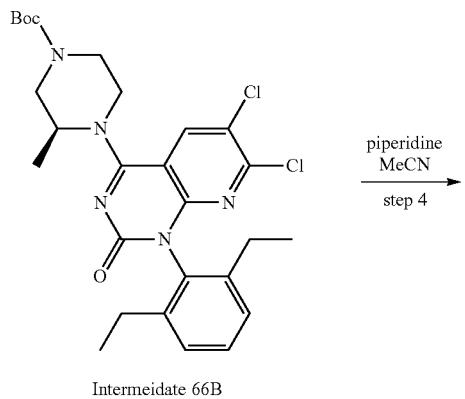

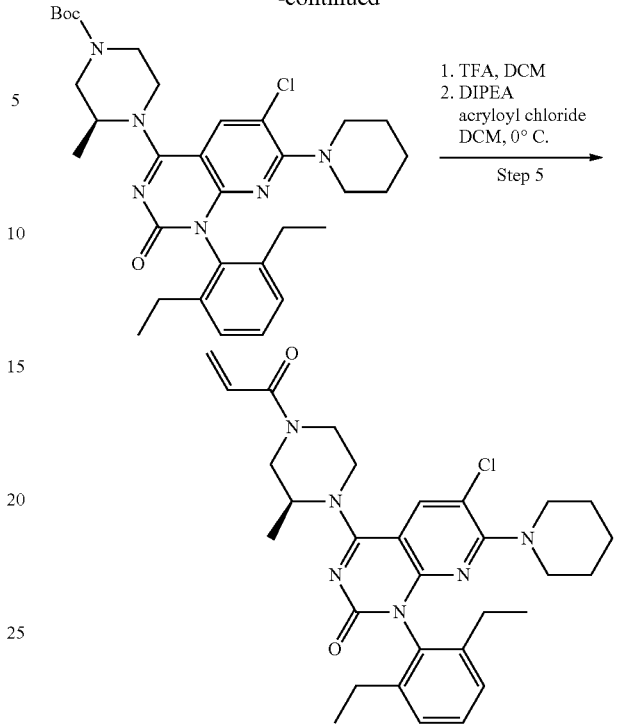

Step 1. 2,5,6-Trichloro-N-((2,6-diethylphenyl)carbamoyl)nicotinamide 2,5,6-Trichloronicotinamide (Intermediate P, 10.1 g, 44.8 mmol) was dissolved in dry THF (200 mL) under nitrogen and the solution was cooled to 0° C. Oxalyl chloride (2 M in DCM, 24 mL, 48 mmol) was added and the mixture was allowed to warm to rt and after stirring for 5 min was heated in a 60° C. bath. After 45 min, the mixture was cooled to 0° C. and triethylamine (13 mL, 92 mmol) and 2,6-diethylanaline (8 mL, 48.6 mmol, Sigma-Aldrich Corporation, St. Louis, Mo., USA) were added. The mixture was stirred for 5 min then allowed to warm to rt. Water (200 mL) and EtOAc (200 mL) were added and the phases mixed and separated. The organic was dried with brine (75 mL) and concentrated in vacuo under reduced pressure. The crude solids were triturated with 25% DCM in heptane (200 mL) and filtered through a sintered glass frit. The solids were dried on the frit and used without further purification. m/z (ESI, +ve ion): 422.0 (M+Na)$^+$.

Step 2. 6,7-Dichloro-1-(2,6-diethylphenyl)pyrido[2,3-d]pyrimidine-2,4(1H,3H)-dione (Intermediate 66A)

2,5,6-Trichloro-N-((2,6-diethylphenyl)carbamoyl)nicotinamide (9.3 g, 23.2 mmol) was dissolved in THF (100 mL) under nitrogen. KHMDS (1 M in THF, 47 mL, 47 mmol) was added using a PE addition funnel over 10 min. An exotherm was observed. Once the addition was complete, the mixture was stirred at rt for 10 min. Satd. ammonium chloride (20 mL), water (100 mL) and EtOAc (200 mL) were added. The organic was concentrated in vacuo and the crude material was triturated with 25% DCM in heptane (100 mL). The solids were collected by filtration to give the desired 6,7-dichloro-1-(2,6-diethylphenyl)pyrido[2,3-d]pyrimidine-2,4(1H,3H)-dione (Intermediate 66A). m/z (ESI, +ve ion): 364.1 (M+H)$^+$.

Step 3. (S)-tert-Butyl 4-(6,7-dichloro-1-(2,6-diethylphenyl)-2-oxo-1,2-dihydropyrido[2,3-d]pyrimidin-4-yl)-3-methylpiperazine-1-carboxylate (Intermediate 66B)

6,7-Dichloro-1-(2,6-diethylphenyl)pyrido[2,3-d]pyrimidine-2,4(1H,3H)-dione (Intermediate 66A, 4.0 g, 11 mmol) was suspended in a mixture of acetonitrile (10 mL) and DIPEA (4 mL, 22.9 mmol) under nitrogen. Phosphorus oxychloride (4 ml, 26.1 mmol) was added followed by 2 drops of DMF. The dark mixture was heated in an 80° C. bath for 20 min. The mixture was concentrated in vacuo and the crude material was co-evaporated with toluene (2×100 mL). The crude product was dissolved in THF (40 mL) and treated with DIPEA (4 mL, 22.9 mmol) and (S)-4-N-Boc-2-methyl piperazine (2.5 g, 12.5 mmol). The mixture was stirred for 10 min then treated with water (200 mL) and EtOAc (200 mL) and the phases mixed and separated. The organic was concentrated in vacuo and purified by silica gel chromatography (eluent: 0-30% EtOAc/DCM) to provide (S)-tert-butyl 4-(6,7-dichloro-1-(2,6-diethylphenyl)-2-oxo-1,2-dihydropyrido[2,3-d]pyrimidin-4-yl)-3-methylpiperazine-1-carboxylate as an off-white solid (Intermediate 66B, 3.71 g, 6.79 mmol, 61.8% yield). m/z (ESI, +ve ion): 546.2 (M+H)$^+$.

Step 4. (S)-tert-Butyl 4-(6-chloro-1-(2,6-diethylphenyl)-2-oxo-7-(piperidin-1-yl)-1,2-dihydropyrido[2,3-d]pyrimidin-4-yl)-3-methylpiperazine-1-carboxylate To a solution of (S)-tert-butyl 4-(6,7-dichloro-1-(2,6-diethylphenyl)-2-oxo-1,2-dihydropyrido[2,3-d]pyrimidin-4-yl)-3-methylpiperazine-1-carboxylate (Intermediate 66B, 72 mg, 0.132 mmol) in acetonitrile (0.66 mL) was added piperidine (20 µL, 0.198 mmol). The reaction mixture was stirred at rt for 1 h then the solvent was concentrated in vacuo to give a solid [m/z (ESI, +ve ion): 595.3 (M+H)$^+$] which was used directly in the following step.

Step 5. 6-Chloro-1-(2,6-diethylphenyl)-4-((2S)-2-methyl-4-(2-propenoyl)-1-piperazinyl)-7-(1-piperidinyl)pyrido[2,3-d]pyrimidin-2(1H)-one A solution of (S)-tert-butyl 4-(6-chloro-1-(2,6-diethylphenyl)-2-oxo-7-(piperidin-1-yl)-1,2-dihydropyrido[2,3-d]pyrimidin-4-yl)-3-methylpiperazine-1-carboxylate (78 mg, 0.131 mmol) in DCM (0.9 mL) was treated with TFA (0.3 mL, 4.0 mmol) at rt and stirred for 15 min. The reaction was concentrated in vacuo to afford (S)-6-chloro-1-(2,6-diethylphenyl)-4-(2-methylpiperazin-1-yl)-7-(piperidin-1-yl)pyrido[2,3-d]pyrimidin-2(1H)-one. m/z (ESI, +ve ion): 495.2 (M+H)$^+$.

A mixture of (S)-6-chloro-1-(2,6-diethylphenyl)-4-(2-methylpiperazin-1-yl)-7-(piperidin-1-yl)pyrido[2,3-d]pyrimidin-2(1H)-one, DIPEA (114 µL, 0.655 mmol) in DCM (2.0 mL) was added acryloyl chloride (10.69 µL, 0.131 mmol) at 0° C. and stirred for 1 h. The mixture was concentrated in vacuo. The crude product was purified by silica gel chromatography (eluent: 0-40% EtOAc-EtOH (3:1)/heptane) to provide 6-chloro-1-(2,6-diethylphenyl)-4-((2S)-2-methyl-4-(2-propenoyl)-1-piperazinyl)-7-(1-piperidinyl)pyrido[2,3-d]pyrimidin-2(1H)-one (60.6 mg, 0.11 mmol, 84% yield) as an off-white solid. $^1$H NMR (400 MHz, DMSO-d$_6$) δ ppm 7.98 (br d, J=4.6 Hz, 1H), 7.27-7.38 (m, 1H), 7.15-7.23 (m, 2H), 6.76-6.91 (m, 1H), 6.11-6.25 (m, 1H), 5.69-5.81 (m, 1H), 4.67-4.84 (m, 1H), 4.38 (br d. J=12.2 Hz, 1H), 4.13 (br d, J=13.1 Hz, 1H), 3.79-4.01 (m, 2H), 3.48-3.64 (m, 2H), 3.23-3.29 (m, 4H), 3.02 (br d, J=2.3 Hz, 1H), 2.13-2.34 (m, 4H), 1.39-1.54 (m, 2H), 1.13-1.29 (m, 6H), 0.92-1.05 (m, 6H). m/z (ESI, +ve ion): 549.2 (M+H)$^+$.

TABLE 66

Compounds 66-2 to 66-33 were prepared following the procedure described in Method 66, Steps 1-5, above as follows:

| Ex. # | Chemical Structure | Name | Method Changes | Reagent |
|---|---|---|---|---|
| 66-2 | (structure shown) | 6-chloro-1-(2,6-diethylphenyl)-7-(3,3-difluoro-1-azetidinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: 3,3-difluoroazetidine (FSSI) |

TABLE 66-continued

Compounds 66-2 to 66-33 were prepared following the procedure described in Method 66, Steps 1-5, above as follows:

| Ex. # | Chemical Structure | Name | Method Changes | Reagent |
|---|---|---|---|---|
| 66-3 | 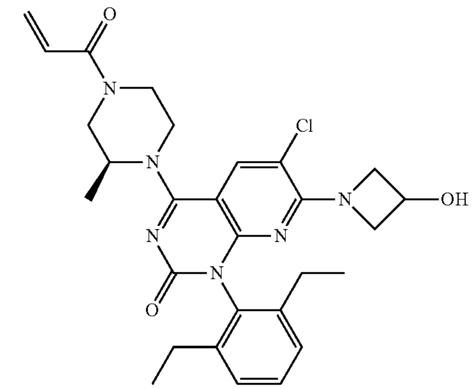 [SMILES: C=CC(=O)N1CCN(c2nc(=O)n(-c3c(CC)cccc3CC)c3nc(N4CC(O)C4)c(Cl)cc23)[C@@H](C)C1] | 6-chloro-1-(2,6-diethylphenyl)-7-(3-hydroxy-1-azetidinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: azetidine-3-ol (FSSI) |
| 66-4 | 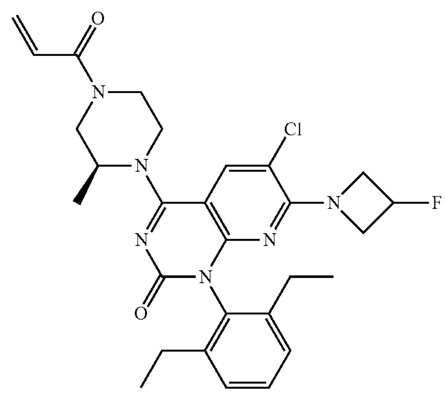 [SMILES: C=CC(=O)N1CCN(c2nc(=O)n(-c3c(CC)cccc3CC)c3nc(N4CC(F)C4)c(Cl)cc23)[C@@H](C)C1] | 6-chloro-1-(2,6-diethylphenyl)-7-(3-fluoro-1-azetidinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: 3-fluoroazetidine (FSSI) |
| 66-5 | 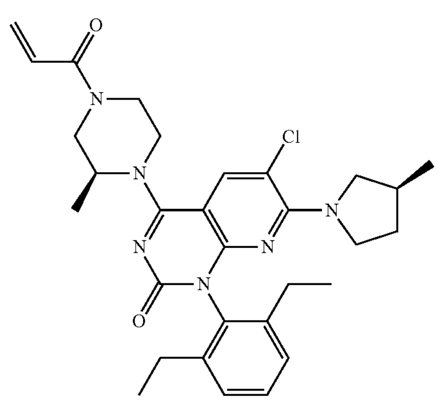 [SMILES: C=CC(=O)N1CCN(c2nc(=O)n(-c3c(CC)cccc3CC)c3nc(N4CC[C@H](C)C4)c(Cl)cc23)[C@@H](C)C1] | 6-chloro-1-(2,6-diethylphenyl)-4-((2S)-2-methyl-4-(2-propenoyl)-1-piperazinyl)-7-((3S)-3-methyl-1-pyrrolidinyl)pyrido[2,3-d]pyrimidin-2(1H)-one | acrylamide formed first then amine displacement | Step 1: 2,6-diethylaniline (Sigma-Aldrich Corporation), Step 4: (S)-3-methylpyrrolidine (FSSI) |

TABLE 66-continued

Compounds 66-2 to 66-33 were prepared following the procedure described in Method 66, Steps 1-5, above as follows:

| Ex. # | Chemical Structure | Name | Method Changes | Reagent |
|---|---|---|---|---|
| 66-6 | 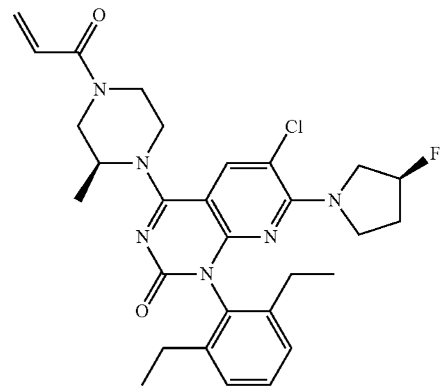 [SMILES: C=CC(=O)N1CCN(c2nc(=O)n(-c3c(CC)cccc3CC)c3nc(N4CC[C@H](F)C4)c(Cl)cc23)[C@@H](C)C1] | 6-chloro-1-(2,6-diethylphenyl)-7-((3S)-3-fluoro-1-pyrrolidinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: (S)-3-fluoropyrrolidine (FSSI) |
| 66-7 | 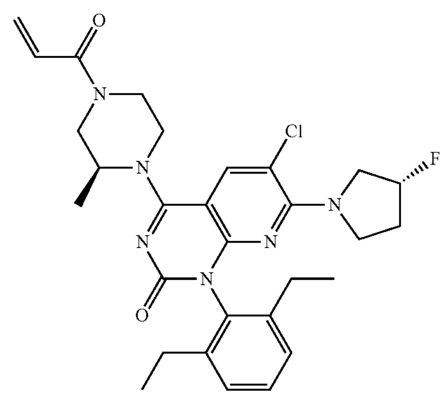 [SMILES: C=CC(=O)N1CCN(c2nc(=O)n(-c3c(CC)cccc3CC)c3nc(N4CC[C@@H](F)C4)c(Cl)cc23)[C@@H](C)C1] | 6-chloro-1-(2,6-diethylphenyl)-7-((3R)-3-fluoro-1-pyrrolidinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: (R)-3-fluoropyrrolidine (FSSI) |
| 66-8 | 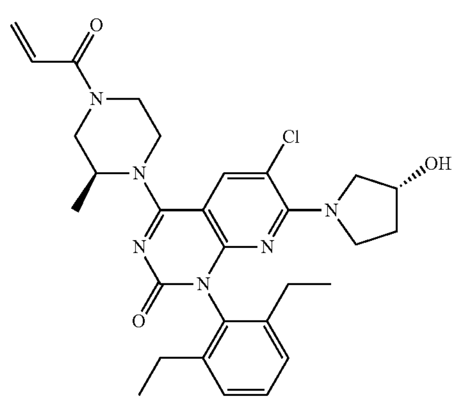 [SMILES: C=CC(=O)N1CCN(c2nc(=O)n(-c3c(CC)cccc3CC)c3nc(N4CC[C@@H](O)C4)c(Cl)cc23)[C@@H](C)C1] | 6-chloro-1-(2,6-diethylphenyl)-7-((3R)-3-hydroxy-1-pyrrolidinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: (R)-pyrrolidin-3-ol (FSSI) |

TABLE 66-continued

Compounds 66-2 to 66-33 were prepared following the procedure described in Method 66, Steps 1-5, above as follows:

| Ex. # | Chemical Structure | Name | Method Changes | Reagent |
|---|---|---|---|---|
| 66-9 | 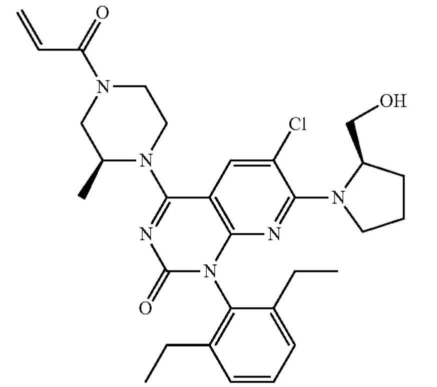 [SMILES: C=CC(=O)N1CCN(c2nc(=O)n(-c3c(CC)cccc3CC)c3nc(N4CCC[C@@H]4CO)c(Cl)cc23)[C@@H](C)C1] | 6-chloro-1-(2,6-diethylphenyl)-7-((2R)-2-(hydroxymethyl)-1-pyrrolidinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: (R)-pyrrolidin-2-ylmethanol (FSSI) |
| 66-10 | 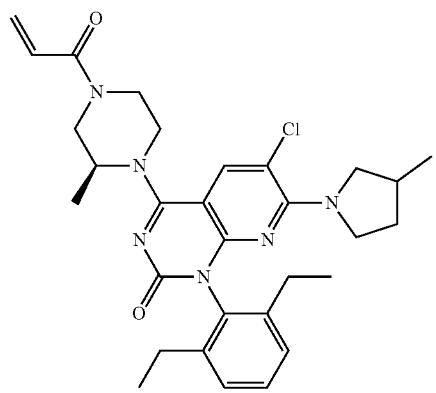 [SMILES: C=CC(=O)N1CCN(c2nc(=O)n(-c3c(CC)cccc3CC)c3nc(N4CCC(C)C4)c(Cl)cc23)[C@@H](C)C1] | 6-chloro-1-(2,6-diethylphenyl)-4-((2S)-2-methyl-4-(2-propenoyl)-1-piperazinyl)-7-(3-methyl-1-pyrrolidinyl)pyrido[2,3-d]pyrimidin-2(1H)-one | acrylamide formed first then amine displacement | Step 1: 2,6-diethylaniline (Sigma-Aldrich Corporation), Step 4: 3-methylpyrrolidine (FSSI) |
| 66-11 | 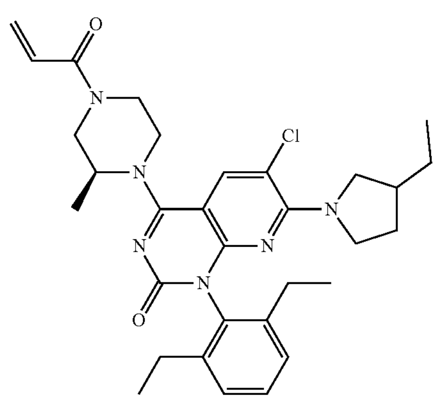 [SMILES: C=CC(=O)N1CCN(c2nc(=O)n(-c3c(CC)cccc3CC)c3nc(N4CCC(CC)C4)c(Cl)cc23)[C@@H](C)C1] | 6-chloro-1-(2,6-diethylphenyl)-7-(3-ethyl-1-pyrrolidinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: 3-ethylpyrrolidine (FSSI) |

TABLE 66-continued

Compounds 66-2 to 66-33 were prepared following the procedure described in Method 66, Steps 1-5, above as follows:

| Ex. # | Chemical Structure | Name | Method Changes | Reagent |
|---|---|---|---|---|
| 66-12 | 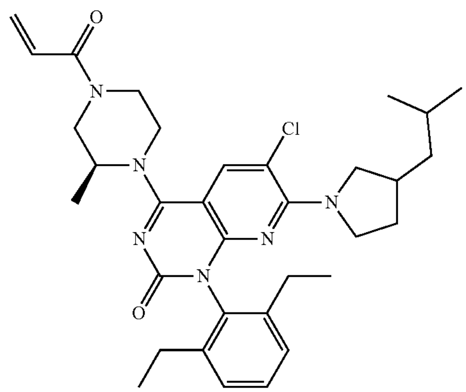 [SMILES: C=CC(=O)N1CCN(c2nc(=O)n(-c3c(CC)cccc3CC)c3nc(N4CCC(CC(C)C)C4)c(Cl)cc23)[C@@H](C)C1] | 6-chloro-1-(2,6-diethylphenyl)-4-((2S)-2-methyl-4-(2-propenoyl)-1-piperazinyl)-7-(3-(2-methylpropyl)-1-pyrrolidinyl)pyrido[2,3-d]pyrimidin-2(1H)-one | acrylamide formed first then amine displacement | Step 1: 2,6-diethylaniline (Sigma-Aldrich Corporation), Step 4: isobutylpyrrolidine (FSSI) |
| 66-13 | 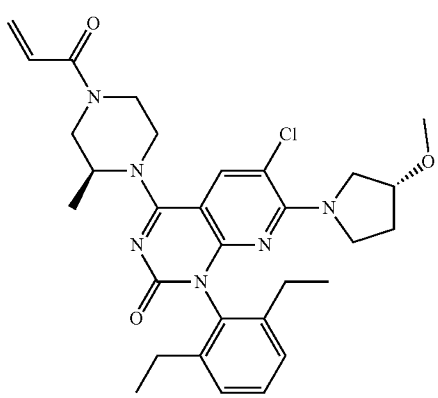 [SMILES: C=CC(=O)N1CCN(c2nc(=O)n(-c3c(CC)cccc3CC)c3nc(N4CC[C@@H](OC)C4)c(Cl)cc23)[C@@H](C)C1] | 6-chloro-1-(2,6-diethylphenyl)-7-((3R)-3-methoxy-1-pyrrolidinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: (R)-3-methoxypyrrolidine (FSSI) |
| 66-14 | 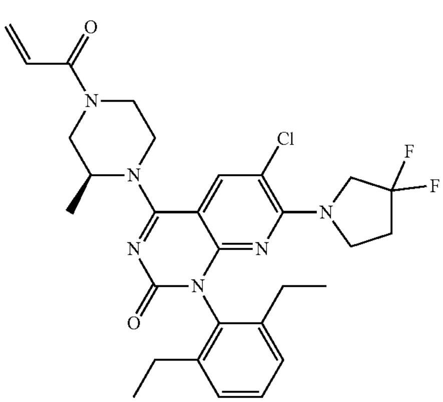 [SMILES: C=CC(=O)N1CCN(c2nc(=O)n(-c3c(CC)cccc3CC)c3nc(N4CCC(F)(F)C4)c(Cl)cc23)[C@@H](C)C1] | 6-chloro-1-(2,6-diethylphenyl)-7-(3,3-difluoro-1-pyrrolidinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: (R)-3-fluoropyrrolidine (FSSI) |

TABLE 66-continued

Compounds 66-2 to 66-33 were prepared following the procedure described in Method 66, Steps 1-5, above as follows:

| Ex. # | Chemical Structure | Name | Method Changes | Reagent |
|---|---|---|---|---|
| 66-15 | 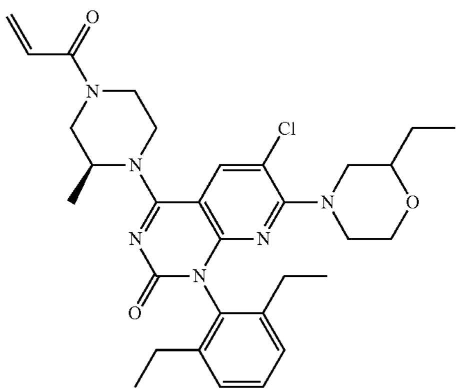 [SMILES: C=CC(=O)N1CCN(c2nc(=O)n(-c3c(CC)cccc3CC)c3nc(N4CCOC(CC)C4)c(Cl)cc23)[C@@H](C)C1] | 6-chloro-1-(2,6-diethylphenyl)-7-(2-ethyl-4-morpholinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: 2-ethylmorpholine (FSSI) |
| 66-16 | 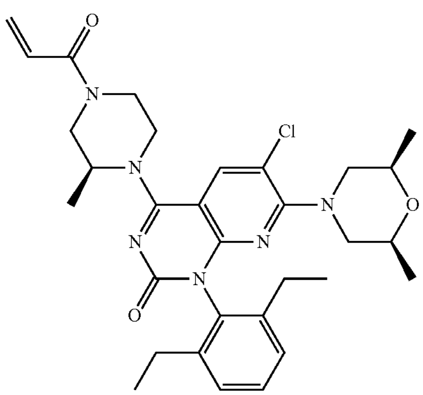 [SMILES: C=CC(=O)N1CCN(c2nc(=O)n(-c3c(CC)cccc3CC)c3nc(N4C[C@@H](C)O[C@@H](C)C4)c(Cl)cc23)[C@@H](C)C1] | 6-chloro-1-(2,6-diethylphenyl)-7-((cis)-2,6-dimethyl-4-morpholinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: (2S,6R)-2,6-dimethylmorpholine (FSSI) |
| 66-17 | 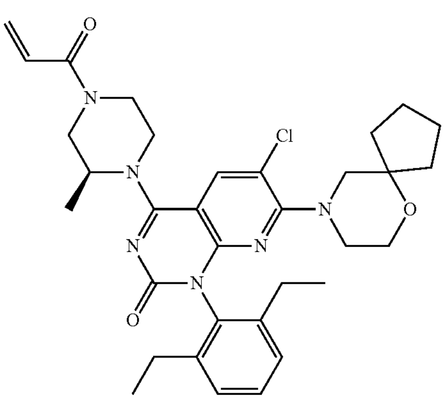 [SMILES: C=CC(=O)N1CCN(c2nc(=O)n(-c3c(CC)cccc3CC)c3nc(N4CCOC5(CCCC5)C4)c(Cl)cc23)[C@@H](C)C1] | 6-chloro-1-(2,6-diethylphenyl)-4-((2S)-2-methyl-4-(2-propenoyl)-1-piperazinyl)-7-(6-oxa-9-azaspiro[4.5]decan-9-yl)pyrido[2,3-d]pyrimidin-2(1H)-one | acrylamide formed first then amine displacement | Step 1: 2,6-diethylaniline (Sigma-Aldrich Corporation), Step 4: 6-oxa-9-azaspiro[4.5]decane (FSSI) |

TABLE 66-continued

Compounds 66-2 to 66-33 were prepared following the procedure described in Method 66, Steps 1-5, above as follows:

| Ex. # | Chemical Structure | Name | Method Changes | Reagent |
|---|---|---|---|---|
| 66-18 | 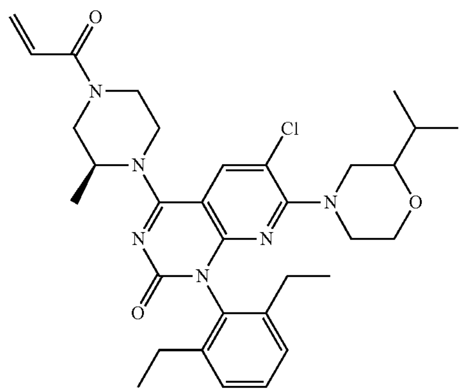 [SMILES: C=CC(=O)N1CCN(c2nc(=O)n(-c3c(CC)cccc3CC)c3nc(N4CCOC(C(C)C)C4)c(Cl)cc23)[C@@H](C)C1] | 6-chloro-1-(2,6-diethylphenyl)-4-((2S)-2-methyl-4-(2-propenoyl)-1-piperazinyl)-7-(2-(2-propanyl)-4-morpholinyl)pyrido[2,3-d]pyrimidin-2(1H)-one | acrylamide formed first then amine displacement | Step 1: 2,6-diethylaniline (Sigma-Aldrich Corporation), Step 4: 2-isopropylmorpholine (FSSI) |
| 66-19 | 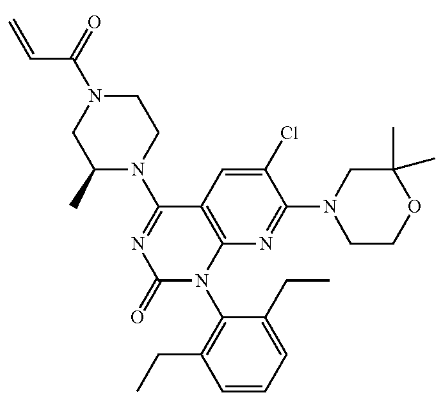 [SMILES: C=CC(=O)N1CCN(c2nc(=O)n(-c3c(CC)cccc3CC)c3nc(N4CCOC(C)(C)C4)c(Cl)cc23)[C@@H](C)C1] | 6-chloro-1-(2,6-diethylphenyl)-7-(2,2-dimethyl-4-morpholinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: 2,2-dimethylmorpholine (FSSI) |
| 66-20 | 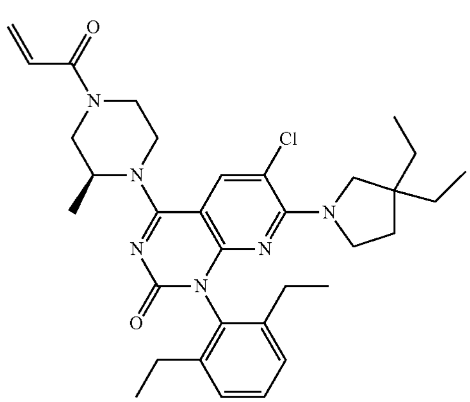 [SMILES: C=CC(=O)N1CCN(c2nc(=O)n(-c3c(CC)cccc3CC)c3nc(N4CCC(CC)(CC)C4)c(Cl)cc23)[C@@H](C)C1] | 6-chloro-1-(2,6-diethylphenyl)-7-(3,3-diethyl-1-pyrrolidinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: 3,3-diethylpyrrolidine (FSSI) |

TABLE 66-continued

Compounds 66-2 to 66-33 were prepared following the procedure described in Method 66, Steps 1-5, above as follows:

| Ex. # | Chemical Structure | Name | Method Changes | Reagent |
|---|---|---|---|---|
| 66-21 | 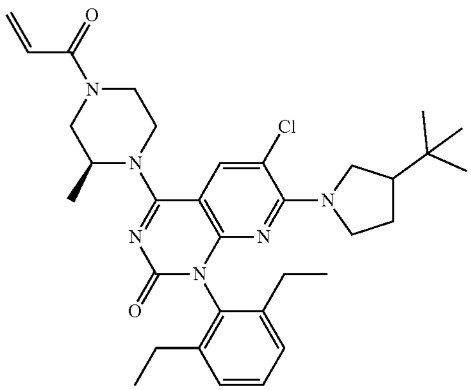 [SMILES: C=CC(=O)N1CCN(c2nc(=O)n(-c3c(CC)cccc3CC)c3nc(N4CCC(C(C)(C)C)C4)c(Cl)cc23)[C@@H](C)C1] | 6-chloro-1-(2,6-diethylphenyl)-7-((3R)-3-(2-methyl-2-propenoyl)-1-pyrrolidinyl)-4-(2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: 3-(tert-butyl)pyrrolidine (FSSI) |
| 66-22 | 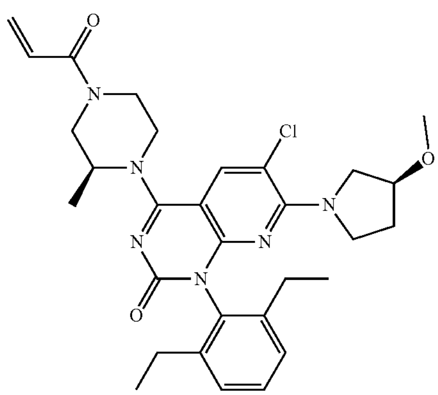 [SMILES: C=CC(=O)N1CCN(c2nc(=O)n(-c3c(CC)cccc3CC)c3nc(N4CC[C@H](OC)C4)c(Cl)cc23)[C@@H](C)C1] | 6-chloro-1-(2,6-diethylphenyl)-7-((3S)-3-methoxy-1-pyrrolidinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: (S)-3-methoxypyrrolidine (FSSI) |
| 66-23 | 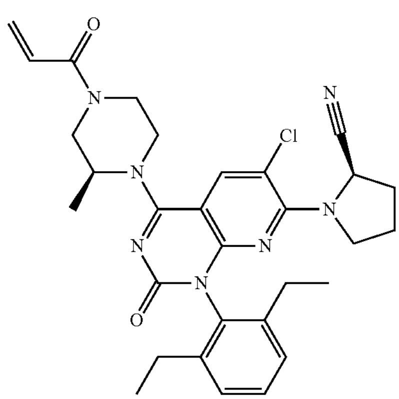 [SMILES: C=CC(=O)N1CCN(c2nc(=O)n(-c3c(CC)cccc3CC)c3nc(N4CCC[C@@H]4C#N)c(Cl)cc23)[C@@H](C)C1] | (2R)-1-(6-chloro-1-(2,6-diethylphenyl)-4-((2S)-2-methyl-4-(2-propenoyl)-1-piperazinyl)-2-oxo-1,2-dihydropyrido[2,3-d]pyrimidin-7-yl)-2-pyrrolidinecarbonitrile | acrylamide formed first then amine displacement | Step 1: 2,6-diethylaniline (Sigma-Aldrich Corporation), Step 4: (R)-pyrrolidine-2-carbonitrile (FSSI) |

TABLE 66-continued

Compounds 66-2 to 66-33 were prepared following the procedure described in Method 66, Steps 1-5, above as follows:

| Ex. # | Chemical Structure | Name | Method Changes | Reagent |
|---|---|---|---|---|
| 66-24 | 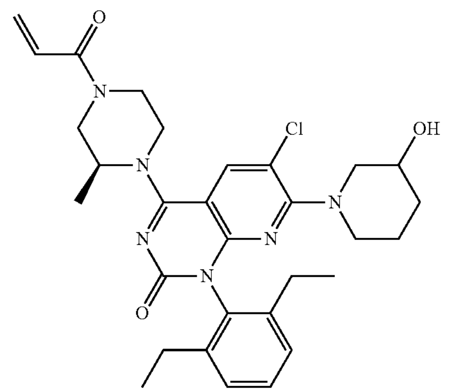 [SMILES: C=CC(=O)N1CCN(c2nc(=O)n(-c3c(CC)cccc3CC)c3nc(N4CCCC(O)C4)c(Cl)cc23)[C@@H](C)C1] | 6-chloro-1-(2,6-diethylphenyl)-7-(3-hydroxy-1-piperazinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: piperidine-3-ol (FSSI) |
| 66-25 | 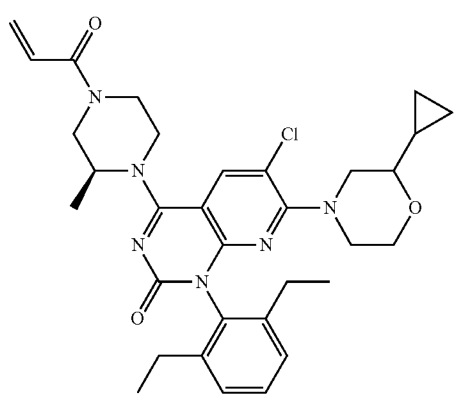 [SMILES: C=CC(=O)N1CCN(c2nc(=O)n(-c3c(CC)cccc3CC)c3nc(N4CCOC(C5CC5)C4)c(Cl)cc23)[C@@H](C)C1] | 6-chloro-7-(2-cyclopropyl-4-morpholinyl)-1-(2,6-diethylphenyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: 3-cyclopropylmorpholine (FSSI) |
| 66-26 | 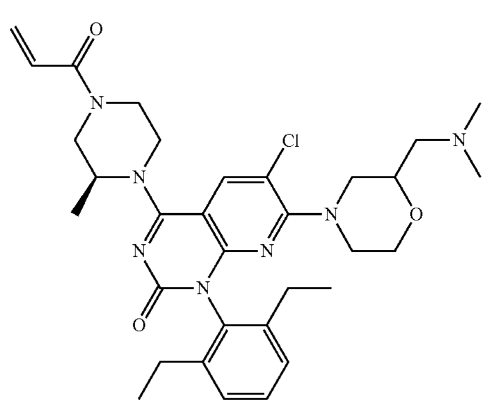 [SMILES: C=CC(=O)N1CCN(c2nc(=O)n(-c3c(CC)cccc3CC)c3nc(N4CCOC(CN(C)C)C4)c(Cl)cc23)[C@@H](C)C1] | 6-chloro-1-(2,6-diethylphenyl)-7-(2-((dimethylamino)methyl)-4-morpholinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: N,N-dimethyl-1-(morpholin-2-yl)methanamine (FSSI) |

TABLE 66-continued

Compounds 66-2 to 66-33 were prepared following the procedure described in Method 66, Steps 1-5, above as follows:

| Ex. # | Chemical Structure | Name | Method Changes | Reagent |
|---|---|---|---|---|
| 66-27 | 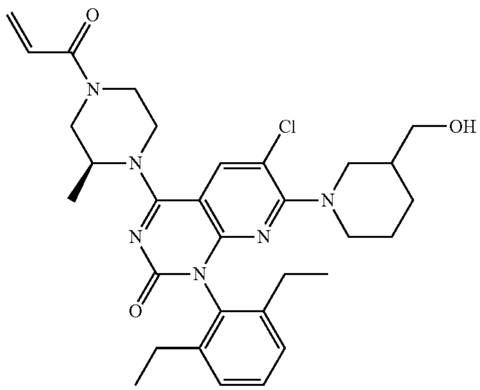 [SMILES: C=CC(=O)N1CCN(c2nc(=O)n(-c3c(CC)cccc3CC)c3nc(N4CCCC(CO)C4)c(Cl)cc23)[C@@H](C)C1] | 6-chloro-1-(2,6-diethylphenyl)-7-(3-(hydroxymethyl)-1-piperindinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: piperidin-3-ylmethanol (FSSI) |
| 66-28 | 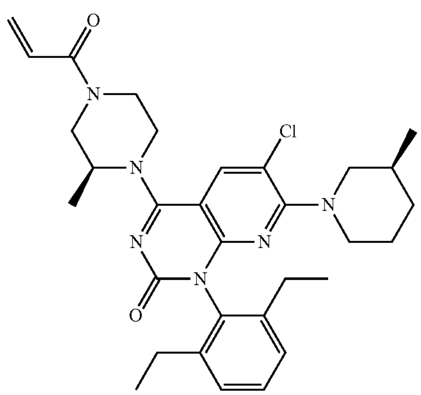 [SMILES: C=CC(=O)N1CCN(c2nc(=O)n(-c3c(CC)cccc3CC)c3nc(N4CCC[C@H](C)C4)c(Cl)cc23)[C@@H](C)C1] | 6-chloro-1-(2,6-diethylphenyl)-7-((3S)-3-methyl-1-piperindinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: (S)-3-methylpiperidine (FSSI) |
| 66-29 | 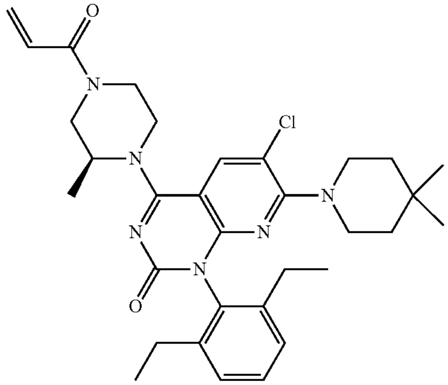 [SMILES: C=CC(=O)N1CCN(c2nc(=O)n(-c3c(CC)cccc3CC)c3nc(N4CCC(C)(C)CC4)c(Cl)cc23)[C@@H](C)C1] | 6-chloro-1-(2,6-diethylphenyl)-7-(4,4-dimethyl-1-piperindinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: 4,4-dimethylpiperidine (FSSI) |

TABLE 66-continued

Compounds 66-2 to 66-33 were prepared following the procedure described in Method 66, Steps 1-5, above as follows:

| Ex. # | Chemical Structure | Name | Method Changes | Reagent |
|---|---|---|---|---|
| 66-30 | 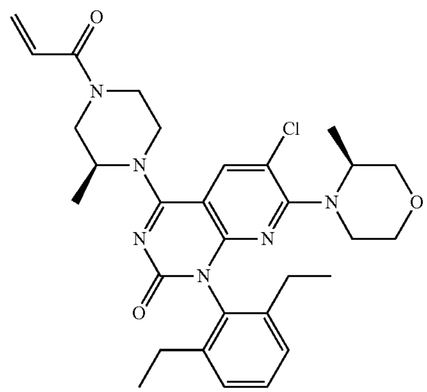 [SMILES: C=CC(=O)N1CCN(c2nc(=O)n(-c3c(CC)cccc3CC)c3nc(N4CCOC[C@@H]4C)c(Cl)cc23)[C@@H](C)C1] | 6-chloro-1-(2,6-diethylphenyl)-7-((3S)-3-methyl-4-morpholinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: (S)-3-methylmorpholine (FSSI) |
| 66-31 | 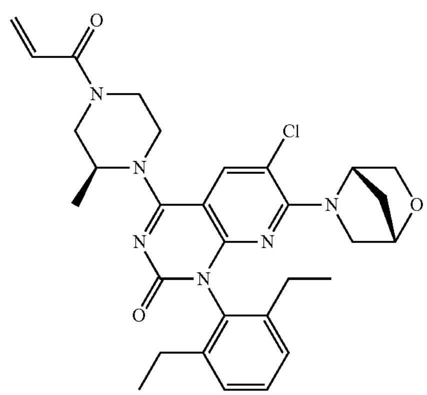 [SMILES: C=CC(=O)N1CCN(c2nc(=O)n(-c3c(CC)cccc3CC)c3nc(N4C[C@@H]5C[C@H]4CO5)c(Cl)cc23)[C@@H](C)C1] | 6-chloro-1-(2,6-diethylphenyl)-4-((2S)-2-methyl-4-(2-propenoyl)-1-piperazinyl)-7-((1S,4S)-2-oxa-5-azabicyclo[2.2.1]heptan-5-yl)pyrido[2,3-d]pyrimidin-2(1H)-one | acrylamide formed first then amine displacement | Step 1: 2,6-diethylaniline (Sigma-Aldrich Corporation), Step 4: (1S,4S)-2-oxa-5-azabicyclo[2.2.1]heptane (FSSI) |
| 66-32 | 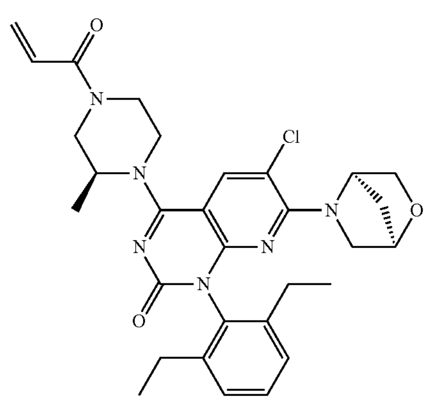 [SMILES: C=CC(=O)N1CCN(c2nc(=O)n(-c3c(CC)cccc3CC)c3nc(N4C[C@H]5C[C@@H]4CO5)c(Cl)cc23)[C@@H](C)C1] | 6-chloro-1-(2,6-diethylphenyl)-4-((2S)-2-methyl-4-(2-propenoyl)-1-piperazinyl)-7-((1R,4R)-2-oxa-5-azabicyclo[2.2.1]heptan-5-yl)pyrido[2,3-d]pyrimidin-2(1H)-one | acrylamide formed first then amine displacement | Step 1: 2,6-diethylaniline (Sigma-Aldrich Corporation), Step 4: (1R,4R)-2-oxa-5-azabicyclo[2.2.1]heptane (FSSI) |

TABLE 66-continued

Compounds 66-2 to 66-33 were prepared following the procedure described in Method 66, Steps 1-5, above as follows:

| Ex. # | Chemical Structure | Name | Method Changes | Reagent |
|---|---|---|---|---|
| 66-33 | 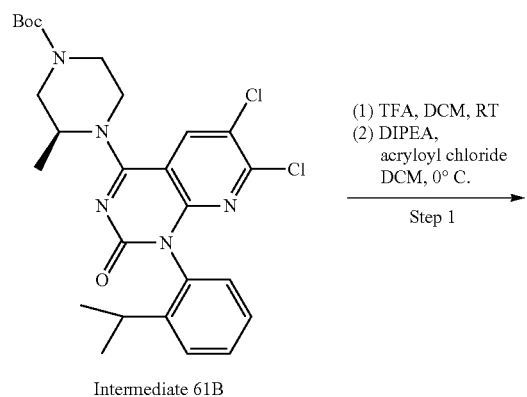 | 6-chloro-1-(2,6-diethylphenyl)-7-((3R)-3-methyl-4-morpholinyl)-4-((2S)-2-methyl-4-(2-propenoyl)-1-piperazinyl)pyrido[2,3-d]pyrimidin-2(1H)-one | acrylamide formed first then amine displacement | Step 1: 2,6-diethylaniline (Sigma-Aldrich Corporation), Step 4: (R)-3-methylmorpholine (FSSI) |

Method 67

Example 67-1: 6-Chloro-7-(3-fluoro-4-pyridinyl)-4-((2S)-2-methyl-4-(2-propenoyl)-1-piperazinyl)-1-(2-(2-propanyl)phenyl)pyrido[2,3-d]pyrimidin-2(1H)-one

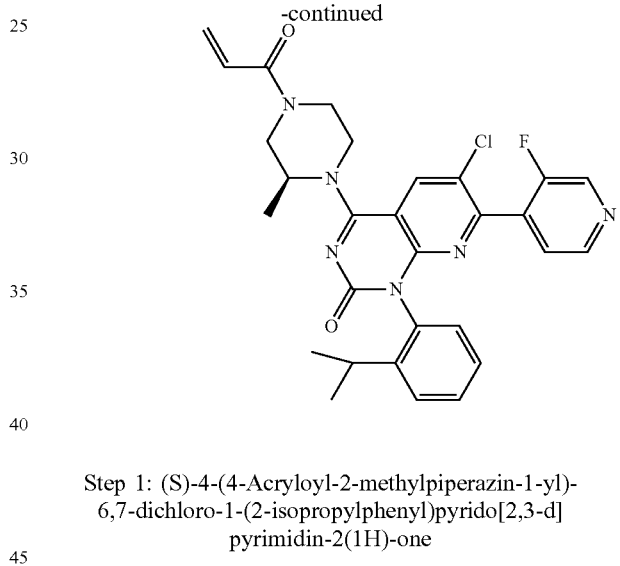

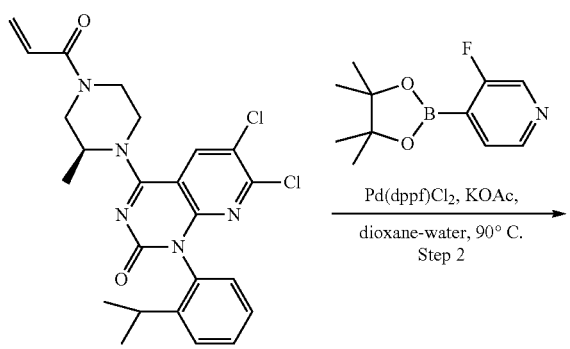

Step 1: (S)-4-(4-Acryloyl-2-methylpiperazin-1-yl)-6,7-dichloro-1-(2-isopropylphenyl)pyrido[2,3-d]pyrimidin-2(1H)-one TFA (7.5 mL, 97 mmol) was added to a solution of (S)-tert-butyl 4-(6,7-dichloro-1-(2-isopropylphenyl)-2-oxo-1,2-dihydropyrido[2,3-d]pyrimidin-4-yl)-3-methylpiperazine-1-carboxylate (Intermediate 61B, 1.2 g, 2.24 mmol) in DCM (15 mL). The mixture was stirred for 25 min at rt and then was concentrated in vacuo. The residue was suspended in DCM (13 mL), cooled to 0° C., and treated with DIPEA (2 mL, 11.2 mmol) followed by acryloyl chloride (1 M in DCM, 2.2 mL, 2.2 mmol). The reaction stirred at 0° C. for 30 min, then was quenched with saturated aqueous sodium bicarbonate (50 mL) and water (50 mL). The layers were partitioned and the aqueous phase was washed with DCM (2×50 mL). The combined organic extracts were dried over MgSO$_4$ and concentrated in vacuo to give crude (S)-4-(4-acryloyl-2-methylpiperazin-1-yl)-6,7-dichloro-1-(2-isopropylphenyl)pyrido[2,3-d]pyrimidin-2(1H)-one which was used without further purification in the following step. m/z (ESI, +ve ion): 485.9 (M+H)$^+$.

Step 2: (S)-4-(4-Acryloyl-2-methylpiperazin-1-yl)-6-chloro-7-(3-fluoropyridin-4-yl)-1-(2-isopropylphenyl)pyrido[2,3-d]pyrimidin-2(1H)-one A mixture of (S)-4-(4-acryloyl-2-methylpiperazin-1-yl)-6,7-dichloro-1-(2-isopropylphenyl)pyrido[2,3-d]pyrimidin-2(1H)-one (Intermediate 67C, 380 mg, 0.78 mmol), 3-fluoro-4-(4,4,5,5-tetramethyl-1,3,2-dioxaborolan-2-yl)pyridine (360 mg, 1.6 mmol), dichloro[1,1'-bis(diphenylphosphino)ferrocene]palladium (II) DCM adduct (57 mg, 0.078 mmol), and potassium acetate (380 mg, 3.9 mmol) in 1,4-dioxane (3.3 mL) and water (0.5 mL) was deoxygenated with argon for 10 min. The mixture was stirred at 90° C. for 1 h, then partitioned between water (50 mL) and EtOAc (50 mL). The organic phase was sequentially washed with water (50 mL) and brine (50 mL), dried over $MgSO_4$, and concentrated in vacuo. The crude product was purified by silica gel chromatography (eluent: 0-75% EtOAc-EtOH (3:1)/heptanes) to provide (S)-4-(4-acryloyl-2-methylpiperazin-1-yl)-6-chloro-7-(3-fluoropyridin-4-yl)-1-(2-isopropylphenyl)pyrido[2,3-d]pyrimidin-2(1H)-one.

$^1$H NMR (400 MHz, DCM-$d_2$) δ ppm 1.03 (d, J=6.8 Hz, 4H), 1.17 (d, J=6.8 Hz, 3H), 1.48 (br d, J=5.2 Hz, 3H), 2.63 (br s, 1H); 2.97-3.13 (m, 1H), 3.18-3.35 (m, 1H), 3.49-3.82 (m, 3H), 3.84-3.96 (m, 1H), 4.00-4.11 (m, 0.5H), 4.15-4.30 (m, 1H), 4.32-4.38 (m, 0.5H), 4.40-4.52 (m, 0.5H), 4.63-4.73 (m, 0.5H), 4.84 (br d, J=2.3 Hz, 0.5H), 4.96-5.07 (m, 0.5H), 5.77 (dd, J=10.5, 2.0 Hz, 1H), 6.32 (dd, J=16.7, 1.8 Hz, 1H), 6.58-6.70 (m, 1H), 7.08 (br d, J=7.7 Hz, 1H), 7.17 (t, J=5.39 Hz, 1H), 7.29 (td, J=7.3, 2.0 Hz, 1H), 7.38-7.47 (m, 2H), 8.12 (s, 1H), 8.44 (d, J=4.6 Hz, 1H), 8.51 (s, 1H). $^{19}$F NMR (376 MHz, DCM-$d_2$) δ ppm −127.69 (s, 1F); m/z (ESI, +ve ion): 547.0 (M+H)$^+$.

TABLE 67

Compounds 67-2 to 67-9 were prepared following the procedure described in Method 67, Steps 1-6, above as follows:

| Ex. # | Chemical Structure | Name | Method Changes | Reagent |
|---|---|---|---|---|
| 67-2 | | 6-chloro-4-((2S)-2-methyl-4-(2-propenoyl)-1-piperazinyl)-7-(1-methyl-3-(trifluoromethyl)-1H-pyrazol-5-yl)-1-(2-(2-propanyl)phenyl)pyrido[2,3-d]pyrimidin-2(1H)-one | Step 2: (1-methyl-3-(trifluoromethyl)-1H-pyrazol-5-yl)boronic acid (Oxchem Corporation) |
| 67-3 | | 6-chloro-7-(1,4-dimethyl-1H-pyrazol-5-yl)-4-((2S)-2-methyl-4-(2-propenoyl)-1-piperazinyl)-1-(2-(2-propanyl)phenyl)pyrido[2,3-d]pyrimidin-2(1H)-one | Step 2: 1,4-dimethyl-5-(4,4,5,5-tetramethyl-1,3,2-dioxaborolan-2-yl)-1H-pyrazole (Combi-Blocks Inc.) |

TABLE 67-continued

Compounds 67-2 to 67-9 were prepared following the procedure described in Method 67, Steps 1-6, above as follows:

| Ex. # | Chemical Structure | Name | Method Changes | Reagent |
|---|---|---|---|---|
| 67-4-1 | 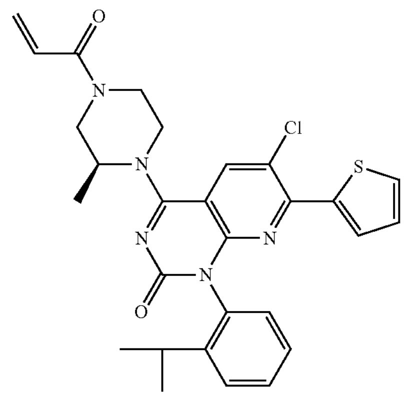 [SMILES: C=CC(=O)N1CCN(c2nc(=O)n(-c3ccccc3C(C)C)c3nc(-c4cccs4)c(Cl)cc23)[C@@H](C)C1] | 6-chloro-4-((2S)-2-methyl-4-(2-propenoyl)-1-piperazinyl)-1-(2-(2-propanyl)phenyl)-7-(2-thiophenyl)pyrido[2,3-d]pyrimidin-2(1H)-one | Step 2: PdCl$_2$(PPh$_3$)$_2$ and Na$_2$CO$_3$ | Step 2: thiophen-2-ylboronic acid (Enamine) |
| 67-4-2 | 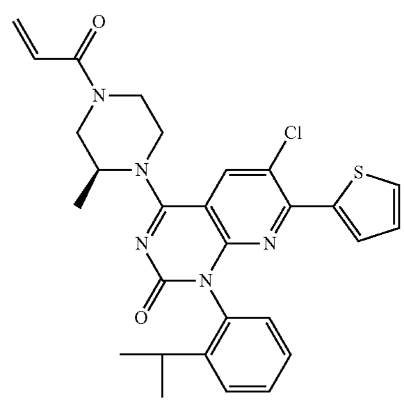 [SMILES: C=CC(=O)N1CCN(c2nc(=O)n(-c3ccccc3C(C)C)c3nc(-c4cccs4)c(Cl)cc23)[C@@H](C)C1] | 6-chloro-4-((2S)-2-methyl-4-(2-propenoyl)-1-piperazinyl)-1-(2-(2-propanyl)phenyl)-7-(2-thiophenyl)pyrido[2,3-d]pyrimidin-2(1H)-one | Step 2: PdCl$_2$(PPh$_3$)$_2$ and Na$_2$CO$_3$ | Step 2: thiophen-2-ylboronic acid (Enamine) |

Method 68

Example 68-1: 7-(2-Chloro-6-hydroxyphenyl)-6-fluoro-1-(2-methyl-6-(2-propanyl)phenyl)-4-((2S)-2-methyl-4-(2-propenoyl)-1-piperazinyl)pyrido[2,3-d]pyrimidin-2(1H)-one

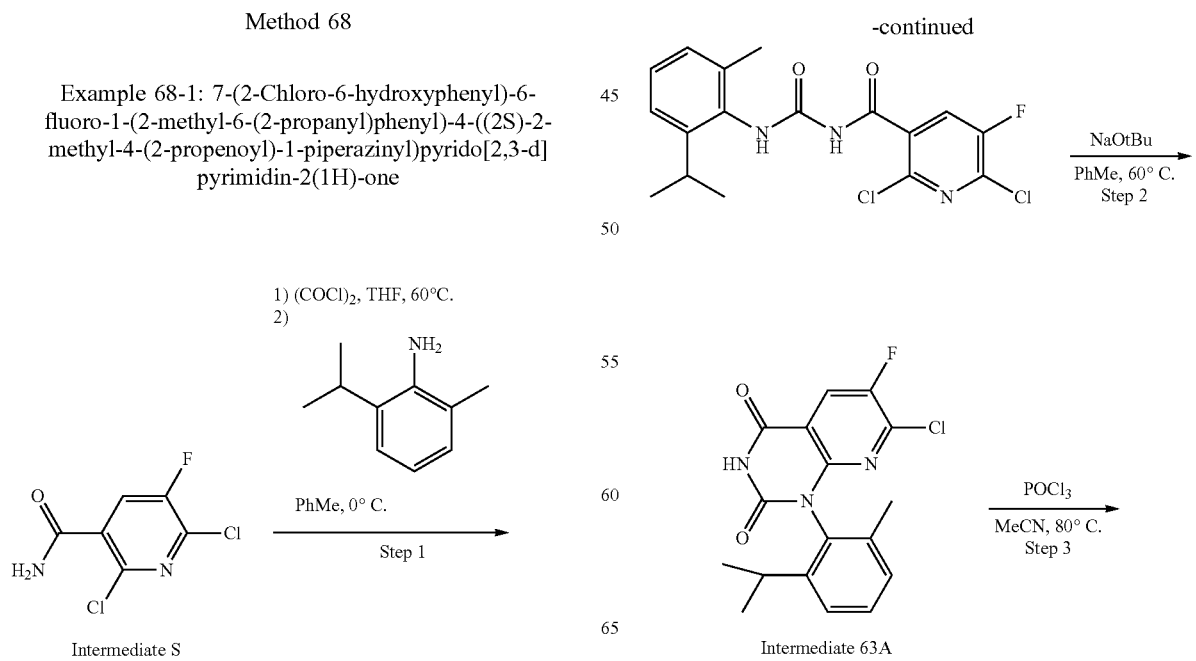

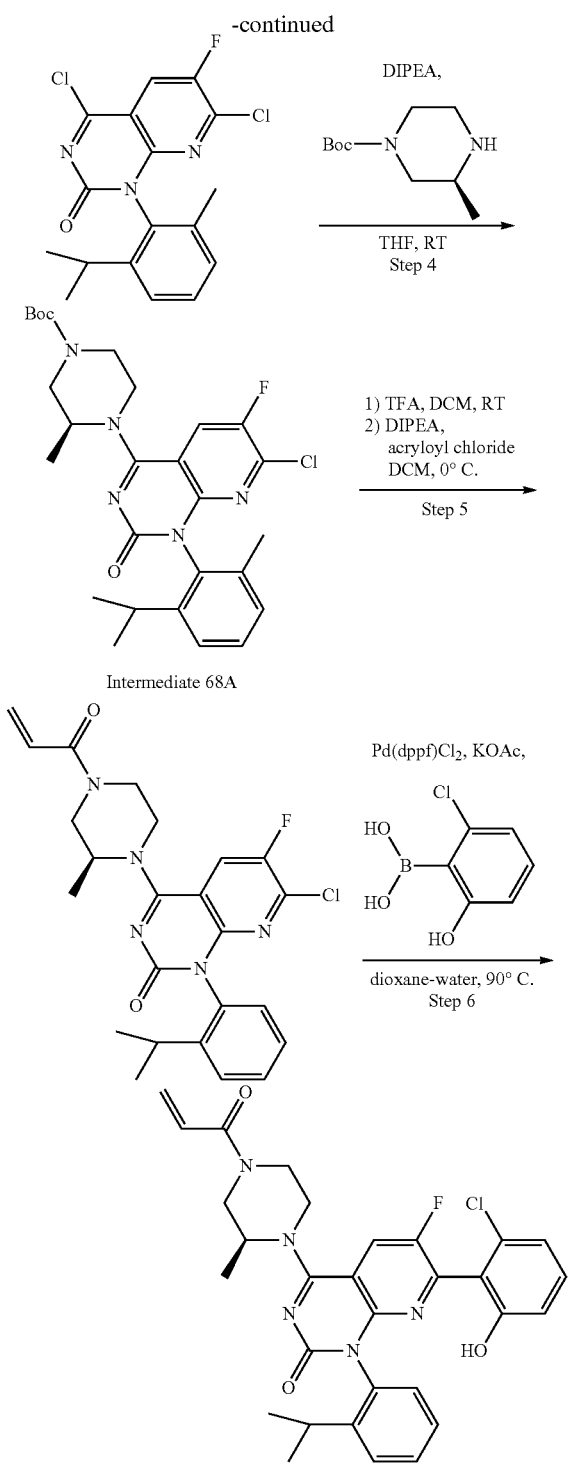

Step 1: 2,6-Dichloro-N-((2-isopropyl-6-methylphenyl)carbamoyl)-5-fluoronicotinamide Oxalyl chloride (2 M in DCM, 9.0 mL, 18 mmol) was added to a mixture of 2,6-dichloro-5-fluoronicotinamide (Intermediate S, 3.75 g, 17.9 mmol) in THF (15 mL) at rt. The mixture heated at 60° C. for 45 min, then cooled to rt and concentrated in vacuo. The crude residue was dissolved in toluene (30 mL) and then cooled to 0° C. in an ice-water bath. A solution of 2-isopropyl-6-methylaniline (2.7 mL, 17 mmol, Enamine, Monmouth Jct., N.J., USA) in toluene (5 mL) was added slowly. The mixture stirred for 5 min, then the reaction was quenched by adding water (200 mL). EtOAc (200 mL) was added and the organic layer was washed with brine (50 mL) and concentrated in vacuo. The residue was triturated with MTBE (75 mL) and the solid was collected by filtration to provide 2,6-dichloro-N-((2-isopropyl-6-methylphenyl)carbamoyl)-5-fluoronicotinamide. m/z (ESI, +ve ion): 406.0 (M+Na)$^+$.

Step 2: 7-Chloro-6-fluoro-1-(2-isopropyl-6-methylphenyl)pyrido[2,3-d]pyrimidine-2,4(1H,3H)-dione (Intermediate 63A)

Sodium tert-butoxide (3.0 g, 31 mmol) was added to a suspension of 2,6-dichloro-5-fluoro-N-((2-isopropyl-6-methylphenyl)carbamoyl)nicotinamide (5.9 g, 15.4 mmol) in toluene (60 mL). The mixture was heated at 60° C. for 10 min and then cooled to rt. The reaction was quenched with satd. ammonium chloride (50 mL) and water (100 mL). The reaction mixture was extracted with EtOAc (200 mL), the organic layer was dried with brine (50 mL), then concentrated in vacuo. The crude product was triturated with MeOH (10 mL) and filtered to afford 7-chloro-6-fluoro-1-(2-isopropyl-6-methylphenyl)pyrido[2,3-d]pyrimidine-2,4 (1H,3H)-dione (Intermediate 63A). m/z (ESI, +ve ion): 348.0 (M+H)$^+$.

Step 3: 4,7-Dichloro-6-fluoro-1-(2-isopropyl-6-methylphenyl)pyrido[2,3-d]pyrimidin-2(1H)-one Phosphorus oxychloride (1.5 mL, 16 mmol) was added to a suspension of 7-chloro-6-fluoro-1-(2-isopropyl-6-methylphenyl)pyrido[2,3-d]pyrimidine-2,4(1H,3H)-dione (Intermediate 63A, 5.3 g, 15.2 mmol) in acetonitrile (75 mL) at rt. The reaction mixture was heated to 80° C. for 80 min, cooled to rt, concentrated in vacuo, and azeotroped with toluene (2×75 mL) to give 4,7-dichloro-6-fluoro-1-(2-isopropyl-6-methylphenyl)pyrido[2,3-d]pyrimidin-2(1H)-one. This material was used without further purification in the following step. m/z (ESI, +ve ion): 366.0 (M+H)$^+$.

Step 4: (S)-tert-Butyl 4-(7-chloro-1-fluoro-1-(2-isopropyl-6-methylphenyl)-2-oxo-1,2-dihydropyrido[2,3-d]pyrimidin-4-yl)-3-methylpiperazine-1-carboxylate (Intermediate 68A)

DIPEA (5.5 mL, 31.5 mmol) was added to a stirring solution of 4,7-dichloro-6-fluoro-1-(2-isopropyl-6-methylphenyl)pyrido[2,3-d]pyrimidin-2(1H)-one (5.55 g, 15.2 mmol) in THF (75 mL), followed by (3S)-1-(tert-butoxycarbonyl)-3-methylpiperazine (3.1 g, 15 mmol, Ark Pharma, Arlington Heights, Ill., USA). The mixture was stirred at rt for 10 min, then satd. ammonium chloride (30 mL), water (100 mL), and EtOAc (200 mL) were added. The organic layer was washed with water (100 mL) and brine (75 mL), and concentrated in vacuo. The crude product was purified by silica gel chromatography (eluent: 0-20% EtOAc-EtOH (3:1)/heptane) to provide (S)-tert-butyl 4-(7-chloro-6-fluoro-1-(2-isopropyl-6-methylphenyl)-2-oxo-1,2-dihydropyrido[2,3-d]pyrimidin-4-yl)-3-methylpiperazine-1-carboxylate (Intermediate 68A). m/z (ESI, +ve ion): 530.2 (M+H)$^+$.

Step 5: (S)-4-(4-Acryloyl-2-methylpiperazin-1-yl)-7-chloro-6-fluoro-1-(2-isopropyl-6-methylphenyl)pyrido[2,3-d]pyrimidin-2(1H)-one TFA (3.8 mL) was added to a solution of (S)-tert-butyl 4-(7-chloro-6-fluoro-1-(2-isopropyl-6-methylphenyl)-2- oxo-1,2-dihydropyrido[2,3-d]pyrimidin-4-yl)-3-methylpiperazine-1-carboxylate (Intermediate 68A, 600 mg, 1.13 mmol) in DCM (7.6 mL). The mixture was stirred for 2 h at rt and then concentrated in vacuo. The resulting residue was re-dissolved in DCM (6 mL) and cooled to 0° C. DIPEA (1.0 mL, 5.6 mmol) and acryloyl chloride. (0.71 M in DCM, 1.6 mL, 1.13 mmol) were sequentially added and the mixture was stirred for 2 h, slowly warming to rt. The reaction mixture was quenched at 0° C. by adding satd. NaHCO$_3$ (30 mL) and water (30 mL), and diluted with DCM (30 mL). The aqueous layer was extracted with DCM (2×30 mL) and the combined organic extracts were dried over MgSO$_4$ and concentrated in vacuo to give crude (S)-4-(4-acryloyl-2-methylpiperazin-1-yl)-7-chloro-6-fluoro-1-(2-isopropyl-6-methylphenyl)pyrido[2,3-d]pyrimidin-2(1H)-one which was used without further purification in the following step. m/z (ESI, +ve ion): 484.0 (M+H)$^+$.

Step 6: 4-((S)-4-Acryloyl-2-methylpiperazin-1-yl)-7-(2-chloro-6-hydroxyphenyl)-6-fluoro-1-(2-isopropyl-6-methylphenyl)pyrido[2,3-d]pyrimidin-2(1H)-one A mixture of (S)-4-(4-acryloyl-2-methylpiperazin-1-yl)-7-chloro-6-fluoro-1-(2-isopropyl-6-methylphenyl)pyrido[2,3-d]pyrimidin-2(1H)-one (300 mg, 0.62 mmol), (2-chloro-6-hydroxyphenyl)boronic acid (160 mg, 0.93 mmol, Aurum Pharmatech LLC, Franklin Park, N.J., USA), Pd(dppf)Cl$_2$ (51 mg, 0.062 mmol), and potassium acetate (300 mg, 3.1 mmol) in 1,4-dioxane (3 mL) and water (0.1 mL) was deoxygenated with argon for 10 min. The resulting mixture was stirred at 90° C. for 2 h, then partitioned between water (50 mL) and EtOAc (50 mL). The aqueous phase washed with EtOAc (2×30 mL). The combined organic extracts were washed with brine (150 mL), dried over MgSO$_4$, and concentrated in vacuo. The crude product was purified by silica gel chromatography (eluent: 0-50% EtOAc-EtOH (3:1)/heptanes) to provide 7-(2-chloro-6-hydroxyphenyl)-6-fluoro-1-(2-methyl-6-(2-propanyl)phenyl)-4-((2S)-2-methyl-4-(2-propenoyl)-1-piperazinyl)pyrido[2,3-d]pyrimidin-2(1H)-one. $^1$H NMR (400 MHz, DMSO-d$_6$) δ ppm 0.86 (br t, J=6.8 Hz, 1H), 0.92 (br dd, J=16.5, 5.7 Hz, 2H), 1.06 (d, J=6.8 Hz, 2H), 1.25 (br s, 1H), 1.30 (br d, J=6.4 Hz, 1H), 1.34 (br d, J=6.6 Hz, 1H), 1.85 (br s, 2H), 2.56 (br d, J=6.6 Hz, 1H), 3.03-3.21 (m, 0.5H), 3.41-3.58 (m, 0.5H), 3.60-3.78 (m, 1.5H), 3.96-4.06 (m, 0.5H), 4.14 (br d, J=12.6 Hz, 0.5H), 4.19-4.33 (m, 1.5H), 4.41 (br d, J=11.0 Hz, 0.5H), 4.86 (br s, 0.5H) 4.93 (br s, 0.5H), 5.76 (dd, J=8, 4.0 Hz, 1H), 6.18 (br s, 0.5H), 6.22 (br s, 0.5H), 6.81-6.88 (m, 1.5H), 6.92 (d, J=8.1 Hz, 1H), 7.05-7.15 (m, 1H), 7.17-7.30 (m, 3H), 8.15-8.41 (m, 1H), 10.13 (br d, J=8.5 Hz, 1H). $^{19}$F NMR (376 MHz, DMSO-d$_6$) δ ppm −129.96−−130.05 (m, 2F); m/z (ESI, +ve ion): 575.9 (M+H)$^+$.

TABLE 68

Compounds 68-2 was prepared following the procedure described in Method 68, Steps 1-6, above as follows:

| Ex. # | Chemical Structure | Name | Method Changes | Reagent |
|---|---|---|---|---|
| 68-2 | ![structure] | 6-fluoro-7-(5-methyl-1H-indazol-4-yl)-1-(2-methyl-6-(2-propanyl)phenyl)-4-((2S)-2-methyl-4-(2-propenoyl)-1-piperazinyl)pyrido[2,3-d]pyrimidin-2(1H)-one | Step 1: 2-isopropyl-6-methylaniline (Enamine), Step 6: 2-(1-methylethyl)-6-methylaniline (Enamine) |

Method 69

Example 69-1: 6-Chloro-4-((2S)-2-methyl-4-(2-propenoyl)-1-piperazinyl)-7-(1-piperidinyl)-1-(2-(2-propanyl)phenyl)pyrido[2,3-d]pyrimidin-2(1H)-one

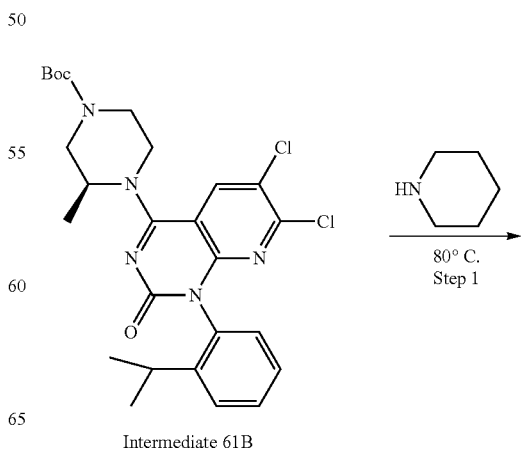

Intermediate 61B

-continued

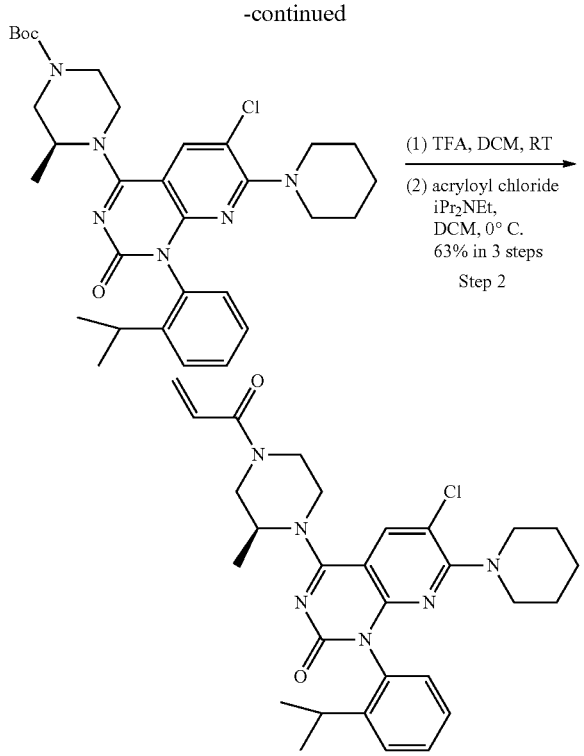

(1) TFA, DCM, RT
(2) acryloyl chloride
iPr₂NEt,
DCM, 0° C.
63% in 3 steps
Step 2

Step 1: tert-Butyl (S)-tert-butyl 4-(6-chloro-1-(2-isopropylphenyl)-2-oxo-7-(piperidin-1-yl)-1,2-dihydropyrido[2,3-d]pyrimidin-4-yl)-3-methylpiperazine-1-carboxylate A 25-mL round-bottomed flask was charged with (S)-tert-butyl 4-(6,7-dichloro-1-(2-isopropylphenyl)-2-oxo-1,2-dihydropyrido[2,3-d]pyrimidin-4-yl)-3-methylpiperazine-1-carboxylate (Intermediate 61B, 45 mg, 0.085 mmol) and piperidine (0.1 mL, 1.01 mmol, Spectrum Chemicals & Laboratory Products, Gardena, Calif., USA). The reaction mixture was stirred and heated at 80° C. for 16 h. The reaction mixture was concentrated in vacuo to give crude (S)-tert-butyl 4-(6-chloro-1-(2-isopropylphenyl)-2-oxo-7-(piperidin-1-yl)-1,2-dihydropyrido[2,3-d]pyrimidin-4-yl)-3-methylpiperazine-1-carboxylate (49 mg) as a yellow solid. m/z (ESI, +ve ion): 581.3 (M+H)⁺. The crude yellow solid was used in next step without purification.

Step 2: 6-Chloro-4-((2S)-2-methyl-4-(2-propenoyl)-1-piperazinyl)-7-(1-piperidinyl)-1-(2-(2-propanyl)phenyl)pyrido[2,3-d]pyrimidin-2(1H)-one To a solution of (S)-tert-butyl 4-(6-chloro-1-(2-isopropylphenyl)-2-oxo-7-(piperidin-1-yl)-1,2-dihydropyrido[2,3-d]pyrimidin-4-yl)-3-methylpiperazine-1-carboxylate (49 mg, 0.084 mmol) in DCM (1 mL) was treated with TFA (1 mL) at rt and stirred for 15 min. The reaction was concentrated in vacuo to afford (S)-6-chloro-1-(2-isopropylphenyl)-4-(2-methylpiperazin-1-yl)-7-(piperidin-1-yl)pyrido[2,3-d]pyrimidin-2(1H)-one. m/z (ESI, +ve ion): 481.3 (M+H)⁺.

A mixture of (S)-6-chloro-1-(2-isopropylphenyl)-4-(2-methylpiperazin-1-yl)-7-(piperidin-1-yl)pyrido[2,3-d]pyrimidin-2(1H)-one and DIPEA (0.07 mL, 0.42 mmol) in DCM (1.0 mL) was added acryloyl chloride (0.26 M in DCM, 0.33 mL, 0.084 mmol) at 0° C. and stirred for 40 min at 0° C. The resulting mixture was concentrated in vacuo. The crude product was purified by silica gel chromatography (eluent: 0-50% of EtOAc/EtOH(3:1)/heptane) to provide pure (S)-4-(4-acryloyl-2-methylpiperazin-1-yl)-6-chloro-1-(2-isopropylphenyl)-7-(piperidin-1-yl)pyrido[2,3-d]pyrimidin-2(1H)-one (28 mg, 0.053 mmol, 62.5% yield) as a light-yellow solid. ¹H NMR (400 MHz, DMSO-d₆) δ ppm 7.85-8.03 (m, 1H), 7.42-7.50 (m, 1H), 7.34-7.42 (m, 1H), 7.26 (t, J=7.5 Hz, 1H), 7.05 (d, J=7.7 Hz, 1H), 6.74-6.92 (m, 1H), 6.19 (br dd, J=17.5, 4.5 Hz, 1H), 5.71-5.78 (m, 1H), 4.68-4.84 (m, 1H), 4.21-4.45 (m, 1H), 3.93-4.19 (m, 2H), 3.35-3.66 (min, 2H), 3.25 (brs, 4H), 2.89-3.19 (m, 1H), 2.45-2.48 (m, 1H), 1.34 (br d, J=3.9 Hz, 3H), 1.20-1.29 (m, 6H), 1.08 (d, J=6.8 Hz, 3H), 0.98 (br d, J=6.8 Hz, 3H). m/z (ESI, +ve ion): 536.3 (M+H)⁺.

TABLE 69

Compounds 69-2 to 69-7 were prepared following the procedure described in Method 69, Steps 1-2, above as follows:

| Ex. # | Chemical Structure | Name | Method Changes | Reagent |
|---|---|---|---|---|
| 69-2 | 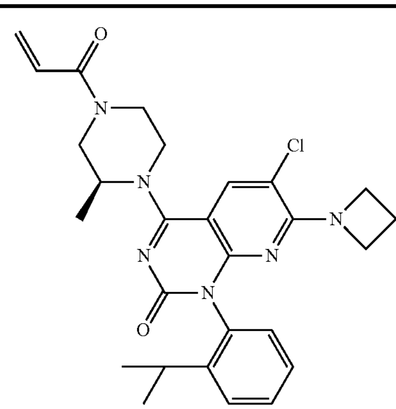 | 7-(1-azetidinyl)-6-chloro-4-((2S)-2-methyl-4-(2-propenoyl)-1-piperazinyl)-1-(2-(2-propanyl)phenyl)pyrido[2,3-d]pyrimidin-2(1H)-one | | Step 1: azetidine (Combi-Blocks Inc.) |

TABLE 69-continued

Compounds 69-2 to 69-7 were prepared following the procedure described in Method 69, Steps 1-2, above as follows:

| Ex. # | Chemical Structure | Name | Method Changes | Reagent |
|---|---|---|---|---|
| 69-3 | 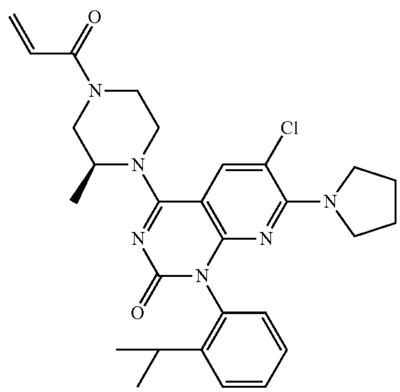 [SMILES: C=CC(=O)N1CCN(c2nc(=O)n(-c3ccccc3C(C)C)c3nc(N4CCCC4)c(Cl)cc23)[C@@H](C)C1] | 6-chloro-4-((2S)-2-methyl-4-(2-propenoyl)-1-piperazinyl)-1-(2-(2-propanyl)phenyl)-7-(1-pyrrolidinyl)pyrido[2,3-d]pyrimidin-2(1H)-one | | Step 1: pyrrolidine (Sigma-Aldrich Corporation) |
| 69-4 | 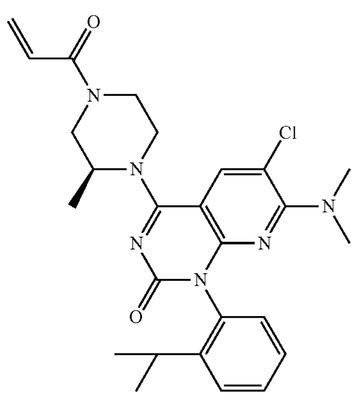 [SMILES: C=CC(=O)N1CCN(c2nc(=O)n(-c3ccccc3C(C)C)c3nc(N(C)C)c(Cl)cc23)[C@@H](C)C1] | 6-chloro-7-(dimethylamino)-4-((2S)-2-methyl-4-(2-propenoyl)-1-piperazinyl)-1-(2-(2-propanyl)phenyl)pyrido[2,3-d]pyrimidin-2(1H)-one | | Step 1: dimethylamine (Sigma-Aldrich Corporation) |
| 69-5 | 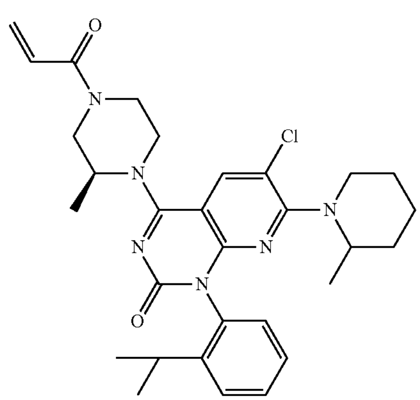 [SMILES: C=CC(=O)N1CCN(c2nc(=O)n(-c3ccccc3C(C)C)c3nc(N4CCCCC4C)c(Cl)cc23)[C@@H](C)C1] | 6-chloro-7-(2-methyl-1-piperazinyl)-4-((2S)-2-methyl-4-(2-propenoyl)-1-piperazinyl)-1-(2-(2-propanyl)phenyl)pyrido[2,3-d]pyrimidin-2(1H)-one | | Step 1: 2-methylpiperidine (Sigma-Aldrich Corporation) |

TABLE 69-continued

Compounds 69-2 to 69-7 were prepared following the procedure described in Method 69, Steps 1-2, above as follows:

| Ex. # | Chemical Structure | Name | Method Changes | Reagent |
|---|---|---|---|---|
| 69-6 | 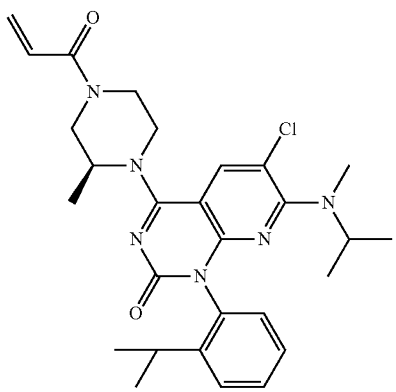 [SMILES: C=CC(=O)N1CCN(c2nc(=O)n(-c3ccccc3C(C)C)c3nc(N(C)C(C)C)c(Cl)cc23)[C@@H](C)C1] | 6-chloro-7-(methyl(2-propanyl)amino)-4-((2S)-2-methyl-4-(2-propenoyl)-1-piperazinyl)-1-(2-(2-propanyl)phenyl)pyrido[2,3-d]pyrimidin-2(1H)-one | | Step 1: N-isopropylmethylamine (Acros Organics) |
| 69-7 | 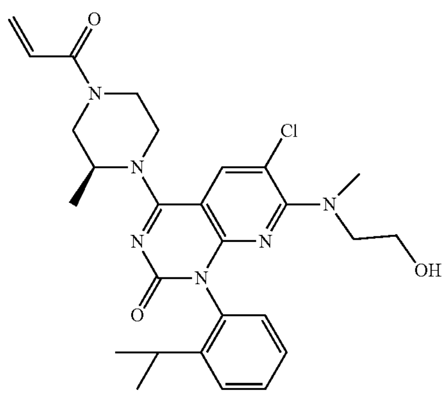 [SMILES: C=CC(=O)N1CCN(c2nc(=O)n(-c3ccccc3C(C)C)c3nc(N(C)CCO)c(Cl)cc23)[C@@H](C)C1] | 6-chloro-7-((2-hydroxyethyl)(methyl)amino)-4-((2S)-2-methyl-4-(2-propenoyl)-1-piperazinyl)-1-(2-(2-propanyl)phenyl)pyrido[2,3-d]pyrimidin-2(1H)-one | | Step 1: 2-(methylamino)ethan-1-ol (Sigma-Aldrich Corporation) |

Method 70

Example 70-1: 7-(6-Amino-3-chloro-2-pyrindinyl)-6-chloro-4-((2S)-2-methyl-4-(2-propenoyl)-1-piperazinyl)-1-(2-(2-propanyl)phenyl)pyrido[2,3-d]pyrimidin-2(1H)-one

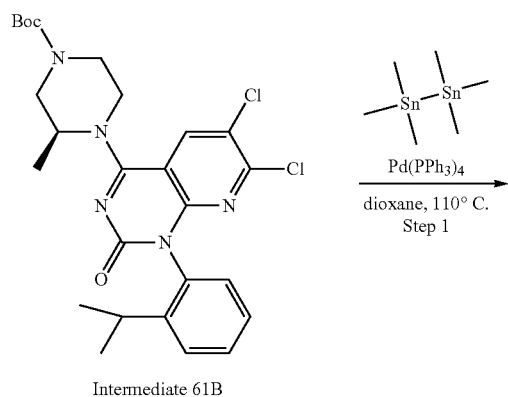

Intermediate 61B

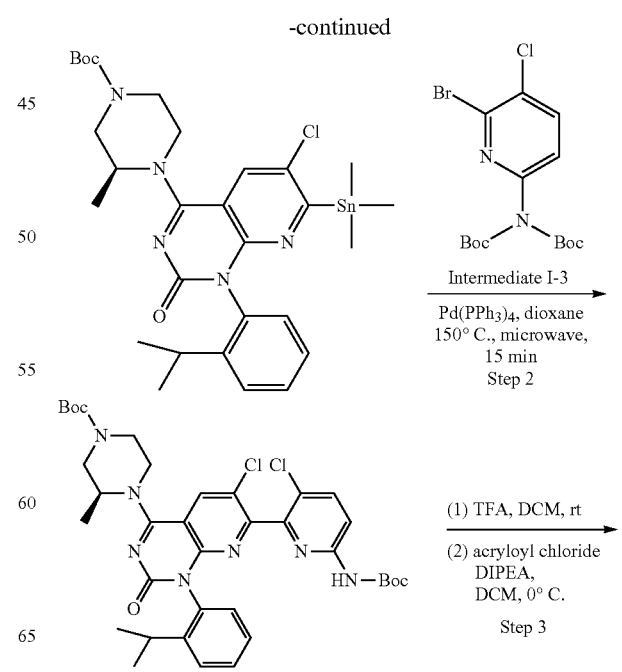

-continued

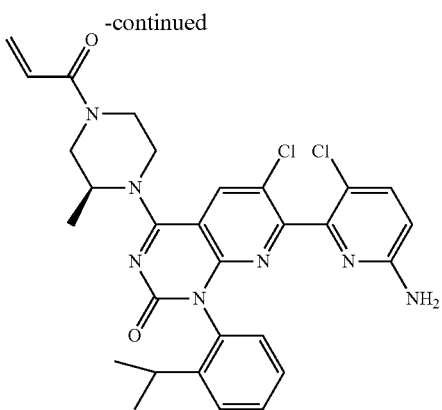

Step 1: (S)-tert-Butyl 4-(6-chloro-1-(2-isopropylphenyl)-2-oxo-7-(trimethylstannyl)-1,2-dihydropyrido[2,3-d]pyrimidin-4-yl)-3-methylpiperazine-1-carboxylate A mixture of (S)-tert-butyl 4-(6,7-dichloro-1-(2-isopropylphenyl)-2-oxo-1,2-dihydropyrido[2,3-d]pyrimidin-4-yl)-3-methylpiperazine-1-carboxylate (Intermediate 61B, 580 mg, 1.09 mmol), tetrakis(triphenylphosphine)palladium (0) (126 mg, 0.11 mmol), and hexamethylditin (1.07 g, 3.27 mmol) in 1,4-dioxane (6.5 mL) was stirred at 110° C. for 20 h. The resulting mixture was concentrated in vacuo. The crude product was purified by silica gel chromatography (eluent: 0-20%/of EtOAc-EtOH(3:1)/heptane) to provide (S)-tert-butyl 4-(6-chloro-1-(2-isopropylphenyl)-2-oxo-7-(trimethylstannyl)-1,2-dihydropyrido[2,3-d]pyrimidin-4-yl)-3-methylpiperazine-1-carboxylate (536 mg, 0.811 mmol, 74.5% yield) as a white solid. m/z (ESI, +ve ion): 662.2 (M+H)$^+$.

Step 2: (S)-tert-Butyl 4-(7-(6-((tert-butoxycarbonyl)amino)-3-chloropyridin-2-yl)-6-chloro-1-(2-isopropylphenyl)-2-oxo-1,2-dihydropyrido[2,3-d]pyrimidin-4-yl)-3-methylpiperazine-1-carboxylate A glass microwave reaction vessel was charged with bis-Boc-2-amino-6-bromo-5-chloropyridine (Intermediate I-3, 130 mg, 0.32 mmol), (S)-tert-butyl 4-(6-chloro-1-(2-isopropylphenyl)-2-oxo-7-(trimethylstannyl)-1,2-dihydropyrido[2,3-d]pyrimidin-4-yl)-3-methylpiperazine-1-carboxylate (210 mg, 0.32 mmol), copper(I) iodide (3.1 mg, 0.02 mmol) and tetrakis(triphenylphosphine)palladium (0) (18 mg, 0.02 mmol) in 1,4-dioxane (1.5 mL). The reaction mixture was stirred and heated in a Emrys Optimizer microwave reactor (Personal Chemistry, Biotage AB, Inc., Upssala, Sweden) at 150° C. for 15 min. The mixture was concentrated in vacuo. The crude product was purified by silica gel chromatography (eluent: 0-50% EtOAc EtOH (3:1)/heptane) to give (S)-tert-butyl 4-(7-(6-((tert-butoxycarbonyl)amino)-3-chloropyridin-2-yl)-6-chloro-1-(2-isopropylphenyl)-2-oxo-1,2-dihydropyrido[2,3-d]pyrimidin-4-yl)-3-methylpiperazine-1-carboxylate (156 mg, 0.22 mmol, 67.8% yield) as a yellow solid. m/z (ESI, +ve ion): 724.3 (M+H)$^+$.

Step 3: 7-(6-Amino-3-chloro-2-pyridinyl)-6-chloro-4-((2S)-2-methyl-4-(2-propenoyl)-1-piperazinyl)-1-(2-(2-propanyl)phenyl)pyrido[2,3-d]pyrimidin-2(1H)-one To a mixture of (S)-tert-butyl 4-(7-(6-amino-3-chloropyridin-2-yl)-6-chloro-1-(2-isopropylphenyl)-2-oxo-1,2-dihydropyrido[2,3-d]pyrimidin-4-yl)-3-methylpiperazine-1-carboxylate (156 mg, 0.22 mmol) in DCM (1.5 mL) was treated with TFA (1.5 mL) at rt and stirred for 50 min. The reaction mixture was concentrated in vacuo to afford (S)-7-(6-amino-3-chloropyridin-2-yl)-6-chloro-1-(2-isopropylphenyl)-4-(2-methylpiperazin-1-yl)pyrido[2,3-d]pyrimidin-2(1H)-one. m/z (ESI, +ve ion): 524.2 (M+H)$^+$.

A mixture of above (S)-7-(6-amino-3-chloropyridin-2-yl)-6-chloro-1-(2-isopropylphenyl)-4-(2-methylpiperazin-1-yl)pyrido[2,3-d]pyrimidin-2(1H)-one and DIPEA (0.2 mL, 1.25 mmol) in DCM (1.5 mL) was added acryloyl chloride (0.25 M in DCM, 1.0 mL, 0.25 mmol) at 0° C. and stirred for 5 min at 0° C. The mixture was concentrated in vacuo. The crude product was purified by silica gel chromatography (eluent: 0-5% of MeOH/DCM) to provide pure (S)-4-(4-acryloyl-2-methylpiperazin-1-yl)-7-(6-amino-3-chloropyridin-2-yl)-6-chloro-1-(2-isopropylphenyl)pyrido[2,3-d]pyrimidin-2(1H)-one (80.6 mg, 0.14 mmol, 55.8% yield) as a light-yellow solid. $^1$H NMR (400 MHz, DMSO-d6) δ ppm 8.39 (br d, J=19.7 Hz, 1H), 7.46 (d, J=8.9 Hz, 1H), 7.37-7.43 (m, 1H), 7.30-7.37 (m, 1H), 7.23 (t, J=7.5 Hz, 1H), 7.06-7.12 (m, 1H), 6.78-6.93 (m, 1H), 6.49 (d, J=8.9 Hz, 1H), 6.27 (br d, J=1.5 Hz, 2H), 6.15-6.24 (m, 1H), 5.76 (dd, J=10.4, 2.3 Hz, 1H), 4.74-5.04 (m, 1H), 3.96-4.47 (m, 3H), 3.36-3.87 (m, 2H), 3.00-3.26 (m, 1H), 2.52-2.60 (m, 1H), 1.32 (br dd, J=16.5, 6.5 Hz, 3H), 1.06 (d, J=6.8 Hz, 3H), 0.98 (d, J=6.8 Hz, 3H). m/z (ESI, +ve ion): 578.2 (M+H)$^+$.

TABLE 70

Compounds 70-2 to 70-4 were prepared following the procedure described in Method 70, Steps 1-3, above as follows:

| Ex. # | Chemical Structure | Name | Method Changes | Reagent |
|---|---|---|---|---|
| 70-2 | 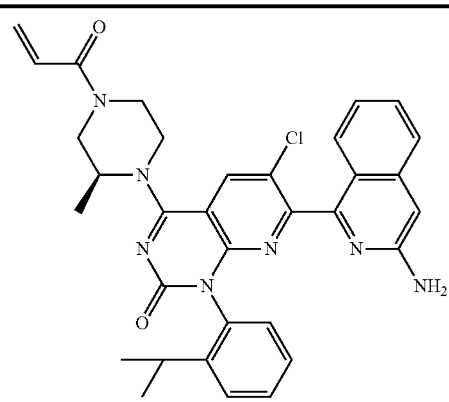 | 7-(3-amino-1-isoquinolinyl)-6-chloro-4-((2S)-2-methyl-4-(2-propenoyl)-1-piperazinyl)-1-(2-(2-propanyl)phenyl)pyrido[2,3-d]pyrimidin-2(1H)-one | Step 2: 1-bromoisoquinolin-3-amine (Maybridge Chemical Co., Ltd.) | |

TABLE 70-continued

Compounds 70-2 to 70-4 were prepared following the procedure described in Method 70, Steps 1-3, above as follows:

| Ex. # | Chemical Structure | Name | Method Changes | Reagent |
|---|---|---|---|---|
| 70-3 | 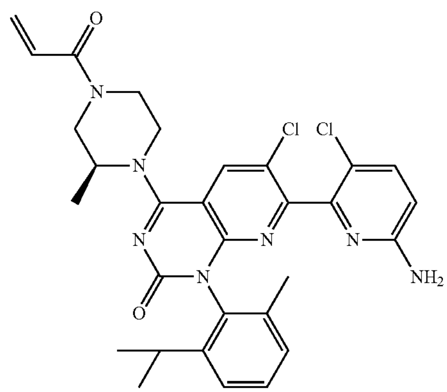 [SMILES: C=CC(=O)N1CCN(c2nc(=O)n(-c3c(C)cccc3C(C)C)c3nc(-c4nc(N)ccc4Cl)c(Cl)cc23)[C@@H](C)C1] | 7-(6-amino-3-chloro-2-pyridinyl)-6-chloro-1-(2-methyl-6-(2-propanyl)phenyl)-4-((2S)-2-methyl-4-(2-propenoyl)-1-piperazinyl)pyrido[2,3-d]pyrimidin-2(1H)-one | | Step 1: (S)-4-(4-acryloyl-2-methylpiperazin-1-yl)-6,7-dichloro-1-(2-isopropyl-6-methylphenyl)pyrido[2,3-d]pyrimidin-2(1H)-one (Example 39, Step 4), Step 2: 2-amino-6-bromo-5-chloropyridine (Combi-Blocks Inc.) |
| 70-4 | 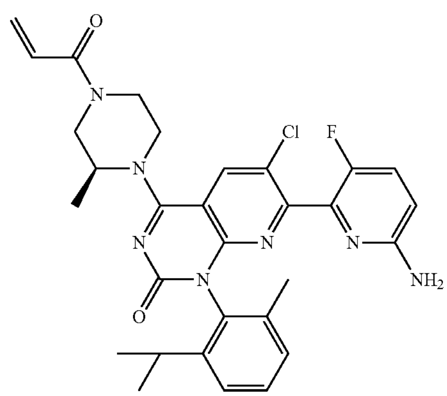 [SMILES: C=CC(=O)N1CCN(c2nc(=O)n(-c3c(C)cccc3C(C)C)c3nc(-c4nc(N)ccc4F)c(Cl)cc23)[C@@H](C)C1] | 7-(6-amino-3-fluoro-2-pyridinyl)-6-chloro-1-(2-methyl-6-(2-propanyl)phenyl)-4-((2S)-2-methyl-4-(2-propenoyl)-1-piperazinyl)pyrido[2,3-d]pyrimidin-2(1H)-one | | Step 1: (S)-4-(4-acryloyl-2-methylpiperazin-1-yl)-6,7-dichloro-1-(2-isopropyl-6-methylphenyl)pyrido[2,3-d]pyrimidin-2(1H)-one (Example 39, Step 4), Step 2: tert-butyl (6-bromo-5-fluoropyridin-2-yl)carbamate (AstaTech, Inc.) |

Method 71

Example 71-1: 7-(6-Amino-3-chloro-2-pyridinyl)-6-fluoro-1-(2-methyl-6-(2-propanyl)phenyl)-4-((2S)-2-methyl-4-(2-propenoyl)-1-piperazinyl)pyrido[2,3-d]pyrimidin-2(1H)-one

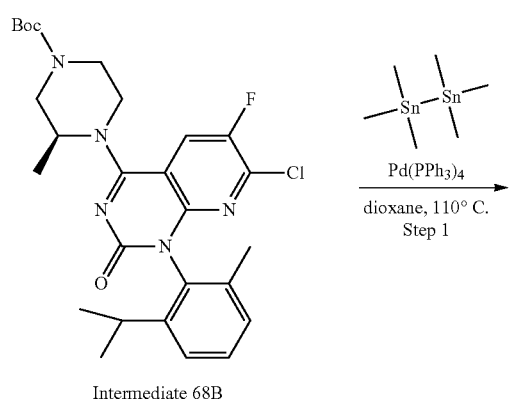

Intermediate 68B

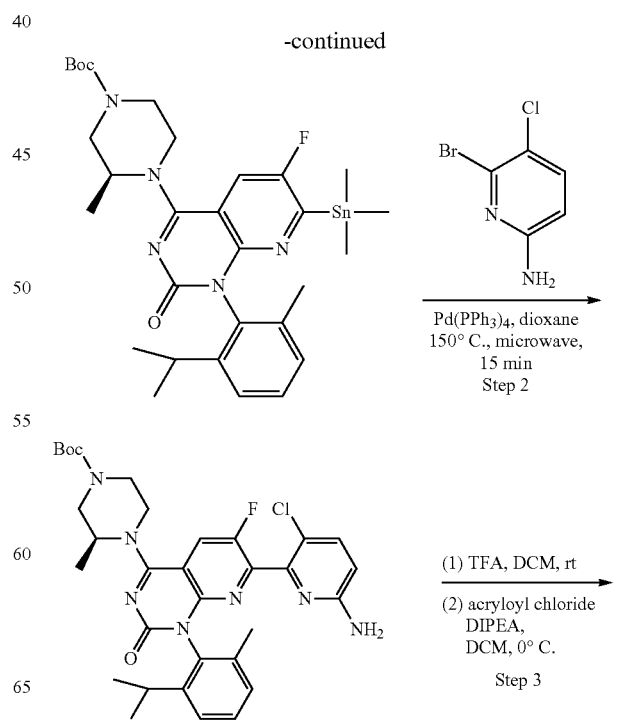

-continued

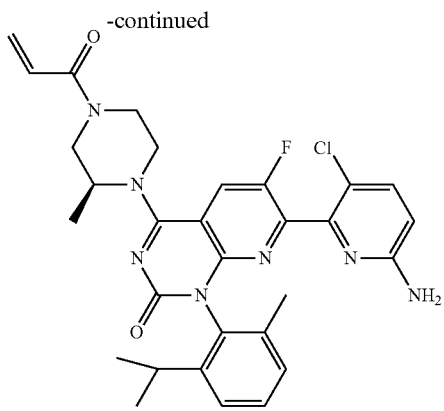

Step 1: tert-Butyl (S)-4-(6-fluoro-1-(2-isopropyl-6-methylphenyl)-2-oxo-7-(trimethylstannyl)-1,2-dihydropyrido[2,3-d]pyrimidin-4-yl)-3-methylpiperazine-1-carboxylate A mixture of tert-butyl (S)-4-(7-chloro-6-fluoro-1-(2-isopropyl-6-methylphenyl)-2-oxo-1,2-dihydropyrido[2,3-d]pyrimidin-4-yl)-3-methylpiperazine-1-carboxylate (Intermediate 68B prepared using Intermediate S according to Method 61, 1.21 g, 2.28 mmol), tetrakis(triphenylphosphine)palladium (0) (0.19 g, 0.16 mmol), and hexamethylditin (1.65 g, 5 mmol) in 1,4-dioxane (6.5 mL) was stirred at 110° C. for 16 h. The mixture was concentrated in vacuo. The crude product was purified by silica gel chromatography (eluent: 0-20% of EtOAc-EtOH (3:1)/heptane) to provide tert-butyl (S)-4-(6-fluoro-1-(2-isopropyl-6-methylphenyl)-2-oxo-7-(trimethylstannyl)-1,2-dihydropyrido[2,3-d]pyrimidin-4-yl)-3-methylpiperazine-1-carboxylate (968 mg, 1.47 mmol, 64.6% yield) as a light yellow foam. m/z (ESI, +ve ion): 660.2 (M+H)$^+$.

Step 2: tert-Butyl (S)-4-(7-(6-amino-3-chloropyridin-2-yl)-6-fluoro-1-(2-isopropyl-6-methylphenyl)-2-oxo-1,2-dihydropyrido[2,3-d]pyrimidin-4-yl)-3-methylpiperazine-1-carboxylate A glass microwave reaction vessel was charged with 2-amino-6-bromo-5-chloropyridine (170 mg, 0.818 mmol, Combi-Blocks Inc., San Diego, Calif., USA), tert-butyl (S)-4-(6-fluoro-1-(2-isopropyl-6-methylphenyl)-2-oxo-7-(trimethylstannyl)-1,2-dihydropyrido[2,3-d]pyrimidin-4-yl)-3-methylpiperazine-1-carboxylate (460 mg, 0.68 mmol), copper(I) iodide (13 mg, 0.07 mmol) and tetrakis(triphenylphosphine)palladium (0) (39 mg, 0.03 mmol) in 1,4-dioxane (3 mL). The reaction mixture was stirred and heated in a Emrys Optimizer microwave reactor (Personal Chemistry, Biotage AB, Inc., Upssala, Sweden) at 150° C. for 15 min. The mixture was concentrated in vacuo. The crude product was purified by silica gel chromatography (eluent: 0-50% of EtOAc-EtOH (3:1)/heptane) to provide tert-butyl (S)-4-(7-(6-amino-3-chloropyridin-2-yl)-6-fluoro-1-(2-isopropyl-6-methylphenyl)-2-oxo-1,2-dihydropyrido[2,3-d]pyrimidin-4-yl)-3-methylpiperazine-1-carboxylate (310 mg, 0.50 mmol, 73.1% yield) as a yellow solid. $^1$H NMR (400 MHz, DMSO-d$_6$) δ ppm 8.28 (dd, J=9.1, 7.5 Hz, 1H), 7.48 (d, J=8.9 Hz, 1H), 7.17-7.32 (m, 2H), 7.12 (br d, J=6.6 Hz, 1H), 6.52 (d, J=8.9 Hz, 1H), 6.31 (s, 2H), 4.82 (br s, 1H), 4.12-4.28 (m, 1H), 3.92-4.08 (m, 1H), 3.73-3.92 (m, 1H), 3.55-3.72 (m, 1H), 3.03-3.29 (m, 2H), 2.54-2.61 (m, 1H), 1.85 (d, J=6.8 Hz, 3H), 1.45 (s, 9H), 1.33 (br t, J=6.4 Hz, 3H), 1.05 (dd, J=6.8, 1.7 Hz, 3H), 0.94 (dd, J=6.7, 4.7 Hz, 3H). m/z (ESI, +ve ion): 622.3 (M+H)$^+$.

Step 3: 7-(6-Amino-3-chloro-2-pyridinyl)-6-fluoro-1-(2-methyl-6-(2-propanyl)phenyl)-4-((2S)-2-methyl-4-(2-propenoyl)-1-piperazinyl)pyrido[2,3-d]pyrimidin-2(1H)-one To a solution of tert-butyl (S)-4-(7-(6-amino-3-chloropyridin-2-yl)-6-fluoro-1-(2-isopropyl-6-methylphenyl)-2-oxo-1,2-dihydropyrido[2,3-d]pyrimidin-4-yl)-3-methylpiperazine-1-carboxylate (306 mg, 0.49 mmol) in DCM (2.0 mL) was treated with TFA (2.0 mL) at rt and stirred for 30 min. The mixture was concentrated in vacuo to afford (S)-7-(6-amino-3-chloropyridin-2-yl)-6-fluoro-1-(2-isopropyl-6-methylphenyl)-4-(2-methylpiperazin-1-yl)pyrido[2,3-d]pyrimidin-2(1H)-one. m/z (ESI, +ve ion): 522.2 (M+H)$^+$.

A mixture of above (S)-7-(6-amino-3-chloropyridin-2-yl)-6-fluoro-1-(2-isopropyl-6-methylphenyl)-4-(2-methylpiperazin-1-yl)pyrido[2,3-d]pyrimidin-2(1H)-one and DIPEA (0.4 mL, 2.46 mmol) in DCM (2.0 mL) was added acryloyl chloride (0.25 M in DCM, 2.0 mL, 0.50 mmol) at 0° C. and stirred for 10 min at 0° C. The reaction mixture was added satd. ammonium chloride (10 mL) and extracted with EtOAc (20 mL). The organic layer was washed with brine (20 mL), dried over Na$_2$SO$_4$, filtered, and concentrated in vacuo. The crude product was purified by silica gel chromatography (eluent: 0-5% of MeOH/DCM) to provide pure 7-(6-amino-3-chloro-2-pyridinyl)-6-fluoro-1-(2-methyl-6-(2-propanyl)phenyl)-4-((2S)-2-methyl-4-(2-propenoyl)-1-piperazinyl)pyrido[2,3-d]pyrimidin-2(1H)-one (211 mg, 0.37 mmol, 74.5% yield) as a yellow solid. $^1$H NMR (400 MHz, DMSO-d$_6$) δ ppm 8.31 (br d, J=7.3 Hz, 1H), 7.48 (d, J=8.9 Hz, 1H), 7.18-7.32 (m, 2H), 7.12 (dd, J=6.8, 1.7 Hz, 1H), 6.76-6.96 (m, 1H), 6.52 (d, J=8.9 Hz, 1H), 6.12-6.42 (m, 3H), 5.72-5.85 (m, 1H), 4.88 (br s, 1H), 4.20-4.47 (m, 2H), 3.92-4.18 (m, 1H), 3.60-3.78 (m, 2H), 3.12-3.29 (m, 1H), 2.54-2.61 (m, 1H), 1.85 (d, J=3.9 Hz, 3H), 1.31 (br t, J=6.5 Hz, 3H), 1.05 (d, J=6.6 Hz, 3H), 0.94 (dd, J=6.7, 3.2 Hz, 3H). $^{19}$F NMR (376 MHz, DMSO-d$_6$) δ ppm −132.10 (br s, 1F). m/z (ESI, +ve ion): 576.2 (M+H)$^+$.

TABLE 71

Compounds 71-2 was prepared following the procedure described in
Method 71, Steps 1-3, above as follows:

| Ex. # | Chemical Structure | Name | Method Changes | Reagent |
|---|---|---|---|---|
| 71-2 | 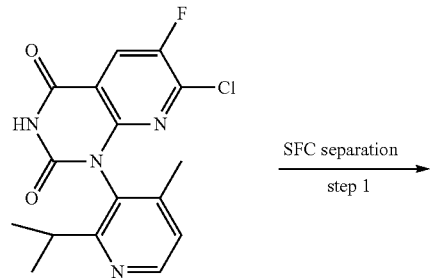 | 7-(3-amino-1-isoquinolinyl)-6-fluoro-1-(2-methyl-6-(2-propanyl)phenyl)-4-((2S)-2-methyl-4-(2-propenoyl)-1-piperazinyl)pyrido[2,3-d]pyrimidin-2(1H)-one | | Step 2: 1-bromoisoquinolin-3-amine (Maybridge Chemical Co., Ltd.) |

Method 72

Example 72-1: (M)-6-Fluoro-7-(5-fluoro-2-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one

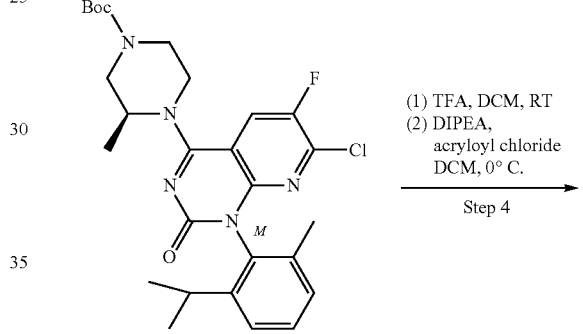

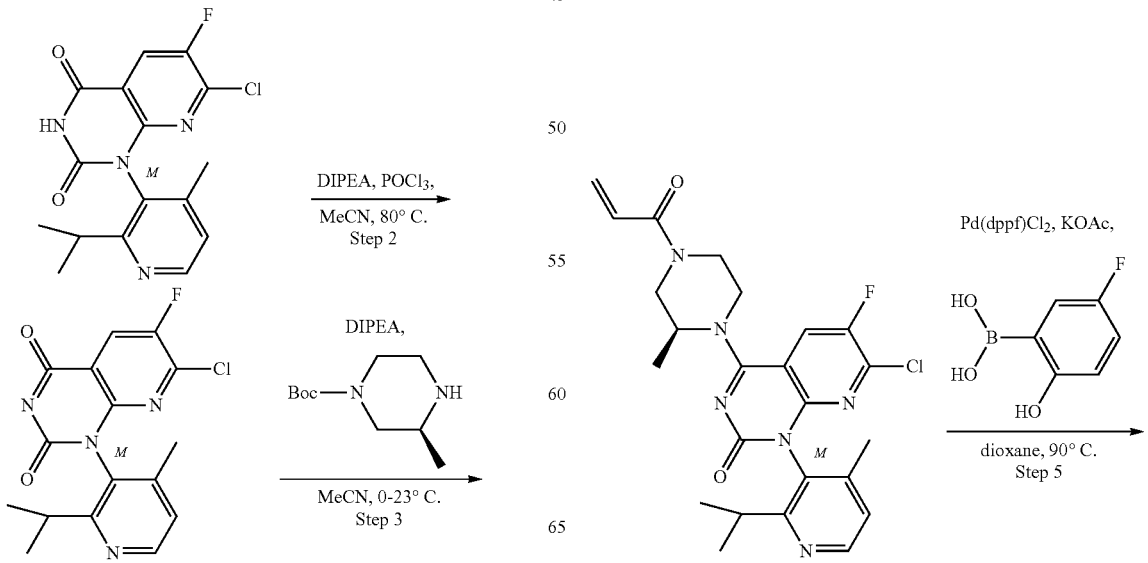

-continued

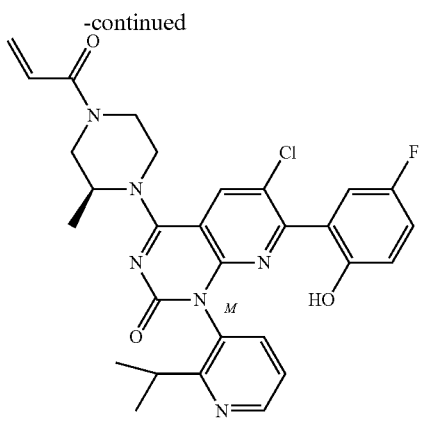

Step 1: 7-Chloro-6-fluoro-1-(2-isopropyl-4-methylpyridin-3-yl)pyrido[2,3-d]pyrimidine-2,4(1H,3H)-dione (Intermediate 72A)

A mixture of atropisomers 7-chloro-6-fluoro-1-(2-isopropyl-4-methylpyridin-3-yl)pyrido[2,3-d]pyrimidine-2,4(1H,3H)-dione (Example 41, Step 3,648 g) was purified by SFC (AD, 150×50 mm, 5 μm, 50% MeOH/CO$_2$, 180 g/min, 102 bar) to obtain two peaks: Peak 1 (P isomer, 230.6 g, >99% ee) and Peak 2 (M isomer, 227.8 g, 97.1% ee, Intermediate 72A).

Step 2: (M)-4,7-Dichloro-6-fluoro-1-(2-isopropyl-4-methylpyridin-3-yl)pyrido[2,3-d]pyrimidin-2(1H)-one To a suspension of (M)-7-chloro-6-fluoro-1-(2-isopropyl-4-methylpyridin-3-yl)pyrido[2,3-d]pyrimidine-2,4(1H,3H)-dione (Intermediate 72A, 2.51 g, 7.19 mmol) in a mixture of acetonitrile (11 mL) and DIPEA (1.9 mL, 11 mmol) was added phosphorous oxychloride (0.87 mL, 9.3 mmol). The mixture was heated at 80° C. for 90 min and then concentrated in vacuo. The crude residue was used without further purification in the following step. m/z (ESI, +ve ion): 367.0 (M+H)$^+$.

Step 3: (M,S)-tert-Butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (Intermediate 65A)

A solution of (M)-4,7-dichloro-6-fluoro-1-(2-isopropyl-4-methylpyridin-3-yl)pyrido[2,3-d]pyrimidin-2(1H)-one (2.64 g, 7.19 mmol) in acetonitrile (11 mL) was cooled in an ice-water bath to 0° C. DIPEA (3.8 mL, 22 mmol) was added, followed by (3S)-1-(tert-butoxycarbonyl)-3-methylpiperazine (1.8 g, 8.7 mmol, Ark Pharm. Inc., Libertyville, Ill., USA). The mixture was allowed to warm to rt and stir for 18 h. The mixture was quenched with satd. NaHCO$_3$ (100 mL). The mixture was diluted with EtOAc (175 mL), and water (75 mL). The aqueous layer was washed with EtOAc (2×100 mL). The combined organic phases were dried over MgSO$_4$ and then concentrated in vacuo. The crude product was purified by silica gel chromatography (eluent: 10-50% EtOAc-EtOH (3:1)/heptane) to provide (M,S)-tert-butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (Intermediate 65A). m/z (ESI, +ve ion): 530.9 (M+H)$^+$.

Step 4: (M,S)-4-(4-Acryloyl-2-methylpiperazin-1-yl)-7-chloro-6-fluoro-1-(2-isopropyl-4-methylpyridin-3-yl)pyrido[2,3-d]pyrimidin-2(1H)-one TFA (10 mL) was added to a solution of (M,S)-tert-butyl 4-(7-chloro-6-fluoro-1-(2-isopropyl-4-methylpyridin-3-yl)-2-oxo-1,2-dihydropyrido[2,3-d]pyrimidin-4-yl)-3-methylpiperaine-1-carboxylate (Intermediate 65A, 3.0 g, 5.7 mmol) in DCM (20 mL). The mixture was stirred for 20 min at rt and then concentrated in vacuo. The resulting residue was re-dissolved in DCM (40 mL) and cooled to 0° C. DIPEA (5.0 mL, 28 mmol) and acryloyl chloride (0.46 mL, 5.7 mmol) were sequentially added and the mixture was stirred for 80 min. The reaction mixture was quenched at 0° C. by adding satd. NaHCO$_3$ (100 mL) and water (50 mL) and diluted with DCM (150 mL). The aqueous layer was extracted with DCM (2×50 mL). The combined organic extracts were dried over MgSO$_4$ and then concentrated in vacuo to give crude (M,S)-4-(4-acryloyl-2-methylpiperazin-1-yl)-7-chloro-6-fluoro-1-(2-isopropyl-4-methylpyridin-3-yl)pyrido[2,3-d]pyrimidin-2(1H)-one which was used without further purification in the following step. m/z (ESI, +ve ion): 485.0 (M+H)$^+$.

Step 5: (M)-6-Fluoro-7-(5-fluoro-2-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one A mixture of (M,S)-4-(4-acryloyl-2-methylpiperazin-1-yl)-7-chloro-6-fluoro-1-(2-isopropyl-4-methylpyridin-3-yl)pyrido[2,3-d]pyrimidin-2(1H)-one (120 mg, 0.25 mmol), (5-fluoro-2-hydroxy)phenylboronic acid (58 mg, 0.37 mmol, Combi-Blocks, San Diego, Calif., USA), Pd(dppf)Cl$_2$ (18 mg, 0.025 mmol), and potassium acetate (120 mg, 1.2 mmol) in 1,4-dioxane (1.2 mL) and one drop of water was deoxygenated with nitrogen for 10 min. The mixture was stirred at 90° C. for 2 h, then was filtered through a plug of silica gel and then partitioned between water (50 mL) and EtOAc (50 mL). The organic phase was washed with water (50 mL) and then with brine (50 mL), dried over MgSO$_4$, filtered, and concentrated in vacuo. The crude product was purified by silica gel chromatography (eluent: 0-100% EtOAc-EtOH (3:1)/heptane) to provide (M)-6-fluoro-7-(5-fluoro-2-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one. $^1$H NMR (400 MHz, DMSO-d$_6$) δ ppm 0.96 (d, J=6.8 Hz, 3H), 1.08 (d, J=6.8 Hz, 3H), 1.33 (d, J=6.8 Hz, 3H), 1.94 (s, 3H), 2.68-2.78 (m, 0.5H), 3.06-3.19 (m, 0.5H), 3.43-3.55 (m, 0.5H), 3.59-3.80 (m, 1.5H), 3.98-4.07 (m, 0.5H), 4.10-4.19 (m, 0.5H), 4.29 (br d, J=13.5 Hz, 1.5H), 4.40 (br d, J=12.7 Hz, 0.5H), 4.91 (br s, 1H), 5.73-5.81 (m, 1H), 6.21 (br d, J=16.4 Hz, 1H), 6.80-6.93 (m, 2H), 7.09 (dd, J=9.4, 3.2 Hz, 1H), 7.18 (td, J=8.5, 3.1 Hz, 1H), 7.26 (d, J=5.0 Hz, 1H), 8.26-8.37 (m, 1H), 8.48 (d, J=5.0 Hz, 1H), 10.35 (s, 1H). $^{19}$F NMR (376 MHz, DMSO-d$_6$) δ ppm −126.02 (s, 1F), −125.16 (s, 1F). m/z (ESI, +ve ion): 561.0 (M+H)$^+$.

TABLE 72

Compounds 72-2 to 72-14 were prepared following the procedure described in Method 72, Steps 1-5, above as follows:

| Ex. # | Chemical Structure | Name | Method Changes | Reagent |
|---|---|---|---|---|
| 72-2 | Single isomer (M) | (M)-7-(4,5-difluoro-2-hydroxyphenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 5: 4,5-difluoro-2-hydroxyphenylboronic acid (Combi-Blocks Inc.) |
| 72-3 | Single isomer (M) | (M)-6-fluoro-7-(3-fluoro-2-hydroxyphenyl)-1-(4-methyl-2-(2-propanyl)-3-pyridinyl)-4-((2S)-2-methyl-4-(2-propenoyl)-4-piperazinyl)pyrido[2,3-d]pyrimidin-2(1H)-one | | Step 5: 3-fluoro-2-hydroxyphenylboronic acid (Frontier Scientific Services Inc.) |
| 72-4 | Single isomer (M) | (M)-6-fluoro-7-(2-hydroxy-6-methylphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 5: (2-hydroxy-6-methylphenyl)boronic acid (Boronic Acid B-1) |

TABLE 72-continued

Compounds 72-2 to 72-14 were prepared following the procedure
described in Method 72, Steps 1-5, above as follows:

| Ex. # | Chemical Structure | Name | Method Changes | Reagent |
|---|---|---|---|---|
| 72-5 | Single isomer (M) | (M)-6-fluoro-7-(2-fluoro-3-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 5: 2-fluoro-3-hydroxybenzeneboronic acid (Combi-Blocks Inc.) |
| 72-6 | single isomer (M) | (M)-7-(2,4-difluoro-5-methoxyphenyl)-6-fluoro-1-(4-methyl)-2-(2-propanyl)-3-pyridinyl)-4-((2S)-(2-methyl-4-(2-propenoyl)-1-piperazinyl)pyrido[2,3-d]pyrimidin-2(1H)-one | | Step 5: 2,4-difluoro-5-methoxyphenylboronic acid (Combi-Blocks Inc.) |
| 72-7 | single isomer (M) | (M)-7-(2,4-difluoro-5-hydroxyphenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step : (2,4-difluoro-5-hydroxyphenyl)boronic acid (Boronic Acid B-2) |

TABLE 72-continued

Compounds 72-2 to 72-14 were prepared following the procedure described in Method 72, Steps 1-5, above as follows:

| Ex. # | Chemical Structure | Name | Method Changes | Reagent |
|---|---|---|---|---|
| 72-8 | single isomer (M) | (M)-7-(2,3-difluoro-6-hydroxyphenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 5: (2,3-difluoro-6-hydroxyphenyl)boronic acid (Boronic Acid B-3) |
| 72-9 | single isomer (M) | (M)-7-(3,6-difluoro-2-hydroxyphenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 5: (3,6-difluoro-2-hydroxyphenyl)boronic acid (Boronic Acid B-4) |
| 72-10 | single isomer (M) | (M)-6-fluoro-7-(6-fluoro-2-hydroxy-3-methylphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 5: (6-fluoro-2-hydroxy-3-methylphenyl)boronic acid (Boronic Acid B-5) |

TABLE 72-continued

Compounds 72-2 to 72-14 were prepared following the procedure described in Method 72, Steps 1-5, above as follows:

| Ex. # | Chemical Structure | Name | Method Changes | Reagent |
|---|---|---|---|---|
| 72-11 | single isomer (M) | (M)-7-(2-amino-6-fluorophenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | Step 5: Pd(PPh$_3$)$_4$ and Na$_2$CO$_3$ | Step 5: (2-amino-6-fluorophenyl)boronic acid hydrochloride (AniChem) |
| 72-12 | single isomer (M) | (M)-7-chloro-4-((2S,6S)-2,6-dimethyl-4-(2-propenoyl)-1-piperazinyl)-6-fluoro-1-(4-methyl-2-(2-propanyl)-3-pyridinyl)pyrido[2,3-d]pyrimidin-2(1H)-one | Omit Step 5 | Step 3: (3S,5S)-1-Boc-3,5-dimethylpiperazine (AstaTech, Inc.) |
| 72-13 | single isomer (M) | (M)-7-(2-amino-6-fluorophenyl)-4-((2S,6S)-2,6-dimethyl-4-(2-propenoyl)-1-piperazinyl)-6-fluoro-1-(4-methyl-2-(2-propanyl)-3-pyridinyl)pyrido[2,3-d]pyrimidin-2(1H)-one | Step 5: Pd(PPh$_3$)$_4$ and Na$_2$CO$_3$ | Step 3: (3S,5S)-1-Boc-3,5-dimethylpiperazine (AstaTech, Inc.) Step 5: (2-amino-6-fluorophenyl)boronic acid pinacol ester (CombiPhos Catalysts, Inc.) |

TABLE 72-continued

Compounds 72-2 to 72-14 were prepared following the procedure described in Method 72, Steps 1-5, above as follows:

| Ex. # | Chemical Structure | Name | Method Changes | Reagent |
|---|---|---|---|---|
| 72-14 | single isomer (M) | (M)-4-((2S,6S)-2,6-dimethyl-4-(2-propenoyl)-1-piperazinyl)-6-fluoro-7-(2-fluorophenyl)-1-(4-methyl-2-(2-propanyl)-3-pyridinyl)pyrido[2,3-d]pyrimidin-2(1H)-one | Step 5: Pd(PPh$_3$)$_4$ and Na$_2$CO$_3$ | Step 3: (3S,5S)-1-boc-3,5-dimethylpiperazine (AstaTech, Inc.) Step 5: (2-fluorophenyl)boronic acid (Combi-Blocks Inc.) |

Method 73

Example 73-1: (M)-7-(2-Amino-6-fluorophenyl)-6-chloro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one

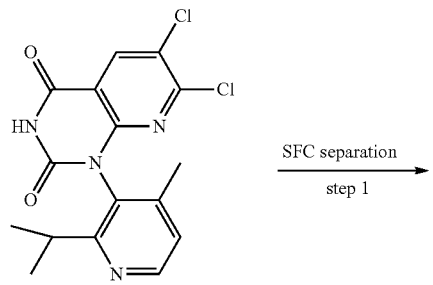

Example 40, Step 3

→ SFC separation, step 1

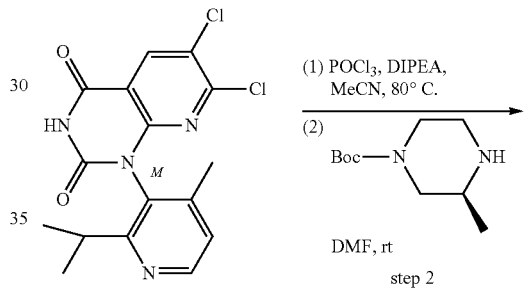

Intermediate 73B (1) POCl$_3$, DIPEA, MeCN, 80° C.

(2) Boc—N⌒NH (3S)-methyl

DMF, rt step 2

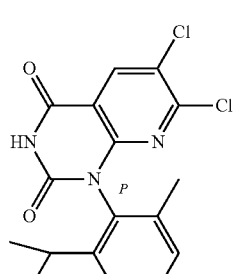

Intermediate 73A

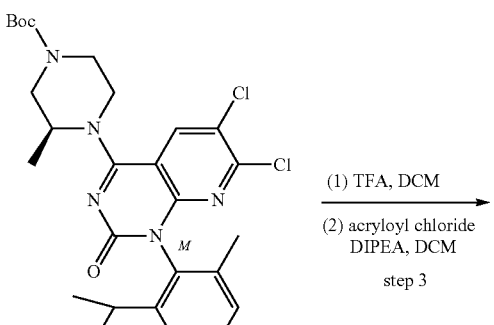

Intermediate 73C (1) TFA, DCM
(2) acryloyl chloride DIPEA, DCM step 3

-continued

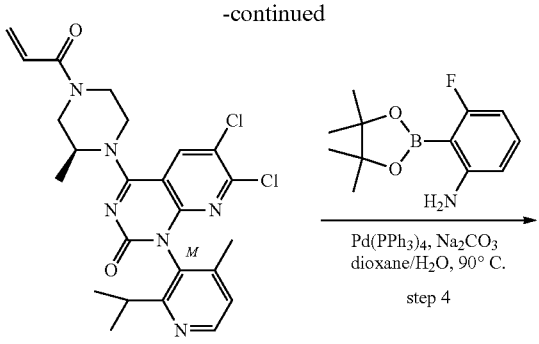

Intermediate 73D

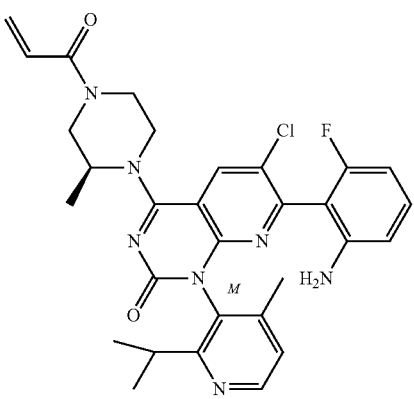

Step 1: 6,7-Dichloro-1-(2-isopropyl-4-methylpyridin-3-yl)pyrido[2,3-d]pyrimidine-2,4(1H,3H)-dione A mixture of atropisomers 6,7-dichloro-1-(2-isopropyl-4-methylpyridin-3-yl)pyrido[2,3-d]pyrimidine-2,4(1H,3H)-dione (Example 40, Step 3, 55.1 g) was purified by SFC (AD, 250×50 mm, 5 μm, 50% MeOH/CO2, 180 g/min, 102 bar) to obtain two peaks: Peak 1 (Intermediate 73A, (P)-isomer, 22.1 g, >99% ee) and Peak 2 ((M)-isomer, 23.2 g, >99% ee). Peak 2 was the desired material (Intermediate 73B).

Step 2: (M)-tert-Butyl (S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate A 250-mL round-bottomed flask was charged with (M)-6,7-dichloro-1-(2-isopropyl-4-methylpyridin-3-yl)pyrido[2,3-d]pyrimidine-2,4(1H,3H)-dione (Intermediate 73B, 5.9 g, 16 mmol) and DIPEA (4.2 mL, 24 mmol) in acetonitrile (65 mL) followed by phosphorous oxychloride (1.8 mL, 19.2 mmol). The mixture was stirred at 80° C. for 1 h. The reaction mixture was concentrated in vacuo to give a brown solid. The crude solid was used in next step without purification. m/z (ESI, +ve ion): 383.0 (M+H)$^+$.

The above crude solid and DIPEA (4.2 mL, 24 mmol) in DMF (50 mL) was treated with (3S)-1-(tert-butoxycarbonyl)-3-methylpiperazine (4.81 g, 24 mmol, Ark Pharm, Inc.) and stirred at rt for 30 min. The resulting mixture was added to ice water (100 mL) and stirred for 15 min. The resulting precipitate was collected by filtration, washed with water, and dried to give (M)-tert-butyl (S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (Intermediate 73C, 7.71 g, 14.1 mmol, 88% yield). $^1$H NMR (400 MHz, DMSO-d$_6$) δ ppm 8.39-8.54 (m, 2H), 7.25 (d, J=5.0 Hz, 1H), 4.87 (br d, J=1.0 Hz, 1H), 4.15 (br d, J=13.3 Hz, 1H), 3.95 (br dd, J=5.9, 4.0 Hz, 1H), 3.83 (br d, J=13.3 Hz, 1H), 3.71 (br t, J=11.0 Hz, 1H), 2.96-3.27 (m, 2H), 2.57-2.64 (m, 1H), 1.94 (s, 3H), 1.45 (s, 9H), 1.32 (d, J=6.6 Hz, 3H), 1.06 (d, J=6.8 Hz, 3H), 1.01 (d, J=6.6 Hz, 3H). m/z (ESI, +ve ion): 547.3 (M+H)$^+$.

Step 3: (M,S-4-(4-Acryloyl-2-methylpiperazin-1-yl)-6,7-dichloro-1-(2-isopropyl-4-methylpyridin-3-yl)pyrido[2,3-d]pyrimidin-2(1H)-one To a solution of (M)-tert-butyl (S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (Intermediate 73C, 2.71 g, 4.95 mmol) in DCM (25 mL) was treated with TFA (10 mL, 134 mmol) at rt and stirred for 20 min. The reaction was concentrated in vacuo to afford (M,S)-6,7-dichloro-1-(2-isopropyl-4-methylpyridin-3-yl)-4-(2-methylpiperazin-1-yl)pyrido[2,3-d]pyrimidin-2(1H)-one as a brown solid. m/z (ESI, +ve ion): 447.2 (M+H)$^+$.

A mixture of (M,S)-6,7-dichloro-1-(2-isopropyl-4-methylpyridin-3-yl)-4-(2-methylpiperazin-1-yl)pyrido[2,3-d]pyrimidin-2(1H)-one and DIPEA (4.3 mL, 24.8 mmol) in DCM (25 mL) was treated with acryloyl chloride (0.36 mL, 4.5 mmol) at 0° C. and stirred for 20 min. The reaction mixture was concentrated in vacuo. The crude product was purified by silica gel chromatography (eluent: 0-60% EtOAc-EtOH(3:1)/heptane) to provide pure (M,S)-4-(4-acryloyl-2-methylpiperazin-1-yl)-6,7-dichloro-1-(2-isopropyl-4-methylpyridin-3-yl)pyrido[2,3-d]pyrimidin-2(1H)-one (Intermediate 73D; 2.28 g, 4.55 mmol, 92% yield) as a light-yellow foam. $^1$H NMR (400 MHz, DMSO-d$_6$) δ ppm 8.50 (d, J=4.8 Hz, 2H), 7.30 (d, J=4.8 Hz, 1H), 6.77-6.94 (m, 1H), 6.20 (br d, J=16.0 Hz, 1H), 5.76 (dd, J=10.5, 2.4 Hz, 1H), 4.92 (br s, 1H), 3.96-4.44 (m, 3H), 3.54-3.85 (m, 2H), 3.00-3.24 (m, 1H), 2.59-2.70 (m, 1H), 1.97 (s, 3H), 1.30 (br d, J=6.6 Hz, 3H), 1.07 (d, J=6.6 Hz, 3H), 1.02 (d, J=6.6 Hz, 3H). m/z (ESI, +ve ion): 501.2 (M+H)$^+$.

Step 4: (M)-7-(2-Amino-6-fluorophenyl)-6-chloro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one A mixture of (M,S)-4-(4-acryloyl-2-methylpiperazin-1-yl)-6,7-dichloro-1-(2-isopropyl-4-methylpyridin-3-yl)pyrido[2,3-d]pyrimidin-2(1H)-one (Intermediate 73D; 1.65 g, 3.28 mmol), tetrakis(triphenylphosphine)palladium (0) (0.38 g, 0.33 mmol, Sigma-Aldrich Corporation). (2-amino-6-fluorophenyl)boronic acid pinacol ester (0.86 g, 3.61 mmol, CombiPhos Catalysts. Inc.) and sodium carbonate (1.74 g, 16.4 mmol) in 1,4-dioxane (11 mL)/water (5.5 mL) was stirred at 90° C. for 80 min. The mixture was treated with water (25 mL) and extracted with EtOAc (2×50 mL). The organic extracts were combined and dried over MgSO$_4$. The solution was filtered and concentrated in vacuo to give a crude product as a yellow solid. The crude product was purified by silica gel chromatography (eluent: 0-70% of EtOAc-EtOH (3:1)/heptane) to provide (M)-7-(2-amino-6-fluorophenyl)-6-chloro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one (1.16 g, 2.01 mmol, 61.3% yield) as a yellow foam. $^1$H NMR (400 MHz, DMSO-d$_6$) δ ppm 8.33-8.48 (m, 2H), 7.18 (d, J=4.8 Hz, 1H), 7.05 (q, J=7.9 Hz, 1H), 6.78-6.95 (m, 1H), 6.44 (d, J=8.3 Hz, 1H), 6.32 (br t, J=8.9 Hz, 1H), 6.21 (br d, J=15.5 Hz, 1H), 5.71-5.81 (m, 1H), 5.05-5.16 (m, 2H), 4.91 (br s, 1H), 4.22-4.48 (m, 2H), 3.96-4.20 (m, 1H), 3.39-3.87 (m, 2H), 3.02-3.24 (m, 1H), 2.59-2.90 (m, 1H), 1.82-2.02 (m, 3H), 1.35 (br d, J=6.6 Hz, 3H), 1.03-1.12 (m, 3H), 0.86-1.02 (m, 3H). $^{19}$F NMR (376 MHz, DMSO-d$_6$) δ ppm −115.51 (br d, J=10.4 Hz), −115.74 (br d, J=13.0 Hz). m/z (ESI, +ve ion): 576.2 (M+H)$^+$.

TABLE 73

Compounds 73-2 to 73-19 were prepared following the procedure described in Method 73, Steps 1-4, above as follows:

| Ex. # | Chemical Structure | Name | Method Changes | Reagent |
|---|---|---|---|---|
| 73-2 | 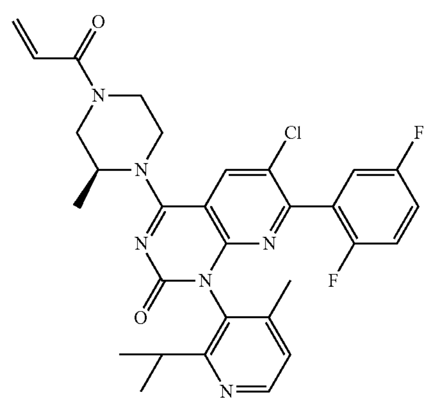 | (M)-6-chloro-7-(2,5-difluorophenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 4: (2,5-difluorophenyl)boronic acid (Combi-Blocks Inc.) |
| 73-3 | 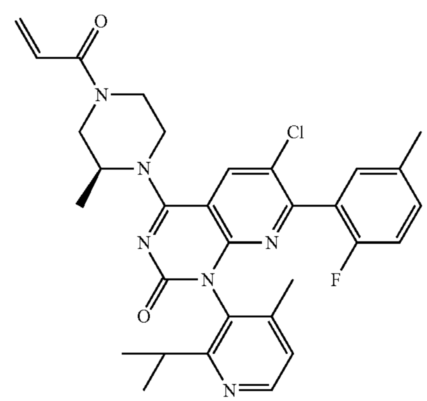 | (M)-6-chloro-7-(2-fluoro-5-methylphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 4: (2-fluoro-5-methylphenyl)boronic acid (Combi-Blocks Inc.) |
| 73-4 | 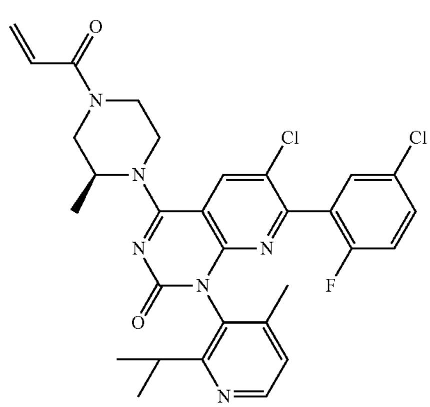 | (M)-6-chloro-7-(5-chloro-2-fluorophenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 4: 5-chloro-2-fluorophenyl boronic acid (Sigma-Aldrich Corporation) |

TABLE 73-continued

Compounds 73-2 to 73-19 were prepared following the procedure described in Method 73, Steps 1-4, above as follows:

| Ex. # | Chemical Structure | Name | Method Changes | Reagent |
|---|---|---|---|---|
| 73-5 | 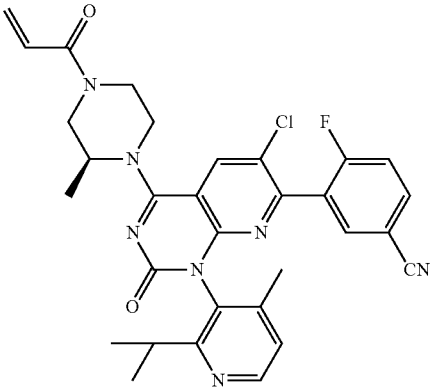 single isomer (M) | (M)-3-(6-chloro-1-(4-methyl-2-(2-propanyl)-3-pyridinyl)-4-((2S)-2-methyl-4-(2-propenoyl)-1-piperazinyl)-2-oxo-1,2-dihydropyrido[2,3-d]pyrimidin-7-yl)-4-fluorobenzonitrile | | Step 4: 5-cyano-2-fluorophenyl boronic acid (Combi-Blocks Inc.) |
| 73-6 | 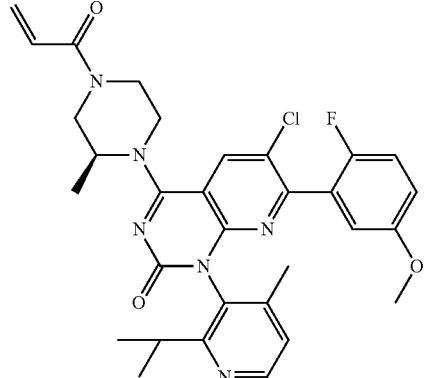 single isomer (M) | (M)-6-chloro-7-(2-fluoro-5-methoxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 4: 2-fluoro-5-methoxybenzeneboronic acid (Combi-Blocks Inc.) |
| 73-7 | 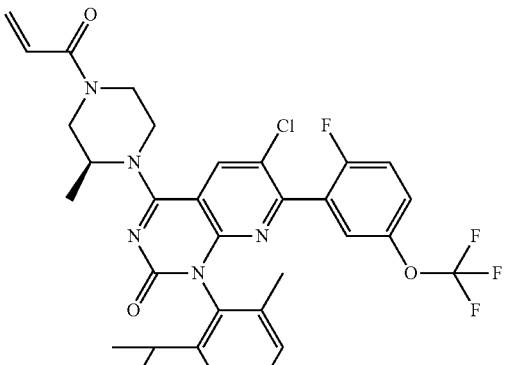 single isomer (M) | (M)-6-chloro-7-(2-fluoro-5-(trifluoromethoxy)phenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 4: 2-fluoro-5-(trifluoromethoxy)benzeneboronic acid (Combi-Blocks Inc.) |

TABLE 73-continued

Compounds 73-2 to 73-19 were prepared following the procedure described in Method 73, Steps 1-4, above as follows:

| Ex. # | Chemical Structure | Name | Method Changes | Reagent |
|---|---|---|---|---|
| 73-8 | single isomer (M) | (M)-6-chloro-7-(2-fluoro-5-(trifluoromethyl)phenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 4: 2-fluoro-5-(trifluoromethyl)benzeneboronic acid (Combi-Blocks Inc.) |
| 73-9 | single isomer (M) | (M)-6-chloro-7-(5-cyclopropyl-2-fluorophenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 4: 5-cyclopropyl-2-fluorophenyl boronic acid (Combi-Blocks Inc.) |
| 73-10 | single isomer (M) | (M)-3-(6-chloro-1-(4-methyl-2-(2-propanyl)-3-pyridinyl)-4-((2S)-2-methyl-4-(2-propenoyl)-1-piperazinyl)-2-oxo-1,2-dihydropyrido[2,3-d]pyrimidin-7-yl)-N-cyclopropyl-4-fluorobenzamide | | Step 4: 5-(cyclopropylcarbamoyl)-2-fluorophenyl boronic acid (Combi-Blocks Inc.) |

TABLE 73-continued

Compounds 73-2 to 73-19 were prepared following the procedure described in Method 73, Steps 1-4, above as follows:

| Ex. # | Chemical Structure | Name | Method Changes | Reagent |
|---|---|---|---|---|
| 73-11 | 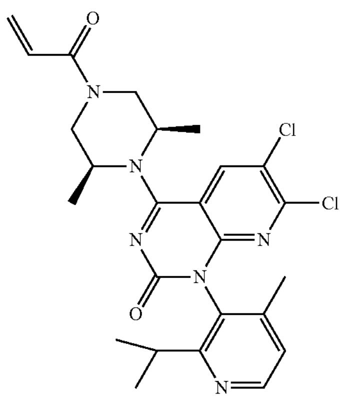 | (M)-6,7-dichloro-4-(cis-2,6-dimethyl-4-(2-propenoyl)-1-piperazinyl)-1-(4-methyl-2-(2-propanyl)-3-pyridinyl)pyrido[2,3-d]pyrimidin-2(1H)-one single isomer (M) | Omit Step 4 | Step 2: (3R,5S)-3,5-dimethyl-piperazine-1-carboxylic acid tert-butyl ester (Combi-Blocks Inc.) |
| 73-12 | 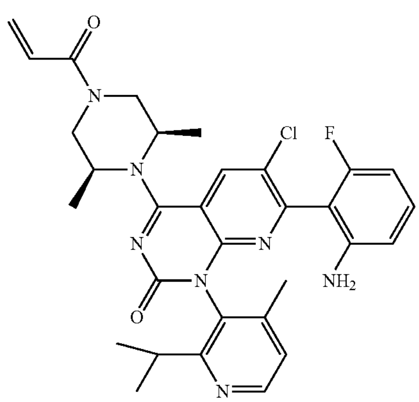 | (M)-7-(2-amino-6-fluorophenyl)-6-chloro-4-(cis-2,6-dimethyl-4-(2-propenoyl)-1-piperazinyl)-1-(4-methyl-2-(2-propanyl)-3-pyridinyl)pyrido[2,3-d]pyrimidin-2(1H)-one Single isomer (M) | | Step 2: (3R,5S)-3,5-dimethyl-piperazine-1-carboxylic acid tert-butyl ester (Combi-Blocks Inc.), Step 4: (2-amino-6-fluorophenyl)boronic acid pinacol ester (CombiPhos Catalysts, Inc.) |
| 73-13 | 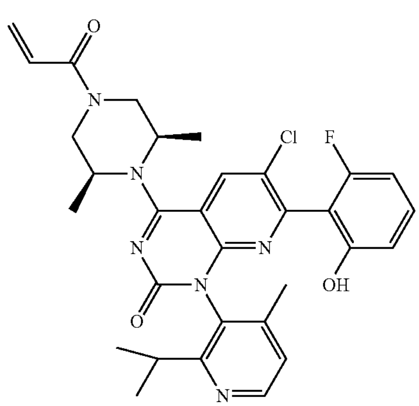 | (M)-6-chloro-4-(cis-2,6-dimethyl-4-(2-propenoyl)-1-piperazinyl)-7-(2-fluoro-6-hydroxyphenyl)-1-(4-methyl-2-(2-propanyl)-3-pyridinyl)pyrido[2,3-d]pyrimidin-2(1H)-one single isomer (M) | | Step 2: (3R,5S)-3,5-dimethyl-piperazine-1-carboxylic acid tert-butyl ester (Combi-Blocks Inc.), Step 4: (2-fluoro-6-hydroxyphenyl)boronic acid (Wuxi) |

TABLE 73-continued

Compounds 73-2 to 73-19 were prepared following the procedure described in Method 73, Steps 1-4, above as follows:

| Ex. # | Chemical Structure | Name | Method Changes | Reagent |
|---|---|---|---|---|
| 73-14 | single isomer (M) | (M)-6,7-dichloro-4-((2S,6S)-2,6-dimethyl-4-(2-propenoyl)-1-piperazinyl)-1-(4-methyl-2-(2-propanyl)-3-pyridinyl)pyrido[2,3-d]pyrimidin-2(1H)-one | Omit Step 4 | Step 2: (3S,5S)-1-Boc-3,5-dimethylpiperazine (AstaTech, Inc.) |
| 73-15 | single isomer (M) | (M)-7-(2-amino-6-fluorophenyl)-6-chloro-4-((2S,6S)-2,6-dimethyl-4-(2-propenoyl)-1-piperazinyl)-1-(4-methyl-2-(2-propanyl)-3-pyridinyl)pyrido[2,3-d]pyrimidin-2(1H)-one | | Step 2: (3S,5S)-1-Boc-3,5-dimethylpiperazine (AstaTech, Inc.), Step 4: (2-amino-6-fluorophenyl)boronic acid pinacol ester (CombiPhos Catalysts, Inc.) |
| 73-16 | single isomer (M) | (M)-6-chloro-4-((2S,6S)-2,6-dimethyl-4-(2-propenoyl)-1-piperazinyl)-7-(2-fluoro-6-hydroxyphenyl)-1-(4-methyl-2-(2-propanyl)-3-pyridinyl)pyrido[2,3-d]pyrimidin-2(1H)-one | | Step 2: (3S,5S)-1-Boc-3,5-dimethylpiperazine (AstaTech, Inc.) Step 4: (2-fluoro-6-hydroxyphenyl)boronic acid (Wuxi) |

TABLE 73-continued

Compounds 73-2 to 73-19 were prepared following the procedure described in Method 73, Steps 1-4, above as follows:

| Ex. # | Chemical Structure | Name | Method Changes | Reagent |
|---|---|---|---|---|
| 73-17 | single isomer (M) | (M)-6,7-dichloro-4-((2R,6R)-2,6-dimethyl-4-(2-propenoyl)-1-piperazinyl)-1-(4-methyl-2-(2-propanyl)-3-pyridinyl)pyrido[2,3-d]pyrimidin-2(1H)-one | Omit Step 4 | Step 2: (3R,5R)-1-Boc-3,5-dimethylpiperazine (AstaTech, Inc.) |
| 73-18 | single isomer (M) | (M)-7-(2-amino-6-fluorophenyl)-6-chloro-4-((2R,6R)-2,6-dimethyl-4-(2-propenoyl)-1-piperazinyl)-1-(4-methyl-2-(2-propanyl)-3-pyridinyl)pyrido[2,3-d]pyrimidin-2(1H)-one | | Step 2: (3R,5R)-1-Boc-3,5-dimethylpiperazine (AstaTech, Inc.), Step 4: (2-amino-6-fluorophenyl)boronic acid pinacol ester (CombiPhos Catalysts, Inc.) |
| 73-19 | single isomer (M) | (M)-6-chloro-4-((2R,6R)-2,6-dimethyl-4-(2-propenoyl)-1-piperazinyl)-7-(2-fluoro-6-hydroxyphenyl)-1-(4-methyl-2-(2-propanyl)-3-pyridinyl)pyrido[2,3-d]pyrimidin-2(1H)-one | | Step 2: (3R,5R)-1-Boc-3,5-dimethylpiperazine (AstaTech, Inc.), Step 4: (2-fluoro-6-hydroxyphenyl)boronic acid (WuXi) |

Method 74
Example 74-1: 7-(2-Fluorophenyl)-6-methyl-4-((2S)-2-methyl-4-(2-propenoyl)-1-piperazinyl)-1-(2-(2-propanyl)phenyl)pyrido[2,3-d]pyrimidin-2(1H)-one
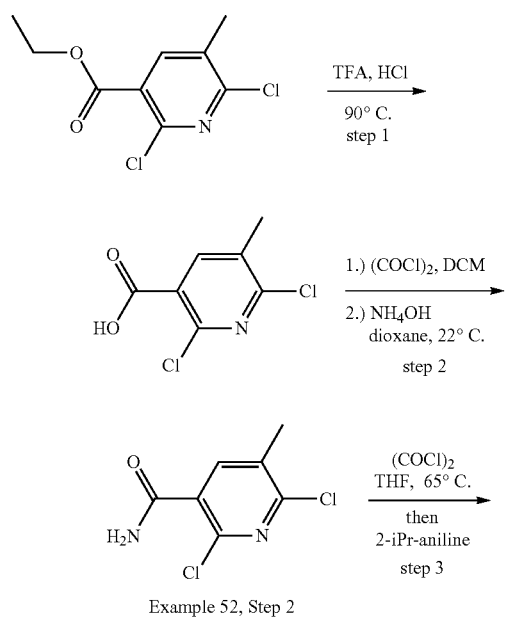
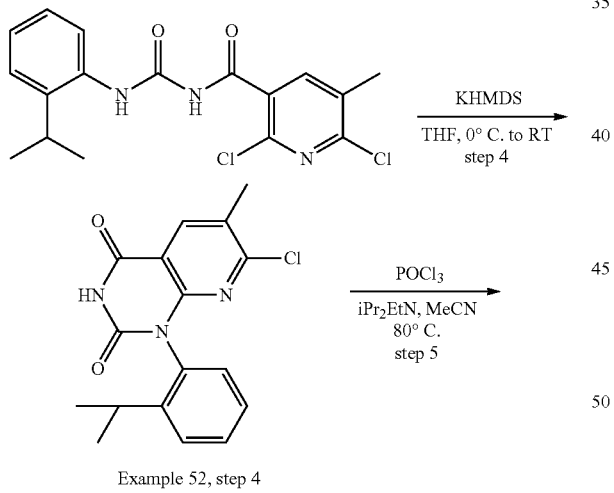
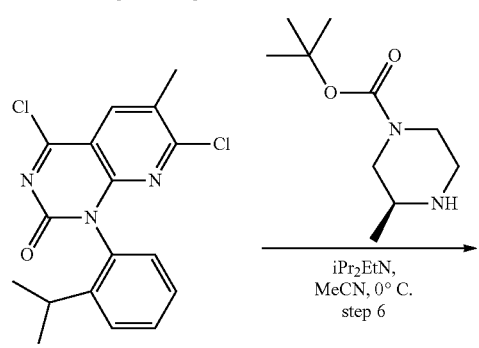
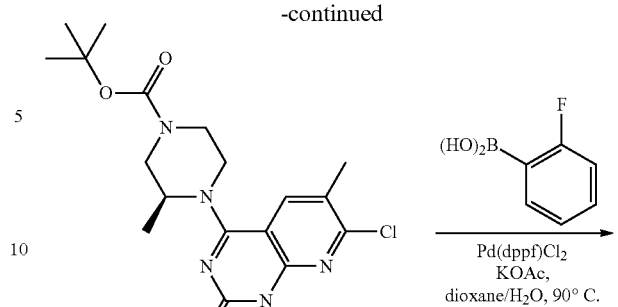
Example 52, step 5
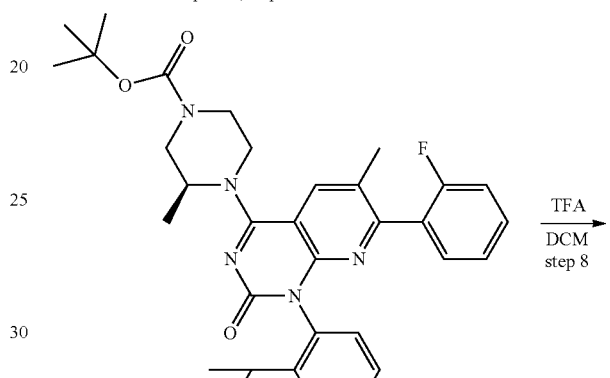
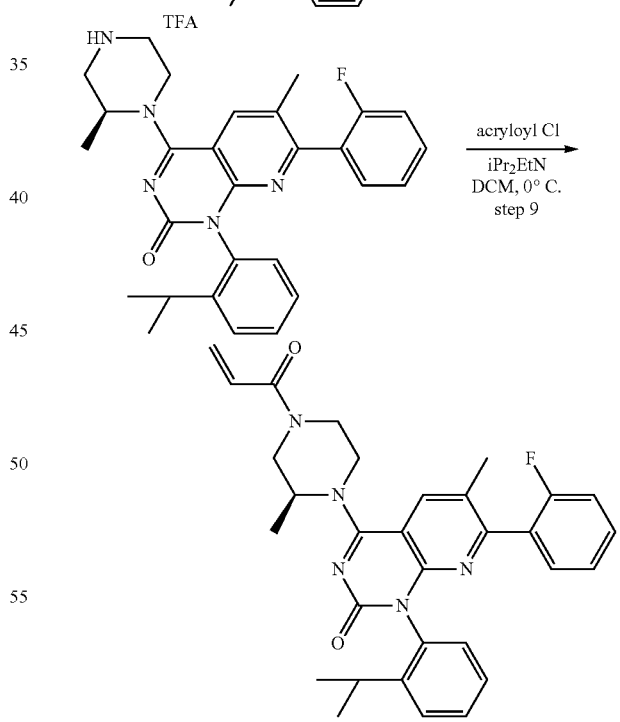
Step 1: 2,6-Dichloro-5-methylnicotinic acid
A mixture of ethyl 2,6-dichloro-5-methylnicotinate (6.49 g, 27.7 mmol, Pharmablock, Inc., Sunnyvale, Calif.) in TFA (30 mL) and 5 N HCl (24 mL) was heated at 90° C. for 16 h. The reaction mixture was allowed to cool to rt and the solvent was partially removed under vacuum. Water was added and the white precipitate obtained was filtered and dried under vacuum to give 2,6-dichloro-5-methylnicotinic acid. m/z (ESI, +ve ion): 205.9 and 207.9 (M+H)$^+$.

Step 2: 2,6-Dichloro-5-methylnicotinamide (Example 52, Step 2)

To a mixture of 2,6-dichloro-5-methylnicotinic acid (4.55 g, 22.1 mmol) in DCM (30 mL) at 0° C. was added oxalyl chloride (2 M in DCM, 16.5 mL, 33 mmol) followed by a couple of drops of DMF. The reaction mixture was allowed to warm to rt for 1 h and the mixture was concentrated in vacuo. The residue was suspended in toluene (15 mL), cooled to 0° C., and treated with 30% aqueous ammonium hydroxide (9.1 mL, 62 mmol). The reaction mixture was stirred at rt for 30 min. The precipitate obtained was filtered, washed with water, and dried under vacuum to give 2,6-dichloro-5-methylnicotinamide (Example 52, Step 2). m/z (ESI, +ve ion): 204.9 and 206.9 (M+H)$^+$.

Step 3: 2,6-Dichloro-N-((2-isopropylphenyl)carbamoyl)-5-methylnicotinamide

A mixture of 2,6-dichloro-5-methylnicotinamide (Example 52, Step 2), 513 mg, 2.50 mmol) and oxalyl chloride (2 M in DCM, 1.38 mL, 2.63 mmol) in THF (10 mL) was stirred with a reflux condenser at 65° C. for 1 h. The reaction mixture was then cooled to rt and 2-isopropylaniline (0.36 mL, 2.63 mmol) was added. The resulting mixture was stirred at rt for 1 h and then the solvent was removed under vacuum. The residue was partitioned between EtOAc and satd. NaHCO$_3$. The organic layer was washed with water, dried over Na$_2$SO$_4$, filtered, and concentrated in vacuo. The residue was triturated with a mixture of heptane:EtOAc (5:1), filtered, and dried under vacuum to give 2,6-dichloro-N-((2-isopropylphenyl)carbamoyl)-5-methylnicotinamide. m/z (ESI, +ve ion): 365.8 and 367.9 (M+H)$^+$.

Step 4: 7-Chloro-1-(2-isopropylphenyl)-6-methylpyrido[2,3-d]pyrimidine-2,4(1H,3H)-dione (Example 52, Step 4)

1 M KHMDS in THF (4.5 mL, 4.5 mmol) was added to a solution of 2,6-dichloro-N-((2-isopropylphenyl)carbamoyl)-5-methylnicotinamide (831 mg, 2.27 mmol) in THF (10 mL) at 0° C., and the resulting mixture was allowed to warm to rt over 2 h. The reaction mixture was then diluted with EtOAc (20 mL) and washed with satd. ammonium chloride (2×10 mL). The organic layer was dried over Na$_2$SO$_4$, filtered, and concentrated in vacuo. The residue was triturated with heptane-EtOAc (5:1). filtered, and dried to give 7-chloro-1-(2-isopropylphenyl)-6-methylpyrido[2,3-d]pyrimidine-2,4(1H,3H)-dione (Example 52, Step 4): $^1$H NMR (400 MHz, DMSO-d$_6$) δ 8.36 (s, 1H), 7.49 (dd, J=8.5, 1.4 Hz, 1H), 7.44 (td, J=6.8, 1.2 Hz, 1H), 7.26-7.33 (m, 1H), 7.23 (dd, J=7.9, 1.7 Hz, 1H), 2.68 (quin, J=6.8 Hz, 1H), 2.34 (s, 3H), 1.08 (d, J=6.8 Hz, 3H), 1.02 (d, J=6.6 Hz, 3H). m/z (ESI, +ve ion): 329.9 and 331.9 (M+H)$^+$.

Step 5: 4,7-Dichloro-1-(2-isopropylphenyl)-6-methylpyrido[2,3-d]pyrimidin-2(1H)-one To a solution of 7-chloro-1-(2-isopropylphenyl)-6-methylpyrido[2,3-d]pyrimidine-2,4(1H,3H)-dione (Example 52, Step 4, 444 mg, 1.35 mmol) and DIPEA (0.7 mL, 4.04 mmol) in acetonitrile (5 mL) was added phosphorus oxychloride (0.13 mL, 1.35 mmol), and the resulting solution was stirred at 80° C. for 2 h. The reaction mixture was concentrated in vacuo to give 4,7-dichloro-1-(2-isopropylphenyl)-6-methylpyrido[2,3-d]pyrimidin-2(1H)-one. m/z (ESI, +ve ion): 343.9 (M+H)$^+$ (quenched with MeOH).

Step 6: tert-Butyl (S)-4-(7-chloro-1-(2-isopropylphenyl)-6-methyl-2-oxo-1,2-dihydropyrido[2,3-d]pyrimidin-4-yl)-3-methylpiperazine-1-carboxylate (Example 52, Step 5)

To a solution of 4,7-dichloro-1-(2-isopropylphenyl)-6-methylpyrido[2,3-d]pyrimidin-2(1H)-one (470 mg, 1.35 mmol) and DIPEA (0.7 mL, 4.04 mmol) in acetonitrile (5 mL) at 0° C. was added tert-butyl (S)-3-methylpiperazine-1-carboxylate (297 mg, 1.48 mmol). The reaction mixture was stirred at 0° C. for 0.5 h and allowed to warm to rt. The reaction mixture was then diluted with EtOAc (10 mL) and washed with water (2×10 mL). The organic layer was dried over Na$_2$SO$_4$, filtered, and concentrated in vacuo. The crude product was purified by silica gel chromatography (eluent: 0-30% EtOAc-EtOH (3:1)/heptane) to provide tert-butyl (S)-4-(7-chloro-1-(2-isopropylphenyl)-6-methyl-2-oxo-1,2-dihydropyrido[2,3-d]pyrimidin-4-yl)-3-methylpiperazine-1-carboxylate (Example 52, Step 5): $^1$H NMR (400 MHz, DMSO-d$_6$) δ 8.16 (d, J=16.2 Hz, 1H), 7.47 (dd, J=6.8, 1.2 Hz, 1H), 7.41 (br t, J=7.3 Hz, 1H), 7.28 (dt, J=7.7, 1.2 Hz, 1H), 7.09 (dt. J=7.8, 1.6 Hz, 1H), 4.70-4.90 (m, 1H), 3.89-4.20 (m, 2H), 3.97-4.09 (m, 2H), 3.76-3.88 (m, 1H), 3.53-3.72 (m, 1H), 2.44 (td, J=6.8, 4.9 Hz, 1H), 2.35 (d, J=0.8 Hz, 3H), 1.45 (s, 9H), 1.25 (br s, 3H), 1.06 (d, J=6.8, 3H), 1.02 (dd, J=6.8, 1.7 Hz, 3H). m/z (ESI, +ve ion): 511.9 and 514.0 (M+H)$^+$.

Step 7: tert-Butyl (S)-4-(7-(2-fluorophenyl)-1-(2-isopropylphenyl)-6-methyl-2-oxo-1,2-dihydropyrido[2,3-d]pyrimidin-4-yl)-3-methylpiperazine-1-carboxylate A mixture of tert-butyl (S)-4-(7-chloro-1-(2-isopropylphenyl)-6-methyl-2-oxo-1,2-dihydropyrido[2,3-d]pyrimidin-4-yl)-3-methylpiperazine-1-carboxylate (Example 52, Step 5, 400 mg, 0.78 mmol), (2-fluorophenyl)boronic acid (197 mg, 1.41 mmol), potassium acetate (383 mg, 3.91 mmol), and Pd(dppf)Cl$_2$ (57 mg, 0.08 mmol) in 1,4-dioxane (6 mL), water (0.06 mL) was stirred at 90° C. for 4 h. The reaction mixture was quenched with satd. NaHCO$_3$ (15 mL) and extracted with EtOAc (20 mL). The organic layer was separated, washed with brine (10 mL), dried over Na$_2$SO$_4$, filtered, and concentrated in vacuo. The crude product was purified by silica gel chromatography (eluent: 0-30% EtOAc-EtOH (3:1)/heptane) to provide tert-butyl (S)-4-(7-(2-fluorophenyl)-1-(2-isopropylphenyl)-6-methyl-2-oxo-1,2-dihydropyrido[2,3-d]pyrimidin-4-yl)-3-methylpiperazine-1-carboxylate as an off-white solid. m/z (ESI, +ve ion): 572.0 (M+H)$^+$.

Step 8: (S)-7-(2-Fluorophenyl)-1-(2-isopropylphenyl)-6-methyl-4-(2-methylpiperazin-1-yl)pyrido[2,3-d]pyrimidin-2(1H)-one To a 50-mL round bottomed flask was added tert-butyl (S)-4-(7-(2-fluorophenyl)-1-(2-isopropylphenyl)-6-methyl-2-oxo-1,2-dihydropyrido[2,3-d]pyrimidin-4-yl)-3-methylpiperazine-1-carboxylate (350 mg, 0.61 mmol), TFA (1.0 mL, 9.18 mmol) and DCM (5 mL). The reaction mixture was stirred at rt for 1 h and the mixture was concentrated in vacuo to provide (S)-7-(2-fluorophenyl)-1-(2-isopropylphenyl)-6-methyl-4-(2-methylpiperazin-1-yl)pyrido[2,3-d]pyrimidin-2(1H)-one. m/z (ESI, +ve ion): 472.0 (M+H)⁺.

Step 9: 7-(2-Fluorophenyl)-6-methyl-4-((2S)-2-methyl-4-(2-propenoyl)-1-piperazinyl)-1-(2-(2-propanyl)phenyl)pyrido[2,3-d]pyrimidin-2(1H)-one To a solution of (S)-7-(2-fluorophenyl)-1-(2-isopropylphenyl)-6-methyl-4-(2-methylpiperazin-1-yl)pyrido[2,3-d]pyrimidin-2(1H)-one (289 mg, 0.61 mmol) and DIPEA (0.43 mL, 2.45 mmol) in DCM (5 mL) at 0° C. was added acryloyl chloride (0.05 mL, 0.61 mmol) in DCM (0.5 mL). The reaction mixture was stirred at 0° C. for 30 min and quenched with satd. NaHCO₃ (5 mL) and extracted with EtOAc (10 mL). The organic layer was separated, washed with brine (5 mL), dried over Na₂SO₄, filtered, and concentrated in vacuo. The crude product was purified by silica gel chromatography (eluent: 0-40% EtOAc-EtOH (3:1)/heptane) followed by prep. HPLC (Phenomenex Gemini column, 10 micron, C18, 100 Å, 150×30 mm, 0.1% TFA in CH₃CN/H₂O, gradient 10% to 100% over 10 min). Fractions containing the title compound were combined and concentrated in vacuo. The residue was partitioned between DCM and satd. NaHCO₃. The organic layer was dried over Na₂SO₄, filtered, and concentrated in vacuo to give 7-(2-fluorophenyl)-6-methyl-4-((2S)-2-methyl-4-(2-propenoyl)-1-piperazinyl)-1-(2-(2-propanyl)phenyl)pyrido[2,3-d]pyrimidin-2(1H)-one. ¹H NMR (400 MHz, DMSO-d₆) δ 8.15 (s, 1H), 7.42-7.49 (m, 1H), 7.39 (dd, J=7.5, 1.0 Hz, 1H), 7.32 (dt, J=7.3, 1.0 Hz, 1H), 7.19-7.29 (m, 3H), 7.15 (dt. J=7.7, 1.4 Hz, 1H), 7.08 (d, J=7.7 Hz, 1H), 6.77-6.97 (m, 1H), 6.20 (dd, J=17.0, 5.0 Hz, 1H), 5.76 (dd, J=10.2, 2.1 Hz, 1H), 4.81 (br s, 1H), 4.10-4.55 (m, 3H), 3.45-3.81 (m, 2H), 2.52-2.56 (m, 1H), 1.35 (d, J=6.6 Hz, 3H), 1.21-1.33 (m, 4H), 1.06 (d, J=6.8 Hz, 3H), 0.94-0.98 (m, 3H). m/z (ESI, +ve ion): 526.0 (M+H)⁺.

TABLE 74

Compounds 74-2 to 74-3 were prepared following the procedure described in Method 74, Steps 1-9, above as follows:

| Ex. # | Chemical Structure | Name | Method Changes | Reagent |
|---|---|---|---|---|
| 74-2 | 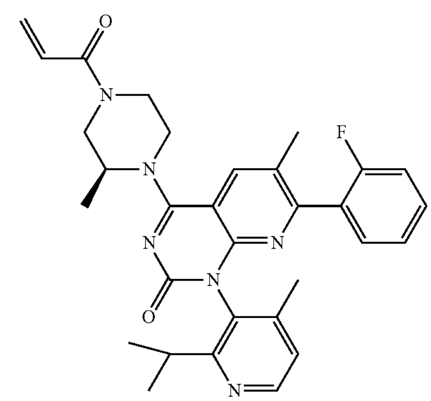 [SMILES: C=CC(=O)N1CCN(c2nc(=O)n(-c3c(C)ccnc3C(C)C)c3nc(-c4ccccc4F)c(C)cc23)[C@@H](C)C1] | 7-(2-fluorophenyl)-6-methyl-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | Step 5 and Step 6 one pot | Step 3: 2-isopropyl-4-methylpyridin-3-amine (Intermediate R), Step 7: (2-fluorophenyl)boronic acid (Combi-Blocks Inc.) |
| 74-3 | 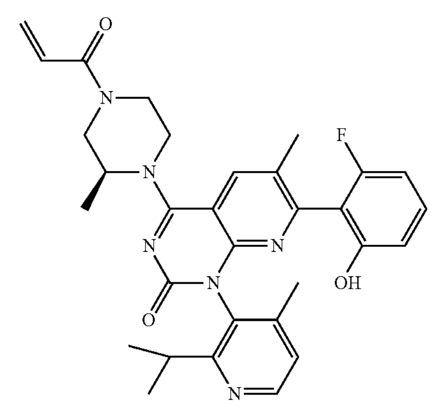 [SMILES: C=CC(=O)N1CCN(c2nc(=O)n(-c3c(C)ccnc3C(C)C)c3nc(-c4c(O)cccc4F)c(C)cc23)[C@@H](C)C1] | 7-(2-fluoro-6-hydroxyphenyl)-6-methyl-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | Step 5 and Step 6 one pot | Step 3: 2-isopropyl-4-methylpyridin-3-amine (Intermediate R), Step 7: (2-fluoro-6-hydroxyphenyl)boronic acid (WuXi) |

Method 75

Example 75-1: (M)-4-(cis-2,6-Dimethyl-4-(2-propenoyl)-1-piperazinyl)-6-fluoro-7-(2-fluoro-6-hydroxyphenyl)-1-(4-methyl-2-(2-propanyl)-3-pyridinyl)pyrido[2,3-d]pyrimidin-2(1H)-one

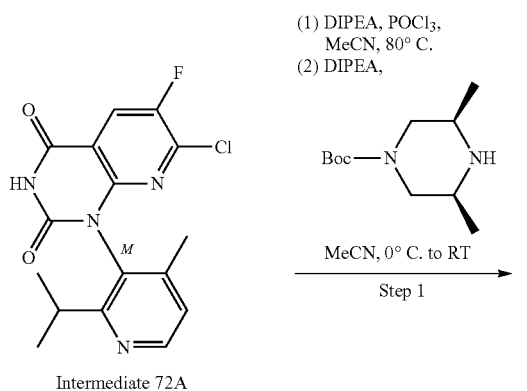

Intermediate 72A

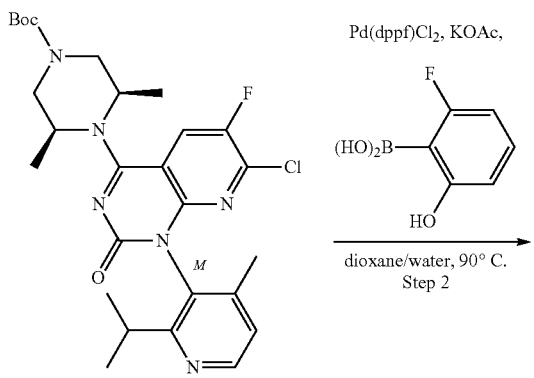

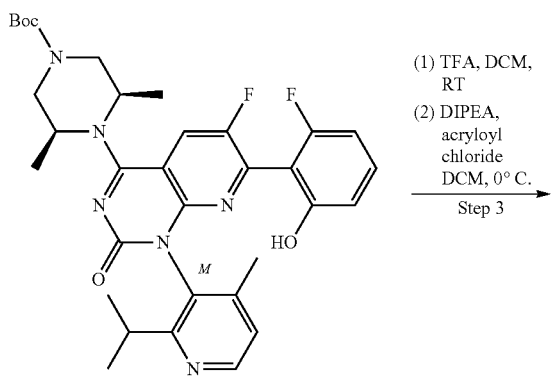

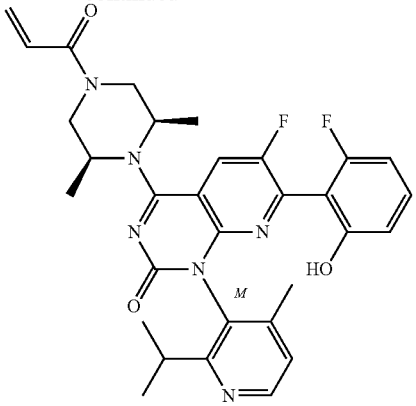

Step 1: (M)-tert-Butyl cis-4-(7-fluoro-6-fluoro-1-(2-isopropyl-4-methylpyridin-3-yl)-2-oxo-1,2-dihydropyrido[2,3-d]pyrimidin-4-yl)-3,5-dimethylpiperazine-1-carboxylate Phosphorous oxychloride (0.072 mL, 0.774 mmol) was added dropwise to a solution of (M)-7-chloro-6-fluoro-1-(2-isopropyl-4-methylpyridin-3-yl)pyrido[2,3-d]pyrimidine-2,4(1H,3H)-dione (Intermediate 72A, 180 mg, 0.52 mmol) and DIPEA (0.14 mL, 0.83 mmol) in acetonitrile (2 mL). This mixture was heated to 80° C. for 3 h. The reaction mixture was cooled to 10° C. and DIPEA (0.27 mL) was added followed by cis-3,5-dimethyl-piperazine-1-carboxylic acid tert-butyl ester (0.122 g, 0.57 mmol). This mixture was allowed to warm to rt and stirred at rt for 18 h. The mixture was poured into ice-cold satd. NaHCO$_3$ and stirred vigorously for 10 min. EtOAc was added and the mixture was separated. The organic extracts were dried over Na$_2$SO$_4$, filtered, and concentrated in vacuo. The crude material was used directly in the following step.

Step 2: (M)-tert-Butyl cis-4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3,5-dimethylpiperazine-1-carboxylate A 100-mL round bottomed flask was charged with (M)-tert-butyl cis-4-(7-chloro-6-fluoro-1-(2-isopropyl-4-methylpyridin-3-yl)-2-oxo-1,2-dihydropyrido[2,3-d]pyrimidin-4-yl)-3,5-dimethylpiperazine-1-carboxylate (281 mg, 0.516 mmol), (2-fluoro-6-hydroxyphenyl)boronic acid (97 mg, 0.62 mmol, Combi-Blocks, San Diego, Calif., USA), dichloro[1,1'-bis(diphenylphosphino)ferrocene]palladium (II) DCM adduct (38 mg, 0.052 mmol), potassium acetate (253 mg, 2.58 mmol), and 1,4-dioxane (5 mL). The mixture was degassed by bubbling nitrogen through the reaction mixture. A drop of water was added and the mixture was stirred at 90° C. for 18 h. The reaction mixture was cooled to rt, partitioned between EtOAc and brine. The aqueous layer was extracted with EtOAc and the combined EtOAc layers were dried over Na$_2$SO$_4$ and concentrated in vacuo. The crude product was purified by silica gel chromatography (eluent: 0-25% EtOAc-EtOH (3:1)/heptane) to provide (M)-tert-butyl (3R,5S)-4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3,5-di methylpiperazine-1-carboxylate (163 mg, 0.263 mmol, 50.9% yield) as an off-white solid. m/z (ESI, +ve ion): 621.2 (M+H)$^+$.

Step 3: (M)-4-(cis-2,6-Dimethyl-4-(2-propenoyl)-1-piperazinyl)-6-fluoro-7-(2-fluoro-hydroxyphenyl)-1-(4-methyl-2-(2-propanyl)-3-pyridinyl)pyrido[2,3-d]pyrimidin-2(1H)-one To a solution of (M)-tert-butyl cis-4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3,5-dimethylpiperazine-1-carboxylate (163 mg, 0.263 mmol) in DCM (1.8 mL) was added TFA (0.59 mL, 7.88 mmol) dropwise. The reaction mixture was stirred at rt for 30 min. The mixture was concentrated in vacuo to give crude product which was used directly in the following step.

To the mixture of (M)-4-(cis-2,6-dimethylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one, and N,N'-diisopropylethylamine (0.21 mL, 1.18 mmol) in DCM (1.7 mL) was added acryloyl chloride (24 µL, 0.293 mmol) at 0° C. and stirred for 30 min. The resulting mixture was concentrated in vacuo and purified by silica gel chromatography (eluent: 0-45% EtOAc-EtOH (3:1)/heptane) to provide (M)-4-(cis-2,6-dimethyl-4-(2-propenoyl)-1-piperazinyl)-6-fluoro-7-(2-fluoro-6-hydroxyphenyl)-1-(4-methyl-2-(2-propanyl)-3-pyridinyl)pyrido[2,3-d]pyrimidin-2(1H)-one (123 mg, 0.214 mmol, 82% yield) as an off-white solid. $^1$H NMR (400 MHz, DMSO-$d_6$) δ 10.21 (s, 1H), 8.39 (d, J=4.77 Hz, 1H), 8.16 (d, J=9.54 Hz, 1H), 7.12-7.35 (m, 2H), 6.90 (dd, J=10.37, 16.59 Hz, 1H), 6.64-6.78 (m, 2H), 6.26 (dd, J=2.38, 16.69 Hz, 1H), 5.77-5.85 (m, 1H), 5.00 (br d, J=2.49 Hz, 2H), 4.23-4.39 (m, 1H), 3.97-4.12 (m, 1H), 3.54-3.69 (m, 1H), 3.29-3.42 (m, 1H), 2.64-2.78 (m, 1H), 1.91 (br s, 3H), 1.47 (dd, J=6.84, 14.10 Hz, 6H), 1.08 (d, J=6.63 Hz, 3H), 0.94 (d, J=6.63 Hz, 3H). $^{19}$F NMR (376 MHz, DMSO-$d_6$) δ −115.68 (br s, 1F), −128.58 (br s, 1F). m/z (ESI, +ve ion): 575.2 (M+H)$^+$.

TABLE 75

Compounds 75-2 to 75-9-2 were prepared following the procedure described in Method 75, Steps 1-3, above as follows:

| Ex. # | Chemical Structure | Name | Method Changes | Reagent |
|---|---|---|---|---|
| 75-2 | 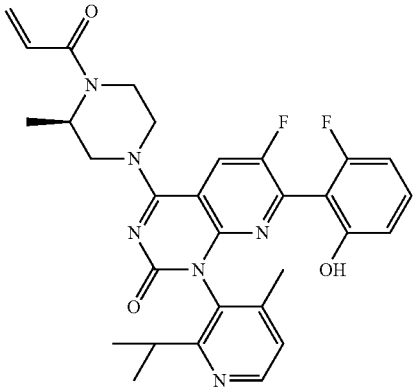 [SMILES: C=CC(=O)N1CCN(c2nc(=O)n(-c3c(C)ccnc3C(C)C)c3nc(-c4c(O)cccc4F)c(F)cc23)C[C@H]1C] single isomer (M) | (M)-6-fluoro-7-(2-fluoro-6-hydroxyphenyl)-1-(4-methyl-2-(2-propanyl)-3-pyridinyl)-4-((3R)-3-methyl-4-(2-propenoyl)-1-piperazinyl)pyrido[2,3-d]pyrimidin-2(1H)-one | | Step 1: (R)-1-Boc-2-methyl-piperazine (J & W Pharmlab, LLC), Step 2: (2-fluoro-6-hydroxyphenyl) boronic acid (Wuxi) |
| 75-3 | 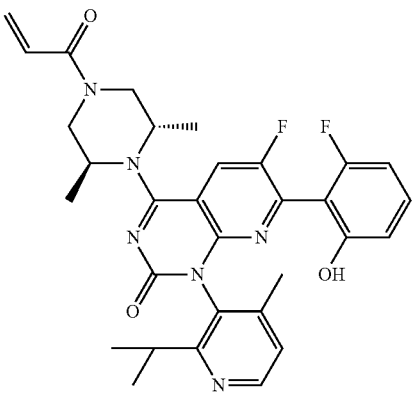 [SMILES: C=CC(=O)N1C[C@H](C)N(c2nc(=O)n(-c3c(C)ccnc3C(C)C)c3nc(-c4c(O)cccc4F)c(F)cc23)[C@@H](C)C1] single isomer (M) | (M)-4-((2S,6S)-2,6-dimethyl-4-(2-propenoyl)-1-piperazinyl)-6-fluoro-7-(2-fluoro-6-hydroxyphenyl)-1-(4-methyl-2-(2-propanyl)-3-pyridinyl)pyrido[2,3-d]pyrimidin-2(1H)-one | | Step 1: tert-butyl (3S,5S)-3,5-dimethylpiperazine-1-carboxylate (eNovation Chemicals LLC), Step 2: (2-fluoro-6-hydroxyphenyl) boronic acid (Wuxi) |

TABLE 75-continued

Compounds 75-2 to 75-9-2 were prepared following the procedure described in Method 75, Steps 1-3, above as follows:

| Ex. # | Chemical Structure | Name | Method Changes | Reagent |
|---|---|---|---|---|
| 75-4 | single isomer (M) | (M)-6-fluoro-7-(2-fluoro-6-hydroxyphenyl)-1-(4-methyl-2-(2-propanyl)-3-pyridinyl)-4-(4-(2-propenoyl)-1-piperazinyl)pyrido[2,3-d]pyrimidin-2(1H)-one | | Step 1: tert-butyl piperazine-1-carboxylate (Combi-blocks Inc.), Step 2: (2-fluoro-6-hydroxyphenyl) boronic acid (Wuxi) |
| 75-5 | single isomer (M) | (M)-6-fluoro-7-(2-fluoro-6-hydroxyphenyl)-1-(4-methyl-2-(2-propanyl)-3-pyridinyl)-4-((2R)-2-methyl-4-(2-propenoyl)-1-piperazinyl)pyrido[2,3-d]pyrimidin-2(1H)-one | | Step 1: (R)-4-Boc-2-methylpiperizine (Sigma-Aldrich Corporation, Step 2: (2-fluoro-6-hydroxyphenyl) boronic acid (Wuxi) |
| 75-6 | single isomer (M) | (M)-N-(1-(6-fluoro-7-(2-fluoro-6-hydroxyphenyl)-1-(4-methyl-2-(2-propanyl)-3-pyridinyl)-2-oxo-1,2-dihydropyrido[2,3-d]pyrimidin-4-yl)-3-azetidinyl)-2-propenamide | | Step 1: 3-(tert-butoxycarbonylamino)azetidine (AstaTech, Inc.) |

TABLE 75-continued

Compounds 75-2 to 75-9-2 were prepared following the procedure described in Method 75, Steps 1-3, above as follows:

| Ex. # | Chemical Structure | Name | Method Changes | Reagent |
|---|---|---|---|---|
| 75-7 | single isomer (M) | (M)-6-fluoro-7-(2-fluoro-6-hydroxyphenyl)-1-(4-methyl-2-(2-propanyl)-3-pyridinyl)-4-((1S,5S)-3-(2-propenoyl)-3,6-diazabicyclo[3.2.0]heptan-6-yl)pyrido[2,3-d]pyrimidin-2(1H)-one | | Step 1: (S,S)-3-Boc-3,6-diazabicyclo[3.2.0]heptane (Synthonix Inc.) |
| 75-8 | single isomer (M) | (M)-7-(2-amino-6-fluorophenyl)-4-((2R,6S)-2,6-dimethyl-4-(2-propenoyl)-1-piperazinyl)-6-fluoro-1-(4-methyl-2-(2-propanyl)-3-pyridinyl)pyrido[2,3-d]pyrimidin-2(1H)-one | Step 2: Pd(PPh₃)₄, K₂CO₃, Step 3: Aqueous workup (basic wash with saturated NaHCO₃) after Boc deprotection, omit DIEA | Step 1: (3R,5S)-3,5-dimethyl-piperazine-1-carboxylic acid tert-butyl ester (Combi-Blocks Inc.), Step 2: (2-amino-6-fluorophenyl) boronic acid pinacol ester (CombiPhos Catalysts) |
| 75-9-1 | single isomer (M and 2S or 2R) | (M)-4-((2S or 2R)-2-(difluoromethyl)-4-(2-propenoyl)-1-piperazinyl)-6-fluoro-7-(2-fluoro-6-hydroxyphenyl)-1-(4-methyl-2-(2-propanyl)-3-pyridinyl)pyrido[2,3-d]pyrimidin-2(1H)-one | Step 3: Aqueous workup (basic wash with saturated NaHCO₃) after Boc deprotection omit DIEA | Step 1: tert-butyl 3-(difluoromethyl)piperazine-1-carboxylate (Enamine) Step 2: potassium trifluoro(2-fluoro-6-hydroxyphenyl)borate (Intermediate Q) |

TABLE 75-continued

Compounds 75-2 to 75-9-2 were prepared following the procedure described in Method 75, Steps 1-3, above as follows:

| Ex. # | Chemical Structure | Name | Method Changes | Reagent |
|---|---|---|---|---|
| 75-9-2 | 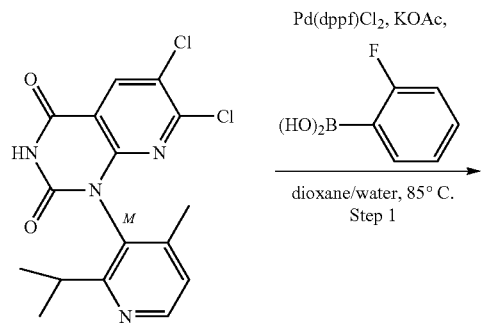 single isomer (M and 2S or 2R) | (M)-4-((2S or 2R)-2-(difluoromethyl)-4-(2-propenoyl)-1-piperazinyl)-6-fluoro-7-(2-fluoro-6-hydroxyphenyl)-1-(4-methyl-2-(2-propanyl)-3-pyridinyl)pyrido[2,3-d]pyrimidin-2(1H)-one | Step 3: Aqueous workup (basic wash with saturated NaHCO$_3$) after Boc deprotection, omit DIEA | Step 1: tert-butyl 3-(difluoromethyl)piperazine-1-carboxylate (Enamine) Step 2: potassium trifluoro(2-fluoro-6-hydroxyphenyl)borate (Intermediate Q) |

Method 76

Example 76-1: (M)-6-Chloro-7-(2-fluorophenyl)-1-(4-methyl-2-(2-propanyl)-3-pyridinyl)-4-((1-(2-propenoyl)-3-azetidinyl)amino)pyrido[2,3-d]pyrimidin-2(1H)-one

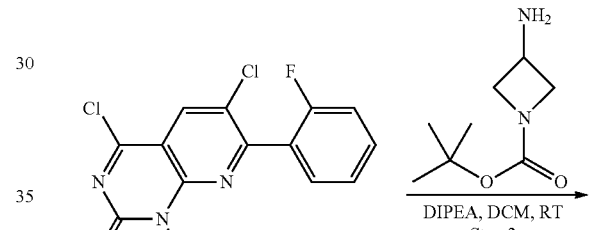

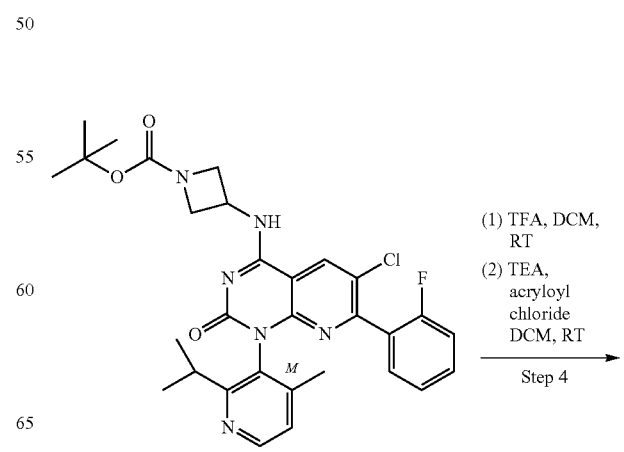

-continued

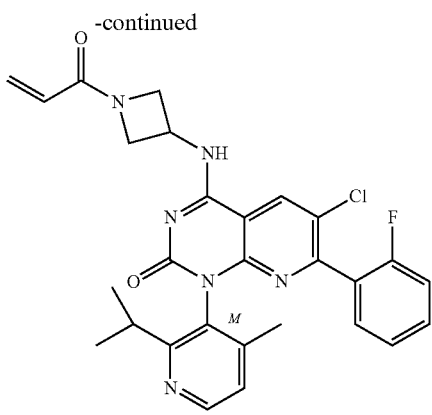

Step 1: (M)-6-Chloro-7-(2-fluorophenyl)-4-hydroxy-1-(2-isopropyl-4-methylpyridin-3-yl)pyrido[2,3-d]pyrimidin-2(1H)-one (Intermediate 76A)

A mixture of (M)-6,7-dichloro-1-(2-isopropyl-4-methylpyridin-3-yl)pyrido[2,3-d]pyrimidine-2,4(1H,3H)-dione (Intermediate 73B, 4.38 g, 12 mmol), 2-fluorophenylboronic acid (2.35 g, 16.8 mmol), (1,1'-bis(diphenylphosphino) ferrocene) dichloropalladium (0.351 g, 0.48 mmol), potassium acetate (5.1 g, 52.0 mmol) in 1,4-dioxane (30 mL) and water (1 mL) was stirred and heated at 85° C. for 15 h. The mixture was cooled to rt and diluted with EtOAc and water. The organic layer was washed with brine, dried over $Na_2SO_4$, filtered, and concentrated in vacuo. The residue was purified by silica gel chromatography (eluent: 0-40% EtOAc/heptane) to provide (M)-6-chloro-7-(2-fluorophenyl)-1-(2-isopropyl-4-methylpyridin-3-yl)pyrido[2,3-d]pyrimidine-2,4(1H,3H)-dione (Intermediate 76A) as white solids. m/z (ESI, +ve ion): 424.9 $(M+H)^+$.

Step 2: (M)-4,6-Dichloro-7-(2-fluorophenyl)-1-(2-isopropyl-4-methylpyridin-3-yl)pyrido[2,3-d]pyrimidin-2(1H)-one To (M)-6-chloro-7-(2-fluorophenyl)-1-(2-isopropyl-4-methylpyridin-3-yl)pyrido[2,3-d]pyrimidine-2,4(1H,3H)-dione (Intermediate 76A, 1.0 g, 2.35 mmol) in acetonitrile (12 mL) was added phosphorous oxychloride (0.4 mL, 4.29 mmol) and DIPEA (1.5 mL, 8.59 mmol). The mixture was stirred and heated at 80° C. for 5 h. The mixture was cooled to rt and concentrated in vacuo then diluted with EtOAc and water. The organic layer was washed with satd. $NaHCO_3$, brine, and dried over dried over $Na_2SO_4$, filtered, and concentrated in vacuo. The crude product was purified by silica gel chromatography (eluent: 0-50% EtOAc/heptane) to provide (M)-4,6-dichloro-7-(2-fluorophenyl)-1-(2-isopropyl-4-methylpyridin-3-yl)pyrido[2,3-d]pyrimidin-2(1H)-one as a yellow solid.

Step 3: (M)-tert-Butyl 3-((6-chloro-7-(2-fluorophenyl)-1-(2-isopropyl-4-methylpyridin-3-yl)-2-oxo-1,2-dihydropyrido[2,3-d]pyrimidin-4-yl)amino)azetidine-1-carboxylate To (M)-4,6-dichloro-7-(2-fluorophenyl)-1-(2-isopropyl-4-methylpyridin-3-yl)pyrido[2,3-d]pyrimidin-2(1H)-one (0.27 g, 0.609 mmol) in DCM (7 mL) was added 1-(tert-butoxycarbonyl)-3-aminoazetidine (0.2 mL, 1.16 mmol) and DIPEA (0.2 mL, 1.15 mmol). The mixture was stirred at rt for 10 min and concentrated in vacuo. The crude product was purified by silica gel chromatography (eluent: 0-40% EtOAc-EtOH (3:1)/heptane) to provide (M)-tert-butyl 3-((6-chloro-7-(2-fluorophenyl)-1-(2-isopropyl-4-methylpyridin-3-yl)-2-oxo-1,2-dihydropyrido[2,3-d]pyrimidin-4-yl)amino)azetidine-1-carboxylate. m/z (ESI, +ve ion): 578.9 $(M+H)^+$.

Step 4: (M)-6-Chloro-7-(2-fluorophenyl)-1-(4-methyl-2-(2-propanyl)-3-pyridinyl)-4-((1-(2-propenoyl)-3-azetidinyl)amino)pyrido[2,3-d]pyrimidin-2(1H)-one A mixture of (M)-tert-butyl 3-((6-chloro-7-(2-fluorophenyl)-1-(2-isopropyl-4-methylpyridin-3-yl)-2-oxo-1,2-dihydropyrido[2,3-d]pyrimidin-4-yl)amino)azetidine-1-carboxylate (0.2 mL, 0.22 mmol) in DCM (3 mL) and TFA (3 mL) was stirred at rt for 30 min. The mixture was concentrated in vacuo and the residue was dissolved in DCM (3 mL) and treated with TEA (0.15 mL, 1.07 mmol). To the mixture was added acryloyl chloride (1.1 M solution in DCM, 0.018 mL, 0.22 mmol). The mixture was stirred at rt for 5 min and concentrated in vacuo. The crude product was purified by silica gel chromatography (eluent: 0-90% EtOAc-EtOH (3:1)/heptane) to provide (M)-6-chloro-7-(2-fluorophenyl)-1-(4-methyl-2-(2-propanyl)-3-pyridinyl)-4-((1-(2-propenoyl)-3-azetidinyl)amino)pyrido[2,3-d]pyrimidin-2(1H)-one as a white solid. $^1$H NMR (400 MHz, DMSO-$d_6$) δ ppm 0.88-0.97 (m, 3H) 1.02-1.10 (m, 3H) 1.88-1.96 (m, 3H) 2.65-2.76 (m, 1H) 4.05-4.19 (m, 1H) 4.23-4.41 (m, 2H) 4.61-4.74 (m, 1H) 4.94-5.08 (m, 1H) 5.67-5.77 (m, 1H) 6.10-6.22 (m, 1H) 6.33-6.49 (m, 1H) 7.15-7.35 (m, 4H) 7.45-7.56 (m, 1H) 8.34-8.43 (m, 1H) 8.96-9.05 (m, 1H) 9.24-9.36 (m, 1H). $^{19}$F NMR (376 MHz, DMSO-$d_6$) δ ppm −117.37−−110.35 (m, 1F). m/z (ESI, +ve ion): 532.8 $(M+H)^+$.

TABLE 76

Compounds 76-2 was prepared following the procedure described in Method 76, Steps 1-4, above as follows:

| Ex. # | Chemical structure | Name | Method Changes | Reagent |
|---|---|---|---|---|
| 76-2 | 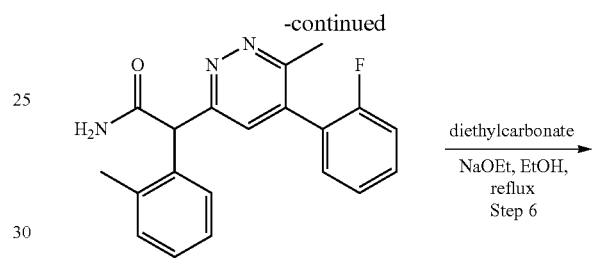 single isomer (M) | (M)-6-chloro-7-(2-fluorophenyl)-1-(4-methyl-2-(2-propanyl)-3-pyridinyl)-4-(methyl(1-(2-propenoyl)-3-azetidinyl)amino)pyrido[2,3-d]pyrimidin-2(1H)-one | | Step 3: tert-butyl 3-(methylamino)azetidine-1-carboxylate (Sigma-Aldrich Corporation) |

Method 77

Example: 77-1: 3-(2-Fluorophenyl)-2-methyl-5-(2-methylphenyl)-8-(4-(2-propenoyl)-1-piperazinyl)-6H-pyrimido[1,6-b]pyridazin-6-one

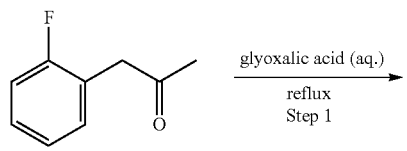 glyoxalic acid (aq.)
reflux
Step 1

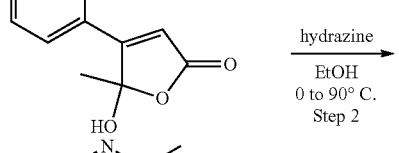 hydrazine
EtOH
0 to 90° C.
Step 2

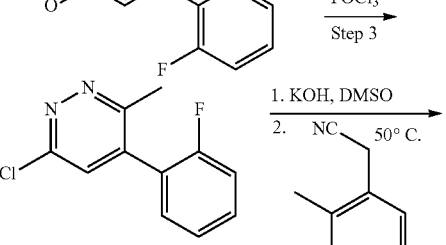 POCl₃
Step 3

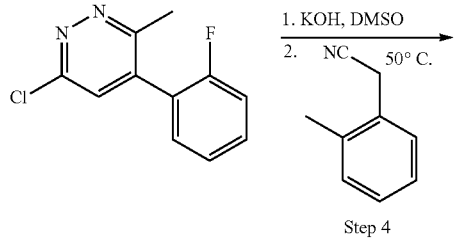 1. KOH, DMSO
2. NC— (2-methylbenzyl)
50° C.
Step 4

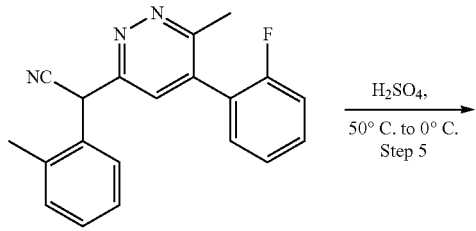 H₂SO₄,
50° C. to 0° C.
Step 5

-continued

 diethylcarbonate
NaOEt, EtOH,
reflux
Step 6

 1. POCl₃
2. DIPEA, DCM, 0° C.
tert-butyl piperazine-1-carboxylate
Step 7

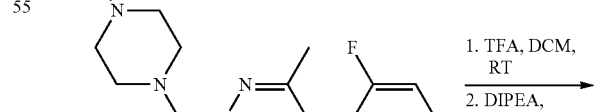 1. TFA, DCM, RT
2. DIPEA, acryloyl chloride, DCM, 0° C.
Step 8

-continued

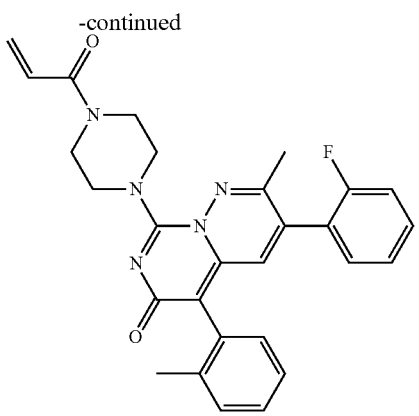

Step 1: 4-(2-Fluorophenyl)-5-hydroxy-5-methyl-furan-2(5H)-one

In a 250-mL round-bottomed flask, 1-(2-fluorophenyl)propan-2-one (5.18 g, 34 mmol) was treated with glyoxalic acid (50 wt % in water, 5.63 mL, 51.1 mmol). The mixture was stirred and heated at 100° C. After heating overnight, the mixture was concentrated in vacuo and co-evaporated with toluene and used in the subsequent step without further purification. m/z (ESI, +ve ion): 209.1 (M+H)$^+$.

Step 2: 5-(2-Fluorophenyl)-6-methylpyridazin-3(2H)-one 4-(2-Fluorophenyl)-5-hydroxy-5-methylfuran-2(5H)-one (7.09 g, 34.1 mmol) in EtOH (50 mL) at 0° C. was treated with hydrazine hydrate (3.34 mL, 68.1 mmol) dropwise forming a suspension. The reaction mixture was stirred and heated at 90° C. overnight. The reaction mixture was concentrated in vacuo and the crude product was purified by silica gel chromatography (eluent: 0-30% DCM-MeOH (4:1)/DCM) to provide 5-(2-fluorophenyl)-6-methylpyridazin-3(2H)-one (2.76 g, 13.5 mmol, 39.7% yield) as a yellow viscous oil. m/z (ESI, +ve ion): 205.1 (M+H)$^+$.

Step 3: 6-Chloro-4-(2-fluorophenyl)-3-methylpyridazine 5-(2-Fluorophenyl)-6-methylpyridazin-3(2H)-one (2.76 g, 13.5 mmol) was treated with phosphorus oxychloride (9 mL, 97 mmol) and the mixture was stirred and heated at 100° C. for 2 h. The reaction mixture was concentrated in vacuo and the residue was treated with DCM and satd. NaHCO$_3$. The aqueous layer was extracted with DCM, dried over Na$_2$SO$_4$, filtered, and concentrated in vacuo. The crude product was purified by silica gel chromatography (eluent: 0-40% EtOAc/heptane) to provide 6-chloro-4-(2-fluorophenyl)-3-methylpyridazine (1.69 g, 7.59 mmol, 56.2% yield) as an orange solid. m/z (ESI, +ve ion): 223.1 (M+H)$^+$.

Step 4: 2-(5-(2-Fluorophenyl)-6-methylpyridazin-3-yl)-2-(o-tolyl)acetonitrile Potassium hydroxide (1.75 g, 31.1 mmol) in DMSO (15 mL) was stirred at rt for 30 min. 2-(o-Tolyl)acetonitrile (1.59 g, 12.1 mmol) in DMSO (9 mL) was added dropwise and the reaction was allowed to stir at rt for 40 min. The reaction mixture was treated with 6-chloro-4-(2-fluorophenyl)-3-methylpyridazine (1.69 g, 7.59 mmol) in DMSO (10 mL) and allowed to stir and heat at 50° C. overnight. Water was added and the reaction mixture was extracted with EtOAc, dried over Na$_2$SO$_4$, filtered, and concentrated in vacuo. The crude product was purified by silica gel chromatography (eluent: 0-40% EtOAc/heptane) to provide 2-(5-(2-fluorophenyl)-6-methylpyridazin-3-yl)-2-(o-tolyl)acetonitrile (2.51 g, 7.91 mmol, 100% yield) as an orange film. m/z (ESI, +ve ion): 318.2 (M+H)$^+$.

Step 5: 2-(5-(2-Fluorophenyl)-6-methylpyridazin-3-yl)-2-(o-tolyl)acetamide 2-(5-(2-Fluorophenyl)-6-methylpyridazin-3-yl)-2-(o-tolyl)acetonitrile (2.51 g, 7.91 mmol) was treated with sulfuric acid (7 mL, 131 mmol) and heated to 50° C. for 2 h. The reaction mixture was cooled to 0° C. in an ice bath and was carefully quenched with NH$_4$H (28%) dropwise (CAUTION: large exotherm). The solution was extracted with DCM, dried over Na$_2$SO$_4$, filtered, and concentrated in vacuo to provide 2-(5-(2-fluorophenyl)-6-methylpyridazin-3-yl)-2-(o-tolyl)acetamide (2.55 g, 7.6 mmol, 96% yield) as a light-orange solid. m/z (ESI, +ve ion): 336.2 (M+H)$^+$.

Step 6: 3-(2-Fluorophenyl)-2-methyl-5-(o-tolyl)-6H-pyrimido[1,6-b]pyridazine-6,8(7H)-dione To the solution of 2-(5-(2-fluorophenyl)-6-methylpyridazin-3-yl)-2-(o-tolyl)acetamide (954 mg, 2.84 mmol) in EtOH (1 mL) was added NaOEt (21 wt. % solution in EtOH 1.9 mL, 5.1 mmol), followed by diethyl carbonate (0.59 mL, 4.84 mmol). The reaction mixture was stirred and heated at reflux for 4.5 h. The reaction mixture was partitioned between EtOAc and aqueous NH$_4$Cl. The aqueous layer was extracted with EtOAc and the combined organic layer was dried over Na$_2$SO$_4$ and concentrated in vacuo. The crude product was triturated with EtOAc. The resulting solids were collected and dried to give 3-(2-fluorophenyl)-2-methyl-5-(o-tolyl)-6H-pyrimido[1,6-b]pyridazine-6,8(7H)-dione (433 mg, 1.2 mmol, 42.1% yield) as a light-yellow solid. $^1$H NMR (400 MHz, CDCl$_3$) δ ppm 8.39 (br s, 1H), 7.38-7.47 (m, 1H), 7.27 (d, J=3.94 Hz, 2H), 7.01-7.22 (m, 4H), 6.75 (s, 1H), 2.27 (s, 3H), 2.18 (s, 3H). $^{19}$F NMR (376 MHz, CDCl$_3$) δ ppm −112.66 (s, 1F). m/z (ESI, +ve ion): 362.1 (M+H)$^+$.

Step 7: tert-Butyl 4-(3-(2-fluorophenyl)-2-methyl-6-oxo-5-(o-tolyl)-6H-pyrimido[1,6-b]pyridazin-8-yl)piperazine-1-carboxylate A mixture of 3-(2-Fluorophenyl)-2-methyl-5-(o-tolyl)-6H-pyrimido[1,6-b]pyridazine-6,8(7H)-dione (253 mg, 0.7 mmol) in phosphorus oxychloride (3 mL, 32.2 mmol) was stirred and heated at 95° C. for 1 h. The reaction mixture was concentrated in vacuo, treated with DCM, cooled in an ice bath and treated with 1-(tert-butoxycarbonyl)-piperazine (196 mg, 1.05 mmol) and DIPEA (0.86 mL, 4.9 mmol). The mixture was allowed to stir at 0° C. After 30 min, the reaction mixture was treated with satd. NaHCO₃ and extracted with DCM, dried over Na₂SO₄, filtered, and concentrated in vacuo. The crude product was purified by silica gel chromatography (eluent: 0-40% EtOAc-EtOH (3:1)/heptane) to provide tert-butyl 4-(3-(2-fluorophenyl)-2-methyl-6-oxo-5-(o-tolyl)-6H-pyrimido[1,6-b]pyridazin-8-yl)piperazine-1-carboxylate (43 mg, 0.081 mmol, 11.6% yield) as a yellow film. $^1$H NMR (400 MHz, CDCl$_3$) δ ppm 7.35-7.49 (m, 1H), 7.28-7.33 (m, 1H), 7.08-7.26 (m, 6H), 6.87 (s, 1H), 3.68 (br dd, J=5.60, 17.83 Hz, 8H), 2.23 (d, J=16.38 Hz, 6H), 1.51 (s, 9H). $^{19}$F NMR (376 MHz, CDCl$_3$) δ ppm −112.92 (s, 1F). m/z (ESI, +ve ion): 530.3 (M+H)⁺.

Step 8: 3-(2-Fluorophenyl)-2-methyl-5-(2-methylphenyl)-8-(4-(2-propenoyl)-1-piperazinyl)-6H-pyrimido 1,6-b pyridazin-6-one tert-Butyl 4-(3-(2-fluorophenyl)-2-methyl-6-oxo-5-(o-tolyl)-6H-pyrimido[1,6-b]pyridazin-8-yl)piperazine-1-carboxylate (39 mg, 0.074 mmol) in DCM (1 mL) was treated with TFA (0.4 mL, 5.2 mmol) and the reaction mixture was allowed to stir at rt for 30 min. The reaction mixture was concentrated in vacuo and the crude residue was treated with DCM, cooled in an ice bath and treated with DIPEA (0.1 mL, 0.59 mmol) and acryloyl chloride (6 μL, 0.074 mmol). After 15 min, the reaction mixture was concentrated in vacuo. The crude product was purified by silica gel chromatography (eluent: 0-40% EtOAc-EtOH (3:1)/heptane) to provide 3-(2-fluorophenyl)-2-methyl-5-(2-methylphenyl)-8-(4-(2-propenoyl)-1-piperazinyl)-6H-pyrimido[1,6-b]pyridazin-6-one (24.7 mg, 0.051 mmol, 69.4% yield) as a yellow solid. $^1$H NMR (400 MHz, CDCl$_3$) δ ppm 7.38-7.49 (m, 1H), 7.27 (br s, 2H), 7.10-7.25 (m, 5H), 6.88 (s, 1H), 6.63 (dd, J=10.57, 16.79 Hz, 1H), 6.36 (dd, J=1.66, 16.79 Hz, 1H), 5.73-5.82 (m, 1H), 3.72-3.98 (m, 8H), 2.26 (s, 3H), 2.21 (s, 3H). $^{19}$F NMR (376 MHz, CDCl$_3$) δ −112.90 (s, 1F). m/z (ESI, +ve ion): 484.3 (M+H)⁺.

TABLE 77

Compounds 77-2 was prepared following the procedure described in Method 77, Steps 1-8, above as follows:

| Ex. # | Chemical structure | Name | Method Changes | Reagent |
|---|---|---|---|---|
| 77-2 | 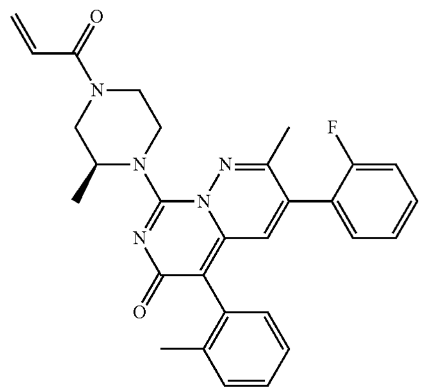 [SMILES: C=CC(=O)N1CCN(c2nc(=O)c(-c3ccccc3C)c3cc(-c4ccccc4F)c(C)nn23)[C@@H](C)C1] | 3-(2-fluorophenyl)-2-methyl-5-(2-methylphenyl)-8-((2S)-2-methyl-4-(2-propenoyl)-1-piperazinyl)-6H-pyrimido[1,6-b]pyridazin-6-one | | Step 7: (3S)-1-(tert-butoxycarbonyl)-3-methylpiperazine (Combi-Blocks Inc.) |

Method 78

Example: 78-1: (M)-6-Chloro-7-(2-fluorophenyl)-1-(4-methyl-2-(2-propanyl)-3-pyridinyl)-4-((3R)-3-methyl-4-(2-propenoyl)-1-piperazinyl)pyrido[2,3-d]pyrimidin-2(1H)-one

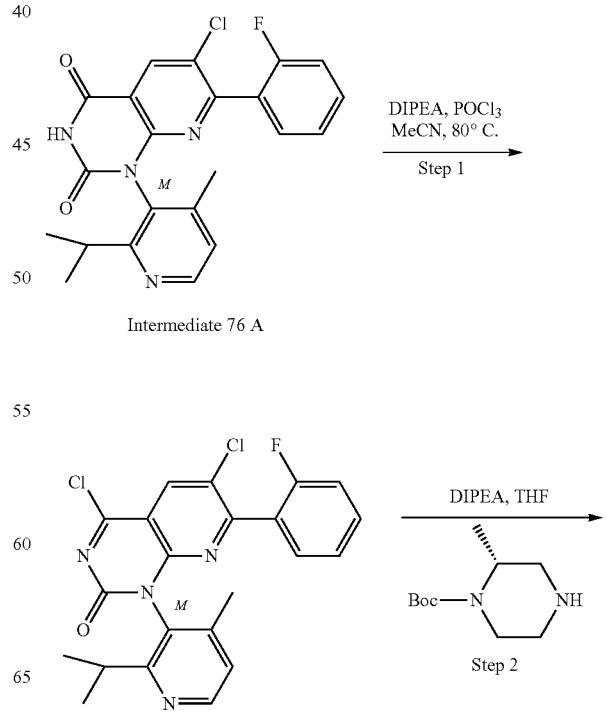

Intermediate 76 A

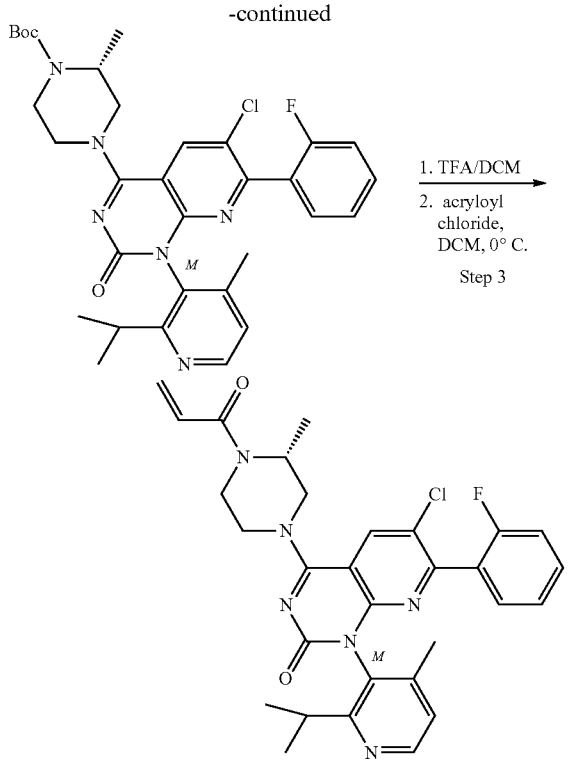

Step 1: (M)-4,6-Dichloro-7-(2-fluorophenyl)-1-(2-isopropyl-4-methylpyridin-3-yl)pyrido[2,3-d]pyrimidin-2(1H)-one To a solution of (M)-6-chloro-7-(2-fluorophenyl)-1-(2-isopropyl-4-methylpyridin-3-yl)pyrido[2,3-d]pyrimidine-2,4(1H,3H)-dione (Intermediate 76A, 0.206 g, 0.484 mmol) and DIPEA (0.25 mL, 1.45 mmol) in acetonitrile (2.4 mL) was added phosphorus oxychloride (0.09 mL, 0.969 mmol) and the mixture was stirred and heated at 80° C. for 1 h. The mixture was concentrated in vacuo to provide (M)-4,6-dichloro-7-(2-fluorophenyl)-1-(2-isopropyl-4-methylpyridin-3-yl)pyrido[2,3-d]pyrimidin-2(1H)-one (0.215 g, 0.485 mmol, 100% yield) as dark red syrup. m/z (ESI, +ve ion): 442.9 (M+H)$^+$. This material was used without further purification in the following step.

Step 2: (M)-tert-Butyl (R)-4-(6-chloro-7-(2-fluorophenyl)-1-(2-isopropyl-4-methylpyridin-3-yl)-2-oxo-1,2-dihydropyrido[2,3-d]pyrimidin-4-yl)-2-methylpiperazine-1-carboxylate To a mixture of (M)-4,6-dichloro-7-(2-fluorophenyl)-1-(2-isopropyl-4-methylpyridin-3-yl)pyrido[2,3-d]pyrimidin-2(1H)-one (0.215 g, 0.485 mmol) in THF (2.4 mL) was added DIPEA (0.25 mL, 1.46 mmol) followed by (R)-1-N-Boc-2-methylpiperazine (0.146 g, 0.727 mmol, Combi-Blocks, Inc., San Diego, Calif., USA) and the mixture was stirred at rt for 2 h. The reaction mixture was quenched with satd. NaHCO$_3$. The mixture was extracted with EtOAc. The organic extract was dried over Na$_2$SO$_4$, the solution was filtered and concentrated in vacuo. The crude product was purified by silica gel chromatography (eluent: 0-100% EtOAc-EtOH (3:1)/heptane) to provide (M)-tert-butyl (R)-4-(6-chloro-7-(2-fluorophenyl)-1-(2-isopropyl-4-methylpyridin-3-yl)-2-oxo-1,2-dihydropyrido[2,3-d]pyrimidin-4-yl)-2-methylpiperazine-1-carboxylate (0.241 g, 0.397 mmol, 82% yield) as a tan solid. $^1$H NMR (400 MHz, DMSO-d$_6$) δ ppm 8.56 (s, 1H), 8.39 (d, J=5.0 Hz, 1H), 7.51 (tdd, J=7.8, 7.8, 5.5, 2.0 Hz, 1H), 7.24-7.34 (m, 2H), 7.16-7.24 (m, 2H), 4.32-4.42 (m, 1H), 4.16-4.31 (m, 2H), 3.72-3.83 (m, 2H), 3.47-3.68 (m, 2H), 2.60-2.69 (m, 1H), 1.95 (s, 3H), 1.45 (s, 9H), 1.24 (d, J=6.6 Hz, 3H), 1.06 (d, J=6.6 Hz, 3H), 0.94 (d, J=6.8 Hz, 3H). $^{19}$F NMR (376 MHz, DMSO-d$_6$) δ ppm −114.02 (s, 1F). m/z (ESI, +ve ion): 607.2 (M+H)$^+$.

Step 3: (M)-6-Chloro-7-(2-fluorophenyl)-1-(4-methyl-2-(2-propanyl)-3-pyridinyl)-4-((3R)-3-methyl-4-(2-propenoyl)-1-piperazinyl)pyrido[2,3-d]pyrimidin-2(1H)-one To a solution of (M)-tert-butyl (R)-4-(6-chloro-7-(2-fluorophenyl)-1-(2-isopropyl-4-methylpyridin-3-yl)-2-oxo-1,2-dihydropyrido[2,3-d]pyrimidin-4-yl)-2-methylpiperazine-1-carboxylate (0.234 g, 0.385 mmol) in DCM (3 mL) was added TFA (3 mL) and the mixture was stirred at rt for 15 min. The mixture was concentrated in vacuo to provide (M,R)-6-chloro-7-(2-fluorophenyl)-1-(2-isopropyl-4-methylpyridin-3-yl)-4-(3-methylpiperazin-1-yl)pyrido[2,3-d]pyrimidin-2(1H)-one as an orange syrup. m/z (ESI, +ve ion): 507.2 (M+H)$^+$.

The crude product was dissolved in DCM (3 mL) and the mixture was cooled to 0° C. and treated with DIPEA (1.0 mL, 5.78 mmol) followed by acryloyl chloride (0.2 M in DCM, 2.0 mL, 0.4 mmol) dropwise and the mixture was stirred at 0° C. for 20 min. The reaction mixture was quenched with satd. NaHCO$_3$ and extracted with DCM. The organic extract was dried over Na$_2$SO$_4$, filtered, and concentrated in vacuo. The crude product was purified by silica gel chromatography (eluent: 0-30% DCM-MeOH (4:1)/DCM) to provide (M)-6-chloro-7-(2-fluorophenyl)-1-(4-methyl-2-(2-propanyl)-3-pyridinyl)-4-((3R)-3-methyl-4-(2-propenoyl)-1-piperazinyl)pyrido[2,3-d]pyrimidin-2(1H)-one (0.158 g, 0.28 mmol, 72.9% yield) as an off-white solid. $^1$H NMR (400 MHz, DMSO-d$_6$) δ ppm 8.60 (s, 1H), 8.39 (d, J=4.8 Hz, 1H), 7.46-7.55 (m, 1H), 7.14-7.34 (m, 4H), 6.81 (dd, J=16.6, 10.4 Hz, 1H), 6.19 (br d, J=16.6 Hz, 1H), 5.69-5.79 (m, 1H), 4.48-4.79 (m, 1H), 4.41 (br dd, J=8.6, 5.1 Hz, 1H), 4.22 (br dd, J=13.6, 2.6 Hz, 1H), 3.94-4.13 (m, 1H), 3.50-3.93 (m, 3H), 2.64 (spt, J=6.7 Hz, 1H), 1.96 (s, 3H), 1.29 (br s, 3H), 1.06 (d, J=6.6 Hz, 3H), 0.95 (d, J=6.6 Hz, 3H). $^{19}$F NMR (376 MHz, DMSO-d$_6$) δ ppm −113.98 (s, 1F). m/z (ESI, +ve ion): 561.2 (M+H)$^+$.

TABLE 78

Compounds 78-2 to 78-18 were prepared following the procedure described in Method 78, Steps 1-4, above as follows:

| Ex. # | Chemical structure | Name | Method Changes | Reagent |
|---|---|---|---|---|
| 78-2 | single isomer (M) | (M)-6-chloro-7-(2-fluorophenyl)-1-(4-methyl-2-(2-propanyl)-3-pyridinyl)-4-(9-(2-propenoyl)-3,9-diazabicyclo[3.3.1]nonan-3-yl)pyrido[2,3-d]pyrimidin-2(1H)-one | | Step 2: tert-butyl 3,9-diazabicyclo[3.3.1]nonane-9-carboxylate (Enamine) |
| 78-3 | single isomer (M) racemic (R/S) | (M)-6-chloro-4-(2-difluoromethyl)-4-(2-propenoyl)-1-piperazinyl)-7-(2-fluorophenyl)-1-(4-methyl-2-(2-propanyl)-3-pyridinyl)pyrido[2,3-d]pyrimidin-2(1H)-one | Step 1 and Step 2: performed as a single step analagous to Example 135, Step 2 | Step 2: tert-butyl 3-(difluoromethyl)piperazine-1-carboxylate (Enamine) |
| 78-4 | single isomer (M) | (M)-6-chloro-7-(2-fluorophenyl)-1-(4-methyl-2-(2-propanyl)-3-pyridinyl)-4-(7-(2-propenoyl)-4,7-diazaspiro[2.5]octan-4-yl)pyrido[2,3-d]pyrimidin-2(1H)-one | Step 1 and Step 2: performed as a single step analagous to Example 135, Step 2 | Step 2: 4,7-diaza-spiro[2.5]octane-7-carboxylic acid tert-butyl ester (J & W Pharmlab, LLC) |

TABLE 78-continued

Compounds 78-2 to 78-18 were prepared following the procedure described in Method 78, Steps 1-4, above as follows:

| Ex. # | Chemical structure | Name | Method Changes | Reagent |
|---|---|---|---|---|
| 78-5 | single isomer (M); racemic (R/S) | (M)-6-chloro-4-(2-(fluoromethyl)-4-(2-propenoyl)-1-piperazinyl)-7-(2-fluorophenyl)-1-(4-methyl-2-(2-propanyl)-3-pyridinyl)pyrido[2,3-d]pyrimidin-2(1H)-one | Step 1 and Step 2: performed as a single step analagous to Example 135, Step 2 | Step 2: 3-fluoromethyl-piperazine-1-carboxylic acid tert-butyl ester (eNovation Chemicals LLC) |
| 78-6 | single isomer (M); racemic (R/S) | (M)-6-chloro-7-(2-fluorophenyl)-4-(2-(hydroxymethyl)-4-(2-propenoyl)-1-piperazinyl)-1-(4-methyl-2-(2-propanyl)-3-pyridinyl)pyrido[2,3-d]pyrimidin-2(1H)-one | Step 1 and Step 2: performed as a single step analagous to Example 135, Step 2 | Step 2: 3-fluoromethyl-piperazine-1-carboxylic acid tert-butyl ester (eNovation Chemicals LLC) |
| 78-7 | single isomer (M) | (M)-6-chloro-4-(cis-2,6-dimethyl-4-(2-propenoyl)-1-piperazinyl)-7-(2-fluorophenyl)-1-(4-methyl-2-(2-propanyl)-3-pyridinyl)pyrido[2,3-d]pyrimidin-2(1H)-one | Step 1 and Step 2: performed as a single step analagous to Example 135, Step 2 | Step 2: cis-3,5-dimethyl-piperazine-1-carboxylic acid tert-butyl ester (AK Scientific, Inc.) |

TABLE 78-continued

Compounds 78-2 to 78-18 were prepared following the procedure described in Method 78, Steps 1-4, above as follows:

| Ex. # | Chemical structure | Name | Method Changes | Reagent |
|---|---|---|---|---|
| 78-8 | single isomer (M) | (M)-6-chloro-4-((2S,6S)-2,6-dimethyl-4-(2-propenoyl)-1-piperazinyl)-7-(2-fluorophenyl)-1-(4-methyl-2-(2-propanyl)-3-pyridinyl)pyrido[2,3-d]pyrimidin-2(1H)-one | Step 1 and Step 2: performed as a single step analagous to Example 135, Step 2 | Step 2: (3S,5S)-1-Boc-3,5-dimethylpiperazine (AstaTech, Inc.) |
| 78-9 | single isomer (M) racemic (R/S) | (M)-6-chloro-7-(2-fluorophenyl)-1-(4-methyl-2-(2-propanyl)-3-pyridinyl)-4-(4-(2-propenoyl)-2-(trifluoromethyl)-1-piperazinyl)pyrido[2,3-d]pyrimidin-2(1H)-one | Step 1 and Step 2: performed as a single step analagous to Example 135, Step 2 | Step 2: 3-trifluoromethyl-piperazine-1-carboxylic acid tert-butyl ester (Anichem Inc.) |
| 78-10 | single isomer (M) | (M)-6-chloro-7-(2-fluorophenyl)-1-(4-methyl-2-(2-propanyl)-3-pyridinyl)-4-((1S,4S)-5-(2-propenoyl)-2,5-diazabicyclo[2.2.1]heptan-2-yl)pyrido[2,3-d]pyrimidin-2(1H)-one | Step 1 and Step 2: performed as a single step analagous to Example 135, Step 2 | Step 2: (1S,4S)-(-)-2-Boc-2,5-diazabicyclo[2.2.1]heptane (Sigma-Aldrich Corporation) |

TABLE 78-continued

Compounds 78-2 to 78-18 were prepared following the procedure described in Method 78, Steps 1-4, above as follows:

| Ex. # | Chemical structure | Name | Method Changes | Reagent |
|---|---|---|---|---|
| 78-11 | single isomer (M) | (M)-6-chloro-7-(2-fluorophenyl)-1-(4-methyl-2-(2-propanyl)-3-pyridinyl)-4-((1R,4R)-5-(2-propenoyl)-2,5-diazabicyclo[2.2.1]heptan-2-yl)pyrido[2,3-d]pyrimidin-2(1H)-one | Step 1 and Step 2: performed as a single step analagous to Example 135, Step 2 | Step 2: (1R,4R)-tert-butyl 2,5-diazabicyclo[2.2.1]heptane-2-carboxylate (AstaTech, Inc.) |
| 78-12 | single isomer (M) | (M)-N-(2-((6-chloro-7-(2-fluorophenyl)-1-(4-methyl-2-(2-propanyl)-3-pyridinyl)-2-oxo-1,2-dihydropyrido[2,3-d]pyrimidin-4-yl)amino)ethyl)-2-propenamide | Step 1 and Step 2: performed as a single step analagous to Example 135, Step 2 | Step 2: N-ethyl-N-isopropylpropan-2-amine (Sigma-Aldrich Corporation) |
| 78-13 | single isomer (M) | (M)-6-chloro-7-(2-fluorophenyl)-1-(4-methyl-2-(2-propanyl)-3-pyridinyl)-4-(3-(2-propenoyl)-3,8-diazabicyclo[3.2.1]octan-8-yl)pyrido[2,3-d]pyrimidin-2(1H)-one | Step 1 and Step 2: performed as a single step analagous to Example 135, Step 2 | Step 2: 3-Boc-3,8-diazabicyclo[3.2.1]octane (Combi-Blocks Inc.) |

TABLE 78-continued

Compounds 78-2 to 78-18 were prepared following the procedure described in Method 78, Steps 1-4, above as follows:

| Ex. # | Chemical structure | Name | Method Changes | Reagent |
|---|---|---|---|---|
| 78-14 | single isomer (M) | (M)-6-chloro-7-(2-fluorophenyl)-4-((2R)-2-(hydroxymethyl)-4-(2-propenoyl)-1-piperazinyl)-1-(4-methyl-2-(2-propanyl)-3-pyridinyl)pyrido[2,3-d]pyrimidin-2(1H)-one | Step 1 and Step 2: performed as a single step analagous to Example 135, Step 2 | Step 2: (3R)-1-(tert-butoxycarbonyl)-3-(hydroxymethyl)piperazine (Synthonix, Inc.) |
| 78-15 | single isomer (M) | (M)-6-chloro-7-(2-fluorophenyl)-1-(4-methyl-2-(2-propanyl)-3-pyridinyl)-4-(4-(2-propenoyl)-1-piperazinyl)pyrido[2,3-d]pyrimidin-2(1H)-one | Step 1 and Step 2: performed as a single step analagous to Example 135, Step 2 | Step 2: tert-butyl piperazine-1-carboxylate (Sigma-Aldrich Corporation) |
| 78-16 | single isomer (M) | (M)-6-chloro-4-((2R,6R)-2,6-dimethyl-4-(2-propenoyl)-1-piperazinyl)-7-(2-fluorophenyl)-1-(4-methyl-2-(2-propanyl)-3-pyridinyl)pyrido[2,3-d]pyrimidin-2(1H)-one | Step 1 and Step 2: performed as a single step analagous to Example 135, Step 2 | Step 2: (3R,5R)-1-Boc-3,5-dimethylpiperazine (AstaTech, Inc.) |

TABLE 78-continued

Compounds 78-2 to 78-18 were prepared following the procedure
described in Method 78, Steps 1-4, above as follows:

| Ex. # | Chemical structure | Name | Method Changes | Reagent |
|---|---|---|---|---|
| 78-17 | single isomer (M) | (M)-6-chloro-7-(2-fluorophenyl)-1-(4-methyl-2-(2-propanyl)-3-pyridinyl)-4-(3-(2-propenoyl)-3,6-diazabicyclo[3.1.1]heptan-6-yl)pyrido[2,3-d]pyrimidin-2(1H)-one | Step 1 and Step 2: performed as a single step analagous to Example 135, Step 2 | Step 2: 3-Boc-3,6-diaza-bicyclo[3.1.1]heptane (Aurum Pharmatech LLC) |
| 78-18 | single isomer (M) | (M)-6-chloro-7-(2-fluorophenyl)-1-(4-methyl-2-(2-propanyl)-3-pyridinyl)-4-((1R,4R)-5-(2-propenoyl)-2,5-diazabicyclo[2.2.2]octan-2-yl)pyrido[2,3-d]pyrimidin-2(1H)-one | Step 1 and Step 2: performed as a single step analagous to Example 135, Step 2 | Step 2: tert-butyl (1R,4R)-2,5-diazabicyclo[2.2.2]octane-2-carboxylate (Synthonix, Inc.) |

Method 79

Example 79-1: (M)-6-Chloro-7-(2-fluorophenyl)-1-(4-methyl-2-(2-propanyl)-3-pyridinyl)-4-((1-(2-propenoyl)-3-azetidinyl)oxy)pyrido[2,3-d]pyrimidin-2(1H)-one

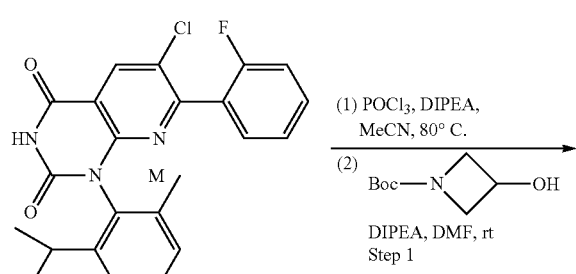

Intermediate 76A

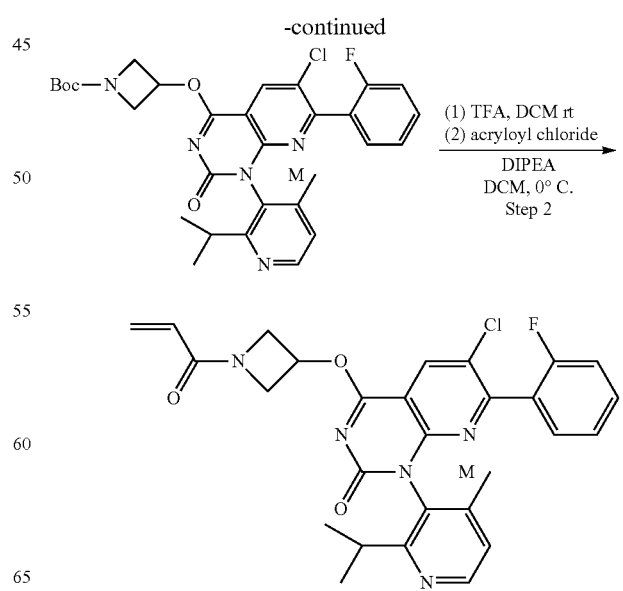

Step 1: (M)-tert-Butyl 3-((6-chloro-7-(2-fluorophenyl)-1-(2-isopropyl-4-methylpyridin-3-yl)-2-oxo-1,2-dihydropyrido[2,3-d]pyrimidin-4-yl)oxy)azetidine-1-carboxylate A 50-mL round-bottomed flask was charged with (M)-6-chloro-7-(2-fluorophenyl)-1-(2-isopropyl-4-methylpyridin-3-yl)pyrido[2,3-d]pyrimidine-2,4(1H,3H)-dione (Intermediate 76A, 256 mg, 0.60 mmol) and DIPEA (0.2 mL, 0.904 mmol) in acetonitrile (3 mL) followed by phosphorous oxychloride (0.1 mL, 0.9 mmol). The mixture was stirred and heated at 80° C. for 40 min. The reaction mixture was concentrated in vacuo to give (M)-4,6-dichloro-7-(2-fluorophenyl)-1-(2-isopropyl-4-methylpyridin-3-yl)pyrido[2,3-d]pyrimidin-2(1H)-one as a brown solid [m/z (ESI, +ve ion): 443 (M+H)$^+$] which was used in next step without purification.

A mixture of the above crude (M)-4,6-dichloro-7-(2-fluorophenyl)-1-(2-isopropyl-4-methylpyridin-3-yl)pyrido[2,3-d]pyrimidin-2(1H)-one (267 mg, 0.6 mmol) in acetonitrile (3 mL) was treated with DIPEA (0.3 mL, 1.81 mmol) followed by 1-Boc-3-(hydroxy)azetidine (313 mg, 1.81 mmol, CNH Technologies, Inc., Woburn, Mass., USA). The reaction mixture was stirred at rt for 24 h then concentrated in vacuo and purified by silica gel chromatography (eluent: 0-30% 3:1 EtOAc-EtOH/heptane) to provide (M)-tert-butyl 3-((6-chloro-7-(2-fluorophenyl)-1-(2-isopropyl-4-methylpyridin-3-yl)-2-oxo-1,2-dihydropyrido[2,3-d]pyrimidin-4-yl)oxy)azetidine-1-carboxylate (51 mg, 0.09 mmol, 14.6% yield) as a light yellow foam. m/z (ESI, +ve ion) 580.3 (M+H)$^+$.

Step 2: (M)-4-((1-Acryloylazetidin-3-yl)oxy)-6-chloro-7-(2-fluorophenyl)-1-(2-isopropyl-4-methylpyridin-3-yl)pyrido[2,3-d]pyrimidin-2(1H)-one To a solution of (M)-tert-butyl 3-((6-chloro-7-(2-fluorophenyl)-1-(2-isopropyl-4-methylpyridin-3-yl)-2-oxo-1,2-dihydropyrido[2,3-d]pyrimidin-4-yl)oxy)azetidine-1-carboxylate (51 mg, 0.9 mmol) in DCM (1 mL) was treated with TFA (1 mL) at rt and stirred for 1 h. The reaction was concentrated to afford (M)-4-(azetidin-3-yloxy)-6-chloro-7-(2-fluorophenyl)-1-(2-isopropyl-4-methylpyridin-3-yl)pyrido[2,3-d]pyrimidin-2(1H)-one as a yellow gum. m/z (ESI, +ve ion) 480.2 (M+H)$^+$.

A mixture of the above (M)-4-(azetidin-3-yloxy)-6-chloro-7-(2-fluorophenyl)-1-(2-isopropyl-4-methylpyridin-3-yl)pyrido[2,3-d]pyrimidin-2(1H)-one and DIPEA (0.08 mL, 0.44 mmol) in DCM (1 mL) was treated with acryloyl chloride (0.25 M in DCM, 0.3 mL, 0.08 mmol) at 0° C. and stirred for 5 min. The reaction mixture was concentrated in vacuo and the crude product was purified by silica gel chromatography (eluent: 0-50% EtOAc-EtOH (3:1)/heptane) to give (M)-4-((1-acryloylazetidin-3-yl)oxy)-6-chloro-7-(2-fluorophenyl)-1-(2-isopropyl-4-methylpyridin-3-yl)pyrido[2,3-d]pyrimidin-2(1H)-one (22 mg, 0.041 mmol, 46.2% yield) as a white solid. 1H NMR (400 MHz, DMSO-d$_6$) δ ppm 8.83 (s, 1H), 8.43 (d, J=4.8 Hz, 1H), 7.47-7.64 (m, 1H), 7.18-7.39 (m, 4H), 6.32-6.51 (m, 1H), 6.16 (dd, J=17.0, 2.1 Hz, 1H), 5.62-5.84 (m, 2H), 4.70-4.85 (m, 1H), 4.54 (td, J=10.4, 3.2 Hz, 1H), 4.44 (br dd, J=11.2, 6.8 Hz, 1H), 4.23-4.37 (m, 1H), 2.76 (dt, J=13.4, 6.8 Hz, 1H), 1.96 (s, 3H), 1.07 (d, J=6.8 Hz, 3H), 0.94 (d, J=6.6 Hz, 3H). 19F NMR (376 MHz, DMSO-d$_6$) δ ppm −114.69 (d, J=4.3 Hz, 1F). m/z (ESI, +ve) 534.1 (M+H)$^+$.

TABLE 79

Compounds 79-2 to 79-5 were prepared following the procedure described in Method 79, Steps 1-3, above as follows:

| Ex. # | Chemical structure | Name | Method Changes | Reagent |
|---|---|---|---|---|
| 79-2 | single isomer (M)<br>racemic (3R/S) | (M)-6-chloro-7-(2-fluorophenyl)-1-(4-methyl-2-(2-propanyl)-3-pyridinyl)-4-((1-(2-propenoyl)-3-pyrrolidinyl)oxy)pyrido[2,3-d]pyrimidin-2(1H)-one | Step 1: (+/−)-1-Boc-3-hydroxypyrrolidine (Combi-Blocks Inc.) |

TABLE 79-continued

Compounds 79-2 to 79-5 were prepared following the procedure described in Method 79, Steps 1-3, above as follows:

| Ex. # | Chemical structure | Name | Method Changes | Reagent |
|---|---|---|---|---|
| 79-3 | 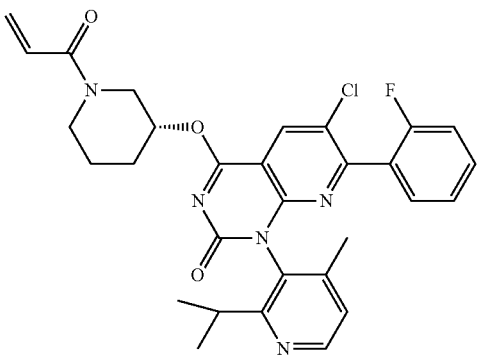 [SMILES: C=CC(=O)N1CCC[C@@H](Oc2nc(=O)n(-c3c(C)ccnc3C(C)C)c3nc(-c4ccccc4F)c(Cl)cc23)C1]<br>single isomer (M and 3R) | (M)-6-chloro-7-(2-fluorophenyl)-1-(4-methyl-2-(2-propanyl)-3-pyridinyl)-4-(((3R)-1-(2-propenoyl)-3-piperidinyl)oxy)pyrido[2,3-d]pyrimidin-2(1H)-one | | Step 1: (R)-1-N-Boc-3-hydroxypiperidine (AstaTech, Inc.) |
| 79-4 | 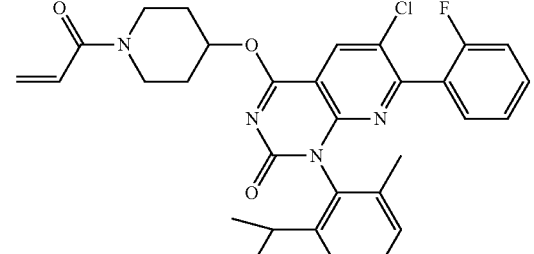<br>single isomer (M) | (M)-6-Chloro-7-(2-fluorophenyl)-1-(4-methyl-2-(2-propanyl)-3-pyridinyl)-4-((1-(2-propenoyl)-4-piperidinyl)oxy)pyrido[2,3-d]pyrimidin-2(1H)-one | | Step 1: tert-butyl 4-hydroxypiperidine-1-carboxylate (Enamine) |
| 79-5 | 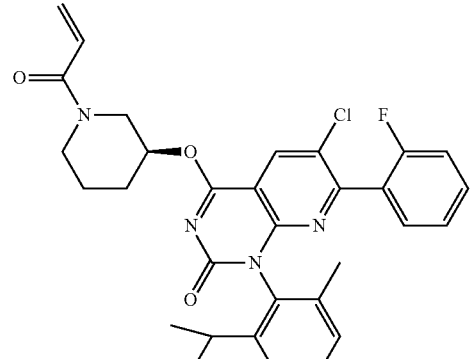<br>single isomer (M) | (M)-6-chloro-7-(2-fluorophenyl)-1-(4-methyl-2-(2-propanyl)-3-pyridinyl)-4-(((3S)-1-(2-propenoyl)-3-piperidinyl)oxy)pyrido[2,3-d]pyrimidin-2(1H)-one | | Step 1: (S)-1-Boc-3-hydroxypiperidine (Sigma-Aldrich Corporation) |

Method 80
Example 80-1: 6-Chloro-1-(4-((dimethylamino)methyl)-2-methyl-6-(2-propanyl)phenyl)-7-(2-fluorophenyl)-4-((2S)-2-methyl-4-(2-propenoyl)-1-piperazinyl)pyrido[2,3-d]pyrimidin-2(1H)-one
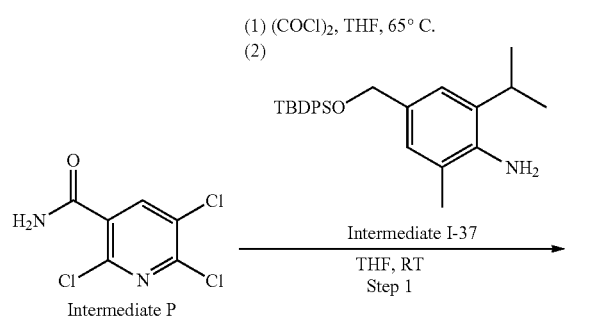
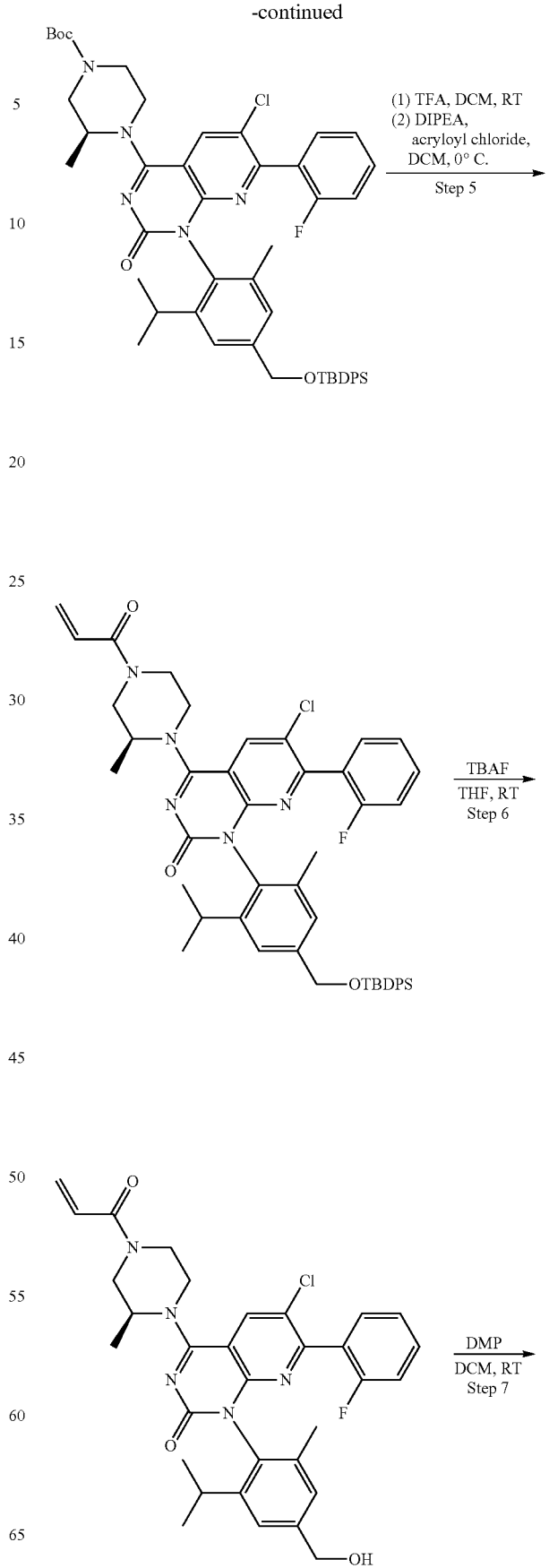

-continued

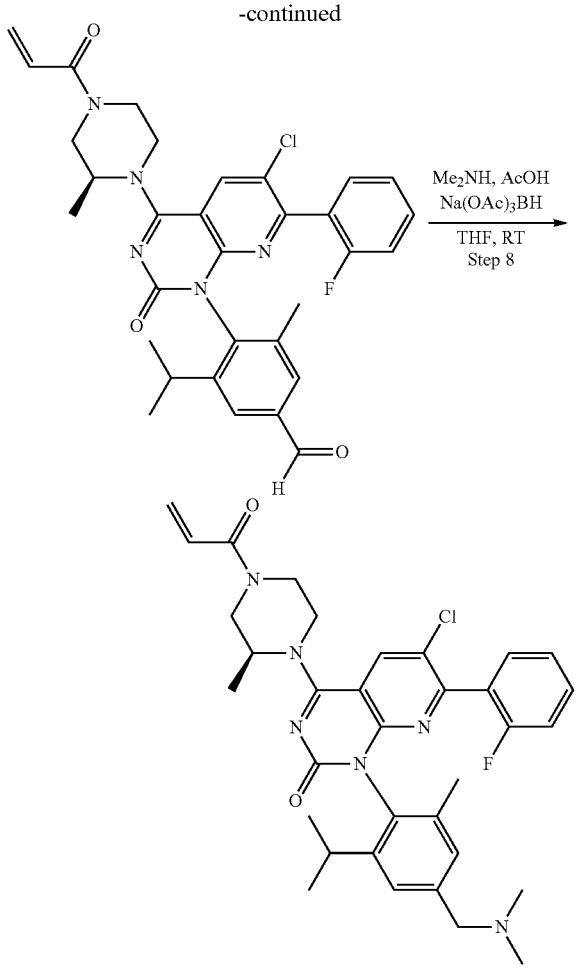

Step 1: N-((4-(((tert-Butyldiphenylsilyl)oxy)methyl)-2-isopropyl-6-methylphenyl)carbamoyl)-2,5,6-trichloronicotinamide To a stirred solution of 2,5,6-trichloronicotinamide (Intermediate P, 1.3 g, 5.5 mmol) in THF (10 mL) was added oxalyl chloride (2 M in DCM, 4.2 mL, 8.4 mmol). After the addition was completed, the reaction mixture was stirred and heated at 65° C. for 2 h. The reaction mixture was cooled, concentrated in vacuo and the crude residue was dissolved in THF (10 mL) and a solution of 4-(((tert-butyldiphenylsilyl)oxy)methyl)-2-isopropyl-6-methylaniline (Intermediate I-37, 2.3 g, 5.5 mmol) in THF (10 mL) was added. After the addition was completed, the solution was maintained at rt for 2 h. The mixture was concentrated in vacuo to provide crude N-((4-(((tert-butyldiphenylsilyl)oxy)methyl)-2-isopropyl-6-methylphenyl)carbamoyl)-2,5,6-trichloronicotinamide which was carried forward in the next step without purification. m/z (ESI, +ve ion): 668.0 (M+H)$^+$.

Step 2: 1-(4-(((tert-Butyldiphenylsilyl)oxy)methyl)-2-isopropyl-6-methylphenyl)-6,7-dichloropyrido[2,3-d]pyrimidine-2,4(1H,3H)-dione To a stirred solution of N-((4-(((tert-butyldiphenylsilyl)oxy)methyl)-2-isopropyl-6-methylphenyl)carbamoyl)-2,5,6-trichloronicotinamide (3.7 g, 5.5 mmol) in THF (20 mL) at 0° C. was added 1 M KHMDS in THF (11 mL, 11 mmol). After 2 h, the reaction was quenched with said. ammonium chloride and diluted with EtOAc. The aqueous layer was extracted with EtOAc and the combined organic extracts were dried over Na$_2$SO$_4$, filtered, and concentrated in vacuo. The crude product was purified by silica gel chromatography (eluent: 0-50% EtOAc/heptane) to provide 1-(4-(((tert-butyldiphenylsilyl)oxy)methyl)-2-isopropyl-6-methylphenyl)-6,7-dichloropyrido[2,3-d]pyrimidine-2,4(1H,3H)-dione. m/z (ESI, +ve ion): 632.0 (M+H)$^+$.

Step 3: tert-Butyl (S)-4-(1-(4-(((tert-butyldiphenylsilyl)oxy)methyl)-2-isopropyl-6-methylphenyl)-6,7-dichloro-2-oxo-1,2-dihydropyrido[2,3-d]pyrimidin-4-yl)-3-methylpiperazine-1-carboxylate To a stirred solution of 1-(4-(((tert-butyldiphenylsilyl)oxy)methyl)-2-isopropyl-6-methylphenyl)-6,7-dichloropyrido[2,3-d]pyrimidine-2,4(1H,3H)-dione (2.8 g, 4.5 mmol) in acetonitrile (20 mL) was added DIPEA (1.2 mL, 6.7 mmol), followed by phosphorus oxychloride (0.63 mL, 6.7 mmol). After the addition was completed, the mixture was stirred and heated at 60° C. for 3 h. The mixture was concentrated in vacuo to provide a crude residue which was dissolved in DCM. The solution was cooled to 0° C. and DIPEA (3.9 mL, 23 mmol) and tert-butyl (S)-3-methylpiperazine-1-carboxylate (0.90 g, 4.5 mmol) were added. After 2 h, the reaction was quenched with water, the aqueous layer was extracted with DCM and the combined organic extracts were dried over Na$_2$SO$_4$, then concentrated in vacuo. The crude product was purified by silica gel chromatography (eluent: 0-50% EtOAc/heptane) to provide tert-butyl (S)-4-(1-(4-(((tert-butyldiphenylsilyl)oxy)methyl)-2-isopropyl-6-methylphenyl)-6,7-dichloro-2-oxo-1,2-dihydropyrido[2,3-d]pyrimidin-4-yl)-3-methylpiperazine-1-carboxylate. $^1$H NMR (400 MHz, DMSO-d$_6$) δ ppm 0.96 (d, J=6.7 Hz, 3H), 1.02 (d, J=6.8 Hz, 3H), 1.08 (s, 9H), 1.31 (dd, J=8.9, 7.1 Hz, 3H), 1.45 (s, 9H), 1.87 (d, J=2.5 Hz, 3H), 2.39-2.47 (m, 1H), 2.96-3.19 (m, 2H), 3.28 (s, 1H), 3.59-3.74 (m, 1H), 3.82 (br d, J=12.0 Hz, 1H), 3.88-4.00 (m, 1H), 4.09-4.23 (m, 1H), 4.83 (s, 3H), 7.10 (s, 1H), 7.31 (s, 1H), 7.41-7.54 (m, 6H), 7.69 (br d, J=7.7 Hz, 4H), 8.42 (d, J=9.5 Hz, 1H).

Step 4: tert-Butyl (S)-4-(1-(4-(((tert-butyldiphenylsilyl)oxy)methyl)-2-isopropyl-6-methylphenyl)-6-chloro-7-(2-fluorophenyl)-2-oxo-1,2-dihydropyrido[2,3-d]pyrimidin-4-yl-3-methylpiperazine-1-carboxylate A mixture of tert-butyl (S)-4-(1-(4-(((tert-butyldiphenylsilyl)oxy)methyl)-2-isopropyl-6-methylphenyl)-6,7-dichloro-2-oxo-1,2-dihydropyrido[2,3-d]pyrimidin-4-yl)-3-methylpiperazine-1-carboxylate (2.8 g, 3.4 mmol), (2-fluorophenyl)boronic acid (0.71 g, 5.1 mmol, CombiBlocks, San Diego, Calif., USA), potassium acetate (1.7 g, 17 mmol), and Pd(dppf)Cl$_2$ (0.25 g, 0.34 mmol) in 1,4-dioxane (20 mL)/water (0.5 mL) was stirred and heated at 90° C. for 3 h. The mixture was cooled to rt and diluted with water. The aqueous mixture was extracted with EtOAc, the combined organic extracts were dried over Na$_2$SO$_4$ and concentrated in vacuo to provide tert-butyl (S)-4-(1-(4-(((tert-butyldiphenylsilyl)oxy)methyl)-2-isopropyl-6-methylphenyl)-6-chloro-7-(2-fluorophenyl)-2-oxo-1,2-dihydropyrido[2,3-d]pyrimidin-4-yl)-3-methylpiperazine-1-carboxylate which was used in the next step without further purification.

Step 5: (S)-4-(4-Acryloyl-2-methylpiperazin-1-yl)-1-(4-(((tert-butyldiphenylsilyl)oxy)methyl)-2-isopropyl-6-methylphenyl)-6-chloro-7-(2-fluorophenyl)pyrido[2,3-d]pyrimidin-2(1H)-one To a solution of tert-butyl (S)-4-(1-(4-(((tert-butyldiphenylsilyl)oxy)methyl)-2-isopropyl-6-methylphenyl)-6-chloro-7-(2-fluorophenyl)-2-oxo-1,2-dihydropyrido[2,3-d]pyrimidin-4-yl)-3-methylpiperazine-1-carboxylate (2.0 g, 2.3 mmol) in DCM (10 mL) was added TFA (3.5 mL, 46 mmol). The reaction was stirred at rt for 3 h and concentrated in vacuo. The residue was dissolved in DCM (10 mL). cooled to 0° C., then treated with DIPEA (2.0 mL, 11 mmol) and acrylovyl chloride (1.1 M in DCM, 2.1 mL, 2.3 mmol). The reaction was stirred at 0° C. for 2 h, the mixture was diluted with water and extracted with DCM. The organic layer was dried over $Na_2SO_4$ and concentrated in vacuo. The crude product was purified by silica gel chromatography (eluent: 0-70% EtOAc/heptane) to provide (S)-4-(4-acryloyl-2-methylpiperazin-1-yl)-1-(4-(((tert-butyldiphenylsilyl)oxy)methyl)-2-isopropyl-6-methylphenyl)-6-chloro-7-(2-fluorophenyl)pyrido[2,3-d]pyrimidin-2(1H)-one. $^1$H NMR (400 MHz, DMSO-$d_6$) δ ppm 0.88-0.94 (m, 3H), 1.03 (s, 9H), 1.24-1.28 (m, 3H), 1.31-1.37 (m, 3H), 1.87 (s, 3H), 3.03-3.33 (m, 2H), 3.58-3.83 (m, 2H), 3.98-4.19 (m, 1H), 4.22-4.48 (m, 2H), 4.76 (s, 2H), 4.93 (br s, 1H), 5.76 (br d, J=10.6 Hz, 1H), 6.13-6.27 (m, 1H), 6.79-6.94 (m, 1H), 7.02 (br s, 1H), 7.17-7.33 (m, 4H), 7.35-7.55 (m, 7H), 7.60-7.68 (m, 4H), 8.44 (br s, 1H). $^{19}$F NMR (377 MHz, DMSO-$d_h$) δ ppm −114.17 (s, 1F).

Step 6: (S)-4-(4-Acryloyl-2-methylpiperazin-1-yl)-6-chloro-7-(2-fluorophenyl)-1-(4-(hydroxymethyl)-2-isopropyl-6-methylphenyl)pyrido[2,3-d]pyrimidin-2(1H)-one (Intermediate 80A)

To a stirred solution of (S)-4-(4-acryloyl-2-methylpiperazin-1-yl)-1-(4-(((tert-butyldiphenylsilyl)oxy)methyl)-2-isopropyl-6-methylphenyl)-6-chloro-7-(2-fluorophenyl)pyrido[2,3-d]pyrimidin-2(1H)-one (270 mg, 0.33 mmol) in THF (5 mL) was added TBAF (1 M in THF, 0.33 mL, 0.33 mmol). The mixture was stirred at rt for 2 h and concentrated in vacuo. The crude product was purified by silica gel chromatography (eluent: 0-50% 3:1 EtOAc-EtOH/heptane) to provide (S)-4-(4-acryloyl-2-methylpiperazin-1-yl)-6-chloro-7-(2-fluorophenyl)-1-(4-(hydroxymethyl)-2-isopropyl-6-methylphenyl)pyrido[2,3-d]pyrimidin-2(1H)-one (Intermediate 80A). $^1$H NMR (400 MHz, DMSO-$d_6$) δ ppm 0.94 (d, J=6.8 Hz, 3H), 1.05 (d, J=6.8 Hz, 3H), 1.33 (d, J=6.8 Hz, 3H), 1.87 (s, 3H), 2.51-2.58 (m, 1H), 3.03-3.28 (m, 1H), 3.41-3.86 (m, 2H), 3.97-4.44 (m, 3H), 4.46 (d, J=5.8 Hz, 2H), 4.92 (br s, 1H), 5.14 (t, J=5.8 Hz, 1H), 5.71-5.81 (m, 1H), 6.20 (br dd, J=16.6, 3.3 Hz, 1H), 6.79-6.94 (m, 1H), 7.05 (s, 1H), 7.16 (s, 1H), 7.18-7.23 (m, 1H), 7.24-7.36 (m, 2H), 7.47-7.56 (m, 1H), 8.43 (br d, J=4.6 Hz, 1H). $^{19}$F NMR (376 MHz, DMSO-$d_6$) δ ppm −114.26 (s, 1F); m/z (ESI, +ve ion): 590.0 (M+H)$^+$.

Step 7: (S)-4-(4-(4-Acryloyl-2-methylpiperazin-1-yl)-6-chloro-7-(2-fluorophenyl)-2-oxopyrido[2,3-d]pyrimidin-1(2H)-yl)-3-isopropyl-5-methylbenzaldehyde To a solution of (S)-4-(4-acryloyl-2-methylpiperazin-1-yl)-6-chloro-7-(2-fluorophenyl)-1-(4-(hydroxymethyl)-2-isopropyl-6-methylphenyl)pyrido[2,3-d]pyrimidin-2(1H)-one (Intermediate 80A, 100 mg, 0.17 mmol) in DCM (3.4 mL) at rt was added Dess-Martin periodinane (110 mg, 0.25 mmol). After 20 min, the reaction was quenched by addition of 1 N sodium thiosulfate (10 mL) and diluted with DCM (5 mL). The layers were partitioned and then the aqueous phase was washed with DCM (2×10 mL). The combined organic extracts were dried over anhydrous sodium sulfate, filtered through Celite®, and concentrated under reduced pressure to afford crude (S)-4-(4-(4-acryloyl-2-methylpiperazin-1-yl)-6-chloro-7-(2-fluorophenyl)-2-oxopyrido[2,3-d]pyrimidin-1(2H)-yl)-3-isopropyl-5-methylbenzaldehyde as a light-yellow foam that was carried forward in the following step without purification. m/z (ESI, +ve ion): 588.0 (M+H)$^+$.

Step 8: 6-Chloro-1-(4-((dimethylamino)methyl)-2-methyl-6-(2-propanyl)phenyl)-7-(2-fluorophenyl)-4-((2S)-2-methyl-4-(2-propenoyl)-1-piperazinyl)pyrido[2,3-d]pyrimidin-2(1H)-one To a solution of (S)-4-(4-(4-acryloyl-2-methylpiperazin-1-yl)-6-chloro-7-(2-fluorophenyl)-2-oxopyrido[2,3-d]pyrimidin-1(2H)-yl)-3-isopropyl-5-methylbenzaldehyde (100 mg, 0.17 mmol) in THF (1.0 mL) at rt was added dimethyl amine solution (2 M in THF, 95 μL, 0.19 mmol), glacial acetic acid (10 μL, 0.17 mmol), and sodium triacetoxyborohydride (72 mg, 0.34 mmol). The resulting cloudy yellow mixture was stirred at rt. After 18 h, the reaction mixture was diluted with EtOAc (10 mL) and water (5 mL), then saturated aqueous sodium bicarbonate (5 mL) was added until the aqueous phase was neutralized. The layers were partitioned and the aqueous phase was extracted with EtOAc (1×20 mL), then the combined organic extracts were dried over anhydrous magnesium sulfate, filtered, and concentrated to afford a light-yellow oil. The crude product was purified by silica gel chromatography (eluent: 0-20% 2 M NH3 in MeOH/DCM) to afford 6-chloro-1-(4-((dimethylamino)methyl)-2-methyl-6-(2-propanyl)phenyl)-7-(2-fluorophenyl)-4-((2S)-2-methyl-4-(2-propenoyl)-1-piperazinyl)pyrido[2,3-d]pyrimidin-2(1H)-one. $^1$H NMR (400 MHz, DMSO-$d_6$) δ ppm 0.92 (d, J=6.8 Hz, 3H), 1.05 (d, J=6.8 Hz, 3H), 1.31-1.36 (m, 3H), 1.87 (s, 3H), 2.14 (s, 6H), 3.02-3.26 (m, 1H), 3.35 (s, 2H), 3.44-3.83 (m, 2H), 3.97-4.47 (m, 3H), 4.93 (br s, 1H), 5.72-5.80 (m, 1H), 6.13-6.28 (m, 1H), 6.79-6.93 (m, 1H), 7.02 (s, 1H), 7.11 (s, 1H), 7.14-7.36 (m, 4H), 7.42-7.56 (m, 1H), 8.43 (br s, 1H). $^{19}$F NMR (376 MHz, DMSO-$d_6$) δ ppm −113.53 (s, 1F). m/z (ESI, +ve ion): 617.2 (M+H)$^+$.

TABLE 80

Compound 80-2 was prepared following the procedure described in Method 80, Steps 1-8, above as follows:

| Ex. # | Chemical structure | Name | Method Changes | Reagent |
|---|---|---|---|---|
| 80-2 | 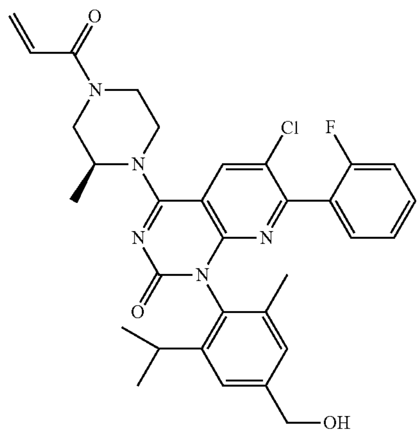 [SMILES: C=CC(=O)N1CCN(c2nc(=O)n(-c3c(C)cc(CO)cc3C(C)C)c3nc(-c4ccccc4F)c(Cl)cc23)[C@@H](C)C1] | 6-chloro-7-(2-fluorophenyl)-1-(4-(hydroxymethyl)-2-methyl-6-(2-propanyl)phenyl)-4-((2S)-2-methyl-4-(2-propenoyl)-1-piperazinyl)pyrido[2,3-d]pyrimidin-2(1H)-one | Omit Step 7 and Step 8 | |

Method 81

Example 81-1: 3-(2-Bromophenyl)-2-methyl-5-(2-methylphenyl)-8-(4-(2-propenoyl)-1-piperazinyl)-6H-pyrimido[1,6-b]pyridazin-6-one

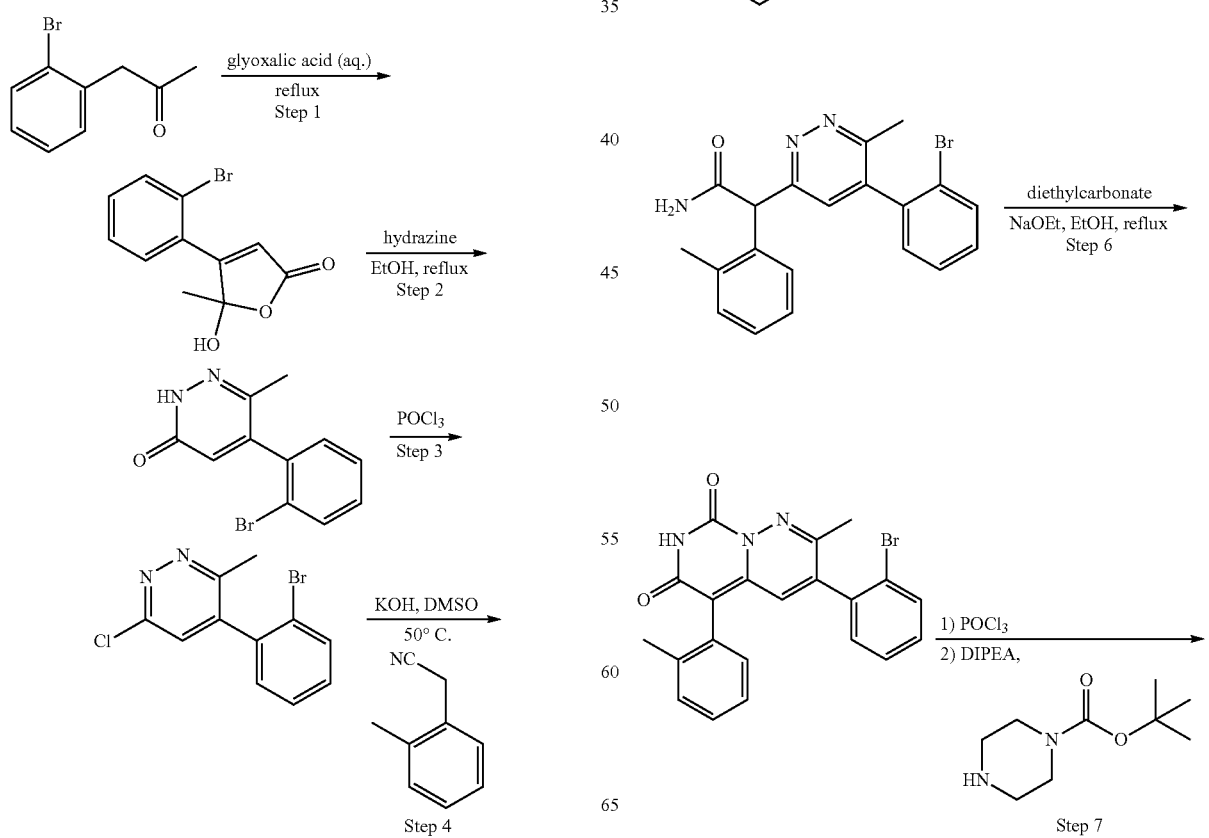

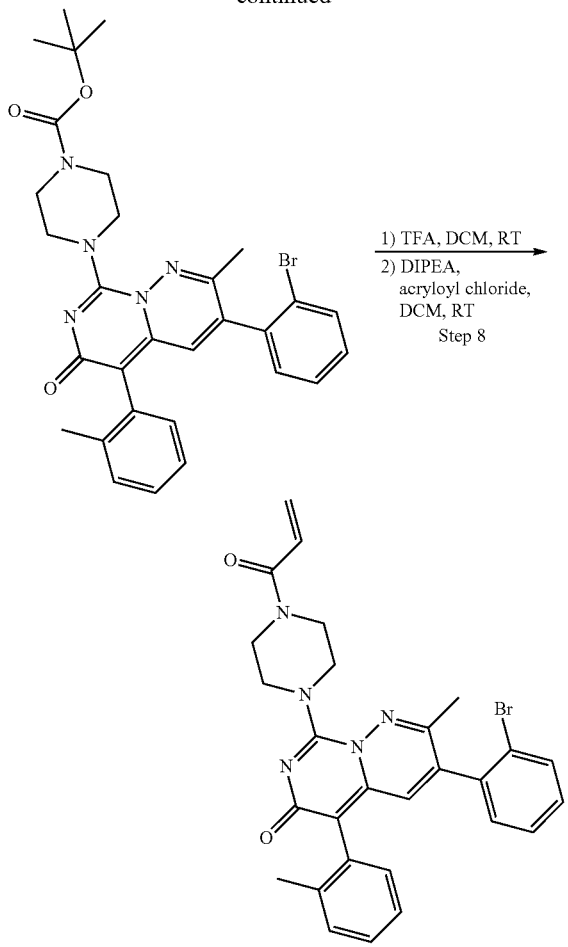

Step 1: 4-(2-Bromophenyl)-5-hydroxy-5-methyl-furan-2(5H)-one 1-(2-Bromophenyl)-2-propanone (5.18 mL, 24.31 mmol, AstaTech Inc., Bristol, Pa.) was treated with glyoxalic acid (50 wt % in water, 4.0 mL, 36.5 mmol). The flask was fitted with a reflux condenser and heated to 100° C. for 24 h. The reaction mixture was concentrated, azeotroped with toluene, and used in the subsequent step without further purification. m/z (ESI, +ve ion): 269.0 (M+H)$^+$.

Step 2: 5-(2-Bromophenyl)-6-methylpyridazin-3(2H)-one 4-(2-Bromophenyl)-5-hydroxy-5-methylfuran-2(5H)-one (6.54 g, 24.3 mmol) in EtOH (50 mL) at 0° C. was treated with hydrazine hydrate (2.39 mL, 48.6 mmol) slowly dropwise forming a suspension. The reaction mixture was then fitted with a reflux condenser and heated to 90° C. overnight. After cooling to rt, it was concentrated to dryness and purified by silica gel chromatography (eluent: 0-30% 4:1 DCM/MeOH in DCM) affording 5-(2-bromophenyl)-6-methylpyridazin-3(2H)-one (3.15 g, 11.9 mmol, 48.8% yield) as a yellow viscous oil. m/z (ESI, +ve ion): 265.0 (M+H)$^+$.

Step 3: 4-(2-Bromophenyl)-6-chloro-3-methylpyridazine 5-(2-Bromophenyl)-6-methylpyridazin-3(2H)-one (3.15 g, 11.9 mmol) was treated with phosphorus oxychloride (8.0 mL, 86 mmol) and heated to 100° C. for 2.5 h. The reaction mixture was concentrated to dryness under reduced pressure and the residue was treated with DCM and stirred for 20 min with a satd. NaHCO$_3$ until the effervescence stopped. The aqueous was then extracted with DCM (3×50 mL), dried over MgSO$_4$, filtered and concentrated. The crude product was purified by silica gel chromatography (eluent: 0-50% EtOAc/heptane) to provide 4-(2-bromophenyl)-6-chloro-3-methylpyridazine (1.97 g, 6.96 mmol, 58.7% yield) as an orange viscous oil. $^1$H NMR (400 MHz, CDCl$_3$) δ ppm 7.73 (1H, dd, J=8.1, 1.0 Hz), 7.60 (1H, dd, J=8.0, 0.9 Hz), 7.43-7.49 (1H, m), 7.38-7.42 (1H, m), 7.27-7.37 (1H, m), 7.13-7.20 (1H, m), 2.53 (3H, s). m/z (ESI, +ve ion): 283.0 (M+H)$^+$.

Step 4: 2-(5-(2-Bromophenyl)-6-methyl)-2-(o-tolyl)acetonitrile

Potassium hydroxide (1.89 g, 33.7 mmol) in DMSO (16 mL) was stirred at rt for 30 min. 2-(o-Tolyl)acetonitrile (1.73 g, 13.2 mmol, Enamine, Monmouth Jct., N.J.) in DMSO (5 mL) was then added dropwise and the reaction was allowed to stir at rt for 40 min (turned orange). The reaction mixture was then treated with 4-(2-bromophenyl)-6-chloro-3-methylpyridazine (2.33 g, 8.22 mmol) and allowed to stir at 50° C. for 4 h, then at rt for 2-d. The reaction mixture was treated with water and extracted with EtOAc (3×50 mL), dried over Na$_2$SO$_4$, filtered and concentrated. The crude product was purified by silica gel chromatography (eluent: 0-50% EtOAc/heptane) to provide 2-(5-(2-bromophenyl)-6-methylpyridazin-3-yl)-2-(o-tolyl)acetonitrile (1.45 g, 3.83 mmol, 46.6% yield) as an orange film. $^1$H NMR (400 MHz, CDCl$_3$) δ 7.64-7.75 (m, 1H), 7.49-7.60 (m, 1H), 7.38-7.47 (m, 1H), 7.31-7.36 (m, 1H), 7.27-7.30 (m, 2H), 7.17-7.25 (m, 2H), 7.07-7.18 (m, 1H), 5.83 (br d, J=9.95 Hz, 1H), 2.54 (s, 3H), 2.35-2.44 (m, 3H). m/z (ESI, +ve ion): 378.1 (M+H)$^+$.

Step 5: 2-(5-(2-Bromophenyl)-6-methylpyridazin-3-yl)-2-(o-tolyl)acetamide 2-(5-(2-Bromophenyl)-6-methylpyridazin-3-yl)-2-(o-tolyl)acetonitrile (1.45 g, 3.83 mmol) was treated with concentrated sulfuric acid (6 mL, 113 mmol) and heated to 50° C. for 2 h. The reaction mixture was then cooled in an ice bath and was carefully quenched with concentrated ammonium hydroxide (28%) slowly dropwise. The precipitate was collected by filtration, washed with water, dried in a vacuum oven overnight affording 2-(5-(2-bromophenyl)-6-methylpyridazin-3-yl)-2-(o-tolyl)acetamide (1.45 g, 3.65 mmol, 95% yield) as an off-white solid. $^1$H NMR (400 MHz, CDCl$_3$) δ 7.68 (br dd, J=3.21, 7.57 Hz, 1H), 7.37-7.47 (m, 2H), 7.32 (br d, J=7.67 Hz, 1H), 7.15-7.23 (m, 5H), 6.78 (br d, J=2.28 Hz, 1H), 5.49-5.6 (m, 2H), 2.53 (s, 3H), 2.43 (d, J=7.46 Hz, 3H). m/z (ESI, +ve ion): 396.0 (M+H)$^+$.

Step 6: 3-(2-Bromophenyl)-2-methyl-5-(o-tolyl)-6H-pyrimido[1,6-b]pyridazine-6,8(7H)-dione To a solution of 2-(5-(2-bromophenyl)-6-methylpyridazin-3-yl)-2-(o-tolyl)acetamide (227 mg, 0.57 mmol) in anhydrous EtOH (3 mL) was added sodium ethoxide (21 wt. % in EtOH, 0.39 mL, 1.03 mmol), followed by diethyl carbonate (0.12 mL, 0.97 mmol). The reaction mixture was heated at reflux for 6 h. Additional sodium ethoxide (21 wt. % in EtOH, 0.2 mL) and diethyl carbonate (0.05 mL) was added and the reaction mixture was refluxed for another 16 h. The reaction mixture was concentrated to dryness and the crude product was purified by silica gel chromatography (eluent: 0-20% MeOH/DCM) to provide 3-(2-bromophenyl)-2-methyl-5-(o-tolyl)-6H-pyrimido[1,6-b]pyridazine-6,8(7H)-dione (200 mg, 0.47 mmol, 83% yield) as a yellow solid. $^1$H NMR (400 MHz, DMSO-d$_6$) δ ppm 11.93-11.99 (1H, m), 7.72-7.77 (1H, m), 7.45-7.51 (1H, m), 7.36-7.43 (2H, m), 7.19-7.31 (3H, m), 7.10-7.19 (1H, m), 6.44-6.51 (1H, m), 2.13 (3H, br d, J=5.8 Hz), 2.03-2.10 (3H, m). m/z (ESI, +ve ion): 422.0 (M+H)$^+$.

Step 7: tert-Butyl 4-(3-(2-bromophenyl)-2-methyl-6-oxo-5-(o-tolyl)-6H-pyrimido[1,6-b]pyridazin-8-yl)piperazine-1-carboxylate 3-(2-Bromophenyl)-2-methyl-5-(o-tolyl)-6H-pyrimido[1,6-b]pyridazine-6,8(7H)-dione (185 mg, 0.438 mmol) in phosphorus oxychloride (2.0 mL, 21.5 mmol) was heated to 95° C. for 45 min. The reaction mixture was concentrated to dryness in vacuo. The resulting residue was treated with DCM (4 mL) and cooled in an ice bath. 1-(tert-Butoxycarbonyl)-piperazine (122 mg, 0.66 mmol) and Hünig's base (0.54 mL, 3.07 mmol) were added, and the reaction mixture was stirred at 0° C. After 10 min, the reaction mixture was treated with a satd. NaHCO$_3$ and extracted with DCM (2×10 mL), dried over MgSO$_4$, filtered and concentrated. The crude product was purified by silica gel chromatography (eluent: 0-20% MeOH/DCM) to provide tert-butyl 4-(3-(2-bromophenyl)-2-methyl-6-oxo-5-(o-tolyl)-6H-pyrimido[1,6-b]pyridazin-8-yl)piperazine-1-carboxylate (11.8 mg, 0.02 mmol, 4.6% yield) as a yellow film. m/z (ESI, +ve ion): 590.1 (M+H)$^+$.

Step 8: 8-(4-Acryloylpiperazin-1-yl)-3-(2-bromophenyl)-2-methyl-5-(o-tolyl)-6H-pyrimido[1,6-b]pyridazin-6-one tert-Butyl 4-(3-(2-bromophenyl)-2-methyl-6-oxo-5-(o-tolyl)-6H-pyrimido[1,6-b]pyridazin-8-yl)piperazine-1-carboxylate (11 mg, 0.019 mmol) in DCM (2 mL) was treated with TFA (0.5 mL, 6.49 mmol), and the reaction mixture was allowed to stir at rt for 15 min. The reaction mixture was concentrated to dryness under reduced pressure. The crude residue was treated with DCM (4 mL). cooled in an ice bath, and treated with Hünig's base (0.1 mL) and acryloyl chloride (1.5 μl, 0.019 mmol). After 10 min, the reaction mixture was treated with saturated NaHCO$_3$, extracted with DCM (2×10 mL), dried over MgSO$_4$, filtered and concentrated. The crude product was purified by silica gel chromatography (eluent: 0-20% MeOH/DCM) to provide 8-(4-acryloylpiperazin-1-yl)-3-(2-bromophenyl)-2-methyl-5-(o-tolyl)-6H-pyrimido[1,6-b]pyridazin-6-one (6.0 mg, 0.011 mmol, 59.2% yield) as a yellow solid. $^1$H NMR (400 MHz, METHANOL-d$_4$) δ ppm 7.74 (1H, br d, J=8.1 Hz), 7.45-7.52 (1H, m), 7.39 (1H, td, J=7.8, 1.7 Hz), 7.30-7.36 (3H, m), 7.23-7.30 (2H, m), 7.16 (1H, br dd, J=8.2, 1.8 Hz), 6.80-6.90 (1H, m), 6.25-6.32 (1H, m), 5.79-5.85 (1H, m), 3.87-3.96 (4H, m), 3.79-3.87 (4H, m), 2.25 (3H, s), 2.19 (3H, br s). m/z (ESI, +ve ion): 544.1 (M+H)$^+$.

TABLE 81

Compounds 81-2 to 81-3 were prepared following the procedure described in Method 81, Steps 1-8, above as follows:

| Ex. # | Chemical structure | Name | Method Changes | Reagent |
| --- | --- | --- | --- | --- |
| 81-2 | 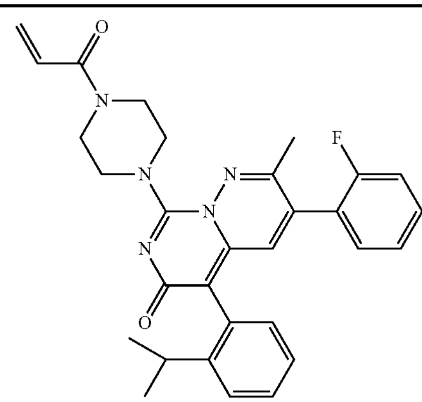 | 3-(2-fluorophenyl)-2-methyl-5-(2-(2-propanyl)phenyl)-8-(4-(2-propenoyl)-1-piperazinyl)-6H-pyrimido[1,6-b]pyridazin-6-one | | Step 4: 2-isopropylbenzylcyanide |
| 81-3 | 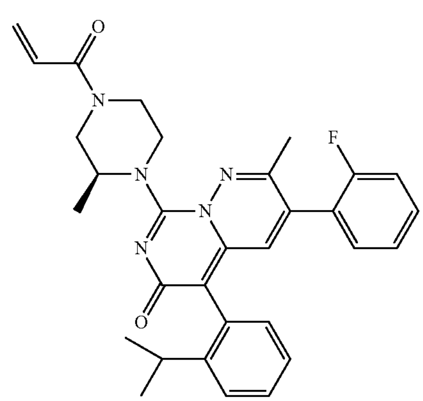 [SMILES: C=CC(=O)N1CCN(c2nc(=O)c(-c3ccccc3C(C)C)c3cc(-c4ccccc4F)c(C)nn23)[C@@H](C)C1] | 3-(2-fluorophenyl)-2-methyl-8-((2S)-2-methyl-4-(2-propenoyl)-1-piperazinyl)-5-(2-(2-propanyl)phenyl)-6H-pyrimido[1,6-b]pyridazin-6-one | | Step 4: 2-isopropylbenzylcyanide, Step 7: tert-butyl (S)-3-methylpiperazine-1-carboxylate |

Method 82

Example 82-1: (M)-6-Chloro-7-(5-methyl-1H-indazol-4-yl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one

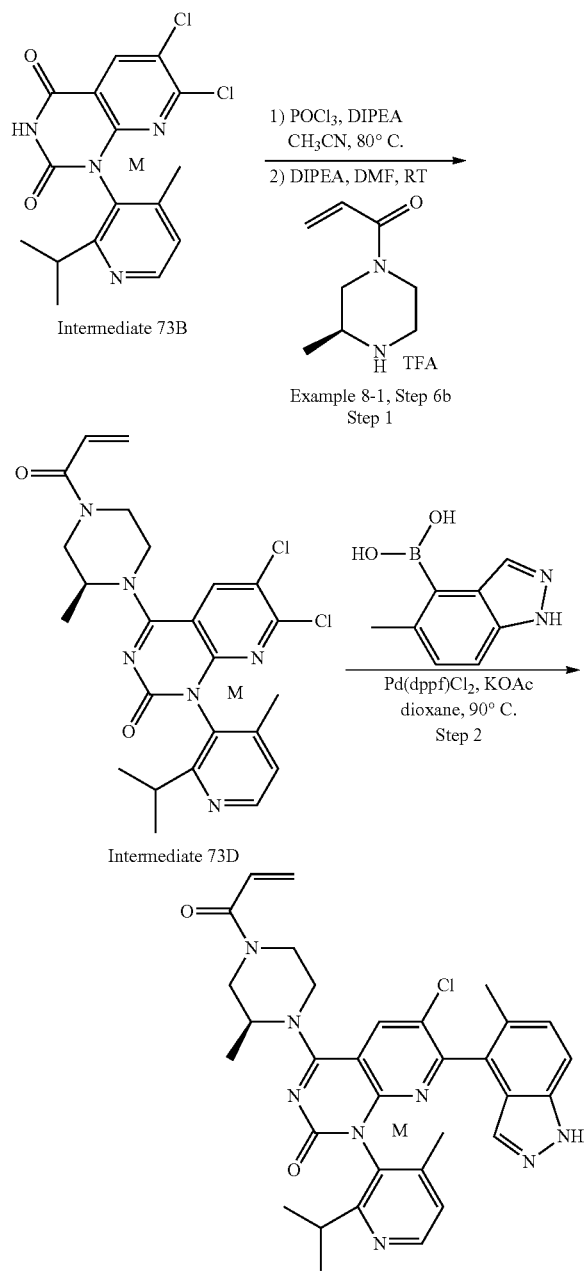

Step 1: (M,S)-4-(4-Acryloyl-2-methylpiperazin-1-yl)-6,7-dichloro-1-(2-isopropyl-4-methylpyridin-3-yl)pyrido[2,3-d]pyrimidin-2(1H)-one To a mixture of (M)-6,7-dichloro-1-(2-isopropyl-4-methylpyridin-3-yl)pyrido[2,3-d]pyrimidine-2,4(1H,3H)-dione (Intermediate 73B, 2.0 g, 5.48 mmol) and N-ethyl-N-isopropylpropan-2-amine (2.86 mL, 16.4 mmol) in acetonitrile (40 mL) was added phosphoryl trichloride (1.0 mL, 11 mmol) at it, and the reaction was heated at 80° C. for 1.5 h. The mixture was concentrated to give the crude (M)-4,6,7-trichloro-1-(2-isopropyl-4-methylpyridin-3-yl)pyrido[2,3-d]pyrimidin-2(1H)-one as thick brown oil which was used in the next step without purification.

The crude product from above reaction was dissolved in DMF (10 mL) and treated with N-ethyl-N-isopropylpropan-2-amine (2.86 mL, 16.4 mmol) followed by (S)-1-(3-methylpiperazin-1-yl)prop-2-en-1-one (TFA salt, Example 8-1, Step 6b, 3.54 g, 5.48 mmol). The mixture was stirred at rt for 10 min, LC-MS showed about 50% conversion to the desired product. After stirring for an additional 16 h, LC-MS indicated complete conversion. The reaction was quenched with water and the resulting mixture was extracted with EtOAc (2×) and DCM. The organic extracts were combined, washed with brine, dried over $Na_2SO_4$ and filtered. The filtrate was concentrated and purified by silica gel chromatography (eluent: 0-60% EtOAc:EtOH (3:1)/heptane) to provide (M,S)-4-(4-acryloyl-2-methylpiperazin-1-yl)-6,7-dichloro-1-(2-isopropyl-4-methylpyridin-3-yl)pyrido[2,3-d]pyrimidin-2(1H)-one (Intermediate 73D; 1.67 g, 3.33 mmol, 60.8% yield) as yellow solid. m/z (ESI, +ve ion): 501.0 $(M+H)^+$.

Step 2: (M)-chloro-7-(5-methyl-1H-indazol-4-yl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one To a pressure vial was added (M,S)-4-(4-acryloyl-2-methylpiperazin-1-yl)-6,7-dichloro-1-(2-isopropyl-4-methylpyridin-3-yl)pyrido[2,3-d]pyrimidin-2(1H)-one (Intermediate 73D: 0.20 g, 0.40 mmol), 5-methyl-1H-indazol-4-boronic acid (0.105 g, 0.598 mmol), [1,1'-bis(diphenylphosphino)ferrocene]-dichloropalladium(II), complex with DCM (0.016 g, 0.02 mmol), potassium acetate (0.196 g, 1.99 mmol) and 1,4-dioxane (10 mL). The vial was purged with N, for 3 min, sealed and then heated at 90° C. for 1 h. The reaction mixture was partitioned between EtOAc and water and the organic layer was washed with brine, dried over $Na_2SO_4$ and filtered. The filtrate was concentrated and purified twice by silica gel chromatography (eluent: 0-60% (EtOAc:EtOH (3:1)/heptane) to provide (M)-4-((S)-4-acryloyl-2-methylpiperazin-1-yl)-6-chloro-1-(2-isopropyl-4-methyl pyridin-3-yl)-7-(5-methyl-1H-indazol-4-yl)pyrido[2,3-d]pyrimidin-2(1H)-one (0.044 g, 0.074 mmol, 18.5% yield) as a light brown solid. $^1$H NMR (DMSO-$d_6$) δ: 12.95-13.29 (m, 1H), 8.48 (br d, J=6.0 Hz, 1H), 8.30 (dd, J=11.2, 5.0 Hz, 1H), 7.40-7.52 (m, 2H), 7.23 (dd, J=8.6, 2.2 Hz, 1H), 7.08-7.18 (m, 1H), 6.81-6.95 (m, 1H), 6.22 (br d, J=16.0 Hz, 1H), 5.74-5.81 (m, 1H), 4.88-5.03 (m, 1H), 4.05-4.47 (m, 3H), 3.50-3.86 (m, 2H), 3.10-3.24 (m, 1H), 2.71-2.86 (m, 1H), 1.86-2.09 (m, 6H), 1.38 (dd, J=6.6, 2.1 Hz, 3H), 1.06 (dd, J=6.6, 3.5 Hz, 3H), 0.76-0.94 (m, 3H). m/z (ESI, +ve ion): 597.2 $(M+H)^+$.

TABLE 82

Compounds 82-2 was prepared following the procedure described in Method 82, Steps 1-2, above as follows:

| Ex. # | Chemical structure | Name | Method Changes | Reagent |
|---|---|---|---|---|
| 82-2 | 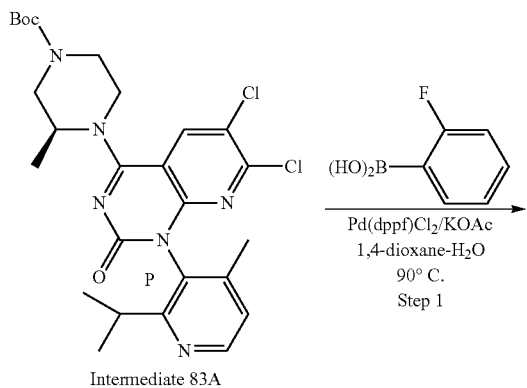 single isomer (M) | (M)-6-chloro-7-(5-fluoro-1H-indazol-4-yl)-1-(4-methyl-2-(2-propanyl)-3-pyridinyl)-4-((2S)-2-methyl-4-(2-propenoyl)-piperazinyl)pyrido[2,3-d]pyrimidin-2(1H)-one | | Step 2: 5-fluoro-4-(4,4,5,5-tetramethyl-1,3,2-dioxaborolan-2-yl)-1H-indazole |

Method 83 and 84

Example 83-1: (P)-6-Chloro-7-(2-fluorophenyl)-1-(5-hydroxy-4-methyl-2-(2-propanyl)-3-pyridinyl)-4-((2S)-2-methyl-4-(2-propenoyl)-1-piperaninyl)pyrido[2,3-d]pyrimidin-2(1H)-one and Example 84-1: (P)-6-chloro-7-(2-fluorophenyl)-1-(4-(hydroxymethyl)-2-(2-propanyl)-3-pyridinyl)-4-((2S)-2-methyl-4-(2-propenoyl)-1-piperazinyl)pyrido[2,3-d]pyrimidin-2(1H)-one

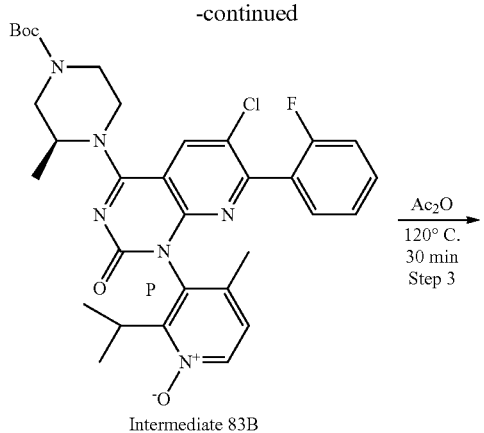

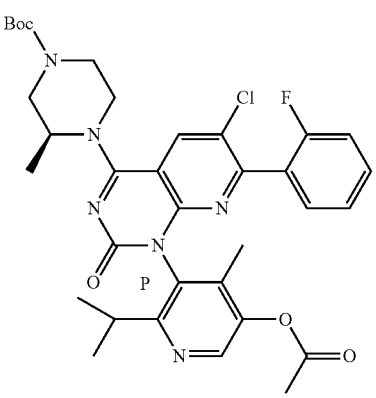

Intermediate 83C

533
-continued

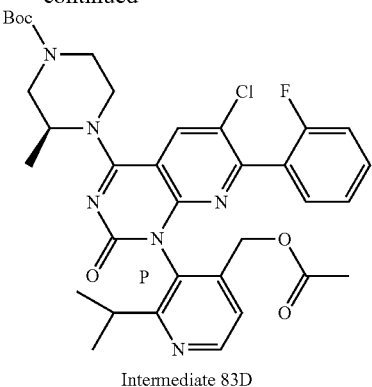
Intermediate 83D

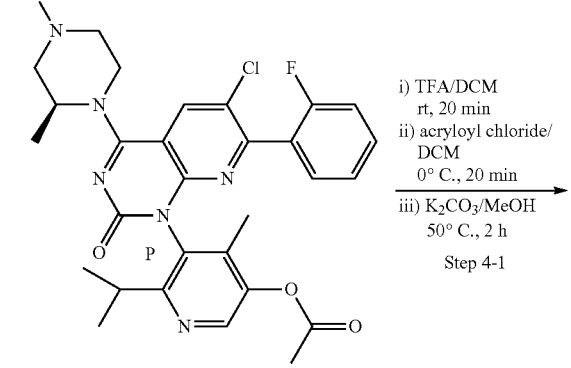

Intermediate 83C

Intermediate 83-1

Intermediate 83D

534
-continued

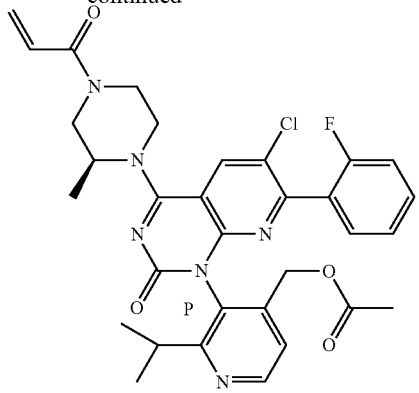
Intermediate 84-1

Step 1: tert-Butyl (P)—(S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate A mixture of tert-butyl (P)—(S)-4-(6,7-dichloro-1-(2-isopropyl-4-methylpyridin-3-yl)-2-oxo-1,2-dihydropyrido[2,3-d]pyrimidin-4-yl)-3-methylpiperazine-1-carboxylate (Intermediate 83A prepared according to Method 73 using Intermediate 73A, 1.00 g, 1.83 mmol), 2-fluorophenylboronic acid (0.307 g, 2.19 mmol), potassium acetate (0.896 g, 9.13 mmol), (1,1'-bis(diphenylphosphino)ferrocene)dichloropalladium-dichloromethane (1:1) (0.075 g, 0.091 mmol) in 1,4-dioxane (18 mL) and water (0.09 mL) and was purged with nitrogen for 5 minutes and stirred and heated at 90° C. After 15 h, the mixture was cooled to rt and diluted with EtOAc (50 mL). The insoluble solids were filtered off and washed with EtOAc (50 mL) and the filtrate concentrated. The crude material was adsorbed onto a plug of silica gel and purified by silica gel chromatography (eluent 0-100% EtOAc/heptanes) to provide tert-butyl (P)—(S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate (0.942 g, 1.55 mmol, 85% yield) as a brown solid. $^1$H NMR (400 MHz, DMSO-$d_6$) δ ppm 8.44 (s, 1H), 8.39 (d, J=4.8 Hz, 1H), 7.48-7.55 (m, 1H), 7.15-7.34 (m, 4H), 4.91 (br s, 1H), 4.26 (br d, J=13.5 Hz, 1H), 3.92-4.01 (m, 1H), 3.85 (br d, J=13.3 Hz, 1H), 3.73 (br t, J=11.1 Hz, 1H), 3.05-3.30 (m, 2H), 2.70 (quin, J=6.7 Hz, 1H), 1.93 (s, 3H), 1.46 (s, 9H), 1.36 (br d, J=6.8 Hz, 3H), 1.06 (d, J=6.8 Hz, 3H), 0.94 (d, J=6.6 Hz, 3H). $^{19}$F NMR (376 MHz, DMSO-$d_6$) δ ppm −114.05 (s, 1F). m/z (ESI, +ve ion): 607.0 (M+H).

Step 2: (P)—(S)-3-(4-(4-(tert-Butoxycarbonyl)-2-methylpiperazin-1-yl)-6-chloro-7-(2-fluorophenyl)-2-oxopyrido[2,3-d]pyrimidin-1(2H)-yl)-2-isopropyl-4-methylpyridine 1-oxide To a cooled mixture of tert-butyl (P)—(S)-4-(6-chloro-7-(2-fluorophenyl)-1-(2-isopropyl-4-methylpyridin-3-yl)-2-oxo-1,2-dihydropyrido[2,3-d]pyrimidin-4-yl)-3-methylpiperazine-1-carboxylate (0.304 g, 0.501 mmol) in chloroform (2.5 mL) at 0° C. was added dropwise a solution of 3-chloroperoxybenzoic acid (0.17 g, 1.0 mmol) in chloroform (2.5 mL) and the mixture was stirred at 0° C. and allowed to warm to rt with stirring. After 18 h, the mixture was quenched with 10% Na2SO3 (50 mL) and the mixture was stirred at rt. The mixture was extracted with DCM (2×50 mL), the organic extracts were washed with satd NaHCO$_3$ (1×100 mL) and dried over Na$_2$SO$_4$. The solution was filtered and concentrated in vacuo to give (P)—(S)-3-(4-(4-(tert-butoxycarbonyl)-2-methylpiperazin-1-yl)-6-chloro-7-(2-fluorophenyl)-2-oxopyrido[2,3-d]pyrimidin-(2H)-yl)-2-isopropyl-4-methylpyridine 1-oxide (Intermediate 83B, 0.312 g, 0.501 mmol, 100% yield) as a light-yellow solid. $^1$H NMR (400 MHz, DMSO-d$_6$) δ ppm 8.46 (s, 1H), 8.12 (d, J=6.6 Hz, 1H), 7.49-7.58 (m, 2H), 7.22-7.36 (m, 7H), 4.93 (br s, 1H), 4.28 (br d, J=13.5 Hz, 1H), 3.94-4.05 (m, 1H), 3.85 (br d, J=13.1 Hz, 1H), 3.74 (br t, J=11.2 Hz, 1H), 3.07-3.28 (min, 2H), 2.82-3.07 (m, 2H), 1.86 (s, 3H), 1.45 (s, 9H), 1.36 (br d, J=6.8 Hz, 3H), 1.18-1.27 (m, 6H), 1.12 (d, J=7.0 Hz, 5H). $^{19}$F NMR (376 MHz, DMSO-d$_6$) δ ppm −14.06 (s, 1F). m/z (ESI, +ve ion): 623.0 (M+H). The crude product was carried on crude for the next step.

Step 3: tert-Butyl (P)—(S)-4-(1-(5-acetoxy-2-isopropyl-4-methylpyridin-3-yl)-6-chloro-7-(2-fluorophenyl)-2-oxo-1,2-dihydropyrido[2,3-d]pyrimidin-4-yl)-3-methylpiperazine-1-carboxylate and tert-Butyl (P)—(S)-(1-(4-(acetoxymethyl)-2-isopropylpyridin-3-yl)-6-chloro-7-(2-fluorophenyl)-2-oxo-1,2-dihydropyrido[2,3-d]pyrimidin-4-yl)-3-methylpiperazine-1-carboxylate A mixture of (P)—(S)-3-(4-(4-(tert-butoxycarbonyl)-2-methylpiperazin-1-yl)-6-chloro-7-(2-fluorophenyl)-2-oxopyrido[2,3-d]pyrimidin-(2H)-yl)-2-isopropyl-4-methylpyridine 1-oxide (Intermediate 83B, 0.31 g, 0.50 mmol) and acetic anhydride (1.9 mL, 20 mmol) was stirred and heated at 120° C. After 30 min. the mixture was cooled to rt and concentrated in vacuo. The crude product was purified by silica gel chromatography (eluent 0-100% EtOAc/heptane) to provide two fractions:

Fraction 1:
tert-Butyl (P)—(S)-4-(1-(5-acetoxy-2-isopropyl-4-methylpyridin-3-yl)-6-chloro-7-(2-fluorophenyl)-2-oxo-1,2-dihydropyrido[2,3-d]pyrimidin-4-yl)-3-methylpiperazine-1-carboxylate (Intermediate 83C, 0.051 g, 0.077 mmol, 15.3% yield) as a yellow solid. $^1$H NMR (400 MHz, DMSO-d$_6$) δ ppm 8.33 (s, 1H), 7.48-7.55 (m, 1H), 7.18-7.34 (m, 4H), 4.96 (br s, 1H), 4.26 (br d, J=13.5 Hz, 1H), 3.93-4.06 (m, 1H), 3.85 (br d, J=12.9 Hz, 1H), 3.69-3.81 (m, 1H), 3.03-3.26 (m, 2H), 2.69-2.77 (m, 1H), 2.34 (s, 3H), 1.46 (s, 12H), 1.35 (br d, J=6.4 Hz, 3H), 1.08 (d, J=6.6 Hz, 3H), 0.92 (d, J=6.6 Hz, 3H). $^{19}$F NMR (376 MHz, DMSO-d$_6$) δ ppm −113.61 (s, 1F). m/z (ESI, +ve ion): 665.0 (M+H).

Fraction 2:
tert-Butyl (P)—(S)-4-(1-(4-(acetoxymethyl)-2-isopropylpyridin-3-yl)-6-chloro-7-(2-fluorophenyl)-2-oxo-1,2-dihydropyrido[2,3-d]pyrimidin-4-yl)-3-methylpiperazine-1-carboxylate (Intermediate 83D, 0.042 g, 0.062 mmol, 12% yield) as a yellow solid. $^1$H NMR (400 MHz, DMSO-d$_6$) δ ppm 8.56 (d, J=4.8 Hz, 1H), 8.43 (s, 1H), 7.46-7.56 (m, 1H), 7.20-7.35 (m, 4H), 4.89 (br s, 1H), 4.77-4.86 (m, 2H), 4.29 (br d, J=13.1 Hz, 1H), 3.95-4.05 (m, 1H), 3.86 (br d, J=13.5 Hz, 1H), 3.64-3.76 (m, 1H), 3.04-3.28 (m, 2H), 2.72 (dt, J=13.5, 6.7 Hz, 1H), 1.86 (s, 3H), 1.46 (s, 9H), 1.38 (br d, J=6.2 Hz, 3H), 1.07 (br d, J=6.6 Hz, 3H), 0.95 (br d, J=6.6 Hz, 3H). $^{19}$F NMR (376 MHz, DMSO-d$_6$) δ ppm −113.85 (br s, 1F). m/z (ESI, +ve ion): 665.0 (M+H).

Step 4-1: (P)-6-Chloro-7-(2-fluorophenyl)-1-(5-hydroxy-4-methyl-2-(2-propanyl)-3-pyridinyl)-4-((2S)-2-methyl-4-(2-propenoyl)-1-piperazinyl)pyrido[2,3-d]pyrimidin-2(1H)-one To a solution of tert-butyl (P)—(S)-4-(1-(5-acetoxy-2-isopropyl-4-methylpyridin-3-yl)-6-chloro-7-(2-fluorophenyl)-2-oxo-1,2-dihydropyrido[2,3-d]pyrimidin-4-yl)-3-methylpiperazine-1-carboxylate (Intermediate 83C, 0.048 g, 0.072 mmol) in DCM (1.8 mL) was added trifluoroacetic acid (1.8 mL) and the mixture was stirred at rt. After 40 min, the mixture was concentrated in vacuo to give (P)—(S)-5-(6-chloro-7-(2-fluorophenyl)-4-(2-methylpiperazin-1-yl)-2-oxopyrido[2,3-d]pyrimidin-1(2H)-yl)-6-isopropyl-4-methylpyridin-3-yl acetate as an orange syrup. m/z (ESI, +ve ion): 565.2 (M+H).

The orange syrup was dissolved in DCM (1.8 mL) and the mixture was cooled to 0° C. To the cooled mixture at 0° C. was added DIPEA (0.19 mL, 1.09 mmol) followed by acryloyl chloride, (0.2 M in DCM, 0.38 mL, 0.076 mmol) dropwise and the mixture was stirred at 0° C. After 10 min, the reaction mixture was concentrated in vacuo to give (P)—(S)-5-(4-(4-acryloyl-2-methylpiperazin-1-yl)-6-chloro-7-(2-fluorophenyl)-2-oxopyrido[2,3-d]pyrimidin-1(2H)-yl)-6-isopropyl-4-methylpyridin-3-yl acetate as a brown syrup. m/z (ESI, +ve ion): 619.2 (M+H).

The brown syrup was dissolved in methanol (3 mL) and treated with anhydrous potassium carbonate (0.04 g, 0.289 mmol) and the mixture was stirred at 50° C. After 2 h, the mixture was concentrated in vacuo and the crude product was purified by silica gel chromatography (eluent 0-50% DCM-MeOH (4:1)/DCM) to provide (P)-6-chloro-7-(2-fluorophenyl)-1-(5-hydroxy-4-methyl-2-(2-propanyl)-3-pyridinyl)-4-((2S)-2-methyl-4-(2-propenoyl)-1-piperazinyl)pyrido[2,3-d]pyrimidin-2(1H)-one (0.018 g, 0.032 mmol, 44% yield) as an off-white solid. $^1$H NMR (400 MHz, DMSO-d$_6$) δ ppm 9.70 (s, 1H), 8.40-8.48 (m, 1H), 8.08 (s, 1H), 7.48-7.56 (m, 1H), 7.25-7.36 (m, 2H), 7.17-7.24 (m, 1H), 6.78-6.93 (m, 1H), 6.15-6.28 (m, 1H), 5.74-5.78 (m, 1H), 4.93 (br s, 1H), 4.23-4.45 (m, 2H), 3.98-4.20 (m, 1H), 3.42-3.83 (m, 2H), 3.04-3.28 (m, 1H), 2.54-2.60 (m, 1H), 1.75 (s, 3H), 1.34 (d, J=6.6 Hz, 3H), 1.01 (d, J=6.8 Hz, 3H), (m, 2H), 3.42-3.84 (m, 2H), 3.06-3.28 (m, 1H), 2.63-2.74 (m, 1H), 1.35 (d, J=6.6 Hz, 3H), 1.07 (d, J=6.8 Hz, 3H), 0.95 (d, J=6.8 Hz, 3H). $^{19}$F NMR (376 MHz, DMSO-$d_6$) δ ppm −113.72 (s, 1F). m/z (ESI, +ve ion): 577.2 (M+H).

TABLE 83 and 84

Compounds 83-2 and 84-2 were prepared following the procedure described in Method 83 and 84, Steps 1-4, above as follows:

| Ex. # | Chemical structure | Name | Method Changes | Reagent |
|---|---|---|---|---|
| 83-2 | *single isomer (M)* | (M)-6-chloro-7-(2-fluorophenyl)-1-(5-hydroxy-4-methyl-2-(2-propanyl)-3-pyridinyl)-4-((2S)-2-methyl-4-(2-propenoyl)-1-piperazinyl)pyrido[2,3-d]pyrimidin-2(1H)-one | | Step 1: (M)-6,7-dichloro-1-(2-isopropyl-4-methylpyridin-3-yl)pyrido[2,3-d]pyrimidine-2,4(1H,3H)-dione (Intermediate 73B) |
| 84-2 | *single isomer (M)* | (M)-6-chloro-7-(2-fluorophenyl)-1-(4-(hydroxymethyl)-2-(2-propanyl)-3-pyridinyl)-4-((2S)-2-methyl-4-(2-propenoyl)-1-piperazinyl)pyrido[2,3-d]pyrimidin-2(1H)-one | | Step 1: (M)-6,7-dichloro-1-(2-isopropyl-4-methylpyridin-3-yl)pyrido[2,3-d]pyrimidine-2,4(1H,3H)-dione (Intermediate 73B) |

0.90 (d, J=6.8 Hz, 3H). $^{19}$F NMR (376 MHz, DMSO-$d_6$) δ ppm −114.11 (s, 1F). m/z (ESI, +ve ion): 577.2 (M+H).

Step 4-2: (P)-6-Chloro-7-(2-fluorophenyl)-1-(4-(hydroxymethyl)-2-(2-propanyl)-3-pyridinyl)-4-((2S)-2-methyl-4-(2-propenoyl)-1-piperazinyl)pyrido[2,3-d]pyrimidin-2(1H)-one Example 84-1 prepared according to Step 4-1 using Intermediate 83D (40 mg, 0.06 mmol) to provide (P)-6-chloro-7-(2-fluorophenyl)-1-(4-(hydroxymethyl)-2-(2-propanyl)-3-pyridinyl)-4-((2S)-2-methyl-4-(2-propenoyl)-1-piperazinyl)pyrido[2,3-d]pyrimidin-2(1H)-one (Example 84-1). $^1$H NMR (400 MHz, DMSO-$d_6$) δ ppm 8.53 (d, J=4.8 Hz, 1H), 8.44 (br d, J=5.8 Hz, 1H), 7.47-7.55 (m, 1H), 7.39 (d, J=5.0 Hz, 1H), 7.24-7.34 (m, 2H), 7.17-7.23 (m, 1H), 6.79-6.94 (m, 1H), 6.21 (br d, J=15.8 Hz, 1H), 5.74-5.79 (m, 1H), 5.32 (t, J=5.6 Hz, 1H), 4.92 (br s, 1H), 4.34 (br d, J=13.9 Hz, 2H), 4.26 (br dd, J=16.0, 5.4 Hz, 1H), 4.05-4.20

Method 85

Example 85-1: 1-(4-(3-Chloro-2-(2-fluorophenyl)-7-(hydroxymethyl)-8-(2-isopropylphenyl)-1,6-naphthyridin-5-yl)prop-2-en-1-one Intermediate P $\xrightarrow{\text{Cu—I, Cs}_2\text{CO}_3\text{, dioxane, 80° C.}}$ Step 1

-continued

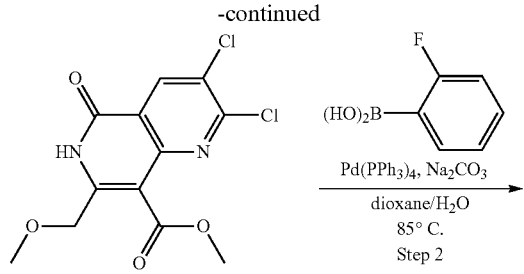

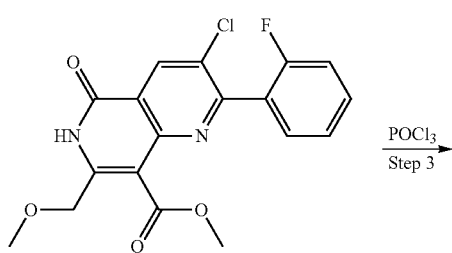

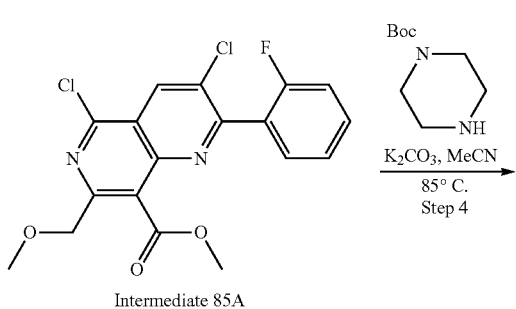

Intermediate 85A

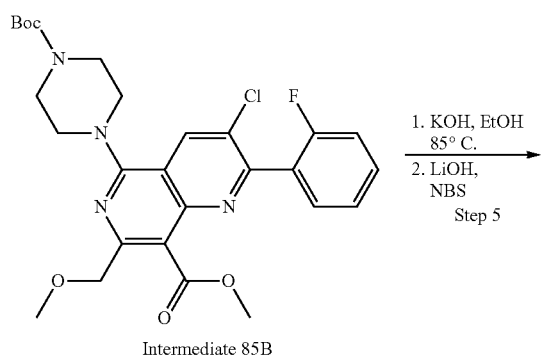

Intermediate 85B

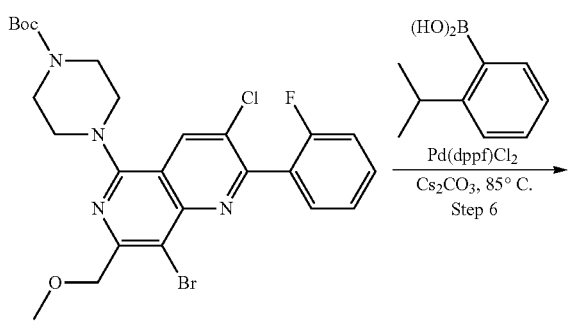

-continued

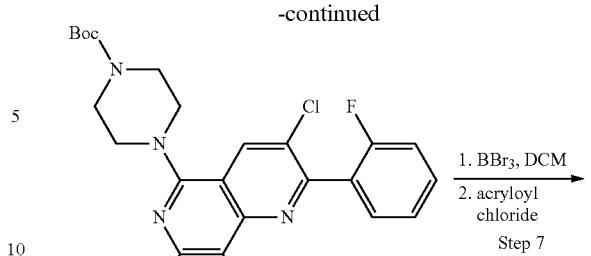

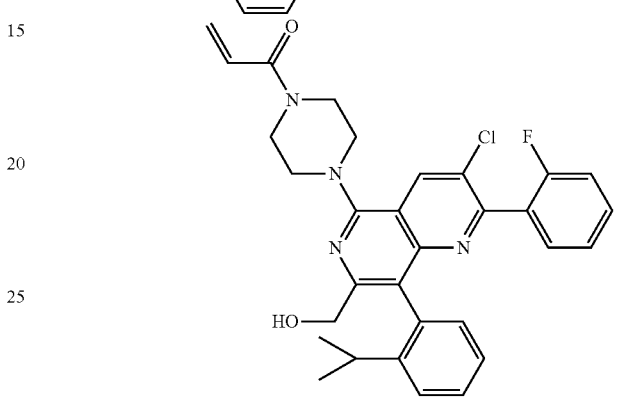

Step 1: Methyl 2,3-dichloro-7-(methoxymethyl)-5-oxo-5,6-dihydro-1,6-naphthyridine-8-carboxylate A mixture of 2,5,6-trichloronicotinamide (Intermediate P, 5.0 g, 22 mmol), 4-methoxy-3-oxo-butanoic acid methyl ester (4.86 mL, 33.3 mmol), copper(I) iodide (0.42 g, 2.22 mmol) and cesium carbonate (14.45 g, 44.4 mmol) was purged with $N_2$ followed by the addition of 1,4-dioxane (110 mL) and the reaction mixture was heated at 80° C. under nitrogen for 16 h. The mixture was quenched with 9:1 sat. $NH_4Cl/NH_4OH$ and extracted with EtOAc. The combined organics were concentrated to give methyl 2,3-dichloro-7-(methoxymethyl)-5-oxo-5,6-dihydro-1,6-naphthyridine-8-carboxylate (4.0 g, 12.6 mmol, 56.9% yield). m/z (ESI, +ve ion): 317.0 (M+H)$^+$. The crude material was used as is in the subsequent step.

Step 2: Methyl 3-chloro-2-(2-fluorophenyl)-7-(methoxymethyl)-5-oxo-5,6-dihydro-1,6-naphthyridine-8-carboxylate A mixture of methyl 2,3-dichloro-7-(methoxymethyl)-5-oxo-5,6-dihydro-1,6-naphthyridine-8-carboxylate (4.0 g, 12.6 mmol), (2-fluorophenyl)boronic acid (2.29 g, 16.4 mmol, Combi-Blocks Inc.), palladium tetrakis (1.46 g, 1.26 mmol) and sodium carbonate (4.01 g, 37.8 mmol) in 1,4-dioxane/water (30/7.5 mL) was heated at 85° C. for 45 min. The reaction was quenched with saturated $NaHCO_3$ and extracted with EtOAc. The crude product was purified by silica gel chromatography (eluent: 0-50% EtOAc:EtOH (3:1)/heptane) to provide methyl 3-chloro-2-(2-fluorophenyl)-7-(methoxymethyl)-5-oxo-5,6-dihydro-1,6-naphthyridine-8-carboxylate (4.0 g, 10.6 mmol, 84% yield) as a yellow solid. m/z (ESI, +ve ion): 377.0 (M+H)$^+$.

Step 3: Methyl 3,5-dichloro-2-(2-fluorophenyl)-7-(methoxymethyl)-1,6-naphthyridine-8-carboxylate (Intermediate 85A)

A solution of methyl 3-chloro-2-(2-fluorophenyl)-7-(methoxymethyl)-5-oxo-5,6-dihydro-1,6-naphthyridine-8-carboxylate (0.30 g, 0.80 mmol) and phosphoryl trichloride (5.0 mL, 54 mmol) was heated at 90° C. for 1 h. The reaction was concentrated in vacuo and the residue was diluted with EtOAc, washed with sat. NaHCO$_3$ and brine. The combined organics were concentrated to afford methyl 3,5-dichloro-2-(2-fluorophenyl)-7-(methoxymethyl)-1,6-naphthyridine-8-carboxylate (Intermediate 85A, 0.3 g, 0.759 mmol, 95% yield) as a brown solid. m/z (ESI, +ve ion): 395.0 (M+H)$^+$.

Step 4: Methyl 5-(4-(tert-butoxycarbonyl)piperazin-1-yl)-3-chloro-2-(2-fluorophenyl)-7-(methoxymethyl)-1,6-naphthyridine-8-carboxylate A mixture of methyl 3,5-dichloro-2-(2-fluorophenyl)-7-(methoxymethyl)-1,6-naphthyridine-8-carboxylate (Intermediate 85A, 0.3 g, 0.76 mmol), tert-butyl piperazine-1-carboxylate (0.42 g, 2.28 mmol), potassium carbonate (0.42 g, 3.04 mmol) and sodium sulfate (1.62 g, 11.4 mmol) in MeCN (12 mL) was heated at 85° C. for 2 h. The reaction was cooled to rt, washed with water and extracted with EtOAc to afford methyl 5-(4-(tert-butoxycarbonyl)piperazin-1-yl)-3-chloro-2-(2-fluorophenyl)-7-(methoxymethyl)-1,6-naphthyridine-8-carboxylate (Intermediate 85B) to be used as is in the next step assuming quantitative yield. m/z (ESI, +ve ion): 545.2 (M+H)$^+$.

Step 5: tert-Butyl 4-(8-bromo-3-chloro-2-(2-fluorophenyl)-7-(methoxymethyl)-1,6-naphthyridin-5-yl)piperazine-1-carboxylate To a solution of methyl 5-(4-(tert-butoxycarbonyl)piperazin-1-yl)-3-chloro-2-(2-fluorophenyl)-7-(methoxymethyl)-1,6-naphthyridine-8-carboxylate (Intermediate 85B, 0.024 g, 0.044 mmol) in EtOH (2 mL) was added KOH (0.15 g, 2.67 mmol) and the resulting mixture was heated at 85° C. for 20 min. The reaction was concentrated to afford 5-(4-(tert-butoxycarbonyl)piperazin-1-yl)-3-chloro-2-(2-fluorophenyl)-7-(methoxymethyl)-1,6-naphthyridine-8-carboxylic acid to be used as is. m/z (ESI, +ve ion): 531.0 (M+H)$^+$.

To 5-(4-(tert-butoxycarbonyl)piperazin-1-yl)-3-chloro-2-(2-fluorophenyl)-7-(methoxymethyl)-1,6-naphthyridine-8-carboxylic acid was added acetonitrile (8 mL) and water (4 mL) followed by the addition of LiOH (0.144 g, 6.03 mmol) and NBS (0.157 g, 0.881 mmol) at rt and the resulting mixture was stirred for 5 min. The reaction mixture was washed with saturated NaHCO$_3$ and extracted with DCM. The combined organics were dried over Na$_2$SO$_4$, filtered, concentrated and purified by silica gel chromatography (eluent: 0-80% EtOAc:EtOH (3:1)/heptane) to provide tert-butyl 4-(8-bromo-3-chloro-2-(2-fluorophenyl)-7-(methoxymethyl)-1,6-naphthyridin-5-yl)piperazine-1-carboxylate as a light yellow solid. m/z (ESI, +ve ion): 565.0 (M+H)$^+$.

Step 6: tert-Butyl 4-(3-chloro-2-(2-fluorophenyl)-8-(2-isopropylphenyl)-7-(methoxymethyl)-1,6-naphthyridin-5-yl)piperazine-1-carboxylate A mixture of tert-butyl 4-(8-bromo-3-chloro-2-(2-fluorophenyl)-7-(methoxymethyl)-1,6-naphthyridin-5-yl)piperazine-1-carboxylate (41 mg, 0.072 mmol). cesium carbonate (165 mg, 0.51 mmol), (1,1'-bis(diphenylphosphino) ferrocene) dichloropalladium (5.3 mg, 7.3 µmol) and [2-(1-methylethyl)phenyl]-boronic acid (59 mg, 0.362 mmol, Combi-Blocks Inc.) was purged with N$_2$ followed by the addition of 1,4-dioxane/water (4/0.4 mL) and the resulting mixture was heated at 85° C. for 1 h. The reaction was cooled to rt, washed with saturated NaHCO$_3$ and extracted with EtOAc. The combined organic extracts were purified by preparative HPLC (Phenomenex Gemini C18 column, 150×30 mm, 10 u, 110 A, 10-95% 0.1% TFA in acetonitrile/water) to afford tert-butyl 4-(3-chloro-2-(2-fluorophenyl)-8-(2-isopropylphenyl)-7-(methoxymethyl)-1,6-naphthyridin-5-yl)piperazine-1-carboxylate as a yellow solid. m/z (ESI, +ve ion): 605.2 (M+H)$^+$.

Step 7: 1-(4-(3-Chloro-2-(2-fluorophenyl)-7-(hydroxymethyl)-8-(2-isopropylphenyl)-1,6-naphthyridin-5-yl)piperazin-1-yl)prop-2-en-1-one To a solution of tert-butyl 4-(3-chloro-2-(2-fluorophenyl)-8-(2-isopropylphenyl)-7-(methoxymethyl)-1,6-naphthyridin-5-yl)piperazine-1-carboxylate (10 mg, 0.017 mmol) in DCM (1 mL) at rt was added BBr$_3$ (2 M in DCM, 1.0 mL, 2.0 mmol) and the resulting mixture was stirred at rt for 1 h. The reaction was washed with saturated NaHCO$_3$ and extracted with DCM. The combined organic extracts were dried over Na$_2$SO$_4$, filtered, and concentrated to afford (3-chloro-2-(2-fluorophenyl)-8-(2-isopropylphenyl)-5-(piperazin-1-yl)-1,6-naphthyridin-7-yl)methanol to be used as is. m/z (ESI, +ve ion): 491.2 (M+H)$^+$.

(3-chloro-2-(2-fluorophenyl)-8-(2-isopropylphenyl)-5-(piperazin-1-yl)-1,6-naphthyridin-7-yl)methanol was dissolved in DCM (3 mL) followed by the addition of acryloyl chloride (2.7 µl, 0.033 mmol) and the resulting mixture was stirred at rt for 4 h. The reaction was washed with sat. NaHCO$_3$, extracted with DCM and purified by preparative HPLC (Phenomenex Gemini C18 column, 150×30 mm, 10 u, 110 A, 10-95% 0.1% TFA in acetonitrile/water) to afford 1-(4-(3-chloro-2-(2-fluorophenyl)-7-(hydroxymethyl)-8-(2-isopropylphenyl)-1,6-naphthyridin-5-yl)piperazin-1-yl)prop-2-en-1-one as a yellow-greenish solid. m/z (ESI, +ve ion): 545.2 (M+H)$^+$. $^1$H NMR (CDCl$_3$) δ: 8.40-8.48 (m, 1H), 7.36-7.44 (m, 3H), 7.27-7.31 (m, 1H), 7.06-7.24 (m, 3H), 6.95-7.03 (m, 1H), 6.60-6.72 (m, 1H), 6.29-6.44 (m, 1H), 5.75-5.84 (m, 1H), 4.47-4.60 (m, 1H), 4.26-4.42 (m, 1H), 3.86-4.10 (m, 4H), 3.57-3.71 (m, 4H), 2.39-2.53 (m, 1H), 1.04-1.08 (m, 3H), 0.98-1.03 (m, 3H)

TABLE 85

Compounds 85-2 to 85-7 were prepared following the procedure described in Method 85, Steps 1-7, above as follows:

| Ex. # | Chemical structure | Name | Method Changes | Reagent |
|---|---|---|---|---|
| 85-2 | 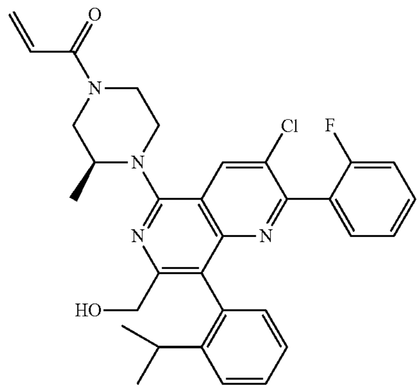 [SMILES: C=CC(=O)N1CCN(c2nc(CO)c(-c3ccccc3C(C)C)c3nc(-c4ccccc4F)c(Cl)cc23)[C@@H](C)C1] | 1-((3S)-4-(3-chloro-2-(2-fluorophenyl)-7-(hydroxymethyl)-8-(2-(2-propanyl)phenyl)-1,6-naphthyridin-5-yl)-3-methyl-1-piperazinyl)-2-propen-1-one | | Step 4: tert-butyl (S)-3-methylpiperazine-1-carboxylate, (Aurum Pharmatech LLC.) |
| 85-3 | 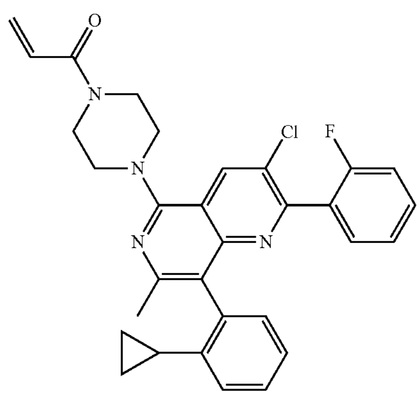 [SMILES: C=CC(=O)N1CCN(c2nc(C)c(-c3ccccc3C3CC3)c3nc(-c4ccccc4F)c(Cl)cc23)CC1] | 1-(4-(3-chloro-8-(2-cyclopropylphenyl)-2-(2-fluorophenyl)-7-methyl-1,6-naphthyridin-5-yl)-1-piperazinyl)-2-propen-1-one | | Step 1: methyl acetoacetate (Sigma-Aldrich Corporation), Step 6: 2-cyclopropylbenzeneboronic acid (CombiPhos Catalysts, Inc.) |
| 85-4 | 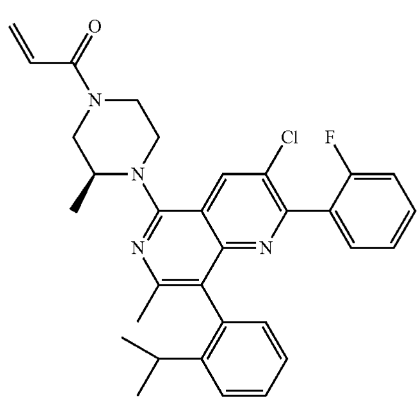 [SMILES: C=CC(=O)N1CCN(c2nc(C)c(-c3ccccc3C(C)C)c3nc(-c4ccccc4F)c(Cl)cc23)[C@@H](C)C1] | 1-((3S)-4-(3-chloro-2-(2-fluorophenyl)-7-methyl-8-(2-(2-propanyl)phenyl)-1,6-naphthyridin-5-yl)-3-methyl-1-piperazinyl)-2-propen-1-one | | Step 1: methyl acetoacetate (Sigma-Aldrich Corporation), Step 4: tert-butyl (S)-3-methylpiperazine-1-carboxylate, (Aurum Pharmatech LLC.) |

TABLE 85-continued

Compounds 85-2 to 85-7 were prepared following the procedure described in Method 85, Steps 1-7, above as follows:

| Ex. # | Chemical structure | Name | Method Changes | Reagent |
|---|---|---|---|---|
| 85-5 | 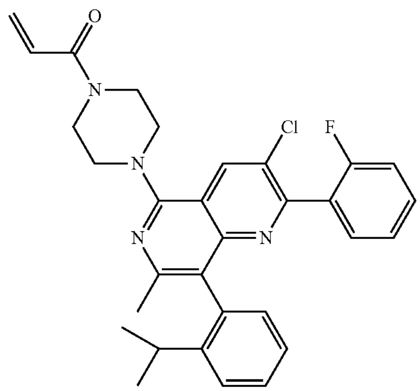 [SMILES: C=CC(=O)N1CCN(c2nc(C)c(-c3ccccc3C(C)C)c3nc(-c4ccccc4F)c(Cl)cc23)CC1] | 1-(4-(3-chloro-2-(2-fluorophenyl)-7-methyl-8-(2-(2-propanyl)phenyl)-1,6-naphthyridin-5-yl)-1-piperazinyl)-2-propen-1-one | | Step 1: methyl acetoacetate (Sigma-Aldrich Corporation) |
| 85-6 | 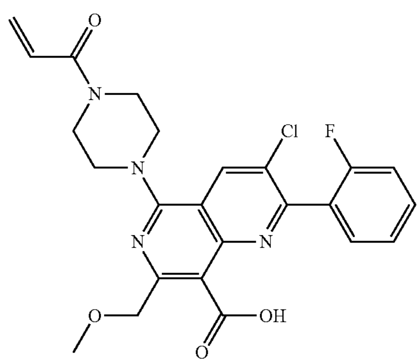 [SMILES: C=CC(=O)N1CCN(c2nc(COC)c(C(=O)O)c3nc(-c4ccccc4F)c(Cl)cc23)CC1] | 3-chloro-2-(2-fluorophenyl)-7-(methoxymethyl)-5-(4-(2-propenoyl)-1-piperazinyl)-1,6-naphthyridine-8-carboxylic acid | Omit NBS bromination in Step 5, Omit step 6, Step 7 performed analogous to Method 80 Step 5 | |
| 85-7 | 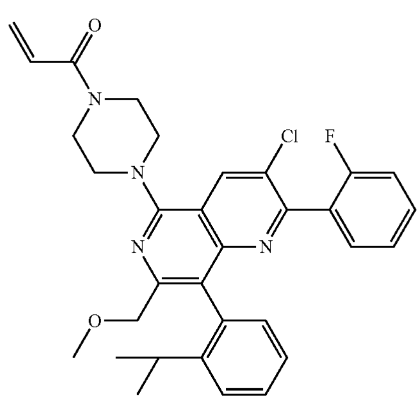 [SMILES: C=CC(=O)N1CCN(c2nc(COC)c(-c3ccccc3C(C)C)c3nc(-c4ccccc4F)c(Cl)cc23)CC1] | 1-(4-(3-chloro-2-(2-fluorophenyl)-7-(methoxymethyl)-8-(2-(2-propanyl)phenyl)-1,6-naphthyridin-5-yl)-1-piperazinyl)-2-propen-1-one | Step 7 performed analogous to Method 80 Step 5 | |

547

Method 86

Example 86-1: 1-((3S)-4-(3-Chloro-7-((dimethyl-amino)methyl)-2-(2-fluorophenyl)-8-(2-isopropylphenyl)-1,6-naphthyridin-5-yl)-3-methylpiperazin-1-yl)prop-2-en-1-one

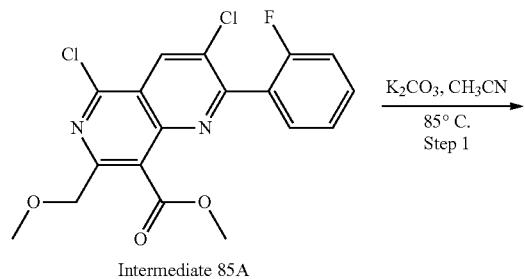

Intermediate 85A

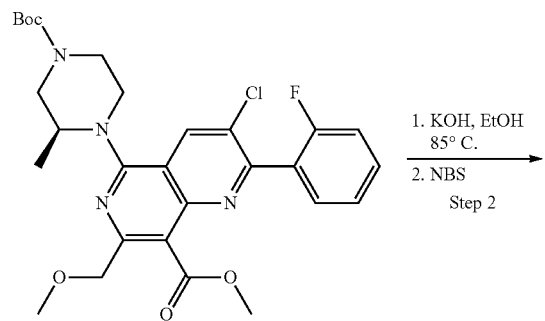

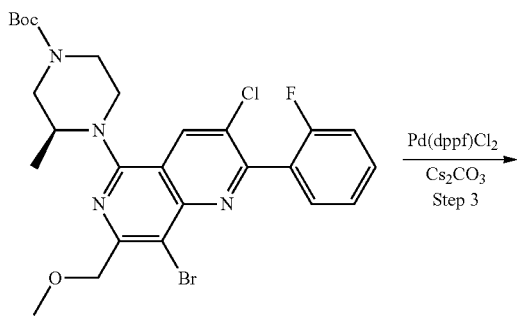

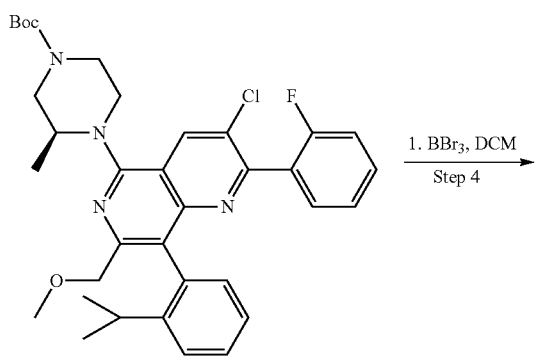

548

-continued

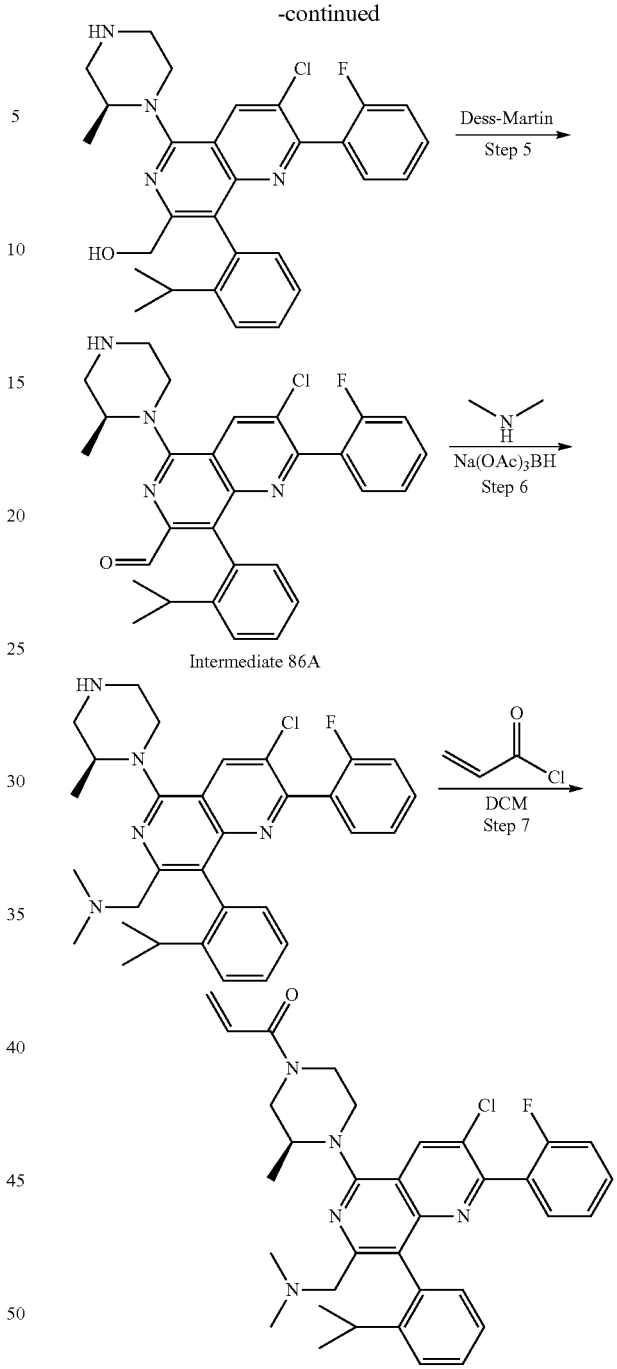

Intermediate 86A

Step 1: Methyl (S)-5-(4-(tert-butoxycarbonyl)-2-methylpiperazin-1-yl)-3-chloro-2-(2-fluorophenyl)-7-(methoxymethyl)-1,6-naphthyridine-8-carboxylate A mixture of methyl 3,5-dichloro-2-(2-fluorophenyl)-7-(methoxymethyl)-1,6-naphthyridine-8-carboxylate (Intermediate 85A, 0.15 g, 0.38 mmol), tert-butyl (S)-3-methylpiperazine-1-carboxylate (0.228 g, 1.14 mmol), potassium carbonate (0.21 g, 1.52 mmol) and sodium sulfate (0.809 g, 5.69 mmol) in $CH_3CN$ (4 mL) was heated at 85° C. for 10 h. The desired product was observed, but starting material was still present. Additional tert-butyl (S)-3-methylpiperazine-1-carboxylate (0.228 g, 1.14 mmol), potassium carbonate (0.21 g, 1.52 mmol) and sodium sulfate (0.809 g, 5.69 mmol) were added. The heating continued for 24 h leading to complete consumption of the starting material. The reaction mixture was cooled to rt, washed with water and extracted with EtOAc. The crude product was purified by silica gel chromatography (eluent: 0-50% EtOAc:EtOH (3:1)/heptane) to provide methyl (S)-5-(4-(tert-butoxycarbonyl)-2-methylpiperazin-1-yl)-3-chloro-2-(2-fluorophenyl)-7-(methoxymethyl)-1,6-naphthyridine-8-carboxylate (0.170 g, 0.304 mmol, 80% yield) as a light brown solid. m/z (ESI, +ve ion): 559.2 (M+H)$^+$.

Step 2: tert-Butyl (S)-4(8-bromo-3-chloro-2-(2-fluorophenyl)-7-(methoxymethyl)-1,6-naphthyridin-5-yl)-3-methylpiperazine-1-carboxylate To a solution of methyl (S)-5-(4-(tert-butoxycarbonyl)-2-methylpiperazin-1-yl)-3-chloro-2-(2-fluorophenyl)-7-(methoxymethyl)-1,6-naphthyridine-8-carboxylate (0.3 g, 0.537 mmol) in EtOH (2 mL) was added KOH (0.15 g, 2.67 mmol) and the resulting mixture was heated at 85° C. for 20 min. The reaction was concentrated to afford (S)-5-(4-(tert-butoxycarbonyl)-2-methylpiperazin-1-yl)-3-chloro-2-(2-fluorophenyl)-7-(methoxymethyl)-1,6-naphthyridine-8-carboxylic acid and used as is. m/z (ESI, +ve ion): 545.2 (M+H)$^+$.

To (S)-5-(4-(tert-butoxycarbonyl)-2-methylpiperazin-1-yl)-3-chloro-2-(2-fluorophenyl)-7-(methoxymethyl)-, 0,6-naphthyridine-8-carboxylic acid was added CH$_3$CN (6 mL) and water (3 mL) followed by the addition of LiOH (1.76 g, 73.5 mmol) and NBS (1.91 g, 10.7 mmol) at rt and the resulting mixture was stirred for 7 min. The reaction mixture was washed with saturated NaHCO$_3$ and extracted with DCM. The combined organics were dried over Na$_2$SO$_4$, filtered, concentrated and purified by silica gel chromatography (eluent: 0-80% EtOAc:EtOH (3:1)/heptane) to provide tert-butyl (S)-4-(8-bromo-3-chloro-2-(2-fluorophenyl)-7-(methoxymethyl)-1,6-naphthyridin-5-yl)-3-methylpiperazine-1-carboxylate (0.248 g, 0.428 mmol, 80% yield) as a yellow solid. m/z (ESI, +ve ion): 579.0 (M+H)$^+$.

Step 3: tert-Butyl (3S)-4-(3-chloro-2-(2-fluorophenyl)-8-(2-isopropylphenyl)-7-(methoxymethyl)-1,6-naphthyridin-5-yl)-3-methylpiperazine-1-carboxylate A mixture of tert-butyl (S)-4-(8-bromo-3-chloro-2-(2-fluorophenyl)-7-(methoxymethyl)-1,6-naphthyridin-5-yl)-3-methylpiperazine-1-carboxylate (0.248 g, 0.428 mmol). cesium carbonate (0.697 g, 2.14 mmol), (1,1'-bis(diphenylphosphino) ferrocene) dichloropalladium (0.031 g, 0.043 mmol) and [2-(1-methylethyl)phenyl]-boronic acid (0.281 g, 1.71 mmol) was purged with N$_2$ followed by the addition of 1,4-dioxane/water (4/0.4 mL) and the resulting mixture was heated at 85° C. for 1 h. The reaction was cooled to rt, washed with sat. NaHCO$_3$ and extracted with EtOAc. The crude product was purified by silica gel chromatography (eluent: 0-40% EtOAc/heptane) to provide tert-butyl (3S)-4-(3-chloro-2-(2-fluorophenyl)-8-(2-isopropylphenyl)-7-(methoxymethyl)-1,6-naphthyridin-5-yl)-3-methylpiperazine-1-carboxylate (0.13 g, 0.21 mmol, 49.1% yield) as a yellow-greenish oil. m/z (ESI, +ve ion): 619.2 (M+H)$^+$. Side product (S)-4-(3-chloro-2-(2-fluorophenyl)-7-(methoxymethyl)-1,6-naphthyridin-5-yl)-3-methylpiperazine-1-carboxylate (Intermediate 86A) was also isolated, as a light yellow oil. m/z (ESI, +ve ion): 501.2 (M+H)$^+$.

Step 4: (3-Chloro-2-(2-fluorophenyl)-8-(2-isopropylphenyl)-5-((S)-2-methylpiperazin-1-yl)-1,6-naphthyridin-7-yl)methanol To a solution of tert-butyl (3S)-4-(3-chloro-2-(2-fluorophenyl)-8-(2-isopropylphenyl)-7-(methoxymethyl)-1,6-naphthyridin-5-yl)-3-methylpiperazine-1-carboxylate (0.13 g, 0.21 mmol) in DCM at 0° C. was added BBr$_3$ (2 M in DCM, 1.05 mL, 2.1 mmol). After complete addition, the ice-bath was removed and the mixture was stirred at rt for 30 min. The reaction mixture was carefully quenched with saturated NaHCO$_3$ and extracted with DCM. The combined organics were dried over Na$_2$SO$_4$, filtered, concentrated and purified by silica gel chromatography (eluent: 0-10% MeOH/DCM) to provide (3-chloro-2-(2-fluorophenyl)-8-(2-isopropylphenyl)-5-((S)-2-methylpiperazin-1-yl)-1,6-naphthyridin-7-yl)methanol (0.046 g, 0.091 mmol, 43.4% yield). m/z (ESI, +ve ion): 505.2 (M+H)$^+$.

Step 5: 3-Chloro-2-(2-fluorophenyl)-8-(2-isopropylphenyl)-5-((S)-2-methylpiperazin-1-yl)-1,6-naphthyridine-7-carbaldehyde To a solution of (3-chloro-2-(2-fluorophenyl)-8-(2-isopropylphenyl)-5-((S)-2-methylpiperazin-1-yl)-1,6-naphthyridin-7-yl)methanol (0.032 g, 0.062 mmol) in DCM (3 mL) at rt was added Dess-Martin periodinane (0.053 g, 0.125 mmol) and the resulting mixture was stirred at rt for 30 min. The reaction was quenched with saturated NaHCO$_3$ and stirred at rt for 30 min. The organic phase was separated, dried over Na$_2$SO$_4$, filtered, concentrated and purified by silica gel chromatography (eluent: 0-10% MeOH/DCM) to provide 3-chloro-2-(2-fluorophenyl)-8-(2-isopropylphenyl)-5-((S)-2-methylpiperazin-1-yl)-1,6-naphthyridine-7-carbaldehyde (0.01 g, 0.02 mmol, 31.9% yield). m/z (ESI, +ve ion): 503.2 (M+H)$^+$.

Step 6: 1-(3-Chloro-2-(2-fluorophenyl)-8-(2-isopropylphenyl)-5-((S)-2-methylpiperazin-1-yl)-1,6-naphthyridin-7-yl)-N,N-dimethylmethanamine To a solution of 3-chloro-2-(2-fluorophenyl)-8-(2-isopropylphenyl)-5-((S)-2-methylpiperazin-1-yl)-1,6-naphthyridine-7-carbaldehyde (0.01 g, 0.02 mmol) in chloroform (3 mL) were added dimethylamine (2.0 M in THF, 0.02 mL, 0.04 mmol) and acetic acid (1.1 µL, 0.020 mmol) and the resulting mixture was stirred at rt for 10 min then sodium triacetoxyborohydride (0.017 g, 0.08 mmol) was added and the stirring continued for 1 h. The reaction was cooled to 0° C. and carefully basified with saturated NaHCO$_3$. The mixture was extracted with DCM, dried over Na$_2$SO$_4$, filtered and concentrated to afford 1-(3-chloro-2-(2-fluorophenyl)-8-(2-isopropylphenyl)-5-((S)-2-methylpiperazin-1-yl)-1,6-naphthyridin-7-yl)-N,N-dimethylmethanamine as a light yellow solid. m/z (ESI, +ve ion): 532.2 (M+H)$^+$.

Step 7: 1-((3S)-4-(3-Chloro-7-((dimethylamino)methyl)-2-(2-fluorophenyl)-8-(2-isopropylphenyl)-1,6-naphthyridin-5-yl)-3-methylpiperazin-1-yl)prop-2-en-1-one To a mixture of 1-(3-chloro-2-(2-fluorophenyl)-8-(2-isopropylphenyl)-5-((S)-2-methylpiperazin-1-yl)-1,6-naphthyridin-7-yl)-N,N-dimethylmethanamine in DCM (3 mL) were added acryloyl chloride (1.9 µL, 0.024 mmol) and Hünig's base (4.2 µL, 0.024 mmol) and the resulting mixture was stirred at rt for 30 min. The reaction was washed with saturated NaHCO$_3$, extracted with DCM and purified by preparative HPLC (Phenomenex Gemini C18 column, 150× 30 mm, 10 u, 110 A, 10-95% 0.1% TFA in acetonitrile/water) to afford 1-((3S)-4-(3-chloro-7-((dimethylamino)methyl)-2-(2-fluorophenyl)-8-(2-isopropylphenyl)-1,6-naphthyridin-5-yl)-3-methylpiperazin-1-yl)prop-2-en-1-one (0.002 g, 3.41 μmol, 17.2% yield) as a yellow solid. ¹H NMR (CDCl₃) δ: 8.37-8.49 (m, 1H), 7.35-7.45 (m, 3H), 7.19-7.23 (m, 1H), 7.02-7.19 (m, 4H), 6.56-6.79 (m, 1H), 6.31-6.44 (m, 1H), 5.71-5.81 (m, 1H), 4.07-4.41 (m, 2H), 3.47-3.83 (m, 5H), 2.66-3.07 (m, 2H), 2.15-2.52 (m, 4H), 1.20-1.29 (m, 6H), 1.04-1.11 (m, 3H), 0.92-1.03 (m, 3H). m/z (ESI, +ve ion): 586.2 (M+H)⁺.

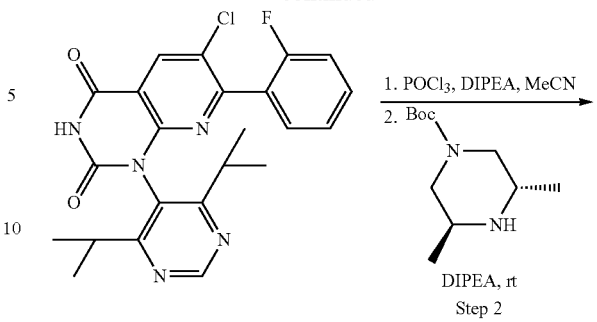

TABLE 86

Compound 86-2 was prepared following the procedure described in Method 86, Steps 1-10, above as follows:

| Ex. # | Chemical structure | Name | Method Changes | Reagent |
|---|---|---|---|---|
| 86-2 | 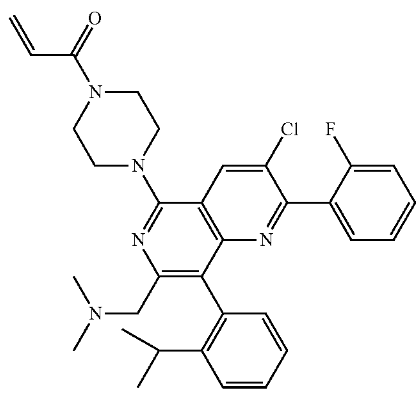 [SMILES: C=CC(=O)N1CCN(c2nc(CN(C)C)c(-c3ccccc3C(C)C)c3nc(-c4ccccc4F)c(Cl)cc23)CC1] | 1-(4-(3-chloro-7-((dimethylamino)methyl)-2-(2-fluorophenyl)-8-(2-(2-propanyl)phenyl)-1,6-naphthyridin-5-yl)-1-piperazinyl)-2-propen-1-one | | Step 1: tert-butyl piperazine-1-carboxylate (Combi-Blocks Inc.) |

Method 87

Example 87-1: 6-Chloro-4-((2S,6S)-2,6-dimethyl-4-(2-propenoyl)-1-piperazinyl)-1-(4,6-di(2-propanyl)-5-pyrimidinyl)-7-(2-fluorophenyl)pyrido[2,3-d]pyrimidin-2(1H)-one

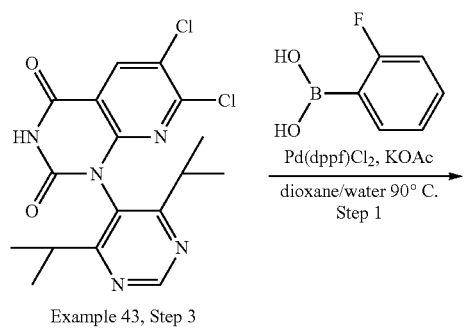

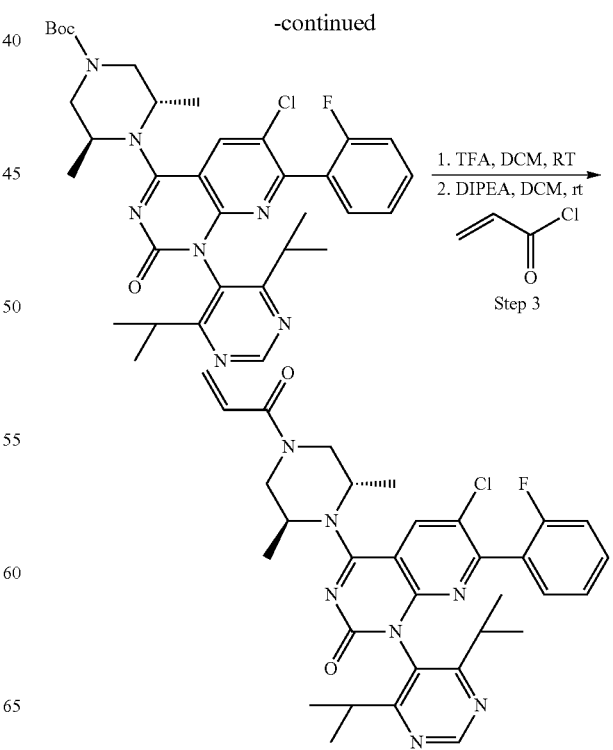

Step 1: 6-Chloro-1-(4,6-diisopropylpyrimidin-5-yl)-7-(2-fluorophenyl)pyrido[2,3-d]pyrimidine-2,4(1H,3H)-dione A solution of 6,7-dichloro-1-(4,6-diisopropylpyrimidin-5-yl)pyrido[2,3-d]pyrimidine-2,4(1H,3H)-dione (Example 43, Step 3, 0.89 g, 2.26 mmol), 2-fluorophenylboronic acid (0.47 g, 3.4 mmol, Small Molecules, Inc., Hoboken, N.J.), (1,1'-bis(diphenylphosphino) ferrocene) dichloropalladium (0.16 g, 0.23 mmol), and potassium phosphate tribasic (1.4 g, 6.8 mmol) in 1,4-dioxane (10 mL) and water (5 mL) was purged with nitrogen and heated to 90° C. for 1 h. The reaction mixture was quenched with saturated $NH_4Cl$ solution, water and extracted with EtOAc (2×). The organic layer was separated, concentrated and purified by silica gel chromatography (eluent: 0-60% EtOAc/heptane) to provide 6-chloro-1-(4,6-diisopropylpyrimidin-5-yl)-7-(2-fluorophenyl)pyrido[2,3-d]pyrimidine-2,4(1H,3H)-dione (0.52 g, 1.15 mmol, 51% yield). $^1$H NMR (400 MHz, DMSO-$d_6$) δ ppm: 12.29 (s, 1H), 9.09 (s, 1H), 8.59 (s, 1H), 7.45-7.55 (m, 1H), 7.23-7.34 (m, 2H), 7.17 (t, J=7.02 Hz, 1H), 2.98 (quin, J=6.63 Hz, 2H), 1.09 (d, J=6.63 Hz, 6H), 0.93 (d, J=6.63 Hz, 6H). $^{19}$F NMR (376 MHz, DMSO-$d_6$) δ ppm: −115.17 (s, 1F). m/z (ESI) M+H: 454.1.

Step 2: tert-Butyl (3S,5S)-4-(6-chloro-1-(4,6-diisopropylpyrimidin-5-yl)-7-(2-fluorophenyl)-2-oxo-1,2-dihydropyrido[2,3-d]pyrimidin-4-yl)-3,5-dimethylpiperazine-1-carboxylate To a solution of 6-chloro-1-(4,6-diisopropylpyrimidin-5-yl)-7-(2-fluorophenyl)pyrido[2,3-d]pyrimidine-2,4(1H,3H)-dione (0.16 g, 0.36 mmol) and N,N-diisopropylethylamine (0.19 mL, 1.1 mmol) in acetonitrile (5 mL) was added phosphorus oxychloride (0.050 mL, 0.54 mmol) dropwise. The mixture was then heated to 80° C. for 1 h and concentrated under vacuum to afford a dark residue. To the residue at 0° C. was added acetonitrile (5 mL) followed by N,N-diisopropylethylamine (0.063 mL, 0.36 mmol) and tert-butyl (3S,5S)-3,5-dimethylpiperazine-1-carboxylate (0.12 g, 0.54 mmol, eNovation Chemicals LLC, Bridgewater, N.J.). This mixture was stirred while warming to rt for 6 h. The reaction mixture was diluted with saturated $NaHCO_3$, and extracted with EtOAc (2×). The organic extracts were combined and concentrated in vacuo to give an oil that was purified by silica gel chromatography (eluent: 0-80% EtOAc:EtOH (3:1)/heptane) to provide tert-butyl (3S,5S)-4-(6-chloro-1-(4,6-diisopropylpyrimidin-5-yl)-7-(2-fluorophenyl)-2-oxo-1,2-dihydropyrido[2,3-d]pyrimidin-4-yl)-3,5-dimethylpiperazine-1-carboxylate (0.20 g, 0.31 mmol, 87° % yield). m/z (ESI) M+H: 650.3.

Step 3: 6-Chloro-4-((2S,6S)-2,6-dimethyl-4-(2-propenoyl)-1-piperazinyl)-1-(4,6-di(2-propanyl)-5-pyrimidinyl)-7-(2-fluorophenyl)pyrido[2,3-d]pyrimidin-2(1H)-one To a solution of tert-butyl (3S,5S)-4-(6-chloro-1-(4,6-diisopropylpyrimidin-5-yl)-7-(2-fluorophenyl)-2-oxo-1,2-dihydropyrido[2,3-d]pyrimidin-4-yl)-3,5-dimethylpiperazine-1-carboxylate (0.20 g, 0.31 mmol) in DCM (5 mL) at rt was added trifluoroacetic acid (1.2 mL, 16 mmol) and the resulting mixture was stirred at rt for 1 h. The reaction was concentrated to give a reddish brown residue. It was re-dissolved in DCM (10 mL) followed by the addition of N,N-diisopropylethylamine (0.22 mL, 1.23 mmol) and a solution of acryloyl chloride (0.03 mL, 0.369 mmol) in DCM (0.5 mL). The reaction was stirred at rt for 10 min, quenched with saturated $NaHCO_3$, water, and extracted with DCM (2×). The combined organics were concentrated and the crude product was purified by silica gel chromatography (eluent: 0-70% EtOAc:EtOH (3:1)/heptane) to provide 6-chloro-4-((2S,6S)-2,6-dimethyl-4-(2-propenoyl)-1-piperazinyl)-1-(4,6-di(2-propanyl)-5-pyrimidinyl)-7-(2-fluorophenyl)pyrido[2,3-d]pyrimidin-2(1H)-one (0.116 g, 0.192 mmol, 62.4% yield). $^1$H NMR (400 MHz, $CDCl_3$) δ ppm: 9.15 (s, 1H), 8.27 (s, 1H), 7.39-7.47 (m, 1H), 7.05-7.23 (m, 3H), 6.63 (dd, J=10.37, 16.79 Hz, 1H), 6.42 (dd, J=1.76, 16.69 Hz, 1H), 5.82 (dd, J=1.87, 10.57 Hz, 1H), 4.38-4.50 (m, 2H), 3.99 (br d, J=10.37 Hz, 2H), 3.92 (br s, 1H), 3.66-3.84 (m, 1H), 2.68 (tt, J=6.71, 13.09 Hz, 2H), 1.46 (br d, J=6.01 Hz, 6H), 1.24 (dd, J=2.70, 6.63 Hz, 6H), 1.05 (t, J=7.15 Hz, 6H). $^{19}$F NMR (376 MHz, $CDCl_3$) δ ppm: −113.37 (s, 1F). m/z (ESI) M+H: 604.3.

TABLE 87

Compounds 87-2 to 87-5 were prepared following the procedure described in Method 87, Steps 1-3, above as follows:

| Ex. # | Chemical structure | Name | Method Changes | Reagent |
|---|---|---|---|---|
| 87-2 | 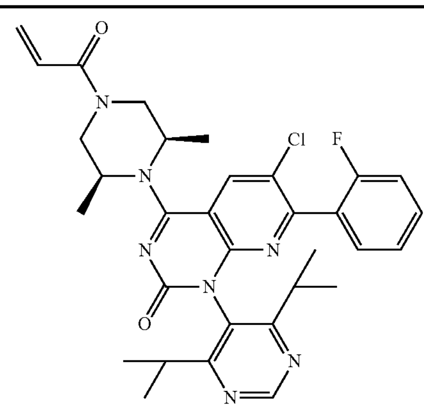 | 6-chloro-4-((2R,6S)-2,6-dimethyl-4-(2-propenoyl)-1-piperazinyl)-1-(4,6-di(2-propanyl)-5-pyrimidinyl)-7-(2-fluorophenyl)pyrido[2,3-d]pyrimidin-2(1H)-one | Step 1: $K_3PO_4$ | Step 2: (3R,5S)-3,5-dimethyl-piperazine-1-carboxylic acid tert-butyl ester (Combi-Blocks Inc.) |

TABLE 87-continued

Compounds 87-2 to 87-5 were prepared following the procedure described in
Method 87, Steps 1-3, above as follows:

| Ex. # | Chemical structure | Name | Method Changes | Reagent |
|---|---|---|---|---|
| 87-3 | 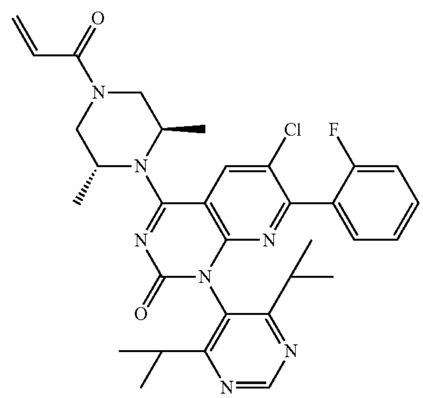 [SMILES: C=CC(=O)N1C[C@@H](C)N(c2nc(=O)n(-c3c(C(C)C)ncnc3C(C)C)c3nc(-c4ccccc4F)c(Cl)cc23)[C@H](C)C1] | 6-chloro-4-(2R,6R)-2,6-dimethyl-4-(2-propenoyl)-1-piperazinyl)-1-(4,6-di(2-propanyl)-5-pyrimidinyl)-7-(2-fluorophenyl)pyrido[2,3-d]pyrimidin-2(1H)-one | Step 1: $K_3PO_4$ | Step 2: (3R,5R)-1-Boc-3,5-dimethylpiperazine (AstaTech, Inc.) |
| 87-4 | 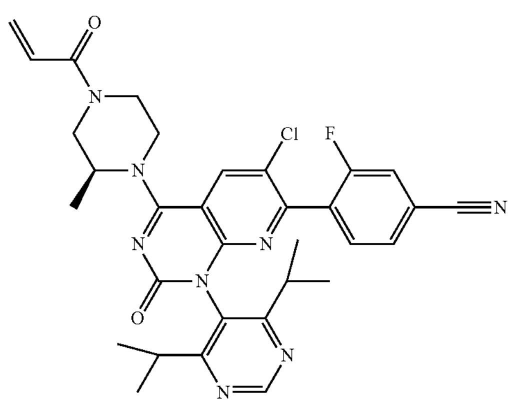 [SMILES: C=CC(=O)N1CCN(c2nc(=O)n(-c3c(C(C)C)ncnc3C(C)C)c3nc(-c4ccc(C#N)cc4F)c(Cl)cc23)[C@@H](C)C1] | 4-(6-chloro-1-(4,6-di(2-propanyl)-5-pyrimidinyl)-4-((2S)-2-methyl-4-(2-propenoyl)-1-piperazinyl)-2-oxo-1,2-dihydropyrido[2,3-d]pyrimidin-7-yl)-3-fluorobenzonitrile | Suzuki coupling in Step 1 performed after Step 2 | Step 2: (S)-4-Boc-2-methylpiperazine (Combi-Blocks Inc.), Step 4: 3-fluoro-4-(4,4,5,5-tetramethyl-1,3,2-dioxaborolan-2-yl)benzonitrile (Combi-Blocks Inc.) |
| 87-5 | 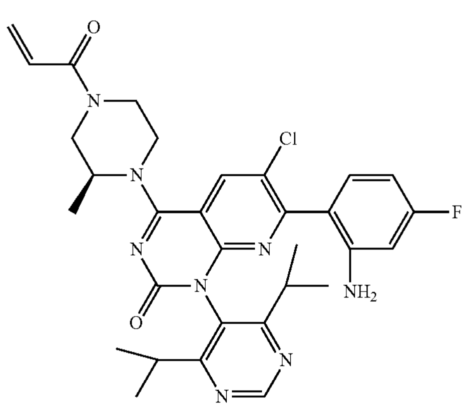 [SMILES: C=CC(=O)N1CCN(c2nc(=O)n(-c3c(C(C)C)ncnc3C(C)C)c3nc(-c4ccc(F)cc4N)c(Cl)cc23)[C@@H](C)C1] | 7-(2-amino-4-fluoropheny-1)-6-chloro-1-(4,6-di(2-propanyl)-5-pyrimidinyl)-4-((2S)-2-methyl-4-(2-propenoyl)-1-piperazinyl)pyrido[2,3-d]pyrimidin-2(1H)-one | Suzuki coupling in Step 1 performed after Step 3 | Step 2: (S)-4-Boc-2-methylpiperazine (Combi-Blocks Inc.), Step 4: 5-fluoro-2-(4,4,5,5-tetramethyl-1,3,2-dioxaborolan-2-yl)aniline (Aurum Pharmatech Inc.) |

Section 2—Individual Examples

Example 88

6-Chloro-7-(2-fluorophenyl)-1-(2-(2-propanyl)phenyl)-4-(4-(2-propenoyl)-1-piperazinyl)-2(1H)-quinazolinone

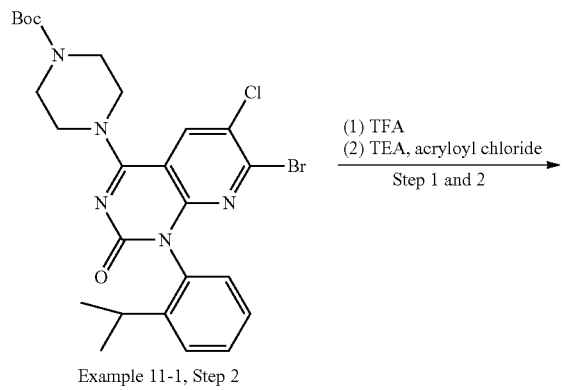

Example 11-1, Step 2

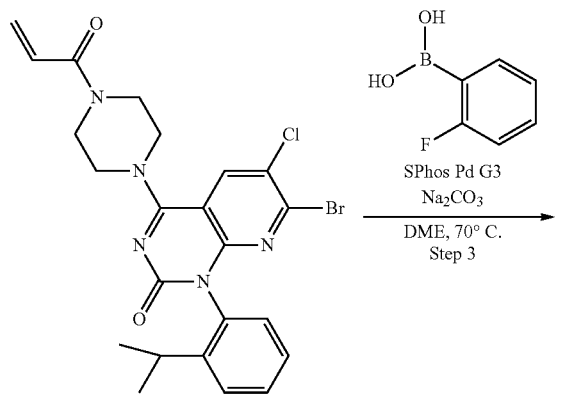

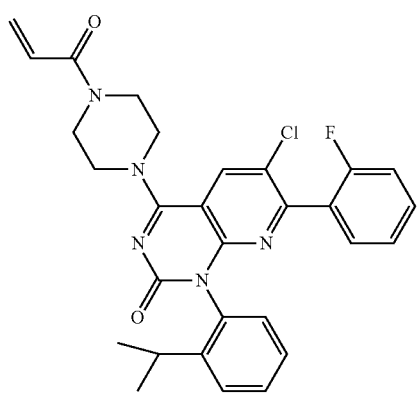

Step 1-1: 7-Bromo-6-chloro-1-(2-isopropylphenyl)-4-(piperazin-1-yl)quinazolin-2(1H)-one TFA (20 mL, 270 mmol) was added to a stirred mixture of tert-butyl 4-(7-bromo-6-chloro-1-(2-isopropylphenyl)-2-oxo-1,2-dihydroquinazolin-4-yl)piperazine-1-carboxylate (Example 11-1, Step 2, 3.52 g, 6.26 mmol) in DCM (20 mL). The reaction mixture was stirred at rt for 1 h. The reaction mixture was concentrated in vacuo to give crude 7-bromo-6-chloro-1-(2-isopropylphenyl)-4-(piperazin-1-yl)quinazolin-2(1H)-one that was used in the subsequent step without purification. m/z (ESI, +ve ion): 460.8 (M+H)$^+$.

Step 1-2: 4-(4-Acryloylpiperazin-1-yl)-7-bromo-6-chloro-1-(2-isopropylphenyl)quinazolin-2(1H)-one Acryloyl chloride (0.61 mL, 7.51 mmol) was added to a stirred solution of 7-bromo-6-chloro-1-(2-isopropylphenyl)-4-(piperazin-1-yl)quinazolin-2(1H)-one (2.89 g, 6.26 mmol) and triethylamine (8.8 mL, 62.6 mmol) in DCM (25 mL). The reaction mixture was stirred at rt for 30 min. The reaction mixture was quenched with saturated ammonium chloride (125 mL) and extracted with DCM (150 mL). The combined organic extracts were dried over MgSO$_4$, filtered, and concentrated in vacuo. The crude product was purified by silica gel chromatography (eluent: 0-75% EtOAc-EtOH (3:1)/heptane) to provide 4-(4-acryloylpiperazin-1-yl)-7-bromo-6-chloro-1-(2-isopropylphenyl)quinazolin-2(1H)-one as a light yellow solid (1.62 g, 3.14 mmol, 50.2% yield). $^1$H NMR (400 MHz, CDCl$_3$) δ ppm 7.79 (1H, s) 7.50-7.57 (2H, m) 7.36-7.42 (1H, m) 7.10 (1H, d, J=7.67 Hz) 6.81 (1H, s) 6.61 (1H, dd, J=16.79, 10.37 Hz) 6.38 (1H, dd, J=16.79, 1.66 Hz) 5.79 (1H, dd, J=10.47, 1.76 Hz) 3.79-3.99 (8H, m) 2.59 (1H, spt, J=6.84 Hz) 1.21 (3H, d, J=6.84 Hz) 1.08 (3H, d, J=6.84 Hz). m/z (ESI, +ve ion): 515.0 (M+H)$^+$.

Step 2: 6-Chloro-7-(2-fluorophenyl)-1-(2-(2-propanyl)phenyl)-4-(4-(2-propenoyl)-1-piperazinyl)-2(1H)-quinazolinone 4-(4-Acryloylpiperazin-1-yl)-7-bromo-6-chloro-1-(2-isopropylphenyl)quinazolin-2(1H)-one (400 mg, 0.775 mmol), 2-fluorobenzeneboronic acid (119 mg, 0.85 mmol, Small Molecules, Inc. New Brunswick, N.J.), (2-dicyclohexylphosphino-2',6'-dimethoxybiphenyl) [2-(2'-amino-1,1'-biphenyl)]palladium(II) methanesulfonate (61 mg, 0.078 mmol) and 2 M Na$_2$CO$_3$ (1.5 mL, 3.0 mmol) were combined in 1,2-dimethoxyethane (5 mL) in a sealed vial under an argon atmosphere. The reaction mixture was stirred at 70° C. for 16 h. The reaction mixture was diluted with water (50 mL) and extracted with EtOAc (75 mL) and the combined organic extracts were washed with brine (100 mL), dried over MgSO$_4$, filtered, and concentrated in vacuo. The crude product was purified by silica gel chromatography (eluent: 0-75% EtOAc-EtOH (3:1)/heptane) to provide 6-chloro-7-(2-fluorophenyl)-1-(2-(2-propanyl)phenyl)-4-(4-(2-propenoyl)-1-piperazinyl)-2(1H)-quinazolinone as a white solid (144 mg, 0.136 mmol, 35% yield). $^1$H NMR (400 MHz, CDCl$_3$) δ ppm 7.87 (1H, s) 7.33-7.54 (4H, m) 7.10-7.22 (4H, m) 6.65 (1H, dd, J=16.79, 10.57 Hz) 6.53 (1H, s) 6.40 (1H, dd, J=16.79, 1.66 Hz) 5.81 (1H, dd, J=10.57, 1.87 Hz) 3.80-4.09 (8H, m) 2.68 (1H, spt, J=6.84 Hz) 1.24 (3H, d, J=6.84 Hz) 1.09 (3H, d, J=6.84 Hz). m/z (ESI, +ve ion): 531.2 (M+H)$^+$.

Example 89

6-Chloro-1-(2,2-dimethylpropyl)-7-(2-fluoro-6-hydroxyphenyl)-4-(4-(2-propenoyl)-1-piperazinyl)-2(1H)-quinazolinone

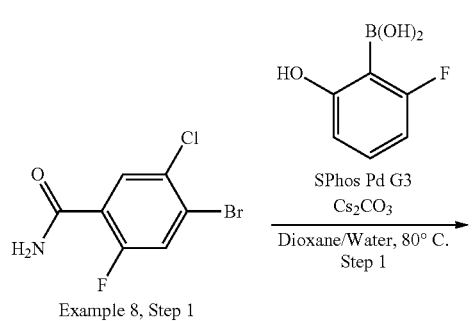

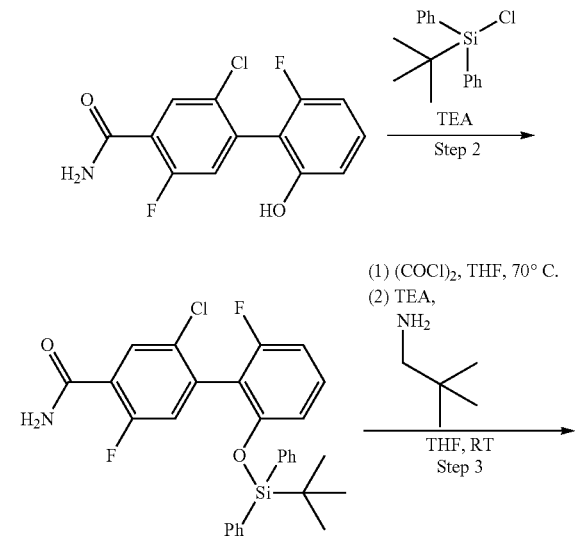

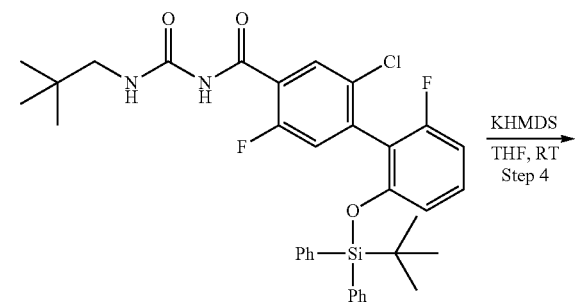

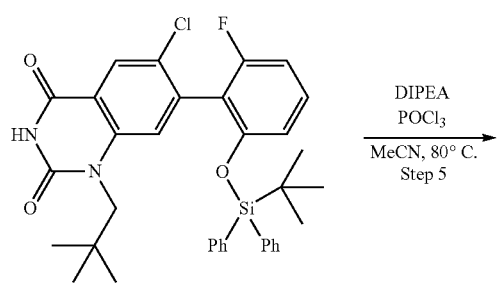

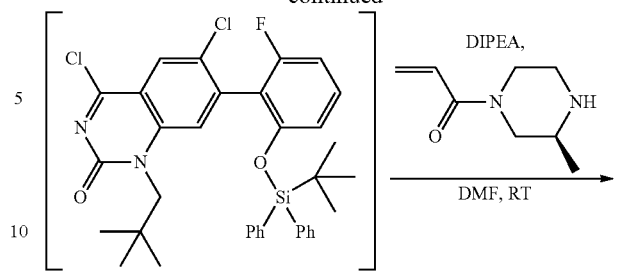

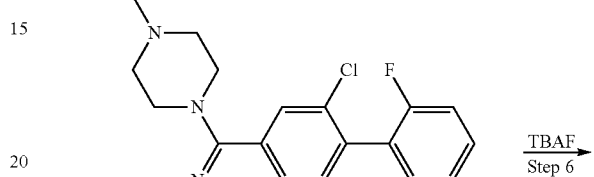

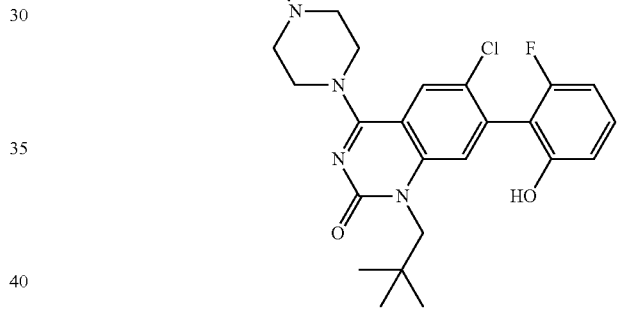

Step 1: 2-Chloro-2',5-difluoro-6'-hydroxy-[1,1'-biphenyl]-4-carboxamide

A mixture of 4-bromo-5-chloro-2-fluorobenzamide (Example 8, Step 1, 2.1 g, 8.32 mmol), 2-fluoro-6-hydroxyphenylboronic acid (1.82 g, 11.65 mmol, Combi-Blocks Inc., San Diego, Calif.), cesium carbonate (5.42 g, 16.6 mmol), and (2-dicyclohexylphosphino-2',6'-dimethoxybiphenyl) [2-(2'-amino-1,1'-biphenyl)]palladium(II) methanesulfonate (0.325 g, 0.416 mmol) in 1,4-dioxane (20 mL) and water (10 mL) was heated to 80° C. under nitrogen and with stirring for 2 h. The reaction mixture was diluted with water and extracted with EtOAc. The organic layer was concentrated in vacuo and purified by silica gel chromatography (eluent: 0-60% EtOAc-EtOH (3:1)/heptane) to provide 2-chloro-2',5-difluoro-6'-hydroxy-[1,1'-biphenyl]-4-carboxamide (1.73 g, 6.1 mmol, 73.3% yield). $^1$H NMR (400 MHz, DMSO-$d_6$) δ 10.13 (s, 1H), 7.91 (br s, 1H), 7.70-7.82 (m, 2H), 7.36 (d, J=10.37 Hz, 1H), 7.28 (q, J=7.95 Hz, 1H), 6.80 (d, J=7.85 Hz, 1H), 6.71-6.77 (m, 1H). $^{19}$F NMR (376 MHz, DMSO-$d_6$) δ −114.15 (s, 1F), −116.71 (s, 1F). m/z (ESI, +ve) 284.0 (M+H)$^+$.

Step 2: 2'-((tert-Butyldiphenylsilyl)oxy)-2-chloro-5, 6'-difluoro-[1,1'-biphenyl]-4-carboxamide To a stirred mixture of 2-chloro-2',5-difluoro-6'-hydroxy-[1,1'-biphenyl]-4-carboxamide (1.73 g, 6.1 mmol) and triethylamine (2.57 mL, 18.3 mmol) in acetonitrile (15 mL) was added tert-butylchlorodiphenylsilane (2.35 mL, 9.15 mmol, Aldrich, St. Louis, Mo.). The reaction mixture was stirred at rt for 1 h, quenched with saturated ammonium chloride and extracted with EtOAc. The organic layer was separated, washed with brine (25 mL), dried over $MgSO_4$, filtered, concentrated in vacuo. The crude product was purified by silica gel chromatography (eluent: 0-50% EtOAc/heptane) to provide the 2'-((tert-butyldiphenylsilyl)oxy)-2-chloro-5,6'-difluoro-[1,1'-biphenyl]-4-carboxamide (2.16 g, 4.14 mmol, 67.8% yield). $^1$H NMR (400 MHz, DMSO-$d_6$) δ 7.86-7.95 (m, 2H), 7.83 (br s, 1H), 7.56-7.63 (m, 5H), 7.40-7.52 (m, 6H), 7.04-7.19 (m, 1H), 6.84-6.94 (m, 1H), 6.24 (d, J=8.29 Hz, 1H), 0.72 (s, 9H). $^{19}$F NMR (376 MHz, DMSO-$d_6$) δ −113.18 (s, 1F), −116.05 (s, 1F). m/z (ESI, +ve ion): 522.2 (M+H)$^+$.

Step 3: 2'-((tert-Butyldiphenylsilyl)oxy)-2-chloro-5, 6'-difluoro-N-(neopentylcarbamoyl)-[1,1'-biphenyl]-4-carboxamide The title compound was prepared according to Method 8, Step 2. m/z (ESI, +ve ion): 635.2 (M+H)$^+$.

Step 4: 7-(2-((tert-Butyldiphenylsilyl)oxy)-6-fluorophenyl)-6-chloro-1-neopentylquinazoline-2,4(1H, 3H)-dione The title compound was prepared according to Method 8, Step 3. m/z (ESI, +ve ion) 615.2 (M+H)$^+$.

Step 5: 4-(4Acryloylpiperazin-1-yl)-7-(2-((tert-butyldiphenylsilyl)oxy)-6-fluorophenyl)-6-chloro-1-neopentylquinazolin-2(1H)-one The title compound was prepared according to Method 59, Step 3. m/z (ESI, +ve ion): 739.2 (M+H)$^+$.

Step 6: 6-Chloro-1-(2,2-dimethylpropyl)-7-(2-fluoro-6-hydroxyphenyl)-4-(4-(2-propenoyl)-1-piperazinyl)-2(1H)-quinazolinone To a solution of 4-(4-acryloylpiperazin-1-yl)-7-(2-((tert-butyldiphenylsilyl)oxy)-6-fluorophenyl)-6-chloro-1-neopentylquinazolin-2(1H)-one (0.20 g, 0.271 mmol) in THF (5 mL) was added tetrabutylammonium fluoride (1.0 M in THF, 1.63 mL, 1.63 mmol, Strem Chemicals, Inc., Newburyport, Mass.). The reaction mixture was stirred at rt for 2 h and quenched with saturated ammonium chloride and extracted with EtOAc (2×). The organic layer was separated and concentrated in vacuo. The crude product was purified by silica gel chromatography (eluent: 0-90% EtOAc-EtOH (3:1)/heptane) to provide 6-chloro-1-(2,2-dimethylpropyl)-7-(2-fluoro-6-hydroxyphenyl)-4-(4-(2-propenoyl)-1-piperazinyl)-2(1H)-quinazolinone. $^1$H NMR (400 MHz, CDCl$_3$) δ 8.15-8.59 (m, 1H), 7.64 (s, 1H), 7.42 (s, 1H), 7.19-7.32 (m, 1H), 6.93 (d, J=8.29 Hz, 1H), 6.71 (t, J=8.60 Hz, 1H), 6.53 (br d, J=10.57 Hz, 1H), 6.30-6.38 (m, 1H), 5.76 (d, J=11.61 Hz, 1H), 3.58-4.00 (m, 10H), 0.93 (s, 9H). $^{19}$F NMR (376 MHz, CDCl$_3$) δ −113.66 (s, 1F). m/z (ESI, +ve ion) 499.3 (M+H)$^+$.

Example 90-1 and 90-2

6-Chloro-7-(2-fluoro-6-hydroxyphenyl)-8-methyl-4-((2S)-2-methyl-4-(2-propenoyl)-1-piperazinyl)-1-(2-(2-propanyl)phenyl)-2(1H)-quinazolinone

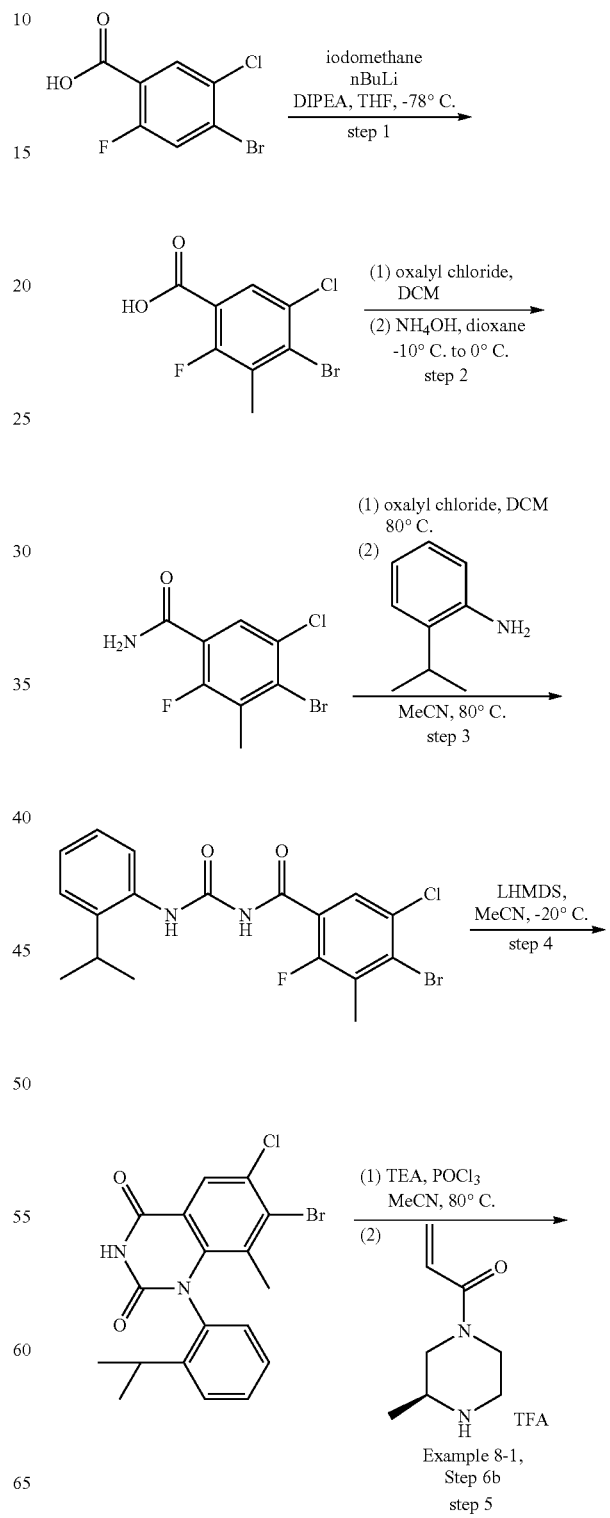

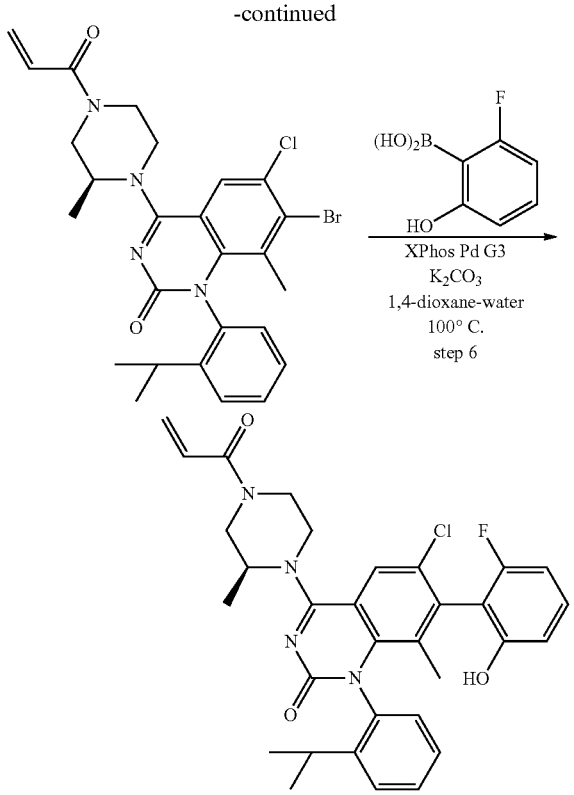

Two separable isomer peaks:
Examples 90-1 and 90-2

Step 1: 4-Bromo-5-chloro-2-fluoro-3-methylbenzoic acid

To a 250-mL 3-neck round-bottomed flask, equipped with an internal temperature probe was added diisopropylamine (2.7 mL, 27 mmol) in THF (47 mL). The reaction mixture was cooled to −78° C. in a dry ice/acetone bath. Then n-butyllithium solution (2.5 M in toluene, 14.2 mL, 35.5 mmol) was added slowly into the reaction mixture. The resulting mixture was allowed to stir 10 min, while the temperature was maintained at −70° C. The mixture was allowed to slowly warm to −40° C., then cooled to −70° C. over 30 min. This mixture was added via cannula to a cold (−78° C.) stirred solution of 4-bromo-5-chloro-2-fluorobenzoic acid (3.0 g, 11.8 mmol, OxChem, Wood Dale, Ill.) in THF (30 mL). The combined reaction mixture was allowed to stir 45 min, while the temperature was maintained at −70° C. The mixture was allowed to slowly warm to −40° C., then cooled to −70° C. over 30 min. Then iodomethane (0.81 mL, 13.0 mmol) was added slowly into the reaction mixture. The resulting mixture was allowed to stir at −72° C. for 45 min and then allowed to slowly warm to −20° C. The mixture was filtered through a pad of Celite and the filtrate was concentrated in vacuo. The residue was triturated with EtOAc and heptane. The precipitate was collected by filtration and washed with heptane. The solids were collected and dried to give 4-bromo-5-chloro-2-fluoro-3-methylbenzoic acid (3.0 g, 11.2 mmol, 95% yield) as a tan solid. $^1$H NMR (400 MHz, DMSO-$d_6$) δ ppm 6.33 (m, 1H) 1.24 (m, 3H). m/z (ESI, +ve ion): 268.9 (M+H)$^+$. This material was used immediately in the subsequent step of the synthesis without further purification as the material is very hygroscopic.

Step 2: 4-Bromo-5-chloro-2-fluoro-3-methylbenzamide

To a 100-mL round-bottomed flask was added 4-bromo-5-chloro-2-fluoro-3-methylbenzoic acid (1.25 g, 4.67 mmol) in DCM (23 mL). Then oxalyl chloride (1.02 mL, 11.7 mmol) and a catalytic amount of DMF (0.01 mL) was added into the reaction mixture. The overall mixture was allowed to stir under an inert ($N_2$) atmosphere for 30 min. The mixture was concentrated in vacuo.

The residue was diluted with 1,4-dioxane (10 mL). The mixture was cooled to −10° C., then ammonium hydroxide (28-30 wt %, 1.78 mL, 46.7 mmol) was added slowly. The resulting mixture was allowed to stir at 0° C. for 30 min. The reaction mixture was concentrated in vacuo and the residue was diluted with EtOAc-heptane (1:1). The resulting precipitate was collected by filtration, washed with heptane, and dried to give 4-bromo-5-chloro-2-fluoro-3-methylbenzamide (0.82 g, 3.08 mmol, 65.8% yield) as a tan solid. $^1$H NMR (400 MHz, DMSO-$d_6$) δ ppm 7.20 (s, 3H) 1.23 (s, 3H). m/z (ESI, +ve ion): 266.0 (M+H)$^+$.

Step 3: 4-Bromo-5-chloro-2-fluoro-N-((2-isopropylphenyl)carbamoyl)-3-methylbenzamide To a 100-mL round-bottomed flask, was added 4-bromo-5-chloro-2-fluoro-3-methylbenzamide (0.8 g, 3.0 mmol), oxalyl chloride (0.45 mL, 5.1 mmol) and a catalytic amount of DMF (2 drops) in 1,2-dichloroethane (15 mL). The mixture was stirred and heated at 80° C. for 2.5 h. The reaction mixture was concentrated in vacuo and the crude material was carried into the next step without further purification.

The crude product was diluted with acetonitrile (10 mL), then 2-(methylethyl)phenylamine (0.49 mL, 3.6 mmol) was added to the reaction mixture. The reaction mixture was allowed to stir at rt for 1 h then filtered and the filtrate was concentrated in vacuo. The crude material was purified by silica gel chromatography (eluent: 0-30% EtOAc/heptane) to provide 4-bromo-5-chloro-2-fluoro-N-((2-isopropylphenyl)carbamoyl)-3-methylbenzamide (0.213 g, 0.498 mmol, 16.6% yield) as tan solid. m/z (ESI, +ve ion): 428.9 (M+H)$^+$.

Step 4: 7-Bromo-6-chloro-1-(2-isopropylphenyl)-8-methylquinazoline-2,4(1H,3H)-dione To a 100-mL round-bottomed flask was added 4-bromo-5-chloro-2-fluoro-N-((2-isopropylphenyl)carbamoyl)-3-methylbenzamide (0.21 g, 0.491 mmol) in THF (4.9 mL). The reaction mixture was cooled to −20° C. in a dilute dry ice/acetone bath. Then KHMDS (1 M in THF, 0.64 mL, 0.64 mmol) was added to the reaction mixture. The resulting reaction mixture was allowed to stir under an inert ($N_2$) atmosphere for 16 h. The reaction was quenched with satd. $NaHCO_3$ and diluted with EtOAc. The layers were separated and the aqueous layer was extracted with EtOAc. The organic extracts were combined and dried over $MgSO_4$, filtered and concentrated in vacuo to afford 7-bromo-6-chloro-1-(2-isopropylphenyl)-8-methylquinazoline-2,4(1H,3H)-dione (0.169 g, 0.415 mmol, 84% yield) as a brown solid. m/z (ESI, +ve ion): 407.0 (M+H)$^+$. This material was carried into the next step without further purification.

Step 5: 4-(4-Acryloylpiperazin-1-yl)-7-bromo-6-chloro-1-(2-isopropylphenyl)-8-methylquinazolin-2(1H)-one To a 100-mL round-bottomed flask was added 7-bromo-6-chloro-1-(2-isopropylphenyl)-8-methylquinazoline-2,4

(1H,3H)-dione (0.169 g, 0.415 mmol) in acetonitrile (4.2 mL). Phosphorus oxychloride (0.23 mL, 2.49 mmol), followed by triethylamine, anhydrous (0.35 mL, 2.49 mmol) was added to the reaction mixture. The reaction mixture was stirred and heated at 80° C. for 45 min. The reaction mixture was concentrated in vacuo and the crude product was used immediately in the next step without further purification.

The crude product was diluted with DCM (4 mL) and treated with a solution of(S)-1-(3-methylpiperazin-1-yl) prop-2-en-1-one 2,2,2-trifluoroacetate (Example 8-1, Step 6b, 0.667 g, 2.49 mmol) in 1,2-dichloroethane (4.2 mL). Triethylamine (0.35 mL, 2.49 mmol) was added and the reaction mixture was allowed to stir under inert ($N_2$) atmosphere for 1 h. The reaction was quenched with satd. ammonium chloride (5 mL) and allowed to stir 10 min. The mixture was diluted with DCM and water, the layers separated and the aqueous layer was extracted with DCM. The combined organic extracts were dried over $MgSO_4$, filtered and concentrated in vacuo. The crude product was purified by silica gel chromatography (eluent: 0-10% MeOH/DCM) to provide (S)-4-(4-acryloyl-2-methylpiperazin-1-yl)-7-bromo-6-chloro-1-(2-isopropylphenyl)-8-methylquinazolin-2(1H)-one (0.06 g, 0.11 mmol, 26.6% yield) as a tan solid. m/z (ESI, +ve ion): 543.0 (M+H)$^+$.

Step 6: 6-Chloro-7-(2-fluoro-6-hydroxyphenyl)-8-methyl-4-((2S)-2-methyl-4-(2-propenoyl)-1-piperazinyl)-1-(2-(2-propanyl)phenyl)-2(1H)-quinazolinone A re-sealable vial was charged with (S)-4-(4-acryloyl-2-methylpiperazin-1-yl)-7-bromo-6-chloro-1-(2-isopropylphenyl)-8-methylquinazolin-2(1H)-one (0.06 g, 0.11 mmol), 2-fluoro-6-hydroxyphenylboronic acid (0.019 g, 0.121 mmol), SPhos Pd G3 (0.004 g, 5 µmol) and potassium carbonate (0.046 g, 0.331 mmol) in 1,4-dioxane (0.9 mL)/water (0.2 mL). The reaction mixture was degassed by bubbling argon into the mixture for 5 min and stirred and heated at 100° C. for 16 h. The reaction was quenched with saturated $NaHCO_3$ and diluted with EtOAc. The layers were separated and the aqueous layer was extracted with EtOAc. The combined organic extracts were dried over $MgSO_4$, filtered and concentrated in vacuo. The crude product was purified by silica gel chromatography (eluent: 0-5% 2 M ammonia in MeOH/CHCl$_3$) to provide 6-chloro-7-(2-fluoro-6-hydroxyphenyl)-8-methyl-4-((2S)-2-methyl-4-(2-propenoyl)-1-piperazinyl)-1-(2-(2-propanyl)phenyl)-2(1H)-quinazolinone (0.010 g, 0.017 mmol, 15.8% yield) as peak a yellow solid (1$^{st}$ eluting peak, Example 90-1): $^1$H NMR (400 MHz, MeOH-d$_4$) δ ppm 7.76-7.91 (m, 1H) 7.32-7.50 (m, 3H) 7.08-7.31 (m, 3H) 6.70-6.86 (m, 1H) 6.55-6.70 (m, 2H) 6.25 (d, J=16.79 Hz, 1H) 5.77 (d, J=10.57 Hz, 1H) 4.17-4.34 (m, 1H) 3.92-4.17 (m, 2H) 3.44-3.72 (m, 3H) 3.12 (d, J=12.02 Hz, 1H) 2.50-2.63 (m, 1H) 1.52-1.66 (m, 1H) 1.18-1.32 (m, 5H) 1.03-1.16 (m, 6H); m/z (ESI, +ve ion): 576.2 (M+H)$^+$ and 6-chloro-7-(2-fluoro-6-hydroxyphenyl)-8-methyl-4-((2S)-2-methyl-4-(2-propenoyl)-1-piperazinyl)-1-(2-(2-propanyl)phenyl)-2(1H)-quinazolinone (0.006 g, 10 µmol, 9% yield) as a light-yellow solid (2$^{nd}$-eluting peak, Example 90-2): $^1$H NMR (400 MHz, MeOH-d$_4$) δ ppm 7.72-7.81 (m, 2H) 7.30-7.39 (m, 2H) 7.06-7.21 (m, 3H) 6.64-6.81 (m, 1H) 6.56-6.61 (m, 1H) 6.53 (t, J=8.45 Hz, 1H) 6.19 (dd, J=16.69, 4.25 Hz, 1H) 5.71 9d, J=12.02 Hz, 1H) 4.47 (s, 1H) 4.33 (d, J=10.99 Hz, 1H) 4.10-4.25 (m, 1H) 3.79-4.04 (m, 1H) 3.61 (d, J=9.33 Hz, 1H) 3.45 (s, 1H) 3.06 (d, J=11.82 Hz, 1H) 2.56-2.68 (m, 1H) 2.47-2.56 (m, 1H) 1.26-1.39 (m, 5H) 0.99-1.09 (m, 6H); m/z (ESI, +ve ion): 576.2 (M+H)$^+$.

Example 91

6-Chloro-7-(2-fluorophenyl)-4-((2S)-2-methyl-4-(2-propenoyl)-1-piperazinyl)-1-(1-(2-propanyl)-1H-imidazol-2-yl)-2(1H)-quinazolinone

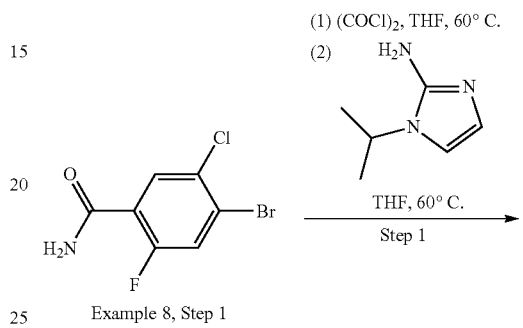

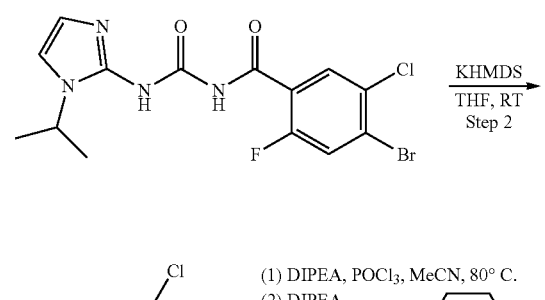

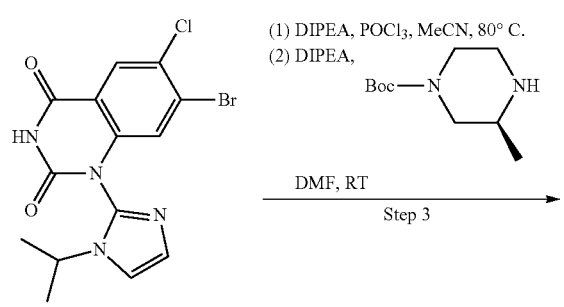

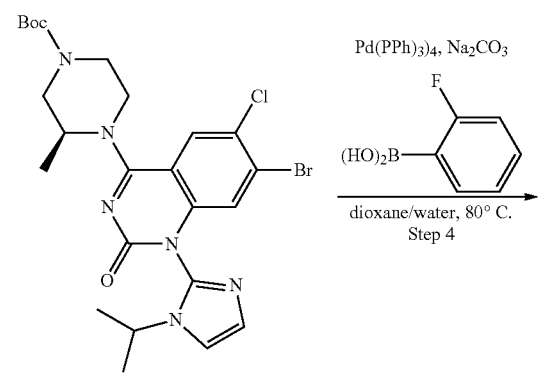

-continued

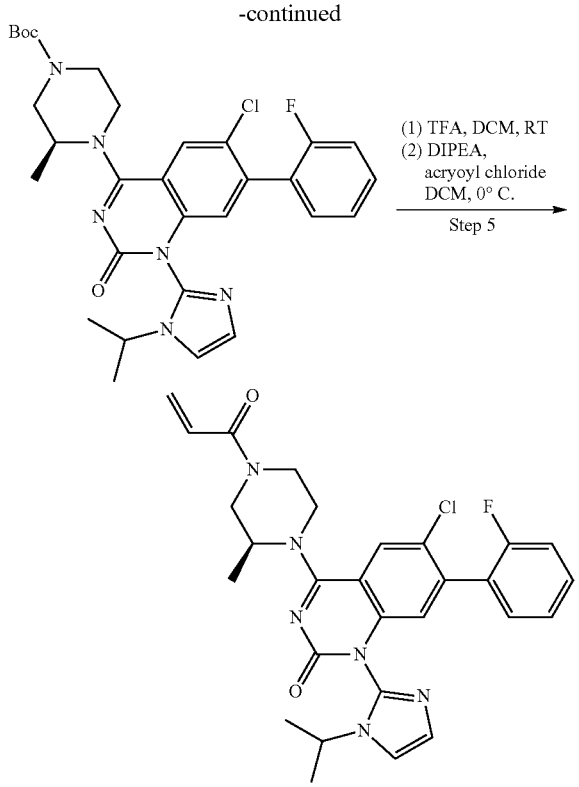

Step 1: 4-Bromo-5-chloro-2-fluoro-N-((1-isopropyl-1H-imidazol-2-yl)carbamoyl)benzamide 4-Bromo-5-chloro-2-fluorobenzamide (Example 8, Step 1, 960 mg, 3.8 mmol) was dissolved in dry THF (4 mL) under nitrogen at rt. Oxalyl chloride (2 M in DCM, 2.2 mL, 4.4 mmol) was added. The mixture was stirred and heated at 60° C. for 2.5 h. 1-(1-Methylethyl)-1H-imidazol-2-amine (485 mg, 3.88 mmol, Oakwood Products, Inc., Estill, S.C., USA) was then added. The resulting mixture was stirred at rt for 1 h. The crude reaction mixture was triturated with heptane (15 mL) and filtered to give 4-bromo-5-chloro-2-fluoro-N-((1-isopropyl-1H-imidazol-2-yl)carbamoyl)benzamide (1.4 g, 3.47 mmol, 91% yield) as a tan solid. m/(ESI, +ve ion): 403.0 (M+H)$^+$.

Step 2. 7-Bromo-6-chloro-1-(1-isopropyl-1H-imidazol-2-yl)quinazoline-2,4(1H,3H)-dione To a solution of 4-bromo-5-chloro-2-fluoro-N-((1-isopropyl-1H-imidazol-2-yl)carbamoyl)benzamide (1.4 g, 3.47 mmol) in THF (35 mL) was added KHMDS (1 M in THF, 6.9 mL, 6.9 mmol) dropwise and the reaction mixture was stirred at rt for 2 h. The reaction mixture was diluted with EtOAc (50 mL), washed with saturated ammonium chloride (20 mL). the organic layer was dried over Na$_2$SO$_4$, and concentrated in vacuo to give 7-bromo-6-chloro-1-(1-isopropyl-1H-imidazol-2-yl)quinazoline-2,4(1H,3H)-dione (0.511 g, 1.33 mmol, 38.4% yield) as a yellow solid. m/z (ESI, +ve ion): 383.0 (M+H)$^+$.

Step 3. (S)-tert-Butyl 4-(7-bromo-6-chloro-1-(1-isopropyl-1H-imidazol-2-yl)-2-oxo-1,2-dihydroquinazolin-4-yl)-3-methylpiperazine-1-carboxylate A mixture of 7-bromo-6-chloro-1-(1-isopropyl-1H-imidazol-2-yl)quinazoline-2,4(1H,3H)-dione (0.78 g, 2.03 mmol), phosphorus oxychloride (0.57 mL, 6.1 mmol), and DIPEA (1.1 mL, 6.1 mmol) in acetonitrile (14 mL) was stirred at 80° C. for 2 h. The reaction mixture was concentrated in vacuo and the crude product was used as is.

The mixture of 7-bromo-4,6-dichloro-1-(1-isopropyl-1H-imidazol-2-yl)quinazolin-2(1H)-one (0.82 g, 2.03 mmol). (3S)-1-(tert-butoxycarbonyl)-3-methylpiperazine (0.61 g, 3.05 mmol, Combi-Blocks, San Diego, Calif.), and DIPEA (1.6 mL, 9.16 mmol) in DMF (14.5 mL) was stirred at rt for 30 min. Ice water (10 mL) was added and stirred for 15 min. The mixture was extracted with EtOAc and the combined organics was washed with brine, dried over Na$_2$SO$_4$ and concentrated. The crude product was purified by silica gel chromatography (eluent: 0-25% EtOAc-EtOH (3:1)/heptane) to provide (S)-tert-butyl 4-(7-bromo-6-chloro-1-(1-isopropyl-1H-imidazol-2-yl)-2-oxo-1,2-dihydroquinazolin-4-yl)-3-methylpiperazine-1-carboxylate (0.607 g, 1.07 mmol, 52.7% yield) as a tan solid. m/z (ESI, +ve ion): 565.1.0 (M+H)$^+$.

Step 4. (S)-tert-Butyl 4-(6-chloro-7-(2-fluorophenyl)-1-(1-isopropyl-1H-imidazol-2-yl)-2-oxo-1,2-dihydroquinazolin-4-yl)-3-methylpiperazine-1-carboxylate A mixture of (S)-tert-butyl 4-(7-bromo-6-chloro-1-(1-isopropyl-1H-imidazol-2-yl)-2-oxo-1,2-dihydroquinazolin-4-yl)-3-methylpiperazine-1-carboxylate (459 mg, 0.811 mmol), 2-fluorophenylboronic acid (170 mg, 1.22 mmol), tetrakis(triphenylphosphine)palladium(0) (94 mg, 0.081 mmol) in a sealed vial was evacuated and flushed with nitrogen two times. 1,4-Dioxane (4 mL) and anhydrous sodium carbonate (215 mg, 2.03 mmol) in water (4 mL) was added and the reaction mixture was heated at 80° C. for 18 h. The aqueous layer was back extracted with EtOAc (2×) and the combined organics was dried over Na$_2$SO$_4$ and concentrated in vacuo. The crude product was purified by silica gel chromatography (eluent: 0-25% EtOAc-EtOH (3:1)/heptane) to provide (S)-tert-butyl 4-(6-chloro-7-(2-fluorophenyl)-1-(1-isopropyl-1H-imidazol-2-yl)-2-oxo-1,2-dihydroquinazolin-4-yl)-3-methylpiperazine-1-carboxylate (178 mg, 0.306 mmol, 37.8% yield) as a light-yellow solid. m/z (ESI, +ve ion): 581.3 (M+H)$^+$.

Step 5. 6-Chloro-7-(2-fluorophenyl)-4-((2S)-2-methyl-4-(2-propenoyl)-1-piperazinyl)-1-(1-(2-propanyl)-1H-imidazol-2-yl)-2(1H)-quinazolinone To a solution of (S)-tert-butyl 4-(6-chloro-7-(2-fluorophenyl)-1-(1-isopropyl-1H-imidazol-2-yl)-2-oxo-1,2-dihydroquinazolin-4-yl)-3-methylpiperazine-1-carboxylate (176 mg, 0.303 mmol) in DCM (2 mL) was added TFA (677 μL, 9.09 mmol) dropwise. The reaction mixture was stirred at rt for 30 min. The mixture was concentrated in vacuo to give crude product which was used directly in the following step.

A mixture of crude (S)-6-chloro-7-(2-fluorophenyl)-1-(1-isopropyl-1H-imidazol-2-yl)-4-(2-methylpiperazin-1-yl)quinazolin-2(1H)-one, DIPEA (0.24 mL, 1.36 mmol) in DCM (2 mL) was added acryloyl chloride (24.70 μL, 0.303 mmol) at 0° C. and stirred for 30 min and the mixture was concentrated in vacuo. The crude product was purified by silica gel chromatography (0-25% EtOAc-EtOH (3:1)/heptane) to provide 6-chloro-7-(2-fluorophenyl)-4-((2S)-2-methyl-4-(2-propenoyl)-1-piperazinyl)-1-(1-(2-propanyl)-1H-imidazol-2-yl)-2(1H)-quinazolinone (100 mg, 0.187 mmol, 61.7% yield) as an off-white solid. $^1$H NMR (400 MHz, DMSO-d$_6$) δ 7.92-8.07 (m, 1H), 7.52 (s, 2H), 7.21-

7.39 (m, 3H), 7.04 (s, 1H), 6.76-6.93 (m, 1H), 6.21 (br d, J=10.57 Hz, 2H), 5.72-5.82 (m, 1H), 4.73-5.09 (m, 1H), 4.52-4.59 (m, 1H), 3.56-4.49 (m, 6H), 1.30-1.42 (m, 6H), 1.17-1.26 (m, 3H). $^{19}$F NMR (376 MHz, DMSO-$d_6$) δ −115.10--114.52 (m, 1F). m/z (ESI, +ve ion): 535.1 (M+H)$^+$.
Example 92
6-Chloro-4-(4-((2E)-4-(dimethylamino)-2-butenoyl)-1-piperazinyl)-7-(2-fluoro-6-hydroxyphenyl)-1-(2-(2-propanyl)phenyl)-2(1H)-quinazolinone
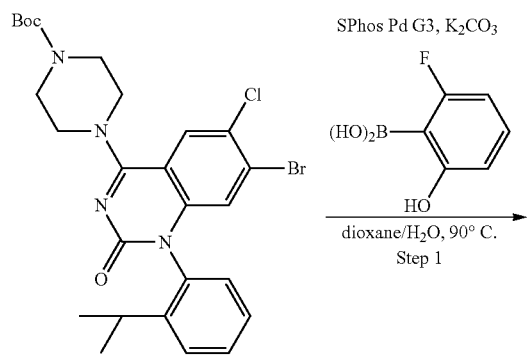
Example 11-1, Step 2
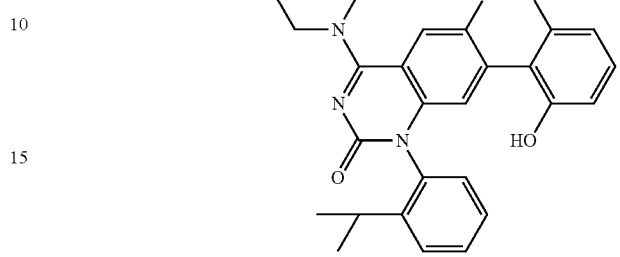
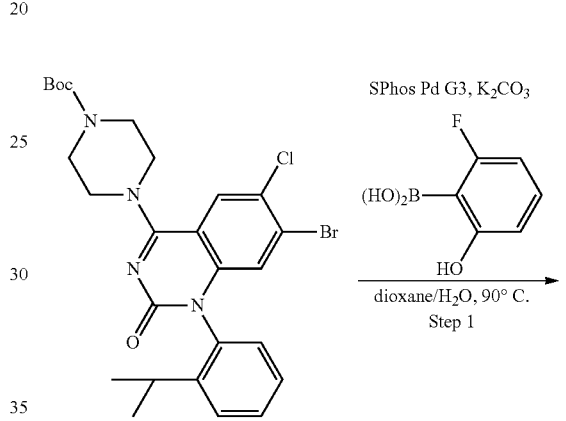
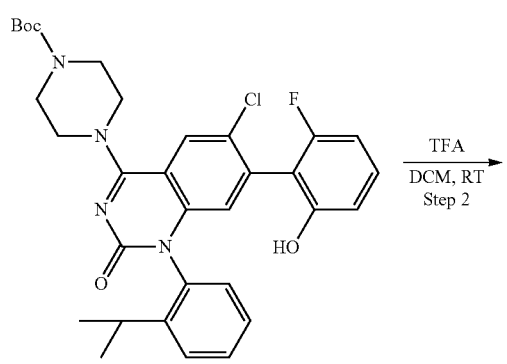
Intermediate 92A
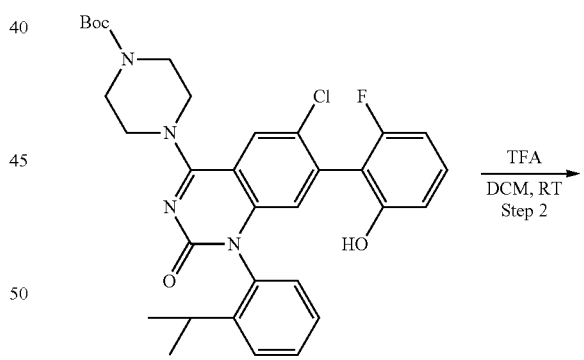
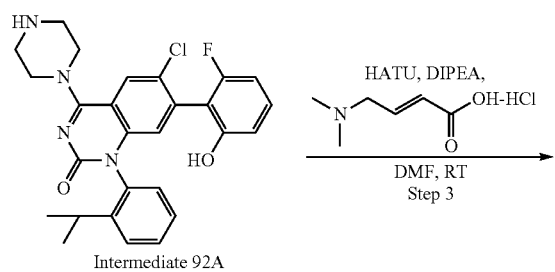
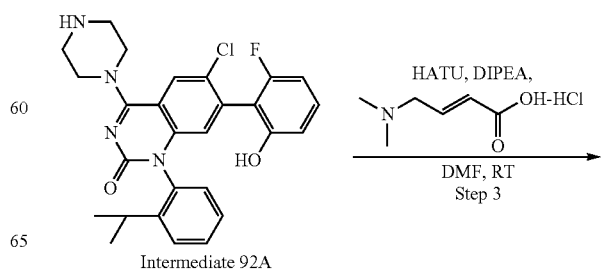
Intermediate 92A -continued

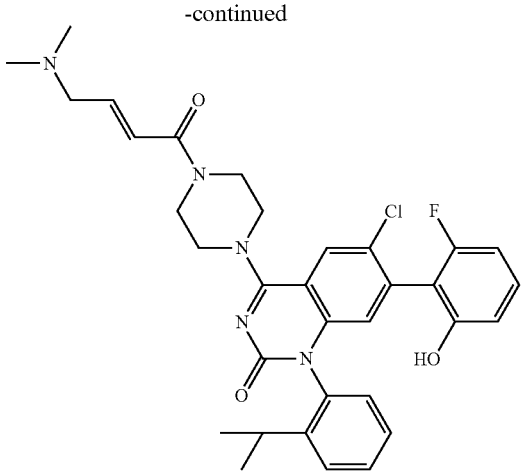

Step 1: tert-Butyl 4-(6-chloro-7-(2-fluoro-6-hydroxyphenyl)-1-(2-isopropylphenyl)-2-oxo-1,2-dihydroquinazolin-4-yl)piperazine-1-carboxylate A mixture of tert-butyl 4-(7-bromo-6-chloro-1-(2-isopropylphenyl)-2-oxo-1,2-dihydroquinazolin-4-yl)piperazine-1-carboxylate (Example 11-1, Step 2, 500 mg, 0.9 mmol), SPhos Pd G3 (39 mg, 0.045 mmol), 2-fluoro-6-hydroxyphenylboronic acid (170 mg, 1.1 mmol, Combi-blocks Inc., San Diego, Calif.) and potassium carbonate (370 mg, 2.7 mmol) in water (1.5 mL), and 1,4-dioxane (6.0 mL) was heated at 90° C. for 16 h. The reaction mixture was diluted with satd NaHCO₃ (10 mL) and extracted with EtOAc. The combined organic layers were dried over Na₂SO₄ and concentrated in vacuo. The crude product was purified by silica gel chromatography (eluent: 0-4% MeOH/DCM) to provide tert-butyl 4-(6-chloro-7-(2-fluoro-6-hydroxyphenyl)-1-(2-isopropylphenyl)-2-oxo-1,2-dihydroquinazolin-4-yl)piperazine-1-carboxylate. m/z (ESI, +ve ion): 593.8 (M+H)⁺.

Step 2: 6-Chloro-7-(2-fluoro-6-hydroxyphenyl)-1-(2-isopropylphenyl)-4-(piperazin-1-yl)quinazolin-2(1H)-one (Intermediate 92A)

TFA (1.2 mL, 16.4 mmol) was added to a solution of tert-butyl 4-(6-chloro-7-(2-fluoro-6-hydroxyphenyl)-1-(2-isopropylphenyl)-2-oxo-1,2-dihydroquinazolin-4-yl)piperazine-1-carboxylate (389 mg, 0.66 mmol) in DCM (8 mL). The mixture was stirred at rt for 3 h and concentrated in vacuo. The crude product was purified by silica gel chromatography (eluent: 0-25% MeOH/DCM) to provide the trifluoroacetate salt of 6-chloro-7-(2-fluoro-6-hydroxyphenyl)-1-(2-isopropylphenyl)-4-(piperazin-1-yl)quinazolin-2(1H)-one (Intermediate 92A). m/z (ESI, +ve ion): 493.0 (M+H)⁺.

Step 3: 6-Chloro-4-(4-((2E)-4-(dimethylamino)-2-butenoyl)-1-piperazinyl)-7-(2-fluoro-6-hydroxyphenyl)-1-(2-(2-propanyl)phenyl)-2(1H)-quinazolinone To a mixture of the trifluoroacetate salt of 6-chloro-7-(2-fluoro-6-hydroxyphenyl)-1-(2-isopropylphenyl)-4-(piperazin-1-yl)quinazolin-2(1H)-one (Intermediate 92A, 0.17 mmol) in DMF (4 mL) was added HATU (67 mg, 0.18 mmol, Matrix Scientific, Columbia, S.C.), trans-4-dimethylaminocrotonoic acid hydrochloride (25 mg, 0.15 mmol, Matrix Scientific, Columbia. S.C.) and DIPEA (0.093 mL, 0.53 mmol). The resulting solution was stirred at rt for 2.5 h, then was partitioned between satd. NaHCO₃ (35 mL) and DCM (50 mL). The organic layer was washed with water, dried over Na₂SO₄ and concentrated in vacuo. The crude product was purified by silica gel chromatography (eluent: 0-30% MeOH/DCM) to provide 6-chloro-4-(4-((2E)-4-(dimethylamino)-2-butenoyl)-1-piperazinyl)-7-(2-fluoro-6-hydroxyphenyl)-1-(2-(2-propanyl)phenyl)-2(1H)-quinazolinone. ¹H NMR (400 MHz, DMSO-d₆) δ ppm 10.10 (br s, 1H), 8.03 (d, J=1.2 Hz, 1H), 7.50-7.56 (m, 1H), 7.45 (t, J=7.5 Hz, 1H), 7.30-7.37 (m, 1H), 7.13-7.25 (m, 2H), 6.59-6.76 (m, 4H), 6.23 (d, J=13.9 Hz, 1H), 3.65-4.07 (m, 8H), 3.06 (d, J=5.2 Hz, 2H), 2.50-2.59 (m, 1H), 2.17 (s, 6H), 0.94-1.12 (m, 6H). m/z (ESI, +ve ion): 604.0 (M+H)⁺.

Example 93

6-Chloro-7-(2-fluorophenyl)-4-((2S)-2-methyl-4-(2-propenoyl)-1-piperazinyl)-1-(2-(trifluoromethyl)phenyl)-2(1H)-quinazolinone

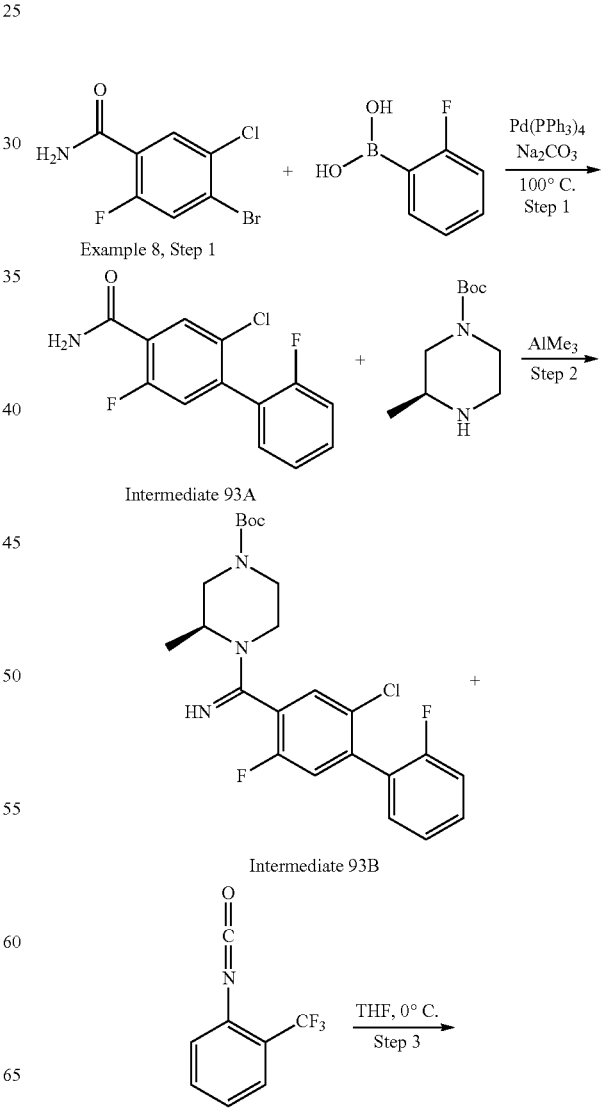

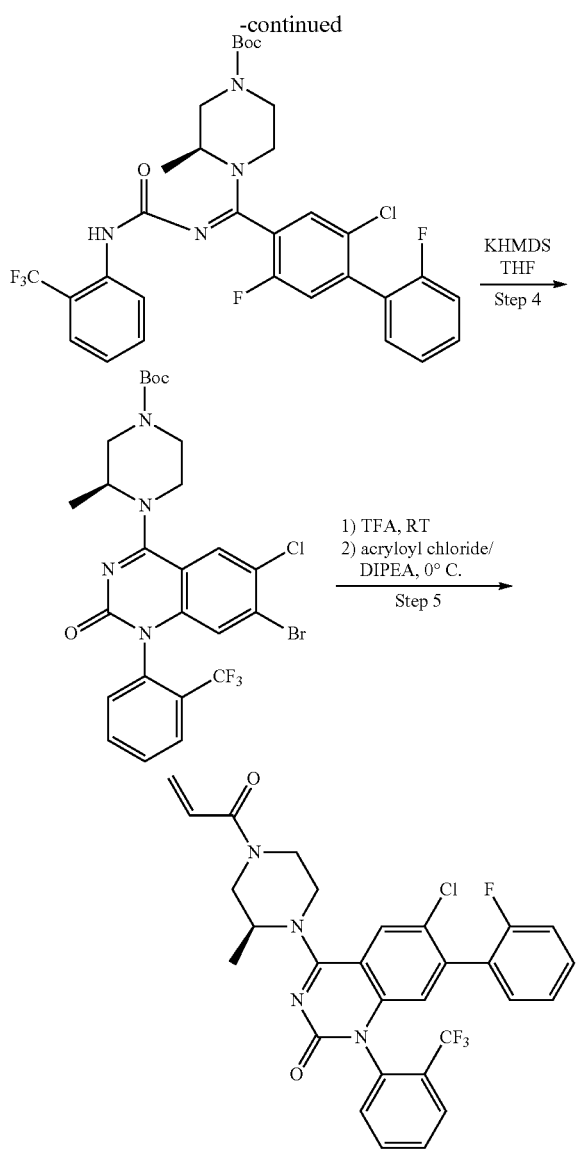

Step 1: 2-Chloro-2',5-difluoro-[1,1'-biphenyl]-4-carboxamide (Intermediate 93A)

A suspension of 4-bromo-5-chloro-2-fluorobenzamide (Example 8, Step 1, 5.0 g, 19.8 mmol), 2-fluorophenylboronic acid (8.31 g, 59.4 mmol, Combi-Blocks, Inc., San Diego, Calif.) tetrakis(triphenylphosphine)palladium(0) (0.458 g, 0.396 mmol), sodium carbonate (10.5 g, 99 mmol) in 1,4-dioxane (35 mL) and water (35 mL) was heated to 100° C. for 6 h. The reaction was then partitioned between EtOAc (100 mL) and 5% NaHCO$_3$ (50 mL). The organic layer was washed with water (50 mL) then brine (5 mL). The organic was dried over MgSO$_4$, filtered and concentrated in vacuo. The crude product was purified by silica gel chromatography (eluent: 0-30% EtOAc-EtOH (3:1)/heptane) to provide 2-chloro-2',5-difluoro-[1,1'-biphenyl]-4-carboxamide (Intermediate 93A): $^1$H NMR (400 MHz, CDCl$_3$) δ 8.26 (d, J=7.05 Hz, 1H), 7.41-7.49 (m, 1H), 7.30-7.36 (m, 1H), 7.16-7.26 (m, 3H), 6.68 (br s, 1H), 5.96 (br s, 1H). $^{19}$F NMR (376 MHz, CDCl$_3$) δ −113.86 (s, 1F), −115.81 (s, 1F). m/z (ESI, +ve ion): 268.1 (M+H)$^+$.

Step 2: tert-Butyl (S)-4-((2-chloro-2',5-difluoro-[1,1'-biphenyl]-4-yl)(imino)methyl)-3-methylpiperazine-1-carboxylate (Intermediate 93B)

To a stirring suspension of 2-chloro-2',5-difluoro-[1,1'-biphenyl]-4-carboxamide (Intermediate 93A, 500 mg, 1.87 mmol) and (S)-4-N-Boc-2-methyl piperazine (412 mg, 2.06 mmol) in toluene (5 mL) at 0° C. under nitrogen was added trimethylaluminum (2 M in toluene, 2.6 mL, 5.23 mmol). The mixture was allowed to stir at 20° C. for 5 min, and then stirred and heated to 110° C. for 1 h. The reaction mixture was cooled to rt, diluted with DCM (20 mL), then quenched with saturated ammonium chloride (2 mL). After 3 min, the suspension was further diluted with THF (15 mL), stirred for 10 min. The suspension was filtered through a pad of Celite, dried over Na$_2$SO$_4$, filtered and concentrated in vacuo to give tert-butyl (S)-4-((2-chloro-2',5-difluoro-[1,1'-biphenyl]-4-yl)(imino)methyl)-3-methylpiperazine-1-carboxylate (Intermediate 93B). m/z (ESI, +ve ion): 450.1 (M+H)$^+$.

Step 3: (S)-tert-Butyl 4-((2-chloro-2',5-difluoro-[1,1'-biphenyl]-4-yl)(((2-(trifluoromethyl)phenyl)carbamoyl)imino)methyl)-3-methylpiperazine-1-carboxylate To a stirring solution of (S)-tert-butyl 4-((2-chloro-2',5-difluoro-[1,1'-biphenyl]-4-yl)imino)methyl)-3-methylpiperazine-1-carboxylate (Intermediate 93B, 100 mg, 0.222 mmol) in THF (1 mL) at 0° C. was added 1-isocyanato-2-(trifluoromethyl)benzene (25.2 µl, 0.167 mmol). The mixture was then purified by silica gel chromatography (eluent: 0-40% EtOAc-EtOH (3:1)/heptane) to provide (S)-tert-butyl 4-((2-chloro-2',5-difluoro-[1,1'-biphenyl]-4-yl)(((2-(trifluoromethyl)phenyl)carbamoyl)imino)methyl)-3-methylpiperazine-1-carboxylate: m/z (ESI, +ve ion): 637.3 (M+H)$^+$.

Step 4: (S)-tert-Butyl 4-(6-chloro-7-(2-fluorophenyl)-2-oxo-1-(2-(trifluoromethyl)phenyl)-1,2-dihydroquinazolin-4-yl)-3-methylpiperazine-1-carboxylate To a stirring solution of (S)-tert-butyl 4-((2-chloro-2',5-difluoro-[1,1'-biphenyl]-4-yl)(((2-(trifluoromethyl)phenyl)carbamoyl)imino)methyl)-3-methylpiperazine-1-carboxylate (200 mg, 0.314 mmol) in THF (2 mL) at 0° C. under argon was added KHMDS (1 M in 2-MeTHF, 314 µL, 0.314 mmol). The cooling bath was removed and the mixture was stirred at 20° C. for 4 h. The reaction was then partitioned between EtOAc (15 mL) and saturated ammonium chloride (5 mL). The organic layer was dried over MgSO$_4$, concentrated in vacuo, and purified by silica gel chromatography (eluent: 0-25% EtOAc-EtOH (3:1)/heptane) to provide (S)-tert-butyl 4-(6-chloro-7-(2-fluorophenyl)-2-oxo-1-(2-(trifluoromethyl)phenyl)-1,2-dihydroquinazolin-4-yl)-3-methylpiperazine-1-carboxylate: $^1$H NMR (400 MHz, CDCl$_3$) δ 7.82-7.91 (m, 1H), 7.68-7.80 (m, 2H), 7.56-7.64 (m, 1H), 7.32-7.43 (m, 2H), 7.05-7.20 (m, 3H), 6.31-6.43 (m, 1H), 4.65-5.00 (m, 1H), 3.80-4.48 (m, 4H), 2.94-3.62 (m, 2H), 1.34-1.58 (m, 12H). m/z (ESI, +ve ion) 617.2 (M+H)$^+$.

Step 5: (S)-4-(4-Acryloyl-2-methylpiperazin-1-yl)-6-chloro-7-(2-fluorophenyl)-1-(2-(trifluoromethyl)phenyl)quinazolin-2(1H)-one A solution of (S)-tert-butyl 4-(6-chloro-7-(2-fluorophenyl)-2-oxo-1-(2-(trifluoromethyl)phenyl)-1,2-dihydroquinazolin-4-yl)-3-methylpiperazine-1-carboxylate (85 mg, 0.138 mmol) in TFA (2 mL) was stirred for 10 min, then concentrated in vacuo. The residue was dissolved in DCM (2 mL), DIPEA (96 µl, 0.551 mmol) added, then chilled to 0° C. To the chilled solution was added acryloyl chloride (11.2 µl, 0.138 mmol). The mixture was then partitioned between EtOAc (5 mL) and saturated NaHCO$_3$ (2 mL). The organic layer was dried over MgSO$_4$, concentrated in vacuo, and purified by silica gel chromatography (eluent: 0-30% EtOAc-EtOH (3:1)/heptane) to provide (S)-4-(4-acryloyl-2-methylpiperazin-1-yl)-6-chloro-7-(2-fluorophenyl)-1-(2-(trifluoromethyl)phenyl)quinazolin-2(1H)-one: $^1$H NMR (400 MHz, CDCl$_3$) δ ppm 1.43-1.69 (m, 3H) 2.95-3.45 (m, 1H) 3.48-4.15 (m, 3H) 4.25-4.87 (m, 2H) 4.88-5.29 (m, 1H) 5.87 (d, J=10.78 Hz, 1H) 6.42-6.50 (m, 2H) 6.59-6.79 (m, 1H) 7.14-7.29 (m, 3H) 7.42-7.51 (m, 2H) 7.69 (dd, J=15.34, 7.88 Hz, 1H) 7.79-7.90 (m, 2H) 7.94 (d, J=8.09 Hz, 1H). 19F NMR (376 MHz, CDCl$_3$) δ −61.42 (s, 1F), −75.99 (s, 1F), − 113.64 (s, 1F). m/z (ESI, +ve ion): 571.1 (M+H)$^+$.

Example 94

6-Chloro-7-cyclopropyl-1-(2,6-diethylphenyl)-4-((2S)-2-methyl-4-(2-propenoyl)-1-piperazinyl)pyrido[2,3-d]pyrimidin-2(1H)-one

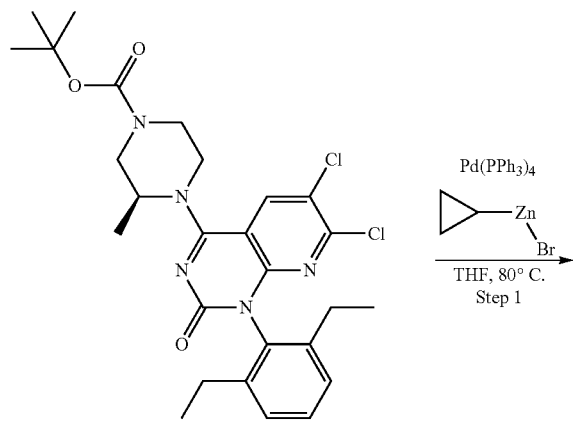

Intermediate 66B

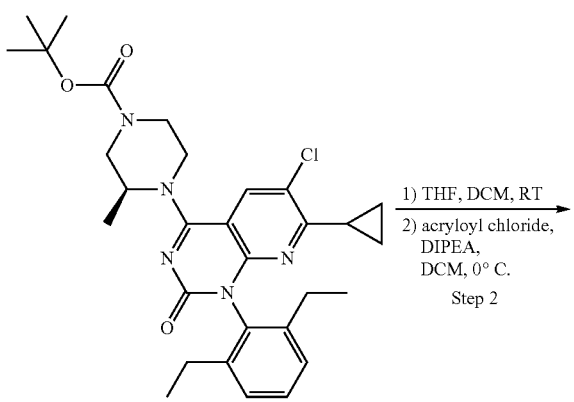

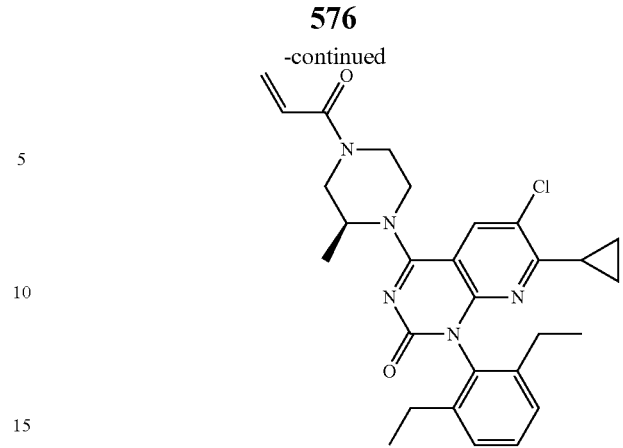

Step 1: (S)-tert-Butyl 4-(6-chloro-7-cyclopropyl-1-(2,6-diethylphenyl)-2-oxo-1,2-dihydropyrido[2,3-d]pyrimidin-4-yl)-3-methylpiperazine-1-carboxylate A mixture of (S)-tert-butyl 4-(6,7-dichloro-1-(2,6-diethylphenyl)-2-oxo-1,2-dihydropyrido[2,3-d]pyrimidin-4-yl)-3-methylpiperazine-1-carboxylate (Intermediate 66B, 90 mg, 0.165 mmol) and tetrakis(triphenylphosphine)palladium(0) (19 mg, 0.016 mmol) in a sealed vial was evacuated and flushed with nitrogen. THF (0.7 mL) was added followed by cyclopropylzinc bromide (362 µL, 0.181 mmol, Rieke Metals. Inc. Lincoln, Nebr.) and the reaction mixture was stirred heated at 80° C. for 2 h. Additional cyclopropylzinc bromide (362 µl, 0.181 mmol) and tetrakis(triphenylphosphine)palladium(0) (5 mg) were added and the resulting mixture was stirred heated at 80° C. for 5 h and at 60° C. overnight. The crude product was purified by silica gel chromatography (eluent: 0-20% EtOAc-EtOH (3:1)/heptane) to provide (S)-tert-butyl 4-(6-chloro-7-cyclopropyl-1-(2,6-diethylphenyl)-2-oxo-1,2-dihydropyrido[2,3-d]pyrimidin-4-yl)-3-methylpiperazine-1-carboxylate (61 mg, 0.11 mmol, 67.1% yield) as a white solid. m/z (ESI, +ve ion): 552.2 (M+H)$^+$.

Step 2: 6-Chloro-7-cyclopropyl-1-(2,6-diethylphenyl)-4-((2S)-2-methyl-4-(2-propenoyl)-1-piperazinyl)pyrido[2,3-d]pyrimidin-2(1H)-one A solution of (S)-tert-butyl 4-(6-chloro-7-cyclopropyl-1-(2,6-diethylphenyl)-2-oxo-1,2-dihydropyrido[2,3-d]pyrimidin-4-yl)-3-methylpiperazine-1-carboxylate (61 mg, 0.10 mmol) in DCM (0.3 mL) was treated with TFA (250 µl, 3.35 mmol) at rt and stirred for 15 min. The mixture was concentrated in vacuo to afford (S)-6-chloro-7-cyclopropyl-1-(2,6-diethylphenyl)-4-(2-methylpiperazin-1-yl)pyrido[2,3-d]pyrimidin-2(1H)-one. m/z (ESI, +ve ion): 452.2 (M+H)$^+$.

A mixture of (S)-6-chloro-7-cyclopropyl-1-(2,6-diethylphenyl)-4-(2-methylpiperazin-1-yl)pyrido[2,3-d]pyrimidin-2(1H)-one and DIPEA (96 µL, 0.55 mmol) in DCM (0.35 mL) was added acryloyl chloride (9.91 µL, 0.122 mmol) at 0° C. and stirred at 0° C. for 40 min. The mixture was concentrated in vacuo and the crude product was purified by silica gel chromatography (eluent: 0-35% EtOAc-EtOH (3:1)/heptane) to provide 6-chloro-7-cyclopropyl-1-(2,6-diethylphenyl)-4-((2S)-2-methyl-4-(2-propenoyl)-1-piperazinyl)pyrido[2,3-d]pyrimidin-2(1H)-one. $^1$H NMR (400 MHz, CDCl$_3$) δ ppm 7.89 (s, 1H), 7.36-7.43 (m, 1H), 7.24 (d, J=7.7 Hz, 2H), 6.53-6.74 (m, 1H), 6.42 (dd, J=1.1, 16.9 Hz, 1H), 5.82 (dd, J=1.8, 10.5 Hz, 1H), 4.97-5.15 (m, 1H), 4.64-4.83 (m, 1H), 4.38-4.58 (m, 1H), 3.96-4.32 (m, 1H), 3.45-3.91 (m, 3H), 2.94-3.34 (m, 1H), 2.08-2.49 (m, 4H), 1.40-1.53 (m, 3H), 1.01-1.16 (m, 6H), 0.93 (br dd, J=3.3, 7.7 Hz, 2H), 0.53-0.68 (m, 2H). m/z (ESI, +ve ion): 506.1 (M+H)+.

Example 95

6,7-Dicyclopropyl-1-(2,6-diethylphenyl)-4-((2S)-2-methyl-4-(2-propenoyl)-1-piperazinyl)pyrido[2,3-d]pyrimidin-2(1H)-one

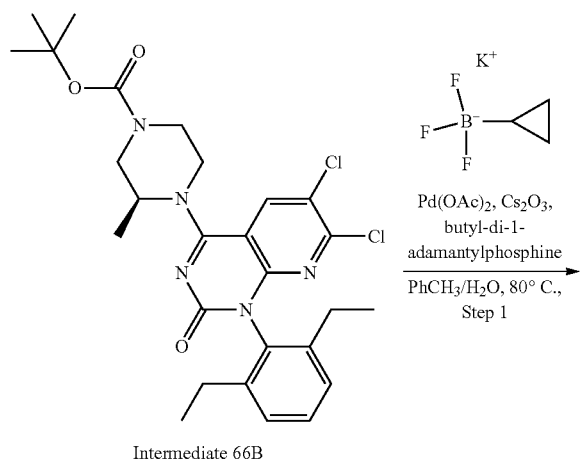

Intermediate 66B

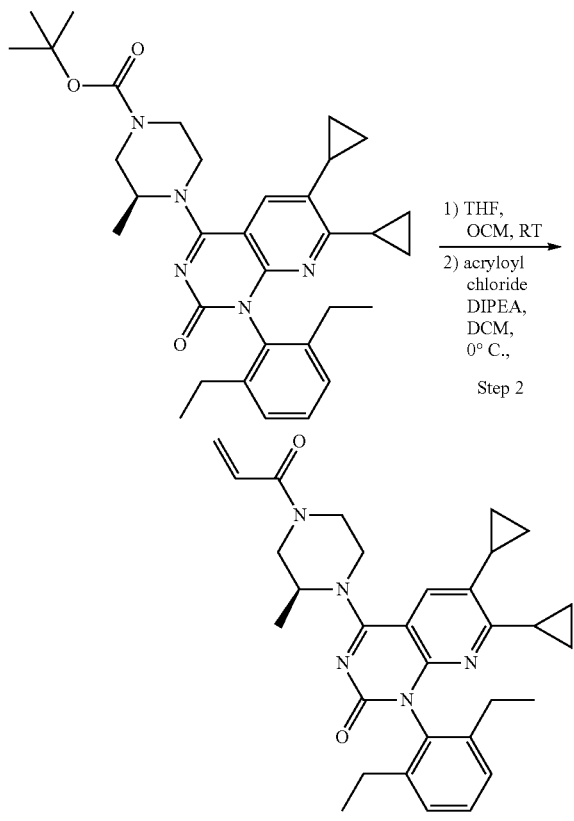

Step 1: (S)-tert-Butyl 4-(6,7-dicyclopropyl-1-(2,6-diethylphenyl)-2-oxo-1,2-dihydropyrido[2,3-d]pyrimidin-4-yl)-3-methylpiperazine-1-carboxylate A mixture of (S)-tert-butyl 4-(6,7-dichloro-1-(2,6-diethylphenyl)-2-oxo-1,2-dihydropyrido[2,3-d]pyrimidin-4-yl)-3-methylpiperazine-1-carboxylate (Intermediate 66B, 75 mg, 0.137 mmol). potassium cyclopropyltrifluoroborate (34.5 mg, 0.233 mmol), palladium(II) acetate (2.5 mg, 11 μmol), butyl-di-1-adamantylphosphine (4.9 mg, 0.014 mmol, Strem Chemicals, Newburyport, Mass.), and cesium carbonate (134 mg, 0.412 mmol) in a sealed vial was evacuated and flushed with nitrogen two times. Toluene (1.4 mL) and water (1.4 mL) was added and the reaction mixture was stirred and heated at 80° C. for 16 h. Added more palladium(II) acetate (2.5 mg, 11 μmol) and butyl-di-1-adamantylphosphine (4.9 mg, 0.014 mmol) and stirred and heated at 100° C. for 18 h. The organic layer was diluted with EtOAc and dried over Na$_2$SO$_4$. The crude product was purified by silica gel chromatography (0-20% EtOAc-EtOH (3:1)/heptane) to provide (S)-tert-butyl 4-(6,7-dicyclopropyl-1-(2,6-diethylphenyl)-2-oxo-1,2-dihydropyrido[2,3-d]pyrimidin-4-yl)-3-methylpiperazine-1-carboxylate (28 mg, 0.05 mmol, 36.6% yield) as an off-white solid.

Step 2: (6,7-Dicyclopropyl-1-(2,6-diethylphenyl)-4-((ZS)-2-methyl-4-(2-propenoyl)-1-piperazinyl)pyrido[2,3-d]pyrimidin-2(1H)-one A solution of (S)-tert-butyl 4-(6,7-dicyclopropyl-1-(2,6-diethylphenyl)-2-oxo-1,2-dihydropyrido[2,3-d]pyrimidin-4-yl)-3-methylpiperazine-1-carboxylate (28 mg, 0.05 mmol) in DCM (0.3 mL) was treated with TFA (100 μL, 1.34 mmol) at rt and stirred for 15 min. The mixture was concentrated in vacuo to afford (S)-6,7-dicyclopropyl-1-(2,6-diethylphenyl)-4-(2-methylpiperazin-1-yl)pyrido[2,3-d]pyrimidin-2(1H)-one. m/z (ESI, +ve ion): 458.3 (M+H)+.

A mixture of (S)-6,7-dicyclopropyl-1-(2,6-diethylphenyl)-4-(2-methylpiperazin-1-yl)pyrido[2,3-d]pyrimidin-2(1H)-one and DIPEA (43.8 μL, 0.251 mmol) in DCM (0.35 mL) was added acryloyl chloride (4.09 μL, 0.05 mmol) at 0° C. and stirred for 40 min at 0° C. The mixture was concentrated in vacuo. The crude product was purified by silica gel chromatography (0-35% EtOAc-EtOH (3:1)/heptane) to provide 6,7-dicyclopropyl-1-(2,6-diethylphenyl)-4-((2S)-2-methyl-4-(2-propenoyl)-1-piperazinyl)pyrido[2,3-d]pyrimidin-2(1H)-one. $^1$H NMR (400 MHz, CDCl$_3$) δ ppm 7.54-7.63 (m, 1H), 7.30-7.38 (m, 1H), 7.20 (d, J=7.5 Hz, 2H), 6.50-6.72 (m, 1H), 6.38 (br d, J=17.0 Hz, 1H), 5.78 (dd, J=1.7, 10.4 Hz, 1H), 4.95-5.10 (m, 1H), 4.57-4.76 (m, 1H), 4.35-4.54 (m, 1H), 4.19 (td, J=1.9, 12.0 Hz, 1H), 3.57-4.02 (m, 2H), 2.91-3.55 (m, 1H), 2.40 (dt, J=4.0, 8.1 Hz, 1H), 2.08-2.36 (m, 4H), 2.00-2.07 (m, 1H), 0.96-1.09 (m, 10H), 0.83 (br dd, J=3.2, 7.8 Hz, 3H), 0.55-0.68 (m, 4H). m/z (ESI, +ve ion): 512.3 (M+H)+.

Example 96

(2R)-1-(6-Chloro-1-(2,6-diethylphenyl)-7-(2-fluorophenyl)-2-oxo-1,2-dihydropyrido[2,3-d]pyrimidin-4-yl)-4-(2-propenoyl)-2-piperazinecarboxylic acid

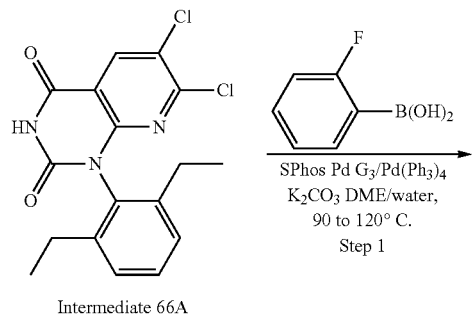

Intermediate 66A

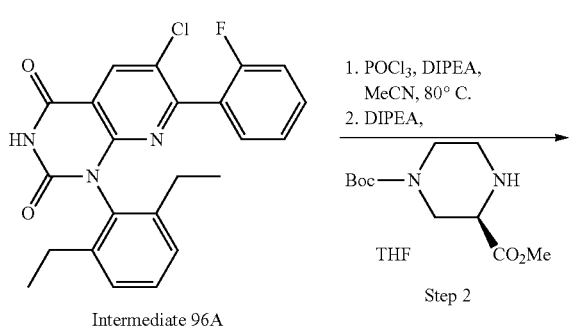

Intermediate 96A

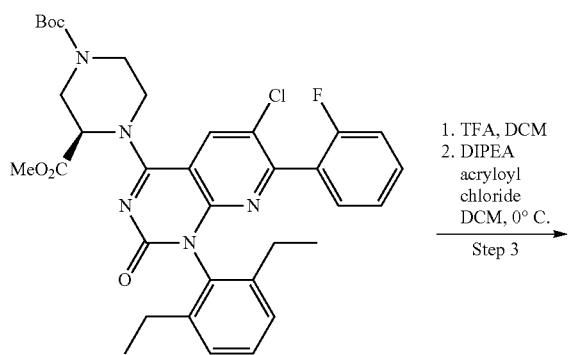

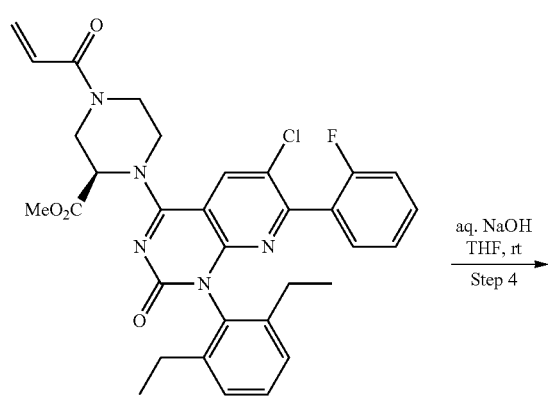

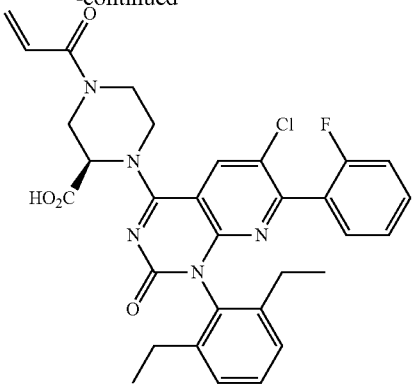

Step 1: 6-Chloro-1-(2,6-diethylphenyl)-7-(2-fluorophenyl)pyrido[2,3-d]pyrimidine-2,4(1H,3H)-dione (Intermediate 96A)

A mixture of SPhos Pd G3 (0.129 g, 0.165 mmol), (2-fluorophenyl)boronic acid (0.461 g, 3.29 mmol, Combi-Blocks, San Diego, Calif.), 6,7-dichloro-1-(2,6-diethylphenyl)pyrido[2,3-d]pyrimidine-2,4(1H,3H)-dione (Intermediate 66A, 1.20 g, 3.29 mmol) and potassium carbonate (1.37 g, 9.88 mmol) in 1,2-dimethoxyethane (8.8 mL)/water (2.2 mL) was heated at 90° C. in a microwave for 1.5 h. The reaction mixture was stirred and heated at 120° C. for 30 min. The mixture was treated with tetrakis(triphenylphosphine) palladium(0) (50 mg, 0.043 mmol) and 2-fluorophenylboronic acid (100 mg, 0.71 mmol) and stirred and heated at 120° C. for 30 min. The mixture was diluted with water (20 mL) and extracted with EtOAc (40 mL). The organic layer was washed with a satd. NaHCO$_3$ and brine, and dried over MgSO$_4$, filtered, and concentrated in vacuo. The crude product was purified by silica gel chromatography (eluent: 0-60% EtOAc/heptane) to provide 6-chloro-1-(2,6-diethylphenyl)-7-(2-fluorophenyl)pyrido[2,3-d]pyrimidine-2,4(1H,3H)-dione (Intermediate 96A, 505.1 mg, 1.19 mmol, 36.2% yield) as a light yellow solid. m/z (ESI, +ve ion): 424.1 (M+H)$^+$.

Step 2: (R)-1-tert-Butyl 3-methyl 4-(6-chloro-1-(2,6-diethylphenyl)-7-(2-fluorophenyl)-2-oxo-1,2-dihydropyrido[2,3-d]pyrimidin-4-yl)piperazine-1,3-dicarboxylate 6-Chloro-1-(2,6-diethylphenyl)-7-(2-fluorophenyl)pyrido[2,3-d]pyrimidine-2,4(1H,3H)-dione (Intermediate 96A, 560 mg, 1.32 mmol) was suspended in a mixture of acetonitrile (7 mL) and DIPEA (0.48 mL, 2.75 mmol) under nitrogen. Phosphorus oxychloride (0.48 mL, 3.14 mmol) was added followed by 2 drops of DMF. The mixture was stirred and heated at 80° C. for 30 min. The mixture was concentrated in vacuo. The residue was co-evaporated with toluene (2×50 mL). The crude product was dissolved in THF (40 mL) and treated with DIPEA (0.48 mL, 2.75 mmol) and (3R)-1,3-piperazinedicarboxylic acid, 1-(1,1-dimethylethyl)

3-methyl ester (0.37 mL, 1.52 mmol, Combi-Blocks, San Diego, Calif.) while cooling in an ice bath. The mixture was stirred and heated at 60° C. for 30 min. Water (100 mL) and EtOAc (100 mL) was added and the layers separated. The organic layer was concentrated in vacuo and purified by silica gel chromatography (eluent: 0-100% EtOAc/heptane) to provide (R)-1-tert-butyl 3-methyl 4-(6-chloro-1-(2,6-diethylphenyl)-7-(2-fluorophenyl)-2-oxo-1,2-dihydropyrido[2,3-d]pyrimidin-4-yl)piperazine-1,3-dicarboxylate (750 mg, 1.15 mmol, 87% yield) as a yellow tar. m/z (ESI, +ve ion): 650.2 (M+H)+.

Step 3: (R)-Methyl 4-acryloyl-1-(6-chloro-1-(2,6-diethylphenyl)-7-(2-fluorophenyl)-2-oxo-1,2-dihydropyrido[2,3-d]pyrimidin-4-yl)piperazine-2-carboxylate To a solution of (R)-1-tert-butyl 3-methyl 4-(6-chloro-1-(2,6-diethylphenyl)-7-(2-fluorophenyl)-2-oxo-1,2-dihydropyrido[2,3-d]pyrimidin-4-yl)piperazine-1,3-dicarboxylate (510 mg, 0.78 mmol) in DCM (5.2 mL) was added TFA (1.75 mL, 23.5 mmol) dropwise. The mixture was stirred at rt for 30 min then concentrated in vacuo to give crude product which was used directly in the following step.

To a mixture of (R)-methyl 1-(6-chloro-1-(2,6-diethylphenyl)-7-(2-fluorophenyl)-2-oxo-1,2-dihydropyrido[2,3-d]pyrimidin-4-yl)piperazine-2-carboxylate, DIPEA (0.62 mL, 3.53 mmol) in DCM (5.2 mL) was added acryloyl chloride (64 µL, 0.784 mmol) at 0° C. and stirred for 30 min. The resulting mixture was concentrated in vacuo and purified by silica gel chromatography (eluent: 0-456 EtOAc-EtOH (3:1)/heptane) to provide (R)-methyl 4-acryoyl-1-(6-chloro-1-(2,6-diethylphenyl)-7-(2-fluorophenyl)-2-oxo-1,2-dihydropyrido[2,3-d]pyrimidin-4-yl)piperazine-2-carboxylate (233 mg, 0.386 mmol, 49.2% yield) as an off-white solid. m/z (ESI, +ve ion): 604.3 (M+H)+.

Step 4: (R)-4-Acryloyl-1-(6-chloro-1-(2,6-diethylphenyl)-7-(2-fluorophenyl)-2-oxo-1,2-dihydropyrido[2,3-d]pyrimidin-4-yl)piperazine-2-carboxylic acid (R)-Methyl 4-acryloyl-1-(6-chloro-1-(2,6-diethylphenyl)-7-(2-fluorophenyl)-2-oxo-1,2-dihydropyrido[2,3-d]pyrimidin-4-yl)piperazine-2-carboxylate (97 mg, 0.161 mmol) in THF (1.6 mL) was treated with 1 N NaOH (1.6 mL, 1.6 mmol) and stirred at rt for 30 min. The mixture was neutralized with 1 N HCl (1.5 mL) to pH 5, then extracted with EtOAc. The combined organic layers were dried over Na$_2$SO$_4$, and concentrated to give (R)-4-acryloyl-1-(6-chloro-1-(2,6-diethylphenyl)-7-(2-fluorophenyl)-2-oxo-1,2-dihydropyrido[2,3-d]pyrimidin-4-yl)piperazine-2-carboxylic acid (80 mg, 0.136 mmol, 84% yield) as an off-white solid. $^1$H NMR (400 MHz, DMSO-d$_6$) δ 8.49-8.59 (m, 1H), 7.43-7.57 (m, 1H), 7.11-7.33 (m, 6H), 6.74-6.91 (m, 1H), 6.17 (br d, J=16.17 Hz, 1H), 5.74-5.82 (m, 1H), 5.18-5.36 (m, 1H), 4.16-4.79 (m, 7H), 2.11-2.27 (m, 4H), 0.89-1.01 (m, 6H). m/z (ESI, +ve ion): 590.3 (M+H)+.

Example 97

6-Chloro-4-((2S)-2-methyl-4-(2-propenoyl)-1-piperazinyl)-7-(2-oxo-1,2-dihydro-3-pyridinyl)-1-(2-(2-propanyl)phenyl)pyrido[2,3-d]pyrimidin-(1H)-one

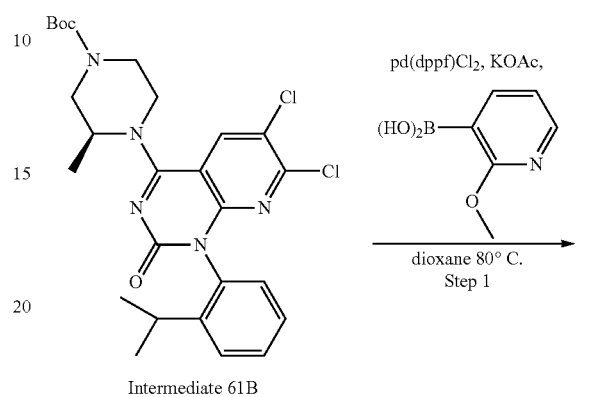

Intermediate 61B

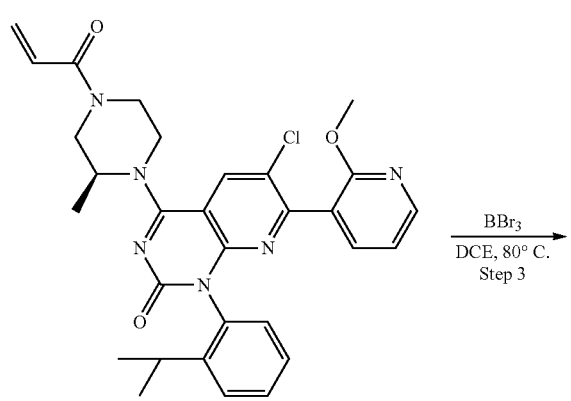

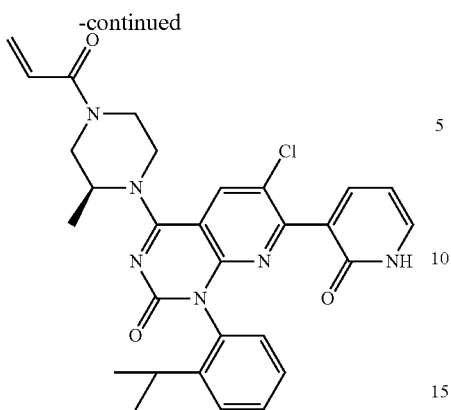

Step 1: (S)-tert-Butyl 4-(6-chloro-1-(2-isopropylphenyl)-7-(2-methoxypyridin-3-yl)-2-oxo-1,2-dihydropyrido[2,3-d]pyrimidin-4-yl)-3-methylpiperazine-1-carboxylate To a solution of (S)-tert-butyl 4-(6,7-dichloro-1-(2-isopropylphenyl)-2-oxo-1,2-dihydropyrido[2,3-d]pyrimidin-4-yl)-3-methylpiperazine-1-carboxylate (Intermediate 61B, 1.0 g, 1.88 mmol) in 1,4-dioxane (13 mL) was added 2-methoxypyridine-3-boronic acid hydrate (0.862 g, 5.63 mmol, Combi-Blocks Inc., San Diego, Calif., USA), potassium acetate (0.921 g, 9.39 mmol), and (1,1'-bis(diphenylphosphino)ferrocene)dichloropalladium-DCM (1:1) (0.153 g, 0.188 mmol). The resulting mixture was then degassed with $N_2$ for 5 min and stirred and heated at 80° C. for 1 h. The mixture was diluted with water (20 mL) and was extracted with EtOAc (2×50 mL). The combined organic extracts were dried over $MgSO_4$ and concentrated in vacuo. The crude product was purified by silica gel chromatography (eluent: 0-10% MeOH/DCM) to provide (S)-tert-butyl 4-(6-chloro-1-(2-isopropylphenyl)-7-(2-methoxypyridin-3-yl)-2-oxo-1,2-dihydropyrido[2,3-d]pyrimidin-4-yl)-3-methylpiperazine-1-carboxylate (1.12 g, 1.85 mmol, 99% yield) as a light yellow solid. m/z (ESI, +ve ion): 604.8 (M+H)$^+$.

Step 2: (S)-4-(4-Acryloyl-2-methylpiperazin-1-yl)-6-chloro-1-(2-isopropylphenyl)-7-(2-methoxypyridin-3-yl)pyrido[2,3-d]pyrimidin-2(1H)-one To a solution of(S)-tert-butyl 4-(6-chloro-1-(2-isopropylphenyl)-7-(2-methoxypyridin-3-yl)-2-oxo-1,2-dihydropyrido[2,3-d]pyrimidin-4-yl)-3-methylpiperazine-1-carboxylate (1.0 g, 1.65 mmol) in DCM (10 mL) was added TFA (2.5 mL, 33.1 mmol). The resulting mixture was then stirred at rt for 1.5 h then concentrated in vacuo to give (S)-6-chloro-1-(2-isopropylphenyl)-7-2-(methoxypyridin-3-yl)-4-(2-methylpiperazin-1-yl)pyrido[2,3-d]pyrimidin-2(1H)-one, TFA salt, which was used in the next step without purification. m/z (ESI, +ve ion): 505.0 (M+H)$^+$.

To a solution of (S)-6-chloro-1-(2-isopropylphenyl)-7-(2-methoxypyridin-3-yl)-4-(2-methylpiperazin-1-yl)pyrido[2,3-d]pyrimidin-2(1H)-one (835 mg, 1.65 mmol), TFA salt in DCM (12 mL) at 0° C. under $N_2$ was added potassium carbonate (1.14 g, 8.27 mmol), DIPEA (1.4 mL, 8.27 mmol), and a solution of acryloyl chloride (0.14 mL, 1.65 mmol) in DCM (2 mL). The resulting mixture was then stirred at 0° C. for 1 h then it was diluted with water (20 mL) and extracted with EtOAc (2×100 mL). The combined organic extracts were dried over $Na_2SO_4$, and concentrated in vacuo. The crude product was purified by silica gel chromatography (eluent: 0-10% MeOH/DCM) to provide (S)-4-(4-acryloyl-2-methylpiperazin-1-yl)-6-chloro-1-(2-isopropylphenyl)-7-(2-methoxypyridin-3-yl)pyrido[2,3-d]pyrimidin-2(1H)-one (900 mg, 1.61 mmol, 97% yield) as a yellow solid. m/z (ESI, +ve ion): 559.1 (M+H)$^+$.

Step 3: (S-4-(4-Acryloyl-2-methylpiperazin-1-yl)-6-chloro-7-(2-hydroxypyridin-3-yl)-1-(2-isopropylphenyl)pyrido[2,3-d]pyrimidin-2(1H)-one To a solution of (S)-4-(4-acryloyl-2-methylpiperazin-1-yl)-6-chloro-1-(2-isopropylphenyl)-7-(2-methoxypyridin-3-yl)pyrido[2,3-d]pyrimidin-2(1H)-one (874 mg, 1.56 mmol) in 1,2-dichloroethane (14 mL) was added boron tribromide (1 M in DCE, 7.8 mL, 7.8 mmol). The mixture was stirred and heated at 75° C. for 12 h and at 80° C. for 5 h. The mixture was carefully quenched with satd. $NaHCO_3$ (20 mL) at 0° C. The mixture was diluted with saturated ammonium chloride (20 mL) and extracted with EtOAc (2×150 mL). The combined organic extracts were then dried over $Na_2SO_4$ and concentrated in vacuo. The residue was purified by preparative HPLC (Phenomenex Gemini C18 column, 150× 30 mm, 10 u, 110 A, 10-100% 0.1% TFA in acetonitrile/water). Pure fractions were concentrated in vacuo. The residue was treated with $NaHCO_3$ (30 mL) and extracted with EtOAc (3×30 mL) and the combined organic extracts were dried over $Na_2SO_4$ and concentrated in vacuo. The crude product was purified by silica gel chromatography (eluent: 0-100% EtOAc-EtOH (3:1)/heptane) to provide (S)-4-(4-acryloyl-2-methylpiperazin-1-yl)-6-chloro-7-(2-hydroxypyridin-3-yl)-1-(2-isopropylphenyl)pyrido[2,3-d]pyrimidin-2(1H)-one (220 mg, 0.202 mmol, 25.8% yield) as a yellow solid. $^1$H NMR (400 MHz, MeOH-d$_4$) δ ppm 8.41 (br s, 1H), 7.60 (dd, J=6.5, 2.2 Hz, 1H), 7.48-7.57 (m, 3H), 7.35-7.41 (m, 1H), 7.20 (d, J=7.5 Hz, 1H), 6.86-7.02 (m, 1H), 6.48 (t, J=6.7 Hz, 1H), 6.36-6.43 (m, 1H), 5.92 (dd, J=10.7, 1.8 Hz, 1H), 5.04-5.20 (m, 1H), 4.45-4.73 (m, 2H), 4.12-4.36 (m, 1H), 3.56-3.99 (m, 2H), 3.18-3.34 (m, 1H), 2.65-2.80 (m, 1H), 1.56 (d, J=6.6 Hz, 3H), 1.27 (d, J=6.8 Hz, 3H), 1.13 (d, J=6.8 Hz, 3H). m/z (ESI, +ve ion): 544.8 (M+H)$^+$.

Example 98

2-(6-Chloro-4-((2S)-2-methyl-4-(2-propenoyl)-1-piperazinyl)-2-oxo-1-(2-(2-propanyl)phenyl)-1,2-dihydropyrido[2,3-d]pyrimidin-7-yl)-3-fluorobenzonitrile

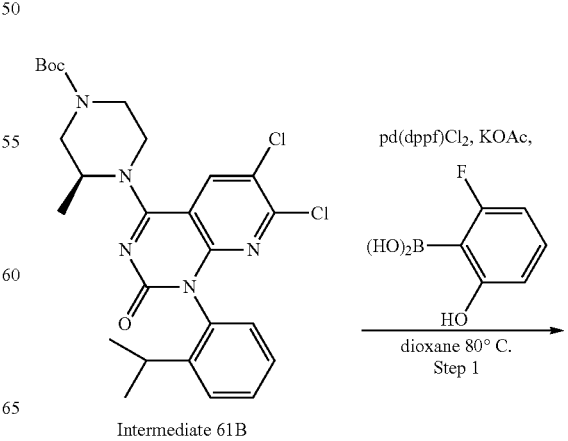

Intermediate 61B

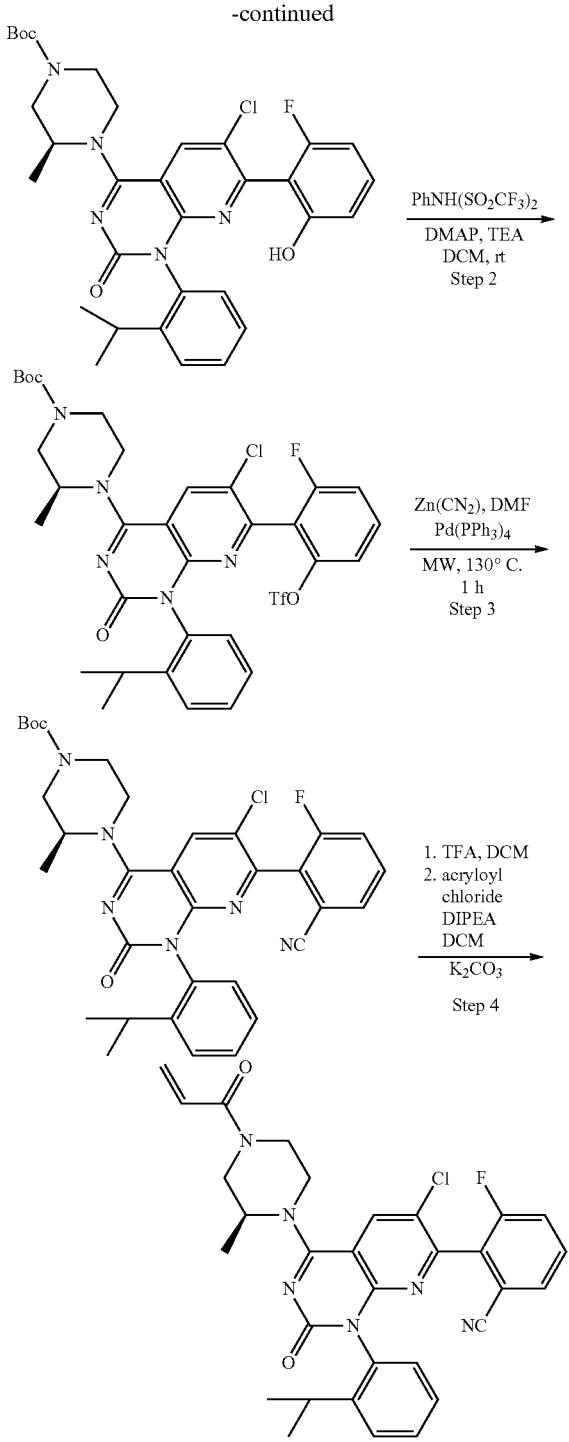

Step 1: (3S)-tert-Butyl 4-(6-chloro-7-(2-fluoro-6-hydroxyphenyl)-1-(2-isopropylphenyl)-2-oxo-1,2-dihydropyrido[2,3-d]pyrimidin-4-yl)-3-methylpiperazine-1-carboxylate To a solution of (S)-tert-butyl 4-(6,7-dichloro-1-(2-isopropylphenyl)-2-oxo-1,2-dihydropyrido[2,3-d]pyrimidin-4-yl)-3-methylpiperazine-1-carboxylate (Intermediate 61B, 1.2 g, 2.25 mmol) in 1,4-dioxane (15 mL) was added 2-fluoro-6-hydroxyphenylboronic acid (1.05 g, 6.76 mmol, Combi-Blocks, San Diego, Calif.), potassium acetate (1.11 g, 11.3 mmol), and (1,1'-bis(diphenylphosphino)ferrocene) dichloropalladium (0.165 g, 0.225 mmol). The mixture was then degassed with $N_2$ for 5 min and stirred at 80° C. for 40 min. The mixture was diluted with water (50 mL) and extracted with EtOAc (2×150 mL) and the combined organic extracts were dried over $Na_2SO_4$ and concentrated in vacuo. The crude product was purified by silica gel chromatography (eluent: 0-15% MeOH/DCM) to provide (3S)-tert-butyl 4-(6-chloro-7-(2-fluoro-6-hydroxyphenyl)-1-(2-isopropylphenyl)-2-oxo-1,2-dihydropyrido[2,3-d]pyrimidin-4-yl)-3-methylpiperazine-1-carboxylate (1.31 g, 2.154 mmol, 96% yield) as a yellow solid. $^1$H NMR (400 MHz, MeOH-$d_4$) δ ppm 8.29 (d, J=4.6 Hz, 1H), 7.28-7.38 (m, 2H), 7.19 (td, J=7.5, 1.6 Hz, 1H), 7.13 (td, J=8.3, 6.7 Hz, 1H), 7.02 (d, J=7.9 Hz, 1H), 6.56 (d, J=8.3 Hz, 1H), 6.50 (t, J=8.8 Hz, 1H), 4.83-4.95 (m, 1H), 4.24-4.34 (m, 1H), 4.05 (br d, J=13.1 Hz, 1H), 3.89-3.94 (m, 1H), 3.63-3.77 (m, 1H), 3.28-3.37 (m, 1H), 3.04-3.22 (m, 1H), 2.44-2.63 (m, 1H), 1.41-1.47 (m, 12H), 1.10 (dd, J=6.8, 1.2 Hz, 3H), 0.96 (d, J=6.8 Hz, 3H). m/z (ESI, +ve ion): 607.8 (M+H)$^+$.

Step 2: (3S)-tert-Butyl 4-(6-chloro-7-(2-fluoro-6-(((trifluoromethyl)sulfonyl)oxy)phenyl)-1-(2-isopropylphenyl)-2-oxo-1,2-dihydropyrido[2,3-d]pyrimidin-4-yl)-3-methylpiperazine-1-carboxylate To a solution of (3S)-tert-butyl 4-(6-chloro-7-(2-fluoro-6-hydroxyphenyl)-1-(2-isopropylphenyl)-2-oxo-1,2-dihydropyrido[2,3-d]pyrimidin-4-yl)-3-methylpiperazine-1-carboxylate (1.24 g, 2.04 mmol) in DCM (14 mL) was added N-phenyl bis-trifluoromethane sulfonimide (0.947 g, 2.65 mmol, Oakwood Products, Inc. Estill, S.C.), DMAP (0.1 g, 0.816 mmol), and TEA (0.57 mL, 4.08 mmol). The mixture was then stirred at rt for 5 h, concentrated in vacuo and the crude product was purified by silica gel column chromatography (eluent: 0-100% EtOAc-EtOH (3:1)/heptane) to provide (3S)-tert-butyl 4-(6-chloro-7-(2-fluoro-6-(((trifluoromethyl)sulfonyl)oxy)phenyl)-1-(2-isopropylphenyl)-2-oxo-1,2-dihydropyrido[2,3-d]pyrimidin-4-yl)-3-methylpiperazine-1-carboxylate (1.32 g, 1.78 mmol, 87% yield). m/z (ESI, +ve ion): 739.7 (M+H)$^+$.

Step 3: (3S)-tert-Butyl 4-(6-chloro-7-(2-cyano-6-fluorophenyl)-1-(2-isopropylphenyl)-2-oxo-1,2-dihydropyrido[2,3-d]pyrimidin-4-yl)-3-methylpiperazine-1-carboxylate To a solution of (3)-tert-butyl 4-(6-chloro-7-(2-fluoro-6-(((trifluoromethyl)sulfonyl)oxy)phenyl)-1-(2-isopropylphenyl)-2-oxo-1,2-dihydropyrido[2,3-d]pyrimidin-4-yl)-3-methylpiperazine-1-carboxylate (1.14 g, 1.54 mmol) in DMF (10 mL) was added zinc cyanide (0.271 g, 2.31 mmol) and tetrakis(triphenylphosphine)palladium(0) (0.712 g, 0.616 mmol). The resulting mixture was degassed with $N_2$ for 5 min and heated at 130° C. for 1 h under microwave irradiation. The mixture was diluted with water (20 mL) and extracted with EtOAc (2×50 mL). The combined organic extracts were dried over $Na_2SO_4$ and concentrated in vacuo. The crude product was purified by silica gel chromatography (eluent: 0-100% EtOAc-EtOH (3:1)/heptane) to provide (3S)-tert-butyl 4-(6-chloro-7-(2-cyano-6-fluorophenyl)-1-(2-isopropylphenyl)-2-oxo-1,2-dihydropyrido[2,3-d]pyrimidin-4-yl)-3-methylpiperazine-1-carboxylate, as a yellow solid, which was used in the next step. m/z (ESI, +ve ion): 616.8 (M+H)$^+$.

Step 4: 2-(4-((S)-4-Acryloyl-2-methylpiperazin-1-yl)-6-chloro-1-(2-isopropylphenyl)-2-oxo-1,2-dihydropyrido[2,3-d]pyrimidin-7-yl)-3-fluorobenzonitrile To a solution of (3S)-tert-butyl 4-(6-chloro-7-(2-cyano-6-fluorophenyl)-1-(2-isopropylphenyl)-2-oxo-1,2-dihydropyrido[2,3-d]pyrimidin-4-yl)-3-methylpiperazine-1-carboxylate (950 mg, 1.54 mmol) in DCM (6 mL) was added TFA (2.3 mL, 30.8 mmol). The mixture was stirred at rt for 30 min then it was concentrated in vacuo to give 2-(6-chloro-1-(2-isopropylphenyl)-4-((S)-2-methylpiperazin-1-yl)-2-oxo-1,2-dihydropyrido[2,3-d]pyrimidin-7-yl)-3-fluorobenzonitrile, TFA salt, as a light yellow oil, which was used in the next step without purification. m/z (ESI, +ve ion): 516.8 (M+H)$^+$.

To a solution of 2-(6-chloro-1-(2-isopropylphenyl)-4-((S)-2-methylpiperazin-1-yl)-2-oxo-1,2-dihydropyrido[2,3-d]pyrimidin-7-yl)-3-fluorobenzonitrile (796 mg, 1.54 mmol), TFA salt in DCM (10 mL) at 0° C. was added potassium carbonate (2.21 g, 15.4 mmol), DIPEA (1.35 mL, 7.7 mmol), and a solution of acryloyl chloride (0.13 mL, 1.54 mmol) in DCM (0.5 mL) dropwise. After addition, the mixture was stirred at 0° C. under N$_2$ for 30 min then the mixture was diluted with water (25 mL) and extracted with EtOAc. The organic layer was washed with brine, dried over MgSO$_4$, and concentrated in vacuo. The crude product was purified by silica gel chromatography (eluent: 0-100% EtOAc-EtOH (3:1)/heptane) to provide 2-(4-((S)-4-acryloyl-2-methylpiperazin-1-yl)-6-chloro-1-(2-isopropylphenyl)-2-oxo-1,2-dihydropyrido[2,3-d]pyrimidin-7-yl)-3-fluorobenzonitrile (420 mg, 0.368 mmol, 47.8% yield) as an off-white solid. $^1$H NMR (400 MHz, MeOH-d$_4$) δ ppm 8.47-8.68 (m, 1H), 7.66-7.73 (m, 2H), 7.55-7.62 (m, 1H), 7.40-7.50 (m, 2H), 7.27-7.36 (m, 1H), 7.11-7.24 (m, 1H), 6.83-6.97 (m, 1H), 6.37 (br d, J=15.5 Hz, 1H), 5.89 (dd, J=10.6, 1.9 Hz, 1H), 5.11 (br d, J=6.6 Hz, 1H), 4.44-4.66 (m, 2H), 4.11-4.31 (m, 1H), 3.61-4.00 (m, 2H), 3.39-3.58 (m, 1H), 2.60-2.87 (m, 1H), 1.51-1.60 (m, 3H), 1.23 (d, J=6.8 Hz, 3H), 0.94-1.03 (m, 3H). $^{19}$F NMR (400 MHz, MeOH-d$_4$) δ: −113.22−−113.10 (m, 1F), −113.87−−113.75 (m, 1F). m/z (ESI, +ve ion): 570.8 (M+H)$^+$.

Example 99

6-Chloro-7-(2-fluorophenyl)-4-((2S)-2-methyl-4-(2-propenoyl)-1-piperazinyl)-1-(5-(2-propanyl)-4-pyrimidinyl)pyrido[2,3-d]pyrimidin-(1H)-one

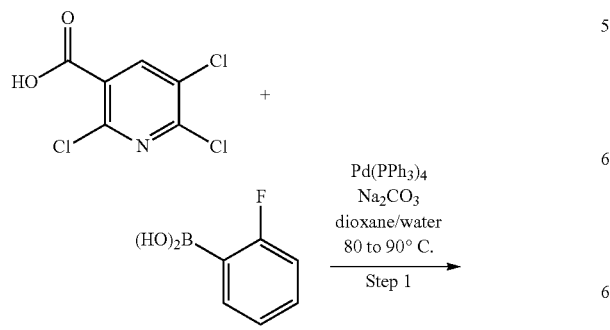

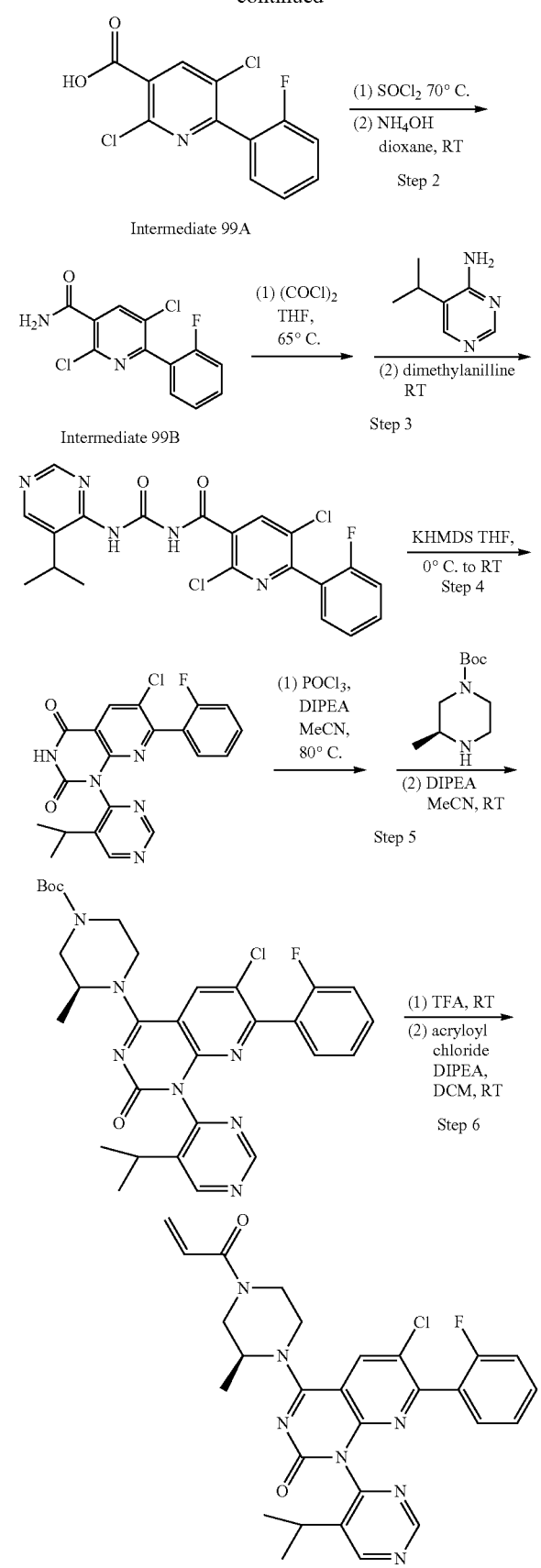

Step 1: 2,5-Dichloro-6-(2-fluorophenyl)nicotinic acid

A mixture of 2,5,6-trichloronicotinic acid (1.03 g, 4.54 mmol, Combi-Blocks, San Diego, Calif.), palladium tetrakis (0.131 g, 0.114 mmol), (2-fluorophenyl)boronic acid (0.699 g, 5.0 mmol, TCI America, Portland, Oreg.). and sodium carbonate (2M in water, 6.82 mL, 13.6 mmol) in 1,4-dioxane (11 mL) was sparged with nitrogen and heated to 80° C. for 1 h followed by 90° C. for 5 h. The reaction mixture was diluted with EtOAc (150 mL), washed with 1 N aqueous citric acid (2×100 mL); the organic layer was separated, dried over anhydrous $Na_2SO_4$. and concentrated in vacuo to give 2,5-dichloro-6-(2-fluorophenyl)nicotinic acid (Intermediate 99A, 1.27 g, 4.43 mmol, 97% yield) as an amber oil. nm/z (ESI, +ve ion): 285.8 $(M+H)^+$.

Step 2

2,5-Dichloro-6-(2-fluorophenyl)nicotinamide. A solution of 2,5-dichloro-6-(2-fluorophenyl)nicotinic acid (Intermediate 99A, 1.27 g, 4.43 mmol) in sulfurous dichloride (13 mL, 177 mmol) was stirred at 70° C. for 30 min. The reaction mixture was concentrated in vacuo to give a dark brown oil. The oil was dissolved in 1,4-dioxane (8.9 mL) and treated with ammonium hydroxide (30% aq., 3.5 mL, 89 mmol) and the mixture was stirred at rt for 5 min. The reaction mixture was diluted with EtOAc (150 mL), added to a separatory funnel, and washed with saturated, aqueous sodium bicarbonate (3×100 mL); the organic layer was separated, dried over anhydrous $Na_2SO_4$, and concentrated in vacuo. The crude product was purified by silica gel chromatography (eluent: 0-80% EtOAc/heptane) to provide crude product as an off-white solid. The solid was stirred in EtOH (8 mL) at rt for 15 min and filtered to give 2,5-dichloro-6-(2-fluorophenyl)nicotinamide (Intermediate 99B, 0.449 g, 1.58 mmol, 36%0 yield) as a white solid. m/z (ESI, +ve ion): 284.8 $(M+H)^+$.

Step 3: 2,5-Dichloro-6-(2-fluorophenyl)-N-((5-isopropylpyrimidin-4-yl)carbamoyl)nicotinamide A mixture of 2,5-dichloro-6-(2-fluorophenyl)nicotinamide (Intermediate 99B, 0.344 g, 1.21 mmol) and oxalyl chloride (2 M in DCM, 0.66 mL, 1.33 mmol) in THF (6.0 mL) was stirred and heated at 65° C. for 45 min. The reaction mixture was removed from the heating block, and 5-isopropylpyrimidin-4-amine (349 mg, 2.54 mmol; Enamine LLC, Monmouth Jct., N.J.) and N,N-dimethylaniline (0.15 mL, 1.21 mmol) were added: the slurry was stirred at rt for 1 h. The reaction mixture was diluted with EtOAc (100 mL), washed with satd. $NaHCO_3$ (2×75 mL): the organic layer was separated, dried over $Na_2SO_4$, and concentrated in vacuo. The crude product was purified by silica gel chromatography (eluent: 0-80% EtOAc/heptane) to provide 2,5-dichloro-6-(2-fluorophenyl)-N-((5-isopropylpyrimidin-4-yl)carbamoyl)nicotinamide (106 mg, 0.236 mmol, 20% yield) as a film. m/z (ESI, +ve ion): 448.0 $(M+H)^+$.

Step 4: 6-Chloro-7-(2-fluorophenyl)-1-(5-isopropylpyrimidin-4-yl)pyrido[2,3-d]pyrimidine-2,4(1H,3H)-dione KHMDS (1 M in THF, 0.47 mL, 0.47 mmol) was added to a solution of 2,5-dichloro-6-(2-fluorophenyl)-N-((5-isopropylpyrimidin-4-yl)carbamoyl)nicotinamide (0.106 g, 0.236 mmol) in THF (2.4 mL) at 0° C. and the mixture was stirred at rt for 2 h. The reaction mixture was diluted with EtOAc (100 mL), washed with satd. ammonium chloride (2×75 mL); the organic layer was separated, dried over $Na_2SO_4$, and concentrated in vacuo. The crude product was purified by silica gel chromatography (eluent: 0-40% EtOAc-EtOH (3:1)/heptane) to provide 6-chloro-7-(2-fluorophenyl)-1-(5-isopropylpyrimidin-4-yl)pyrido[2,3-d]pyrimidine-2,4(1H,3H)-dione (10 mg, 0.024 mmol, 10% yield) as an off-white solid. m/z (ESI, +ve ion): 411.8 $(M+H)^+$.

Step 5: (S)-tert-Butyl 4-(6-chloro-7-(2-fluorophenyl)-1-(5-isopropylpyrimidin-4-yl)-2-oxo-1,2-dihydropyrido[2,3-d]pyrimidin-4-yl)-3-methylpiperazine-1-carboxylate A brown solution of 6-chloro-7-(2-fluorophenyl)-1-(5-isopropylpyrimidin-4-yl)pyrido[2,3-d]pyrimidine-2,4(1H,3H)-dione (0.011 g, 0.027 mmol), phosphorus oxychloride (0.003 mL, 0.032 mmol), and DIPEA (0.014 mL, 0.08 mmol) in acetonitrile (0.3 mL) was stirred at 80° C. for 1 h. The reaction mixture was concentrated in vacuo. A solution of the resulting oil, (S)-tert-butyl 3-methylpiperazine-1-carboxylate (5.9 mg, 0.029 mmol), and DIPEA (0.014 mL, 0.08 mmol) in acetonitrile (0.27 mL) was stirred at rt for 30 min. The reaction mixture was diluted with EtOAc (50 mL), washed with satd $NaHCO_3$ (50 mL). The organic layer was dried over $Na_2SO_4$, and concentrated in vacuo. The crude product was purified by silica gel chromatography (eluent: 0-60% EtOAc-EtOH (3:1)/heptane) to provide (S)-tert-butyl 4-(6-chloro-7-(2-fluorophenyl)-1-(5-isopropylpyrimidin-4-yl)-2-oxo-1,2-dihydropyrido[2,3-d]pyrimidin-4-yl)-3-methylpiperazine-1-carboxylate (5 mg, 8 μmol, 32% yield) as a brown oil. m/z (ESI, +ve ion): 593.9 $(M+H)^+$.

Step 6: (S)-4-(4-Acryloyl-2-methylpiperazin-1-yl)-6-chloro-7-(2-fluorophenyl)-1-(5-isopropylpyrimidin-4-yl)pyrido[2,3-d]pyrimidin-2(1H)-one A solution of (S)-tert-butyl 4-(6-chloro-7-(2-fluorophenyl)-1-(5-isopropylpyrimidin-4-yl)-2-oxo-1,2-dihydropyrido[2,3-d]pyrimidin-4-yl)-3-methylpiperazine-1-carboxylate (5 mg, 8.42 μmol) in TFA (0.032 mL, 0.421 mmol) was stirred at rt for 15 min. The reaction mixture was concentrated in vacuo. A solution of the resulting oil, acryloyl chloride in DCM (0.019 mL, 9.3 μmol), and DIPEA (0.4 mL, 0.025 mmol) in DCM (0.1 mL) was stirred at rt for 30 min. The reaction mixture was diluted with EtOAc (50 mL). washed with satd $NaHCO_3$ (50 mL). The organic layer was dried over $Na_2SO_4$, and concentrated in vacuo. The crude product was purified by silica gel chromatography (eluent: 0-100% EtOAc-EtOH (3:1)/heptane) to provide (S)-4-(4-acryloyl-2-methylpiperazin-1-yl)-6-chloro-7-(2-fluorophenyl)-1-(5-isopropylpyrimidin-4-yl)pyrido[2,3-d]pyrimidin-2(1H)-one (4.9 mg, 8.9 μmol) as an off-white solid. $^1$H NMR (400 MHz, $CDCl_3$) δ ppm 9.16 (d, J=1.2 Hz, 1H) 8.94 (s, 1H) 8.13 (s, 1H) 7.46-7.53 (m, 1H) 7.20-7.28 (m, 2H) 7.17 (t, J=9.2 Hz, 1H) 6.58-6.78 (m, 1H) 6.43-6.52 (m, 1H) 5.89 (dd, J=10.5, 1.8 Hz, 1H) 4.26-5.33 (m, 3H) 3.88-4.16 (m, 1H) 3.55-3.85 (m, 2H) 3.00-3.44 (m, 1H) 2.78-2.97 (m, 1H) 1.51-1.63 (m, 3H) 1.37-1.42 (m, 3H) 1.21 (d, J=6.8 Hz, 3H). $^{19}$F NMR (377 MHz, $CDCl_3$) δ −112.43 (br d, J=25.1 Hz, 1F). m/z (ESI, +ve ion): 548.0 $(M+H)^+$.

Example 100

6-Chloro-7-(2-fluoro-6-hydroxyphenyl)-4-((2S)-2-methyl-4-(2-propenoyl)-1-piperazinyl)-1-phenylpyrido[2,3-d]pyrimidin-2(1H)-one

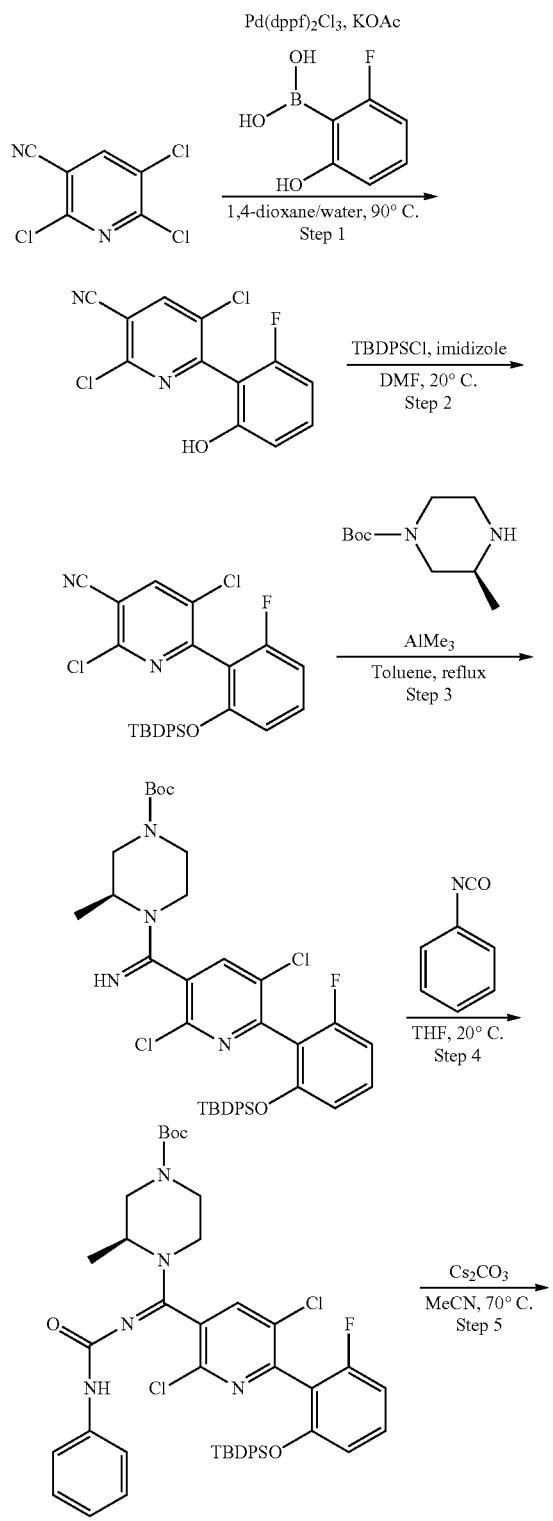

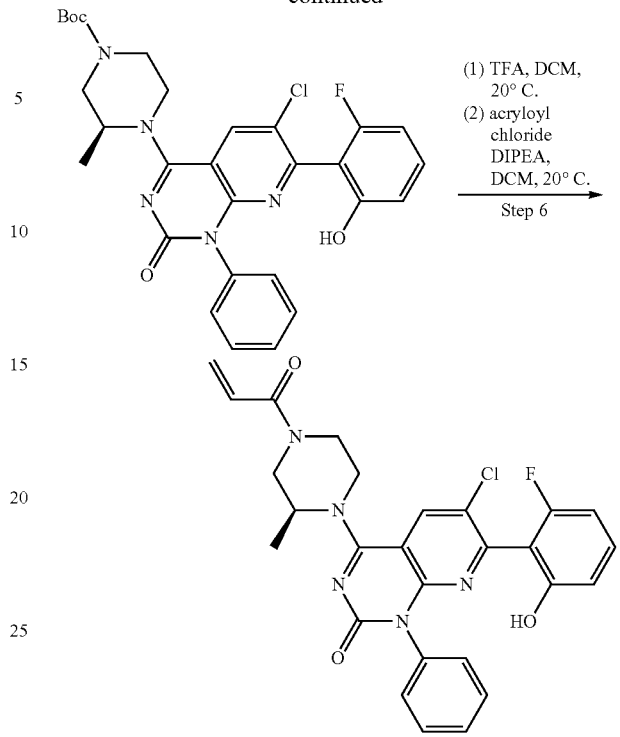

Step 1: 2,5-Dichloro-6-(2-fluoro-6-hydroxyphenyl)nicotinonitrile

A suspension of 2,5,6-trichloronicotinonitrile (500 mg, 2.41 mmol), (2-fluoro-6-hydroxyphenyl)boronic acid (413 mg, 2.65 mmol, Combi-Blocks, San Diego, Calif.), [1,1'-bis(diphenylphosphino)ferrocene]dichloropalladium(II), complex with DCM (98 mg, 0.121 mmol), potassium acetate (710 mg, 7.23 mmol) in 1,4-dioxane (5 mL)/water (0.5 mL) was sparged with argon for 2 min and stirred and heated at 90° C. for 45 min. The reaction was partitioned between EtOAc (30 mL) and 5% NaHCO$_3$ (10 mL). The organic layer was dried over MgSO$_4$, concentrated in vacuo. The crude product was purified by silica gel chromatography (eluent; 0-10% EtOAc-EtOH (3:1)/heptane) to provide 2,5-dichloro-6-(2-fluoro-6-hydroxyphenyl)nicotinonitrile. $^1$H NMR (400 MHz, CDCl$_3$) δ 8.15 (s, 1H), 7.33-7.44 (m, 1H), 7.10 (br s, 1H), 6.86 (d, J=7.67 Hz, 1H), 6.77 (t, J=17.60 Hz, 1H). $^{19}$F NMR (376 MHz, CDCl$_3$) δ −108.52 (s, 1F). m/z (ESI, +ve ion): 283.0 (M+H)$^+$.

Step 2: 6-(2-((tert-Butyldiphenylsilyl)oxy)-6-fluorophenyl)-2,5-dichloronicotinonitrile To a solution of 2,5-dichloro-6-(2-fluoro-6-hydroxyphenyl)nicotinonitrile (200 mg, 0.707 mmol) and imidazole (96 mg, 1.41 mmol) in DMF (2 mL) at 20° C. was added tert-butyldiphenylchlorosilane (0.27 mL, 1.06 mmol) then stirred for 1 h. The reaction was then partitioned between EtOAc (10 mL) and satd. NaHCO$_3$ (10 mL). The organic was washed with water, brine, dried over MgSO$_4$, concentrated in vacuo. The crude product was purified by silica gel chromatography (eluent: 0-10% EtOAc/heptane) to provide 6-(2-((tert-butyldiphenylsilyl)oxy)-6-fluorophenyl)-2,5-dichloronicotinonitrile: $^1$H NMR (400 MHz, CDCl$_3$) δ ppm 8.11 (s, 1H), 7.33-7.68 (m, 12H), 6.95-7.07 (m, 1H), 6.66-6.78 (m, 1H), 6.28-6.36 (m, 1H), 0.80 (s, 9H).

Step 3: tert-Butyl (3S)-4-((6-(2-((tert-butyldiphenyl-silyl)oxy)-6-fluorophenyl)-2,5-dichloropyridin-3-yl)(imino)methyl)-3-methylpiperazine-1-carboxylate To a stirring suspension of 6-(2-((tert-butyldiphenylsilyl)oxy)-6-fluorophenyl)-2,5-dichloronicotinonitrile (200 mg, 0.384 mmol) and (S)-4-N-Boc-2-methylpiperazine (169 mg, 0.844 mmol) in toluene (2 mL) at 20° C. under argon was added trimethylaluminum (2 M in toluene, 0.42 mL, 0.84 mmol) dropwise over a 2 min period. After 5 min, the reaction was heated to 115° C. for 90 min. After cooling to 20° C., the reaction was added dropwise to a slurry of silica gel (2 g) in EtOAc (10 mL). The mixture was concentrated in vacuo and the crude product was purified by silica gel chromatography (eluent: isocratic 100% EtOAc) to provide tert-butyl (3S)-4-((6-(2-((tert-butyldiphenylsilyl)oxy)-6-fluorophenyl)-2,5-dichloropyridin-3-yl)(imino)methyl)-3-methylpiperazine-1-carboxylate. $^1$H NMR (400 MHz, CDCl$_3$ δ 7.74-7.87 (m, 1H), 7.65-7.72 (m, 4H), 7.42-7.50 (m, 2H), 7.34-7.41 (m, 4H), 6.92-7.02 (m, 1H), 6.68-6.78 (m, 1H), 6.22-6.32 (m, 1H), 3.77-4.28 (m, 3H), 3.07-3.41 (m, 2H), 2.80-3.06 (m, 1H), 1.51-1.70 (m, 3H), 1.41-1.49 (m, 9H), 1.22-1.36 (m, 3H), 0.71-0.81 (m, 9H). m/z (ESI, +ve ion): 721.1 (M+H)$^+$.

Step 4: (3S)-tert-Butyl 4-((6-(2-((tert-butyldiphenyl-silyl)oxy)-6-fluorophenyl)-2,5-dichloropyridin-3-yl)((phenylcarbamoyl)imino)methyl)-3-methylpiperazine-1-carboxylate To a stirring solution of (3S)-tert-butyl 4-((6-(2-((tert-butyldiphenylsilyl)oxy)-6-fluorophenyl)-2,5-dichloropyridin-3-yl)(imino)methyl)-3-methylpiperazine-1-carboxylate (300 mg, 0.416 mmol) in THF (3 mL) at 20° C. was added a solution of phenyl isocyanate (45.4 µL, 0.416 mmol) in THF (0.5 mL) over a period of 1 min. The reaction was concentrated in vacuo to give (3S)-tert-butyl 4-((6-(2-((tert-butyldiphenylsilyl)oxy)-6-fluorophenyl)-2,5-dichloropyridin-3-yl)((phenylcarbamoyl)imino)methyl)-3-methylpiperazine-1-carboxylate: m/z (ESI, +ve ion): 840.2 (M+H)$^+$.

Step 5: (3S)-tert-Butyl 4-(6-chloro-7-(2-fluoro-6-hydroxyphenyl)-2-oxo-1-phenyl-1,2-dihydropyrido[2,3-d]pyrimidin-4-yl)-3-methylpiperazine-1-carboxylate A suspension of (3S)-tert-butyl 4-((6-(2-((tert-butyldiphenylsilyl)oxy)-6-fluorophenyl)-2,5-dichloropyridin-3-yl)((phenylcarbamoyl)imino)methyl)-3-methylpiperazine-1-carboxylate (250 mg, 0.297 mmol) and cesium carbonate (484 mg, 1.49 mmol) was heated to 70° C. for 3 h. The reaction was then partitioned between EtOAc (20 mL) and 5% NaHCO$_3$ (10 mL). The organic was washed with brine, dried over MgSO$_4$, concentrated in vacuo, azeotroped with heptane (3×10 mL). The crude product was purified by silica gel chromatography (eluent: 0-40% EtOAc-EtOH (3:1)/heptane) to provide (3S)-tert-butyl 4-(6-chloro-7-(2-fluoro-6-hydroxyphenyl)-2-oxo-1-phenyl-1,2-dihydropyrido[2,3-d]pyrimidin-4-yl)-3-methylpiperazine-1-carboxylate. $^1$H NMR (400 MHz, CDCl$_3$) δ 8.67 (s, 1H), 8.08 (s, 1H), 7.56-7.64 (m, 2H), 7.48-7.55 (m, 1H), 7.27-7.33 (m, 3H), 6.63-6.77 (m, 2H), 4.80-5.01 (m, 1H), 4.16-4.53 (m, 2H), 3.91-4.14 (m, 1H), 3.54-3.75 (m, 1H), 3.02-3.37 (m, 2H), 1.50-1.59 (m, 9H). $^{19}$F NMR (376 MHz, CDCl$_3$) δ -104.98 (s, 1F), -112.06 (s, 1F). m/z (ESI, +ve ion): 566.2 (M+H)$^+$.

Step 6: 4-((S)-4-Acryloyl-2-methylpiperazin-1-yl)-6-chloro-7-(2-fluoro-6-hydroxyphenyl)-1-phenylpyrido[2,3-d]pyrimidin-2(1H)-one A solution of (3S)-tert-butyl 4-(6-chloro-7-(2-fluoro-6-hydroxyphenyl)-2-oxo-1-phenyl-1,2-dihydropyrido[2,3-d]pyrimidin-4-yl)-3-methylpiperazine-1-carboxylate (44 mg, 0.078 mmol) in DCM was treated with TFA (1 mL) and stirred for 15 min at 20° C. The reaction was then concentrated under reduced pressure, and the residue dissolved in DCM (1 mL) with DIPEA (67.9 µl, 0.389 mmol). To this was added a diluted solution of acryloyl chloride (6.3 µl, 0.078 mmol) in 0.06 mL DCM. The reaction was directly purified by silica gel chromatography (eluent: 0-50% EtOAc-EtOH (3:1)/heptane) to provide 4-((S)-4-acryloyl-2-methylpiperazin-1-yl)-6-chloro-7-(2-fluoro-6-hydroxyphenyl)-1-phenylpyrido[2,3-d]pyrimidin-2(1H)-one. $^1$H NMR (400 MHz, DMSO-d$_6$) δ 10.07 (br s, 1H), 8.35-8.38 (m, 1H), 8.31-8.40 (m, 1H), 7.43 (t, J=15.10 Hz, 2H), 7.34 (dd, J=7.05, 14.72 Hz, 1H), 7.20-7.29 (m, 3H), 6.79-6.93 (m, 1H), 6.72 (d, J=8.29 Hz, 1H), 6.67 (t, J=17.60 Hz, 1H), 6.15-6.27 (m, 1H), 5.77 (dd, J=2.28, 10.16 Hz, 1H), 4.81-4.95 (m, 1H), 4.27-4.45 (m, 1H), 3.97-4.27 (m, 2H), 3.57-3.80 (m, 2H), 3.34-3.53 (m, 1H), 1.34 (d, J=6.84 Hz, 3H). $^{19}$F NMR (376 MHz, DMSO-d$_6$) δ -113.43 (s, 1F), -113.44 (s, 1F), -114.38 (s, 1F), -115.34 (s, 1F), -115.35 (s, 1F). m/z (ESI, +ve ion): 520.1 (M+H)$^+$.

Example 101

6-Chloro-7-(2-fluorophenyl)-4-((2S)-2-methyl-4-(2-propenoyl)-1-piperazinyl)-1-(2-(2-methylpropyl)-3-pyridinyl)pyrido[2,3-d]pyrimidin-2(1H)-one

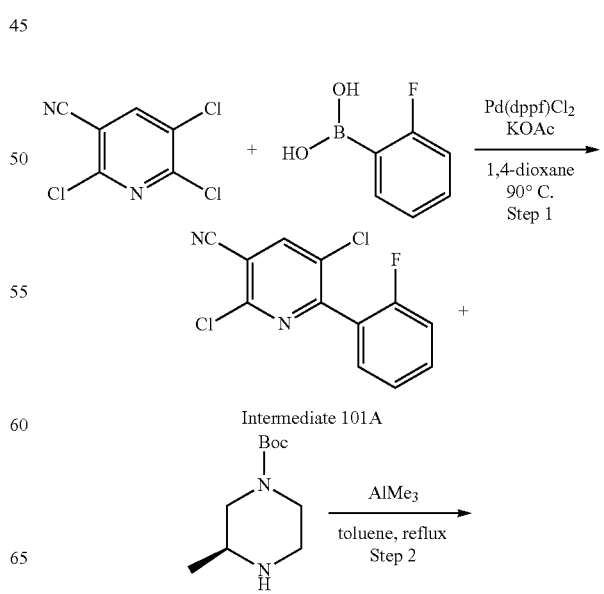

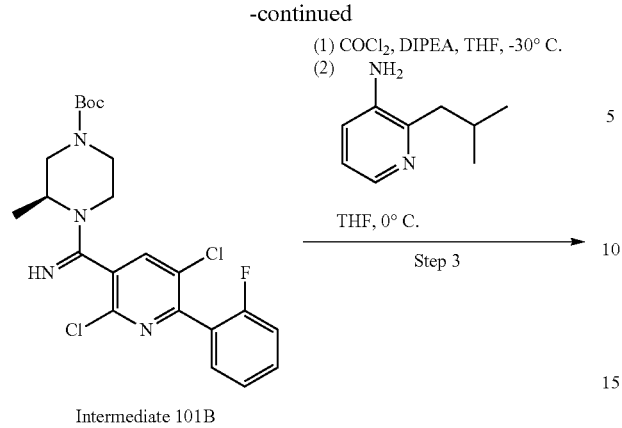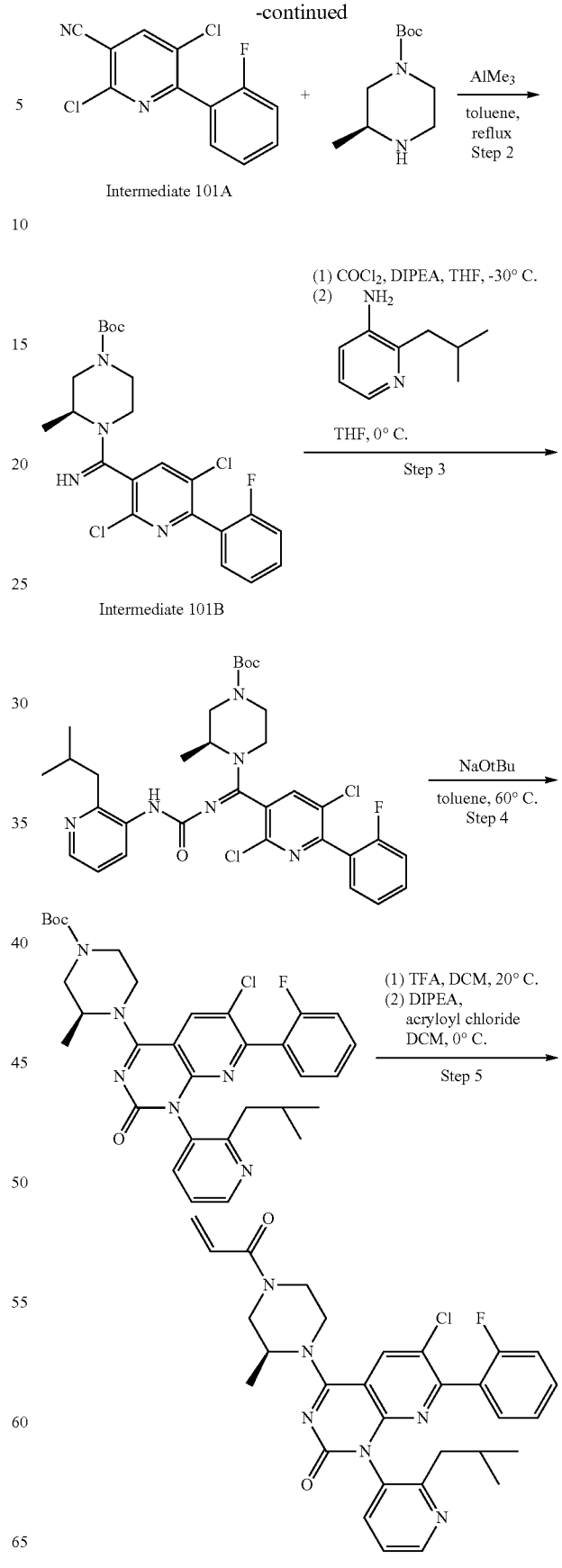

Step 1: 2,5-Dichloro-6-(2-fluorophenyl)nicotinonitrile (Intermediate 101A)

A suspension of 2,5,6-trichloronicotinonitrile (4.5 g, 21.7 mmol), 2-fluorophenylboronic acid (3.34 g, 23.9 mmol), [1,1'-bis(diphenylphosphino)ferrocene]-dichloropalladium (II), complex with DCM (0.177 g, 0.217 mmol), potassium acetate (6.39 g, 65.1 mmol) in 1,4-dioxane (50 mL) was sparged with argon for 5 min then heated at 90° C. for 50 min. The reaction was partitioned between EtOAc (150 mL) and 5% NaHCO$_3$ (50 mL). The organic was washed with brine (20 mL), dried over MgSO$_4$, and concentrated in vacuo. The crude product was purified by silica gel chromatography (eluent: 0-10% MTBE/heptane) to provide 2,5-dichloro-6-(2-fluorophenyl)nicotinonitrile (Intermediate 101A). $^1$H NMR (400 MHz, CDCl$_3$) δ 8.09 (s, 1H), 7.44-7.56 (m, 2H), 7.27-7.33 (m, 1H), 7.19 (dd, J=9.33, 19.70 Hz, 1H). $^{19}$F NMR (376 MHz, CDCl$_3$) δ −111.88 (s, 1F). m/z (ESI, +ve ion): 267.0 (M+H)$^+$.

Step 2: (S)-tert-Butyl 4-((2,5-dichloro-6-(2-fluorophenyl)pyridin-3-yl)(imino)methyl)-3-methylpiperazine-1-carboxylate (Intermediate 101B)

To a stirring solution of 2,5-dichloro-6-(2-fluorophenyl)nicotinonitrile (Intermediate 101A, 1.0 g, 3.74 mmol) and (S)-4-Boc-2-methylpiperazine (1.65 g, 8.24 mmol) in toluene (10 mL) at 20° C. under argon was added trimethylaluminum (2 M in toluene, 4.12 mL, 8.24 mmol) at a rate that did not exceed an internal temp of 30° C. After 15 min, the reaction was heated to reflux for 2 h. The reaction was cooled to 25° C. then added dropwise to a suspension of silica gel (10 g) in EtOAc (40 mL). The mixture was concentrated in vacuo and purified by silica gel chromatography (eluent: 0-100%6 EtOAc/heptane) to provide (S)-tert-butyl 4-((2,5-dichloro-6-(2-fluorophenyl)pyridin-3-yl)(imino)methyl)-3-methylpiperazine-1-carboxylate (Intermediate 101B). $^1$H NMR (400 MHz, CDCl$_3$) δ 7.72 (s, 1H), 7.45-7.52 (m, 2H), 7.27-7.31 (m, 1H), 7.14-7.22 (m, 1H), 3.80-4.25 (m, 3H), 2.75-3.50 (m, 4H), 1.48 (s, 9H), 1.27 (d, J=7.05 Hz, 3H). $^{19}$F NMR (376 MHz, CDCl$_3$) δ −112.76 (s, 1F). m/z (ESI, +ve ion): 467.1 (M+H)$^+$.

Step 3: tert-Butyl (S)-4-((2,5-dichloro-6-(2-fluorophenyl)pyridin-3-yl)(((2-isobutylpyridin-3-yl)carbamoyl)imino)methyl)-3-methylpiperazine-1-carboxylate To a stirring diluted solution of phosgene solution (15% in toluene, 1.6 mL, 2.25 mmol) in THF (0.3 mL) at −30° C. was added a solution of tert-butyl (S)-4-((2,5-dichloro-6-(2-fluorophenyl)pyridin-3-yl)imino)methyl)-3-methylpiperazine-1-carboxylate (Intermediate 101B, 420 mg, 0.899 mmol) and DIPEA (0.47 mL, 2.7 mmol) in THF (8 mL). The cooling bath was removed and reaction warmed to 5° C. A solution of 2-isobutylpyridin-3-amine (236 mg, 1.57 mmol, CombiPhos, Trenton, N.J.) in THF (2.3 mL) was then added. The reaction was stirred for 10 min then partitioned between EtOAc (20 mL) and satd. NaHCO$_3$ (10 mL). The organic was then washed with brine (2 mL), dried over MgSO$_4$, and concentrated in vacuo. The crude product was purified by silica gel chromatography (eluent: 0-60% EtOAc-EtOH (3:1)/heptane) to provide tert-butyl (S)-4-((2,5-dichloro-6-(2-fluorophenyl)pyridin-3-yl)(((2-isobutylpyridin-3-yl)carbamoyl)imino)methyl)-3-methylpiperazine-1-carboxylate: m/z (ESI, +ve ion): 643.2 (M+H)$^+$.

Step 4: tert-Butyl (S)-4-(6-chloro-7-(2-fluorophenyl)-1-(2-isobutylpyridin-3-yl)-2-oxo-1,2-dihydropyrido[2,3-d]pyrimidin-4-yl)-3-methylpiperazine-1-carboxylate A suspension of (S)-tert-butyl 4-((((2-(tert-butyl)pyridin-3-yl)carbamoyl)imino)(2,5-dichloro-6-(2-fluorophenyl)pyridin-3-yl)methyl)-3-methylpiperazine-1-carboxylate (320 mg, 0.497 mmol) and sodium tert-butoxide (96 mg, 0.994 mmol) in toluene (3 mL) was heated to 60° C. for 30 min. The reaction was then partitioned between EtOAc (10 mL) and satd. NaHCO$_3$ (1 mL). The organic was dried over MgSO$_4$, filtered, and concentrated in vacuo to give tert-butyl (S)-4-(6-chloro-7-(2-fluorophenyl)-1-(2-isobutylpyridin-3-yl)-2-oxo-1,2-dihydropyrido[2,3-d]pyrimidin-4-yl)-3-methylpiperazine-1-carboxylate.

Step 5: 6-Chloro-7-(2-fluorophenyl)-4-((2S)-2-methyl-4-(2-propenoyl)-1-piperazinyl)-1-(2-(2-methylpropyl)-3-pyridinyl)pyrido[2,3-d]pyrimidin-2(1H)-one tert-Butyl (S)-4-(6-chloro-7-(2-fluorophenyl)-1-(2-isobutylpyridin-3-yl)-2-oxo-1,2-dihydropyrido[2,3-d]pyrimidin-4-yl)-3-methylpiperazine-1-carboxylate was stirred in DCM (2 mL) and TFA (2 mL) at 20° C. for 10 min. The mixture was concentrated in vacuo and the residue was dissolved in DCM (5 mL), brought to 0° C. and DIPEA (434 μl, 2.49 mmol) was added followed by acryloyl chloride (40.5 μl, 0.497 mmol). After 5 min then reaction was diluted with DCM (5 mL) and washed with satd. NaHCO$_3$ (5 mL). The organic was washed with brine (2 mL), dried over MgSO$_4$, and concentrated in vacuo. The crude product was purified by silica gel chromatography (eluent: 0-75% EtOAc-EtOH (3:1)/heptane) to provide 6-chloro-7-(2-fluorophenyl)-4-((2S)-2-methyl-4-(2-propenoyl)-1-piperazinyl)-1-(2-(2-methylpropyl)-3-pyridinyl)pyrido[2,3-d]pyrimidin-2(1H)-one. $^1$H NMR (400 MHz, CDCl$_3$) δ ppm 8.60 (dd, J=1.45, 4.77 Hz, 1H), 8.07 (d, J=4.15 Hz, 1H), 7.51 (d, J=8.09 Hz, 1H), 7.37-7.45 (m, 1H), 7.23-7.28 (m, 1H), 7.13-7.22 (m, 2H), 7.06-7.13 (m, 1H), 6.52-6.72 (m, 1H), 6.41 (dd, J=1.87, 17.00 Hz, 1H), 5.81 (dd, J=1.45, 10.37 Hz, 1H), 4.25-5.16 (m, 3H), 3.51-4.08 (m, 3H), 2.95-3.35 (m, 1H), 2.36-2.47 (m, 2H), 2.08-2.24 (m, 1H), 1.39-1.61 (m, 3H), 0.82 (dd, J=2.07, 6.63 Hz, 3H), 0.77 (d, J=6.63 Hz, 3H). $^{19}$F NMR (376 MHz, CDCl$_3$) δ ppm −112.21 (s, 1F). m/z (ESI, +ve ion): 561.2 (M+H)$^+$.

Example 102

7-(2-Fluorophenyl)-6-methyl-1-(2-methyl-6-(2-propanyl)phenyl)-4-((2S)-2-methyl-4-(2-propenoyl)-1-piperazinyl)pyrido[2,3-d]pyrimidin-2(1H)-one

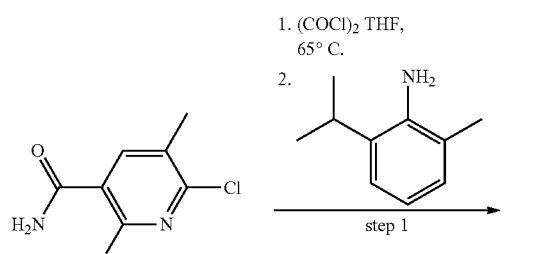

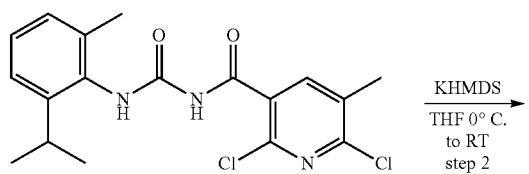

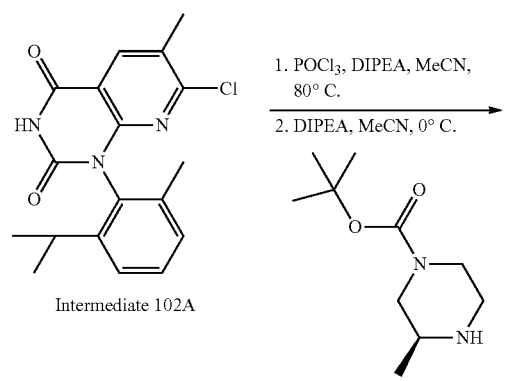

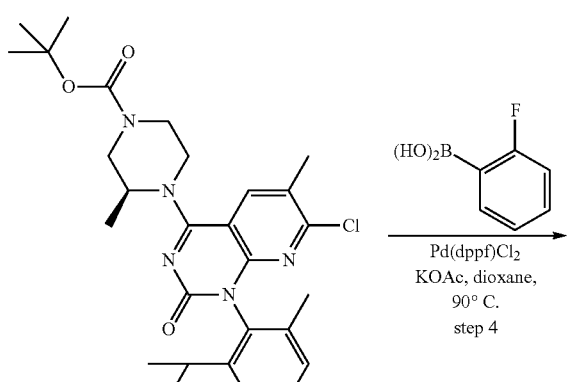

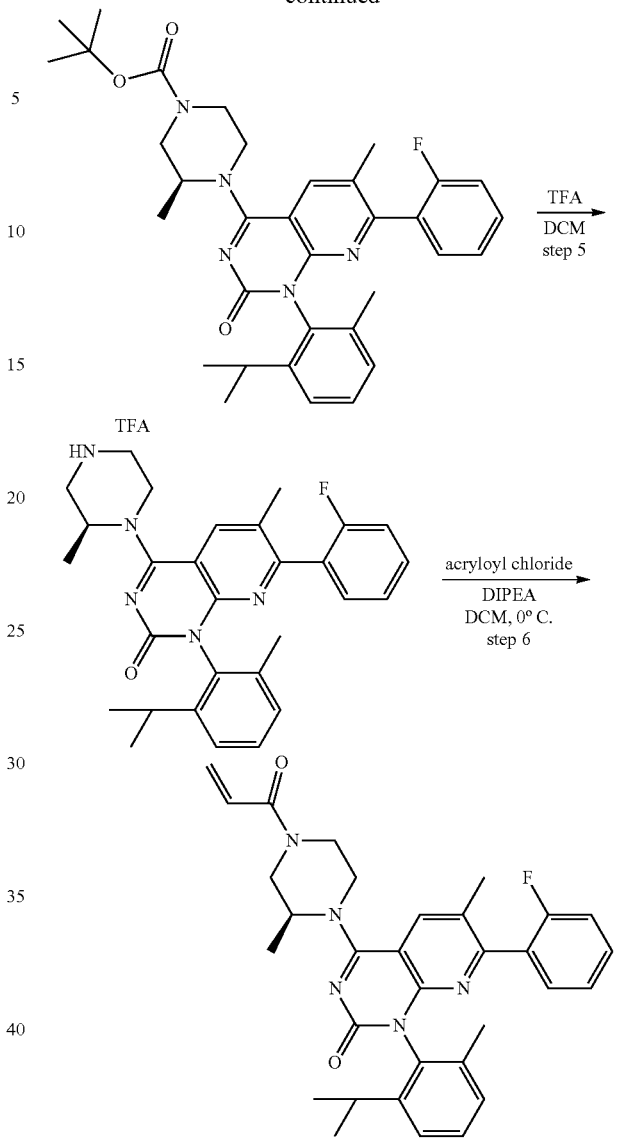

Step 1: 2,6-Dichloro-N-((2-isopropyl-6-methylphenyl)carbamoyl)-5-methylnicotinamide Oxalyl chloride (2 M in DCM, 4.37 mL, 8.74 mmol) was added to a solution of 2,6-dichloro-5-methylnicotinamide (Example 52, Step 2, 1.63 g, 7.95 mmol) in THF (30 mL), the reaction mixture was heated to 65° C. After 40 min, the reaction mixture was cooled to 0° C. and 2-isopropyl-6-methylaniline (1.25 g, 8.35 mmol, Advanced ChemBlocks, Inc., Burlingame, Calif.) was added. Stirring was continued for 1 h at rt, followed by concentrating the reaction mixture in vacuo. The residue was partitioned between EtOAc (50 mL) and satd. ammonium chloride (10 mL). The organic layer was washed with water, dried over $Na_2SO_4$, filtered, and concentrated in vacuo. The residue was triturated with a mixture of heptane-EtOAc (5:1). The precipitate was filtered, and dried to give 2,6-dichloro-N-((2-isopropyl-6-methylphenyl)carbamoyl)-5-methylnicotinamide: m/z (ESI, +ve ion): 379.9 and 381.9 (M+H)$^+$.

Step 2: 7-Chloro-1-(2-isopropyl-6-methylphenyl)-6-methylpyrido[2,3-d]pyrimidine-2,4(1H,3H)-dione (Intermediate 102A)

KHMDS (1 M in THF, 12.5 mL, 12.5 mmol) was added to a solution of 2,6-dichloro-N-((2-isopropyl-6-methylphenyl)carbamoyl)-5-methylnicotinamide (2.38 g, 6.26 mmol) in THF (25 mL) at 0° C. After completed addition, the reaction mixture was allowed to warm to rt over 16 h. The reaction mixture was then partitioned between EtOAc (20 mL) and satd. ammonium chloride (20 mL). The organic layer was separated, dried over Na$_2$SO$_4$, filtered, and concentrated in vacuo. The residue was triturated with a mixture of heptane-EtOAc (5:1). The precipitate was filtered off, and dried to give 7-chloro-1-(2-isopropyl-6-methylphenyl)-6-methylpyrido[2,3-d]pyrimidine-2,4(1H,3H)-dione (Intermediate 102A) as an off-white solid: $^1$H NMR (400) MHz, DMSO-d$_6$) δ 12.03 (s, 1H), 8.41 (s, 1H), 7.27-7.45 (m, 2H), 7.21 (br d, J=6.6 Hz, 1H), 2.63 (dt, J=13.7, 7.0H z, 1H), 2.36 (s, 3H), 1.96 (s, 3H), 1.08 (br d, J=6.8 Hz, 3H), 0.99 (br d, J=6.6 Hz, 3H). m/z (ESI, +ve) 343.9 and 346.0 (M+H)$^+$.

Step 3: tert-Butyl (S-4-(7-chloro-1-(2-isopropyl-6-methylphenyl)-6-methyl-2-oxo-1,2-dihydropyrido[2,3-d]pyrimidin-4-yl)-3-methylpiperazine-1-carboxylate (Intermediate 102B)

Phosphorus oxychloride (0.7 mL, 7.49 mmol) was added to a solution of 7-chloro-1-(2-isopropyl-6-methylphenyl)-6-methylpyrido[2,3-d]pyrimidine-2,4(1H,3H)-dione (Intermediate 102A, 1.98 g, 5.76 mmol) and iPr$_2$NEt (1.51 mL, 8.64 mmol) in acetonitrile (20 mL). The resulting solution was heated to 80° C. After 2 h, the reaction mixture was cooled to 0° C. and iPr$_2$NEt (5.0 mL, 28 mmol) was added, followed by tert-butyl (S)-3-methylpiperazine-1-carboxylate (2.42 g, 12.1 mmol, Combi-Blocks, San Diego, Calif.). The reaction mixture was stirred at 0° C. for 0.5 h and allowed to warm to rt over 2 h. EtOAc (10 mL) was added to the reaction mixture. The organic phase was separated, washed with water (2×10 mL), dried over Na$_2$SO$_4$, and concentrated in vacuo. The crude product was purified by silica gel chromatography (eluent: 0-30% EtOAc:EtOH (3:1) in heptane) to give tert-butyl (S)-4-(7-chloro-1-(2-isopropyl-6-methylphenyl)-6-methyl-2-oxo-1,2-dihydropyrido[2,3-d]pyrimidin-4-yl)-3-methylpiperazine-1-carboxylate (Intermediate 102B) as an off-white solid: m/z (ESI, +ve) 526.0 (M+H)$^+$.

Step 4: tert-Butyl (S)-4-(7-(2-fluorophenyl)-1-(2-isopropyl-6-methylphenyl)-6-methyl-2-oxo-1,2-dihydropyrido[2,3-d]pyrimidin-4-yl)-3-methylpiperazine-1-carboxylate A mixture of tert-butyl (S)-4-(7-chloro-1-(2-isopropyl-6-methylphenyl)-6-methyl-2-oxo-1,2-dihydropyrido[2,3-d]pyrimidin-4-yl)-3-methylpiperazine-1-carboxylate (Intermediate 102B, 557 mg, 1.06 mmol), (2-fluorophenyl)boronic acid (267 mg, 1.91 mmol, Combi-Blocks, San Diego, Calif.), potassium acetate (520 mg, 5.29 mmol), and Pd(dppf)Cl$_2$ (77 mg, 0.11 mmol) in 1,4-dioxane (7 mL) and water (0.05 mL) was heated to 90° C. for 30 min. The reaction mixture was quenched with satd NaHCO$_3$ (15 mL) and extracted with EtOAc (20 mL). The organic layer was separated, washed with brine (10 mL), dried over Na$_2$SO$_4$, and concentrated in vacuo. The crude product was purified by silica gel chromatography (eluent: 0-40% EtOAc-EtOH (3:1)/heptane) to provide tert-butyl (S)-4-(7-(2-fluorophenyl)-1-(2-isopropyl-6-methylphenyl)-6-methyl-2-oxo-1,2-dihydropyrido[2,3-d]pyrimidin-4-yl)-3-methylpiperazine-1-carboxylate as an off-white solid: m/z (ESI, +ve ion): 586.1 (M+H)$^+$.

Step 5: (S)-7-(2-Fluorophenyl)-1-(2-isopropyl-6-methylphenyl)-6-methyl-4-(2-methylpiperazin-1-yl)pyrido[2,3-d]pyrimidin-2(1H)-one trifluoroacetate TFA (3 mL, 26.4 mmol) was added to a solution of tert-butyl (S)-4-(7-(2-fluorophenyl)-1-(2-isopropyl-6-methylphenyl)-6-methyl-2-oxo-1,2-dihydropyrido[2,3-d]pyrimidin-4-yl)-3-methylpiperazine-1-carboxylate (515 mg, 0.88 mmol) in DCM (6 mL). The reaction mixture was stirred at rt. After 30 min, the mixture was concentrated in vacuo to provide (S)-7-(2-fluorophenyl)-1-(2-isopropyl-6-methylphenyl)-6-methyl-4-(2-methylpiperazin-1-yl)pyrido[2,3-d]pyrimidin-2(1H)-one trifluoroacetate. m/z (ESI, +ve ion): 486.0 (M+H)$^+$.

Step 6: 7-(2-Fluorophenyl)-6-methyl-1-(2-methyl-6-(2-propanyl)phenyl)-4-((2S)-2-methyl-4-(2-propenoyl)-1-piperazinyl)pyrido[2,3-d]pyrimidin-2(1H)-one A solution of acryloyl chloride (0.075 mL, 0.92 mmol) in DCM (1 mL) was added to a reaction mixture of (S)-7-(2-fluorophenyl)-1-(2-isopropyl-6-methylphenyl)-6-methyl-4-(2-methylpiperazin-1-yl)pyrido[2,3-d]pyrimidin-2(1H)-one trifluoroacetate (527 mg, 0.88 mmol) and DIPEA (0.61 mL, 3.52 mmol) in DCM (6 mL) at 0° C. The reaction mixture was warmed to rt, stirred for 30 min and then quenched with satd NaHCO$_3$ (5 mL). The mixture was extracted with EtOAc (10 mL). The organic layer was separated, washed with brine (5 mL), dried over Na$_2$SO$_4$, filtered, and concentrated in vacuo. The crude product was purified by silica gel chromatography (eluent: 0-50% EtOAc-EtOH (3:1)/heptane) to provide 7-(2-fluorophenyl)-6-methyl-1-(2-methyl-6-(2-propanyl)phenyl)-4-((2S)-2-methyl-4-(2-propenoyl)-1-piperazinyl)pyrido[2,3-d]pyrimidin-2(1H)-one as an off-white solid. $^1$H NMR (400 MHz, DMSO-d$_6$) δ ppm 8.22 (s, 1H), 7.41-7.53 (m, 1H), 7.19-7.31 (m, 4H), 7.16 (td, J=7.5, 1.7 Hz, 1H), 7.11 (dd, J=6.1, 2.6 Hz, 1H), 6.81-6.95 (m, 1H), 6.21 (dd, J=16.1, 7.1, 1H), 5.78 (dd, J=10.2, 2.3 Hz, 1H), 4.87-4.93 (m, 1H), 3.94-4.55 (m, 3H), 3.57-3.70 (m, 2H), 2.49-2.53 (m, 1H), 2.19 (s, 3H), 1.87 (s, 3H), 1.33 (d, J=6.6 Hz, 3H), 1.25 (br s, 1H), 1.06 (d, J=6.8 Hz, 3H), 0.93 (dd, J=6.6, 3.7 Hz, 3H). m/z (ESI, +ve ion): 540.0 (M+H)$^+$.

Example 103

6-Chloro-1-(2,6-diethylphenyl)-7-(2-fluorophenyl)-4-((2S)-2-methyl-4-(2-propenoyl)-1-piperazinyl)-2(1H)-quinazolinone

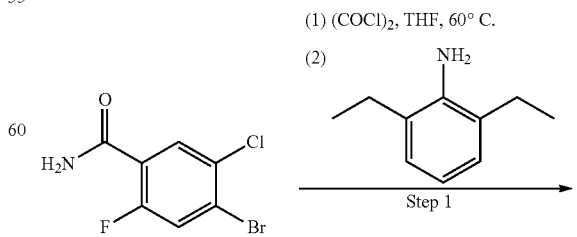

Example 8,
Step 1

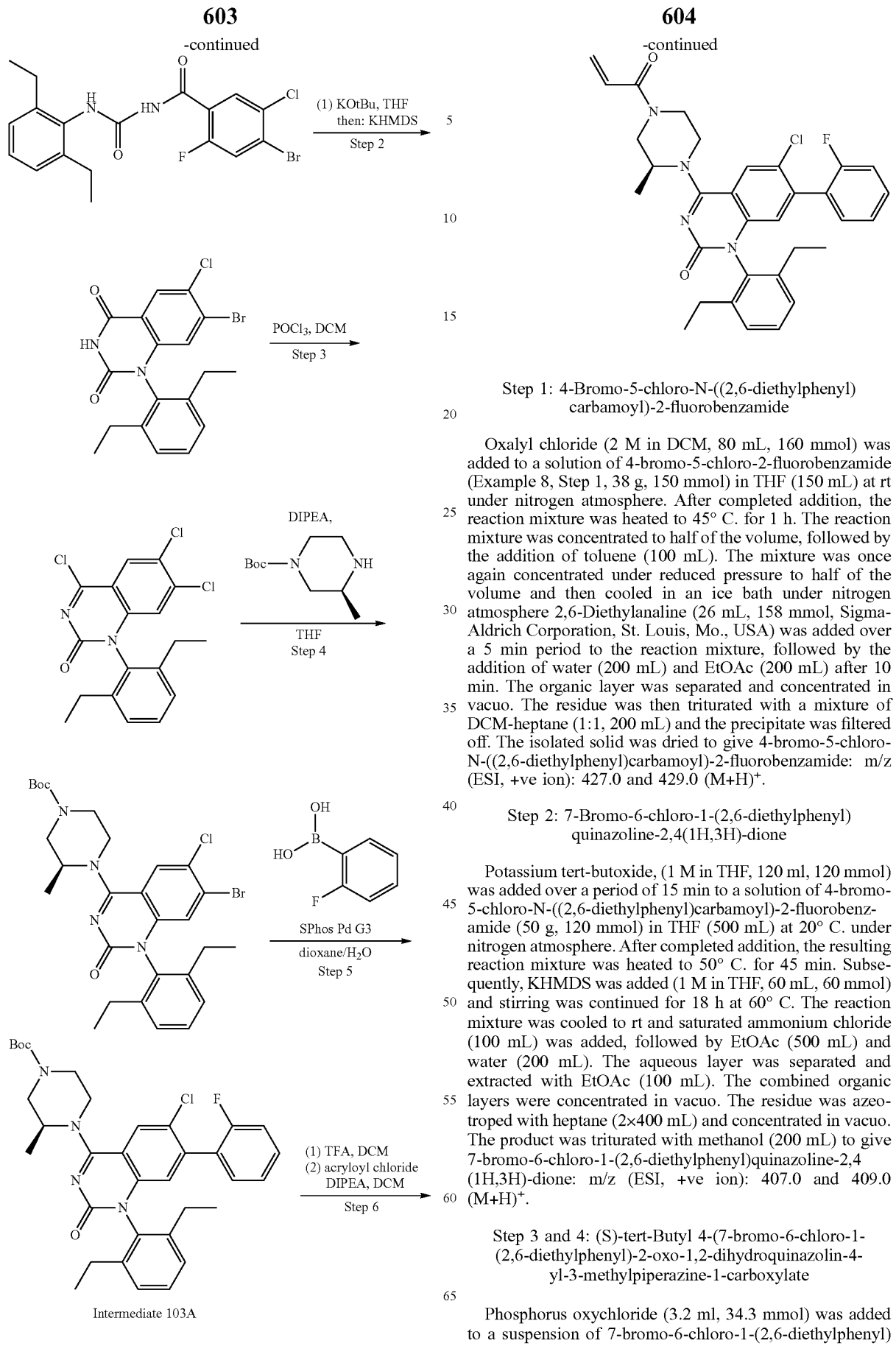

Step 1: 4-Bromo-5-chloro-N-((2,6-diethylphenyl)carbamoyl)-2-fluorobenzamide

Oxalyl chloride (2 M in DCM, 80 mL, 160 mmol) was added to a solution of 4-bromo-5-chloro-2-fluorobenzamide (Example 8, Step 1, 38 g, 150 mmol) in THF (150 mL) at rt under nitrogen atmosphere. After completed addition, the reaction mixture was heated to 45° C. for 1 h. The reaction mixture was concentrated to half of the volume, followed by the addition of toluene (100 mL). The mixture was once again concentrated under reduced pressure to half of the volume and then cooled in an ice bath under nitrogen atmosphere 2,6-Diethylanaline (26 mL, 158 mmol, Sigma-Aldrich Corporation, St. Louis, Mo., USA) was added over a 5 min period to the reaction mixture, followed by the addition of water (200 mL) and EtOAc (200 mL) after 10 min. The organic layer was separated and concentrated in vacuo. The residue was then triturated with a mixture of DCM-heptane (1:1, 200 mL) and the precipitate was filtered off. The isolated solid was dried to give 4-bromo-5-chloro-N-((2,6-diethylphenyl)carbamoyl)-2-fluorobenzamide: m/z (ESI, +ve ion): 427.0 and 429.0 (M+H)$^+$.

Step 2: 7-Bromo-6-chloro-1-(2,6-diethylphenyl)quinazoline-2,4(1H,3H)-dione

Potassium tert-butoxide, (1 M in THF, 120 ml, 120 mmol) was added over a period of 15 min to a solution of 4-bromo-5-chloro-N-((2,6-diethylphenyl)carbamoyl)-2-fluorobenzamide (50 g, 120 mmol) in THF (500 mL) at 20° C. under nitrogen atmosphere. After completed addition, the resulting reaction mixture was heated to 50° C. for 45 min. Subsequently, KHMDS was added (1 M in THF, 60 mL, 60 mmol) and stirring was continued for 18 h at 60° C. The reaction mixture was cooled to rt and saturated ammonium chloride (100 mL) was added, followed by EtOAc (500 mL) and water (200 mL). The aqueous layer was separated and extracted with EtOAc (100 mL). The combined organic layers were concentrated in vacuo. The residue was azeotroped with heptane (2×400 mL) and concentrated in vacuo. The product was triturated with methanol (200 mL) to give 7-bromo-6-chloro-1-(2,6-diethylphenyl)quinazoline-2,4(1H,3H)-dione: m/z (ESI, +ve ion): 407.0 and 409.0 (M+H)$^+$.

Step 3 and 4: (S)-tert-Butyl 4-(7-bromo-6-chloro-1-(2,6-diethylphenyl)-2-oxo-1,2-dihydroquinazolin-4-yl-3-methylpiperazine-1-carboxylate Phosphorus oxychloride (3.2 ml, 34.3 mmol) was added to a suspension of 7-bromo-6-chloro-1-(2,6-diethylphenyl)

quinazoline-2,4(1H,3H)-dione (7.0 g, 17.2 mmol) and DIPEA (7.0 ml, 40 mmol) in DCM (50 mL) under nitrogen atmosphere. The reaction mixture was stirred at rt for 30 min and then heated to 60° C. for 1 h. The reaction mixture was concentrated in vacuo and the residue was azeotroped with toluene (2×100 mL). The residue was dissolved in THF (100 mL) and the solution was placed under nitrogen atmosphere. DIPEA (7.0 ml, 40.1 mmol) and (S)-4-N-Boc-2-methyl piperazine (3.44 g, 17.2 mmol, Combi-Blocks, San Diego, Calif.) were added and the reaction mixture stirred at rt. After 10 min, water (200 mL) and EtOAc (300 mL) were added. The organic layer was washed with saturated ammonium chloride (200 mL) and brine (75 mL), and concentrated in vacuo. The crude product was purified by silica gel chromatography (eluent: 0-40% EtOAc-EtOH (3:1)/DCM) to provide (S)-tert-butyl 4-(7-bromo-6-chloro-1-(2,6-diethylphenyl)-2-oxo-1,2-dihydroquinazolin-4-yl)-3-methylpiperazine-1-carboxylate. m/z (ESI, +ve on): 589.1 and 591.2 (M+H)+.

Step 5: (S)-tert-Butyl 4-(6-chloro-1-(2,6-diethylphenyl)-7-(2-fluorophenyl)-2-oxo-1,2-dihydroquinazolin-4-yl)-3-methylpiperazine-1-carboxylate (Intermediate 103A)

A suspension of (S)-tert-butyl 4-(7-bromo-6-chloro-1-(2,6-diethylphenyl)-2-oxo-1,2-dihydroquinazolin-4-yl)-3-methylpiperazine-1-carboxylate (1.2 g, 2.03 mmol), 2-fluorobenzeneboronic acid (0.43 g, 3.1 mmol, Combi-Blocks, Inc., San Diego, Calif., USA), SPhos Pd G3 (0.119 g, 0.153 mmol), and potassium carbonate (0.84 g, 6.1 mmol) in 1,4-dioxane (8 mL) and water (4 mL) was sparged with argon for 2 min then heated to 80° C. for 1.5 h. The reaction was partitioned between EtOAc (40 mL) and saturated NaHCO3 (20 mL). The organic layer was washed with brine (5 mL) and concentrated in vacuo. The residue was purified by silica gel chromatography (eluent: 0-30% EtOAc-EtOH (3:1)/heptane) to provide (S)-tert-butyl 4-(6-chloro-1-(2,6-diethylphenyl)-7-(2-fluorophenyl)-2-oxo-1,2-dihydroquinazolin-4-yl)-3-methylpiperazine-1-carboxylate (Intermediate 103A). m/z (ESI, +ve ion): 605.2 (M+H)+.

Step 6: 6-Chloro-1-(2,6-diethylphenyl)-7-(2-fluorophenyl)-4-((2S)-2-methyl-4-(2-propenoyl)-1-piperazinyl)-2(1H)-quinazolinone TFA (4 mL) was added to a solution of (S)-tert-butyl 4-(6-chloro-1-(2,6-diethylphenyl)-7-(2-fluorophenyl)-2-oxo-1,2-dihydroquinazolin-4-yl)-3-methylpiperazine-1-carboxylate (Intermediate 103A, 1.1 g, 1.82 mmol) in DCM rt. After 30 min, the mixture was concentrated in vacuo and the residue was azeotroped with heptane (20 mL). The residue was dissolved in DCM (10 mL), followed by the addition of DIPEA (0.95 mL, 5.45 mmol). The reaction mixture was cooled to 0° C. followed by the addition of acryloyl chloride (0.22 mL, 2.73 mmol). The cooling bath was removed, and stirring was continued for 30 min at rt. The reaction mixture was quenched with satd. NaHCO3 (20 mL) and the aqueous was extracted with DCM (10 mL). The combined organic layers were dried over MgSO4 and concentrated in vacuo. The crude product was purified by silica gel chromatography (eluent: 10-40% EtOAc-EtOH (3:1)/heptane), followed by SFC purification (OJ-H column (30×250 mm, 5 μm), 15% (20 mM NH3 in MeOH) in supercritical CO2), to give (S)-4-(4-acryloyl-2-methylpiperazin-1-yl)-6-chloro-1-(2,6-diethylphenyl)-7-(2-fluorophenyl)quinazolin-2(1H)-one. 1H NMR (400 MHz, CDCl3) δ ppm 7.83 (br s, 1H), 7.34-7.42 (m, 2H), 7.26-7.28 (m, 3H), 7.07-7.20 (m, 3H), 6.52-6.73 (m, 1H), 6.45-6.48 (m, 1H), 6.39 (dd, J=1.66, 16.79 Hz, 1H), 5.79 (dd, J=1.87, 10.57 Hz, 1H), 4.78-5.13 (m, 1H), 4.21-4.77 (m, 2H), 3.51-4.09 (m, 3H), 2.95-3.36 (m, 1H), 2.34-2.48 (m, 2H), 2.19-2.33 (m, 2H), 1.48 (d, J=9.33 Hz, 3H), 1.06-1.15 (m, 6H). 19F NMR (377 MHz, CDCl3) δ ppm −113.93 (s, 1F). m/z (ESI, +ve ion): 559.3 (M+H)+.

Example 104

6-Chloro-7-(2-fluorophenyl)-4-((2S)-2-methyl-4-(2-propenoyl)-1-piperazinyl)-1-(3-(2-propanyl)-2-pyridinyl)-2(1H)-quinazolinone

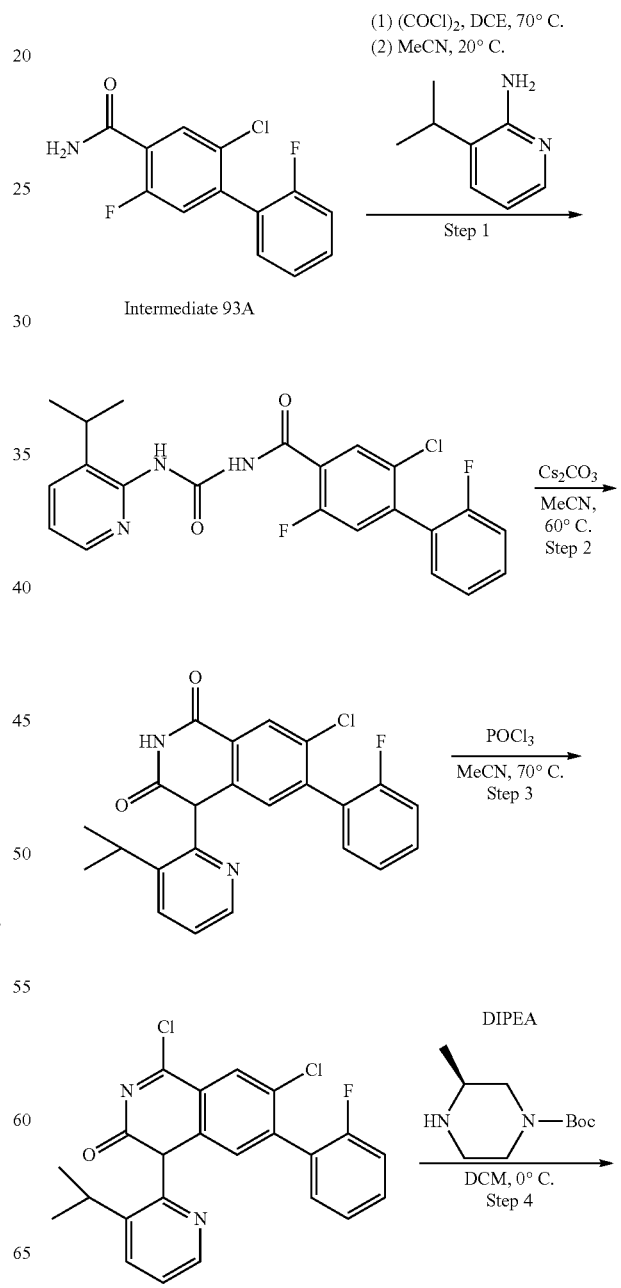

-continued

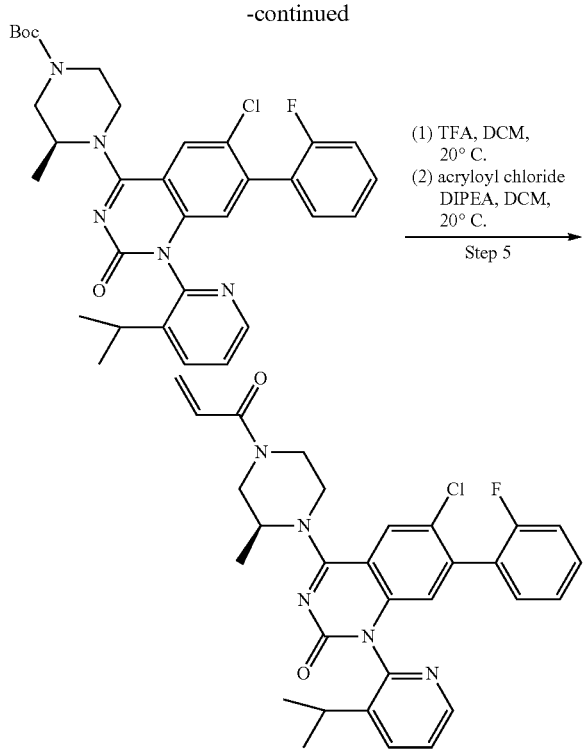

Step 1: 2-Chloro-2',5-difluoro-N-((3-isopropylpyridin-2-yl)carbamoyl)-[1,1'-biphenyl]-4-carboxamide Oxalyl chloride (2 M in DCM, 3.4 mL, 6.8 mmol) was added over a 1 min period to a suspension of 2-chloro-2',5-difluoro-[1,1'-biphenyl]-4-carboxamide (Intermediate 93A, 1.2 g, 4.5 mmol) in 1,2-dichloroethane (12 mL) at 20° C. under nitrogen atmosphere. The resulting solution was stirred for 5 min at rt and then heated to 70° C. for 1 hr. The reaction was concentrated in vacuo to afford an oil. The oil was dissolved in acetonitrile (5 mL), and a solution of 3-(propan-2-yl)pyridin-2-amine (0.76 ml, 5.6 mmol, Enamine LLC, Princeton N.J.) in MeCN (5 mL) was added dropwise at rt. After 10 min, the reaction mixture was concentrated in vacuo. The crude product was purified by silica gel chromatography (eluent: 10-30% EtOAc-EtOH (3:1)/heptane) to provide 2-chloro-2',5-difluoro-N-((3-isopropylpyridin-2-yl)carbamoyl)-[1,1'-biphenyl]-4-carboxamide. m/z (ESI, +ve ion): 430.1 (M+H)+.

Step 2: 6-Chloro-7-(2-fluorophenyl)-1-(3-isopropylpyridin-2-yl)quinazoline-2,4(1H,3H)-dione A suspension of 2-chloro-2',5-difluoro-N-((3-isopropylpyridin-2-yl)carbamoyl)-[1,1'-biphenyl]-4-carboxamide (700 mg, 1.63 mmol) and cesium carbonate (1.59 g, 4.89 mmol) in acetonitrile (10 mL) was heated to 50° C. for 45 min. The reaction temperature was increased to 80° C. and the reaction mixture was partitioned between EtOAc (50 mL) and water (30 mL) after 30 min. The organic layer was separated, washed with saturated NaHCO₃ (10 mL) and brine (10 mL). The organic layer was dried over MgSO₄, concentrated in vacuo, and the crude product was purified by silica gel chromatography (eluent: 15-40% EtOAc-EtOH (3:1)/heptane) to provide 6-chloro-7-(2-fluorophenyl)-1-(3-isopropylpyridin-2-yl)quinazoline-2,4(1H,3H)-dione: $^1$H NMR (400 MHz, DMSO-d₆) δ ppm 12.07 (s, 1H), 8.46-8.52 (m, 1H), 8.15-8.18 (m, 1H), 8.07-8.12 (m, 1H), 7.54-7.63 (m, 1H), 7.43-7.53 (m, 1H), 7.14-7.34 (m, 4H), 6.14-6.17 (m, 1H), 2.79-2.93 (m, 1H), 1.02-1.23 (m, 6H). $^{19}$F NMR (376 MHz, DMSO-d₆) δ ppm −114.35 (s, 1F), −115.03 (s, 1F). m/z (ESI, +ve ion): 410.1 (M+H)+.

Steps 3 and 4: (S)-tert-Butyl 4-(6-chloro-7-(2-fluorophenyl)-1-(3-isopropylpyridin-2-yl)-2-oxo-1,2-dihydroquinazolin-4-yl)-3-methylpiperazine-1-carboxylate A suspension of 6-chloro-7-(2-fluorophenyl)-1-(3-isopropylpyridin-2-yl)quinazoline-2,4(1H,3H)-dione (0.28 g, 0.683 mmol), DIPEA (0.6 ml, 3.42 mmol), and phosphoroxychloride (0.13 ml, 1.37 mmol) in acetonitrile (3 mL) was heated to 70° C. for 75 min. The mixture was concentrated in vacuo. The residue was dissolved in THF (3 mL). the solution was placed under nitrogen atmosphere and DIPEA (0.6 ml, 3.42 mmol) added. The reaction mixture was cooled to 0° C. and (S)-4-N-Boc-2-methyl piperazine (0.164 g, 0.82 mmol, Combi-Blocks. San Diego, Calif.) added. The cooling bath was removed and the reaction mixture was stirred at rt for 15 min. The reaction mixture was partitioned between EtOAc (30 mL) and satd. NaHCO₃ (15 mL). The organic layer was separated, dried over MgSO₄ and concentrated in vacuo. The crude product was purified by silica gel chromatography (eluent: 0-100% EtOAc/heptane) to provide (S)-tert-butyl 4-(6-chloro-7-(2-fluorophenyl)-1-(3-isopropylpyridin-2-yl)-2-oxo-1,2-dihydroquinazolin-4-yl)-3-methylpiperazine-1-carboxylate. $^1$H NMR (400 MHz, CDCl₃) δ ppm 8.46-8.52 (m, 1H), 7.87-7.92 (m, 1H), 7.76-7.81 (m, 1H), 7.41-7.46 (m, 1H), 7.34-7.41 (m, 1H), 7.06-7.20 (m, 3H), 6.31-6.37 (m, 1H), 4.64-5.03 (m, 1H), 3.86-4.45 (m, 4H), 3.44-3.82 (m, 1H), 2.93-3.42 (m, 2H), 2.76-2.90 (m, 1H), 1.42-1.54 (m, 12H), 1.28-1.33 (m, 3H), 1.05-1.10 (m, 3H). $^{19}$F NMR (376 MHz, CDCl₃) δ ppm −113.81 (s, 1F). m/z (ESI, +ve ion): 592.3 (M+H)+.

Step 5: 6-Chloro-7-(2-fluorophenyl)-4-((2S)-2-methyl-4-(2-propenoyl)-1-piperazinyl)-1-(3-(2-propanyl)-2-pyridinyl)-2(1H)-quinazolinone A solution of (S)-tert-butyl 4-(6-chloro-7-(2-fluorophenyl)-1-(3-isopropylpyridin-2-yl)-2-oxo-1,2-dihydroquinazolin-4-yl)-3-methylpiperazine-1-carboxylate (200 mg, 0.338 mmol) in TFA (1 mL) was stirred at rt for 15 min. The reaction mixture was concentrated in vacuo, and the residue was azeotroped with heptane (20 mL). The residue was dissolved in DCM (2 mL) and DIPEA (0.3 ml, 1.69 mmol) added to the solution, followed by addition of acryloyl chloride (41.3 μl, 0.507 mmol). After 5 min the reaction mixture was diluted with DCM (5 mL) and washed with satd. NaHCO₃ (5 mL). The organic layer was separated, washed with brine (1 mL), dried over MgSO₄ and concentrated in vacuo. The crude product was purified by silica gel chromatography (eluent: 0-75% EtOAc-EtOH (3:1)/heptane) to provide (S)-4-(4-acryloyl-2-methylpiperazin-1-yl)-6-chloro-7-(2-fluorophenyl)-1-(3-isopropylpyridin-2-yl)quinazolin-2(1H)-one. $^1$H NMR (400 MHz, CDCl₃) δ ppm 8.54-8.61 (m, 1H), 7.96 (dd, J=1.87, 7.67 Hz, 1H), 7.87 (s, 1H), 7.50 (dd, J=4.77, 7.88 Hz, 1H), 7.42-7.47 (m, 1H) 7.21-7.28 (m, 2H), 7.18 (t, J=18.00 Hz, 1H), 6.57-6.77 (m, 1H), 6.41-6.51 (m, 2H), 5.88 (d, J=10.57 Hz, 1H), 4.86-5.24 (m, 1H), 4.36-4.85 (m, 2H), 3.30-3.98 (m, 3H), 2.97-3.27 (m, 1H), 2.80-2.94 (m, 1H), 1.45-1.69 (m, 3H), 1.37 (d, J=6.84 Hz, 3H), 1.16 (d, J=6.84 Hz, 3H). $^{19}$F NMR (376 MHz, CDCl$_3$) δ ppm −113.78 (s, 1F). m/z (ESI, +ve ion): 546.2 (M+H)$^+$.

Example 105

6-Chloro-7-(2-fluorophenyl)-4-((2S)-2-methyl-4-(2-propenoyl)-1-piperazinyl)-1-(4-(2-propanyl)-1,3-thiazol-5-yl)-2(1H)-quinazolinone

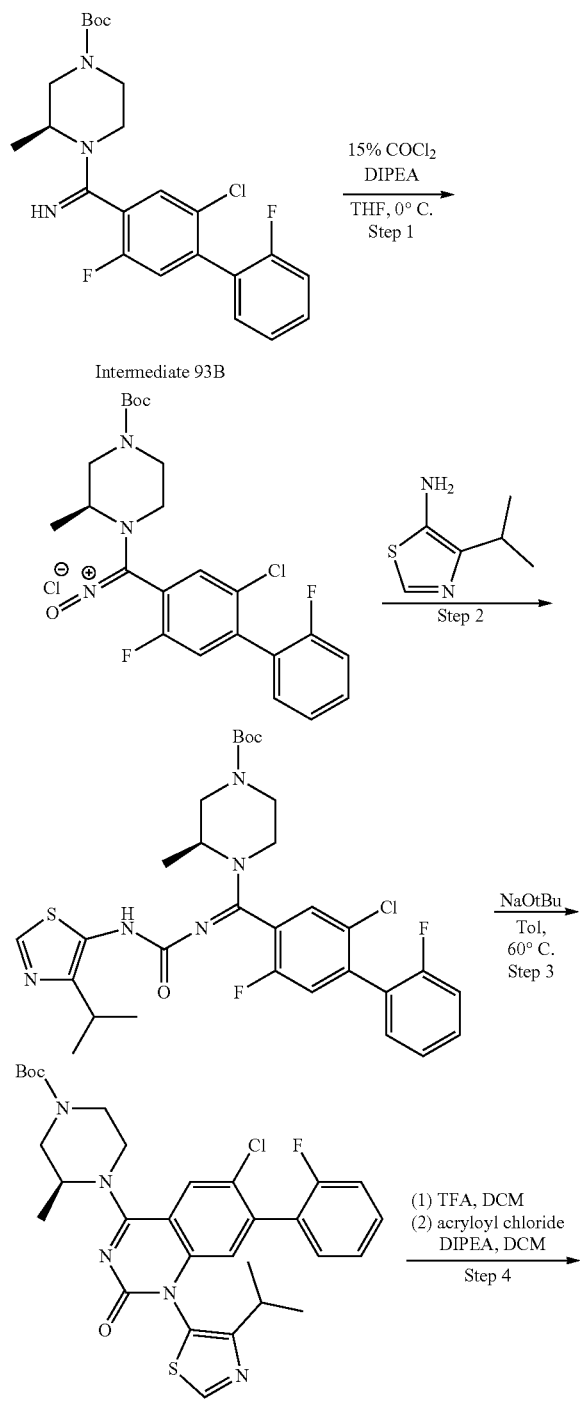

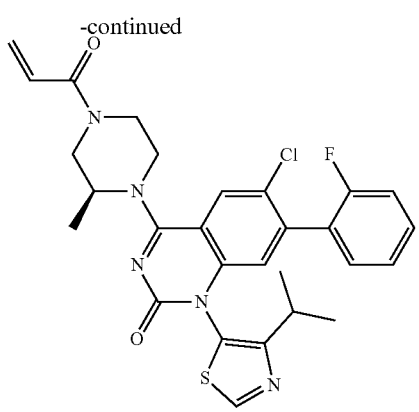

Steps 1 and 2: (S)-tert-Butyl 4-((2-chloro-2',5-difluoro-[1,1'-biphenyl]-4-yl)(((4-isopropylthiazol-5-yl)carbamoyl)imino)methyl)-3-methylpiperazine-1-carboxylate A solution of phosgene (15% in toluene, 4.76 mL, 6.67 mmol) in THF (5.0 mL) was placed under nitrogen atmosphere and cooled to 0° C. A solution of (S)-tert-butyl 4-((2-chloro-2',5-difluoro-[1,1'-biphenyl]-4-yl)(imino)methyl)-3-methylpiperazine-1-carboxylate (Intermediate 93B, 1.0 g, 2.22 mmol) and DIPEA (1.2 ml, 6.67 mmol) in THF (15 mL) was added dropwise over a period of 3 min. After additional 5 min reaction time, 4-isopropylthiazol-5-amine (0.948 g, 6.67 mmol, Enamine LLC, Princeton N.J.) was added in one portion. The reaction mixture was diluted with THF (15 mL), and stirred at rt for 30 min. The reaction mixture was partitioned between EtOAc (20 mL) and saturated NaHCO$_3$ (20 mL). The organic phase was dried over MgSO$_4$ and concentrated in vacuo. The crude product was purified by silica gel chromatography (eluent: 10-30% EtOAc-EtOH (3:1)/heptane) to provide (S)-tert-butyl 4-((2-chloro-2',5-difluoro-[1,1'-biphenyl]-4-yl)((4-isopropylthiazol-5-yl)carbamoyl)imino)methyl)-3-methylpiperazine-1-carboxylate: $^1$H NMR (400 MHz, CDCl$_3$) δ ppm 8.36 (s, 1H), 7.30-7.49 (m, 3H), 7.06-7.24 (m, 4H), 4.50-5.20 (m, 1H), 3.62-4.40 (m, 3H), 2.70-3.44 (m, 5H), 1.46-1.54 (m, 10H), 1.18-1.41 (m, 22H), 0.82-0.92 (m, 5H). m/z (ESI, +ve ion): 608.2 (M+H)$^+$.

Step 3: (S)-tert-Butyl 4-(6-chloro-7-(2-fluorophenyl)-1-(4-isopropylthiazol-5-yl)-2-oxo-1,2-dihydroquinazolin-4-yl)-3-methylpiperazine-1-carboxylate A suspension of (S)-tert-butyl 4-((2-chloro-2',5-difluoro-[1,1'-biphenyl]-4-yl)(((4-isopropylthiazol-5-yl)carbamoyl)imino)methyl)-3-methylpiperazine-1-carboxylate (1.5 g, 2.43 mmol) and sodium tert-butoxide (0.583 g, 6.07 mmol) in toluene (15 mL) was heated to 60° C. for 20 min. The reaction mixture was diluted with EtOAc (20 mL), and washed with satd. NaHCO$_3$ (10 mL). The organic layer was separated, washed with brine (5 mL), dried over MgSO$_4$, and concentrated in vacuo to give (S)-tert-butyl 4-(6-chloro-7-(2-fluorophenyl)-1-(4-isopropylthiazol-5-yl)-2-oxo-1,2-dihydroquinazolin-4-yl)-3-methylpiperazine-1-carboxylate. m/z (ESI, +ve ion): 598.3 (M+H)$^+$.

Step 4: 6-Chloro-7-(2-fluorophenyl)-4-((2S)-2-methyl-4-(2-propenoyl)-1-piperazinyl)-1-(4-(2-propanyl)-1,3-thiazol-5-yl)-2(1H)-quinazolinone TFA (5 mL) was added to a solution of (S)-tert-butyl 4-(6-chloro-7-(2-fluorophenyl)-1-(4-isopropylthiazol-5-yl)-

2-oxo-1,2-dihydroquinazolin-4-yl)-3-methylpiperazine-1-carboxylate (1.45 g, 2.42 mmol) in DCM (10 mL). The reaction mixture was stirred for 15 min at rt and concentrated in vacuo. The residue was azeotroped with heptane (20 mL) and the resulting residue was dissolved in DCM (15 mL). DIPEA (2.1 ml, 12.1 mmol) and a solution of acryloyl chloride (0.247 ml, 3.03 mmol) in DCM (2 mL) were added. After 10 min, the reaction mixture was diluted with DCM (15 mL) and satd NaHCO$_3$ (25 mL). The organic layer was separated, washed with brine (5 mL), dried over MgSO$_4$ and concentrated in vacuo. The crude product was purified by silica gel chromatography (eluent: 0-60% EtOAc-EtOH (3:1)/heptane) to provide (S)-4-(4-acryloyl-2-methylpiperazin-1-yl)-6-chloro-7-(2-fluorophenyl)-1-(4-isopropylthiazol-5-yl)quinazolin-2(1H)-one. $^1$H NMR (400 MHz, (CDCl$_3$) δ ppm 8.89 (s, 1H), 7.75-7.83 (m, 1H), 7.38-7.47 (m, 1H), 7.11-7.25 (m, 3H), 6.75 (s, 1H), 6.48-6.70 (m, 1H), 6.40 (dd, J=1.45, 16.79 Hz, 1H), 5.77-5.84 (m, 1H), 5.80 (d, J=10.57 Hz, 1H), 4.79-5.15 (m, 1H), 4.23-4.78 (m, 2H), 3.49-4.08 (m, 2H), 2.93-3.32 (m, 1H), 2.66-2.85 (m, 1H), 2.07-2.11 (m, 1H), 1.49 (d, J=20.52 Hz, 3H), 1.23-1.29 (m, 3H), 1.19 (d, J=7.26 Hz, 3H). $^{19}$F NMR (376 MHz, CDCl$_3$) δ ppm −113.83 (s, 1F). m/z (ESI, +ve ion): 552.2 (M+H)$^+$.

Example 106

6-Chloro-7-(2-fluoro-6-hydroxyphenyl)-1-(2-methyl-6-(2-propanyl)phenyl)-4-((2S)-2-methyl-4-(2-propenoyl)-1-piperazinyl)-2(1H)-quinazolinone

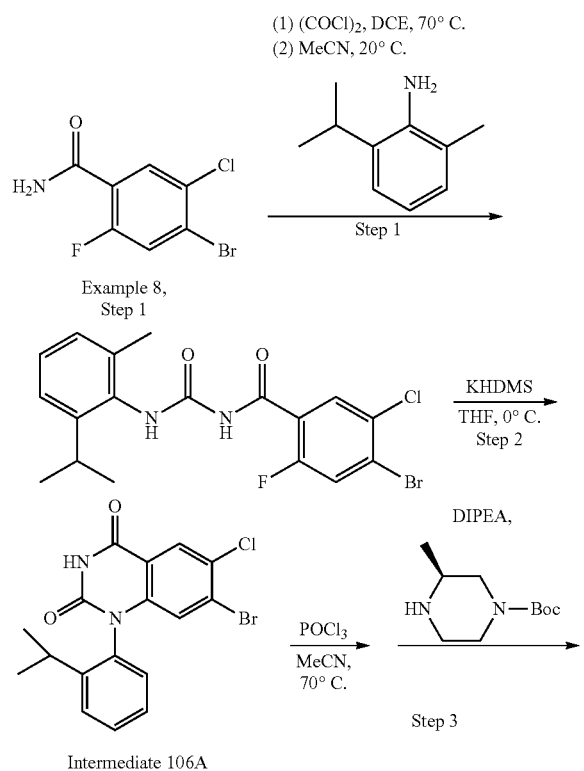

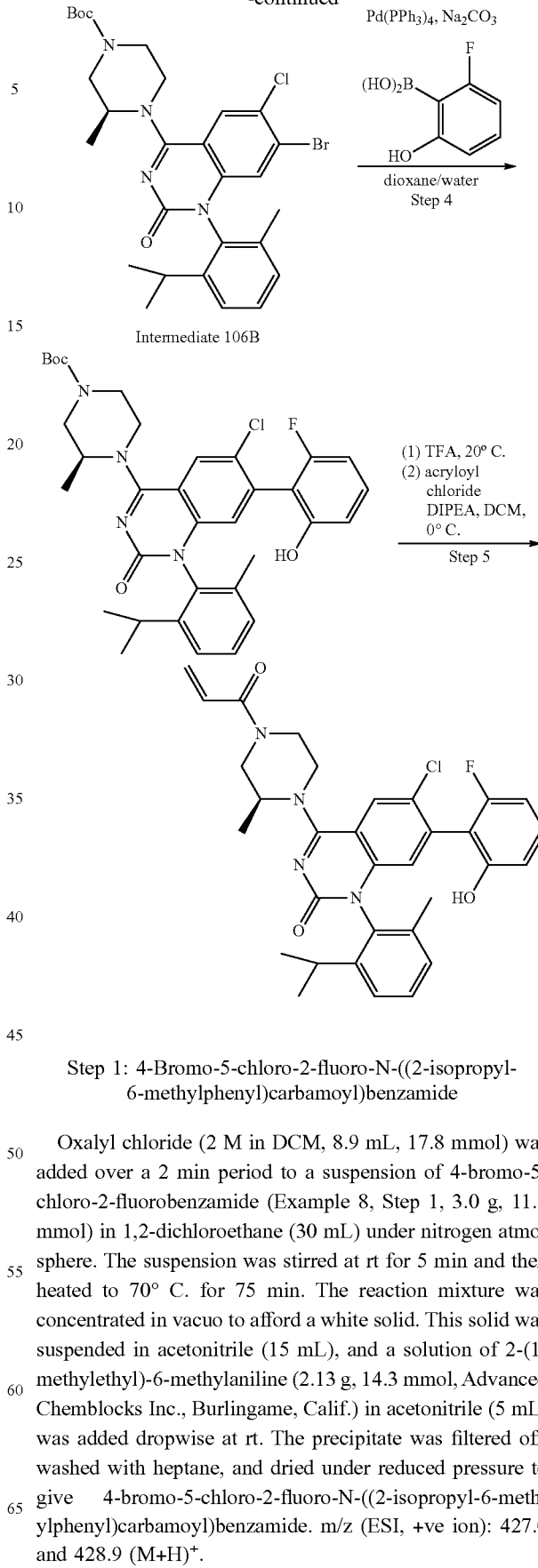

Step 1: 4-Bromo-5-chloro-2-fluoro-N-((2-isopropyl-6-methylphenyl)carbamoyl)benzamide Oxalyl chloride (2 M in DCM, 8.9 mL, 17.8 mmol) was added over a 2 min period to a suspension of 4-bromo-5-chloro-2-fluorobenzamide (Example 8, Step 1, 3.0 g, 11.9 mmol) in 1,2-dichloroethane (30 mL) under nitrogen atmosphere. The suspension was stirred at rt for 5 min and then heated to 70° C. for 75 min. The reaction mixture was concentrated in vacuo to afford a white solid. This solid was suspended in acetonitrile (15 mL), and a solution of 2-(1-methylethyl)-6-methylaniline (2.13 g, 14.3 mmol, Advanced Chemblocks Inc., Burlingame, Calif.) in acetonitrile (5 mL) was added dropwise at rt. The precipitate was filtered off, washed with heptane, and dried under reduced pressure to give 4-bromo-5-chloro-2-fluoro-N-((2-isopropyl-6-methylphenyl)carbamoyl)benzamide. m/z (ESI, +ve ion): 427.0 and 428.9 (M+H)$^+$.

Step 2: 7-Bromo-6-chloro-1-(2-isopropyl-6-methylphenyl)quinazoline-2,4(1H,3H)-dione (Intermediate 106A)

KHMDS (1 M in THF, 20.6 mL, 20.6 mmol) was added portion-wise over a period of 10 min to a suspension of 4-bromo-5-chloro-2-fluoro-N-((2-isopropyl-6-methylphenyl)carbamoyl)benzamide (4.4 g, 10.3 mmol) in THF (30 mL) cooled to 0° C. under nitrogen atmosphere. The reaction mixture was allowed to warm to rt and stirred for 18 h. The reaction mixture was then partitioned between EtOAc (100 mL) and satd. NaHCO$_3$ (50 mL). The organic layer was washed with brine (20 mL), dried over MgSO$_4$, and concentrated in vacuo to give 7-bromo-6-chloro-1-(2-isopropyl-6-methylphenyl)quinazoline-2,4(1H,3H)-dione (Intermediate 106A). m/z (ESI, +ve ion): 407.0 and 409.0 (M+H)$^+$.

Step 3: (S)-tert-Butyl 4-(7-bromo-6-chloro-1-(2-isopropyl-6-methylphenyl)-2-oxo-1,2-dihydroquinazolin-4-yl)-3-methylpiperazine-1-carboxylate (Intermediate 106B)

A suspension of 7-bromo-6-chloro-1-(2-isopropyl-6-methylphenyl)quinazoline-2,4(1H,3H)-dione (Intermediate 106A, 2.9 g, 7.11 mmol), DIPEA (3.7 ml, 21.3 mmol), and phosphorous oxychloride (1.3 mL, 14.2 mmol) in acetonitrile (30 mL) was heated to 70° C. for 2 h. The reaction mixture was concentrated in vacuo, and the residue was azeotroped with heptane (30 mL). The residue was dissolved in THF (30 mL), and placed under nitrogen atmosphere, followed by the addition of DIPEA (3.7 ml, 21.3 mmol). The solution was cooled to 0° C. and (S)-4-N-Boc-2-methyl piperazine (1.78 g, 8.89 mmol, Combi-Blocks, San Diego, Calif.) was added. The cooling bath was removed and the reaction mixture was partitioned between EtOAc (120 mL) and saturated NaHCO$_3$ (50 mL) after 15 min. The organic layer was separated, dried over MgSO$_4$, and concentrated in vacuo. The crude product was purified by silica gel chromatography (eluent: 0-20% EtOAc:EtOH (3:1)/heptane) to provide tert-butyl (S)-4-(7-bromo-6-chloro-1-(2-isopropyl-6-methylphenyl)-2-oxo-1,2-dihydroquinazolin-4-yl)-3-methylpiperazine-1-carboxylate (Intermediate 106B). m/z (ESI, +ve ion): 589.1 and 590.2 (M+H)$^+$.

Step 4: tert-Butyl (3S)-4-(6-chloro-7-(2-fluoro-6-hydroxyphenyl)-1-(2-isopropyl-6-methylphenyl)-2-oxo-1,2-dihydroquinazolin-4-yl)-3-methylpiperazine-1-carboxylate A suspension of tert-butyl (S)-4-(7-bromo-6-chloro-1-(2-isopropyl-6-methylphenyl)-2-oxo-1,2-dihydroquinazolin-4-yl)-3-methylpiperazine-1-carboxylate (Intermediate 106B, 1.2 g, 2.03 mmol), (2-fluoro-6-hydroxyphenyl)boronic acid (0.634 g, 4.07 mmol, Combi-Blocks, San Diego, Calif.), tetrakis(triphenylphosphine)palladium(0) (0.235 g, 0.203 mmol), sodium carbonate (0.43 g, 4.07 mmol) in 1,4-dioxane (10 mL) and degassed water (10 mL) was sparged with argon for 1 min and then heated to 90° C. After 5 h, the reaction mixture was partitioned between EtOAc (30 mL) and satd. NaHCO$_3$ (10 mL). The organic layer was separated, washed with brine, dried over MgSO$_4$, and concentrated in vacuo. The crude product was purified by silica gel chromatography (eluent: 0-30% EtOAc/heptane) to provide tert-butyl (3S)-4-(6-chloro-7-(2-fluoro-6-hydroxyphenyl)-1-(2-isopropyl-6-methylphenyl)-2-oxo-1,2-dihydroquinazolin-4-yl)-3-methylpiperazine-1-carboxylate. $^1$H NMR (400 MHz, CDCl$_3$) δ ppm 7.81-7.86 (m, 1H), 7.27-7.49 (m, 3H), 7.04-7.24 (m, 4H), 6.58-6.70 (m, 2H), 6.48 (d, J=2.90 Hz, 1H), 4.64-4.97 (m, 1H), 3.75-4.32 (m, 3H), 2.87-3.74 (m, 3H), 2.50-2.68 (m, 1H), 1.93-2.00 (m, 3H), 1.49-1.53 (m, 9H), 1.37-1.46 (m, 3H), 1.10-1.19 (m, 3H), 0.96-1.05 (m, 3H), 0.84-0.92 (m, 3H). $^{19}$F NMR (376 MHz, CDCl$_3$) δ ppm −113.54-113.76 (m, 1F). m/z (ESI, +ve ion): 621.2 (M+H)$^+$.

Step 5: 6-Chloro-7-(2-fluoro-6-hydroxyphenyl)-1-(2-methyl-6-(2-propanyl)phenyl)-4-((2S)-2-methyl-4-(2-propenoyl)-1-piperazinyl)-2(1H)-quinazolinone A solution of tert-butyl (3S)-4-(6-chloro-7-(2-fluoro-6-hydroxyphenyl)-1-(2-isopropyl-6-methylphenyl)-2-oxo-1,2-dihydroquinazolin-4-yl)-3-methylpiperazine-1-carboxylate (780 mg, 1.26 mmol) in TFA (5 mL) was stirred for 30 min. The reaction mixture was concentrated in vacuo. The residue was dissolved in DCM (10 mL) and cooled to ° C. DIEA (1097 µl, 6.28 mmol) and a solution of acryloyl chloride (102 µl, 1.26 mmol) in DCM (2 mL) and were added. After 10 min, the reaction was washed with satd. NaHCO$_3$ (10 mL). The organic layer was separated, dried over MgSO$_4$ and concentrated in vacuo. The crude product was purified by silica gel chromatography (eluent: 0-100% EtOAc-EtOH (3:1)/heptane) to provide 4-((S)-4-acryloyl-2-methylpiperazin-1-yl)-6-chloro-7-(2-fluoro-6-hydroxyphenyl)-1-(2-isopropyl-6-methylphenyl)quinazolin-2(1H)-one. $^1$H NMR (400 MHz, CDCl$_3$) δ ppm 7.84 (s, 1H), 7.26-7.37 (m, 2H), 7.08-7.18 (m, 2H), 6.71 (d, J=8.29 Hz, 1H), 6.54-6.67 (m, 2H), 6.51 (d, J=3130.75 Hz, 1H), 6.38 (d, J=16.38 Hz, 1H), 5.79 (d, J=10.37 Hz, 1H), 4.72-5.14 (m, 1H), 4.17-4.71 (m, 2H), 3.76-4.02 (m, 1H), 3.44-3.75 (m, 2H), 2.92-3.30 (m, 1H), 2.44-2.71 (m, 1H), 1.90-2.01 (m, 3H), 1.35-1.54 (m, 3H), 1.14 (dd, J=6.84, 11.61 Hz, 3H), 0.97-1.05 (m, 3H). $^{19}$F NMR (376 MHz, CDCl$_3$) δ ppm −114.04--113.40 (m, 1F). m/z (ESI, +ve ion): 575.2 (M+H)$^+$.

Example 107

1-(2,6-Diethylphenyl)-7-(2-fluoro-6-hydroxyphenyl)-4-((2S)-2-methyl-4-(2-propenoyl)-1-piperazinyl)pyrido[2,3-d]pyrimidin-2(1H)-one

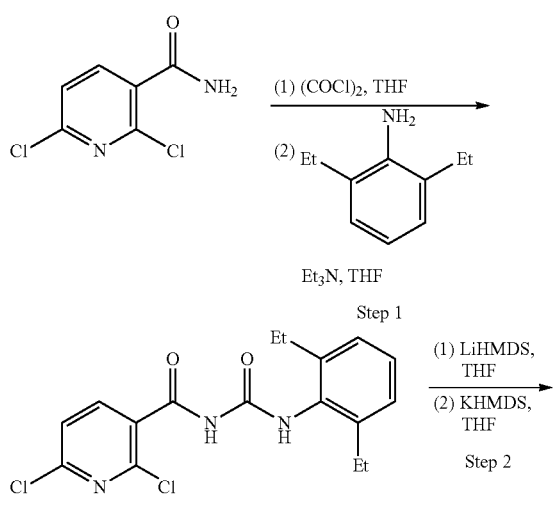

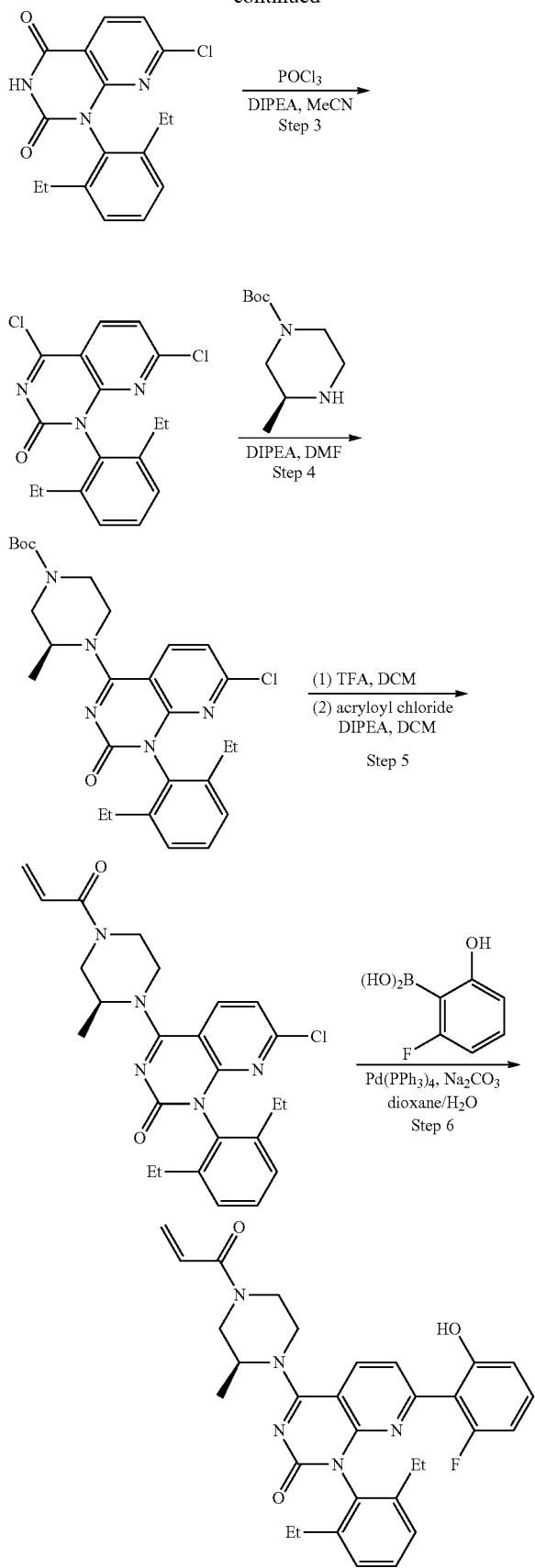

Step 1

2,6-Dichloro-N-((2,6-diethylphenyl)carbamoyl)nicotinamide

Oxalyl chloride (2M in DCM, 10 ml, 20 mmol) was added to a solution of 2,6-dichloronicotinamide (3.6 g, 18.9 mmol) in THF (100 mL) under nitrogen atmosphere. The reaction mixture stirred for 5 min at rt and then heated to 60° C. After 40 min, toluene (75 mL) was added, the reaction mixture was concentrated to half of the volume, followed by the addition of $Et_3N$ (6 ml, 42.7 mmol) and 2,6-diethylaniline (3.3 mL, 20 mmol, Sigma-Aldrich Corporation, St. Louis, Mo., USA). The reaction mixture was stirred for 10 min and EtOAc (200 mL) and water (200 mL) were added. The organic layer was separated and concentrated in vacuo. The crude product was suspended in heptane-EtOAc (9:1, 75 mL). The precipitate was filtered off and the solid was used without further purification. m/z (ESI, +ve ion): 366.0 $(M+H)^+$.

Step 2: 7-Chloro-1-(2,6-diethylphenyl)pyrido[2,3-d]pyrimidine-2,4(1H,3H)-dione

LiHMDS (1 M in THF, 25 mL, 25 mmol) was added to a solution of 2,6-dichloro-N-((2,6-diethylphenyl)carbamoyl)nicotinamide (4.0 g, 11 mmol) in THF (100 mL). The reaction mixture was stirred at rt overnight. Additional KHMDS (1 M in THF, 10 mL) was added and the mixture was stirred for another hour. Satd ammonium chloride (20 mL), water (200 mL) and EtOAc (300 mL) were added. The organic layer was separated, washed with brine and concentrated in vacuo. The crude product was used without further purification. m/z (ESI, +ve ion): 330.0 $(M+H)^+$.

Step 3: 4,7-Dichloro-1-(2,6-diethylphenyl)pyrido[2,3-d]pyrimidin-2(1H)-one

Phosphorus oxychloride (1.6 mL, 10.3 mmol) was added to a mixture of 7-chloro-1-(2,6-diethylphenyl)pyrido[2,3-d]pyrimidine-2,4(1H,3H)-dione (1.1 g, 3.4 mmol) and DIPEA (1.8 mL, 10.3 mmol) in acetonitrile (23 mL). The resulting reaction mixture was heated at 80° C. for 30 min and subsequently concentrated in vacuo to give the 4,7-dichloro-1-(2,6-diethylphenyl)pyrido[2,3-d]pyrimidin-2(1H)-one as a brown solid. The product was used without further purification in the next step. m/z (ESI, +ve ion): 349.0 $(M+H)^+$.

Step 4: (S)-tert-Butyl 4-(7-chloro-1-(2,6-diethylphenyl)-2-oxo-1,2-dihydropyrido[2,3-d]pyrimidin-4-yl)-3-methylpiperazine-1-carboxylate A reaction mixture of 4,7-dichloro-1-(2,6-diethylphenyl)pyrido[2,3-d]pyrimidin-2(1H)-one (1.2 g, 3.4 mmol), (S)-tert-butyl 3-methylpiperazine-1-carboxylate (1.0 g, 5.1 mmol) and DIPEA (1.8 mL, 10 mmol) in DMF (15 mL) was stirred at rt for 15 min. Ice water (30 mL) was added and stirring was continued for 5 min. The precipitate was filtered off, washed with water, and dried to give (S)-tert-butyl 4-(7-chloro-1-(2,6-diethylphenyl)-2-oxo-1,2-dihydropyrido[2,3-d]pyrimidin-4-yl)-3-methylpiperazine-1-carboxylate (1.7 g, 97% yield), as a yellow solid. m/z (ESI, +ve ion): 513.2 $(M+H)^+$.

Step 5: (S)-4-(4-acryloyl-2-methylpiperazin-1-yl)-7-chloro-1-(2,6-diethylphenyl)pyrido[2,3-d]pyrimidin-2(1H)-one TFA (5.0 mL, 67 mmol) was added at rt to a solution of (S)-tert-butyl 4-(7-chloro-1-(2,6-diethylphenyl)-2-oxo-1,2- dihydropyrido[2,3-d]pyrimidin-4-yl)-3-methylpiperazine-1-carboxylate (1.7 g, 3.3 mmol) in DCM (10 mL). After 30 min, the reaction mixture was concentrated in vacuo to afford (S)-7-chloro-1-(2,6-diethylphenyl)-4-(2-methylpiperazin-1-yl)pyrido[2,3-d]pyrimidin-2(1H)-one, as a yellow solid. m/z (ESI, +ve ion): 412.2 (M+H)$^+$.

Acryloyl chloride (0.3 mL, 3.7 mmol) was added to a mixture of (S)-7-chloro-1-(2,6-diethylphenyl)-4-(2-methylpiperazin-1-yl)pyrido[2,3-d]pyrimidin-2(1H)-one, and DIPEA (2.3 mL, 13.3 mmol) in DCM (10 mL) at 0° C. After 1 h, the resulting mixture was concentrated in vacuo. The crude product was purified by silica gel chromatography (eluent: 0-100% of EtOAc-EtOH (3:1)/heptane) to provide (S)-4-(4-acryloyl-2-methylpiperazin-1-yl)-7-chloro-1-(2,6-diethylphenyl)pyrido[2,3-d]pyrimidin-2(1H)-one (1.6 g, 3.43 mmol) as a yellow solid. m/z (ESI, +ve ion): 466.2 (M+H)$^+$.

Step 6: (S)-4-(4-Acryloyl-2-methylpiperazin-1-yl)-1-(2,6-diethylphenyl)-7-(2-fluoro-6-hydroxyphenyl)pyrido[2,3-d]pyrimidin-2(1H)-one A mixture of tetrakis(triphenylphosphine)palladium (24.8 mg, 0.021 mmol), (S)-4-(4-acryloyl-2-methylpiperazin-1-yl)-7-chloro-1-(2,6-diethylphenyl)pyrido[2,3-d]pyrimidin-2(1H)-one (200 mg, 0.429 mmol), sodium carbonate (91 mg, 0.86 mmol) and 2-fluoro-6-hydroxyphenylboronic acid (134 mg, 0.86 mmol, Combi-Blocks, San Diego, Calif.) in 1,4-dioxane (2.0 mL)/water (1.0 mL) was heated to 80° C. for 3 h. The reaction mixture was diluted with water (10 mL) and extracted with EtOAc (20 mL). The organic layer was separated, dried over Na$_2$SO$_4$, and concentrated in vacuo. The resulting crude product was purified by silica gel chromatography (eluent: 0-100% EtOAc-EtOH (3:1)/heptane) to provide (S)-4-(4-acryloyl-2-methylpiperazin-1-yl)-1-(2,6-diethylphenyl)-7-(2-fluoro-6-hydroxyphenyl)pyrido[2,3-d]pyrimidin-2(1H)-one (50 mg, 0.092 mmol, 22% yield) as a yellow solid. $^1$H NMR (400 MHz, DMSO-d$_6$) δ ppm 11.67 (br. s., 1H) 8.48 (m, 1H) 7.75 (d, J=8.0 Hz, 1H) 7.41 (t, J=8.0 Hz, 1H) 7.29 (m, 3H) 6.85 (m, 1H) 6.76 (m, 1H) 6.62 (d, J=8.0 Hz, 1H) 6.20 (br m., 1H) 5.76 (m, 1H) 4.87 (br. m., 1H) 4.42 (br. m., 0.5H) 4.30 (br. m., 2H) 4.16 (br. m., 0.5H) 3.64 (br. m., 2H) 3.48 (br. m., 0.5H) 3.13 (br. m., 0.5H) 2.23 (m, 4H) 1.34 (d, J=8.0 Hz, 3H) 0.98 (m, 6H). m/z (ESI, +ve ion): 542.2 (M+H)$^+$.

Example 108

6-Ethyl-7-(2-fluorophenyl)-4-((2S)-2-methyl-4-(2-propenoyl)-1-piperazinyl)-1-(2-(2-propanyl)phenyl)-2(1H)-pteridinone

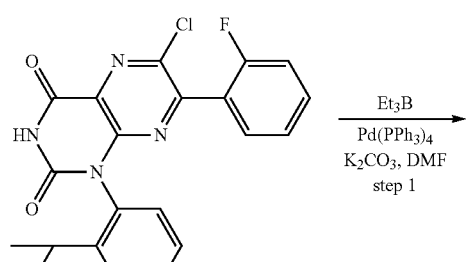

Intermediate Y

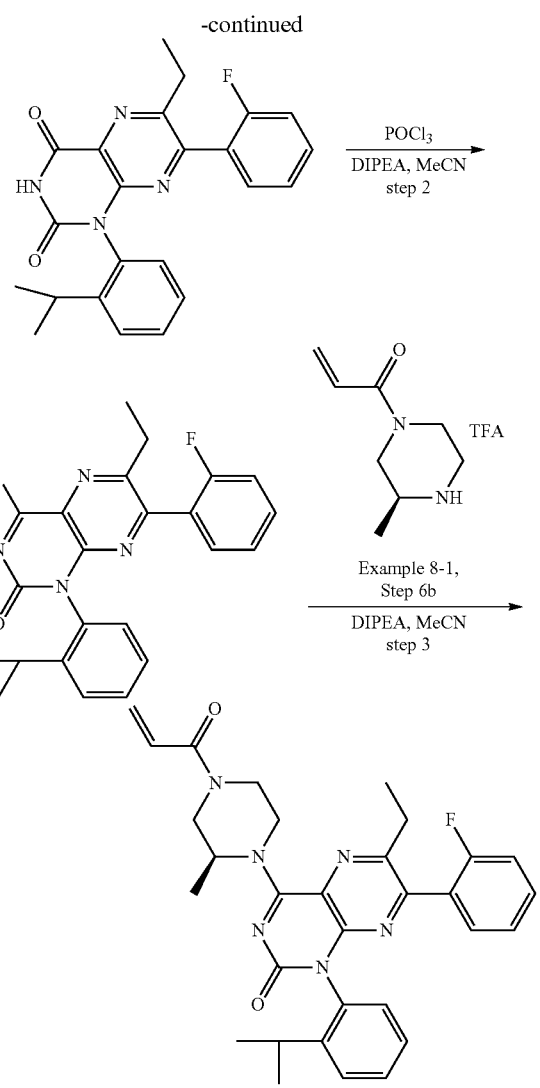

Step 1: 6-Ethyl-7-(2-fluorophenyl)-1-(2-isopropylphenyl)pteridine-2,4(1H,3H)-dione A reaction mixture of 6-chloro-7-(2-fluorophenyl)-1-(2-isopropylphenyl)pteridine-2,4(1H,3H)-dione (Intermediate Y, 0.69 g, 1.68 mmol), tetrakis(triphenylphosphine)palladium (0.097 g, 0.08 mmol), triethylborane (1 M in THF, 3.0 mL, 3.0 mmol), and potassium carbonate (0.35 g, 2.5 mmol) in DMF (2.0 mL) was purged with nitrogen for 5 min and then heated to 90° C. for 1 h. The reaction mixture was allowed to cool to rt and was partitioned between EtOAc and satd. ammonium chloride. The organic layer was dried over Na$_2$SO$_4$, and concentrated in vacuo. The crude product was purified by silica gel chromatography (eluent: 0-50% EtOAc/heptane) to provide 6-ethyl-7-(2-fluorophenyl)-1-(2-isopropylphenyl)pteridine-2,4(1H,3H)-dione as a light yellow solid. m/z (ESI, +ve ion): 405.0 (M+H)$^+$.

Step 2: 4-Chloro-6-ethyl-7-(2-fluorophenyl)-1-(2-isopropylphenyl)pteridin-2(1H)-one Phosphorus oxychloride (0.043 mL, 0.46 mmol) was added to a solution of 6-ethyl-7-(2-fluorophenyl)-1-(2-isopropylphenyl)pteridine-2,4(1H,3H)-dione (187 mg, 0.46 mmol), and DIPEA (0.14 mL, 0.79 mmol) in acetonitrile (4 mL). The resulting solution was heated 80° C. for 45 min. The reaction mixture was concentrated in vacuo to give 4-chloro-6-ethyl-7-(2-fluorophenyl)-1-(2-isopropylphenyl) pteridin-2(1H)-one. m/z (ESI, +ve ion): 418.9 (M+H)+.

Step 3: 6-Ethyl-7-(2-fluorophenyl)-4-((2S)-2-methyl-4-(2-propenoyl)-1-piperazinyl)-1-(2-(2-propanyl)phenyl)-2(1H)-pteridinone A solution of (S)-1-(3-methylpiperazin-1-yl)prop-2-en-1-one (TFA salt, Example 8-1, Step 6b, 372 mg, 0.56 mmol) in acetonitrile (0.5 mL) was added to a solution of 4-chloro-6-ethyl-7-(2-fluorophenyl)-1-(2-isopropylphenyl)pteridin-2(1H)-one (194 mg, 0.46 mmol), and DIPEA (0.32 mL, 1.84 mmol) in acetonitrile (3 mL) at 0° C. The reaction mixture was stirred at 0° C. for 1 h. The reaction mixture was warmed to rt, diluted with EtOAc (10 mL) and washed with water. The organic layer was dried over Na₂SO₄. and concentrated in vacuo. The crude product was purified by silica gel chromatography (eluent: 0-50% EtOAc-EtOH (3:1)/heptane) to provide 6-ethyl-7-(2-fluorophenyl)-4-((2S)-2-methyl-4-(2-propenoyl)-1-piperazinyl)-1-(2-(2-propanyl)phenyl)-2(1H)-pteridinone. ¹H NMR (400 MHz, DMSO-d₆) δ 7.48-7.63 (m, 2H), 7.41 (dt, J=7.9, 2.1 Hz, 1H), 7.19-7.37 (m, 4H), 7.10 (dt, J=7.7, 1.0 Hz, 1H), 6.80-6.95 (m, 1H), 6.21 (br d, J=16.8 Hz, 1H), 5.76 (dd, J=11.0, 1.4 Hz, 1H), 5.04-5.46 (m, 1H), 3.86-5.07 (m, 2H), 3.59-3.76 (m, 3H), 3.57-3.58 (m, 2H), 2.61-2.75 (m, 2H), 1.29-1.45 (m, 3H), 1.21 (t, J=7.4 Hz, 3H), 1.02-1.12 (m, 3H), 0.96 (d, J=6.8 Hz, 3H). m/z (ESI, +ve ion): 541.1 (M+H)+.

Example 109

7-(2-Fluorophenyl)-6-methoxy-4-((2S)-2-methyl-4-(2-propenoyl)-1-piperazinyl)-1-(2-(2-propanyl)phenyl)-2(1H)-pteridinone

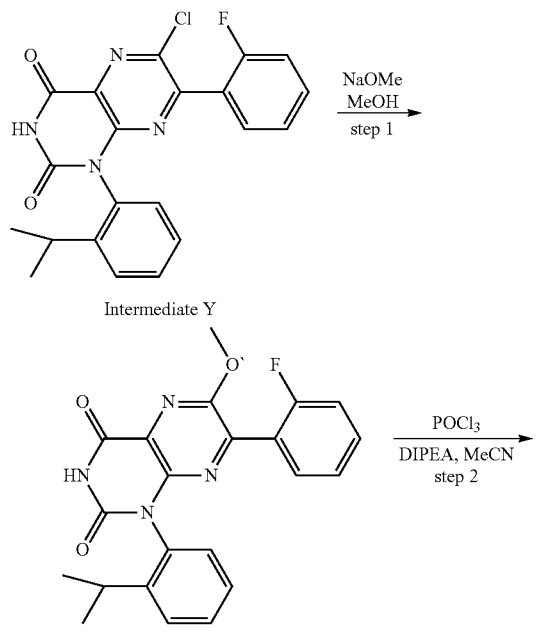

Intermediate Y

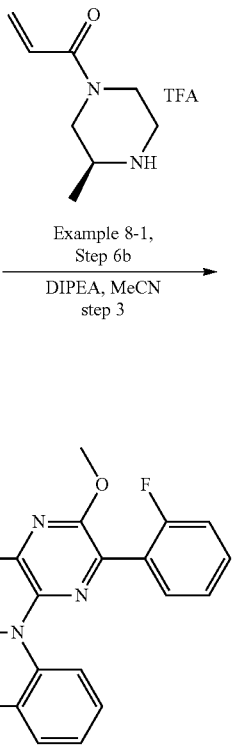

Step 1: 7-(2-Fluorophenyl)-1-(2-isopropylphenyl)-6-methoxypteridine-2,4(1H,3H)-dione A microwave reaction vessel was charged with 6-chloro-7-(2-fluorophenyl)-1-(2-isopropylphenyl)pteridine-2,4(1H,3H)-dione (Intermediate Y, 0.34 g, 0.83 mmol), sodium methoxide (0.5 M in MeOH, 5 mL, 2.5 mmol) and MeOH (4 mL). The reaction mixture was stirred and heated in a microwave reactor to 100° C. for 1 h. The reaction mixture was concentrated in vacuo and the residue was partitioned between EtOAc (10 mL) and satd. ammonium chloride (10 mL). The organic layer was washed with water, dried over Na₂SO₄, and concentrated in vacuo. The crude product was purified by silica gel chromatography (eluent: 0-40% EtOAc/heptane) to provide 7-(2-fluorophenyl)-1-(2-isopropylphenyl)-6-methoxypteridine-2,4(1H,3H)-dione as a light yellow solid: ¹H NMR (400 MHz, DMSO-d₆) δ ppm 12.04 (s, 1H), 7.49-7.55 (m, 1H), 7.46 (d, J=7.3 Hz, 1H), 7.40 (dt, J=8.1, 4.2 Hz, 1H), 7.22-7.33 (m, 5H), 3.98 (s, 3H), 2.84 (quin, J=6.8 Hz, 1H), 1.11 (d, J=6.8 Hz, 3H), 1.02 (d, J=6.8 Hz, 3H). m/z (ESI, +ve ion): 406.9 (M+H)+.

Step 2: 4-Chloro-7-(2-fluorophenyl)-1-(2-isopropylphenyl)-6-methoxypteridin-2(1H)-one Phosphorus oxychloride (0.03 mL, 0.32 mmol) was added to a solution of 7-(2-fluorophenyl)-1-(2-isopropylphenyl)-6-methoxypteridine-2,4(1H,3H)-dione (131 mg, 0.32 mmol), and DIPEA (0.096 mL, 0.55 mmol) in acetonitrile (3 mL). The reaction mixture was heated to 80° C. for 1.5 h. The reaction mixture was concentrated in vacuo to give 4-chloro-7-(2-fluorophenyl)-1-(2-isopropylphenyl)-6-methoxypteridin-2(1H)-one. m/z (ESI, +ve ion): 420.8 (M+H)+.

Step 3: 7-(2-Fluorophenyl)-6-methoxy-4-((2S)-2-methyl-4-(2-propenoyl)-1-piperazinyl)-1-(2-(2-propanyl)phenyl)-2(1H)-pteridinone A solution of (S)-1-(3-methylpiperazin-1-yl)prop-2-en-1-one (TFA salt, Example 8-1, Step 6b, 259 mg, 0.39 mmol) in acetonitrile (0.5 mL) was added to a solution of 4-chloro-7-(2-fluorophenyl)-1-(2-isopropylphenyl)-6-methoxypteridin-2(1H)-one (136 mg, 0.32 mmol), and DIPEA (0.23 mL, 1.28 mmol) in acetonitrile (3 mL) at 0° C. The reaction mixture was stirred at 0° C. for 1 h. The reaction mixture was allowed to warm to rt and then diluted with EtOAc (10 mL) and washed with water. The organic layer was dried over Na$_2$SO$_4$, and concentrated in vacuo. The crude product was purified by silica gel chromatography (eluent: 0-50% EtOAc-EtOH (3:1)/heptane) to provide 7-(2-fluorophenyl)-6-methoxy-4-((2S)-2-methyl-4-(2-propenoyl)-1-piperazinyl)-1-(2-(2-propanyl)phenyl)-2(1H)-pteridinone as a light yellow solid. $^1$H NMR (400 MHz, DMSO-d$_6$) δ ppm 7.47-7.55 (m, 1H), 7.43 (dt, J=7.9, 1.3 Hz, 1H), 7.36 (tt, J=7.5, 1.4 Hz, 1H), 7.25-7.32 (m, 3H), 7.23 (dd, J=7.0, 1.4 Hz, 1H), 7.11 (td, J=7.8, 1.0 Hz, 1H), 6.79-6.97 (m, 1H), 6.21 (br d, J=16.8 Hz, 1H), 5.76 (dd, J=10.5, 2.0 Hz, 1H), 4.00-4.53 (m, 3H), 3.96 (s, 3 H), 3.37-3.83, m, 2H), 2.56-2.74 (m, 2H), 1.21-1.51 (m, 4H), 1.10 (t, J=6.3 Hz, 3H), 0.98 (d, J=5.8 Hz, 3H). m/z (ESI, +ve ion) 542.9 (M+H)$^+$.

Example 110

6-Chloro-7-(2-fluorophenyl)-4-((2S)-2-methyl-4-(2-propenoyl)-1-piperazinyl)-1-(2-(2-propanyl)phenyl)pyrido[3,2-d]pyrimidin-2(1H)-one

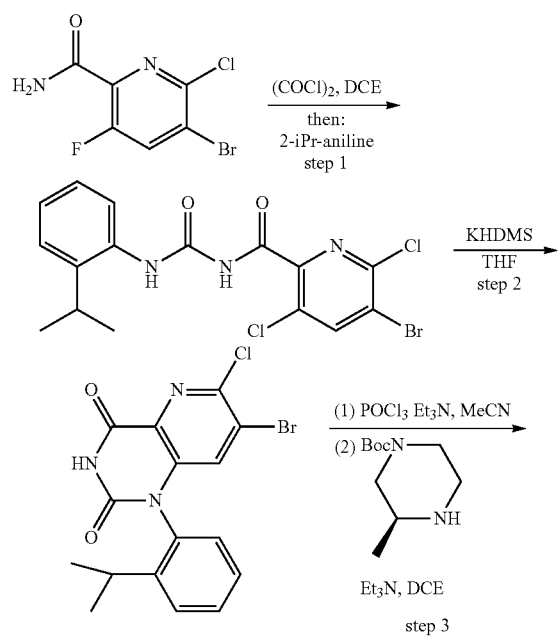

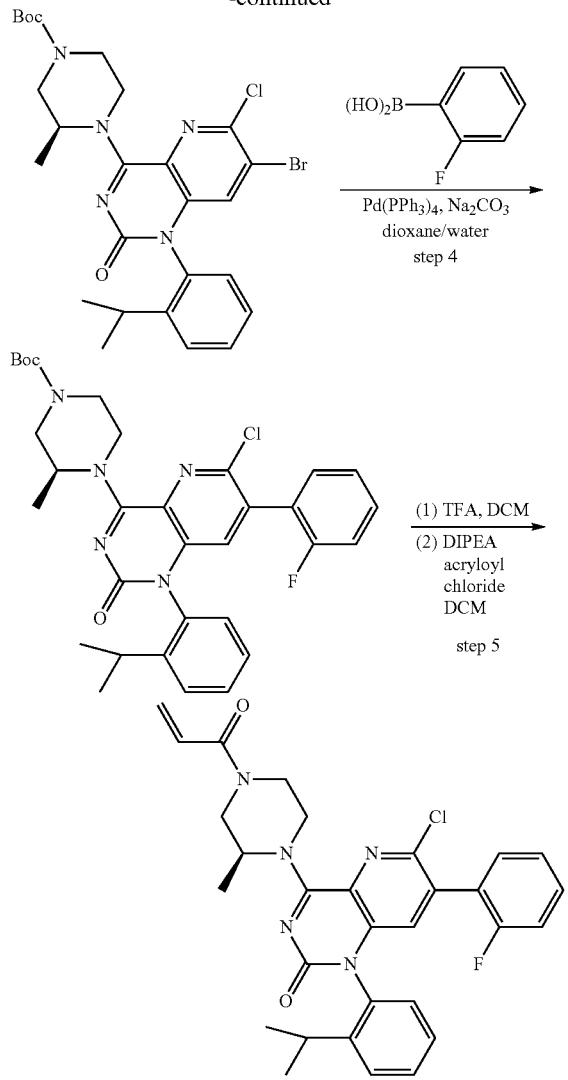

Step 1: 5-Bromo-3,6-dichloro-N-((2-isopropylphenyl)carbamoyl)picolinamide

This material was prepared according to Method 8, Step 2, using 5-bromo-3,6-dichloropicolinamide (3.3 g, 12 mmol, Sigma-Aldrich Corporation, St. Louis, Mo., USA) and 2-isopropylaniline (2.0 mL, 15 mmol, Sigma-Aldrich Corporation, St. Louis, Mo., USA). m/z (ESI, +ve ion): 429.8 (M+H)$^+$.

Step 2: 7-Bromo-6-chloro-1-(2-isopropylphenyl)pyrido[3,2-d]pyrimidine-2,4(1H,3H)-dione This material was prepared according to Method 8, Step 3, using 5-bromo-3,6-dichloro-N-((2-isopropylphenyl)carbamoyl)picolinamide (2.55 g, 5.91 mmol). m/z (ESI, +ve ion): 393.8 (M+H)$^+$.

Step 3: (S)-tert-Butyl 4-(7-bromo-6-chloro-1-(2-isopropylphenyl)-2-oxo-1,2 dihydropyrido[3,2-d]pyrimidin-4-yl)-3-methylpiperazine-1-carboxylate This material was prepared in 44%0/overall yield (1.5 g) according to Method 8, Steps 5 and 6, using 7-bromo-6- chloro-1-(2-isopropylphenyl)pyrido[3,2-d]pyrimidine-2,4 (1H,3H)-dione (2.3 g, 5.9 mmol) and tert-butyl (S)-3-methylpiperazine-1-carboxylate (1.6 g, 8.0 mmol). $^1$H NMR (400 MHz, MeOH-d$_4$) δ ppm 7.62 (d, J=7.32 Hz 1H), 7.58 (t, J=7.46 Hz, 1H), 7.44 (t, J=6.86 Hz, 1H), 7.19 (t, J=6.27 Hz, 1H), 7.14 (s, 1H), 4.83-6.12 (m, 2H), 3.51-4.34 (m, 3H), 3.35-3.46 (m, 1H), 3.05-3.26 (m, 1H), 2.44-2.76 (m, 1H), 1.40-1.57 (m, 12H), 1.19-1.22 (m, 3H), 1.04-1.11 (m, 3H). m/z (ESI, +ve ion): 576.0 (M+H)$^+$.

Step 4: (S)-tert-Butyl 4-(6-chloro-7-(2-fluorophenyl)-1-(2-isopropylphenyl)-2-oxo-1,2-dihydropyrido[3,2-d]pyrimidin-4-yl)-3-methylpiperazine-1-carboxylate A reaction mixture of (2-fluorophenyl)boronic acid (0.1 g, 0.715 mmol, Combi-Blocks, Inc., San Diego, Calif.), palladium tetrakis (0.032 g, 0.028 mmol, Strem Chemicals. Newburyport, Mass., USA), saturated sodium bicarbonate (1.0 mL, 1.19 mmol), and (S)-tert-butyl 4-(7-bromo-6-chloro-1-(2-isopropylphenyl)-2-oxo-1,2-dihydropyrido[3,2-d]pyrimidin-4-yl)-3-methylpiperazine-1-carboxylate (0.30 g, 0.52 mmol) in 1,4-dioxane (5.0 mL) and water (0.1 mL) was placed under nitrogen atmosphere and heated to 70° C. After 1 h, sodium carbonate (0.032 mL, 0.755 mmol) was added and the mixture was heated for an additional 16 h. The reaction mixture was allowed to cool to rt and diluted with EtOAc (15 mL) and brine (5 mL). The organic layer was dried over Na$_2$SO$_4$, and purified by silica gel chromatography (eluent: 20-70% EtOAc/heptane) to provide (S)-tert-butyl 4-(6-chloro-7-(2-fluorophenyl)-1-(2-isopropylphenyl)-2-oxo-1,2-dihydropyrido[3,2-d]pyrimidin-4-yl)-3-methylpiperazine-1-carboxylate (0.22 g, 0.372 mmol, 71.5% yield). $^1$H NMR (400 MHz, CDCl$_3$) δ ppm 7.31-7.55 (m, 4H), 7.08-7.23 (m, 4H), 6.81 (s, 1H), 5.41-6.29 (m, 1H), 4.88-5.23 (m, 1H), 3.85-4.30 (m, 2H), 3.33 (br s, 3H), 2.66-2.80 (m, 1H), 1.52 (s, 12H), 1.20-1.28 (m, 3H), 1.03-1.13 (m, 3H). $^{19}$F NMR (377 MHz, CDCl$_3$) δ −113.72, 113.75 (2s, 1F). m/z (ESI, +ve ion): 592.1 (M+H)$^+$.

Step 5: (S)-4-(4-Acryloyl-2-methylpiperazin-1-yl)-6-chloro-7-(2-fluorophenyl)-1-(2-isopropylphenyl)pyrido[3,2-d]pyrimidin-2(1H)-one TFA (1.5 mL, 19.6 mmol) was added to a mixture of (S)-tert-butyl 4-(6-chloro-7-(2-fluorophenyl)-1-(2-isopropylphenyl)-2-oxo-1,2-dihydropyrido[3,2-d]pyrimidin-4-yl)-3-methylpiperazine-1-carboxylate (0.34 g, 0.574 mmol) in DCM (8 mL). After 1 h, the solvent was evaporated under reduced pressure. The residue was dissolved in EtOAc and washed with satd NaHCO$_3$ and brine. The organic layer was dried over Na$_2$SO$_4$, and concentrated in vacuo. The residue was taken up in DCM (5 mL), followed by the addition of DIPEA (0.25 mL, 1.44 mmol) and acryloyl chloride (0.06 mL, 0.738 mmol). After 30 min. EtOAc was added and the mixture was washed with satd NaHCO$_3$ and brine. The organic layer was dried over Na$_2$SO$_4$, and concentrated in vacuo. The crude product was purified by silica gel chromatography (eluent: 5-40% EtOAc-EtOH (3:1)/heptane) to give (S)-4-(4-acryloyl-2-methylpiperazin-1-yl)-6-chloro-7-(2-fluorophenyl)-1-(2-isopropylphenyl)pyrido[3,2-d]pyrimidin-2(1H)-one (0.249 g, 0.456 mmol, 79% yield) as a white powder. $^1$H NMR (400 MHz, CDCl$_3$) δ ppm 7.25-7.51 (m, 4H), 7.05-7.18 (m, 4H), 6.78 (s, 1H), 6.58 (br d, J=9.95 Hz, 1H), 6.32-6.39 (m, 1H), 5.83-6.31 (m, 1H), 5.74 (br d. J=10.16 Hz, 1H), 4.84-5.67 (m, 1H), 4.58 (br s, 1H), 3.01-4.07 (m, 4H), 2.56-2.80 (m, 1H), 1.45 (br, 3H), 1.19 (d, J=6.84 Hz, 3H), 1.03 (d, J=6.84 Hz, 3H). $^{19}$F NMR (376 MHz, (CDCl$_3$) 5-113.73 (br d, J=10.41 Hz, 1F). m/z (ESI, +ve ion): 545.9 (M+H)$^+$.

Example 111

6-Chloro-7-(2-fluorophenyl)-1-(4-methyl-2-(2-propanyl)-3-pyridinyl)-4-((2S)-2-methyl-4-(2-propenoyl)-1-piperazinyl)-2(1H)-pteridinone

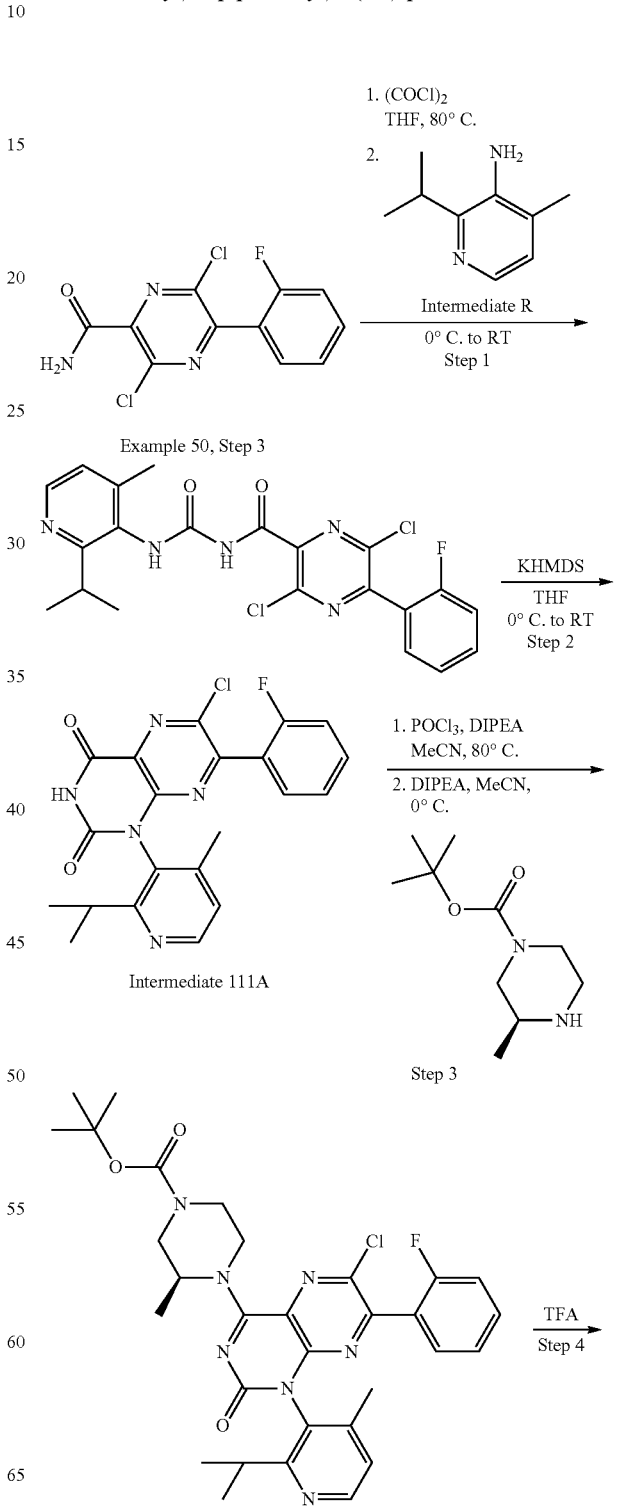

-continued

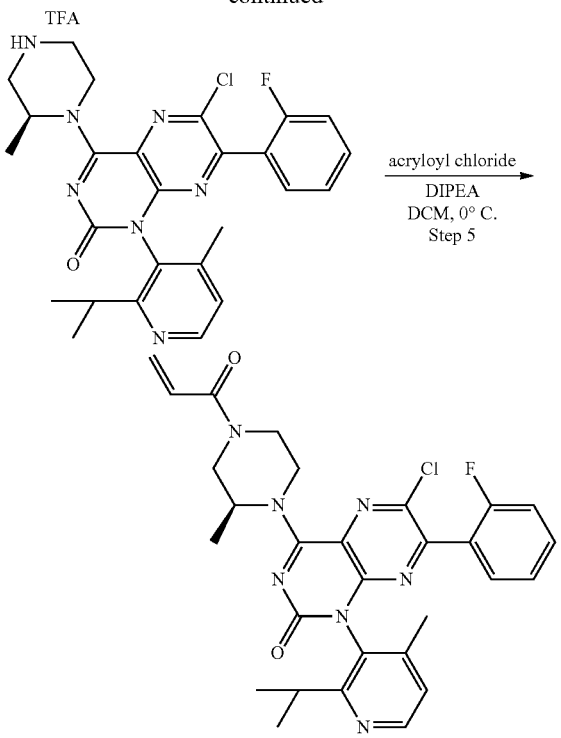

Step 1: 3,6-Dichloro-5-(2-fluorophenyl)-N-((2-isopropyl-4-methylpyridin-3-yl)carbamoyl)pyrazine-2-carboxamide A mixture of 3,6-dichloro-5-(2-chloride (2 M in DCM 2.8 mL, 5.6 mmol) in THF (25 mL) was heated to 80° C. for 2 h. The reaction mixture was then cooled to 0° C. and 2-isopropyl-4-methylpyridin-3-amine (Intermediate R, 0.8 g, 5.34 mmol) was added. The cold bath was removed and stirring was continued at rt for 45 min. The reaction mixture was concentrated in vacuo, the residue was taken up in EtOAc. and sonicated. The precipitate was filtered off and dried to give 3,6-dichloro-5-(2-fluorophenyl)-N-((2-isopropyl-4-methylpyridin-3-yl)carbamoyl)pyrazine-2-carboxamide as a light yellow solid. m/z (ESI, +ve ion): 461.8 and 463.8 (M+H)$^+$.

Step 2: 6-Chloro-7-(2-fluorophenyl)-1-(2-isopropyl-4-methylpyridin-3-yl)pteridine-2,4(1H,3H)-dione (Intermediate 111A)

KHMDS (1 M in THF, 5.3 mL, 5.3 mmol) was added to a solution of 3,6-dichloro-5-(2-fluorophenyl)-N-((2-isopropyl-4-methylpyridin-3-yl)carbamoyl)pyrazine-2-carboxamide (1.22 g, 2.64 mmol) in THF (15 mL) at 0° C. The reaction mixture was allowed to warm to rt over a period of 1 h. The reaction mixture was then diluted with EtOAc and washed with satd. ammonium chloride. The organic layer was dried over Na$_2$SO$_4$, and concentrated in vacuo. The crude product was purified by silica gel chromatography (eluent: 0-50% EtOAc/heptane) to provide 6-chloro-7-(2-fluorophenyl)-1-(2-isopropyl-4-methylpyridin-3-yl)pteridine-2,4(1H,3H)-dione (Intermediate 111A) as a light yellow solid: H NMR (400 MHz, DMSO-d$_6$) δ ppm 12.40 (s, 1H), 8.44 (br d, J=4.6 Hz, 1H), 7.52-7.62 (m, 1H), 7.28-7.39 (m, 3H), 7.21 (br d, J=4.6 Hz, 1H), 3.03 (dt, J=12.7, 6.4 Hz, 1H), 2.07 (s, 3H), 1.07 (br d, J=6.6 Hz, 3H), 0.95 (br d, J=6.4 Hz, 3H). m/z (ESI, +ve) 425.9 and 427.9 (M+H)$^+$.

Step 3: tert-Butyl (S)-4-(6-chloro-7-(2-fluorophenyl)-1-(2-isopropyl-4-methylpyridin-3-yl)-2-oxo-1,2-dihydropteridin-4-yl)-3-methylpiperazine-1-carboxylate Phosphorus oxychloride (0.11 mL, 1.2 mmol) was added to a solution of 6-chloro-7-(2-fluorophenyl)-1-(2-isopropyl-4-methylpyridin-3-yl)pteridine-2,4(1H,3H)-dione (Intermediate 111A, 341 mg, 0.8 mmol), and DIPEA (0.24 mL, 1.36 mmol) in acetonitrile (5 mL). The reaction mixture was heated to 80° C. for 30 min and then cooled to 0° C. DIPEA (0.42 mL, 2.4 mmol) was added, followed by tert-butyl (S)-3-methylpiperazine-1-carboxylate (241 mg, 1.2 mmol, Combi-Blocks, San Diego, Calif.) in acetonitrile (1 mL). The reaction mixture was stirred at 0° C. for 30 min and the allowed to warm to rt. The reaction mixture was diluted with EtOAc (10 mL) and washed with water. The organic layer was dried over Na$_2$SO$_4$, and concentrated in vacuo. The crude product was purified by silica gel chromatography (eluent: 0-3% MeOH/DCM) to provide tert-butyl (S)-4-(6-chloro-7-(2-fluorophenyl)-1-(2-isopropyl-4-methylpyridin-3-yl)-2-oxo-1,2-dihydropteridin-4-yl)-3-methylpiperazine-1-carboxylate as a light yellow solid. m/z (ESI, +ve ion): 607.8 and 609.8 (M+H)$^+$.

Step 4: (S)-6-Chloro-7-(2-fluorophenyl)-1-(2-isopropyl-4-methylpyridin-3-yl)-4-(2-methylpiperazin-1-yl)pteridin-2(1H)-one TFA (0.8 mL, 7.23 mmol) was added to a solution of tert-butyl (S)-4-(6-chloro-7-(2-fluorophenyl)-1-(2-isopropyl-4-methylpyridin-3-yl)-2-oxo-1,2-dihydropteridin-4-yl)-3-methylpiperazine-1-carboxylate (293 mg, 0.48 mmol) in DCM (5 mL). After 30 min, the reaction mixture was concentrated in vacuo to provide (S)-6-chloro-7-(2-fluorophenyl)-1-(2-isopropyl-4-methylpyridin-3-yl)-4-(2-methylpiperazin-1-yl)pteridin-2(1H)-one trifluoroacetate. m/z (ESI, +ve ion): 507.8 and 509.8 (M+H)$^+$.

Step 5: 6-Chloro-7-(2-fluorophenyl)-1-(4-methyl-2-(2-propanyl)-3-pyridinyl)-4-((2S)-2-methyl-4-(2-propenoyl)-1-piperazinyl)-2(1H)-pteridinone A solution of acryloyl chloride (0.039 mL, 0.51 mmol) in DCM (0.5 mL) was added to a solution of (S)-6-chloro-7-(2-fluorophenyl)-1-(2-isopropyl-4-methylpyridin-3-yl)-4-(2-methylpiperazin-1-yl)pteridin-2(1H)-one (245 mg, 0.48 mmol) and iPr$_2$NEt (0.34 mL, 1.93 mmol) in DCM (5 mL) at 0° C. The reaction mixture was stirred at 0° C. for 30 min, quenched with satd. NaHCO$_3$ (5 mL) and extracted with EtOAc (10 mL). The organic layer was washed with brine (5 mL), dried over Na$_2$SO$_4$, and concentrated in vacuo. The crude product was purified by silica gel chromatography (eluent: 0-40% EtOAc-EtOH (3:1)/heptane) to provide 6-chloro-7-(2-fluorophenyl)-1-(4-methyl-2-(2-propanyl)-3-pyridinyl)-4-((2S)-2-methyl-4-(2-propenoyl)-1-piperazinyl)-2(1H)-pteridinone as an off-white solid. $^1$H NMR (400 MHz, DMSO-d$_6$) δ ppm 8.41 (d, J=4.8 Hz, 1H), 7.50-7.66 (m, 1H), 7.26-7.42 (m, 3H), 7.20 (d, J=4.8 Hz, 1H), 6.89 (br dd, J=16.6, 10.8 Hz, 1H), 6.22 (br d, J=17.2 Hz, 1H), 5.76 (dd, J=10.2, 1.9 Hz, 1H), 4.15-4.40 (m, 2H), 3.65-3.75 (m, 2H), 3.50-3.61 (m, 2H), 2.75-2.91 (m, 1H), 1.95-2.01 (m, 3H), 1.21-1.54 (m, 4H), 1.07 (t, J=5.9 Hz, 3H), 0.96 (dd, J=6.6, 4.2 Hz, 3H). m/z (ESI, +ve ion) 561.8 and 563.8 (M+H)$^+$.

Example 112

(M)-6,7-Dichloro-1-(2-methyl-6-(2-propanyl)phenyl)-4-((2S)-2-methyl-4-(2-propenoyl)-1-piperazinyl)pyrido[2,3-d]pyrimidin-2(1H)-one

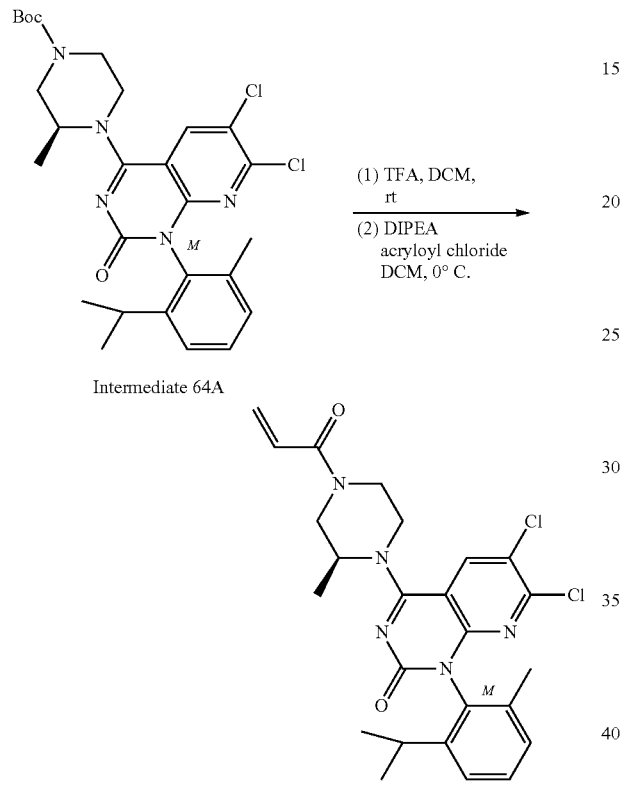

Intermediate 64A

TFA (0.8 mL) was added to a solution of (M)-(S)-tert-butyl 4-(6,7-dichloro-1-(2-isopropyl-6-methylphenyl)-2-oxo-1,2-dihydropyrido[2,3-d]pyrimidin-4-yl)-3-methylpiperazine-1-carboxylate (Intermediate 64A, 105 mg, 0.192 mmol) in DCM (1.5 mL). The resulting mixture was stirred for 30 min at rt and concentrated in vacuo. The resulting residue was re-dissolved in DCM (1 mL) and the solution was cooled to 0° C. DIPEA (0.17 mL, 0.96 mmol) and acryloyl chloride, (0.38 M in DCM, 0.5 mL, 0.19 mmol) were sequentially added and the resulting mixture was stirred for 2 h. The reaction mixture was cooled to 0° C., followed by the addition of satd. NaHCO$_3$ (10 mL), water (25 mL) and DCM (25 mL). The aqueous layer was extracted with DCM (2×20 mL). The combined organic extracts were dried over MgSO$_4$ and concentrated in vacuo. The crude product was purified by silica gel chromatography (eluent: 0-100% EtOAc-EtOH (3:1)/heptane) to provide (M)-6,7-dichloro-1-(2-methyl-6-(2-propanyl)phenyl)-2-propenoyl)-1-piperazinyl)pyrido[2,3-d]pyrimidin-2(1H)-one. $^1$H NMR (400 MHz, DMSO-d$_6$) δ ppm 0.99 (d, J=6.8 Hz, 3H), 1.05 (d, J=6.8 Hz, 3H), 1.28 (br d, J=6.6 Hz, 3H), 1.89 (s, 3H), 2.38-2.46 (m, 1H), 2.93-3.12 (m, 0.5H), 3.18-3.27 (m, 0.5H), 3.35-3.46 (m, 0.5H), 3.62 (d, J=11.6 Hz, 1H), 3.73 (q, J=11.7 Hz, 1H), 3.95-4.05 (m, 0.5H), 4.11-4.19 (m, 1.5H), 4.24-4.31 (m, 0.5H), 4.32-4.44 (m, 0.5H), 4.90 (br s, 1H), 5.69-5.80 (m, 1H), 6.20 (br d, J=16.6 Hz, 1H), 6.77-6.94 (m, 1H), 7.18 (dd, J=7.2, 1.4 Hz, 1H), 7.27-7.37 (m, 2H), 8.47 (br s, 1H). m/z (ESI. +ve ion): 500.0 (M+H)$^+$.

Example 113

7-(5-Chloro-2-hydroxyphenyl)-6-fluoro-1-(2-methyl-6-(2-propanyl)phenyl)-4-((2S)-2-methyl-4-(2-propenoyl)-1-piperazinyl)pyrido[2,3-d]pyrimidin-2(1H)-one. (M Atropisomer from P1, No X-Ray)

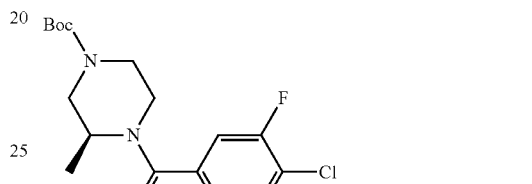

Intermediate 68A

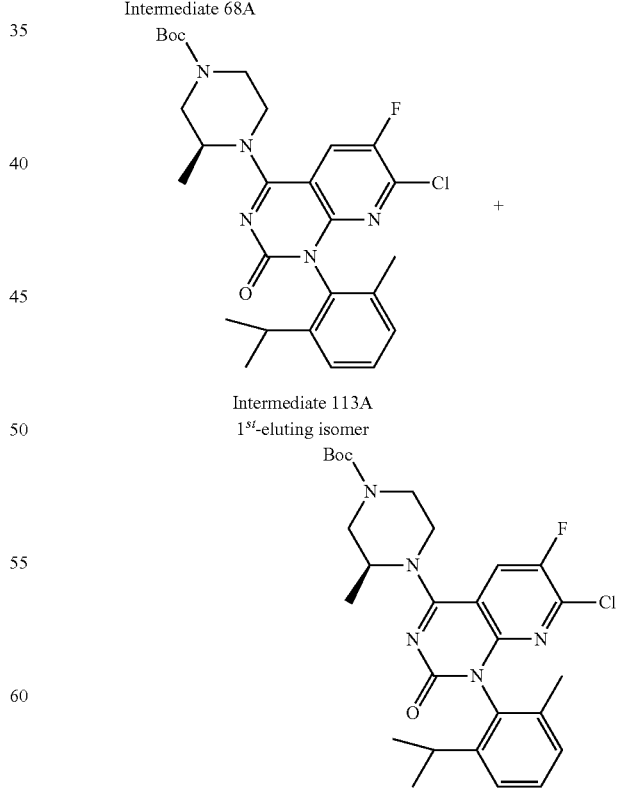

Intermediate 113A
1$^{st}$-eluting isomer

Intermediate 113B
2$^{nd}$-eluting isomer

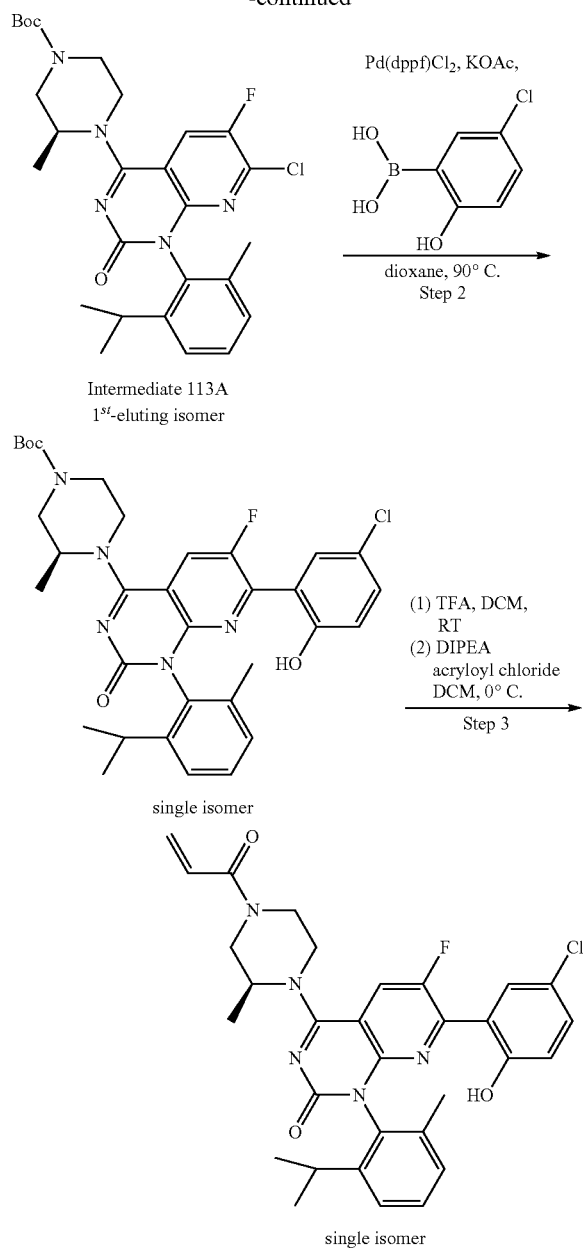

Step 1: (S)-tert-Butyl 4-(7-chloro-6-fluoro-1-(2-isopropyl-6-methylphenyl)-2-oxo-1,2-dihydropyrido[2,3-d]pyrimidin-4-yl)-3-methylpiperazine-1-carboxylate (Intermediate 113A)

Atropisomers of (S)-tert-butyl 4-(7-chloro-6-fluoro-1-(2-isopropyl-6-methylphenyl)-2-oxo-1,2-dihydropyrido[2,3-d]pyrimidin-4-yl)-3-methylpiperazine-1-carboxylate (Intermediate 68A) were separated by SFC [(S,S) Whelk-01, 30×250 mm, 40% iPrOH/CO₂, 100 g/min, 100 bar] to give (S)-tert-butyl 4-(7-chloro-6-fluoro-1-(2-isopropyl-6-methylphenyl)-2-oxo-1,2-dihydropyrido[2,3-d]pyrimidin-4-yl)-3-methylpiperazine-1-carboxylate (1S-eluting isomer, Intermediate 113A) and (S)-tert-butyl 4-(7-chloro-6-fluoro-1-(2-isopropyl-6-methylphenyl)-2-oxo-1,2-dihydropyrido[2,3-d]pyrimidin-4-yl)-3-methylpiperazine-1-carboxylate ($2^{nd}$-eluting isomer, Intermediate 113B). m/z (ESI, +ve ion): 530.0 (M+H)⁺.

Step 2: (S)-tert-Butyl 4-(7-(5-chloro-2-hydroxyphenyl)-6-fluoro-1-(2-isopropyl-6-methylphenyl)-2-oxo-1,2-dihydropyrido[2,3-d]pyrimidin-4-yl)-3-methylpiperazine-1-carboxylate A reaction mixture of (S)-tert-butyl 4-(7-chloro-6-fluoro-1-(2-isopropyl-6-methylphenyl)-2-oxo-1,2-dihydropyrido[2,3-d]pyrimidin-4-yl)-3-methylpiperazine-1-carboxylate (Intermediate 113A, 400 mg, 0.76 mmol), 5-chloro-2-hydroxyphenylboronic acid (195 mg, 1.13 mmol, CombiPhos Catalyst. Trenton, N.J.), Pd(dppf)Cl₂ (62 mg, 0.075 mmol), potassium acetate (370 mg, 3.8 mmol) in 1,4-dioxane (3.7 mL), and water (0.1 mL) was purged with nitrogen for 10 min. The reaction mixture was heated 90° C. for 90 min, and was then partitioned between water (50 mL) and EtOAc (50 mL). The aqueous phase was extracted with EtOAc. The combined organic layers were dried over MgSO₄ and concentrated in vacuo to give (S)-tert-butyl 4-(7-(5-chloro-2-hydroxyphenyl)-6-fluoro-1-(2-isopropyl-6-methylphenyl)-2-oxo-1,2-dihydropyrido[2,3-d]pyrimidin-4-yl)-3-methylpiperazine-1-carboxylate which was used without further purification in the following step. m/z (ESI. +ve ion): 622.2 (M+H)⁺.

Step 3: (S)-4-(4-Acryloyl-2-methylpiperazin-1-yl)-7-(5-chloro-2-hydroxyphenyl)-6-fluoro-1-(2-isopropyl-6-methylphenyl)pyrido[2,3-d]pyrimidin-2(1H)-one TFA (2.5 mL) was added to a solution of (S)-tert-butyl 4-(7-(5-chloro-2-hydroxyphenyl)-6-fluoro-1-(2-isopropyl-6-methylphenyl)-2-oxo-1,2-dihydropyrido[2,3-d]pyrimidin-4-yl)-3-methylpiperazine-1-carboxylate (470 mg, 0.76 mmol) in DCM (5 mL). The resulting mixture was stirred for 30 min at rt and then concentrated in vacuo. The resulting residue was re-dissolved in DCM (3 mL) and cooled to 0° C. DIPEA (0.66 mL, 3.8 mmol) and acryloyl chloride (0.38 M in DCM, 2 mL, 0.76 mmol) were sequentially added and the resulting mixture was stirred for 5 h. The reaction mixture was cooled to 0° C., followed by the addition of satd. NaHCO₃ (20 mL), water (20 mL) and DCM (15 mL). The aqueous layer was extracted with DCM. The combined organic extracts were dried over MgSO₄ and then concentrated in vacuo. The crude product was purified by silica gel chromatography (eluent: 0-60% EtOAc-EtOH (3:1)/heptane) to provide 7-(5-chloro-2-hydroxyphenyl)-6-fluoro-1-(2-methyl-6-(2-propanyl)phenyl)-4-((2S)-2-methyl-4-(2-propenoyl)-1-piperazinyl)pyrido[2,3-d]pyrimidin-2(1H)-one. ¹H NMR (400 MHz, DMSO-d₆) δ ppm 0.97 (br d, J=6.8 Hz, 3H), 1.07 (br d, J=6.6 Hz, 3H), 1.31 (br d, J=6.4 Hz, 3H), 1.88 (br s, 3H), 3.03-3.19 (m, 0.5H), 3.42-3.54 (m, 0.5H), 3.61-3.78 (m, 1.5H), 4.03 (br d, J=7.5 Hz, 0.5H), 4.15 (br d, J=13.1 Hz, 0.5H), 4.20-4.33 (m, 1.5H), 4.41 (br d, J=12.9 Hz, 0.5H), 4.89 (br s, 1H) 5.72-5.83 (m, 1H) 6.21 (br d, J=15.8 Hz, 1H), 6.78-6.96 (m, 2H) 7.19 (br d, J=6.6 Hz, 1H), 7.26-7.44 (m, 4H) 8.31 (br t, J=10.1 Hz, 1H), 10.69 (br s, 1H). ¹⁹F NMR (376 MHz, DMSO-d₆) δ ppm −126.4 (s, 1F). m/z (ESI, +ve ion): 576.2 (M+H)⁺.

Example 114

7-(5-Chloro-2-hydroxyphenyl)-6-fluoro-1-(2-methyl-6-(2-propanyl)phenyl)-4-((2S)-2-methyl-4-(2-propenoyl)-1-piperazinyl)pyrido[2,3-d]pyrimidin-2(1H)-one. (P Atropisomer from Peak 2, No X-Ray)

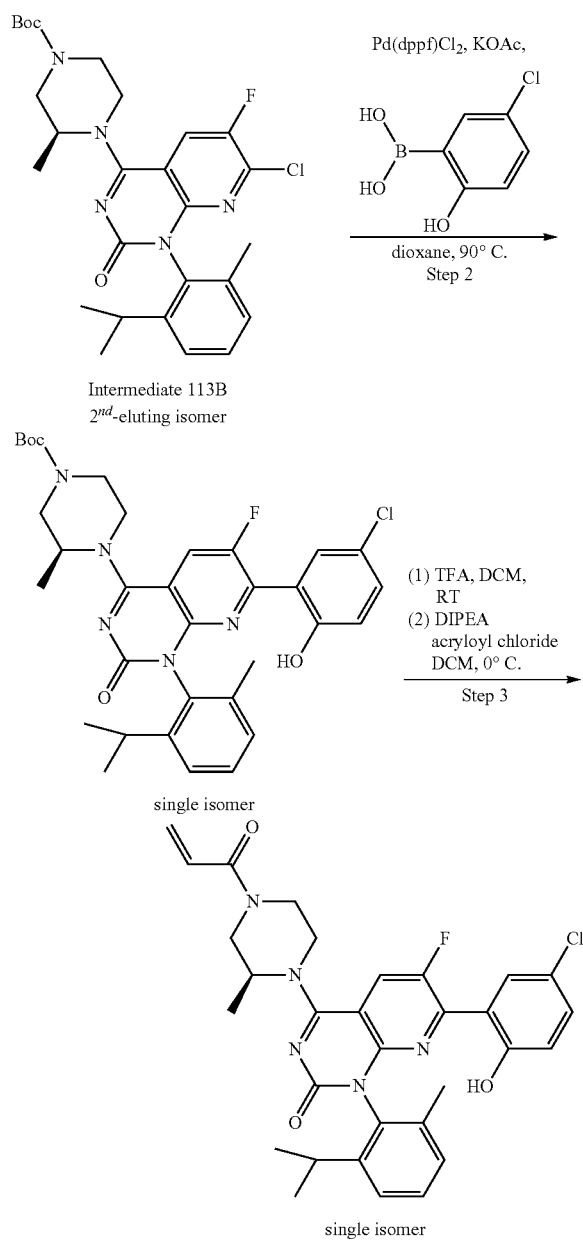

Step 1: (S)-tert-Butyl 4-(7-(5-chloro-2-hydroxyphenyl)-6-fluoro-1-(2-isopropyl-6-methylphenyl)-2-oxo-1,2-dihydropyrido[2,3-d]pyrimidin-4-yl)-3-methylpiperazine-1-carboxylate A mixture of (S)-tert-butyl 4-(7-chloro-6-fluoro-1-(2-isopropyl-6-methylphenyl)-2-oxo-1,2-dihydropyrido[2,3-d]pyrimidin-4-yl)-3-methylpiperazine-1-carboxylate (Intermediate 113B, 400 mg, 0.76 mmol), 5-chloro-2-hydroxyphenylboronic acid (220 mg, 1.28 mmol, CombiPhos Catalyst, Trenton, N.J., USA), Pd(dppf)Cl$_2$ (78 mg, 0.096 mmol), potassium acetate (370 mg, 3.8 mmol) in 1,4-dioxane (3.7 mL), and water (0.1 mL) was purged with argon for 10 min. The reaction mixture was heated to 70° C. for 18 h, followed by partitioning between water (50 mL) and EtOAc (50 mL). The aqueous layer was washed with EtOAc. The combined organic extracts were dried over MgSO$_4$ and concentrated in vacuo to give (S)-tert-butyl 4-(7-(5-chloro-2-hydroxyphenyl)-6-fluoro-1-(2-isopropyl-6-methylphenyl)-2-oxo-1,2-dihydropyrido[2,3-d]pyrimidin-4-yl)-3-methylpiperazine-1-carboxylate which was used without further purification in the following step. m/z (ESI, +ve ion): 622.2 (M+H)$^+$.

Step 2: (S)-4-(4-acryloyl-2-methylpiperazin-1-yl)-7-(5-chloro-2-hydroxyphenyl)-6-fluoro-1-(2-isopropyl-6-methylphenyl)pyrido[2,3-d]pyrimidin-2(1H)-one TFA (2.5 mL) was added to a solution of (S)-tert-butyl 4-(7-(5-chloro-2-hydroxyphenyl)-6-fluoro-1-(2-isopropyl-6-methylphenyl)-2-oxo-1,2-dihydropyrido[2,3-d]pyrimidin-4-yl)-3-methylpiperazine-1-carboxylate (470 mg, 0.76 mmol) in DCM (5 mL). The resulting mixture was stirred for 30 min at rt and then concentrated in vacuo. The resulting residue was dissolved in DCM (3 mL). The solution was cooled to 0° C. and DIPEA (0.66 mL, 3.8 mmol) and acryloyl chloride (0.38 M in DCM, 2 mL, 0.76 mmol) were sequentially added. The resulting mixture was allowed to warm to rt. After 5 h, the reaction mixture was cooled to 0° C. and quenched by adding satd. NaHCO$_3$ (20 mL), water and DCM. The aqueous layer was extracted with DCM. The combined organic extracts were dried over MgSO$_4$ and then concentrated in vacuo. The crude product was purified by silica gel chromatography (eluent: 0-60% EtOAc-EtOH (3:1)/heptane) to provide 7-(5-Chloro-2-hydroxyphenyl)-6-fluoro-1-(2-methyl-6-(2-propanyl)phenyl)-4-((2S)-2-methyl-4-(2-propenoyl)-1-piperazinyl)pyrido[2,3-d]pyrimidin-2(1H)-one. $^1$H NMR (400 MHz, DMSO-d$_6$) δ ppm 0.97 (br d, J=6.8 Hz, 3H), 1.07 (br d, J=6.6H, 3H), 1.32 (br d, J=6.4 Hz, 3H), 1.89 (br s, 3H), 3.03-3.19 (m, 0.5H), 3.42-3.54 (m, 0.5H), 3.61-3.78 (m, 1.5H), 4.03 (br d, J=7.5 Hz, 0.5H), 4.15 (br d, J=13.1 Hz, 0.5H), 4.20-4.33 (m, 1.5H), 4.41 (br d, J=12.9 Hz, 0.5H), 4.89 (br s, 1H) 5.72-5.83 (m, 1H) 6.21 (br d, J=15.8 Hz, 1H), 6.78-6.96 (m, 2H) 7.19 (br d, J=6.6 Hz, 1H), 7.26-7.44 (m, 4H) 8.31 (br t, J=10.1 Hz, 1H), 10.69 (br s, 1H). $^{19}$F NMR (376 MHz, DMSO-d$_6$) δ ppm −126.4 (s, 1F). m/z (ESI, +ve ion): 576.2 (M+H)$^+$.

Example 115

Mixture of (M)-6-chloro-7-((2R)-2-methyl-1-piperidinyl)-4-((2S)-2-methyl-4-(2-propenoyl)-1-piperazinyl)-1-(2-(2-propanyl)phenyl)pyrido[2,3-d]pyrimidin-2(1H)-one and (M)-6-chloro-7-((2S)-2-methyl-1-piperidinyl)-4-((2S)-2-methyl-4-(2-propenoyl)-1-piperazinyl)-1-(2-(2-propanyl)phenyl)pyrido[2,3-d]pyrimidin-2(1H)-one

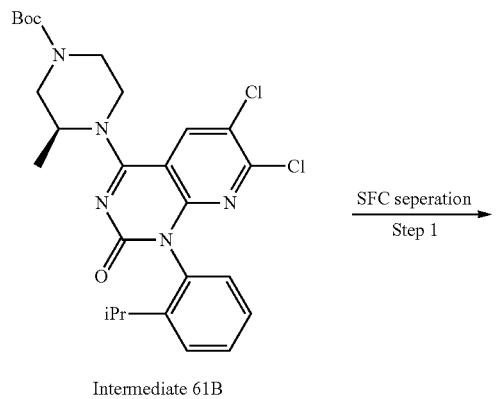

Intermediate 61B

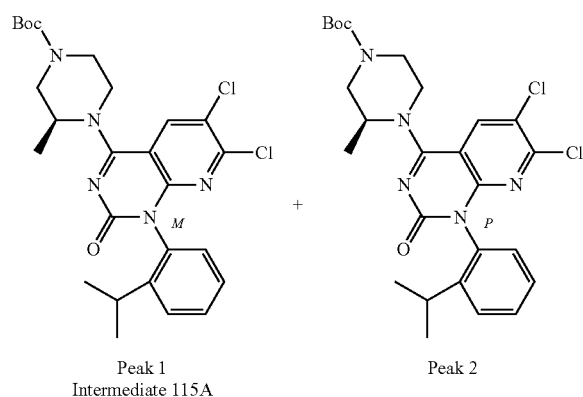

Peak 1
Intermediate 115A

Peak 2

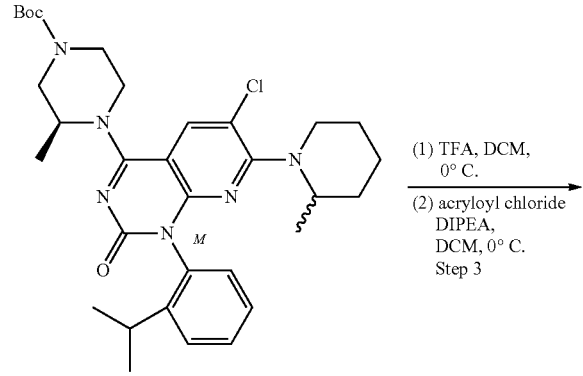

(1) TFA, DCM, 0° C.
(2) acryloyl chloride DIPEA, DCM, 0° C.
Step 3

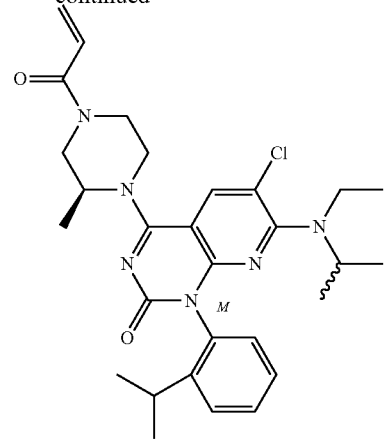

Step 1: (M)-(S)-tert-Butyl 4-(6,7-dichloro-1-(2-isopropylphenyl)-2-oxo-1,2-dihydropyrido[2,3-d]pyrimidin-4-yl)-3-methylpiperazine-1-carboxylate (Intermediate 115A)

A mixture of atropisomers Intermediate 61B (1.87 g) was purified by SFC (ID, 21×250 mm, 5 mm, 50% MeOH (with 20 mM NH$_3$)/CO$_2$, 50 mL/min, 100 bar) to obtain two peaks:

Peak 1 ((M)-isomer: Intermediate 115A, 720 mg, 97.5% ee). $^1$H NMR (400 MHz, DMSO-d6) δ ppm 8.41 (s, 1H), 7.46-7.51 (m, 1H), 7.39-7.45 (m, 1H), 7.29 (td, J=7.5, 1.6 Hz, 1H), 7.12 (dd, J=7.7, 1.0 Hz, 1H), 4.88 (brs, 1H), 4.06 (br d, J=13.3 Hz, 1H), 3.88-4.00 (m, 1H), 3.83 (br d, J=13.3 Hz, 1H), 3.72 (br t, J=10.9 Hz, 1H), 2.92-3.14 (m, 1H), 2.39-2.48 (m, 2H), 1.45 (s, 9H), 1.30 (d, J=6.6 Hz, 3H), 1.07 (d, J=6.8 Hz, 3H), 1.01 (d, J=6.8 Hz, 3H). m/z (ESI, +ve ion) 532.3 (M+H)$^+$.

Peak 2 ((P)-isomer, 698 mg, 98% ee). $^1$H NMR (400 MHz, DMSO-d$_6$) δ ppm 8.37 (s, 1H), 7.47-7.52 (m, 1H), 7.40-7.46 (m, 1H), 7.30 (td, J=7.5, 1.5 Hz, 1H), 7.12 (dd, J=7.8, 0.9 Hz, 1H), 4.77 (br s, 1H), 4.19 (br d, J=13.5 Hz, 1H), 3.90-4.05 (m, 1H), 3.82 (br d, J=13.5 Hz, 1H), 3.62 (br t, J=11.4 Hz, 1H), 3.02-3.18 (m, 1H), 2.41-2.50 (m, 2H), 1.45 (s, 9H), 1.34 (d, J=6.6 Hz, 3H), 1.08 (d, J=6.8 Hz, 3H), 1.02 (d, J=6.6 Hz, 3H). m/z (ESI, +ve ion): 532.3 (M+H)$^+$.

Step 2: (M)-(3S)-tert-Butyl 4-(6-chloro-1-(2-isopropylphenyl)-7-(2-methylpiperidin-1-yl)-2-oxo-1,2-dihydropyrido[2,3-d]pyrimidin-4-yl)-3-methylpiperazine-1-carboxylate 2-Methylpiperidine (0.09 mL, 0.94 mmol) was added to a solution of (M)-(S)-tert-butyl 4-(6,7-dichloro-1-(2-isopropylphenyl)-2-oxo-1,2-dihydropyrido[2,3-d]pyrimidin-4-yl)-3-methylpiperazine-1-carboxylate (Intermediate 115A, 100 mg, 0.19 mmol) in DMF (1.0 mL). After 2 h, ice water (2 mL) was added and stirring was continued for 5 min. The resulting precipitate was filtered off, washed with water, and dried to give (M)-(3S)-tert-butyl 4-(6-chloro-1-(2-isopropylphenyl)-7-(2-methylpiperidin-1-yl)-2-oxo-1,2-dihydropyrido[2,3-d]pyrimidin-4-yl)-3-methylpiperazine-1-carboxylate (113 mg, 0.190 mmol) as a white solid. m/z (ESI, +ve ion): 595.3 (M+H)$^+$.

Step 3: Mixture of (M)-4-((S)-4-acryloyl-2-methylpiperazin-1-yl)-6-chloro-1-(2-isopropylphenyl)-7-((R)-2-methylpiperidin-1-yl)pyrido[2,3-d]pyrimidin-2(1H)-one and (M-4-((S)-4-acryloyl-2-methylpiperazin-1-yl)-6-chloro-1-(2-isopropylphenyl)-7-((S)-2-methylpiperidin-1-yl)pyrido[2,3-d]pyrimidin-2(1H)-one TFA (1.0 mL, 13.4 mmol) was added to a solution of (M)-(3S)-tert-butyl 4-(6-chloro-1-(2-isopropylphenyl)-7-(2-methylpiperidin-1-yl)-2-oxo-1,2-dihydropyrido[2,3-d]pyrimidin-4-yl)-3-methylpiperazine-1-carboxylate (112 mg, 0.19 mmol) in DCM (1.0 mL) at 0° C. After 2 h, the reaction mixture was concentrated under reduced pressure to afford 6-chloro-1-(2-isopropylphenyl)-4-((S)-2-methylpiperazin-1-yl)-7-2-methylpiperidin-1-yl)pyrido[2,3-d]pyrimidin-2 (1H)-one. m/z (ESI, +ve ion): 495.2 (M+H)$^+$.

Acryloyl chloride (0.25 M in DCM, 0.8 mL, 0.19 mmol) was added to a mixture of (M)-6-chloro-1-(2-isopropylphenyl)-4-((S)-2-methylpiperazin-1-yl)-7-(2-methylpiperidin-1-yl)pyrido[2,3-d]pyrimidin-2(1H)-one and DIPEA (0.2 mL, 0.94 mmol) in DCM (1.0 mL) at 0° C. After 10 min, the resulting mixture was concentrated in vacuo and the crude product was purified by silica gel chromatography (eluent: 0-3% MeOH/DCM) to provide a mixture of (M)-6-chloro-7-((2R)-2-methyl-1-piperidinyl)-4-((2S)-2-methyl-4-(2-propenoyl)-1-piperazinyl)-1-(2-(2-propanyl)phenyl)pyrido[2,3-d]pyrimidin-2(1H)-one and (M)-6-chloro-7-((2S)-2-methyl-1-piperidinyl)-4-((2S)-2-methyl-4-(2-propenoyl)-1-piperazinyl)-1-(2-(2-propanyl)phenyl)pyrido[2,3-d]pyrimidin-2(1)-one (76 mg, 0.14 mmol, 73.8% yield) as a light-yellow solid. $^1$H NMR (400 MHz, DMSO-d$_6$) δ ppm 7.85-8.04 (m, 1H), 7.35-7.49 (m, 2H), 7.22-7.33 (m, 1H), 6.96-7.12 (m, 1H), 6.75-6.94 (m, 1H), 6.19 (br dd, J=16.6, 5.8 Hz, 1H), 5.67-5.82 (m, 1H), 4.60-4.95 (m, 1H), 3.87-4.46 (m, 4H), 3.40-3.77 (m, 3H), 3.02-3.21 (m, 1H), 2.80-2.97 (m, 1H), 2.56-2.74 (m, 1H), 1.19-1.62 (m, 9H), 1.05-1.14 (m, 3H), 0.88-1.05 (m, 6H). m/z (ESI, +ve ion): 549.2 (M+H)$^+$.

Example 116

1-((3S)-4-(6-Chloro-1-(2,6-diethylphenyl)-7-(2-fluorophenyl)-2-sulfanylidene-1,2-dihydro-4-quinazolinyl)-3-methyl-1-piperazinyl)-2-propen-1-one

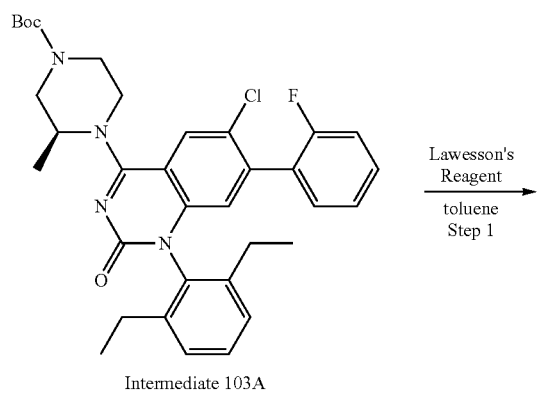

Intermediate 103A

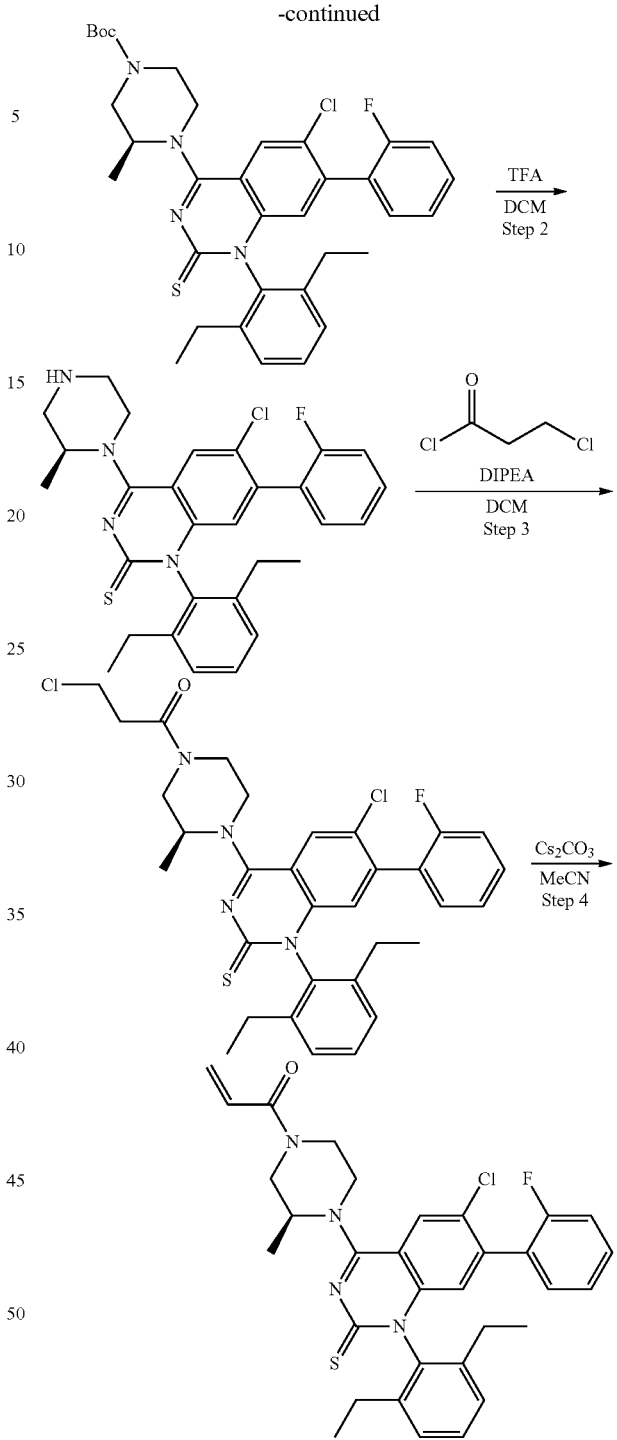

Step 1: (S)-tert-Butyl 4-(6-chloro-1-(2,6-diethylphenyl)-7-(2-fluorophenyl)-2-thioxo-1,2-dihydroquinazolin-4-yl)-3-methylpiperazine-1-carboxylate A suspension of (S)-tert-butyl 4-(6-chloro-1-(2,6-diethylphenyl)-7-(2-fluorophenyl)-2-oxo-1,2-dihydroquinazolin-4-yl)-3-methylpiperazine-1-carboxylate (Intermediate 103A, 0.70 g, 1.16 mmol) and Lawesson's reagent (0.468 g, 1.16 mmol, Sigma-Aldrich Corporation, St. Louis, Mo., USA) in toluene (7 mL) was heated to 110° C. for 4 h. The reaction mixture was cooled to rt and then partitioned between EtOAc (30 mL) and 5% aqueous NaHCO₃ (20 mL). The organic phase was washed with brine, dried over MgSO4, and concentrated in vacuo. The crude product was purified by silica gel chromatography (eluent: 0-25% EtOAc-EtOH (3:1)/heptane) to provide (S)-tert-butyl 4-(6-chloro-1-(2,6-diethylphenyl)-7-(2-fluorophenyl)-2-thioxo-1,2-dihydroquinazolin-4-yl)-3-methylpiperazine-1-carboxylate. m/z (ESI, +ve ion): 621.2 (M+H)⁺.

Steps 2 and 3: (S)-3-Chloro-1-(4-(6-chloro-1-(2,6-diethylphenyl)-7-(2-fluorophenyl)-2-thioxo-1,2-dihydroquinazolin-4-yl)-3-methylpiperazin-1-yl)propan-1-one A solution of (S)-tert-butyl 4-(6-chloro-1-(2,6-diethylphenyl)-7-(2-fluorophenyl)-2-thioxo-1,2-dihydroquinazolin-4-yl)-3-methylpiperazine-1-carboxylate (50 mg, 0.08 mmol) in TFA (1 mL) was stirred at rt for 5 min. The reaction mixture was concentrated under reduced pressure and the residue was dissolved in DCM (1 mL). The solution was placed under nitrogen atmosphere and DIPEA (70.3 µl, 0.402 mmol) was added. The reaction mixture was cooled to −30° C. and a solution of 3-chloropropionyl chloride (284 µl, 0.32 mmol, Sigma-Aldrich Corporation, St. Louis, Mo.) in DCM (2 mL) was added. The reaction mixture was concentrated under reduced pressure and the crude product was purified by silica gel chromatography (eluent: 0-30% EtOAc-EtOH (3:1)/heptane) to provide (S)-3-chloro-1-(4-(6-chloro-1-(2,6-diethylphenyl)-7-(2-fluorophenyl)-2-thioxo-1,2-dihydroquinazolin-4-yl)-3-methylpiperazin-1-yl)propan-1-one. m/z (ESI, +ve ion): 611.2 (M+H)⁺.

Step 4: 1-((3S)-4-(6-chloro-1-(2,6-diethylphenyl)-7-(2-fluorophenyl)-2-sulfanylidene-1,2-dihydro-4-quinazolinyl)-3-methyl-1-piperazinyl)-2-propen-1-one A suspension of (S)-3-chloro-1-(4-(6-chloro-1-(2,6-diethylphenyl)-7-(2-fluorophenyl)-2-thioxo-1,2-dihydroquinazolin-4-yl)-3-methylpiperazin-1-yl)propan-1-one (15 mg, 0.025 mmol) and cesium carbonate (32 mg, 0.098 mmol) in acetonitrile (0.4 mL) was heated to 75° C. for 4 h. The reaction mixture was partitioned between EtOAc (8 mL) and satd. NaHCO₃ (1 mL). The organic layer was dried over MgSO₄, concentrated in vacuo, and purified by silica gel chromatography (eluent: 0-40% EtOAc-EtOH (3:1)/heptane) to provide 1-((3S)-4-(6-chloro-1-(2,6-diethylphenyl)-7-(2-fluorophenyl)-2-sulfanylidene-1,2-dihydro-4-quinazolinyl)-3-methyl-1-piperazinyl)-2-propen-1-one. ¹H NMR (400 MHz, CDCl₃) δ ppm 7.84 (s, 1H), 7.35-7.47 (m, 2H), 7.30 (d, J=7.67 Hz, 2H), 7.19 (dd, J=7.05, 14.72 Hz, 1H), 7.09-7.16 (m, 2H), 6.54-6.82 (m, 1H), 6.50-6.53 (m, 1H), 6.41 (d, J=16.59 Hz, 1H), 5.81 (dd, J=2.07, 10.78 Hz, 1H), 4.83-5.30 (m, 1H), 4.54-4.81 (m, 1H), 4.29-4.53 (m, 1H), 3.57-4.16 (m, 3H), 2.96-3.36 (m, 1H), 2.41-2.54 (m, 2H), 2.10-2.31 (m, 2H), 1.51 (d, J=17.41 Hz, 3H), 1.11-1.19 (m, 6H). ¹⁹F NMR (376 MHz, CDCl₃) δ ppm −113.90 (s, 1F). m/z (ESI, +ve ion): 575.2 (M+H)⁺.

Example 117

1-(4-(2-Azidoethoxy)-2-(2-propanyl)phenyl)-6-chloro-4-((2S)-2-methyl-4-(2-propenoyl)-1-piperazinyl)-7-(1-piperidinyl)pyrido[2,3-d]pyrimidin-2(1H)-one

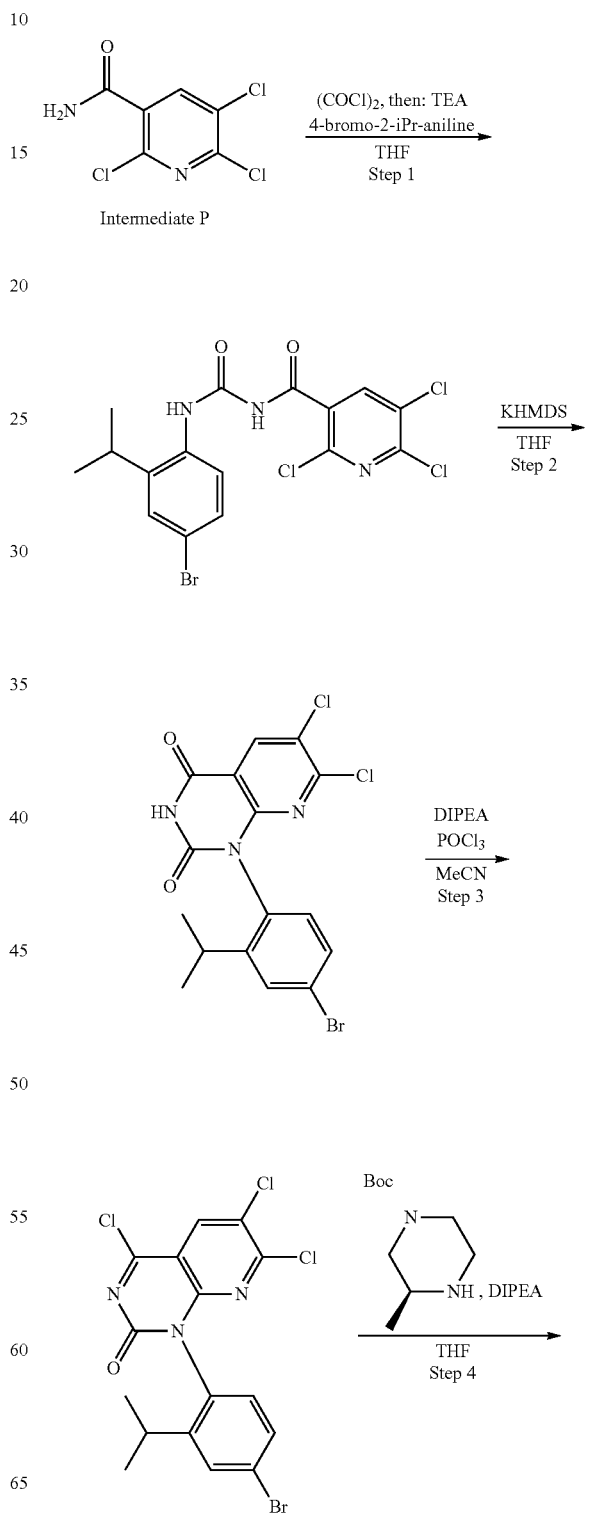

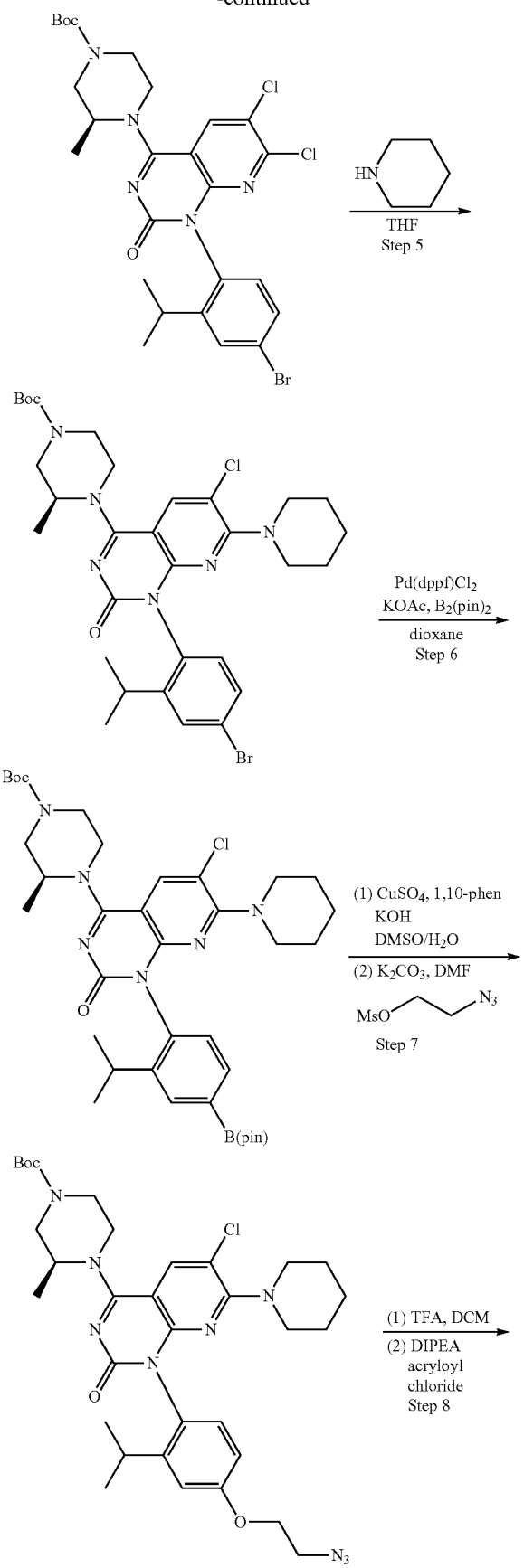

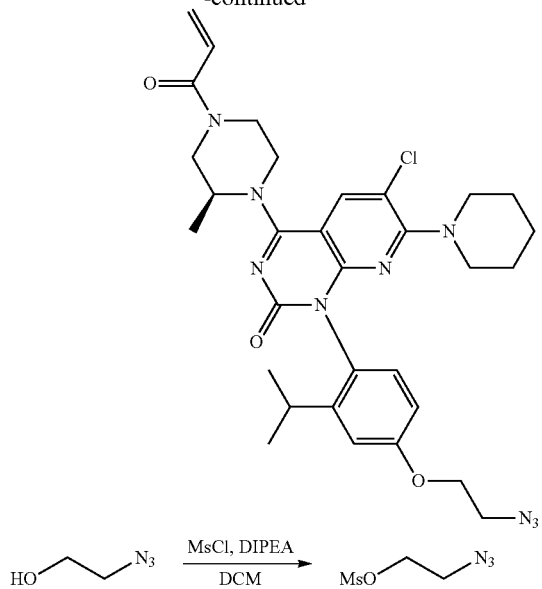

Step 1: N-((4-Bromo-2-isopropylphenyl)carbamoyl)-2,5,6-trichloronicotinamide

A solution of 2,5,6-Trichloronicotinamide (Intermediate P, 1.92 g, 8.52 mmol) in THF (30 mL) was placed under nitrogen atmosphere and cooled to −78° C. Oxalyl chloride (2.0 M in DCM, 4. 6 mL, 9.2 mmol) was added over a period of 2 min. The reaction mixture was allowed to warm to rt over a period of 5 min and subsequently heated to 60° C. for 45 min. The reaction mixture was cooled to −78° C. and a solution of TEA (2.5 mL, 17.5 mmol) and 4-bromo-2-isopropylaniline (2.0 g, 9.2 mmol, Oakwood Products, Inc. Estill, S.C.) in THF (4 mL) was added. The reaction mixture was stirred for 5 min then allowed to warm to rt. Water (50 mL) and EtOAc (100 mL) were added. The organic layer was washed with brine (75 mL), dried over MgSO4, and concentrated in vacuo to give N-((4-bromo-2-isopropylphenyl)carbamoyl)-2,5,6-trichloronicotinamide (3.99 g, 8.57 mmol, 100% yield) as a tan foam. $^1$H NMR (400 MHz, DMSO-$d_6$) δ ppm 11.48 (1H, br s), 10.13 (1H, br s), 8.57-8.65 (1H, m), 7.77 (1H, br d, J=8.7 Hz), 7.48 (1H, d, J=2.3 Hz), 7.39-7.44 (1H, m), 3.08 (1H, dqd, J=13.5, 6.8, 6.8, 6.8, 6.6 Hz), 1.23 (6H, d, J=6.6 Hz). m/z (ESI, +ve ion): 487.9 and 490.0 (M+Na)$^+$.

Step 2: 1-(4-Bromo-2-isopropylphenyl)-6,7-dichloropyrido[2,3-d]pyrimidine-2,4(1H,3H)-dione KHMDS (0.5 M in toluene, 36.1 mL, 18.0 mmol) was added over a period of 5 min to a solution of N-((4-bromo-2-isopropylphenyl)carbamoyl)-2,5,6-trichloronicotinamide (3.96 g, 8.51 mmol) in THF (40 mL) under nitrogen atmosphere. After 15 min, satd. ammonium chloride (50 mL), water (50 mL) and EtOAc (100 mL) were added. The organic layer was washed with water (100 mL) and brine (75 mL), dried over MgSO$_4$, and concentrated in vacuo. The residue was triturated with heptane (40 mL) and the precipitate was filtered off to give 1-(4-bromo-2-isopropylphenyl)-6,7-dichloropyrido[2,3-d]pyrimidine-2,4(1H,3H)-dione (3.12 g, 7.27 mmol, 85% yield) as a tan amorphous solid. $^1$H NMR (400 MHz, DMSO-$d_6$) δ ppm 12.14 (1H, s), 8.54 (1H, s), 7.68 (1H, d, J=2.3 Hz), 7.50-7.56 (1H, m), 7.26 (1H, d, J=8.5 Hz), 2.72-2.81 (1H, sept., J=8.0 Hz), 1.09 (3H, d, J=6.8 Hz), 1.04 (3H, d, J=6.8 Hz). m/z (ESI, +ve ion): 428.0 and 430.0 (M+H)$^+$.

Steps 3-4: (S)-tert-Butyl 4-(1-(4-bromo-2-isopropylphenyl)-6,7-dichloro-2-oxo-1,2-dihydropyrido[2,3-d]pyrimidin-4-yl)-3-methylpiperazine-1-carboxylate 1-(4-Bromo-2-isopropylphenyl)-6,7-dichloropyrido[2,3-d]pyrimidine-2,4(1H,3H)-dione (3.12 g, 7.27 mmol) was added to mixture of DIPEA (2.7 mL, 15.2 mmol) in acetonitrile (7 mL) under nitrogen atmosphere. Phosphorus oxychloride (2.7 mL, 17.3 mmol) was added followed by 2 drops of DMF. The reaction mixture was heated to 80° C. for 30 min. The reaction mixture was concentrated in vacuo and azeotroped with toluene. The crude product was dissolved in THF (40 mL) and treated with DIPEA (2.7 mL, 15.2 mmol) and (S)-4-N-Boc-2-methyl piperazine (1.66 g, 8.27 mmol, Combi-Blocks, San Diego, Calif.). After 30 min, water (200 mL) and EtOAc (200 mL) were added. The organic layer was separated and concentrated in vacuo. The crude product was purified by silica gel chromatography (eluent: 0-30% EtOAc/DCM) to provide (S)-tert-butyl 4-(1-(4-bromo-2-isopropylphenyl)-6,7-dichloro-2-oxo-1,2-dihydropyrido[2,3-d]pyrimidin-4-yl)-3-methylpiperazine-1-carboxylate (3.43 g, 5.61 mmol, 77% yield) as an orange foam. $^1$H NMR (400 MHz, DMSO-d$_6$) δ ppm 8.41 (1H, d, J=15.5 Hz), 7.66 (1H, d, J=1.9 Hz), 7.47-7.55 (1H, m), 7.13 (1H, dd, J=8.3, 3.1 Hz), 4.84-4.94 (1H, m), 4.75-4.84 (1H, m), 4.18 (1H, br d, J=13.7 Hz), 3.92-4.11 (4H, m), 3.79-3.87 (1H, m), 3.52-3.79 (1H, m), 3.38 (1H, br d, J=1.7 Hz), 3.01-3.30 (2H, m), 1.41-1.51 (9H, m), 1.28-1.36 (3H, m), 1.08 (3H, d, J=6.8 Hz), 1.02 (3H, d, J=6.8 Hz). m/z (ESI, +ve ion): 610.0 and 612.0 (M+H)$^+$.

Step 5: (S)-tert-Butyl 4-(1-(4-bromo-2-isopropylphenyl-6-chloro-2-oxo-7-(piperidin-1-yl)-1,2-dihydropyrido[2,3-d]pyrimidin-4-yl)-3-methylpiperazine-1-carboxylate Piperidine (0.09 mL, 0.91 mmol) was added to a solution of (S)-tert-butyl 4-(1-(4-bromo-2-isopropylphenyl)-6,7-dichloro-2-oxo-1,2-dihydropyrido[2,3-d]pyrimidin-4-yl)-3-methylpiperazine-1-carboxylate (370 mg, 0.61 mmol) in THF (5 mL). Water was added to the reaction mixture after 10 min. The reaction mixture was extracted with EtOAc (50 mL). The organic layer was separated, washed with brine, dried over MgSO4, and concentrated in vacuo. The crude product was purified by silica gel chromatography (eluent: 0-30% DCM-MeOH (4:1)/DCM) to provide (S)-tert-butyl 4-(1-(4-bromo-2-isopropylphenyl)-6-chloro-2-oxo-7-(piperidin-1-yl)-1,2-dihydropyrido[2,3-d]pyrimidin-4-yl)-3-methylpiperazine-1-carboxylate (323 mg, 0.49 mmol, 81% yield) as an yellow foam. $^1$H NMR (400 MHz, DMSO-d$_6$) δ ppm 7.93 (1H, d, J=4.6 Hz), 7.61 (1H, d, J=2.3 Hz), 7.46 (1H, dt, J=8.3, 1.1 Hz), 7.05 (1H, d, J=8.1 Hz), 4.71 (1H, br d, J=8.7 Hz), 3.98-4.13 (1H, m), 3.95 (1H, br s), 3.80 (1H, br d, J=13.3 Hz), 3.46-3.62 (1H, m), 3.22-3.28 (3H, m), 3.06 (1H, br s), 1.47-1.55 (2H, m), 1.44 (9H, s), 1.33-1.41 (4H, m), 1.28 (3H, t, J=5.7 Hz), 1.08 (3H, d, J=6.8 Hz), 0.98 (3H, d, J=6.8 Hz). m/z (ESI, +ve ion): 659.2 and 661.1 (M+H)$^+$.

Step 6: (S)-tert-Butyl 4-(6-chloro-1-(2-isopropyl-4-(4,4,5,5-tetramethyl-1,3,2-dioxaborolan-2-yl)phenyl)-2-oxo-7-(piperidin-1-yl)-1,2-dihydropyrido[2,3-d]pyrimidin-4-yl)-3-methylpiperazine-1-carboxylate A reaction mixture of bis(pinacolato)diboron (141 mg, 0.55 mmol, Sigma-Aldrich Corporation, St. Louis, Mo.), [1,1'-bis(diphenylphosphino)ferrocene]-dichloropalladium (II) (38 mg, 0.046 mmol), potassium acetate (227 mg, 2.31 mmol) and (S)-tert-butyl 4-(1-(4-bromo-2-isopropylphenyl)-6-chloro-2-oxo-7-(piperidin-1-yl)-1,2-dihydropyrido [2,3-d]pyrimidin-4-yl)-3-methylpiperazine-1-carboxylate (305 mg, 0.46 mmol) in 1,4-dioxane (7.0 mL) was purged with argon and subsequently heated in a microwave to 100° C. for 1.5 h. The reaction mixture was partitioned between water and EtOAc (25 mL). The organic phase was separated, washed with brine, dried over MgSO4, and concentrated in vacuo. The crude product was purified by silica gel chromatography (eluent: 0-30% DCM-MeOH (4:1)/DCM) to provide (S)-tert-butyl 4-(6-chloro-1-(2-isopropyl-4-(4,4,5,5-tetramethyl-1,3,2-dioxaborolan-2-yl)phenyl)-2-oxo-7-(piperidin-1-yl)-1,2-dihydropyrido[2,3-d]pyrimidin-4-yl)-3-methylpiperazine-1-carboxylate (313 mg, 0.44 mmol, 96% yield) as a light brown foam. m/z (ESI, +ve ion): 707.3 (M+H)$^+$.

Step 7: (S)-tert-Butyl 4-(6-chloro-1-(4-hydroxy-2-isopropylphenyl)-2-oxo-7-(piperidin-1-yl)-1,2-dihydropyrido[2,3-d]pyrimidin-4-yl)-3-methylpiperazine-1-carboxylate Step 1

A reaction mixture of (S)-tert-Butyl 4-(6-chloro-1-(2-isopropyl-4-(4,4,5,5-tetramethyl-1,3,2-dioxaborolan-2-yl)phenyl)-2-oxo-7-(piperidin-1-yl)-1,2-dihydropyrido[2,3-d]pyrimidin-4-yl)-3-methylpiperazine-1-carboxylate (313 mg, 0.44 mmol), 1,10-phenanthroline (16 mg, 0.089 mmol), copper(II) sulfate, (7.0 mg, 0.044 mmol), potassium hydroxide (75 mg, 1.33 mmol) in water (3 mL) and DMSO (1 mL) was allowed to stir under air at rt for 2 h. The reaction mixture was quenched with satd. ammonium chloride and extracted with EtOAc (50 mL). The organic phase was separated, washed with brine, dried over MgSO4, and concentrated in vacuo. The crude product was purified by silica gel chromatography (eluent: 0-60% DCM-MeOH (4:1)/DCM) to provide (S)-tert-butyl 4-(6-chloro-1-(4-hydroxy-2-isopropylphenyl)-2-oxo-7-(piperidin-1-yl)-1,2-dihydropyrido[2,3-d]pyrimidin-4-yl)-3-methylpiperazine-1-carboxylate (150 mg, 0.25 mmol, 56.8% yield). $^1$H NMR (400 MHz, CDCl$_3$) δ ppm 7.67 (1H, s), 6.72-6.79 (2H, m), 6.62-6.72 (1H, m), 6.49-6.56 (1H, m), 4.63-4.92 (1H, m), 4.10-4.26 (2H, m), 3.87-4.07 (1H, m), 3.43-3.71 (1H, m), 3.27-3.39 (4H, m), 2.97-3.27 (1H, m), 2.52 (1H, dt, J=13.4, 6.7 Hz), 1.93 (3H, br s), 1.53-1.69 (6H, m), 1.34-1.48 (1H, m), 1.24 (9H, s), 1.20 (3H, dd, J=6.8, 1.9 Hz), 0.93-1.00 (3H, m). m/z (ESI, +ve ion): 597.4 (M+H)$^+$.

Step 2

A reaction mixture of (S)-tert-butyl 4-(6-chloro-1-(4-hydroxy-2-isopropylphenyl)-2-oxo-7-(piperidin-1-yl)-1,2-dihydropyrido[2,3-d]pyrimidin-4-yl)-3-methylpiperazine-1-carboxylate (150 mg, 0.25 mmol), potassium carbonate (35 mg, 0.251 mmol), and 2-azidoethyl methanesulfonate (50 mg, 0.3 mmol, synthesis below) in DMF (3 mL) was heated to 50° C. for 6 h. The reaction mixture was treated with brine and satd. ammonium chloride and extracted with EtOAc (50 mL). The organic phase was separate, washed with brine (20 mL), dried over MgSO4, and concentrated in vacuo. The crude product was purified by silica gel chromatography (eluent: 0-50% DCM-MeOH (4:1)/DCM) to provide (S)-tert-butyl 4-(6-chloro-1-(4-hydroxy-2-isopropylphenyl)-2-oxo-7-(piperidin-1-yl)-1,2-dihydropyrido[2,3-d]pyrimidin- 4-yl)-3-methylpiperazine-1-carboxylate (150 mg, 0.251 mmol) as a light yellow oil. $^1$H NMR (400 MHz, CDCl$_3$) δ ppm 7.67 (1H, s), 6.94-7.00 (2H, m), 6.81 (1H, dd, J=8.6, 2.8 Hz), 4.61-4.87 (1H, m), 4.15-4.24 (3H, m), 3.87-4.07 (1H, m), 3.63 (2H, t, J=5.0 Hz), 3.28-3.39 (4H, m), 3.01-3.33 (3H, m), 2.59 (1H, dt, J=13.1, 6.4 Hz), 1.65 (2H, s), 1.54-1.59 (2H, m), 1.45-1.54 (11H, m), 1.41 (4H, br dd, J=6.2, 2.7 Hz), 1.19 (3H, d, J=6.8 Hz), 1.02 (3H, d, J=6.8 Hz). m/z (ESI, +ve ion): 666.3 (M+H)$^+$.

Step 8: 1-(4-(2-Azidoethoxy)-2-(2-propanyl)phenyl)-6-chloro-4-((2S)-2-methyl-4-(2-propenoyl)-1-piperazinyl)-7-(1-piperidinyl)pyrido[2,3-d]pyrimidin-2(1H)-one TFA (1 mL, 13 mmol) was added to a solution of (S)-tert-butyl 4-(1-(4-(2-azidoethoxy)-2-isopropylphenyl)-6-chloro-2-oxo-7-(piperidin-1-yl)-1,2-dihydropyrido[2,3-d]pyrimidin-4-yl)-3-methylpiperazine-1-carboxylate (26 mg, 0.039 mmol) in DCM (2 mL). After 30 min, the reaction mixture was concentrated in vacuo and the residue was taken up in DCM (2 mL). DIPEA (0.034 mL, 0.2 mmol) was added, the mixture was cooled to 0° C. and acryloyl chloride (3.5 μL, 0.043 mmol) was added. After 5 min, the reaction mixture was treated with satd. NaHCO$_3$ and extracted with DCM. The organic phase was separated, dried over MgSO4, and concentrated in vacuo. The crude product was purified by silica gel chromatography (eluent: 0-50% DCM-MeOH (4:1)/DCM) to provide 1-(4-(2-azidoethoxy)-2-(2-propanyl)phenyl)-6-chloro-4-((2S)-2-methyl-4-(2-propenoyl)-1-piperazinyl)-7-(1-piperidinyl)pyrido[2,3-d]pyrimidin-2(1H)-one as a light yellow solid. $^1$H NMR (400 MHz; DMSO-d$_6$) δ ppm 7.94 (1H, br t, J=5.2 Hz), 6.93-7.03 (2H, m), 6.78-6.93 (2H, m), 6.14-6.26 (1H, m), 5.72-5.80 (1H, m), 4.66-4.84 (1H, m), 4.31-4.42 (1H, m), 4.19-4.28 (2H, m), 3.94-4.19 (2H, m), 3.65-3.72 (2H, m), 3.47-3.64 (2H, m), 3.24-3.30 (3H, m), 2.94-3.09 (2H, m), 2.41-2.48 (1H, m), 1.44-1.57 (2H, m), 1.39 (4H, br d, J=4.6 Hz), 1.22-1.30 (3H, m), 1.08 (3H, d, J=6.8 Hz), 0.98 (3H, br d, J=6.6 Hz). m/z (ESI, +ve ion): 620.3 (M+H)$^+$.

2-Azidoethyl methanesulfonate

A mixture of 2-azidoethanol (30 mg, 0.35 mmol, Aurum Pharmatech LLC, Franklin Park, N.J.) and DIPEA (0.18 mL, 1.03 mmol) in DCM (3 mL) was cooled to 0° C., followed by the addition of methanesulfonyl chloride (30 μL, 0.38 mmol). The reaction mixture was allowed to stir at 0° C. for 30 min. The reaction mixture was treated with brine and extracted with DCM. The organic phase was separated, dried over MgSO$_4$ and concentrated in vacuo to give 2-azidoethyl methanesulfonate which was used immediately as a solution in DMF (3 mL) in Step 7.

Example 118

6-Chloro-1-(2,6-diethylphenyl)-7-(2-fluorophenyl)-4-(1-(2-propenoyl)-4-piperidinyl)pyrido[2,3-d]pyrimidin-2(1H)-one

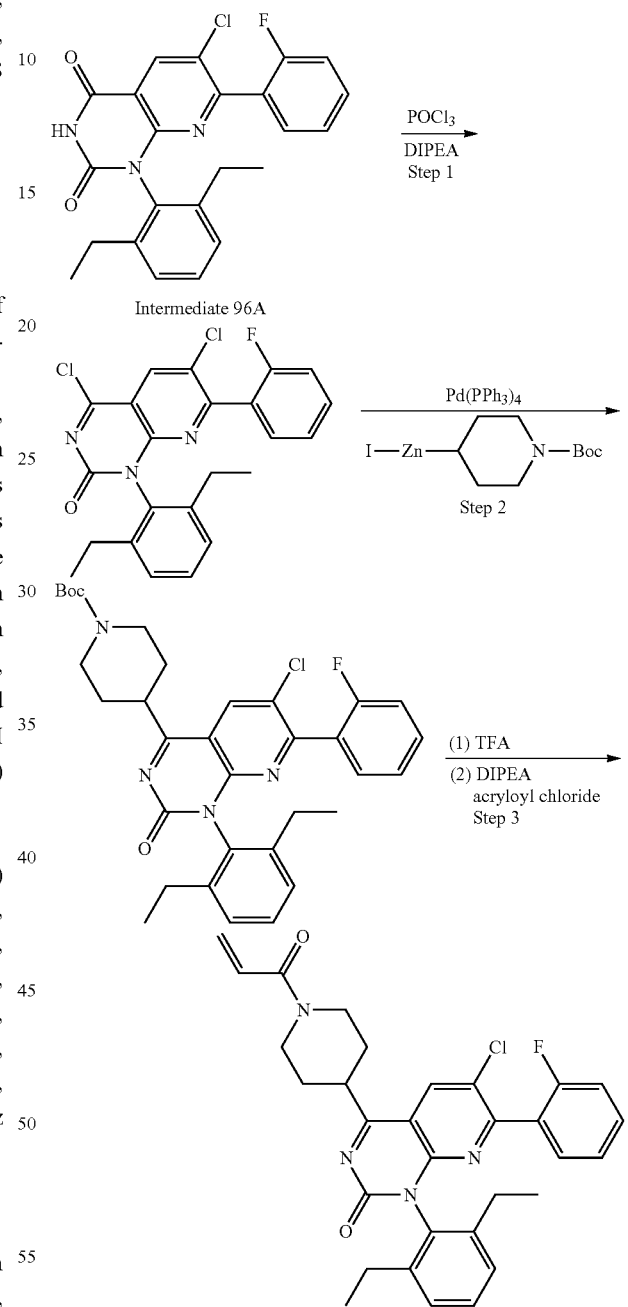

Step 1: 4,6-Dichloro-1-(2,6-diethylphenyl)-7-(2-fluorophenyl)pyrido[2,3-d]pyrimidin-2(1H)-one DIPEA (0.43 mL, 2.5 mmol) and phosphorus oxychloride (0.43 mL, 2.8 mmol) were subsequently added to a solution of 6-chloro-1-(2,6-diethylphenyl)-7-(2-fluorophenyl)pyrido[2,3-d]pyrimidine-2,4(1H,3H)-dione (Intermediate 96A, 500 mg, 1.2 mmol) in acetonitrile (5 mL) under nitrogen atmosphere. Two drops of DMF were added and the reaction mixture was heated to 80° C. for 45 min. The reaction mixture was concentrated in vacuo to give crude 4,6-dichloro-1-(2,6-diethylphenyl)-7-(2-fluorophenyl)pyrido[2,3-d]pyrimidin-2(1H)-one, which was used in the next step without purification.

Step 2: tert-Butyl 4-(6-chloro-1-(2,6-diethylphenyl)-7-(2-fluorophenyl)-2-oxo-1,2-dihydropyrido[2,3-d]pyrimidin-4-yl)piperidine-1-carboxylate A mixture of 4,6-Dichloro-1-(2,6-diethylphenyl)-7-(2-fluorophenyl)pyrido[2,3-d]pyrimidin-2(1H)-one (530 mg, 1.2 mmol), [1-(tert-butoxycarbonyl)piperidin-4-yl]zinc iodide (0.5 M in THF, 23.8 mL. 11.9 mmol, Rieke Metals, Inc., Lincoln, Nebr.) and tetrakis(triphenylphosphine) palladium(0) (69 mg, 0.06 mmol) in THF (2.0 mL) was heated to 80° C. under nitrogen atmosphere. After 30 min, ice was added to the reaction mixture, followed by 5 N NaOH (10 mL). The reaction mixture was extracted with EtOAc. The organic layer washed with brine, dried over MgSO4, and concentrated in vacuo. The crude product was purified by silica gel chromatography (eluent: 0-80% EtOAc/heptane) to provide tert-butyl 4-(6-chloro-1-(2,6-diethylphenyl)-7-(2-fluorophenyl)-2-oxo-1,2-dihydropyrido[2,3-d]pyrimidin-4-yl)piperidine-1-carboxylate (180 mg, 0.31 mmol, 25.8% yield). m/z (ESI, +ve ion): 491.2 (M-Boc)⁺.

Step 3: 4-(1-Acryloylpiperidin-4-yl)-6-chloro-1-(2,6-diethylphenyl)-7-(2-fluorophenyl)pyrido[2,3-d]pyrimidin-2(1H)-one TFA (1.5 mL, 19.5 mmol) was added to a solution of tert-butyl 4-(6-chloro-1-(2,6-diethylphenyl)-7-(2-fluorophenyl)-2-oxo-1,2-dihydropyrido[2,3-d]pyrimidin-4-yl)piperidine-1-carboxylate (180 mg, 0.31 mmol) in DCM (3 mL) at rt. After 45 min, the reaction mixture was concentrated in vacuo to afford 6-chloro-1-(2,6-diethylphenyl)-7-(2-fluorophenyl)-4-(piperidin-4-yl)pyrido[2,3-d]pyrimidin-2(1H)-one. The residue was dissolved in DCM (3 mL) and the solution was cooled to 0° C. DIPEA (0.27 mL, 1.53 mmol) and by acryloyl chloride (0.025 mL, 0.31 mmol) were sequentially added and the reaction mixture was allowed to stir at 0° C. for 15 min. The reaction mixture was treated with saturated NaHCO3 and extracted with DCM. The organic layer was dried over MgSO4, and concentrated in vacuo. The crude product was purified by silica gel chromatography (eluent: 0-50% DCM-MeOH (4:1)/DCM), followed by additional purification by RP-HPLC (Gemini Phenomenex; 30×150 mm, 5 u, 20-90% 0.1% TFA/CH₃CN in 0.1% TFA/water, 45 mL/min). The combined fractions were concentrated, the solid was dissolved in MeOH-DCM (1:5) and the solution was filtered through an Agilent PL-HCO₃ MP SPE column to provide 4-(1-acryloylpiperidin-4-yl)-6-chloro-1-(2,6-diethylphenyl)-7-(2-fluorophenyl)pyrido[2,3-d]pyrimidin-2(1H)-one (60 mg, 0.11 mmol, 36.1% yield) as a light yellow solid. ¹H NMR (400 MHz, DMSO-d₆) δ ppm 8.14-8.25 (1H, m), 8.10 (1H, s), 7.38-7.59 (1H, m), 7.20-7.35 (2H, m), 7.09-7.20 (3H, m), 6.75-6.93 (1H, m), 6.06-6.20 (1H, m), 5.63-5.74 (1H, m), 4.36-4.69 (1H, m), 4.03-4.35 (1H, m), 2.56-2.66 (2H, m), 2.23-2.36 (4H, m), 2.19 (1H, dt, J=14.1, 7.1 Hz), 1.86-2.09 (2H, m), 1.44-1.68 (2H, m), 0.87-1.06 (6H, m). ¹⁹F NMR (376 MHz, DMSO-d₆) δ ppm −114.37 (1F, s), −114.45 (1F, s), −114.50 (1F, s). m/z (ESI, +ve ion): 545.2 (M+H)⁺.

Example 119

6-Chloro-7-(2-fluoro-6-hydroxyphenyl)-4-((2S)-2-methyl-4-(2-propenoyl)-1-piperazinyl)pyrido[2,3-d]pyrimidin-2(1H)-one

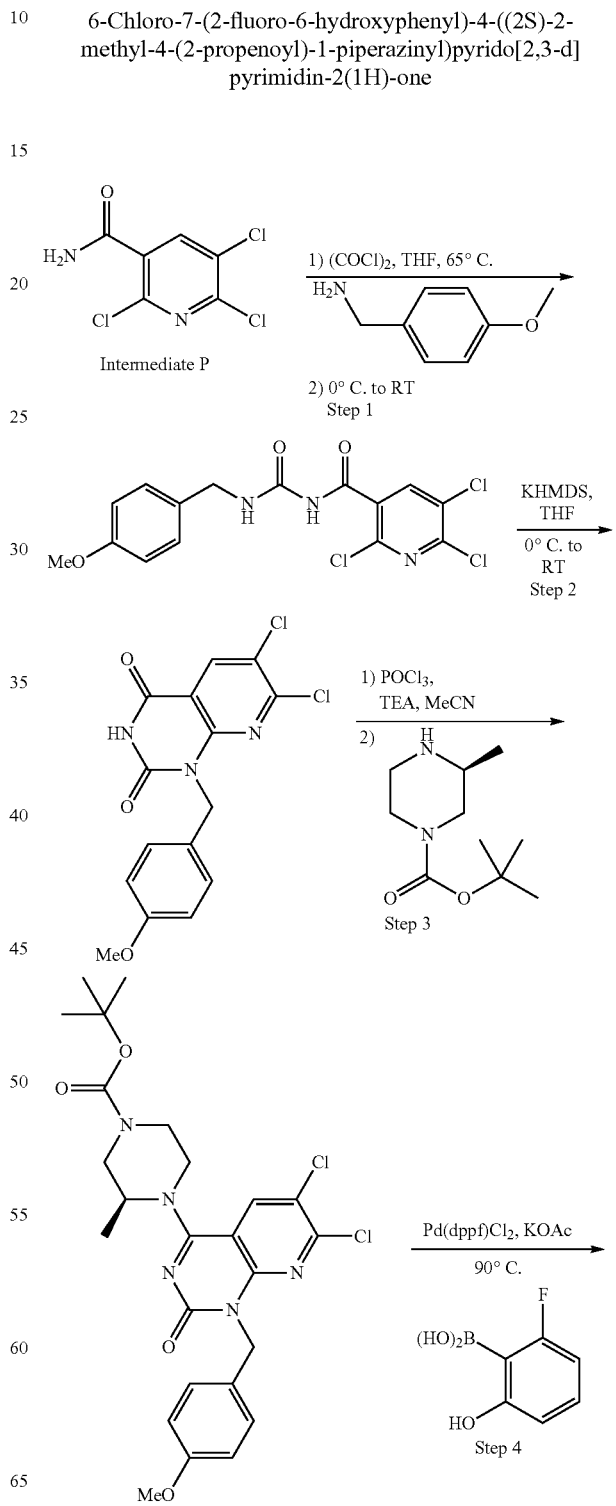

-continued

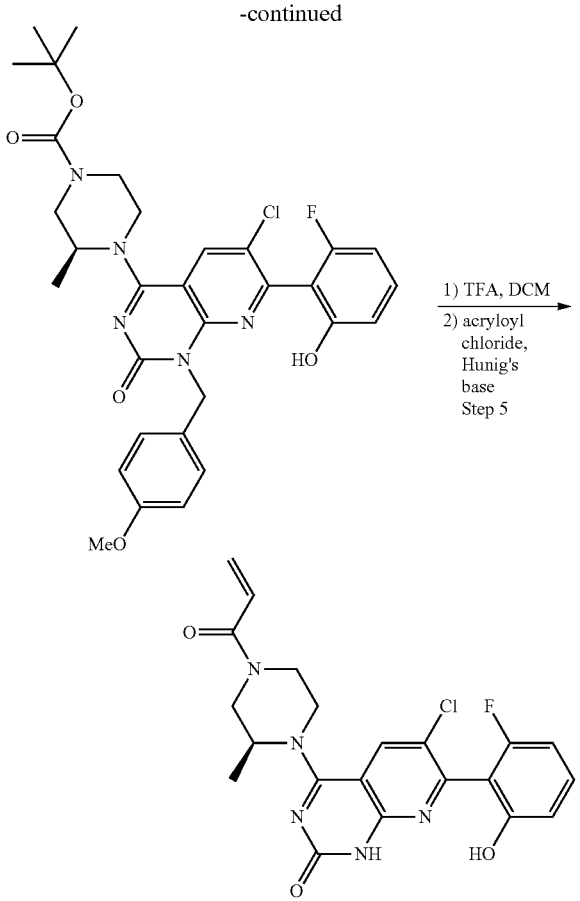

1) TFA, DCM
2) acryloyl chloride, Hunig's base
Step 5

Step 1: 2,5,6-Trichloro-N-((4-methoxybenzyl)carbamoyl)nicotinamide

A Oxalyl chloride (2.0 M in DCM, 6.65 mL, 13.3 mmol) was added to a suspension of 2,5,6-trichloronicotinamide (Intermediate P, 2.0 g, 8.87 mmol) in THF (20 mL). The reaction mixture was heated to 65° C. for 1 h. The reaction mixture was cooled to rt and concentrated in vacuo. The residue was taken up in toluene (20 mL), the solution was cooled to 0° C. and 4-methoxybenzylamine (1.2 mg, 8.87 mmol, Sigma-Aldrich Corporation % St. Louis, Mo.) was added dropwise. The ice bath was removed and stirring was continued for 30 min. The reaction mixture was concentrated in vacuo and the crude residue was dried under reduced pressure to provide a pale yellow solid. The product was used in the subsequent step without further purification. m/z (ESI, +ve ion): 410.0 and 412.0 (M+H)$^+$.

Step 2. 6,7-Dichloro-1-(4-4-methoxybenzyl)pyrido[2,3-d]pyrimidine-2,4-(1H,3H)-dione KHMDS (1 M in THF, 17.8 mL, 17.8 mmol) was added to a solution of 2,5,6-trichloro-N-((4-methoxybenzyl)carbamoyl)nicotinamide (3.45 g, 8.88 mmol) in THF (20 mL) at 0° C. After 5 min. the reaction mixture was quenched with brine and extracted with EtOAc. The organic phase was dried over MgSO$_4$. and concentrated in vacuo to provide 6,7-dichloro-1-(4-methoxybenzyl)pyrido[2,3-d]pyrimidine-2,4(1H,3H)-dione (3.12 g, 8.86 mmol, 100% yield) as a light orange. m/z (ESI, ve ion) 352.1 (M+H)$^+$. The product was used in the subsequent step without further purification.

Step 3: ter-Butyl (S)-4-(6,7-dichloro-1-(4-methoxybenzyl)-2-oxo-1,2-dihydropyrido[2,3-d]pyrimidin-4-yl)-3-methylpiperazine-1-carboxylate TEA (1.0 mL, 7.1 mmol) and phosphorus oxychloride (0.34 mL, 3.41 mmol) were added to a solution of 6,7-dichloro-1-(4-methoxybenzyl)pyrido[2,3-d]pyrimidine-2,4(1H,3H)-dione (1.0 g, 2.84 mmol) in acetonitrile (10 mL) under nitrogen atmosphere. The reaction mixture was heated to 60° C. After 1 h, the reaction mixture was cooled to 0° C. and treated with TEA (1.0 mL) and (S)-4-N-Boc-2-methylpiperazine (0.597 g, 2.98 mmol, Combi-Blocks, San Diego, Calif.). The ice bath was removed and after 30 min, the reaction mixture was quenched with brine and extracted with EtOAc (100 mL). The organic extract was washed with brine (40 mL), water (30 mL) and brine (50 mL), dried over MgSO4, and concentrated in vacuo. The crude product was purified by silica gel chromatography (eluent: 0-100% EtOAc/heptane) to provide tert-butyl (S)-4-(6,7-dichloro-1-(4-methoxybenzyl)-2-oxo-1,2-dihydropyrido[2,3-d]pyrimidin-4-yl)-3-methylpiperazine-1-carboxylate (321 mg, 0.6 mmol, 21.1% yield) as a light orange foam. $^1$H NMR (400 MHz, DMSO-d$_6$) δ ppm 8.32 (1H, s), 7.30 (2H, d, J=8.7 Hz), 6.82-6.88 (2H, m), 5.22 (2H, s), 4.66-4.78 (1H, m), 4.03 (2H, q, J=7.0 Hz), 3.84-3.96 (1H, m), 3.73-3.81 (1H, m), 3.70 (3H, s), 3.59 (1H, br t, J=11.2 Hz), 2.95-3.11 (1H, br, m), 1.43 (9H, s), 1.27 (3H, br d, J=6.6 Hz). m/z (ESI, +ve ion): 534.2 (M+H)$^+$.

Step 4: tert-Butyl (3S)-4-(6-chloro-7-(2-fluoro-6-hydroxyphenyl)-1-(4-methoxybenzyl)-2-oxo-1,2-dihydropyrido[2,3-d]pyrimidin-4-yl)-3-methylpiperazine-1-carboxylate A reaction mixture of tert-butyl (S)-4-(6,7-dichloro-1-(4-methoxybenzyl)-2-oxo-1,2-dihydropyrido[2,3-d]pyrimidin-4-yl)-3-methylpiperazine-1-carboxylate (320 mg, 0.6 mmol), {1,1'-bis(diphenylphosphino)ferrocene}dichloropalladium(II) (22 mg, 0.03 mmol), potassium acetate (294 mg, 2.99 mmol), (2-fluoro-6-hydroxyphenyl)boronic acid (112 mg, 0.719 mmol) and 1,4-dioxane (6 mL) was sparged with argon for 5 min. Four drops of water were added and the mixture was heated to 90° C. for 1 h. The reaction mixture was cooled to rt and partitioned between water (10 mL) and EtOAc (20 mL). The aqueous phase was extracted with DCM (20 mL). The combined organic phases were washed with brine (20 mL), dried over MgSO4, and concentrated in vacuo. The crude product was purified by silica gel chromatography (eluent: 0-40% DCM-MeOH (4:1)/DCM) to provide tert-butyl (3S)-4-(6-chloro-7-(2-fluoro-6-hydroxyphenyl)-1-(4-methoxybenzyl)-2-oxo-1,2-dihydropyrido[2,3-d]pyrimidin-4-yl)-3-methylpiperazine-1-carboxylate (363 mg, 0.596 mmol, 99% yield) as a light orange solid. $^1$H NMR (400 MHz, DMSO-d$_6$) δ ppm 10.21 (1H, br d, J=2.7 Hz), 8.29 (1H, d, J=2.5 Hz), 7.34 (1H, d, J=7.0 Hz), 7.28 (2H, d, J=8.7 Hz), 6.80-6.87 (1H, m), 6.78 (3H, d, J=8.7 Hz), 5.26 (2H, br d, J=4.8 Hz), 4.69-4.78 (1H, m), 4.03-4.13 (1H, m), 3.83-3.99 (1H, m), 3.60-3.80 (1H, m), 3.68 (3H, s), 2.99-3.20 (2H, m), 1.43 (9H, s), 1.30 (3H, br dd, J=6.0, 3.5 Hz). $^{19}$F NMR (376 MHz, DMSO-d$_6$) δ ppm −115.21 (1F, s), −115.24 (1F, s). m/z (ESI, +ve ion): 610.3 (M+H)$^+$.

Step 5: 4-((S)-4-Acryloyl-2-methylpiperazin-1-yl)-6-chloro-7-(2-fluoro-6-hydroxyphenyl)pyrido[2,3-d]pyrimidin-2(1H)-one A mixture of tert-butyl (3S)-4-(6-chloro-7-(2-fluoro-6-hydroxyphenyl)-1-(4-methoxybenzyl)-2-oxo-1,2-dihydropyrido[2,3-d]pyrimidin-4-yl)-3-methylpiperazine-1-carboxylate (363 mg, 0.6 mmol) and TFA (3 mL, 38.9 mmol) was heated to 60° C. for 4 h. The reaction mixture was concentrated in vacuo and the crude residue was dissolved in DCM (10 mL). The solution was cooled to 0° C. and treated with DIPEA (0.52 mL, 2.98 mmol) and acryloyl chloride (0.05 mL, 0.6 mmol). After 15 min, the reaction mixture was quenched with satd NaHCO$_3$ and extracted with DCM. The organic phase was dried over MgSO$_4$, and concentrated in vacuo. The crude product was purified by silica gel chromatography (eluent: 0-100% DCM-MeOH (4:1)/DCM) to provide 4-((S)-4-acryloyl-2-methylpiperazin-1-yl)-6-chloro-7-(2-fluoro-6-hydroxyphenyl)pyrido[2,3-d]pyrimidin-2(1H)-one (55.8 mg, 0.13 mmol, 21.1% yield) as a light yellow solid. $^1$H NMR (400 MHz, DMSO-d$_6$) δ ppm 11.52 (1H, s), 10.17 (1H, s), 8.26 (1H, br s), 7.23-7.41 (1H, m), 6.69-6.90 (3H, m), 6.19 (1H, br d, J=15.8 Hz), 5.70-5.78 (1H, m), 4.77 (1H, br s), 4.35 (1H, br d, J=11.6 Hz), 4.24 (1H, br d, J=13.3 Hz), 4.02-4.19 (2H, m), 3.97 (1H, br d, J=13.5 Hz), 3.52-3.71 (1H, m), 1.28 (3H, br d, J=6.6 Hz). $^{19}$F NMR (376 MHz, DMSO-d$_6$) δ ppm −115.41 (1F, s). m/z (ESI, +ve ion): 444.1 (M+H)$^+$.

Examples 120 and 121

1-(2,2-Dimethylpropyl)-7-(2-fluorophenyl)-4-((2S)-2-methyl-4-(2-propenoyl)-1-piperazinyl)-1,8-naphthyridin-2(1H)-one and 6-chloro-1-(2,2-dimethylpropyl)-7-(2-fluorophenyl)-4-((2S)-2-methyl-4-(2-propenoyl)-1-piperazinyl)-1,8-naphthyridin-2(1H)-one

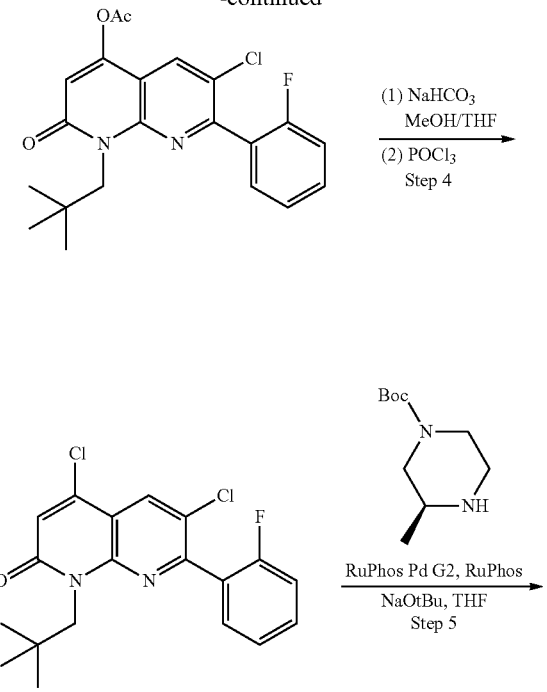
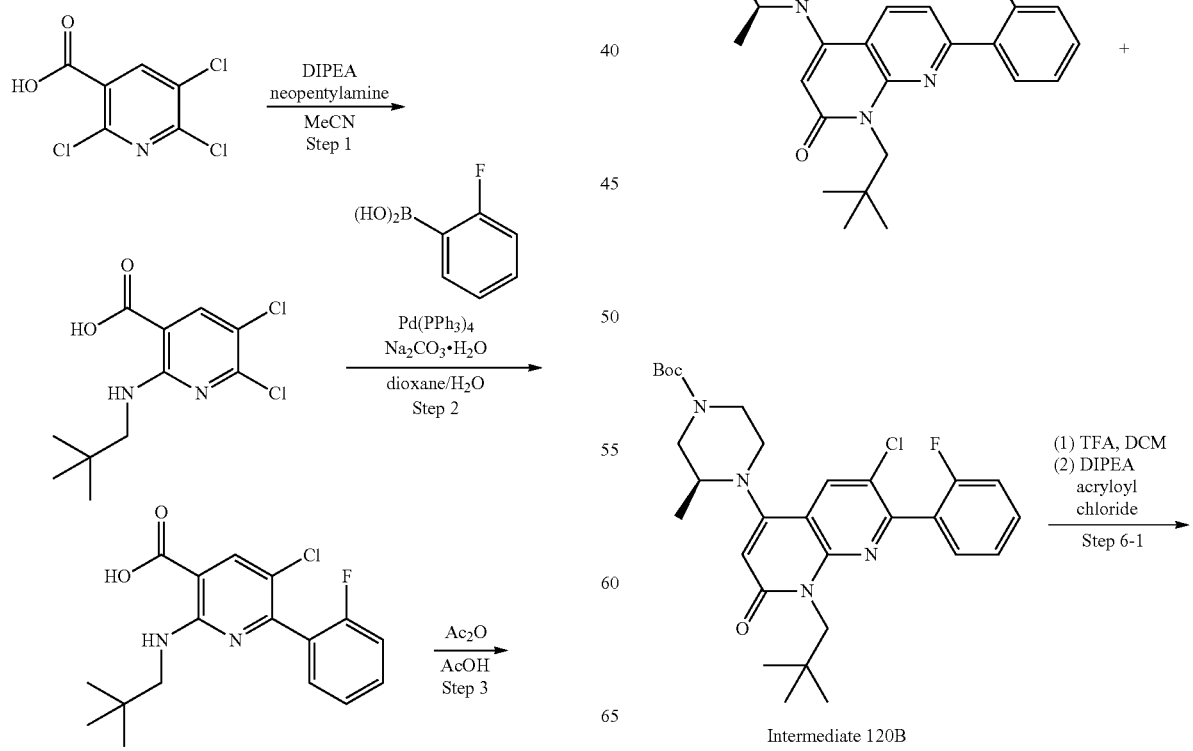

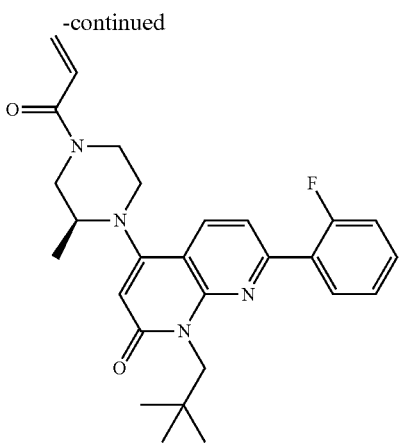

Example 120

Intermediate 120B (1) TFA, DCM
(2) DIPEA
acryloyl chloride

Step 6-2

Example 121

Step 1: 5,6-Dichloro-2-(neopentylamino)nicotinic acid

DIPEA (7.6 mL, 43.7 mmol) and neopentylamine (2.6 mL, 21.9 mmol) were added to a solution of 2,5,6-trichloronicotinic acid (3.3 g, 14.6 mmol, Combi-Blocks, Inc., San Diego, Calif., USA) in MeCN (20 mL). The reaction mixture was heated to 80° C. The reaction mixture was concentrated in vacuo and the crude product was purified by silica gel chromatography (eluent: 15-50% EtOAc/heptane and 3% AcOH in EtOAc/heptane) to provide 5,6-dichloro-2-(neopentylamino)nicotinic acid (2.96 g, 10.7 mmol, 73.3% yield) as a light yellow solid. $^1$H NMR (400 MHz, DMSO-$d_6$) δ ppm 8.42-8.53 (1H, m), 8.14 (1H, s), 3.26 (2H. s), 0.91-0.98 (9H, s). m/z (ESI, +ve ion): 277.0 and 279.0 (M+H)$^+$.

Step 2: 5-Chloro-6-(2-fluorophenyl)-2-(neopentylamino)nicotinic acid

A mixture of 2-fluorobenzeneboronic acid (1.14 g, 8.15 mmol, Combi-Blocks, San Diego, Calif.), tetrakis(triphenylphosphine) palladium(0) (0.448 g, 0.388 mmol), sodium carbonate monohydrate (2.89 g, 23.3 mmol) and 5,6-dichloro-2-(neopentylamino)nicotinic acid (2.15 g, 7.76 mmol) in 1,4-dioxane (29 mL) and water (9.7 mL) was placed under nitrogen atmosphere and heated to 90° C. After 1.5 h, the pH of the reaction mixture was adjusted to pH 4 and the mixture was extracted with EtOAc (100 mL). The organic phase was washed with brine, dried over MgSO$_4$, and concentrated in vacuo. The crude product was purified by silica gel chromatography (eluent: 20-80% (3% AcOH in EtOAc/heptane) to provide 5-chloro-6-(2-fluorophenyl)-2-(neopentylamino)nicotinic acid (2.45 g, 7.27 mmol, 94% yield) as a yellow solid. $^1$H NMR (400 MHz, DMSO-$d_6$) δ ppm 8.36 (1H, br t, J=5.1 Hz), 8.13 (1H, s), 7.51-7.58 (1H, m), 7.45 (1H, td, J=7.5, 1.8 Hz), 7.30-7.37 (2H, m), 3.27 (2H, s), 0.91-0.96 (9H, s). $^{19}$F NMR (376 MHz, DMSO-$d_6$) δ ppm −114.23 (1F, s). m/z (ESI, +ve ion): 337.1 (M+1)$^+$.

Step 3: 6-Chloro-7-(2-fluorophenyl)-1-neopentyl-2-oxo-1,2-dihydro-1,8-naphthyridin-4-yl acetate A mixture of 5-chloro-6-(2-fluorophenyl)-2-(neopentylamino)nicotinic acid (2.43 g, 7.22 mmol) in acetic anhydride (15 mL, 159 mmol) and acetic acid (10 mL) was heated to 125° C. for 2.5 h. The reaction mixture was concentrated in vacuo and the crude product was purified by silica gel chromatography (eluent: 0-60% EtOAc/heptane) to provide 6-chloro-7-(2-fluorophenyl)-1-neopentyl-2-oxo-1,2-dihydro-1,8-naphthyridin-4-yl acetate (1.41 g, 3.5 mmol, 48.5% yield) as an orange foam. $^1$H NMR (400 MHz, DMSO-$d_6$) δ ppm 8.52 (1H, s), 7.58-7.65 (1H, m), 7.54 (1H, td, J=7.6, 1.9 Hz), 7.37-7.44 (2H, m), 6.76 (1H, s), 4.32 (2H, s), 2.48 (3H, s), 0.89 (9H, s). $^{19}$F NMR (376 MHz, DMSO-$d_6$) δ ppm −114.32 (1F, s). m/z (ESI, +ve ion): 403.1 (M+1)$^+$.

Step 4: 4,6-Dichloro-7-(2-fluorophenyl)-1-neopentyl-1,8-naphthyridin-2(1H)-one (Intermediate 120A)

Step 4-1

A reaction mixture of satd. NaHCO$_3$ (5 mL) and 6-chloro-7-(2-fluorophenyl)-1-neopentyl-2-oxo-1,2-dihydro-1,8-naphthyridin-4-yl acetate (1.41 g, 3.5 mmol) in MeOH (10 mL) and THF (5.0 mL) was heated to 50° C. for 30 min. Ice was added to the reaction mixture and the pH of the reaction mixture was adjusted to pH 4 with 5 N HCl. The reaction mixture was extracted with EtOAc (40 mL). The organic layer was washed with brine, dried over MgSO$_4$, and concentrated. The crude product was purified by silica gel chromatography (eluent: 0-80% (3% AcOH in EtOAc)/heptane) to provide 6-chloro-7-(2-fluorophenyl)-4-hydroxy-1-neopentyl-1,8-naphthyridin-2(1)-one (1.08 g, 2.99 mmol, 85% yield) as a light yellow solid. $^1$H NMR (400 MHz, DMSO-$d_6$) δ ppm 11.94 (1H, br s), 8.32 (1H, s), 7.56-7.63 (1H, m), 7.51 (1H, td, J=7.5, 1.8 Hz), 7.35-7.43 (2H, m), 5.97 (1H, s), 4.25 (2H, s), 0.87 (9H, s). $^{19}$F NMR (376 MHz, DMSO-$d_6$) δ ppm −114.37 (1F, s). m/z (ESI, +ve ion): 361.1 (M+1)$^+$.

Step 4-2

A mixture of 6-chloro-7-(2-fluorophenyl)-4-hydroxy-1-neopentyl-1,8-naphthyridin-2(1H)-one (1.05 g, 2.91 mmol) and phosphorus oxychloride (5.0 mL, 32.6 mmol) was heated to 95° C. for 1 h. The reaction mixture was cooled to rt and poured onto ice and extracted with EtOAc. The organic layer was washed with satd. NaHCO$_3$, 5 N NaOH and then brine, dried over MgSO$_4$, and concentrated in vacuo. The crude product was purified by silica gel chromatography (eluent: 0-50% EtOAc/heptane) to provide 4,6-dichloro-7-(2-fluorophenyl)-1-neopentyl-1,8-naphthyridin-2(1H)-one (Intermediate 120A, 727 mg, 1.92 mmol, 65.8% yield) as an off-white solid. $^1$H NMR (400 MHz, DMSO-d$_6$) δ ppm 8.47 (1H, s), 7.62 (1H, br dd, J=8.0, 1.8 Hz), 7.53 (1H, t, J=7.0 Hz), 7.38-7.45 (2H, m), 7.18 (1H, s), 4.31 (2H, s), 0.89 (9H, s). $^{19}$F NMR (376 MHz, DMSO-d$_6$) δ ppm −114.16 (1F, s). m/z (ESI, +ve ion): 379.1 (M+1)$^+$.

Step 5: (S)-tert-Butyl 4-(7-(2-fluorophenyl)-1-neopentyl-2-oxo-1,2-dihydro-1,8-naphthyridin-4-yl)-3-methylpiperazine-1-carboxylate and (S)-tert-butyl 4-(6-chloro-7-(2-fluorophenyl)-1-neopentyl-2-oxo-1,2-dihydro-1,8-naphthyridin-4-yl)-3-methylpiperazine-1-carboxylate A mixture of (S)-tert-butyl 3-methylpiperazine-1-carboxylate (113 mg, 0.564 mmol, Combi-Blocks, San Diego, Calif.), 4,6-dichloro-7-(2-fluorophenyl)-1-neopentyl-1,8-naphthyridin-2(1H)-one (Intermediate 120A, 110 mg, 0.28 mmol), sodium tert-butoxide (108 mg, 1.13 mmol), 2-dicyclohexylphosphino-2',6'-di-i-propoxy-1,1'-biphenyl (13 mg, 0.028 mmol, Strem chemicals, Inc., Newburyport, Mass.) and chloro-(2-dicyclohexylphosphino-2',6'-diisopropoxy-1,1'-biphenyl)[2-(2'-amino-1,1'-biphenyl)]palladium(II) (22 mg, 0.028 mmol, Sigma-Aldrich Corporation, St. Louis, Mo.) in of THF (3 mL) was sparged with argon and then heated to 100° C. for 2 h. The reaction mixture was treated with water and extracted with EtOAc. The organic phase was washed with brine, dried over MgSO$_4$, and concentrated in vacuo. The crude product was purified by silica gel chromatography (eluent: 0-50% EtOAc/heptane) to provide two products. (S)-tert-butyl 4-(7-(2-fluorophenyl)-1-neopentyl-2-oxo-1,2-dihydro-1,8-naphthyridin-4-yl)-3-methylpiperazine-1-carboxylate (79.9 mg, 0.157 mmol, 55.7% yield) was obtained as a yellow film. $^1$H NMR (400 MHz, CDCl$_3$) δ ppm 8.20 (1H, td, J=7.8, 1.8 Hz), 8.12 (1H, d, J=8.3 Hz), 7.72 (1H, dd, J=8.2, 2.0 Hz), 7.41-7.48 (1H, m), 7.33 (1H, t, J=7.6 Hz), 7.20 (1H, dd, J=11.3, 8.6 Hz), 6.20 (1H, s), 4.59 (2H, br d, J=14.5 Hz), 3.84-4.03 (1H, m), 3.61-3.65 (3H, m), 3.29-3.49 (2H, m), 2.86 (1H, br d, J=11.8 Hz), 1.51 (9H, s), 1.06 (3H, d, J=6.2 Hz), 1.02 (9H, s). $^{19}$F NMR (376 MHz, CDCl$_3$) δ ppm −113.26 (1F, s), −115.13 (1F, s). m/z (ESI, +ve ion): 509.3 (M+1). (S)-tert-Butyl 4-(6-chloro-7-(2-fluorophenyl)-1-neopentyl-2-oxo-1,2-dihydro-1,8-naphthyridin-4-yl)-3-methylpiperazine-1-carboxylate (Intermediate 120B, 7.4 mg, 0.014 mmol, 4.8% yield) was isolated as a light yellow film. $^1$H NMR (400 MHz, CDCl$_3$) δ ppm 8.08 (1H, s), 7.43-7.50 (2H, m), 7.28-7.30 (1H, m), 7.18 (1H, t, J=9.1 Hz), 6.21 (1H, s), 4.34-4.46 (2H, m), 3.79-3.97 (1H, br. s), 3.58-3.62 (3H, m), 3.42 (1H, br d, J=11.0 Hz), 3.26-3.38 (1H, m), 2.75-2.87 (1H, m), 1.48 (9H, s), 1.05 (3H, d, J=5.8 Hz), 0.93 (9H, s). $^{19}$F NMR (376 MHz, CDCl$_3$) δ ppm −113.26 (1F, s), −113.31 (1F, s), −114.79 (1F, s). m/z (ESI, +ve ion): 543.2 (M+1)$^+$.

Step 6-1: 1-(2,2-Dimethylpropyl)-7-(2-fluorophenyl)-4-((2S)-2-methyl-4-(2-propenoyl)-1-piperazinyl)-1,8-naphthyridin-2(1H)-one (Example 120)

TFA (0.5 mL, 6.49 mmol) was added to a solution of (S)-tert-butyl 4-(7-(2-fluorophenyl)-1-neopentyl-2-oxo-1,2-dihydro-1,8-naphthyridin-4-yl)-3-methylpiperazine-1-carboxylate (79.9 mg, 0.157 mmol) in DCM (2.0 mL) at rt. After 30 min, the reaction mixture was concentrated in vacuo. The residue was dissolved in DCM (2.0 mL) and the solution was cooled to 0° C. DIPEA (0.14 mL, 0.79 mmol) and acryloyl chloride (0.013 mL, 0.157 mmol) were sequentially added and the reaction mixture was allowed to stir for 15 min at 0° C. The reaction mixture was treated with said NaHCO$_3$ and extracted with DCM. The organic phase was dried over MgSO$_4$, and concentrated in vacuo. The crude product was purified by silica gel chromatography (eluent: 0-30% DCM-MeOH (4:1)/DCM) to provide 1-(2,2-dimethylpropyl)-7-(2-fluorophenyl)-4-((2S)-2-methyl-4-(2-propenoyl)-1-piperazinyl)-1,8-naphthyridin-2(1H)-one (Example 120). $^1$H NMR (400 MHz, DMSO-d$_6$) δ ppm 8.31 (1H, d, J=7.8 Hz), 8.13 (1H, td, J=7.9, 1.7 Hz), 7.72 (1H, dd, J=8.2, 2.0 Hz), 7.49-7.61 (1H, m), 7.36-7.46 (2H, m), 6.78-6.95 (1H, m), 6.06-6.23 (2H, m), 5.72 (1H, d, J=2.1 Hz), 4.49 (1H, br d, J=11.0 Hz), 4.41 (1H, br s), 4.28 (1H, br d, J=10.2 Hz), 3.91-4.14 (1H, m), 3.82 (2H, br d, J=10.4 Hz), 3.52-3.68 (1H, m), 3.29-3.33 (1H, m), 2.85-3.02 (1H, m), 0.92 (9H, s). $^{19}$F NMR (376 MHz, DMSO-d$_6$) δ ppm −114.14 (1F, s), −115.54 (1F, s). m/z (ESI, +ve ion): 463.3 (M+1)$^+$.

Step 6-2: 6-Chloro-1-(2,2-dimethylpropyl)-7-(2-fluorophenyl)-4-((2S)-2-methyl-4-(2-propenoyl)-1-piperazinyl)-1,8-naphthyridin-2(1H)-one (Example 121)

TFA (0.5 mL, 6.49 mmol) was added to a solution of (S)-tert-butyl 4-(6-chloro-7-(2-fluorophenyl)-1-neopentyl-2-oxo-1,2-dihydro-1,8-naphthyridin-4-yl)-3-methylpiperazine-1-carboxylate (Intermediate 120B, 7.4 mg, 0.014 mmol) in DCM (1 mL). After 30 min, the reaction mixture was concentrated in vacuo. The residue was dissolved in DCM (1 mL) and the solution was cooled to 0° C. DIPEA (0.012 mL, 0.068 mmol) and acryloyl chloride (1.1 μl, 0.014 mmol) were sequentially added and the reaction mixture was allowed to stir for 15 min at 0° C. The reaction mixture was treated with satd. NaHCO$_3$ and extracted with DCM. The organic phase was dried over MgSO$_4$, and concentrated in vacuo. The crude product was purified by silica gel chromatography (eluent: 0-20% DCM-MeOH (4:1)/DCM) to provide 6-chloro-1-(2,2-dimethylpropyl)-7-(2-fluorophenyl)-4-((2S)-2-methyl-4-(2-propenoyl)-1-piperazinyl)-1,8-naphthyridin-2(1H)-one (Example 121). $^1$H NMR (400 MHz, MeOH-d$_4$) δ ppm 8.35 (1H, s), 7.48-7.65 (2H, m), 7.32-7.42 (1H, m), 7.27 (1H, br t, J=9.2 Hz), 6.86 (1H, br d, J=10.4 Hz), 6.24-6.40 (2H, m), 5.75-5.93 (1H, m), 4.46 (1H, br s), 4.39 (1H, br d, J=9.7 Hz), 4.32 (1H, br d, J=12.0 Hz), 4.02-4.19 (1H, m), 3.98 (1H, br d, J=10.0 Hz), 3.86 (1H, br s), 3.64-3.82 (1H, m), 3.40-3.60 (1H, m), 3.02 (1H, br d, J=12.0 Hz), 1.07 (3H, br d, J=5.8 Hz), 0.93 (9H, s). $^{19}$F NMR (376 MHz, MeOH-d4) δ ppm −115.68 (1F, s). m/z (ESI, +ve ion): 497.2 (M+1)$^+$.

Examples 122 and 123

6-Chloro-1-(2,2-dimethylpropyl)-7-(2-fluorophenyl)-4-(4-(2-propenoyl)-1-piperazinyl)-1,8-naphthyridin-2(1H)-one and 1-(2,2-dimethylpropyl)-7-(2-fluorophenyl)-4-(4-(2-propenoyl)-1-piperazinyl)-1,8-naphthyridin-2(1H)-one

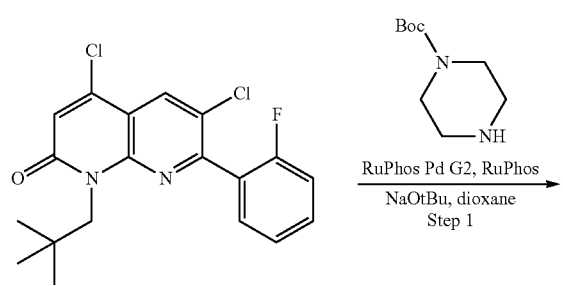

Intermediate 120A

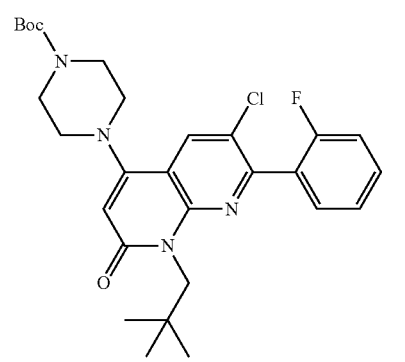

+

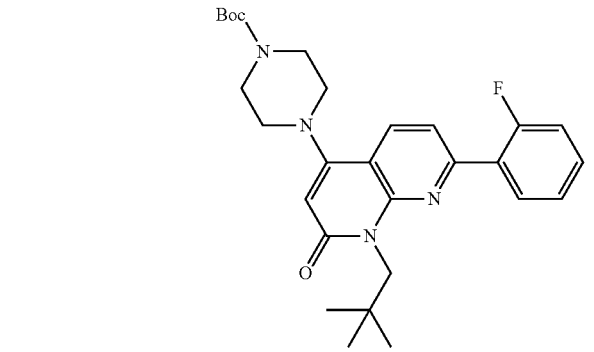

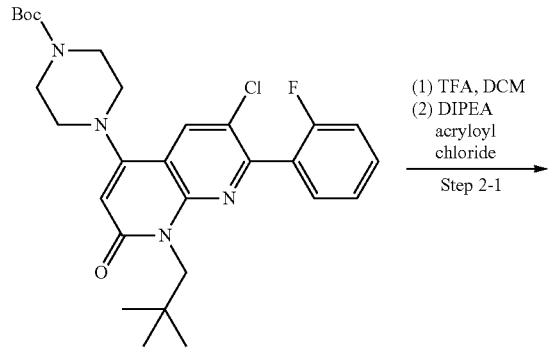

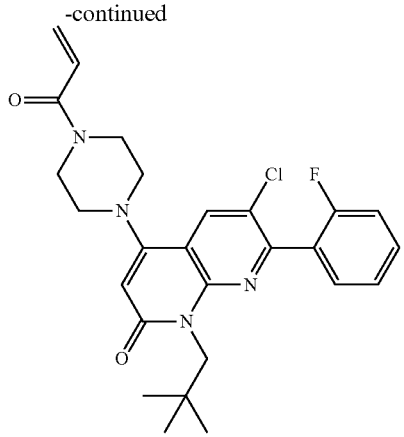

Example 122

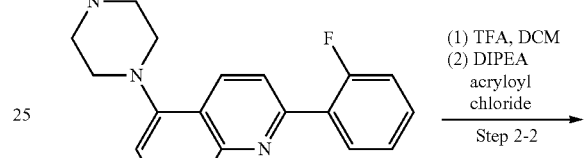

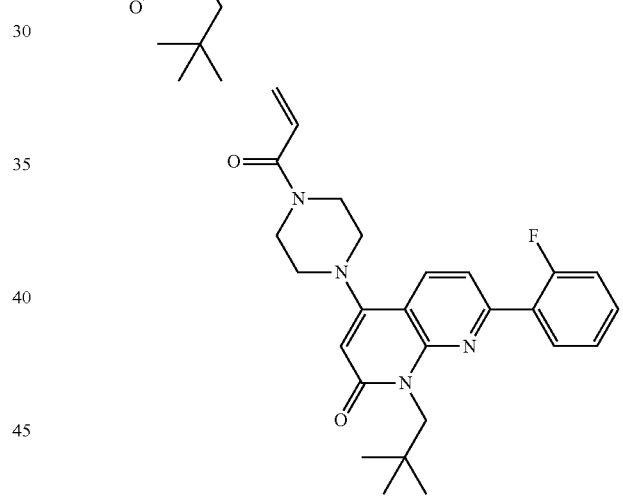

Example 123

Step 1: tert-Butyl 4-(6-chloro-7-(2-fluorophenyl)-1-neopentyl-2-oxo-1,2-dihydro-1,8-naphthyridin-4-yl)piperazine-1-carboxylate and tert-butyl 4-(7-(2-fluorophenyl)-1-neopentyl-2-oxo-1,2-dihydro-1,8-naphthyridin-4-yl)piperazine-1-carboxylate A mixture of tert-butyl piperazine-1-carboxylate (183 mg, 0.98 mmol), 4,6-dichloro-7-(2-fluorophenyl)-1-neopentyl-1,8-naphthyridin-2(1H)-one (Intermediate 120A, 310 mg, 0.82 mmol), sodium tert-butoxide (173 mg, 1.80 mmol), 2-dicyclohexylphosphino-2',6'-di-iso-propoxy-1,1'-biphenyl (38.1 mg, 0.082 mmol, Strem Chemicals, Inc., Newburyport, Mass.) and chloro-(2-dicyclohexylphosphino-2',6'-di-isopropoxy-1,1'-biphenyl)[2-(2'-amino-1,1'-biphenyl)]palladium(II) (64 mg, 0.082 mmol, Sigma-Aldrich Corporation, St. Louis, Mo., USA) in 1,4-dioxane (10 mL) was sparged with argon and heated to 80° C. for 45 min. The reaction mixture was treated with water and extracted with EtOAc. The organic phase was washed with brine, dried over MgSO$_4$, and concentrated in vacuo. The crude product was purified by silica gel chromatography (eluent: 0-70% EtOAc/heptane) to provide two products. tert-Butyl 4-(6-chloro-7-(2-fluorophenyl)-1-neopentyl-2-oxo-1,2-dihydro-1,8-naphthyridin-4-yl)piperazine-1-carboxylate (201 mg, 0.38 mmol, 46.5% yield) was obtained as a yellow foam. $^1$H NMR (400 MHz, CDCl$_3$) δ ppm 8.05 (1H, s), 7.45-7.55 (1H, m), 7.27-7.38 (1H, m), 7.15-7.24 (2H, m), 6.21 (1H, s), 4.41 (2H, br s), 3.63-3.75 (4H, m), 3.05-3.16 (4H, m), 1.51 (9H, s), 0.95 (9H, s). $^{19}$F NMR (376 MHz, CDCl$_3$) δ ppm −113.23 (1F, s). m/z (ESI, +ve ion): 529.3 (M+H)$^+$. tert-Butyl 4-(7-(2-fluorophenyl)-1-neopentyl-2-oxo-1,2-dihydro-1,8-naphthyridin-4-yl)piperazine-1-carboxylate (48 mg, 0.097 mmol, 12% yield) was isolated as a light yellow film. $^1$H NMR (400 MHz, CDCl$_3$) δ ppm 8.19 (1H, td, J=7.9, 1.8 Hz), 8.03-8.09 (1H, m), 7.72 (1H, dd, J=8.2, 2.0 Hz), 7.38-7.50 (1H, m), 7.32 (1H, td, J=7.6, 1.2 Hz), 7.20 (1H, ddd, J=11.8, 8.2, 0.9 Hz), 6.17 (1H, s), 4.57 (2H, br s), 3.65-3.72 (4H, m), 3.10 (4H, br s), 1.51 (9H, s), 1.01 (8H, s). $^{19}$F NMR (376 MHz, CDCl$_3$) δ ppm −115.07 (1F, s). m/z (ESI, +ve ion): 495.2 (M+H)$^+$.

Step 2-1: 6-Chloro-1-(2,2-dimethylpropyl)-7-(2-fluorophenyl)-4-(4-(2-propenoyl)-1-piperazinyl)-1,8-naphthyridin-2(1H)-one (Example 122)

TFA (0.5 mL, 6.49 mmol) was added to a solution of tert-butyl 4-(6-chloro-7-(2-fluorophenyl)-1-neopentyl-2-oxo-1,2-dihydro-1,8-naphthyridin-4-yl)piperazine-1-carboxylate (175 mg, 0.33 mmol) in DCM (3 mL) at rt. After 15 min, the reaction mixture was concentrated in vacuo. The residue was dissolved in DCM (3 mL) and the solution was cooled to 0° C. DIPEA (0.29 mL, 1.65 mmol) and acryloyl chloride (0.027 mL, 0.33 mmol) were sequentially added and the reaction mixture was allowed to stir for 10 min at 0° C. The reaction mixture was treated with satd. NaHCO$_3$ and extracted with DCM. The organic phase was dried over MgSO$_4$, and concentrated in vacuo. The crude product was purified by silica gel chromatography (eluent: 0-20% DCM-MeOH (4:1)/DCM) to provide 6-chloro-1-(2,2-dimethylpropyl)-7-(2-fluorophenyl)-4-(4-(2-propenoyl)-1-piperazinyl)-1,8-naphthyridin-2(1H)-one (Example 122). $^1$H NMR (400 MHz, DMSO-d$_6$) δ ppm 8.25 (1H, s), 7.57-7.66 (1H, m), 7.54 (1H, td, J=7.5, 2.0 Hz), 7.36-7.45 (2H, m), 6.86 (1H, dd, J=16.7, 10.5 Hz), 6.09-6.25 (2H, m), 5.71-5.79 (1H, m), 4.28 (2H, s), 3.76-3.91 (4H, m), 3.15 (4H, br s), 0.88 (9H, s). $^{19}$F NMR (376 MHz, DMSO-d$_6$) δ ppm −114.11 (1F, s). m/z (ESI, +ve ion): 483.2 (M+H)$^+$. Step 2-2: 1-(2,2-Dimethylpropyl)-7-(2-fluorophenyl)-4-(4-(2-propenoyl)-1-piperazinyl)-1,8-naphthyridin-2(1H)-one (Example 123).

TFA (0.5 mL, 6.49 mmol) was added to a solution of tert-butyl 4-(7-(2-fluorophenyl)-1-neopentyl-2-oxo-1,2-dihydro-1,8-naphthyridin-4-yl)piperazine-1-carboxylate (48 mg, 0.097 mmol) in DCM (3 mL) at rt. After 25 min. the reaction mixture was concentrated in vacuo. The residue was dissolved in DCM (3 mL) and the solution was cooled to 0° C. DIPEA (0.085 mL, 0.49 mmol) and acryloyl chloride (7.9 μL, 0.097 mmol) were sequentially added and the reaction mixture was allowed to stir for 10 min at 0° C. The reaction mixture was treated with saturated NaHCO$_3$, extracted with DCM. The organic phase was dried over MgSO$_4$, and concentrated in vacuo. The crude product was purified by silica gel chromatography (eluent: 0-20% DCM-MeOH (4:1)/DCM) to provide 1-(2,2-dimethylpropyl)-7-(2-fluorophenyl)-4-(4-(2-propenoyl)-1-piperazinyl)-1,8-naphthyridin-2(1H)-one (Example 123). $^1$H NMR (400 MHz; DMSO-d$_6$) δ ppm 8.30 (1H, d, J=8.3 Hz), 8.10-8.19 (1H, m), 7.71-7.79 (1H, m), 7.52-7.61 (1H, m), 7.32-7.48 (2H, m), 6.81-6.93 (1H, m), 6.11-6.22 (1H, m), 6.05-6.11 (1H, m), 5.68-5.81 (1H, m), 4.44 (2H, br s), 3.82 (4H, br s), 3.06-3.20 (4H, m), 0.88-0.95 (9H, s). $^{19}$F NMR (376 MHz, DMSO-d$_6$) δ ppm −115.48 (1F, s). m/z (ESI, +ve ion): 449.2 (M+H)$^+$.

Example 124

6-Chloro-1-(2,2-dimethylpropyl)-7-(2-fluorophenyl)-4-(1-(i-propenoyl)-1,2,3,6-tetrahydro-4-pyridinyl)-1,8-naphthyridin-2(1H)-one

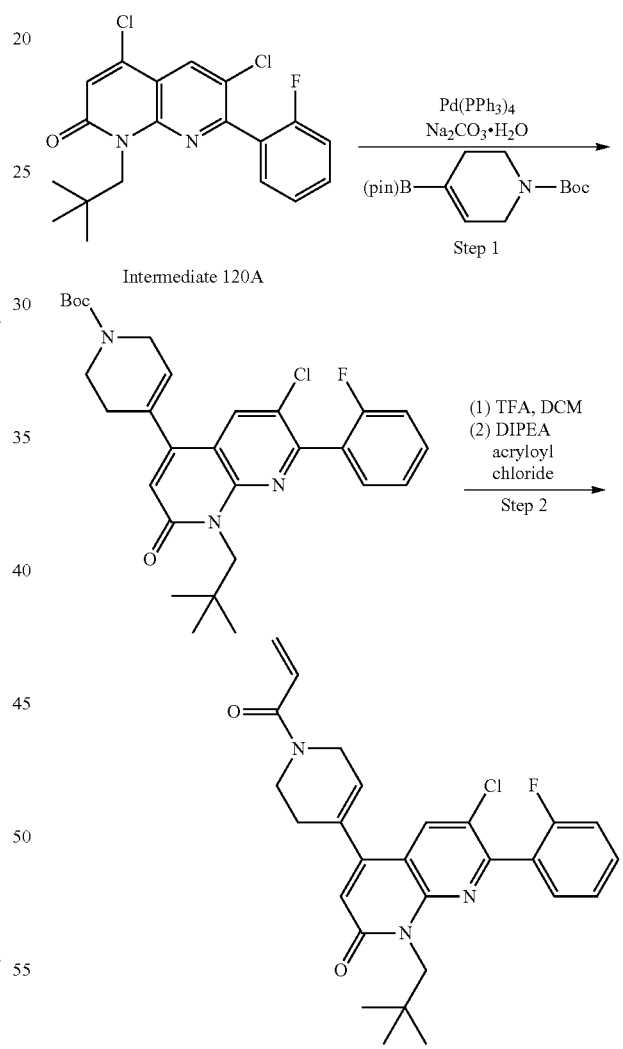

Step 1: tert-Butyl 4-(6-chloro-7-(2-fluorophenyl)-1-neopentyl-2-oxo-1,2-dihydro-1,8-naphthyridin-4-yl)-5,6-dihydropyridine-1(2H)-carboxylate A mixture of tert-butyl 4-(4,4,5,5-tetramethyl-1,3,2-dioxaborolan-2-yl)-5,6-dihydropyridine-1(2H)-carboxylate (92 mg, 0.299 mmol, Combi-Blocks, San Diego, Calif.), tetrakis(triphenylphosphine)palladium(0) (15.7 mg, 0.014 mmol), sodium carbonate monohydrate (101 mg, 0.815 mmol), and 4,6-dichloro-7-(2-fluorophenyl)-1-neopentyl-1,8-naphthyridin-2(1H)-one (Intermediate 120A, 103 mg, 0.272 mmol) in 1,4-dioxane (2.0 mL) and water (0.7 mL) was placed under a nitrogen atmosphere and heated to 110° C. for 30 min. The reaction mixture was cooled to rt, treated with brine and extracted with EtOAc (20 mL). The organic phase was washed with brine, dried over $MgSO_4$, and concentrated in vacuo. The crude product was purified by silica gel chromatography (eluent: 0-100% EtOAc/heptane) to provide tert-butyl 4-(6-chloro-7-(2-fluorophenyl)-1-neopentyl-2-oxo-1,2-dihydro-1,8-naphthyridin-4-yl)-5,6-dihydropyridine-1(2H)-carboxylate (128 mg, 0.24 mmol, 90% yield) as a light yellow solid. $^1$H NMR (400 MHz, DMSO-$d_6$) δ ppm 8.23 (1H, s), 7.57-7.67 (1H, m), 7.46-7.57 (1H, m), 7.35-7.46 (2H, m), 6.67 (1H, s), 6.02 (1H, brs), 4.33 (2H, s), 4.01-4.13 (2H, m), 3.62 (2H, br t, J=5.5 Hz), 2.37-2.48 (2H, m), 1.41-1.48 (9H, s), 0.85-0.91 (9H, s). $^{19}$F NMR (376 MHz, DMSO-$d_6$) δ ppm −114.23 (1F, s). m/z (ESI, +ve ion): 526.3 (M+H)$^+$.

Step 2: 6-Chloro-1-(2,2-dimethylpropyl)-7-(2-fluorophenyl)-4-(1-(2-propenoyl)-1,2,3,6-tetrahydro-4-pyridinyl)-1,8-naphthyridin-2(1H)-one TFA (0.5 mL, 6.49 mmol) was added to a solution of tert-butyl 4-(6-chloro-7-(2-fluorophenyl)-1-neopentyl-2-oxo-1,2-dihydro-1,8-naphthyridin-4-yl)-5,6-dihydropyridine-1(2H)-carboxylate (117 mg, 0.222 mmol) in DCM (3 mL) at rt. After 20 min, the reaction mixture was concentrated in vacuo. The residue was dissolved in DCM (1 mL) and the solution was cooled to 0° C. DIPEA (0.19 mL, 1.11 mmol) and by acryloyl chloride (0.018 mL, 0.22 mmol) were sequentially added and the reaction mixture was allowed to stir for 10 min at 0° C. The reaction mixture was treated with satd. $NaHCO_3$ and extracted with DCM. The organic layer was dried over $MgSO_4$, and concentrated in vacuo. The crude product was purified by silica gel chromatography (eluent: 0-30% DCM-MeOH (4:1/DCM) to provide 6-chloro-1-(2,2-dimethylpropyl)-7-(2-fluorophenyl)-4-(1-(2-propenoyl)-1,2,3,6-tetrahydro-4-pyridinyl)-1,8-naphthyridin-2(1H)-one. $^1$H NMR (400 MHz, DMSO-$d_6$) δ ppm 8.28 (1H, s), 7.59-7.66 (1H, m), 7.50-7.56 (1H, m), 7.36-7.46 (2H, m), 6.76-7.01 (1H, m), 6.68 (1H, s), 6.13-6.24 (1H, m), 5.99-6.11 (1H, m), 5.74 (1H, br d, J=10.2 Hz), 4.19-4.44 (6H, m), 3.80-3.92 (2H, m), 0.90 (9H, s). $^{19}$F NMR (376 MHz, DMSO-$d_6$) δ ppm −114.23 (1F, s). m/z (ESI, +ve ion): 480.2 (M+H)$^+$.

Example 125

6-Chloro-1-(2,2-dimethylpropyl)-7-(2-fluorophenyl)-4-(1-(2-propenoyl)-4-piperidinyl)-1,8-naphthyridin-2(1)-one

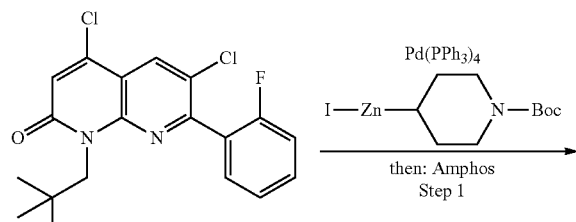

Intermediate 120A

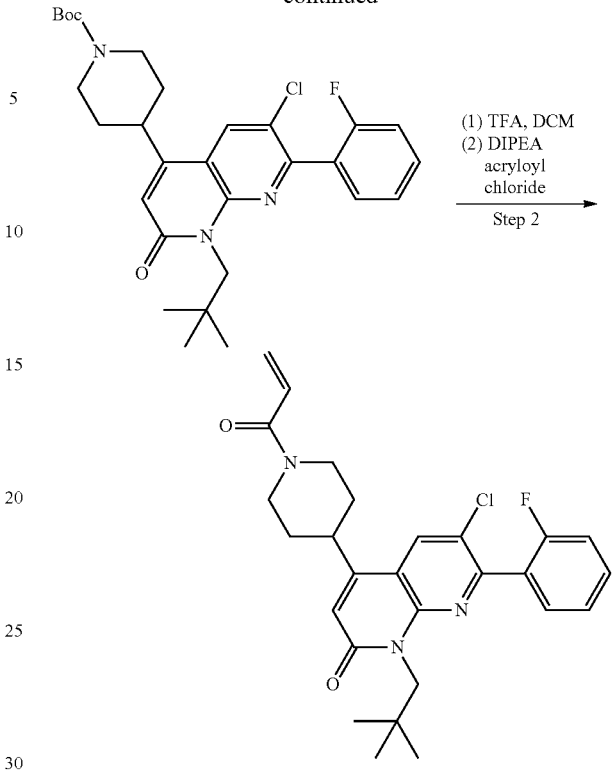

Step 1: tert-Butyl 4-(6-chloro-7-(2-fluorophenyl)-1-neopentyl-2-oxo-1,2-dihydro-1,8-naphthyridin-4-yl)piperidine-1-carboxylate

[1-(tert-Butoxycarbonyl)piperidin-4-yl]zinc iodide (0.5 M in THF, 0.28 mL, 0.14 mmol) was added to a mixture of 4,6-dichloro-7-(2-fluorophenyl)-1-neopentyl-1,8-naphthyridin-2(1H)-one (Intermediate 120A, 11 mg, 0.028 mmol) and tetrakis(triphenylphosphine) palladium (0) (1.6 mg, 1.41 μmol) in THF (3.0 mL) under nitrogen atmosphere. The reaction mixture was heated to 80° C. for 20 min. Additional [1-(tert-butoxycarbonyl)piperidin-4-yl]zinc iodide, (0.5 M in THF, 0.28 mL, 0.14 mmol, Rieke Metals, Inc., Lincoln, Nebr.) and bis(di-tert-butyl(4-dimethylaminophenyl)phosphine)dichloropalladium(II) (3 mg, 4 μmol, Sigma-Aldrich Corporation, St. Louis, Mo.) were added and heating to 80° C. was continued for 40 min. The reaction mixture was cooled to rt, treated with 5 N NaOH (2 mL) and extracted with EtOAc. The organic phase was washed with brine, dried over $MgSO_4$. and concentrated in vacuo. The crude product was purified by silica gel chromatography (eluent: 0-80% EtOAc/heptane) to provide tert-butyl 4-(6-chloro-7-(2-fluorophenyl)-1-neopentyl-2-oxo-1,2-dihydro-1,8-naphthyridin-4-yl)piperidine-1-carboxylate (10.7 mg, 0.02 mmol, 71.8% yield). $^1$H NMR (400 MHz, CDCl$_3$) δ ppm 8.07 (1H, s), 7.42-7.53 (2H, m), 7.27-7.34 (1H, m), 7.20 (1H, t, J=9.0 Hz), 6.67 (1H, s), 4.46 (1H, br s), 4.34 (2H, br dd, J=3.6, 1.8 Hz), 2.98-3.07 (1H, m), 2.86-2.98 (2H, m), 1.95 (2H, br d, J=13.1 Hz), 1.65-1.73 (2H, m), 1.61 (2H, s), 0.95 (9H, s) 123912-2-3. $^{19}$F NMR (376 MHz, CDCl$_3$) δ ppm −113.28 (1F, s).

Step 2: 6-Chloro-1-(2,2-dimethylpropyl)-7-(2-fluorophenyl)-4-(1-(2-propenoyl)-4-piperidinyl)-1,8-naphthyridin-2(1H)-one TFA (0.5 mL, 6.49 mmol) was added to a solution of tert-butyl 4-(6-chloro-7-(2-fluorophenyl)-1-neopentyl-2-oxo-1,2-dihydro-1,8-naphthyridin-4-yl)piperidine-1-carboxylate (10 mg, 0.019 mmol) in DCM (1 mL) at rt. After 30 min, the reaction mixture was concentrated in vacuo. The residue was dissolved in DCM (1 mL) and the solution was cooled to 0° C. DIPEA (0.017 mL, 0.095 mmol) and acryloyl chloride (1.5 µL, 0.019 mmol) were sequentially added and the reaction mixture was allowed to stir for 10 min at 0° C. The reaction mixture was treated with satd. NaHCO$_3$ and extracted with DCM. The organic phase was dried over MgSO$_4$, and concentrated in vacuo. The crude product was purified by silica gel chromatography (eluent: 0-30% DCM-MeOH (4:1)/DCM) to provide 6-chloro-1-(2,2-dimethylpropyl)-7-(2-fluorophenyl)-4-(1-(2-propenoyl)-4-piperidinyl)-1,8-naphthyridin-2(1H)-one. $^1$H NMR (400 MHz, DMSO-d$_6$) δ ppm 8.68 (1H, s), 7.57-7.65 (1H, m), 7.53 (1H, td, J=7.5, 1.9 Hz), 7.36-7.44 (2H, m), 6.85 (1H, dd, J=16.8, 10.6 Hz), 6.64 (1H, s), 6.12 (1H, dd, J=16.7, 2.4 Hz), 5.69 (1H, dd, J=10.5, 2.4 Hz), 4.58-4.68 (1H, m), 4.27-4.36 (2H, m), 4.15-4.27 (1H, m), 3.46-3.57 (1H, m), 2.84-2.96 (1H, m), 2.42 (1H, br s), 1.93 (2H, br d, J=12.4 Hz), 1.49-1.68 (2H, m), 0.88 (9H, s). $^{19}$F NMR (376 MHz, DMSO-d$_6$) δ ppm −114.30 (1F, s). m/z (ESI, +ve ion): 482.2 (M+H)$^+$.

Examples 126 and 127

6-Chloro-7-(2-fluorophenyl)-4-((2S)-2-methyl-4-(2-propenoyl)-1-piperazinyl)-1-(2-(2-propanyl)phenyl)-1,8-naphthyridin-2(1H)-one and 7-(2-fluorophenyl)-4-((2S)-2-methyl-4-(2-propenoyl)-1-piperazinyl)-1-(2-(2-propanyl)phenyl)-1,8-naphthyridin-2(1H)-one

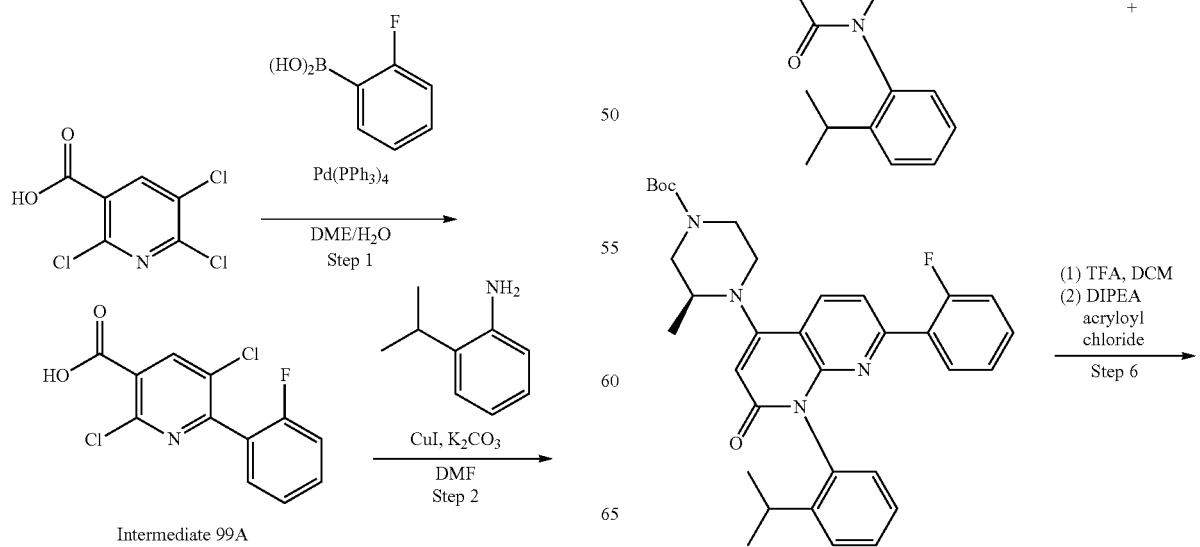

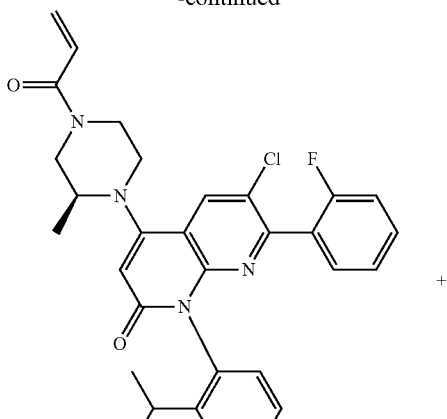

Example 126

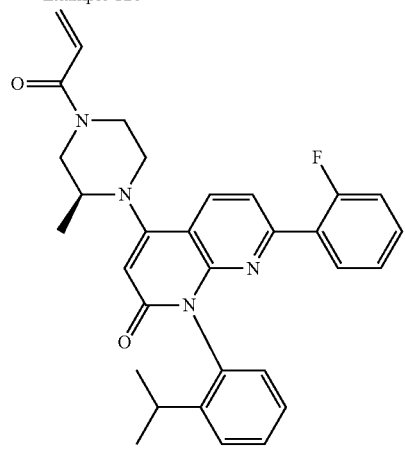

Example 127

Step 1: 2,5-Dichloro-6-(2-fluorophenyl)nicotinic acid

A mixture of 2,5,6-trichloronicotinic acid (580 mg, 2.56 mmol, Combi-Blocks, Inc., San Diego, Calif.), (2-fluorophenyl)boronic acid (376 mg, 2.69 mmol, Combi-Blocks, Inc., San Diego, Calif.), potassium carbonate (1.06 g, 7.68 mmol) and tetrakis(triphenylphosphine) palladium (0) (148 mg, 0.13 mmol) in 1,2-dimethoxyethane (12.8 mL)/water (4.3 mL) was heated to 100° C. in a microwave for 1 h. The reaction mixture was diluted with water (50 mL) and the pH was adjusted to pH 4 with 5 N HCl. The reaction mixture was extracted with EtOAc (50 mL). The organic layer was washed with brine, dried over MgSO$_4$, and concentrated in vacuo to provide 2,5-dichloro-6-(2-fluorophenyl)nicotinic acid (Intermediate 99A). $^1$H NMR (400 MHz, DMSO-d$_6$) δ ppm 8.50 (1H, s), 7.61-7.69 (1H, m), 7.49-7.61 (1H, m), 7.32-7.46 (2H, m). $^{19}$F NMR (376 MHz, DMSO-d$_6$) δ ppm −114.25 (1F, s). m/z (ESI, +ve ion): 286.0 (M+H)$^+$.

Step 2: 5-Chloro-6-(2-fluorophenyl)-2-((2-isopropylphenyl)amino)nicotinic acid

A mixture of copper(I) iodide (62 mg, 0.33 mmol), 2-isopropylaniline (1.35 g, 9.96 mmol, Sigma Aldrich), 2,5-dichloro-6-(2-fluorophenyl)nicotinic acid (950 mg, 3.32 mmol) and potassium carbonate (1.61 g, 11.6 mmol) in DMF (12 mL) was sparged with argon and then heated in a microwave to 150° C. for 90 min. The reaction mixture was treated with water and the pH was adjusted to pH 4 with 5 N HCl. The reaction mixture was extracted with EtOAc (50 mL). The organic phase was washed with brine, dried over MgSO$_4$, and concentrated in vacuo. The crude product was purified by silica gel chromatography (eluent: 10-50% (3% AcOH in EtOAc)/heptane) to provide 5-chloro-6-(2-fluorophenyl)-2-((2-isopropylphenyl)amino)nicotinic acid (330 mg, 0.86 mmol, 25.8% yield) as a bright yellow solid. $^1$H NMR (400 MHz, MeOH-d$_4$) δ ppm 8.36 (1H, s), 7.93 (1H, dd, J=7.8, 1.6 Hz), 7.39-7.53 (2H, m), 7.24-7.33 (2H, m), 7.16-7.23 (1H, m), 7.03-7.13 (2H, m), 3.21-3.31 (3H, m), 1.24-1.31 (6H, m). $^{19}$F NMR (376 MHz, MeOH-d4) δ ppm −115.50 (1F, s). m/z (ESI, +ve ion): 385.1 (M+H)$^+$.

Step 3: 6-Chloro-7-(2-fluorophenyl)-4-hydroxy-1-(2-isopropylphenyl)-1,8-naphthyridin-2(1H)-one Step 3-1

A mixture of 5-chloro-6-(2-fluorophenyl)-2-((2-isopropylphenyl)amino)nicotinic acid (186 mg, 0.483 mmol) and CDI (86 mg, 0.531 mmol) in THF (3 mL) was heated to 50° C. for 1 h and then stirred at rt for additional 1.5 h. In a separate flask, isopropylmagnesium chloride (2.0 M in THF, 1.1 mL, 2.2 mmol) was added to a solution of mono-benzyl malonate (200 mg, 1 mmol, Sigma-Aldrich Corporation, St. Louis, Mo.) in THF (3 mL) at 0° C. After 30 min, the reaction was heated to 50° C. for 1.5 h. Both solutions were cooled to 0° C. and the magnesium malonate solution was added dropwise to the nicotinic acid solution. The ice bath was removed and the mixture was allowed to warm to rt overnight. 5 N HCl was added dropwise to the reaction mixture until it became clear. The solution was extracted with EtOAc (40 mL). The organic extract was washed with brine, dried over MgSO$_4$, and concentrated in vacuo. The crude product was purified by silica gel chromatography (eluent: 0-20% EtOAc/heptane) to provide benzyl 3-(5-chloro-6-(2-fluorophenyl)-2-((2-isopropylphenyl)amino)pyridin-3-yl)-3-oxopropanoate (152 mg, 0.3 mmol, 61% yield) as a bright yellow oil. $^{19}$F NMR (376 MHz, CDCl$_3$) δ ppm −112.46 (1F, s), −112.54 (1F, s). m/z (ESI, +ve ion): 517.1 (M+H)$^+$.

Step 3-2

5 N NaOH (0.6 mL, 3 mmol) was added to a solution of benzyl 3-(5-chloro-6-(2-fluorophenyl)-2-((2-isopropylphenyl)amino)pyridin-3-yl)-3-oxopropanoate (150 mg, 0.29 mmol) in MeOH (3.0 mL) and THF (3.0 mL) at 50° C. After 30 min, the reaction mixture was concentrated in vacuo. The crude residue was diluted with water, the pH was adjusted to pH 4 with 5 N HCl and the mixture was extracted with EtOAc. The organic phase was washed with brine, dried over MgSO$_4$, and concentrated in vacuo. The residue was purified by silica gel chromatography (eluent: 0-60% EtOAc/heptane) to provide 6-chloro-7-(2-fluorophenyl)-4-hydroxy-1-(2-isopropylphenyl)-1,8-naphthyridin-2(1H)-one (76.2 mg, 0.186 mmol, 63.4% yield) as a white solid. $^1$H NMR (400 MHz, CDCl$_3$) δ ppm 8.26 (1H, s), 7.40-7.47 (2H, m), 7.32-7.39 (1H, m), 7.25-7.32 (1H, m), 7.10-7.20 (2H, m), 7.03-7.10 (3H, m), 6.47 (1H, s), 2.55 (1H, quin, J=6.8 Hz), 1.17 (3H, d, J=6.8 Hz), 1.00 (3H, d, J=6.8 Hz). $^{19}$F NMR (376 MHz, CDCL$_3$) δ ppm −112.89 (1F, s). m/z (ESI, +ve ion): 409.1 (M+H)$^+$.

Step 4: 4,6-Dichloro-7-(2-fluorophenyl)-1-(2-isopropylphenyl)-1,8-naphthyridin-2(1H)-one A mixture of 6-chloro-7-(2-fluorophenyl)-4-hydroxy-1-(2-isopropylphenyl)-1,8-naphthyridin-2(1H)-one (97.8 mg, 0.239 mmol) and phosphorus oxychloride (1.0 mL, 6.5 mmol) was heated to 95° C. for 2 h. The reaction mixture was concentrated in vacuo and the residue was dissolved in EtOAc. The solution was washed with satd. NaHCO$_3$, dried over MgSO$_4$. and concentrated in vacuo. The crude product was purified by silica gel chromatography (eluent: 0-80% EtOAc/heptane) to provide 4,6-dichloro-7-(2-fluorophenyl)-1-(2-isopropylphenyl)-1,8-naphthyridin-2(1H)-one (101 mg, 0.26 mmol, 99% yield) as a white foam. $^1$H NMR (400 MHz, CDCl$_3$) δ ppm 8.37 (1H, s), 7.35-7.45 (3H, m), 7.27-7.31 (1H, m), 7.09-7.18 (2H, m), 7.01-7.09 (3H, m), 2.53 (1H, dt, J=13.7, 6.8 Hz), 1.16 (3H, d, J=6.8 Hz), 1.00 (3H, d, J=6.8 Hz). $^{19}$F NMR (376 MHz, CDCl$_3$) δ ppm −112.74 (1F, s). m/z (ESI, +ve ion): 427.1 (M+H)$^+$.

Step 5: (S)-tert-Butyl 4-(6-chloro-7-(2-fluorophenyl)-1-(2-isopropylphenyl)-2-oxo-1,2-dihydro-1,8-naphthyridin-4-yl)-3-methylpiperazine-1-carboxylate and (S)-tert-butyl 4-(7-(2-fluorophenyl)-1-(2-isopropylphenyl)-2-oxo-1,2-dihydro-1,8-naphthyridin-4-yl)-3-methylpiperazine-1-carboxylate A mixture of (S)-tert-butyl 3-methylpiperazine-1-carboxylate (61.3 mg, 0.306 mmol), 4,6-dichloro-7-(2-fluorophenyl)-1-(2-isopropylphenyl)-1,8-naphthyridin-2(1H)-one (110 mg, 0.26 mmol), sodium tert-butoxide (54 mg, 0.56 mmol), 2-dicyclohexylphosphino-2',6'-di-i-propoxy-1,1'-biphenyl (12 mg, 0.026 mmol) and chloro-(2-dicyclohexylphosphino-2',6'-diisopropoxy-1,1'-biphenyl)[2-(2'-amino-1,1'-biphenyl)]palladium(II) (20 mg, 0.026 mmol) 1,4-dioxane (5 mL) was sparged with argon and heated to 80° C. for 45 min. The reaction mixture was treated with water and extracted with EtOAc. The organic phase was washed with brine, dried over MgSO$_4$, and concentrated in vacuo. The crude product was purified by silica gel chromatography (eluent: 0-80% EtOAc/heptane) to provide a 1:1 mixture of(S)-tert-butyl 4-(6-chloro-7-(2-fluorophenyl)-1-(2-isopropylphenyl)-2-oxo-1,2-dihydro-1,8-naphthyridin-4-yl)-3-methylpiperazine-1-carboxylate and (S)-tert-butyl 4-(7-(2-fluorophenyl)-1-(2-isopropylphenyl)-2-oxo-1,2-dihydro-1,8-naphthyridin-4-yl)-3-methylpiperazine-1-carboxylate (58.2 mg, 0.098 mmol, 38.6% yield). $^{19}$F NMR (376 MHz, CDCl$_3$) δ ppm −112.81 (1F, s), −112.86 (1F, s), −114.56 (1F, s), −114.58 (1F, s), −114.62 (1F, s). m/z (ESI, +ve ion): 591.3 (M+H)$^+$ and 557.3 (M+H)+(ca. 1:1 ratio). The mixture was used in the subsequent step without separation.

Step 6: 6-Chloro-7-(2-fluorophenyl)-4-((2S)-2-methyl-4-(2-propenoyl)-1-piperazinyl)-1-(2-(2-propanyl)phenyl)-1,8-naphthyridin-2(1H)-one (Example 126) and 7-(2-fluorophenyl)-4-((2S)-2-methyl-4-(2-propenoyl)-1-piperazinyl)-1-(2-(2-propanyl)phenyl)-1,8-naphthyridin-2(1H)-one (Example 127)

Step 6-1

TFA (0.5 mL, 6.49 mmol) was added to a 1:1 mixture of (S)-tert-butyl 4-(6-chloro-7-(2-fluorophenyl)-1-(2-isopropylphenyl)-2-oxo-1,2-dihydro-1,8-naphthyridin-4-yl)-3-methylpiperazine-1-carboxylate and (S)-tert-butyl 4-(7-(2-fluorophenyl)-1-(2-isopropylphenyl)-2-oxo-1,2-dihydro-1, 8-naphthyridin-4-yl)-3-methylpiperazine-1-carboxylate (58 mg, 0.098 mmol) in DCM (3 mL at rt. After 20 min. the reaction mixture was concentrated in vacuo. The resulting residue was dissolved in DCM (3 mL) and cooled to 0° C. DIPEA (0.086 mL, 0.491 mmol) and acryloyl chloride (8.0 μl, 0.098 mmol) were sequentially added and the reaction mixture was allowed to stir for 10 min at 0° C. The reaction mixture was treated with satd. NaHCO$_3$, and extracted with DCM. The organic phase was dried over MgSO$_4$, and concentrated in vacuo. The crude products were purified by silica gel chromatography (eluent: 0-30% DCM-MeOH (4:1)/DCM) to provide two products. 6-chloro-7-(2-fluorophenyl)-4-((2S)-2-methyl-4-(2-propenoyl)-1-piperazinyl)-1-(2-(2-propanyl)phenyl)-1,8-naphthyridin-2(1H)-one (Example 126). $^1$H NMR (400 MHz, DMSO-d$_6$) δ ppm 8.33 (1H, d, J=5.0 Hz), 7.45-7.51 (1H, m), 7.40-7.45 (1H, m), 7.35 (1H, t, J=7.6 Hz), 7.14-7.32 (4H, m), 7.05-7.14 (1H, m), 6.88 (1H, br s), 6.28 (1H, d, J=14.5 Hz), 6.14-6.24 (1H, m), 5.73-5.78 (1H, m), 4.32 (1H, br d, J=12.4 Hz), 3.97-4.16 (1H, m), 3.89 (2H, br d, J=18.9 Hz), 3.60-3.75 (1H, m), 3.00 (1H, br d, J=8.7 Hz), 2.37-2.44 (1H, m), 2.08 (1H, s), 0.99-1.09 (6H, m), 0.96 (3H, t, J=7.3 Hz). $^{19}$F NMR (376 MHz, DMSO-d$_6$) δ ppm −114.06 (1F, s), −114.17 (1F, s), −114.20 (1F, s). m/z (ESI, +ve ion): 545.2 (M+H)$^+$.

7-(2-Fluorophenyl)-4-((2S)-2-methyl-4-(2-propenoyl)-1-piperazinyl)-1-(2-(2-propanyl)phenyl)-1,8-naphthyridin-2(1H)-one (Example 127). $^1$H NMR (400 MHz, DMSO-d$_6$) δ ppm 8.37 (1H, dd, J=8.3, 3.3 Hz), 7.75 (1H, d, J=7.9 Hz), 7.50-7.53 (1H, m), 7.39-7.49 (3H, m), 7.26-7.35 (2H, m), 7.13-7.19 (1H, m), 7.07-7.13 (1H, m), 6.82-6.97 (1H, m), 6.14-6.24 (2H, m), 5.72-5.79 (1H, m), 4.29-4.41 (1H, m), 4.03-4.16 (1H, m), 3.82-4.01 (3H, m), 3.59 (1H, br d, J=8.5 Hz), 3.01-3.09 (1H, m), 1.08 (3H, t, J=7.4 Hz), 1.02 (3H, br d, J=3.3 Hz), 0.95 (2H, d, J=6.8 Hz), 0.91 (2H, d, J=6.8 Hz) $^{19}$F NMR (376 MHz, DMSO-d$_6$) δ ppm −115.14 (1F, s), −115.16 (1F, s), −115.18 (1F, s). m/z (ESI, +ve ion): 511.2 (M+H)$^+$.

Example 128

7-Bromo-6-chloro-4-(4-(2-propenoyl)-1-piperazinyl)-1-(2-(trifluoromethyl)phenyl)-2(1H)-quinazolinone

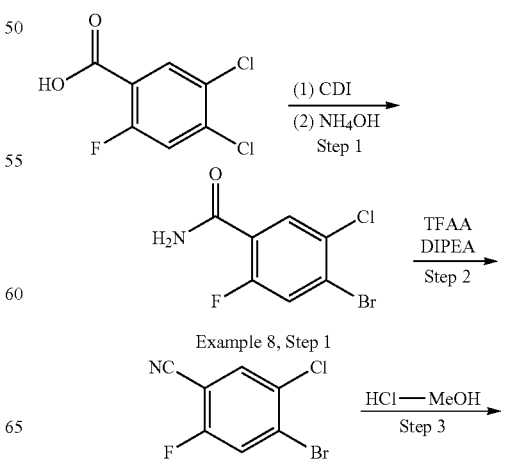

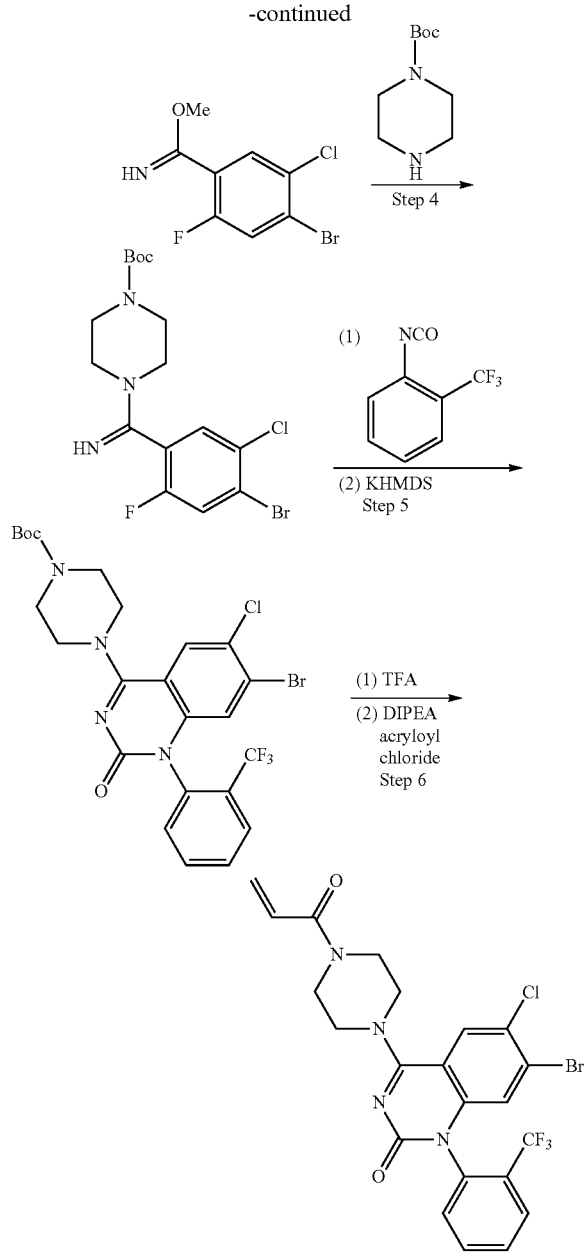

Step 1 and Step 2:
4-Bromo-5-chloro-2-fluorobenzonitrile 1,1'-Carbonyldiimidazole (7.0 g, 43 mmol) was added to a solution of 4-bromo-5-chloro-2-fluorobenzoic acid (10 g, 40 mmol, Oxychem, Dallas, Tex.) in THF (100 mL) at rt. After 3 h, the reaction mixture was cooled to 0° C. and ammonium hydroxide (20.5 ml, 158 mmol) was added dropwise over a period of 5 min. The reaction was then partitioned between EtOAc (200 mL) and satd. NaHCO$_3$ (100 mL). The organic layer was washed with 1 M HCl (50 mL), brine (20 mL), dried over MgSO$_4$, and concentrated in vacuo to afford 4-bromo-5-chloro-2-fluorobenzamide (Example 8, Step 1). The crude residue was dissolved in THF (100 mL), and DIPEA (35 ml, 200 mmol) was added. The reaction mixture was cooled to −30° C. and 2,2,2-trifluoroacetic anhydride (16.72 ml, 118 mmol) was added dropwise while the internal temp was monitored (not to exceed an internal temp of −20° C.). After completed addition, the reaction mixture was allowed to warm to 10° C., followed by partitioning between EtOAc (200 mL) and satd. NaHCO$_3$ (100 mL). The organic phase was washed with 1 M HCl (50 mL) and sat. NaCl (20 mL), dried over MgSO$_4$, and concentrated in vacuo. The residue was triturated with MTBE to give 4-bromo-5-chloro-2-fluorobenzonitrile. $^1$H NMR (400 MHz, CDCl$_3$) δ 7.71 (d, J=6.22 Hz, 1H), 7.56 (d, J=7.88 Hz, 1H).

Step 3:
Methyl-4-bromo-5-chloro-2-fluorobenzimidate

A mixture of 4-Bromo-5-chloro-2-fluorobenzonitrile (0.60 g, 2.6 mmol) in methanolic HCl (10 mL) was stirred at rt for 18 h. The mixture was concentrated in vacuo to give methyl-4-bromo-5-chloro-2-fluorobenzimidate. m/z (ESI, +ve ion): 266.0 and 268.0 (M+H)$^+$.

Step 4: tert-Butyl 4-((4-bromo-5-chloro-2-fluorophenyl)(imino)methyl)piperazine-1-carboxylate A mixture of methyl 4-bromo-5-chloro-2-fluorobenzimidate (2.2 g, 8.3 mmol) and pyridine (20 mL) was stirred at rt for 5 min, followed by the addition of tert-butyl piperazine-1-carboxylate (1.5 g, 8.3 mmol). After 5 min, the reaction mixture was heated to 80° C. for 5 h. The reaction mixture was partitioned between EtOAc (150 mL) and satd. NaHCO$_3$ (100 mL). The organic phase was washed with brine (10 mL), dried over MgSO$_4$, and concentrated in vacuo to give tert-butyl 4-((4-bromo-5-chloro-2-fluorophenyl)(imino)methyl)piperazine-1-carboxylate. m/z (ESI, +ve ion): 420.0 and 422.0 (M+H)$^+$.

Step 5: tert-Butyl 4-(7-bromo-6-chloro-2-oxo-1-(2-(trifluoromethyl)phenyl)-1,2-dihydroquinazolin-4-yl)piperazine-1-carboxylate 2-(Trifluoromethyl)phenyl isocyanate (0.22 ml, 1.43 mmol, Sigma-Aldrich Corporation, St. Louis, Mo.) was added to a suspension of tert-butyl 4-((4-bromo-5-chloro-2-fluorophenyl)imino)methyl)piperazine-1-carboxylate (0.6 g, 1.43 mmol) in THF (3 mL) at rt under nitrogen atmosphere. The reaction mixture was cooled to 0° C. and KHMDS (1M in THF, 1.4 ml, 1.4 mmol) was added dropwise over a period of 3 min. The reaction mixture was then partitioned between EtOAc (50 mL) and saturated ammonium chloride (10 mL). The organic extract was dried over MgSO$_4$, concentrated in vacuo and the crude product was purified by silica gel chromatography (eluent: 0-30% EtOAc-EtOH (3:1)/heptane) to provide tert-butyl 4-(7-bromo-6-chloro-2-oxo-1-(2-(trifluoromethyl)phenyl)-1,2-dihydroquinazolin-4-yl)piperazine-1-carboxylate. $^1$H NMR (400 MHz, CDCl$_3$) δ ppm 7.91 (d, J=7.67 Hz, 1H), 7.80 (t, 1=14.70 Hz, 1H), 7.77 (s, 1H), 7.68 (dd, J=7.26, 15.34 Hz, 1H), 7.36 (d, J=7.67 Hz, 1H), 6.68 (s, 1H), 3.91-3.99 (m, 2H), 3.76-3.86 (m, 2H), 3.65-3.75 (m, 2H), 3.55-3.64 (m, 2H), 1.48-1.52 (m, 9H), $^{19}$F NMR (376 MHz, CDCl$_3$) δ ppm −60.60 (s, 1F): m/z (ESI, +ve ion): 587.0 and 589.0 (M+H)$^+$.

Step 6: 4-(4-Acryloylpiperazin-1-yl)-7-bromo-6-chloro-1-(2-(trifluoromethyl)phenyl)quinazolin-2(1H)-one A solution of tert-butyl 4-(7-bromo-6-chloro-2-oxo-1-(2-(trifluoromethyl)phenyl)-1,2-dihydroquinazolin-4-yl)piperazine-1-carboxylate (300 mg, 0.51 mmol) in TFA (2 mL) was stirred at rt for 15 min. The reaction was then concentrated in vacuo. The residue was dissolved in DCM (1 mL) and the solution was cooled to 0° C. DIPEA (0.45 mL, 2.55 mmol) and a solution of acryloyl chloride (45.8 µL, 0.561 mmol) in DCM (0.2 mL) were added dropwise and the reaction mixture was allowed to stir at 0° C. for 2 h. The reaction was then partitioned between EtOAc (15 mL) and satd. NaHCO₃ (15 mL). The organic layer was dried over MgSO₄ and concentrated in vacuo. The crude product was purified by silica gel chromatography (eluent: 0-40% EtOAc-EtOH (3:1)/heptane) to provide 4-(4-acryloylpiperazin-1-yl)-7-bromo-6-chloro-1-(2-(trifluoromethyl)phenyl)quinazolin-2(1H)-one. ¹H NMR (400 MHz, CDCl₃) δ ppm 7.92 (d, J=7.67 Hz, 1H), 7.76-7.84 (m, 2H), 7.69 (t, J=15.10 Hz, 1H), 7.36 (d, J=7.46 Hz, 1H), 6.68-6.71 (m, 1H), 6.59 (dd, J=10.57, 17.00 Hz, 1H), 6.38 (dd, J=1.87, 16.79 Hz, 1H), 5.79 (dd, J=1.87, 10.37 Hz, 1H), 3.74-4.08 (m, 8H). ¹⁹F NMR (376 MHz, CDCl₃) δ ppm −61.44 (s, 3F); m/z (ESI, +ve ion): 541.0 and 543.0 (M+H)⁺.

Example 129

(M)-6-Chloro-7-(2-fluoro-6-hydroxyphenyl)-1-(4-methyl-2-(2-propanyl)-3-pyridinyl)-4-((3R)-3-methyl-4-(2-propenoyl)-1-piperazinyl)pyrido[2,3-d]pyrimidin-2(1H)-one

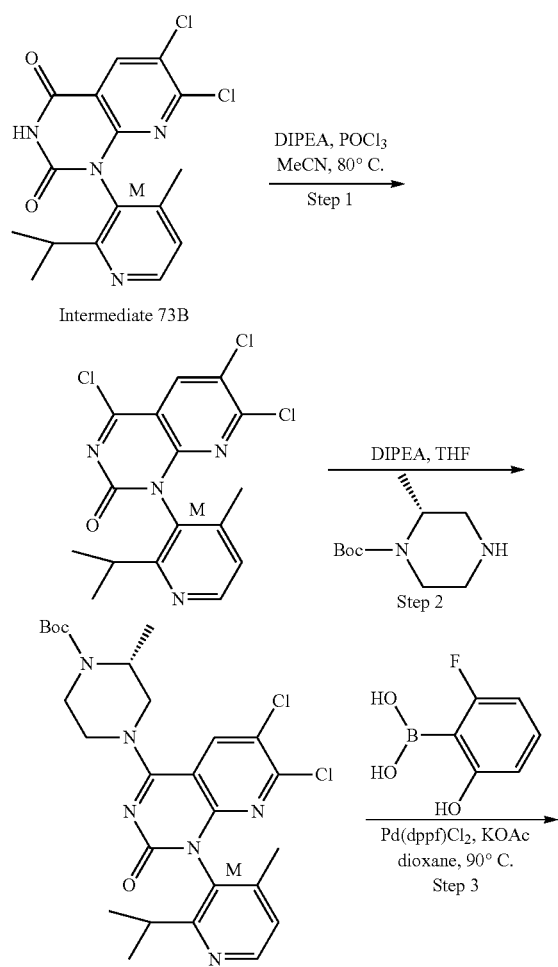

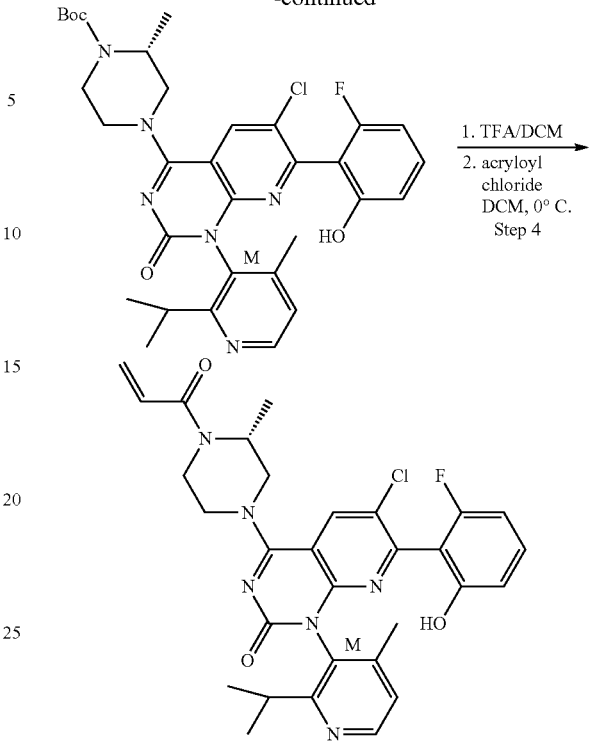

Step 1: (M)-4,6,7-Trichloro-1-(2-isopropyl-4-methylpyridin-3-yl)pyrido[2,3-d]pyrimidin-2(1H)-one Phosphorus oxychloride (0.5 mL, 5.5 mmol) was added to a mixture of (M)-6,7-dichloro-1-(2-isopropyl-4-methylpyridin-3-yl)pyrido[2,3-d]pyrimidine-2,4(1H,3H)-dione (Intermediate 73B, 1.005 g, 2.75 mmol) and DIPEA (1.4 mL, 8.2 mmol) in acetonitrile (13.8 mL). The reaction mixture was heated to 80° C. for 1 h. The reaction mixture was concentrated in vacuo to provide (M)-4,6,7-trichloro-1-(2-isopropyl-4-methylpyridin-3-yl)pyrido[2,3-d]pyrimidin-2(1H)-one (1.056 g, 2.75 mmol, 100% yield). m/z (ESI, +ve ion): 382.9 (M+H)⁺. The crude product was used in the next step without further purification.

Step 2: tert-Butyl (M)-(R)-4-(6,7-dichloro-1-(2-isopropyl-4-methylpyridin-3-yl)-2-oxo-1,2-dihydropyrido[2,3-d]pyrimidin-4-yl)-2-methylpiperazine-1-carboxylate DIPEA (1.4 mL, 8.2 mmol) and (R)-1-N-Boc-2-methylpiperazine (0.827 g, 4.13 mmol, Sigma-Aldrich Corporation, St. Louis, Mo., USA) were added to a solution of (M)-4,6,7-trichloro-1-(2-isopropyl-4-methylpyridin-3-yl)pyrido[2,3-d]pyrimidin-2(1H)-one (1.056 g, 2.75 mmol) in THF (13.8 ml) at rt. After 2 h, the reaction mixture was quenched with satd. NaHCO₃ and extracted with EtOAc. The organic extract was dried over Na₂SO₄, and concentrated in vacuo to give the crude material. The crude product was purified by silica gel chromatography (eluent: 0% to 100% EtOAc/heptane) to provide tert-butyl (M)-(R)-4-(6,7-dichloro-1-(2-isopropyl-4-methylpyridin-3-yl)-2-oxo-1,2-dihydropyrido[2,3-d]pyrimidin-4-yl)-2-methylpiperazine-1-carboxylate (1.274 g, 2.326 mmol, 85% yield) as yellow solid. ¹H NMR (400 MHz, DMSO-d₆) δ ppm 8.58 (s, 1H), 8.48 (d, J=5.0 Hz, 1H), 7.25 (d, J=4.8 Hz, 1H), 4.28-4.37 (m, 1H), 4.18-4.28 (m, 1H), 4.13 (br dd, J=13.6, 2.0 Hz, 1H), 3.70-3.81 (m, 2 H), 3.45-3.63 (m, 2H), 2.57 (quin, J=6.6 Hz, 1H), 1.96 (s, 9H), 1.44 (s, 9H), 1.19 (br d, J=6.6 Hz, 3H), 1.05 (d, J=6.6 Hz, 3H), 1.00) (d, J=6.6 Hz, 3H). m/z (ESI, +ve ion): 547.0 (M+H)+.

Step 3: tert-Butyl (M)-(2R)-4-(6-chloro-7-(2-fluoro-6-hydroxyphenyl)-1-(2-isopropyl-4-methylpyridin-3-yl)-2-oxo-1,2-dihydropyrido[2,3-d]pyrimidin-4-yl)-2-methylpiperazine-1-carboxylate A mixture of tert-butyl (M)-(R)-4-(6,7-dichloro-1-(2-isopropyl-4-methylpyridin-3-yl)-2-oxo-1,2-dihydropyrido[2,3-d]pyrimidin-4-yl)-2-methylpiperazine-1-carboxylate (0.315 g, 0.576 mmol), (2-fluoro-6-hydroxyphenyl)boronic acid (0.135 g, 0.863 mmol, CombiBlocks, San Diego, Calif.), potassium acetate (0.282 g, 2.88 mmol), (1,1'-bis(diphenylphosphino)ferrocene)dichloropalladium-dichloromethane (1:1) (0.047 g, 0.058 mmol) in 1,4-dioxane (5.7 mL) and water (0.03 mL) was heated to 90° C. for 16 h. The reaction mixture was concentrated under reduced pressure and the crude product was purified by silica gel chromatography (eluent: 0-50% DCM-MeOH (4:1)/DCM) to provide tert-butyl (M)-(2R)-4-(6-chloro-7-(2-fluoro-6-hydroxyphenyl)-1-(2-isopropyl-4-methylpyridin-3-yl)-2-oxo-1,2-dihydropyrido[2,3-d]pyrimidin-4-yl)-2-methylpiperazine-1-carboxylate (0.1287 g, 0.207 mmol, 35.9% yield) as a tan solid. $^1$H NMR (400 MHz, DMSO-$d_6$) δ ppm 10.10 (br s, 1H), 8.53 (s, 1H), 8.37 (d, J=4.8 Hz, 1H), 7.19-7.27 (m, 1H), 7.17 (br d, J=4.6 Hz, 1H), 6.70 (d, J=8.3 Hz, 1H), 6.66 (br t, J=8.7 Hz, 1H), 4.35 (br d, J=13.1 Hz, 1H), 4.17-4.31 (m, 2H), 3.51-3.84 (m, 4H), 2.58-2.71 (m, 1H), 1.91 (br s, 3H), 1.45 (s, 9H), 1.26 (br d, J=6.4 Hz, 3H), 1.06 (d, -=6.6 Hz, 3H), 0.92 (br d, J=6.4 Hz, 3H). $^{19}$F NMR (376 MHz, DMSO-$d_6$) δ ppm −115.89 (br d, J=288.7 Hz, 1F). m/z (ESI, +ve ion): 623.0 (M+H)+.

Step 4: (M)-6-Chloro-7-(2-fluoro-6-hydroxyphenyl)-1-(4-methyl-2-(2-propanyl)-3-pyridinyl)-4-((3R)-3-methyl-4-(2-propenoyl)-1-piperazinyl)pyrido[2,3-d]pyrimidin-2(1H)-one TFA (1.9 ml) was added to a solution of tert-butyl (M)-(2R)-4-(6-chloro-7-(2-fluoro-6-hydroxyphenyl)-1-(2-isopropyl-4-methylpyridin-3-yl)-2-oxo-1,2-dihydropyrido[2,3-d]pyrimidin-4-yl)-2-methylpiperazine-1-carboxylate (0.121 g, 0.194 mmol) in DCM (1.9 mL) at rt. After 30 min, the reaction mixture was concentrated in vacuo to provide (M)-6-chloro-7-(2-fluoro-6-hydroxyphenyl)-1-(2-isopropyl-4-methylpyridin-3-yl)-4-((R)-3-methylpiperazin-1-yl)pyrido[2,3-d]pyrimidin-2(1H)-one. m/z (ESI +ve ion): 523.0 (M+H)+.

The crude product was dissolved in DCM (1.940 mL) and the solution was cooled to 0° C. DIPEA (0.507 mL, 2.91 mmol) and acryloyl chloride (0.2 M solution in DCM, 1 mL, 0.19 mmol) were sequentially added and the reaction mixture was allowed to stir for 30 min at 0° C. The reaction mixture was quenched with satd. NaHCO$_3$ and extracted with DCM. The organic extract was dried over Na$_2$SO$_4$, and concentrated in vacuo. The crude product was purified by silica gel chromatography (eluent: 0-50%/o DCM-MeOH (4:1)/DCM) to provide (M)-6-chloro-7-(2-fluoro-6-hydroxyphenyl)-1-(4-methyl-2-(2-propanyl)-3-pyridinyl)-4-((3R)-3-methyl-4-(2-propenoyl)-1-piperazinyl)pyrido[2,3-d]pyrimidin-2(1H)-one (0.0532 g, 0.092 mmol, 47.5% yield) as a light-yellow solid. $^1$H NMR (400 MHz, DMSO-$d_6$) δ ppm 10.11 (br s, 1H), 8.56 (s, 1H), 8.37 (d, J=4.8 Hz, 1H), 7.23 (q, J=8.1 Hz, 1H), 7.17 (d, J=4.8 Hz, 1H), 6.81 (dd, J=16.7, 10.5 Hz, 1H), 6.70 (d, J=8.3 Hz, 1H), 6.66 (br t, J=8.8 Hz, 1H), 6.19 (br d, J=16.8 Hz, 1H), 5.71-5.78 (m, 1H), 4.46-4.78 (m, 1H), 4.39 (br dd, J=8.1, 4.8 Hz, 1H), 4.22 (br d, J=8.9 Hz, 1H), 3.96-4.14 (m, 1H), 3.56-3.92 (m, 3H), 2.57-2.71 (m, 1H), 1.93 (br s, 3H), 1.30 (br s, 3H), 1.06 (d, J=6.6 Hz, 3H), 0.92 (br d, J=6.4 Hz, 3H). $^{19}$F NMR (376 MHz, DMSO-$d_6$) δ ppm −115.87 (br d, J=284.4 Hz, 1F). m/z (ESI, +ve ion): 577.0 (M+H)+.

Example 130

1-(4-(3-Chloro-2-(2-fluorophenyl)-8-(2-(2-propanyl)phenyl)-1,6-naphthyridin-5-yl)-1-piperazinyl)-2-propen-1-one

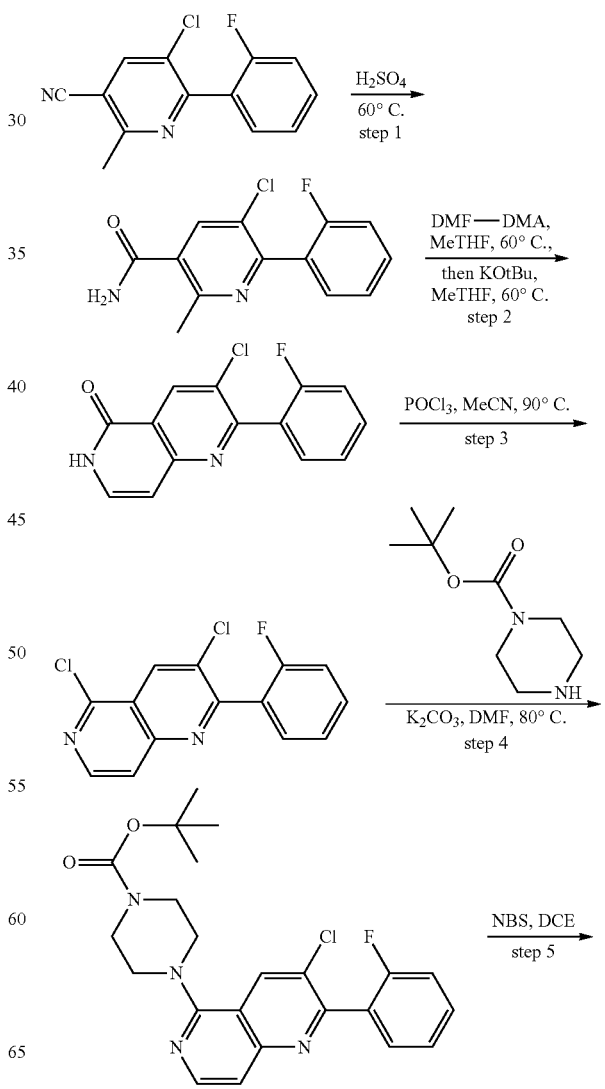

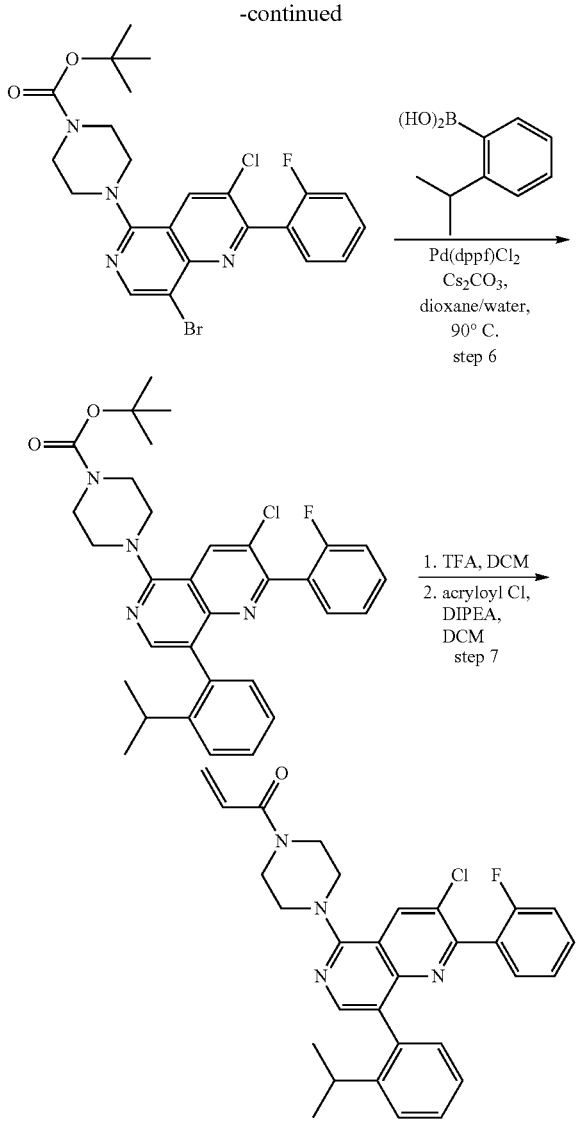

Step 1:
5-Chloro-6-(2-fluorophenyl)-2-methylnicotinamide

A mixture of 5-chloro-6-(2-fluorophenyl)-2-methylnicotinonitrile (0.69 g, 2.81 mmol, prepared from Intermediate 101A similarly to Kubelka, Tomas et al. Organic & Biomolecular Chemistry, 11(28), 4702-4718; 2103) and conc. sulfuric acid (4.7 mL, 84 mmol) was heated to 60° C. After 2 h, the reaction mixture was poured over ice-water, stirred for 15 min and extracted with EtOAc (15 mL). The organic phase was washed with NaOH (1 N) and water, dried over anhydrous sodium sulfate and concentrated to provide 5-chloro-6-(2-fluorophenyl)-2-methylnicotinamide. $^1$H NMR (400 MHz, DMSO-$d_6$) δ 8.07 (br s, 1H), 8.01 (s, 1H), 2 (br s, 1H), 7.55 (q, J=5.8 Hz, 1H), 7.47 (t, J=7.9 Hz, 1H), 7.28-7.41 (m, 2H), 2.57 (s, 3H). m/z (ESI, +ve ion): 265.0 M+H)$^+$.

Step 2: 3-Chloro-2-(2-fluorophenyl)-1,6-naphthyridin-5(6H)-one

A mixture of 5-chloro-6-(2-fluorophenyl)-2-methylnicotinamide (0.548 g, 2.07 mmol) and N,N-dimethylformamide dimethyl acetal (0.3 mL, 2.4 mmol, Sigma-Aldrich, Inc., St. Louis, Mo.) in MeTHF (15 mL) was heated to 60° C. for 1 h. The solvent was partially removed under reduced pressure and the residue was taken up in MeTHF (5 mL), followed by the addition of KOtBu (3.1 mL, 3.1 mmol, 1 M in THF). The reaction mixture was heated to 60° C. After 1 h, the reaction mixture was diluted with satd. aqueous ammonium chloride and extracted with EtOAc (10 mL). The organic phase was separated, washed with water, dried over anhydrous sodium sulfate and concentrated under reduced pressure. The crude product was purified by silica gel chromatography (eluent: 0-40% 3:1 EtOAc heptane) to provide 3-chloro-2-(2-fluorophenyl)-1,6-naphthyridin-5(6H)-one. $^1$H NMR (400 MHz, CDCl$_3$) δ 10.05 (br s, 1H), 8.75 (s, 1H), 7.46-7.56 (m, 2H), 7.28-7.37 (m, 2H), 7.18-7.24 (m, 1H), 6.85 (d, J=7.5 Hz, 1H). m/z (ESI, +ve ion): 274.9 (M+H)$^+$.

Step 3: 3,5-Dichloro-2-(2-fluorophenyl)-1,6-naphthyridine

Phosphorus oxychloride (0.4 mL, 4.5 mmol) was added to a solution of 3-chloro-2-(2-fluorophenyl)-1,6-naphthyridin-5(6H)-one (0.25 g, 0.91 mmol) in acetonitrile (5 mL). The reaction mixture was heated to 90° C. After 1 h, the reaction mixture was partially concentrated under vacuo. The residue was poured over ice-water, stirred for several minutes and neutralized with satd. aqueous NaHCO$_3$. The mixture was extracted with EtOAc (10 mL). The organic layer was separated, washed with water, dried over anhydrous sodium sulfate and concentrated under reduced pressure to provide 3,5-dichloro-2-(2-fluorophenyl)-1,6-naphthyridine. m/z (ESI, +ve ion): 292.9 (M+H)$^+$.

Step 4: tert-Butyl 4-(3-chloro-2-(2-fluorophenyl)-1,6-naphthyridin-5-yl)piperazine-1-carboxylate A mixture of 3,5-dichloro-2-(2-fluorophenyl)-1,6-naphthyridine (0.197 g, 0.67 mmol), K$_2$CO$_3$ (0.279 g, 2.02 mmol), tert-butyl piperazine-1-carboxylate (0.188 g, 1.0 mmol) in DMF (5 mL) was heated to 80° C. After 16 h, the reaction mixture was diluted with EtOAc (10 mL), and washed with water (1×) and brine (1×). The organic layer was dried over anhydrous sodium sulfate and concentrated under reduced pressure. The crude product was purified by silica gel chromatography (eluent: 0-1% MeOH/DCM) to provide tert-butyl 4-(3-chloro-2-(2-fluorophenyl)-1,6-naphthyridin-5-yl)piperazine-1-carboxylate. $^1$H NMR (400 MHz, CDCl$_3$) δ 8.43 (s, 1H), 8.36 (br d, J=5.8 Hz, 1H), 7.46-7.59 (m, 3H), 7.32 (t, J=7.1 Hz, 1H), 7.21 (br t, J=9.0 Hz, 1H), 3.72 (br s, 4H), 3.45 (br s, 4H), 1.51 (s, 9H). m/z (ESI, +ve ion): 443.0 (M+H)$^+$.

Step 5: tert-Butyl 4-(8-bromo-3-chloro-2-(2-fluorophenyl)-1,6-naphthyridin-5-yl)piperazine-1-carboxylate NBS (51 mg, 0.29 mmol) was added to a mixture of tert-butyl 4-(3-chloro-2-(2-fluorophenyl)-1,6-naphthyridin-5-yl)piperazine-1-carboxylate (128 mg, 0.29 mmol) in DCE (4 mL) at room temperature. After 30 min, the reaction mixture was partitioned between DCM and water. The organic layer was separated, washed with satd. aqueous NaHCO$_3$, dried over anhydrous sodium sulfate and concentrated under reduced pressure to obtain tert-butyl 4-(8-bromo-3-chloro-2-(2-fluorophenyl)-1,6-naphthyridin-5-yl)

piperazine-1-carboxylate. m/z (ESI, +ve ion): 522.8 (M+H)⁺. The product was taken onto the next step without further purification.

Step 6: tert-Butyl 4-(3-chloro-2-(2-fluorophenyl)-8-(2-isopropylphenyl)-1,6-naphthyridin-5-yl)piperazine-1-carboxylate A mixture of tert-butyl 4-(8-bromo-3-chloro-2-(2-fluorophenyl)-1,6-naphthyridin-5-yl)piperazine-1-carboxylate (145 mg, 0.28 mmol), cesium carbonate (272 mg, 0.83 mmol), [1,1'-bis(diphenylphosphino)ferrocene]-dichloropalladium (II) (20 mg, 0.03 mmol), and (2-isopropylphenyl)boronic acid (91 mg, 0.56 mmol, Combi-Blocks, San Diego, Calif., USA) in dioxane (3 mL) and water (0.3 mL) was heated to 90° C. for 1 h. The reaction mixture was diluted with EtOAc (10 mL) and washed with water (1×) and brine (1×). The organic layer was dried over anhydrous sodium sulfate and concentrated under reduced pressure. The crude product was purified by silica gel chromatography (eluent: 0-30% EtOAc-EtOH(3:1)/heptane) to provide tert-butyl 4-(3-chloro-2-(2-fluorophenyl)-8-(2-isopropylphenyl)-1,6-naphthyridin-5-yl)piperazine-1-carboxylate. ¹H NMR (400 MHz, CHLOROFORM-d) δ 8.47 (s, 1H), 8.25 (s, 1H), 7.34-7.44 (m, 3H), 7.32 (dd, J=7.3, 1.7 Hz, 1H), 7.14-7.24 (m, 3H), 7.11 (t, J=9.1 Hz, 1H), 3.69-3.79 (m, 4H), 3.49 (br s, 4H), 2.70 (quin, J=6.8 Hz, 1H), 1.52 (s, 9H), 1.08 (d, J=6.6 Hz, 3H), 1.04 (d, J=6.8 Hz, 3H). m/z (ESI, +ve ion): 561.0 (M+H)⁺.

Step 7: 1-(4-(3-Chloro-2-(2-fluorophenyl)-8-(2-(2-propanyl)phenyl)-1,6-naphthyridin-5-yl)-2-piperazinyl)-2-propen-1-one Trifluoroacetic acid (1.5 mL) was added to a solution of tert-butyl 4-(3-chloro-2-(2-fluorophenyl)-8-(2-isopropylphenyl)-1,6-naphthyridin-5-yl)piperazine-1-carboxylate (123 mg, 0.24 mmol) in DCM (3 mL). The reaction was stirred for 30 min at room temperature, and then concentrated under reduced pressure. The residue was dissolved in DCM (5 mL), followed by the addition of DIPEA (0.165 mL, 0.95 mmol) and acryloyl chloride (0.02 mL, 0.24 mmol). The reaction mixture was stirred for 30 min at room temperature, diluted with EtOAc (30 mL) and washed with saturated aqueous sodium bicarbonate solution (10 mL) and brine (5 mL). The organic layer was dried over anhydrous sodium sulfate and concentrated under reduced pressure. The crude product was purified by silica gel chromatography (eluent: 0-30% EtOAc (3:1)/heptane) to provide 1-(4-(3-chloro-2-(2-fluorophenyl)-8-(2-(2-propanyl)phenyl)-1,6-naphthyridin-5-yl)-1-piperazinyl)-2-propen-1-one. ¹H NMR (40 MHz, DMSO-d₆) δ 8.71 (s, 1H), 8.23 (s, 1H), 7.48-7.61 (m, 1H), 7.28-7.42 (m, 5H), 7.20 (td, J=7.5, 1.7 Hz, 1H), 7.16 (dd, J=7.1, 1.0 Hz, 1H), 6.89 (dd, J=16.7, 10.5 Hz, 1H), 6.18 (dd, J=16.7, 2.4 Hz, 1H), 5.75 (dd, J=10.4, 2.9 Hz, 1H), 3.87 (br s, 4H), 3.52 (br s, 4H), 2.59 (quin, J=6.8 Hz, 1H), 1.03 (d, J=6.8 Hz, 3H), 0.98 (d, J=6.8 Hz, 3H). m/z (ESI, +ve ion): 515.0 (M+H)⁺.

Example 131

Methyl 5-(4-acryloylpiperazin-1-yl)-3-chloro-2-(2-fluorophenyl)-7-methyl-1,6-naphthyridine-8-carboxylate -continued

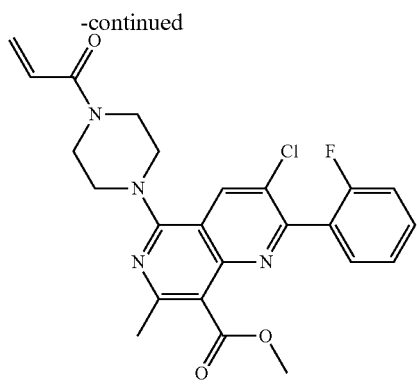

Step 1. Methyl 2,3-dichloro-7-methyl-5-oxo-5,6-dihydro-1,6-naphthyridine-8-carboxylate A mixture of 2,5,6-trichloronicotinamide (Intermediate P, 4.0 g, 17.74 mmol), methyl acetoacetate (2.89 ml, 26.6 mmol, Sigma-Aldrich Corporation, St. Louis, Mo., USA), copper(I) iodide (0.337 g, 1.774 mmol) and cesium carbonate (11.56 g, 35.5 mmol) in 1,4-dioxane (89 ml) was purged with nitrogen and subsequently heated to 80° C. for 17 h. The reaction mixture was quenched with a mixture of 9:1 sat. NH$_4$Cl/NH$_4$OH and extracted with EtOAc. The organic phase was separated and concentrated under reduced pressure. The crude product was purified by silica gel chromatography (eluent: 0-5% MeOH/DCM) to provide methyl 2,3-dichloro-7-methyl-5-oxo-5,6-dihydro-1,6-naphthyridine-8-carboxylate (3.0 g, 10.45 mmol, 58.9% yield) as a brown solid. m/z (ESI, +ve ion): 287.0 (M+H)$^+$.

Step 2. Methyl 3-chloro-2-(2-fluorophenyl)-7-methyl-5-oxo-5,6-dihydro-1,6-naphthyridine-8-carboxylate A mixture of (2-fluorophenyl)boranediol (0.205 mL, 1.467 mmol, Combi-Blocks Inc.), methyl 2,3-dichloro-7-methyl-5-oxo-5,6-dihydro-1,6-naphthyridine-8-carboxylate (324 mg, 1.129 mmol), potassium acetate (0.44 g, 4.51 mmol), and [1,1'-bis(diphenylphosphino)ferrocene]dichloropalladium(II) (92 mg, 0.113 mmol) in 1,4-dioxane (5 mL) was purged with nitrogen for 1 min. Water (0.833 mL) was added and the resulting mixture was heated to 90° C. for 1.5 h. The reaction mixture was treated with brine and extracted with EtOAc (2×40 mL). The organic phase was separated, dried over MgSO$_4$, and concentrated under reduced pressure. The crude product was purified by silica gel chromatography (eluent: 0-30%/(20% MeOH/DCM)/DCM) to provide methyl 3-chloro-2-(2-fluorophenyl)-7-methyl-5-oxo-5,6-dihydro-1,6-naphthyridine-8-carboxylate (340.9 mg, 0.983 mmol, 87% yield) as a bright yellow solid. m/z (ESI, +ve ion): 347.0 (M+H)$^+$.

Step 3. Methyl 3,5-dichloro-2-(2-fluorophenyl)-7-methyl-7-methyl-1,6-naphthyridine-8-carboxylate A mixture of methyl 3-chloro-2-(2-fluorophenyl)-7-methyl-5-oxo-5,6-dihydro-1,6-naphthyridine-8-carboxylate (0.250 g, 0.721 mmol) and POCl3 (3.0 mL, 32.2 mmol) was heated to 90° C. for 1 h. The reaction mixture was concentrated under reduced pressure and the residue was diluted with EtOAc. The organic phase was washed with sat. NaHCO$_3$ and brine, and concentrated under reduced pressure. The crude product was purified by silica gel chromatography (eluent: 0-10% EtOAc/heptane) to provide methyl 3,5-dichloro-2-(2-fluorophenyl)-7-methyl-1,6-naphthyridine-8-carboxylate (0.133 g, 0.364 mmol, 50.5% yield) as a light yellow solid. m/z (ESI, +ve ion): 365.0 (M+H)$^+$.

Step 4. Methyl 5-(4-(tert-butoxycarbonyl)piperazin-1-yl)-3-chloro-2-(2-fluorophenyl)-7-methyl-1,6-naphthyridine-8-carboxylate A mixture of methyl 3,5-dichloro-2-(2-fluorophenyl)-7-methyl-1,6-naphthyridine-8-carboxylate (0.0113 g, 0.031 mmol), tert-butyl piperazine-1-carboxylate (6.92 mg, 0.037 mmol), potassium carbonate (6.41 mg, 0.046 mmol) and some Na$_2$SO$_4$ in CH$_3$CN (2 mL) was stirred at rt overnight. Additional portions of tert-butyl piperazine-1-carboxylate (6.92 mg, 0.037 mmol), potassium carbonate (6.41 mg, 0.046 mmol) and Na$_2$SO$_4$ were added and the reaction was heated to 80° C. After 4 h, the reaction mixture was cooled to rt, washed with water and extracted with EtOAc. The organic phase was separated and concentrated under reduced pressure to afford methyl 5-(4-(tert-butoxy carbonyl)piperazin-1-yl)-3-chloro-2-(2-fluorophenyl)-7-methyl-1,6-naphthyridine-8-carboxylate (Intermediate 131A) as a light yellow oil. m/z (ESI, +ve ion): 515.0 (M+H)$^+$.

Step 5. Methyl 5-(4-acryloylpiperazin-1-yl)-3-chloro-2-(2-fluorophenyl)-7-methyl-1,6-naphthyridine-8-carboxylate TFA (1.0 mL, 12.98 mmol) was added to a solution of methyl 5-(4-(tert-butoxycarbonyl)piperazin-1-yl)-3-chloro-2-(2-fluorophenyl)-7-methyl-1,6-naphthyridine-8-carboxylate (Intermediate 131A) in DCM (1 mL) at rt. After 15 min, the reaction mixture was concentrated under reduced pressure to afford methyl 3-chloro-2-(2-fluorophenyl)-7-methyl-5-(piperazin-1-yl)-1,6-naphthyridine-8-carboxylate. m/z (ESI, +ve ion): 415.0 (M+H)$^+$. The residue was dissolved in DCM (3 mL), followed by the addition of DIPEA (0.016 mL, 0.093 mmol) and acryloyl chloride (2.51 µl, 0.031 mmol). The resulting mixture was stirred at rt for 30 min and subsequently washed with sat. NaHCO$_3$, and sat. NH$_4$Cl. Extraction with DCM, was followed by concentrating the organic phase under reduced pressure. The residue was purified by RP-HPLC to afford methyl 5-(4-acryloylpiperazin-1-yl)-3-chloro-2-(2-fluorophenyl)-7-methyl-1,6-naphthyridine-8-carboxylate (0.0048 g, 10.24 µmol, 33.1% yield). $^1$H NMR (DMSO-d$_6$) δ: 8.58-8.65 (m, 1H), 7.58-7.68 (m, 1H), 7.51-7.60 (m, 1H), 7.36-7.46 (m, 2H), 6.78-6.92 (m, 1H), 6.10-6.24 (m, 1H), 5.69-5.79 (m, 1H), 3.75-3.89 (m, 7H), 3.55-3.65 (m, 4H), 2.46-2.48 (m, 3H). m/z (ESI, +ve ion): 469.0 (M+H)$^+$.

Example 132

2-(6-Chloro-7-(2-fluorophenyl)-4-((2S)-2-methyl-4-(2-propenoyl)-1-piperazinyl)-2-oxopyrido[2,3-d]pyrimidin-1(2H)-yl)-3-(2-propanyl)benzoic acid

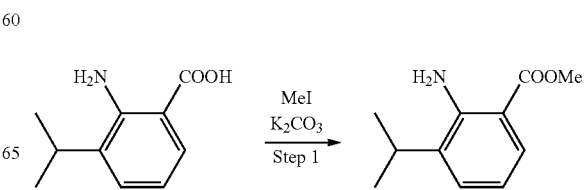

-continued

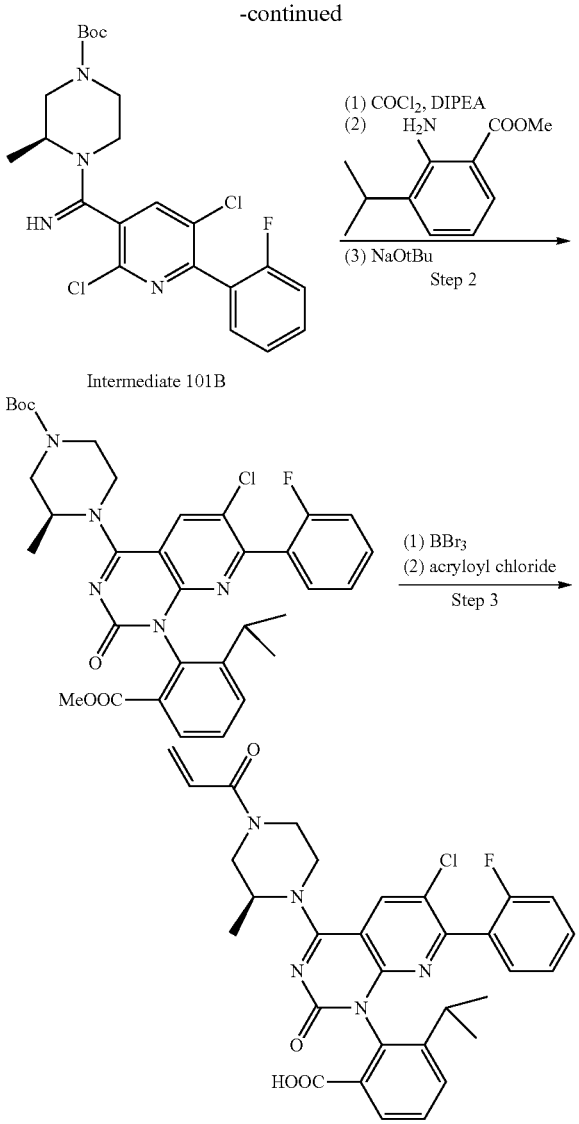

Step 1: Methyl 2-amino-3-isopropylbenzoate

Potassium carbonate (19 g, 130 mmol) was added to a solution of 2-amino-3-(propan-2-yl)benzoic acid (10 g, 56 mmol, Enamine, Monmouth Jct., N.J.) in DMF (100 mL). The suspension was stirred for 30 min, followed by the addition of iodomethane (5 ml, 73 mmol). After 72 h, the reaction mixture was partitioned between EtOAc (200 mL) and water (750 mL). The aqueous layer was extracted with EtOAc (100 mL). The combined organic extracts were washed with sat. NaCl, dried over MgSO$_4$, and concentrated under reduced pressure to provide methyl 2-amino-3-isopropylbenzoate. m/z (ESI, +ve ion): 194.1 (M+H)$^+$.

Step 2: tert-Butyl (S)-4-(6-chloro-7-(2-fluoro-7-(2-fluorophenyl)-1-(2-isopropyl-6-(methoxycarbonyl)phenyl)-2-oxo-1,2-dihydropyrido[2,3-d]pyrimidin-4-yl)-3-methylpiperazine-1-carboxylate A mixture of tert-butyl (S)-4-(((2,5-dichloro-6-(2-fluorophenyl)pyridin-3-yl)imino)methyl)-3-methylpiperazine-1-carboxylate (Intermediate 101B, 2.5 g, 5.4 mmol) and DIPEA (2.0 ml, 12 mmol) in THF (20 mL) was added dropwise over a period of 6 min to solution of phosgene solution (15% in toluene, 7.6 ml, 11 mmol) in THF (23 mL; 3:1 dilution ratio) cooled 0° C. (internal temp not to exceed 5° C.). Subsequently, a solution of methyl 2-amino-3-isopropylbenzoate (2.3 g, 12 mmol, from Step 1) in THF (10 mL) was added. After 10 min, the reaction mixture was partitioned between EtOAc (200 mL) and 5% NaHCO$_3$ (100 mL). The organic extract was washed twice with sat. NaCl (25 mL), dried over MgSO$_4$, and concentrated under reduced pressure to afford an oil. The oil was taken up in toluene (30 mL), the solution was cooled to 0° C., and sodium tert-butoxide (0.77 g, 8.0 mmol) was added. The ice bath was removed and the reaction mixture was allowed to stir for 30 min. The reaction mixture was then partitioned between EtOAc (75 mL) and 5% NaHCO$_3$ (50 mL). The organic extract was washed with sat. NaCl (25 mL), dried over MgSO$_4$, and concentrated under reduced pressure. The residue was purified by silica gel chromatography (eluent: 0-30% EtOAc-EtOH (3:1)/heptane) to provide tert-butyl (S)-4-(6-chloro-7-(2-fluorophenyl)-1-(2-isopropyl-6-(methoxycarbonyl)phenyl)-2-oxo-1,2-dihydropyrido[2,3-d]pyrimidin-4-yl)-3-methylpiperazine-1-carboxylate. m/z (ESI, +ve ion): 650.3 (M+H)$^+$.

Step 3: 2-(6-Chloro-7-(2-fluorophenyl)-4-((2S)-2-methyl-4-(2-propenoyl)-1-piperazinyl)-2-oxopyrido[2,3-d]pyrimidin-1(2H)-yl)-3-(2-propanyl)benzoic acid Boron tribromide (1 M in hexanes, 13.5 mL, 13.5 mmol) was added dropwise to a solution of tert-butyl (S)-4-(6-chloro-7-(2-fluorophenyl)-1-(2-isopropyl-6-(methoxycarbonyl)phenyl)-2-oxo-1,2-dihydropyrido[2,3-d]pyrimidin-4-yl)-3-methylpiperazine-1-carboxylate (2.2 g, 3.4 mmol) in DCM (30 mL) at 0° C. under nitrogen atmosphere. The suspension was stirred for 2 h at rt and then cooled back down to 0° C. DCM (20 mL) and an aqueous solution of sodium carbonate (5.7 g, 54 mmol in 80 mL of water) were added dropwise. The biphasic suspension was treated with a solution of acryloyl chloride (0.207 ml, 2.54 mmol) in DCM (2 mL). The pH was adjusted to pH=1 with 2 M HCl. The organic was separated, and the aqueous phase was further extracted with DCM (25 mL). The combined organic extracts were dried over MgSO$_4$, and concentrated under reduced pressure. The residue was purified by silica gel chromatography (eluent: 30-65% EtOAc-EtOH (3:1)/2% AcOH/heptane) to provide 2-(6-chloro-7-(2-fluorophenyl)-4-((2S)-2-methyl-4-(2-propenoyl)-1-piperazinyl)-2-oxopyrido[2,3-d]pyrimidin-1(2H)-yl)-3-(2-propanyl)benzoic acid. $^1$H NMR (400 MHz, CDCl$_3$) 8.05 (s, 1H), 8.01 (br s, 1H), 7.63 (d, J=7.88 Hz, 1H), 7.45 (t, J=15.80 Hz, 1H), 7.33-7.40 (m, 1H), 7.02-7.18 (m, 3H), 6.47-6.83 (m, 1H), 6.32-6.44 (m, 1H), 5.79 (d, J=9.54 Hz, 1H), 2.94-5.17 (m, 7H), 2.73-2.92 (m, 1H), 2.09 (s, 1H), 1.37-1.58 (m, 3H), 1.18-1.25 (m, 3H), 1.05 (d, J=5.80 Hz, 3H). $^{19}$F NMR (376 MHz, CDCl$_3$) δ −112.26 (s, 1F). m/z (ESI, +ve ion): 590.2 (M+H)$^+$.

Example 133

6-Chloro-1-(4-chloro-6-(2-propanyl)-5-pyrimidinyl)-7-(2-fluorophenyl)-4-((2S)-2-methyl-4-(2-propenoyl)-1-piperazinyl)pyrido[2,3-d]pyrimidin-2(1H)-one

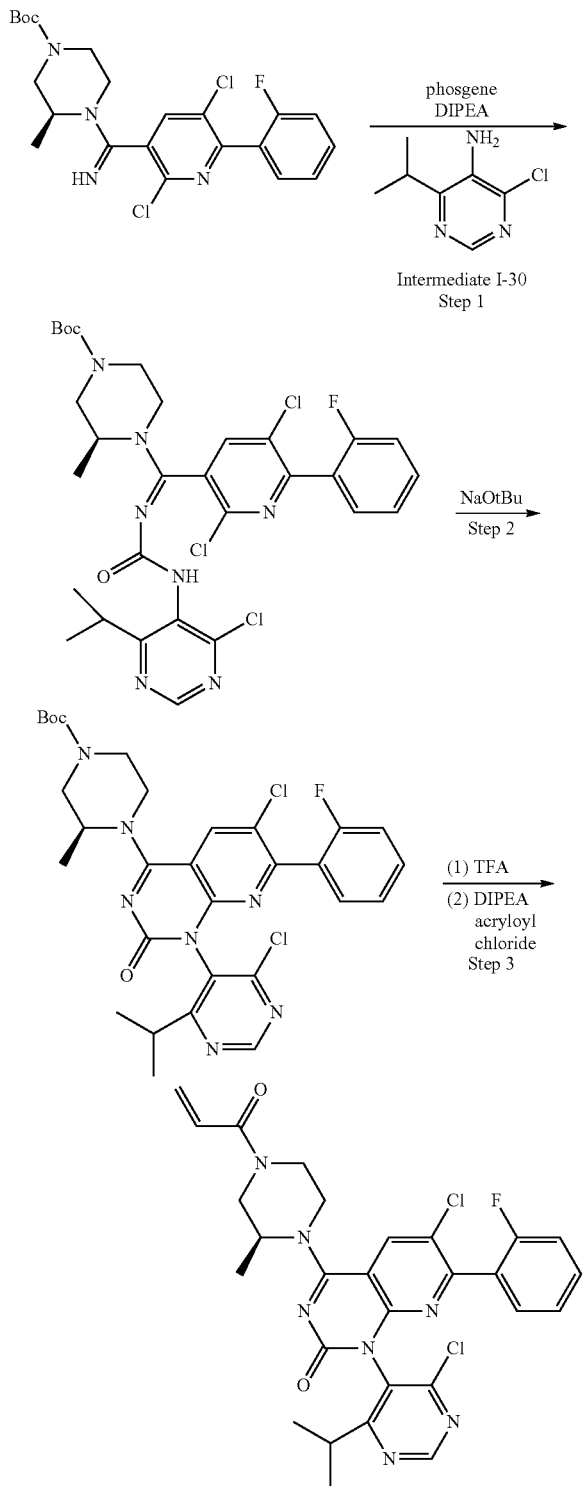

Step 1: tert-Butyl (S,E)-4-((((4-chloro-6-isopropylpyrimidin-5-yl)carbamoyl)imino)(2,5-dichloro-6-(2-fluorophenyl)pyridin-3-yl)methyl)-3-methylpiperazine-1-carboxylate A mixture of 4-chloro-6-isopropylpyrimidin-5-amine (Intermediate I-30, 0.43 g, 2.5 mmol), tert-butyl (S)-4-((2,5-dichloro-6-(2-fluorophenyl)pyridin-3-yl)(imino)methyl)-3-methylpiperazine-1-carboxylate (Intermediate 101B; 0.39 g, 0.83 mmol), and DIPEA (0.4 mL, 2.5 mmol) in tetrahydrofuran (8 mL) was added dropwise to a phosgene solution (15% in toluene: 1.2 mL, 1.67 mmol) at 0° C. After 30 min. additional phosgene (15% in toluene: 0.20 mL) was added and the reaction mixture was stirred for additional 15 min at 0° C. The ice bath was removed and stirring was continued at rt for 30 min. The reaction mixture was diluted with EtOAc (100 mL), and washed with saturated, aqueous sodium bicarbonate (2×50 mL). The organic layer was separated, dried over anhydrous $Na_2SO_4$, and concentrated in vacuo to give tert-butyl (S,E)-4-((((4-chloro-6-isopropylpyrimidin-5-yl)carbamoyl)imino)(2,5-dichloro-6-(2-fluorophenyl)pyridin-3-yl)methyl)-3-methylpiperazine-1-carboxylate. m/z (ESI, +ve ion): 664.0/665.9 (M+1)$^+$. The product was used in the next step without further purification.

Step 2: tert-Butyl (S)-4-(6-chloro-1-(4-chloro-6-isopropylpyrimidin-5-yl)-7-(2-fluorophenyl)-2-oxo-1,2-dihydropyrido[2,3-d]pyrimidin-4-yl)-3-methylpiperazine-1-carboxylate A mixture of tert-butyl (S,E)-4-((((4-chloro-6-isopropylpyrimidin-5-yl)carbamoyl)imino)(2,5-dichloro-6-(2-fluorophenyl)pyridin-3-yl)methyl)-3-methylpiperazine-1-carboxylate (0.56 g, 0.84 mmol) and sodium tert-butoxide (0.160 g, 1.67 mmol) in toluene (8 mL) was stirred at RT for 15 min. The reaction mixture was diluted with EtOAc (50 mL), and washed with saturated, aqueous ammonium chloride (2×50 mL). The organic layer was separated, dried over anhydrous $Na_2SO_4$ and concentrated under reduced pressure. The crude product was purified by silica gel chromatography (eluent: 0-80% EtOAc/heptane) to provide tert-butyl (S)-4-(6-chloro-1-(4-chloro-6-isopropylpyrimidin-5-yl)-7-(2-fluorophenyl)-2-oxo-1,2-dihydropyrido[2,3-d]pyrimidin-4-yl)-3-methylpiperazine-1-carboxylate (374 mg, 0.595 mmol, 62% yield) as a yellow foam. m/z (ESI, +ve ion): 628.0 (M+1)$^+$.

Step 3: 6-Chloro-1-(4-chloro-6-(2-propanyl)-5-pyrimidinyl)-7-(2-fluorophenyl)-4-((2S)-2-methyl-4-(2-propenoyl)-1-piperazinyl)pyrido[2,3-d]pyrimidin-2(1H)-one A solution of tert-butyl (S)-4-(6-chloro-1-(4-chloro-6-isopropylpyrimidin-5-yl)-7-(2-fluorophenyl)-2-oxo-1,2-dihydropyrido[2,3-d]pyrimidin-4-yl)-3-methylpiperazine-1-carboxylate (0.019 g, 0.030 mmol) in TFA (150 µL, 1.51 mmol) was stirred at RT for 10 min. The reaction mixture was concentrated under reduced pressure and the residue was taken up in DCM (0.3 mL). Acryloyl chloride (0.5 M in DCM: 0.060 mL, 0.030 mmol), and DIPEA (0.016 mL, 0.091 mmol) were added and after 15 min, the reaction mixture was diluted with EtOAc (50 mL). The mixture was washed with saturated, aqueous sodium bicarbonate (2×20 mL). The organic layer was separated, dried over anhydrous $Na_2SO_4$, and concentrated in vacuo. The crude product was purified by silica gel chromatography (eluent: 0-80%

EtOAc-EtOH (3:1)/heptane) to provide 6-chloro-1-(4-chloro-6-(2-propanyl)-5-pyrimidinyl)-7-(2-fluorophenyl)-4-((2S)-2-methyl-4-(2-propenoyl)-1-piperazinyl)pyrido[2,3-d]pyrimidin-2(1H)-one (8 mg, 0.014 mmol, 45% yield) as an off-white film. $^1$H NMR (400 MHz, CDCl$_3$) δ 8.93 (s, 1H) 8.12 (s, 1H) 7.41-7.19 (m, 1H) 7.15-7.25 (m, 2H) 7.12 (br t, J=9.3 Hz, 1H) 6.52-6.71 (m, 1H) 6.36-6.46 (m, 1H) 5.82 (br d, J=11.0 Hz, 1H) 4.25-5.29 (m, 3H) 3.53-4.08 (m, 3H) 2.75-3.37 (m, 2H) 1.46-1.60 (m, 3H) 1.28 (br d, J=6.2 Hz, 3H) 1.09 (br d, J=6.4 Hz, 3H). $^{19}$F NMR (377 MHz, CDCl$_3$) δ −112.3-−112.6 (m, 1F). m/z (ESI, +ve ion): 581.8 (M+1)$^+$.

Example 134

1-((3S)-4-(3-Chloro-2-(2-fluorophenyl)-7-methoxy-8-(2-methylphenyl)-1,6-naphthyridin-5-yl)-3-methyl-1-piperazinyl)-2-propen-1-one

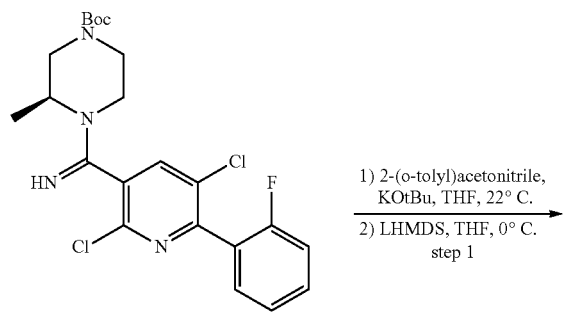

Intermediate 101B

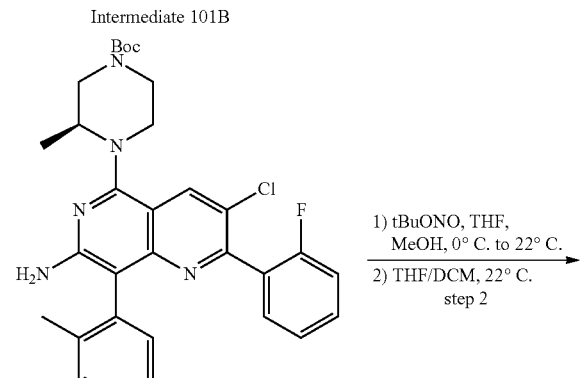

Intermediate 134A

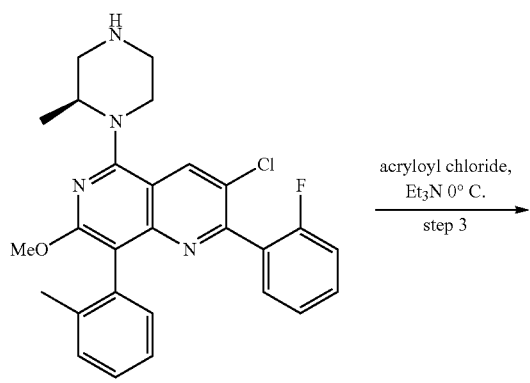

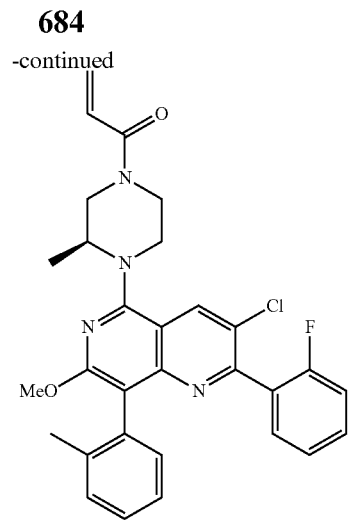

Step 1: (3S)-tert-Butyl 4-(7-amino-3-chloro-2-(2-fluorophenyl)-8-(o-tolyl)-1,6-naphthyridin-5-yl)-3-methylpiperazine-1-carboxylate (Intermediate 134A)

2-(o-Tolyl)acetonitrile (0.3 g, 2.3 mmol, Enamine, Monmouth Jct., N.J.) was added to a solution of potassium tert-butoxide (2.3 mL, 2.3 mmol) in THF (2.3 mL) at rt and the reaction mixture was stirred for 15 min before adding to a solution of tert-butyl (S)-4-((2,5-dichloro-6-(2-fluorophenyl)pyridin-3-yl)(imino)methyl)-3-methylpiperazine-1-carboxylate (Intermediate 101B, 485 mg, 1.038 mmol) in THF (4 mL). This mixture was stirred for 30 min, followed by quenching with saturated aqueous ammonium chloride solution and extraction with ethyl acetate (2×). The combined organic extracts were washed with water and dried over anhydrous sodium sulfate, and concentrated in vacuo to give a yellow oil. The oil was purified by silica gel chromatography (eluent: 50-100% EtOAc/heptane) to provide a yellow oil: m/z (ESI, +ve) 562.1 (M+H)$^+$. This material was dissolved in THF (5 mL) and cooled to 0° C. LHMDS (1 M in THF, 2.1 mL, 2.1 mmol) was added and the mixture was stirred for 2 h at 0° C. Saturated aqueous ammonium chloride solution was added and the mixture was extracted with ethyl acetate (2×). The combined extracts were dried over anhydrous magnesium sulfate, and concentrated in vacuo to give yellow oil. The crude material was purified by silica gel chromatography (eluent: 0-20% EtOAc/heptane) to provide (3S)-tert-butyl 4-(7-amino-3-chloro-2-(2-fluorophenyl)-8-(o-tolyl)-1,6-naphthyridin-5-yl)-3-methylpiperazine-1-carboxylate (Intermediate 134A): m/z (ESI, +ve) 562.1 (M+H)$^+$.

Step 2: 3-Chloro-2-(2-fluorophenyl)-7-methoxy-5-((S)-2-methylpiperazin-1-yl)-8-(o-tolyl)-1,6-naphthyridine Trifluoroacetic acid (0.03 mL, 0.33 mmol) and tert-butyl nitrite (0.044 mL, 0.33 mmol, Sigma-Aldrich Corporation. St. Louis, Mo., USA) were added to a solution of (3S)-tert-butyl 4-(7-amino-3-chloro-2-(2-fluorophenyl)-8-(o-tolyl)-1,6-naphthyridin-5-yl)-3-methylpiperane-1-carboxylate (Intermediate 134A, 37 mg, 0.066 mmol) in anhydrous methanol (0.5 mL) at 0° C. The reaction mixture was allowed to warm to room temperature over a period of 2 h. Ethyl acetate and saturated aqueous sodium bicarbonate solution were added. The organic layer separated, and dried over anhydrous magnesium sulfate, and concentrated in vacuo to give an oil.

This material was taken up in a mixture of DCM/TFA (1:1, v/v, 2 mL total volume) and the reaction mixture was stirred for 30 min at room temperature. The solvent was removed in vacuo and the oil was partitioned between aqueous 2N sodium carbonate solution and DCM. The organic layer was separated, dried over anhydrous magnesium sulfate, filtered, and concentrated in vacuo to give an oil. The oil was purified by silica gel chromatography (eluent: 0-5% MeOH (2M $NH_3$)/heptane) to provide 3-chloro-2-(2-fluorophenyl)-7-methoxy-5-((S)-2-methylpiperazin-1-yl)-8-(o-tolyl)-1,6-naphthyridine: m/z (ESI, +ve) 476.9 (M+H)$^+$.

Step 3: 1-((3)-4-(3-Chloro-2-(2-fluorophenyl)-7-methoxy-8-(2-methylphenyl)-1,6-naphthyridin-5-yl)-3-methyl-1-piperazinyl)-2-propen-1-one Acryloyl chloride (3.0 μL, 0.038 mmol) and triethylamine (5 μL, 0.038 mmol) were added to an ice cold solution of 3-chloro-2-(2-fluorophenyl)-7-methoxy-5-((S)-2-methylpiperazin-1-yl)-8-(o-tolyl)-1,6-naphthyridine (15 mg, 0.031 mmol) in DCM (0.2 mL). The mixture was stirred for 30 min, followed by the addition of water. The organic layer was separated, dried over anhydrous magnesium sulfate, and concentrated in vacuo to give an oil. The oil was purified by silica gel chromatography (eluent: 0-50% EtOAc/heptane) to provide 1-((3S)-4-(3-chloro-2-(2-fluorophenyl)-7-methoxy-8-(2-methylphenyl)-1,6-naphthyridin-5-yl)-3-methyl-1-piperazinyl)-2-propen-1-one. $^1$H NMR (400 MHz, $CDCl_3$) δ ppm 8.35 (br s, 1H) 7.33-7.43 (m, 2H) 7.04-7.25 (m, 6H) 6.58-6.72 (m, 1H) 6.39 (dd, J=16.79, 1.45 Hz, 1H) 5.77 (dd, J=10.57, 1.66 Hz, 1H) 4.00-4.42 (m, 2H) 3.92-3.98 (m, 3H) 3.60 (br s, 5H) 2.07 (d, J=10.37 Hz, 3H) 1.29 (br t, J=5.08 Hz, 3H). $^{19}$F NMR (376 MHz, DMSO-$d_6$) δ −113.0 (s, 1F). m/z (ESI, +ve ion) 531.0 (M+H)$^+$.

Example 135

(M)-6-Chloro-7-(2-fluorophenyl)-1-(4-methyl-2-(2-propanyl)-3-pyridinyl)-4-((1R,5S)-6-(2-propenoyl)-3,6-diazabicyclo[3.1.1]heptan-3-yl)pyrido[2,3-d]pyrimidin-2(1H)-one

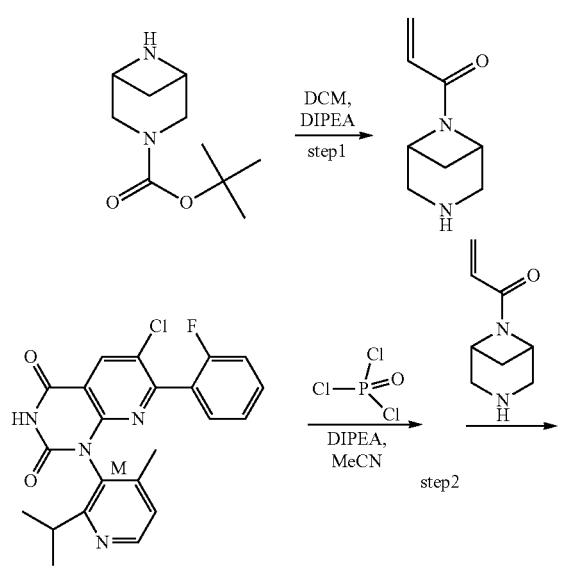

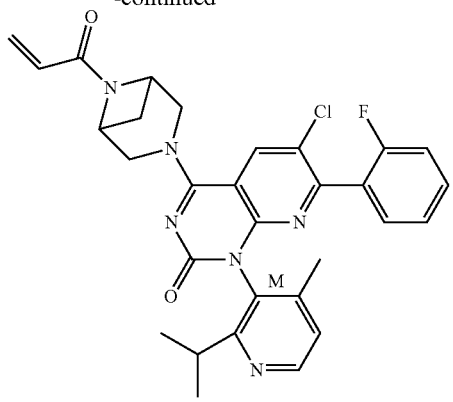

Step 1: 1-(3,6-diazabicyclo[3.1.1]heptan-6-yl)prop-2-en-1-one

DIPEA (0.15 mL, 0.85 mmol) was added to a solution of 3-Boc-3,6-diaza-bicyclo[3.1.1]heptane (0.15 g, 0.757 mmol, Aurum Pharmatech LLC, Franklin Park, N.J.) in DCM (1 mL), followed by 2-propenoyl chloride (0.5 M, 0.5 mL, 0.25 mmol). After 10 min, trifluoroacetic acid (0.019 mL, 0.259 mmol) was added to the reaction mixture. Stirring was continued for 30 min, followed by the removal of solvents under reduced pressure. m/z (ESI, +ve ion) 153.1.

Step 2: (M)-6-Chloro-7-(2-fluorophenyl)-1-(4-methyl-2-(2-propanyl)-3-pyridinyl)-4-((1R,5S)-6-(2-propenoyl)-3,6-diazabicyclo[3.1.1]heptan-3-yl)pyrido[2,3-d]pyrimidin-2(1H)-one Phosphoryl trichloride (0.04 mL, 0.429 mmol) was added to a solution of (M)-6-chloro-7-(2-fluorophenyl)-1-(2-isopropyl-4-methylpyridin-3-yl)pyrido[2,3-d]pyrimidine-2,4 (1H,3H)-dione (Intermediate 76A, 0.110 g, 0.259 mmol), and DIPEA (0.3 mL, 1.722 mmol) in acetonitrile (1.0 mL). The mixture was heated to 80° C. for 30 min. The reaction mixture was cooled to 0° C. and a solution of the amine obtained in Step 1 in DCM (2 mL) was added. The reaction mixture was allowed to warm to rt. After 16 h, the reaction mixture was diluted with EtOAc (10 mL) and washed with saturated aqueous sodium bicarbonate (2×5 mL) and brine (5 mL). The organic phase was concentrated in vacuo. The crude product purified by silica gel chromatography (eluent: 10-60% EtOAc-EtOH (3:1)/heptane) to provide (M)-6-chloro-7-(2-fluorophenyl)-1-(4-methyl-2-(2-propanyl)-3-pyridinyl)-4-((1R,5S)-6-(2-propenoyl)-3,6-diazabicyclo[3.1.1]heptan-3-yl)pyrido[2,3-d]pyrimidin-2(1H)-one (67 mg, 0.120 mmol, 46.3%6 yield). $^1$H NMR (400 MHz, DMSO-$d_6$) δ 8.86 (s, 1H), 8.37 (d, J=4.98 Hz, 1H), 7.47-7.53 (m, 1H), 7.15-7.32 (m, 4H), 6.52 (dd, J=10.16, 17.00 Hz, 1H), 6.18 (dd, J=2.07, 17.00 Hz, 1H), 5.70-5.76 (m, 1H), 4.86 (br s, 1H), 4.54 (br s, 1H), 4.37 (br d, J=12.44 Hz, 4H), 2.63-2.76 (m, 2H), 1.91 (s, 3H), 1.72 (d, J=8.91 Hz, 1H), 1.05 (d, J=6.63 Hz, 3H), 0.91 (d, J=6.63 Hz, 3H). $^{19}$F NMR (376 MHz, DMSO-$d_6$) δ −114.25 (s, 1F). m/z (ESI, +ve ion) 559.1.

Example 136

1-(6-Amino-4-methyl-2-(2-propanyl)-3-pyridinyl)-6-chloro-7-(2-fluorophenyl)-4-((2S)-2-methyl-4-(2-propenoyl)-1-piperazinyl)pyrido[2,3-d]pyrimidin-2(1H)-one

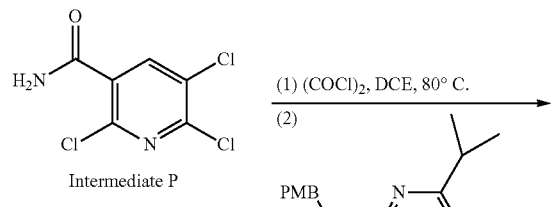

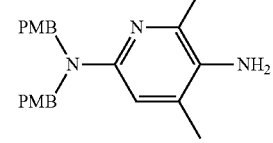

Intermediate I-33
Step 1

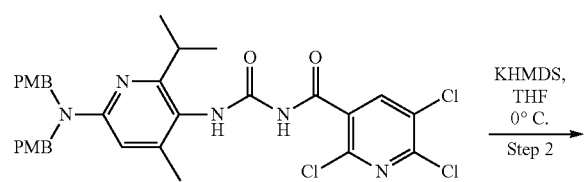

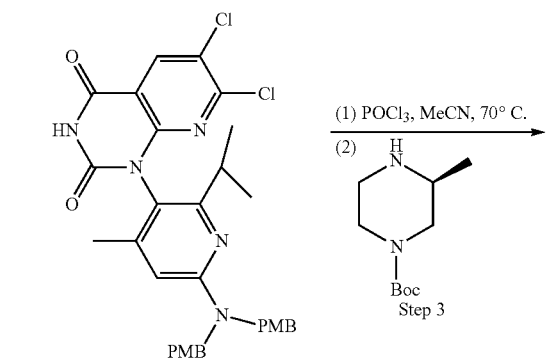

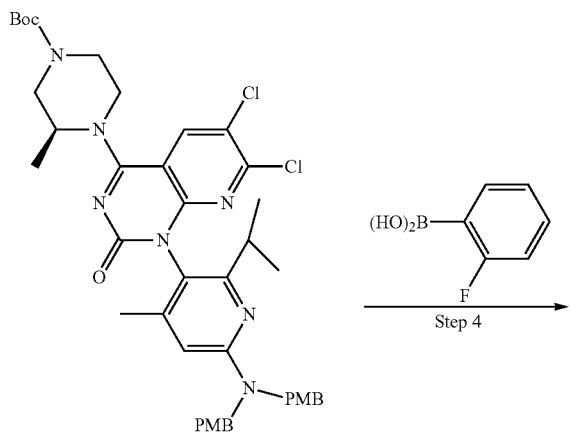

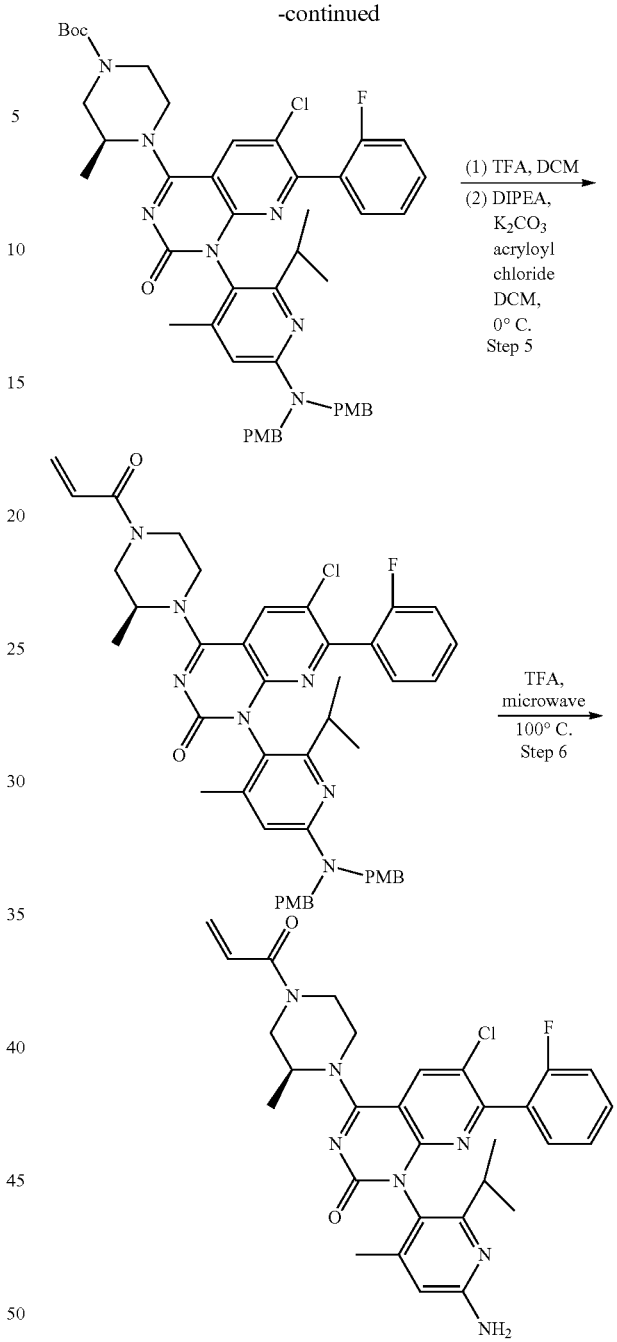

Step 1: N-((6-(Bis(4-methoxybenzyl)amino)-2-isopropyl-4-methylpyridin-3-yl)carbamoyl)-2,5,6-trichloronicotinamide Oxalyl chloride (2 M in DCM, 0.46 mL, 0.91 mmol) was added to a solution of 2,5,6-trichloronicotinamide (Intermediate P, 187 mg, 0.831 mmol) in 1,2-dichloroethane (10 mL) under nitrogen atmosphere. The resulting mixture was heated to 80° C. for 1 hour. The mixture was cooled to room temperature and a solution of 6-isopropyl-N2,N2-bis(4-methoxybenzyl)-4-methylpyridine-2,5-diamine (Intermediate I-33, 337 mg, 0.831 mmol) in MeCN (5 mL) was added. After 1 h, the mixture was quenched with saturated NH₄Cl (5 mL) and diluted with saturated NaHCO₃ (25 mL). The mixture was extracted with EtOAc (2×100 mL). The combined organic extracts were dried over MgSO$_4$ and concentrated under reduced pressure. The crude product was purified by silica gel chromatography (eluent: 0-100% EtOAc-EtOH (3:1)/heptane) to provide N-((6-(bis(4-methoxybenzyl)amino)-2-isopropyl-4-methylpyridin-3-yl)carbamoyl)-2,5,6-trichloronicotinamide as a yellow solid. m/z (ESI, +ve ion): 656.0 (M+H)$^+$. The product was used in the next step without further purification.

Step 2: 1-(6-(Bis(4-methoxybenzyl)amino)-2-isopropyl-4-methylpyridin-3-yl)-6,7-dichloropyrido[2,3-d]pyrimidine-2,4(1H,3H)-dione KHMDS (1M in THF, 1.662 mL, 1.662 mmol) was added dropwise to a solution of N-((6-(bis(4-methoxybenzyl)amino)-2-isopropyl-4-methylpyridin-3-yl)carbamoyl)-2,5,6-trichloronicotinamide (546 mg, 0.831 mmol) in tetrahydrofuran (15 mL) at 0° C. under nitrogen atmosphere. After completed addition, the reaction mixture was stirred at 0° C. for 30 mins. The reaction mixture was quenched with saturated NH$_4$Cl (5 mL), diluted with saturated NaHCO$_3$ (16 mL) and extracted with EtOAc (2×100 mL). The combined organic extracts were dried over MgSO$_4$ and concentrated under reduced pressure. The crude product was purified by silica gel chromatography (eluent: 0-100% EtOAc-EtOH (3:1)/heptane) to provide 1-(6-(bis(4-methoxybenzyl)amino)-2-isopropyl-4-methylpyridin-3-yl)-6,7-dichloro-pyrido[2,3-d]pyrimidine-2,4(1H,3H)-dione (476 mg, 0.767 mmol, 92% yield) as a yellow solid. m/z (ESI, +ve ion): 620.0 (M+H)$^+$.

Step 3: tert-Butyl (S)-4-(1-(6-(bis(4-methoxybenzyl)amino)-2-isopropyl-4-methylpyridin-3-yl)-6,7-dichloro-2-oxo-1,2-dihydropyrido[2,3-d]pyrimidin-4-yl)-3-methylpiperazine-1-carboxylate 1,1'-Dimethyltriethylamine (0.46 mL, 2.66 mmol) and phosphorus oxide chloride (0.18 mL, 1.898 mmol) were added to a solution of 1-(6-(bis(4-methoxybenzyl)amino)-2-isopropyl-4-methylpyridin-3-yl)-6,7-dichloropyrido[2,3-d]pyrimidine-2,4(1H,3H)-dione (471 mg, 0.759 mmol) in acetonitrile (8 mL). The resulting mixture was heated to 70° C. under nitrogen atmosphere for 30 mins. The reaction mixture was cooled to room temperature and a mixture of (3S)-1-(tert-butoxycarbonyl)-3-methylpiperazine (0.30 mL, 1.518 mmol, Combi-Blocks, San Diego, Calif.) and 1,1'-dimethyltriethylamine (0.46 mL, 2.66 mmol) in MeCN (4 mL) was added. After 30 mins., the reaction mixture was diluted with water (20 mL) and extracted with EtOAc (2×50 mL). The combined organic extracts were dried over MgSO4 and concentrated under reduced pressure. The crude product was purified by silica gel chromatography (eluent: 0-80% EtOAc-EtOH (3:1)/heptane) to provide tert-butyl (S)-4-(1-(6-(bis(4-methoxybenzyl)amino)-2-isopropyl-4-methylpyridin-3-yl)-6,7-dichloro-2-oxo-1,2-dihydropyrido[2,3-d]pyrimidin-4-yl)-3-methylpiperazine-1-carboxylate as a yellow solid. m/z (ESI, +ve ion): (M-i-C$_4$H$_8$=746.0)

Step 4: tert-Butyl (S)-4-(l-(6-(bis(4-methoxybenzyl)amino)-2-isopropyl-4-methylpyridin-3-yl)-6-chloro-7-(2-fluorophenyl)-2-oxo-1,2-dihydropyrido[2,3-d]pyrimidin-4-yl)-3-methylpiperazine-1-carboxylate A mixture of tert-butyl (S)-4-(1-(6-(bis(4-methoxybenzyl)amino)-2-isopropyl-4-methylpyridin-3-yl)-6,7-dichloro-2-oxo-1,2-dihydropyrido[2,3-d]pyrimidin-4-yl)-3-methylpiperazine-1-carboxylate (609 mg, 0.759 mmol), (2-fluorophenyl)boranediol (212 mg, 1.517 mmol, Combi-Blocks, San Diego, Calif.), (1,1'-bis(diphenylphosphino)ferrocene) dichloropalladium (56 mg, 0.076 mmol), and potassium acetate (371 mg, 3.79 mmol). in 1,4-dioxane (7 mL) was heated to 80° C. under nitrogen atmosphere for 1 hour. The reaction mixture was diluted with saturated NaHCO$_3$ (10 mL) and extracted with EtOAc (2×50 mL). The combined organic extracts were dried over MgSO$_4$ and concentrated under reduced pressure. The crude product was purified by silica gel chromatography (eluent: 0-100% EtOAc-EtOH (3:1)/heptane) to provide tert-butyl (S)-4-(1-(6-(bis(4-methoxybenzyl)amino)-2-isopropyl-4-methylpyridin-3-yl)-6-chloro-7-(2-fluorophenyl)-2-oxo-1,2-dihydropyrido[2,3-d]pyrimidin-4-yl)-3-methylpiperazine-1-carboxylate (654 mg, 0.758 mmol, 100% yield) as a yellow solid. m/z (ESI, +ve ion): 862.2 (M+H)

Step 5: (S)-4-(4-Acryloyl-2-methylpiperazin-1-yl)-1-(6-(bis(4-methoxybenzyl)amino)-2-isopropyl-4-methylpyridin-3-yl)-6-chloro-7-(2-fluorophenyl)pyrido[2,3-d]pyrimidin-2(1H)-one Trifluoroacetic acid (1.1 mL, 15.17 mmol) was added to a solution of tert-butyl (S)-4-(1-(6-(bis(4-methoxybenzyl)amino)-2-isopropyl-4-methylpyridin-3-yl)-6-chloro-7-(2-fluorophenyl)-2-oxo-1,2-dihydropyrido[2,3-d]pyrimidin-4-yl)-3-methylpiperazine-1-carboxylate (654 mg, 0.758 mmol) in dichloromethane (5 mL). After 1 h, the reaction mixture was concentrated in vacuo to provide (S)-1-(6-(bis(4-methoxybenzyl)amino)-2-isopropyl-4-methylpyridin-3-yl)-6-chloro-7-(2-fluorophenyl)-4-(2-methylpiperazin-1-yl)pyrido[2,3-d]pyrimidin-2(1H)-one as the TFA salt. m/z (ESI, +ve ion): 762.2 (M+H)$^+$ The residue was dissolved in DCM (7 mL), placed under nitrogen atmosphere and cooled to 0° C. Potassium carbonate (523 mg, 3.79 mmol), 1,1'-dimethyltriethylamine (2 mL, 11.37 mmol). and a solution of 2-propenoyl chloride (0.062 mL, 0.758 mmol) in DCM (0.3 mL) were added. The resulting mixture was stirred for 15 min at 0° C. The reaction mixture was quenched with saturated NaHCO$_3$ (10 mL) and extracted with EtOAc (2×30 mL). The combined organic extracts were dried over MgSO$_4$ and concentrated in vacuo. The crude product was purified by silica gel chromatography (eluent: 0-100% EtOAc-EtOH (3:1)/heptane) to provide (S)-4-(4-acryloyl-2-methylpiperazin-1-yl)-1-(6-(bis(4-methoxybenzyl)amino)-2-isopropyl-4-methylpyridin-3-yl)-6-chloro-7-(2-fluorophenyl)pyrido[2,3-d]pyrimidin-2(1H)-one. m/z (ESI, +ve ion): 816.5 (M+H)$^+$ Step 6: 1-(6-Amino-4-methyl-2-(2-propanyl)-3-pyridinyl)-6-chloro-7-(2-fluorophenyl)-4-((2S)-2-methyl-4-(2-propenoyl)-1-piperazinyl)pyrido[2,3-d]pyrimidin-2(1H)-one A solution of (S)-4-(4-acryloyl-2-methylpiperazin-1-yl)-1-(6-(bis(4-methoxybenzyl)amino)-2-isopropyl-4-methylpyridin-3-yl)-6-chloro-7-(2-fluorophenyl)pyrido[2,3-d]pyrimidin-2(1H)-one (568 mg, 0.696 mmol) in TFA (3.6 mL, 48.7 mmol) was heated to 100° C. for 10 min in a microwave. The reaction mixture was concentrated under reduced pressure and the residue was taken up in DCM (20 mL). Saturated NaHCO$_3$ (50 mL) was added slowly at 0° C. After completed addition, the organic layer was separated, dried over MgSO$_4$, and concentrated in vacuo. The crude product was purified by silica gel chromatography (eluent: 0-10% MeOH (2M NH$_3$/heptane) to provide 1-(6-amino-4- methyl-2-(2-propanyl)-3-pyridinyl)-6-chloro-7-(2-fluoro-phenyl)-4-((2S)-2-methyl-4-(2-propenoyl)-1-piperazinyl)pyrido[2,3-d]pyrimidin-2(1H)-one (165 mg, 0.143 mmol, 41.2% yield), yellow solid, TFA salt. ¹H NMR (DMSO-d₆) δ: 8.40 (br s, 1H), 7.48-7.60 (m, 1H), 7.22-7.36 (m, 3H), 6.78-6.93 (m, 1H), 6.15-6.25 (m, 2H), 5.70-5.84 (m, 3H), 4.79-5.03 (m, 1H), 4.22-4.49 (m, 2H), 3.96-4.19 (m, 2H), 3.40-3.83 (m, 2H), 3.01-3.29 (m, 2H), 1.73 (s, 3H), 1.29-1.35 (m, 3H), 0.99 (d, J=6.8 Hz, 3H), 0.86-0.89 (n, 3H). ¹⁹F NMR (DMSO-d₆) δ: −114.09 (s, 1F), −114.13 (s, 1F). m/z (ESI, +ve ion): 576.0 (M+H)⁺

Example 137

6-Chloro-7-(2-fluorophenyl)-1-(4-methyl-6-ozo-2-(2-propanyl)-1,6-dihydro-3-pyridinyl)-4-((2S)-2-methyl-4-(2-propenoyl)-1-piperazinyl)pyrido[2,3-d]pyrimidin-2(1H)-one

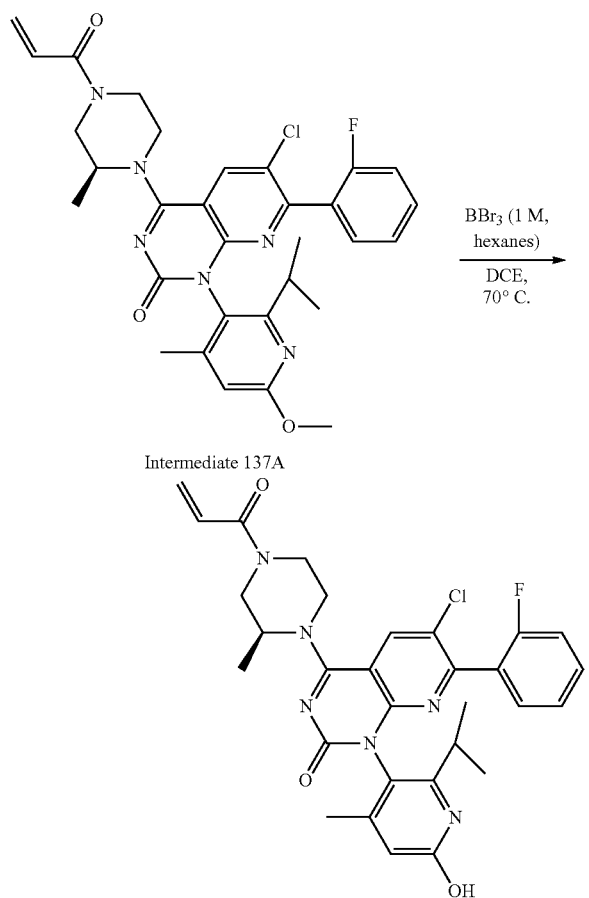

Intermediate 137A

Boron tribromide (1 M in hexanes, 2.6 mL, 2.6 mmol) was added dropwise to a solution of (S)-4-(4-acryloyl-2-methylpiperazin-1-yl)-6-chloro-7-(2-fluorophenyl)-1-(2-isopropyl-6-methoxy-4-methylpyridin-3-yl)pyrido[2,3-d]pyrimidin-2(1H)-one (Intermediate 137A prepared according to Method 136 using Intermediate I-32, 258 mg, 0.436 mmol) in 1,2-dichloroethane (4 mL). After completed addition, the reaction mixture was heated to 70° C. for 7 hours. The reaction mixture was cooled to 0° C. and slowly quenched with saturated NaHCO₃ (5 mL). The mixture was extracted with EtOAc (2×100 mL) and the combined organic extracts were dried over MgSO₄ and concentrated in vacuo. The crude product was purified by silica gel chromatography (eluent: 0-100% EtOAc-EtOH (3:1)/heptane) to provide 6-chloro-7-(2-fluorophenyl)-1-(4-methyl-6-oxo-2-(2-propanyl)-1,6-dihydro-3-pyridinyl)-4-((2S)-2-methyl-4-(2-propenoyl)-1-piperazinyl)pyrido[2,3-d]pyrimidin-2(1H)-one (10 mg, 8.66 μmol, 2.0% yield) as a yellow solid. ¹H NMR (DMSO-d₆) δ: 11.18-11.46 (m, 1H), 8.41 (br d, J=3.1 Hz, 1H), 7.55 (br s, 1H), 7.33 (br d, J=4.8 Hz, 3H), 6.56-6.96 (m, 1H), 6.02-6.28 (m, 2H), 5.76 (br d, J=9.1 Hz, 1H), 4.76-5.06 (m, 1H), 4.07-4.49 (m, 3H), 3.48-4.06 (m, 3H), 2.87-3.14 (m, 1H), 1.69 (br s, 3H), 1.33 (br d, J=5.8 Hz, 3H), 1.07 (br s, 3H), 0.94 (br s, 3H). ¹⁹F NMR (376 MHz, DMSO-d₆) δ −114.09 (s, 1F). m/z (ESI, +ve ion): 577.1 (M+H)⁺

Example 138

1-((3S)-4-(3-Chloro-8-(2,6-di(2-propanyl)phenyl)-2-(2-fluorophenyl)pyrido[2,3-d]pyridazin-5-yl)-3-methyl-1-piperazinyl)-2-propen-1-one

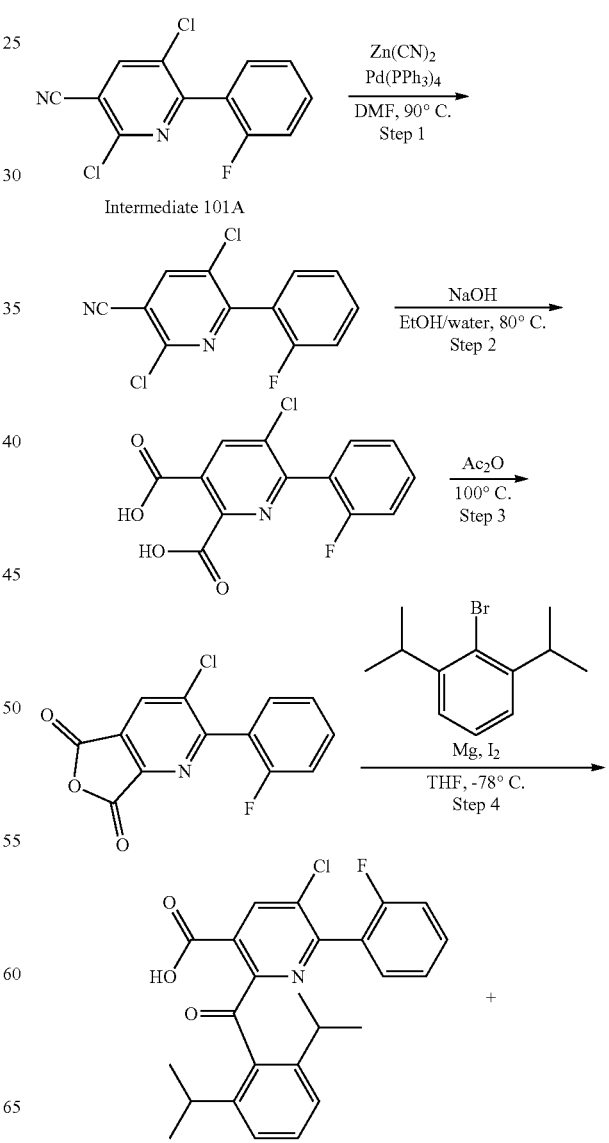

693

-continued

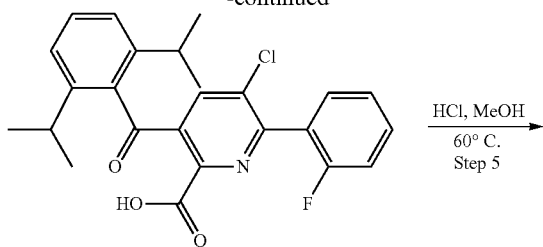

HCl, MeOH
60° C.
Step 5

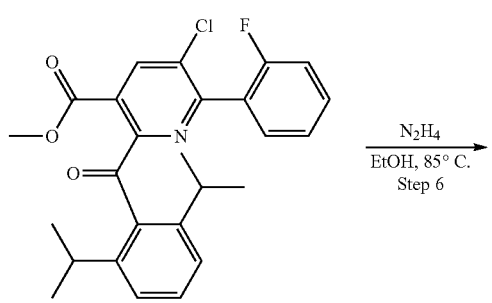

N₂H₄
EtOH, 85° C.
Step 6

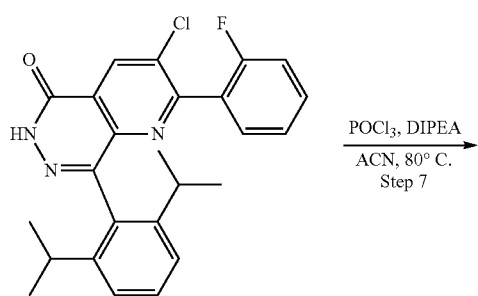

POCl₃, DIPEA
ACN, 80° C.
Step 7

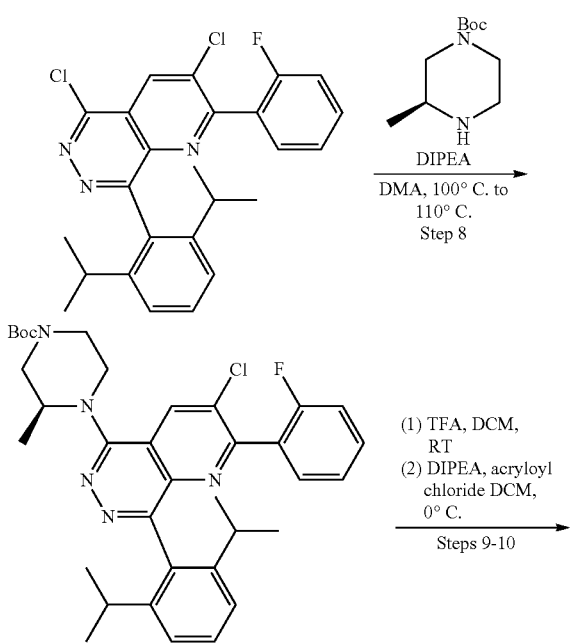

DIPEA
DMA, 100° C. to 110° C.
Step 8

(1) TFA, DCM, RT
(2) DIPEA, acryloyl chloride DCM, 0° C.
Steps 9-10

694

-continued

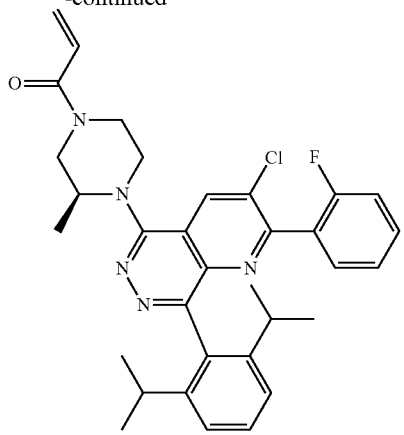

Step 1: 5-Chloro-6-(2-fluorophenyl)pyridine-2,3-dicarbonitrile

A mixture of 2,5-dichloro-6-(2-fluorophenyl)nicotinonitrile (Intermediate 101A, 50 mg, 0.187 mmol), zinc cyanide (0.013 mL, 0.206 mmol), and tetrakis(triphenylphosphine)palladium (21.6 mg, 0.019 mmol) in N,N-dimethylformamide (1 mL) were heated at 90° C. for 3 h under an argon atmosphere. The reaction mixture was cooled to room temperature and partitioned between EtOAc (50 mL) and 1 M aqueous NaOH (30 mL). The organic layer was separated, washed with brine (25 mL), dried over MgSO₄, filtered, and concentrated in vacuo. The crude product was purified by silica gel chromatography (eluent: 0-25% EtOAc/heptane) to provide 5-chloro-6-(2-fluorophenyl)pyridine-2,3-dicarbonitrile as a white solid (38 mg, 0.147 mmol, 79% yield). $^1$H NMR (400 MHz, CDCl₃) δ ppm 8.19 (1H, s) 7.50-7.58 (1H, m) 7.42-7.48 (1H, m) 7.28-7.34 (1H, m) 7.17-7.23 (1H, m). m/z (ESI, +ve ion ion): 258.0 (M+H)⁺.

Step 2: 5-Chloro-6-(2-fluorophenyl)pyridine-2,3-dicarboxylic acid

Sodium hydroxide (5 N aqueous, 3 mL, 15.00 mmol) was added to a solution of 5-chloro-6-(2-fluorophenyl)pyridine-2,3-dicarbonitrile (338 mg, 1.312 mmol) in ethanol (5 mL). The reaction mixture was stirred at 80° C. for 3 h. The reaction mixture was cooled to room temperature and diluted with saturated aqueous ammonium chloride (50 mL). The aqueous solution was acidified with 2 N aqueous HCl and extracted with EtOAc (75 mL). The organic extract was separated, washed with brine (50 mL), dried over MgSO₄, filtered, and concentrated to give 5-chloro-6-(2-fluorophenyl)pyridine-2,3-dicarboxylic acid as an off-white solid (377 mg, 1.275 mmol, 97% yield). m/z (ESI, +ve ion ion): 296.0 (M+H)⁺.

Step 3: 3-Chloro-2-(2-fluorophenyl)furo[3,4-b]pyridine-5,7-dione

A mixture of 5-chloro-6-(2-fluorophenyl)pyridine-2,3-dicarboxylic acid (342 mg, 1.157 mmol) in acetic anhydride (2 mL, 21.16 mmol) was heated at 100° C. for 1.5 h. The reaction mixture was concentrated to give 3-chloro-2-(2-fluorophenyl)furo[3,4-b]pyridine-5,7-dione as an orange solid. The crude product was used without further purification in the next step.

Step 4: 5-Chloro-2-(2,6-diisopropylbenzoyl)-6-(2-fluorophenyl)nicotinic acid with 5-chloro-3-(2,6-diisopropylbenzoyl)-6-(2-fluorophenyl)picolinic acid 2-Bromo-1,3-diisopropylbenzene (1.00 g, 4.15 mmol, Combi-Blocks, San Diego, Calif.) was added to a mixture of magnesium turnings (106 mg, 4.35 mmol) and iodine (3 mg, 0.012 mmol) in tetrahydrofuran (6 mL) under an argon atmosphere. The reaction mixture was heated to 65° C. for 2.5 h. The reaction mixture was cooled to room temperature and 5 mL of the Grignard solution were added dropwise to a stirred solution of 3-chloro-2-(2-fluorophenyl)furo[3,4-b]pyridine-5,7-dione (321 mg, 1.156 mmol) in tetrahydrofuran (5 mL) at −78° C. under an argon atmosphere. The reaction mixture was stirred at −78° C. for 1 h and then allowed to warm to room temperature and stir for another 1 h. The reaction mixture was quenched with saturated aqueous ammonium chloride (50 mL) and extracted with EtOAc (75 mL). The organic layer was separated, washed with brine (60 mL), dried over $MgSO_4$, filtered, and concentrated in vacuo to give approximately a 1:4 mixture of 5-chloro-2-(2,6-diisopropylbenzoyl)-6-(2-fluorophenyl)nicotinic acid with 5-chloro-3-(2,6-diisopropylbenzoyl)-6-(2-fluorophenyl)picolinic acid. m/z (ESI, +ve ion ion): 440.1 $(M+H)^+$.

Step 5: Methyl 5-chloro-2-(2,6-diisopropylbenzoyl)-6-(2-fluorophenyl)nicotinate Hydrogen chloride (4.0 M in 1,4-dioxane, 1.4 mL, 5.67 mmol) was added to a solution of the product mixture from the previous step (499 mg, 1.134 mmol) in methanol (5 mL). The reaction mixture was stirred at 60° C. for 23 h. The reaction mixture was quenched with saturated aqueous sodium bicarbonate (50 mL) and extracted with EtOAc (100 mL). The organic layer was separated, washed with brine (50 mL), dried over $MgSO_4$, filtered, and concentrated in vacuo. The crude product was purified by silica gel chromatography (eluent: 0-20% EtOAc/heptane) to provide two products. The first peak to elute provided methyl 5-chloro-2-(2,6-diisopropylbenzoyl)-6-(2-fluorophenyl)nicotinate as a white solid (45 mg, 0.099 mmol, 8.74% yield). $^1$H NMR (400 MHz, $CDCl_3$) δ ppm 8.02 (1H, s) 7.32-7.40 (1H, m) 7.26-7.32 (1H, m) 7.02-7.23 (5H, m) 3.97 (3H, s) 2.76 (2H, spt, J=6.50 Hz) 1.07 (12H, d, J=6.60 Hz). m/z (ESI, +ve ion ion): 454.2 $(M+H)^+$.

Step 6: 3-chloro-8-(2,6-diisopropylphenyl)-2-(2-fluorophenyl)pyrido[2,3-d]pyridazin-5(6H)-one Hydrazine hydrate (0.049 mL, 0.991 mmol) was added to a solution of methyl 5-chloro-2-(2,6-diisopropylbenzoyl)-6-(2-fluorophenyl)nicotinate (45 mg, 0.099 mmol) in ethanol (0.5 mL). The reaction mixture was heated at 85° C. for 24 h. The reaction mixture was cooled to room temperature and concentrated in vacuo. The crude product was purified by silica gel chromatography (eluent: 0-50% EtOAc-EtOH (3:1)/heptane) to provide 3-chloro-8-(2,6-diisopropylphenyl)-2-(2-fluorophenyl)pyrido[2,3-d]pyridazin-5(6H)-one as a white solid (48 mg, 0.110 mmol, 111% yield). $^1$H NMR (400 MHz, $CDCl_3$) δ ppm 10.68 (1H, s) 8.84 (1H, s) 7.35-7.45 (2H, m) 7.07-7.23 (5H, m) 2.46 (2H, spt, J=6.74 Hz) 1.14 (6H, d, J=6.84 Hz) 0.99 (6H, d, J=6.63 Hz). m/z (ESI, +ve ion ion): 436.3 $(M+H)^+$.

Step 7: 3,5-dichloro-8-(2,6-diisopropylphenyl)-2-(2-fluorophenyl)pyrido[2,3-d]pyridazine Phosphorous oxychloride (0.062 mL, 0.661 mmol) was added to a s mixture of 3-chloro-8-(2,6-diisopropylphenyl)-2-(2-fluorophenyl)pyrido[2,3-d]pyridazin-5(6H)-one (48 mg, 0.110 mmol) and N,N-diisopropylethylamine (0.04 mL, 0.220 mmol) in acetonitrile (0.5 mL). The reaction mixture was heated at 80° C. for 19 h. The reaction mixture was concentrated in vacuo. The crude product was purified by silica gel chromatography (eluent: 0-100% EtOAc/heptane) to provide 3,5-dichloro-8-(2,6-diisopropylphenyl)-2-(2-fluorophenyl)pyrido[2,3-d]pyridazine as a yellow solid (33 mg, 0.073 mmol, 66.0% yield). m/z (ESI, +ve ion ion): 454.2 $(M+H)^+$.

Step 8: tert-butyl (S)-4-(3-chloro-8-(2,6-diisopropylphenyl)-2-(2-fluorophenyl)pyrido[2,3-d]pyridazin-5-yl)-3-methylpiperazine-1-carboxylate A mixture of 3,5-dichloro-8-(2,6-diisopropylphenyl)-2-(2-fluorophenyl)pyrido[2,3-d]pyridazine (29 mg, 0.064 mmol), tert-butyl (S)-3-methylpiperazine-1-carboxylate (63.9 mg, 0.319 mmol, Combi-Blocks, San Diego, Calif.), and N,N-diisopropylethylamine (0.06 mL, 0.3 mmol) in N,N-dimethylacetamide (0.30 mL) was heated at 100° C. for 2 h and at 110° C. for another 3 h. The reaction mixture was cooled to 100° C. and stirred overnight for 16 h. The reaction mixture was heated at 110° C. and stirred for another 4 h. The reaction mixture was cooled to room temperature, quenched with saturated aqueous ammonium chloride (25 ml), and extracted with EtOAc (30 mL). The organic layer was separated, washed with brine (20 mL), dried over $MgSO_4$, filtered, and concentrated in vacuo. The crude product was purified by silica gel chromatography (eluent: 0-30% EtOAc/heptane) to provide tert-butyl (S)-4-(3-chloro-8-(2,6-diisopropylphenyl)-2-(2-fluorophenyl)pyrido[2,3-d]pyridazin-5-yl)-3-methylpiperazine-1-carboxylate as a yellow solid (31 mg, 0.050 mmol, 79% yield). $^1$H NMR (400 MHz, $CDCl_3$) 5 ppm 8.46 (1H, s) 7.38-7.48 (2H, m) 7.10-7.28 (5H, m) 3.46-4.28 (7H, m) 2.20-2.33 (2H, m) 1.54 (9H, s) 1.34 (3H, d, J=6.40 Hz) 1.11-1.16 (6H, m) 0.94-0.99 (6H, m). m/z (ESI, +ve ion ion): 618.3 $(M+H)^+$.

Step 9: (S)-3-chloro-8-(2,6-diisopropylphenyl)-2-(2-fluorophenyl)-5-(2-methylpiperazin-1-yl)pyrido[2,3-d]pyridazine Trifluoroacetic acid (0.3 mL, 3.35 mmol) was added to a solution of tert-butyl (S)-4-(3-chloro-8-(2,6-diisopropylphenyl)-2-(2-fluorophenyl)pyrido[2,3-d]pyridazin-5-yl)-3-methylpiperazine-1-carboxylate (31 mg, 0.050 mmol) in dichloromethane (0.3 mL). The reaction mixture was stirred at room temperature for 15 min. The reaction mixture was concentrated in vacuo to give (S)-3-chloro-8-(2,6-diisopropylphenyl)-2-(2-fluorophenyl)-5-(2-methylpiperazin-1-yl)pyrido[2,3-d]pyridazine as an orange solid. m/z (ESI, +ve ion ion): 518.3 $(M+H)^+$. The product was used in the next step without further purification.

Step 10: 1-((3S)-4-(3-Chloro-8-(2,6-di(2-propanyl)phenyl)-2-(2-fluorophenyl)pyrido[2,3-d]pyridazin-5-yl)-3-methyl-1-piperazinyl)-2-propen-1-one Acryloyl chloride (4.89 µl, 0.060 mmol) was added to a stirred mixture of (S)-3-chloro-8-(2,6-diisopropylphenyl)-2-(2-fluorophenyl)-5-(2-methylpiperazin-1-yl)pyrido[2,3-d]pyridazine (26 mg, 0.050 mmol) and N,N-diisopropylethylamine (0.03 mL, 0.151 mmol) in dichloromethane (0.5 mL) at 0° C. After 15 min, the reaction mixture was diluted with DCM (25 mL) and washed with saturated aqueous ammonium chloride (15 ml). The organic layer was separated, dried over MgSO₄, filtered, and concentrated in vacuo. The crude product was purified by silica gel chromatography (eluent: 0-60% EtOAc/heptane) to provide 1-((3S)-4-(3-Chloro-8-(2,6-di(2-propanyl)phenyl)-2-(2-fluorophenyl)pyrido[2,3-d]pyridazin-5-yl)-3-methyl-1-piperazinyl)-2-propen-1-one as a yellow solid (14 mg, 0.024 mmol, 48.8% yield). ¹H NMR (400 MHz, CDCl₃) δ ppm 8.49 (1H, s) 7.40-7.52 (2H, m) 7.12-7.32 (5H, m) 6.63-6.79 (1H, m) 6.45 (1H, d, J=16.79 Hz) 5.83 (1H, d, J=10.40 Hz) 3.56-4.48 (7H, m) 2.21-2.35 (2H, m) 1.38 (3H, br s) 1.11-1.20 (6H, m) 0.96-1.02 (6H, m). m/z (ESI, +ve ion ion): 572.3 (M+H)⁺.

Example 139

1-(2-Amino-4,6-di(2-propanyl)-5-pyrimidinyl)-6-chloro-7-(2-fluorophenyl)-4-((2S)-2-methyl-4-(2-propenoyl)-1-piperazinyl)pyrido[2,3-d]pyrimidin-2(1H)-one

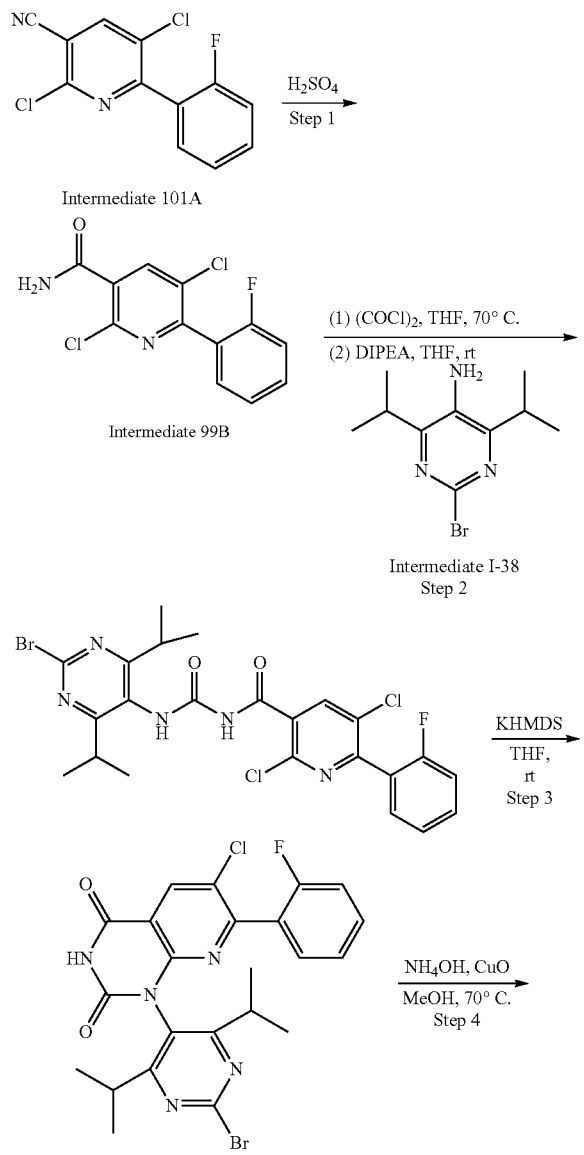

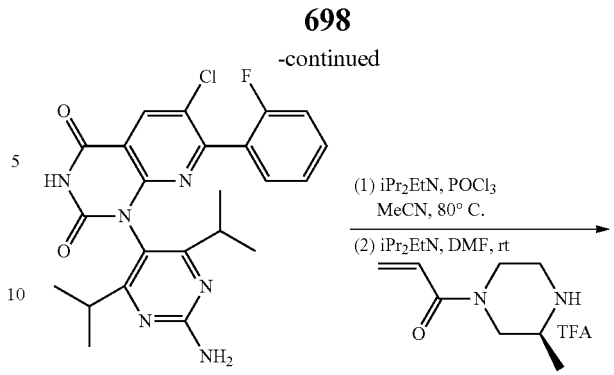

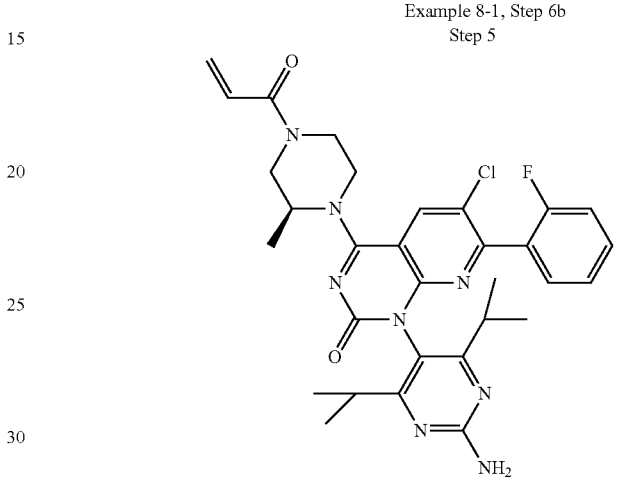

Step 1: 2,5-dichloro-6-(2-fluorophenyl)nicotinamide

A suspension of 2,5-dichloro-6-(2-fluorophenyl)nicotinonitrile (Intermediate 101A, 5.1 g, 19.10 mol) in sulfuric acid (10.2 ml, 191 mmol) was heated at 50° C. for 18 hrs. The reaction mixture was poured onto ice water (200 mL). The precipitate was filtered off, washed and dried to afford 2,5-dichloro-6-(2-fluorophenyl)nicotinamide (Intermediate 99B, 5.5 g, 19.29 mmol, 100% yield) as white solid. ¹H NMR (400 MHz, DMSO-d₆) δ ppm 7.34-7.43 (m, 2H) 7.52 (td, J=7.62, 1.76 Hz, 1H) 7.57-7.65 (m, 1H) 7.92 (br s, 1H) 8.18 (br s, 1H) 8.27 (s, 1H). m/z (ESI, +ve ion): 284.9 (M+H).

Step 2: N-((2-bromo-4,6-diisopropylpyrimidin-5-yl)carbamoyl)-2,5-dichloro-6-(2-fluorophenyl)nicotinamide Oxalyl chloride (2 M in DCM, 2.6 mL, 5.2 mol) was added to a suspension of 2,5-dichloro-6-(2-fluorophenyl)nicotinamide (Intermediate 99B, 0.98 g, 3.44 m, 191 mmol) in tetrahydrofuran (15 mL). The reaction mixture was heated at 65° C. for 2.5 hrs. Additional oxalyl chloride (2 M in DCM, 2.6 mL, 5.2 mmol) was added and the reaction mixture was heated for one additional hour. The reaction mixture was concentrated under reduced pressure and the oil was taken up in THF (15 mL). 2-Bromo-4,6-diisopropylpyrimidin-5-amine (Intermediate I-38, 0.976 g, 3.78 mmol) was added and the reaction mixture was stirred at rt for 60 min. The solvent was removed under reduced pressure and the residue was purified by silica gel chromatography (eluent: 0-30% EtOAc/heptane) to provide N-((2-bromo-4,6-diisopropylpyrimidin-5-yl)carbamoyl)-2,5-dichloro-6-(2- fluorophenyl)nicotinamide (1. g, 1.932 mmol, 56.2% yield). This product was carried to the next step without further purification.

m/z (ESI, +ve ion): 569.8/571.8 (M+H).

Step 3: 1-(2-bromo-4,6-diisopropylpyrimidin-5-yl)-6-chloro-7-(2-fluorophenyl)pyrido[2,3-d]pyrimidine-2,4(1H,3H)-dione KHMDS (IM in THF, 3.9 mL, 3.9 mmol) was added to a solution of N-((2-bromo-4,6-diisopropylpyrimidin-5-yl)carbamoyl)-2,5-dichloro-6-(2-fluorophenyl)nicotinamide (1.1 g, 1.932 mmol) in tetrahydrofuran (25 mL) at rt. After 30 min, the reaction mixture was cooled to 5° C., and saturated $NH_4Cl$ was added. Stirring was continued for 30 min. The suspension was diluted with water and extracted with EtOAc. The organic extracts were washed with brine, dried over $Na_2SO_4$, and concentrated under reduced pressure. The crude product was purified by silica gel chromatography (0-40% EtOAc/heptane) to provide 1-(2-bromo-4,6-diisopropylpyrimidin-5-yl)-6-chloro-7-(2-fluorophenyl)pyrido[2,3-d]pyrimidine-2,4(1H,3H)-dione (0.303 g, 0.569 mmol, 29.4% yield) as light yellow solid. m/z (ESI, +ve ion ion): 531.8/533.8 (M+H).

Step 4: 1-(2-amino-4,6-diisopropylpyrimidin-5-yl)-6-chloro-7-(2-fluorophenyl)pyrido[2,3-d]pyrimidine-2,4(1H,3H)-dione A mixture of 1-(2-bromo-4,6-diisopropylpyrimidin-5-yl)-(6-chloro-7-(2-fluorophenyl)pyrido[2,3-d]pyrimidine-2,4 (1H,3H)-dione (0.28 g, 0.526 mmol), copper (I) oxide (30 mg, 0.158 mmol), ammonium hydroxide (28.0-30%. $NH_3$ basis, 3.6 ml, 26.3 mmol) and methanol (3.5 mL) was heated at 70° C. for 19 hrs. The reaction mixture was concentrated in vacuo. The residue was taken up in EtOAc and saturated $NH_4Cl$. The separated organic layer was washed with water and brine, dried over $Na_2SO_4$ and then filtered. The crude product was purified by silica gel chromatography (eluent: 0-40% (EtOAc:EtOH)(3:1)/heptane) to provide 1-(2-amino-4,6-diisopropylpyrimidin-5-yl)-6-chloro-7-(2-fluorophenyl) pyrido[2,3-d]pyrimidine-2,4(1H,3H)-dione (0.164 g, 0.350 mmol, 66.6% yield) as white solid.

$^1H$ NMR (400 MHz, DMSO-$d_6$) δ ppm 0.86 (d, J=6.63 Hz, 6H) 1.02 (d, J=6.63 Hz, 6H) 2.68 (quin, J=6.69 Hz, 2H) 6.58 (s, 2H) 7.21 (td, J=7.52, 1.55 Hz, 1H) 7.28-7.35 (m, 2H) 7.48-7.56 (m, 1H) 8.54 (s, 1H) 12.15 (s, 1H). m/z (ESI, +ve ion ion): 469.0 (M+H).

Step 5: 1-(2-Amino-4,6-di(2-propanyl)-5-pyrimidinyl)-6-chloro-7-(2-fluorophenyl)-4-((2S)-2-methyl-4-(2-propenoyl)-1-piperazinyl)pyrido[2,3-d]pyrimidin-2(1H)-one Phosphoryl trichloride (0.035 mL, 0.371 mmol) was added to a mixture of 1-(2-amino-4,6-diisopropylpyrimidin-5-yl)-6-chloro-7-(2-fluorophenyl)pyrido[2,3-d]pyrimidine-2,4(1H,3H)-dione (0.087 g, 0.186 mmol) and DIPEA (0.1 mL, 0.557 mmol) in acetonitrile (5 ml). The reaction was heated at 80° C. for 30 min. Additional phosphoryl trichloride (0.035 mL, 0.371 mmol) was added and heating was continued for additional 15 min. The mixture was concentrated under reduced pressure to give 1-(2-amino-4,6-diisopropylpyrimidin-5-yl)-4,6-dichloro-7-(2-fluorophenyl) pyrido[2,3-d]pyrimidin-2(1H)-one as brown oil which was used in the next step without purification.

The crude product from the above reaction was dissolved in DMF (2 mL). DIPEA (0.097 ml, 0.557 mmol) and (S)-1-(3-methylpiperazin-1-yl)prop-2-en-1-one (TFA salt, Example 8-1, Step 6b, 0.132 g, 0.204 mmol). were added to the solution and the reaction mixture was stirred at RT for 1 hr. The reaction was quenched with water and the mixture was extracted with EtOAc. The organic extracts were washed with brine, dried over $Na_2SO_4$ and concentrated under reduced pressure. The crude product was purified by silica gel chromatography (0-50% EtOAc-EtOH (3:1)/heptane) to provide 1-(2-amino-4,6-di(2-propanyl)-5-pyrimidinyl)-6-chloro-7-(2-fluorophenyl)-4-((2S)-2-methyl-4-(2-propenoyl)-1-piperazinyl)pyrido[2,3-d]pyrimidin-2(1H)-one (0.057 g, 0.094 mmol, 50.8% yield) as yellow solid. $^1H$ NMR (400 MHz, DMSO-$d_6$) δ ppm 0.85 (br d, J=6.01 Hz, 6H) 1.00 (br d, J=6.01 Hz, 6H) 1.33 (br d, J=6.01 Hz, 3H) 3.01-3.26 (m, 2H) 3.42-3.85 (m, 3H) 3.98-4.47 (m, 3H) 4.94 (br s, 1H) 5.76 (br d, J=10.16 Hz, 1H) 6.21 (br d, J=1.00 Hz, 1H) 6.48 (br s, 2H) 6.77-6.96 (m, 1H) 7.18-7.26 (m, 1H) 7.27-7.41 (m, 2H) 7.49-7.59 (m, 1H) 8.43 (br s, 1H). m/z (ESI, +ve ion ion): 605.1 (M+H).

Example 140

6-Chloro-1-(4-(dimethylamino)-6-(2-propanyl)-5-pyrimidinyl)-7-(2-fluorophenyl)-4-((2S)-2-methyl-4-(2-propenoyl)-1-piperazinyl)pyrido[2,3-d]pyrimidin-2(1H)-one

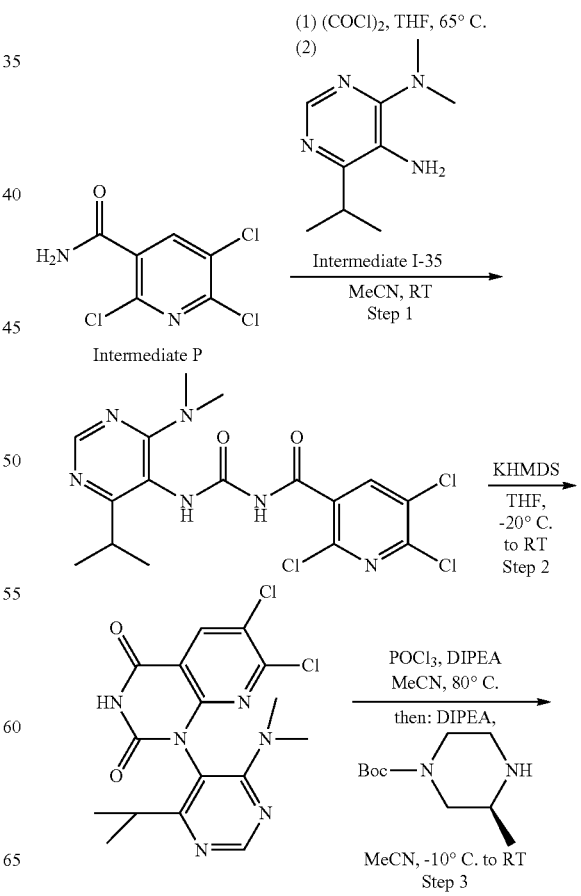

-continued

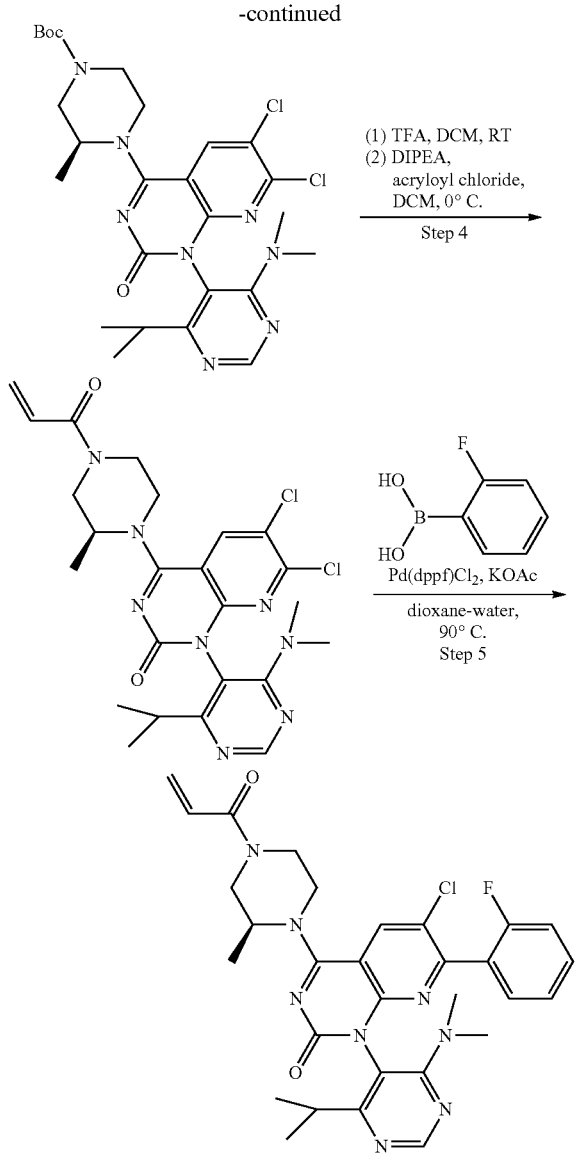

Step 1: 2,5,6-Trichloro-N-((4-(dimethylamino)-6-isopropylpyrimidin-5-yl)carbamoyl)nicotinamide Oxalyl chloride solution (2 M in DCM, 6.3 mL, 13 mmol) was added to a suspension of 2,5,6-trichloronicotinamide (Intermediate P, 2.7 g, 12 mmol) in THF (40 mL). The reaction mixture was heated at 65° C. After 4.5 h. the mixture was concentrated under reduced pressure. A solution of 6-isopropyl-N, $N^4$-dimethylpyrimidine-4,5-diamine (Intermediate I-35, 2.4 g, 13 mmol) in acetonitrile (40 mL) was added to the residue. And the resulting reaction mixture was stirred for 30 min at rt. The reaction mixture was concentrated under reduced pressure and the residue was purified by silica gel chromatography (eluent: 0-100% EtOAc/heptanes) to provide 2,5,6-trichloro-N-((4-(dimethylamino)-6-isopropylpyrimidin-5-yl)carbamoyl)nicotinamide. m/z (ESI, +ve ion ion): 430.9 (M+H)$^+$.

Step 2: 6,7-Dichloro-1-(4-(dimethylamino)-6-isopropylpyrimidin-5-yl)pyrido[2,3-d]pyrimidine-2,4 (1H,3H)-dione KHMDS (1 M in THF, 16 mL, 16 mmol) was added to a solution of 2,5,6-trichloro-N-((4-(dimethylamino)-6-isopropylpyrimidin-5-yl)carbamoyl)nicotinamide (2.7 g, 6.3 mmol) in THF (63 mL) at −20° C. After completed addition, the solution was allowed to warm to rt. After 2 h, the reaction mixture was quenched with saturated aqueous ammonium chloride (100 mL), then diluted with EtOAc (150 mL) and brine (50 mL). The layers were partitioned and the aqueous layer was extracted with EtOAc (1×50 mL). The combined organic extracts were dried over anhydrous magnesium sulfate, filtered, and then concentrated in vacuo. The crude product was purified by silica gel chromatography (eluent: 0-100% EtOAc-EtOH (3:1)/heptanes) to afford 6,7-dichloro-1-(4-(dimethylamino)-6-isopropylpyrimidin-5-yl) pyrido[2,3-d]pyrimidine-2,4(1H,3H)-dione. m/z (ESI, +ve ion ion): 395.0 (M+H)$^+$.

Step 3: tert-Butyl (S)-4-(6,7-dichloro-1-(4-(dimethylamino)-6-isopropylpyrimidin-5-yl)-2-oxo-1,2-dihydropyrido[2,3-d]pyrimidin-4-yl)-3-methylpiperazine-1-carboxylate DIPEA (0.2 mL, 1.3 mmol) and phosphorous oxychloride (0.11 mL, 1.2 mmol) were sequentially added to a solution of 6,7-dichloro-1-(4-(dimethylamino)-6-isopropylpyrimidin-5-yl)pyrido[2,3-d]pyrimidine-2,4(1H,3H)-dione (390 mg, 1.0 mmol) in acetonitrile (7 mL). After completed addition, the reaction mixture was heated at 80° C. for 1 h. The reaction mixture was cooled to −10° C. and DIPEA (0.34 mL, 2.0 mmol) was added, followed by the addition of a solution of (S)-4-Boc-2-methylpiperazine (590 mg, 3.0 mmol, Combi-Blocks, San Diego, Calif.) in acetonitrile (5.5 mL). The cold bath was removed and the reaction mixture was allowed to warm to room temperature. After 1 h. DIPEA (0.34 mL, 2.0 mmol) was added, followed by ice. The reaction mixture was diluted with EtOAc (50 mL) and the layers were partitioned. The aqueous phase was washed with EtOAc (50 mL) and then the combined organic extracts were washed with brine (200 mL), dried over anhydrous magnesium sulfate, filtered, and concentrated under reduced pressure. The crude product was purified by silica gel chromatography (eluent: 0-60% EtOAc-EtOH (3:1)/heptanes) to provide tert-butyl (S)-4-(6,7-dichloro-1-(4-(dimethylamino)-6-isopropylpyrimidin-5-yl)-2-oxo-1,2-dihydropyrido[2,3-d]pyrimidin-4-yl)-3-methylpiperazine-1-carboxylate. m/z (ESI, +ve ion ion): 577.0 (M+H)$^+$.

Step 4: (S-4-(4-Acryloyl-2-methylpiperazin-1-yl)-6,7-dichloro-1-(4-(dimethylamino)-6-isopropylpyrimidin-5-yl)pyrido[2,3-d]pyrimidin-2(1H)-one trifluoroacetic acid (1.5 mL, 20 mmol) was added to a solution of tert-butyl (S)-4-(6,7-dichloro-1-(4-(dimethylamino)-6-isopropylpyrimidin-5-yl)-2-oxo-1,2-dihydropyrido[2,3-d]pyrimidin-4-yl)-3-methylpiperazine-1-carboxylate (300 mg, 0.52 mmol) in DCM (3 mL) at rt. After 2.5 h, the reaction mixture was concentrated in vacuo and the residue was dissolved in DCM (6 mL). The solution was cooled to 0° C., and DIPEA (0.45 mL, 2.6 mmol) and acryloyl chloride (50 μL, 0.62 mmol) were added. The reaction mixture was stirred for 1.5 h at 0° C., and subsequently diluted with saturated aqueous sodium bicarbonate (40 mL) and DCM (40 mL). The layers were partitioned and the aqueous phase was extracted with DCM (2×50 mL). The combined organic extracts were dried over anhydrous magnesium sulfate, filtered, and concentrated to afford crude (S)-4-(4-acryloyl-2-methylpiperazin-1-yl)-6,7-dichloro-1-(4-(dimethylamino)-6-isopropylpyrimidin-5-yl)pyrido[2,3-d]pyrimidin-2(1H)-one. m/z (ESI, +ve ion ion): 531.0 (M+H)$^+$. The product was used in the next step without further purification Step 5: 6-Chloro-1-(4-(dimethylamino)-6-(2-propanyl)-5-pyrimidinyl)-7-(2-fluorophenyl)-4-((2S)-2-methyl-4-(2-propenoyl)-1-piperazinyl)pyrido[2,3-d]pyrimidin-2(1H)-one A mixture of (S)-4-(4-acryloyl-2-methylpiperazin-1-yl)-6,7-dichloro-1-(4-(dimethylamino)-6-isopropylpyrimidin-5-yl)pyrido[2,3-d]pyrimidin-2(1H)-one (280 mg, 0.52 mmol), 2-fluorophenylboronic acid (250 mg, 1.8 mmol, Combi-Blocks. San Diego, Calif., USA), Pd(dppf)Cl$_2$ (38 mg, 0.052 mmol), and potassium acetate (260 mg, 2.6 mmol) in 1,4-dioxane (2.5 mL) was purged with nitrogen. One drop of water was added and the reaction mixture was stirred at 90° C. for 15 h. The reaction mixture was cooled to rt, diluted with EtOAc (80 mL), and then sequentially washed with pH 7 buffer (75 mL), water (75 mL), and brine (75 mL). The organic phase was dried over anhydrous magnesium sulfate, filtered, and concentrated under reduced pressure. The residue was purified by silica gel chromatography (eluent: 0-75% EtOAc-EtOH (3:1)/heptanes) to afford 6-chloro-1-(4-(dimethylamino)-6-(2-propanyl)-5-pyrimidinyl)-7-(2-fluorophenyl)-4-((2S)-2-methyl-4-(2-propenoyl)-1-piperazinyl)pyrido[2,3-d]pyrimidin-2(1H)-one as a mixture of isomers. $^1$H NMR (400 MHz, DMSO-d$_6$) δ ppm 0.84-0.89 (m, 3H), 1.01 (d, J=6.6 Hz, 3H), 1.32 (d, J=6.6 Hz, 3H), 2.54 (br d, J=6.4 Hz, 1H), 2.84 (s, 6H), 3.02-3.29 (m, 1H), 3.40-3.83 (m, 2H), 4.07-4.49 (m, 3H), 4.94 (br s, 1H), 5.71-5.82 (m, 1H), 6.20 (br d, J=15.6 Hz, 1H), 6.76-6.93 (m, 1H), 7.22-7.38 (m, 3H), 7.50-7.60 (m, 1H), 8.43 (s, 1H), 8.48 (br s, 1H); $^{19}$F{H} NMR (376 MHz, DMSO-d$_6$) δ ppm −113.72 (s, 1F); m/z (ESI, +ve ion ion): 591.2 (M+H)$^+$.

Example 141

4-(6-Chloro-7-(2-fluorophenyl)-4-((2S)-2-methyl-4-(2-propenoyl)-1-piperazinyl)-2-oxopyrido[2,3-d]pyrimidin-1(2H)-yl)-3-methyl-5-(2-propanyl)benzoic acid

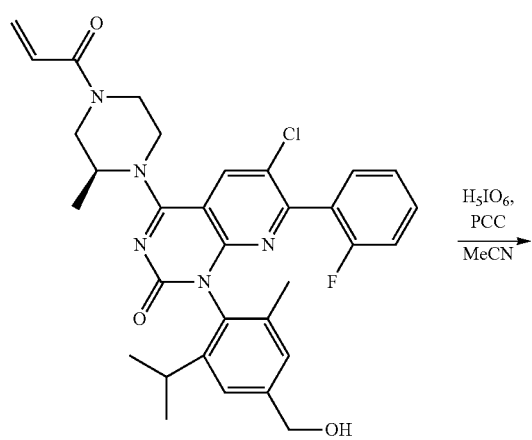

Intermediate 80A

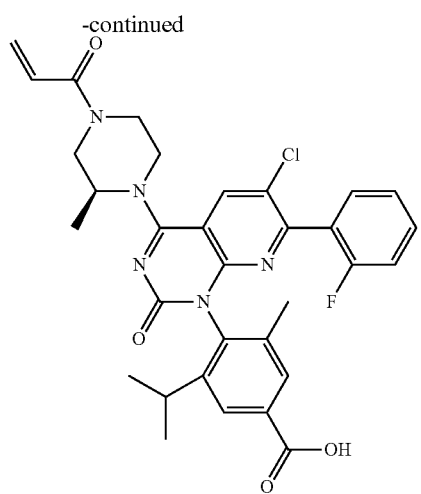

A solution of H$_5$IO$_6$ (0.3 mL, 1.403 mmol) in MeCN (10 mL) was stirred for 15 min, followed by addition of (S)-4-(4-acryloyl-2-methylpiperazin-1-yl)-6-chloro-7-(2-fluorophenyl)-1-(4-(hydroxymethyl)-2-isopropyl-6-methylphenyl)pyrido[2,3-d]pyrimidin-2(1H)-one (Intermediate 80A, 376.4 mg, 0.638 mmol). The reaction mixture was cooled to 0° C. and pyridinium chlorochromate (21 mg, 0.1 mmol, Sigma-Aldrich Corporation, St. Louis, Mo., USA) was added. Stirring was continued for 3 h at 0° C., and for 16 h at rt. The reaction mixture was quenched by the addition of water and neutralized with saturated aqueous NaHCO$_3$. The mixture was extracted with DCM (3×). The combined extracts were dried over Na$_2$SO$_4$, concentrated under reduced pressure. The crude product was purified by silica gel chromatography (0-100% EtOAc/EtOH/Heptane) to give 4-(6-chloro-7-(2-fluorophenyl)-4-((2S)-2-methyl-4-(2-propenoyl)-1-piperazinyl)-2-oxopyrido[2,3-d]pyrimidin-1(2H)-yl)-3-methyl-5-(2-propanyl)benzoic acid. $^1$H NMR (DMSO-d$_6$) δ: 12.68-13.20 (m, 1H), 8.46 (br d, J=4.6 Hz, 1H), 7.66-7.81 (m, 2H), 7.47-7.53 (m, 1H), 7.18-7.32 (m, 3H), 6.77-6.94 (m, 1H), 6.21 (br d, J=16.8 Hz, 1H), 5.70-5.82 (m, 1H), 4.95 (br s, 1H), 4.11-4.47 (m, 3H), 4.03 (q, J=7.0 Hz, 1H), 3.43-3.84 (m, 2H), 3.04-3.19 (m, 1H), 2.55-2.64 (m, 1H), 1.95 (s, 3H), 1.34 (d, J=6.6 Hz, 3H), 1.08 (d, J=6.8 Hz, 3H), 0.96 (dd, J=6.7, 2.0 Hz, 3H). $^{19}$F NMR (376.5 MHz, DMSO-d$_6$) δ: −114.11 (d, J=11.3 Hz, 1F). m/z (ESI, +ve ion) 604.0 (M+H)$^+$.

Example 142-1 and 142-2

2-(6-Chloro-7-(2-fluorophenyl)-4-((2S)-2-methyl-4-(2-propenoyl)-1-piperazinyl)-2-oxopyrido[2,3-d]pyrimidin-1(2H)-yl)-3-(2-propanyl)benzamide

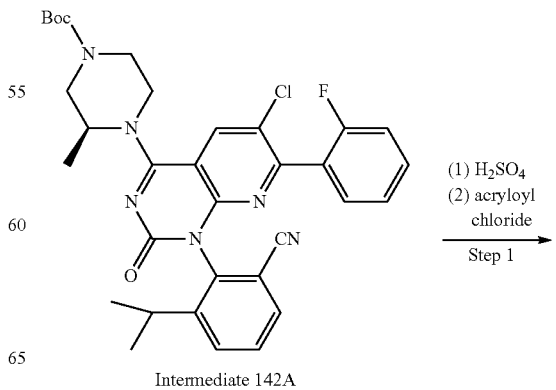

Intermediate 142A

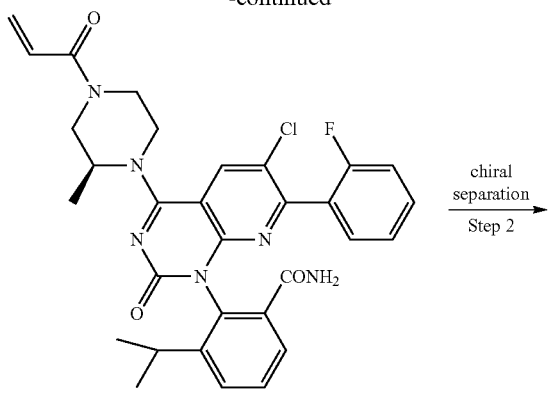

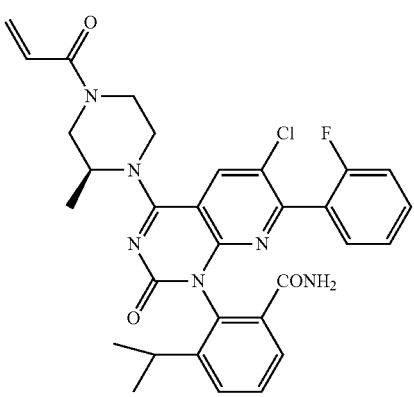

Example 142-1
(1st-eluting isomer)

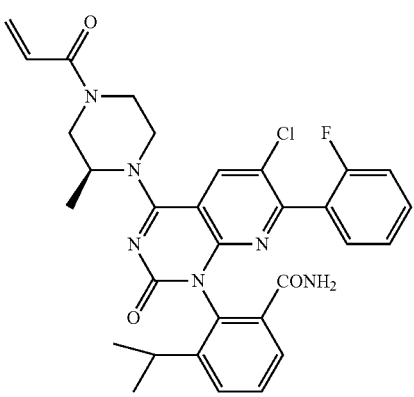

Example 142-2
(2nd-eluting isomer)

Step 1: 2-(6-Chloro-7-(2-fluorophenyl)-4-((2S)-2-methyl-4-(2-propenoyl)-1-piperazinyl)-2-oxopyrido[2,3-d]pyrimidin-(2H)-yl)-3-(2-propanyl)benzamide A suspension tert-butyl (S)-4-(6-chloro-1-(2-cyano-6-isopropylphenyl)-7-(2-fluorophenyl)-2-oxo-1,2-dihydropyrido[2,3-d]pyrimidin-4-yl)-3-methylpiperazine-1-carboxylate (Intermediate 142A prepared according to Method 54, 500 mg, 0.810 mmol, using commercial 2-amino-3-isopropyl-benzonitrile (1.0 g; 6.3 mmol: Enamine, Monmouth Jct., N.J., USA)) in sulfuric acid (1.7 mL, 32.4 mmol) was stirred at rt for 24 h. The reaction mixture added dropwise onto a mixture of ice (200 mL) and DCM (50 mL). Potassium phosphate dibasic (7.0 g, 41 mmol) was added to the mixture, followed by 1 M NaOH (50 mL). The organic was separated, and the aqueous layer was further extracted with DCM (50 mL). The combined organic extracts were dried over MgSO$_4$, and concentrated under reduced pressure. The residue was taken up in DCM (10 mL) and DIPEA (283 μL, 1.620 mmol) was added. The solution was cooled to 0° C., followed by the addition of a solution of acryloyl chloride (33 μL, 0.41 mmol) in DCM (1 mL). After 10 min, the reaction mixture was quenched with sat. NaHCO$_3$ (5 mL). The organic layer was separated, dried over MgSO$_4$, and concentrated under reduced pressure. The crude residue was purified by silica gel chromatography (eluent: 0-70% EtOAc-EtOH (3:1)/heptane) to provide 2-(6-chloro-7-(2-fluorophenyl)-4-((2S)-2-methyl-4-(2-propenoyl)-1-piperazinyl)-2-oxopyrido[2,3-d]pyrimidin-1(2H)-yl)-3-(2-propanyl)benzamide.

Step 2: 2-(6-Chloro-7-(2-fluorophenyl)-4-((2S)-2-methyl-4-(2-propenoyl)-1-piperazinyl)-2-oxopyrido[2,3-d]pyrimidin-1(2H)-yl)-3-(2-propanyl)benzamide The mixture of atropisomers was purified by NPLC (Chiralcel OX—H (21×250 mm, 5 um), 35% isocratic MeOH:EtOH):1)/heptane, 35 mL/min to afford two fractions:

Example 142-1 (1st-Eluting Isomer 2-(6-chloro-7-(2-fluorophenyl)-4-((2S)-2-methyl-4-(2-propenoyl)-1-piperazinyl)-2-oxopyrido[2,3-d]pyrimidin-1(2H)-yl)-3-(2-propanyl)benzamide. $^1$H NMR (400 MHz, DMSO-dc) δ 8.29-8.37 (m, 1H), 7.38-7.49 (m, 4H), 7.34 (dd, J=7.88, 15.34 Hz, 1H), 7.10-7.25 (m, 3H), 6.95 (br s, 1H), 6.71-6.86 (m, 1H), 6.14 (d, J=15.34 Hz, 1H), 5.69 (dd, J=2.07, 10.37 Hz, 1H), 4.79-4.94 (m, 1H), 3.90-4.40 (m, 3H), 3.28-3.78 (m, 2H), 2.92-3.19 (m, 1H), 2.62-2.74 (m, 1H), 1.23 (d, J=6.43 Hz, 3H), 1.02 (d, J=6.84 Hz, 3H), 0.91 (d, J=7.05 Hz, 3H). m/z (ESI, +ve ion) M+1=589.3.

Example 142-2 (2nd-Eluting Isomer)

2-(6-chloro-7-(2-fluorophenyl)-4-((2S)-2-methyl-4-(2-propenoyl)-1-piperazinyl)-2-oxopyrido[2,3-d]pyrimidin-1(2H)-yl)-3-(2-propanyl)benzamide. $^1$H NMR (400 MHz, DMSO-d$_6$) δ 8.38 (d, J=6.22 Hz, 1H), 7.45-7.58 (m, 4H), 7.41 (t, J=13.70 Hz, 1H), 7.19-7.32 (m, 3H), 7.03 (s, 1H), 6.78-6.94 (m, 1H), 6.21 (dd, J=6.43, 16.59 Hz, 1H), 5.76 (d, J=10.37 Hz, 1H), 4.76-4.90 (m, 1H), 4.26-4.49 (m, 1H), 3.98-4.25 (m, 2H), 3.38-3.76 (m, 2H), 2.99-3.30 (m, 1H), 2.64-2.79 (m, 1H), 1.30 (d, J=6.63 Hz, 3H), 0.96-1.16 (m, 6H). $^{19}$F NMR (376 MHz, DMSO-d$_6$) δ −113.26 (s, 1F). $^{19}$F NMR (376 MHz, DMSO-d$_6$) δ −113.21 (s, 1F). m/z (ESI, +ve ion) M+1=589.3.

Example 143

7-(2-Fluorophenyl)-6-methyl-1-(4-methyl-2-(2-propanyl)-3-pyridinyl)-4-((2S)-2-methyl-4-(2-propenoyl)-1-piperazinyl)-2(1H)-pteridinone

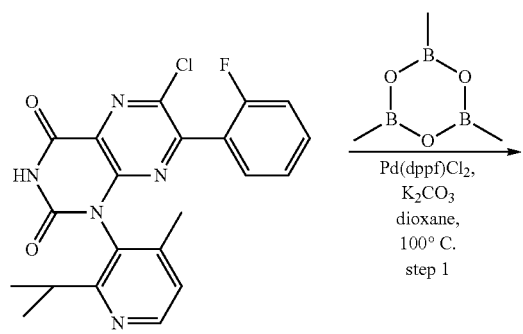

Intermediate 111A

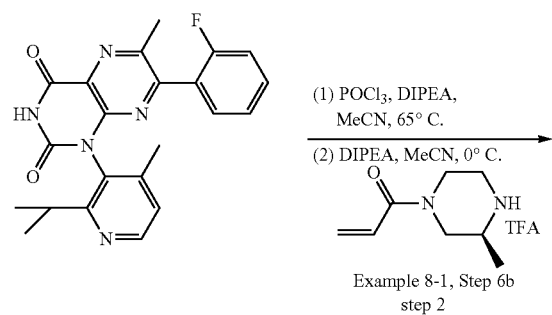

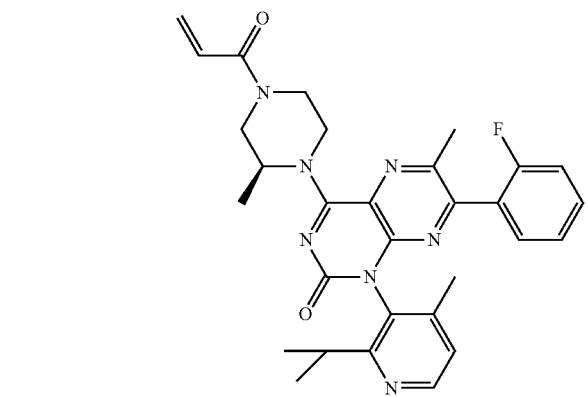

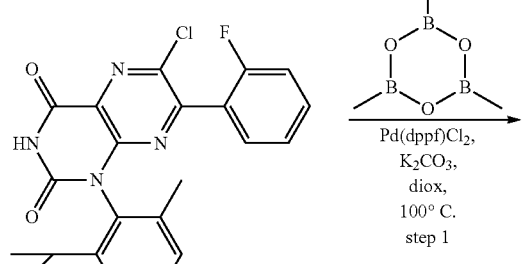

Intermediate 111A

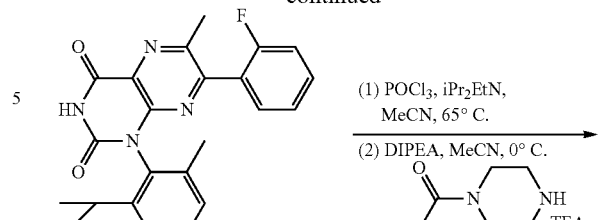

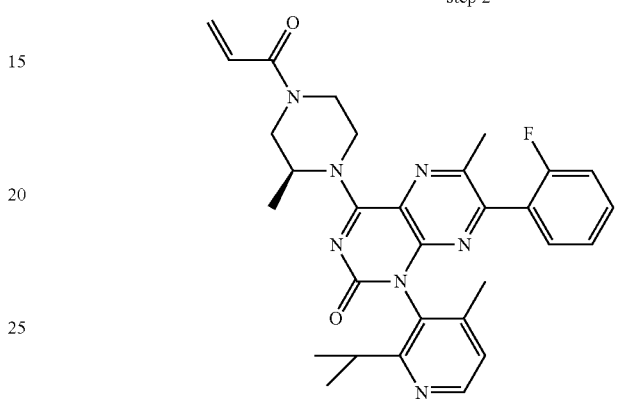

Step 1: 7-(2-Fluorophenyl)-1-(2-isopropyl-4-methylpyridin-3-yl)-6-methylpteridine-2,4(1H,3H)-dione A mixture of 6-chloro-7-(2-fluorophenyl)-1-(2-isopropyl-4-methylpyridin-3-yl)pteridine-2,4(1H,3H)-dione (Intermediate 111A, 0.50 g, 1.17 mmol), potassium carbonate (0.324 g, 2.34 mmol), [1,1'-bis(diphenylphosphino)ferrocene]-dichloropalladium (II) (86 mg, 0.12 mmol) and trimethylboroxine (0.3 mL, 2.34 mmol, Sigma-Aldrich, Inc., St. Louis, Mo.) in dioxane (5 mL) and water (0.5 mL) was heated in a microwave to 100° C. for 1.5 h. The reaction mixture was diluted with EtOAc (10 mL), then washed with water and brine. The organic layer was dried over anhydrous sodium sulfate, filtered and concentrated under reduced pressure. The crude product was purified by silica gel chromatography (eluent: 0-70% EtOAc-EtOH (3:1)/heptane) to provide 7-(2-fluorophenyl)-1-(2-isopropyl-4-methylpyridin-3-yl)-6-methylpteridine-2,4(1H,3H)-dione. m/z (ESI, +ve ion ion): 406.0 (M+H)$^+$.

Step 2: 7-(2-Fluorophenyl)-6-methyl-1-(4-methyl-2-(2-propanyl)-3-pyridinyl)-4-((2S)-2-methyl-4-(2-propenoyl)-1-piperazinyl)-2(1H)-pteridinone phosphorus oxychloride (0.09 mL, 0.94 mmol) was added to a mixture of 7-(2-fluorophenyl)-1-(2-isopropyl-4-methylpyridin-3-yl)-6-methylpteridine-2,4(1H,3H)-dione (0.254 g, 0.63 mmol), and DIPEA (0.1 mL, 1.06 mmol) in acetonitrile (5 mL). The reaction mixture was heated to 65° C. for 30 min, then cooled to room temperature and concentrated under reduced pressure. The residue was dissolved in acetonitrile (5 mL) and the solution was cooled to 0° C. DIPEA (0.4 mL, 2.52 mmol), and a solution of (S)-1-(3-methylpiperazin-1-yl)prop-2-en-1-one (TFA salt, Example 8-1, Step 6b, 0.52 mg, 0.75 mmol) in acetonitrile (0.5 mL) were added. The resulting reaction mixture was stirred at rt for 1 h and then was diluted with EtOAc (10 mL). The mixture was washed with water and brine. The organic layer was separated, dried over anhydrous sodium sulfate, and concentrated under reduced pressure. The residue was purified by silica gel chromatography (eluent: 0-60% 3:1 EtOAc-EtOH/heptane) to provide 7-(2-fluorophenyl)-6-methyl-1-(4-methyl-2-(2-propanyl)-3-pyridinyl)-4-((2S)-2-methyl-4-(2-propenoyl)-1-piperazinyl)-2(1H)-pteridinone.
$^1$H NMR (400 MHz, DMSO-d$_6$) δ 8.41 (d, J=4.8 Hz, 1H), 7.47-7.60 (m, 1H), 7.26-7.38 (m, 3H), 7.20 (d, J=5.0 Hz, 1H), 6.81-6.95 (m, 1H), 6.21 (br d, J=16.8 Hz, 1H), 5.76 (dd, J=10.6, 1.9 Hz, 1H), 4.61-5.43 (m, 1H), 3.49-4.47 (m, 4H), 2.68-2.88 (m, 1H), 2.45 (d, J=0.6 Hz, 3H), 1.95 (br d, J=14.5 Hz, 3H), 1.34-1.56 (m, 2H), 1.22-1.51 (m, 3H), 1.07 (t, J=6.1 Hz, 3H), 0.94 (dd, J=6.8, 1.4 Hz, 3H). m/z (ESI, +ve ion ion): 542.2 (M+H)$^+$.

Example 144

3-Chloro-2-(2-fluorophenyl)-7-methyl-N,N-di(2-propanyl)-5-(4-(2-propenoyl)-1-piperazinyl)-1,6-naphthyridine-8-carboxamide

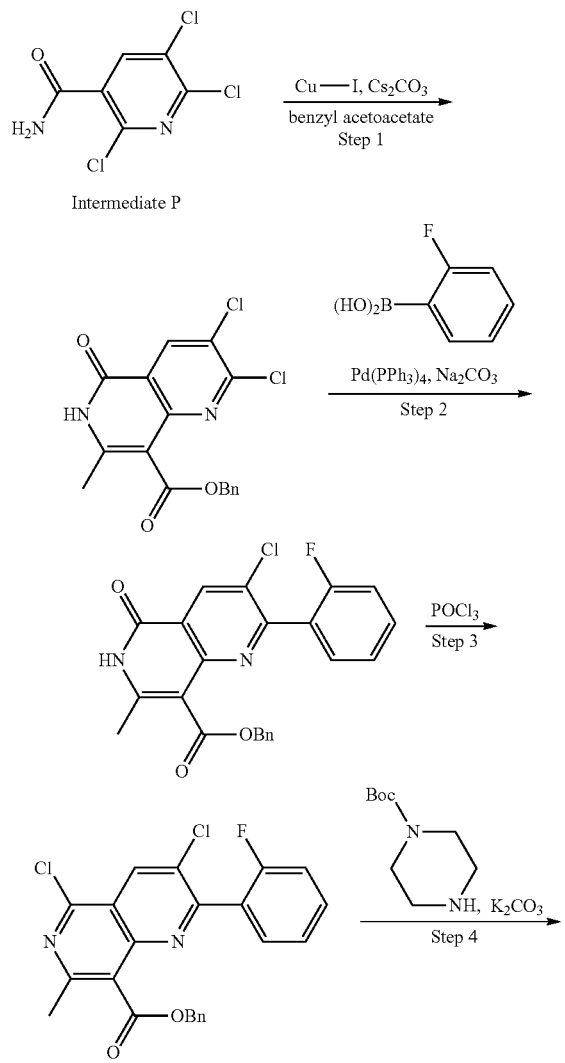

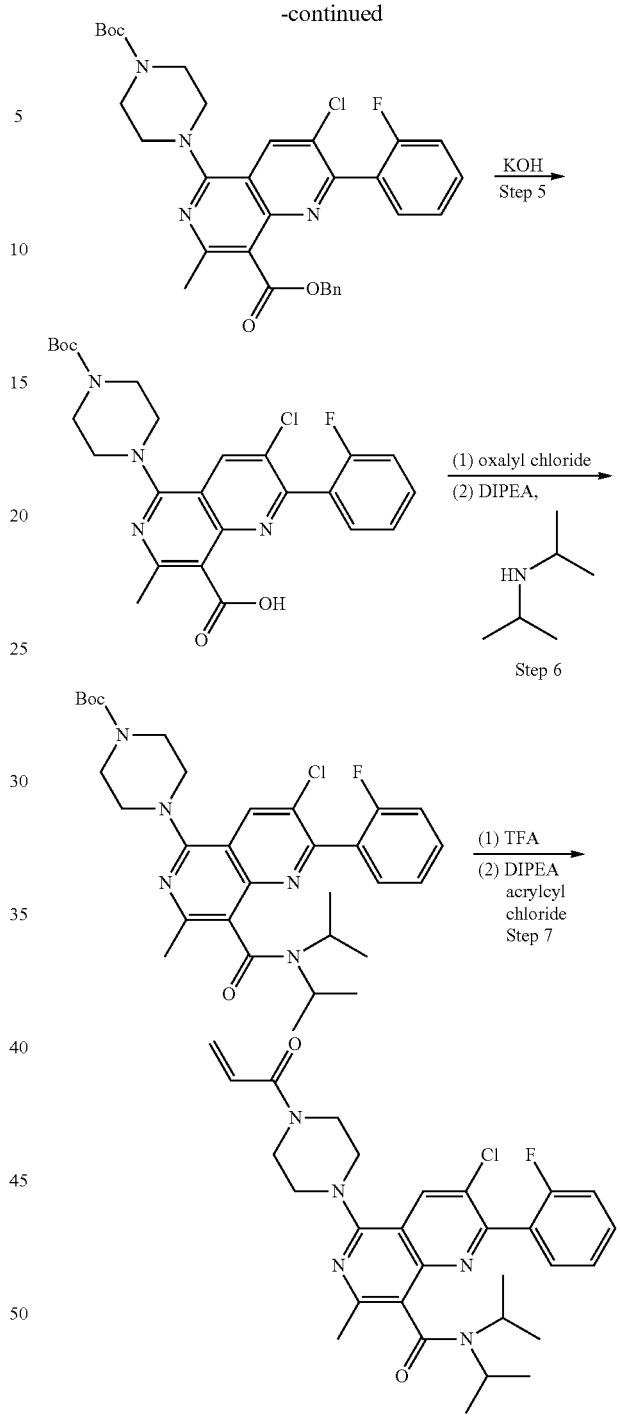

Step 1: Benzyl 2,3-dichloro-7-methyl-5-oxo-5,6-dihydro-1,6-naphthyridine-8-carboxylate A mixture of 2,5,6-trichloronicotinamide (Intermediate P, 4.0 g, 17.74 mmol), copper(I) iodide (337 mg, 1.774 mmol) and cesium carbonate (11.56 g, 35.5 mmol) was purged with nitrogen for 5 min, followed by the addition of 1,4-dioxane (89 mL) and benzyl acetoacetate (4.6 mL, 26.6 mmol). The reaction mixture was heated to 80° C. overnight. The reaction mixture was cooled to rt and quenched with a 9:1 mixture of sat. NH$_4$Cl/NH$_4$OH. The aqueous layer was extracted with EtOAc. The combined organic layers were dried over MgSO$_4$, and concentrated in vacuo. The crude product was purified by silica gel chromatography (eluent: 0-5% MeOH/DCM) to provide benzyl 2,3-dichloro-7-methyl-5-oxo-5,6-dihydro-1,6-naphthyridine-8-carboxylate (2.51 g, 6.91 mmol, 39.0% yield) as a brown solid. m/z (ESI, +ve ion): 363.0 (M+H)$^+$.

Step 2: Benzyl 3-chloro-2-(2-fluorophenyl)-7-methyl-5-oxo-5,6-dihydro-1,6-naphthyridine-8-carboxylate A mixture of benzyl 2,3-dichloro-7-methyl-5-oxo-5,6-dihydro-1,6-naphthyridine-8-carboxylate (2.50 g, 6.88 mmol), (2-fluorophenyl)boranediol (1.25 g, 8.95 mmol, Combi-Blocks Inc., San Diego, Calif. 3371495), palladium tetrakis (0.79 g, 0.688 mmol) and sodium carbonate (2.19 g, 20.65 mmol) in 1,4-dioxane/water (30/7.5 mL) was heated at 85° C. for 45 min. The reaction mixture was quenched with sat. NaHCO$_3$ and extracted with EtOAc. The combined organic extracts were dried over MgSO$_4$, filtered and concentrated in vacuo. The crude product was purified by silica gel chromatography (eluent: 0-5% MeOH/DCM) to provide benzyl 3-chloro-2-(2-fluorophenyl)-7-methyl-5-oxo-5,6-dihydro-1,6-naphthyridine-8-carboxylate (2.0 g, 4.73 mmol, 68.7% yield) as an orange solid. m/z (ESI, +ve ion): 423.0 (M+H)$^+$.

Step 3: Benzyl 3,5-dichloro-2-(2-fluorophenyl)-7-methyl-1,6-naphthyridine-8-carboxylate A solution of benzyl 3-chloro-2-(2-fluorophenyl)-7-methyl-5-oxo-5,6-dihydro-1,6-naphthyridine-8-carboxylate (2.0 g, 4.73 mmol) and POCl$_3$ (10 mL, 107 mmol) was heated at 90° C. for 1 h. The reaction mixture was concentrated in vacuo. The residue was diluted with EtOAc, washed with sat. NaHCO$_3$ and brine. The combined organic extracts were dried over MgSO$_4$, filtered and concentrated in vacuo. The crude residue was purified by silica gel chromatography (eluent: 0-50% EtOAc/heptane) to provide benzyl 3,5-dichloro-2-(2-fluorophenyl)-7-methyl-1,6-naphthyridine-8-carboxylate (1.20 g, 2.72 mmol, 57.5% yield) as an orange solid. m/z (ESI, +ve ion): 441.0 (M+H)$^+$.

Step 4: Benzyl 5-(4-(tert-butoxycarbonyl)piperazin-1-yl)-3-chloro-2-(2-fluorophenyl)-7-methyl-1,6-naphthyridine-8-carboxylate A mixture of benzyl 3,5-dichloro-2-(2-fluorophenyl)-7-methyl-1,6-naphthyridine-8-carboxylate (0.400 g, 0.906 mmol), tert-butyl piperazine-1-carboxylate (0.506 g, 2.72 mmol), potassium carbonate (0.501 g, 3.63 mmol) and sodium sulfate (1.287 g, 9.06 mmol) in CH$_3$CN (12 mL) was heated at 85° C. for 2 h. The reaction mixture was cooled to rt, washed with water and extracted with EtOAc. The organic phase was concentrated under reduced pressure to afford benzyl 5-(4-(tert-butoxycarbonyl)piperazin-1-yl)-3-chloro-2-(2-fluorophenyl)-7-methyl-1,6-naphthyridine-8-carboxylate (0.501 g, 0.848 mmol, 94% yield)—to be used as is. m/z (ESI, +ve ion): 591.2 (M+H)$^+$.

Step 5: 5-(4-(tert-Butoxycarbonyl)piperazin-1-yl)-3-chloro-2-(2-fluorophenyl)-7-methyl-1,6-naphthyridine-8-carboxylic acid To a solution of benzyl 5-(4-(tert-butoxycarbonyl)piperazin-1-yl)-3-chloro-2-(2-fluorophenyl)-7-methyl-1,6-naphthyridine-8-carboxylate (0.015 g, 0.025 mmol) in EtOH (3 mL) was added KOH (0.014 g, 0.254 mmol) and the reaction mixture was heated at 80° C. for 30 min. The reaction mixture was cooled to rt, acidified with 5 N HCl and extracted with DCM. The combined organic layers were dried over Na$_2$SO$_4$, filtered, and concentrated in vacuo, to afford 5-(4-(tert-butoxycarbonyl)piperazin-1-yl)-3-chloro-2-(2-fluorophenyl)-7-methyl-1,6-naphthyridine-8-carboxylic acid (0.009 g, 0.018 mmol, 70.8% yield) as a bright yellow oil—to be used as is. m/z (ESI, +ve ion): 501.0 (M+H)$^+$.

Step 6: tert-Butyl 4-(3-chloro-8-(diisopropylcarbamoyl)-2-(2-fluorophenyl)-7-methyl-1,6-naphthyridin-5-yl)piperazine-1-carboxylate Oxalyl chloride (2 M in DCM, 0.02 mL, 0.051 mmol) and a cat. amount of DMF were added to a solution of 5-(4-(tert-butoxycarbonyl)piperazin-1-yl)-3-chloro-2-(2-fluorophenyl)-7-methyl-1,6-naphthyridine-8-carboxylic acid (0.009 g, 0.018 mmol, 70.8% yield) in DCM (3 mL). The resulting reaction mixture was stirred at rt. After 1 h, the reaction mixture was concentrated in vacuo. The residue was taken up in THF (3 mL) and (N-(l-methylethyl)-2)propanamine (5 µL, 0.05 mmol), and DIPEA (4 µL, 0.025 mmol) were added. The reaction mixture was stirred for 40 min, washed with sat. NaHCO$_3$, sat. NH$_4$Cl and extracted with EtOAc. The combined organic extracts were dried over MgSO$_4$, filtered and concentrated in vacuo. The crude residue was purified by RP-HPLC to afford tert-butyl 4-(3-chloro-8-(diisopropylcarbamoyl)-2-(2-fluorophenyl)-7-methyl-1,6-naphthyridin-5-yl)piperazine-1-carboxylate (0.005 g, 8.56 µmol, 33.7% yield) as a yellow solid. m/z (ESI, +ve ion): 584.2 (M+H)$^+$.

Step 7: 3-Chloro-2-(2-fluorophenyl)-7-methyl-N,N-di(2-propanyl)-5-(4-(2-propenoyl)-1-piperazinyl)-1,6-naphthyridine-8-carboxamide TFA (1.0 mL, 12.98 mmol) was added to a solution of tert-butyl 4-(3-chloro-8-(diisopropylcarbamoyl)-2-(2-fluorophenyl)-7-methyl-1,6-naphthyridin-5-yl)piperazine-1-carboxylate (0.005 g, 8.56 µmol) in DCM (1 mL). The resulting mixture was stirred at rt for 15 min. The reaction mixture was concentrated in vacuo, to afford 3-chloro-2-(2-fluorophenyl)-N,N-diisopropyl-7-methyl-5-(piperazin-1-yl)-1,6-naphthyridine-8-carboxamide—to be used as is. m/z (ESI, +ve ion): 484.2 (M+H)$^+$.

DIPEA (6 µl, 0.034 mmol) and acryloyl chloride (0.7 µL, 8.56 µmol) were added to a solution of 3-chloro-2-(2-fluorophenyl)-N,N-diisopropyl-7-methyl-5-(piperazin-1-yl)-1,6-naphthyridine-8-carboxamide in DCM (2 mL). The resulting mixture was stirred at rt for 20 min. The reaction mixture was washed with sat. NaHCO$_3$, sat. NH$_4$Cl and extracted with DCM. The combined organic layers were dried over Na$_2$SO$_4$, filtered and concentrated in vacuo. The crude product was purified by silica gel chromatography (eluent: 0-50% EtOAc-EtOH (3:1)/heptane) to provide 3-chloro-2-(2-fluorophenyl)-7-methyl-N,N-di(2-propanyl)-5-(4-(2-propenoyl)-1-piperazinyl)-1,6-naphthyridine-8-carboxamide (0.0025 g, 4.65 µmol, 54.3% yield). $^1$H NMR (DMSO-d$_6$) &: 8.52-8.71 (m, 1H), 7.57-7.67 (m, 1H), 7.48-7.56 (m, 1H), 7.35-7.45 (m, 2H), 6.82-6.92 (m, 1H), 6.12-6.22 (m, 1H), 5.71-5.75 (m, 1H), 3.77-3.91 (m, 4H), 3.48-3.53 (m, 5H), 2.44-2.46 (m, 4H), 1.45-1.53 (m, 3H), 1.34-1.42 (m, 3H), 1.02-1.09 (m, 3H), 0.88-0.97 (m, 3H). m/z (ESI, +ve ion): 538.2 (M+H)⁺.

Example 145

(M)-4-((2S)-4-((2E)-4-(Dimethylamino)-2-butenoyl)-2-methyl-piperazinyl)-6-fluoro-7-(2-fluoro-6-hydroxyphenyl)-1-(4-methyl-2-(2-propanyl)-3-pyridinyl)pyrido[2,3-d]pyrimidin-2(1H)-one

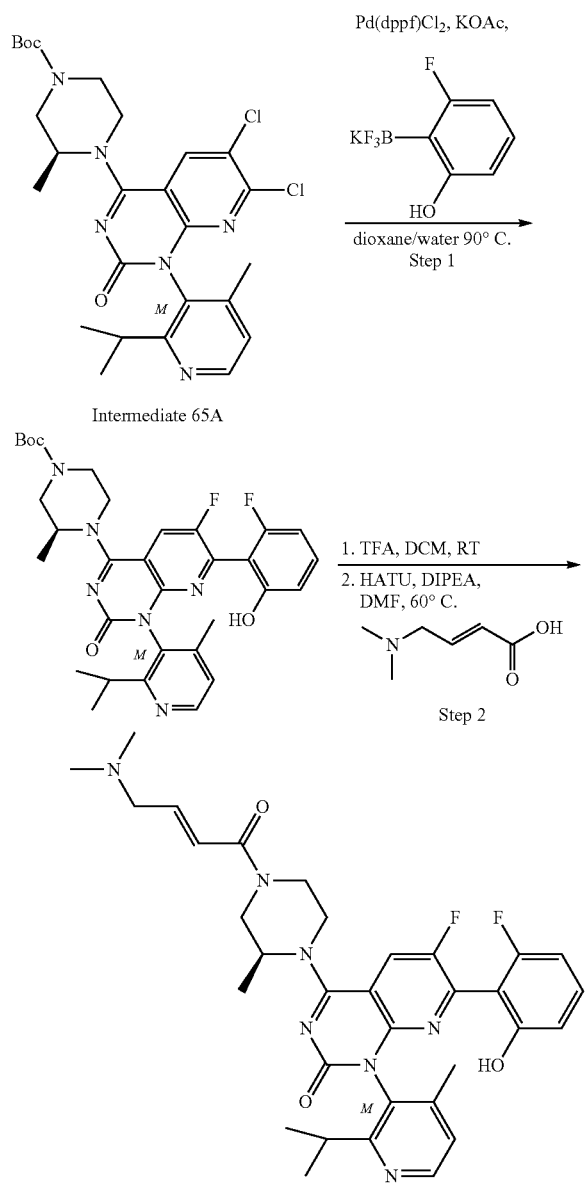

Step 1: tert-Butyl (M)-(3S)-4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate A mixture of tert-butyl (M)-(S)-4-(7-chloro-6-fluoro-1-(2-isopropyl-4-methylpyridin-3-yl)-2-oxo-1,2-dihydropyrido[2,3-d]pyrimidin-4-yl)-3-methylpiperazine-1-carboxylate (Intermediate 65A, 4.3 g, 8.10 mmol), potassium trifluoro(2-fluoro-6-hydroxyphenyl)borate (2.87 g, 10.53 mmol, Wuxi, Shanghai, China), potassium acetate (3.18 g, 32.4 mmol), and [1,1'-bis(diphenylphosphino)ferrocene]dichloropalladium(II) (0.661 g, 0.810 mmol) in 1,4-dioxane (80 mL) was purged with nitrogen for 1 min. Degassed water (14 mL) was added and the resulting mixture was heated to 90° C. for 1 h. The reaction mixture was quenched with saturated NaHCO₃ solution, diluted with water, and extracted with EtOAc (2×) and DCM. The combined organic extracts were dried over MgSO₄, and concentrated in vacuo. The crude product was purified by silica gel chromatography (eluent: 0-60% EtOAc-EtOH (3:1)/heptane) to provide tert-butyl (M)-(3S)-4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate (4.52 g, 7.45 mmol, 92% yield). ¹H NMR (400 MHz, DMSO-d₆) δ: 10.19 (br s, 1H), 8.38 (d, J=4.98 Hz, 1H), 8.26 (dd, J=9.23, 12.54 Hz, 1H), 7.23-7.28 (m, 1H), 7.18 (d, J=5.01 Hz, 1H), 6.72 (d, J=7.98 Hz, 1H), 6.68 (t, J=8.94 Hz, 1H), 4.77-4.98 (m, 1H), 4.24 (br t, J=14.20 Hz, 1H), 3.93-4.08 (m, 1H), 3.84 (br d, J=12.85 Hz, 1H), 3.52-3.75 (m, 1H), 3.07-3.28 (m, 1H), 2.62-2.74 (m, 1H), 1.86-1.93 (m, 3H), 1.43-1.48 (m, 9H), 1.35 (dd, J=6.84, 10.78 Hz, 3H), 1.26-1.32 (m, 1H), 1.07 (dd, J=1.66, 6.63 Hz, 3H), 0.93 (dd, J=2.07, 6.63 Hz, 3H). ¹⁹F NMR (376 MHz, DMSO-d₆) δ: −115.65 (s, 1F), −128.62 (s, 1F). m/z (ESI, +ve ion): 607.3 (M+H)⁺.

Step 2: (M)-4-((2S)-4-((2E)-(Dimethylamino)-2-butenoyl)-2-methyl-1-piperazinyl)-6-fluoro-7-(2-fluoro-6-hydroxyphenyl)-1-(4-methyl-2-(2-propanyl)-3-pyridinyl)pyrido[2,3-d]pyrimidin-2(1H)-one A solution of tert-butyl (M)-(3S)-4-(6-fluoro-7-(2-fluoro-6-hydroxyphenyl)-1-(2-isopropyl-4-methylpyridin-3-yl)-2-oxo-1,2-dihydropyrido[2,3-d]pyrimidin-4-yl)-3-methylpiperazine-1-carboxylate (0.320 g, 0.527 mmol) and trifluoroacetic acid (2 mL, 26.4 mmol) in dichloromethane (5 mL) was stirred at rt for 1 h. The reaction mixture was concentrated in vacuo. The residue was taken up in in DMF (5 mL) and trans-4-dimethylaminocrotonic acid hydrochloride (0.114 g, 0.686 mmol), [(dimethylamino)(([1,2,3]triazolo[4,5-b]pyridin-3-yloxy))methylidene]dimethylazanium hexafluorophosphate (0.6 g, 1.582 mmol), and N,N-diisopropylethylamine (0.6 mL, 3.2 mmol) were added. After 12 h, additional portions of trans-4-dimethylaminocrotonic acid hydrochloride (0.11 g, 0.69 mmol, Small Molecules, Inc., Jackson Street, Hoboken, N.J.), [(dimethylamino)(([1,2,3]triazolo[4,5-b]pyridin-3-yloxy))methylidene]dimethylazanium hexafluorophosphate (0.60 g, 1.6 mmol) and N,N-diisopropylethylamine (0.60 mL, 3.2 mmol) were added The reaction mixture was heated to 60° C. for an additional 12 h. The reaction mixture was diluted with saturated NaHCO₃ and water. The aqueous layer was extracted with EtOAc, and DCM. The organic layers were combined, dried over MgSO₄, and concentrated in vacuo. The crude residue was purified by silica gel chromatography (eluent: 0-15% MeOH/DCM) to provide the (M)-4-((2S)-4-((2E)-4-(dimethylamino)-2-butenoyl)-2-methyl-1-piperazinyl)-6-fluoro-7-(2-fluoro-6-hydroxyphenyl)-1-(4-methyl-2-(2-propanyl)-3-pyridinyl)pyrido[2,3-d]pyrimidin-2(1H)-one (0.20 g, 0.33 mmol, 62% yield). ¹H NMR (400 MHz, DMSO-d₆) δ 10.20 (br s, 1H), 8.39 (d, J=4.98 Hz, 1H), 8.24-8.33 (m, 1H), 7.23-7.31 (m, 1H), 7.19 (d, J=4.98 Hz, 1H), 6.62-6.76 (m, 4H), 4.91 (br s, 1H), 4.21-4.44 (m, 2H), 3.90-4.19 (m, 1H), 3.43-3.79 (m, 2H), 3.13-3.27 (m, 1H), 3.09 (br d, J=4.56 Hz, 2H), 2.67-2.76 (m, 1H), 2.19 (s, 6H), 1.90 (s, 3H), 1.35 (d, J=6.63 Hz, 3H), 1.08 (d, J=6.63 Hz, 3H), 0.94 (d, J=6.63 Hz, 3H). $^{19}$F NMR (376 MHz, DMSO-$d_6$) δ −115.63 (s, 1F), −128.63 (s, 1F). m/z (ESI, +ve ion): 618.3 (M+H)$^+$.

Example 146

3-Chloro-2-(2-fluorophenyl)-8-(2-(2-propanyl)phenyl)-5-(4-(2-propenoyl)-1-piperazinyl)-1,6-naphthyridine-7-carbonitrile

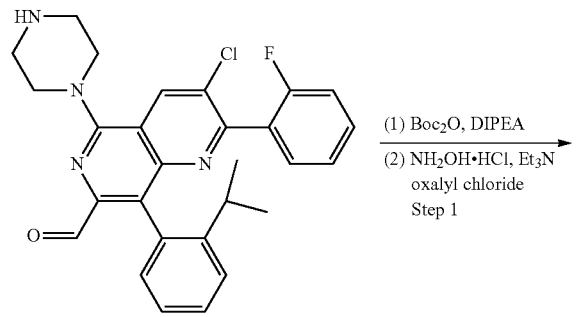

Intermediate 146A

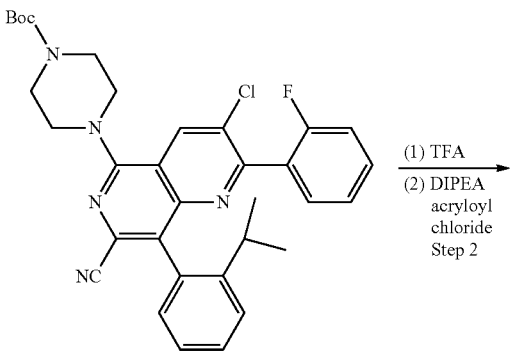

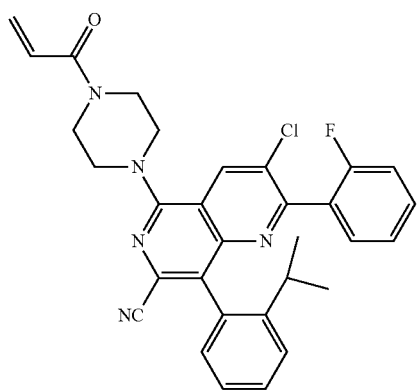

Step 1: tert-Butyl 4-(3-chloro-7-cyano-2-(2-fluorophenyl)-8-(2-isopropylphenyl)-1,6-naphthyridin-5-yl)piperazine-1-carboxylate Boc anhydride (0.01 mL, 0.049 mmol) and DIPEA (9 μL, 0.05 mmol) were added to a solution of 3-chloro-2-(2-fluorophenyl)-8-(2-isopropylphenyl)-5-(piperazin-1-yl)-1,6-naphthyridine-7-carbaldehyde (Intermediate 146A, prepared analogously to Method 86, steps 1-5, using tert-butyl (S)-3-methylpiperazine-1-carboxylate, 0.020 g, 0.041 mmol) in THF (2 mL). The resulting reaction mixture was stirred at rt for 3 h, then washed with sat. NH$_4$Cl and extracted with EtOAc. The combined organic extracts were dried over Na$_2$SO$_4$, filtered and concentrated to afford tert-butyl 4-(3-chloro-2-(2-fluorophenyl)-7-formyl-8-(2-isopropylphenyl)-1,6-naphthyridin-5-yl)piperazine-1-carboxylate to be used as is. m/z (ESI, +ve ion): 589.2 (M+H)$^+$.

Triethylamine (6 μl, 0.043 mmol) and hydroxyamine hydrochloride (30 mg, 0.043 mmol) were added to a solution of tert-butyl 4-(3-chloro-2-(2-fluorophenyl)-7-formyl-8-(2-isopropylphenyl)-1,6-naphthyridin-5-yl)piperazine-1-carboxylate in MeCN (5 mL). The resulting mixture was stirred and heated at reflux for 2 h. Oxalyl chloride (2 M in DCM, 0.020 mL, 0.041 mmol) was added and the heating was continued for 45 min. The reaction mixture was concentrated under reduced pressure, the residue was washed with water and extracted with DCM. The combined organic layers were dried over Na$_2$SO$_4$, filtered and concentrated under reduced pressure to afford tert-butyl 4-(3-chloro-7-cyano-2-(2-fluorophenyl)-8-(2-isopropylphenyl)-1,6-naphthyridin-5-yl)piperazine-1-carboxylate as a yellow solid—to be used as is. m/z (ESI, +ve ion): 586.2 (M+H)$^+$.

Step 2: 3-Chloro-2-(2-fluorophenyl)-8-((2-propanyl)phenyl)-5-(4-(2-propenoyl)-1-piperazinyl)-1,6-naphthyridine-7-carbonitrile TFA (1.0 mL, 12.98 mmol) was added to a solution of tert-butyl 4-(3-chloro-7-cyano-2-(2-fluorophenyl)-8-(2-isopropylphenyl)-1,6-naphthyridin-5-yl)piperazine-1-carboxylate (0.024 g, 0.041 mmol) in DCM (1 mL). The resulting mixture was stirred at rt for 20 min and concentrated under reduced pressure to afford 3-chloro-2-(2-fluorophenyl)-8-(2-isopropylphenyl)-5-(piperazin-1-yl)-1,6-naphthyridine-7-carbonitrile—to be used as is. m/z (ESI, +ve ion): 486.0 (M+H)$^+$.

DIPEA (0.021 mL, 0.123 mmol) and acryloyl chloride (4 μl, 0.049 mmol) were added to a solution of 3-Chloro-2-(2-fluorophenyl)-8-(2-isopropylphenyl)-5-(piperazin-1-yl)-1,6-naphthyridine-7-carbonitrile in DCM (3 mL). The resulting mixture was stirred at rt for 30 min. The reaction mixture was washed with sat. NaHCO$_3$ and extracted with DCM. The organic phase was concentrated under reduced pressure. The residue was purified by silica gel chromatography (eluent: 0-10% MeOH/DCM) to provide 3-chloro-2-(2-fluorophenyl)-8-(2-(2-propanyl)phenyl)-5-(4-(2-propenoyl)-1-piperazinyl)-1,6-naphthyridine-7-carbonitrile (0.0112 g, 0.021 mmol, 50.6% yield) as a yellow solid. $^1$H NMR (CDCl$_3$) δ: 8.43-8.47 (m, 1H), 7.39-7.48 (m, 3H), 7.27-7.33 (m, 1H), 7.06-7.21 (m, 4H), 6.59-6.73 (m, 1H), 6.30-6.44 (m, 1H), 5.74-5.84 (m, 1H), 3.83-4.06 (m, 4H), 3.62-3.71 (m, 4H), 2.41-2.55 (m, 1H), 1.11-1.16 (m, 3H), 1.03-1.08 (m, 3H). m/z (ESI, +ve ion): 540.0 (M+H)$^+$.

Example 147

3-Chloro-2-(2-fluorophenyl)-8-(2-(2-propanyl)phenyl)-5-(4-(2-propenoyl)-1-piperazinyl)-1,6-naphthyridine-7-carboxamide

Example 148

1-(4-(3-Chloro-7-(difluoromethyl)-2-(2-fluorophenyl)-8-(2-(2-propanyl)phenyl)-1,6-naphthyridin-5-yl)-1-piperazinyl)-2-propen-1-one

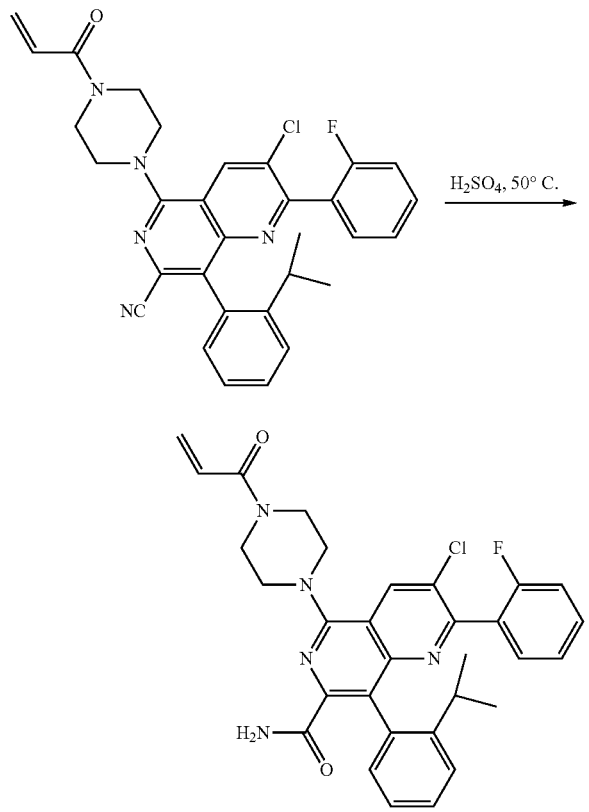

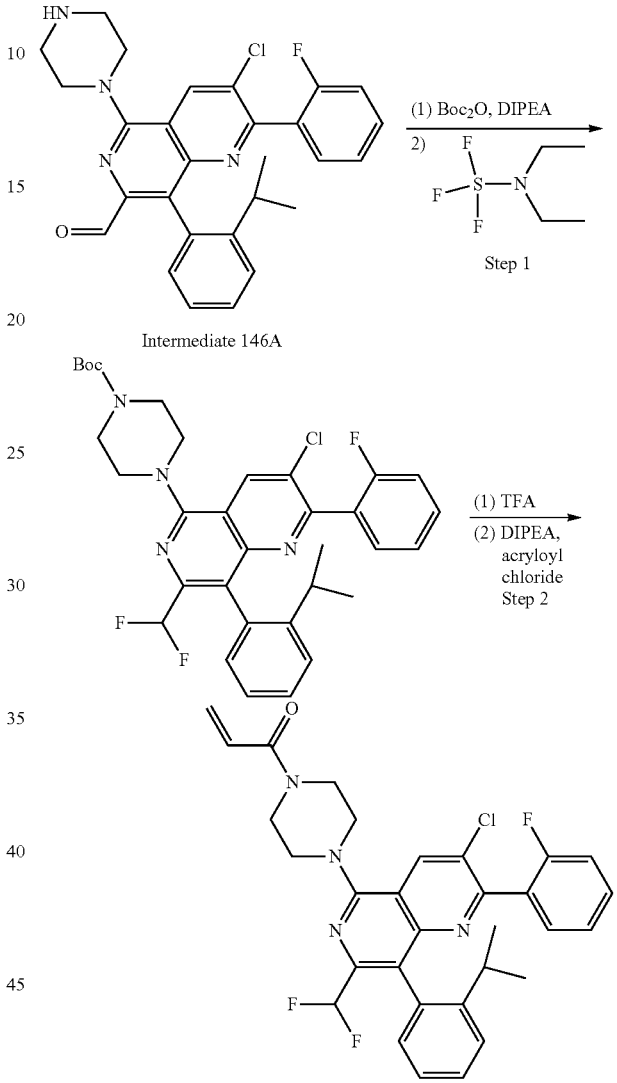

Example 146

A mixture of 5-(4-acryloylpiperazin-1-yl)-3-chloro-2-(2-fluorophenyl)-8-(2-isopropylphenyl)-1,6-naphthyridine-7-carbonitrile (Example 146, 4.5 mg, 8.33 μmol) and conc. sulfuric acid (2.0 mL, 37.5 mmol was heated to 50° C. for 3 h. Cold sat. NaHCO$_3$ was added to the reaction mixture, followed by extraction with DCM. The combined organic extracts were concentrated under reduced pressure and the crude product was purified by silica gel chromatography (eluent: 0-50% EtOAc-EtOH (3:1)/heptane) to provide 3-chloro-2-(2-fluorophenyl)-8-(2-(2-propanyl)phenyl)-5-(4-(2-propenoyl)-1-piperazinyl)-1,6-naphthyridine-7-carboxamide (0.0037 g, 6.63 μmol, 80% yield) as yellow solid. $^1$H NMR (CDCl$_3$) δ: 8.44-8.49 (m, 1H), 7.37-7.47 (m, 2H), 7.32-7.35 (m, 2H), 7.27-7.32 (m, 1H), 7.14-7.19 (m, 3H), 7.07-7.13 (m, 1H), 6.97-7.01 (m, 1H), 6.59-6.72 (m, 1H), 6.33-6.43 (m, 1H), 5.76-5.85 (m, 1H), 3.86-4.10 (m, 4H), 3.53-3.67 (m, 4H), 2.40-2.52 (m, 1H), 1.08-1.11 (m, 3H), 0.96-1.01 (m, 3H). m/z (ESI, +ve ion): 558.2 (M+H)$^+$.

Step 1: tert-Butyl 4-(3-chloro-7-(difluoromethyl)-2-(2-fluorophenyl)-8-(2-isopropylphenyl)-1,6-naphthyridin-5-yl)piperazine-1-carboxylate Boc anhydride (0.4 ml, 1.6 mmol) and DIPEA (0.3 ml, 1.6 mmol) were added to a solution of 3-chloro-2-(2-fluorophenyl)-8-(2-isopropylphenyl)-5-(piperazin-1-yl)-1,6-naphthyridine-7-carbaldehyde (Intermediate 146A, 0.6 g, 1.3 mmol) in THF (2 mL) at rt. After 3 h, the reaction mixture was washed with sat. NH$_4$Cl and extracted with EtOAc. The combined organic layers were dried over Na$_2$SO$_4$, and concentrated under reduced pressure. The crude residue was purified by silica gel chromatography (eluent: 0-50%/o EtOAc-EtOH (3:1)/heptane) to provide tert-butyl 4-(3-chloro-2-(2-fluorophenyl)-7-formyl-8-(2-isopropylphenyl)-1,6-naphthyridin-5-yl)piperazine-1-carboxylate. m/z (ESI, +ve ion): 589.2 (M+H)$^+$.

A solution of tert-butyl 4-(3-chloro-2-(2-fluorophenyl)-7-formyl-8-(2-isopropylphenyl)-1,6-naphthyridin-5-yl)piperazine-1-carboxylate (0.050 g, 0.085 mmol) in DCM (5 mL) was cooled to −20° C., followed by the dropwise addition of (diethylamino)trifluorosulfur (0.03 ml, 0.187 mmol, Sigma-Aldrich Corporation, St. Louis, Mo., USA). After complete addition, the reaction was brought to rt and stirred for 2 h. The reaction mixture was quenched with ice and sat. NaHCO$_3$ and extracted with DCM. The organic phase was concentrated under reduced pressure and the residue was purified by silica gel chromatography (eluent: 0-50% EtOAc-EtOH (3:1)/heptane) to provide tert-butyl 4-(3-chloro-7-(difluoromethyl)-2-(2-fluorophenyl)-8-(2-isopropylphenyl)-1,6-naphthyridin-5-yl)piperazine-1-carboxylate (0.011 g, 0.018 mmol, 21.2% yield) as a yellow solid. m/z (ESI, +ve ion): 611.2 (M+H)$^+$.

Step 2: 1-(4-(3-Chloro-7-(difluoromethyl)-2-(2-fluorophenyl)-8-(2-(2-propanyl)phenyl)-1,6-naphthyridin-5-yl)-1-piperazinyl)-2-propen-1-one TFA (1.0 mL, 12.98 mmol) was added to a solution of tert-butyl 4-(3-chloro-7-(difluoromethyl)-2-(2-fluorophenyl)-8-(2-isopropylphenyl)-1,6-naphthyridin-5-yl)piperazine-1-carboxylate (0.011 g, 0.018 mmol) in DCM (1 mL) at rt. After 20 min, the reaction mixture was concentrated in vacuo. The residue was dissolved in DCM (3 mL), followed by the addition of DIPEA (9 μl, 0.05 mmol) and acryloyl chloride (1.8 μl, 0.022 mmol). The resulting mixture was stirred at rt for 30 min. The reaction mixture was washed with sat. NaHCO$_3$ and extracted with DCM. The organic phase was concentrated under reduced pressure and the residue was purified by silica gel chromatography (eluent: 0-10% MeOH/DCM) to provide 1-(4-(3-chloro-7-(difluoromethyl)-2-(2-fluorophenyl)-8-(2-(2-propanyl)phenyl)-1,6-naphthyridin-5-yl)-1-piperazinyl)-2-propen-1-one (0.0026 g, 4.60 μmol, 25.6% yield) as a yellow solid. $^1$H NMR (CDCl$_3$) δ: 8.42-8.51 (m, 1H), 7.37-7.45 (m, 3H), 7.27-7.31 (m, 1H), 7.19-7.25 (m, 1H), 7.05-7.19 (m, 3H), 6.58-6.74 (m, 1H), 6.17-6.53 (m, 2H), 5.71-5.84 (m, 1H), 3.85-4.06 (m, 4H), 3.59-3.75 (m, 4H), 2.41-2.53 (m, 1H), 0.99-1.07 (m, 6H). m/z (ESI, +ve ion): 565.2 (M+H)$^+$.

Example 149

1-(4-(3-Chloro-8-(((2S,5S)-2,5-dimethyl-1-pyrrolidinyl)carbonyl)-2-(2-fluorophenyl)-7-(hydroxymethyl)-1,6-naphthyridin-5-yl)-1-piperazinyl)-2-propen-1-one

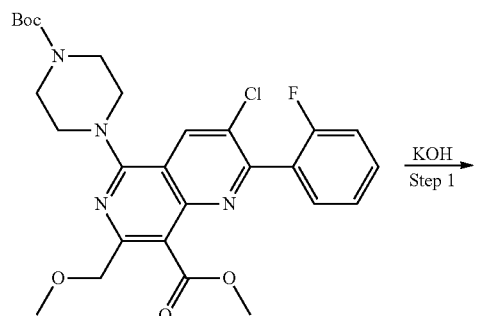

Intermediate 85B

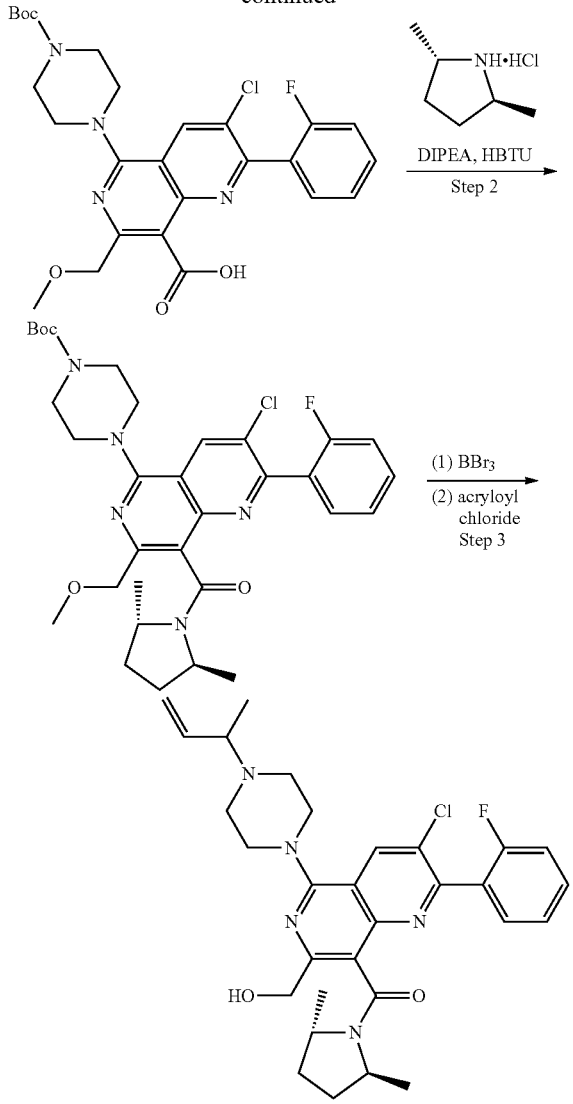

Step 1: 5-(4-(tert-Butoxycarbonyl)piperazin-1-yl)-3-chloro-2-(2-fluorophenyl)-7-(methoxymethyl)-1,6-naphthyridine-8-carboxylic acid A mixture of KOH (1.491 g, 26.6 mmol) and a solution of methyl 5-(4-(tert-butoxycarbonyl)piperazin-1-yl)-3-chloro-2-(2-fluorophenyl)-7-(methoxymethyl)-1,6-naphthyridine-8-carboxylate (Intermediate 85B, 1.0 g, 1.8 mmol) in EtOH (20 mL), was heated to 85° C. for 30 min. The reaction mixture was cooled to rt, acidified with 5 N HCl and extracted with DCM. The combined organic extracts were dried over Na$_2$SO$_4$, and concentrated to afford 5-(4-(tert-butoxycarbonyl)piperazin-1-yl)-3-chloro-2-(2-fluorophenyl)-7-(methoxymethyl)-1,6-naphthyridine-8-carboxylic acid (0.920 g, 1.733 mmol, 45.7% yield) as a yellow solid. m/z (ESI, +ve ion): 531.0 (M+H)$^+$.

Step 2: tert-Butyl 4-(3-chloro-8-((2S,5S)-2,5-dimethylpyrrolidine-1-carbonyl)-2-(2-fluorophenyl)-7-(methoxymethyl)-1,6-naphthyridin-5-yl)piperazine-1-carboxylate DIPEA (0.8 ml, 4.7 mmol), (2S,5S)-2,5-dimethylpyrrolidine hydrochloride (0.255 g, 1.883 mmol, J&W Pharmlab, LLC, Levittown, Pa.) and HBTU (0.536 g, 1.412 mmol, Oakwood Products, Inc. Estill, S.C.) were added to a solution of 5-(4-(tert-butoxycarbonyl)piperazin-1-yl)-3-chloro-2-(2-fluorophenyl)-7-(methoxymethyl)-1,6-naphthyridine-8-carboxylic acid (0.50 g, 0.94 mmol) in DCM (2 mL) at 0° C. The ice bath was removed and stirring was continued at rt for 15 h. The reaction mixture was diluted with DCM (10 mL) and washed with water. The organic phase was concentrated under reduced pressure and the crude product was purified by silica gel chromatography (eluent: 0-100% EtOAc/heptane) to provide tert-butyl 4-(3-chloro-8-((2S,5S)-2,5-dimethylpyrrolidine-1-carbonyl)-2-(2-fluorophenyl)-7-(methoxymethyl)-1,6-naphthyridin-5-yl)piperazine-1-carboxylate (0.184 g, 0.301 mmol, 31.9% yield) as a light yellow solid with some impurities. m/z (ESI, +ve ion): 612.2 (M+H)+.

Step 3 1-(4-(3-Chloro-8-(((2S,5S)-2,5-dimethyl-1-pyrrolidinyl)carbonyl)-2-(2-fluorophenyl)-7-(hydroxymethyl)-1,6-naphthyridin-5-yl)-1-piperazinyl)-2-propen-1-one BBr$_3$ (1 M solution in hexanes, 1.5 mL, 1.5 mmol) was added dropwise to a solution of tert-butyl 4-(3-chloro-8-((2S,5S)-2,5-dimethylpyrrolidine-1-carbonyl)-2-(2-fluorophenyl)-7-(methoxymethyl)-1,6-naphthyridin-5-yl)piperazine-1-carboxylate (0.184 g, 0.301 mmol) in DCM (5 mL) at 0° C. After complete addition the ice-bath was removed and stirring was continued at rt for 45 min. The reaction was cooled to 0° C., treated with sat. NaHCO$_3$ and extracted with DCM. The combined organic layers were dried over Na$_2$SO$_4$, filtered and purified by silica gel chromatography (eluent: 0-10% MeOH/heptane) to provide (3-chloro-2-(2-fluorophenyl)-7-(hydroxymethyl)-5-(piperazin-1-yl)-1,6-naphthyridin-8-yl)((2S,5S)-2,5-dimethylpyrrolidin-1-yl)methanone (0.0047 g, 9.44 µmol, 3.14% yield) as a yellow solid. m/z (ESI, +ve ion): 498.0 (M+H)+.

Acryloyl chloride (3.0 µL, 0.037 mmol) was added to a solution of the above compound in DCM (2 mL) at rt. After 30 min, the reaction mixture was washed with sat. NaHCO$_3$ and extracted with DCM. The organic phase was concentrated under reduced pressure and purified by reverse-phase preparative HPLC using a Phenimenex Gemini column, 5 micron, C18, 110 Å, AXIA, 150×30 mm, 0.1% TFA in CH3CN/H2O, gradient 10% to 90% over 15 min to afford 1-(4-(3-chloro-8-(((2S,5S)-2,5-dimethyl-1-pyrrolidinyl)carbonyl)-2-(2-fluorophenyl)-7-(hydroxymethyl)-1,6-naphthyridin-5-yl)-1-piperazinyl)-2-propen-1-one as a yellow solid. $^1$H NMR (CDCl$_3$) δ: 8.36-8.42 (m, 1H), 7.45-7.59 (m, 2H), 7.27-7.30 (m, 1H), 7.14-7.24 (m, 1H), 6.57-6.72 (m, 1H), 6.33-6.43 (m, 1H), 5.74-5.84 (m, 1H), 4.89-4.97 (m, 1H), 4.67-4.75 (m, 1H), 4.43-4.54 (m, 1H), 3.75-4.08 (m, 5H), 3.63-3.76 (m, 5H), 1.51-1.62 (m, 2H), 1.42-1.49 (m, 2H), 1.21-1.26 (m, 3H), 0.85-0.92 (m, 3H). m/z (ESI, +ve ion): 552.2 (M+H)+.

Example 150

1-((3S)-4-(3-Chloro-2-(2-fluorophenyl)-7-(hydroxymethyl)-1,6-naphthyridin-5-yl)-3-methyl-1-piperazinyl)-2-propen-1-one

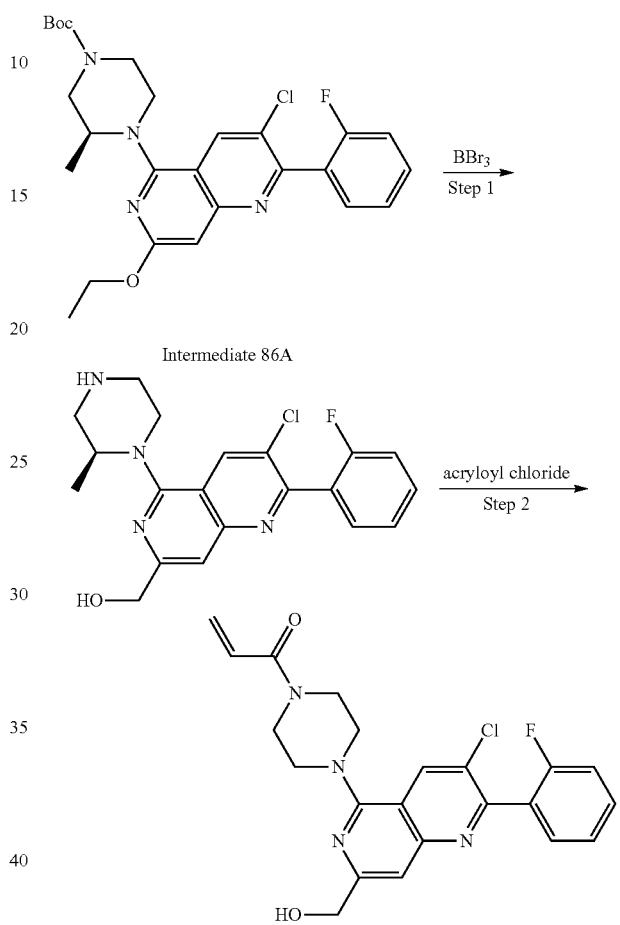

Step 1: (S)-(3-Chloro-2-(2-fluorophenyl)-5-(2-methylpiperazin-1-yl)-1,6-naphthyridin-7-yl)methanol BBr$_3$ (1 M in hexanes, 1.4 mL, 1.4 mmol) was added to a solution of tert-butyl (S)-4-(3-chloro-2-(2-fluorophenyl)-7-(methoxymethyl)-1,6-naphthyridin-5-yl)-3-methylpiperazine-1-carboxylate (Intermediate 86A, 0.080 g, 0.16 mmol) in DCM (5 mL) at 0° C. After complete addition, the ice-bath was removed and the mixture was stirred at rt for 40 min. The reaction mixture was slowly quenched with sat. NaHCO$_3$ and extracted with DCM. The combined organic layers were dried over Na$_2$SO$_4$, concentrated and purified by silica gel chromatography (eluent: 0-10% MeOH/DCM) to provide (S)-(3-chloro-2-(2-fluorophenyl)-5-(2-methylpiperazin-1-yl)-1,6-naphthyridin-7-yl)methanol as a yellow solid. m/z (ESI, +ve ion): 387.2 (M+H)+.

Step 2. 1-((3S)-4-(3-Chloro-2-(2-fluorophenyl)-7-(hydroxymethyl)-1,6-naphthyridin-5-yl)-3-methyl-1-piperazinyl)-2-propen-1-one Acryloyl chloride (0.013 mL, 0.160 mmol) was added to a suspension of (S)-(3-chloro-2-(2-fluorophenyl)-5-(2- methylpiperazin-1-yl)-1,6-naphthyridin-7-yl)methanol in DCM (5 mL) at rt. After 45 min, the reaction mixture was washed with sat. NaHCO₃ and extracted with DCM. The solvent was removed under reduced pressure and the residue was purified by silica gel chromatography (eluent: 0-10% MeOH/DCM) to provide 1-((3S)-4-(3-chloro-2-(2-fluorophenyl)-7-(hydroxymethyl)-1,6-naphthyridin-5-yl)-3-methyl-1-piperazinyl)-2-propen-1-one (0.018 g, 0.041 mmol, 25.6% yield) as a yellow solid. ¹H NMR (DMSO-d₆) δ: 8.58-8.63 (m, 1H), 7.58-7.70 (m, 2H), 7.49-7.55 (m, 1H), 7.38-7.46 (m, 2H), 6.78-6.96 (m, 1H), 6.13-6.25 (m, 1H), 5.70-5.80 (m, 1H), 5.47-5.56 (m, 1H), 4.55-4.69 (m, 2H), 4.08-4.23 (m, 2H), 3.72-4.08 (m, 3H), 3.56-3.69 (m, 1H), 3.45-3.55 (m, 1H), 1.03-1.11 (m, 3H). m/z (ESI, +ve ion): 441.2 (M+H)⁺.

Example 151

(M)-6-Chloro-7-(2-fluorophenyl)-1-(4-methyl-1-oxido-2-(2-propanyl)-3-pyridinyl)-4-((2S)-2-methyl-4-(2-propenoyl)-1-piperazinyl)pyrido[2,3-d]pyrimidin-2(1H)-one

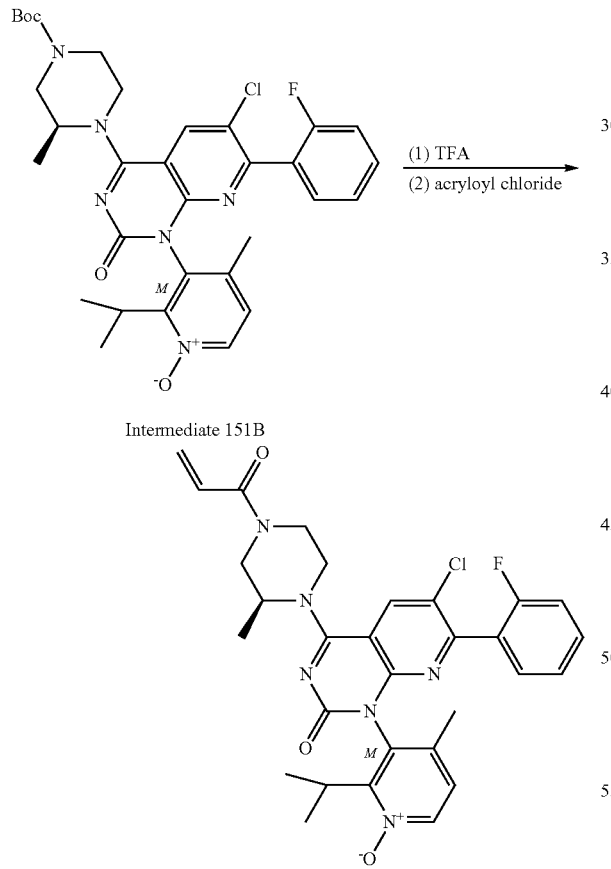

Trifluoroacetic acid (1.8 mL) was added to a solution of (M)-(S)-3-(4-(4-(tert-butoxycarbonyl)-2-methylpiperazin-1-yl)-6-chloro-7-(2-fluorophenyl)-2-oxopyrido[2,3-d]pyrimidin-1(2H)-yl)-2-isopropyl-4-methylpyridine 1-oxide (Intermediate 151B prepared according to Example 83 using Intermediate 73C, 0.0665 g, 0.107 mmol) in DCM (1.8 mL) at rt. After 10 min, the mixture was concentrated in vacuo to give (M)-(S)-3-(6-chloro-7-(2-fluorophenyl)-4-(2-methylpiperazin-1-yl)-2-oxopyrido[2,3-d]pyrimidin-1(2H)-yl)-2-isopropyl-4-methylpyridine 1-oxide. m/z (ESI, +ve ion): 523.2 (M+H).

The residue was dissolved in DCM (1.78 mL) and the solution was cooled to 0° C. DIPEA (0.3 mL, 1.7 mmol) and acryloyl chloride (0.2 M in DCM, 0.6 mL, 0.12 mmol) were sequentially added and the reaction mixture was allowed to stir for 20 min at 0° C. The reaction mixture was quenched with satd. NaHCO₃ (50 mL) and extracted with DCM (2 f 50 mL). The organic extract was dried over Na₂SO₄ and concentrated in vacuo. The crude product was purified by silica gel chromatography (eluent 0-60% DCM-MeOH (4:1)/DCM) to provide (M)-6-chloro-7-(2-fluorophenyl)-1-(4-methyl-1-oxido-2-(2-propanyl)-3-pyridinyl)-4-((2S)-2-methyl-4-(2-propenoyl)-1-piperazinyl)pyrido[2,3-d]pyrimidin-2(1H)-one (0.054 g, 0.093 mmol, 87% yield) as tan solid. ¹H NMR (400 MHz, DMSO-d₆) δ ppm 8.48 (br d, J=4.6 Hz, 1H), 8.12 (d, J=6.6 Hz, 1H), 7.50-7.57 (m, 1H), 7.22-7.36 (m, 4H), 6.79-6.93 (m, 1H), 6.21 (br d, J=16.8 Hz, 1H), 5.73-5.80 (m, 1H), 4.97 (br s, 1H), 4.24-4.45 (m, 2H), 3.99-4.20 (m, 1H), 3.40-3.87 (m, 2H), 3.05-3.29 (m, 1H), 2.85-3.04 (m, 1H), 1.87 (s, 3H), 1.34 (d, J=6.6 Hz, 3H), 1.22 (br d, J=6.6 Hz, 3H), 1.12 (d, J=6.8 Hz, 3H). ¹⁹F NMR (376 MHz, DMSO-d₆) δ ppm −114.03 (s, 1F). m/z (ESI, +ve ion): 577.2 (M+H).

Example 152

(M)-6-Chloro-1-(4-(((dimethylamino)methyl)-2-(2-propanyl)-3-pyridinyl)-7-(2-fluorophenyl)-4-((2S)-2-methyl-4-(2-propenoyl)-1-piperazinyl)pyrido[2,3-d]pyrimidin-2(1H1)-one

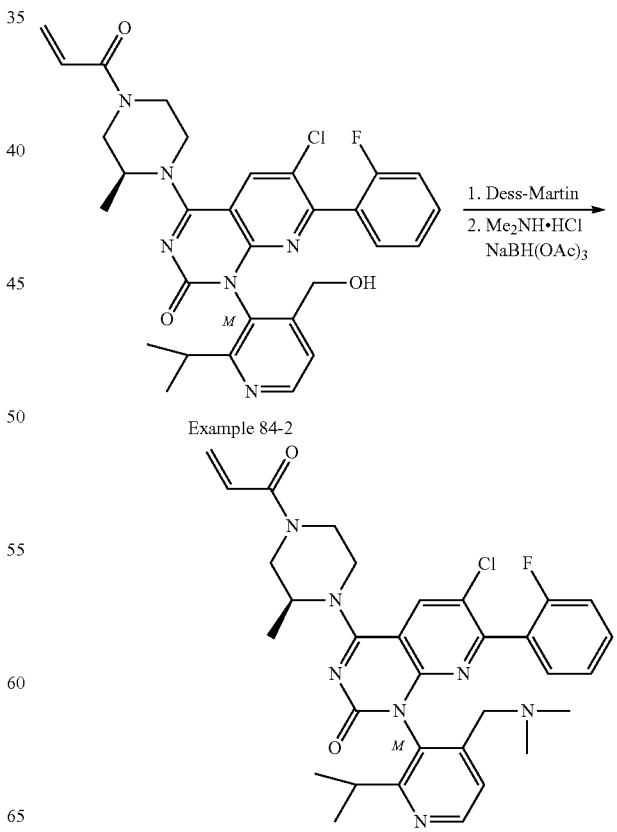

Dess-Martin periodinane (0.084 g, 0.198 mmol, Sigma-Aldrich Corporation, St. Louis, Mo. USA) was added to a solution of (M)-6-chloro-7-(2-fluorophenyl)-1-(4-(hydroxymethyl)-2-(2-propanyl)-3-pyridinyl)-4-((2S)-2-methyl-4-(2-propenoyl)-1-piperazinyl)pyrido[2,3-d]pyrimidin-2(1H)-one (Example 84-2, 0.0763 g, 0.132 mmol) in DCM (2.6 mL). The resulting reaction mixture was stirred at rt. After 50 min, the mixture was quenched with 10% $Na_2S_2O_3$ (50 mL). The mixture was extracted with DCM (2×50 mL). The organic extract was washed with brine (1×50 mL), dried over $Na_2SO_4$ and concentrated in vacuo to give (M)-(S)-3-(4-(4-acryloyl-2-methylpiperazin-1-yl)-6-chloro-7-(2-fluorophenyl)-2-oxopyrido[2,3-d]pyrimidin-1(2H)-yl)-2-isopropylisonicotinaldehyde (0.076 g, 0.132 mmol, 100% yield). m/z (ESI, +ve ion): 575.0 (M+H). The crude product was carried on crude for the next step.

Dimethylamine hydrochloride (11 mg, 0.13 mmol, Sigma-Aldrich Corporation, St. Louis, Mo., USA) was added to a solution of (M)-(S)-3-(4-(4-acryloyl-2-methylpiperazin-1-yl)-6-chloro-7-(2-fluorophenyl)-2-oxopyrido[2,3-d]pyrimidin-1(2H)-yl)-2-isopropylisonicotinaldehyde (0.076 g, 0.132 mmol) in DCM (2.64 mL). After 15 min, sodium triacetoxyborohydride (0.056 g, 0.264 mmol) was added to the reaction mixture and stirring was continued for 1.5 h. The crude product was purified by silica gel chromatography (eluent 0-50% DCM-MeOH (4:1)/DCM) to provide (M)-6-chloro-1-(4-((dimethylamino)methyl)-2-(2-propanyl)-3-pyridinyl)-7-(2-fluorophenyl)-4-((2S)-2-methyl-4-(2-propenoyl)-1-piperazinyl)pyrido[2,3-d]pyrimidin-2(1H)-one (0.0431 g, 0.071 mmol, 54.0% yield) as white solid. $^1$H NMR (400 MHz, DMSO-$d_6$) δ ppm 8.48 (d, J=5.0 Hz, 1H), 8.46 (br s, 1H), 7.45-7.54 (m, 1H), 7.22-7.34 (m, 3H), 7.16 (td, J=7.4, 1.6 Hz, 1H), 6.79-6.93 (m, 1H), 6.21 (br d, J=16.2 Hz, 1H), 5.73-5.80 (m, 1H), 4.95 (br s, 1H), 4.23-4.47 (m, 2H), 3.99-4.21 (m, 1H), 3.41-3.83 (m, 3H), 2.98-3.08 (m, 2H), 2.74 (dt. J=13.3, 6.6 Hz, 1H), 1.91 (s, 6H), 1.34 (br d, J=6.6 Hz, 3H), 1.08 (d, J=6.6 Hz, 3H), 0.96 (d, J=6.6 Hz, 3H). $^{19}$F NMR (376 MHz, DMSO-$d_6$) δ ppm −114.42 (s, 1F). m/z (ESI, +ve ion): 604.0 (M+H).

Example 153

1-((3S)-4-(7-Amino-3-chloro-2-(2-fluorophenyl)-8-(o-tolyl)-1,6-naphthyridin-5-yl)-3-methylpiperazin-1-yl)prop-2-en-1-one

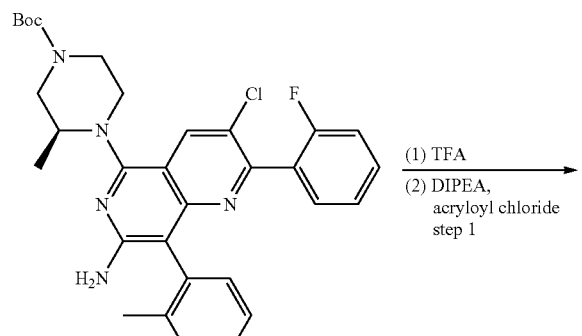

Intermediate 134A

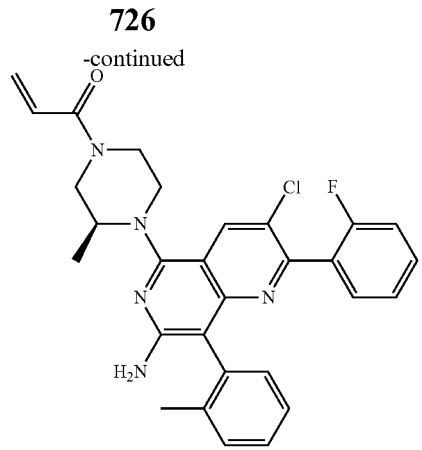

Step 1: 1-((3S)-4-(7-Amino-3-chloro-2-(2-fluorophenyl)-8-(o-tolyl)-1,6-naphthyridin-5-yl)-3-methylpiperazin-1-yl)prop-2-en-1-one Trifluoroacetic acid (1 mL) was added to a solution of tert-butyl (3S)-4-(7-amino-3-chloro-2-(2-fluorophenyl)-8-(o-tolyl)-1,6-naphthyridin-5-yl)-3-methylpiperazine-1-carboxylate (Intermediate 134A; 34 mg, 0.06 mmol) in DCM (2 mL), and the resulting mixture was stirred at room temperature for 1 h. The mixture was then concentrated in vacuo, and the residue was dissolved in DCM (2 mL). DIPEA (0.051 mL, 0.29 mmol) and acryloyl chloride (5 μL, 0.06 mmol) in DCM (0.5 mL) were sequentially added, and the resulting mixture was stirred at room temperature for 30 min. The mixture was then diluted with EtOAc (30 mL) and sequentially washed with saturated aqueous sodium bicarbonate solution (10 mL) and brine (5 mL). The organic layer was separated, dried over anhydrous sodium sulfate, and concentrated in vacuo. The crude product was purified by silica gel chromatography (eluent: 0-2% MeOH/DCM) to provide 1-((3S)-4-(7-amino-3-chloro-2-(2-fluorophenyl)-8-(o-tolyl)-1,6-naphthyridin-5-yl)-3-methylpiperazin-1-yl)prop-2-en-1-one. $^1$H NMR (400 MHz, DMSO-$d_6$) δ 8.35 (d, J=7.9 Hz, 1H), 7.44-7.56 (m, 1H), 7.19-7.37 (m, 6H), 7.12-7.18 (m, 1H), 6.82-6.96 (m, 1H), 6.19 (dd, J=16.4, 6.4 Hz, 1H), 5.74 (dd, J=10.6, 2.1 Hz, 1H), 5.44 (br d, J=4.6 Hz, 2H), 3.57-4.24 (m, 5H), 3.32-3.53 (m, 2H), 1.99 (d, J=16.6 Hz, 3H), 1.12 (br d, J=4.8 Hz, 3H). m/z (ESI, +ve ion): 515.9 (M+H)$^+$.

Example 154

1-((3S)-4-(7-Fluoro-3-chloro-2-(2-fluorophenyl)-8-(o-tolyl)-1,6-naphthyridin-5-yl)-3-methylpiperazin-1-yl)prop-2-en-1-one

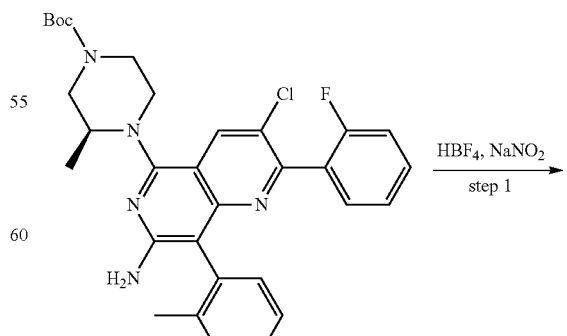

Intermediate 134A

727

-continued

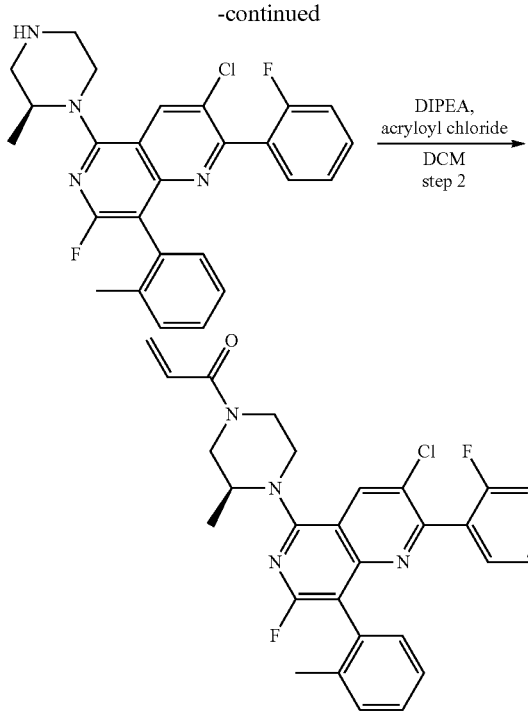

Step 1: 3-Chloro-7-fluoro-2-(2-fluorophenyl)-5-((S)-2-methylpiperazin-1-yl)-8-(o-tolyl)-1,6-naphthyridine Sodium nitrite (4 mg, 0.06 mmol, Acros, Geel, Belgium) was slowly added to a mixture of tert-butyl (3S)-4-(7-amino-3-chloro-2-(2-fluorophenyl)-8-(o-tolyl)-1,6-naphthyridin-5-yl)-3-methylpiperazine-1-carboxylate (Intermediate 134A: 17 mg, 0.03 mmol) and tetrafluoroboric acid (0.4 mL, Sigma-Aldrich Corporation, St. Louis, Mo., USA) at 0° C., and the resulting mixture was stirred at ° C. for 10 min, then at room temperature for 30 min. The mixture was then cooled to 0° C., treated with saturated aqueous sodium bicarbonate solution, and extracted with EtOAc. The organic layer was separated, dried over sodium sulfate, and concentrated in vacuo to give 3-chloro-7-fluoro-2-(2-fluorophenyl)-5-((S)-2-methylpiperazin-1-yl)-8-(o-tolyl)-1,6-naphthyridine as an orange solid. m/z (ESI, +ve ion): 464.9 (M+H)$^+$.

Step 2: 1-((3S)-4-(7-Fluoro-3-chloro-(2-fluorophenyl)-8-(o-tolyl)-1,6-naphthyridin-5-yl)-3-methylpiperazin-1-yl)prop-2-en-1-one Acryloyl chloride (0.5 M in DCM, 0.052 mL, 0.03 mmol) was added to a mixture of 3-chloro-7-fluoro-2-(2-fluorophenyl)-5-((S)-2-methylpiperazin-1-yl)-8-(o-tolyl)-1,6-naphthyridine (12 mg, 0.03 mmol), DIPEA (0.023 mL, 0.13 mmol) and DCM (1 mL) at 0° C., and the resulting mixture was stirred at 0° C. for 30 min. The mixture was then diluted with EtOAc (5 mL), and the organic layer was separated and sequentially washed with saturated aqueous sodium bicarbonate solution (5 mL) and brine (5 mL). then dried over sodium sulfate and concentrated in vacuo. The crude product was purified by silica gel chromatography (eluent: 0-1%

728

MeOH/DCM) to provide 1-((3S)-4-(7-Fluoro-3-chloro-2-(2-fluorophenyl)-8-(o-tolyl)-1,6-naphthyridin-5-yl)-3-methylpiperazin-1-yl)prop-2-en-1-one. $^1$H NMR (400 MHz, CDCl$_3$) 8.38 (s, 1H), 7.35-7.50 (m, 2H), 7.27-7.32 (m, 4H), 7.20 (td, J=7.7, 0.8 Hz, 1H), 7.12 (t, J=9.1 Hz, 1H), 6.52-6.77 (m, 1H), 6.38 (dd, J=16.9, 1.76 Hz, 1H), 5.78 (dd, J=10.6, 1.7 Hz, 1H), 4.19-4.58 (m, 2H), 3.42-4.08 (m, 5H), 2.12 (d, J=13.5 Hz, 3H), 1.32 (br t, J=5.5 Hz, 3H). m/z (ESI, +ve ion): 518.9 (M+H)$^+$.

Example 155

1-(2-Amino-6-(2-propanyl)phenyl)-6-chloro-7-(2-fluorophenyl)-4-((2S)-2-methyl-4-(2-propenoyl)-1-piperazinyl)pyrido[2,3-d]pyrimidin-2(1H)-one

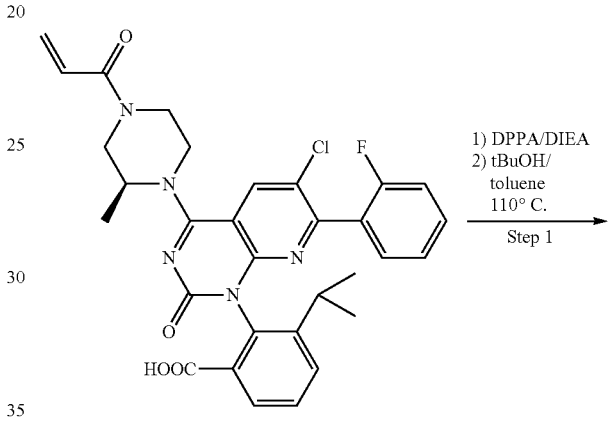

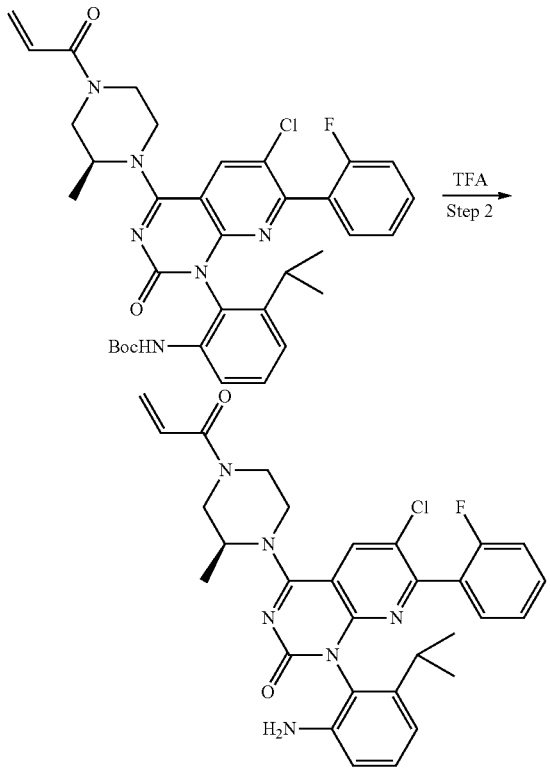

Step 1: tert-Butyl (S)-(2-(4-(4-acryloyl-2-methylpiperazin-1-yl)-6-chloro-7-(2-fluorophenyl)-2-oxopyrido[2,3-d]pyrimidin-1(2H)-yl)-3-isopropylphenyl)carbamate A solution of (S)-2-(4-(4-acryloyl-2-methylpiperazin-1-yl)-6-chloro-7-(2-fluorophenyl)-2-oxopyrido[2,3-d]pyrimidin-1(2H)-yl)-3-isopropylbenzoic acid (Example 132, 650 mg, 1.102 mmol), diphenyl phosphoryl azide (358 µl, 1.652 mmol, Sigma-Aldrich Corporation, St. Louis, Mo., USA), and DIPEA (250 µl, 1.432 mmol) in THF (6 mL) was stirred at 20° C. for 18 h. The mixture was then concentrated in vacuo, and the residue was dissolved in toluene (5 mL) and tert-butyl alcohol (1047 µl, 11.02 mmol). The resulting solution was heated to 110° C. for 4 hrs. The reaction mixture was then partitioned between EtOAc (20 mL) and 5% NaHCO$_3$ (20 mL). The organic layer was separated, dried over MgSO$_4$, and concentrated under reduced pressure. Purification of the residue by silica gel chromatography (eluent: 30-60% EtOAc-EtOH (3:1)/heptane) provided tert-butyl (S)-(2-(4-(4-acryloyl-2-methylpiperazin-1-yl)-6-chloro-7-(2-fluorophenyl)-2-oxopyrido[2,3-d]pyrimidin-1(2H)-yl)-3-isopropylphenyl)carbamate. m/z (ESI, +ve ion): 661.3 (M+H)$^+$.

Step 2: 1-(2-Amino-6-(2-propanyl)phenyl)-6-chloro-7-(2-fluorophenyl)-4-((2S)-2-methyl-4-(2-propenoyl)-1-piperazinyl)pyrido[2,3-d]pyrimidin-2(1H)-one A solution of tert-butyl (S)-(2-(4-(4-acryloyl-2-methylpiperazin-1-yl)-6-chloro-7-(2-fluorophenyl)-2-oxopyrido[2,3-d]pyrimidin-1(2H)-yl)-3-isopropylphenyl)carbamate (350 mg, 0.529 mmol) in TFA was stirred at 20° C. for 15 min. The solvent was then removed under reduced pressure, and the residue was partitioned between EtOAc (20 mL) and sat. NaHCO$_3$ (10 mL). The organic layer was separated and sequentially washed with brine, dried over MgSO4, and concentrated in vacuo. Chromatographic purification of the residue (eluent: 0-80% EtOAc-EtOH (3:1)/heptane) furnished 1-(2-amino-6-(2-propanyl)phenyl)-6-chloro-7-(2-fluorophenyl)-4-((2S)-2-methyl-4-(2-propenoyl)-1-piperazinyl)pyri do[2,3-d]pyrimidin-2(1H)-one. $^1$H NMR (400 MHz, CDCl$_3$) δ 8.05 (s, 1H), 7.34-7.45 (m, 1H), 7.04-7.25 (m, 4H), 6.84 (d, J=7.67 Hz, 1H), 6.71 (d, J=7.88 Hz, 1H), 6.51-6.66 (m, 1H), 6.40 (d, J=15.55 Hz, 1H), 5.80 (d, J=12.02 Hz, 1H), 4.19-5.22 (m, 3H), 3.47-4.07 (m, 3H), 2.92-3.34 (m, 1H), 2.34-2.77 (m, 3H), 1.51 (d, J=24.26 Hz, 3H), 1.13 (d, J=6.84 Hz, 3H), 0.98 (dd, J=1.87, 6.43 Hz, 3H). $^{19}$F NMR (376 MHz, CDCl$_3$) δ −111.78 (s, 1F). m/z (ESI, +ve ion): 561.2 (M+H)$^+$.

Example 156

Methyl 4-(6-chloro-7-(2-fluorophenyl)-4-((2S)-2-methyl-4-(2-propenoyl)-1-piperazinyl)-2-oxopyrido[2,3-d]pyrimidin-1(2H)-yl)-3-methyl-5-(2-propanyl)benzoate

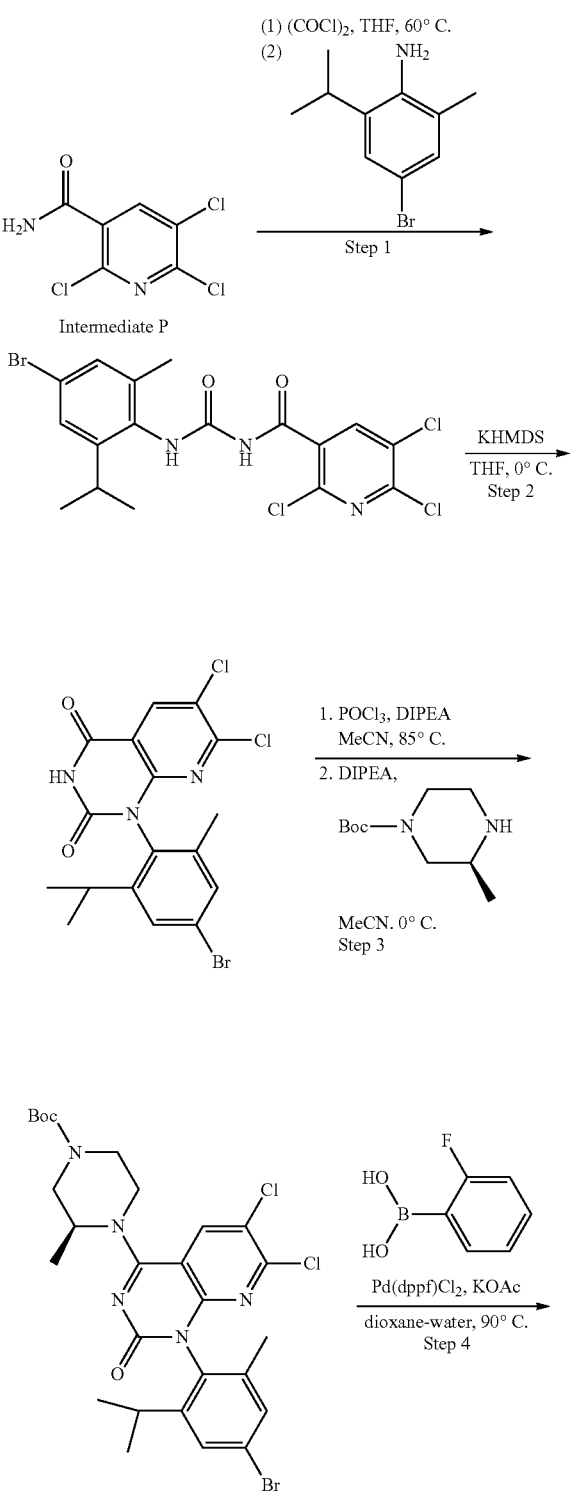

-continued

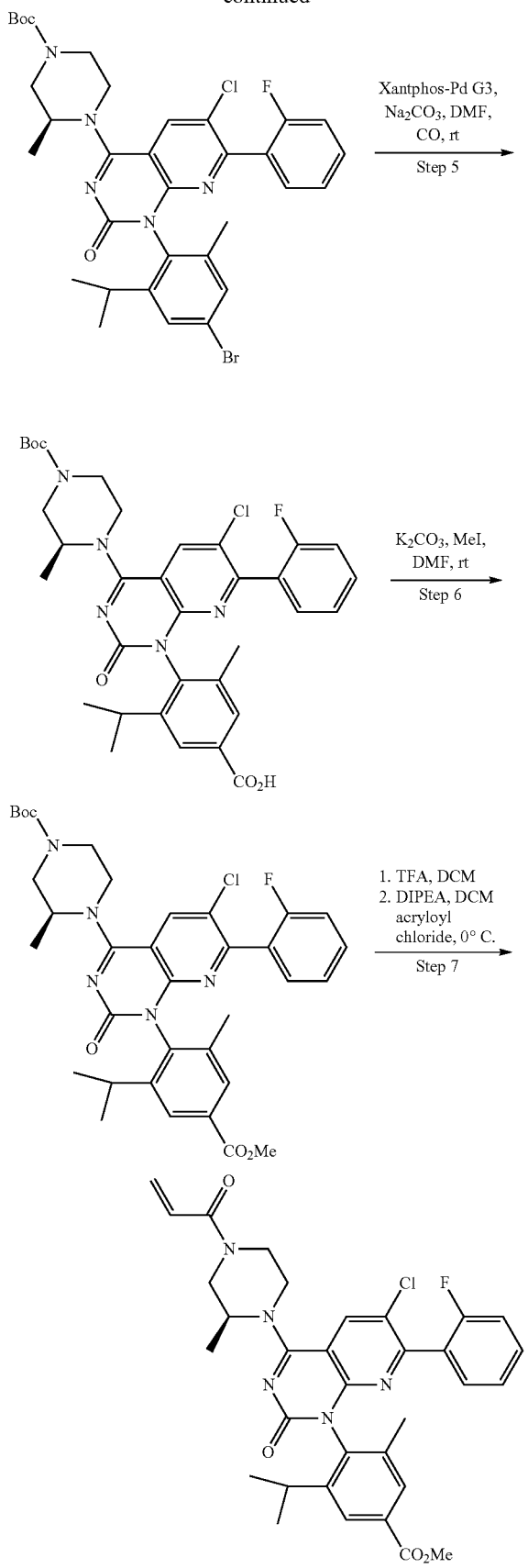

Xantphos-Pd G3,
Na₂CO₃, DMF,
CO, rt
Step 5

K₂CO₃, MeI,
DMF, rt
Step 6

1. TFA, DCM
2. DIPEA, DCM
acryloyl
chloride, 0° C.
Step 7

Step 1: N-((4-Bromo-2-isopropyl-6-methylphenyl)carbamoyl)-2,5,6-trichloronicotinamide Oxalyl chloride (2 M in DCM, 3.33 mL, 6.65 mmol) was added to 2,5,6-trichloronicotinamide (Intermediate P, 1 g, 4.44 mmol) in THF (10 mL), and the resulting mixture was stirred at 60° C. for 2 h. The reaction mixture was then cooled, concentrated to dryness under reduced pressure, and co-evaporated with heptane to give 2,5,6-trichloronicotinoyl isocyanate. 2,5,6-Trichloronicotinoyl isocyanate was then taken up in THF (15 mL), and 4-bromo-2-isopropyl-6-methylaniline (1.012 g, 4.44 mmol, Aurum Pharmatech. Franklin Park, N.J.) was added. The reaction mixture was stirred for 2 h, then concentrated in vacuo to provide N-((4-bromo-2-isopropyl-6-methylphenyl)carbamoyl)-2,5,6-trichloronicotinamide (2.12 g, 4.42 mmol, 100% yield), which was used in the next step without further purification. MS (ESI, +ve ion) m/z: 501.6 (M+Na)⁺.

Step 2: 1-(4-Bromo-2-isopropyl-6-methylphenyl)-6,7-dichloropyrido[2,3-d]pyrimidine-2,4(1H,3H)-dione Potassium bis(trimethylsilyl)amide (1 M in THF, 8.8 mL, 8.8 mmol) was added, dropwise, to a stirred solution of N-((4-bromo-2-isopropyl-6-methylphenyl)carbamoyl)-2,5,6-trichloronicotinamide (2.12 g, 4.42 mmol) in tetrahydrofuran (15 mL) at 0° C. After the addition was complete, the reaction mixture was stirred for 2 h. Water was then added, and the mixture was extracted with EtOAc (3×). The extracts were dried over MgSO4, concentrated in vacuo, and used to the next step without further purification.

Step 3: tert-Butyl (S)-4-(1-(4-bromo-2-isopropyl-6-methylphenyl)-6,7-dichloro-2-oxo-1,2-dihydropyrido[2,3-d]pyrimidin-4-yl)-3-methylpiperazine-1-carboxylate DIPEA (1.169 mL, 6.60 mmol) and POCl₃ (0.615 mL, 6.60 mmol) were sequentially added to a stirred solution of 1-(4-bromo-2-isopropyl-6-methylphenyl)-6,7-dichloropyrido[2,3-d]pyrimidine-2,4(1H,3H)-dione (1.95 g, 4.40 mmol) in MeCN (20 mL). After the addition was complete, the reaction mixture was stirred at 85° C. for 2 h. The reaction mixture was then cooled, concentrated in vacuo, and co-evaporated with heptane to give crude 1-(4-bromo-2-isopropyl-6-methylphenyl)-4,6,7-trichloropyrido[2,3-d]pyrimidin-2(1H)-one This material was taken up in DCM (20 mL) and cooled to 0° C. DIPEA (3.90 mL, 22.0 mmol) and tert-butyl (S)-3-methylpiperazine-1-carboxylate (0.881 g, 4.40 mmol) were sequentially added, and the resulting mixture was stirred at 0° C. for 3 h. Water was added, and the organic layer was separated, dried over MgSO₄, and concentrated in vacuo. Chromatographic purification of the residue (eluent: 40% EtOAc/heptane) furnished tert-butyl (S)-4-(1-(4-bromo-2-isopropyl-6-methylphenyl)-6,7-dichloro-2-oxo-1,2-dihydropyrido[2,3-d]pyrimidin-4-yl)-3-methylpiperazine-1-carboxylate (1.39 g, 2.22 mmol, 51% yield). ¹H NMR (DMSO-d₆) δ 8.43 (br d, J=7.9 Hz, 1H), 7.45 (br d, J=14.9 Hz, 2H), 4.75-4.92 (m, 1H), 4.10-4.22 (m, 1H), 3.90-4.05 (m, 1H), 3.82 (br d, J=12.2 Hz, 1H), 3.59-3.75 (m, 1H), 3.18-3.29 (m, 1H), 2.97-3.15 (m, 1H), 2.40-2.47 (m, 1H), 1.88 (br s, 3H), 1.44 (s, 9H), 1.31 (br t, J=6.6 Hz, 3H), 1.04 (br d, J=6.4 Hz, 3H), 0.98 (br d, J=6.6 Hz, 3H). m/z (ESI, +ve ion): 626.0 (M+H)⁺.

Step 4: tert-Butyl (S)-4-(1-(4-bromo-2-isopropyl-6-methylphenyl)-6-chloro-7-(2-fluorophenyl)-2-oxo-1,2-dihydropyrido[2,3-d]pyrimidin-4-yl)-3-methyl piperazine-1-carboxylate A mixture of tert-butyl (S)-4-(1-(4-bromo-2-isopropyl-6-methylphenyl)-6,7-dichloro-2-oxo-1,2-dihydropyrido[2,3-d]pyrimidin-4-yl)-3-methylpiperazine-1-carboxylate (1.08 g, 1.73 mmol), (2-fluorophenyl)boronic acid (267 mg, 1.91 mmol, Combi-Blocks, San Diego, Calif.), sodium carbonate (551 mg, 5.20 mmol), and tetrakis(triphenylphosphine)palladium(0) (100 mg, 0.087 mmol) in 1,4-dioxane (20 mL)/water (4 mL) was sparged with argon, then heated at 90° C. for 16 h. The reaction mixture was then cooled, concentrated in vacuo, and water was added. The precipitated solid was collected by filtration and dried in vacuo. Chromatographic purification of this solid (silica gel, eluent: 0-50% EtOAc/heptane) provided tert-butyl (S)-4-(1-(4-bromo-2-isopropyl-6-methylphenyl)-6-chloro-7-(2-fluorophenyl)-2-oxo-1,2-dihydropyrido[2,3-d]pyrimidin-4-yl)-3-methylpiperazine-1-carboxylate (889 mg, 1.30 mmol, 74.9% yield). $^1$H NMR (DMSO-$d_6$) δ 8.42 (s, 1H), 7.48-7.60 (m, 1H), 7.37 (br d, J=6.8 Hz, 1H), 7.26-7.35 (m, 3H), 7.19-7.25 (m, 1H), 4.89 (br s, 1H), 4.20-4.28 (m, 1H), 3.90-4.03 (m, 2H), 3.84 (br d, J=13.1 Hz, 1H), 3.71 (br t, J=11.9 Hz, 1H), 3.05-3.22 (m, 1H), 2.52-2.63 (m, 1H), 1.88 (s, 3H), 1.45 (s, 9H), 1.35 (br d, J=5.6 Hz, 3H), 1.05 (br d, J=6.4 Hz, 3H), 0.85-0.96 (m, 3H). mm/z (ESI, +ve): 685.8 (M+H)$^+$.

Step 5: (S)-4-(4-(4-(tert-Butoxycarbonyl)-2-methylpiperazin-1-yl)-6-chloro-7-(2-fluorophenyl)-2-oxopyrido[2,3-d]pyrimidin-1(2H)-yl)-3-isopropyl-5-methylbenzoic acid A mixture of tert-butyl (S)-4-(1-(4-bromo-2-isopropyl-6-methylphenyl)-6-chloro-7-(2-fluorophenyl)-2-oxo-1,2-dihydropyrido[2,3-d]pyrimidin-4-yl)-3-methylpiperazine-1-carboxylate (678 mg, 0.990 mmol), methanesulfonato[9,9-dimethyl-4,5-bis(diphenylphosphino)xanthene][2'-amino-1,1'-biphenyl]palladium(II) dichloromethane adduct (205 mg, 0.198 mmol, Strem Chemicals, Newburyport, Mass.), sodium carbonate (315 mg, 2.97 mmol), and water (0.178 mL, 9.90 mmol) in DMF (10 mL) was stirred in a 2-necked flask. $CO_{(g)}$ was bubbled through the mixture for 10 min, then the mixture was heated to 80° C. with very slow bubbling $CO_{(g)}$ for 2 h. The mixture was subsequently cooled, and water was added. 2 N HCl was added to adjust the pH to 4, precipitating a gray solid. This solid was collected, washed with water, and dried in vacuo to provide (S)-4-(4-(4-(tert-butoxycarbonyl)-2-methylpiperazin-1-yl)-6-chloro-7-(2-fluorophenyl)-2-oxopyrido[2,3-d]pyrimidin-1(2H)-yl)-3-isopropyl-5-methylbenzoic acid (643 mg, 0.989 mmol, 100% yield), which was used in the next step without further purification. m/z (ESI, +ve): 650.0 (M+H)$^+$.

Step 6: tert-Butyl (S)-4-(6-chloro-7-(2-fluorophenyl)-1-(2-isopropyl-4-(methoxycarbonyl)-6-methylphenyl)-2-oxo-1,2-dihydropyrido[2,3-d]pyrimidin-4-yl)-3-methylpiperazine-1-carboxylate Iodomethane (0.692 mL, 1.38 mmol) was added to a mixture of (S)-4-(4-(4-tert-butoxycarbonyl)-2-methylpiperazin-1-yl)-6-chloro-7-(2-fluorophenyl)-2-oxopyrido[2,3-d]pyrimidin-1(2H)-yl)-3-isopropyl-5-methylbenzoic acid (600 mg, 0.923 mmol) and $K_2CO_3$ (191 mg, 1.38 mmol) in DMF (10 mL), and the resulting mixture was stirred at RT for 2 h. Water was then added, and the precipitated solid was collected, washed with water, and dried in vacuo. Chromatographic purification of this solid (silica gel, eluent: 40% EtOAc/heptane) provided tert-butyl (S)-4-(6-chloro-7-(2-fluorophenyl)-1-(2-isopropyl-4-(methoxycarbonyl)-6-methylphenyl)-2-oxo-1,2-dihydropyrido[2,3-d]pyrimidin-4-yl)-3-methylpiperazine-1-carboxylate (436 mg, 0.657 mmol, 71.2% yield). $^1$H NMR (DMSO-$d_6$) δ 8.43 (br s, 1H), 7.79 (s, 1H), 7.74 (s, 1H), 7.46-7.55 (m, 1H), 7.23-7.33 (m, 2H), 7.15-7.22 (m, 1H), 4.90 (br s, 1H), 4.25 (br d, J=13.9 Hz, 1H), 3.92-4.05 (m, 1H), 3.84 (s, 4H), 3.66-3.77 (m, 1H), 3.32-3.39 (m, 1H), 3.07-3.26 (m, 1H), 2.55-2.65 (m, 1H), 1.95 (s, 3H), 1.45 (s, 9H), 1.36 (br d, J=6.4 Hz, 3H), 1.08 (br d, J=6.6 Hz, 3H), 0.93-0.98 (m, 3H). $^{19}$F NMR (DMSO-$d_6$) δ −114.16 (br d, J=8.7 Hz, 1F). m/z (ESI, +ve): 664.0 (M+H)$^+$.

Step 7: Methyl 4-(6-chloro-7-(2-fluorophenyl)-4-((2S)-2-methyl-4-(2-propenoyl)-1-piperazinyl)-2-oxopyrido[2,3-d]pyrimidin-1(2H)-yl)-3-methyl-5-(2-propanyl)benzoate TFA (0.483 mL, 6.26 mmol) was added to a solution of tert-butyl (S)-4-(6-chloro-7-(2-fluorophenyl)-1-(2-isopropyl-4-(methoxycarbonyl)-6-methylphenyl)-2-oxo-1,2-dihydropyrido[2,3-d]pyrimidin-4-yl)-3-methylpiperazine-1-carboxylate (208 mg, 0.313 mmol) in DCM (5 mL), and the resulting mixture was stirred at rt for 2 h, then concentrated to dryness in vacuo. The residue was partitioned between saturated aqueous $NaHCO_3$ and DCM, and the organic layer was separated. The aqueous layer was extracted with DCM (3×), and all organic extracts were then combined, dried over $Na_2SO_4$ and concentrated in vacuo to give methyl (S)-4-(6-chloro-7-(2-fluorophenyl)-4-(2-methyl piperazin-1-yl)-2-oxopyrido[2,3-d]pyrimidin-1(2H)-yl)-3-isopropyl-5-methylbenzoate as a yellow solid that was used without further purification. m/z (ESI, +ve): 563.9 (M+H)$^+$.

DIPEA (0.073 mL, 0.420 mmol) and acryloyl chloride (0.255 mL, 0.280 mmol) were sequentially added to a solution of methyl (S)-4-(6-chloro-7-(2-fluorophenyl)-4-(2-methylpiperazin-1-yl)-2-oxopyrido[2,3-d]pyrimidin-1(2H)-yl)-3-isopropyl-5-methylbenzoate (158 mg, 0.280 mmol) in DCM (5 mL) at 0° C., and the resulting mixture was stirred at 0° C. for 2 h. The mixture was then concentrated in vacuo, and the residue was purified by silica gel chromatography (eluent: 0-30% EtOAc-EtOH (3:1) heptane) to provide methyl 4-(6-chloro-7-(2-fluorophenyl)-4-((2S)-2-methyl-4-(2-propenoyl)-1-piperazinyl)-2-oxopyrido[2,3-d]pyrimidin-1(2H)-yl)-3-methyl-5-(2-propanyl)benzoate. $^1$H NMR (DMSO-$d_6$) δ 8.46 (br s, 1H), 7.71-7.83 (m, 2H), 7.50 (br d, J=6.2 Hz, 1H), 7.24-7.34 (m, 2H), 7.16-7.23 (m, 1H), 6.79-6.92 (m, 1H), 6.21 (br d, J=16.8 Hz, 1H), 5.76 (br d, J=10.6 Hz, 1H), 4.95 (br s, 1H), 4.24-4.46 (m, 2H), 3.99-4.21 (m, 1H), 3.85 (s, 3H), 3.77 (br d, J=9.1 Hz, 1H), 3.43-3.69 (m, 1H), 3.04-3.25 (m, 1H), 2.61 (br d, J=5.8 Hz, 1H), 1.96 (br s, 3H), 1.34 (br d, J=6.4 Hz, 3H), 1.08 (br d, J=6.4 Hz, 3H), 0.96 (br d, J=6.4 Hz, 3H). $^{19}$F NMR (DMSO-$d_6$) δ −114.16 (br d, J=11.3 Hz, 1F). m/z (ESI, +ve): 618.0 (M+H)$^+$.

735
Example 157
4-((2S,5R)-4-acryloyl-2,5-dimethylpiperazin-1-yl)-1-(2-isopropylphenyl)-7-phenyl-5,6,7,8-tetrahydropyrido[3,4-d]pyrimidin-2(1H)-one
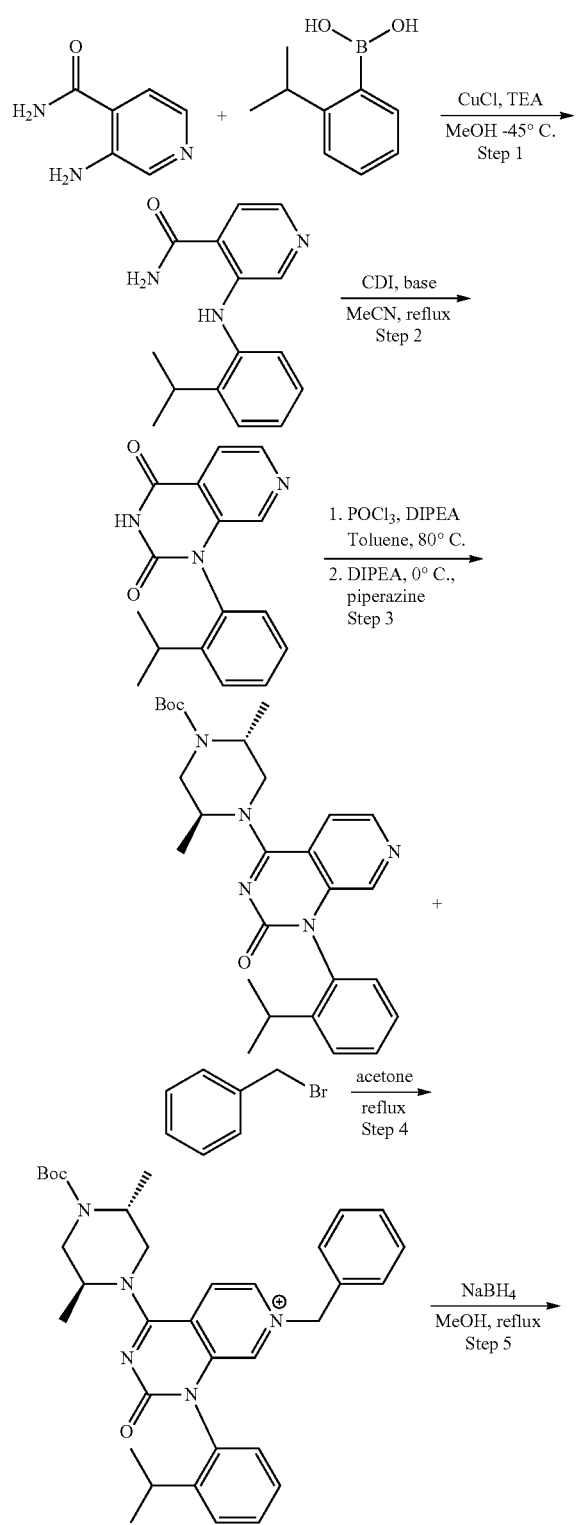
736
-continued
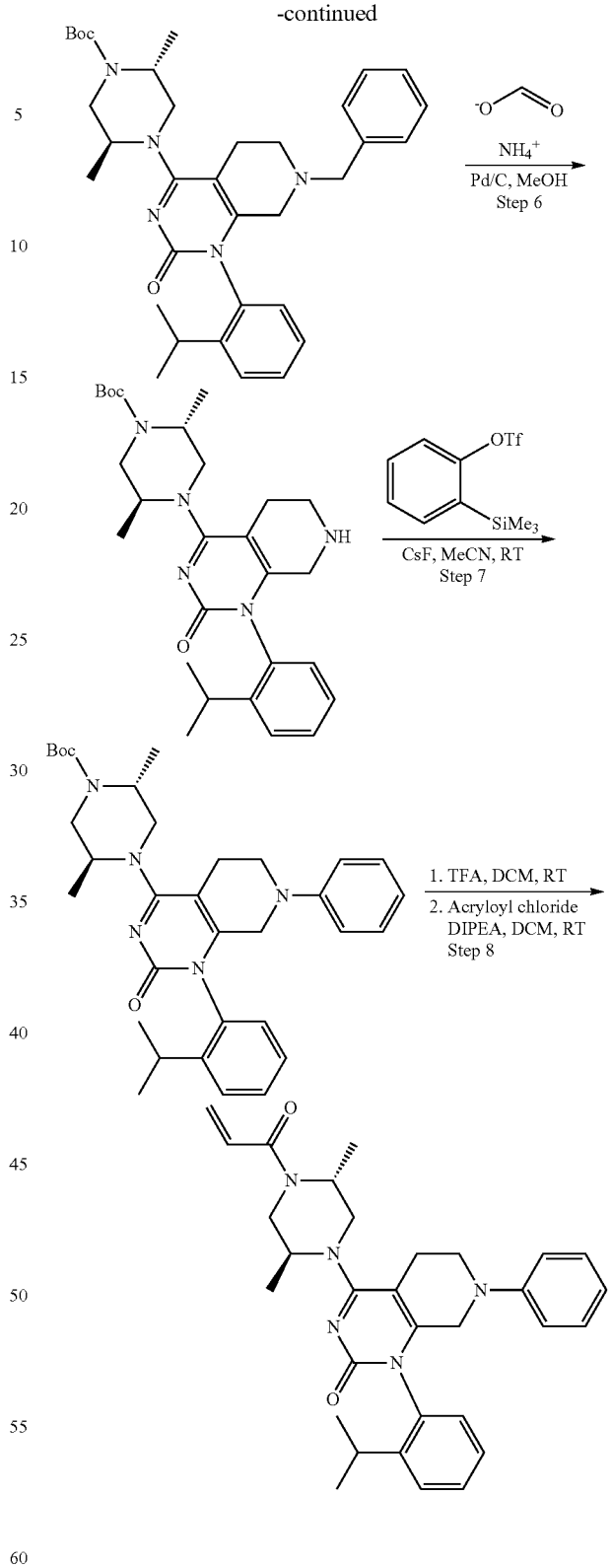
Step 1:
3-((2-isopropylphenyl)amino)isonicotinamide
A mixture of [2-(1-methylethyl)phenyl]-boronic acid (8.97 g, 54.7 mmol), [2-(1-methylethyl)phenyl]-boronic acid (8.97 g, 54.7 mmol), copper chloride (0.541 g, 5.47 mmol) and TEA (2.54 ml, 18.23 mmol) was purged with $N_2$ followed by the addition of MeOH (100 mL) and the resulting mixture was stirred at rt overnight. The reaction was quenched with a 9:1 sat. NH$_4$Cl/NH$_4$OH, and extracted with DCM. The combined organics were dried over Na$_2$SO$_4$, filtered, concentrated and chromatographed on silica gel using 0-5% MeOH in DCM to afford 3-((2-isopropylphenyl) amino)isonicotinamide (0.97 g, 3.80 mmol, 10.42% yield) as a yellow solid. m/z (ESI, +ve ion): 256 (M+H)$^+$. $^1$H NMR (400 MHz, DMSO-d$_6$) δ ppm 9.65 (s, 1H), 8.32-8.38 (m, 1H), 8.20 (s, 1H), 7.96 (d, J=5.2 Hz, 1H), 7.78 (br s, 1H), 7.60 (d, J=5.2 Hz, 1H), 7.39 (dd, J=7.6, 1.6 Hz, 1H), 7.28-7.32 (m, 1H), 7.15-7.25 (m, 2H), 3.04-3.19 (m, 1H), 1.19 (d, J=6.8 Hz, 6H).

Step 2: 1-(2-isopropylphenyl)pyrido[3,4-d]pyrimidine-2,4(1H,3H)-dione

A mixture of 3-((2-isopropylphenyl)amino)isonicotinamide (1.51 g, 5.91 mmol), pyridine (1.435 ml, 17.74 mmol) and CDI (2.88 g, 17.74 mmol) in MeCN (100 mL) was heated at 85° C. overnight. The mixture was quenched with sat. NaHCO$_3$, and extracted with EtOAc. The combined organics were dried over Na$_2$SO$_4$, filtered, concentrated and chromatographed on silica gel using 0-50% EtOAc in heptane to afford 1-(2-isopropylphenyl)pyrido[3,4-d]pyrimidine-2,4(1H,3H)-dione (1.3 g, 4.62 mmol, 78% yield) as a white solid. m/z (ESI, +ve ion): 281.8 (M+H)$^+$. $^1$H NMR (400 MHz, DMSO-d$_6$) δ ppm 12.03 (s, 1H), 8.48 (d, J=5.2 Hz, 1H), 7.92 (d, J=5.0 Hz, 1H), 7.70 (s, 1H), 7.54-7.66 (m, 2H), 7.42-7.47 (m, 1H), 7.32-7.41 (m, 1H), 2.71-2.85 (m, 1H), 1.13 (d, J=6.8 Hz, 3H), 1.05 (d, J=6.8 Hz, 3H).

Step 3: tert-butyl (2R,5S)-4-(1-(2-isopropylphenyl)-2-oxo-1,2-dihydropyrido[3,4-d]pyrimidin-4-yl)-2,5-dimethylpiperazine-1-carboxylate A suspension of 1-(2-isopropylphenyl)pyrido[3,4-d]pyrimidine-2,4(1H,3H)-dione (0.186 g, 0.661 mmol) in toluene (3 mL) was added 1,1'-dimethyltriethylamine (1.155 mL, 6.61 mmol) and phosphorous oxychloride (0.308 mL, 3.31 mmol) and the resulting mixture was heated at 80° C. After 5 min, the mixture went into solution and the heating continued for 30 min. LCMS showed complete conversion to desired intermediate. The reaction mixture was cooled to 0° C. and 10 equiv DIEA was added followed by (2R,5S)-tert-butyl 2,5-dimethylpiperazine-1-carboxylate (0.213 mL, 0.992 mmol). This mixture was stirred with warming to rt over 1 h at which time LCMS showed conversion to desired product. The mixture was poured into cold satd. NaHCO$_3$ solution and stirred vigorously for 10 min. The mixture was extracted with EtOAc, the combined organics were dried over Na$_2$SO$_4$, filtered, concentrated and chromatographed on silica gel using 0-40% EtOAc in heptane to afford tert-butyl (2R,5S)-4-(1-(2-isopropylphenyl)-2-oxo-1,2-dihydropyrido[3,4-d]pyrimidin-4-yl)-2,5-dimethylpiperazine-1-carboxylate (0.281 g, 0.588 mmol, 89% yield) as a light yellow foam. m/z (ESI, +ve ion): 477.8 (M+H)$^+$. $^1$H NMR (400 MHz, DMSO-d$_6$) δ ppm 8.39 (dd, J=5.4, 2.9 Hz, 1H), 7.72-7.80 (m, 2H), 7.50-7.65 (m, 2H), 7.38-7.47 (m, 1H), 7.21-7.31 (m, 1H), 4.72-4.85 (m, 1H), 4.23-4.43 (m, 1H), 4.00-4.14 (m, 2H), 3.67-3.81 (m, 2H), 3.40-3.60 (m, 1H), 1.45 (s, 9H), 1.31 (dd, J=9.1, 6.6 Hz, 3H), 1.15-1.21 (m, 3H), 1.11 (dd, J=6.6, 4.8 Hz, 3H), 1.00 (dd, J=6.8, 4.8 Hz, 3H).

Step 4: 7-benzyl-4-((2S,5R)-4-(tert-butoxycarbonyl)-2,5-dimethylpiperazin-1-yl)-1-(2-isopropylphenyl)-2-oxo-1,2-dihydropyrido[3,4-d]pyrimidin-7-ium A mixture of tert-butyl (2R,5S)-4-(1-(2-isopropylphenyl)-2-oxo-1,2-dihydropyrido[3,4-d]pyrimidin-4-yl)-2,5-dimethylpiperazine-1-carboxylate (0.36 g, 0.754 mmol) and (bromomethyl)benzene (0.193 mL, 1.131 mmol) in acetone (20 mL) was heated to reflux for 1 h. Some product was observed, mostly starting material. More (bromomethyl) benzene (0.193 mL, 1.131 mmol) was added and the resulting mixture was heated to reflux overnight. The mixture was brought to rt, concentrated and chromatographed on a small amount of silica gel using 0-10% MeOH in DCM to afford 7-benzyl-4-((2S,5R)-4-(tert-butoxycarbonyl)-2,5-dimethylpiperazin-1-yl)-1-(2-isopropylphenyl)-2-oxo-1,2-dihydropyrido[3,4-d]pyrimidin-7-ium (0.401 g, 0.705 mmol, 94% yield) as a yellow solid. m/z (ESI, +ve ion): 567.8 (M+H)$^+$. $^1$H NMR (400 MHz, DMSO-d$_6$) δ ppm 8.84 (br d, J=6.8 Hz, 1H), 8.30-8.40 (m, 2H), 7.56-7.65 (m, 2H), 7.34-7.48 (m, 6H), 7.25 (d, J=8.1 Hz, 1H), 5.87-5.90 (m, 2H), 4.66-4.76 (m, 1H), 4.24-4.46 (m, 1H), 4.01-4.15 (m, 1H), 3.66-3.87 (m, 2H), 3.41-3.61 (m, 1H), 2.58-2.66 (m, 1H), 1.45 (s, 9H), 1.34 (t, J=5.5 Hz, 3H), 1.18 (dd, J=14.5, 6.8 Hz, 3H), 1.08 (d, J=6.8 Hz, 3H), 0.95 (dd, J=10.8, 6.8 Hz, 3H).

Step 5: tert-butyl (2R,5S)-4-(7-benzyl-1-(2-isopropylphenyl)-2-oxo-1,2,5,6,7,8-hexahydropyrido[3,4-d]pyrimidin-4-yl)-2,5-dimethylpiperazine-1-carboxylate 7-benzyl-4-((2S,5R)-4-(tert-butoxycarbonyl)-2,5-dimethylpiperazin-1-yl)-1-(2-isopropylphenyl)-2-oxo-1,2-dihydropyrido[3,4-d]pyrimidin-7-ium was dissolved in 80% aq. MeOH (20 mL) and brought to 0° C. Then. NaBH$_4$ (0.570 g, 15.08 mmol) was added and the resulting mixture was heated to reflux for 20 min. The reaction went to completion, brought to rt, carefully quenched with sat. NaHCO$_3$ and extracted with DCM. The combined organics were dried over Na$_2$SO$_4$, filtered and concentrated to afford tert-butyl (2R,5S)-4-(7-benzyl-1-(2-isopropylphenyl)-2-oxo-1,2,5,6,7,8-hexahydropyrido[3,4-d]pyrimidin-4-yl)-2,5-dimethylpiperazine-1-carboxylate. m/z (ESI, +ve ion): 571.8 (M+H)$^+$.

Step 6: tert-butyl (2R,5S)-4-(1-(2-isopropylphenyl)-2-oxo-1,2,5,6,7,8-hexahydropyrido[3,4-d]pyrimidin-4-yl)-2,5-dimethylpiperazine-1-carboxylate To a solution of tert-butyl (2R,5S)-4-(7-benzyl-1-(2-isopropylphenyl)-2-oxo-1,2,5,6,7,8-hexahydropyrido[3,4-d] pyrimidin-4-yl)-2,5-dimethylpiperazine-1-carboxylate (0.280 g, 0.490 mmol) in MeOH (15 mL) was added palladium 10 wt. % on activated carbon (0.365 g, 0.343 mmol) and ammonium formate (0.309 g, 4.90 mmol) and the resulting mixture was heated to reflux. After 20 min the starting material was consumed and desired mass was observed. The mixture was brought to rt, filtered through celite, concentrated and chromatographed on silica gel using 0-100% 3:1EtOAc/EtOH in heptane to afford tert-butyl (2R,5S)-4-(1-(2-isopropylphenyl)-2-oxo-1,2,5,6,7,8-hexahydropyrido[3,4-d]pyrimidin-4-yl)-2,5-dimethylpiperazine-1-carboxylate (0.105 g, 0.218 mmol, 44.5% yield) as a white solid. m/z (ESI, +ve ion): 481.8 (M+H)$^+$. $^1$H NMR (400 MHz, DMSO-d$_6$) δ ppm 7.39-7.51 (m, 2H), 7.25-7.34 (m, 1H), 7.13-7.18 (m, 1H), 7.03-7.11 (m, 1H), 4.38-4.53 (m, 1H), 4.12-4.38 (m, 1H), 3.93-4.06 (m, 1H), 3.58-3.74 (m, 2H), 3.40-3.49 (m, 2H), 2.98-3.16 (m, 2H), 2.73-2.94 (m, 2H), 2.36-2.46 (m, 2H), 1.41-1.47 (m, 9H), 1.10-1.19 (m, 8H), 1.03-1.10 (m, 4H).

Steps 7 & 8: 4-((2S,5R)-4-acryloyl-2,5-dimethylpiperazin-1-yl)-1-(2-isopropylphenyl)-7-phenyl-5,6,7,8-tetrahydropyrido[3,4-d]pyrimidin-2(1H)-one, 3386882

A solution of tert-butyl (2R,5S)-4-(1-(2-isopropylphenyl)-2-oxo-1,2,5,6,7,8-hexahydropyrido[3,4-d]pyrimidin-4- yl)-2,5-dimethylpiperazine-1-carboxylate (0.060 g, 0.125 mmol) in acetonitrile (2 mL) was added to a stirring mixture of 2-(trimethylsilyl)phenyl triflate (0.056 g, 0.187 mmol) and cesium fluoride (0.057 g, 0.374 mmol) in acetonitrile (2 mL). The reaction mixture was stirred at rt for 1 hour, concentrated, diluted with water and extracted with EtOAc. The organic was concentrated to give a crude tert-butyl (2R,5S)-4-(1-(2-isopropylphenyl)-2-oxo-7-phenyl-1,2,5,6,7,8-hexahydropyrido[3,4-d]pyrimidin-4-yl)-2,5-dimethylpiperazine-1-carboxylate. m/z (ESI, +ve ion): 558.3 (M+H)⁺. This crude intermediate was dissolved in DCM (2 mL) and treated with TFA (0.288 mL, 3.74 mmol). The resulting mixture was stirred at rt for 1 hour and then concentrated in vacuo. The residue was suspended in DCM (2 mL) and treated with TEA (0.087 mL, 0.623 mmol) followed by acryloyl chloride (0.020 mL, 0.249 mmol). The reaction was stirred at rt for 10 minutes, quenched with water, and extracted with DCM. The organic was concentrated and the residue purified with ISCO using 0-100% EtOAc/EtOH (3:1) in heptane to afford 4-((2S,5R)-4-acryloyl-2,5-dimethylpiperazin-1-yl)-1-(2-isopropylphenyl)-7-phenyl-5,6,7,8-tetrahydropyrido[3,4-d]pyrimidin-2(1H)-one (0.008 g, 7.82 μmol, 6.28% yield) as a mixture of atropisomers. m/z (ESI, +ve ion): 512.4 (M+H)⁺. ¹H NMR (400 MHz, CHLOROFORM-d) δ 7.44-7.50 (m, 2H), 7.28-7.36 (m, 1H), 7.22 (t, J=7.88 Hz, 2H), 7.10-7.16 (m, 1H), 6.86 (t, J=7.26 Hz, 1H), 6.68 (br d, J=7.67 Hz, 2H), 6.35 (br t, J=15.96 Hz, 1H), 5.75 (br t, J=10.26 Hz, 1H), 4.85-5.02 (m, 1H), 4.19-4.44 (m, 1H), 3.89-4.05 (m, 1H), 3.75-3.89 (m, 1H), 3.49-3.74 (m, 4H), 3.30-3.46 (m, 1H), 3.03-3.28 (m, 1H), 2.80-2.93 (m, 1H), 2.54-2.80 (m, 2H), 1.77 (td, J=6.63, 13.27 Hz, 1H), 1.17-1.31 (m, 12H).

Section 3—Synthesis of Intermediates

Intermediate I-1

2-(1-(Trifluoromethyl)cyclopropyl)aniline

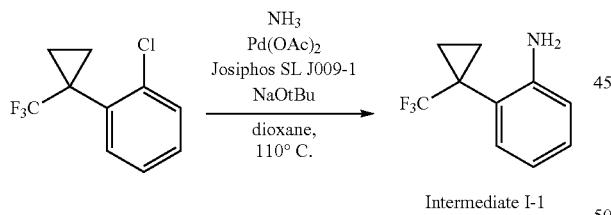

Intermediate I-1

Ammonia (0.5 M in dioxane, 20.4 mL, 10.20 mmol) was added to a mixture of 1-chloro-2-(1-trifluoromethyl-cyclopropyl)-benzene (0.90 g, 4.08 mmol, Oakwood Products, Inc. Estill, S.C.), palladium (II) acetate (0.046 g, 0.204 mmol, Sigma-Aldrich Corporation, St. Louis, Mo., USA), (R)-(−)-1-[(S)-2-(dicyclohexylphosphino)ferrocenyl]ethyldi-tert-butylphosphine (0.226 g, 0.408 mmol, Sigma-Aldrich Corporation, St. Louis, Mo., USA), and sodium tert-butoxide (0.588 g, 6.12 mmol, Sigma-Aldrich Corporation, St. Louis, Mo., USA), and the resulting mixture was heated at 110° C. in a sealed vial under an argon atmosphere for 6 h. The reaction mixture was subsequently cooled to rt, diluted with water, and extracted with EtOAc (100 mL). The organic layer was separated, washed with brine, dried over MgSO₄, filtered, and concentrated in vacuo. The crude product was purified by silica gel chromatography (eluent: 0-25% EtOAc/heptane) to provide 2-(1-(trifluoromethyl) cyclopropyl)aniline as an orange oil (Intermediate I-1, 650 mg, 3.23 mmol, 79% yield). ¹H NMR (400 MHz, CDCl₃) δ ppm 7.25-7.29 (1H, m) 7.11-7.17 (1H, m) 6.75 (1H, td, J=7.46, 1.04 Hz) 6.69 (1H, dd, J=8.09, 1.04 Hz) 3.98 (2H, br s) 1.40-1.45 (2H, m) 1.04-1.09 (2H, m). m/z (ESI, +ve ion): 201.9 (M+H)⁺.

Intermediate I-2

3-Cyclopropylpyridin-2-amine

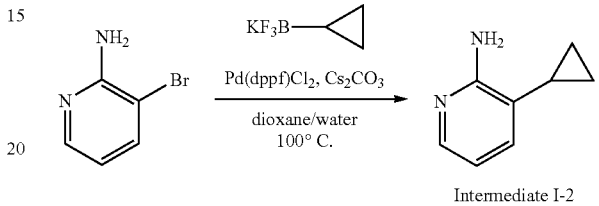

Intermediate I-2

A mixture of 2-amino-3-bromopyridine (5.15 g, 29.8 mmol), cyclopropyl trifluoroborate potassium salt (8.81 g, 59.6 mmol: Combi-Blocks, Inc., San Diego, Calif., USA), (1,1'-bis(diphenylphosphino)ferrocene) dichloropalladium (1.14 g, 1.56 mmol), and cesium carbonate (29 g, 89 mmol) in 1,4-dioxane (68 mL)/water (7 mL) was sparged with nitrogen then stirred at 100° C. for 7 h. The reaction mixture was then diluted with EtOAc and washed with water. The organic layer was separated, dried over anhydrous Na₂SO₄, and concentrated in vacuo. The crude product was purified by silica gel chromatography (eluent: 0-70% EtOAc-EtOH (3:1)/heptane) to provide 3-cyclopropylpyridin-2-amine (Intermediate I-2, 2.66 g, 19.8 mmol, 67% yield) as an amber oil. ¹H NMR (400 MHz, CDCl₃) δ ppm 7.94 (dd, J=5.0, 1.2 Hz, 1H) 7.22-7.26 (m, 1H) 6.60 (dd, J=7.3, 5.2 Hz, 1H) 4.71 (br s, 2H) 1.57-1.68 (m, 1H) 0.88-0.96 (m, 2H) 0.56-0.63 (m, 2H). m/z (ESI, +ve ion): 135.1 (M+H)⁺.

Intermediate I-3

Di-tert-butyl (6-bromo-5-chloropyridin-2-yl)-2-imidodicarbonate

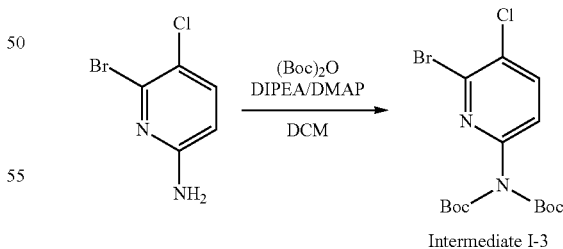

Intermediate I-3

A mixture of 2-amino-6-bromo-5-chloropyridine (1.03 g, 4.96 mmol, Combi-Blocks Inc., San Diego, Calif., USA), DMAP (60.1 mg, 0.49 mmol), DIPEA (2.17 mL, 12.41 mmol), and di-tert-butyl dicarbonate (2.709 g, 12.41 mmol) in DCM (24.8 mL) was stirred at rt for 18 h. The mixture was then diluted with satd. ammonium chloride (20 mL) and extracted with DCM (3×). The combined extracts were washed with water, dried over Na₂SO₄, filtered, and concentrated in vacuo. Chromatographic purification of the residue (silica gel, eluent: 0-10% EtOAc/heptane) provided di-tert-butyl (6-bromo-5-chloropyridin-2-yl)-2-imidodicarbonate (Intermediate I-3, 314 mg, 0.77 mmol, 16% yield) as a white solid. $^1$H NMR (400 MHz, DMSO-d$_6$) δ ppm 8.17 (d, J=8.3 Hz, 1H), 7.57 (d, J=8.3 Hz, 1H), 1.42 (s, 18H). m/z (ESI, +ve) 429.0 (M+Na)$^+$.

Intermediate I-4

4-(1-Methylcyclopropyl)pyrimidin-5-amine

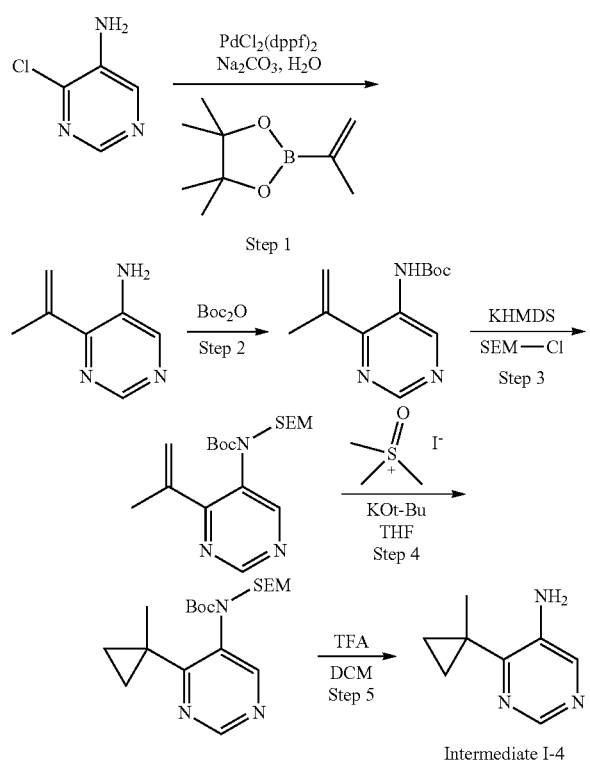

Intermediate I-4

Step 1: 4-(Prop-1-en-2-yl)pyrimidin-5-amine. A mixture of 4-chloropyrimidin-5-amine (1.75 g, 13.5 mmol, Frontier Scientific. Inc., Logan, Utah), 4,4,5,5-tetramethyl-2-(prop-1-en-2-yl)-1,3,2-dioxaborolane (4.54 g, 27.0 mmol, CombiBlocks, San Diego, Calif.), sodium carbonate (5.73 g, 54.0 mmol). and Pd(dppf)Cl$_2$ (1.483 g, 2.026 mmol) in 1,4-dioxane (20 mL)/water (2 mL) was heated at 90° C. for 5 h. The reaction mixture was then cooled, diluted with water, and extracted with EtOAc. The combined extracts were dried over MgSO$_4$ and concentrated in vacuo. Chromatographic purification of the residue (silica gel, eluent: 0-50% EtOAc-EtOH (3:1)/heptane) provided 4-(prop-1-en-2-yl)pyrimidin-5-amine as amber oil. $^1$H NMR (400 MHz, CDCl$_3$) δ ppm 8.66 (s, 1H), 8.25 (br s, 1H), 5.60 (s, 1H), 5.47 (s, 1H), 3.95 (br s, 2H), 2.18 (s, 3H). m/z (ESI, +ve ion): 136.1 (M+H)$^+$.

Step 2: tert-Butyl (4-(prop-1-en-2-yl)pyrimidin-5-yl)carbamate

A mixture of 4-(prop-1-en-2-yl)pyrimidin-5-amine (1.17 g, 8.66 mmol) and Boc-anhydride (3.01 mL, 13.0 mmol) in DMF (10 mL) was stirred at rt for 4 h, then at 50° C. for 16 h. The reaction mixture was then cooled, diluted with water, and extracted with EtOAc. The combined extracts were dried over MgSO$_4$, concentrated in vacuo, and purified by silica gel chromatography (eluent: 0-40% EtOAc/heptane) to provide tert-butyl (4-(prop-1-en-2-yl)pyrimidin-5-yl)carbamate (699 mg, 2.97 mmol, 34% yield). $^1$H NMR (400 MHz, CDCl$_3$) δ ppm 9.46 (s, 1H), 8.87 (s, 1H), 6.84 (br s, 1H), 5.54-5.71 (m, 1H), 5.32 (s, 1H), 2.18 (s, 3H), 1.53 (s, 10H). m/z (ESI, +ve ion): 236.1 (M+H)$^+$.

Step 3: tert-Butyl (4-(prop-1-en-2-yl)pyrimidin-5-yl)((2-(trimethylsilyl)ethoxy)methyl)carbamate KHMDS (1 M in THF, 2.45 mL, 2.45 mmol) was added to a solution of tert-butyl (4-(prop-1-en-2-yl)pyrimidin-5-yl)carbamate (525 mg, 2.231 mmol) in THF (8 mL) at 0° C., and the resulting mixture was stirred at 0° C. for 30 min. 2-(Trimethylsilyl)ethoxymethyl chloride (0.44 mL, 2.45 mmol) was then added, and the resulting mixture was stirred at rt for 2 h. The reaction mixture was then diluted with satd. ammonium chloride and extracted with EtOAc. The combined extracts were dried over MgSO$_4$, concentrated in vacuo, and purified by silica gel chromatography (eluent: 0-40% EtOAc/heptane) to furnish tert-butyl (4-(prop-1-en-2-yl)pyrimidin-5-yl)((2-(trimethylsilyl)ethoxy)methyl)carbamate (618 mg, 1.69 mmol, 76% yield). $^1$H NMR (400 MHz, CDCl$_3$) δ ppm 9.05 (s, 1H), 8.49-8.66 (m, 1H), 5.25-5.53 (m, 3H), 4.39 (br d, J=1.7 Hz, 1H), 3.62 (br s, 2H), 2.13 (s, 3H), 1.31-1.55 (m, 9H), 0.93 (br s, 2H), 0.00 (br s, 9H). m/z (ESI, +ve): 366.2 (M+H)$^+$.

Step 4: tert-Butyl (4-(1-methylcyclopropyl)pyrimidin-5-yl)((2-(trimethylsilyl)ethoxy) methyl)carbamate Potassium 2-methylpropan-2-olate (2.03 mL, 2.03 mmol) was added, dropwise, to a stirred solution of trimethylsulfoxonium iodide (446 mg, 2.029 mmol) in dimethyl sulfoxide (6.00 mL), and the resulting mixture was stirred at rt for 1 h. This mixture was then added to a solution of tert-butyl (4-(prop-1-en-2-yl)pyrimidin-5-yl)((2-(trimethylsilyl)ethoxy)methyl)carbamate (618 mg, 1.691 mmol) in THF (6 mL). and the resulting mixture was stirred at rt for 4 h, then at 60° C. for 16 h. The reaction was then diluted with satd. ammonium chloride and extracted with EtOAc. The combined extracts were dried over MgSO$_4$ and concentrated in vacuo to give tert-butyl (4-(1-methylcyclopropyl) pyrimidin-5-yl)((2-(trimethylsilyl)ethoxy) methyl)carbamate, which was used in the next step without further purification. m/z (ESI, +ve ion): 380.1 (M+H)$^+$.

Step 5: 4-(1-Methylcyclopropyl)pyrimidin-5-amine (Intermediate I-4)

TFA (1 mL) was added to a stirred suspension of tert-butyl (4-(1-methylcyclopropyl)pyrimidin-5-yl)((2-(trimethylsilyl) ethoxy)methyl)carbamate (0.587 g, 1.546 mmol) in DCM (5 mL), and the resulting mixture was stirred at rt for 3 h, then concentrated in vacuo. The residue was treated with water, and satd. aq. Na2CO$_3$ was added to achieve a pH of 9. The resulting mixture was extracted with DCM, and the combined extracts were dried over Na$_2$SO$_4$, concentrated in vacuo, and purified by silica gel chromatography (eluent: 0-50% EtOAc-EtOH (3:1)/heptane) to provide 4-(1-methylcyclopropyl)pyrimidin-5-amine (Intermediate I-4, 0.195 g, 1.31 mmol, 85% yield). $^1$H NMR (40 MHz, CDCl$_3$) δ: 8.61

(s, 1H), 8.14 (s, 1H), 3.72-4.21 (m, 2H), 1.42 (s, 3H), 0.97-1.03 (m, 2H), 0.83-0.88 (m, 2H). m/z (ESI, +ve): 150.1 (M+H)+.

Intermediate I-5

4-Isopropyl-6-methylpyrimidin-5-amine

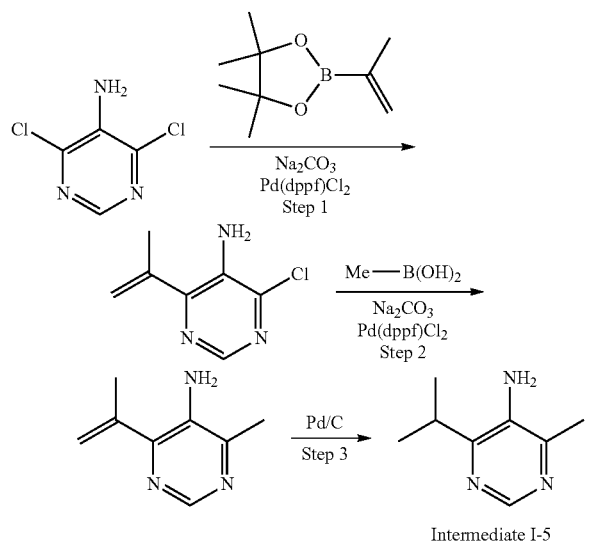

Intermediate I-5

Step 1: 4-Chloro-6-(prop-1-en-2-yl)pyrimidin-5-amine

A mixture of 4,6-dichloro-5-aminopyrimidine (5.00 g, 30.5 mmol), 2-isopropenylboronic acid, pincol ester (6.15 g, 36.6 mmol, Combi-Blocks, San Diego, Calif.), Pd(dppf)Cl₂ (2.23 g, 3.05 mmol), and sodium carbonate (9.69 g, 91 mmol) in a mixture of 1,4-dioxane (40 mL) and water (10 mL) was sparged with N₂ then heated at 95° C. for 2 h. The mixture was cooled to rt, satd. aq. NaHCO₃ was added, and the resulting mixture was extracted with EtOAc. The combined extracts were concentrated in vacuo, and the residue was purified by silica gel chromatography (eluent: 0-40% EtOAc/heptane) to provide 4-chloro-6-(prop-1-en-2-yl)pyrimidin-5-amine (1.24 g, 7.31 mmol, 24% yield) as a yellow oil. m/z (ESI, +ve ion): 170.0 (M+H)+.

Step 2: 4-Methyl-6-(prop-1-en-2-yl)pyrimidin-5-amine

A mixture of 4-chloro-6-(prop-1-en-2-yl)pyrimidin-5-amine (2.0 g, 11.79 mmol), methylboronic acid (3.53 g, 59.0 mmol, Combi-Blocks, San Diego, Calif.), Pd(dppf)Cl₂ (0.863 g, 1.179 mmol) and sodium carbonate (6.25 g, 59.0 mmol) in 1,4-dioxane (40 mL) and water (10 mL) was sparged with N₂, then heated at 95° C. for 17 h. The mixture was then cooled to rt, diluted with satd. aq. NaHCO₃, and extracted with EtOAc. The combined extracts were concentrated in vacuo. and the residue was purified by silica gel chromatography (eluent: 0-5% MeOH/DCM) to provide 4-methyl-6-(prop-1-en-2-yl)pyrimidin-5-amine (1.3 g, 8.71 mmol, 73.9% yield). m/z (ESI, +ve ion): 150.2 (M+H)+.

Step 3: 4-Isopropyl-6-methylpyrimidin-5-amine (Intermediate I-5)

Palladium 10 wt. % on activated carbon (0.522 g, 0.491 mmol) was added to a solution of 4-methyl-6-(prop-1-en-2-yl)pyrimidin-5-amine (1.464 g, 9.81 mmol) in EtOH (30 mL), and the resulting suspension was stirred under hydrogen gas (30 psi) for 1.5 h. The resulting mixture was subsequently filtered through Celite, and the filtrate was concentrated in vacuo to provide 4-isopropyl-6-methylpyrimidin-5-amine (Intermediate I-5, 1.48 g, 9.79 mmol, 100% yield) as a brown oil. ¹H NMR (400 MHz, DMSO-d₆) δ: 7.96-8.30 (m, 1H), 4.94-5.11 (m, 2H), 3.12-3.27 (m, 1H), 2.22-2.31 (m, 3H), 1.13-1.16 (m, 6H). m/z (ESI, +ve ion): 152.2 (M+H)+.

Intermediate I-6

3-(tert-Butyl)pyrazin-2-amine

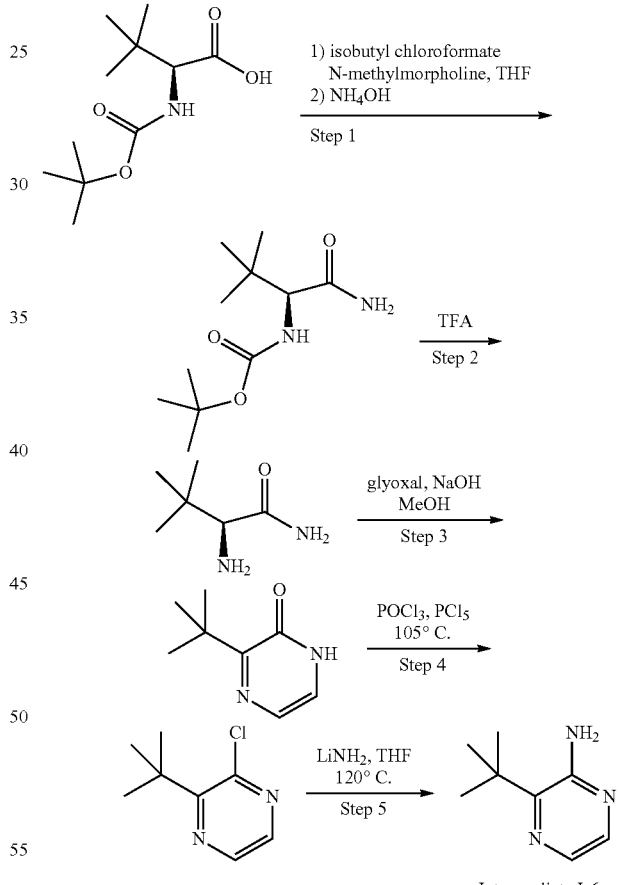

Intermediate I-6

Step 1: tert-Butyl (S)-(1-amino-3,3-dimethyl-1-oxobutan-2-yl)carbamate

Isobutyl chloroformate (8.9 mL, 68.7 mmol) was added dropwise to a solution of Boc-L-tert-leucine (14.4 g, 62.4 mmol, Alfa Aesar, Tewksbury, Mass.), and the resulting mixture was stirred at 0° C. for 30 min. Ammonium hydroxide (30% aq.; 16.2 mL, 125 mmol) was added, and the resulting mixture was allowed to warm to rt and to stir for 1.5 h. The reaction mixture was then concentrated in vacuo, and the residue was taken up in EtOAc (150 mL) and sequentially washed with 1 N aqueous citric acid (2×75 mL) and satd. NaHCO₃ (2×75 mL). The organic layer was dried over anhydrous Na₂SO₄, filtered, and concentrated in vacuo to give tert-butyl (S)-(1-amino-3,3-dimethyl-1-oxobutan-2-yl)carbamate (14.03 g, 60.9 mmol, 98% yield) as a colorless hygroscopic oil. ¹H NMR (400 MHz, DMSO-d₆) δ ppm 7.31 (br s, 1H) 7.02 (br s, 1H) 6.29 (br d, J=9.5 Hz, 1H) 3.79 (br d, J=9.5 Hz, 1H) 1.38 (s, 9H) 0.89 (s, 9H). m/z (ESI, +ve ion): 253.1 (M+Na)⁺.

Step 2: (S)-2-Amino-3,3-dimethylbutanamide

TFA (46.9 mL, 609 mmol) was added to a solution of tert-butyl (S)-(1-amino-3,3-dimethyl-1-oxobutan-2-yl)carbamate (14.03 g, 60.9 mmol) in DCM (200 mL) at 0° C., and the resulting mixture was stirred at 0° C. for 15 min, then at rt for 6 h. The reaction mixture was subsequently concentrated in vacuo to give (S)-2-amino-3,3-dimethylbutanamide TFA salt which was used without further purification. m/z (ESI, +ve ion): 131.1 (M+H)⁺.

Step 3: 3-(tert-Butyl)pyrazin-2(1H)-one

Sodium hydroxide (10 N, aq.; 30.5 mL, 305 mmol) was added to a solution of (S)-2-amino-3,3-dimethylbutanamide TFA salt (13.90 g, 60.9 mmol) and glyoxal (40% aqueous; 7.8 mL, 60.9 mmol, Sigma-Aldrich Corporation, St. Louis, Mo., USA) in MeOH (61 mL), and the resulting mixture was stirred at rt for 1 h. Acetic acid (1 mL) and was then added, and the resulting mixture was diluted with EtOAc (200 mL) and washed with satd. ammonium chloride (4×75 mL). The organic layer was then separated, dried over Na₂SO₄, filtered, and concentrated in vacuo to give 3-(tert-butyl)pyrazin-2(1H)-one (8.71 g, 57.2 mmol, 94% yield) as an amber oil. ¹H NMR (400 MHz, CDCl₃) δ 11.27 (br. s., 1H) 7.42-7.45 (m, 1H) 7.09-7.12 (m, 1H) 1.40 (s, 9H). m/z (ESI, +ve ion): 153.1 (M+H)⁺.

Step 4: 2-(tert-Butyl)-3-chloropyrazine

A mixture of 3-(tert-butyl)pyrazin-2(1H)-one (5.28 g, 34.7 mmol) and pentachloro-phosphane (14.5 g, 69.4 mmol) in phosphorous oxychloride (64.7 mL, 694 mmol) was stirred at 105° C. for 16 h. The reaction mixture was concentrated in vacuo, and the residue was diluted with EtOAc (150 mL). Satd aq. NaHCO₃ (100 mL) was slowly added (until bubbling ended). The organic layer was then separated and sequentially washed with satd. NaHCO₃ (2×75 mL), dried over anhydrous Na₂SO₄, and concentrated in vacuo. Chromatographic purification of the residue (silica gel, eluent: 0-30% EtOAc/heptane) provided 2-(tert-butyl)-3-chloropyrazine (1.27 g, 7.43 mmol, 21.4% yield) as a viscous yellow liquid. ¹H NMR (400 MHz, CDCl₃) δ 8.42 (s, 1H) 8.20 (s, 1H) 1.52 (s, 9H). m/z (ESI, +ve ion): 171.1 (M+H)⁺.

Step 5: 3-(tert-Butyl)pyrazin-2-amine (Intermediate I-6)

A mixture of 2-(tert-butyl)-3-chloropyrazine (1.27 g, 7.43 mmol) and lithium amide (0.512 g, 22.3 mmol, Sigma-Aldrich Corporation, St. Louis, Mo., USA) in THF (7.4 mL) was heated in a microwave reactor at 120° C. for 6 h. The reaction mixture was then diluted with EtOAc (150 mL) and washed with satd. ammonium chloride (3×100 mL). The organic layer was separated, dried over Na₂SO₄, and concentrated in vacuo. Chromatographic purification of the residue (silica gel, eluent: 0-90% EtOAc-EtOH (3:1)/heptane) provided 3-(tert-butyl)pyrazin-2-amine (Intermediate I-6, 367 mg, 2.43 mmol, 33% yield). ¹H NMR (400 MHz, CDCl₃) δ 7.86 (d, J=2.5 Hz, 1H) 7.82 (d, J=2.7 Hz, 1H) 4.64 (br s, 2H) 1.39 (s, 9H). m/z (ESI, +ve ion): 152.0 (M+H)⁺.

Intermediate I-7

1-Benzyl-3-cyclopropyl-1H-pyrazol-4-amine

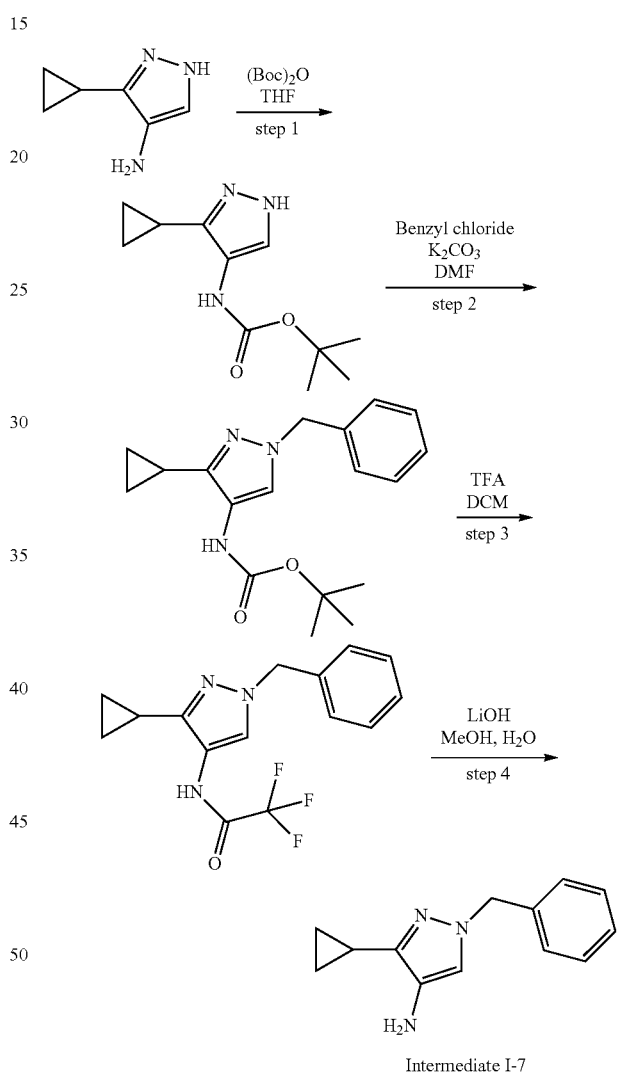

Intermediate I-7

Step 1: tert-Butyl (3-cyclopropyl-1H-pyrazol-4-yl)carbamate

A mixture of 3-cyclopropyl-1H-pyrazol-4-amine (1.52 mL, 12.3 mmol, Enamine, Monmouth Jct., N.J.) and di-tert-butyl dicarbonate (2.83 g, 13.0 mmol) in THF (40 mL) was stirred at rt for 6 h. The reaction mixture was then concentrated in vacuo, and the crude material was treated with DCM. The resulting solid was collected by filtration and dried in vacuo to provide tert-butyl (3-cyclopropyl-1H- pyrazol-4-yl)carbamate. $^1$H NMR (400 MHz, DMSO-d$_6$) δ ppm 11.68-12.48 (1H, m), 8.10-8.73 (1H, m), 7.08-7.83 (1H, m), 1.74-2.02 (1H, m), 1.44 (9H, s), 0.57-0.96 (4H, m). m/z (ESI, +ve ion) 224.2 (M+H)$^+$.

Step 2: tert-Butyl (1-benzyl-3-cyclopropyl-1H-pyrazol-4-yl)carbamate

A mixture of tert-butyl (3-cyclopropyl-1H-pyrazol-4-yl)carbamate (1.52 g, 6.83 mmol) and potassium carbonate (1.98 g, 14.3 mmol) in DMF (10 mL) was stirred at rt for 50 min. (Chloromethyl)benzene (0.9 mL, 8.19 mmol, Sigma-Aldrich, St. Louis, Mo.) was then added, and the resulting mixture was stirred at rt for 48 h. The reaction mixture was subsequently diluted with water and repeatedly extracted with EtOAc. The combined extracts were washed with water, dried by passing through a Chem Elut extraction cartridge (eluting with EtOAc), and concentrated in vacuo. Chromatographic purification of the residue (silica gel, eluent: 0-60% EtOAc/heptane) provided tert-butyl (1-benzyl-3-cyclopropyl-1H-pyrazol-4-yl)carbamate. $^1$H NMR (400 MHz, CDCl$_3$) δ ppm 7.62 (1H, br s), 7.27-7.35 (3H, m), 7.17-7.22 (2H, m), 6.25 (1H, br s), 5.15 (2H, s), 1.62-1.69 (1H, m), 1.50 (9H, s), 0.88 (2H, dt, J=8.3, 2.6 Hz), 0.79-0.84 (2H, m). m/z (ESI, +ve ion) 314.2 (M+H)$^+$.

Step 3: N-(1-Benzyl-3-cyclopropyl-1H-pyrazol-4-yl)-2,2,2-trifluoroacetamide

TFA (10 mL, 130 mmol) was slowly added to a solution of tert-butyl (1-benzyl-3-cyclopropyl-1H-pyrazol-4-yl)carbamate (1.79 g, 5.71 mmol) in DCM (10 mL) at 0° C., and the resulting mixture was subsequently stirred at rt for 1 h. The mixture was then concentrated in vacuo, and the residue was taken up in EtOAc (20 mL). Satd NaHCO$_3$ was slowly added, and the organic layer was separated. The aqueous layer was extracted with EtOAc, then saturated with NaCl and further extracted with EtOAc. The combined organic extracts were dried by passing through a Chem Elut extraction cartridge (eluting with EtOAc), then concentrated in vacuo. Chromatographic purification of the residue (silica gel, eluent: 30-100%/o EtOAc/heptane) provided N-(1-benzyl-3-cyclopropyl-1H-pyrazol-4-yl)-2,2,2-trifluoroacetamide. $^1$H NMR (400 MHz, CDCl$_3$) δ ppm 7.91 (1H, s), 7.81 (1H, br s), 7.30-7.37 (3H, m), 7.19-7.24 (2H, m), 5.20 (2H, s), 1.69 (1H, tt, J=8.3, 5.1 Hz), 0.94-1.00 (2H, m), 0.84-0.89 (2H, m). m/z (ESI, +ve ion): 310.2 (M+H)$^+$.

Step 4: 1-Benzyl-3-cyclopropyl-1H-pyrazol-4-amine (Intermediate I-7)

A solution of lithium hydroxide hydrate (0.216 g, 5.15 mmol) in water (5 mL) was added to a solution of N-(1-benzyl-3-cyclopropyl-1H-pyrazol-4-yl)-2,2,2-trifluoroacetamide (1.06 g, 3.43 mmol) in MeOH (20 mL), and the resulting mixture was stirred at rt for 72 h, then at 55° C. for 24 h. The reaction mixture was subsequently partitioned between satd. ammonium chloride (30 mL) and EtOAc (30 mL). The aqueous layer was extracted with EtOAc. The combined organic extracts were dried by passing through a Chem Elut extraction cartridge (eluting with EtOAc) and concentrated in vacuo to provide 1-benzyl-3-cyclopropyl-1H-pyrazol-4-amine (Intermediate I-7). $^1$H NMR (400 MHz, CDCl$_3$) δ ppm 7.28-7.36 (m, 3H), 7.13-7.19 (m, 2H), 6.86 (s, 1H), 5.12 (s, 2H), 2.09-2.22 (m, 2H), 1.67-1.78 (m, 1H), 0.80-0.92 (m, 4H). m/z (ESI, +ve ion) 214.2 (M+H)$^+$.

Intermediate I-8

3-Isopropyl-N$^1$,N$^1$,5-trimethylbenzene-1,4-diamine

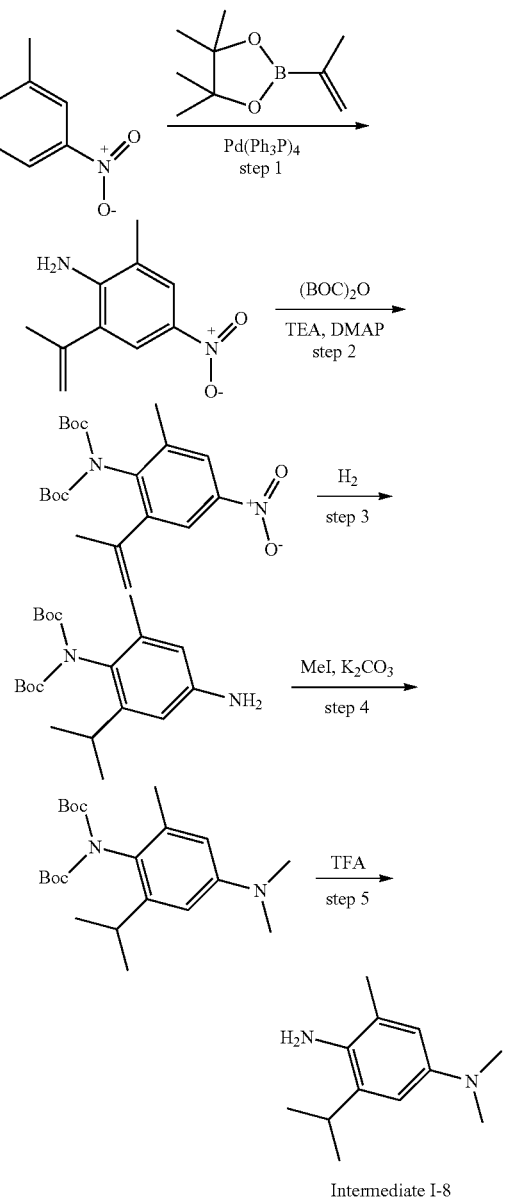

Intermediate I-8

Step 1: 2-Methyl-4-nitro-6-(prop-1-en-2-yl)aniline

A mixture of 2-isopropenylboronic acid, pincol ester (6.84 g, 40.7 mmol, Combi-Blocks, San Diego, Calif.), 2-amino-3-bromo-5-nitrotoluene (4.7 g, 20.34 mmol), sodium carbonate (anhydrous, powder; 2.56 mL, 61.0 mmol), tetrakis (triphenylphosphine)palladium(0) (2.35 g, 2.03 mmol) in 1,2-dimethoxyethane (100 mL) and water (25 mL) was stirred under N$_{2(g)}$ at 80° C. for 18 h. The mixture was then diluted with satd. aq. NaHCO$_3$ (150 mL) and extracted with EtOAc. The combined extracts were dried over Na$_2$SO$_4$ and concentrated in vacuo. Chromatographic purification of the residue (silica gel, eluent: 0-10% MeOH/DCM) furnished 2-methyl-4-nitro-6-(prop-1-en-2-yl)aniline (3.28 g, 17.1 mmol, 84% yield) as a yellow solid. $^1$H NMR (400 MHz, CDCl$_3$) δ ppm 7.92 (d, J=2.1 Hz, 1H), 7.86 (d, J=2.5 Hz, 1H), 5.41 (t, J=1.7 Hz, 1H), 5.11 (s, 1H), 2.23 (s, 3H), 2.08 (s, 3H), 1.53 (br s, 2H). m/z (ESI, +ve ion): 192.9 (M+H)$^+$.

Step 2: Bis(2-methyl-2-propanyl) (2-methyl-4-nitro-6-(1-propen-2-yl)phenyl)-2-imidodicarbonate A mixture of 2-methyl-4-nitro-6-(prop-1-en-2-yl)aniline (3.25 g, 16.91 mmol), triethylamine (7.13 mL, 50.7 mmol), DMAP (1.033 g, 8.45 mmol), and di-tert-butyl dicarbonate (11.78 mL, 50.7 mmol) in THF (40 mL) was stirred under N$_{2(g)}$ at rt for 17 h. The reaction mixture was then diluted with satd. aq. NaHCO$_3$ and extracted with DCM. The combined extracts were dried over Na$_2$SO$_4$ and concentrated in vacuo. Chromatographic purification of the residue (silica gel, eluent: 0-5% MeOH/DCM) gave bis(2-methyl-2-propanyl) (2-methyl-4-nitro-6-(1-propen-2-yl)phenyl)-2-imidodicarbonate (4.1 g, 10.5 mmol, 62% yield) as yellow solid. $^1$H NMR (400 MHz, CDCl$_3$) δ 8.01 (d, J=2.5 Hz, 1H), 7.95 (d, J=2.5 Hz, 1H), 5.27 (t, J=1.6 Hz, 1H), 4.99 (s, 1H), 2.29 (s, 3H), 2.06 (s, 3H), 1.40 (s, 18H).

Step 3: Bis(2-methyl-2-propanyl) (4-amino-2-methyl-6-(2-propanyl)phenyl)-2-imidodicarbonate A suspension of palladium (10% on activated wood carbon, reduced, 50% water wet paste; 0.046 mL, 5.22 mmol) in EtOAc (10 mL) was added to a solution of bis(2-methyl-2-propanyl) (2-methyl-4-nitro-6-(1-propen-2-yl)phenyl)-2-imidodicarbonate (4.1 g, 10.5 mmol) in EtOH (50 mL), and the resulting mixture stirred under H$_{2(g)}$ (40 psi) at rt for 2 h. The resulting mixture was then filtered through a pad of Celite, and the Celite pad was washed with EtOH and EtOAc. The combined filtrates were concentrated in vacuo to provide bis(2-methyl-2-propanyl) (4-amino-2-methyl-6-(2-propanyl)phenyl)-2-imidodicarbonate as a yellow solid, which was used in the next step without purification. $^1$H NMR (400 MHz, CDCl$_3$) δ ppm 6.45 (d, J=2.7 Hz, 1H), 6.39 (d, J=2.5 Hz, 1H), 3.50-4.12 (m, 2H), 2.90 (quin, J=6.9 Hz, 1H), 2.06 (s, 3H), 1.38 (s, 18H), 1.14 (s, 3H), 1.13 (s, 3H). m/z (ESI, +ve ion): 365.1 (M+H)$^+$.

Step 4: Bis(2-methyl-2-propanyl) (4-(dimethylamino)-2-methyl-6-(2-propanyl)phenyl)-2-imidodicarbonate Potassium carbonate (1.38 g, 10.0 mmol) and a solution of iodomethane (1.25 mL, 20.0 mmol) in N-methyl-2-pyrrolidinone (3 mL) were sequentially added to a solution of bis(2-methyl-2-propanyl) (4-amino-2-methyl-6-(2-propanyl)phenyl)-2-imidodicarbonate (3.65 g, 10.01 mmol) in N-methyl-2-pyrrolidinone (70 mL), and the resulting mixture was stirred at rt overnight. Additional potassium carbonate (690 mg, 5 mmol) and iodomethane (0.6 mL) were added, and the resulting mixture was stirred at rt for 7 h. The mixture was then diluted with satd. aq. NaHCO$_3$ (50 mL) and extracted with EtOAc. The organic layer was separated, dried over MgSO$_4$. and concentrated in vacuo. Chromatographic purification of the residue (silica gel, eluent: 0-100% EtOAc-EtOH (3:1)/heptane) provided bis(2-methyl-2-propanyl) (4-(dimethylamino)-2-methyl-6-(2-propanyl)phenyl)-2-imidodicarbonate (1.75 g, 4.46 mmol, 45% yield) as a light yellow solid. m/z (ESI, +ve ion): 393.0 (M+H)+.

Step 5: 3-Isopropyl-N$^1$,N$^1$,5-trimethylbenzene-1,4-diamine (Intermediate I-8)

TFA (9.97 mL, 134 mmol) was added to a solution of bis(2-methyl-2-propanyl) (4-(dimethylamino)-2-methyl-6-(2-propanyl)phenyl)-2-imidodicarbonate (1.75 g, 4.46 mmol) in DCM (15 mL), and the resulting mixture was stirred at rt for 30 min before being concentrated in vacuo. The residue was dissolved in DCM, satd. aq. NaHCO$_3$ was added, and the resulting mixture was stirred at rt for 15 min. The organic layer was separated, and the aqueous layer was extracted with DCM. The combined organic extracts were then dried over MgSO$_4$ and concentrated in vacuo. Chromatographic purification of the residue (silica gel, eluent: 0-5% 2 M ammonia in MeOH/DCM) provided 3-isopropyl-N$^1$,N$^1$,5-trimethylbenzene-1,4-diamine (Intermediate I-8, 842 mg, 4.38 mmol, 98% yield) as yellow oil. $^1$H NMR (400 MHz, CDCl$_3$) δ ppm 6.19-6.86 (m, 2H), 2.62-3.10 (m, 7H), 2.09-2.34 (m, 3H), 1.27 (s, 3H), 1.26 (s, 3H). m, (ESI, +ve ion): 193.1 (M+H)$^+$.

Intermediate I-9

2-Cyclopropyl-6-methylaniline

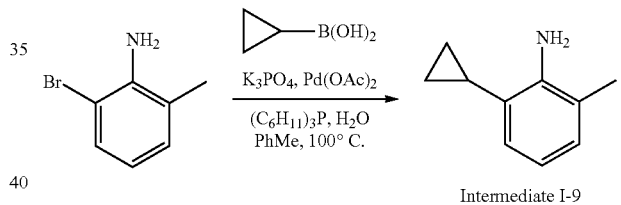

Intermediate I-9

A mixture of 2-amino-3-bromotoluene (10.0 mL, 53.7 mmol, Combi-Blocks, San Diego, Calif.), 1-boronocyclopropane (23.1 mL, 269 mmol, Small Molecules. Inc., Jackson Street, Hoboken, N.J.), tricyclohexylphosphine (3.01 g, 10.8 mmol, Strem Chemicals, Newburyport, Mass.), palladium(II) acetate (2.413 g, 10.75 mmol, Strem Chemicals, Newburyport, Mass.), and potassium phosphate tribasic (17.6 mL, 215 mmol) in toluene (400 mL) and water (40.0 mL) was sparged with N$_2$ for 5 min and then stirred at 100° C. for 1.5 h. The mixture was cooled to rt, diluted with satd. aq. NaHCO$_3$, and extracted with EtOAc. The combined extracts were dried over MgSO$_4$ and concentrated in vacuo. Chromatographic purification of the residue (silica gel, eluent: 0-100% EtOAc-EtOH (3:1)/heptane) yielded 2-cyclopropyl-6-methylaniline (Intermediate I-9, 6.85 g, 46.5 mmol, 87% yield) as a yellow liquid. $^1$H NMR (400 MHz, CDCl$_3$) δ: 6.95 (dd, J=7.7, 2.5 Hz, 2H), 6.65 (t, J=7.6 Hz, 1H), 3.82-4.45 (m, 2H), 2.20 (s, 3H), 1.65-1.73 (m, 1H), 0.88-0.94 (m, 2H), 0.58-0.63 (m, 2H). m/z (ESI, +ve ion): 148.1 (M+H)$^+$.

Intermediate I-10

3-(Prop-1-en-2-yl)pyridin-2-amine

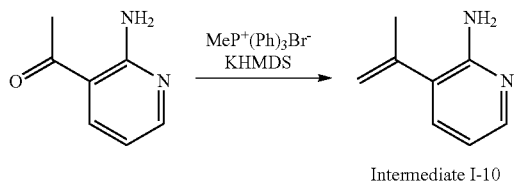

Intermediate I-10

KHMDS (1 M in THF, 19 mL, 19 mmol) was slowly added to an ice-cooled suspension of methyltriphenylphosphonium bromide (7.0 g, 20 mmol, Sigma-Aldrich Corporation, St. Louis, Mo., USA) in THF (20 mL), and the resulting mixture was stirred at 0° C. for 5 min, then at rt for 15 min. A suspension of 1-(2-amino-3-pyridinyl)-1-ethanone (2.0 g, 15 mmol, BIONET/Key Organics, Bedford, Mass., USA) in THF (15 mL) was then added, and the resulting mixture was stirred at rt for 30 min. The mixture was subsequently diluted with satd. aq. ammonium chloride, water, and EtOAc. The organic layer was separated, washed with brine, and concentrated in vacuo. Chromatographic purification of the residue (silica gel, eluent: 0-100% EtOAc/heptane) provided 3-(prop-1-en-2-yl)pyridin-2-amine (Intermediate I-10, 1.56 g, 11.63 mmol, 79% yield). m/z (ESI, +ve ion): 135.2 (M+H)$^+$.

Intermediate I-11

3,5-Diisopropyl-1H-pyrazol-4-amine

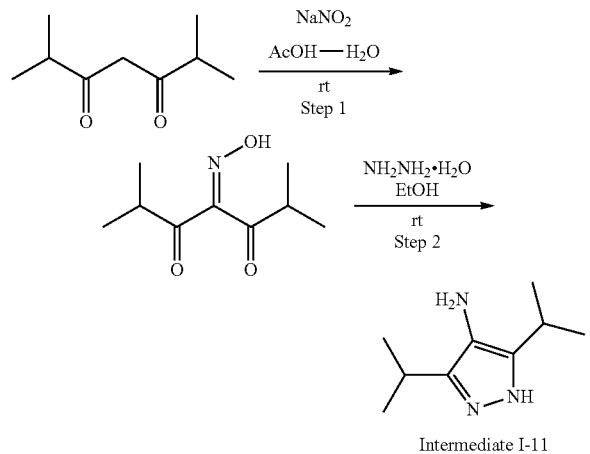

Step 1: 4-(Hydroxyimino)-2,6-dimethylheptane-3,5-dione

A solution of sodium nitrite (4.0 g, 58 mmol) in water (5.3 mL) was added dropwise to a solution of 2,6-dimethyl-3,5-heptanedione (1.648 ml, 9.60 mmol, Acros Organics, NJ. USA) in acetic acid (27 mL), and the resulting mixture was stirred at rt for 3 h. The reaction mixture was then extracted with EtOAc, and the extract was sequentially washed with satd. aq. NaHCO$_3$, dried over Na$_2$SO$_4$, filtered, and concentrated in vacuo. Chromatographic purification of the residue (silica gel. eluent: 30-50% EtOAc/heptane) gave 4-(hydroxyimino)-2,6-dimethylheptane-3,5-dione (0.370 g, 2.00 mmol, 21% yield) as yellow syrup. m/z (ESI, +ve ion): 207.9 (M+Na)$^+$.

Step 2: 3,5-Diisopropyl-1H-pyrazol-4-amine (Intermediate I-11)

Hydrazine hydrate (0.93 mL, 19 mmol) was added dropwise to an ice-cooled mixture of 4-(hydroxyimino)-2,6-dimethylheptane-3,5-dione (0.35 g, 1.9 mmol) in EtOH (6.3 mL), and the resulting mixture was allowed to warm to rt and stir for 40 h. The reaction mixture was subsequently concentrated in vacuo, and the residue was partitioned between EtOAc and 2 N HCl. The acidic aqueous layer was washed with EtOAc, then neutralized with 2 N NaOH. The neutralized aqueous layer was extracted with EtOAc, and the extract was then dried over Na$_2$SO$_4$, filtered, and concentrated in vacuo. Chromatographic purification of the residue (silica gel, eluent: 50-100% EtOAc/heptane) gave 3,5-diisopropyl-1H-pyrazol-4-amine (Intermediate I-11, 0.203 g, 1.21 mmol, 64% yield) as off-white solid. $^1$H NMR (400 MHz, DMSO-d$_6$) δ ppm 11.37 (br s, 1H), 3.09 (br s, 2H), 2.90 (dt, J=13.4, 6.6 Hz, 2H), 1.15 (d, J=6.8 Hz, 12H). m/z (ESI, +ve ion): 168.2 (M+H)$^+$.

Intermediate I-12

4-Methyl-3-propylpyridin-2-amine

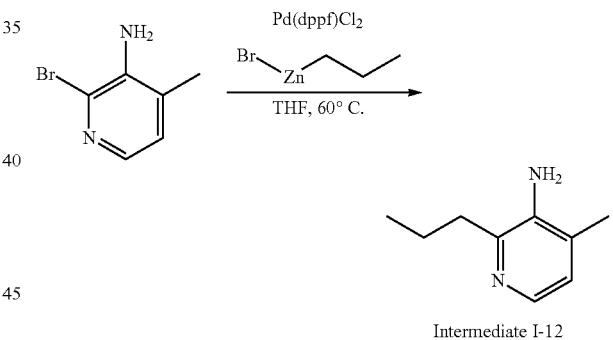

Intermediate I-12 n-Propylzinc bromide (64 ml, 32 mmol, Sigma Aldrich, St. Louis, Mo., USA) was added to a mixture of (1,1'-bis (diphenylphosphino) ferrocene)dichloropalladium (0.982 g, 1.34 mmol, Sigma Aldrich, St. Louis, Mo., USA) and 3-amino-2-bromo-4-picoline (5.0 g, 27 mmol, Combi-Blocks. San Diego, Calif., USA) in THF (30 mL), and the resulting mixture was stirred at 60° C. for 19 h. Additional n-propylzinc bromide (12 mL, 1.5 mmol) was added, and heating was continued for 1 h. The reaction mixture was then cooled to rt and treated with water (25 mL), followed by 5 N NaOH and additional water. The resulting mixture was stirred for 10 min and then was extracted with EtOAc. The organic layer was separated and sequentially washed with (1:1) brine-5 N NaOH, dried over sodium sulfate, and concentrated in vacuo. Chromatographic purification of the residue (silica gel, eluent: 0-80% EtOAc-EtOH (3:1)/heptane) provided 4-methyl-3-propylpyridin-2-amine (Intermediate I-12) as an oil. $^1$H NMR (400 MHz, CDCl$_3$) δ ppm 1.00-1.08 (m, 3H) 1.74-1.83 (m, 2H) 2.13-2.20 (m, 3H)

2.62-2.74 (m, 2H) 3.42-3.73 (m, 2H) 6.71-6.99 (m, 1H) 7.83-7.98 (m, 1H). m/z (ESI, +ve ion): 151.1 (M+H)⁺.

Intermediate I-13

2-Isopropyl-4-(trifluoro-methyl)pyridin-3-amine

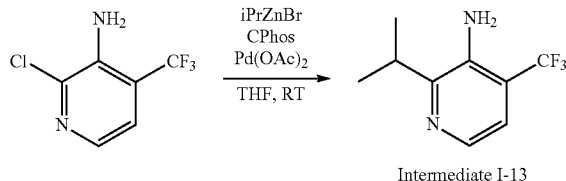

Intermediate I-13

2-Chloro-3-amino-4-(trifluoromethyl)pyridine (3.90 ml, 19.8 mmol, Aurum Pharmatech LLC, Franklin Park, N.J.), palladium(II) acetate (0.22 g, 0.99 mmol), and CPhos (0.87 g, 2.0 mmol, Sigma Aldrich, St. Louis, Mo., USA) were combined in a three-necked flask, and headspace of the flask was flushed with N2 for 10 min. THF (10 mL) and 2-propylzinc bromide (50 mL, 25 mmol, Sigma Aldrich, St. Louis, Mo., USA) were sequentially added, and the resulting mixture was stirred at rt for 1.5 h. The reaction mixture was then diluted with satd. aq. ammonium chloride and EtOAc. and organic layer was separated and sequentially washed with brine, dried over sodium sulfate, and concentrated in vacuo. Chromatographic purification of the residue (silica gel, eluent: 0-15% EtOAc/heptane) provided 2-isopropyl-4-(trifluoro-methyl)pyridin-3-amine (Intermediate I-13) as an oil. ¹H NMR (400 MHz, CDCl₃) δ ppm 1.22-1.31 (m, 6H) 2.94-3.10 (m, 1H) 3.99-4.31 (m, 2H) 7.03-7.13 (m, 1H) 7.90-8.08 (m, 1H). ¹⁹F NMR (376 MHz, CDCl₃) δ ppm −64.41 (s, 1F). m/z (ESI, +ve ion): 205.1 (M+H)⁺.

Intermediate I-14

N,N,4-Trimethylpyridine-2,3-diamine

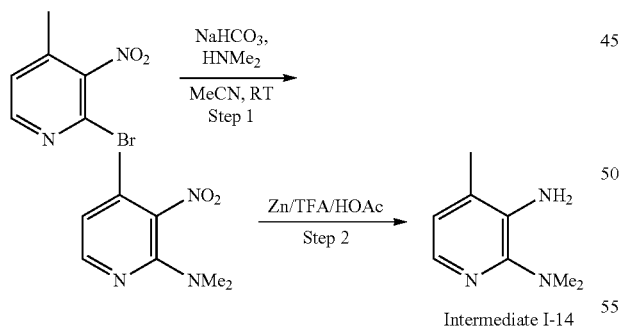

Intermediate I-14

Step 1: N,N,4-Trimethyl-3-nitropyridin-2-amine

A mixture of 2-bromo-3-nitro-4-methyl pyridine (7.18 ml, 33.1 mmol, Combi-Blocks, San Diego, Calif., USA), sodium bicarbonate (4.16 g, 49.6 mmol), and dimethylamine (2M in THF, 24 mL, 48 mmol, Sigma-Aldrich Corporation. St. Louis, Mo. USA) in acetonitrile (30 mL) was stirred at rt for 6 h, then diluted with EtOAc and washed with brine. The organic layer was separated, dried over Na₂SO₄, filtered, and concentrated in vacuo. Chromatographic purification of the residue (silica gel, eluent: 0-10% EtOAc/heptane) provided N,N,4-trimethyl-3-nitropyridin-2-amine as yellow solid.

Step 2: N,N,4-Trimethylpyridine-2,3-diamine

Zinc nanopowder (0.708 ml, 77 mmol, Sigma Aldrich. St. Louis, Mo., USA) was added, portion-wise, to a mixture of N,N,4-trimethyl-3-nitropyridin-2-amine (2.8 g, 15 mmol), acetic acid (10 mL), and TFA (5 mL) at 0° C., and the resulting mixture was stirred at 0° C. for 4 h. The reaction mixture was then diluted with EtOAc and concentrated in vacuo. 5 N NaOH (20 mL) was slowly added to the residue, followed by solid NaOH to adjust the pH to 10. (9:1) CHCl₃/iPrOH was added, and the resulting mixture was stirred for 5 min, then filtered through a pad of Celite. The organic layer was separated, and the aqueous layer was extracted with (9:1) CHCl₃/iPrOH. The combined organic extracts were dried over sodium sulfate and concentrated in vacuo to give N,N,4-trimethylpyridine-2,3-diamine (Intermediate I-14) as a white solid. ¹H NMR (400 MHz, DMSO-d₆) δ ppm 2.04-2.15 (m, 3H) 2.57-2.67 (m, 6H) 4.44-4.62 (m, 2H) 6.64-6.74 (m, 1H) 7.41-7.55 (m, 1H). m/z (ESI, +ve ion): 152.1 (M+H)⁺.

Intermediate I-15

6-Amino-5-ethylnicotinonitrile

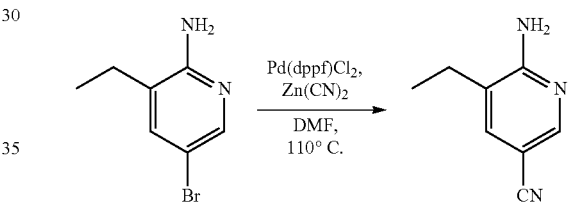

Intermediate I-15

A mixture of 5-bromo-3-ethylpyridin-2-amine (850 mg, 4.23 mmol), dicyanozinc (745 mg, 6.34 mmol), and Pd(dppf)Cl₂ (619 mg, 0.846 mmol) in DMF (8 mL) was stirred at 110° C. for 24 h. Water was added to the cooled reaction mixture, and the precipitated solid was collected by filtration, washed with water, an dried in vacuo. Chromatographic purification of the residue (silica gel, eluent: 0-50% EtOAc-EtOH (3:1)/heptane) provided 6-amino-5-ethylnicotinonitrile (Intermediate I-15). m/z (ESI, +ve ion): 148.1 (M+H)⁺.

Intermediate I-16

4-Isopropyl-2-methylpyridin-3-amine

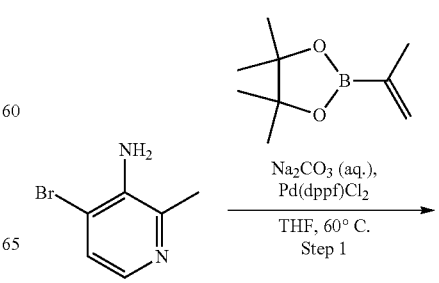

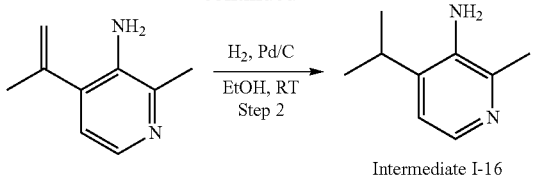

Intermediate I-16

Step 1: 2-Methyl-4-(prop-1-en-2-yl)pyridin-3-amine. A mixture of 4-bromo-2-methylpyridin-3-amine (1.43 g, 7.66 mmol, Chem-Impex International, Inc., Wood Dale, Ill.), dichloro[1,1'-bis(diphenylphosphino)ferrocene]dichloride palladium(II) DCM adduct (0.063 g, 0.077 mmol), 2-isopropenylboronic acid, pincol ester (2.317 g, 13.79 mmol, Combi-Blocks, San Diego, Calif.), and aqueous sodium carbonate (10% solution in 14 mL of water; 1.62 g, 15.3 mmol) in 1,4-dioxane (25 mL) was sparged with $N_{2(g)}$ for 3 min, then heated at 110° C. for 1 h. The reaction mixture was subsequently partitioned between EtOAc and brine. The aqueous layer was further extracted with EtOAc, and the combined organic extracts were dried over $Na_2SO_4$, filtered, and concentrated in vacuo. Chromatographic purification of the residue (silica gel, eluent: 0-50% EtOAc-EtOH (3:1)/heptane) provided 2-methyl-4-(prop-1-en-2-yl)pyridin-3-amine (1.14 g, 7.66 mmol, 100% yield) as light-yellow oil. m/z (ESI, +ve ion): 149.1 $(M+H)^+$.

Step 2: 4-Isopropyl-2-methylpyridin-3-amine (Intermediate I-16)

A mixture of 2-methyl-4-(prop-1-en-2-yl)pyridin-3-amine (1.14 g, 7.66 mmol) and palladium (10 wt. % on activated carbon: 407 mg, 0.383 mmol) in ethanol was stirred under hydrogen gas (20 psi) for 3 h. The reaction mixture was then filtered through a pad of Celite and concentrated in vacuo to provide 4-isopropyl-2-methylpyridin-3-amine (Intermediate I-16, 1.08 g, 7.19 mmol, 94% yield) as a light-yellow viscous oil. $^1$H NMR (400 MHz, $CDCl_3$) δ ppm 7.93 (d, J=5.18 Hz, 1H), 6.93 (d, J=5.18 Hz, 1H), 3.62 (br s, 2H), 2.89 (td, J=6.82, 13.53 Hz, 1H), 2.44 (s, 3H), 1.26 (d, J=8.0 Hz, 6H). m/z (ESI, +ve ion): 151.1 (M+H).

Intermediate I-17

3-Isopropyl-6-methylpyridin-2-amine

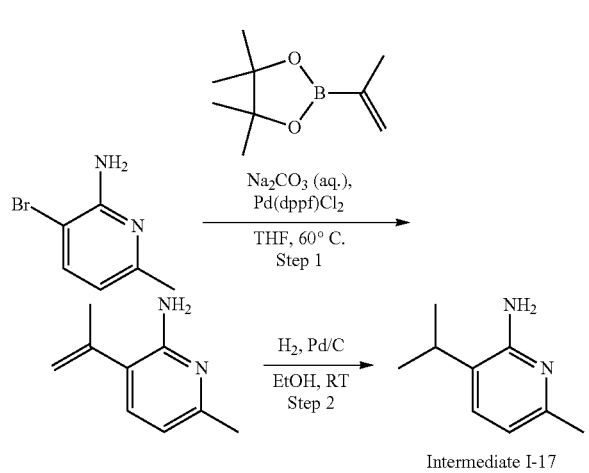

Intermediate I-17

Step 1: 6-Methyl-3-(prop-1-en-2-yl)pyridin-2-amine

A mixture of 2-amino-3-bromo-6-methylpyridine (5 g, 26.7 mmol, Waterstone Technology, LLC, Carmel, Ind.), dichloro[1,1'-bis(diphenylphosphino)ferrocene]dichloride palladium(II) DCM adduct (0.218 g, 0.267 mmol), 2-isopropenylboronic acid, pincol ester (8.09 g, 48.1 mmol, Combi-Blocks, San Diego, Calif.), and aqueous sodium carbonate (10% solution in 51 mL of water; 5.67 g, 53.5 mmol) in 1,4-dioxane (89 mL) was sparged with $N_2$), for 3 min, then stirred at 110° C. for 2 h. The reaction mixture was then partitioned between EtOAc and brine. The aqueous layer was further extracted with EtOAc, and the combined organic extracts were then dried over $Na_2SO_4$ and concentrated in vacuo. Chromatographic purification of the residue (silica gel, eluent: 0-40% EtOAc-EtOH (3:1)/heptane) gave 6-methyl-3-(prop-1-en-2-yl)pyridin-2-amine (3.65 g, 24.6 mmol, 92% yield) as a white solid. m/z (ESI, +ve ion): 149.1 $(M+H)^+$.

Step 2: 3-Isopropyl-6-methylpyridin-2-amine (Intermediate I-17)

A mixture of 6-methyl-3-(prop-1-en-2-yl)pyridin-2-amine (3.45 g, 23.28 mmol) and palladium (10 wt. % on activated carbon; 1.24 g, 1.16 mmol) in ethanol (40 mL) was stirred under hydrogen gas (20 psi) for 2 h. The reaction mixture was then filtered through a pad of Celite and concentrated in vacuo to provide 3-isopropyl-6-methylpyridin-2-amine (Intermediate I-17, 3.25 g, 21.6 mmol, 93% yield) as a colorless, viscous oil. $^1$H NMR (400 MHz, $CDCl_3$) δ 7.28 (d, J=8.50 Hz, 1H), 6.34 (d, J=8.29 Hz, 1H), 4.42 (br s, 2H), 3.00 (td, J=6.87, 13.84 Hz, 1H), 2.38 (s, 3H), 1.16 (d, J=6.84 Hz, 6H). m/z (ESI, +ve ion): 151.1 $(M+H)^+$.

Intermediate I-18

3-(Prop-1-en-2-yl)pyrazin-2-amine

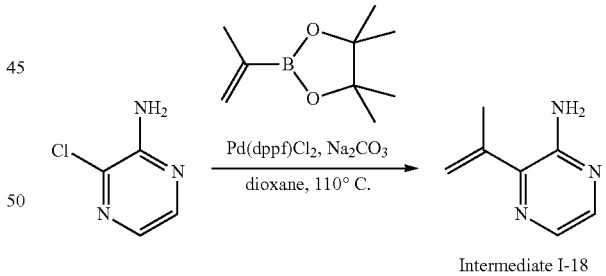

Intermediate I-18

A mixture of 2-amino-3-chloropyrazine (1.0 g, 7.7 mmol, Synchem Inc., Elk Grove, Ill.), {1,1'-bis(diphenylphosphino)ferrocene} dichloropalladium(II) (0.57 g, 0.77 mmol), isopropenylboronic acid pinacol ester (2.9 mL, 15 mmol, Combi-Blocks, San Diego, Calif.), and 10% aq. sodium carbonate (25 mL, 23 mmol) in 1,4-dioxane (13 mL) was sparged with $N_{2(g)}$ for 3 min, then heated at 110° C. for 16 h. The reaction mixture was then cooled to rt, filtered through a pad of Celite, and concentrated in vacuo. The residue was taken up in EtOAc, re-filtered, and concentrated in vacuo to provide 3-(prop-1-en-2-yl)pyrazin-2-amine (Intermediate I-18), which was used without purification. m/z (ESI, +ve ion): 136.0 $(M+H)^+$.

Intermediate I-19

3-Ethylpyrazin-2-amine

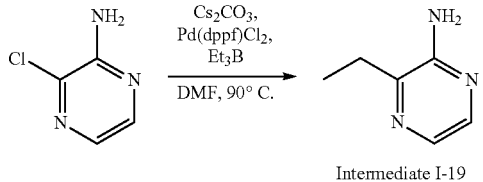

Intermediate I-19

A 3-necked 250 mL round-bottomed flask was charged with cesium carbonate (22.64 g, 69.5 mmol), 2-amino-3-chloropyrazine (3 g, 23.16 mmol, Synchem Inc., Elk Grove Village, Ill.), and {1,1'-bis(diphenylphosphino)ferrocene} dichloropalladium(II) (1.69 g, 2.32 mmol, Strem Chemicals, Newburyport, Mass.). A reflux condenser was attached, and the apparatus was sealed. The vessel was evacuated and backfilled with nitrogen. DMF (66.2 mL) was added, followed by triethylborane (1.0 M in THF; 42 mL, 42 mmol; Sigma-Aldrich Corporation, St. Louis, Mo., USA). The reaction was then stirred in a pre-heated 90° C. oil bath for 1 h. The reaction mixture was cooled to rt, water was added, and the resulting mixture was extracted with DCM (2×). The combined extracts were dried over $MgSO_4$ and concentrated in vacuo. The crude residue was taken up in MeOH and loaded onto a column composed of Si-propylsulfonic acid (Silicyle). The column was flushed with 4 column volumes of MeOH before eluting the title compound with 4 column volumes of 2M ammonia in MeOH. The filtrate was concentrated in vacuo, and the residue was purified by silica gel chromatography (eluent: 0-20% 2 M $NH_3$ in MeOH/DCM) to provide 3-ethylpyrazin-2-amine (Intermediate I-19, 2.34 g, 19.0 mmol, 82% yield) as a brown oil. $^1$H NMR (400 MHz, DMSO-$d_6$) δ ppm 7.75 (d, J=2.70 Hz, 1H) 7.65 (d, J=2.70 Hz, 1H) 6.13 (br s, 2H) 2.60 (q, J=7.39 Hz, 2H) 1.17 (t, J=7.46 Hz, 3H).

Intermediate I-20

1-(2-Aminopyridin-3-yl)cyclopropanecarbonitrile

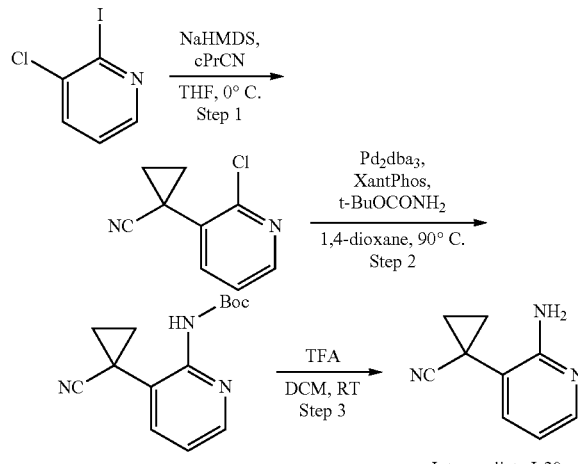

Intermediate I-20

Step 1: 1-(2-Chloropyridin-3-yl)cyclopropanecarbonitrile

Sodium bis(trimethylsilyl)amide (1 M in THF, 22.37 mL, 22.37 mmol) was added, dropwise, to a solution of 2-chloro-3-iodopyridine (4.12 g, 17.2 mmol, Alfa Aesar, A Johnson Matthey Company, Ward Hill, Mass.) and cyclopropanecarbonitrile (1.7 ml, 22.4 mmol, Sigma-Aldrich St. Louis, Mo., USA) in THF (100 mL) at −78° C., and the resulting mixture was warmed to 0° C. over 3 h. Satd aq. ammonium chloride solution was added to neutralize excess base, and the resulting mixture was partitioned between EtOAc and water. The organic layer was separated and sequentially washed with brine, dried over $MgSO_4$ and concentrated in vacuo. Chromatographic purification of the residue (silica gel, eluent: 0-60% EtOAc/heptane) provided 1-(2-chloropyridin-3-yl)cyclopropane-1-carbonitrile (1.21 g, 6.77 mmol, 39% yield) as a brown solid.

Step 2: tert-Butyl (3-(1-cyanocyclopropyl)pyridin-2-yl)carbamate

A mixture of tris(dibenzylideneacetone)dipalladium (0) (0.205 g, 0.224 mmol, Strem Chemicals, Newburyport, Mass.), 9,9-dimethyl-4,5-bis(bis[3,5-dimethyl-4-methoxyphenyl]phosphino)xanthene (XantPhos; 0.259 g, 0.448 mmol, Strem Chemicals, Newburyport, Mass.), cesium carbonate (2.92 g, 8.96 mmol, Strem Chemicals, Newburyport, Mass.), tert-butyl carbamate (1.574 g, 13.44 mmol, Sigma-Aldrich), and 1-(2-chloropyridin-3-yl)cyclopropane-1-carbonitrile (0.8 g, 4.48 mmol) in 1,4-dioxane (14.9 mL) was stirred under $N_{2(g)}$ at 90° C. for 16 h. The reaction mixture was then cooled to rt and partitioned between EtOAc and water. The organic layer was separated and sequentially washed with brine, dried over $MgSO_4$ and concentrated in vacuo to provide material which was used without further purification in the subsequent step.

Step 3: 1-(2-Aminopyridin-3-yl)cyclopropane-1-carbonitrile (Intermediate I-20)

To the product obtained in step 2 was added DCM (30 mL) and TFA (8.62 mL, 112 mmol), and the resulting mixture was stirred at rt overnight. The reaction mixture was then concentrated in vacuo, and the crude product was purified by silica gel chromatography (eluent: 0-20% 2 M $NH_3$ in MeOH/DCM) to afford 1-(2-aminopyridin-3-yl)cyclopropane-1-carbonitrile (Intermediate I-20, 0.705 g, 4.43 mmol, 96% yield (2 steps)) as a brown solid. $^1$H NMR (400 MHz, DMSO-$d_6$) δ ppm 8.00 (br d, J=2.70 Hz, 2H) 7.93 (d, J=6.84 Hz, 1H) 7.05 (d, J=1.66 Hz, 1H) 6.52 (dd, J=6.84, 1.87 Hz, 1H) 2.51 (s, 3H) 1.97-2.04 (m, 2H) 1.69-1.77 (m, 2H).

Intermediate I-21

4-Cyclopropyl-2-methylpyridin-3-amine

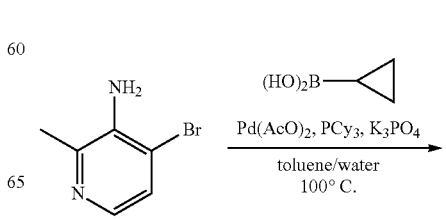

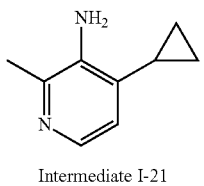

Intermediate I-21

A mixture of 3-amino-4-bromo-2-methylpyridine (1.47 g, 7.86 mmol; Chem-Impex, Wood Dale, Ill.), cyclopropylboronic acid (2.02 g, 23.58 mmol: Small Molecules, Inc., Hoboken, N.J., USA). tricyclohexylphosphine (0.44 g, 1.57 mmol), palladium acetate (0.35 g, 1.47 mmol), and potassium phosphate (5.00 g, 23.58 mmol) in toluene (4 mL) and water (0.4 mL) was sparged with $N_{2(g)}$ and then stirred at 100° C. for 2 h. The reaction mixture was diluted with EtOAc and washed with water. The organic layer was dried over $Na_2SO_4$ and concentrated in vacuo. Chromatographic purification of the residue (silica gel, eluent: 0-50% EtOAc-EtOH (3:1)/heptane) provided 4-cyclopropyl-2-methylpyridin-3-amine (Intermediate I-21) as a yellow oil. $^1$H NMR (400 MHz, CDCl$_3$) δ ppm 7.87 (d, J=5.0 Hz, 1H), 6.80 (d, J=5.0 Hz, 1H), 3.89 (br s, 2H), 2.45 (s, 3H), 1.67 (tt, J=8.3, 5.5 Hz, 1H), 0.92-1.03 (m, 2H), 0.59-0.69 (m, 2H). m/z (ESI, +ve) 149.0 (M+H)$^+$.

Intermediate I-22

1-(tert-Butyl)-4-methyl-1H-pyrazol-5-amine

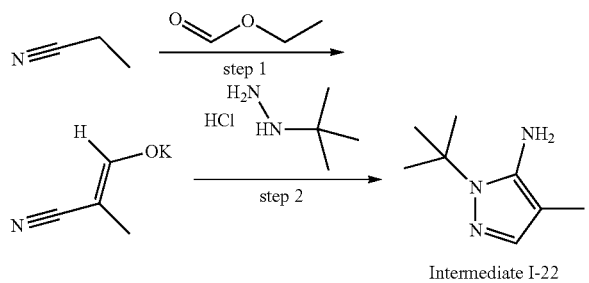

Intermediate I-22

Step 1: (E)-2-Cyanoprop-1-en-1-olate

A solution of ethyl formate (2.5 mL, 33.7 mmol) and propionitrile (2.0 mL, 28.0 mmol) in THF (15 mL) was slowly added to a solution of potassium tert-butoxide (1 M in THF, 60 mL, 60.0 mmol), and the resulting mixture was stirred at rt for 16 h. The reaction mixture was then concentrated in vacuo, and the residue was slurred in ether (5 mL) and filtered. The collected solids were washed with ethyl ether and dried in vacuo to give potassium (L)-2-cyanoprop-1-en-1-olate (3.35 g, 99%). $^1$H NMR (400 MHz, CDCl$_3$) δ (8.1, 7.9, ~1:2.6); 1.5, 1.4 (~2.5:1).

Step 2: 1-(tert-Butyl)-4-methyl-1H-pyrazol-5-amine (Intermediate I-22)

Acetic acid (8 mL, 139 mmol) and tert-butylhydrazine hydrochloride (5.0 g, 40 mmol) were sequentially added to a solution of potassium (E)-2-cyanoprop-1l-en-1-olate (3.0 g, 25 mmol) in EtOH (50 mL), and the resulting mixture was stirred at 80° C. for 4 h. The reaction mixture was then concentrated in vacuo, and satd. aq. NaHCO$_3$ (30 mL) was slowly added to the residue. 5 N NaOH and solid Na$_2$CO$_3$ were added until a slightly basic pH was achieved, and the resulting mixture was extracted with DCM (3$_x$). The combined extracts were dried over MgSO$_4$, filtered, and concentrated in vacuo. Chromatographic purification of the residue (silica gel. eluent: 10-50% EtOAc/DCM) provided 1-(tert-butyl)-4-methyl-1H-pyrazol-5-amine (Intermediate I-22, 3.20 g, 20.9 mmol, 94% yield) as a light yellow liquid. $^1$H NMR (400 MHz, CDCl$_3$) δ 7.13 (s, 1H), 3.28 (br s, 2H), 1.90 (s, 3H), 1.65 (s, 9H). m/z (ESI, +ve ion) 154.1 (M+H)$^+$.

Intermediate I-23

2-(tert-Butyl)pyridin-3-amine

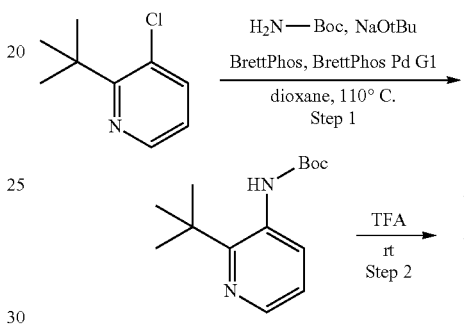

Intermediate I-23

Step 1: tert-Butyl (2-(tert-butyl)pyridin-3-yl)carbamate

A pressure vial was charged 2-(tert-butyl)-3-chloropyridine (0.100 g, 0.589 mmol, Aris Pharmaceutical Inc., Levittown, Pa.), tert-butyl carbamate (0.345 g, 2.95 mmol, Sigma-Aldrich Corporation, St Louis, Mo., USA), sodium tert-butoxide (0.283 g, 2.95 mmol, Sigma-Aldrich Corporation, St. Louis, Mo. USA), 2-(dicyclohexylphosphino)-3,6-dimethoxy-2'-4'-6'-tri-i-propyl-1,1'-biphenyl (9.49 mg, 0.018 mmol, Strem Chemicals, Newburyport, Mass.), chloro [2-(dicyclohexylphosphino)-3,6-dimethoxy-2',4',6'-triisopropyl-1,1'-biphenyl][2-(2-aminoethyl)phenyl]palladium (II) (0.019 g, 0.024 mmol, Strem Chemicals, Newburyport, Mass.) and dioxane (3 mL). The vial was flushed with $N_{2(g)}$ for 5 min, then sealed and heated at 110° C. for 18 h. Satd aq. ammonium chloride was added to neutralize excess base, and the reaction mixture was then partitioned between EtOAc and water. The separated organic layer was washed with brine, dried over Na$_2$SO$_4$ filtered, and concentrated in vacuo. Chromatographic purification of the residue (silica gel, eluent: 0-50% EtOAc-EtOH (3:1)/heptane) provided tert-butyl (2-(tert-butyl)pyridin-3-yl)carbamate (0.045 g, 0.180 mmol, 31% yield) as brown oil. $^1$H NMR (400 MHz, CDCl$_3$) δ ppm 1.45 (s, 9H) 1.52 (s, 9H) 6.41 (br s, 1H) 7.14 (dd, J=8.09, 4.56 Hz, 1H) 7.95 (br d, J=7.46 Hz, 1H) 8.31 (dd, J=4.56, 1.66 Hz, 1H).

Step 2: 2-(tert-Butyl)pyridin-3-amine (Intermediate I-23)

A mixture of tert-butyl (2-(tert-butyl)pyridin-3-yl)carbamate (0.042 g, 0.168 mmol) and TFA (1.0 mL, 12.98 mmol) was stirred at rt for 20 min, then concentrated in vacuo to give 2-(tert-butyl)pyridin-3-amine (Intermediate I-23) as brown solid. m/z (ESI, +ve ion): 151.2 (M+H)+.

Intermediate I-24

2-(5-(Difluoromethoxy)-2-fluorophenyl)-4,4,5,5-tetramethyl-1,3,2-dioxaborolane

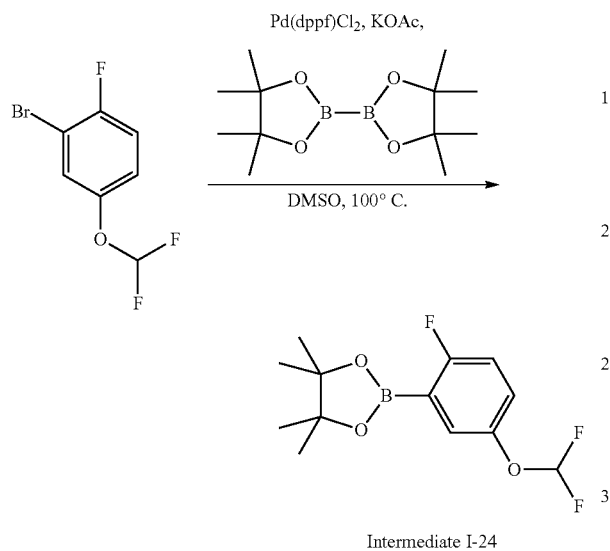

Intermediate I-24

A mixture of 2-bromo-4-(difluoromethoxy)-1-fluoro-benzene (1.50 g, 6.22 mmol, Enamine, Monmouth Jct., N.J.), bis(pinacolato)diboron (2.37 g, 9.34 mmol, Frontier Scientific. Inc., Logan, Utah), potassium acetate (1.83 g, 18.67 mmol), and dichloro[1,1'-bis(diphenylphosphino)ferrocene]palladium (II) DCM adduct (0.46 g, 0.62 mmol, Strem Chemicals, Inc., Newburyport, Mass.) in DMSO (5 mL) was stirred at 100° C. for 24 h. The reaction mixture was then cooled to rt and partitioned between EtOAc and water. The organic layer was separated and sequentially washed with brine, dried over $Na_2SO_4$ and concentrated in vacuo. Chromatographic purification of the residue (silica gel, eluent: 0-10% EtOAc/heptane) provided 2-(5-(difluoromethoxy)-2-fluorophenyl)-4,4,5,5-tetramethyl-1,3,2-dioxaborolane (Intermediate I-24, 1.33 g, 4.62 mmol, 74% yield) as a green-yellow oil. $^1$H NMR (400 MHz, DMSO-$d_6$) δ ppm 7.30-7.42 (m, 2H), 6.97-7.29 (m, 2H), 1.30 (s, 12H). m/z (ESI, +ve ion) 289 (M+H)+.

Intermediate I-25

4,6-Dicyclopropylpyrimidin-5-amine

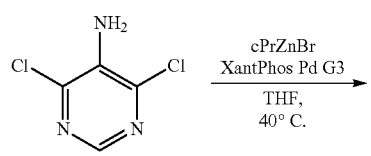

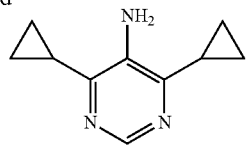

Intermediate I-25

Cyclopropylzinc bromide (0.5 M in THF, 75 ml, 37.5 mmol) was added to a mixture of 5-amine-4,6-dichloropyrimidine (2.05 g, 12.50 mmol, Sigma-Aldrich Corporation, St. Louis, Mo., USA) and [(4,5-bis(diphenylphosphino)-9,9-dimethylxanthene)-2-(2'-amino-1,1'-biphenyl)]palladium (II) methanesulfonate (1.186 g, 1.250 mmol, Sigma-Aldrich Corporation, St. Louis, Mo., USA) in THF (25 mL) under an argon atmosphere, and the resulting mixture was stirred at 40° C. for 2.5 h. The reaction mixture was then diluted with satd. aq. $NaHCO_3$ and extracted with EtOAc (2×). The combined extracts were washed with brine, dried over MgSO4, filtered, and concentrated in vacuo. Chromatographic purification of the residue (silica gel, eluent: 0-100% EtOAc/heptane) furnished 4,6-dicyclopropylpyrimidin-5-amine (Intermediate I-25) as an orange solid (1.80 g, 10.2 mmol, 82% yield). $^1$H NMR (400 MHz, CDCl$_3$) δ ppm 8.40 (1H, s) 3.91 (2H, br s) 1.81-1.89 (2H, m) 1.00-1.12 (8H, m). m/z (ESI, +ve ion): 176.1 (M+H)+.

Intermediate I-26

2-Fluoro-6-isopropylaniline

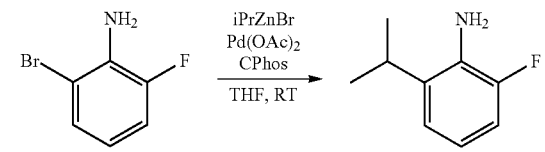

Intermediate I-26

2-Propylzinc bromide (0.50 M in THF, 16 mL, 7.9 mmol, Sigma-Aldrich Corporation, St. Louis, Mo. USA) was added to a stirred mixture of 2-bromo-6-fluoroaniline (1.00 g, 5.26 mmol, Acros, Geel, Belgium), palladium (II) acetate (0.059 g, 0.263 mmol), and 2-dicyclohexylphosphino-2',6'-dimethylamino-1,1'-biphenyl (0.230 g, 0.526 mmol, Strem Chemicals, Newburyport, Mass.) in THF (10 mL), and the resulting mixture was stirred under Ar$_{(g)}$ in a sealed vial at rt for 3 h. The reaction mixture was then diluted with satd. aq. ammonium chloride and extracted with EtOAc. The organic extract was then washed with brine, dried over MgSO$_4$, filtered, and concentrated in vacuo. Chromatographic purification of the residue (silica gel, eluent: 0-25% EtOAc in heptane) gave 2-fluoro-6-isopropylaniline as a yellow oil (Intermediate I-26, 618 mg, 4.03 mmol, 77% yield). $^1$H NMR (400 MHz, CDCl$_3$) δ ppm 6.92 (1H, d, J=7.88 Hz) 6.86 (1H, ddd, J=10.73, 8.14, 1.24 Hz) 6.69 (1H, td, J=7.88, 5.60 Hz) 3.70 (2H, br s) 2.92 (1H, spt, J=6.84 Hz) 1.26 (6H, d, J=6.84 Hz). m/z (ESI, +ve ion): 154.1 (M+H)+.

Intermediate I-27

3-Isopropylpyrazin-2-amine

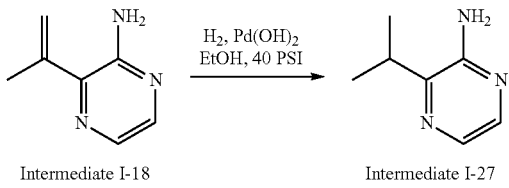

Intermediate I-18 → Intermediate I-27

A mixture of 3-(prop-1-en-2-yl)pyrazin-2-amine (Intermediate I-18, 2.00 g, 14.80 mmol) and palladium hydroxide on activated carbon (0.208 g, 1.480 mmol) in EtOH (34.6 mL) was stirred at rt under hydrogen gas (40 psi) for 16 h. The reaction mixture was then filtered through a plug of Celite, and the filter cake was rinsed with EtOH. The combined filtrates were concentrated in vacuo to provide crude 3-isopropylpyrazin-2-amine (Intermediate I-27), which was used without further purification. m/z (ESI, +ve ion): 138.2 (M+H)$^+$.

Intermediate I-28

4-Isopropyl-2,6-dimethyl-pyrimidin-5-amine

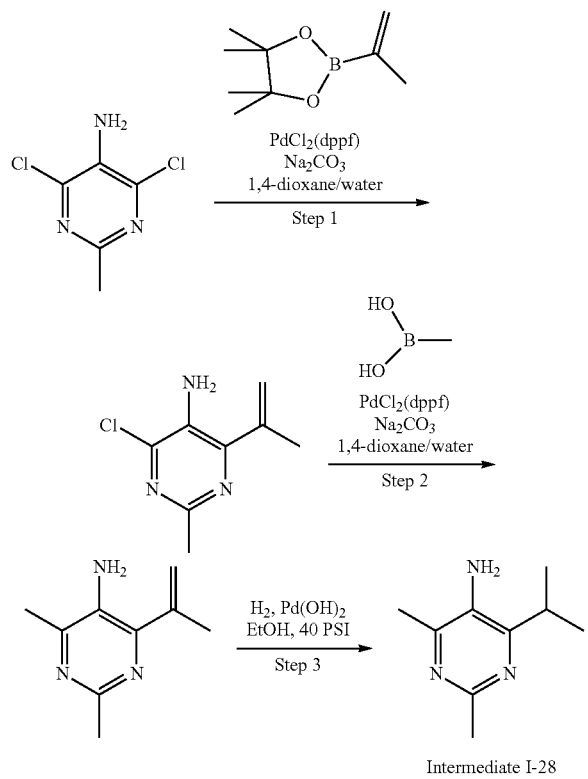

Step 1: 4-Chloro-2-methyl-6-(prop-1-en-2-yl)pyrimidin-5-amine

A mixture of 4,6-dichloro-2-methylpyrimidin-5-amine (1.5 g, 8.4 mmol, Sigma-Aldrich Corporation, St. Louis, Mo., USA), 2-isopropenylboronic acid, pincol ester (1.6 g, 9.7 mmol), sodium carbonate (2.7 g, 25 mmol), and PdCl$_2$(dppf) (0.62 g, 0.84 mmol) in 1,4-dioxane (34 mL) and water (8.4 mL) was sparged with Ar$_{(g)}$ for 5 min, then heated at 100° C. for 16 h. After cooling to rt, the resulting mixture was diluted with EtOAc and poured in heptane. The precipitated solid was collected by filtration and washed with heptane to provide 4-chloro-2-methyl-6-(prop-1-en-2-yl)pyrimidin-5-amine as tan solid. m/z (ESI, +ve ion): 184.1 (M+H)$^+$.

Step 2: 2,4-Dimethyl-6-(prop-1-en-2-yl)pyrimidin-5-amine

A mixture of 4-chloro-2-methyl-6-(prop-1-en-2-yl)pyrimidin-5-amine (1.30 g, 7.08 mmol), methaneboronic acid (0.847 g, 14.16 mmol), PdCl$_2$(dppf) (0.518 g, 0.708 mmol), and sodium carbonate (2.251 g, 21.24 mmol) in 1,4-dioxane (28.3 mL) and water (7.1 mL) was sparged with Ar$_{(g)}$ for 5 min, then stirred at 100° C. for 16 h. After cooling to rt, the reaction mixture was diluted with EtOAc and poured into heptane. The resulting mixture was sonicated for 3 min, then filtered through a pad of Celite. The filtrate was concentrated in vacuo to provide 2,4-dimethyl-6-(prop-1-en-2-yl)pyrimidin-5-amine. m/z (ESI, +ve ion): 164.1 (M+H)$^+$.

Step 3: 4-Isopropyl-2,6-dimethylpyrimidin-5-amine (Intermediate I-28)

A mixture of 2,4-dimethyl-6-(prop-1-en-2-yl)pyrimidin-5-amine (0.944 g, 5.78 mmol) and palladium hydroxide on activated carbon (0.081 g, 0.578 mmol) in EtOH (17.9 mL) was stirred under hydrogen gas (40 psi) at rt for 2 h. The reaction mixture was then filtered through a plug of Celite, and the filter cake was rinsed with ethanol. The combined filtrates were concentrated in vacuo, and the residue was triturated with cold heptane and EtOAc. The resulting solid was collected by vacuum filtration and washed with heptane to provide 4-isopropyl-2,6-dimethylpyrimidin-5-amine (Intermediate I-28, 0.173 g, 1.05 mmol, 18% yield) as tan solid. m/z (ESI, +ve ion): 166.3 (M+H)$^+$.

Intermediate I-29

4,6-Diisopropyl-2-methyl-pyrimidin-5-amine

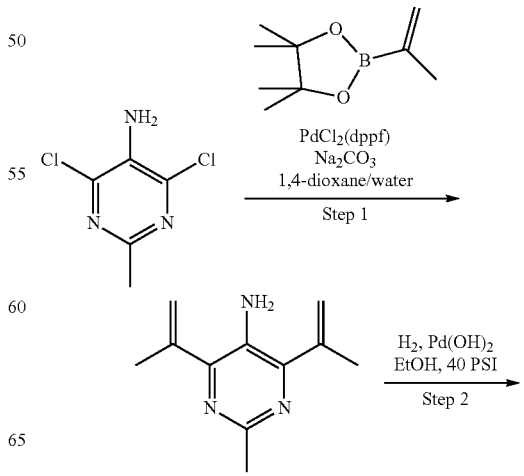

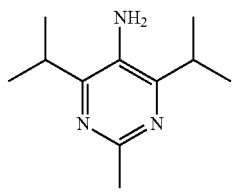

Intermediate I-29

Step 1: 2-Methyl-4,6-di(prop-1-en-2-yl)pyrimidin-5-amine

A mixture of 4,6-dichloro-2-methylpyrimidin-5-amine (2.87 g, 15.64 mmol, Sigma-Aldrich Corporation, St. Louis, Mo., USA), 2-isopropenylboronic acid, pincol ester (5.91 g, 35.2 mmol), (1,1'-bis(diphenylphosphino) ferrocene)dichloropalladium (1.14 g, 1.56 mmol) and sodium carbonate (4.97 g, 46.9 mmol) in 1,4-dioxane (83 mL) and water (20.8 mL) was sparged with $Ar_{(g)}$ for 5 min, then stirred at 100° C. for 16 h. After cooling to rt, the reaction mixture was then diluted with EtOAc (20 mL) and poured into heptane. The resulting mixture was sonicated for 3 min, then filtered through a pad of Celite. The filtrate was concentrated in vacuo to provide 2-methyl-4,6-di(prop-1-en-2-yl)pyrimidin-5-amine, which was used without further purification. m/z (ESI, +ve ion): 190.2 $(M+H)^+$.

Step 2: 4,6-Diisopropyl-2-methylpyrimidin-5-amine (Intermediate I-29)

A mixture of 2-methyl-4,6-di(prop-1-en-2-yl)pyrimidin-5-amine (2.96 g, 15.64 mmol) and palladium hydroxide on activated carbon (0.220 g, 1.564 mmol) in EtOH (39.1 mL) was stirred under hydrogen gas (40 psi) at rt for 16 h. The reaction mixture was then filtered through a plug of Celite, and the filtrate was concentrated in vacuo. The residue was triturated with cold heptane and EtOAc, and the resulting solid was collected by vacuum filtration and dried in vacuo to provide 4,6-diisopropyl-2-methylpyrimidin-5-amine (Intermediate I-29) as a tan solid. $^1$H NMR (400 MHz, DMSO-$d_6$) δ ppm 4.73 (s, 2H) 3.17 (spt, J=6.70 Hz, 2H) 2.35-2.41 (m, 3H) 1.12 (d, J=6.63 Hz, 12H). m/z (ESI, +ve ion): 194.2 $(M+H)^+$.

Intermediate I-30

4-Chloro-6-isopropylpyrimidin-5-amine

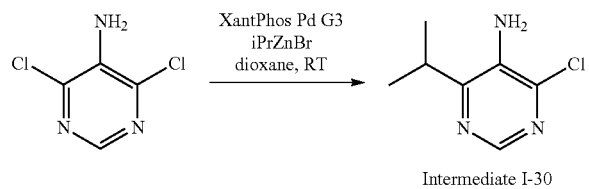

Intermediate I-30

A mixture of 4,6-dichloropyrimidin-5-amine (2.45 g, 15.0 mmol, Sigma Aldrich, St. Louis, Mo.), XantPhos Pd G3 (0.77 g, 0.75 mmol), and 2-propylzinc bromide in THF (31.4 mL, 15.7 mmol) in 1,4-dioxane (15 mL) was sparged with nitrogen and then stirred at rt for 16 h. The reaction mixture was diluted with EtOAc (150 mL) and washed with saturated aqueous ammonium chloride (3×75 mL). The organic layer was then separated, dried over $Na_2SO_4$, filtered, and concentrated in vacuo. Chromatographic purification of the residue (silica gel, eluent: 0-40% EtOAc/heptane) provided 4-chloro-6-isopropylpyrimidin-5-amine (Intermediate I-30, 1.67 g, 9.71 mmol, 65% yield) as a yellow-brown solid. $^1$H NMR (400 MHz, $CDCl_3$) δ 8.39 (s, 1H) 4.08 (br s, 2H) 3.01 (spt, J=7.0 Hz, 1H) 1.31 (br d, J=6.8 Hz, 6H). m/z (ESI, +ve ion): 171.9 (M+1).

Intermediate I-31

3-Isopropyl-N1,N1-dimethylbenzene-1,2-diamine

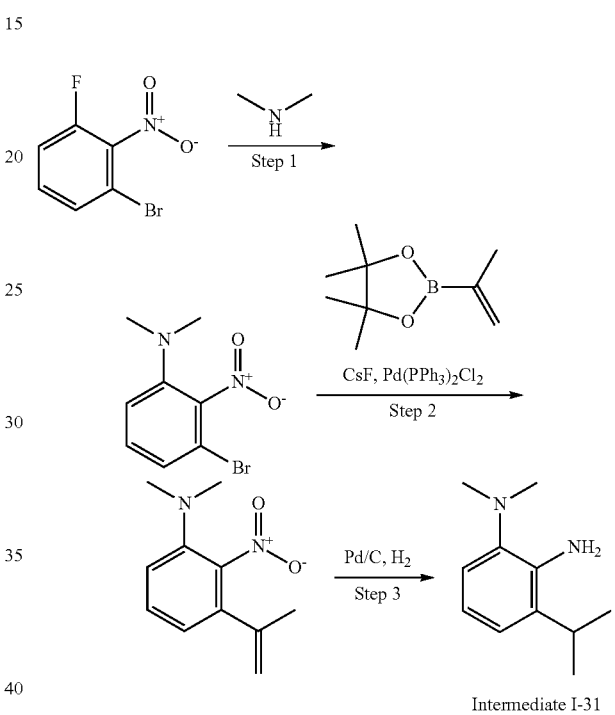

Intermediate I-31

Step 1: 3-Bromo-N,N-dimethyl-2-nitroaniline

Dimethylamine (2 M in THF: 100 mL, 200 mmol) was added to a solution of 2-bromo-6-fluoronitrobenzene (4.4 g, 20.0 mmol, Apollo Scientific Ltd., Stockport, UK) in ethanol (20 mL), and the resulting mixture was stirred at rt for 18 hours before being concentrated in vacuo. The residue was diluted with EtOAc (30 mL) and saturated $NaHCO_3$ (50 mL) was added. The mixture was extracted with EtOAc (2×150 mL), and the combined organic extracts were then dried over $Na_2SO_4$ and concentrated in vacuo. Chromatographic purification of the residue (silica gel, eluent: 0-100% EtOAc/heptane) provided 3-bromo-N,N-dimethyl-2-nitroaniline (4.72 g, 19.3 mmol, 96% yield) as a yellow oil. $^1$H NMR ($CDCl_3$) δ: 7.16-7.25 (m, 2H), 7.07 (dd, J=6.6, 2.9 Hz, 1H), 2.83 (s, 6H). m/z (ESI, +ve ion) 244.9 (M+H).

Step 2: N,N-Dimethyl-2-nitro-3-(prop-1-en-2-yl) aniline

A mixture of 3-bromo-N,N-dimethyl-2-nitroaniline (4.7 g, 19 mmol), 2-isopropenylboronic acid. pincol ester (9.61 g, 57.2 mmol), trans-dichlorobis(triphenyl-phosphine)palladium(II) (1.337 g, 1.906 mmol), and cesium fluoride (14.44 g, 95 mmol) in 1,4-dioxane (80 mL) and water (40.0 mL) was sparged with N$_{2(g)}$ for 5 min and then stirred at 80° C. for 2.5 h. The reaction mixture was then diluted with saturated aq. NaHCO$_3$ (50 mL) and extracted with EtOAc (1×150 mL). The organic extract was separated, dried over MgSO$_4$, filtered, and concentrated in vacuo. Chromatographic purification of the residue (silica gel, eluent 0-100% EtOAc-EtOH (3:1)/heptane) provided N,N-dimethyl-2-nitro-3-(prop-1-en-2-yl)aniline (3.93 g, 19.1 mmol, 100% yield) as yellow oil. $^1$H NMR (CDCl$_3$) δ: 7.31-7.37 (m, 1H), 7.11 (dd, J=8.2, 0.9 Hz, 1H), 6.91 (dd, J=7.6, 1.1 Hz, 1H), 5.17 (t, J=1.6 Hz, 1H), 4.97 (s, 1H), 2.81 (s, 6H), 2.07 (s, 3H). m/z (ESI, +ve ion) 207.1 (M+H).

Step 3: 3-Isopropyl-N$^1$,N$^1$-dimethylbenzene-1,2-diamine (Intermediate I-31)

A mixture of N,N-dimethyl-2-nitro-3-(prop-1-en-2-yl)aniline (3.9 g, 19 mmol) and palladium 10 wt. % on activated carbon (0.4 g) in ethanol (40 mL) was stirred under H$_2$ (45 psig) at rt for 4 h. The reaction mixture was then filtered through Celite (washing with EtOAc (3×50 mL)), and the combined filtrates were concentrated in vacuo. Chromatographic purification of the residue (silica gel, eluent 0-5% 2 M NH$_3$ in MeOH/DCM) provided 3-isopropyl-N$^1$,N$^1$-dimethylbenzene-1,2-diamine (Intermediate I-31, 2.2 g, 12.3 mmol, 65% yield) as a yellow liquid. $^1$H NMR (CDCl$_3$) δ: 6.95 (d, J=7.7 Hz, 2H), 6.74-6.80 (m, 1H), 3.95-4.28 (m, 2H), 2.93 (quin, J=6.8 Hz, 1H), 2.68 (s, 6H), 1.28 (d, J=6.8 Hz, 6H). m/z (ESI, +ve ion) 179.1 (M+H).

Intermediate I-32

2-Isopropyl-6-methoxy-4-methylpyridin-3-amine

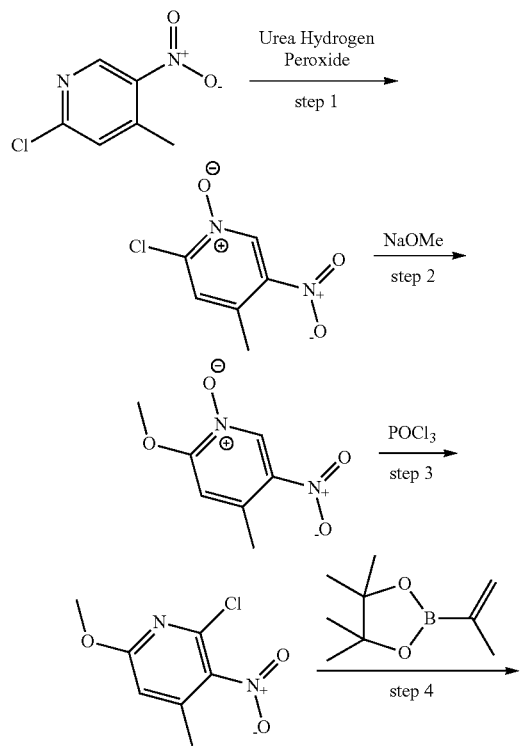

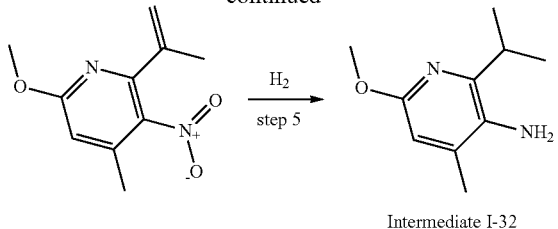

Intermediate I-32

Step 1: 2-Chloro-4-methyl-5-nitropyridine 1-oxide

Urea hydrogen peroxide (4.93 g, 52.4 mmol) was added in three portions to a solution of 2-chloro-4-methyl-5-nitropyridine (4.52 g, 26.2 mmol, Matrix Scientific, Haram Cairo—Egypt) in dichloromethane (45 mL) at 0° C. 2,2,2-Trifluoroacetic anhydride (7.40 mL, 52.4 mmol) was then added, dropwise, and the resulting mixture was stirred at rt for 4 h. Water (140 mL) was added, and the resulting mixture was stirred at rt for 30 mins. The aqueous and organic layers were tested for peroxide (Quantofix test strip; Macherey-Nagel, Doren, Germany; <1 mg/L peroxide present), and the organic layer was separated. The aqueous layer was extracted with DCM (3×100 mL), and all organic layers were then combined, washed saturated aq. NaHCO$_3$ (50 mL), dried over MgSO$_4$, and concentrated in vacuo. Chromatographic purification of the residue (silica gel, eluent: 0-100% EtOAc/heptane) provided 2-chloro-4-methyl-5-nitropyridine 1-oxide (3.68 g, 19.5 mmol, 75% yield) as a yellow solid. $^1$H NMR (CDCl$_3$) δ: 9.02 (s, 1H), 7.51 (s, 1H), 2.64 (s, 3H). m/z (ESI, +ve ion): 188.9 (M+H)$^+$.

Step 2: 2-Methoxy-4-methyl-5-nitropyridine 1-oxide

Sodium methoxide (0.5 M in MeOH; 55.7 mL, 27.8 mmol) was added, dropwise, to a solution of 2-chloro-4-methyl-5-nitropyridine 1-oxide (3.5 g, 18.6 mmol) in methanol (100 mL) at 0° C., and the resulting mixture was stirred at 0° C. for 2 hours, then at room temperature for 2 hours. The reaction mixture was then concentrated in vacuo, and the residue was purified by silica gel chromatography (eluent: 0-20% MeOH/DCM) to provide 2-methoxy-4-methyl-5-nitropyridine 1-oxide (990 mg, 5.38 mmol, 29% yield) as a yellow solid. $^1$H NMR (CDCl$_3$) δ: 9.11 (s, 1H), 6.80 (s, 1H), 4.20 (s, 3H), 2.73 (s, 3H). m/z (ESI, +ve ion): 185.0 (M+H)$^+$.

Step 3: 2-Chloro-6-methoxy-4-methyl-3-nitropyridine

Phosphorus oxychloride (13.2 ml, 141 mmol) was slowly added to 2-methoxy-4-methyl-5-nitropyridine 1-oxide (1.3 g, 7.06 mmol) at 0° C., and the resulting mixture was then heated to 70° C. and stirred for 3 hours. The mixture was subsequently concentrated in vacuo, and the residue was taken up in EtOAc (150 mL) and sequentially washed with saturated aq. NaHCO$_3$ (50 mL), dried over MgSO$_4$, and concentrated in vacuum. Chromatographic purification of the residue (silica gel, 0%-100% EtOAc/heptane) provided 2-chloro-6-methoxy-4-methyl-3-nitropyridine (684 mg, 3.38 mmol, 48% yield) as a white solid. $^1$H NMR (METHANOL-d4) δ: 6.79 (s, 1H), 3.96 (s, 3H), 2.32 (s, 3H). m/z (ESI, +ve ion): 202.9 (M+H)$^+$.

Step 4: 6-Methoxy-4-methyl-3-nitro-2-(prop-1-en-2-yl)pyridine

A mixture of 2-chloro-6-methoxy-4-methyl-3-nitropyridine (684 mg, 3.38 mmol), 2-isopropenylboronic acid, pincol ester (1.702 g, 10.13 mmol), cesium carbonate (3300 mg, 10.13 mmol), trans-dichlorobis(triphenyl-phosphine)palladium (II) (237 mg, 0.338 mmol) in 1,2-dimethoxyethane (20 mL) and water (4.00 mL) was sparged with $N_{2(g)}$ for 5 mins and then stirred at 80° C. for 3 hours. Additional 2-isopropenylboronic acid, pincol ester (1.70 g, 10.13 mmol), cesium carbonate (3.30 g, 10.13 mmol), and trans-dichlorobis(triphenyl-phosphine)palladium (1H) (237 mg, 0.338 mmol) were then added, the resulting mixture was stirred at 80° C. for 3 h. The mixture was then cooled to room temperature, diluted with saturated aq. $NaHCO_3$ (30 mL), and extracted with EtOAc (2×120 mL). The combined extracts were then dried over $MgSO_4$ and concentrated in vacuo. Chromatographic purification of the residue (silica gel, 0%-100% EtOAc/heptane) provided 6-methoxy-4-methyl-3-nitro-2-(prop-1-en-2-yl)pyridine as a yellow solid, which was used in the next step without further purification. m/z (ESI, +ve ion): 209.0 $(M+H)^+$.

Step 5: 2-Isopropyl-6-methoxy-4-methylpyridin-3-amine (Intermediate I-32)

A mixture of 6-methoxy-4-methyl-3-nitro-2-(prop-1-en-2-yl)pyridine (703 mg, 3.38 mmol) and palladium (10 wt. % on activated carbon; 70 mg) in ethanol (22 mL) was stirred under $H_{2(g)}$ (40 psi) at rt for 4.5 h and then filtered through Celite (washing with EtOAc (5×30 mL)). The combined filtrates were concentrated in vacuo, and the residue chromatographically purified (silica gel, 0%-5% $NH_3$ 2M in MeOH/DCM) to provided 2-isopropyl-6-methoxy-4-methylpyridin-3-amine (Intermediate I-32, 193 mg, 1.07 mmol, 32% yield) as a yellow liquid. $^1$H NMR ($CDCl_3$) δ: 6.35 (s, 1H), 3.86 (s, 3H), 3.06 (dt, J=13.4, 6.9 Hz, 1H), 2.19 (s, 3H), 1.27 (d, J=6.6 Hz, 6H). m/z (ESI, +ve ion): 181.1 $(M+H)^+$.

Intermediate I-33

6-Isopropyl-N2,N2-bis(4-methoxybenzyl)-4-methylpyridine-2,5-diamine

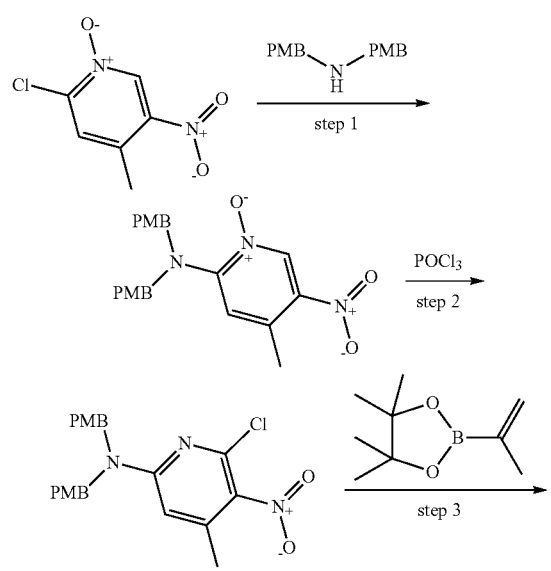

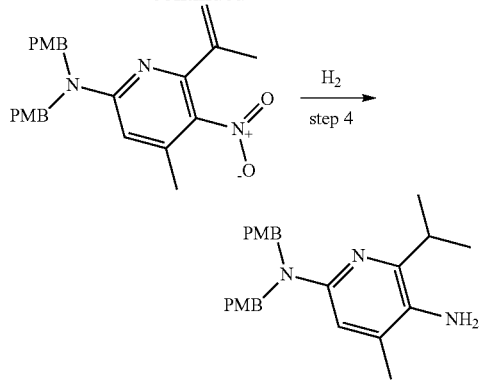

Intermediate I-33

PMB = p-methoxybenzyl

Step 1: 2-(Bis(4-methoxybenzyl)amino)-4-methyl-5-nitropyridine 1-oxide

A mixture of 2-chloro-4-methyl-5-nitropyridine 1-oxide (2.3 g, 12.20 mmol; product of step 2 in preparation of Intermediate I-32), bis(4-methoxybenzyl)-amine (3.45 g, 13.42 mmol), and sodium carbonate (anhydrous, powder; 2.6 g, 24.39 mmol) in toluene (70 mL) was stirred at 70° C. for 16 h. Additional sodium carbonate (anhydrous, powder; 2.6 g, 24.39 mmol) and bis(4-methoxybenzyl)-amine (3.45 g, 13.42 mmol) were added, and the resulting mixture was stirred at 90° C. for 2 h. The reaction mixture was then filtered, and the filter cake washed with DCM (3×100 mL). The combined filtrates were concentrated in vacuo and the residue chromatographically purified (silica gel, 0%-10% MeOH/DCM) to provide 2-(bis(4-methoxybenzyl)amino)-4-methyl-5-nitropyridine 1-oxide (2.75 g, 6.72 mmol, 55% yield) as a brown solid. $^1$H NMR ($CDCl_3$) δ: 9.11 (s, 1H), 7.26 (d, J=8.7 Hz, 4H), 6.92 (d, J=8.7 Hz, 4H), 6.60 (s, 1H), 4.77 (s, 4H), 3.87 (s, 6H), 2.59 (s, 3H). m/z (ESI, +ve ion): 410.0 $(M+H)^+$.

Step 2: 6-Chloro-N,N-bis(4-methoxybenzyl)-4-methyl-5-nitropyridin-2-amine

Phosphorus oxychloride (12.29 ml, 132 mmol) was added, dropwise, to a solution of 2-(bis(4-methoxybenzyl)amino)-4-methyl-5-nitropyridine 1-oxide (2.7 g, 6.59 mmol) in N,N'-diisopropylethylamine (27.6 mL, 158 mmol) at 0° C. and the resulting mixture was heated to 70° C. and stirred for 10 mins. The reaction mixture was then concentrated in vacuo and the residue diluted with ice water (20 mL) and EtOAc (100 mL). The resulting mixture was stirred as saturated aq. $NaHCO_3$ (50 mL) was slowly added until a pH of 10-11 was achieved. The resulting mixture was then stirred at room temperature for 30 mins before the organic layer was separated, dried over MgSO4, and concentrated in vacuo. Chromatographic purification of the residue (silica gel, 0%-100% EtOAc/heptane) provided 6-chloro-N,N-bis(4-methoxybenzyl)-4-methyl-5-nitropyridin-2-amine (1.62 g, 3.77 mmol, 57% yield) as a yellow solid. $^1$H NMR (METHANOL-d4) δ: 7.15 (br d, J=8.7 Hz, 4H), 6.87 (d, J=8.7 Hz, 4H), 6.44 (s, 1H), 4.72 (s, 4H), 3.77 (s, 6H), 2.21 (s, 3H). m/z (ESI, +ve ion): 427.9 $(M+H)^+$.

Step 3: N,N-Bis(4-methoxybenzyl)-4-methyl-5-nitro-6-(prop-1-en-2-yl)pyridin-2-amine A mixture of 6-chloro-N,N-bis(4-methoxybenzyl)-4-methyl-5-nitropyridin-2-amine (1.59 g, 3.72 mmol), 2-isopropenylboronic acid, pincol ester (1.873 g, 11.15 mmol), cesium carbonate (3.63 g, 11.15 mmol), and trans-dichlorobis(triphenyl-phosphine)palladium (II) (0.261 g, 0.372 mmol) in 1,2-dimethoxyethane (20 mL) and water (4.00 mL) was sparged with $N_2$, for 5 min and then stirred at 80° C. for 3 h. Additional 2-isopropenylboronic acid, pincol ester (1.873 g, 11.15 mmol), cesium carbonate (3.63 g, 11.2 mmol), and trans-dichlorobis(triphenyl-phosphine)palladium (II) (0.261 g, 0.372 mmol) were then added, and the resulting mixture was stirred at 80° C. for 1 hour. After cooling to rt, saturated aq. $NaHCO_3$ (30 mL) was added, and the resulting mixture was extracted with EtOAc (2×120 mL). The combined extracts were dried over $MgSO_4$ and concentrated in vacuo. Chromatographic purification of the residue (silica gel, 0%-100% EtOAc:EtOH (3:1)/heptane) provided N,N-bis(4-methoxybenzyl)-4-methyl-5-nitro-6-(prop-1-en-2-yl)pyridin-2-amine (1.00 g, 2.31 mmol, 62% yield) as a yellow solid. m/z (ESI, +ve ion): 434.0 $(M+H)^+$.

Step 4: 6-Isopropyl-$N^2$,$N^2$-bis(4-methoxybenzyl)-4-methylpyridine-2,5-diamine (Intermediate I-33)

A mixture of N,N-bis(4-methoxybenzyl)-4-methyl-5-nitro-6-(prop-1-en-2-yl)pyridin-2-amine (1.00 g, 2.31 mmol) and palladium, 10 w. % on activated carbon (0.1 g) in ethanol (15 mL) and ethyl acetate (15 mL) was then stirred under $H_{2(g)}$ (40 psi) at rt for 1.5 hours, then under $H_{2(g)}$ (30 psi) at rt for 16 hours. The mixture was subsequently filtered through Celite (washing with EtOAc (2×100 mL)), and the combined filtrates were concentrated in vacuo. Chromatographic purification of the residue (silica gel, 0%-10% ammonia in MeOH 2M/heptane) provided 6-isopropyl-$N^2$,$N^2$-bis(4-methoxybenzyl)-4-methylpyridine-2,5-diamine (Intermediate I-33, 340 mg, 0.838 mmol, 36% yield) as a yellow oil. $^1H$ NMR ($CDCl_3$) δ: 7.26 (br d, J=7.3 Hz, 4H), 6.90 (br d, J=7.9 Hz, 4H), 6.13-6.26 (m, 1H), 4.56-4.83 (m, 4H), 3.87 (s, 8H), 3.02-3.19 (m, 1H), 2.17 (br d, J=10.4 Hz, 3H), 1.34 (br d, J=5.6 Hz, 6H). m/z (ESI, +ve ion): 406.1 $(M+H)^+$.

Intermediate I-34

4-Cyclopropyl-6-methylpyrimidin-5-amine

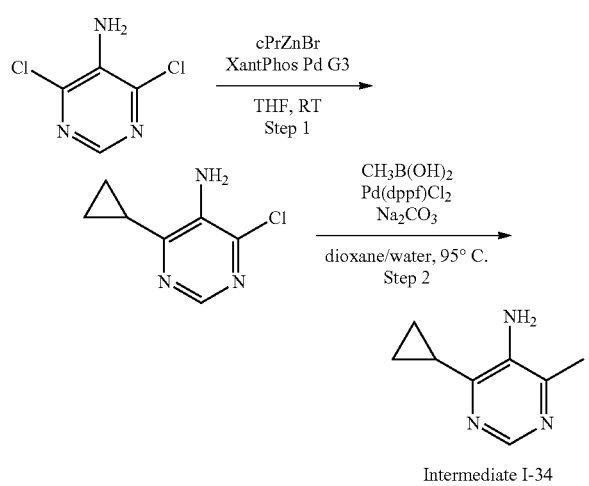

Intermediate I-34

Step 1: 4-chloro-6-cyclopropylpyrimidin-5-amine

Cyclopropylzinc bromide (0.5 M in THF, 47.0 ml, 23.48 mmol) was added to a mixture of 4,6-dichloro-5-aminopyrimidine (3.50 g, 21.34 mmol) and XantPhos Pd G3 (1.012 g, 1.067 mmol) under an argon atmosphere, and the resulting mixture was stirred at room temperature for 17 h. The reaction mixture was then diluted with EtOAc (500 mL) and washed with water (400 mL). The organic layer was separated, washed with brine (300 mL), dried over $MgSO_4$, filtered, and concentrated in vacuo. Chromatographic purification of the residue (silica gel, 0 to 50% EtOAc in heptane) gave 4-chloro-6-cyclopropylpyrimidin-5-amine as a light-yellow solid (1.36 g, 8.02 mmol, 38% yield). $^1H$ NMR (400 MHz, $CDCl_3$) δ ppm 8.27 (1H, s) 4.18 (2H, br s) 1.81-1.89 (1H, m) 1.14-1.19 (2H, m) 1.06-1.13 (2H, m). m/z (ESI, +ve ion): 170.1 $(M+H)^+$.

Step 2: 4-cyclopropyl-6-methylpyrimidin-5-amine (Intermediate I-34)

A mixture of 4-Chloro-6-cyclopropylpyrimidin-5-amine (1.36 g, 8.02 mmol), methylboronic acid (2.400 g, 40.1 mmol), (1,1'-bis(diphenylphosphino) ferrocene)dichloropalladium (0.587 g, 0.802 mmol), and sodium carbonate (2.0 M, aqueous, 20.05 mL, 40.1 mmol) in 1,4-dioxane (40 mL) was stirred under an argon atmosphere at 95° C. for 22 h. The reaction mixture was then diluted with water (100 mL) and extracted three times with EtOAc (100 mL). The organic layers were combined, washed with brine (150 mL), dried over $MgSO_4$, filtered, and concentrated in vacuo. Chromatographic purification of the residue (silica gel, 0 to 100% EtOAc in heptane) gave 4-cyclopropyl-6-methylpyrimidin-5-amine as a green solid (Intermediate I-34, 737 mg, 4.94 mmol, 62% yield). $^1H$ NMR (400 MHz, $CDCl_3$) δ ppm 8.43 (1H, s) 3.73 (2H, br s) 2.40 (3H, s) 1.79-1.89 (1H, m) 1.07-1.13 (2H, m) 1.01-1.07 (2H, m). m/z (ESI, +ve ion): 150.2 $(M+H)^+$.

Intermediate I-35

6-Isopropyl-$N^4$,$N^4$-dimethylpyrimidine-4,5-diamine

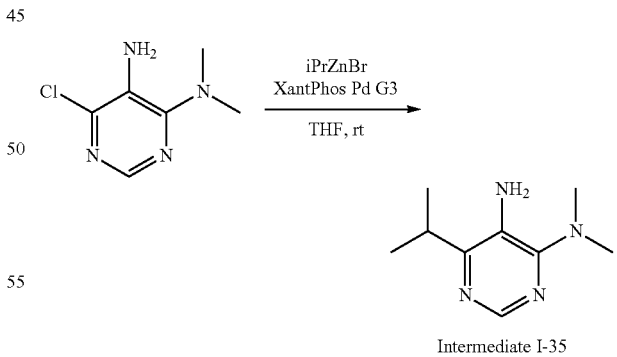

Intermediate I-35

To a nitrogen-sparged solution of 6-chloro-4-dimethylamino-pyrimidine-5-amine (2.00 g, 11.6 mmol, Enamine, Kiev, Ukraine) in THF (11.6 mL) was added isopropylzinc bromide (0.5 M in THF, 40.6 mL, 20.3 mmol) and XantPhos Pd G3 (0.55 g, 0.58 mmol). The resulting mixture was stirred at room temperature for 2 h and then filtered through a pad of Celite®. The filter cake was rinsed with EtOAc, and the collected filtrate was concentrated in vacuo. Chromatographic purification of the residue (silica gel, eluent: 0-100% 3:1 EtOAc-EtOH in heptanes) afforded 6-isopropyl-N⁴,N⁴-dimethylpyrimidine-4,5-diamine (Intermediate I-35). ¹H NMR (400 MHz, DMSO-d₆) δ ppm 1.14 (d, J=6.6 Hz, 6H), 2.80 (s, 6H), 3.20 (sept, J=6.6 Hz, 1H), 4.60 (br s, 2H), 8.11 (s, 1H); m/z (ESI, +ve ion): 181.2 (M+H)⁺.

Intermediate I-36

4,6-di-Isopropyl-2-methoxypyrimidin-5-amine

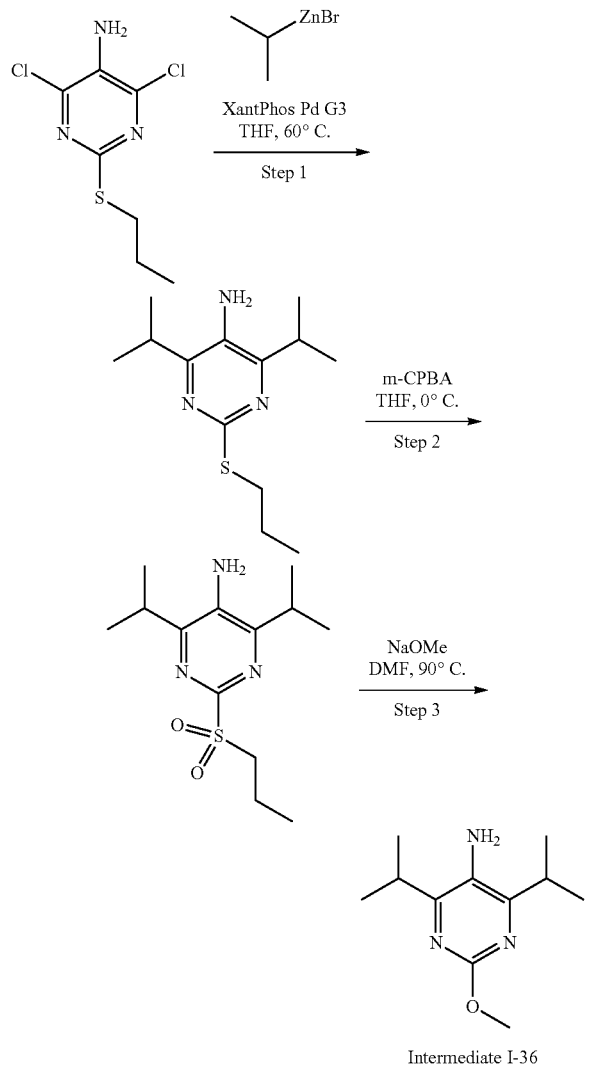

Intermediate I-36

Step 1: 4,6-Diisopropyl-2-(propylthio)pyrimidin-5-amine

A mixture of 4,6-dichloro-2-(propylthio)pyrimidin-5-amine (2.45 g, 10.29 mmol) and tetrahydrofuran (20.6 mL) was spared with argon gas for 5 min, then 2-propylzinc bromide (0.5 M in THF, 61.7 mL, 30.9 mmol) and Xantphos Pd G3 (Sigma-Aldrich, St. Louis, Mo.: 0.293 g, 0.309 mmol) were sequentially added. The resulting mixture was heated to 60° C. and stirred for 2 h, then cooled to rt. Sat. aq. NH₄Cl (30 mL) was added, and the resulting mixture was stirred for 10 min, then diluted with EtOAc and brine (10 mL). The organic layer was separated, and the aqueous layer was extracted with EtOAc. The combined organic extracts were dried over MgSO₄, filtered, and concentrated in vacuo. Chromatographic purification of the residue (silica gel, 0-30% EtOAc/Heptane) provided 4,6-diisopropyl-2-(propylthio)pyrimidin-5-amine (1.75 g, 6.91 mmol, 67% yield) as a tan oil. ¹H NMR (400 MHz, DMSO-d₆) δ ppm 4.80 (s, 2H) 3.13-3.25 (m, 2H) 2.91-3.05 (m, 2H) 1.66 (sxt, J=7.26 Hz, 2H) 1.12 (d, J=6.63 Hz, 12H) 0.96 (t, J=7.36 Hz, 3H). m/z (ESI, +ve ion): 254.1 (M+H)⁺.

Step 2: 4,6-Diisopropyl-2-(propylsulfonyl)pyrimidin-5-amine

A mixture of 4,6-diisopropyl-2-(propylthio)pyrimidin-5-amine (1.56 g, 6.16 mmol) and 3-chloroperoxybenzoic acid (3.45 g, 15.4 mmol) in THF (30.8 mL) was stirred at rt for 45 min, then cooled to 0° C. Sat. aq. NaHCO₃ was added slowly (3×10 mL portions) over 20 min. The resulting mixture was diluted with 4:1 EtOAc/MeOH and brine (20 mL), and the organic layer was separated. The aqueous layer was extracted with EtOAc, and the combined organic extracts were then dried over MgSO₄, filtered, and concentrated in vacuo. The residue was diluted with DMF (20 mL) and agitated by sonication to provide a homogeneous mixture. The mixture was slowly poured into water (100 mL), and the precipitated solid was collected by filtration, then washed with water and dried in a reduced-pressure oven at 45° C. overnight to afforded 4,6-diisopropyl-2-(propylsulfonyl)pyrimidin-5-amine (1.65 g, 5.76 mmol, 94% yield) as tan solid. ¹H NMR (400 MHz, DMSO-d₆) δ ppm 6.08 (br s, 2H) 3.48-3.68 (m, 3H) 1.79 (br s, 2H) 1.29 (br s, 12H) 1.07 (br s, 4H). m/z (ESI, +ve ion): 286.2 (M+H)⁺.

Step 3: 4,6-diisopropyl-2-methoxypyrimidin-5-amine (Intermediate I-36)

A mixture of 4,6-diisopropyl-2-(propylsulfonyl)pyrimidin-5-amine (0.300 g, 1.05 mmol) and sodium methoxide (0.5 M in MeOH, 3.4 mL, 1.68 mmol) in N,N-dimethylformamide (3.5 mL) was stirred in a sealed vial at 90° C. for 16 h. Additional sodium methoxide (0.5 M in MeOH, 3.4 mL, 1.68 mmol) was subsequently added, and the resulting mixture was stirred at 90° C. for an additional 16 h. After cooling, the reaction mixture was partitioned between EtOAc and sat. aq. NH₄Cl. The organic layer was separated, and the aqueous layer was extracted with EtOAc. The combined organic extracts were then dried over MgSO₄, filtered, and concentrated in vacuo. The residue was triturated with EtOAc and heptane, and the collected solids were washed with heptane and dried to provide 4,6-diisopropyl-2-methoxypyrimidin-5-amine (Intermediate I-36, 0.095 g, 0.454 mmol, 43% yield) as tan oil. m/z (ESI, +ve ion): 210.2 (M+H)⁺.

Intermediate I-37

4-(((tert-Butyldiphenylsilyl)oxy)methyl)-2-isopropyl-6-methylaniline

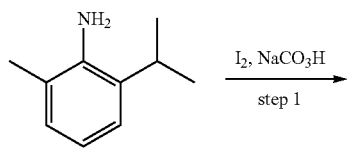

step 1

-continued

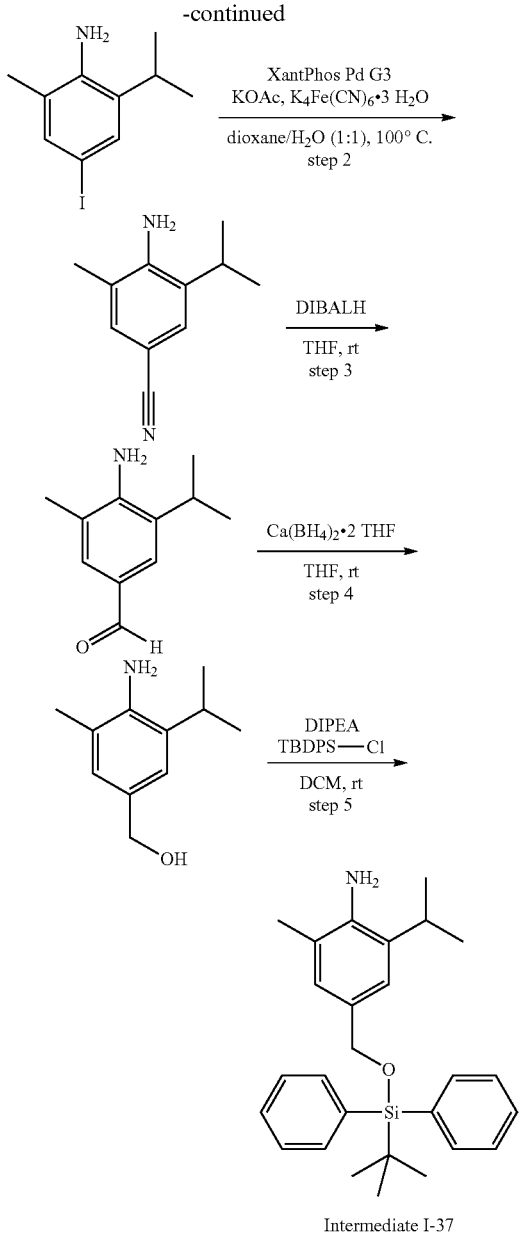

Intermediate I-37

Step 1: 4-Iodo-2-isopropyl-6-methylaniline

To a suspension of 2-isopropyl-6-methylaniline (3.2 mL, 20 mmol, Advanced Chemblocks Inc., Burlingame, Calif., USA), and sodium bicarbonate (3.4 g, 40 mmol) in DCM (20 mL) and water (20 mL) was added iodine (5.4 g, 21 mmol) in three portions. After 90 min, the 1 N sodium thiosulfate (30 mL) was added, and the resulting mixture was partitioned between DCM (30 mL) and water (10 mL). The organic layer was separated, and the aqueous layer was extracted with DCM (100 mL). The combined organic layers were then sequentially washed with brine (300 mL), dried over magnesium sulfate, filtered, and concentrated in vacuo. Chromatographic purification of the residue (silica gel, eluent: 0-30% EtOAc in heptanes) afforded 4-iodo-2-isopropyl-6-methylaniline as a red-purple oil. $^1$H NMR (400 MHz, DMSO-$d_6$) δ ppm 1.11 (d, J=6.8 Hz, 6H), 2.04 (s, 3H), 2.97 (sept, J=6.8 Hz, 1H), 4.73 (s, 2H), 7.08-7.10 (s, 1H), 7.10-7.13 (m, 1H); m/z (ESI, +ve ion) 275.9 (M+H)$^+$.

Step 2: 4-Amino-3-isopropyl-5-methylbenzonitrile

A nitrogen-sparged suspension of 4-iodo-2-isopropyl-6-methylaniline (2.2 g, 7.9 mmol), XantPhos Pd G3 (170 mg, 0.20 mmol), potassium acetate (580 mg, 5.9 mmol), and potassium hexacyanoferrate(II) trihydrate (5.0 g, 12 mmol) in 1,4-dioxane (20 mL) and water (20 mL) was vigorously stirred at 100° C. for 4 h. The reaction mixture was then partitioned between water (200 mL) and EtOAc (150 mL). The organic layer was separated, and the aqueous layer was extracted with EtOAc (2×70 mL). The combined organic extracts were then dried over magnesium sulfate, filtered, and concentrated in vacuo. Chromatographic purification of the residue (silica gel, eluent: 0-40% EtOAc in heptanes) afforded 4-amino-3-isopropyl-5-methylbenzonitrile as an amber oil. $^1$H NMR (400 MHz, DMSO-$d_6$) δ ppm 1.09-1.18 (m, 6H), 2.08 (s, 3H), 3.02 (sept, J=6.6 Hz, 1H), 5.59 (br s, 2H), 7.20 (br s, 1H), 7.22 (br s, 1H): m/z (ESI, +ve ion) 175.1 (M+H)$^+$.

Step 3: 4-Amino-3-isopropyl-5-methylbenzaldehyde

Diisobutylaluminum hydride (1 M in toluene, 17 mL, 17 mmol) was added, dropwise, to a room temperature solution of 4-amino-3-isopropyl-5-methylbenzonitrile (1.2 g, 6.9 mmol) in THF (34 mL). After 20 min, the reaction mixture was cooled to 0° C. and 1 M aq. Rochelle salt (35 mL) was added. The resulting mixture was stirred for 45 min, and the organic layer was then separated. The aqueous layer was extracted with EtOAc (1×70 mL), and the combined organic extracts were then sequentially washed with brine (300 mL), dried over magnesium sulfate, filtered through Celite®, and concentrated in vacuo. Chromatographic purification of the residue (silica gel, eluent: 0-15% EtOAc in heptanes) afforded 4-amino-3-isopropyl-5-methylbenzaldehyde as a thick yellow oil. $^1$H NMR (400 MHz, DMSO-$d_6$) δ ppm 1.17 (d, J=6.6 Hz, 6H), 2.14 (s, 3H), 3.06 (spt, J=6.6 Hz, 1H), 5.75 (s, 2H), 7.35 (s, 1H), 7.44 (s, 1H), 9.59 (s, 1H); m/z (ESI, +ve ion) 178.1 (M+H)$^+$.

Step 4: (4-Amino-3-isopropyl-5-methylphenyl)methanol

Calcium borohydride bis(tetrahydrofuran) (1.8 g, 8.2 mmol) was added to a stirred solution of 4-amino-3-isopropyl-5-methylbenzaldehyde (970 mg, 5.5 mmol) in THF (8 mL), and the resulting mixture was stirred at rt for 2 h. Saturated aqueous NH$_4$Cl (30 mL) was then slowly added, and the resulting mixture was extracted with (3×20 mL). The combined organic extracts were washed with brine, dried over sodium sulfate, filtered, and concentrated in vacuo to give crude (4-amino-3-isopropyl-5-methylphenyl)methanol, which was used without purification. m/z (ESI, +ve ion) 180.2 (M+H)$^+$.

Step 5: 4-(((tert-Butyldiphenylsilyl)oxy)methyl)-2-isopropyl-6-methylaniline (Intermediate I-37)

DIPEA (1.4 mL, 8.2 mmol) and tert-butyl(chloro)diphenylsilane (1.7 mL, 6.6 mmol) were sequentially added to a solution of (4-amino-3-isopropyl-5-methylphenyl)methanol (710 mg, 4.0 mmol) in DCM (10 mL), and the resulting mixture was stirred at room temperature for 4 h. The reaction mixture was then concentrated in vacuo and the residue chromatographically purified (silica gel, eluent: 0-40% EtOAc in heptanes) to provide 4-(((tert-butyldiphenylsilyl)oxy)methyl)-2-isopropyl-6-methylaniline (Intermediate I-37). m/z (ESI, +ve ion) 418.1 (M+H)⁺.

Intermediate I-38

2-Bromo-4,6-diisopropylpyrimidin-5-amine

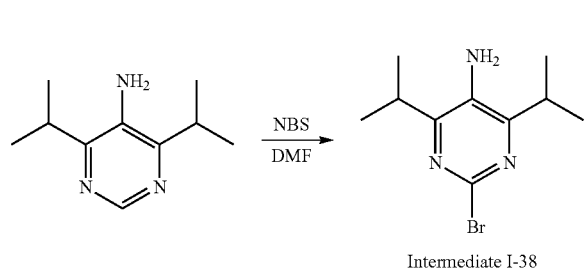

Intermediate I-38

A mixture of 4,6-diisopropylpyrimidin-5-amine (1 g, 5.58 mmol, Intermediate U), 1-bromopyrrolidine-2,5-dione (1.191 g, 6.69 mmol), and DMF (5 mL) was heated at 70° C. in a sealed pressure vial for 4 h, then cooled to rt and diluted with water. The resulting mixture was extracted with EtOAc, and the combined extracts were washed with brine, dried over Na₂SO₄, filtered, and concentrated in vacuo. Chromatographic purification of the residue (silica gel, 0-40% EtOAc/heptane) furnished 2-bromo-4,6-diisopropylpyrimidin-5-amine (Intermediate I-38) as brown oil. ¹H NMR (400 MHz, DMSO-d₆) δ ppm 1.12 (d, J=6.63 Hz, 12H) 3.12-3.27 (m, 2H) 5.27 (s, 2H). m/z (ESI, +ve ion): 258.0/260.0 (M+H)⁺

Intermediate I-39

4-Isopropyl-6-methoxypyrimidin-5-amine

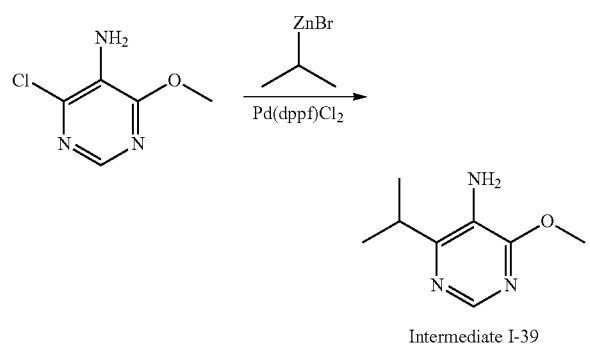

Intermediate I-39

Isopropylmagnesium bromide (9.4 mL, 4.70 mmol) was added to a stirred mixture of 4-chloro-6-methoxypyrimidin-5-amine (0.50 g, 3.1 mmol, Frontier Scientific Inc., Newark, Del.), Pd(dppf)Cl₂ (0.23 g, 0.31 mmol), and THF (5 mL), and the resulting mixture was heated at 60° C. for 16 h. After cooling, 5 N NaOH was added, and the resulting mixture was extracted with EtOAc (3×). The combined extracts were washed with brine, dried over MgSO₄, and concentrated in vacuo. Chromatographic purification of the residue (silica gel, 40% EtOAc/heptane) gave 4-isopropyl-6-methoxypyrimidin-5-amine (Intermediate I-39, 482 mg, 91%). ¹H NMR (CDCl₃) δ: 8.18 (s, 1H), 3.92 (s, 3H), 3.57 (br s, 2H), 2.91 (dt, J=13.5, 6.7 Hz, 1H), 1.19 (br d, J=6.8 Hz, 6H). m/z (ESI, +ve ion) 168.1 (M+H)⁺.

Intermediate I-40

2-(((tert-Butyldiphenylsilyl)oxy)methyl)-6-isopropylaniline

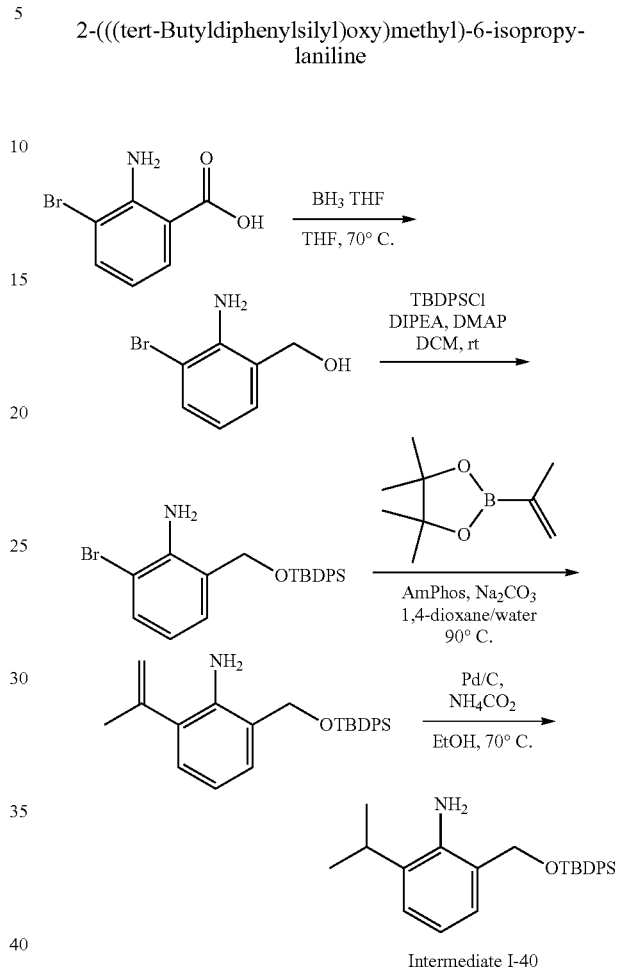

Intermediate I-40

Step 1: (2-Amino-3-bromophenyl)methanol

Borane tetrahydrofuran complex (1.0 M solution in THF, 23.4 mL, 23.4 mmol) was added, dropwise over 20 min, to a mixture of 2-amino-3-bromobenzoic acid (2.02 g, 9.34 mmol, Sigma-Aldrich, St. Louis, Mo., USA) and THF (30 mL) at 0° C. The resulting mixture was allowed to warm to rt and stir for 30 min before being stirred at 70° C. for 20 h. The reaction mixture was subsequently cooled to 0° C., and MeOH (~5 mL) and ice-water (30 mL) were sequentially added. The aqueous layer was saturated with solid NaCl, and the resulting mixture was extracted with EtOAc (2×40 mL). The combined extracts were dried over sodium sulfate, filtered and concentrated in vacuo. Chromatographic purification of the residue (silica gel, 10-50% EtOAc in heptane) furnished (2-amino-3-bromophenyl)methanol as a white solid (1.83 g, 9.04 mmol, 97% yield). m/z (ESI, +ve ion): 184.0 (M+H)⁺.

Step 2: 2-Bromo-6-(((tert-butyldiphenylsilyl)oxy)methyl)aniline tert-Butyldiphenylsilyl chloride (2.0 mL, 7.66 mmol, Sigma-Aldrich) was added to a mixture of (2-amino-3- bromophenyl)methanol (1.19 g, 5.89 mmol), DIPEA (3.6 mL, 20.6 mmol), DMAP (0.035 g, 0.28 mmol), and DCM (20 mL). The resulting mixture was stirred at rt for 24 h, then concentrated in vacuo. Chromatographic purification of the residues (silica gel, 0-50% EtOAc in heptane) provided 2-bromo-6-(((tert-butyldiphenylsilyl)oxy)methyl)aniline (2.42 g, 5.50 mmol, 93% yield) as a clear oil. m/z (ESI, +ve ion): 462.2 (M+Na)$^+$.

Step 3: 2-(((tert-butyldiphenylsilyl)oxy)methyl)-6-(prop-1-en-2-yl)aniline

A mixture of 2-bromo-6-(((tert-butyldiphenylsilyl)oxy) methyl)aniline (2.22 g, 5.04 mmol), (4,4,5,5-tetramethyl-1,3,2-dioxaborolan-2-yl)isopropene (1.23 mL, 6.55 mmol, Combi-Blocks, Inc.), bis-(di-tert-butyl(4-dimethylaminophenyl)phosphine)dichloropalladium(II) (0.432 g, 0.610 mmol, Sigma-Aldrich). sodium carbonate (2 M aq solution: 6.30 mL, 12.60 mmol), and 1,4-dioxane (25 mL) was sparged with Ar$_{(g)}$ for 5 min, then stirred at 90° C. for 3 h. After cooling to rt, water (30 mL) was added, and the resulting mixture was extracted with EtOAc (2×30 mL). The combined extracts were dried over sodium sulfate, filtered, and concentrated in vacuo. Chromatographic purification of the residue (silica gel, 0-20% EtOAc in heptane) gave 2-(((tert-butyldiphenylsilyl)oxy)methyl)-6-(prop-1-en-2-yl) aniline (1.80 g, 4.49 mmol, 89% yield) as a blue-green tinged oil.

Step 4: 2-(((tert-Butyldiphenylsilyl)oxy)methyl)-6-isopropylaniline (Intermediate I-40)

A mixture of 2-(((tert-butyldiphenylsilyl)oxy)methyl)-6-(prop-1-en-2-yl)aniline (1.80 g, 4.48 mmol), palladium, 10 wt. % (dry basis) on activated carbon (wet, Degussa type E101 NEW; 0.477 g, 0.224 mmol), ammonium formate (2.83 g, 44.8 mmol), and EtOH (20 mL) was stirred at 70° C. for 30 min. The mixture was then cooled to rt and filtered through a pad of diatomaceous earth. The filtrate was concentrated in vacuo, and the residue was partitioned between EtOAc (30 mL) and water (30 mL). The organic layer was separated and sequentially washed with water (10 mL), dried over sodium sulfate, filtered, and concentrated in vacuo to afford 2-(((tert-butyldiphenylsilyl)oxy)methyl)-6-isopropylaniline (Intermediate I-40, 1.73 g, 4.29 mmol, 96% yield) as clear paste. $^1$H NMR (400 MHz, CDCl$_3$) δ ppm 7.71 (4H, dd, J=7.9, 1.5 Hz), 7.37-7.46 (6H, m), 7.13 (1H, dd, J=7.7, 1.2 Hz), 6.74-6.79 (1H, m), 6.66-6.72 (1H, m), 4.75 (2H, s), 4.42 (2H, br d, J=1.5 Hz), 2.98 (1H, dt, J=13.5, 6.8 Hz), 1.31 (6H, d, J=6.6 Hz), 1.07 (9H, s). m/z (ESI, +ve ion): 426.2 (M+Na).

Intermediate I-41

4-Isopropyl-1H-pyrrol-3-amine

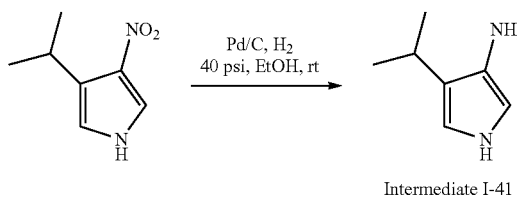

Intermediate I-41

A mixture of 3-isopropyl-4-nitro-1H-pyrrole (0.806 g, 5.23 mmol: Enamine, Monmouth Jct., N.J.), palladium, 10 wt. % (dry basis) on activated carbon (wet, Degussa type e101 ne/w; 0.566 g, 2.66 mmol) and EtOH (20 mL) was stirred under hydrogen gas (40-45 psi) at rt for 2.5 h. The reaction mixture was then filtered through a pad of diatomaceous earth and the filtrate was concentrated in vacuo to give 4-isopropyl-1H-pyrrol-3-amine (Intermediate I-41, 0.760 g, 70 wt %, 0.366 mmol) as a mixture with unreacted starting material. This mixture was used in subsequent reactions without further purification. $^1$H NMR (400 MHz, DMSO-d$_6$) δ ppm 9.51 (br s, 1H), 6.19 (t, J=2.38 Hz, 1H), 6.03 (t, J=2.38 Hz, 1H), 3.23-3.30 (m, 2H), 2.68 (td, J=6.82, 13.53 Hz, 1H), 1.10 (d, J=6.84 Hz, 6H). m/z (ESI, +ve ion): 125.2 (M+H)$^+$.

Section 4—Synthesis of Boronic Acids

Boronic Acid B-1

(2-Hydroxy-6-methylphenyl)boronic acid

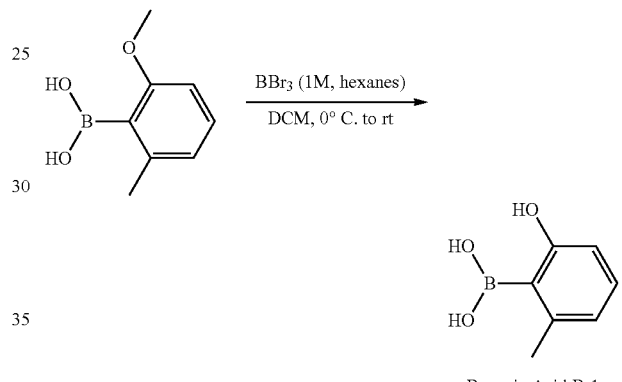

Boronic Acid B-1

Boron tribromide (1 M in hexanes, 6 mL, 6 mmol) was added, dropwise, to a solution of (2-methoxy-6-methylphenyl)boronic acid (330 mg, 2.0 mmol, Combi-Blocks Inc., San Diego, Calif., USA) in DCM (6 mL) at 0° C. The resulting mixture was allowed to warm to rt and stir for 90 min before being re-cooled to 0° C. Ice was added, and the resulting biphasic mixture was warmed to rt and partitioned between EtOAc and water. The organic layer was separated, and the aqueous layer was extracted with EtOAc. The combined organic extracts were then dried over MgSO$_4$, filtered, and concentrated in vacuo to afford (2-hydroxy-6-methylphenyl)boronic acid (Boronic Acid B-1) as an orange oil, which was used without purification.

Boronic Acid B-2

(2,4-Difluoro-5-hydroxyphenyl)boronic acid

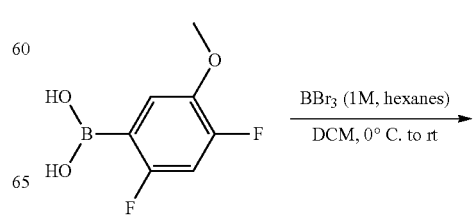

-continued

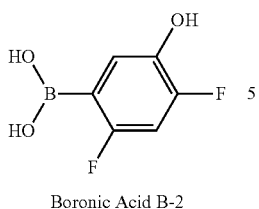

Boronic Acid B-2

(2,4-Difluoro-5-hydroxyphenyl)boronic acid (Boronic Acid B-2) was prepared using 2,4-difluoro-5-methoxyphenylboronic acid (380 mg, 2.0 mmol, Combi-Blocks, San Diego, Calif.) according to the procedure described for Boronic Acid B-1.

Boronic Acid B-3

(2,3-Difluoro-6-hydroxyphenyl)boronic acid

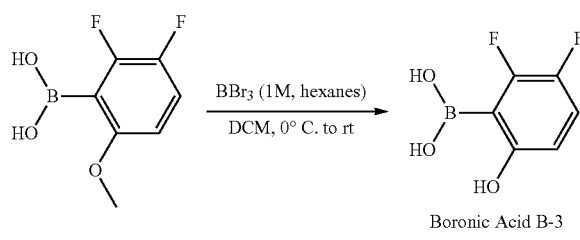

Boronic Acid B-3

(2,3-Difluoro-6-hydroxyphenyl)boronic acid (Boronic Acid B-3) was prepared using 2,3-difluoro-6-methoxybenzeneboronic acid (380 mg, 2.0 mmol, Combi-Blocks, San Diego, Calif.) according to the procedure described for Boronic Acid B-1.

Boronic Acid B-4

(3,6-Difluoro-2-hydroxyphenyl)boronic acid

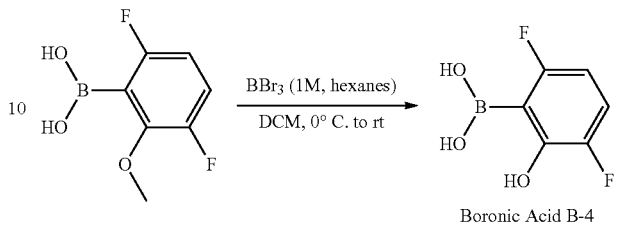

Boronic Acid B-4

(3,6-Difluoro-2-hydroxyphenyl)boronic acid (Boronic Acid B-4) was prepared using 3,6-difluoro-2-methoxybenzeneboronic acid (380 mg, 2.0 mmol, Aurum Pharmatech LLC, Franklin Park, N.J.) according to the procedure described for Boronic Acid B-1.

Boronic Acid B-5

(6-Fluoro-2-hydro-3-methylphenyl)boronic acid

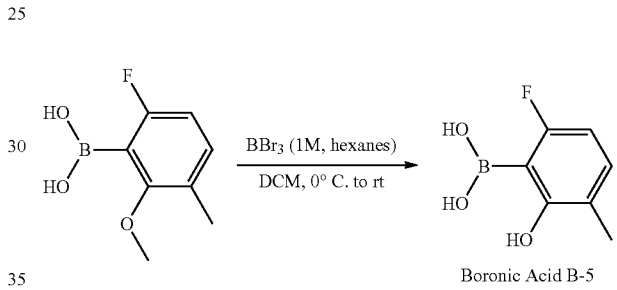

Boronic Acid B-5

(6-Fluoro-2-hydroxy-3-methylphenyl)boronic acid (Boronic Acid B-5) was prepared using 6-fluoro-2-methoxy-3-methylphenylboronic acid (370 mg, 2.0 mmol, Aurum Pharmatech LLC, Franklin Park, N.J.) according to the procedure described for Boronic Acid B-1.

Separated Compound Examples, Including Isomers and Some Atropisomers

| Ex. # | Chemical Structure | Name | Racemic SM/ separation conditions |
|---|---|---|---|
| 9-17-1 | (1st-eluting isomer) | 7-bromo-6-chloro-4-((2S)-2-methyl-4-(2-propenoyl)-1-piperazinyl)-1-(2-(2-propanyl)phenyl)-2(1H)-quinazolinone | SFC Whelk-01 (S,S), 21 × 250 mm, 5 μm, 40% MeOH (with 20 mM $NH_3$)/$CO_2$, 80 g/min, 102 bar |

-continued

| Ex. # | Chemical Structure | Name | Racemic SM/ separation conditions |
|---|---|---|---|
| 9-17-2 | 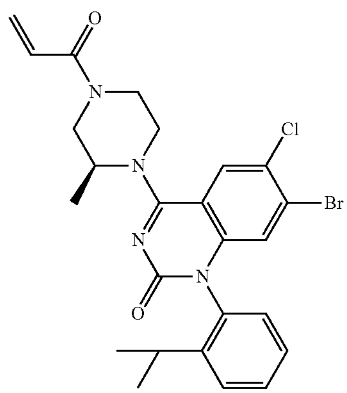 [SMILES: C=CC(=O)N1CCN(c2nc(=O)n(-c3ccccc3C(C)C)c3cc(Br)c(Cl)cc23)[C@@H](C)C1] | 7-bromo-6-chloro-4-((2S)-2-methyl)-4-(2-propenoyl)-1-piperazinyl)-1-(2-(2-propanyl)phenyl)-2(1H)-quinazolinone<br><br>2nd-eluting isomer | SFC Whelk-01 (S,S), 21 × 250 mm, 5 μm, 40% MeOH (with 20 mM $NH_3$)/$CO_2$, 80 g/min, 102 bar |
| 54-9-1 | 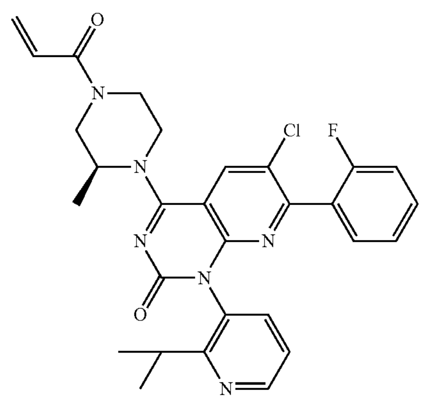 | 6-chloro-7-(2-fluorophenyl)-4-((2S)-2-methyl-4-(2-propenoyl)-1-piperazinyl)-1-(2-(2-propanyl)-3-pyridinyl)pyrido[2,3-d]pyrimidin-2(1H)-one<br><br>1st-eluting isomer | SFC Whelk-01 (S,S) (250 × 21 mm, 5 μm), 45% MeOH ($NH_3$)/$CO_2$ B, 70 g/min, 102 bar |
| 54-9-2 | 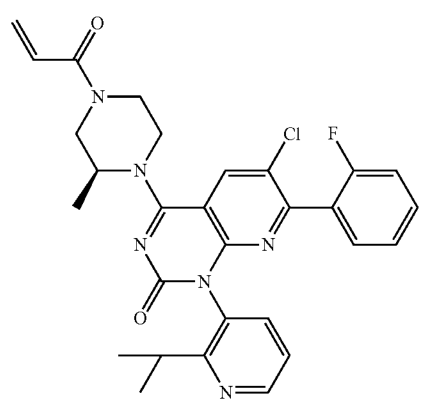 [SMILES: C=CC(=O)N1CCN(c2nc(=O)n(-c3cccnc3C(C)C)c3nc(-c4ccccc4F)c(Cl)cc23)[C@@H](C)C1] | 6-chloro-7-(2-fluorophenyl)-4-((2S)-2-methyl-4-(2-propenoyl)-1-piperazinyl)-1-(2-(2-propanyl)-3-pyridinyl)pyrido[2,3-d]pyrimidin-2(1H)-one<br><br>2nd-eluting isomer | SFC-Whelk-01 (S,S) (250 × 21 mm, 5 μm), 45% methanol ($NH_3$)/$CO_2$, 70 g/min, 102 bar |

-continued

| Ex. # | Chemical Structure | Name | Racemic SM/ separation conditions |
|---|---|---|---|
| 54-10-1 | 1st-eluting isomer | 6-chloro-1-(2-cyclobutylphenyl)-7-(2-fluoro-6-hydroxyphenyl)-4-((2S)-2-methyl-4-(2-propenoyl)-1-piperazinyl)pyrido[2,3-d]pyrimidin-2(1H)-one | SFC Whelk-01 (S,S) (250 × 21 mm, 5 μm), 60% MeOH/CO$_2$, 55 g/min, 102 bar |
| 54-10-2 | 2nd-eluting isomer | 6-chloro-1-(2-cyclobutylphenyl)-7-(2-fluoro-6-hydroxyphenyl)-4-((2S)-2-methyl-4-(2-propenoyl)-1-piperazinyl)pyrido[2,3-d]pyrimidin-2(1H)-one | SFC Whelk-01 (S,S) (250 × 21 mm, 5 μm), 60% MeOH/CO$_2$, 55 g/min, 102 bar |
| 54-11-1 | 1st-eluting isomer | 6-chloro-7-(2-fluoro-6-hydroxyphenyl)-4-((2S)-2-methyl-4-(2-propenoyl)-1-piperazinyl)-1-(2-(2-propanyl)-3-pyridinyl)pyrido[2,3-d]pyrimidin-2(1H)-one | SFC OD (250 × 21 mm, 5 μm), 60% MeOH/CO$_2$, 80 g/min, 120 bar |

| Ex. # | Chemical Structure | Name | Racemic SM/ separation conditions |
|---|---|---|---|
| 54-11-2 | 2nd-eluting isomer | 6-chloro-7-(2-fluoro-6-hydroxyphenyl)-4-((2S)-2-methyl-4-(2-propenoyl)-1-piperazinyl)-1-(2-(2-propanyl)-3-pyridinyl)pyrido[2,3-d]pyrimidin-2(1H)-one | SFC OD (250 × 21 mm, 5 μm), 60% MeOH/CO$_2$, 80 g/min, 120 bar |
| 54-12-1 | 1st-eluting isomer | 6-chloro-1-(2-cyclobutylphenyl)-7-(2-fluorophenyl)-4-((2S)-2-methyl-4-(2-propenoyl)-1-piperazinyl)pyrido[2,3-d]pyrimidin-2(1H)-one | SFC OZ-H (21 × 250 mm, 5 μm), 35% MeOH/CO$_2$, 50 ml/min, 100 bar |
| 54-12-2 | 2nd-eluting isomer | 6-chloro-1-(2-cyclobutylphenyl)-7-(2-fluorophenyl)-4-((2S)-2-methyl-4-(2-propenoyl)-1-piperazinyl)pyrido[2,3-d]pyrimidin-2(1H)-one | SFC OZ-H (21 × 250 mm, 5 μm), 35% MeOH/CO$_2$, 50 ml/min, 100 bar |

| Ex. # | Chemical Structure | Name | Racemic SM/ separation conditions |
|---|---|---|---|
| 54-17-1 | 1st-eluting isomer (M) | (M)-6-chloro-7-(2-fluoro-6-hydroxyphenyl)-1-(2-methyl-4-(2-propanyl)-3-pyridinyl)-4-((2S)-2-methyl-4-(2-propenoyl)-1-piperazinyl)pyrido[2,3-d]pyrimidin-2(1H)-one | SFC IC (250 × 20 mm, 10 μm), 30% MeOH/CO$_2$, 70 g/min, 103 bar |
| 54-17-2 | 2nd-eluting isomer (P) | (P)-6-chloro-7-(2-fluoro-6-hydroxyphenyl)-1-(2-methyl-4-(2-propanyl)-3-pridinyl)-4-((2S)-2-methyl-4-(2-propenoyl)-1-piperazinyl)pyrido[2,3-d]pyrimidin-2(1H)-one | SFC (250 × 20 mm, 10 μm), 30% MeOH/CO$_2$, 70 g/min, 103 bar |
| 54-18-1 | 1st-eluting isomer | 6-chloro-7-(2-fluorophenyl)-1-(2-methyl-4-(2-propanyl)-3-pyridinyl)-4-((2S)-2-methyl-4-(2-propenoyl)-1-piperazinyl)pyrido[2,3-d]pyrimidin-2(1H)-one | SFC Whelk-01 (S,S) (250 × 21 mm, 5 μm), 35% MeOH/CO$_2$, 80 g/min, 102 bar |

-continued

| Ex. # | Chemical Structure | Name | Racemic SM/ separation conditions |
|---|---|---|---|
| 54-18-2 | 2$^{nd}$-eluting isomer | 6-chloro-7-(2-fluorophenyl)-1-(2-methyl-4-(2-propanyl)-3-pyridinyl)-4-((2S)-2-methyl-4-(2-propenoyl)-1-piperazinyl)pyrido[2,3-d]pyrimidin-2(1H)-one | SFC whelk-01 (S,S) (250 × 21 mm, 5 μm); 35% MeOH/CO$_2$, 80 g/min, 102 bar |
| 54-27-1 | 1$^{st}$-eluting isomer | 6-chloro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | SFC Chiralpak IC (21 × 150 mm, 5 μm), 50% MeOH/CO$_2$, 50 mL/min, 100 bar |
| 54-27-2 | 2nd-eluting isomer | 6-chloro-7-(2-fluoro-6-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | SFC Chiralpak IC (21 × 150 mm, 5 μm), 50% MeOH/CO$_2$, 50 mL/min, 100 bar |

-continued

| Ex. # | Chemical Structure | Name | Racemic SM/ separation conditions |
|---|---|---|---|
| 54-43-1 | 1st-eluting isomer | 6-chloro-7-(2-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | SFC Whelk 01 (S,S) (250 × 21 mm, 5 μm), 50% MeOH (with 20 mM NH$_3$)/CO$_2$, 65 g/min, 102 bar |
| 54-43-2 | 2nd-eluting isomer | 6-chloro-7-(2-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | SFC Whelk 01 (S,S) (250 × 21 mm, 5 μm), 50% MeOH (with 20 mM NH$_3$)/CO$_2$, 65 g/min, 102 bar |
| 54-51-1 | 1st-eluting isomer | 6-chloro-7-(5-(difluoromethoxy)-2-fluorophenyl)-4-((2S)-2-methyl-4-(2-propenoyl)-1-piperazinyl)-1-(2-(2-propanyl)phenyl)pyrido[2,3-d]pyrimidin-2(1H)-one | SFC Whelk 01 (S,S) (250 × 21 mm, 5 μm), 60% MeOH (with 20 mM NH$_3$)/CO$_2$, 65 g/min, 102 bar |

-continued

| Ex. # | Chemical Structure | Name | Racemic SM/ separation conditions |
|---|---|---|---|
| 54-51-2 | 2nd-eluting isomer | 6-chloro-7-(5-(difluoromethoxy)-2-fluorophenyl)-4-((2S)-2-methyl-4-(2-propenoyl)-1-piperazinyl)-1-(2-(2-propanyl)phenyl)pyrido[2,3-d]pyrimidin-2(1H)-one | SFC Whelk 01 (S,S) (250 × 21 mm, 5 μm), 60% MeOH (with 20 mM $NH_3$)/$CO_2$, 65 g/min, 102 bar |
| 54-56-1 | 1st-eluting isomer | 6-chloro-7-(2-fluoro-6-hydroxyphenyl)-4-((2S)-2-methyl-4-(2-propenoyl)-1-piperazinyl)-1-(2-methylsulfonyl)phenyl)pyrido-[2,3-d]pyrimidin-2(1H)-one | SFC Chiralpak IC (250 × 21 mm, 5 μm), 50% MeOH/$CO_2$, 50 mL/min, 100 bar |
| 54-56-2 | 2nd-eluting isomer | 6-chloro-7-(2-fluoro-6-hydroxyphenyl)-4-((2S)-2-methyl-4-(2-propenoyl)-4-piperazinyl)-1-(2-methylsulfonyl)phenyl)pyrido[2,3-d]pyrimidin-2(1H)-one | SFC Chiralpak IC (250 × 21 mm, 5 μm), 50% MeOH/$CO_2$, 50 mL/min, 100 bar |

| Ex. # | Chemical Structure | Name | Racemic SM/ separation conditions |
|---|---|---|---|
| 54-71-1 | 1st-eluting isomer (M) | (M)-6-chloro-7-(2-fluoro-6-hydroxyphenyl)-1-(4-methyl-1-(2-propanyl)-1H-pyrazol-5-yl)-4-((2S)-2-methyl-4-(2-propenoyl)-1-piperazinyl)pyrido[2,3-d]pyrimidin-2(1H)-one | SFC Whelk-01 (S,S) (21 × 250 mm, 5 μm), 30% MeOH/$CO_2$, 80 g/min, 175 bar |
| 54-71-2 | 2nd-eluting isomer (P) | (P)-6-chloro-7-(2-fluoro-6-hydroxyphenyl)-1-(4-methyl-1-(2-propanyl)-1H-pyrazol-5-yl)-4-((2S)-2-methyl-4-(2-propenoyl)-1-piperazinyl)pyrido[2,3-d]pyrimidin-2(1H)-one | SFC (Whelk-01 S,S) (21 × 250 mm, 5 μm), 30% MeOH/$CO_2$, 80 g/min, 175 bar |
| 54-73-1 | 1st-eluting isomer | 6-chloro-7-(2-fluoro-6-hydroxyphenyl)-1-(2-methoxy-6-(2-propanyl)phenyl)-4-((2S)-2-methyl-4-(2-propenoyl)-1-piperazinyl)pyrido[2,3-d]pyrimidin-2(1H)-one | SFC (S,S) Whelk-01 (250 × 21 mm, 5u), 45% MeOH/$CO_2$ 60 g/min, 189 bar. |

| Ex. # | Chemical Structure | Name | Racemic SM/ separation conditions |
|---|---|---|---|
| 54-73-2 | 2nd-eluting isomer | 6-chloro-7-(2-fluoro-6-hydroxyphenyl)-1-(2-methoxy-6-(2-propanyl)phenyl)-4-((2S)-2-methyl-4-(2-propenoyl)-1-piperazinyl) pyrido[2,3-d]pyrimidin-2(1H)-one | SFC (S,S) Whelk-01 (250 × 21 mm, 5u), 45% MeOH/CO$_2$ 60 g/min, 189 bar. |
| 54-75-1 | 1st-eluting isomer | 6-chloro-7-(1-cyclohexen-1-yl)-4-((2S)-2-methyl-4-(2-propenoyl)-1-piperazinyl)-1-(2-(2-propanyl)phenyl) pyrido[2,3-d]pyrimidin-2(1H)-one | SFC Whelk-01 (S,S) (21 × 250 mm, 5 μm), 45% MeOH/CO$_2$, 80 mL/min, 102 bar |
| 54-75-2 | 2nd-eluting isomer | 6-chloro-7-(1-cyclohexen-1-yl)-4-((2S)-2-methyl-4-(2-propenoyl)-1-piperazinyl)-1-(2-(2-propanyl)phenyl) pyrido[2,3-d]pyrimidin-2(1H)-one | STC Whelk-01 (S,S) (21 × 250 mm, 5 μm, 45% MeOH/CO$_2$, 80 mL/min, 102 bar |

-continued

| Ex. # | Chemical Structure | Name | Racemic SM/ separation conditions |
|---|---|---|---|
| 54-77-1 | 1st-eluting isomer | 6-chloro-7-(4-fluoro-2-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | SFC Chiralpak AS-H (30 × 250 mm), 25% MeOH/CO$_2$, 80 mL/min, 100 bar |
| 54-77-2 | 2nd-eluting isomer | 6-chloro-7-(4-fluoro-2-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | SR: Chiralpak AS-H (30 × 250 mm), 25% MeOH/CO$_2$, 80 mL/min, 100 bar |
| 54-78-1 | 1st-eluting isomer | 6-chloro-7-(5-fluoro-2-hydroxyphenyl)-4-((2S)-2-methyl)-4-(2-propenoyl)-1-piperazinyl)-1-(2-(2-propanyl)phenyl)pyrido[2,3-d]pyrimidin-2(1H)-one | SFC Chiralpak AS-H (30 × 250 mm), 20% MeOH/CO$_2$, 80 mL/min, 100 bar |

-continued

| Ex. # | Chemical Structure | Name | Racemic SM/ separation conditions |
|---|---|---|---|
| 54-78-2 | *2nd-eluting isomer* | 6-chloro-7-(5-fluoro-2-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | SFC Chiralpak AS-H (30 × 250 mm), 20% MeOH/CO$_2$, 80 mL/min, 100 bar |
| 54-84-1 | *1$^{st}$-eluting isomer* | 6-chloro-7-(2-chlorophenyl)-4-((2S)-2-methyl-4-(2-propenoyl)-1-piperazinyl)-1-(2-(2-propanyl)phenyl pyrido[2,3-d]pyrimidin-2(1H)-one | SFC OD (150 × 21 mm, 5 μm), 25% iPrOH/MeCN (1:1)/CO$_2$, 80 g/min, 140 bar |
| 54-84-2 | *2nd-eluting isomer* | 6-chloro-7-(2-chlorophenyl)-4-((2S)-2-methyl)-4-(2-propenoyl)-1-piperazinyl)-1-(2-(2-propanyl)phenyl)pyrido[2,3-d]pyrimidin-2(1H)-one | SFC OD (150 × 21 mm, 5 μm), 25% iPrOH/MeCN (1:1)/CO$_2$, 80 g/min, 140 bar |

| Ex. # | Chemical Structure | Name | Racemic SM/ separation conditions |
|---|---|---|---|
| 54-85-1 | 1st-eluting isomer (P) | (P)-6-chloro-7-(2,4-difluorophenyl)-4-((2S)-2-methyl-4-(2-propenoyl)-1-piperazinyl)-1-(2-(2-propanyl)phenyl) pyrido[2,3-d]pyrimidin-2(1H)-one | SFC Whelk-01 (S,S) (250 × 21 mm, 5 μm), 60% MeOH (with 20 mM NH$_3$)/CO$_2$, 65 g/min, 102 bar |
| 54-85-2 | 2nd-eluting isomer (M) | (M)-6-chloro-7-(2,4-difluorophenyl)-4-((2S)-2-methyl-4-(2-propenoyl)-1-piperazinyl)-1-(2-(2-propanyl)phenyl) pyrido[2,3-d]pyrimidin-2(1H)-one | SFC Whelk-01 (S,S) (250 × 21 mm, 5 μm), 60% MeOH (with 20 mM NH$_3$)/CO$_2$, 65 g/min, 102 bar |
| 54-86-1 | 1st-eluting isomer | 6-chloro-7-(2-fluorophenyl)-4-((2S)-2-methyl-4-(2-propenoyl)-1-piperazinyl)-1-(2-(2-propanyl)phenyl) pyrido[2,3-d]pyrimidin-2(1H)-one | SFC Whelk-01 (S,S) (250 × 21 mm, 5 μm), 45% MeOH (with 20 mM NH$_3$)/CO$_2$, 75 g/min, 102 bar |

| Ex. # | Chemical Structure | Name | Racemic SM/ separation conditions |
|---|---|---|---|
| 54-86-2 | 2nd-eluting isomer | 6-chloro-7-(2-fluorophenyl)-4-((2S)-2-methyl-4-(2-propenoyl)-1-piperazinyl)-1-(2-(2-propanyl)phenyl)pyrido[2,3-d]pyrimidin-2(1H)-one | SFC Whelk-01 (S,S) (250 × 21 mm, 5 μm) 45% MeOH (with 20 mM $NH_3$)/CO2, 75 g/min, 102 bar |
| 54-88-1 | 1st-eluting isomer | 6-chloro-7-(2-fluoro-5-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | SFC Chiralpak ID (250 × 21 mm, 5 μm), 70% MeOH (with 20 mM $NH_3$)/$CO_2$, 65 g/min, 110 bar |
| 54-88-2 | 2nd-eluting isomer | 6-chloro-7-(2-fluoro-5-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | SFC Chiralpak ID (250 × 21 mm, 5 μm), 70% MeOH (with 20 mM $NH_3$)/$CO_2$, 65 g/min, 110 bar |

-continued

| Ex. # | Chemical Structure | Name | Racemic SM/ separation conditions |
|---|---|---|---|
| 54-90-1 | 1st-eluting isomer | 6-chloro-7-(2-chloro-5-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | SFC Chiralpak ID (250 × 21 mm, 5 μm), 75% MeOH (with 20 mM $NH_3$)/$CO_2$, 65 g/min, 102 bar |
| 54-90-2 | 2nd-eluting isomer | 6-chloro-7-(2-chloro-5-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | SFC Chiralpak ID (250 × 21 mm, 5 μm), 75% MeOH (with 20 mM $NH_3$)/$CO_2$, 65 g/min, 102 bar |
| 54-91-1 | 1st-eluting isomer | 6-chloro-7-(2,3-dichloro-5-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | SFC Chiralpak ID (250 × 21 mm, 5 μm), 35% MeOH (with 20 mM $NH_3$)/$CO_2$, 65 g/min, 102 bar |

-continued

| Ex. # | Chemical Structure | Name | Racemic SM/ separation conditions |
|---|---|---|---|
| 54-91-2 | 2nd-eluting isomer | 6-chloro-7-(2,3-dichloro-5-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | SFC Chiralpak ID (250 × 21 mm, 5 μm), 35% MeOH (with 20 mM $NH_3$)/$CO_2$, 65 g/min, 102 bar |
| 54-97-1 | 1st-eluting isomer (P) | (P)-6-chloro-7-(2-fluoro-6-hydroxyphenyl)-1-(2-(1-methylcyclopropyl)phenyl)-4-((2S)-2-methyl-4-(2-propenoyl)-1-piperazinyl)pyrido[2,3-d]pyrimidin-2(1H)-one | SFC Chiralcel OX-H (21 × 250 mm, 5 μm), 35% MeOH/$CO_2$, 80 g/min, 102 bar |
| 54-97-2 | 2nd-eluting isomer (M) | (M)-6-chloro-7-(2-fluoro-6-hydroxyphenyl)-1-(2-(1-methylcyclopropyl)phenyl)-4-((2S)-2-methyl-4-(2-propenoyl)-1-piperazinyl)pyrido[2,3-d]pyrimidin-2(1H)-one | SFC Chiralcel OX-H (21 × 250 mm, 5 μm), 35% MeOH/$CO_2$, 80 g/min, 102 bar |

-continued

| Ex. # | Chemical Structure | Name | Racemic SM/ separation conditions |
|---|---|---|---|
| 54-99-1 | 1st-eluting isomer | 6-chloro-7-(2-fluorophenyl)-1-(2-(1-methylcyclopropyl)phenyl)-4-((2S)-2-methyl-4-(2-propenoyl)-1-piperazinyl)pyrido[2,3-d]pyrimidin-2(1H)-one | SFC Whelk-01 (S,S) (250 × 21 mm, 5 μm), 40% MeOH (with 20 mM NH$_3$)/CO$_2$, 60 g/min, 102 bar |
| 54-99-2 | 2nd-eluting isomer | 6-chloro-7-(2-fluorophenyl)-1-(2-(1-methylcyclopropyl)phenyl)-4-((2S)-2-methyl-4-(2-propenoyl)-1-piperazinyl)pyrido[2,3-d]pyrimidin-2(1H)-one | SFC Whelk-01 (S,S) (250 × 21 mm, 5 μm), 40% MeOH (with 20 mM NH$_3$)/CO$_2$, 60 g/min, 102 bar |
| 54-103-1 | 1st-eluting isomer | 6-chloro-7-(2-fluoro-6-hydroxyphenyl)-1-(2-(2-methyl-2-propanyl)-3-pyridinyl)-4-((2S)-2-methyl-4-(2-propenoyl)-1-piperazinyl)pyrido[2,3-d]pyrimidin-2(1H)-one | NPLC Chiralcel AZ-H (21.2 × 250 mm, 5 μm), 35% EtOH/heptane, 30 mL/min |

| Ex. # | Chemical Structure | Name | Racemic SM/ separation conditions |
|---|---|---|---|
| 54-103-2 | 2nd-eluting isomer | 6-chloro-7-(2-fluoro-6-hydroxyphenyl)-1-(2-(2-methyl-2-propanyl)-3-pyridinyl)-4-((2S)-2-methyl-4-(2-propenoyl)-1-piperazinyl)pyrido[2,3-d]pyrimidin-2(1H)-one | NPLC Chiralcel AZ-H (21.2 × 250 mm 5 μm), 35% EtOH/heptane, 30 mL/min |
| 54-104-1 | 1st-eluting isomer (P) | (P)-6-chloro-1-(2-dimethylamino)-6-(2-propanyl)phenyl)-7-(2-fluorophenyl)-4-((2S)-2-methyl-4-(2-propenoyl)-1-piperazinyl)pyrido[2,3-d]pyrimidin-2(1H)-one | SFC Whelk-01 (250 × 20), 35% Ethanol at 60 ml/min, 200 Bar |
| 54-104-2 | 2nd-eluting isomer (M) | (M)-6-chloro-1-(2-dimethylamino)-6-(2-propanyl)phenyl)-7-(2-fluorophenyl)-4-((2S)-2-methyl-4-(2-propenoyl)-1-piperazinyl)pyrido[2,3-d]pyrimidin-2(1H)-one | SFC Whelk-01 (250 × 20), 35% Ethanol at 60 ml/min, 200 Bar |

| Ex. # | Chemical Structure | Name | Racemic SM/ separation conditions |
|---|---|---|---|
| 54-107-1 | 1st-eluting isomer | 6-chloro-7-(2-fluorophenyl)-1-(4-methoxy-6-(2-propanyl)-5-pyrimidinyl)-4-((2S)-2-methyl-4-(2-propenoyl)-1-piperazinyl)pyrido[2,3-d]pyrimidin-2(1H)-one | SFC (Chiralpak ID (250 × 21 mm, 5 μm), 35% MeOH (with 20 mM NH3)/CO2, 65 g/min, 102 bar) |
| 54-107-2 | 2nd-eluting isomer | 6-chloro-7-(2-fluorophenyl)-1-(4-methoxy-6-(2-propanyl)-5-pyrimidinyl)-4-((2S)-2-methyl-4-(2-propenoyl)-1-piperazinyl)pyrido[2,3-d]pyrimidin-2(1H)-one | SFC (Chiralpak ID (250 × 21 mm, 5 μm), 35% MeOH (with 20 mM NH3)/CO2, 65 g/min, 102 bar) |
| 54-110-1 | 1st-eluting isomer | 6-chloro-7-(2-fluorophenyl)-1-(4-(2-methyl-2-propanyl)-5-pyrimidinyl)-4-((2S)-2-methyl-4-(2-propenoyl)-1-piperazinyl)pyrido[2,3-d]pyrimidin-2(1H)-one | R,R-Whelk-01, 250 × 20, 50% methanol at 60 ml/min, 193 Bar, 254-nm 541 mg/20 mL DCM/MeOH (1:1) 0.5 mL Injection |

| Ex. # | Chemical Structure | Name | Racemic SM/ separation conditions |
|---|---|---|---|
| 54-110-2 | 2nd-eluting isomer | 6-chloro-7-(2-fluorophenyl)-1-(4-(2-methyl-2-propanyl)-5-pyrimidinyl)-4-((2S)-2-methyl-4-(2-propenoyl)-1-piperazinyl) pyrido[2,3-d]pyrimidin-2(1H)-one | R,R-Whelk-01, 250 × 20, 50% methanol at 60 ml/min, 193 Bar, 254-nm 541 mg/20 mL DCM/MeOH (1:1) 0.5 mL Injection |
| 54-112-1 | 1st-eluting isomer | 6-chloro-7-(2-fluorophenyl)-1-(2-(2-methyl-2-propanyl)-3-pyridinyl)-4-((2S)-2-methyl-4-(2-propenoyl)-1-piperazinyl) pyrido[2,3-d]pyrimidin-2(1H)-one | Normal Phase Liquid Chromatography. ISOCRATIC_35C_IPA_10MIN |
| 54-112-2 | 2nd-eluting isomer | 6-chloro-7-(2-fluorophenyl)-1-(2-(2-methyl-2-propanyl)-3-pyridinyl)-4-((2S)-2-methyl-4-(2-propenoyl)-1-piperazinyl) pyrido[2,3-d]pyrimidin-2(1H)-one | Normal Phase Liquid Chromatography. ISOCRATIC_35C_IPA_10MIN |

-continued

| Ex. # | Chemical Structure | Name | Racemic SM/ separation conditions |
|---|---|---|---|
| 55-4-1 | 1st-eluting isomer | 6-chloro-1-(2,4-dimethyl-6-(2-propanyl)-5-pyrimidinyl)-7-(2-fluoro-6-hydroxyphenyl)-4-((2S)-2-methyl-4-(2-propenoyl)-1-piperazinyl) pyrido[2,3-d]pyrimidin-2(1H)-one | Chiralpak IC (250 × 20), 25% Methanol at 60 ml/min, 165 Bar, 220-nm |
| 55-4-2 | 2nd-eluting isomer | 6-chloro-1-(2,4-dimethyl-6-(2-propanyl)-5-pyrimidinyl)-7-(2-fluoro-6-hydroxyphenyl)-4-((2S)-2-methyl-4-(2-propenoyl)-1-piperazinyl) pyrido[2,3-d]pyrimidin-2(1H)-one | Chiralpak IC (250 × 20), 25% Methanol at 60 ml/min, 165 Bar, 220-nM |
| 55-7-1 | 1st-eluting isomer | 6-chloro-1-(2-(dimethylamino)-4-methyl-3-pyridinyl)-7-(2-fluorophenyl)-4-((2S)-2-methyl-4-(2-propenoyl)-1-piperazinyl) pyrido[2,3-d]pyrimidin-2(1H)-one | SFC (OX (250 × 21 mm, 5 μm), 50% MeOH/CO2, 65 g/min, 102 bar) |

-continued

| Ex. # | Chemical Structure | Name | Racemic SM/ separation conditions |
|---|---|---|---|
| 55-7-2 | 2nd-eluting isomer | 6-chloro-1-(2-(dimethylamino)-4-methyl-3-pyridinyl)-7-(2-fluorophenyl)-4-((2S)-2-methyl-4-(2-propenoyl)-1-piperazinyl)pyrido[2,3-d]pyrimidin-2(1H)-one | SFC (OX (250 × 21 mm, 5 μm), 50% MeOH/CO2, 65 g/min, 102 bar) |
| 55-8-1 | 1st-eluting isomer (M) | (M)-6-chloro-1-(2-ethyl-6-methylphenyl)-7-(2-fluoro-6-hydroxyphenyl)-4-((2S)-2-methyl-4-(2-propenoyl)-1-piperazinyl)pyrido[2,3-d]pyrimidin-2(1H)-one | SFC Chiralpak AD-H (20 × 250 mm, 5 μm), 30% iPrOH/CO$_2$, 50 mL/min, 100 bar |
| 55-8-2 | 2nd-eluting isomer (P) | (P)-6-chloro-1-(2-ethyl-6-methylphenyl)-7-(2-fluoro-6-hydroxyphenyl)-4-((2S)-2-methyl-4-(2-propenoyl)-1-piperazinyl)pyrido[2,3-d]pyrimidin-2(1H)-one | SFC Chiralpak AD-H (20 × 250 mm, 5 μm, 30% iPrOH/CO$_2$, 50 mL/min, 100 bar |

| Ex. # | Chemical Structure | Name | Racemic SM/ separation conditions |
|---|---|---|---|
| 55-9-1 | 1st-eluting isomer | 6-chloro-1-(2-ethyl-6-methylphenyl)-7-(2-fluorophenyl)-4-((2S)-2-methyl-4-(2-propenoyl)-1-piperazinyl) pyrido[2,3-d]pyrimidin-2(1H)-one | NPLC Chiralpak IF (21.2 × 250 mm, 5 μm), 20% MeOH:EtOH (50:50)/heptane, 25 mL/min |
| 55-9-2 | 2nd-eluting isomer | 6-chloro-1-(2-ethyl-6-methylphenyl)-7-(2-fluorophenyl)-methyl-4-(2-propenoyl)-1-piperazinyl) pyrido[2,3-d]pyrimidin-2(1H)-one | NPLC Chiralpak IF (21.2 × 250 mm, 5 μm), 20% MeOH:EtOH (50:50)/heptane, 25 mL/min |
| 55-10-1 | 1st-eluting isomer | 6-chloro-1-(2-ethyl-4-methyl-3-pyridinyl)-7-(2-fluoro-6-hydroxyphenyl)-4-((2S)-2-methyl-4-(2-propenoyl)-1-piperazinyl) pyrido[2,3-d]pyrimidin 2(1H)-one | NPLC Chiralpak IC (21.2 × 150 mm, 5 μm), 40% MeOH:EtOH (50:50)/heptane, 22 mL/min |

-continued

| Ex. # | Chemical Structure | Name | Racemic SM/ separation conditions |
|---|---|---|---|
| 55-10-2 | 2nd-eluting isomer | 6-chloro-1-(2-ethyl-4-methyl-3-pyridinyl)-7-(2-fluoro-6-hydroxyphenyl)-4-((2S)-2-methyl-4-(2-propenoyl)-1-piperazinyl)pyrido[2,3-d]pyrimidin-2(1H)-one | NPLC Chiralpak IC (21.2 × 150 mm, 5 μm), 40% MeOH:EtOH (50:50)/heptane, 22 mL/min |
| 55-13-1 | 1st-eluting isomer | 6-chloro-7-(2-fluorophenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | SFC Whelk-01 (R,R) (20 × 250 mm, 5 μm), 40% MeOH/60% $CO_2$, 60 mL/min, 102 bar |
| 55-13-2 | 2nd-eluting isomer | 6-chloro-7-(2-fluorophenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | SFC Whelk-01 (R,R) (20 × 250 mm, 5 μm), 40% MeOH/60% $CO_2$, 60 mL/min, 102 bar |

| Ex. # | Chemical Structure | Name | Racemic SM/ separation conditions |
|---|---|---|---|
| 55-14-1 | 1st-eluting isomer | 6-chloro-7-(2-fluoro-6-hydroxyphenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | SFC Whelk-01 (R,R) (20 × 250 mm, 5 μm), 40% MeOH/60% $CO_2$, 60 mL/min, 102 bar |
| 55-14-2 | 2nd-eluting isomer | 6-chloro-7-(2-fluoro-6-hydroxyphenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | SFC Whelk-01 (R,R) (20 × 250 mm, 5 μm), 40% MeOH/60% $CO_2$, 60 mL/min, 102 bar |
| 55-15-1 | 1st-eluting isomer (P) | (P)-6-chloro-1-(2-cyclopropyl-6-methylphenyl)-7-(2-fluoro-6-hydroxyphenyl)-4-((2S)-2-methyl-4-(2-propenoyl)-1-piperazinyl)pyrido[2,3-d]pyrimidin-2(1H)-one | SFC Chiralcel AS (250 × 30 mm, 5 μm), 20% EtOH/$CO_2$, 170 g/min, 103 bar |

| Ex. # | Chemical Structure | Name | Racemic SM/ separation conditions |
|---|---|---|---|
| 55-15-2 | 2nd-eluting isomer (M) | (M)-6-chloro-1-(2-cyclopropyl-6-methylphenyl)-7-(2-fluoro-6-hydroxyphenyl)-4-((2S)-2-methyl-4-(2-propenoyl)-1-piperazinyl)pyrido[2,3-d]pyrimidin-2(1H)-one | SFC Chiralcel AS (250 × 30 mm, 5 μm), 20% EtOH/$CO_2$, 170 g/min, 103 bar |
| 55-16-1 | 1st-eluting isomer (P) | (P)-6-chloro-1-(4-(dimethylamino)-2-methyl-6-(2-propanyl)phenyl)-7-(2-fluorophenyl)-4-((2S)-2-methyl-4-(2-propenoyl)-1-piperazinyl)pyrido[2,3-d]pyrimidin-2(1H)-one | SFC Chiralpak (250 × 20 mm) 50% Methanol at 50 ml/min, 180 Bar, 220-nm |
| 55-16-2 | 2nd-eluting isomer (M) | (M)-6-chloro-1-(4-(dimethylamino)-2-methyl-6-(2-propanyl)phenyl)-7-(2-fluorophenyl)-4-((2S)-2-methyl-4-(2-propenoyl)-1-piperazinyl)pyrido[2,3-d]pyrimidin-2(1H)-one | SFC Chiralpak (250 × 20 mm) 50% Methanol at 50 ml/min, 180 Bar, 220-nm |

| Ex. # | Chemical Structure | Name | Racemic SM/ separation conditions |
|---|---|---|---|
| 55-23-1 | 1st-eluting isomer | 6-chloro-7-(2-fluoro-6-hydroxyphenyl)-1-(3-(2-methyl-2-propanyl)-2-pyrazinyl)-4-((2S)-2-methyl-4-(2-propenoyl)-1-piperazinyl)pyrido[2,3-d]pyrimidin-2(1H)-one | NPLC ChiralPak IC-H (21 × 250 mm, 5 μm), 40% (MeOH/EtOH, 1:1)/heptane; 30 mL/min |
| 55-23-2 | 2nd-eluting isomer | 6-chloro-7-(2-fluoro-6-hydroxyphenyl)-1-(3-(2-methyl-2-propanyl)-2-pyrazinyl)-4-((2S)-2-methyl-4-(2-propenoyl)-1-piperazinyl)pyrido[2,3-d]pyrimidin-2(1H)-one | NPLC ChiralPak IC-H (21 × 250 mm, 5 μm), 40% (MeOH/EtOH, 1:1)/heptane; 30 mL/min |
| 55-26-1 | 1st-eluting isomer (P) | (P)-6-chloro-7-(2-fluorophenyl)-1-(2-hydroxy-6-(2-propanyl)phenyl)-4-((2S)-2-methyl-4-(2-propenoyl)-1-piperazinyl)pyrido[2,3-d]pyrimidin-2(1H)-one | SFC IE (250 × 21 mm, 5 μ), 50% MeOH/CO$_2$, 80 g/min, 102 bar) |

| Ex. # | Chemical Structure | Name | Racemic SM/ separation conditions |
|---|---|---|---|
| 55-26-2 | 2nd-eluting isomer (M) | (M)-6-chloro-7-(2-fluorophenyl)-1-(2-hydroxy-6-(2-propanyl)phenyl)-4-((2S)-2-methyl-4-(2-propenoyl)-1-piperazinyl)pyrido[2,3-d]pyrimidin-2(1H)-one | SFC IE (250 × 21 mm, 5 μ, 50% MeOH/$CO_2$, 80 g/min, 102 bar) |
| 55-38-1 | 1st-eluting isomer (P) | (P)-6-chloro-7-(2-fluorophenyl)-1-(4-methyl-1-(2-methyl-2-propanyl)-1H-pyrazol-5-yl)-4-((2S)-2-methyl-4-(2-propenoyl)-1-piperazinyl)pyrido[2,3-d]pyrimidin-2(1H)-one | SFC (OZ-H column (5 μm, 46 × 150 mm), 40% MeOH/CO2, 70 mL/min, 100 bar) |
| 55-38-2 | 2nd-eluting isomer (M) | (M)-6-chloro-7-(2-fluorophenyl)-1-(4-methyl-1-(2-methyl-2-propanyl)-1H-pyrazol-5-yl)-4-((2S)-2-methyl-4-(2-propenoyl)-1-piperazinyl)pyrido[2,3-d]pyrimidin-2(1H)-one | SFC (OZ-H column (5 μm, 46 × 150 mm), 40% MeOH/CO2, 70 mL/min, 100 bar) |

| Ex. # | Chemical Structure | Name | Racemic SM/ separation conditions |
|---|---|---|---|
| 55-39-1 | 1st-eluting isomer | 6-chloro-7-(2,5-difluorophenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | R,R-Whelk-01, (5 micron, 250 × 20 mm id), 60% CO2, 40% MeOH, 60 ml/min, ambient temperature, 102 Bar 220-nm |
| 55-39-2 | 2nd-eluting isomer | 6-chloro-7-(2,5-difluorophenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | R,R-Whelk-01, (5 micron, 250 × 20 mm id), 60% CO2, 40% MeOH, 60 ml/min, ambient temperature, 102 Bar, 220-nm |
| 55-40-1 | 1st-eluting isomer | 6-chloro-7-(2-fluoro-5-methylphenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | R,R-Whelk-01, (5 micron, 250 × 20 mm id), 60% CO2, 40% MeOH, 60 ml/min, ambient temperature, 102 Bar, 220-nm |

| Ex. # | Chemical Structure | Name | Racemic SM/ separation conditions |
|---|---|---|---|
| 55-40-2 | 2nd-eluting isomer | 6-chloro-7-(2-fluoro-5-methylphenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | R,R-Whelk-01, (5 micron, 250 × 20 mm id), 60% CO2, 40% MeOH, 60 ml/min, ambient temperature, 102 Bar, 220-nm |
| 55-43-1 | 1st-eluting isomer | 6-chloro-7-(2-fluorophenyl)-1-(2-(hydroxymethyl)-6-(2-propanyl)phenyl)-4-((2S)-2-methyl-4-(2-propenoyl)-1-piperazinyl)pyrido[2,3-d]pyrimidin-2(1H)-one | SFC (Chiralpak IE (150 × 20 mm, 5 μm), 50% MeOH/CO2, 60 mL/min, 165 bar) |
| 55-43-2 | 2nd-eluting isomer | 6-chloro-7-(2-fluorophenyl)-1-(2-(hydroxymethyl)-6-(2-propanyl)phenyl)-4-((2S)-2-methyl-4-(2-propenoyl)-1-piperazinyl)pyrido[2,3-d]pyrimidin-2(1H)-one | SFC (Chiralpak IE (150 × 20 mm, 5 μm), 50% MeOH/CO2, 60 mL/min, 165 bar) |

| Ex. # | Chemical Structure | Name | Racemic SM/ separation conditions |
|---|---|---|---|
| 56-1-1 | 1st-eluting isomer | 6-chloro-7-(2-fluoro-6-hydroxy-phenyl)-4-[(2S)-2-methyl-4-prop-2-enoyl-piperazin-1-yl]-1-[2-(pentafluoro-$\lambda^6$-sulfanyl)phenyl]pyrido[2,3-d]pyrimidin-2-one | NPLC Whelk-O1 (S,S) (21.1 × 250 mm, 5 um), 60% (MeOH/EtOH, 1:1)/heptane, 25 mL/min |
| 56-1-2 | 2nd-eluting isomer | 6-chloro-7-(2-fluoro-6-hydroxy-phenyl)-4-[(2S)-2-methyl-4-prop-2-enoyl-piperazin-1-yl]-1-[2-(pentafluoro-$\lambda^6$-sulfanyl)phenyl]pyrido[2,3-d]pyrimidin-2-one | NPLC Whelk-O1 (S,S) (21.1 × 250 mm, 5 um), 60% (MeOH/EtOH, 1:1)/heptane, 25 mL/min |
| 56-5-1 | 1st-eluting isomer | 6-chloro-1-(2-cyclopropyl-6-methylphenyl)-7-(2-fluorophenyl)-4-((2S)-2-methyl-4-(2-propenoyl)-1-piperazinyl)pyrido[2,3-d]pyrimidin-2(1H)-one | SFC Chiralcel OX-H (21 × 250 mm, 5 μm) 30% MeOH/CO$_2$, 100 bar |

-continued

| Ex. # | Chemical Structure | Name | Racemic SM/ separation conditions |
|---|---|---|---|
| 56-5-2 | 2nd-eluting isomer | 6-chloro-1-(2-cyclopropyl-6-methylphenyl)-7-(2-fluorophenyl)-4-((2S)-2-methyl-4-(2-propenoyl)-1-piperazinyl)pyrido[2,3-d]pyrimidin-2(1H)-one | SFC Chiralcel OX-H (21 × 250 mm, 5 μm 30% MeOH/$CO_2$, 100 bar |
| 56-7-1 | 1st-eluting isomer | 7-(5-amino-2-chlorophenyl)-6-chloro-4-((2S)-2-methyl-4-(2-propenoyl)-1-piperazinyl)-1-(2-(2-propanyl)phenyl)pyrido[2,3-d]pyrimidin-2(1H)-one | SFC ID (21 × 250 mm, 5 μm), 60% MeOH (with 20 mM $NH_3$)/$CO_2$, 50 mL/min, 100 bar |
| 56-7-2 | 2nd-eluting isomer | 7-(5-amino-2-chlorophenyl)-6-chloro-4-((2S)-2-methyl-4-(2-propenoyl)-1-piperazinyl)-1-(2-(2-propanyl)phenyl)pyrido[2,3-d]pyrimidin-2(1H)-one | SFC ID (21 × 250 mm, 5 μm), 60% MeOH (with 20 mM $NH_3$)/$CO_2$, 50 mL/min, 100 bar |

-continued

| Ex. # | Chemical Structure | Name | Racemic SM/ separation conditions |
|---|---|---|---|
| 57-1-1 | 1st-eluting isomer | 1-(2-ethyl-4-methyl-3-pyridinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | SFC IC (21 × 150 mm, 5 μm), 65% MeOH/CO$_2$, 50 mL/min, 100 bar |
| 57-1-2 | 2nd-eluting isomer | 1-(2-ethyl-4-methyl-3-pyridinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | SFC IC (21 × 150 mm, 5 μm), 65% MeOH/CO$_2$, 50 mL/min, 100 bar |
| 57-6-1 | 1$^{st}$-eluting isomer (P) | (P)-6-fluoro-7-(2-fluoro-6-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | SFC Welk-01 (S,S) (21 × 250 mm, 5 μm), 35% MeOH with 20 mM NH$_3$/CO$_2$, 50 mL/min, 100 bar |

| Ex. # | Chemical Structure | Name | Racemic SM/ separation conditions |
|---|---|---|---|
| 57-6-2 | 2nd eluting isomer (M) | (M)-6-fluoro-7-(2-fluoro-6-hydroxyphenyl)-4-((2S)-2-methyl-4-(2-propenoyl)-1-piperazinyl)-1-(2-(2-propanyl)phenyl)pyrido[2,3-d]pyrimidin-2(1H)-one | SFC Welk-01 (S,S) (21 × 250 mm, 5 μm), 35% MeOH with 20 mM $NH_3/CO_2$, 50 mL/min, 100 bar |
| 57-7-1 | 1st-eluting isomer | 6-fluoro-7-(2-fluorophenyl)-4-((2S)-2-methyl-4-(2-propenoyl)-1-piperazinyl)-1-(2-(2-propanyl)phenyl)pyrido[2,3-d]pyrimidin-2(1H)-one | SFC Whelk-01 (S,S) (21 × 250 mm, 5 μm), 35% MeOH with 20 mM $NH_3/CO_2$, 50 mL/min, 100 bar |
| 57-7-2 | 2nd-eluting isomer | 6-fluoro-7-(2-fluorophenyl)-4-((2S)-2-methyl-4-(2-propenoyl)-1-piperazinyl)-1-(2-(2-propanyl)phenyl)pyrido[2,3-d]pyrimidin-2(1H)-one | SFC Whelk-01 (S,S) (21 × 250 mm, 5 μm), 35% MeOH with 20 mM $NH_3/CO_2$, 50 mL/min, 100 bar |

-continued

| Ex. # | Chemical Structure | Name | Racemic SM/ separation conditions |
|---|---|---|---|
| 57-8-1 | 1st-eluting isomer | 7-(2-chlorophenyl)-6-fluoro-4-((2S)-2-methyl-4-(2-propenoyl)-1-piperazinyl)-1-(2-(2-propanyl)phenyl)pyrido[2,3-d]pyrimidin-2(1H)-one | SFC Whelk-01 (S,S) (21 × 250 mm, 5 μm) 40% MeOH/ 60% $CO_2$, 50 mL/min, 100 bar |
| 57-8-2 | 2nd-eluting isomer | 7-(2-chlorophenyl)-6-fluoro-4-((2S)-2-methyl-4-(2-propenoyl)-1-piperazinyl)-1-(2-(2-propanyl)phenyl)pyrido[2,3-d]pyrimidin-2(1H)-one | SFC Whelk-01 (S,S) (21 × 250 mm, 5 μm), 40% MeOH/ 60% $CO_2$, 50 mL/min, 100 bar |
| 57-13-1 | 1st-eluting isomer | 1-(2-ethyl-6-methylphenyl)-6-fluoro-7-(2-fluorophenyl)-4-((2S)-2-methyl-4-(2-propenoyl)-1-piperazinyl)pyrido[2,3-d]pyrimidin-2(1H)-one | SFC Chiralpak IC, (21 × 250 mm, 5 μm), 35% MeOH/$CO_2$, 70 mL/min, 100 bar |

| Ex. # | Chemical Structure | Name | Racemic SM/ separation conditions |
|---|---|---|---|
| 57-13-2 | 2nd-eluting isomer | 1-(2-ethyl-6-methylphenyl)-6-fluoro-7-(2-fluorophenyl)-4-((2S)-2-methyl-4-(2-propenoyl)-1-piperazinyl)pyrido[2,3-d]pyrimidin-2(1H)-one | SFC Chiralpak IC, (21 × 250 mm, 5 μm), 35% MeOH/$CO_2$, 70 mL/min, 100 bar |
| 57-14-1 | 1st-eluting isomer | 1-(2-ethyl-6-methylphenyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | SFC OX-H (21 × 250 mm, 5 μm), 20% MeOH/$CO_2$, 60 mL/min, 100 bar |
| 57-14-2 | 2nd-eluting isomer | 1-(2-ethyl-6-methyphenyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | SFC OX-H (21 × 250 mm, 5 μm), 20% MeOH/$CO_2$, 60 mL/min, 100 bar |

-continued

| Ex. # | Chemical Structure | Name | Racemic SM/ separation conditions |
|---|---|---|---|
| 57-15-1 | 1st-eluting isomer | 1-(2-chloro-6-(2-propanyl)phenyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | SFC OX-H (21 × 250 mm, 5 μm), 40% MeOH/$CO_2$, 80 mL/min, 100 bar |
| 57-15-2 | 2nd-eluting isomer | 1-(2-chloro-6-(2-propanyl)phenyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | SFC OX-H (21 × 250 mm, 5 μm), 40% MeOH/$CO_2$, 80 mL/min, 100 bar |
| 57-16-1 | 1st-eluting isomer | 1-(2-ethyl-4-methyl-3-pyridinyl)-6-fluoro-7-(2-fluorophenyl)-4-((2S)-2-methyl-4-(2-propenoyl)-1-piperazinyl)pyrido[2,3-d]pyrimidin-2(1H)-one | SFC Chiralcel OD-H (20 × 250 mm, 5 μm), 30% MeOH/$CO_2$, 50 mL/min, 100 bar |

| Ex. # | Chemical Structure | Name | Racemic SM/ separation conditions |
|---|---|---|---|
| 57-16-2 | 2nd-eluting isomer | 1-(2-ethyl-4-methyl-3-pyridinyl)-6-fluoro-7-(2-fluorophenyl)-4-((2S)-2-methyl-4-(2-propenoyl)-1-piperazinyl)pyrido[2,3-d]pyrimidin-2(1H)-one | SFC Chiralcel OD-H (20 × 250 mm, 5 μm), 30% MeOH/CO$_2$, 50 mL/min, 100 bar |
| 57-17-1 | 1st-eluting isomer | 6-fluoro-7-(2-fluoro-6-hydroxyphenyl)-1-(2-methyl-6-(2-methyl-2-propanyl)phenyl)-4-((2S)-2-methyl-4-(2-propenoyl)-1-piperazinyl)pyrido[2,3-d]pyrimidin-2(1H)-one | SFC Chiralpak AD-H (21 × 250 mm, 5 μm), 20% MeOH/CO$_2$, 100 g/min, 102 bar |
| 57-17-2 | 2nd-eluting isomer | 6-fluoro-7-(2-fluoro-6-hydroxyphenyl)-1-(2-methyl-6-(2-methyl-2-propanyl)phenyl)-4-((2S)-2-methyl-4-(2-propenoyl)-1-piperazinyl)pyrido[2,3-d]pyrimidin-2(1H)-one | SFC Chiralpak AD-H (21 × 250 mm, 5 μm), 20% MeOH/CO$_2$, 100 g/min, 102 bar |

-continued

| Ex. # | Chemical Structure | Name | Racemic SM/ separation conditions |
|---|---|---|---|
| 58-1-1 | 1st-eluting isomer | 6-fluoro-7-(2-fluoro-6-hydroxyphenyl)-1-(2-(2-methyl-2-propanyl)phenyl)-4-((2S)-2-methyl-4-(2-propenoyl)-1-piperazinyl)pyrido[2,3-d]pyrimidin-2(1H)-one | SFC Welk-01 (S,S) (21 × 150 mm, 5 μm), 55% MeOH/CO$_2$, 70 mL/min, 110 bar |
| 58-1-2 | 2nd-eluting isomer | 6-fluoro-7-(2-fluoro-6-hydroxyphenyl)-1-(2-(2-methyl-2-propanyl)phenyl)-4-((2S)-2-methyl-4-(2-propenoyl)-1-piperazinyl)pyrido[2,3-d]pyrimidin-2(1H)-one | SFC Welk-01 (S,S) (21 × 150 mm, 5 μm), 55% MeOH/CO$_2$, 70 mL/min, 110 bar |
| 58-2-1 | 1$^{st}$-eluting isomer | 6-fluoro-7-(2-fluoro-6-hydroxyphenyl)-4-((2S)-2-methyl-4-(2-propenoyl)-1-piperazinyl)-1-(4-methyl-2-propyl-3-pyridinyl)pyrido[2,3-d]pyrimidin-2(1H)-one | SFC Chiralpak IC (21 × 150 mm, 5 μm), 60% MeOH/CO$_2$, 50 mL/min, 100 bar |

| Ex. # | Chemical Structure | Name | Racemic SM/ separation conditions |
|---|---|---|---|
| 58-2-2 | 2nd-eluting isomer | 6-fluoro-7-(2-fluoro-6-hydroxyphenyl)-4-((2S)-2-methyl-4-(2-propenoyl)-1-piperazinyl)-1-(4-methyl-2-propyl-3-pyridinyl)pyrido[2,3-d]pyrimidin-2(1H)-one | SFC Chiralpak IC (21 × 150 mm, 5 μm), 60% MeOH/CO$_2$, 50 mL/min, 100 bar |
| 58-3-1 | 1st-eluting isomer | 6-fluoro-7-(2-fluoro-6-hydroxyphenyl)-4-((2S)-2-methyl-4-(2-propenoyl)-1-piperazinyl)-1-(2-(2-propanyl)-4-(trifluoromethyl)-3-pyridinyl)pyrido[2,3-d]pyrimidin-2(1H)-one | SFC Chiralpak IC (21 × 150 mm, 5 μm), 60% MeOH/CO$_2$, 50 mL/min, 100 bar |
| 58-3-2 | 2nd-eluting isomer | 6-fluoro-7-(2-fluoro-6-hydroxyphenyl)-4-((2S)-2-methyl-4-(2-propenoyl)-1-piperazinyl)-1-(2-(2-propanyl)-4-(trifluoromethyl)-3-pyridinyl)pyrido[2,3-d]pyrimidin-2(1H)-one | SFC Chiralpak IC (21 × 150 mm, 5 μm), 60% MeOH/CO$_2$, 50 mL/min, 100 bar |

-continued

| Ex. # | Chemical Structure | Name | Racemic SM/ separation conditions |
|---|---|---|---|
| 58-4-1 | 1st-eluting isomer | 6-fluoro-7-(2-fluorophenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | SFC Chiralpak IC (20 × 150 mm), 60% MeOH/$CO_2$, 70 mL/min, 100 bar |
| 58-4-2 | 2nd-eluting isomer | 6-fluoro-7-(2-fluorophenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | SFC Chiralpak IC (20 × 150 mm), 60% MeOH/$CO_2$, 70 mL/min, 100 bar |
| 58-5-1 | 1st-eluting isomer | 6-fluoro-7-(2-fluoro-5-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | NPLC Chiralpak IF (21.2 × 250 mm, 5 μm), 35% 20 mM $NH_3$ in MeOH:EtOH (50:50)/heptane, 22 mL/min |

-continued

| Ex. # | Chemical Structure | Name | Racemic SM/ separation conditions |
|---|---|---|---|
| 58-5-2 | (2nd-eluting isomer) | 6-fluoro-7-(2-fluoro-5-hydroxyphenyl)-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | NPLC Chiralpak IF (21.2 × 250 mm, 5 μm), 35% 20 mM NH$_3$ in MeOH:EtOH (50:50)/heptane, 22 mL/min |
| 58-6-1 | (1st-eluting isomer) | 7-(5-amino-2-fluorophenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | NPLC Chiralpak OZ-H (21.2 × 25 cm × 5 μm), 40% MeOH:EtOH (50:50)/heptane, 20 ml/min |
| 58-6-2 | (2nd-eluting isomer) | 7-(5-amino-2-fluorophenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | NPLC Chiralpak OZ-H (21.2 × 25 cm × 5 um), 40% MeOH:EtOH (50:50)/heptane, 20 mL/min |

| Ex. # | Chemical Structure | Name | Racemic SM/ separation conditions |
|---|---|---|---|
| 58-7-1 | 1st-eluting isomer | 7-(2,3-dichloro-5-hydroxyphenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | NPLC Chiralpak IF (250 × 21 mm, 5 μm), 20% MPB: MeOH:EtOH (50:50)/heptane, 22 mL/min |
| 58-7-2 | 2nd-eluting isomer | 7-(2,3-dichloro-5-hydroxyphenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | NPLC Chiralpak IF (250 × 21 mm, 5 μm), 20% MPB: MeOH:ETOH (50:50)/heptane, 22 mL/min |
| 58-8-1 | 1st-eluting isomer | 7-(5-amino-2-chlorophenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | SFC Chiralpak IC (30 × 250 mm, 5 μm), 55% MeOH/CO$_2$, 160 mL/min, 100 bar |

| Ex. # | Chemical Structure | Name | Racemic SM/ separation conditions |
|---|---|---|---|
| 58-8-2 | 2nd-eluting isomer | 7-(5-amino-2-chlorophenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | SFC Chiralpak IC (30 × 250 mm, 5 μm), 55% MeOH/CO$_2$, 160 mL/min, 100 bar |
| 58-9-1 | 1st-eluting isomer | 7-(2-chloro-6-hydroxyphenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | SFC Chiralpak IC (30 × 250 mm, 20 μm), 55% MeOH/CO$_2$, 160 mL/min, 110 bar |
| 58-9-2 | 2nd-eluting isomer | 7-(2-chloro-6-hydroxyphenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | SFC Chiralpak IC (30 × 250 mm, 20 μm), 55% MeOH/CO$_2$, 160 mL/min, 110 bar |

| Ex. # | Chemical Structure | Name | Racemic SM/ separation conditions |
|---|---|---|---|
| 58-10-1 | 1st-eluting isomer | 7-(2,4-difluorophenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | NPLC ChiralPak IC (21 × 150 mm, 5 μm), 70% MPB:IPA/heptane, 20 mL/min |
| 58-10-2 | 2nd-eluting isomer | 7-(2,4-difluorophenyl)-6-fluoro-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | NPLC ChiralPak IC (21 × 150 mm, 5 μm), 70% MPB:IPA/heptane, 20 mL/min |
| 58-11-1 | 1st-eluting isomer | 6-fluoro-7-(2-fluoro-6-hydroxyphenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | NPLC IC (21 × 250 mm, 5 μm), 20% MTB:EtOH/heptane, 25 mL/min |

| Ex. # | Chemical Structure | Name | Racemic SM/ separation conditions |
|---|---|---|---|
| 58-11-2 | *2nd-eluting isomer* | 6-fluoro-7-(2-fluoro-6-hydroxyphenyl)-1-(4-methyl-6-(2-propanyl)-5-pyrimidinyl)-4-((2S)-2-methyl-4-(2-propenoyl)-1-piperazinyl)pyrido[2,3-d]pyrimidin-2(1H)-one | NPLC IC (21 × 250 mm, 5 μm), 20% MTB:EtOH/heptane, 25 mL/min |
| 58-13-1 | *1st-eluting isomer* | 1-(2-cyclopropyl-6-methylphenyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | SFC Chiralpak AS-H (250 × 21.2 mm, 5 μm), 25% IPOH 100 g/min (218 bar), 102 bar |
| 58-13-2 | *2nd-eluting isomer* | 1-(2-cyclopropyl-6-methylphenyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | SFC Chiralpak AS-H (250 × 21.2 mm, 5 μm), 25% IPOH 100 g/min (218 bar), 102 bar |

-continued

| Ex. # | Chemical Structure | Name | Racemic SM/ separation conditions |
|---|---|---|---|
| 58-15-1 | 1st-eluting isomer | 6-fluoro-7-(2-fluoro-6-hydroxyphenyl)-1-(2-methyl-4-(2-propanyl)-3-pyridinyl)-4-((2S)-2-methyl-4-(2-propenoyl)-1-piperazinyl)pyrido[2,3-d]pyrimidin-2(1H)-one | SFC Welk-01 (R,R) (250 × 21 mm, 5 μm), 65% MeOH/CO$_2$, 80 g/min, 103 |
| 58-15-2 | 2nd-eluting isomer | 6-fluoro-7-(2-fluoro-6-hydroxyphenyl)-1-(2-methyl-4-(2-propanyl)-3-pyridinyl)-4-((2S)-2-methyl-4-(2-propenoyl)-1-piperazinyl)pyrido[2,3-d]pyrimidin-2(1H)-one | SFC Welk-01 (R,R) (250 × 21 mm, 5 μm), 65% MeOH/CO$_2$, 80 g/min, 103 |
| 58-16-1 | 1st-eluting isomer | 6-fluoro-7-(2-fluorophenyl)-1-(2-methyl-4-(2-propanyl)-3-pyridinyl)-4-methyl-4-(2-propenoyl)-1-piperazinyl)pyrido[2,3-d]pyrimidin-2(1H)-one | SFC Welk-01 (R,R) (21 × 25 cm, 5 μm), 50% MeOH/CO$_2$, 60 mL/min, 100 bar |

| Ex. # | Chemical Structure | Name | Racemic SM/ separation conditions |
|---|---|---|---|
| 58-16-2 | *2nd-eluting isomer* | 6-fluoro-7-(2-fluorophenyl)-1-(2-methyl-4-(2-propanyl)-3-pyridinyl)-4-((2S)-2-methyl-4-(2-propenoyl)-1-piperazinyl)pyrido[2,3-d]pyrimidin-2(1H)-one | SFC Welk-01 (R,R) (21 × 25 cm, 5 μm), 50% MeOH/CO$_2$, 60 mL/min, 100 bar |
| 58-17-1 | *1st-eluting isomer* | 6-fluoro-7-(2-fluorophenyl)-1-(2-(2-methyl-2-propanyl)phenyl)-4-((2S)-2-methyl-4-(2-propenoyl)-1-piperazinyl)pyrido[2,3-d]pyrimidin-2(1H)-one | SFC Welk-01 (S,S) (21 × 150 mm, 5 μm), 40% MeOH/CO$_2$, 65 mL/min, 102 bar |
| 58-17-2 | *2nd-eluting isomer* | 6-fluoro-7-(2-fluorophenyl)-1-(2-(2-methyl-2-propanyl)phenyl)-4-((2S)-2-methyl-4-(2-propenoyl)-1-piperazinyl)pyrido[2,3-d]pyrimidin-2(1H)-one | SFC Welk-01 (S,S) (21 × 150 mm, 5 μm), 40% MeOH/CO$_2$, 65 mL/min, 102 bar |

| Ex. # | Chemical Structure | Name | Racemic SM/ separation conditions |
|---|---|---|---|
| 58-18-1 | 1st-eluting isomer | 6-fluoro-7-(2-fluoro-6-hydroxyphenyl)-1-(2-methyl-6-(2-propanyl)phenyl)-4-((2S)-2-methyl-4-(2-propenoyl)-1-piperazinyl)pyrido[2,3-d]pyrimidin-2(1H)-one | SFC AD (30 × 250 mm, 5 μm), 60% iPrOH/$CO_2$, 95 g/min, 170 bar |
| 58-18-2 | 2nd-eluting isomer | 6-fluoro-7-(2-fluoro-6-hydroxyphenyl)-1-(2-methyl-6-(2-propanyl)phenyl)-4-((2S)-2-methyl-4-(2-propenoyl)-1-piperazinyl)pyrido[2,3-d]pyrimidin-2(1H)-one | SFC AD (30 × 250 mm, 5 μm), 60% iPrOH/$CO_2$, 95 g/min, 170 bar |
| 58-19-1 | 1st-eluting isomer | 1-(4-cyclopropyl-2-methyl-3-pyridinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | SFC OD-H (250 × 20 mm, 5 μm), 30% MeOH/$CO_2$, 60 ml/min, 100 bar |

-continued

| Ex. # | Chemical Structure | Name | Racemic SM/ separation conditions |
|---|---|---|---|
| 58-19-2 | 2$^{nd}$-eluting isomer | 1-(4-cyclopropyl-2-methyl-3-pyridinyl)-6-fluoro-7-(2-fluoro-6-hydroxyphenyl)-4-((2S)-2-methyl-4-(2-propenoyl)-1-piperazinyl)pyrido[2,3-d]pyrimidin-2(1H)-one | SFC OD-H (250 × 20 mm, 5 μm), 30% MeOH/CO$_2$, 60 ml/min, 100 bar |
| 58-20-1 | 1$^{st}$-eluting isomer | 1-(4-cyclopropyl-2-methyl-3-pyridinyl)-6-fluoro-7-(2-fluorophenyl)-4-((2S)-2-methyl-4-(2-propenoyl)-1-piperazinyl)pyrido[2,3-d]pyrimidin-2(1H)-one | NPLC, Chiralpak AZ-H (21.2 × 25 cm, 5 μm, MeOH:EtOH (50:50)/heptane, 30 mL/min |
| 58-20-2 | 2$^{nd}$-eluting isomer | 1-(4-cyclopropyl-2-methyl-3-pyridinyl)-6-fluoro-7-(2-fluorophenyl)-4-((2S)-2-methyl-4-(2-propenoyl)-1-piperazinyl)pyrido[2,3-d]pyrimidin-2(1H)-one | NPLC, Chiralpak AZ-H (21.2 × 25 cm, 5 μm, MeOH:EtOH (50:50)/heptane, 30 mL/min |

-continued

| Ex. # | Chemical Structure | Name | Racemic SM/ separation conditions |
|---|---|---|---|
| 59-1-1 | 1st-eluting isomer | 6-fluoro-7-(2-fluoro-6-hydroxyphenyl)-4-((2S)-2-methyl-4-(2-propenoyl)-1-piperazinyl)-1-(2-(1-(trifluoromethyl)cyclopropyl)phenyl)pyrido[2,3-d]pyrimidin-2(1H)-one | NPLC Chiralpak IE (21 × 150 mm, 5 μm), 30% 1:1 MeOH:EtOH/heptane, 30 mL/min |
| 59-1-2 | 2nd-eluting isomer | 6-fluoro-7-(2-fluoro-6-hydroxyphenyl)-4-((2S)-2-methyl-4-(2-propenoyl)-1-piperazinyl)-1-(2-(1-(trifluoromethyl)cyclopropyl)phenyl)pyrido[2,3-d]pyrimidin-2(1H)-one | NPLC Chiralpak IE (21 × 150 mm, 5 μm), 30% 1:1 MeOH:EtOH/heptane, 30 mL/min |
| 59-2-1 | 1st-eluting isomer | 6-fluoro-7-(2-fluoro-6-hydroxyphenyl)-1-(2-fluoro-6-(2-propanyl)phenyl)-4-((2S)-2-methyl-4-(2-propenoyl)-1-piperazinyl)pyrido[2,3-d]pyrimidin-2(1H)-one | SFC Whelk-01 (S,S) (21 × 250 mm, 5 μm), 50% MeOH/CO$_2$, 50 g/min, 212 bar |

-continued

| Ex. # | Chemical Structure | Name | Racemic SM/ separation conditions |
|---|---|---|---|
| 59-2-2 | 2nd-eluting isomer | 6-fluoro-7-(2-fluoro-6-hydroxyphenyl)-1-(2-fluoro-6-(2-propanyl)phenyl)-4-(2S)-2-methyl-4-(2-propenoyl)-1-piperazinyl)pyrido[2,3-d]pyrimidin-2(1H)-one | SFC Whelk-01 (S,S) (21 × 250 mm, 5 μm), 50% MeOH/CO$_2$, 50 g/min, 212 bar |
| 59-3-1 | 1$^{st}$-eluting isomer | 6-fluoro-7-(2-fluorophenyl)-1-(2-fluoro-6-(2-propanyl)phenyl)-4-((2S)-2-methyl-4-(2-propenoyl)-1-piperazinyl)pyrido[2,3-d]pyrimidin-2(1H)-one | NPLC (Whelk-01 (S,S), 21 × 250 mm, 5 μm, Heptane/(1:1 MeOH:EtOH), 32 mg/mL) |
| 59-3-2 | 2$^{nd}$-eluting isomer | 6-fluoro-7-(2-fluorophenyl)-1-(2-fluoro-6-(2-propanyl)phenyl)-4-((2S)-2-methyl-4-(2-propenoyl)-1-piperazinyl)pyrido[2,3-d]pyrimidin-2(1H)-one | NPLC (Whelk-01 (S,S), 21 × 250 mm, 5 μm, Heptane/(1:1 MeOH:EtOH), 32 mg/mL) |

-continued

| Ex. # | Chemical Structure | Name | Racemic SM/ separation conditions |
|---|---|---|---|
| 60-20-1 | 1st-eluting isomer (M) | (M)-2-(6-chloro-7-(2-fluorophenyl)-4-((2S)-2-methyl-4-(2-propenoyl)-1-piperazinyl)-2-oxopyrido[2,3-d]pyrimidin-1(2H)-yl)-3-(2-propanyl)benzonitrile | SFC OD (250 × 21 mm, 5 μ), 25% MeOH/CO$_2$, 80 g/min, 100 bar |
| 60-20-2 | 2nd-eluting isomer (P) | (P)-2-(6-chloro-7-(2-fluorophenyl)-4-((2S)-2-methyl-4-(2-propenoyl)-1-piperazinyl)-2-oxopyrido[2,3-d]pyrimidin-1(2H)-yl)-3-(2-propanyl)benzonitrile | SFC OD (250 × 21 mm, 5 μ), 25% MeOH/CO$_2$, 80 g/min, 100 bar |
| 60-24-1 | 1st-eluting isomer (M) | (M)-6-chloro-7-(2-fluoro-6-hydroxyphenyl)-1-(2-(2-propanyl)phenyl)-4-(4-(2-propenoyl)-1-piperazinyl)pyrido[2,3-d]pyrimidin-2(1H)-one | SFC IC (150 × 21 mm, 5 μm), 40% MeOH (with 20 mM NH$_3$)/CO$_2$, 80 g/min, 102 bar |

-continued

| Ex. # | Chemical Structure | Name | Racemic SM/ separation conditions |
|---|---|---|---|
| 60-24-2 | 2nd-eluting isomer (P) | (P)-6-chloro-7-(2-fluoro-6-hydroxyphenyl)-1-(2-(2-propanyl)phenyl)-4-(4-(2-propenoyl)-1-piperazinyl)pyrido[2,3-d]pyrimidin-2(1H)-one | SFC IC (150 × 21 mm, 5 µm), 40% MeOH (with 20 mM NH$_3$)/CO$_2$, 80 g/min, 102 bar |
| 60-30-1 | 1$^{st}$-eluting isomer | 6-chloro-1-(4-cyclopropyl-6-methyl-5-pyrimidinyl)-7-(2-fluorophenyl)-4-((2S)-2-methyl-4-(2-propenoyl)-1-piperazinyl)pyrido[2,3-d]pyrimidin-2(1H)-one | SFC (Whelk-01 (R,R), 21 × 250 mm, 5 µm, 35% MeOH/CO$_2$, 75 g/mL, 102 bar) |
| 60-30-2 | 2$^{nd}$-eluting isomer | 6-chloro-1-(4-cyclopropyl-6-methyl-5-pyrimidinyl)-7-(2-fluorophenyl)-4-((2S)-2-methyl-4-(2-propenoyl)-1-piperazinyl)pyrido[2,3-d]pyrimidin-2(1H)-one | SFC (Whelk-01 (R,R), 21 × 250 mm, 5 µm, 35% MeOH/CO$_2$, 75 g/mL, 102 bar) |

-continued

| Ex. # | Chemical Structure | Name | Racemic SM/ separation conditions |
|---|---|---|---|
| 62-1-1 | 1st-eluting isomer | 6-chloro-7-(2-fluorophenyl)-4-((2S)-2-methyl-4-(2-propenoyl)-1-piperazinyl)-1-(2-(2-propanyl)phenyl)-2(1H)-quinazolinone | SFC Whelk-01 (S,S) (21 × 250 mm, 5 μm), 40% MeOH with 20 mM $NH_3/CO_2$, 50 mL/min, 165 bar |
| 62-1-2 | 2nd-eluting isomer | 6-chloro-7-(2-fluorophenyl)-4-((2S)-2-methyl-4-(2-propenoyl)-1-piperazinyl)-1-(2-(2-propanyl)phenyl)-2(1H)-quinazolinone | SFC Whelk-01 (S,S) (21 × 250 mm, 5 μm), 40% MeOH with 20 mM $NH_3/CO_2$, 50 mL/min, 165 bar |
| 67-4-1 | 1st-eluting isomer | 6-chloro-4-((2S)-2-methyl-4-(2-propenoyl)-1-piperazinyl)-1-(2-(2-propanyl)phenyl)-7-(2-thiophenyl)pyrido[2,3-d]pyrimidin-2(1H)-one | SFC Whelk-01 (R,R) (250 × 21 mm, 5 μm), 40% MeOH/CO2, 70 g/min, 102 bar |

| Ex. # | Chemical Structure | Name | Racemic SM/ separation conditions |
|---|---|---|---|
| 67-4-2 | *2nd-eluting isomer* | 6-chloro-4-((2S)-2-methyl-4-(2-propenoyl)-1-piperazinyl)-1-(2-(2-propanyl)phenyl)-7-(2-thiophenyl)pyrido[2,3-d]pyrimidin-2(1H)-one | SFC Whelk-01 (R,R) (250 × 21 mm, 5 μm), 40% MeOH/CO2, 70 g/min, 102 bar |
| 68-1-1 | *1st-eluting isomer* | 7-(2-chloro-6-hydroxyphenyl)-6-fluoro-1-(2-methyl-6-(2-propanyl)phenyl)-4-((2S)-2-methyl-4-(2-propenoyl)-1-piperazinyl)pyrido[2,3-d]pyrimidin-2(1H)-one | NPLC Chiralpak AZ-H (21.2 × 250 mm, 5 μm), 20% MeOH:EtOH (50:50)/heptane, 22 mL/min |
| 68-1-2 | *2nd-eluting isomer* | 7-(2-chloro-6-hydroxyphenyl)-6-fluoro-1-(2-methyl-6-(2-propanyl)phenyl)-4-((2S)-2-methyl-4-(2-propenoyl)-1-piperazinyl)pyrido[2,3-d]pyrimidin-2(1H)-one | NPLC Chiralpak AZ-H (21.2 × 250 mm, 5 μm), 20% MeOH:EtOH (50:50)/heptane, 22 mL/min |

-continued

| Ex. # | Chemical Structure | Name | Racemic SM/ separation conditions |
|---|---|---|---|
| 68-2-1 | 1st-eluting isomer | 6-fluoro-7-(5-methyl-1H-indazol-4-yl)-1-(2-methyl-6-(2-propanyl)phenyl)-4-((2S)-2-methyl-4-(2-propenoyl)-1-piperazinyl)pyrido[2,3-d]pyrimidin-2(1H)-one | NPLC Chiralpak IF (21.2 × 250 mm, 5 µm), 35% MeOH:EtOH (50:50)/heptane, 25 mL/min |
| 68-2-2 | 2nd-eluting isomer | 6-fluoro-7-(5-methyl-1H-indazol-4-yl)-1-(2-methyl-6-(2-propanyl)phenyl)-4-((2S)-2-methyl-4-(2-propenoyl)-1-piperazinyl)pyrido[2,3-d]pyrimidin-2(1H)-one | NPLC Chiralpak IF (21.2 × 250 mm, 5 µm), 35% MeOH:EtOH (50:50)/heptane, 25 mL/min |
| 69-1-1 | 1st-eluting isomer | 6-chloro-4-((2S)-2-methyl-4-(2-propenoyl)-1-piperazinyl)-7-(1-piperidinyl)-1-(2-(2-propanyl)phenyl)pyrido[2,3-d]pyrimidin-2(1H)-one | SFC Whelk-01 (S,S) (250 × 21 mm, 5 µm), 50% MeOH (with 20 mM NH$_3$)/CO$_2$, 65 g/min, 102 bar |

-continued

| Ex. # | Chemical Structure | Name | Racemic SM/ separation conditions |
|---|---|---|---|
| 69-1-2 | 2nd-eluting isomer | 6-chloro-4-((2S)-2-methyl-4-(2-propenoyl)-1-piperazinyl)-7-(1-piperidinyl)-1-(2-(2-propanyl)phenyl) pyrido[2,3-d]pyrimidin-2(1H)-one | SFC Whelk-01 (S,S) (250 × 21 mm, 5 μm), 50% MeOH (with 20 mM $NH_3$)/$CO_2$, 65 g/min, 102 bar |
| 71-1-1 | 1st-eluting isomer | 7-(6-amino-3-chloro-2-pyridinyl)-6-fluoro-1-(2-methyl-6-(2-propanyl)phenyl)-4-((2S)-2-methyl-4-(2-propenoyl)-1-piperazinyl) pyrido[2,3-d]pyrimidin-2(1H)-one | NPLC Chiralpak IF (21.2 × 250 mm, 5 μm), 50% Isopropanol (50:50)/heptane, 22 mL/min |
| 71-1-2 | 2nd-eluting isomer | 7-(6-amino-3-chloro-2-pyridinyl)-6-fluoro-1-(2-methyl-6-(2-propanyl)phenyl)-4-((2S)-2-methyl-4-(2-propenoyl)-1-piperazinyl) pyrido[2,3-d]pyrimidin-2(1H)-one | NPLC Chiralpak IF (21.2 × 250 mm, 5 μm), 50% Isopropanol (50:50)/heptane, 22 mL/min |

-continued

| Ex. # | Chemical Structure | Name | Racemic SM/ separation conditions |
|---|---|---|---|
| 71-2-1 | 1st-eluting isomer | 7-(3-amino-1-isoquinolinyl)-6-fluoro-1-(2-methyl-6-(2-propanyl)phenyl)-4-((2S)-2-methyl-4-(2-propenoyl)-1-piperazinyl)pyrido[2,3-d]pyrimidin-2(1H)-one | NPLC Chiralpak IF (21.2 × 250 mm, 5 μm), 40% MeOH:EtOH (50:50)/heptane, 22 mL/min |
| 71-2-2 | 2nd-eluting isomer | 7-(3-amino-1-isoquinolinyl)-6-fluoro-1-(2-methyl-6-(2-propanyl)phenyl)-4-((2S)-2-methyl-4-(2-propenoyl)-1-piperazinyl)pyrido[2,3-d]pyrimidin-2(1H)-one | NPLC Chiralpak IF (21.2 × 250 mm, 5 μm), 40% MeOH:EtOH (50:50)/heptane, 22 mL/min |
| 74-1-1 | 1st-eluting isomer | 7-(2-fluorophenyl)-6-methyl-4-((2S)-2-methyl-4-(2-propenoyl)-1-piperazinyl)-1-(2-(2-propanyl)phenyl)pyrido[2,3-d]pyrimidin-2(1H)-one | SFC Whelk-01 (S,S) (21 × 250 mm, 5 μm), 50% MeOH/CO$_2$, 65 g/min, 102 bar |

-continued

| Ex. # | Chemical Structure | Name | Racemic SM/ separation conditions |
|---|---|---|---|
| 74-1-2 | 2nd-eluting isomer | 7-(2-fluorophenyl)-6-methyl-4-((2S)-2-methyl-4-(2-propenoyl)-1-piperazinyl)-1-(2-(2-propanyl)phenyl)pyrido[2,3-d]pyrimidin-2(1H)-one | SFC Whelk-01 (S,S) (21 × 250 mm, 5 μm), 50% MeOH/$CO_2$, 65 g/min, 102 bar |
| 74-2-1 | 1st-eluting isomer | 7-(2-fluorophenyl)-6-methyl-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | SFC (ChiralPak IC (150 × 21 mm, 5 μm), 6:4 MeOH/CO2, 50 g/min, 102 bar) |
| 74-2-2 | 2nd-eluting isomer | 7-(2-fluorophenyl)-6-methyl-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | SFC (ChiralPak IC (150 × 21 mm, 5 μm), 6:4 MeOH/CO2, 50 g/min, 102 bar) |

-continued

| Ex. # | Chemical Structure | Name | Racemic SM/ separation conditions |
|---|---|---|---|
| 74-3-1 | 1st-eluting isomer | 7-(2-fluoro-6-hydroxyphenyl)-6-methyl-1-(4-methyl-2-(2-propanyl)-3-pyridinyl)-4-((2S)-2-methyl-4-(2-propenoyl)-1-piperazinyl)pyrido[2,3-d]pyrimidin-2(1H)-one | SFC (ChiralPak IC, (21 × 250 mm, 5 um), 50% MeOH/CO$_2$, 60 g/min, 100 bar) |
| 74-3-2 | 2nd-eluting isomer | 7-(2-fluoro-6-hydroxyphenyl)-6-methyl-1-(4-methyl-2-(2-propanyl)-((2S)-2-methyl-4-(2-propenoyl)-1-piperazinyl)pyrido[2,3-d]pyrimidin-2(1H)-one | SFC (ChiralPak IC, (21 × 250 mm, 5 um), 50% MeOH/CO$_2$, 60 g/min, 100 bar) |
| 75-9-1 | 1st-eluting isomer (M and 2S or 2R) | (M)-4-(2-(difluoromethyl)-4-(2-propenoyl)-1-piperazinyl)-6-fluoro-7-(2-fluoro-6-hydroxyphenyl)-1-(4-methyl-2-(2-propanyl)-3-pyridinyl)pyrido[2,3-d]pyrimidin-2(1H)-one | SFC (ChiralPak OX, 21 × 150 mmm, 5 um; 20% MeOH/CO$_2$, 80 g/min, 140 bar) |

-continued

| Ex. # | Chemical Structure | Name | Racemic SM/ separation conditions |
|---|---|---|---|
| 75-9-2 | 2nd-eluting isomer (M and 2S or 2R) | (M)-4-(2-(difluoromethyl)-4-(2-propenoyl)-1-piperazinyl)-6-fluoro-7-(2-fluoro-6-hydroxyphenyl)-1-(4-methyl-2-(2-propanyl)-3-pyridinyl)pyrido[2,3-d]pyrimidin-2(1H)-one | SFC (ChiralPak OX, 21 × 150 mmm, 5 um; 20% MeOH/CO$_2$, 80 g/min, 140 bar |
| 78-3-1 | 1st-eluting isomer (M and 2S) | (M)-6-chloro-4-((2S)-2-(difluoromethyl)-4-(2-propenoyl)-1-piperazinyl)-7-(2-fluorophenyl)-1-(4-methyl-2-(2-propanyl)-3-pyridinyl)pyrido[2,3-d]pyrimidin-2(1H)-one | SFC (ChiralPak OX, 21 × 250 mm, 5 um), 25% MeOH/CO$_2$, 70 g/min, 191 bar) |
| 78-3-2 | 2nd-eluting isomer (M and 2R) | (M)-6-chloro-4-((2R)-2-(difluoromethyl)-4-(2-propenoyl)-1-piperazinyl)-7-(2-fluorophenyl)-1-(4-methyl-2-(2-propanyl)-3-pyridinyl)pyrido[2,3-d]pyrimidin-2(1H)-one | SFC (ChiralPak OX, 21 × 250 mm, 5 um), 25% MeOH/CO$_2$, 70 g/min, 191 bar) |

| Ex. # | Chemical Structure | Name | Racemic SM/ separation conditions |
|---|---|---|---|
| 78-9-1 | 1st-eluting isomer (M and 2S or 2R) | (M)-6-chloro-7-(2-fluorophenyl)-1-(4-methyl-2-(2-propanyl)-3-pyridinyl)-4-((2S)-4-(2-propenoyl)-2-(trifluoromethyl)-1-piperazinyl)pyrido[2,3-d]pyrimidin-2(1H)-one | SFC (ChiralPak OX, 21 × 250 mm, 5 um; 35% MeOH/CO$_2$, 60 g/min, 102 bar) |
| 78-9-2 | 2nd-eluting isomer (M and 2S or 2R) | (M)-6-chloro-7-(2-fluorophenyl)-1-(4-methyl-2-(2-propanyl)-3-pyridinyl)-4-((2R)-4-(2-propenoyl)-2-(trifluoromethyl)-1-piperazinyl)pyrido[2,3-d]pyrimidin-2(1H)-one | SFC (ChiralPak OX, 21 × 250 mm, 5 um; 35% MeOH/CO$_2$, 60 g/min, 102 bar) |
| 80-1-1 | 1st-eluting isomer (M) | (M)-6-chloro-1-(4-((dimethylamino)methyl)-2-methyl-6-(2-propanyl)phenyl)-7-(2-fluorophenyl)-4-((2S)-2-methyl-4-(2-propenoyl)-1-piperazinyl)pyrido[2,3-d]pyrimidin-2(1H)-one | SFC (ChiralPak OX, 21 × 150 mmm, 5 um; 45% MeOH (with 20 mM NH3)/CO$_2$, 80 g/min, 110 bar) |

| Ex. # | Chemical Structure | Name | Racemic SM/ separation conditions |
|---|---|---|---|
| 80-1-2 | 2nd-eluting isomer (P) | (P)-6-chloro-1-(4-((dimethylamino)methyl)-2-methyl-6-(2-propanyl)phenyl)-7-(2-fluorophenyl)-4-((2S)-2-methyl-4-(2-propenoyl)-1-piperazinyl)pyrido[2,3-d]pyrimidin-2(1H)-one | SFC (ChiralPak OX, 21 × 150 mmm, 5 um; 45% MeOH (with 20 mM NH3)/CO2, 80 g/min, 110 bar) |
| 80-2-1 | 1st-eluting isomer | 6-chloro-7-(2-fluorophenyl)-1-(4-(hydroxymethyl)-2-methyl-6-(2-propanyl)phenyl)-4-((2S)-2-methyl-4-(2-propenoyl)-1-piperazinyl)pyrido[2,3-d]pyrimidin-2(1H)-one | SFC (Chiralpak ID (250 × 21 mm, 5 μm), 35% MeOH (with 20 mM NH3)/CO2, 65 g/min, 102 bar) |
| 80-2-2 | 2nd-eluting isomer | 6-chloro-7-(2-fluorophenyl)-1-(4-(hydroxymethyl)-2-methyl-6-(2-propanyl)phenyl)-4-((2S)-2-methyl-4-(2-propenoyl)-1-piperazinyl)pyrido[2,3-d]pyrimidin-2(1H)-one | SFC (Chiralpak ID (250 × 21 mm, 5 μm), 35% MeOH (with 20 mM NH3)/CO2, 65 g/min, 102 bar) |

-continued

| Ex. # | Chemical Structure | Name | Racemic SM/ separation conditions |
|---|---|---|---|
| 88-1 | 1st-eluting isomer | 6-chloro-7-(2-fluorophenyl)-1-(2-(2-propanyl)phenyl)-4-(4-(2-propenoyl)-1-piperazinyl)-2(1H)-quinazolinone | SFC ID (21 × 250 mm, 5 μm), 50% MeOH with 20 mM $NH_3/CO_2$, 50 mL/min, 227 bar |
| 88-2 | 2nd-eluting isomer | 6-chloro-7-(2 fluorophenyl)-1-(2-(2-propanyl)phenyl)-4-(4-(2-propenoyl)-1-piperazinyl)-2(1H)-quinazolinone | SFC ID (21 × 250 mm, 5 μm), 50% MeOH with 20 mM $NH_3/CO_2$, 50 mL/min, 227 bar |
| 98-1 | 1st-eluting isomer | 2-(6-chloro-4-((2S)-2-methyl-4-(2-propenoyl)-1-piperazinyl)-2-oxo-1-(2-(2-propanyl)phenyl)-1,2-dihydropyrido[2,3-d]pyrimidin-7-yl)-3-fluorobenzonitrile | SFC Chiralpak IC (4.6 × 150 mm, 5 μm), 50% MeOH/$CO_2$, 4 mL/min, 100 bar |

-continued

| Ex. # | Chemical Structure | Name | Racemic SM/ separation conditions |
|---|---|---|---|
| 98-2 | 2nd-eluting isomer | 2-(6-chloro-4-((2S)-2-methyl-4-(2-propenoyl)-1-piperazinyl)-2-oxo-1-(2-(2-propanyl)phenyl)-1,2-dihydropyrido[2,3-d]pyrimidin-7-3-fluorobenzonitrile | SFC Chiralpak IC (4.6 × 150 mm, 5 μm), 50% MeOH/CO$_2$, 4 mL/min, 100 bar |
| 102-1 | 1st-eluting isomer | 7-(2-fluorophenyl)-6-methyl-1-(2-methyl-6-(2-propanyl)phenyl)-4-((2S)-2-methyl-4-(2-propenoyl)-1-piperazinyl)pyrido[2,3-d]pyrimidin-2(1H)-one | NPLC Chiralpak IF (21.2 × 250 mm, 5 μm), MeOH:EtOH (50:50)/heptane, 25 mL/min) |
| 102-2 | 2nd-eluting isomer | 7-(2-fluorophenyl)-6-methyl-1-(2-methyl-6-(2-propanyl)phenyl)-4-((2S)-2-methyl-4-(2-propenoyl)-1-piperazinyl)pyrido[2,3-d]pyrimidin-2(1H)-one | NPLC Chiralpak IF (21.2 × 250 mm, 5 μm), MeOH:EtOH (50:50)/heptane, 25 mL/min) |

-continued

| Ex. # | Chemical Structure | Name | Racemic SM/ separation conditions |
|---|---|---|---|
| 110-1 | 1st-eluting isomer | 6-chloro-7-(2-fluorophenyl)-4-((2S)-2-methyl-4-(2-propenoyl)-1-piperazinyl)-1-(2-(2-propanyl)phenyl)pyrido[3,2-d]pyrimidin-2(1H)-one | SFC Whelk-01 (S,S) (21 × 150 mm, 5 μm, 65% MeOH/CO$_2$, 50 mL/min 100 bar |
| 110-2 | 2nd-eluting isomer | 6-chloro-7-(2-fluorophenyl)-4-((2S)-2-methyl-4-(2-propenoyl)-1-piperazinyl)-1-(2-(2-propanyl)phenyl)pyrido[3,2-d]pyrimidin-2(1H)-one | SFC Whelk-01 (S,S) (21 × 150 mm, 5 μm, 65% MeOH/CO$_2$, 50 mL/min, 100 bar |
| 111-1 | 1st-eluting isomer | 6-chloro-7-(2-fluorophenyl)-1-(4-methyl-2-(2-propanyl)-3-pyridinyl)-4-((2S)-2-methyl-4-(2-propenoyl)-1-piperazinyl)-2(1H)-pteridinone | NPLC IC (21.2 × 150 mm, 5 μm), MeOH:EtOH (40:60)/heptane, 30 mL/min) |

-continued

| Ex. # | Chemical Structure | Name | Racemic SM/ separation conditions |
|---|---|---|---|
| 111-2 | 2nd-eluting isomer | 6-chloro-7-(2-fluorophenyl)-1-(4-methyl-2-(2-propanyl)-3-pyridinyl)-4-((2S)-2-methyl-4-(2-propenoyl)-1-piperazinyl)-2(1H)-pteridinone | NPLC IC (21.2 × 150 mm, 5 μm), MeOH:EtOH (40:60)/heptane, 30 mL/min) |
| 140-1 | 1st-eluting isomer | 6-chloro-1-(4-(dimethylamino)-6-(2-propanyl)-5-pyrimidinyl)-7-(2-fluorophenyl)-4-((2S)-2-methyl-4-(2-propenoyl)-1-piperazinyl) pyrido[2,3-d]pyrimidin-2(1H)-one | SFC (Whelk-01 (S,S) (250 × 20 mm, 5 u), 30%, MeOH/CO$_2$ 60 mL/min, 200 bar.) |
| 140-2 | 2nd-eluting isomer | 6-chloro-1-(4-dimethylamino)-6-(2-propanyl)-5-pyrimidinyl)-7-(2-fluorophenyl)-4-((2S)-2-methyl-4-(2-propenoyl)-1-piperazinyl) pyrido[2,3-d]pyrimidin-2(1H)-one | SFC (Whelk-01 (S,S) (250 × 20 mm, 5 u), 30% MeOH/CO$_2$ 60 mL/min, 200 bar.) |

| Ex. # | Chemical Structure | Name | Racemic SM/ separation conditions |
|---|---|---|---|
| 142-1 | 1<sup>st</sup>-eluting isomer | 2-(6-chloro-7-(2-fluorophenyl)-4-((2S)-2-methyl-4-(2-propenoyl)-1-piperazinyl)-2-oxopyrido[2,3-d]pyrimidin-1(2H)-yl)-3-(2-propanyl)benzamide | NPLC (Chiralcel OX-H (21 × 250 mm, 5 um), 35% isocratic MeOH:EtOH):1)/heptane, 35 ml/min |
| 142-2 | 2<sup>nd</sup>-eluting isomer | 2-(6-chloro-7-(2-fluorophenyl)-4-((2S)-2-methyl-4-(2-propenoyl)-1-piperazinyl)-2-oxopyrido[2,3-d]pyrimidin-1(2H)-yl)-3-(2-propanyl)benzamide | NPLC (Chiralcel OX-H (21 × 250 mm, 5 um), 35% isocratic MeOH:EtOH):1)/heptane, 35 ml/min |
| 143-1 | 1<sup>st</sup>-eluting isomer | 7-(2-fluorophenyl)-6-methyl-1-(4-methyl-2-(2-propanyl)-3-pyridinyl)-4-((2S)-2-methyl-4-(2-propenoyl)-1-piperazinyl)-2(1H)-pteridinone | Chiral IF (250 × 20 mm, 5 μm), 50:50 CO$_2$:MeOH, 60 g/min, 205 bar) |

-continued

| Ex. # | Chemical Structure | Name | Racemic SM/ separation conditions |
|---|---|---|---|
| 143-2 | 2nd-eluting isomer | 7-(2-fluorophenyl)-6-methyl-1-(4-methyl-2-(2-propanyl)-3-pyridinyl)-4-((2S)-2-methyl-4-(2-propenoyl)-1-piperazinyl)-2(1H)-pteridinone | Chiral IF (250 × 20 mm, 5 μm), 50:50 $CO_2$:MeOH, 60 g/min, 205 bar) |
| 155-1 | 1st-eluting isomer | 1-(2-amino-6-(2-propanyl)phenyl)-6-chloro-7-(2-fluorophenyl)-4-((2S)-2-methyl-4-(2-propenoyl)-1-piperazinyl) pyrido[2,3-d]pyrimidin-2(1H)-one | SFC (Chiralcel ODH, 20 × 250 mm, 5 μm, 45% MeOH/$CO_2$, 70 mL/min, 204 bar). |
| 155-2 | 2nd-eluting isomer | 1-(2-amino-6-(2-propanyl)phenyl)-6-chloro-7-(2-fluorophenyl)-4-((2S)-2-methyl-4-(2-propenoyl)-1-piperazinyl) pyrido[2,3-d]pyrimidin-2(1H)-one | SFC (Chiralcel ODH, 20 × 250 mm, 5 μm, 45% MeOH/$CO_2$, 70 mL/min, 204 bar). |

TABLE 88

Analytical Data

| Ex. # | LRMS: m/z (ESI, +ve ion): $(M + H)^+$ | NMR |
|---|---|---|
| 8-8 | 534.2 | $^1$H NMR (400 MHz, $CDCl_3$) δ ppm 8.68 (s, 1H), 8.20 (s, 1H), 7.28-7.37 (m, 2H), |

TABLE 88-continued

Analytical Data

| Ex. # | LRMS: m/z (ESI, +ve ion): (M + H)+ | NMR |
|---|---|---|
| | | 7.25 (s, 1H), 7.25 (d, J = 4.32 Hz, 1H), 6.59-6.78 (m, 3H), 6.39-6.46 (m, 1H), 5.80-5.86 (m, 1H), 4.07 (br s, 4H), 3.96 (br s, 2H), 3.89 (br s, 2H), 2.05 (s, 6H). $^{19}$F NMR (376 MHz, CDCl$_3$) δ ppm −104.53 (s, 1F). |
| 9-17 | 529.1 | $^1$H NMR (400 MHz, DMSO-d$_6$) δ ppm 7.91-8.08 (m, 1 H), 7.49-7.67 (m, 2 H), 7.41 (br d, J = 5.8 Hz, 1 H), 7.21 (br s, 1 H), 6.76-6.98 (m, 1 H), 6.52-6.67 (m, 1 H), 6.09-6.29 (m, 1 H), 5.75 (br s, 1 H), 4.61-4.96 (m, 1 H), 4.23-4.48 (m, 1 H), 3.93-4.21 (m, 2 H), 3.50-3.77 (m, 1 H), 3.33-3.49 (m, 1 H), 3.23-3.28 (m, 1 H), 2.94-3.24 (m, 1 H), 1.27 (br d, J = 9.3 Hz, 6 H), 1.09 (br s, 3 H). |
| 9-17-1 | 529.1 | $^1$H NMR (400 MHz, DMSO-d$_6$) δ ppm 7.97 (br s, 1 H), 7.58-7.63 (m, 1 H), 7.50-7.57 (m, 1 H), 7.41 (td, J = 7.5, 1.5 Hz, 1 H), 7.21 (dd, J = 7.8, 1.1 Hz, 1 H), 6.76-6.95 (m, 1 H), 6.58 (s, 1 H), 6.12-6.25 (m, 1 H), 5.71-5.80 (m, 1 H), 4.72 (br s, 1 H), 4.22-4.44 (m, 1 H), 3.94-4.22 (m, 2 H), 3.37-3.68 (m, 2 H), 3.01-3.24 (m, 1 H), 2.43-2.47 (m, 1 H), 1.31 (br d, J = 6.6 Hz, 3 H), 1.09 (d, J = 6.8 Hz, 3 H), 1.01 (d, J = 6.8 Hz, 3 H). |
| 9-17-2 | 529.1 | $^1$H NMR (400 MHz, DMSO-d$_6$) δ ppm 8.00 (s, 1 H), 7.58-7.64 (m, 1 H), 7.51-7.58 (m, 1 H), 7.38-7.46 (m, 1 H), 7.21 (d, J = 7.0 Hz, 1 H), 6.77-6.94 (m, 1 H), 6.58 (s, 1 H), 6.12-6.26 (m, 1 H), 5.70-5.81 (m, 1 H), 4.77-4.93 (m, 1 H), 4.23-4.48 (m, 1 H), 3.97-4.20 (m, 2 H), 3.34-3.83 (m, 2 H), 2.92-3.27 (m, 1 H), 2.43-2.49 (m, 1 H), 1.29 (br d, J = 6.4 Hz, 3 H), 1.10 (d, J = 6.6 Hz, 3 H), 1.02 (d, J = 6.8 Hz, 3 H). |
| 54-1 | 560.2 | $^1$H NMR (400 MHz, DMSO-d$_6$) δ ppm 10.07 (s, 1 H), 8.29-8.42 (m, 1 H), 7.19-7.29 (m, 3 H), 7.14 (br d, J = 6.2 Hz, 1 H), 7.06 (br d, J = 5.4 Hz, 1 H), 6.79-6.93 (m, 1 H), 6.61-6.74 (m, 2 H), 6.20 (br d, J = 16.2 Hz, 1 H), 5.71-5.80 (m, 1 H), 4.73-5.04 (m, 1 H), 3.96-4.49 (m, 3 H), 3.42-3.91 (m, 2 H), 3.20-3.27 (m, 1 H), 1.41-1.63 (m, 1 H), 1.28-1.40 (m, 3 H), 0.47-0.67 (m, 3 H), 0.41 (br s, 1 H). $^{19}$F NMR (376 MHz, DMSO-d$_6$) δ ppm −115.37 (s, 1F). |
| 54-2 | 498.1 | $^1$H NMR (400 MHz, CDCl$_3$) δ ppm 8.00 (s, 1H), 7.51-7.58 (m, 2H), 7.35 (t, J = 7.56 Hz, 1H), 7.25 (t, J = 9.39 Hz, 1H), 6.54-6.70 (m, 1H), 6.37-6.44 (m, 1H), 5.81 (dd, J = 1.66, 10.57 Hz, 1H), 5.21-5.37 (m, 1H), 4.87-5.03 (m, 1H), 4.60-4.83 (m, 1H), 4.31-4.56 (m, 1H), 3.80-4.10 (m, 1H), 3.51-3.78 (m, 2H), 2.91-3.32 (m, 1H), 2.24-2.37 (m, 2H), 1.89 (quint, J = 6.92, 13.98 Hz, 2H), 1.46 (br d, J = 11.82 Hz, 3H), 0.85 (t, J = 7.46 Hz, 6H). |
| 54-3 | 438.1 | $^1$H NMR (400 MHz, CDCl$_3$) δ ppm 7.91 (s, 1H), 6.48-6.70 (m, 1H), 6.34-6.41 (m, 1H), 5.78 (dd, J = 1.76, 10.47 Hz, 1H), 5.07-5.20 (m, 1H), 4.63-4.93 (m, 1H), 4.37-4.60 (m, 1H), 3.78-4.35 (m, 2H), 3.45-3.74 (m, 2H), 2.86-3.24 (m, 1H), 2.18-2.32 (m, 2H), 1.85-1.95 (m, 2H), 1.36-1.44 (m, 3H), 0.82 (t, J = 7.46 Hz, 6H). |
| 54-4 | 534.2 | $^1$H NMR (400 MHz, CDCl$_3$) δ ppm 7.94 (s, 1H), 7.36-7.43 (m, 1H), 7.22-7.29 (m, 2H), 6.58-6.73 (m, 1H), 6.41-6.48 (m, |

TABLE 88-continued

Analytical Data

| Ex. # | LRMS: m/z (ESI, +ve ion): (M + H)+ | NMR |
|---|---|---|
| | | 1H), 5.84 (dd, J = 1.76, 10.47 Hz, 1H), 5.06-5.16 (m, 1H), 4.70-4.85 (m, 1H), 4.41-4.60 (m, 1H), 3.84-4.11 (m, 1H), 3.56-3.84 (m, 3H), 2.97-3.39 (m, 1H), 2.17-2.44 (m, 4H), 1.79-1.88 (m, 2H), 1.50-1.57 (m, 2H), 1.41-1.48 (m, 4H), 1.32 (br s, 3H), 1.04-1.16 (m, 6H). |
| 54-5 | 566.2 | $^1$H NMR (400 MHz, CDCl$_3$) δ ppm 8.03 (s, 1H), 7.36 (dt, J = 6.74, 8.24 Hz, 1H), 6.91 (d, J = 8.29 Hz, 1H), 6.78 (t, J = 8.91 Hz, 1H), 6.50-6.67 (m, 1H), 6.35-6.44 (m, 1H), 5.80 (dd, J = 1.76, 10.47 Hz, 1H), 4.86-5.05 (m, 0.5H), 4.54-4.81 (m, 3H), 4.35-4.54 (m, 1H), 4.17-4.33 (m, 0.5H), 3.76-4.06 (m, 1H), 3.48-3.75 (m, 2H), 3.04-3.04 (m, 1H), 3.06 (br s, 1H), 1.38-1.53 (m, 3H), 1.02-1.12 (m, 2H), 0.99 (s, 2H). $^{19}$F NMR (376 MHz, CDCl$_3$) δ ppm −69.32 (s, 3F), −110.17 (s, 3F). |
| 54-6 | 512.2 | $^1$H NMR (400 MHz, DMSO-d$_6$) δ ppm 10.01 (br s, 1H), 8.13 (br s, 1H), 7.12-7.20 (m, 1H), 6.57-6.72 (m, 3H), 5.96-6.06 (m, 1H), 5.54-5.61 (m, 1H), 4.64 (br s, 1H), 4.03-4.26 (m, 1H), 3.98 (br s, 4H), 3.46 (br d, J = 13.68 Hz, 2H), 2.80-3.09 (m, 1H), 1.11 (d, J = 6.43 Hz, 3H), 0.76 (s, 3H), 0.43 (br s, 2H), −0.04-0.04 (m, 2H). $^{19}$F NMR (376 MHz, DMSO-d$_6$) δ ppm −115.36 (s, 1F). |
| 54-7 | 526.1 | $^1$H NMR (400 MHz, CDCl$_3$) δ ppm 8.06 (s, 1H), 7.35 (dt, J = 6.53, 8.34 Hz, 1H), 6.89 (d, J = 8.29 Hz, 1H), 6.76 (t, J = 8.91 Hz, 1H), 6.46-6.68 (m, 1H), 6.35-6.42 (m, 1H), 5.79 (dd, J = 1.66, 10.37 Hz, 1H), 4.98-5.14 (m, 2H), 4.59-4.86 (m, 1H), 4.36-4.55 (m, 1H), 4.17-4.34 (m, 1H), 3.38-4.06 (m, 2H), 3.09-3.26 (m, 1H), 2.88-3.07 (m, 5H). $^{19}$F NMR (376 MHz, CDCl$_3$) δ ppm −69.11 (s, 3F), −110.02 (s, 1F). |
| 54-8 | 522.2 | $^1$H NMR (400 MHz, CDCl$_3$) δ ppm 8.10 (s, 1H), 7.35 (d, J = 7.46 Hz, 1H), 7.22 (d, J = 7.67 Hz, 2H), 6.58 (dd, J = 0.83, 17.21 Hz, 1H), 6.16-6.30 (m, 1H), 6.05 (dd, J = 0.83, 10.57 Hz, 1H), 5.86 (tdd, J = 6.32, 10.39, 16.97 Hz, 1H), 5.15-5.28 (m, 2H), 4.85 (br s, 1H), 4.28 (br d, J = 13.06 Hz, 1H), 3.60-3.79 (m, 1H), 3.14-3.16 (m, 1H), 2.92-3.13 (m, 3H), 2.83 (br d, J = 11.40 Hz, 1H), 2.17-2.42 (m, 6H), 1.03-1.11 (m, 6H). |
| 54-9 | 547.2 | $^1$H NMR (400 MHz, DMSO-d$_6$) δ ppm 8.54 (dd, J = 4.7, 1.6 Hz, 1H), 8.37-8.47 (m, 1H), 7.61 (dd, J = 7.9, 1.7 Hz, 1H), 7.46-7.55 (m, 1H), 7.16-7.36 (m, 4H), 6.77-6.94 (m, 1H), 6.15-6.28 (m, 1H), 5.78 (d, J = 2.3 Hz, 1H), 4.82-5.05 (m, 1H), 3.98-4.46 (m, 4H), 3.35-3.88 (m, 2H), 2.63-2.81 (m, 1H), 1.34 (dd, J = 9.7, 6.8 Hz, 3H), 1.10 (d, J = 6.6 Hz, 3H), 0.99 (dd, J = 6.7, 1.6 Hz, 3H). $^{19}$F NMR (376 MHz, DMSO-d$_6$) δ ppm −113.71 (d, 1F). |
| 54-9-1 | 547.2 | $^1$H NMR (400 MHz, DMSO-d$_6$) δ ppm 8.54 (dd, J = 1.56, 4.66 Hz, 1H), 8.42 (br d, J = 6.01 Hz, 1H), 7.62 (dd, J = 1.45, 7.88 Hz, 1H), 7.45-7.56 (m, 1H), 7.18-7.35 (m, 4H), 6.77-6.96 (m, 1H), 6.22 (br d, J = 16.17 Hz, 1H), 5.73-5.82 (m, 1H), 4.90 (br d, J = 7.26 Hz, 1H), 3.94-4.46 (m, 4H), 3.55-3.85 (m, 2H), 2.75-2.85 (m, 1H), 1.36 (d, J = 6.63 Hz, 3H), 1.10 (d, J = 6.63 Hz, 3H), 0.99 (d, J = 6.84 |

TABLE 88-continued

| | Analytical Data | |
|---|---|---|
| Ex. # | LRMS: m/z (ESI, +ve ion): (M + H)+ | NMR |
| 54-9-2 | 547.2 | Hz, 3H). ¹⁹F NMR (376 MHz, DMSO-d₆) δ ppm −113.68 (s, 1F). ¹H NMR (400 MHz, DMSO-d₆) δ ppm 8.51-8.59 (m, 1H), 8.45 (br s, 1H), 7.57-7.65 (m, 1H), 7.44-7.55 (m, 1H), 7.14-7.36 (m, 4H), 6.77-6.96 (m, 1H), 6.21 (br d, J = 15.55 Hz, 1H), 5.71-5.82 (m, 1H), 4.98 (br s, 1H), 3.37-4.48 (m, 7H), 1.33 (br d, J = 6.22 Hz, 3H), 1.10 (br d, J = 6.43 Hz, 3H), 0.99 (br d, J = 6.63 Hz, 3H). ¹⁹F NMR (376 MHz, DMSO-d₆) δ ppm −113.74 (s, 1F). |
| 54-10 | 574.1 | ¹H NMR (400 MHz, DMSO-d₆) δ ppm 10.10 (br s, 1H), 8.37 (br d, J = 15.5 Hz, 1H), 7.19-7.34 (m, 5H), 7.03-7.19 (m, 1H), 6.77-6.94 (m, 1H), 6.72 (s, 1H), 6.20 (br d, J = 16.4 Hz, 1H), 5.77 (s, 1H), 4.71-5.02 (m, 1H), 3.94-4.48 (m, 3H), 2.95-3.86 (m, 4H), 1.55-2.06 (m, 6H), 0.82-0.91 (m, 3H). ¹⁹F NMR (376 MHz, DMSO-d₆) δ ppm −115.34 (br s, 1F), −115.72 (br s, 1F). |
| 54-10-1 | 574.1 | ¹H NMR (400 MHz, DMSO-d₆) δ ppm 10.31 (br s, 1H), 8.35 (br s, 1H), 7.17-7.36 (m, 4H), 7.07 (br d, J = 7.46 Hz, 1H), 6.75-6.93 (m, 1H), 6.59-6.73 (m, 2H), 6.19 (br dd, J = 5.49, 16.90 Hz, 1H), 5.73-5.83 (m, 1H), 3.98-4.92 (m, 7H), 1.47-2.05 (m, 7H), 1.32-1.34 (d, 3H, J = 5.6 Hz). ¹⁹F NMR (376 MHz, DMSO-d₆) δ ppm −116.08--115.15 (m, 1F). |
| 54-10-2 | 574.1 | ¹H NMR (400 MHz, DMSO-d₆) δ ppm 8.38 (br s, 1H), 7.17-7.37 (m, 4H), 7.10 (br d, J = 7.26 Hz, 1H), 6.78-6.97 (m, 1H), 6.58-6.75 (m, 2H), 6.20 (br d, J = 16.59 Hz, 1H), 5.77-5.80 (m, 1H), 4.93 (br s, 1H), 3.95-4.45 (m, 3H), 3.38-3.86 (m, 2H), 2.92-3.26 (m, 1H), 1.53-2.08 (m, 7H), 1.30 (br d, J = 6.63 Hz, 3H). ¹⁹F NMR (376 MHz, DMSO-d₆) δ ppm −115.53 (br d, J = 158.66 Hz, 1F). |
| 54-11 | 563.2 | ¹H NMR (400 MHz, DMSO-d₆) δ ppm 8.49-8.56 (m, 1H), 8.32-8.45 (m, 1H), 7.57 (br d, J = 5.60 Hz, 1H), 7.18-7.34 (m, 2H), 6.79-6.93 (m, 1H), 6.59-6.75 (m, 2H), 6.22 (br d, J = 15.55 Hz, 1H), 5.78 (d, J = 2.28 Hz, 1H), 5.76 (s, 1H), 3.57-5.11 (m, 8H), 1.30-1.39 (m, 3H), 1.18 (t, J = 7.05 Hz, 3H), 1.08 (br d, J = 6.63 Hz, 3H), 0.98 (br d, J = 6.63 Hz, 3H). ¹⁹F NMR (376 MHz, DMSO-d₆) δ ppm −115.43--115.30 (m, 1F), −115.54 (br s, 1F). |
| 54-11-1 | 563.2 | ¹H NMR (400 MHz, DMSO-d₆) δ ppm 8.50 (d, J = 4.56 Hz, 1H), 8.41 (br s, 1H), 7.55 (br s, 1H), 7.29 (dd, J = 4.77, 7.88 Hz, 1H), 7.16-7.26 (m, 1H), 6.76-6.93 (m, 1H), 6.57-6.71 (m, 2H), 6.20 (br dd, J = 4.35, 17.21 Hz, 1H), 5.73-5.83 (m, 1H), 4.97 (br d, J = 1.45 Hz, 1H), 3.88-4.50 (m, 6H), 2.64-2.67 (m, 1H), 1.30 (br d, J = 6.22 Hz, 3H), 1.06 (br d, J = 6.63 Hz, 3H), 0.96 (br d, J = 6.63 Hz, 3H). ¹⁹F NMR (377 MHz, DMSO-d₆) δ ppm −115.45 (br d, J = 56.35 Hz, 1F). |
| 54-11-2 | 563.2 | ¹H NMR (400 MHz, DMSO-d₆) δ ppm 9.92-10.23 (m, 1H), 8.52 (dd, J = 1.45, 4.56 Hz, 1H), 8.30-8.43 (m, 1H), 7.56 (br d, J = 6.63 Hz, 1H), 7.16-7.34 (m, 2H), 6.76-6.94 (m, 1H), 6.56-6.72 (m, 2H), 6.12-6.26 (m, 1H), 5.78 (d, J = 2.28 Hz, 1H), 4.85 (br dd, J = 2.80, 6.32 Hz, 1H), 3.16-3.24 (m, 1H), 3.40-4.47 (m, 5H), 2.66-2.79 (m, 1H), 1.36 (br d, |

TABLE 88-continued

| | Analytical Data | |
|---|---|---|
| Ex. # | LRMS: m/z (ESI, +ve ion): (M + H)⁺ | NMR |
| | | J = 6.43 Hz, 3H), 1.08 (d, J = 6.63 Hz, 3H), 0.98 (d, J = 6.63 Hz, 3H). ¹⁹F NMR (377 MHz, DMSO-d₆) δ ppm −115.62--115.32 (m, 1F). |
| 54-12 | 558.2 | ¹H NMR (400 MHz, DMSO-d₆) δ ppm 8.34-8.46 (m, 1H), 7.46-7.57 (m, 1H), 7.18-7.40 (m, 7H), 6.77-6.95 (m, 1H), 6.21 (br dd, J = 17.0, 3.9 Hz, 1H), 5.75-5.80 (m, 1H), 4.78-5.01 (m, 1H), 3.60-4.49 (m, 7H), 1.71-2.11 (m, 5H), 1.56-1.69 (m, 1H), 1.33 (dd, J = 6.3, 4.5 Hz, 3H). ¹⁹F NMR (377 MHz, DMSO-d₆) δ ppm −113.50 (m, 1F), −113.54 (m, 1F). |
| 54-12-1 | 558.2 | ¹H NMR (400 MHz, DMSO-d₆) δ ppm 8.41 (br d, J = 4.8 Hz, 1H), 7.47-7.58 (m, 1H), 7.09-7.43 (m, 7H), 6.76-6.95 (m, 1H), 6.13-6.29 (m, 1H), 5.77 (br dd, J = 10.5, 2.2 Hz, 1H), 4.94 (s, 1H), 3.95-4.47 (m, 4H), 3.60-3.85 (m, 3H), 1.54-2.15 (m, 6H), 1.33 (br d, J = 6.6 Hz, 3H). ¹⁹F NMR (377 MHz, DMSO-d₆) δ ppm −113.54 (m, 1F). |
| 54-12-2 | 558.2 | ¹H NMR (400 MHz, DMSO-d₆) δ ppm 8.38 (br s, 1H), 7.45-7.57 (m, 1H), 7.07-7.41 (m, 7H), 6.72-6.94 (m, 1H), 6.12-6.29 (m, 1H), 5.72-5.83 (m, 1H), 4.83 (br d, J = 1.7 Hz, 1H), 3.95-4.51 (m, 7H), 1.57-2.16 (m, 6H), 1.33 (br d, J = 6.4 Hz, 3H). ¹⁹F NMR (377 MHz, DMSO-d₆) δ ppm −113.60 (m, 1F). |
| 54-13 | 552.2 | ¹H NMR (400 MHz, MeOH-d₄) δ ppm 8.35-8.48 (m, 1H), 7.49-7.77 (m, 1H), 7.18-7.35 (m, 2H), 7.07 (s, 1H), 6.75-6.93 (m, 1H), 6.46-6.73 (m, 1H), 6.25-6.37 (m, 1H), 5.84 (dd, J = 10.7, 1.8 Hz, 1H), 4.95-5.28 (m, 1H), 4.35-4.67 (m, 2H), 3.66-4.29 (m, 5H), 1.27-1.36 (m, 9H). ¹⁹F NMR (377 MHz, DMSO-d₆) δ ppm −116.80 (m, 1F). |
| 54-14 | 577.3 | ¹H NMR (400 MHz, DMSO-d₆) δ ppm 10.07 (br s, 1H), 8.36 (br s, 1H), 7.75 (d, J = 8.1 Hz, 1H), 7.19-7.31 (m, 1H), 7.13 (d, J = 8.1 Hz, 1H), 6.76-6.92 (m, 1H), 6.63-6.74 (m, 2H), 6.20 (br d, J = 17.0 Hz, 1H), 5.71-5.80 (m, 1H), 4.77-4.98 (m, 1H), 3.96-4.44 (m, 3H), 3.51-3.80 (m, 2H), 3.07-3.14 (m, 2H), 2.45 (s, 3H), 1.33-1.34 (m, 3H), 1.21 (d, J = 6.8 Hz, 6H). ¹⁹F NMR (377 MHz, DMSO-d₆) δ ppm −115.17 (m, 1F). |
| 54-15 | 533.2 | ¹H NMR (400 MHz, DMSO-d₆) δ ppm 8.38 (br d, J = 4.56 Hz, 1H), 8.34-8.51 (m, 1H), 7.86 (dd, J = 1.24, 7.67 Hz, 1H), 7.48-7.57 (m, 1H), 7.42 (dd, J = 4.77, 7.67 Hz, 1H), 7.17-7.35 (m, 3H), 6.77-6.95 (m, 1H), 6.22 (br d, J = 16.79 Hz, 1H), 5.72-5.82 (m, 1H), 4.77-5.13 (m, 1H), 3.80-4.48 (m, 4H), 3.64 (dq, J = 4.04, 6.46 Hz, 2H), 2.31-2.41 (m, 2H), 1.26 (d, J = 6.22 Hz, 3H), 1.06 (dt, J = 1.66, 7.57 Hz, 3H). ¹⁹F NMR (376 MHz, DMSO-d₆) δ ppm −113.59 (br s, 1F), −113.65 (s, 1F). |
| 54-16 | 549.2 | ¹H NMR (400 MHz, DMSO-d₆) δ ppm 10.00-10.20 (m, 1H), 8.31-8.45 (m, 2H), 7.81 (br s, 1H), 7.40 (dd, J = 4.77, 7.67 Hz, 1H), 7.16-7.31 (m, 1H), 6.77-6.94 (m, 1H), 6.61-6.75 (m, 2H), 6.13-6.29 (m, 1H), 5.72-5.84 (m, 1H), 4.73-5.14 (m, 1H), 3.75-4.48 (m, 4H), 3.63 (qd, J = 6.50, 10.37 Hz, 2H), 2.22-2.38 (m, 2H), 1.25-1.29 (m, 3H), 1.04 (br t, J = 6.95 Hz, 3H). ¹⁹F NMR (376 MHz, |

TABLE 88-continued

| | Analytical Data | |
|---|---|---|
| Ex. # | LRMS: m/z (ESI, +ve ion): (M + H)⁺ | NMR |
| 54-17 | 577.3 | DMSO-d₆) δ ppm −115.16(br s, 1F), −116.09 (s, 1F). ¹H NMR (400 MHz, DMSO-d₆) δ ppm 10.11 (s, 1H), 8.43 (br s, 1H), 8.34 (d, J = 5.2 Hz, 1H), 7.18-7.31 (m, 2H), 6.78-6.93 (m, 1H), 6.62-6.75 (m, 2H), 6.21 (br d, J = 16.6 Hz, 1H), 5.78 (d, J = 2.3 Hz, 1H), 4.82-5.07 (m, 1H), 4.22-4.44 (m, 2H), 3.97-4.21 (m, 1H), 3.40-3.88 (m, 2H), 3.04-3.22 (m, 1H), 2.56 (br d, J = 3.3 Hz, 1H), 2.07 (br s, 3H), 1.30-1.39 (m, 3H), 1.07 (d, J = 6.8 Hz, 3H), 0.93 (br d, J = 6.6 Hz, 3H). ¹⁹F NMR (377 MHz, DMSO-d₆) δ ppm −115.72 (br d, J = 12.1 Hz, 1F), −116.13 (br d, J = 7.8 Hz, 1F). |
| 54-17-1 | 577.3 | ¹H NMR (400 MHz, DMSO-d₆) δ ppm 10.11 (s, 1H), 8.44 (br d, J = 4.35 Hz, 1H), 8.34 (d, J = 5.18 Hz, 1H), 7.21-7.30 (m, 2H), 6.78-6.93 (m, 1H), 6.62-6.74 (m, 2H), 6.21 (br d, J = 16.59 Hz, 1H), 5.76 (dd, J = 2.07, 10.57 Hz, 1H), 4.96 (br s, 1H), 3.97-4.45 (m, 3H), 3.58-3.86 (m, 2H), 3.42-4.46 (m, 1H), 3.17 (d, J = 5.18 Hz, 1H), 2.05 (br d, J = 9.54 Hz, 3H), 1.33 (br d, J = 6.43 Hz, 3H), 1.07 (d, J = 6.84 Hz, 3H), 0.93 (br d, J = 6.43 Hz, 3H). ¹⁹F NMR (376 MHz, DMSO-d₆) δ ppm −115.73 (br s, 1F), −116.14 (br s, 1F). |
| 54-17-2 | 577.3 | ¹H NMR (400 MHz, DMSO-d₆) δ ppm 10.11 (br s, 1H), 8.43 (br s, 1H), 8.34 (d, J = 5.18 Hz, 1H), 7.20-7.29 (m, 2H), 6.78-6.93 (m, 1H), 6.63-6.73 (m, 2H), 6.23 (br s, 1H), 5.76 (dd, J = 2.18, 10.47 Hz, 1H), 4.94 (br s, 1H), 3.40-4.46 (m, 6H), 3.17 (d, J = 5.18 Hz, 1H), 2.07 (br s, 3H), 1.35 (br d, J = 6.43 Hz, 3H), 1.07 (d, J = 6.84 Hz, 3H), 0.93 (br d, J = 6.43 Hz, 3H). ¹⁹F NMR (376 MHz, DMSO-d₆) δ ppm −115.70 (br s, 1F), −116.12 (br s, 1F). |
| 54-18 | 561.2 | ¹H NMR (400 MHz, DMSO-d₆) δ ppm 8.46 (br d, J = 3.7 Hz, 1H), 8.36 (d, J = 5.2 Hz, 1H), 7.46-7.57 (m, 1H), 7.17-7.35 (m, 4H), 6.77-6.96 (m, 1H), 6.21 (br d, J = 16.0 Hz, 1H), 5.78 (d, J = 2.3 Hz, 1H), 4.96 (br d, J = 3.5 Hz, 1H), 4.24-4.45 (m, 1H), 3.97-4.22 (m, 1H), 3.39-3.85 (m, 2H), 2.91-3.16 (m, 1H), 2.43 (q, J = 7.0 Hz, 1H), 2.17 (s, 1H), 2.09 (d, J = 3.1 Hz, 3H), 1.34 (dd, J = 6.7, 2.0 Hz, 3H), 1.07 (d, J = 6.8 Hz, 3H), 0.95 (d, J = 6.4 Hz, 3H). ¹⁹F NMR (376 MHz, DMSO-d₆) δ ppm −114.04 (s, 1F), −114.07 (s, 1F). |
| 54-18-1 | 561.2 | ¹H NMR (400 MHz, DMSO-d₆) δ ppm 8.47 (br s, 1H), 8.36 (d, J = 5.18 Hz, 1H), 7.47-7.56 (m, 1H), 7.17-7.33 (m, 4H), 6.76-6.97 (m, 1H), 6.21 (br d, J = 16.59 Hz, 1H), 5.75-5.81 (m, 1H), 4.96 (br s, 1H), 3.40-4.45 (m, 5H), 3.02-3.24 (m, 1H), 2.58 (m, 1H), 2.09 (s, 3H), 1.34 (d, J = 6.63 Hz, 3H), 1.07 (d, J = 6.84 Hz, 3H), 0.94 (d, J = 6.84 Hz, 3H). ¹⁹F NMR (376 MHz, DMSO-d₆) δ ppm −114.04 (s, 1F). |
| 54-18-2 | 561.2 | ¹H NMR (400 MHz, DMSO-d₆) δ ppm 8.46 (br d, J = 4.56 Hz, 1H), 8.36 (d, J = 5.18 Hz, 1H), 7.45-7.58 (m, 1H), 7.13-7.35 (m, 4H), 6.77-6.95 (m, 1H), 6.20 (br d, J = 16.79 Hz, 1H), 5.77 (br d, J = 2.28 Hz, 1H), 4.96 (br s, 1H), 3.43-4.47 (m, 5H), 3.21 (br s, 1H), 3.02-3.16 (m, 1H), 2.09 (s, 3H), 1.33 (d, J = 6.63 |

TABLE 88-continued

| | Analytical Data | |
|---|---|---|
| Ex. # | LRMS: m/z (ESI, +ve ion): (M + H)⁺ | NMR |
| | | Hz, 3H), 1.06 (d, J = 6.84 Hz, 3H), 0.94 (d, J = 6.84 Hz, 3H). ¹⁹F NMR (376 MHz, DMSO-d₆) δ ppm −114.07 (s, 1F). |
| 54-19 | 559.0 | ¹H NMR (400 MHz, DMSO-d₆) δ ppm 10.36-9.85 (m, 1H), 8.53 (d, J = 16.4 Hz, 1H), 7.54-7.36 (m, 3H), 7.33-7.19 (m, 2H), 6.85-6.64 (m, 3H), 6.19 (m, 1H), 5.79-5.69 (m, 1H), 4.72-4.45 (m, 1H), 4.44-4.31 (m, 1H), 4.29-3.95 (m, 2H), 3.89-3.61 (m, 3H), 3.91-3.54 (m, 1H), 3.43-3.33 (m, 1H), 1.37-1.20 (m, 3H); ¹⁹F NMR (376 MHz, DMSO-d₆): δ ppm −73.41 ppm (s, 1F) |
| 54-20 | 548.0 | ¹H NMR (400 MHz, DMSO-d₆) δ ppm 8.71-8.58 (m, 2H), 8.49 (dd, J = 2.4, 7.4 Hz, 1H), 7.55-7.47 (m, 1H), 7.34-7.17 (m, 3H), 6.86-6.76 (m, 1H), 6.19 (m, 1H), 5.79-5.70 (m, 1H), 4.40 (m, 1H), 4.34-4.10 (m, 1H), 4.10-3.90 (m, 2H), 3.79 (m, 2H), 2.97-2.73 (m, 2H), 1.22-1.12 (m, 3H), 1.08-0.99 (m, 3H), 0.86 (t, J = 6.8 Hz, 3H); ¹⁹F NMR (376 MHz, DMSO-d₆): δ ppm −113.78-−113.97 ppm (m, 1F). |
| 54-21 | 563.9 | ¹H NMR (400 MHz, DMSO-d₆) δ ppm 10.12 (br d, J = 5.0 Hz, 1H), 8.65 (s, 1H), 8.58 (d, J = 11.6 Hz, 1H), 8.48 (t, J = 2.2 Hz, 1H), 7.23 (br d, J = 7.3 Hz, 1H), 6.86-6.75 (m, 1H), 6.72-6.62 (m, 2H), 6.21 (m, 1H), 5.74 (m, 1H), 4.53 (s, 1H), 4.48-4.29 (m, 1H), 4.23-3.89 (m, 2H), 3.76 (br s, 2H), 2.93-2.70 (m, 2H), 1.30 (m, 3H), 1.18-1.09 (m, 3H), 1.03 (m, 3H); ¹⁹F NMR (376 MHz, DMSO-d₆) δ ppm −115.15-−116.05 (m, 1F). |
| 54-22 | 582.0 | ¹H NMR (400 MHz, DMSO-d₆) δ ppm 8.42 (br d, J = 3.3 Hz, 1 H), 7.23-7.32 (m, 2 H), 7.12-7.21 (m, 3 H), 6.92-7.03 (m, 2 H), 6.80-6.90 (m, 1 H), 6.15-6.25 (m, 1 H), 5.74-5.80 (m, 1 H), 4.86-4.96 (m, 1 H), 4.36-4.46 (m, 1 H), 4.22-4.35 (m, 2 H), 4.10-4.20 (m, 1 H), 3.98-4.09 (m, 1 H), 3.62-3.81 (m, 2 H), 2.10-2.29 (m, 4 H), 1.33 (d, J = 6.6 Hz, 3 H), 0.97 (td, J = 7.5, 2.8 Hz, 6 H), 0.65 (br dd, J = 8.2, 1.8 Hz, 2 H), 0.50 (br d, J = 3.5 Hz, 2 H). |
| 54-23 | 584.0 | ¹H NMR (400 MHz, DMSO-d₆) δ ppm 8.42 (br d, J = 3.9 Hz, 1 H), 7.33-7.39 (m, 2 H), 7.18-7.28 (m, 2 H), 7.13 (d, J = 7.7 Hz, 2 H), 6.99 (d, J = 7.5 Hz, 1 H), 6.80-6.93 (m, 1 H), 6.15-6.26 (m, 1 H), 5.73-5.81 (m, 1 H), 4.93 (br d, J = 8.1 Hz, 1 H), 4.05-4.48 (m, 3 H), 3.42-3.83 (m, 2 H), 3.03-3.15 (m, 1 H), 2.54-2.62 (m, 1 H), 2.08-2.29 (m, 4 H), 1.33 (d, J = 6.6 Hz, 3 H), 0.76-1.09 (m, 12 H). |
| 54-24 | 550.8 | ¹H NMR (400 MHz, DMSO-d₆) δ ppm 10.02-10.35 (m, 1 H), 8.75 (s, 1 H), 8.28-8.54 (m, 1 H), 7.23-7.33 (m, 1 H), 6.79-6.92 (m, 1 H), 6.63-6.78 (m, 2 H), 6.14-6.25 (m, 1 H), 5.71-5.81 (m, 1 H), 4.66-5.26 (m, 1 H), 3.84-4.56 (m, 4 H), 3.47-3.71 (m, 1 H), 2.90-3.28 (m, 2 H), 1.25-1.48 (m, 3 H), 0.28-0.70 (m, 4 H) |
| 54-25 | 551.9 | ¹H NMR (400 MHz, DMSO-d₆) δ ppm 10.00-10.20 (m, 1 H), 8.26-8.50 (m, 1 H), 7.48 (d, J = 1.7 Hz, 1 H), 7.26 (q, J = 8.0 Hz, 1 H), 6.78-6.93 (m, 1 H), 6.63-6.77 (m, 2 H), 6.16-6.25 (m, 1 H), 6.13 (s, 1 H), 5.72-5.80 (m, 1 H), 4.73-5.13 (m, 1 H), 3.95-4.47 (m, 5 |

TABLE 88-continued

Analytical Data

| Ex. # | LRMS: m/z (ESI, +ve ion): (M + H)+ | NMR |
|---|---|---|
| | | H), 3.54-3.95 (m, 2 H), 1.14-1.41 (m, 9 H). |
| 54-26 | 563.9 | $^1$H NMR (400 MHz, DMSO-d$_6$) δ ppm 10.13 (br s, 1 H), 9.11 (s, 1 H), 8.60 (br s, 1 H), 8.44 (br d, J = 13.5 Hz, 1 H), 7.24 (q, J = 8.1 Hz, 1 H), 6.79-6.93 (m, 1 H), 6.71 (d, J = 8.3 Hz, 1 H), 6.66 (br t, J = 8.6 Hz, 1 H), 6.21 (br d, J = 16.2 Hz, 1 H), 5.73-5.81 (m, 1 H), 4.83-5.09 (m, 1 H), 3.99-4.48 (m, 3 H), 3.36-3.92 (m, 2 H), 3.20-3.27 (m, 1 H), 2.70-2.85 (m, 1 H), 1.35 (br dd, J = 11.9, 6.3 Hz, 3 H), 1.10 (d, J = 6.6 Hz, 3 H), 1.00 (br d, J = 6.2 Hz, 3 H). |
| 54-27 | 577.0 | $^1$H NMR (400 MHz, DMSO-d$_6$) δ ppm 10.10 (br d, J = 2.9 Hz, 1 H), 8.43 (br d, J = 6.8 Hz, 1 H), 8.37 (d, J = 4.8 Hz, 1 H), 7.20-7.27 (m, 1 H), 7.17 (br d, J = 4.6 Hz, 1 H), 6.78-6.93 (m, 1 H), 6.70 (d, J = 8.3 Hz, 1 H), 6.66 (t, J = 8.9 Hz, 1 H), 6.14-6.26 (m, 1 H), 5.72-5.80 (m, 1 H), 4.87-5.03 (m, 1 H), 4.24-4.46 (m, 2 H), 3.98-4.20 (m, 1 H), 3.40-3.86 (m, 2 H), 3.17 (d, J = 5.2 Hz, 1 H), 2.67-2.78 (m, 1 H), 1.84-1.98 (m, 3 H), 1.34 (br t, J = 7.6 Hz, 3 H), 1.07 (d, J = 6.6 Hz, 3 H), 0.93 (br d, J = 6.6 Hz, 3 H). |
| 54-27-1 | 577.0 | $^1$H NMR (400 MHz, CDCl$_3$) δ ppm 8.61 (d, J = 5.2 Hz, 1 H), 8.37 (br s, 1 H), 8.17 (s, 1 H), 7.28-7.33 (m, 1 H), 6.75 (d, J = 8.1 Hz, 1 H), 6.53-6.72 (m, 2 H), 6.43 (dd, J = 16.6, 1.7 Hz, 1 H), 5.84 (dd, J = 10.4, 1.7 Hz, 1 H), 4.32-5.17 (m, 3 H), 3.55-4.15 (m, 3 H), 3.01-3.35 (m, 1 H), 2.87 (br d, J = 1.7 Hz, 1 H), 2.10 (br s, 3 H), 1.58 (br d, J = 17.0 Hz, 3 H), 1.30 (br d, J = 6.2 Hz, 3 H), 1.13 (br d, J = 6.2 Hz, 3 H). |
| 54-27-2 | 577.0 | $^1$H NMR (400 MHz, CDCl$_3$) δ ppm 8.61 (d, J = 5.0 Hz, 1 H), 8.39 (br s, 1 H), 8.18 (s, 1 H), 7.28-7.31 (m, 1 H), 6.75 (d, J = 8.3 Hz, 1 H), 6.55-6.71 (m, 2 H), 6.40-6.47 (m, 1 H), 5.81-5.87 (m, 1 H), 4.25-5.36 (m, 3 H), 3.54-4.16 (m, 3 H), 2.99-3.40 (m, 1 H), 2.72-2.93 (m, 1 H), 2.11 (br s, 3 H), 1.42-1.73 (m, 3 H), 1.30 (br d, J = 6.4 Hz, 3 H), 1.12 (br d, J = 5.8 Hz, 3 H). |
| 54-28 | 563.9 | $^1$H NMR (400 MHz, DMSO-d$_6$) δ ppm 10.15 (br s, 1 H), 8.38 (br d, J = 34.8 Hz, 1 H), 7.51 (d, J = 1.9 Hz, 1 H), 7.26 (q, J = 8.0 Hz, 1 H), 6.79-6.93 (m, 1 H), 6.64-6.78 (m, 2 H), 6.13-6.26 (m, 2 H), 5.70-5.80 (m, 1 H), 4.72-5.13 (m, 1 H), 3.97-4.48 (m, 4 H), 3.45-3.93 (m, 2 H), 3.21 (br d, J = 2.7 Hz, 1 H), 2.26-2.47 (m, 2 H), 1.88-2.18 (m, 2 H), 1.52-1.72 (m, 2 H), 1.34 (br dd, J = 28.1, 6.5 Hz, 3 H). |
| 54-29 | 547.8 | $^1$H NMR (400 MHz, DMSO-d$_6$) δ ppm 8.42 (br d, J = 31.9 Hz, 1 H), 7.51-7.59 (m, 2 H), 7.24-7.37 (m, 3 H), 6.77-6.93 (m, 1 H), 6.16-6.26 (m, 2 H), 5.74-5.81 (m, 1 H), 4.79-5.11 (m, 1 H), 3.98-4.52 (m, 4 H), 3.36-3.94 (m, 2 H), 3.18-3.26 (m, 1 H), 2.29-2.47 (m, 2 H), 2.16 (br d, J = 3.5 Hz, 1 H), 1.94-2.06 (m, 1 H), 1.55-1.76 (m, 2 H), 1.34 (dd, J = 21.8, 6.6 Hz, 3 H). |
| 54-30 | 571.9 | $^1$H NMR (400 MHz, DMSO-d$_6$) δ ppm 8.51 (br s, 1H), 7.63 (d, J = 7.88 Hz, 2H), 7.45-7.57 (m, 2H), 7.23-7.35 (m, 3H), 6.86 (br d, J = 16.17 Hz, 1H), 6.21 (br d, J = 14.93 Hz, 1H), 5.74-5.79 (m, 1H), |

TABLE 88-continued

| | Analytical Data | |
|---|---|---|
| Ex. # | LRMS: m/z (ESI, +ve ion): $(M+H)^+$ | NMR |
| | | 5.01 (br s, 1H), 4.36 (br d, J = 12.44 Hz, 2H), 4.04 (br d, J = 14.10 Hz, 1H), 3.79 (br s, 1H), 3.64 (br d, J = 15.55 Hz, 1H), 3.01-3.26 (m, 1H), 1.34 (d, J = 6.63 Hz, 3H). $^{19}$F NMR (377 MHz, DMSO-d$_6$) δ ppm −113.03 (s, 1F). |
| 54-31 | 532.0 | $^1$H NMR (400 MHz, MeOH-d$_4$) δ ppm 8.39 (br d, J = 3.73 Hz, 1H), 7.27-7.48 (m, 4H), 7.11-7.24 (m, 4H), 6.78-6.90 (m, 1H), 6.31 (br dd, J = 4.77, 16.38 Hz, 1H), 5.83 (dd, J = 1.87, 10.57 Hz, 1H), 5.04 (br s, 1H), 4.39-4.62 (m, 2H), 4.04-4.25 (m, 1H), 3.84 (br d, J = 12.65 Hz, 1H), 3.54-3.76 (m, 1H), 3.10-3.26 (m, 1H), 2.37 (q, J = 7.53 Hz, 2H), 1.48 (br d, J = 6.63 Hz, 3H), 1.08 (t, J = 7.57 Hz, 3H). $^{19}$F NMR (376 MHz, MeOH-d$_4$) δ ppm −114.72 (br s, 1F). |
| 54-32 | 538.0 | $^1$H NMR (400 MHz, MeOH-d$_4$) δ ppm 8.37-8.44 (m, 1H), 7.53-7.62 (m, 1H), 7.39-7.49 (m, 4H), 7.09-7.31 (m, 3H), 6.76-6.90 (m, 1H), 6.31 (br d, J = 17.00 Hz, 1H), 5.83 (dd, J = 1.87, 10.57 Hz, 1H), 5.00 (br s, 1H), 4.34-4.61 (m, 2H), 4.01-4.28 (m, 1H), 3.47-3.94 (m, 2H), 3.06-3.27 (m, 1H), 1.42-1.52 (m, 3H). $^{19}$F NMR (377 MHz, MeOH-d$_4$) δ ppm −114.36 (br d, J = 6.94 Hz, 1F). |
| 54-33 | 587.8 | $^1$H NMR (400 MHz, DMSO-d$_6$) δ ppm 10.19 (br s, 1H), 8.46 (br d, J = 13.27 Hz, 1H), 7.58 (br s, 2H), 7.40-7.49 (m, 1H), 7.20-7.29 (m, 1H), 6.84 (br d, J = 6.63 Hz, 1H), 6.62-6.74 (m, 2H), 6.21 (br d, J = 14.93 Hz, 1H), 5.73-5.79 (m, 1H), 5.04 (br s, 1H), 3.40-4.48 (m, 5H), 2.93-3.21 (m, 1H), 1.34 (br d, J = 13.89 Hz, 3H). $^{19}$F NMR (377 MHz, DMSO-d$_6$) δ ppm −115.40 (s, 1F). |
| 54-34 | 548.0 | $^1$H NMR (400 MHz, CDCl$_3$) δ ppm 8.14-8.18 (m, 1H), 7.49 (br d, J = 4.15 Hz, 2H), 7.41 (br s, 1H), 7.34 (br s, 1H), 7.23-7.32 (m, 1H), 7.17 (br s, 1H), 6.59-6.75 (m, 3H), 6.42 (br d, J = 17.00 Hz, 1H), 5.86 (br d, J = 10.37 Hz, 1H), 4.28-5.24 (m, 3H), 3.52-4.18 (m, 3H), 3.05-3.37 (m, 1H), 2.40 (br d, J = 9.12 Hz, 2H), 1.45-1.64 (m, 3H), 1.11-1.19 (m, 3H). $^{19}$F NMR (377 MHz, CDCl$_3$) δ ppm −106.57 (br s, 1F). |
| 54-35 | 553.7 | $^1$H NMR (400 MHz, CDCl$_3$) δ ppm 8.15 (br s, 1H), 7.47-7.56 (m, 1H), 7.34-7.44 (m, 4H), 7.32 (br s, 1H), 7.18 (br d, J = 6.43 Hz, 1H), 6.54-6.72 (m, 3H), 6.32 (br d, J = 16.79 Hz, 1H), 5.81 (br d, J = 10.16 Hz, 1H), 4.78-5.09 (m, 1H), 4.33-4.69 (m, 2H), 3.46-4.17 (m, 3H), 1.42-1.54 (m, 3H). $^{19}$F NMR (377 MHz, CDCl$_3$) δ ppm −108.45 (br, 1F). |
| 54-36 | 563.2 | 1H NMR (400 MHz, DMSO-d$_6$) δ ppm 10.05-10.19 (m, 1 H) 8.68 (s, 1 H) 8.32-8.52 (m, 2 H) 7.13-7.30 (m, 1 H) 6.78-6.96 (m, 1 H) 6.60-6.76 (m, 2 H) 6.15-6.28 (m, 1 H) 5.71-5.80 (m, 1 H) 4.81-5.05 (m, 1 H) 4.25-4.49 (m, 2 H) 4.12-4.24 (m, 1 H) 3.93-4.09 (m, 1 H) 3.75-3.91 (m, 1 H) 3.57-3.75 (m, 1 H) 1.29-1.43 (m, 3 H) 1.14 (br d, J = 6.63 Hz, 3 H) 0.95-1.09 (m, 3 H). |
| 54-37 | 550.2 | $^1$H NMR (400 MHz, DMSO-d$_6$) δ ppm 10.06-10.23 (m, 1 H) 8.62 (d, J = 2.49 Hz, 1 H) 8.32-8.53 (m, 2 H) 7.18-7.29 (m, 1 H) 6.76-6.93 (m, 1 H) 6.59-6.74 (m, 2 H) 6.11-6.27 (m, 1 H) 5.74-5.78 (m, 1 H) 4.76-5.16 (m, 1 H) 3.77-4.51 |

TABLE 88-continued

Analytical Data

| Ex. # | LRMS: m/z (ESI, +ve ion): (M + H)+ | NMR |
|---|---|---|
| | | (m, 4 H) 3.47-3.74 (m, 2 H) 2.92-3.31 (m, 2 H) 1.28-1.44 (m, 3 H) 1.01-1.15 (m, 3 H). |
| 54-38 | 534.0 | $^1$H NMR (400 MHz, DMSO-d$_6$) δ ppm 8.66 (d, J = 2.49 Hz, 1 H) 8.40-8.55 (m, 2 H) 7.47-7.58 (m, 1 H) 7.19-7.37 (m, 3 H) 6.78-6.94 (m, 1 H) 6.22 (br dd, J = 15.86, 0.73 Hz, 1 H) 5.73-5.80 (m, 1 H) 4.72-5.15 (m, 1 H) 4.22-4.51 (m, 2 H) 3.98-4.21 (m, 1 H) 3.81-3.96 (m, 1 H) 3.59-3.79 (m, 1 H) 3.36-3.58 (m, 1 H) 2.99-3.28 (m, 1 H) 2.53-2.63 (m, 2 H) 1.30-1.43 (m, 3 H) 1.13 (t, J = 7.57 Hz, 3 H). |
| 54-39 | 570.0 | $^1$H NMR (400 MHz, DMSO-d$_6$) δ ppm 8.54 (d, J = 5.39 Hz, 1 H) 8.42 (br s, 1 H) 7.50-7.59 (m, 1 H) 7.47 (d, J = 1.45 Hz, 1 H) 7.25-7.38 (m, 4 H) 6.78-6.93 (m, 1 H) 6.22 (br d, J = 16.79 Hz, 1 H) 5.75-5.80 (m, 1 H) 4.93 (br dd, J = 2.28, 1.45 Hz, 1 H) 4.25-4.46 (m, 2 H) 3.99-4.19 (m, 1 H) 3.55-3.85 (m, 2 H) 3.03-3.27 (m, 1 H) 1.91-2.02 (m, 2 H) 1.63-1.73 (m, 2 H) 1.35 (br d, J = 6.63 Hz, 3 H). |
| 54-40 | 586.0 | $^1$H NMR (400 MHz, DMSO-d$_6$) δ ppm 10.07 (br d, J = 2.90 Hz, 1 H) 8.52 (d, J = 5.39 Hz, 1 H) 8.39 (br s, 1 H) 7.30-7.36 (m, 2 H) 7.25-7.28 (m, 1 H) 7.21-7.30 (m, 1 H) 6.79-6.94 (m, 1 H) 6.73 (d, J = 8.29 Hz, 1 H) 6.69 (t, J = 8.81 Hz, 1 H) 6.16-6.28 (m, 1 H) 5.74-5.81 (m, 1 H) 4.84-5.02 (m, 1 H) 4.20-4.47 (m, 2 H) 3.99-4.19 (m, 1 H) 3.69-3.87 (m, 1 H) 3.41-3.67 (m, 1 H) 3.02-3.26 (m, 1 H) 1.95 (br d, J = 2.70 Hz, 2 H) 1.64 (br d, J = 6.43 Hz, 2 H) 1.35 (dd, J = 3.42, 0.93 Hz, 3 H). |
| 54-41 | 548.9 | $^1$H NMR (400 MHz, MeOH-d$_4$) δ ppm 8.71 (br s, 2H), 8.50-8.56 (m, 1H), 7.19-7.28 (m, 1H), 6.77-6.93 (m, 1H), 6.66 (d, J = 8.3 Hz, 1H), 6.60 (t, J = 8.8 Hz, 1H), 6.33 (br d, J = 16.6 Hz, 1H), 5.84 (dd, J = 10.7, 1.8 Hz, 1H), 5.14 (br s, 1H), 4.40-4.64 (m, 2H), 4.04-4.29 (m, 2H), 3.92 (br s, 1H), 3.53-3.81 (m, 1H), 2.25 (br s, 6H), 1.51 (br d, J = 4.8 Hz, 3H). |
| 54-42 | 562.8 | $^1$H NMR (400 MHz, MeOH-d$_4$) δ ppm 8.46 (br s, 1H), 7.41-7.48 (m, 1H), 7.27-7.36 (m, 2H), 7.18-7.26 (m, 2H), 6.84-7.01 (m, 1H), 6.64-6.76 (m, 2H), 6.40 (br d, J = 15.5 Hz, 1H), 5.92 (dd, J = 10.6, 1.7 Hz, 1H), 5.10 (br d, J = 4.6 Hz, 1H), 4.45-4.72 (m, 2H), 4.11-4.34 (m, 1H), 3.55-3.97 (m, 2H), 3.17-3.36 (m, 1H), 2.61 (s, 6H), 1.54-1.60 (m, 3H). |
| 54-43 | 543.8 | $^1$H NMR (400 MHz, MeOH-d$_4$) δ ppm 8.42-8.51 (m, 1H), 7.52-7.62 (m, 3H), 7.42 (td, J = 7.5, 1.7 Hz, 1H), 7.30-7.37 (m, 1H), 7.24 (d, J = 7.9 Hz, 1H), 6.85-7.00 (m, 3H), 6.37-6.45 (m, 1H), 5.93 (dd, J = 10.7, 1.8 Hz, 1H), 5.08-5.21 (m, 1H), 4.48-4.71 (m, 2H), 4.12-4.35 (m, 1H), 3.56-3.98 (m, 2H), 2.75 (br d, J = 6.2 Hz, 1H), 1.57 (br d, J = 6.6 Hz, 3H), 1.28 (d, J = 6.8 Hz, 3H), 1.12 (d, J = 6.8 Hz, 3H). |
| 54-43-1 | 543.8 | $^1$H NMR (400 MHz, DMSO-d$_6$) δ ppm 9.78 (br s, 1H), 8.28 (br s, 1H), 7.39-7.46 (m, 1H), 7.34 (t, J = 7.5 Hz, 1H), 7.22 (q, J = 7.2 Hz, 2H), 7.12 (d, J = 8.1 Hz, 1H), 7.00 (br d, J = 7.3 Hz, 1H), 6.85 (br d, J = 8.1 Hz, 1H), 6.75-6.81 (m, 1H), 6.21 (br d, J = 17.0 Hz, 1H), 5.73-5.79 (m, |

TABLE 88-continued

Analytical Data

| Ex. # | LRMS: m/z (ESI, +ve ion): (M + H)+ | NMR |
|---|---|---|
| | | 1H), 4.82 (br s, 1H), 3.97-4.46 (m, 3H), 3.42-3.73 (m, 2H), 3.04-3.25 (m, 1H), 2.56 (br d, J = 6.4 Hz, 1H), 1.36 (d, J = 6.6 Hz, 3H), 1.08 (d, J = 6.8 Hz, 3H), 1.00 (d, J = 6.8 Hz, 3H). |
| 54-43-2 | 543.8 | $^1$H NMR (400 MHz, DMSO-$d_6$) δ ppm 9.79 (br s, 1H), 8.32 (br s, 1H), 7.40-7.44 (m, 1H), 7.34 (t, J = 7.6 Hz, 1H), 7.22 (q, J = 6.8 Hz, 2H), 7.12 (d, J = 7.9 Hz, 1H), 7.00 (br d, J = 6.4 Hz, 1H), 6.85 (br d, J = 8.1 Hz, 1H), 6.76-6.81 (m, 1H), 6.15-6.27 (m, 1H), 5.72-5.80 (m, 1H), 4.95 (br s, 1H), 4.26-4.48 (m, 1H), 4.00-4.23 (m, 2H), 3.39-3.86 (m, 2H), 2.95-3.25 (m, 1H), 2.53-2.72 (m, 1H), 1.31 (br d, J = 6.4 Hz, 3H), 1.08 (d, J = 6.8 Hz, 3H), 1.01 (br d, J = 6.8 Hz, 3H). |
| 54-44 | 546.8 | $^1$H NMR (400 MHz, MeOH-$d_4$) δ ppm 8.33-8.45 (m, 1H), 7.40-7.50 (m, 2H), 7.29 (td, J = 7.5, 1.7 Hz, 1H), 7.09 (br d, J = 7.9 Hz, 1H), 6.74-6.89 (m, 1H), 6.24-6.33 (m, 1H), 5.81 (dd, J = 10.6, 1.9 Hz, 1H), 4.90-5.16 (m, 1H), 4.31-4.57 (m, 2H), 4.01-4.23 (m, 1H), 3.34-3.94 (m, 2H), 3.08-3.25 (m, 1H), 2.61-2.75 (m, 1H), 2.26 (s, 3H), 1.86 (s, 3H), 1.40-1.53 (m, 3H), 1.16 (d, J = 6.8 Hz, 3H), 0.95 (d, J = 6.8 Hz, 3H). |
| 54-45 | 531.8 | $^1$H NMR (400 MHz, MeOH-$d_4$) δ ppm 8.25-8.41 (m, 2H), 7.66-7.69 (m, 1H), 7.53-7.64 (m, 2H), 7.42 (td, J = 7.4, 1.6 Hz, 1H), 7.16-7.28 (m, 1H), 6.79-6.97 (m, 1H), 6.36 (br d, J = 16.8 Hz, 1H), 5.88 (dd, J = 10.5, 1.8 Hz, 1H), 4.95-5.19 (m, 1H), 4.40-4.66 (m, 2H), 4.07-4.29 (m, 1H), 3.93 (s, 3H), 3.40-3.90 (m, 3H), 3.14-3.34 (m, 1H), 2.58-2.72 (m, 1H), 1.52 (br s, 3H), 1.24 (d, J = 6.6 Hz, 3H), 1.05 (d, J = 6.8 Hz, 3H). |
| 54-46 | 517.1 | $^1$H NMR (400 MHz, MeOH-$d_4$) δ ppm 8.25 (br s, 1H), 7.51-7.61 (m, 2H), 7.37-7.45 (m, 1H), 7.32-7.35 (m, 1H), 7.19 (d, J = 7.9 Hz, 1H), 6.92 (dd, J = 2.5, 1.2 Hz, 1H), 6.76-6.89 (m, 1H), 6.31 (br dd, J = 16.8, 3.9 Hz, 1H), 6.25 (dd, J = 3.9, 2.7 Hz, 1H), 5.83 (dd, J = 10.7, 2.0 Hz, 1H), 4.95-5.07 (m, 1H), 4.31-4.60 (m, 2H), 4.02-4.23 (m, 1H), 3.52-3.89 (m, 2H), 3.11-3.27 (m, 1H), 2.54-2.73 (m, 1H), 1.46 (br d, J = 5.4 Hz, 3H), 1.20 (d, J = 6.8 Hz, 3H), 1.01 (d, J = 7.0 Hz, 3H). |
| 54-47 | 518.0 | $^1$H NMR (400 MHz, MeOH-$d_4$) δ ppm 8.39 (br s, 1H), 7.75 (d, J = 1.0 Hz, 1H), 7.53-7.63 (m, 2H), 7.38-7.45 (m, 1H), 7.20 (d, J = 7.9 Hz, 1H), 7.10 (d, J = 3.5 Hz, 1H), 6.83-6.99 (m, 1H), 6.61 (dd, J = 3.5, 1.7 Hz, 1H), 6.39 (br d, J = 16.2 Hz, 1H), 5.90 (dd, J = 10.6, 1.9 Hz, 1H), 5.05-5.18 (m, 1H), 4.43-4.65 (m, 2H), 4.09-4.31 (m, 1H), 3.55-3.94 (m, 1H), 3.42-3.98 (m, 1H), 3.17 (s, 1H), 2.59-2.73 (m, 1H), 1.52-1.58 (m, 3H), 1.25 (d, J = 6.8 Hz, 3H), 1.10 (d, J = 7.0 Hz, 3H). |
| 54-48 | 550.0 | $^1$H NMR (400 MHz, DMSO-$d_6$) δ ppm 10.23 (br s, 1H), 8.86 (s, 1H), 8.45 (br d, J = 4.6 Hz, 1H), 7.22-7.30 (m, 1H), 6.80-6.91 (m, 1H), 6.65-6.75 (m, 2H), 6.21 (br d, J = 15.8 Hz, 1H), 5.73-5.80 (m, 1H), 4.96 (br s, 1H), 4.26-4.46 (m, 2H), 4.00-4.19 (m, 1H), 3.73-3.86 (m, 1H), 3.42-3.69 (m, 1H), 3.05-3.15 (m, 1H), 2.16 (br s, 3H), 2.13 (br s, 3H), 1.35 (d, J = 6.6 Hz, 3H). |

TABLE 88-continued

Analytical Data

| Ex. # | LRMS: m/z (ESI, +ve ion): (M + H)+ | NMR |
|---|---|---|
| 54-49 | 603.8 | ¹H NMR (400 MHz, DMSO-d₆) δ ppm 10.07 (br s, 1H), 8.37 (br s, 1H), 7.52-7.60 (m, 1H), 7.29-7.39 (m, 3H), 7.21-7.28 (m, 1H), 6.78-6.92 (m, 1H), 6.72 (d, J = 8.3 Hz, 1H), 6.66 (t, J = 8.8 Hz, 1H), 6.21 (br d, J = 16.6 Hz, 1H), 5.71-5.82 (m, 1H), 4.87 (br d, J = 8.5 Hz, 1H), 3.99-4.46 (m, 3H), 3.67-3.85 (m, 1H), 3.37-3.66 (m, 1H), 3.02-3.27 (m, 1H), 1.33 (br d, J = 5.2 Hz, 3H). |
| 54-50 | 560.0 | ¹H NMR (400 MHz, DMSO-d₆) δ ppm 10.03 (br s, 1H), 8.37-8.53 (m, 1H), 7.35-7.41 (m, 1H), 7.27-7.34 (m, 1H), 7.16-7.24 (m, 2H), 6.94-7.11 (m, 1H), 6.79 (ddd, J = 16.6, 10.5, 5.9 Hz, 1H), 6.58-6.72 (m, 2H), 6.47 (dt, J = 16.7, 10.0 Hz, 1H), 6.16 (ddt, J = 16.8, 4.2, 2.2 Hz, 1H), 5.69 (ddd, J = 10.2, 6.0, 2.3 Hz, 1H), 5.22-5.43 (m, 1H), 4.90-5.10 (m, 1H), 4.27-4.50 (m, 1H), 3.94-4.22 (m, 1H), 3.54-3.94 (m, 2H), 2.57-2.69 (m, 1H), 1.94-2.15 (m, 2H), 1.05 (td, J = 6.8, 1.6 Hz, 3H), 0.95 (t, J = 6.9 Hz, 3H). |
| 54-51 | 612.2 | ¹H NMR (400 MHz, DMSO-d₆) δ ppm 8.35-8.49 (1 H, m), 7.31-7.47 (4 H, m), 7.24 (1 H, td, J = 7.5, 1.5 Hz), 7.11-7.17 (2 H, m), 7.01 (1 H, dd, J = 5.6, 2.9 Hz), 6.78-6.92 (1 H, m), 6.13-6.26 (1 H, m), 5.73-5.83 (1 H, m), 4.79-5.03 (1 H, m), 4.00-4.47 (3 H, m), 3.36-3.89 (2 H, m), 2.97-3.27 (1 H, m), 2.54-2.61 (1 H, m), 1.34 (3 H, dd, J = 16.6, 6.6 Hz), 1.09 (3 H, d, J = 6.8 Hz), 0.99 (3 H, dd, J = 6.8, 2.3 Hz). |
| 54-51-1 | 612.2 | ¹H NMR (400 MHz, DMSO-d₆) δ ppm 8.39 (br d, J = 6.0 Hz, 1 H), 7.32-7.44 (m, 4 H), 7.23 (td, J = 7.5, 1.3 Hz, 1 H), 6.94-7.16 (m, 3 H), 6.78-6.93 (m, 1 H), 6.21 (br d, J = 16.4 Hz, 1 H), 5.76 (dd, J = 10.5, 2.2 Hz, 1 H), 4.78-4.92 (m, 1 H), 3.96-4.47 (m, 3 H), 3.41-3.79 (m, 2 H), 3.06-3.25 (m, 1 H), 2.55-2.63 (m, 1 H), 1.35 (d, J = 6.6 Hz, 3 H), 1.08 (d, J = 6.8 Hz, 3 H), 0.98 (d, J = 6.8 Hz, 3 H) |
| 54-51-2 | 612.0 | ¹H NMR (400 MHz, DMSO-d₆) δ ppm 8.33-8.49 (m, 1 H), 7.29-7.48 (m, 4 H), 7.23 (td, J = 7.5, 1.3 Hz, 1 H), 6.94-7.18 (m, 3 H), 6.78-6.92 (m, 1 H), 6.21 (br d, J = 17.0 Hz, 1 H), 5.73-5.81 (m, 1 H), 4.97 (br s, 1 H), 3.97-4.48 (m, 3 H), 3.35-3.88 (m, 2 H), 2.95-3.25 (m, 1 H), 2.55 (br d, J = 6.6 Hz, 1 H), 1.31 (br d, J = 6.6 Hz, 3 H), 1.08 (d, J = 6.8 Hz, 3 H), 0.99 (d, J = 6.8 Hz, 3 H). |
| 54-52 | 554.0 | ¹H NMR (400 MHz, DMSO-d₆) δ ppm 10.03 (br s, 1H), 8.37-8.53 (m, 1H), 7.35-7.41 (m, 1H), 7.27-7.34 (m, 1H), 7.16-7.24 (m, 2H), 6.94-7.11 (m, 1H), 6.79 (ddd, J = 16.6, 10.5, 5.9 Hz, 1H), 6.58-6.72 (m, 2H), 6.47 (dt, J = 16.7, 10.0 Hz, 1H), 6.16 (ddt, J = 16.8, 4.2, 2.2 Hz, 1H), 5.69 (ddd, J = 10.2, 6.0, 2.3 Hz, 1H), 5.22-5.43 (m, 1H), 4.90-5.10 (m, 1H), 4.27-4.50 (m, 1H), 3.94-4.22 (m, 1H), 3.54-3.94 (m, 2H), 2.57-2.69 (m, 1H), 1.94-2.15 (m, 2H), 1.05 (td, J = 6.8, 1.6 Hz, 3H), 0.95 (t, J = 6.9 Hz, 3H). |
| 54-53 | 574.0 | ¹H NMR (400 MHz, DMSO-d₆) δ ppm 10.07-10.23 (m, 1H), 8.86 (d, J = 1.9 Hz, 1H), 8.35-8.50 (m, 2H), 7.50-7.60 (m, 1H), 7.20-7.28 (m, 1H), 6.78-6.91 (m, 1H), 6.63-6.73 (m, 2H), 6.21 (br d, J = 16.6 Hz, 1H), 5.72-5.79 (m, 1H), 4.77- |

TABLE 88-continued

Analytical Data

| Ex. # | LRMS: m/z (ESI, +ve ion): (M + H)+ | NMR |
|---|---|---|
| | | 5.15 (m, 1H), 4.39 (br d, J = 11.6 Hz, 1H), 3.96-4.30 (m, 2H), 3.49-3.95 (m, 2H), 2.97-3.27 (m, 1H), 2.27-2.43 (m, 2H), 1.28-1.42 (m, 3H), 1.01-1.10 (m, 3H). |
| 54-54 | 560.0 | $^1$H NMR (400 MHz, DMSO-d$_6$) δ ppm 9.02 (s, 1H), 8.61 (d, J = 1.5 Hz, 1H), 8.46-8.54 (m, 1H), 7.50-7.58 (m, 1H), 7.27-7.36 (m, 3H), 6.79-6.94 (m, 1H), 6.15-6.25 (m, 1H), 5.69-5.81 (m, 1H), 4.95 (br s, 1H), 4.10-4.46 (m, 3H), 3.39-4.08 (m, 3H), 2.98-3.26 (m, 1H), 1.29-1.38 (m, 3H), 1.15 (tt, J = 6.1, 3.0 Hz, 1H), 1.05 (d, J = 6.6 Hz, 3H), 0.95 (ddd, J = 9.5, 5.9, 3.4 Hz, 1H), 0.57-0.69 (m, 2H). |
| 54-55 | 575.9 | $^1$H NMR (400 MHz, DMSO-d$_6$) δ ppm 10.14 (br s, 1H), 9.00 (s, 1H), 8.54 (s, 1H), 8.39-8.50 (m, 1H), 7.20-7.29 (m, 1H), 6.78-6.91 (m, 1H), 6.62-6.75 (m, 2H), 6.20 (br d, J = 16.2 Hz, 1H), 5.70-5.79 (m, 1H), 4.93 (br d, J = 2.1 Hz, 1H), 4.21-4.47 (m, 2H), 3.56-4.20 (m, 3H), 3.32-3.56 (m, 1H), 1.27-1.38 (m, 3H), 1.01-1.04 (m, 1H), 0.94 (br s, 1H), 0.62 (br d, J = 2.7 Hz, 1H), 0.53 (br s, 1H). |
| 54-56 | 598.2 | $^1$H NMR (400 MHz, DMSO-d$_6$) δ ppm 9.97-10.21 (m, 1H), 8.43 (br s, 1H), 7.99-8.06 (m, 1H), 7.76-7.84 (m, 1H), 7.63-7.72 (m, 1H), 7.46 (br d, J = 6.43 Hz, 1H), 7.22 (q, J = 7.95 Hz, 1H), 6.75-6.95 (m, 1H), 6.69 (d, J = 8.29 Hz, 1H), 6.64 (t, J = 8.81 Hz, 1H), 6.15-6.27 (m, 1H), 5.76 (dd, J = 2.07, 10.57 Hz, 1H), 4.72-5.06 (m, 1H), 3.82-4.52 (m, 4H), 3.55-3.71 (m, 1H), 3.02 (s, 3H), 1.32 (br s, 3H). $^{19}$F NMR (376 MHz, DMSO-d$_6$) δ −116.16−−113.68 (m, 1F). |
| 54-56-1 | 620.0 (M + Na) | $^1$H NMR (400 MHz, DMSO-d$_6$) δ ppm 9.40-10.69 (1 H, m), 8.39 (1 H, br s), 8.02 (1 H, d, J = 7.9 Hz), 7.76-7.84 (1 H, m), 7.64-7.71 (1 H, m), 7.46 (1 H, br d, J = 7.3 Hz), 7.18-7.29 (1 H, m), 6.76-6.95 (1 H, m), 6.70 (1 H, d, J = 8.3 Hz), 6.64 (1 H, t, J = 8.8 Hz), 6.21 (1 H, br d, J = 16.4 Hz), 5.73-5.81 (1 H, m), 4.74-4.95 (1 H, m), 3.96-4.49 (3 H, m), 3.57-3.76 (2 H, m), 3.02 (3 H, s), 1.33 (3 H, br s). $^{19}$F NMR (376 MHz, DMSO-d$_6$) δ ppm −115.01 (br d, J = 311.24 Hz, 1F). |
| 54-56-2 | 598.2 | $^1$H NMR (400 MHz, DMSO-d$_6$) δ ppm 9.77-10.37 (1 H, m), 8.43 (1 H, br s), 7.99-8.07 (1 H, m), 7.75-7.85 (1 H, m), 7.67 (1 H, td, J = 7.7, 1.1 Hz), 7.46 (1 H, br d, J = 4.4 Hz), 7.18-7.27 (1 H, m), 6.79-6.93 (1 H, m), 6.70 (1 H, d, J = 8.3 Hz), 6.64 (1 H, t, J = 8.9 Hz), 6.21 (1 H, br d, J = 16.0 Hz), 5.71-5.81 (1 H, m), 4.84-5.07 (1 H, m), 4.00-4.49 (3 H, m), 3.72-3.93 (1 H, m), 3.54-3.69 (1 H, m), 3.02 (3 H, s), 1.31 (3 H, br s). $^{19}$F NMR (376 MHz, DMSO-d$_6$) δ ppm −114.97 (br d, J = 312.98 Hz, 1F). |
| 54-57 | 563.2 | $^1$H NMR (400 MHz, DMSO-d$_6$) δ ppm 10.09 (1 H, br s), 8.31-8.48 (2 H, m), 7.89 (1 H, br d, J = 7.7 Hz), 7.40 (1 H, dd, J = 7.8, 4.7 Hz), 7.18-7.27 (1 H, m), 6.79-6.94 (1 H, m), 6.60-6.73 (2 H, m), 6.15-6.27 (1 H, m), 5.71-5.80 (1 H, m), 4.74-5.11 (1 H, m), 4.39 (1 H, br d, J = 3.9 Hz), 3.97-4.34 (2 H, m), 3.48-3.94 (2 H, m), 2.99-3.26 (1 H, m), 2.54-2.61 (1 H, m), 1.28-1.42 (3 H, m), 1.10 (3 H, d, J = 6.8 Hz), 1.00 (3 H, br d, |

TABLE 88-continued

Analytical Data

| Ex. # | LRMS: m/z (ESI, +ve ion): (M + H)⁺ | NMR |
|---|---|---|
| | | J = 6.8 Hz). ¹⁹F NMR (376 MHz, DMSO-d₆) δ ppm −115.59-−115.28 (m, 1F). |
| 54-58 | 545.2 | ¹H NMR (400 MHz, DMSO-d₆) δ ppm 10.18 (br s, 1H), 8.34-8.53 (m, 1H), 7.91-8.00 (m, 1H), 7.75-7.84 (m, 1H), 7.48-7.63 (m, 2H), 7.19-7.29 (m, 1H), 6.77-6.93 (m, 1H), 6.60-6.73 (m, 2H), 6.21 (br d, J = 16.38 Hz, 1H), 5.73-5.82 (m, 1H), 4.77-5.15 (m, 1H), 3.99-4.49 (m, 3H), 3.55-3.96 (m, 2H), 2.93-3.21 (m, 1H), 1.35 (br d, J = 19.28 Hz, 3H). ¹⁹F NMR (376 MHz, DMSO-d₆) δ ppm −115.73-−114.94 (m, 1F). |
| 54-59 | 561.0 | ¹H NMR (400 MHz, CDCl₃) δ ppm 8.59 (1 H, d, J = 5.18 Hz) 8.47 (1 H, s) 8.15 (1 H, d, J = 2.90 Hz) 7.21-7.32 (2 H, m) 6.55-6.75 (3 H, m) 6.39-6.48 (1 H, m) 5.84 (1 H, d, J = 10.37 Hz) 2.98-5.21 (7 H, m) 1.44-1.70 (4 H, m) 0.56-0.89 (4 H, m). |
| 54-60 | 560.2 | ¹H NMR (400 MHz, CDCl₃) δ ppm 8.05 (s, 1 H) 7.35-7.41 (m, 1 H) 7.28-7.33 (m, 1 H) 7.19 (s, 1 H) 7.17 (s, 1 H) 7.11-7.16 (m, 2 H) 7.04-7.10 (m, 1 H) 6.51-6.70 (m, 1 H) 6.39 (dd, J = 16.8, 1.5 Hz, 1 H) 5.79 (dd, J = 10.5, 1.8 Hz, 1 H) 4.21-5.15 (m, 3 H) 3.53-4.06 (m, 3 H) 2.97-3.31 (m, 1 H) 2.17-2.42 (m, 4 H) 1.48 (br d, J = 17.6 Hz, 3 H) 1.01-1.12 (m, 6 H). ¹⁹F NMR (376 MHz, CDCl₃) δ ppm −112.16 (s, 1 F) |
| 54-61 | 499.9 | ¹H NMR (400 MHz, CDCl₃) δ ppm 8.02 (s, 1 H) 7.37-7.45 (m, 1 H) 7.20-7.31 (m, 2 H) 6.55-6.68 (m, 1 H) 6.40 (dd, J = 16.7, 1.6 Hz, 1 H) 5.74-5.85 (m, 1 H) 4.17-5.13 (m, 3 H) 3.50-4.07 (m, 3 H) 2.99-3.34 (m, 1 H) 2.14-2.44 (m, 4 H) 1.47 (br d, J = 12.2 Hz, 3 H) 1.05-1.16 (m, 6 H). |
| 54-62 | 541.8 | ¹H NMR (400 MHz, CDCl₃) δ ppm 8.07 (s, 1 H) 7.62 (s, 1 H) 7.60 (d, J = 1.7 Hz, 1 H) 7.31-7.44 (m, 4 H) 7.24 (s, 1 H) 7.22 (s, 1 H) 6.53-6.72 (m, 1 H) 6.41 (dd, J = 16.7, 1.3 Hz, 1 H) 5.81 (dd, J = 10.4, 1.9 Hz, 1 H) 4.22-5.21 (m, 3 H) 3.51-4.09 (m, 3 H) 2.96-3.35 (m, 1 H) 2.17-2.48 (m, 4 H) 1.50 (br d, J = 19.5 Hz, 3 H) 1.03-1.13 (m, 6 H). |
| 54-63 | 557.9 | ¹H NMR (400 MHz, CDCl₃) δ ppm 9.87 (s, 1 H) 8.15 (s, 1 H) 8.08 (dd, J = 8.4, 1.3 Hz, 1 H) 7.46-7.53 (m, 1 H) 7.35 (s, 1 H) 7.33 (s, 1 H) 7.27-7.32 (m, 1 H) 6.83-6.91 (m, 2 H) 6.53-6.70 (m, 1 H) 6.42 (dd, J = 16.7, 1.3 Hz, 1 H) 5.82 (dd, J = 10.5, 1.8 Hz, 1 H) 4.23-5.24 (m, 3 H) 3.55-4.09 (m, 3 H) 3.00-3.36 (m, 1 H) 2.20-2.47 (m, 4 H) 1.43-1.59 (m, 3 H) 1.07-1.15 (m, 6 H). |
| 54-64 | 575.9 | ¹H NMR (400 MHz, CDCl₃) δ ppm 8.02 (s, 1 H) 7.17-7.24 (m, 1 H) 7.00-7.08 (m, 3 H) 6.77 (td, J = 8.3, 2.3 Hz, 1 H) 6.56-6.69 (m, 2 H) 6.53 (dt, J = 9.5, 2.3 Hz, 1 H) 6.34-6.43 (m, 1 H) 5.79 (dd, J = 10.5, 1.8 Hz, 1 H) 3.80-5.14 (m, 4 H) 3.46-3.72 (m, 2 H) 2.94-3.32 (m, 1 H) 2.24 (dt, J = 14.8, 7.2 Hz, 2 H) 2.09 (br s, 2 H) 1.38-1.52 (m, 3 H) 0.97 (t, J = 7.6 Hz, 6 H). ¹⁹F NMR (376 MHz, CDCl₃) δ ppm −110.85 (s, 1 F). |
| 54-65 | 577.8 | ¹H NMR (400 MHz, CDCl₃) δ ppm 8.07 (s, 1 H) 7.26-7.36 (m, 2 H) 7.17 (s, 1 H) 7.15 (s, 1 H) 6.89 (t, J = 8.3 Hz, 2 H) 6.48-6.69 (m, 1 H) 6.38 (dd, J = 16.6, 1.7 Hz, 1 H) 5.79 (dd, J = 10.4, 1.9 Hz, 1 |

TABLE 88-continued

| | Analytical Data | |
|---|---|---|
| Ex. # | LRMS: m/z (ESI, +ve ion): (M + H)+ | NMR |
| | | H) 4.19-5.13 (m, 3 H) 3.67-4.08 (m, 2 H) 2.97-3.67 (m, 2 H) 2.17-2.40 (m, 4 H) 1.41-1.52 (m, 3 H) 1.01-1.09 (m, 6 H). $^{19}$F NMR (377 MHz, CDCl$_3$) δ ppm −112.42--112.68 (m, 2 F). |
| 54-66 | 596.3 | $^1$H NMR (400 MHz, CDCl$_3$) δ ppm 10.78 (br. s., 1 H) 8.16 (s, 1 H) 7.40-7.50 (m, 1 H) 7.20 (t, J = 8.3 Hz, 2 H) 7.02-7.15 (m, 3 H) 6.59 (br d, J = 6.6 Hz, 1 H) 6.34-6.46 (m, 1 H) 5.74-5.85 (m, 1 H) 4.26-5.24 (m, 3 H) 3.01-4.04 (m, 4 H) 2.17-2.48 (m, 4 H) 2.06 (br s, 3 H) 1.39-1.62 (m, 3 H) 1.00-1.13 (m, 6 H). |
| 54-67 | 543.8 | $^1$H NMR (400 MHz, CDCl$_3$) δ ppm 7.91 (s, 1 H) 7.39-7.48 (m, 1 H) 7.15-7.24 (m, 2 H) 7.05-7.15 (m, 3 H) 6.97-7.03 (m, 1 H) 6.86-6.95 (m, 1 H) 6.44-6.71 (m, 2 H) 6.39 (dd, J = 16.8, 1.7 Hz, 1 H) 5.79 (dd, J = 10.6, 1.7 Hz, 1 H) 4.23-4.93 (m, 3 H) 3.79-4.06 (m, 1 H) 3.42-3.68 (m, 2 H) 2.97-3.22 (m, 2 H) 2.84-2.95 (m, 1 H) 2.42-2.61 (m, 2 H) 1.41-1.58 (m, 3 H). $^{19}$F NMR (377 MHz, CDCl$_3$) δ ppm −111.78 (br d, J = 31.2 Hz, 1 F). |
| 54-68 | 563.8 | $^1$H NMR (400 MHz, CDCl$_3$) δ ppm 7.98 (s, 1 H) 7.32-7.40 (m, 1 H) 7.24-7.30 (m, 1 H) 7.20 (td, J = 7.4, 1.9 Hz, 1 H) 7.09-7.15 (m, 1 H) 7.02-7.09 (m, 1 H) 6.61 (d, J = 8.5 Hz, 3 H) 6.36 (dd, J = 16.6, 1.7 Hz, 1 H) 5.76 (dd, J = 10.5, 1.8 Hz, 1 H) 4.18-5.09 (m, 3 H) 3.78-4.01 (m, 1 H) 3.68-3.71 (m, 6 H) 3.67 (br d, J = 7.0 Hz, 1 H) 3.54 (br d, J = 1.9 Hz, 1 H) 2.92-3.25 (m, 1 H) 1.45 (br d, J = 19.5 Hz, 3 H). $^{19}$F NMR (377 MHz, CDCl$_3$) δ ppm −112.01 (s, 1 F). |
| 54-69 | 547.8 | $^1$H NMR (400 MHz, CDCl$_3$) δ ppm 8.69 (s, 1 H) 8.13 (s, 1 H) 7.30-7.36 (m, 1 H) 7.25-7.29 (m, 2 H) 7.24 (s, 1 H) 6.72 (d, J = 8.5 Hz, 1 H) 6.68 (dd, J = 10.2, 8.5 Hz, 1 H) 6.54-6.65 (m, 1 H) 6.42 (dd, J = 16.8, 1.5 Hz, 1 H) 5.82 (dd, J = 10.5, 1.8 Hz, 1 H) 4.27-5.25 (m, 3 H) 3.85-4.09 (m, 1 H) 3.50-3.85 (m, 2 H) 2.99-3.32 (m, 1 H) 2.05 (br d, J = 2.3 Hz, 6 H) 1.51 (br d, J = 18.7 Hz, 3 H). $^{19}$F NMR (377 MHz, CDCl$_3$) δ ppm −104.7 (s, 1 F) −104.8 (s, 1 F). |
| 54-70 | 566.0 | $^1$H NMR (400 MHz, DMSO-d$_6$) δ ppm 10.13 (s, 1 H), 8.41 (br d, J = 7.3 Hz, 1 H), 7.32 (s, 1 H), 7.23-7.31 (m, 1 H), 6.78-6.92 (m, 1 H), 6.66-6.77 (m, 2 H), 6.21 (br d, J = 16.2 Hz, 1 H), 5.73-5.80 (m, 1 H), 4.96 (br s, 1 H), 3.94-4.45 (m, 4 H), 3.79 (br s, 1 H), 3.38-3.69 (m, 1 H), 3.00-3.28 (m, 1 H), 1.69 (br s, 3 H), 1.34 (br t, J = 7.0 Hz, 3 H), 1.12-1.28 (m, 6 H). $^{19}$F NMR (376 MHz, DMSO-d$_6$) δ ppm −73.42 (s, 1 F), −115.68 (br dd, J = 81.9, 12.6 Hz, 1 F) |
| 54-71-1 | 565.8 | $^1$H NMR (400 MHz, DMSO-d$_6$) δ ppm 10.12 (br s, 1 H), 8.42 (br s, 1 H), 7.32 (s, 1 H), 7.22-7.31 (m, 1 H), 6.78-6.93 (m, 1 H), 6.66-6.77 (m, 2 H), 6.21 (br d, J = 16.4 Hz, 1 H), 5.76 (dd, J = 10.4, 2.1 Hz, 1 H), 4.98 (br s, 1 H), 3.94-4.46 (m, 4 H), 3.81 (br s, 1 H), 3.37-3.69 (m, 1 H), 2.99-3.29 (m, 1 H), 1.69 (br s, 3 H), 1.33 (br d, J = 6.4 Hz, 3 H), 1.20 (br dd, J = 39.1, 6.3 Hz, 6 H). $^{19}$F NMR (376 MHz, DMSO-d$_6$) δ ppm −115.65 (br d, J = 80.6 Hz, 1 F). |

TABLE 88-continued

Analytical Data

| Ex. # | LRMS: m/z (ESI, +ve ion): (M + H)⁺ | NMR |
|---|---|---|
| 54-71-2 | 566.0 | ¹H NMR (400 MHz, DMSO-d₆) δ ppm 10.13 (s, 1 H), 8.40 (br s, 1 H), 7.32 (s, 1 H), 7.23-7.31 (m, 1 H), 6.78-6.93 (m, 1 H), 6.66-6.77 (m, 2 H), 6.21 (br d, J = 16.6 Hz, 1 H), 5.73-5.79 (m, 1 H), 4.94 (br s, 1 H), 3.95-4.45 (m, 4 H), 3.78 (br d, J = 2.1 Hz, 1 H), 3.40-3.68 (m, 1 H), 3.01-3.28 (m, 1 H), 1.68 (br s, 3 H), 1.35 (br d, J = 6.6 Hz, 3 H), 1.21 (br dd, J = 38.7, 6.5 Hz, 6 H). ¹⁹F NMR (376 MHz, DMSO-d₆) δ ppm −115.69 (br d, J = 84.1 Hz, 1 F). |
| 54-71 | 568.0 | ¹H NMR (400 MHz, DMSO-d₆) δ ppm 8.39-8.49 (m, 1 H), 7.30-7.46 (m, 3 H), 7.24 (td, J = 8.5, 2.3 Hz, 1 H), 6.78-6.93 (m, 1 H), 6.21 (br d, J = 16.4 Hz, 1 H), 5.73-5.79 (m, 1 H), 4.96 (br s, 1 H), 4.22-4.45 (m, 2 H), 3.98-4.20 (m, 2 H), 3.80 (br s, 1 H), 3.38-3.68 (m, 1 H), 3.01-3.28 (m, 1 H), 1.71 (d, J = 2.9 Hz, 3 H), 1.34 (t, J = 6.2 Hz, 3 H), 1.21 (dd, J = 36.7, 6.6 Hz, 6 H), ¹⁹F NMR (376 MHz, DMSO-d₆) δ ppm −106.98 (t, J = 8.7 Hz, 1 F), −109.32 (t, J = 10.4 Hz, 1 F). |
| 54-72 | 578.0 | ¹H NMR (400 MHz, DMSO-d₆) δ ppm 12.24 (s, 1 H), 8.38 (br s, 1 H), 7.50-7.59 (m, 1 H), 7.29-7.37 (m, 2 H), 7.22-7.28 (m, 1 H), 6.78-6.93 (m, 1 H), 6.14-6.25 (m, 1 H), 5.76 (dd, J = 10.3, 2.4 Hz, 1 H), 4.89 (br s, 1 H), 4.19-4.45 (m, 2 H), 3.96-4.19 (m, 1 H), 3.37-3.79 (m, 2 H), 2.99-3.27 (m, 1 H), 2.56 (br s, 2 H), 1.31 (d, J = 6.6 Hz, 3 H), 0.91-1.07 (m, 12 H). ¹⁹F NMR (376 MHz, DMSO-d₆) δ ppm −114.47 (s, 1 F). |
| 54-73 | 592.3 | ¹H NMR (400 MHz, CDCl₃) δ ppm 8.51 (br s, 1H), 8.06-8.15 (m, 1H), 7.45 (dd, J = 7.67, 16.17 Hz, 1H), 7.08 (d, J = 8.29 Hz, 1H), 6.95 (d, J = 7.88 Hz, 1H), 6.74 (d, J = 8.29 Hz, 1H), 6.50-6.70 (m, 2H), 6.40 (d, J = 17.21 Hz, 1H), 5.82 (dd, J = 1.66, 10.37 Hz, 1H), 4.17-5.42 (m, 3H), 3.80-4.07 (m, 1H), 3.68-3.71 (m, 3H), 2.68-3.07 (m, 3H), 1.38-1.77 (m, 5H), 1.23 (d, J = 7.05 Hz, 3H), 1.03 (d, J = 7.05 Hz, 3H). ¹⁹F NMR (376 MHz, CDCl₃) δ ppm −106.01 (s, 1F). |
| 54-73-1 | 592.3 | H NMR (400 MHz, DMSO-d₆) δ 8.56 (br s, 1H), 7.79-7.85 (m, 2H), 7.59 (t, J = 16.00 Hz, 1H), 7.48-7.55 (m, 1H), 7.25-7.37 (m, 2H), 7.19-7.25 (m, 1H), 6.78-6.97 (m, 1H), 6.22 (d, J = 16.38 Hz, 1H), 5.77 (dd, J = 2.28, 10.37 Hz, 1H), 4.98-5.18 (m, 1H), 4.23-4.47 (m, 2H), 3.99-4.22 (m, 1H), 3.79-3.96 (m, 1H), 3.39-3.72 (m, 1H), 3.04-3.28 (m, 1H), 2.70-2.81 (m, 1H), 1.34 (d, J = 6.84 Hz, 3H), 1.11 (d, J = 6.84 Hz, 3H), 0.98 (d, J = 6.84 Hz, 3H). ¹⁹F NMR (376 MHz, DMSO-d₆) δ −113.69 (s, 1F). |
| 54-73-2 | 592.3 | ¹H NMR (400 MHz, DMSO-d₆) δ 8.51 (d, J = 6.84 Hz, 1H), 7.78-7.85 (m, 2H), 7.58 (t, J = 15.30 Hz, 1H), 7.49-7.55 (m, 1H), 7.26-7.36 (m, 2H), 7.18-7.25 (m, 1H), 6.79-6.95 (m, 1H), 6.15-6.28 (m, 1H), 5.77 (dd, J = 2.28, 9.95 Hz, 1H), 4.87-5.02 (m, 1H), 4.25-4.48 (m, 2H), 4.00-4.23 (m, 1H), 3.43-3.82 (m, 2H), 3.08-3.28 (m, 1H), 2.70-2.80 (m, 1H), 1.36 (d, J = 6.63 Hz, 3H), 1.11 (d, J = 6.84 Hz, 3H), 0.99 (d, J = 6.63 Hz, 3H). ¹⁹F NMR (376 MHz, DMSO-d₆) δ −113.70 (s, 1F). |

TABLE 88-continued

| | Analytical Data | |
|---|---|---|
| Ex. # | LRMS: m/z (ESI, +ve ion): (M + H)+ | NMR |
| 54-74 | 596.9 | ¹H NMR (400 MHz, DMSO-d₆) δ ppm 1.23 (br d, J = 6.2 Hz, 3 H), 2.96-3.01 (m, 0.5 H), 3.08-3.22 (m, 0.5 H), 3.45-3.73 (m, 1.5 H), 3.89-4.01 (m, 0.5 H), 4.03-4.17 (m, 1.5 H), 4.23-4.27 (m, 0.5 H), 4.31-4.46 (m, 0.5 H) 4.67 (br s, 0.5 H), 4.76 (br s, 0.5 H) 5.69-5.80 (m, 1 H) 6.19 (br d, J = 16.4 Hz, 1 H), 6.62-6.76 (m, 2 H), 6.76-6.90 (m, 1 H), 7.08 (br s, 2 H), 7.18 (br s, 3 H), 7.22-7.29 (m, 1 H), 7.30-7.39 (m, 2 H), 7.40-7.47 (m, 2 H), 7.48-7.61 (m, 1 H), 8.27 (br s, 1 H), 9.98-10.29 (m, 1 H); ¹⁹F NMR (376 MHz, DMSO-d₆) δ ppm −115.27 (s, 1 F), −114.88 (s, 1 F). |
| 54-75 | 532.3 | ¹H NMR (400 MHz, DMSO-d₆) δ ppm 0.96 (d, J = 6.8 Hz, 3 H), 1.07 (d, J = 6.8 Hz, 3 H), 1.23-1.30 (m, 4 H), 1.33 (d, J = 6.6 Hz, 2 H), 1.50-1.51 (m, 4 H), 1.89-2.05 (m, 2 H), 2.12 (br s, 2 H), 2.42-2.49 (m, 1 H), 2.94-3.13 (m, 0.5 H) 3.16-3.23 (m, 0.5 H), 3.36-3.48 (m, 0.5 H), 3.52-3.66 (m, 1 H), 3.68-3.79 (m, 0.5 H), 3.95-4.08 (m, 0.5 H), 4.14 (br d, J = 12.7 Hz, 1 H), 4.27 (br d, J = 13.5 Hz, 1 H), 4.38 (br d, J = 12.2 Hz, 0.5 H), 4.79 (br s, 0.5 H), 4.92 (br s, 0.5 H) 5.69-5.81 (m, 1 H), 6.12-6.25 (m, 1 H), 6.26-6.33 (m, 1 H), 6.75-6.94 (m, 1 H), 7.08 (d, J = 7.9 Hz, 1 H), 7.24-7.32 (m, 1 H), 7.35-7.42 (m, 1 H), 7.43-7.52 (m, 1 H), 8.23 (br d, J = 18.0 Hz, 1 H). |
| 54-75-1 | 532.0 | ¹H NMR (400 MHz, DMSO-d₆) δ ppm 0.96 (br d, J = 6.6 Hz, 3 H), 1.07 (br d, J = 6.6 Hz, 3 H), 1.17-1.37 (m, 9 H), 1.50 (br s, 4 H), 1.85-2.05 (m, 2 H), 2.12 (br s, 2 H), 2.46 (sept, J = 6.8 Hz, 1 H), 2.90-3.08 (m, 0.5 H), 3.15-3.26 (m, 0.5 H), 3.34-3.43 (m, 0.5 H), 3.55-3.67 (m, 0.5 H), 3.69-3.84 (m, 1 H), 3.96-4.07 (m, 0.5 H), 4.14 (br d, J = 11.8 Hz, 1.5 H), 4.28 (br d, J = 13.3 Hz, 0.5 H), 4.39 (br d, J = 13.7 Hz, 0.5 H), 4.92 (br s, 1 H) 5.67-5.85 (m, 1 H), 6.20 (br d, J = 16.6 Hz, 1 H), 6.28 (br s, 1 H), 6.79-6.93 (m, 1 H), 7.08 (br d, J = 7.7 Hz, 1 H), 7.28 (br t, J = 7.3 Hz, 1 H), 7.35-7.52 (m, 2 H), 8.25 (br s, 1 H). |
| 54-75-2 | 532.0 | ¹H NMR (400 MHz, DMSO-d₆) δ ppm 0.96 (d, J = 6.8 Hz, 3 H), 1.07 (d, J = 6.8 Hz, 3 H), 1.20-1.28 (m, 4 H), 1.33 (d, J = 6.6 Hz, 3 H), 1.47-1.54 (m, 4 H), 1.87-2.06 (m, 2 H), 2.10-2.15 (m, 2 H), 2.42-2.47 (m, 1 H), 3.02-3.14 (m, 0.5 H), 3.14-3.21 (m, 0.5 H), 3.38-3.51 (m, 0.5 H), 3.54-3.67 (m, 1.5 H), 4.00 (br d, J = 13.5 Hz, 0.5 H), 4.14 (br d, J = 12.7 Hz, 0.5 H), 4.27 (br d, J = 13.5 Hz, 1.5 H), 4.38 (br d, J = 12.4 Hz, 0.5 H), 4.79 (br s, 1 H), 5.70-5.79 (m, 1 H), 6.20 (br d, J = 16.6 Hz, 1 H), 6.26-6.33 (m, 1 H), 6.85 (td, J = 16.4, 11.0 Hz, 1 H), 7.04-7.11 (m, 1 H), 7.27 (td, J = 7.5, 1.5 Hz, 1 H), 7.36-7.43 (m, 1 H), 7.43-7.50 (m, 1 H), 8.21 (br s, 1 H). |
| 54-76 | 533.9 | ¹H NMR (400 MHz, DMSO-d₆) δ ppm 0.95 (d, J = 6.8 Hz, 3 H), 1.08 (d, J = 6.8 Hz, 3 H), 1.31 (dd, J = 10.9, 6.7 Hz, 3 H), 2.22-2.27 (m, 2 H), 2.98-3.12 (m, 0.5 H), 3.15-3.26 (m, 0.5 H) 3.56-3.66 (m, 3 H), 3.68-3.79 (m, 0.5 H), 3.83-3.87 (m, 1.5 H), 3.96-4.06 (m, |

TABLE 88-continued

Analytical Data

| Ex. # | LRMS: m/z (ESI, +ve ion): (M + H)⁺ | NMR |
|---|---|---|
| | | 0.5 H) 4.09-4.21 (m, 1 H), 4.26 (br d, J = 13.9 Hz, 1 H), 4.33-4.45 (m, 0.5 H), 4.82 (br s, 0.5 H), 4.91 (br s, 0.5 H), 5.73-5.81 (m, 1 H), 6.20 (br d, J = 16.8 Hz, 1 H), 6.75-6.93 (m, 2 H), 7.07 (d, J = 7.9 Hz, 1 H), 7.24-7.33 (m, 1 H), 7.38-7.44 (m, 1 H), 7.45-7.53 (m, 1 H), 8.26 (br dd, J = 12.4, 4.0 Hz, 1 H). |
| 54-77 | 562.0 | ¹H NMR (400 MHz, DMSO-d₆) δ ppm 0.99 (dd, J = 6.8, 3.5 Hz, 3 H), 1.08 (d, J = 6.8 Hz, 3 H), 1.33 (dd, J = 18.5, 6.6 Hz, 3 H), 2.52-2.61 (m, 1 H), 2.92-3.16 (m, 1 H), 3.57-3.69 (m, 1 H), 3.72-3.86 (m, 0.5 H), 3.95-4.09 (m, 0.5 H), 4.15 (br d, J = 12.6 Hz, 1 H), 4.29 (br d, J = 13.3 Hz, 1 H), 4.41 (br d, J = 12.9 Hz, 0.5 H), 4.81 (br s, 0.5 H), 4.95 (br s, 0.5 H), 5.72-5.81 (m, 1 H), 6.21 (br d, J = 16.8 Hz, 1 H), 6.58-6.71 (m, 2 H), 6.77-6.94 (m, 1 H), 7.01-7.05 (m, 1 H), 7.11 (d, J = 7.7 Hz, 1 H), 7.24 (t, J = 7.6 Hz, 1 H), 7.32-7.39 (m, 1 H), 7.39-7.45 (m, 1 H), 8.20-8.40 (m, 1 H), 10.35 (br s, 1 H). ¹⁹F NMR (376 MHz, DMSO-d₆) δ ppm −110.19 (s, 1 F), −110.13 (s, 1 F). |
| 54-77-1 | 562.0 | ¹H NMR (400 MHz, DMSO-d₆) δ ppm 0.99 (d, J = 6.8 Hz, 3 H), 1.08 (d, J = 6.8 Hz, 3 H), 1.35 (d, J = 6.6 Hz, 3 H), 2.53-2.60 (m, 1 H), 3.12 (br t, J = 11.2 Hz, 0.5 H), 3.22 (br d, J = 13.1 Hz, 0.5 H) 3.41-3.53 (m, 0.5 H) 3.58-3.74 (m, 1.5 H), 4.02 (br d, J = 13.7 Hz, 0.5 H), 4.11-4.21 (m, 0.5 H), 4.30 (br d, J = 13.5 Hz, 1.5 H), 4.41 (br d, J = 13.3 Hz, 0.5 H), 4.82 (br s, 1 H), 5.73-5.81 (m, 1 H), 6.21 (br d, J = 16.8 Hz, 1 H), 6.59-6.70 (m, 2 H), 6.86 (td, J = 16.1, 10.6 Hz, 1 H), 7.04 (t, J = 7.7 Hz, 1 H), 7.12 (dd, J = 7.9, 1.0 Hz, 1 H), 7.24 (td, J = 7.5, 1.5 Hz, 1 H), 7.32-7.39 (m, 1 H), 7.39-7.46 (m, 1 H), 8.28 (br d, J = 6.4 Hz, 1 H), 10.34 (br s, 1 H). ¹⁹F NMR (376 MHz, DMSO-d₆) δ ppm −110.11 (s, 1 F). |
| 54-77-2 | 562.0 | ¹H NMR (400 MHz, DMSO-d₆) δ ppm 0.99 (d, J = 6.8 Hz, 3 H), 1.08 (d, J = 6.8 Hz, 3 H), 1.30 (br d, J = 6.6 Hz, 3 H), 2.52-2.59 (m, 1 H), 2.95-3.09 (m, 0.5 H), 3.23-3.27 (m, 0.5 H), 3.38-3.44 (m, 0.5 H), 3.63 (br d, J = 11.2 Hz, 0.5 H), 3.75-3.82 (m, 1 H), 4.04 (br d, J = 13.7 Hz, 0.5 H), 4.15 (br d, J = 12.0 Hz, 1.5 H), 4.29 (br d, J = 13.3 Hz, 0.5 H), 4.41 (br d, J = 12.4 Hz, 0.5 H), 4.95 (br s, 1 H), 5.71-5.81 (m, 1 H), 6.21 (br d, J = 15.7 Hz, 1 H), 6.57-6.69 (m, 2 H), 6.79-6.93 (m, 1 H), 7.03 (dd, J = 8.5, 6.8 Hz, 1 H), 7.12 (d, J = 7.0 Hz, 1 H), 7.24 (td, J = 7.5, 1.5 Hz, 1 H), 7.32-7.39 (m, 1 H), 7.40-7.45 (m, 1 H), 8.33 (br s, 1 H), 10.34 (br s, 1 H). ¹⁹F NMR (376 MHz, DMSO-d₆) δ ppm −110.18 (s, 1 F). |
| 54-78 | 562.0 | ¹H NMR (400 MHz, DMSO-d₆) δ ppm 1.01 (br d, J = 5.8 Hz, 3 H), 1.08 (br d, J = 6.4 Hz, 3 H), 1.33 (br dd, J = 18.9, 6.2 Hz, 3 H), 2.52-2.60 (m, 1 H), 2.97-3.17 (m, 0.5 H), 3.18-3.28 (m, 0.5 H), 3.35-3.54 (m, 0.5 H), 3.57-3.71 (m, 1 H), 3.76-3.83 (m, 0.5 H), 3.94-4.08 (m, 0.5 H), 4.15 (br d, J = 11.4 Hz, 1 H), 4.30 (br d, J = 13.3 Hz, 1 H), 4.41 (br d, J = 12.4 Hz, 0.5 H), 4.82 (br s, 0.5 H), |

TABLE 88-continued

| | Analytical Data | |
|---|---|---|
| Ex. # | LRMS: m/z (ESI, +ve ion): $(M + H)^+$ | NMR |
| | | 4.95 (br s, 0.5 H), 5.76 (br d, J = 10.8 Hz, 1 H), 6.21 (br d, J = 16.2 Hz, 1 H), 6.77 (br d, J = 8.1 Hz, 1 H), 6.85 (br dd, J = 8.5, 4.4 Hz, 2 H), 7.02-7.16 (m, 2 H), 7.24 (br t, J = 7.3 Hz, 1 H), 7.36 (br t, J = 7.3 Hz, 1 H), 7.40-7.47 (m, 1 H), 8.25-8.41 (m, 1 H), 9.79 (br s, 1 H). $^{19}$F NMR (376 MHz, DMSO-$d_6$) δ ppm −126.12 (s, 1 F), −126.10 (s, 1 F). |
| 54-78-1 | 562.0 | $^1$H NMR (400 MHz, DMSO-$d_6$) δ ppm 1.00 (d, J = 6.8 Hz, 3 H), 1.08 (d, J = 6.8 Hz, 3 H), 1.35 (d, J = 6.6 Hz, 3 H), 2.56 (dt, J = 13.4, 6.6 Hz, 1 H), 3.05-3.15 (m, 0.5 H), 3.19-3.27 (m, 0.5 H), 3.48 (br t, J = 11.7 Hz, 0.5 H), 3.57-3.72 (m, 1.5 H), 4.02 (br d, J = 13.5 Hz, 0.5 H), 4.16 (br d, J = 12.2 Hz, 0.5 H), 4.24-4.35 (m, 1.5 H), 4.41 (br d, J = 12.9 Hz, 0.5 H), 4.82 (br s, 1 H), 5.71-5.81 (m, 1 H), 6.21 (br d, J = 16.6 Hz, 1 H), 6.78 (dd, J = 8.8, 3.2 Hz, 1 H), 6.85 (dd, J = 8.9, 4.8 Hz, 1 H), 7.04-7.10 (m, 1 H), 7.10-7.15 (m, 1 H), 7.24 (td, J = 7.5, 1.4 Hz, 1 H), 7.32-7.38 (m, 1 H), 7.39-7.46 (m, 1 H), 8.29 (br d, J = 6.2 Hz, 1 H), 9.79 (br s, 1 H). $^{19}$F NMR (376 MHz, DMSO-$d_6$) δ ppm −126.10 (s, 1 F). |
| 54-78-2 | 562.0 | $^1$H NMR (400 MHz, DMSO-$d_6$) δ ppm 1.01 (d, J = 6.6 Hz, 3 H), 1.08 (d, J = 6.8 Hz, 3 H), 1.31 (br d, J = 6.6 Hz, 3 H), 2.52-2.61 (m, 1 H), 3.03 (br t, J = 10.9 Hz, 0.5 H), 3.26 (br d, J = 12.9 Hz, 0.5 H), 3.41 (br t, J = 11.5 Hz, 0.5 H), 3.64 (br d, J = 12.7 Hz, 0.5 H), 3.72-3.90 (m, 1 H), 4.04 (br d, J = 13.7 Hz, 0.5 H), 4.16 (br d, J = 12.4 Hz, 1.5 H), 4.25-4.36 (m, 0.5 H), 4.42 (br d, J = 12.9 Hz, 0.5 H), 4.95 (br s, 1 H), 5.70-5.81 (m, 1 H), 6.21 (br d, J = 16.4 Hz, 1 H), 6.77 (dd, J = 8.7, 3.1 Hz, 1 H), 6.85 (dd, J = 9.0, 4.7 Hz, 1 H), 7.04-7.10 (m, 1 H), 7.12 (d, J = 8.1 Hz, 1 H), 7.21-7.27 (m, 1 H), 7.36 (t, J = 7.4 Hz, 1 H), 7.41-7.46 (m, 1 H), 8.35 (br s, 1 H), 9.80 (br s, 1 H). $^{19}$F NMR (376 MHz, DMSO-$d_6$) δ ppm −126.12 (s, 1 F). |
| 54-79 | 578.0 | $^1$H NMR (400 MHz, DMSO-$d_6$) δ ppm 0.97 (dd, J = 16.2, 6.8 Hz, 3 H), 1.07 (dd, J = 6.6, 4.4 Hz, 3 H), 1.29-1.40 (m, 3 H), 2.52-2.61 (m, 1 H), 2.99-3.18 (m, 0.5 H), 3.22-3.27 (m, 0.5 H), 3.37-3.56 (m, 0.5 H), 3.59-3.73 (m, 1 H), 3.75-3.87 (m, 0.5 H), 3.96-4.08 (m, 0.5 H), 4.10-4.23 (m, 1 H), 4.29 (br d, J = 13.1 Hz, 1 H), 4.41 (br d, J = 11.8 Hz, 0.5 H), 4.75-4.89 (m, 0.5 H), 4.94 (br s, 0.5 H), 5.72-5.80 (m, 1 H), 6.15-6.27 (m, 1 H), 6.77-6.85 (m, 1 H), 6.90 (br t, J = 8.3 Hz, 1 H), 7.02-7.10 (m, 1 H), 7.16-7.26 (m, 2 H), 7.32 (t, J = 7.4 Hz, 1 H), 7.35-7.42 (m, 1 H), 8.32-8.43 (m, 1 H), 10.01 (br s, 0.5 H), 10.05 (br s, 0.5 H). |
| 54-80 | 472.2 | $^1$H NMR (400 MHz, DMSO-$d_6$) δ ppm 8.51 (s, 1 H), 7.37-7.55 (m, 2 H), 7.29 (td, J = 7.6, 1.5 Hz, 1 H), 7.10 (dd, J = 7.9, 1.0 Hz, 1 H), 6.83 (dd, J = 16.7, 10.5 Hz, 1 H), 6.18 (dd, J = 16.7, 2.4 Hz, 1 H), 5.66-5.85 (m, 1 H), 3.89-4.04 (m, 4 H), 3.68-3.87 (m, 4 H), 3.33 (br s, 1 H), 1.06-1.11 (m, 3 H), 0.99-1.04 (m, 3 H). |
| 54-82 | 562.2 | $^1$H NMR (400 MHz, DMSO-$d_6$) δ ppm 8.38 (br s, 1 H), 7.19-7.32 (m, 2 H), 7.08-7.19 (m, 2 H), 6.79-6.97 (m, 3 |

TABLE 88-continued

Analytical Data

| Ex. # | LRMS: m/z (ESI, +ve ion): (M + H)+ | NMR |
|---|---|---|
| | | H), 6.70-6.78 (m, 2 H), 6.20 (br d, J = 16.8 Hz, 1 H), 5.70-5.81 (m, 1 H), 4.75-4.96 (m, 1 H), 4.23-4.44 (m, 1 H), 3.96-4.21 (m, 2 H), 3.36-3.78 (m, 2 H), 2.97-3.26 (m, 1 H), 2.36-2.47 (m, 1 H), 1.29 (t, J = 6.8 Hz, 3 H), 1.01 (d, J = 6.6 Hz, 3 H), 0.75 (d, J = 6.8 Hz, 3 H). |
| 54-84 | 562.1 | $^1$H NMR (400 MHz, DMSO-$d_6$) δ ppm 8.30-8.51 (m, 1 H), 7.50-7.57 (m, 1 H), 7.44-7.49 (m, 1 H), 7.37-7.43 (m, 2 H), 7.30-7.35 (m, 1 H), 7.17-7.29 (m, 2 H), 7.07-7.15 (m, 1 H), 6.78-6.93 (m, 1 H), 6.22 (br d, J = 16.6 Hz, 1 H), 5.68-5.83 (m, 1 H), 4.74-5.08 (m, 1 H), 3.95-4.46 (m, 3 H), 3.38-3.89 (m, 2 H), 3.01-3.28 (m, 1 H), 2.53-2.60 (m, 1 H), 1.34 (dd, J = 16.6, 6.6 Hz, 3 H), 1.08 (d, J = 6.8 Hz, 3 H), 0.98 (dd, J = 6.7, 1.6 Hz, 3 H). |
| 54-84-1 | 562.2 | $^1$H NMR (400 MHz, DMSO-$d_6$)) δ ppm 8.39 (br d, J = 4.8 Hz, 1 H), 7.50-7.55 (m, 1 H), 7.45 (td, J = 7.7, 1.7 Hz, 1 H), 7.36-7.43 (m, 2 H), 7.29-7.35 (m, 1 H), 7.18-7.25 (m, 2 H), 7.07-7.12 (m, 1 H), 6.79-6.94 (m, 1 H), 6.21 (br d, J = 17.4 Hz, 1 H), 5.76 (dd, J = 10.4, 2.3 Hz, 1 H), 4.85 (br s, 1 H), 4.24-4.49 (m, 2 H), 3.96-4.22 (m, 1 H), 3.43-3.79 (m, 2 H), 3.13-3.24 (m, 1 H), 2.53-2.60 (m, 1 H), 1.35 (d, J = 6.6 Hz, 3 H), 1.07 (d, J = 6.8 Hz, 3 H), 0.97 (d, J = 6.8 Hz, 3 H). |
| 54-84-2 | 562.2 | $^1$H NMR (400 MHz, DMSO-$d_6$) δ ppm 8.45 (br s, 1 H), 7.51-7.57 (m, 1 H), 7.46 (td, J = 7.7, 1.9 Hz, 1 H), 7.37-7.43 (m, 2 H), 7.30-7.36 (m, 1 H), 7.17-7.26 (m, 2 H), 7.04-7.15 (m, 1 H), 6.79-6.94 (m, 1 H), 6.22 (br d, J = 16.6 Hz, 1 H), 5.73-5.80 (m, 1 H), 4.97 (br s, 1 H), 4.27-4.46 (m, 2 H), 4.01-4.23 (m, 2 H), 3.59-3.90 (m, 2 H), 2.98-3.28 (m, 1 H), 2.54-2.60 (m, 1 H), 1.32 (br d, J = 6.6 Hz, 3 H), 1.08 (d, J = 6.8 Hz, 3 H), 0.99 (d, J = 6.8 Hz, 3 H). |
| 54-85 | 564.2 | $^1$H NMR (400 MHz, DMSO-$d_6$) δ ppm 8.30-8.51 (m, 1 H), 7.41-7.47 (m, 1 H), 7.32-7.41 (m, 2 H), 7.22-7.30 (m, 2 H), 7.15-7.22 (m, 1 H), 7.12 (d, J = 7.9 Hz, 1 H), 6.78-6.94 (m, 1 H), 6.14-6.28 (m, 1 H), 5.74-5.79 (m, 1 H), 4.79-5.03 (m, 1 H), 3.97-4.47 (m, 3 H), 3.56-3.88 (m, 2 H), 3.38-3.54 (m, 1 H), 2.54-2.61 (m, 1 H), 1.34 (dd, J = 15.5, 6.6 Hz, 3 H), 1.09 (d, J = 6.8 Hz, 3 H), 0.98 (dd, J = 6.8, 2.1 Hz, 3 H). |
| 54-85-1 | 564.2 | $^1$H NMR (400 MHz, DMSO-$d_6$) δ ppm 8.37 (br d, J = 5.8 Hz, 1 H), 7.31-7.45 (m, 3 H), 7.14-7.31 (m, 3 H), 7.12 (dd, J = 7.9, 1.0 Hz, 1 H), 6.78-6.93 (m, 1 H), 6.14-6.26 (m, 1 H), 5.73-5.80 (m, 1 H), 4.85 (br d, J = 1.0 Hz, 1 H), 4.24-4.48 (m, 2 H), 3.97-4.20 (m, 1 H), 3.40-3.78 (m, 2 H), 3.19-3.27 (m, 1 H), 2.54-2.62 (m, 1 H), 1.35 (d, J = 6.6 Hz, 3 H), 1.08 (d, J = 6.8 Hz, 3 H), 0.96 (d, J = 6.8 Hz, 3 H). $^{19}$F NMR (376 MHz, DMSO-$d_6$) δ ppm −107.14 (d, J = 8.7 Hz, 1 F), −109.05 (br d, J = 8.7 Hz, 1 F). |
| 54-85-2 | 564.2 | $^1$H NMR (400 MHz, DMSO-$d_6$) δ ppm 8.43 (br s, 1 H), 7.32-7.47 (m, 3 H), 7.14-7.31 (m, 3 H), 7.08-7.14 (m, 1 H), 6.77-6.94 (m, 1 H), 6.13-6.26 (m, 1 H), 5.76 (dd, J = 10.5, 2.4 Hz, 1 H), 4.96 (br s, 1 H), 3.97-4.46 (m, 3 H), 3.36- |

TABLE 88-continued

Analytical Data

| Ex. # | LRMS: m/z (ESI, +ve ion): (M + H)+ | NMR |
|---|---|---|
| | | 3.89 (m, 2 H), 2.98-3.28 (m, 1 H), 2.53-2.58 (m, 1 H), 1.31 (br d, J = 6.6 Hz, 3 H), 1.08 (d, J = 6.8 Hz, 3 H), 0.97 (d, J = 6.8 Hz, 3 H). $^{19}$F NMR (376 MHz, DMSO-d$_6$) δ ppm −107.17 (br d, J = 8.7 Hz, 1 F), −109.12 (br d, J = 8.7 Hz, 1 F) |
| 54-86 | 546.2 | $^1$H NMR (400 MHz, DMSO-d$_6$) δ ppm 8.29-8.52 (m, 1 H), 7.37-7.62 (m, 2 H), 7.15-7.37 (m, 5 H), 7.12 (br d, J = 6.6 Hz, 1 H), 6.74-6.96 (m, 1 H), 6.09-6.29 (m, 1 H), 5.76 (br d, J = 9.5 Hz, 1 H), 4.78-5.04 (m, 1 H), 3.95-4.48 (m, 3 H), 3.41-3.90 (m, 2 H), 2.94-3.18 (m, 1 H), 2.56-2.62 (m, 1 H), 1.27-1.40 (m, 3 H), 1.08 (br d, J = 5.8 Hz, 3 H), 0.98 (br d, J = 4.8 Hz, 3 H). $^{19}$F NMR (376 MHz, DMSO-d$_6$) δ ppm −113.69 (br s, 1 F). |
| 54-86-1 | 546.2 | $^1$H NMR (400 MHz, DMSO-d$_6$) δ ppm 8.36 (br d, J = 5.0 Hz, 1 H), 7.46-7.54 (m, 1 H), 7.37-7.44 (m, 1 H), 7.16-7.37 (m, 5 H), 7.11 (dd, J = 7.9, 1.0 Hz, 1 H), 6.77-6.93 (m, 1 H), 6.21 (br d, J = 16.6 Hz, 1 H), 5.71-5.80 (m, 1 H), 4.85 (br d, J = 1.2 Hz, 1 H), 4.23-4.46 (m, 2 H), 3.92-4.20 (m, 1 H), 3.39-3.78 (m, 2 H), 3.05-3.26 (m, 1 H), 2.53-2.61 (m, 1 H), 1.35 (d, J = 6.6 Hz, 3 H), 1.07 (d, J = 6.8 Hz, 3 H), 0.97 (d, J = 6.8 Hz, 3 H). $^{19}$F NMR (376 MHz, DMSO-d$_6$) δ ppm −113.69 (s, 1 F). |
| 54-86-2 | 546.2 | $^1$H NMR (400 MHz, DMSO-d$_6$) δ ppm 8.42 (br s, 1 H), 7.46-7.55 (m, 1 H), 7.39-7.44 (m, 1 H), 7.16-7.37 (m, 5 H), 7.12 (dd, J = 7.8, 0.9 Hz, 1 H), 6.80-6.95 (m, 1 H), 6.21 (br d, J = 16.4 Hz, 1 H), 5.73-5.79 (m, 1 H), 4.97 (br s, 1 H), 4.24-4.49 (m, 1 H), 3.98-4.23 (m, 2 H), 3.37-3.86 (m, 2 H), 2.97-3.25 (m, 1 H), 2.53-2.58 (m, 1 H), 1.31 (br d, J = 6.6 Hz, 3 H), 1.08 (d, J = 6.8 Hz, 3 H), 0.98 (d, J = 6.8 Hz, 3 H). $^{19}$F NMR (376 MHz, DMSO-d$_6$) δ ppm −113.76 (s, 1 F). |
| 54-87 | 622.1 | $^1$H NMR (400 MHz, DMSO-d$_6$) δ ppm 9.95 (s, 1 H), 8.39 (br d, J = 14.9 Hz, 1 H), 7.37-7.46 (m, 2 H), 7.33 (t, J = 7.5 Hz, 1 H), 7.23 (t, J = 7.2 Hz, 1 H), 7.09 (d, J = 7.7 Hz, 1 H), 6.79-6.93 (m, 1 H), 6.76 (dd, J = 8.7, 2.9 Hz, 1 H), 6.54 (d, J = 2.7 Hz, 1 H), 6.21 (br d, J = 16.2 Hz, 1 H), 5.71-5.81 (m, 1 H), 4.78-5.03 (m, 1 H), 3.95-4.48 (m, 3 H), 3.38-3.88 (m, 2 H), 2.98-3.23 (m, 1 H), 2.54-2.62 (m, 1 H), 1.33 (br dd, J = 13.4, 6.5 Hz, 3 H), 1.07 (d, J = 6.6 Hz, 3 H), 0.99 (br d, J = 6.4 Hz, 3 H). |
| 54-88 | 562.2 | $^1$H NMR (400 MHz, DMSO-d$_6$) δ ppm 9.61 (s, 1 H), 8.27-8.43 (m, 1 H), 7.38-7.48 (m, 1 H), 7.30-7.38 (m, 1 H), 7.19-7.28 (m, 1 H), 7.02-7.15 (m, 2 H), 6.78-6.93 (m, 2 H), 6.50 (dd, J = 5.7, 3.0 Hz, 1 H), 6.21 (br d, J = 16.6 Hz, 1 H), 5.71-5.81 (m, 1 H), 4.77-5.04 (m, 1 H), 3.97-4.45 (m, 2 H), 3.38-3.87 (m, 2 H), 2.94-3.27 (m, 1 H), 2.53-2.60 (m, 1 H), 1.33 (br dd, J = 18.2, 6.6 Hz, 3 H), 1.08 (d, J = 6.8 Hz, 3 H), 0.98 (dd, J = 6.7, 2.0 Hz, 3 H). $^{19}$F NMR (376 MHz, DMSO-d$_6$) δ ppm −126.97 (s, 1 F), −127.03 (s, 1 F). |
| 54-88-1 | 562.1 | $^1$H NMR (400 MHz, DMSO-d$_6$) δ ppm 9.66 (br d, J = 1.0 Hz, 1 H), 8.40 (br s, 1 H), 7.40-7.47 (m, 1 H), 7.33-7.40 (m, 1 H), 7.25 (td, J = 7.5, 1.5 Hz, 1 H), 7.03- |

TABLE 88-continued

Analytical Data

| Ex. # | LRMS: m/z (ESI, +ve ion): $(M + H)^+$ | NMR |
|---|---|---|
| | | 7.16 (m, 2 H), 6.77-6.94 (m, 2 H), 6.51 (dd, J = 5.8, 3.1 Hz, 1 H), 6.21 (br d, J = 15.5 Hz, 1 H), 5.73-5.81 (m, 1 H), 4.97 (br s, 1 H), 4.01-4.45 (m, 3 H), 3.38-3.89 (m, 2 H), 3.21-3.28 (m, 1 H), 2.61 (br s, 1 H), 1.31 (br d, J = 6.4 Hz, 3 H), 1.09 (d, J = 6.8 Hz, 3 H), 0.99 (d, J = 6.8 Hz, 3 H). $^{19}$F NMR (376 MHz, DMSO-$d_6$) δ ppm −127.06 (br s, 1 F). |
| 54-88-2 | 562.1 | $^1$H NMR (400 MHz, DMSO-$d_6$) δ ppm 9.67 (br s, 1 H), 8.34 (br d, J = 5.6 Hz, 1 H), 7.40-7.48 (m, 1 H), 7.32-7.39 (m, 1 H), 7.25 (td, J = 7.6, 1.5 Hz, 1 H), 7.02-7.17 (m, 2 H), 6.76-6.94 (m, 2 H), 6.51 (dd, J = 5.8, 3.1 Hz, 1 H), 6.22 (br d, J = 16.6 Hz, 1 H), 5.72-5.81 (m, 1 H), 4.84 (br s, 1 H), 4.25-4.45 (m, 2 H), 3.96-4.23 (m, 1 H), 3.40-3.76 (m, 2 H), 3.19-3.26 (m, 1 H), 2.55-2.63 (m, 1 H), 1.36 (d, J = 6.6 Hz, 3 H), 1.09 (d, J = 6.8 Hz, 3 H), 0.98 (d, J = 6.8 Hz, 3 H). $^{19}$F NMR (376 MHz, DMSO-$d_6$) δ ppm −127.02 (br s, 1 F). |
| 54-89 | 592.2 | $^1$H NMR (400 MHz, DMSO-$d_6$) δ ppm 8.33-8.49 (m, 1 H), 7.37-7.47 (m, 2 H), 7.33 (t, J = 7.5 Hz, 1 H), 7.23 (td, J = 7.5, 1.5 Hz, 1 H), 7.10 (d, J = 7.9 Hz, 1 H), 7.03 (dd, J = 8.9, 2.9 Hz, 1 H), 6.78-6.94 (m, 1 H), 6.73 (d, J = 3.1 Hz, 1 H), 6.11-6.27 (m, 1 H), 5.69-5.87 (m, 1 H), 4.76-5.02 (m, 1 H), 3.96-4.46 (m, 3 H), 3.74-3.88 (m, 1 H), 3.70 (s, 3 H), 3.39-3.65 (m, 1 H), 2.96-3.19 (m, 1 H), 2.54-2.60 (m, 1 H), 1.28-1.39 (m, 3 H), 1.07 (d, J = 6.8 Hz, 3 H), 1.00 (br d, J = 6.8 Hz, 3 H). |
| 54-90 | 578.2 | $^1$H NMR (400 MHz, DMSO-$d_6$) δ ppm 9.93 (s, 1 H), 8.28-8.50 (m, 1 H), 7.38-7.45 (m, 1 H), 7.34 (t, J = 7.5 Hz, 1 H), 7.19-7.29 (m, 2 H), 7.10 (br d, J = 7.9 Hz, 1 H), 6.74-6.96 (m, 2 H), 6.54 (dd, J = 2.6, 1.8 Hz, 1 H), 6.21 (br d, J = 16.0 Hz, 1 H), 5.71-5.81 (m, 1 H), 4.76-5.04 (m, 1 H), 3.97-4.46 (m, 3 H), 3.39-3.91 (m, 2 H), 3.00-3.28 (m, 1 H), 2.54-2.65 (m, 1 H), 1.34 (br dd, J = 17.3, 6.5 Hz, 3 H), 1.08 (d, J = 6.8 Hz, 3 H), 0.99 (br d, J = 6.0 Hz, 3 H). |
| 54-90-1 | 578.2 | $^1$H NMR (400 MHz, DMSO-$d_6$) δ ppm 9.85-10.11 (m, 1 H), 8.42 (br s, 1 H), 7.38-7.45 (m, 1 H), 7.34 (t, J = 7.0 Hz, 1 H), 7.19-7.31 (m, 2 H), 7.10 (d, J = 7.9 Hz, 1 H), 6.78-6.93 (m, 2 H), 6.54 (d, J = 2.9 Hz, 1 H), 6.21 (br d, J = 15.5 Hz, 1 H), 5.77 (dd, J = 10.5, 2.2 Hz, 1 H), 4.96 (br s, 1 H), 4.26-4.47 (m, 1 H), 3.99-4.24 (m, 2 H), 3.39-3.92 (m, 2 H), 2.95-3.20 (m, 1 H), 2.55-2.61 (m, 1 H), 1.32 (br d, J = 6.2 Hz, 3 H), 1.08 (d, J = 6.8 Hz, 3 H), 0.99 (br d, J = 6.8 Hz, 3 H) |
| 54-90-2 | 578.2 | $^1$H NMR (400 MHz, DMSO-$d_6$) δ ppm 9.97 (br d, J = 2.5 Hz, 1 H), 8.35 (br d, J = 5.6 Hz, 1 H), 7.37-7.43 (m, 1 H), 7.30-7.37 (m, 1 H), 7.18-7.29 (m, 2 H), 7.09 (d, J = 7.7 Hz, 1 H), 6.78-6.95 (m, 2 H), 6.53 (d, J = 2.9 Hz, 1 H), 6.21 (br d, J = 16.8 Hz, 1 H), 5.72-5.82 (m, 1 H), 4.83 (br s, 1 H), 4.23-4.46 (m, 2 H), 3.97-4.21 (m, 1 H), 3.45-3.77 (m, 2 H), 3.08-3.26 (m, 1 H), 2.54-2.60 (m, 1 H), 1.35 (d, J = 6.8 Hz, 3 H), 1.07 (d, J = 6.8 Hz, 3 H), 0.98 (br d, J = 6.8 Hz, 3 H). |

TABLE 88-continued

Analytical Data

| Ex. # | LRMS: m/z (ESI, +ve ion): $(M + H)^+$ | NMR |
|---|---|---|
| 54-91 | 612.0 | $^1$H NMR (400 MHz, DMSO-d$_6$) δ ppm 10.64 (br s, 1 H), 8.31-8.48 (m, 1 H), 7.37-7.47 (m, 1 H), 7.34 (t, J = 7.5 Hz, 1 H), 7.23 (t, J = 7.5 Hz, 1 H), 7.09 (br d, J = 7.9 Hz, 1 H), 7.03 (d, J = 2.3 Hz, 1 H), 6.77-6.95 (m, 1 H), 6.52 (s, 1 H), 6.21 (br d, J = 17.0 Hz, 1 H), 5.72-5.82 (m, 1 H), 4.76-5.02 (m, 1 H), 3.95-4.48 (m, 3 H), 3.37-3.90 (m, 2 H), 2.96-3.20 (m, 1 H), 2.62 (br s, 1 H), 1.33 (br dd, J = 16.4, 6.6 Hz, 3 H), 1.07 (d, J = 6.8 Hz, 3 H), 0.97 (br d, J = 5.8 Hz, 3 H). |
| 54-91-1 | 612.0 | $^1$H NMR (400 MHz, DMSO-d$_6$) δ ppm 10.60 (br s, 1 H), 8.43 (br s, 1 H), 7.38-7.44 (m, 1 H), 7.31-7.37 (m, 1 H), 7.23 (td, J = 7.5, 1.5 Hz, 1 H), 7.09 (d, J = 7.9 Hz, 1 H), 7.03 (d, J = 2.7 Hz, 1 H), 6.79-6.93 (m, 1 H), 6.53 (d, J = 2.7 Hz, 1 H), 6.15-6.26 (m, 1 H), 5.69-5.82 (m, 1 H), 4.96 (br s, 1 H), 3.98-4.46 (m, 3 H), 3.38-3.91 (m, 2 H), 2.96-3.23 (m, 1 H), 2.53-2.60 (m, 1 H), 1.31 (br d, J = 6.6 Hz, 3 H), 1.07 (d, J = 6.6 Hz, 3 H), 0.97 (br d, J = 6.0 Hz, 3 H). |
| 54-91-2 | 612.0 | $^1$H NMR (400 MHz, DMSO-d$_6$) δ ppm 10.37-10.89 (br s, 1 H), 8.38 (br d, J = 5.0 Hz, 1 H), 7.37-7.44 (m, 1 H), 7.29-7.37 (m, 1 H), 7.23 (td, J = 7.6, 1.5 Hz, 1 H), 7.09 (d, J = 7.7 Hz, 1 H), 7.03 (d, J = 2.7 Hz, 1 H), 6.77-6.95 (m, 1 H), 6.53 (d, J = 2.9 Hz, 1 H), 6.21 (br d, J = 16.4 Hz, 1 H), 5.71-5.80 (m, 1 H), 4.84 (br d, J = 3.7 Hz, 1 H), 4.23-4.45 (m, 2 H), 3.94-4.21 (m, 1 H), 3.41-3.80 (m, 2 H), 3.07-3.26 (m, 1 H), 2.53-2.60 (m, 1 H), 1.35 (d, J = 6.6 Hz, 3 H), 1.07 (d, J = 6.8 Hz, 3 H), 0.97 (br d, J = 6.2 Hz, 3 H). |
| 54-92 | 547.1 | $^1$H NMR (400 MHz, DMSO-d$_6$) δ ppm 8.41 (2 H, m), 7.79-7.91 (1 H, m), 7.58 (1 H, dt, J = 8.6, 4.4 Hz), 7.36-7.46 (1 H, m), 7.32 (1 H, t, J = 7.4 Hz), 7.18-7.25 (1 H, m), 7.06-7.15 (1 H, m), 6.76-6.97 (1 H, m), 6.21 (1 H, br dd, J = 15.8, 3.9 Hz), 5.72-5.80 (1 H, m), 4.77-5.06 (1 H, m), 3.95-4.50 (3 H, m), 3.43-3.92 (2 H, m), 2.97-3.23 (1 H, m), 2.58 (1 H, m), 1.29-1.40 (3 H, m), 1.06 (3 H, d, J = 6.8 Hz), 0.97 (3 H, d, J = 6.8 Hz). $^{19}$F NMR (376 MHz, DMSO-d$_6$) δ ppm −123.46 (s, 1 F). |
| 54-93 | 565.1 | $^1$H NMR (400 MHz, DMSO-d$_6$) δ ppm 8.58 (1 H, d, J = 2.1 Hz), 8.30-8.53 (1 H, m), 8.09 (1 H, td, J = 9.3, 2.3 Hz), 7.37-7.47 (1 H, m), 7.27-7.37 (1 H, m), 7.19-7.26 (1 H, m), 7.10 (1 H, dd, J = 7.5, 3.5 Hz), 6.78-6.93 (1 H, m), 6.14-6.27 (1 H, m), 5.73-5.80 (1 H, m), 4.76-5.04 (1 H, m), 4.01-4.43 (3 H, m), 3.38-3.88 (2 H, m), 3.20-3.29 (1 H, m), 2.54-2.60 (1 H, m), 1.29-1.40 (3 H, m), 1.06 (3 H, d, J = 6.8 Hz), 0.97 (3 H, d, J = 6.8 Hz). $^{19}$F NMR (376 MHz, DMSO-d$_6$) δ ppm −119.09 (dd, J = 7.8, 4.3 Hz, 1 F), −120.99-−120.85 (m, 1 F). |
| 54-94 | 563.2 | $^1$H NMR (400 MHz, DMSO-d$_6$) δ ppm 8.56 (dt, J = 4.6, 1.2 Hz, 1 H), 8.37-8.51 (m, 1 H), 8.05 (dd, J = 8.3, 1.2 Hz, 1 H), 7.52 (dd, J = 8.2, 4.7 Hz, 1 H), 7.35-7.41 (m, 1 H), 7.32 (t, J = 7.2 Hz, 1 H), 7.17-7.26 (m, 1 H), 7.06-7.13 (m, 1 H), 6.77-6.94 (m, 1 H), 6.15-6.29 (m, 1 H), 5.71-5.82 (m, 1 H), 4.79-5.05 (m, 1 H), 4.03-4.45 (m, 3 H), 3.39-3.87 (m, 2 H), |

TABLE 88-continued

| | Analytical Data | |
|---|---|---|
| Ex. # | LRMS: m/z (ESI, +ve ion): $(M + H)^+$ | NMR |
| | | 2.99-3.29 (m, 1 H), 2.52-2.57 (m, 1 H), 1.34 (br dd, J = 15.8, 6.6 Hz, 3 H), 1.07 (d, J = 6.8 Hz, 3 H), 0.97 (d, J = 6.2 Hz, 3 H). |
| 54-95 | 578.2 | $^1$H NMR (400 MHz, DMSO-$d_6$) δ ppm 8.34-8.48 (m, 1 H), 7.96 (s, 1 H), 7.39-7.45 (m, 1 H), 7.32-7.39 (m, 1 H), 7.24 (t, J = 7.5 Hz, 1 H), 7.10 (br d, J = 7.9 Hz, 1 H), 6.78-6.96 (m, 1 H), 6.34 (s, 2 H), 6.16-6.26 (m, 2 H), 5.73-5.82 (m, 1 H), 4.78-5.04 (m, 1 H), 4.07-4.49 (m, 3 H), 3.36-3.93 (m, 2 H), 2.97-3.28 (m, 1 H), 2.53-2.61 (m, 1 H), 1.34 (dd, J = 15.5, 6.6 Hz, 3 H), 1.08 (d, J = 6.8 Hz, 3 H), 0.97 (d, J = 6.8 Hz, 3 H). |
| 54-96 | 544.3 | $^1$H NMR (400 MHz, DMSO-$d_6$) δ ppm 8.36 (br s, 1 H), 7.98 (dd, J = 4.9, 1.8 Hz, 1 H), 7.42-7.54 (m, 2 H), 7.33-7.42 (m, 1 H), 7.26 (td, J = 7.5, 1.5 Hz, 1 H), 7.11-7.17 (m, 1 H), 6.79-6.94 (m, 1 H), 6.58 (ddd, J = 7.6, 4.9, 0.8 Hz, 1 H), 6.13-6.27 (m, 1 H), 5.81 (s, 1 H), 4.90 (br s, 1 H), 3.98-4.48 (m, 3 H), 3.38-3.82 (m, 2 H), 3.01-3.13 (m, 1 H), 2.55-2.65 (m, 1 H), 1.29-1.37 (m, 3 H), 1.09 (d, J = 6.8 Hz, 3 H), 0.95 (dd, J = 6.8, 2.7 Hz, 3 H). |
| 54-97 | 574.1 | $^1$H NMR (400 MHz, DMSO-$d_6$) δ ppm 10.05 (br s, 1 H), 8.24-8.54 (m, 1 H), 7.35-7.48 (m, 1 H), 7.15-7.34 (m, 3 H), 7.07 (br d, J = 5.8 Hz, 1 H), 6.75-6.95 (m, 1 H), 6.56-6.74 (m, 2 H), 6.19 (br d, J = 16.4 Hz, 1 H), 5.71-5.78 (m, 1 H), 4.71-5.04 (m, 1 H), 3.97-4.50 (m, 3 H), 3.44-3.77 (m, 2 H), 3.07-3.29 (m, 1 H), 1.38 (br d, J = 6.4 Hz, 2 H), 1.02 (s, 3 H), 0.61-0.74 (m, 1 H), 0.41-0.55 (m, 1 H), 0.33-0.41 (m, 1 H), 0.26 (br s, 1 H). $^{19}$F NMR (376 MHz, DMSO-$d_6$) δ ppm −115.42 (br d, J = 29.5 Hz, 1 F). |
| 54-97-1 | 574.2 | $^1$H NMR (400 MHz, DMSO-$d_6$) δ ppm 10.05 (br s, 1 H), 8.45 (s, 1 H), 7.35-7.49 (m, 1 H), 7.16-7.35 (m, 1 H), 7.07 (br d, J = 6.8 Hz, 1 H), 6.76-6.94 (m, 1 H), 6.58-6.75 (m, 2 H), 6.20 (br dd, J = 16.6, 3.7 Hz, 1 H), 5.71-5.81 (m, 1 H), 4.91 (br s, 1 H), 4.26-4.52 (m, 1 H), 3.96-4.24 (m, 2 H), 3.37-3.82 (m, 2 H), 2.85-3.13 (m, 1 H), 1.26 (br s, 3 H), 1.02 (s, 3 H), 0.62-0.74 (m, 1 H), 0.33-0.58 (m, 2 H), 0.27 (br d, J = 3.3 Hz, 1 H). $^{19}$F NMR (376 MHz, DMSO-$d_6$) δ ppm −115.42 (1 F, br d, J = 29.5 Hz). |
| 54-97-2 | 574.2 | $^1$H NMR (400 MHz, DMSO-$d_6$) δ ppm 10.06 (br s, 1 H), 8.35 (br s, 1 H), 7.41 (br d, J = 7.9 Hz, 1 H), 7.13-7.34 (m, 3 H), 7.07 (br d, J = 5.8 Hz, 1 H), 6.75-6.93 (m, 1 H), 6.58-6.72 (m, 2 H), 6.19 (br d, J = 16.6 Hz, 1 H), 5.68-5.84 (m, 1 H), 4.79 (br s, 1 H), 4.19-4.46 (m, 2 H), 3.93-4.19 (m, 1 H), 3.45-3.75 (m, 2 H), 3.07-3.25 (m, 1 H), 1.38 (br d, J = 6.2 Hz, 3 H), 1.02 (s, 3 H), 0.67 (br d, J = 3.7 Hz, 1 H), 0.31-0.58 (m, 2 H), 0.26 (br s, 1 H). $^{19}$F NMR (376 MHz, DMSO-d6) δ ppm −115.39 (1 F, br s). |
| 54-98 | 498.2 | $^1$H NMR (400 MHz, DMSO-$d_6$) δ ppm 8.33-8.61 (m, 1 H), 7.49 (dd, J = 7.5, 1.5 Hz, 1 H), 7.37 (dtd, J = 18.5, 7.5, 7.5, 1.5 Hz, 2 H), 7.14 (dd, J = 7.5, 1.7 Hz, 1 H), 6.70-6.96 (m, 1 H), 6.19 (br d, J = 16.8 Hz, 1 H), 5.75 (br d, J = 10.6 Hz, 1 H), 4.66-4.99 (m, 1 H), 3.87-4.50 (m, 3 H), 3.23-3.80 (m, 3 H), 1.34 (d, J = 6.6 |

TABLE 88-continued

Analytical Data

| Ex. # | LRMS: m/z (ESI, +ve ion): (M + H)+ | NMR |
|---|---|---|
| | | Hz, 3 H), 1.03 (d, J = 2.9 Hz, 3 H), 0.66-0.79 (m, 1 H), 0.26-0.54 (m, 3 H). |
| 54-99 | 558.2 | $^1$H NMR (400 MHz, DMSO-d$_6$) δ ppm 8.34-8.55 (m, 1 H), 7.46-7.57 (m, 1 H), 7.39-7.45 (m, 1 H), 7.17-7.35 (m, 5 H), 7.11-7.17 (m, 1 H), 6.76-6.96 (m, 1 H), 6.20 (br d, J = 16.4 Hz, 1 H), 5.76 (dd, J = 10.7, 1.8 Hz, 1 H), 4.74-5.00 (m, 1 H), 3.90-4.52 (m, 3 H), 3.36-3.81 (m, 2 H), 2.89-3.27 (m, 1 H), 1.21-1.44 (m, 3 H), 1.01 (s, 3 H), 0.70 (dt, J = 6.0, 2.7 Hz, 1 H), 0.27-0.48 (m, 3 H). $^{19}$F NMR (376 MHz, DMSO-d$_6$) δ ppm −113.60 (1 F, s), −113.62 (1 F, br s). |
| 54-99-1 | 558.2 | $^1$H NMR (400 MHz, DMSO-d$_6$) δ ppm 8.48 (br s, 1 H), 7.47-7.57 (m, 1 H), 7.43 (br d, J = 6.6 Hz, 1 H), 7.17-7.33 (m, 5 H), 7.14 (br d, J = 6.6 Hz, 1 H), 6.76-6.95 (m, 1 H), 6.20 (br d, J = 16.6 Hz, 1 H), 5.76 (br d, J = 10.4 Hz, 1 H), 4.93 (br s, 1 H), 3.95-4.54 (m, 3 H), 3.34-3.83 (m, 2 H), 2.85-3.20 (m, 1 H), 1.26 (br s, 3 H), 1.02 (s, 3 H), 0.70 (br d, J = 7.0 Hz, 1 H), 0.41 (br t, J = 9.2 Hz, 2 H), 0.29-0.36 (m, 1 H). $^{19}$F NMR (377 MHz, DMSO-d$_6$) δ ppm −113.60 (1 F, s) |
| 54-99-2 | 558.2 | $^1$H NMR (400 MHz, DMSO-d$_6$) δ ppm 8.39 (br s, 1 H), 7.46-7.55 (m, 1 H), 7.42 (br d, J = 6.2 Hz, 1 H), 7.18-7.36 (m, 5 H), 7.15 (br d, J = 6.4 Hz, 1 H), 6.75-6.93 (m, 1 H), 6.20 (br d, J = 16.8 Hz, 1 H), 5.76 (br d, J = 10.0 Hz, 1 H), 4.81 (br s, 1 H), 3.91-4.43 (m, 3 H), 3.42-3.75 (m, 2 H), 3.11-3.25 (m, 1 H), 1.38 (br d, J = 6.0 Hz, 3 H), 1.01 (s, 3 H), 0.70 (br d, J = 8.3 Hz, 1 H), 0.40 (br s, 2 H), 0.33 (br d, J = 7.7 Hz, 1 H). $^{19}$F NMR (377 MHz, DMSO-d$_6$) δ ppm −113.61 (1 F, s). |
| 54-100 | 605.0 | $^1$H NMR (400 MHz, DMSO-d$_6$) δ ppm 1.28-1.36 (m, 3 H) 2.52-2.63 (m, 1 H) 2.71 (br d, J = 1.45 Hz, 2 H) 2.96-3.17 (m, 1 H) 3.25 (br d, J = 4.15 Hz, 4 H) 3.36-4.56 (m, 6 H) 4.73-5.00 (m, 1 H) 5.65-5.87 (m, 1 H) 6.20 (br d, J = 16.38 Hz, 1 H) 6.56-6.74 (m, 2 H) 6.76-6.95 (m, 1 H) 7.14-7.28 (m, 4 H) 7.30-7.37 (m, 1 H) 8.39 (br d, J = 11.61 Hz, 1 H) 10.03 (br s, 1 H). |
| 54-101 | 577.0 | $^1$H NMR (400 MHz, DMSO-d$_6$) δ ppm 0.71 (br d, J = 6.63 Hz, 6 H) 1.26-1.40 (m, 3 H) 1.70-1.87 (m, 1 H) 2.08-2.29 (m, 2 H) 3.08-3.28 (m, 1 H) 3.38-3.92 (m, 2 H) 4.04-4.49 (m, 3 H) 4.74-5.13 (m, 1 H) 5.73-5.81 (m, 1 H) 6.14-6.27 (m, 1 H) 6.60-6.72 (m, 2 H) 6.75-6.94 (m, 1 H) 7.17-7.28 (m, 1 H) 7.37 (dd, J = 7.57, 4.66 Hz, 1 H) 7.76 (br d, J = 5.60 Hz, 1 H) 8.31-8.48 (m, 2 H) 9.98-10.18 (m, 1 H). |
| 54-102 | 560.9 | $^1$H NMR (400 MHz, DMSO-d$_6$) δ ppm 0.67-0.77 (m, 6 H) 1.33 (dd, J = 16.79, 6.63 Hz, 3 H) 1.68-1.87 (m, 1 H) 2.15-2.31 (m, 2 H) 3.24-3.86 (m, 4 H) 4.12-4.44 (m, 2 H) 4.80-5.07 (m, 1 H) 5.72-5.80 (m, 1 H) 6.20 (br d, J = 17.21 Hz, 1 H) 6.77-6.95 (m, 1 H) 7.14-7.20 (m, 1 H) 7.22-7.33 (m, 2 H) 7.38 (dd, J = 7.67, 4.77 Hz, 1 H) 7.45-7.56 (m, 1 H) 7.79 (d, J = 6.84 Hz, 1 H) 8.37 (d, J = 4.77 Hz, 1 H) 8.39-8.48 (m, 1 H). |
| 54-103 | 577.0 | $^1$H NMR (400 MHz, DMSO-d$_6$) δ ppm 1.09-1.17 (m, 9 H) 1.23-1.31 (m, 3 H) 3.03-3.27 (m, 1 H) 3.34-3.82 (m, 2 H) 4.04-4.53 (m, 3 H) 4.79-5.00 (m, 1 H) |

TABLE 88-continued

| | Analytical Data | |
|---|---|---|
| Ex. # | LRMS: m/z (ESI, +ve ion): (M + H)+ | NMR |
| | | 5.73-5.80 (m, 1 H) 6.20 (br d, J = 17.21 Hz, 1 H) 6.66 (t, J = 8.81 Hz, 1 H) 6.71 (d, J = 8.50 Hz, 1 H) 6.76-6.92 (m, 1 H) 7.20-7.27 (m, 1 H) 7.30 (dd, J = 7.88, 4.56 Hz, 1 H) 7.47 (br d, J = 5.80 Hz, 1 H) 8.41 (br d, J = 4.56 Hz, 1 H) 8.52 (dd, J = 4.35, 1.45 Hz, 1 H) 10.10 (s, 1 H). |
| 54-103-1 | 577.0 | $^1$H NMR (400 MHz, DMSO-$d_6$) δ ppm 1.13 (s, 9 H) 1.33 (br d, J = 6.43 Hz, 3 H) 3.45-3.80 (m, 2 H) 4.03-4.42 (m, 3 H) 4.89 (br s, 1 H) 5.71-5.81 (m, 1 H) 6.20 (br d, J = 16.79 Hz, 1 H) 6.65 (br t, J = 8.71 Hz, 1 H) 6.70 (d, J = 8.09 Hz, 1 H) 6.77-6.91 (m, 1 H) 7.19-7.27 (m, 1 H) 7.30 (dd, J = 7.77, 4.46 Hz, 1 H) 7.43-7.52 (m, 1 H) 8.40 (br s, 1 H) 8.52 (dd, J = 4.35, 1.45 Hz, 1 H) 10.11 (br s, 1 H). |
| 54-103-2 | 577.0 | $^1$H NMR (400 MHz, DMSO-$d_6$) δ ppm 1.14 (s, 9 H) 1.29 (br s, 3 H) 2.95-3.26 (m, 1 H) 3.37-3.79 (m, 2 H) 4.06-4.51 (m, 3 H) 4.88 (br s, 1 H) 5.73-5.79 (m, 1 H) 6.14-6.26 (m, 1 H) 6.64 (br t, J = 8.81 Hz, 1 H) 6.69 (d, J = 8.29 Hz, 1 H) 6.77-6.94 (m, 1 H) 7.22 (q, J = 7.88 Hz, 1 H) 7.30 (dd, J = 7.77, 4.46 Hz, 1 H) 7.46 (br d, J = 7.46 Hz, 1 H) 8.42 (br s, 1 H) 8.52 (dd, J = 4.46, 1.55 Hz, 1 H) 10.11 (br s, 1 H). |
| 54-104 | 589.1 | 1H NMR (DMSO-d6) δ: 8.42 (br s, 1H), 7.43-7.55 (m, 1H), 7.22-7.32 (m, 3H), 7.12-7.19 (m, 1H), 7.02-7.10 (m, 2H), 6.77-6.94 (m, 1H), 6.20 (br dd, J = 17.3, 3.8 Hz, 1H), 5.76 (dd, J = 10.5, 2.4 Hz, 1H), 4.80-4.99 (m, 1H), 4.21-4.48 (m, 2H), 3.97-4.19 (m, 1H), 3.35-3.82 (m, 2H), 3.00-3.26 (m, 1H), 2.31-2.41 (m, 7H), 1.29-1.35 (m, 3H), 1.08 (d, J = 6.8 Hz, 3H), 0.89 (dd, J = 6.8, 1.9 Hz, 3H). 19F NMR (DMSO-d6) δ: −114.28 (s, 1F), −114.30 (s, 1F) |
| 54-104-1 | 589.1 | 1H NMR (DMSO-d6) δ: 8.41 (br d, J = 7.3 Hz, 1H), 7.45-7.55 (m, 1H), 7.23-7.32 (m, 3H), 7.15 (td, J = 7.5, 1.7 Hz, 1H), 7.07 (t, J = 7.0 Hz, 2H), 6.79-6.93 (m, 1H), 6.16-6.24 (m, 1H), 5.73-5.78 (m, 1H), 4.92 (br s, 1H), 4.23-4.43 (m, 2H), 3.99-4.18 (m, 1H), 3.41-3.79 (m, 2H), 3.03-3.28 (m, 1H), 2.53-2.70 (m, 1H), 2.36 (s, 6H), 1.33 (d, J = 6.8 Hz, 3H), 1.08 (d, J = 6.8 Hz, 3H), 0.89 (d, J = 6.8 Hz, 3H). 19F NMR (DMSO-d6) δ: −114.28 (s, 1F) |
| 54-104-2 | 589.1 | 1H NMR (DMSO-d6) δ: 8.42 (br s, 1H), 7.45-7.54 (m, 1H), 7.23-7.33 (m, 3H), 7.16 (td, J = 7.4, 1.6 Hz, 1H), 7.06 (t, J = 8.1 Hz, 2H), 6.77-6.95 (m, 1H), 6.12-6.28 (m, 1H), 5.74-5.79 (m, 1H), 4.84-4.98 (m, 1H), 4.21-4.48 (m, 2H), 3.99-4.19 (m, 1H), 3.38-3.76 (m, 2H), 3.01-3.28 (m, 1H), 2.53-2.69 (m, 1H), 2.37 (s, 6H), 1.31 (br d, J = 6.4 Hz, 3H), 1.08 (d, J = 6.8 Hz, 3H), 0.90 (d, J = 6.8 Hz, 3H). 19F NMR (DMSO-d6) δ: −114.30 (s, 1F) |
| 54-105 | 590.9 | 1H NMR (DMSO-d6) δ: 8.44 (br d, J = 6.8 Hz, 1H), 7.47-7.58 (m, 1H), 7.20-7.35 (m, 3H), 6.79-6.94 (m, 1H), 6.60 (s, 1H), 6.20 (br dd, J = 16.0, 3.3 Hz, 1H), 5.73-5.80 (m, 1H), 4.83-5.04 (m, 1H), 4.25-4.46 (m, 2H), 3.99-4.20 (m, 1H), 3.84 (s, 3H), 3.59-3.73 (m, 1H), 3.40-3.52 (m, 1H), 2.55-2.71 (m, 2H), 1.86 (d, J = 1.5 Hz, 3H), 1.33 (t, J = 6.9 Hz, 3H), 1.07 (d, J = 6.6 Hz, 3H), 0.93 (d, J = 5.8 |

TABLE 88-continued

Analytical Data

| Ex. # | LRMS: m/z (ESI, +ve ion): (M + H)+ | NMR |
|---|---|---|
| | | Hz, 3H). 19F NMR (DMSO-d6) δ: −114.26 (s, 1F), −114.29 (s, 1F) |
| 54-106 | 550.0 | ¹H NMR (DMSO-d₆) δ: 12.15-12.37 (m, 1H), 8.37 (br d, J = 3.9 Hz, 1H), 7.50-7.63 (m, 1H), 7.23-7.41 (m, 3H), 6.77-6.99 (m, 1H), 6.20 (br dd, J = 17.0, 3.7 Hz, 1H), 5.70-5.81 (m, 1H), 4.79-4.95 (m, 1H), 3.96-4.44 (m, 4H), 3.56-3.78 (m, 2H), 3.02-3.26 (m, 1H), 2.27 (br d, J = 5.6 Hz, 4H), 1.31 (d, J = 6.8 Hz, 3H), 0.95 (t, J = 7.6 Hz, 6H). ¹⁹F NMR (DMSO-d₆) δ: −114.13 (s, 1F) |
| 54-107 | 578.0 | ¹H NMR (DMSO-d₆) δ: 8.75 (s, 1H), 8.40-8.51 (m, 1H), 7.49-7.59 (m, 1H), 7.27-7.37 (m, 2H), 7.19-7.26 (m, 1H), 6.80-6.92 (m, 1H), 6.21 (br d, J = 16.4 Hz, 1H), 5.77 (br d, J = 10.4 Hz, 1H), 4.88-5.08 (m, 1H), 4.26-4.43 (m, 2H), 3.99-4.05 (m, 1H), 3.82 (s, 3H), 3.59-3.79 (m, 1H), 3.35-3.53 (m, 1H), 3.10 (br d, J = 11.4 Hz, 1H), 2.78-2.91 (m, 1H), 1.30-1.38 (m, 3H), 1.10 (br d, J = 6.2 Hz, 3H), 0.97 (br d, J = 6.2 Hz, 3H); ¹⁹F NMR (DMSO-d₆) δ: −116.16--112.75 (m, 1F) |
| 54-107-1 | 578.0 | ¹H NMR (DMSO-d₆) δ: 8.75 (s, 1H), 8.47 (br s, 1H), 7.53 (br d, J = 6.6 Hz, 1H), 7.25-7.38 (m, 2H), 7.19-7.25 (m, 1H), 6.80-6.93 (m, 1H), 6.21 (br d, J = 16.6 Hz, 1H), 5.77 (br d, J = 10.4 Hz, 1H), 5.03 (br s, 1H), 4.26-4.44 (m, 2H), 3.98-4.21 (m, 1H), 3.84-3.91 (m, 1H), 3.82 (s, 3H), 3.39-3.67 (m, 1H), 3.03-3.27 (m, 1H), 2.79-2.92 (m, 1H), 1.33 (br d, J = 6.2 Hz, 3H), 1.10 (br d, J = 6.4 Hz, 3H), 0.97 (br d, J = 6.4 Hz, 3H) 124230-13-1. ¹⁹F NMR (DMSO-d₆) δ: −117.02--111.34 (m, 1F) |
| 54-107-2 | 578.0 | ¹H NMR (DMSO-d₆) δ: 8.75 (s, 1H), 8.44 (br s, 1H), 7.49-7.61 (m, 1H), 7.26-7.37 (m, 2H), 7.17-7.25 (m, 1H), 6.79-6.92 (m, 1H), 6.21 (br d, J = 16.2 Hz, 1H), 5.76 (br d, J = 10.4 Hz, 1H), 4.93 (br s, 1H), 4.26-4.44 (m, 2H), 3.99-4.19 (m, 1H), 3.82 (s, 3H), 3.75 (br d, J = 9.7 Hz, 1H), 3.43-3.68 (m, 1H), 3.08-3.28 (m, 1H), 2.78-2.89 (m, 1H), 1.36 (br d, J = 6.4 Hz, 3H), 1.10 (br d, J = 6.4 Hz, 3H), 0.98 (br d, J = 6.4 Hz, 3H) ¹⁹F NMR (DMSO-d₆) δ: −114.07 (s, 1F) |
| 54-108 | 564.0 | ¹H NMR (DMSO-d₆) δ: 8.43 (br d, J = 13.9 Hz, 1H), 8.21 (s, 1H), 7.51-7.60 (m, 1H), 7.26-7.38 (m, 3H), 6.79-6.92 (m, 1H), 6.14-6.26 (m, 1H), 5.76 (br d, J = 10.6 Hz, 1H), 4.83-5.05 (m, 1H), 4.21-4.43 (m, 2H), 3.95-4.19 (m, 1H), 3.68-3.89 (m, 1H), 3.35-3.66 (m, 1H), 3.03-3.24 (m, 1H), 2.83-2.97 (m, 1H), 1.33 (br t, J = 7.6 Hz, 3H), 1.06 (br d, J = 6.4 Hz, 3H), 0.95 (br d, J = 6.4 Hz, 3H). ¹⁹F NMR (DMSO-d₆) δ: −113.49 (br d, J = 15.6 Hz, 1F) |
| 54-109 | 535.2 | ¹H NMR (400 MHz, METHANOL-d₄) δ 8.34 (br d, J = 4.56 Hz, 1H), 7.44-7.53 (m, 1H), 7.32 (dt, J = 1.66, 7.36 Hz, 1H), 7.20-7.26 (m, 1H), 7.13-7.20 (m, 1H), 6.75-6.92 (m, 1H), 6.65 (d, J = 2.07 Hz, 1H), 6.58 (d, J = 2.07 Hz, 1H), 6.30 (br dd, J = 3.32, 16.59 Hz, 1H), 5.82 (dd, J = 1.87, 10.57 Hz, 1H), 4.90-5.11 (m, 1H), 4.31-4.63 (m, 2H), 3.99-4.25 (m, 1H), 3.50-3.87 (m, 2H), 3.08-3.29 (m, 1H), 2.47 (td, J = 6.84, 13.68 Hz, 1H), 1.45 (br t, J = 7.98 Hz, 3H), 1.07 (d, |

TABLE 88-continued

Analytical Data

| Ex. # | LRMS: m/z (ESI, +ve ion): (M + H)+ | NMR |
|---|---|---|
| | | J = 6.84 Hz, 3H), 1.01 (d, J = 6.84 Hz, 3H). $^{19}$F NMR (376 MHz, METHANOL-d$_4$) δ ppm −114.76 (s, 1F). |
| 54-110 | 562.2 | $^1$H NMR (400 MHz, DMSO-d$_6$) δ ppm 1.17 (d, J = 2.49 Hz, 9 H) 1.27-1.39 (m, 3 H) 2.97-3.29 (m, 1 H) 3.45-3.85 (m, 2 H) 4.09-4.49 (m, 3 H) 4.85-5.05 (m, 1 H) 5.71-5.82 (m, 1 H) 6.21 (br d, J = 16.59 Hz, 1 H) 6.74-6.97 (m, 1 H) 7.20-7.38 (m, 3 H) 7.47-7.59 (m, 1 H) 8.42-8.54 (m, 1 H) 8.57 (d, J = 1.66 Hz, 1 H) 9.12 (s, 1 H) |
| 54-110-1 | 562.2 | $^1$H NMR (400 MHz, DMSO-d$_6$) δ ppm 1.17 (s, 9 H) 1.30 (br d, J = 6.01 Hz, 3 H) 2.95-3.29 (m, 1 H) 3.34-3.86 (m, 2 H) 3.97-4.52 (m, 3 H) 4.98 (br s, 1 H) 5.67-5.84 (m, 1 H) 6.21 (br d, J = 17.21 Hz, 1 H) 6.86 (br d, J = 13.06 Hz, 1 H) 7.20-7.36 (m, 3 H) 7.45-7.58 (br s, 1 H) 8.56 (s, 1 H) 9.11 (s, 1 H) |
| 54-110-2 | 562.1 | $^1$H NMR (400 MHz, DMSO-d$_6$) δ ppm 1.17 (s, 9 H) 1.35 (d, J = 6.63 Hz, 3 H) 3.09-3.26 (m, 1 H) 3.43-3.81 (m, 2 H) 3.98-4.42 (m, 3 H) 4.92 (br s, 1 H) 5.72-5.83 (m, 1 H) 6.21 (br d, J = 16.59 Hz, 1 H) 6.76-6.97 (m, 1 H) 7.22-7.36 (m, 3 H) 7.47-7.59 (m, 1 H) 8.46 (br d, J = 7.46 Hz, 1 H) 8.57 (s, 1 H) 9.12 (s, 1 H) |
| 54-111 | 536.2 | $^1$H NMR (500 MHz, CHLOROFORM-d) δ ppm 1.01-1.21 (m, 7 H) 1.47 (br s, 2 H) 1.55 (br d, J = 3.66 Hz, 1 H) 2.55-2.67 (m, 1 H) 2.87-3.13 (m, 1 H) 3.23 (br s, 1 H) 3.55 (br s, 1 H) 3.58-3.70 (m, 1 H) 3.86 (br d, J = 13.43 Hz, 1 H) 3.95-4.08 (m, 1 H) 4.74 (br d, J = 12.82 Hz, 1 H) 5.74-5.85 (m, 1 H) 6.40 (br d, J = 16.48 Hz, 1 H) 6.53-6.70 (m, 1 H) 7.10 (t, J = 9.16 Hz, 1 H) 7.13-7.22 (m, 1 H) 7.37-7.46 (m, 1 H) 7.38-7.45 (m, 1 H) 8.00 (s, 1 H) |
| 54-112 | 560.9 | $^1$H NMR (400 MHz, DMSO-d$_6$) δ ppm 1.15 (d, J = 2.28 Hz, 9 H) 1.24-1.41 (m, 3 H) 2.92-3.23 (m, 1 H) 3.41-3.81 (m, 2 H) 4.07-4.51 (m, 3 H) 4.82-5.05 (m, 1 H) 5.69-5.82 (m, 1 H) 6.20 (br d, J = 16.79 Hz, 1 H) 6.76-6.97 (m, 1 H) 7.19-7.36 (m, 4 H) 7.45-7.60 (m, 2 H) 8.38-8.50 (m, 1 H) 8.54 (dd, J = 4.56, 1.45 Hz, 1 H) |
| 54-112-1 | 560.9 | $^1$H NMR (400 MHz, DMSO-d$_6$) δ ppm 1.16 (s, 9 H) 1.35 (d, J = 6.63 Hz, 3 H) 3.07-3.26 (m, 1 H) 3.42-4.46 (m, 5 H) 4.89 (br s, 1 H) 5.77 (dd, J = 10.47, 1.97 Hz, 1 H) 6.21 (br d, J = 16.59 Hz, 1 H) 6.72-6.96 (m, 1 H) 7.20-7.37 (m, 4 H) 7.46-7.61 (m, 2 H) 8.43 (br d, J = 7.46 Hz, 1 H) 8.55 (dd, J = 4.35, 1.45 Hz, 1 H) |
| 54-112-2 | 560.9 | $^1$H NMR (400 MHz, DMSO-d$_6$) δ ppm 1.15 (s, 9 H) 1.27 (d, J = 4.15 Hz, 3 H) 2.92-3.27 (m, 1 H) 3.34-4.54 (m, 5 H) 4.93 (br s, 1 H) 5.76 (dd, J = 10.47, 2.18 Hz, 1 H) 6.10-6.30 (m, 1 H) 6.73-6.99 (m, 1 H) 7.16-7.37 (m, 4 H) 7.43-7.58 (m, 2 H) 8.48 (br s, 1 H) 8.53 (dd, J = 4.46, 1.76 Hz, 1 H) |
| 55-1 | 566.9 | $^1$H NMR (400 MHz, DMSO-d$_6$) δ ppm 10.18 (br s, 1 H), 8.40 (br d, J = 13.1 Hz, 1 H), 7.25-7.32 (m, 1 H), 6.79-6.91 (m, 1 H), 6.68-6.79 (m, 2 H), 6.20 (br d, J = 16.6 Hz, 1 H), 5.74-5.79 (m, 1 H), 4.93 (br d, J = 27.8 Hz, 1 H), 3.97-4.46 (m, 3 H), 3.36-3.88 (m, 2 H), 2.98-3.28 (m, 1 H), 2.85-2.97 (m, 1 H), 1.92 (br d, |

TABLE 88-continued

Analytical Data

| Ex. # | LRMS: m/z (ESI, +ve ion): (M + H)+ | NMR |
|---|---|---|
| | | J = 6.0 Hz, 3 H), 1.33 (dd, J = 12.6, 6.6 Hz, 3 H), 1.10 (d, J = 6.8 Hz, 3 H), 1.05 (dd, J = 6.9, 2.6 Hz, 3 H). $^{19}$F NMR (376 MHz, DMSO-d$_6$) δ ppm −115.73 (br dd, J = 82.4, 10.4 Hz, 1 F). |
| 55-2 | 607.4 | 1H NMR (500 MHz, DMSO-d6) δ ppm 10.17 (s, 1 H) 9.04 (s, 1 H) 8.46 (d, J = 9.43 Hz, 1 H) 7.20-7.26 (m, 1 H) 6.87 (td, J = 15.86, 10.57 Hz, 1 H) 6.70 (d, J = 8.18 Hz, 1 H) 6.66 (t, J = 8.51 Hz, 1 H) 6.18-6.24 (m, 1 H) 5.75-5.79 (m, 1 H) 4.99 (br s, 1 H) 4.26-4.43 (m, 2 H) 4.02-4.20 (m, 1 H) 3.61-3.86 (m, 2 H) 3.07-3.29 (m, 1 H) 2.70 (br s, 2 H) 1.34 (br d, J = 6.49 Hz, 3 H) 1.08 (d, J = 6.49 Hz, 6 H) 0.93 (br d, J = 10.51 Hz, 3 H) 0.92 (br d, J = 10.51 Hz, 3 H) |
| 55-3 | 582.0 | $^1$H NMR (500 MHz, DMSO-d$_6$) δ ppm 10.23 (br s, 1 H) 8.50 (s, 1 H) 8.34-8.44 (m, 1 H) 7.24-7.29 (m, 1 H) 6.81-6.90 (m, 1 H) 6.73 (d, J = 8.28 Hz, 1 H) 6.69 (t, J = 8.54 Hz, 1 H) 6.17-6.24 (m, 1 H) 5.76 (dd, J = 10.32, 2.01 Hz, 1 H) 4.85-5.07 (m, 1 H) 4.25-4.40 (m, 2 H) 3.99-4.18 (m, 1 H) 3.83 (s, 3 H) 3.80 (s, 3 H) 3.57-3.75 (m, 1 H) 3.31-3.34 (m, 1 H) 3.11-3.24 (m, 1 H) 1.25-1.36 (m, 3 H). |
| 55-4 | 592.3 | $^1$H NMR (500 MHz, DMSO-d$_6$) δ ppm 10.21 (s, 1 H) 8.40-8.47 (m, 1 H) 7.26 (q, J = 7.96 Hz, 1 H) 6.82-6.91 (m, 1 H) 6.66-6.74 (m, 2 H) 6.21 (br dd, J = 17.32, 9.28 Hz, 1 H) 5.77 (dd, J = 10.44, 2.01 Hz, 1 H) 4.98 (br s, 1 H) 4.24-4.44 (m, 2 H) 4.00-4.19 (m, 1 H) 3.78 (br s, 1 H) 3.64 (br d, J = 12.85 Hz, 1 H) 3.04-3.28 (m, 1 H) 2.64-2.75 (m, 1 H) 2.57 (s, 3 H) 2.04 (br d, J = 12.20 Hz, 3 H) 1.34 (br t, J = 7.27 Hz, 3 H) 1.06 (d, J = 6.62 Hz, 3 H) 0.92 (br t, J = 7.20 Hz, 3 H). |
| 55-4-1 | 592.3 | $^1$H NMR (400 MHz, DMSO-d$_6$) δ ppm 10.15 (br s, 1 H) 8.43 (br s, 1 H) 7.25 (q, J = 8.09 Hz, 1 H) 6.79-6.92 (m, 1 H) 6.65-6.75 (m, 2 H) 6.21 (br d, J = 16.17 Hz, 1 H) 5.73-5.79 (m, 1 H) 4.94 (br s, 1 H) 4.33-4.42 (m, 1 H) 4.21-4.33 (m, 1 H) 3.99-4.18 (m, 1 H) 3.77 (br d, J = 6.84 Hz, 1 H) 3.52-3.70 (m, 1 H) 3.12-3.28 (m, 1 H) 2.69 (br dd, J = 12.44, 6.01 Hz, 1 H) 2.54-2.60 (m, 3 H) 2.05 (br d, J = 10.37 Hz, 3 H) 1.35 (d, J = 6.63 Hz, 3 H) 1.07 (d, J = 6.63 Hz, 3 H) 0.92 (br s, 3 H) |
| 55-4-2 | 592.3 | $^1$H NMR (400 MHz, DMSO-d$_6$) δ ppm 10.16 (br s, 1 H) 8.45 (br s, 1 H) 7.20-7.30 (m, 1 H) 6.85 (br dd, J = 15.96, 10.37 Hz, 1 H) 6.64-6.76 (m, 2 H) 6.21 (br d, J = 16.79 Hz, 1 H) 5.71-5.80 (m, 1 H) 4.98 (br s, 1 H) 4.25-4.43 (m, 2 H) 4.04 (br d, J = 13.89 Hz, 1 H) 3.80 (br s, 1 H) 3.52-3.72 (m, 1 H) 3.06-3.24 (m, 1 H) 2.68-2.78 (m, 1 H) 2.55-2.59 (m, 3 H) 1.97-2.10 (m, 3 H) 1.33 (br d, J = 6.63 Hz, 3 H) 1.07 (d, J = 6.84 Hz, 3 H) 0.92 (br s, 3 H) |
| 55-5 | 605.2 | $^1$H NMR (400 MHz, DMSO-d$_6$) δ ppm 8.49 (br s, 1 H) 7.52 (q, J = 7.26 Hz, 1 H) 7.26-7.36 (m, 2 H) 7.16-7.22 (m, 1 H) 6.81-6.93 (m, 1 H) 6.22 (br d, J = 16.79 Hz, 1 H) 5.75-5.81 (m, 1 H) 4.99 (br s, 1 H) 4.26-4.39 (m, 2 H) 4.01-4.21 (m, 1 H) 3.81 (br d, J = 10.99 Hz, 1 H) 3.44- |

TABLE 88-continued

| | Analytical Data | |
|---|---|---|
| Ex. # | LRMS: m/z (ESI, +ve ion): $(M + H)^+$ | NMR |
| | | 3.70 (m, 1 H) 3.08-3.29 (m, 1 H) 2.64-2.72 (m, 2 H) 2.60 (s, 3 H) 1.35 (d, J = 6.63 Hz, 3 H) 1.07 (d, J = 6.63 Hz, 6 H) 0.92 (d, J = 6.63 Hz, 6 H). |
| 55-6 | 601.8 | $^1$H NMR (400 MHz, DMSO-$d_6$) δ ppm 1.29-1.40 (m, 3 H) 1.97-2.02 (m, 1 H) 3.12-3.20 (m, 1 H) 3.34-3.89 (m, 3 H) 3.99-4.11 (m, 1 H) 4.13-4.46 (m, 2 H) 4.76-5.07 (m, 1 H) 5.75-5.80 (m, 2 H) 6.07-6.28 (m, 1 H) 6.61-6.75 (m, 2 H) 6.77-6.95 (m, 1 H) 7.17-7.30 (m, 2 H) 7.32-7.54 (m, 3 H) 8.27-8.52 (m, 1 H) 9.85-10.25 (m, 1 H). $^{19}$F NMR (377 MHz, DMSO-$d_6$) δ ppm −118.84−−113.86 (m, 1 F) −65.29−−59.73 (m, 1 F). |
| 55-7 | 561.8 | $^1$H NMR (400 MHz, DMSO-$d_6$) δ ppm 1.28-1.41 (m, 3 H) 1.88-1.94 (m, 3 H) 2.69-2.80 (m, 6 H) 3.01-3.28 (m, 1 H) 3.53-3.82 (m, 3 H) 4.20-4.43 (m, 3 H) 4.84-5.04 (m, 1 H) 5.67-5.87 (m, 1 H) 6.05-6.31 (m, 1 H) 6.72-6.95 (m, 2 H) 7.22-7.39 (m, 3 H) 7.48-7.62 (m, 1 H) 7.92-8.10 (m, 1 H) 8.40-8.55 (m, 1 H). |
| 55-7-1 | 562.0 | 1H NMR (400 MHz, DMSO-d6) δ ppm 1.26-1.42 (m, 3 H) 1.80-1.97 (m, 3 H) 2.64-2.78 (m, 6 H) 2.93-3.16 (m, 1 H) 3.35-3.82 (m, 3 H) 3.96-4.48 (m, 3 H) 4.84-5.03 (m, 1 H) 5.67-5.88 (m, 1 H) 6.13-6.31 (m, 1 H) 6.67-6.76 (m, 1 H) 6.79-6.96 (m, 1 H) 7.23-7.42 (m, 3 H) 7.46-7.67 (m, 1 H) 7.94-8.05 (m, 1 H) 8.37-8.52 (m, 1 H) 19F NMR (376 MHz, DMSO-d6) δ ppm −115.62−−111.23 (m, 1 F) |
| 55-7-2 | 562.0 | 1H NMR (400 MHz, DMSO-d6) δ ppm 1.29-1.47 (m, 3 H) 1.79-2.00 (m, 3 H) 2.63-2.80 (m, 6 H) 3.03-3.25 (m, 1 H) 3.39-3.86 (m, 3 H) 3.94-4.49 (m, 3 H) 4.84-5.08 (m, 1 H) 5.70-5.89 (m, 1 H) 6.12-6.30 (m, 1 H) 6.65-6.79 (m, 1 H) 6.80-7.01 (m, 1 H) 7.22-7.42 (m, 3 H) 7.45-7.66 (m, 1 H) 7.92-8.09 (m, 1 H) 8.35-8.52 (m, 1 H) 19F NMR (376 MHz, DMSO-d6) δ ppm −113.31 (br s, 1 F) |
| 55-8 | 562.1 | $^1$H NMR (400 MHz, CDCl$_3$) δ ppm 8.62 (br s, 1H), 8.14 (s, 1H), 7.36-7.42 (m, 1H), 7.28-7.33 (m, 2H), 7.23-7.26 (m, 1H), 6.54-6.74 (m, 3H), 6.42 (dd, J = 1.45, 16.79 Hz, 1H), 5.83 (dd, J = 1.76, 10.47 Hz, 1H), 4.23-5.26 (m, 3H), 3.51-4.09 (m, 3H), 2.93-3.37 (m, 1H), 2.23-2.47 (m, 2H), 1.99-2.06 (m, 3H), 1.42-1.62 (m, 3H), 1.08-1.17 (m, 3H). $^{19}$F NMR (377 MHz, CDCl$_3$) δ ppm −75.95 (s, 0.06F), −105.18-104.05 (m, 1F). |
| 55-8-1 | 562.0 | $^1$H NMR (400 MHz, DMSO-$d_6$) δ ppm 10.11 (s, 1H), 8.39 (br s, 1H), 7.09-7.26 (m, 4H), 6.79-6.91 (m, 1H), 6.70 (d, J = 7.97 Hz, 1H), 6.65 (t, J = 8.81 Hz, 1H), 6.20 (br d, J = 16.17 Hz, 1H), 5.73-5.78 (m, 1H), 4.88 (br s, 1H), 3.97-4.43 (m, 3H), 3.46-3.84 (m, 2H), 3.02 (br d, J = 12.23 Hz, 1H), 2.22 (br s, 2H), 1.81-1.97 (m, 3H), 1.34 (br d, J = 5.80 Hz, 3H), 0.96 (br t, J = 7.15 Hz, 3H). $^{19}$F NMR (376 MHz, DMSO-$d_6$) δ ppm −115.87 (br d, J = 41.62 Hz, 1F). |
| 55-8-2 | 562.0 | $^1$H NMR (400 MHz, DMSO-$d_6$) δ ppm 10.10 (s, 1H), 8.41 (br s, 1H), 7.09-7.26 (m, 4H), 6.79-6.91 (m, 1H), 6.70 (d, J = 8.03 Hz, 1H), 6.65 (t, J = 8.52 Hz, 1H), 6.20 (br d, J = 16.38 Hz, 1H), 5.73-5.78 (m, 1H), 4.93 (br s, 1H), 3.99-4.49 (m, |

TABLE 88-continued

Analytical Data

| Ex. # | LRMS: m/z (ESI, +ve ion): (M + H)+ | NMR |
|---|---|---|
| | | 3H), 3.58-3.84 (m, 2H), 2.97-3.25 (m, 1H), 2.23 (br s, 2H), 1.81-1.92 (m, 3H), 1.27-1.35 (m, 3H), 0.92-0.99 (m, 3H). $^{19}$F NMR (376 MHz, DMSO-d$_6$) δ ppm −115.87 (br d, J = 79.76 Hz, 1F). |
| 55-9 | 546.0 | $^1$H NMR (400 MHz, CDCl$_3$) δ ppm 8.05 (s, 1H), 7.35-7.43 (m, 1H), 7.24 (d, J = 7.67 Hz, 1H), 7.06-7.21 (m, 5H), 6.50-6.74 (m, 1H), 6.37-6.44 (m, 1H), 5.80 (dd, J = 1.76, 10.47 Hz, 1H), 4.21-5.23 (m, 3H), 3.50-4.08 (m, 3H), 2.91-3.33 (m, 1H), 2.33 (br d, J = 15.34 Hz, 2H), 2.01 (br s, 3H), 1.41-1.57 (m, 3H), 1.04-1.12 (m, 3H). $^{19}$F NMR (376 MHz, CDCl$_3$) δ ppm −112.06 (s, 1F). |
| 55-9-1 | 546.0 | $^1$H NMR (400 MHz, DMSO-d$_6$) δ ppm 8.44 (br s, 1H), 7.51 (br d, J = 7.26 Hz, 1H), 7.11-7.33 (m, 6H), 6.78-6.93 (m, 1H), 6.21 (br d, J = 16.17 Hz, 1H), 5.76 (br d, J = 10.57 Hz, 1H), 4.93 (br s, 1H), 3.96-4.52 (m, 3H), 3.41-3.85 (m, 2H), 2.94-3.24 (m, 1H), 2.17-2.32 (m, 2H), 1.81-1.99 (m, 3H), 1.32 (br d, J = 6.43 Hz, 3H), 0.97 (br t, J = 7.46 Hz, 3H). $^{19}$F NMR (376 MHz, DMSO-d$_6$) δ ppm −113.77 (s, 1F). |
| 55-9-2 | 546.0 | $^1$H NMR (400 MHz, DMSO-d$_6$) δ ppm 8.42 (br s, 1H), 7.10-7.58 (m, 7H), 6.87 (br s, 1H), 6.23 (br s, 1H), 5.77 (br s, 1H), 4.90 (br s, 1H), 4.27 (br s, 3H), 3.55-3.83 (m, 3H), 2.15-2.28 (m, 2H), 1.90 (br s, 3H), 1.34 (br s, 3H), 0.91-1.06 (m, 3H). $^{19}$F NMR (377 MHz, DMSO-d$_6$) δ ppm −113.77 (br s, 1F). |
| 55-10 | 563.0 | $^1$H NMR (400 MHz, CDCl$_3$) δ ppm 8.43-8.58 (m, 2H), 8.16 (br s, 1H), 7.34 (s, 1H), 7.23 (br s, 1H), 6.57-6.75 (m, 3H), 6.40-6.46 (m, 1H), 5.83 (br d, J = 10.99 Hz, 1H), 3.47-5.34 (m, 6H), 2.96-3.36 (m, 1H), 2.47-2.72 (m, 2H), 2.04-2.13 (m, 3H), 1.44-1.54 (m, 3H), 1.16-1.24 (m, 3H). $^{19}$F NMR (376 MHz, CDCl$_3$) δ ppm −105.6 (br s, 1F) |
| 55-10-1 | 563.0 | $^1$H NMR (400 MHz, DMSO-d$_6$) δ ppm 10.16 (br s, 1H), 8.41 (br s, 1H), 8.34 (d, J = 4.98 Hz, 1H), 7.16-7.27 (m, 2H), 6.80-6.91 (m, 1H), 6.62-6.73 (m, 2H), 6.21 (br d, J = 16.59 Hz, 1H), 5.74-5.79 (m, 1H), 4.92 (br s, 1H), 3.94-4.47 (m, 3H), 3.41-3.82 (m, 2H), 3.02-3.23 (m, 1H), 2.28-2.41 (m, 2H), 1.88-1.99 (m, 3H), 1.35 (br d, J = 3.94 Hz, 3H), 0.98-1.06 (m, 3H). $^{19}$F NMR (376 MHz, DMSO-d$_6$) δ ppm −116.55--115.55 (m, 1F). |
| 55-10-2 | 563.0 | $^1$H NMR (400 MHz, DMSO-d$_6$) δ ppm 10.14 (br s, 1H), 8.44 (br s, 1H), 8.34 (d, J = 4.98 Hz, 1H), 7.17-7.27 (m, 2H), 6.80-6.92 (m, 1H), 6.63-6.73 (m, 2H), 6.21 (br d, J = 17.21 Hz, 1H), 5.74-5.79 (m, 1H), 4.96 (br s, 1H), 3.97-4.51 (m, 3H), 3.39-3.88 (m, 2H), 2.98-3.19 (m, 1H), 2.21-2.43 (m, 2H), 1.92 (br d, J = 14.10 Hz, 3H), 1.33 (br d, J = 5.60 Hz, 3H), 1.03 (br s, 3H). $^{19}$F NMR (376 MHz, DMSO-d$_6$) δ ppm −115.87 (br d, J = 118.77 Hz, 1F). |
| 55-11 | 551.0 | $^1$H NMR (400 MHz, DMSO-d$_6$) δ ppm 8.37-8.48 (m, 1 H), 7.52-7.61 (m, 1 H), 7.30-7.40 (m, 3 H), 6.78-6.93 (m, 1 H), 6.21 (br d, J = 16.6 Hz, 1 H), 5.73-5.80 (m, 1 H), 4.94 (br d, J = 28.0 Hz, 1 H), 3.97-4.46 (m, 3 H), 3.43-3.89 (m, 2 H), 3.01-3.29 (m, 1 H), 2.94 (dtd, |

TABLE 88-continued

| | Analytical Data | |
|---|---|---|
| Ex. # | LRMS: m/z (ESI, +ve ion): (M + H)+ | NMR |
| | | J = 13.9, 7.0, 7.0, 4.0 Hz, 1 H), 1.95 (s, 3 H), 1.33 (dd, J = 12.9, 6.6 Hz, 3 H), 1.07 (dd, J = 23.0, 7.0 Hz, 6 H). $^{19}$F NMR (376 MHz, DMSO-$d_6$) δ ppm −114.08 (d, J = 2.6 Hz, 1 F). |
| 55-12 | 569.0 | $^1$H NMR (400 MHz, DMSO-$d_6$) δ ppm 8.44 (br d, J = 15.5 Hz, 1 H), 7.38-7.48 (m, 2 H), 7.26 (td, J = 8.5, 2.3 Hz, 1 H), 6.78-6.92 (m, 1 H), 6.21 (br d, J = 16.2 Hz, 1 H), 5.73-5.80 (m, 1 H), 4.93 (br d, J = 30.3 Hz, 1 H), 3.96-4.46 (m, 3 H), 3.35-3.87 (m, 2 H), 3.00-3.28 (m, 1 H), 2.94 (dtd, J = 13.9, 6.9, 6.9, 4.0 Hz, 1 H), 1.94 (s, 3 H), 1.32 (dd, J = 13.6, 6.7 Hz, 3 H), 1.07 (dd, J = 23.2, 7.0 Hz, 6 H). $^{19}$F NMR (376 MHz, DMSO-$d_6$) δ ppm −106.95 (dd, J = 9.5, 3.5 Hz, 1 F), −109.44 (dd, J = 9.1, 3.0 Hz, 1 F). |
| 55-13 | 562.0 | $^1$H NMR (400 MHz, DMSO-$d_6$) δ ppm 8.98 (s, 1H), 8.49 (br d, J = 6.0 Hz, 1H), 7.47-7.59 (m, 1H), 7.31 (br d, J = 8.1 Hz, 3H), 6.78-6.95 (m, 1H), 6.21 (br dd, J = 17.5, 4.0 Hz, 1H), 5.67-5.81 (m, 1H), 4.94-5.07 (m, 1H), 4.83-4.94 (m, 1H), 4.27-4.42 (m, 2H), 3.88-4.27 (m, 2H), 3.58-3.86 (m, 1H), 2.73-2.84 (m, 1H), 2.15 (d, J = 3.5 Hz, 3H), 1.36 (d, J = 6.8 Hz, 3H), 1.09 (d, J = 6.6 Hz, 3H), 0.96 (d, J = 6.6 Hz, 3H). |
| 55-13-1 | 562.2 | $^1$H NMR (400 MHz, DMSO-$d_6$) δ ppm 8.97 (s, 1H), 8.49 (br d, J = 5.2 Hz, 1H), 7.18-7.36 (m, 4H), 6.80-6.94 (m, 1H), 6.17-6.28 (m, 1H), 5.73-5.84 (m, 1H), 4.93-5.05 (m, 1H), 4.28-4.45 (m, 3H), 4.02-4.20 (m, 1H), 3.62-3.89 (m, 1H), 3.44-3.54 (m, 1H), 2.74-2.85 (m, 1H), 2.14 (s, 3H), 1.36 (d, J = 6.6 Hz, 3H), 1.09 (d, J = 6.6 Hz, 3H), 0.96 (d, J = 6.6 Hz, 3H). |
| 55-13-2 | 562.2 | $^1$H NMR (400 MHz, DMSO-$d_6$) δ ppm 8.98 (s, 1H), 8.49 (br d, J = 4.8 Hz, 1H), 7.49-7.57 (m, 1H), 7.18-7.39 (m, 3H), 6.81-6.95 (m, 1H), 6.22 (br dd, J = 18.0, 4.1 Hz, 1H), 5.77 (d, J = 1.0 Hz, 1H), 4.94-5.05 (m, 1H), 4.34 (br d, J = 13.9 Hz, 2H), 4.00-4.21 (m, 1H), 3.77-3.89 (m, 1H), 3.44-3.69 (m, 1H), 3.12 (br d, J = 2.5 Hz, 1H), 2.74-2.81 (m, 1H), 2.15 (s, 3H), 1.36 (d, J = 6.6 Hz, 3H), 1.09 (d, J = 6.6 Hz, 3H), 0.96 (d, J = 6.6 Hz, 3H). |
| 55-14 | 578.2 | $^1$H NMR (400 MHz, DMSO-$d_6$) δ ppm 10.15 (s, 1H), 8.95 (s, 1H), 8.46 (br d, J = 3.3 Hz, 1H), 7.26 (br d, J = 7.7 Hz, 1H), 6.80-6.93 (m, 1H), 6.63-6.77 (m, 2H), 6.21 (d, J = 1.0 Hz, 1H), 5.77 (d, J = 1.0 Hz, 1H), 4.87-5.08 (m, 1H), 4.72-4.87 (m, 1H), 4.27-4.46 (m, 1H), 4.27-4.37 (m, 1H), 4.00-4.19 (m, 1H), 3.76-3.92 (m, 1H), 3.58-3.69 (m, 1H), 3.18 (d, J = 5.4 Hz, 3H), 2.73-2.85 (m, 1H), 1.36 (br t, J = 6.5 Hz, 3H), 1.10 (d, J = 6.6 Hz, 3H), 0.95 (br s, 3H). |
| 55-14-1 | 578.2 | $^1$H NMR (400 MHz, DMSO-$d_6$) δ ppm 10.15 (s, 1H), 8.95 (s, 1H), 8.47 (br d, J = 1.5 Hz, 1H), 7.26 (d, J = 7.3 Hz, 1H), 6.81-6.93 (m, 1H), 6.65-6.74 (m, 2H), 6.22 (br dd, J = 14.1, 4.1 Hz, 1H), 5.77 (d, J = 1.0 Hz, 1H), 4.97-5.06 (m, 1H), 4.26-4.43 (m, 2H), 3.80-3.95 (m, 1H), 3.57-3.70 (m, 2H), 3.08-3.19 (m, 1H), 2.75-2.83 (m, 1H), 1.35 (br d, J = 6.6 Hz, 3H), 1.13 (d, J = 14.9 Hz, 6H), 1.06 (d, J = 6.0 Hz, 3H). |

TABLE 88-continued

| | Analytical Data | |
|---|---|---|
| Ex. # | LRMS: m/z (ESI, +ve ion): (M + H)+ | NMR |
| 55-14-2 | 578.2 | ¹H NMR (400 MHz, DMSO-d₆) δ ppm 10.15 (s, 1H), 8.95 (s, 1H), 8.45 (br d, J = 5.8 Hz, 1H), 7.26 (d, J = 7.0 Hz, 1H), 6.82-6.93 (m, 1H), 6.66-6.74 (m, 2H), 6.24 (br d, J = 2.3 Hz, 1H), 5.73-5.80 (m, 1H), 4.92-5.04 (m, 1H), 4.30-4.44 (m, 2H), 3.93 (td, J = 6.0, 2.9 Hz, 2H), 3.61-3.86 (m, 1H), 3.29 (s, 2H), 2.72-2.84 (m, 1H), 2.11 (br d, J = 11.2 Hz, 2H), 1.37 (br d, J = 6.4 Hz, 3H), 1.13 (d, J = 14.9 Hz, 3H), 1.06 (d, J = 6.2 Hz, 3H). |
| 55-15 | 574.0 | ¹H NMR (400 MHz, DMSO-d₆) δ ppm 0.23-0.42 (m, 1 H), 0.44-0.56 (m, 2 H), 0.57-0.67 (m, 1 H), 1.29-1.39 (m, 3 H), 1.41-1.56 (m, 1 H), 1.91 (br s, 3 H), 2.98-3.20 (m, 0.5 H), 3.41-3.55 (m, 0.5 H), 3.58-3.79 (m, 1.5 H), 3.94-4.07 (m, 0.5 H), 4.08-4.18 (m, 0.5 H), 4.20-4.34 (m, 1.5 H), 4.35-4.46 (m, 0.5 H), 4.87 (br s, 1 H), 5.72-5.81 (m, 1 H), 6.20 (br dd, J = 15.9, 4.0 Hz, 1 H), 6.67 (t, J = 8.9 Hz, 1 H), 6.71 (d, J = 8.3 Hz, 1 H), 6.77-6.85 (m, 1 H), 6.87 (br d, J = 6.6 Hz, 1 H), 7.07-7.18 (m, 2 H), 7.19-7.28 (m, 1 H), 8.31-8.46 (m, 1 H), 10.10 (br s, 1 H). ¹⁹F NMR (376 MHz, DMSO-d₆) δ ppm −115.94 (s, 1 F), −115.46 (s, 1 F). |
| 55-15-1 | 574.2 | 1H NMR (400 MHz, DMSO-d₆) δ ppm 10.03-10.26 (m, 1 H) 8.43 (br s, 1 H) 7.20-7.29 (m, 1 H) 7.07-7.19 (m, 2 H) 6.79-6.95 (m, 2 H) 6.60-6.76 (m, 2 H) 6.21 (br dd, J = 16.27, 3.42 Hz, 1 H) 5.77 (dd, J = 10.47, 2.38 Hz, 1 H) 4.87-5.05 (m, 1 H) 4.12-4.50 (m, 3 H) 3.86-4.10 (m, 1 H) 3.58-3.84 (m, 2 H) 3.37-3.53 (m, 1 H) 2.92-3.19 (m, 1 H) 1.92 (br s, 3 H) 1.40-1.63 (m, 1 H) 1.32 (br d, J = 5.18 Hz, 3 H) 1.02-1.09 (m, 3 H) 0.57-0.70 (m, 1 H) 0.44-0.59 (m, 2 H) 0.27-0.43 (m, 1 H). |
| 55-15-2 | 574.0 | 1H NMR (400 MHz, DMSO-d₆) δ ppm 9.98-10.26 (m, 1 H) 8.30-8.48 (m, 1 H) 7.20-7.28 (m, 1 H) 7.06-7.20 (m, 2 H) 6.76-6.94 (m, 2 H) 6.59-6.75 (m, 2 H) 6.13-6.26 (m, 1 H) 5.72-5.81 (m, 1 H) 4.78-4.97 (m, 1 H) 4.10-4.45 (m, 3 H) 3.85-4.07 (m, 1 H) 3.59-3.84 (m, 2 H) 3.39-3.56 (m, 1 H) 3.04-3.27 (m, 1 H) 1.81-2.05 (m, 3 H) 1.35 (br d, J = 6.43 Hz, 2 H) 1.13 (d, J = 15.13 Hz, 1 H) 1.01-1.08 (m, 3 H) 0.57-0.69 (m, 1 H) 0.43-0.56 (m, 2 H) 0.29-0.43 (m, 1 H). |
| 55-16 | 603.0 | ¹H NMR (400 MHz, DMSO-d₆) δ ppm 8.40 (br s, 1H), 7.47-7.56 (m, 1H), 7.30-7.34 (m, 1H), 7.26-7.30 (m, 1H), 7.20-7.25 (m, 1H), 6.76-6.96 (m, 1H), 6.46 (s, 2H), 6.16-6.25 (m, 1H), 5.74-5.78 (m, 1H), 4.89 (br s, 1H), 4.20-4.46 (m, 2H), 3.98-4.18 (m, 1H), 3.38-3.80 (m, 2H), 3.22-3.29 (m, 1H), 2.95-3.30 (m, 1H), 2.90 (s, 6H), 1.81 (s, 3H), 1.31 (br d, J = 6.4 Hz, 3H), 1.25 (br s, 3H), 1.04 (d, J = 6.6 Hz, 3H). |
| 55-16-1 | 603.0 | 1H NMR (DMSO-d6) δ: 8.40 (br s, 1H), 7.44-7.57 (m, 1H), 7.30-7.34 (m, 1H), 7.26-7.30 (m, 1H), 7.20-7.25 (m, 1H), 6.78-6.94 (m, 1H), 6.46 (s, 2H), 6.20 (br dd, J = 15.7, 4.7 Hz, 1H), 5.73-5.79 (m, 1H), 4.88 (br d, J = 6.0 Hz, 1H), 4.22-4.47 (m, 2H), 3.97-4.19 (m, 1H), 3.39-3.80 (m, 2H), 3.16 (br d, J = 6.0 Hz, 1H), 2.90 (s, 6H), 2.39-2.46 (m, 1H), |

TABLE 88-continued

Analytical Data

| Ex. # | LRMS: m/z (ESI, +ve ion): (M + H)+ | NMR |
|---|---|---|
| | | 1.81 (s, 3H), 1.32 (d, J = 6.6 Hz, 3H), 1.04 (d, J = 6.8 Hz, 3H), 0.93 (d, J = 6.8 Hz, 3H). 19F NMR (DMSO-d6) δ: −114.32 (s, 1F) |
| 55-16-2 | 603.0 | 1H NMR (DMSO-d6) δ: 8.40 (br s, 1H), 7.43-7.58 (m, 1H), 7.32 (d, J = 10.6 Hz, 1H), 7.26-7.29 (m, 1H), 7.20-7.25 (m, 1H), 6.74-6.96 (m, 1H), 6.46 (s, 2H), 6.15-6.25 (m, 1H), 5.73-5.79 (m, 1H), 4.89 (br s, 1H), 4.20-4.46 (m, 2H), 3.97-4.18 (m, 1H), 3.40-3.82 (m, 2H), 2.97-3.25 (m, 1H), 2.90 (s, 6H), 2.43 (dt, J = 13.6, 6.8 Hz, 1H), 1.81 (s, 3H), 1.31 (d, J = 6.6 Hz, 3H), 1.04 (d, J = 6.8 Hz, 3H), 0.94 (d, J = 6.8 Hz, 3H). 19F NMR (DMSO-d6) δ: −114.29 (s, 1F) |
| 55-17 | 569.2 | $^{1}$H NMR (400 MHz, DMSO-$d_6$) δ ppm 9.98-10.25 (1 H, m), 8.91 (1 H, s), 8.29-8.47 (1 H, m), 7.22-7.30 (1 H, m), 6.78-6.92 (1 H, m), 6.63-6.77 (2 H, m), 6.21 (1 H, br d, J = 17.0 Hz), 5.72-5.80 (1 H, m), 4.72-5.13 (1 H, m), 3.97-4.48 (3 H, m), 3.48-3.93 (2 H, m), 3.09-3.28 (1 H, m), 2.83 (1 H, br s), 1.28-1.41 (3 H, m), 1.14 (3 H, d, J = 6.8 Hz), 1.06 (3 H, br d, J = 6.6 Hz). $^{19}$F NMR (376 MHz, DMSO-$d_6$) δ −116.01--114.85 (m, 1F). |
| 55-18 | 553.2 | $^{1}$H NMR (400 MHz, DMSO-$d_6$) δ 9.03 (d, J = 1.45 Hz, 1H), 8.41 (br s, 1H), 7.50-7.59 (m, 1H), 7.28-7.36 (m, 3H), 6.78-6.93 (m, 1H), 6.21 (br d, J = 16.38 Hz, 1H), 5.72-5.80 (m, 1H), 4.94 (br s, 1H), 4.22-4.45 (m, 2H), 3.98-4.20 (m, 1H), 3.70-3.87 (m, 1H), 3.61 (br d, J = 13.89 Hz, 1H), 3.01-3.28 (m, 1H), 2.64-2.76 (m, 1H), 1.33 (dd, J = 4.77, 6.22 Hz, 3H), 1.11 (d, J = 6.63 Hz, 3H), 1.01 (dd, J = 1.87, 6.84 Hz, 3H). $^{19}$F NMR (376 MHz, DMSO-$d_6$) δ −113.55 (br d, J = 33.81 Hz, 1F). |
| 55-19 | 553.2 | $^{1}$H NMR (400 MHz, DMSO-$d_6$) δ 8.93 (d, J = 0.83 Hz, 1H), 8.34-8.47 (m, 1H), 7.49-7.58 (m, 1H), 7.23-7.37 (m, 3H), 6.78-6.93 (m, 1H), 6.21 (br d, J = 16.59 Hz, 1H), 5.73-5.80 (m, 1H), 4.79-5.09 (m, 1H), 3.95-4.46 (m, 3H), 3.56-3.92 (m, 2H), 3.09-3.28 (m, 1H), 2.84-3.08 (m, 1H), 1.29-1.40 (m, 3H), 1.16 (d, J = 6.84 Hz, 3H), 1.08 (d, J = 6.63 Hz, 3H). $^{19}$F NMR (376 MHz, DMSO-$d_6$) δ −113.74--113.54 (m, 1F). |
| 55-20 | 640.2 | $^{1}$H NMR (400 MHz, DMSO-$d_6$) δ ppm 10.11 (1 H, s), 8.34 (1 H, br s), 7.72 (1 H, s), 7.27-7.36 (1 H, m), 7.17-7.26 (3 H, m), 7.07-7.15 (2 H, m), 6.84 (1 H, br d, J = 15.8 Hz), 6.70-6.80 (2 H, m), 6.20 (1 H, br d, J = 16.6 Hz), 5.72-5.80 (1 H, m), 5.21 (2 H, s), 4.87 (1 H, br s), 4.26-4.44 (1 H, m), 4.10-4.24 (1 H, m), 3.39-3.82 (2 H, m), 3.00-3.27 (1 H, m), 1.39-1.51 (1 H, m), 1.32 (3 H, br d, J = 6.6 Hz), 1.12-1.17 (1 H, m), 0.49-0.63 (4 H, m). $^{19}$F NMR (376 MHz, DMSO-$d_6$) δ −113.74--113.54 (m, 1F). |
| 55-21 | 550.2 | $^{1}$H NMR (400 MHz, MeOH-$d_4$) δ ppm 8.36 (br s, 1H), 7.52 (s, 1H), 7.25 (dt, J = 6.84, 8.29 Hz, 1H), 6.83 (dt, J = 11.30, 16.33 Hz, 1H), 6.58-6.72 (m, 2H), 6.24-6.36 (m, 1H), 5.82 (dd, J = 1.87, 10.57 Hz, 1H), 5.01 (br s, 1H), 4.39-4.54 (m, 2H), 4.03-4.23 (m, 1H), 3.53-3.86 (m, |

TABLE 88-continued

Analytical Data

| Ex. # | LRMS: m/z (ESI, +ve ion): (M + H)+ | NMR |
|---|---|---|
| | | 2H), 3.08-3.26 (m, 1H), 1.58-1.69 (m, 1H), 1.47 (br d, J = 6.63 Hz, 3H), 0.61-0.75 (m, 4H). |
| 55-22 | 560.9 | $^1$H NMR (400 MHz, CDCl$_3$) δ ppm 8.48 (s, 2 H) 8.09 (s, 1 H) 7.37-7.47 (m, 1 H) 7.05-7.19 (m, 3 H) 6.51-6.72 (m, 1 H) 6.35-6.47 (m, 1 H) 5.82 (dd, J = 10.5, 1.8 Hz, 1 H) 3.84-5.20 (m, 4 H) 2.99-3.71 (m, 3 H) 2.28-2.43 (m, 4 H) 1.43-1.58 (m, 3 H) 1.07-1.14 (m, 6 H). $^{19}$F NMR (377 MHz, CDCl$_3$) δ ppm −112.50 (s, 1 F). |
| 55-23 | 577.8 | $^1$H NMR (400 MHz, CDCl$_3$) δ ppm 8.70 (s, 1 H) 8.50 (s, 1 H) 8.12 (br s, 1 H) 8.08 (br s, 1 H) 7.23-7.33 (m, 1 H) 6.73 (br d, J = 8.5 Hz, 1 H) 6.68 (br t, J = 9.1 Hz, 1 H) 6.50-6.64 (m, 1 H) 6.36-6.46 (m, 1 H) 5.82 (br d, J = 10.6 Hz, 1 H) 4.17-5.40 (m, 3 H) 3.79-4.05 (m, 1 H) 2.79-3.64 (m, 2 H) 1.48-1.68 (m, 3 H) 1.33 (s, 9 H). $^{19}$F NMR (377 MHz, CDCl$_3$) δ ppm −106.58−−106.84 (m, 1 F). |
| 55-23-1 | 578.0 | $^1$H NMR (400 MHz, CDCl$_3$) δ ppm 8.70 (s, 1 H) 8.49 (s, 1 H) 8.12 (br s, 2 H) 7.20-7.34 (m, 1 H) 6.52-6.77 (m, 3 H) 6.35-6.45 (m, 1 H) 5.82 (br d, J = 10.2 Hz, 1 H) 4.15-5.06 (m, 3 H) 3.66-3.92 (m, 4 H) 1.40 (br d, J = 6.4 Hz, 3 H) 1.32 (br s, 9 H). $^{19}$F NMR (377 MHz, CDCl$_3$) δ ppm −108.81−−107.93 (m, 1 F). |
| 55-23-2 | 578.0 | $^1$H NMR (400 MHz, CDCl$_3$) δ ppm 8.71 (s, 1 H) 8.51 (s, 1 H) 8.08 (br s, 1 H) 8.05 (br s, 1 H) 7.28-7.33 (m, 1 H) 6.74 (br d, J = 8.7 Hz, 1 H) 6.69 (br t, J = 9.0 Hz, 1 H) 6.51-6.65 (m, 1 H) 6.35-6.46 (m, 1 H) 5.82 (br d, J = 10.4 Hz, 1 H) 4.42-4.95 (m, 3 H) 3.52-4.11 (m, 3 H) 3.01-3.41 (m, 1 H) 1.64 (br s, 3 H) 1.33 (s, 9 H). $^{19}$F NMR (377 MHz, CDCl$_3$) δ ppm −108.75−−108.31 (m, 1 F). |
| 55-24 | 560.9 | $^1$H NMR (400 MHz, DMSO-d$_6$) δ ppm 10.13 (s, 1 H), 8.31-8.48 (m, 2 H), 7.82 (br d, J = 7.3 Hz, 1 H), 7.42 (dd, J = 7.7, 4.8 Hz, 1 H), 7.19-7.28 (m, 1 H), 6.77-6.92 (m, 1 H), 6.71 (d, J = 8.3 Hz, 1 H), 6.66 (br t, J = 8.8 Hz, 1 H), 6.20 (br d, J = 16.4 Hz, 1 H), 5.72-5.78 (m, 1 H), 4.68-5.07 (m, 3 H), 3.92-4.46 (m, 3 H), 2.98-3.89 (m, 3 H), 1.85 (br s, 3 H), 1.25-1.40 (m, 3 H). $^{19}$F NMR (376 MHz, DMSO-d$_6$) δ ppm −115.39 (br d, J = 36.4 Hz, 1 F). |
| 55-25 | 575.0 | $^1$H NMR (400 MHz, DMSO-d$_6$) δ ppm 10.22 (br s, 1 H), 8.27-8.47 (m, 1 H), 8.17 (d, J = 5.0 Hz, 1 H), 7.23 (q, J = 7.9 Hz, 1 H), 7.13 (br d, J = 4.4 Hz, 1 H), 6.76-6.93 (m, 1 H), 6.61-6.75 (m, 2 H), 6.14-6.26 (m, 1 H), 5.72-5.80 (m, 1 H), 4.64-5.15 (m, 1 H), 3.47-4.49 (m, 5 H), 2.91-3.27 (m, 1 H), 2.76 (br s, 2 H), 2.04-2.31 (m, 2 H), 1.55-1.78 (m, 4 H), 1.25-1.45 (m, 3 H). $^{19}$F NMR (376 MHz, DMSO-d$_6$) δ ppm −115.88 (br d, J = 596.5 Hz, 1 F). |
| 55-26 | 562.3 | $^1$H NMR (400 MHz, CDCl$_3$) δ ppm 8.04 (s, 1H), 7.34-7.43 (m, 1H), 7.18-7.24 (m, 1H), 7.04-7.18 (m, 3H), 6.90 (d, J = 7.26 Hz, 1H), 6.74 (d, J = 8.29 Hz, 1H), 6.48-6.67 (m, 1H), 6.39 (dd, J = 1.24, 16.59 Hz, 1H), 5.79 (dd, J = 1.87, 10.57 Hz, 1H), 4.78-5.21 (m, 1H), 4.16-4.76 (m, 2H), 3.35-4.05 (m, 3H), 2.92-3.32 (m, 1H), 2.42-2.68 (m, 1H), 1.74 (br s, 1H), 1.44 |

TABLE 88-continued

Analytical Data

| Ex. # | LRMS: m/z (ESI, +ve ion): (M + H)+ | NMR |
|---|---|---|
| | | (d, J = 22.18 Hz, 3H), 1.16 (d, J = 6.84 Hz, 3H), 0.99 (d, J = 6.84 Hz, 3H). $^{19}$F NMR (376 MHz, CDCl$_3$) δ ppm −112.04 (s, 1F). |
| 55-26-1 | 562.3 | $^1$H NMR (400 MHz, CHLOROFORM-d) δ 8.04 (s, 1H), 7.34-7.43 (m, 1H), 7.18-7.24 (m, 1H), 7.04-7.18 (m, 3H), 6.90 (d, J = 7.26 Hz, 1H), 6.74 (d, J = 8.29 Hz, 1H), 6.48-6.67 (m, 1H), 6.39 (dd, J = 1.24, 16.59 Hz, 1H), 5.79 (dd, J = 1.87, 10.57 Hz, 1H), 4.78-5.21 (m, 1H), 4.16-4.76 (m, 2H), 3.35-4.05 (m, 3H), 2.92-3.32 (m, 1H), 2.42-2.68 (m, 1H), 1.74 (br s, 1H), 1.44 (d, J = 22.18 Hz, 3H), 1.16 (d, J = 6.84 Hz, 3H), 0.99 (d, J = 6.84 Hz, 3H). $^{19}$F NMR (376 MHz, CHLOROFORM-d) δ −112.04 (s, 1F). |
| 55-26-2 | 562.3 | $^1$H NMR (400 MHz, CHLOROFORM-d) δ 8.03-8.03 (m, 1H), 8.03 (s, 1H), 7.33-7.43 (m, 1H), 7.17-7.24 (m, 1H), 7.03-7.17 (m, 3H), 6.89 (d, J = 7.46 Hz, 1H), 6.73 (d, J = 7.88 Hz, 1H), 6.47-6.67 (m, 1H), 6.39 (d, J = 16.59 Hz, 1H), 5.79 (dd, J = 1.87, 10.16 Hz, 1H), 4.74-5.18 (m, 1H), 4.26-4.73 (m, 2H), 3.41-4.04 (m, 3H), 3.00-3.29 (m, 1H), 2.48-2.70 (m, 1H), 1.49 (d, J = 27.16 Hz, 3H), 1.16 (d, J = 6.84 Hz, 3H), 1.00 (d, J = 6.84 Hz, 3H). $^{19}$F NMR (376 MHz, CHLOROFORM-d) δ −112.06 (s, 1F). |
| 55-27 | 543.2 | $^1$H NMR (400 MHz, DMSO-d$_6$) δ ppm 8.52-8.57 (1 H, m), 8.30-8.36 (1 H, m), 7.71-7.79 (1 H, m), 7.31-7.38 (1 H, m), 7.15-7.28 (2 H, m), 7.06-7.15 (2 H, m), 6.70-6.85 (1 H, m), 6.13 (1 H, br d, J = 16.4 Hz), 5.64-5.71 (1 H, m), 4.84 (1 H, br s), 4.21 (1 H, br d, J = 13.5 Hz), 3.90-4.03 (1 H, m), 3.30-3.65 (2 H, m), 3.57 (1 H, br d, J = 13.9 Hz), 2.22-2.32 (1 H, m), 2.07-2.20 (4 H, m), 1.25 (3 H, br d, J = 6.6 Hz), 0.83-0.96 (6 H, m). |
| 55-28 | 543.2 | $^1$H NMR (400 MHz, DMSO-d$_6$) δ ppm 8.61 (1 H, s), 8.62 (2 H, d, J = 4.8 Hz), 8.41-8.49 (1 H, m), 7.94 (1 H, dt, J = 7.9, 1.9 Hz), 7.48 (1 H, dd, J = 8.0, 4.9 Hz), 7.28-7.39 (1 H, m), 7.17-7.28 (2 H, m), 6.81-6.93 (1 H, m), 6.22 (1 H, br dd, J = 16.2, 1.9 Hz), 5.73-5.80 (1 H, m), 4.82-4.97 (1 H, m), 4.29 (2 H, br d, J = 13.7 Hz), 3.98-4.22 (1 H, m), 3.55-3.80 (2 H, m), 2.16-2.29 (4 H, m), 1.34 (3 H, d, J = 6.6 Hz), 0.99 (3 H, br t, J = 7.6 Hz), 0.98 (3 H, br t, J = 7.6 Hz). |
| 55-29 | 557.2 | $^1$H NMR (400 MHz, DMSO-d$_6$) δ ppm 8.49 (2 H, br dd, J = 4.9, 1.8 Hz), 7.56 (1 H, dd, J = 7.9, 1.7 Hz), 7.22-7.33 (2 H, m), 7.17 (2 H, d, J = 7.5 Hz), 6.81-6.97 (1 H, m), 6.24 (1 H, br d, J = 1.7 Hz), 6.20 (1 H, br d, J = 1.5 Hz), 5.75-5.81 (1 H, m), 4.88-4.99 (1 H, m), 4.40 (1 H, br s), 4.25-4.35 (1 H, m), 4.05 (1 H, br d, J = 14.3 Hz), 3.71-3.90 (1 H, m), 3.66 (1 H, br d, J = 11.2 Hz), 2.15-2.29 (4 H, m), 2.12 (3 H, s), 1.34 (3 H, d, J = 6.6 Hz), 0.98 (6 H, td, J = 7.6, 3.1 Hz). |
| 55-30 | 604.1 | $^1$H NMR (400 MHz, DMSO-d$_6$) δ ppm 8.54 (1 H, s), 7.47-7.55 (1 H, m), 7.23-7.33 (3 H, m), 7.13-7.21 (2 H, m), 6.80 (1 H, br d, J = 8.3 Hz), 6.17 (1 H, br d, J = 16.6 Hz), 5.71-5.81 (1 H, m), 5.49 (1 H, br s), 5.37 (1 H, br s), 4.68 (1 H, br d, J = 6.0 Hz), 4.54 (1 H, br d, J = 12.0 Hz), 4.41 (1 H, br d, J = 13.5 Hz), 4.28 (1 H, br s), 3.92-4.15 (1 H, m), 3.83 (1 H, br d, |

TABLE 88-continued

Analytical Data

| Ex. # | LRMS: m/z (ESI, +ve ion): (M + H)+ | NMR |
|---|---|---|
| | | J = 11.8 Hz), 3.68 (3 H, s), 2.21 (4 H, q, J = 7.3 Hz), 0.92-1.01 (6 H, m). ¹⁹F NMR (376 MHz, DMSO-d₆) δ ppm −113.80 (1 F, s). |
| 55-31 | 578.2 | ¹H NMR (400 MHz, DMSO-d₆) δ ppm 10.15 (1 H, s), 8.99 (1 H, s), 8.41-8.51 (1 H, m), 7.18-7.29 (1 H, m), 6.79-6.94 (1 H, m), 6.72 (1 H, d, J = 7.9 Hz), 6.68 (1 H, t, J = 8.5 Hz), 6.16-6.28 (1 H, m), 5.73-5.81 (1 H, m), 4.87-5.07 (1 H, m), 4.23-4.49 (2 H, m), 3.95-4.23 (1 H, m), 3.58-3.93 (1 H, m), 3.43-3.57 (1 H, m), 3.06-3.21 (1 H, m), 2.34-2.47 (4 H, m), 1.35 (3 H, br d, J = 6.6 Hz), 1.05 (6 H, q, J = 6.5 Hz). ¹⁹F NMR (376 MHz, DMSO-d₆) δ ppm −115.86 (1 F, s), −115.89 (1 F, s), −115.92 (1 F, s). |
| 55-32 | 564.2 | ¹H NMR (400 MHz, DMSO-d₆) δ ppm 10.22 (1 H, br d, J = 4.1 Hz), 8.33 (1 H, br s), 7.32-7.39 (1 H, m), 7.29 (2 H, d, J = 8.5 Hz), 6.76-6.88 (5 H, m), 6.19 (1 H, br dd, J = 16.3, 5.7 Hz), 5.72-5.78 (1 H, m), 5.20-5.33 (2 H, m), 4.73-4.85 (1 H, m), 4.04-4.40 (3 H, m), 3.94-4.04 (2 H, m), 3.70 (3 H, s), 2.96-3.25 (1 H, m), 1.28 (3 H, s). ¹⁹F NMR (376 MHz, DMSO-d₆) δ ppm −115.21 (1 F, s), −115.23 (1 F, s) |
| 55-33 | 442.1 | ¹H NMR (400 MHz, DMSO-d₆) δ ppm 8.32 (1 H, br s), 7.58-7.65 (2 H, m), 7.36-7.43 (2 H, m), 6.77-6.89 (1 H, m), 6.16-6.22 (1 H, m), 5.71-5.77 (1 H, m), 4.77 (1 H, br s), 4.25-4.36 (1 H, m), 3.96-4.14 (2 H, m), 3.51-3.68 (2 H, m), 3.42-3.49 (3 H, s), 3.00 (1 H, br s), 1.27 (3 H, d, J = 6.6 Hz). ¹⁹F NMR (376 MHz, DMSO-d₆) δ ppm −113.46 (1 F, s). |
| 55-34 | 458.1 | ¹H NMR (400 MHz, DMSO-d₆) δ ppm 10.17 (1 H, br d, J = 5.2 Hz), 8.30 (1 H, br s), 7.29-7.39 (1 H, m), 6.75-6.89 (3 H, m), 6.17 (1 H, br s), 6.21 (1 H, br s), 5.72-5.77 (1 H, m), 4.76 (1 H, br s), 4.20-4.43 (1 H, m), 4.13 (1 H, br s), 3.51-3.69 (2 H, m), 3.44 (3 H, s), 3.01 (1 H, br s), 1.28 (3 H, br d, J = 6.4 Hz). ¹⁹F NMR (376 MHz, DMSO-d₆) δ ppm −115.27 (1 F, s), −115.30 (1 F, s). |
| 55-35 | 580.2 | ¹H NMR (400 MHz, DMSO-d₆) δ ppm 9.03 (1 H, s), 8.45-8.54 (1 H, m), 7.36-7.47 (1 H, m), 7.28-7.35 (1 H, m), 7.17-7.26 (1 H, m), 6.81-6.94 (1 H, m), 6.22 (1 H, br d, J = 16.6 Hz), 5.76-5.81 (1 H, m), 4.98 (1 H, br s), 4.27-4.45 (2 H, m), 4.05-4.17 (1 H, m), 3.65-3.88 (1 H, m), 3.48 (1 H, br s), 3.06-3.20 (1 H, m), 2.35-2.49 (4 H, m), 1.35 (3 H, d, J = 6.8 Hz), 1.07 (6 H, t, J = 7.5 Hz). ¹⁹F NMR (376 MHz, DMSO-d₆) δ ppm −106.73 (1 F, s), −106.75 (1 F, s), −109.35 (1 F, s), −109.38 (1 F, s). |
| 55-36 | 478.1 | ¹H NMR (400 MHz, DMSO-d₆) δ ppm 13.15 (1 H, s), 8.33-8.40 (1 H, m), 7.70 (1 H, s), 7.59 (1 H, d, J = 8.5 Hz), 7.33-7.39 (1 H, m), 6.78-6.93 (1 H, m), 6.16-6.25 (1 H, m), 5.74-5.80 (1 H, m), 4.77-4.92 (1 H, m), 4.10-4.39 (3 H, m), 3.98-4.05 (1 H, m), 3.56-3.78 (2 H, m), 3.44 (3 H, s), 2.27 (3 H, s), 1.31 (3 H, br t, J = 6.3 Hz). |
| 55-37 | 620.0 | ¹H NMR (400 MHz, DMSO-d₆) δ ppm 8.40 (br s, 1 H) 7.41-7.49 (m, 1 H) 7.19-7.29 (m, 2 H) 7.13 (t, J = 6.96 Hz, 1 H) 6.74-6.85 (m, 1 H) 6.14 (br d, J = 15.76 Hz, 1 H) 5.66-5.73 (m, 1 H) 4.90 (br s, |

TABLE 88-continued

Analytical Data

| Ex. # | LRMS: m/z (ESI, +ve ion): (M + H)+ | NMR |
|---|---|---|
| | | 1 H) 4.17-4.31 (m, 2 H) 3.90-4.04 (m, 1 H) 3.84 (s, 3 H) 3.73 (br d, J = 9.12 Hz, 1 H) 3.57 (br d, J = 12.44 Hz, 1 H) 2.96-3.12 (m, 1 H) 2.52-2.62 (m, 2 H) 1.28 (d, J = 6.63 Hz, 3 H) 0.99 (d, J = 6.63 Hz, 6 H) 0.84 (d, J = 6.63 Hz, 6 H) |
| 55-38 | 564.0 | $^1$H NMR (400 MHz, DMSO-$d_6$) δ 8.39-8.52 (m, 1H), 7.55 (br s, 1H), 7.28-7.37 (m, 4H), 6.85 (br d, J = 8.91 Hz, 1H), 6.20 (br d, J = 15.96 Hz, 1H), 5.76 (br d, J = 10.16 Hz, 1H), 4.85-5.05 (m, 1H), 4.32-4.44 (m, 1H), 4.28 (br s, 1H), 3.96-4.20 (m, 1H), 3.68-3.86 (m, 1H), 3.45-3.68 (m, 1H), 3.17 (br d, J = 5.60 Hz, 1H), 1.61 (s, 3H), 1.28-1.37 (m, 12H). $^{19}$F NMR (377 MHz, DMSO-$d_6$) δ −113.95 (br s, 1F). |
| 55-38-1 | 564.0 | $^1$H NMR (400 MHz, DMSO-$d_6$) δ 8.44 (br s, 1H), 7.53-7.59 (m, 1H), 7.28-7.37 (m, 4H), 6.79-6.89 (m, 1H), 6.20 (br d, J = 15.96 Hz, 1H), 5.74-5.78 (m, 1H), 4.91 (br s, 1H), 4.37 (br d, J = 13.27 Hz, 2H), 3.96-4.19 (m, 1H), 3.73 (br d, J = 11.20 Hz, 1H), 3.44-3.65 (m, 1H), 3.09-3.25 (m, 1H), 1.61 (s, 3H), 1.32-1.38 (m, 12H). $^{19}$F NMR (376 MHz, DMSO-$d_6$) δ −113.94 (s, 1F). |
| 55-38-2 | 564.0 | $^1$H NMR (400 MHz, DMSO-$d_6$) δ 8.49 (br s, 1H), 7.52-7.58 (m, 1H), 7.28-7.37 (m, 4H), 6.80-6.91 (m, 1H), 6.21 (br d, J = 16.59 Hz, 1H), 5.74-5.79 (m, 1H), 5.00 (br s, 1H), 4.23-4.47 (m, 2H), 4.00-4.20 (m, 1H), 3.79 (br s, 1H), 3.63 (br d, J = 12.85 Hz, 1H), 2.95-3.28 (m, 1H), 1.61 (s, 3H), 1.34 (s, 9H), 1.29 (br d, J = 6.22 Hz, 3H). $^{19}$F NMR (376 MHz, DMSO-$d_6$) δ −113.94 (s, 1F). |
| 55-39 | 580.2 | $^1$H NMR (DMSO-$d_6$) δ: 8.94-9.02 (m, 1H), 8.48-8.58 (m, 1H), 7.36-7.45 (m, 2H), 7.04-7.18 (m, 1H), 6.78-6.98 (m, 1H), 6.12-6.31 (m, 1H), 5.73-5.83 (m, 1H), 4.91-5.05 (m, 1H), 4.27-4.47 (m, 2H), 4.01-4.26 (m, 1H), 3.59-3.89 (m, 2H), 3.46-3.59 (m, 1H), 2.71-2.86 (m, 1H), 2.11-2.20 (m, 3H), 1.32-1.38 (m, 3H), 1.07-1.11 (m, 3H), 0.92-1.00 (m, 3H) |
| 55-39-1 | 580.2 | $^1$H NMR (DMSO-$d_6$) δ: 8.95-9.03 (m, 1H), 8.47-8.57 (m, 1H), 7.34-7.47 (m, 2H), 7.08-7.18 (m, 1H), 6.76-6.96 (m, 1H), 6.14-6.29 (m, 1H), 5.75-5.82 (m, 1H), 4.92-5.05 (m, 1H), 4.26-4.47 (m, 2H), 4.00-4.24 (m, 1H), 3.74-3.92 (m, 1H), 3.41-3.71 (m, 2H), 2.73-2.87 (m, 1H), 2.11-2.19 (m, 3H), 1.31-1.40 (m, 3H), 1.10 (s, 3H), 0.92-1.00 (m, 3H) |
| 55-39-2 | 580.2 | $^1$H NMR (DMSO-$d_6$) δ: 8.96-9.01 (m, 1H), 8.46-8.57 (m, 1H), 7.35-7.44 (m, 2H), 7.08-7.17 (m, 1H), 6.79-6.95 (m, 1H), 6.16-6.30 (m, 1H), 5.74-5.82 (m, 1H), 4.92-5.06 (m, 1H), 4.26-4.47 (m, 2H), 4.00-4.22 (m, 1H), 3.75-3.92 (m, 1H), 3.41-3.72 (m, 2H), 2.73-2.85 (m, 1H), 2.10-2.20 (m, 3H), 1.31-1.40 (m, 3H), 1.04-1.14 (m, 3H), 0.92-0.99 (m, 3H) |
| 55-40 | 576.2 | $^1$H NMR (DMSO-$d_6$) δ: 8.93-9.01 (m, 1H), 8.45-8.51 (m, 1H), 7.27-7.36 (m, 1H), 7.15-7.23 (m, 1H), 6.98-7.04 (m, 1H), 6.80-6.95 (m, 1H), 6.16-6.29 (m, 1H), 5.76-5.82 (m, 1H), 4.91-5.05 (m, 1H), 4.27-4.48 (m, 2H), 3.98-4.23 (m, 1H), 3.59-3.89 (m, 2H), 3.45-3.55 (m, 1H), 2.70-2.84 (m, 1H), 2.22-2.30 (m, |

TABLE 88-continued

Analytical Data

| Ex. # | LRMS: m/z (ESI, +ve ion): (M + H)+ | NMR |
|---|---|---|
| | | 3H), 2.13-2.19 (m, 3H), 1.32-1.39 (m, 3H), 1.06-1.13 (m, 3H), 0.93-1.01 (m, 3H) |
| 55-40-1 | 576.2 | $^1$H NMR (DMSO-$d_6$) δ: 8.93-9.02 (m, 1H), 8.41-8.54 (m, 1H), 7.28-7.38 (m, 1H), 7.13-7.25 (m, 1H), 6.96-7.06 (m, 1H), 6.79-6.95 (m, 1H), 6.14-6.28 (m, 1H), 5.72-5.81 (m, 1H), 4.90-5.05 (m, 1H), 4.25-4.47 (m, 2H), 4.00-4.22 (m, 1H), 3.74-3.90 (m, 1H), 3.57-3.71 (m, 1H), 3.41-3.59 (m, 1H), 2.73-2.87 (m, 1H), 2.22-2.30 (m, 3H), 2.08-2.21 (m, 3H), 1.33-1.39 (m, 3H), 1.07-1.11 (m, 3H), 0.96-1.01 (m, 3H) |
| 55-40-2 | 576.2 | $^1$H NMR (DMSO-$d_6$) δ: 8.94-9.02 (m, 1H), 8.44-8.53 (m, 1H), 7.27-7.41 (m, 1H), 7.15-7.26 (m, 1H), 6.99-7.07 (m, 1H), 6.81-6.95 (m, 1H), 6.13-6.31 (m, 1H), 5.70-5.85 (m, 1H), 4.90-5.07 (m, 1H), 4.27-4.47 (m, 2H), 4.00-4.25 (m, 1H), 3.74-3.91 (m, 1H), 3.57-3.72 (m, 1H), 3.42-3.55 (m, 1H), 2.75-2.85 (m, 1H), 2.24-2.31 (m, 3H), 2.12-2.19 (m, 3H), 1.31-1.41 (m, 3H), 1.07-1.14 (m, 3H), 0.95-1.02 (m, 3H) |
| 55-41 | 537.2 | $^1$H NMR (DMSO-$d_6$) δ: 8.32-8.64 (m, 1H), 8.02-8.08 (m, 1H), 7.60-7.73 (m, 1H), 7.52-7.59 (m, 1H), 7.24-7.50 (m, 2H), 6.78-6.96 (m, 1H), 6.14-6.27 (m, 1H), 5.77-5.81 (m, 1H), 5.07-5.23 (m, 1H), 4.78-4.96 (m, 1H), 3.89-4.54 (m, 4H), 3.55-3.75 (m, 1H), 2.86-3.11 (m, 1H), 1.37-1.44 (m, 3H), 1.29-1.35 (m, 3H), 1.21-1.27 (m, 3H) |
| 55-42 | 536.2 | $^1$H NMR (400 MHz, DMSO-$d_6$) δ 12.44-12.75 (m, 1H), 8.35 (br s, 1H), 7.60-7.70 (m, 1H), 7.50-7.58 (m, 1H), 7.28-7.38 (m, 3H), 6.85 (td, J = 11.84, 15.29 Hz, 1H), 6.20 (br d, J = 16.79 Hz, 1H), 5.71-5.80 (m, 1H), 4.74-5.02 (m, 1H), 3.97-4.47 (m, 3H), 3.37-3.85 (m, 2H), 2.97-3.25 (m, 1H), 2.67-2.78 (m, 1H), 1.31 (br d, J = 6.22 Hz, 3H), 1.05 (br d, J = 1.66 Hz, 6H). $^{19}$F NMR (376 MHz, DMSO-$d_6$) δ ppm −113.92 (s, 1F). |
| 55-43 | 576.2 | $^1$H NMR (400 MHz, CHLOROFORM-d) δ ppm 8.10 (1 H, s), 7.35-7.45 (4 H, m), 7.05-7.19 (3 H, m), 6.53-6.73 (1 H, m), 6.37-6.47 (1 H, m), 5.82 (1 H, d, J = 10.4 Hz), 4.54-5.22 (2 H, m), 4.37-4.53 (1 H, m), 4.36 (2 H, br s), 3.87 (1 H, br s), 3.63 (1 H, br s), 2.98-3.37 (1 H, m), 2.54 (1 H, br s), 2.11-2.46 (1 H, m), 1.65 (3 H, br s), 1.22-1.28 (1 H, m), 1.18 (3 H, d, J = 6.8 Hz), 0.96-1.03 (3 H, m). $^{19}$F NMR (376 MHz, CHLOROFORM-d) δ ppm −112.66 (s, 1F) |
| 55-43-1 | 576.2 | $^1$H NMR (400 MHz, DMSO-$d_6$) δ 8.41 (br d, J = 5.60 Hz, 1H), 7.46-7.54 (m, 1H), 7.16-7.39 (m, 6H), 6.79-6.94 (m, 1H), 6.21 (br d, J = 16.38 Hz, 1H), 5.73-5.80 (m, 1H), 5.00 (t, J = 5.70 Hz, 1H), 4.89 (br d, J = 1.66 Hz, 1H), 4.26-4.46 (m, 2H), 3.97-4.25 (m, 3H), 3.42-3.79 (m, 2H), 3.08-3.28 (m, 1H), 1.35 (d, J = 6.63 Hz, 3H), 1.05 (d, J = 6.84 Hz, 3H), 0.95 (d, J = 6.84 Hz, 3H) [Note: One proton was not observed]. $^{19}$F NMR (376 MHz, DMSO-$d_6$) δ ppm −113.64 (s, 1F). |
| 55-43-2 | 576.2 | $^1$H NMR (400 MHz, DMSO-$d_6$) δ 8.44 (br s, 1H), 7.46-7.55 (m, 1H), 7.16-7.39 (m, 6H), 6.79-6.94 (m, 1H), 6.21 (br d, |

TABLE 88-continued

Analytical Data

| Ex. # | LRMS: m/z (ESI, +ve ion): (M + H)+ | NMR |
|---|---|---|
| | | J = 16.59 Hz, 1H), 5.73-5.80 (m, 1H), 5.00 (t, J = 5.70 Hz, 1H), 4.95 (br s, 1H), 3.98-4.48 (m, 5H), 3.71-3.87 (m, 1H), 3.38-3.70 (m, 1H), 3.01-3.28 (m, 1H), 1.32 (br d, J = 6.63 Hz, 3H), 1.06 (d, J = 6.63 Hz, 3H), 0.96 (d, J = 6.84 Hz, 3H) [Note: One proton was not observed]. $^{19}$F NMR (376 MHz, DMSO-$d_6$) δ ppm −113.64 (s, 1F). |
| 56-1 | 646.0 | $^1$H NMR (400 MHz, CDCl$_3$) δ ppm 8.27 (br s, 1 H) 8.09 (br d, J = 13.1 Hz, 1 H) 8.03 (br d, J = 8.1 Hz, 1 H) 7.69-7.80 (m, 1 H) 7.57-7.69 (m, 1 H) 7.20-7.34 (m, 1 H) 6.64-6.74 (m, 2 H) 6.49-6.64 (m, 1 H) 6.34-6.43 (m, 1 H) 5.81 (br d, J = 10.6 Hz, 1 H) 4.16-5.41 (m, 3 H) 2.78-4.07 (m, 4 H) 1.49-1.68 (m, 3 H). $^{19}$F NMR (377 MHz, CDCl$_3$) δ ppm 66.87 (br d, J = 150.9 Hz, 1 F) −106.06−−104.79 (m, 1 F). |
| 56-1-1 | 646.0 | $^1$H NMR (400 MHz, CDCl$_3$) δ ppm 8.26 (br s, 1 H) 8.09 (br s, 1 H) 8.01 (br d, J = 8.3 Hz, 1 H) 7.67-7.76 (m, 1 H) 7.55-7.67 (m, 1 H) 7.17-7.31 (m, 2 H) 6.62-6.71 (m, 2 H) 6.59 (br d, J = 9.7 Hz, 1 H) 6.31-6.43 (m, 1 H) 5.79 (br d, J = 10.6 Hz, 1 H) 4.43-5.42 (m, 2 H) 3.96-4.38 (m, 2 H) 3.59-3.94 (m, 2 H) 2.62-3.35 (m, 1 H) 1.39 (br s, 3 H). $^{19}$F NMR (377 MHz, CDCl$_3$) δ ppm 66.88 (br d, J = 150.9 Hz, 1 F) −105.63 (br d, J = 33.2 Hz, 1 F). |
| 56-1-2 | 646.0 | $^1$H NMR (400 MHz, CDCl$_3$) δ ppm 8.18-8.45 (m, 1 H) 8.08 (s, 1 H) 8.03 (br d, J = 8.3 Hz, 1 H) 7.68-7.78 (m, 1 H) 7.58-7.68 (m, 1 H) 7.19-7.32 (m, 2 H) 6.64-6.77 (m, 2 H) 6.51-6.64 (m, 1 H) 6.34-6.44 (m, 1 H) 5.81 (br d, J = 10.4 Hz, 1 H) 4.38-4.97 (m, 3 H) 3.79-4.29 (m, 1 H) 3.40-3.71 (m, 2 H) 3.17 (br s, 1 H) 1.50-1.64 (m, 3 H), $^{19}$F NMR (377 MHz, CDCl$_3$) δ ppm 66.86 (br dd, J = 150.9, 22.1 Hz, 1 F) −105.84 (br s, 1 F). |
| 56-2 | 606.2 | $^1$H NMR (400 MHz, DMSO-$d_6$) δ ppm 9.05 (s, 1 H) 8.46 (br s, 1 H) 7.01-7.09 (m, 1 H) 6.81-6.93 (m, 1 H) 6.44 (br d, J = 8.29 Hz, 1 H) 6.31 (br s, 1 H) 6.21 (br d, J = 17.00 Hz, 1 H) 5.77 (br d, J = 10.37 Hz, 1 H) 5.08 (br d, J = 7.46 Hz, 2 H) 4.89-5.02 (m, 1 H) 4.31-4.46 (m, 1 H) 4.27 (br d, J = 12.65 Hz, 1 H) 4.02-4.20 (m, 1 H) 3.83 (br s, 1 H) 3.43-3.72 (m, 1 H) 2.86 (br s, 1 H) 2.61 (br s, 1 H) 1.35 (br s, 3 H) 0.98-1.13 (m, 10 H) 0.83-0.92 (m, 3 H). |
| 56-3 | 566.9 | $^1$H NMR (400 MHz, DMSO-$d_6$) δ ppm 8.92 (d, J = 4.1 Hz, 1H), 8.54-8.49 (m, 1H), 7.66-7.19 (m, 4H), 6.84-6.67 (m, 1H), 6.18 (br d, J = 16.2 Hz, 1H), 5.75 (m, 1H), 4.57-4.42 (m, 1H), 4.34 (m, 1H), 4.22 (m, 1H), 4.13-3.93 (m, 1H), 3.83 (m, 1H), 3.70 (m, 2H), 1.71-1.51 (m, 1H), 1.34-1.25 (m, 3H), 0.76 (m, 4H); $^{19}$F NMR (377 MHz, DMSO-$d_6$) δ ppm −73.41 (s, 1F). |
| 56-4 | 550.8 | $^1$H NMR (400 MHz, DMSO-$d_6$) δ ppm 8.94 (d, J = 6.2 Hz, 1H), 8.54 (d, J = 6.2 Hz, 1H), 7.60-7.46 (m, 2H), 7.43-7.30 (m, 3H), 6.80 (dd, J = 10.5, 16.7 Hz, 1H), 6.18 (br d, J = 17.4 Hz, 1H), 5.75 (m, 1H), 4.70-4.42 (m, 1H), 4.35 (m, 1H), 4.27-4.11 (m, 1H), 4.03 (m, 1H), 3.92-3.75 (m, 1H), 3.70 (m, 2H), 1.72-1.59 (m, 1H), 1.33-1.25 (m, 3H), 0.84-0.70 (m, |

TABLE 88-continued

Analytical Data

| Ex. # | LRMS: m/z (ESI, +ve ion): (M + H)⁺ | NMR |
|---|---|---|
| | | 3H). ¹⁹F NMR (377 MHz, DMSO-d₆) δ = −112.96−−112.89 (m 1F). |
| 56-5 | 558.2 | ¹H NMR (400 MHz, DMSO-d₆) δ ppm 0.32-0.43 (m, 1 H), 0.50-0.58 (m, 2 H), 0.60-0.69 (m, 1 H), 1.29-1.37 (m, 3 H), 1.38-1.47 (m, 1 H), 1.94 (s, 3 H), 3.02-3.15 (m, 0.5 H), 3.20-3.27 (m, 0.5 H), 3.58-3.79 (m, 1.5 H), 4.10-4.20 (m, 0.5 H), 4.21-4.30 (m, 1.5 H), 4.37-4.45 (m, 0.5 H), 4.91 (br s, 1 H), 5.72-5.80 (m, 1 H), 6.20 (br d, J = 16.2 Hz, 1 H), 6.79-6.92 (m, 2 H), 7.08-7.14 (m, 1 H), 7.14-7.20 (m, 1 H), 7.21-7.34 (m, 3 H), 7.47-7.55 (m, 1 H) 8.43 (br s, 1 H). ¹⁹F NMR (376 MHz, DMSO-d₆) δ ppm −113.66 (s, 1 F), −113.59 (s, 1 F). |
| 56-5-1 | 557.9 | ¹H NMR (400 MHz, DMSO-d₆) δ ppm 0.31-0.43 (m, 1 H), 0.49-0.59 (m, 2 H), 0.60-0.69 (m, 1 H), 1.33 (d, J = 6.6 Hz, 3 H), 1.38-1.50 (m, 1 H), 1.94 (s, 3 H), 3.03-3.14 (m, 0.5 H), 3.17 (d, J = 5.2 Hz, 3 H), 3.21-3.28 (m, 0.5 H), 3.4-3.53 (m, 0.5 H), 3.57-3.67 (m, 0.5 H), 3.68-3.81 (m, 1 H), 3.97-4.05 (m, 0.5 H), 4.14 (br d, J = 12.9 Hz, 0.5 H), 4.28 (br d, J = 13.5 Hz, 1.5 H), 4.40 (br d, J = 13.1 Hz, 0.5 H), 4.91 (br s, 1 H), 5.72-5.80 (m, 1 H), 6.20 (br dd, J = 15.7, 5.1 Hz, 1 H), 6.79-6.92 (m, 2 H), 7.06-7.14 (m, 1 H), 7.14-7.20 (m, 1 H), 7.21-7.36 (m, 3 H), 7.45-7.57 (m, 1 H), 8.43 (br s, 1 H). ¹⁹F NMR (376 MHz, DMSO-d₆) δ ppm −113.59 (s, 1 F). |
| 56-5-2 | 557.9 | ¹H NMR (400 MHz, DMSO-d₆) δ ppm 0.30-0.43 (m, 1 H), 0.48-0.58 (m, 2 H), 0.60-0.69 (m, 1 H), 1.32 (br d, J = 6.4 Hz, 3 H), 1.41-1.48 (m, 1 H), 1.94 (s, 3 H), 3.07 (br t, J = 11.2 Hz, 0.5 H), 3.17 (d, J = 5.2 Hz, 1 H), 3.22-3.29 (m, 0.5 H), 3.40-3.51 (m, 0.5 H), 3.59-3.81 (m, 1.5 H), 4.03 (br d, J = 13.9 Hz, 0.5 H), 4.11-4.20 (m, 0.5 H), 4.21-4.34 (m, 1.5 H), 4.35-4.46 (m, 0.5 H), 4.91 (br s, 1 H), 5.71-5.82 (m, 1 H), 6.21 (br d, J = 16.4 Hz, 1 H), 6.78-6.94 (m, 2 H), 7.07-7.14 (m, 1 H), 7.14-7.20 (m, 1 H), 7.21-7.35 (m, 3 H), 7.43-7.59 (m, 1 H). 8.44 (br s, 1 H). ¹⁹F NMR (376 MHz, DMSO-d₆) δ ppm −113.65 (s, 1 F). |
| 56-6 | 621.0 | ¹H NMR (400 MHz, DMSO-d₆) δ ppm 8.37 (br d, J = 14.3 Hz, 1 H), 7.37-7.44 (m, 1 H), 7.33 (t, J = 7.0 Hz, 1 H), 7.16-7.28 (m, 2 H), 7.08 (br d, J = 7.7 Hz, 1 H), 6.77-6.93 (m, 1 H), 6.52 (dd, J = 8.7, 2.7 Hz, 1 H), 6.27-6.34 (m, 1 H), 6.21 (br d, J = 16.4 Hz, 1 H), 5.76 (dd, J = 10.3, 2.4 Hz, 1 H), 5.41 (s, 2 H), 4.76-5.01 (m, 1 H), 3.96-4.44 (m, 3 H), 3.37-3.88 (m, 2 H), 2.99-3.15 (m, 1 H), 2.54-2.60 (m, 1 H), 1.33 (br dd, J = 12.5, 6.5 Hz, 3 H), 1.07 (d, J = 6.8 Hz, 3 H), 0.99 (br d, J = 6.6 Hz, 3 H). |
| 56-7 | 577.2 | ¹H NMR (400 MHz, DMSO-d₆) δ ppm 8.29-8.42 (m, 1 H), 7.37-7.44 (m, 1 H), 7.33 (t, J = 7.0 Hz, 1 H), 7.23 (td, J = 7.5, 1.2 Hz, 1 H), 7.04-7.13 (m, 2 H), 6.77-6.92 (m, 1 H), 6.58 (dd, J = 8.7, 2.7 Hz, 1 H), 6.29 (t, J = 2.5 Hz, 1 H), 6.21 (br d, J = 16.6 Hz, 1 H), 5.76 (dd, J = 10.5, 2.4 Hz, 1 H), 5.38 (s, 2 H), 4.75-5.01 (m, 1 H), 3.94-4.46 (m, 3 H), 3.38-3.86 (m, 2 H), 2.93-3.15 (m, 1 H), 2.59 |

TABLE 88-continued

Analytical Data

| Ex. # | LRMS: m/z (ESI, +ve ion): (M + H)+ | NMR |
|---|---|---|
| | | (br s, 1 H), 1.33 (br dd, J = 16.8, 6.6 Hz, 3 H), 1.04-1.10 (m, 3 H), 0.97 (br d, J = 6.8 Hz, 3 H). |
| 56-7-1 | 577.1 | $^1$H NMR (400 MHz, DMSO-$d_6$) δ ppm 8.39 (1 H, br s), 7.36-7.43 (1 H, m), 7.33 (1 H, br t, J = 7.5 Hz), 7.20-7.27 (1 H, m), 7.05-7.12 (2 H, m), 6.76-6.92 (1 H, m), 6.58 (1 H, dd, J = 8.6, 2.6 Hz), 6.28 (1 H, d, J = 2.5 Hz), 6.13-6.25 (1 H, m), 5.70-5.81 (1 H, m), 5.38 (2 H, s), 4.96 (1 H, br s), 3.97-4.47 (3 H, m), 3.34-3.87 (2 H, m), 2.98-3.24 (1 H, m), 2.54-2.60 (1 H, m), 1.31 (3 H, br d, J = 6.4 Hz), 1.07 (3 H, br d, J = 6.8 Hz), 0.98 (3 H, br d, J = 6.8 Hz). |
| 56-7-2 | 577.3 | $^1$H NMR (400 MHz, DMSO-$d_6$) δ ppm 8.34 (1 H, br s), 7.29-7.45 (2 H, m), 7.19-7.27 (1 H, m), 7.04-7.12 (2 H, m), 6.77-6.92 (1 H, m), 6.58 (1 H, dd, J = 8.7, 2.7 Hz), 6.29 (1 H, d, J = 2.7 Hz), 6.21 (1 H, br d, J = 16.2 Hz), 5.72-5.81 (1 H, m), 5.38 (2 H, s), 4.83 (1 H, br s), 4.23-4.45 (2 H, m), 3.96-4.22 (1 H, m), 3.44-3.74 (2 H, m), 3.07-3.27 (1 H, m), 2.54 (1 H, br s), 1.35 (3 H, d, J = 6.6 Hz), 1.07 (3 H, d, J = 6.8 Hz), 0.97 (3 H, br d, J = 6.6 Hz). |
| 56-8 | 594.2 | $^1$H NMR (400 MHz, DMSO-$d_6$) δ ppm 8.39 (br dd, J = 13.2, 4.7 Hz, 1 H), 7.34-7.53 (m, 4 H), 7.20-7.30 (m, 3 H), 6.93-7.17 (m, 2 H), 6.78-6.93 (m, 1 H), 6.21 (br d, J = 16.4 Hz, 1 H), 5.72-5.83 (m, 1 H), 4.80-5.05 (m, 1 H), 3.96-4.49 (m, 3 H), 3.34-3.87 (m, 2 H), 2.95-3.26 (m, 1 H), 2.54-2.62 (m, 1 H), 1.33 (dd, J = 10.4, 6.6 Hz, 3 H), 1.09 (d, J = 6.8 Hz, 3 H), 0.97 (dd, J = 6.8, 3.9 Hz, 3 H). $^{19}$F NMR (376 MHz, DMSO-$d_6$) δ ppm −82.02 (br s, 1 F), −82.04 (d, J = 5.2 Hz, 1 F). |
| 56-9 | 576.2 | $^1$H NMR (400 MHz, DMSO-$d_6$) δ ppm 8.31-8.46 (m, 1 H), 7.40-7.47 (m, 1 H), 7.31-7.39 (m, 1 H), 7.17-7.28 (m, 2 H), 7.13 (d, J = 7.5 Hz, 1 H), 7.04 (dt, J = 9.1, 3.7 Hz, 1 H), 6.78-6.94 (m, 1 H), 6.68 (dd, J = 5.4, 3.3 Hz, 1 H), 6.13-6.27 (m, 1 H), 5.70-5.82 (m, 1 H), 4.77-5.04 (m, 1 H), 3.99-4.44 (m, 3 H), 3.69-3.88 (m, 1 H), 3.66 (s, 3 H), 3.37-3.63 (m, 1 H), 2.96-3.26 (m, 1 H), 2.52-2.60 (m, 1 H), 1.33 (dd, J = 17.0, 6.6 Hz, 3 H), 1.05-1.13 (m, 3 H), 0.96-1.02 (m, 3 H). |
| 56-10 | 594.2 | $^1$H NMR (400 MHz, DMSO-$d_6$) δ ppm 8.39 (br d, J = 16.2 Hz, 1 H), 7.44-7.58 (m, 1 H), 7.36-7.43 (m, 1 H), 7.15-7.35 (m, 5 H), 7.10 (br d, J = 7.7 Hz, 1 H), 6.96-7.05 (m, 1 H), 6.77-6.92 (m, 1 H), 6.21 (br d, J = 16.8 Hz, 1 H), 5.71-5.81 (m, 1 H), 4.76-5.04 (m, 1 H), 3.94-4.47 (m, 3 H), 3.37-3.88 (m, 2 H), 2.96-3.21 (m, 1 H), 2.54-2.62 (m, 1 H), 1.33 (br dd, J = 14.3, 6.6 Hz, 3 H), 1.04-1.11 (m, 3 H), 0.95 (br d, J = 6.6 Hz, 3 H). |
| 57-1 | 547.0 | $^1$H NMR (400 MHz, DMSO-$d_6$) δ ppm 10.23 (d, J = 1.2 Hz, 1 H), 8.37 (d, J = 5.0 Hz, 1 H), 8.24-8.34 (m, 1 H), 7.19-7.32 (m, 2 H), 6.79-6.93 (m, 1 H), 6.74 (d, J = 8.3 Hz, 1 H), 6.69 (t, J = 8.9 Hz, 1 H), 6.21 (br d, J = 17.2 Hz, 1 H), 5.73-5.79 (m, 1 H), 4.84-5.00 (m, 1 H), 3.95-4.47 (m, 3 H), 3.02-3.82 (m, 3 H), 2.35-2.45 (m, 2 H), 1.93 (s, 3 H), 1.33 (dd, J = 9.4, 6.7 Hz, 3 H), 1.03 (td, J = 7.5, |

TABLE 88-continued

| | Analytical Data | |
|---|---|---|
| Ex. # | LRMS: m/z (ESI, +ve ion): (M + H)+ | NMR |
| | | 1.6 Hz, 3 H). $^{19}$F NMR (377 MHz, DMSO-d$_6$) δ ppm −115.66 (d, J = 6.1 Hz, 1 F), −128.33 (br s, 1 F). |
| 57-1-1 | 547.0 | $^1$H NMR (400 MHz, DMSO-d$_6$) δ ppm 10.32 (br s, 1 H), 8.35 (d, J = 5.0 Hz, 1 H), 8.27 (br t, J = 10.5 Hz, 1 H), 7.26 (q, J = 8.1 Hz, 1 H), 7.20 (d, J = 5.0 Hz, 1 H), 6.86 (dt, J = 16.0, 11.2 Hz, 1 H), 6.71 (br d, J = 8.3 Hz, 1 H), 6.66 (br t, J = 8.8 Hz, 1 H), 6.21 (br d, J = 16.4 Hz, 1 H), 5.73-5.79 (m, 1 H), 4.89 (br s, 1 H), 3.95-4.47 (m, 3 H), 3.44-3.77 (m, 2 H), 3.08-3.25 (m, 1 H), 2.32-2.42 (m, 2 H), 1.92 (s, 3 H), 1.34 (d, J = 6.6 Hz, 3 H), 1.03 (t, J = 7.5 Hz, 3 H). $^{19}$F NMR (376 MHz, DMSO-d$_6$) δ ppm −115.73 (br s, 1 F), −128.27 (br s, 1 F). |
| 57-1-2 | 547.0 | $^1$H NMR (400 MHz, DMSO-d$_6$) δ ppm 10.27 (br s, 1 H), 8.35 (d, J = 5.0 Hz, 1 H), 8.26-8.33 (m, 1 H), 7.23-7.31 (m, 1 H), 7.20 (d, J = 5.0 Hz, 1 H), 6.86 (dt, J = 16.2, 11.2 Hz, 1 H), 6.72 (d, J = 8.3 Hz, 1 H), 6.67 (br t, J = 8.9 Hz, 1 H), 6.21 (br d, J = 16.6 Hz, 1 H), 5.73-5.79 (m, 1 H), 4.88-4.98 (m, 1 H), 3.97-4.47 (m, 3 H), 3.40-3.80 (m, 2 H), 3.03-3.28 (m, 1 H), 2.31-2.43 (m, 2 H), 1.93 (s, 3 H), 1.32 (d, J = 6.6 Hz, 3 H), 1.03 (t, J = 7.5 Hz, 3 H). $^{19}$F NMR (376 MHz, DMSO-d$_6$) δ ppm −115.69 (br s, 1 F), −128.35 (br s, 1 F). |
| 57-2 | 532.3 | $^1$H NMR (400 MHz, DMSO-d$_6$) δ ppm 8.71 (d, J = 2.49 Hz, 1 H) 8.52 (dd, J = 2.28, 0.83 Hz, 1 H) 8.28-8.42 (m, 1 H) 7.48-7.59 (m, 1 H) 7.21-7.36 (m, 3 H) 6.77-6.93 (m, 1 H) 6.21 (br d, J = 16.79 Hz, 1 H) 5.69-5.79 (m, 1 H) 4.82-5.07 (m, 1 H) 4.40 (br d, J = 13.68 Hz, 1 H) 4.18-4.33 (m, 1 H) 3.98-4.17 (m, 1 H) 3.59-3.75 (m, 1 H) 3.03-3.28 (m, 1 H) 2.82-2.95 (m, 1 H) 1.28-1.42 (m, 3 H) 1.12-1.28 (m, 4 H) 1.04 (d, J = 6.84 Hz, 3 H). |
| 57-3 | 548.2 | $^1$H NMR (500 MHz, DMSO-d$_6$) δ ppm 10.25 (br s, 1 H) 8.66 (d, J = 2.47 Hz, 1 H) 8.49 (d, J = 2.47 Hz, 1 H) 8.23-8.37 (m, 1 H) 7.24-7.29 (m, 1 H) 6.81-6.91 (m, 1 H) 6.72 (d, J = 8.19 Hz, 1 H) 6.68 (t, J = 8.65 Hz, 1 H) 6.20 (br dd, J = 17.06, 9.02 Hz, 1 H) 5.75-5.78 (m, 1 H) 5.02 (br s, 1 H) 4.87 (br s, 1 H) 4.36-4.44 (m, 1 H) 4.22-4.31 (m, 1 H) 3.99-4.17 (m, 1 H) 3.57-3.66 (m, 1 H) 3.30-3.32 (m, 1 H) 3.24 (br t, J = 12.78 Hz, 1 H) 3.16 (d, J = 5.19 Hz, 1 H) 2.77-2.84 (m, 1 H) 2.52-2.55 (m, 1 H) 1.21-1.40 (m, 4 H) 1.10-1.16 (m, 3 H) 1.02 (d, J = 6.62 Hz, 3 H). |
| 57-4 | 590.2 | $^1$H NMR (400 MHz, DMSO-d$_6$) δ ppm 10.20 (br s, 1 H) 9.05 (s, 1 H) 8.27-8.37 (m, 1 H) 7.23-7.30 (m, 1 H) 6.80-6.93 (m, 1 H) 6.72 (d, J = 7.94 Hz, 1 H) 6.68 (t, J = 8.89 Hz, 1 H) 6.21 (br d, J = 16.59 Hz, 1 H) 5.74-5.80 (m, 1 H) 4.97 (br s, 1 H) 4.24-4.44 (m, 2 H) 3.95-4.20 (m, 1 H) 3.69-3.80 (m, 1 H) 3.47-3.70 (m, 1 H) 3.06-3.27 (m, 1 H) 2.69 (br d, J = 6.22 Hz, 2 H) 1.35 (d, J = 6.63 Hz, 3 H) 1.08 (d, J = 6.43 Hz, 6 H) 0.93 (d, J = 6.63 Hz, 6 H). |
| 57-5 | 574.3 | $^1$H NMR (400 MHz, DMSO-d$_6$) δ ppm 9.14 (br s, 1 H) 8.43 (br s, 1 H) 7.59 (br s, 1 H) 7.35 (br s, 2 H) 7.29 (br s, 1 H) |

TABLE 88-continued

| | Analytical Data | |
|---|---|---|
| Ex. # | LRMS: m/z (ESI, +ve ion): (M + H)$^+$ | NMR |
| | | 6.91 (br s, 1 H) 6.26 (br d, J = 14.10 Hz, 1 H) 5.73-5.90 (m, 1 H) 5.02 (br s, 1 H) 4.41 (br d, J = 13.68 Hz, 2 H) 4.05-4.26 (m, 1 H) 3.81 (br s, 1 H) 3.51-3.73 (m, 1 H) 3.00-3.26 (m, 1 H) 2.78 (br s, 2 H) 1.40 (br s, 3 H) 1.14 (br s, 6 H) 0.97 (br s, 6 H). |
| 57-6 | 545.5 | $^1$H NMR (400 MHz, CDCl$_3$) δ ppm 0.96-1.07 (m, 3 H) 1.19-1.24 (m, 3 H) 1.40-1.53 (m, 3 H) 2.47-2.81 (m, 1 H) 2.94-3.37 (m, 1 H) 3.40-3.96 (m, 3 H) 3.99-4.34 (m, 1 H) 4.37-4.92 (m, 2 H) 5.77-5.86 (m, 1 H) 6.36-6.45 (m, 1 H) 6.52-6.75 (m, 3 H) 7.07-7.20 (m, 1 H) 7.27-7.30 (m, 1 H) 7.36-7.44 (m, 1 H) 7.48-7.59 (m, 2 H) 7.83-7.91 (m, 1 H) 9.44-9.51 (m, 1 H). |
| 57-6-1 | 545.9 | $^1$H NMR (400 MHz, DMSO-d$_6$) δ ppm 0.91-1.13 (m, 6 H) 1.30-1.41 (m, 3 H) 3.07-3.29 (m, 1 H) 3.42-3.73 (m, 2 H) 3.95-4.49 (m, 3 H) 4.73-4.93 (m, 1 H) 5.67-5.85 (m, 1 H) 6.12-6.27 (m, 1 H) 6.59-6.77 (m, 2 H) 6.79-6.99 (m, 1 H) 7.04-7.14 (m, 1 H) 7.20-7.30 (m, 2 H) 7.30-7.37 (m, 1 H) 7.37-7.45 (m, 1 H) 7.98-8.36 (m, 1 H) 10.00-10.33 (m, 1 H). $^{19}$F NMR (376 MHz, DMSO-d$_6$) δ ppm −137.27−−124.40 (m, 1 F) −117.37−−111.23 (m, 1 F). |
| 57-6-2 | 545.9 | $^1$H NMR (400 MHz, DMSO-d$_6$) δ ppm 0.91-1.15 (m, 6 H) 1.26-1.41 (m, 3 H) 2-95-3.28 (m, 1 H) 3.39-3.83 (m, 2 H) 3.96-4.24 (m, 2 H) 4.23-4.51 (m, 1 H) 4.80-5.16 (m, 1 H) 5.61-5.89 (m, 1 H) 6.07-6.31 (m, 1 H) 6.58-6.78 (m, 2 H) 6.79-6.98 (m, 1 H) 7.03-7.16 (m, 1 H) 7.18-7.50 (m, 4 H) 8.05-8.44 (m, 1 H) 9.98-10.38 (m, 1 H). $^{19}$F NMR (376 MHz, DMSO-d$_6$) δ ppm −130.73−−127.48 (m, 1 F) −115.98 (br d, J = 8.67 Hz, 1 F) |
| 57-7 | 529.8 | $^1$H NMR (400 MHz, CDCl$_3$) δ ppm 7.75-7.84 (m, 1H), 7.37-7.50 (m, 3H), 7.28-7.35 (m, 2H), 7.06-7.20 (m, 3H), 6.50-6.74 (m, 1H), 6.36-6.47 (m, 1H), 5.76-5.87 (m, 1H), 4.21-5.18 (m, 3H), 3.52-4.09 (m, 3H), 2.91-3.40 (m, 1H), 2.49-2.79 (m, 1H), 1.34-1.53 (m, 3H), 1.17-1.25 (m, 3H), 0.99-1.07 (m, 3H). $^{19}$F NMR (376 MHz, DMSO-d$_6$) δ ppm −132.17 (br d, J = 2.60 Hz, 1 F) −121.88−−113.23 (m, 1 F). |
| 57-7-1 | 529.8 | $^1$H NMR (400 MHz, CDCl$_3$) δ ppm 0.98-1.10 (m, 3 H) 1.16-1.25 (m, 3 H) 1.36-1.55 (m, 3 H) 2.55-2.76 (m, 1 H) 3.01-3.31 (m, 1 H) 3.49-3.80 (m, 2 H) 3.81-4.11 (m, 1 H) 4.26-4.40 (m, 1 H) 4.44-4.63 (m, 1 H) 4.65-4.84 (m, 1 H) 4.96-5.10 (m, 1 H) 5.77-5.86 (m, 1 H) 6.36-6.46 (m, 1 H) 6.52-6.74 (m, 1 H) 7.08-7.20 (m, 3 H) 7.28-7.34 (m, 2 H) 7.38-7.50 (m, 3 H) 7.74-7.82 (m, 1 H). $^{19}$F NMR (376 MHz, CDCl$_3$) δ ppm −133.13−−123.04 (m, 1 F) −117.27−−105.74 (m, 1 F). |
| 57-7-2 | 529.8 | $^1$H NMR (400 MHz, CDCl$_3$) δ ppm 0.98-1.11 (m, 3 H) 1.17-1.25 (m, 3 H) 1.42-1.55 (m, 3 H) 2.56-2.79 (m, 1 H) 2.89-3.37 (m, 1 H) 3.51-4.11 (m, 3 H) 4.18-5.18 (m, 3 H) 5.72-5.89 (m, 1 H) 6.29-6.48 (m, 1 H) 6.51-6.75 (m, 1 H) 7.04-7.21 (m, 3 H) 7.28-7.34 (m, 2 H) 7.37-7.52 (m, 3 H) 7.71-7.88 (m, 1 H). $^{19}$F NMR (376 MHz, CDCl$_3$) δ ppm −130.54−−120.73 (m, 1 F) −116.12−−107.18 (m, 1 F). |

TABLE 88-continued

Analytical Data

| Ex. # | LRMS: m/z (ESI, +ve ion): (M + H)+ | NMR |
|---|---|---|
| 57-8-1 | 545.9 | $^1$H NMR (400 MHz, DMSO-d$_6$) δ ppm 0.92-1.14 (m, 6 H) 1.27-1.40 (m, 3 H) 2.53-2.64 (m, 1 H) 3.03-3.27 (m, 1 H) 3.44-3.77 (m, 2 H) 3.94-4.50 (m, 3 H) 4.76-4.95 (m, 1 H) 5.67-5.85 (m, 1 H) 6.10-6.33 (m, 1 H) 6.75-7.00 (m, 1 H) 7.07-7.62 (m, 9 H) 8.17-8.37 (m, 1 H) $^{19}$F NMR (376 MHz, DMSO-d$_6$) δ ppm −129.46 (br s, 1 F). |
| 57-8-2 | 545.9 | $^1$H NMR (400 MHz, DMSO-d$_6$) δ ppm 0.92-1.15 (m, 6 H) 1.20-1.41 (m, 3 H) 3.34-3.52 (m, 1 H) 3.51-3.85 (m, 3 H) 3.93-4.49 (m, 3 H) 4.77-5.11 (m, 1 H) 5.64-5.84 (m, 1 H) 6.09-6.33 (m, 1 H) 6.69-6.99 (m, 1 H) 7.01-7.67 (m, 9 H) 8.14-8.52 (m, 1 H). $^{19}$F NMR (376 MHz, DMSO-d$_6$) δ ppm −129.53 (s, 1 F). |
| 57-9 | 530.9 | $^1$H NMR (400 MHz, DMSO-d$_6$) δ ppm 0.98-1.06 (m, 3 H) 1.10-1.17 (m, 3 H) 1.29-1.43 (m, 3 H) 2.62-2.71 (m, 1 H) 3.04-3.18 (m, 1 H) 3.62-3.69 (m, 1 H) 3.71-3.85 (m, 1 H) 3.95-4.18 (m, 1 H) 4.19-4.32 (m, 1 H) 4.33-4.48 (m, 1 H) 4.77-5.09 (m, 1 H) 5.69-5.86 (m, 1 H) 6.11-6.30 (m, 1 H) 6.76-6.98 (m, 1 H) 7.16-7.39 (m, 3 H) 7.42-7.62 (m, 2 H) 7.89-8.01 (m, 1 H) 8.20-8.44 (m, 2 H). $^{19}$F NMR (376 MHz, DMSO-d$_6$) δ ppm −132.88--125.27 (m, 1 F) −116.79--109.76 (m, 1 F). |
| 57-10 | 546.8 | $^1$H NMR (400 MHz, DMSO-d$_6$) δ ppm 0.69-1.18 (m, 6 H) 1.27-1.74 (m, 3 H) 2.88-3.34 (m, 2 H) 3.42-3.92 (m, 2 H) 3.94-4.56 (m, 3 H) 4.74-5.14 (m, 1 H) 5.64-5.93 (m, 1 H) 6.07-6.38 (m, 1 H) 6.51-7.00 (m, 3 H) 7.17-7.61 (m, 2 H) 7.79-8.06 (m, 1 H) 8.12-8.54 (m, 2 H) 9.95-10.37 (m, 1 H). $^{19}$F NMR (376 MHz, DMSO-d$_6$) δ ppm −133.17--124.10 (m, 1 F) −115.21 (br d, J = 6.93 Hz, 1 F). |
| 57-11 | 553.0 | $^1$H NMR (400 MHz, DMSO-d$_6$) δ ppm 10.21 (br s, 1 H), 9.02 (s, 1 H), 8.19-8.29 (m, 1 H), 7.26-7.34 (m, 1 H), 6.79-6.92 (m, 1 H), 6.76 (d, J = 8.3 Hz, 1 H), 6.71 (t, J = 9.0 Hz, 1 H), 6.14-6.26 (m, 1 H), 5.73-5.79 (m, 1 H), 4.91 (br d, J = 3.1 Hz, 1 H), 4.20-4.44 (m, 2 H), 3.96-4.18 (m, 1 H), 3.40-3.79 (m, 2 H), 3.17 (d, J = 5.2 Hz, 1 H), 2.61-2.72 (m, 1 H), 1.28-1.36 (m, 3 H), 1.10 (d, J = 6.6 Hz, 3 H), 1.02 (d, J = 6.6 Hz, 3 H). |
| 57-12 | 536.9 | $^1$H NMR (400 MHz, DMSO-d$_6$) δ ppm 9.07 (d, J = 0.6 Hz, 1 H), 8.23-8.35 (m, 1 H), 7.54-7.62 (m, 1 H), 7.30-7.44 (m, 3 H), 6.79-6.93 (m, 1 H), 6.20 (br d, J = 17.0 Hz, 1 H), 5.76 (dd, J = 10.5, 2.4 Hz, 1 H), 4.81-5.01 (m, 1 H), 3.97-4.46 (m, 3 H), 3.36-3.83 (m, 2 H), 3.17 (d, J = 5.2 Hz, 1 H), 2.68-2.80 (m, 1 H), 1.32 (dd, J = 10.3, 6.7 Hz, 3 H), 1.12 (d, J = 6.8 Hz, 3 H), 1.03 (d, J = 6.8 Hz, 3 H) |
| 57-13-1 | 530.0 | $^1$H NMR (400 MHz, DMSO-d$_6$) δ ppm 8.26-8.36 (m, 1H), 7.49-7.59 (m, 1H), 7.15-7.36 (m, 6H), 6.80-6.92 (m, 1H), 6.21 (br d, J = 16.17 Hz, 1H), 5.76 (br d, J = 10.37 Hz, 1H), 4.89 (br s, 1H), 3.83-4.50 (m, 3H), 3.41-3.74 (m, 2H), 3.04-3.25 (m, 1H), 2.20-2.32 (m, 2H), 1.90 (s, 3H), 1.33 (br d, J = 6.22 Hz, 3H), 0.99 (br t, J = 7.36 Hz, 3H). $^{19}$F NMR (377 MHz, DMSO-d$_6$) δ ppm −113.78 (br d, J = 32.95 Hz, 1F), −129.66 (br d, J = 32.94 Hz, 1F). |

TABLE 88-continued

Analytical Data

| Ex. # | LRMS: m/z (ESI, +ve ion): (M + H)+ | NMR |
|---|---|---|
| 57-13-2 | 530.0 | $^1$H NMR (400 MHz, DMSO-d$_6$) δ ppm 8.28-8.37 (m, 1H), 7.49-7.59 (m, 1H), 7.15-7.36 (m, 6H), 6.86 (q, J = 12.99 Hz, 1H), 6.21 (br d, J = 15.96 Hz, 1H), 5.76 (br d, J = 10.37 Hz, 1H), 4.91 (br s, 1H), 3.97-4.46 (m, 3H), 3.38-3.84 (m, 2H), 2.99-3.27 (m, 1H), 2.20-2.30 (m, 2H), 1.91 (s, 3H), 1.31 (br d, J = 6.01 Hz, 3H), 0.98 (br t, J = 7.46 Hz, 3H). $^{19}$F NMR (377 MHz, DMSO-d$_6$) δ −113.79 (br d, J = 32.08 Hz, 1F), −129.68 (br d, J = 32.07 Hz, 1F). |
| 57-14-1 | 546.0 | $^1$H NMR (400 MHz, DMSO-d$_6$) δ ppm 10.19 (br s, 1H), 8.25 (br s, 1H), 7.04-7.43 (m, 4H), 6.59-6.97 (m, 3H), 6.20 (br d, J = 14.72 Hz, 1H), 5.76 (br d, J = 8.29 Hz, 1H), 4.86 (br s, 1H), 3.93-4.47 (m, 3H), 3.45-3.79 (m, 2H), 2.98-3.23 (m, 1H), 2.23 (br s, 2H), 1.87 (br s, 3H), 1.33 (br s, 3H), 0.87-1.08 (m, 3H). $^{19}$F NMR (377 MHz, DMSO-d$_6$) δ ppm 115.46 (br s, 1F), −128.77 (br s, 1F). |
| 57-14-2 | 546.0 | $^1$H NMR (400 MHz, DMSO-d$_6$) δ ppm 10.29 (br s, 1H), 8.28 (br s, 1H), 7.10-7.31 (m, 4H), 6.78-6.93 (m, 1H), 6.64-6.76 (m, 2H), 6.20 (br d, J = 15.96 Hz, 1H), 5.76 (br d, J = 10.16 Hz, 1H), 4.91 (br s, 1H), 3.90-4.51 (m, 3H), 3.44-3.76 (m, 2H), 2.99-3.09 (m, 1H), 2.23 (br d, J = 7.05 Hz, 2H), 1.88 (br s, 3H), 1.30 (br d, J = 5.18 Hz, 3H), 0.96 (br t, J = 7.15 Hz, 3H). $^{19}$F NMR (377 MHz, DMSO-d$_6$) δ ppm −115.52 (br d, J = 4.34 Hz, 1F), −128.74 (br s, 1F). |
| 57-15-1 | 580.0 | $^1$H NMR (400 MHz, DMSO-d$_6$) δ ppm 10.18 (s, 1H), 8.23-8.33 (m, 1H), 7.38 (br s, 3H), 7.27 (q, J = 7.81 Hz, 1H), 6.79-6.92 (m, 1H), 6.64-6.76 (m, 2H), 6.21 (br d, J = 16.79 Hz, 1H), 5.76 (br d, J = 10.57 Hz, 1H), 4.90 (br s, 1H), 4.24-4.47 (m, 2H), 3.95-4.23 (m, 1H), 3.68 (br s, 2H), 3.06-3.20 (m, 1H), 2.61-2.70 (m, 1H), 1.33 (br d, J = 6.22 Hz, 3H), 1.09 (br d, J = 6.43 Hz, 3H), 0.99 (br d, J = 6.43 Hz, 3H). $^{19}$F NMR (377 MHz, DMSO-d$_6$) δ ppm −115.21 (br d, J = 4.33 Hz, 1F), −128.38 (br s, 1F). |
| 57-15-2 | 580.0 | $^1$H NMR (400 MHz, DMSO-d$_6$) δ ppm 10.19 (s, 1H), 8.29 (br t, J = 9.54 Hz, 1H), 7.38 (br s, 3H), 7.20-7.35 (m, 1H), 6.79-6.92 (m, 1H), 6.64-6.76 (m, 2H), 6.21 (br d, J = 16.59 Hz, 1H), 5.76 (br d, J = 10.57 Hz, 1H), 4.94 (br s, 1H), 4.24-4.48 (m, 2H), 3.95-4.21 (m, 1H), 3.42-3.80 (m, 2H), 3.06-3.28 (m, 1H), 2.61-2.69 (m, 1H), 1.32 (br d, J = 6.43 Hz, 3H), 1.09 (br d, J = 6.43 Hz, 3H), 0.98 (br d, J = 6.43 Hz, 3H). $^{19}$F NMR (377 MHz, DMSO-d$_6$) δ ppm −115.21 (br d, J = 5.20 Hz, 1F), −128.38 (br s, 1F). |
| 57-16 | 530.9 | $^1$H NMR (400 MHz, DMSO-d$_6$) δ ppm 8.39 (d, J = 5.0 Hz, 1 H), 8.29-8.38 (m, 1 H), 7.51-7.59 (m, 1 H), 7.21-7.38 (m, 4 H), 6.78-6.94 (m, 1 H), 6.21 (br d, J = 16.6 Hz, 1 H), 5.74-5.80 (m, 1 H), 4.93 (br s, 1 H), 4.23-4.46 (m, 2 H), 4.09 (br dd, J = 47.8, 13.2 Hz, 1 H), 3.40-3.82 (m, 2 H), 3.03-3.30 (m, 1 H), 2.31-2.46 (m, 2 H), 1.96 (d, J = 1.7 Hz, 3 H), 1.33 (t, J = 6.4 Hz, 3 H), 1.05 (td, J = 7.5, 2.4 Hz, 3 H). $^{19}$F NMR (376 MHz, DMSO-d$_6$) δ ppm −113.86 (dd, J = 31.6, 3.0 Hz, 1 F), −129.26 (br dd, J = 31.2, 7.8 Hz, 1 F). |

TABLE 88-continued

| | Analytical Data | |
|---|---|---|
| Ex. # | LRMS: m/z (ESI, +ve ion): (M + H)$^+$ | NMR |
| 57-16-1 | 531.1 | $^1$H NMR (400 MHz, DMSO-d$_6$) δ ppm 8.39 (d, J = 5.0 Hz, 1 H), 8.27-8.37 (m, 1 H), 7.50-7.60 (m, 1 H), 7.21-7.38 (m, 4 H), 6.86 (dt, J = 16.4, 10.9 Hz, 1 H), 6.21 (br d, J = 16.6 Hz, 1 H), 5.73-5.80 (m, 1 H), 4.92 (br s, 1 H), 4.24-4.46 (m, 2 H), 3.98-4.20 (m, 1 H), 3.42-3.82 (m, 2 H), 3.05-3.29 (m, 1 H), 2.31-2.46 (m, 2 H), 1.96 (s, 3 H), 1.34 (d, J = 6.8 Hz, 3 H), 1.02-1.08 (m, 3 H), $^{19}$F NMR (376 MHz, DMSO-d$_6$) δ ppm −113.85 (d, J = 31.2 Hz, 1 F), −129.25 (d, J = 32.1 Hz, 1 F). |
| 57-16-2 | 530.9 | $^1$H NMR (400 MHz, DMSO-d$_6$) δ ppm 8.39 (d, J = 5.0 Hz, 1 H), 8.30-8.38 (m, 1 H), 7.51-7.59 (m, 1 H), 7.21-7.38 (m, 4 H), 6.80-6.94 (m, 1 H), 6.21 (br d, J = 16.8 Hz, 1 H), 5.73-5.80 (m, 1 H), 4.94 (br s, 1 H), 4.23-4.47 (m, 2 H), 4.03 (br d, J = 13.7 Hz, 1 H), 3.39-3.83 (m, 2 H), 3.03-3.29 (m, 1 H), 2.40 (dt, J = 14.6, 7.3 Hz, 2 H), 1.96 (s, 3 H), 1.32 (d, J = 6.6 Hz, 3 H), 1.00-1.08 (m, 3 H), $^{19}$F NMR (376 MHz, DMSO-d$_6$) δ ppm −113.86 (d, J = 32.1 Hz, 1 F), −129.27 (br d, J = 32.1 Hz, 1 F). |
| 57-17 | 574.0 | $^1$H NMR (400 MHz, DMSO-d$_6$) δ ppm 10.20 (br s, 1 H), 8.15-8.41 (m, 1 H), 7.37 (br d, J = 8.1 Hz, 1 H), 7.09-7.33 (m, 3 H), 6.77-6.93 (m, 1 H), 6.63-6.75 (m, 2 H), 6.19 (br d, J = 16.2 Hz, 1 H), 5.72-5.80 (m, 1 H), 4.69-5.02 (m, 1 H), 3.92-4.52 (m, 3 H), 3.48-3.76 (m, 2 H), 2.85-3.28 (m, 1 H), 1.73 (s, 3 H), 1.15-1.41 (m, 3 H), 1.11 (s, 9 H), $^{19}$F NMR (376 MHz, DMSO-d$_6$) δ ppm −115.54 (br s, 1 F), −128.97 (br s, 1 F). |
| 57-17-1 | 574.0 | $^1$H NMR (400 MHz, DMSO-d$_6$) δ ppm 10.17 (s, 1 H), 8.16-8.27 (m, 1 H), 7.37 (d, J = 7.3 Hz, 1 H), 7.10-7.32 (m, 3 H), 6.84 (dt, J = 16.5, 10.7 Hz, 1 H), 6.64-6.76 (m, 2 H), 6.19 (br d, J = 16.6 Hz, 1 H), 5.72-5.79 (m, 1 H), 4.78 (br s, 1 H), 3.94-4.44 (m, 3 H), 3.57 (br s, 2 H), 3.11-3.29 (m, 1 H), 1.73 (s, 3 H), 1.36 (br d, J = 5.4 Hz, 3 H), 1.11 (s, 9 H), $^{19}$F NMR (376 MHz, DMSO-d$_6$) δ ppm −115.52 (d, J = 6.1 Hz, 1 F), −128.98 (br s, 1 F). |
| 57-17-2 | 574.0 | $^1$H NMR (400 MHz, DMSO-d$_6$) δ ppm 10.17 (s, 1 H), 8.36 (br d, J = 8.1 Hz, 1 H), 7.37 (br d, J = 8.1 Hz, 1 H), 7.10-7.33 (m, 3 H), 6.75-6.94 (m, 1 H), 6.63-6.75 (m, 2 H), 6.20 (br d, J = 14.9 Hz, 1 H), 5.76 (br d, J = 8.7 Hz, 1 H), 4.89-5.01 (m, 1 H), 3.95-4.53 (m, 3 H), 3.54-3.77 (m, 2 H), 2.84-2.99 (m, 1 H), 1.73 (s, 3 H), 1.16-1.25 (m, 3 H), 1.11 (s, 9 H). $^{19}$F NMR (376 MHz, DMSO-d$_6$) δ ppm −115.53 (br s, 1 F), −128.98 (br d, J = 30.3 Hz, 1 F). |
| 57-18 | 543.0 | $^1$H NMR (400 MHz, DMSO-d$_6$) δ ppm 8.32 (br t, J = 10.1 Hz, 1H), 8.28 (d, J = 5.0 Hz, 1H), 7.51-7.60 (m, 1H), 7.27-7.38 (m, 3H), 7.14 (d, J = 4.8 Hz, 1H), 6.80-6.92 (m, 1H), 6.20 (br d, J = 16.6 Hz, 1H), 5.69-5.80 (m, 1H), 4.92 (br d, J = 1.5 Hz, 1H), 4.24-4.46 (m, 2H), 3.97-4.19 (m, 1H), 3.42-3.66 (m, 1H), 3.05-3.30 (m, 1H), 1.97 (s, 3H), 1.65 (br s, 1H), 1.33 (d, J = 6.6 Hz, 3H), 0.90 (td, J = 5.4, 2.6 Hz, 1H), 0.80-0.87 (m, 1H), 0.70-0.79 (m, 1H), 0.60-0.70 (m, 1H). |
| 58-1 | 560.2 | $^1$H NMR (400 MHz, DMSO-d$_6$) δ ppm 10.13 (br d, J = 2.07 Hz, 1H), 8.16-8.29 |

TABLE 88-continued

Analytical Data

| Ex. # | LRMS: m/z (ESI, +ve ion): (M + H)+ | NMR |
|---|---|---|
| | | (m, 1H), 7.55 (d, J = 7.67 Hz, 1H), 7.18-7.34 (m, 3H), 6.95 (d, J = 7.67 Hz, 1H), 6.78-6.91 (m, 1H), 6.63-6.76 (m, 2H), 6.14-6.25 (m, 1H), 5.76 (dd, J = 2.07, 10.37 Hz, 1H), 4.75-4.89 (m, 1H), 3.92-4.53 (m, 3H), 3.45-3.74 (m, 2H), 2.90-3.24 (m, 1H), 1.22-1.36 (m, 3H), 1.12 (s, 9H). $^{19}$F NMR (377 MHz, DMSO-d$_6$) δ ppm −114.88 (br d, J = 8.0 Hz, 1 F), −129.19 (m, 1 F). |
| 58-1-1 | 560.2 | $^1$H NMR (400 MHz, DMSO-d$_6$) δ ppm 10.15 (1 H, br d, J = 2.7 Hz), 8.28 (1 H, br d, J = 7.9 Hz), 7.55 (1 H, d, J = 7.7 Hz), 7.17-7.36 (3 H, m), 6.95 (1 H, br d, J = 7.5 Hz), 6.85 (1 H, br d, J = 10.0 Hz), 6.61-6.75 (2 H, m), 6.12-6.27 (1 H, m), 5.76 (1 H, dd, J = 10.5, 2.2 Hz), 4.78-4.94 (1 H, m), 3.53-4.54 (5 H, m), 2.89-3.09 (1 H, m), 1.25 (3 H, br s), 1.12 (9 H, s). $^{19}$F NMR (376 MHz, DMSO-d$_6$) δ −114.90 (br d, J = 6.93 Hz, 1F), −129.13 (br d, J = 9.54 Hz, 1F). |
| 58-1-2 | 560.2 | $^1$H NMR (400 MHz, DMSO-d$_6$) δ ppm 10.15 (1 H, s), 8.16-8.28 (1 H, m), 7.55 (1 H, dd, J = 8.1, 1.2 Hz), 7.18-7.34 (3 H, m), 6.95 (1 H, dd, J = 7.9, 1.2 Hz), 6.78-6.90 (1 H, m), 6.64-6.76 (2 H, m), 6.20 (1 H, br d, J = 16.4 Hz), 5.72-5.80 (1 H, m), 4.81 (1 H, br s), 3.94-4.45 (3 H, m), 3.45-3.72 (2 H, m), 3.10-3.26 (1 H, m), 1.33 (3 H, d, J = 6.6 Hz), 1.12 (9 H, s). $^{19}$F NMR (376 MHz, DMSO-d$_6$) δ ppm −114.88 (d, J = 7.80 Hz, 1F), −129.18 (br d, J = 6.94 Hz, 1F). |
| 58-2 | 560.9 | $^1$H NMR (400 MHz, DMSO-d$_6$) δ ppm 0.68-0.77 (m, 3 H) 1.27-1.38 (m, 3 H) 1.46-1.62 (m, 2 H) 1.88-1.95 (m, 3 H) 2.26-2.38 (m, 2 H) 3.40-3.80 (m, 2 H) 3.90-4.20 (m, 1 H) 4.21-4.49 (m, 2 H) 4.76-5.01 (m, 1 H) 5.65-5.85 (m, 1 H) 6.08-6.32 (m, 1 H) 6.62-6.77 (m, 2 H) 6.81-6.93 (m, 1 H) 7.17-7.22 (m, 1 H) 7.24-7.32 (m, 1 H) 8.20-8.33 (m, 1 H) 8.33-8.38 (m, 1 H) 10.10-10.31 (m, 1 H). $^{19}$F NMR (376 MHz, DMSO-d$_6$) δ ppm −128.39 (br s, 1 F) −115.68 (d, J = 5.20 Hz, 1 F). |
| 58-2-1 | 560.9 | $^1$H NMR (400 MHz, DMSO-d$_6$) δ ppm 0.66-0.80 (m, 3 H) 1.27-1.42 (m, 3 H) 1.47-1.64 (m, 2 H) 1.84-2.00 (m, 3 H) 2.23-2.40 (m, 2 H) 3.04-3.28 (m, 1 H) 3.43-3.79 (m, 2 H) 3.90-4.48 (m, 3 H) 4.75-5.00 (m, 1 H) 5.68-5.84 (m, 1 H) 6.09-6.28 (m, 1 H) 6.63-6.76 (m, 2 H) 6.78-6.96 (m, 1 H) 7.15-7.22 (m, 1 H) 7.23-7.34 (m, 1 H) 8.22-8.32 (m, 1 H) 8.33-8.40 (m, 1 H) 10.04-10.33 (m, 1 H). $^{19}$F NMR (377 MHz, DMSO-d$_6$) δ ppm −128.74−−128.20 (m, 1 F) −115.99−−115.49 (m, 1 F). |
| 58-2-2 | 560.9 | $^1$H NMR (400 MHz, DMSO-d$_6$) δ ppm 0.66-0.84 (m, 3 H) 1.26-1.37 (m, 3 H) 1.46-1.63 (m, 2 H) 1.84-1.99 (m, 3 H) 2.23-2.40 (m, 2 H) 2.97-3.29 (m, 1 H) 3.39-3.81 (m, 2 H) 3.86-4.52 (m, 3 H) 4.78-5.00 (m, 1 H) 5.65-5.86 (m, 1 H) 6.09-6.29 (m, 1 H) 6.62-6.77 (m, 2 H) 6.79-6.93 (m, 1 H) 7.13-7.23 (m, 1 H) 7.23-7.37 (m, 1 H) 8.14-8.42 (m, 2 H) 10.07-10.30 (m, 1 H). $^{19}$F NMR (377 MHz, DMSO-d$_6$) δ ppm −130.83−−126.15 (m, 1 F) −115.67 (br s, 1 F). |
| 58-3 | 614.8 | $^1$H NMR (400 MHz, DMSO-d$_6$) δ ppm 0.92-1.02 (m, 3 H) 1.07-1.14 (m, 3 H) |

TABLE 88-continued

Analytical Data

| Ex. # | LRMS: m/z (ESI, +ve ion): (M + H)+ | NMR |
|---|---|---|
| | | 1.26-1.40 (m, 3 H) 2.66-2.86 (m, 1 H) 2.98-3.30 (m, 1 H) 3.40-3.82 (m, 2 H) 3.96-4.19 (m, 1 H) 4.21-4.50 (m, 2 H) 4.85-5.05 (m, 1 H) 5.71-5.82 (m, 1 H) 6.14-6.27 (m, 1 H) 6.61-6.75 (m, 2 H) 6.77-7.00 (m, 1 H) 7.20-7.40 (m, 1 H) 7.56-7.81 (m, 1 H) 8.17-8.49 (m, 1 H) 8.68-9.06 (m, 1 H) 10.05-10.38 (m, 1 H). $^{19}$F NMR (376 MHz, DMSO-$d_6$) δ ppm −130.25−−125.57 (m, 1 F) −115.78 (br s, 1 F) −64.99−−59.43 (m, 1 F) |
| 58-3-1 | 614.8 | $^1$H NMR (400 MHz, DMSO-$d_6$) δ ppm 0.94-1.02 (m, 3 H) 1.07-1.15 (m, 3 H) 1.28-1.35 (m, 3 H) 2.63-2.84 (m, 1 H) 2.91-3.29 (m, 1 H) 3.38-3.83 (m, 2 H) 3.98-4.48 (m, 3 H) 4.92-5.06 (m, 1 H) 5.71-5.82 (m, 1 H) 6.12-6.28 (m, 1 H) 6.61-6.75 (m, 2 H) 6.78-6.96 (m, 1 H) 7.14-7.40 (m, 1 H) 7.60-7.83 (m, 1 H) 8.22-8.49 (m, 1 H) 8.70-9.01 (m, 1 H) 9.92-10.43 (m, 1 H). $^{19}$F NMR (376 MHz, DMSO-$d_6$) δ ppm −130.83−−126.15 (m, 1 F) −118.25−−114.45 (m, 1 F) −66.16−−60.02 (m, 1 F). |
| 58-3-2 | 614.8 | $^1$H NMR (400 MHz, DMSO-$d_6$) δ ppm 0.91-1.03 (m, 3 H) 1.07-1.16 (m, 3 H) 1.30-1.43 (m, 3 H) 2.63-2.85 (m, 1 H) 3.09-3.28 (m, 1 H) 3.49-3.84 (m, 2 H) 3.95-4.49 (m, 3 H) 4.80-5.01 (m, 1 H) 5.68-5.82 (m, 1 H) 6.12-6.35 (m, 1 H) 6.61-6.75 (m, 2 H) 6.77-7.00 (m, 1 H) 7.17-7.35 (m, 1 H) 7.61-7.77 (m, 1 H) 8.21-8.39 (m, 1 H) 8.78-8.92 (m, 1 H) 10.15-10.25 (m, 1 H). $^{19}$F NMR (376 MHz, DMSO-$d_6$) δ ppm −127.98 (br s, 1 F) −120.01−−112.69 (m, 1 F) −62.35 (br d, J = 24.28 Hz, 1 F). |
| 58-4 | 545.2 | $^1$H NMR (400 MHz, DMSO-$d_6$) δ ppm 8.42 (d, J = 4.8 Hz, 1H), 8.30-8.37 (m, 1H), 7.54 (br d, J = 8.1 Hz, 1H), 7.15-7.39 (m, 4H), 6.78-6.93 (m, 1H), 6.20 (br dd, J = 15.4, 4.7 Hz, 1H), 5.76 (d, J = 1.0 Hz, 1H), 4.93 (br s, 1H), 4.24-4.45 (m, 2H), 4.01 (br s, 1H), 3.58-3.78 (m, 1H), 3.39-3.54 (m, 1H), 3.28 (s, 1H), 3.06-3.17 (m, 1H), 2.66-2.78 (m, 1H), 1.93 (d, J = 1.7 Hz, 2H), 1.33 (dd, J = 6.6, 2.5 Hz, 3H), 1.07 (d, J = 6.8 Hz, 3H), 0.94 (dd, J = 6.6, 2.5 Hz, 3H). |
| 58-4-1 | 545.2 | $^1$H NMR (400 MHz, DMSO-$d_6$) δ ppm 8.44 (d, J = 4.8 Hz, 1H), 8.35 (br s, 1H), 7.55 (br d, J = 6.2 Hz, 1H), 7.21-7.37 (m, 5H), 6.81-6.94 (m, 1H), 6.21 (br d, J = 17.4 Hz, 1H), 5.72-5.82 (m, 2H), 4.93 (br d, J = 2.7 Hz, 1H), 4.24-4.45 (m, 2H), 3.95-4.19 (m, 1H), 3.62-3.78 (m, 1H), 2.72 (br s, 1H), 1.94 (s, 3H), 1.34 (d, J = 6.6 Hz, 3H), 1.08 (d, J = 6.6 Hz, 3H), 0.96 (d, J = 6.8 Hz, 3H). |
| 58-4-2 | 545.2 | $^1$H NMR (400 MHz, DMSO-$d_6$) δ ppm 8.40-8.46 (m, 1H), 8.35 (br s, 1H), 7.55 (br dd, J = 4.8, 1.5 Hz, 1H), 7.18-7.39 (m, 4H), 6.88 (br d, J = 17.4 Hz, 1H), 6.22 (br d, J = 16.2 Hz, 1H), 5.71-5.83 (m, 1H), 4.95 (br s, 1H), 4.83-4.90 (m, 1H), 4.22-4.44 (m, 1H), 3.96-4.23 (m, 1H), 3.96-3.98 (m, 1H), 3.73 (br d, J = 3.5 Hz, 2H), 2.66-2.75 (m, 1H), 1.95 (s, 3H), 1.33 (br d, J = 6.6 Hz, 3H), 1.08 (br d, J = 6.6 Hz, 3H), 0.91-0.99 (m, 3H). |
| 58-5 | 561.2 | $^1$H NMR (400 MHz, DMSO-$d_6$) δ ppm 9.70 (s, 1H), 8.45 (d, J = 4.8 Hz, 1H), 8.32 (br d, J = 3.3 Hz, 1H), 7.23 (d, J = 4.8 Hz, 1H), 7.12 (t, J = 9.3 Hz, 1H), 6.84- |

TABLE 88-continued

Analytical Data

| Ex. # | LRMS: m/z (ESI, +ve ion): $(M + H)^+$ | NMR |
|---|---|---|
| | | 6.91 (m, 2H), 6.58 (dd, J = 5.6, 3.1 Hz, 1H), 6.21 (br d, J = 15.3 Hz, 1H), 5.77 (d, J = 1.0 Hz, 1H), 4.89-4.98 (m, 1H), 4.88 (br d, J = 2.1 Hz, 1H), 4.25-4.37 (m, 2H), 4.22 (s, 1H), 3.60-3.76 (m, 2H), 2.68-2.75 (m, 1H), 1.94 (d, J = 1.9 Hz, 3H), 1.34 (dd, J = 6.4, 4.1 Hz, 3H), 1.08 (d, J = 6.4 Hz, 3H), 0.96 (dd, J = 6.6, 2.5 Hz, 3H). |
| 58-5-1 | 561.2 | $^1$H NMR (400 MHz, DMSO-d$_6$) δ ppm 9.63-9.80 (m, 1H), 8.41-8.50 (m, 1H), 8.24-8.39 (m, 1H), 7.18-7.29 (m, 1H), 7.06-7.17 (m, 1H), 6.82-6.94 (m, 2H), 6.54-6.63 (m, 1H), 6.12-6.28 (m, 1H), 5.72-5.83 (m, 1H), 4.88-5.00 (m, 1H), 4.37-4.47 (m, 1H), 4.25-4.37 (m, 2H), 3.96-4.23 (m, 1H), 3.59-3.82 (m, 2H), 2.64-2.80 (m, 1H), 1.88-1.98 (m, 3H), 1.28-1.37 (m, 3H), 1.04-1.10 (m, 3H), 0.90-0.98 (m, 3H). |
| 58-5-2 | 561.2 | $^1$H NMR (400 MHz, DMSO-d$_6$) δ ppm 9.53-9.94 (m, 1H), 8.39-8.50 (m, 1H), 8.24-8.39 (m, 1H), 7.19-7.28 (m, 1H), 7.04-7.16 (m, 1H), 6.80-6.94 (m, 2H), 6.52-6.65 (m, 1H), 6.15-6.29 (m, 1H), 5.71-5.82 (m, 1H), 4.86-4.99 (m, 1H), 4.24-4.35 (m, 2H), 3.97-4.21 (m, 1H), 3.59-3.78 (m, 2H), 2.65-2.77 (m, 1H), 1.87-1.99 (m, 3H), 1.30-1.39 (m, 3H), 1.06-1.11 (m, 3H), 0.94-0.99 (m, 3H). |
| 58-6 | 560.2 | $^1$H NMR (400 MHz, DMSO-d$_6$) δ ppm 8.40-8.46 (m, 1H), 8.22-8.36 (m, 1H), 7.18-7.25 (m, 1H), 6.91-6.99 (m, 1H), 6.80-6.91 (m, 1H), 6.60-6.70 (m, 1H), 6.32-6.40 (m, 1H), 6.15-6.27 (m, 1H), 5.73-5.81 (m, 1H), 5.06-5.20 (m, 2H), 4.86-5.00 (m, 1H), 4.24-4.47 (m, 2H), 3.97-4.20 (m, 1H), 3.60-3.80 (m, 2H), 2.63-2.77 (m, 2H), 1.87-2.00 (m, 3H), 1.29-1.38 (m, 3H), 1.03-1.13 (m, 3H), 0.91-1.00 (m, 3H). |
| 58-6-1 | 560.2 | $^1$H NMR (400 MHz, DMSO-d$_6$) δ ppm 8.39-8.46 (m, 1H), 8.25-8.35 (m, 1H), 7.18-7.25 (m, 1H), 6.93-6.99 (m, 1H), 6.79-6.92 (m, 1H), 6.62-6.69 (m, 1H), 6.33-6.39 (m, 1H), 6.15-6.26 (m, 1H), 5.73-5.80 (m, 1H), 5.07-5.20 (m, 2H), 4.88-4.99 (m, 1H), 4.26-4.47 (m, 2H), 3.96-4.24 (m, 2H), 3.59-3.80 (m, 2H), 2.64-2.77 (m, 1H), 1.91-1.99 (m, 3H), 1.30-1.38 (m, 3H), 1.06-1.10 (m, 3H), 0.92-0.98 (m, 3H). |
| 58-6-2 | 560.2 | $^1$H NMR (400 MHz, DMSO-d$_6$) δ ppm 8.41-8.46 (m, 1H), 8.22-8.34 (m, 1H), 7.18-7.25 (m, 1H), 6.92-7.01 (m, 1H), 6.79-6.91 (m, 1H), 6.60-6.71 (m, 1H), 6.32-6.39 (m, 1H), 6.15-6.27 (m, 1H), 5.72-5.81 (m, 1H), 5.01-5.27 (m, 2H), 4.85-4.98 (m, 1H), 4.24-4.47 (m, 2H), 3.97-4.20 (m, 1H), 3.59-3.80 (m, 2H), 2.64-2.77 (m, 2H), 1.89-1.99 (m, 3H), 1.30-1.39 (m, 3H), 1.06-1.11 (m, 3H), 0.94-0.98 (m, 3H). |
| 58-7 | 611.2 | $^1$H NMR (400 MHz, DMSO-d$_6$) δ ppm 10.38-10.68 (m, 1H), 8.23-8.52 (m, 1H), 7.17-7.25 (m, 1H), 7.05-7.14 (m, 1H), 6.80-6.94 (m, 1H), 6.60-6.66 (m, 1H), 6.16-6.27 (m, 1H), 5.73-5.81 (m, 1H), 4.86-5.01 (m, 1H), 4.23-4.47 (m, 2H), 3.98-4.21 (m, 1H), 3.60-3.85 (m, 2H), 2.63-2.79 (m, 2H), 1.86-1.98 (m, 3H), 1.29-1.38 (m, 3H), 1.04-1.13 (m, 3H), 0.88-1.00 (m, 3H). |

TABLE 88-continued

| | Analytical Data | |
|---|---|---|
| Ex. # | LRMS: m/z (ESI, +ve ion): (M + H)$^+$ | NMR |
| 58-7-1 | 611.0 | $^1$H NMR (400 MHz, DMSO-d$_6$) δ ppm 10.46-10.68 (m, 1H), 8.28-8.46 (m, 2H), 7.16-7.27 (m, 1H), 7.05-7.14 (m, 1H), 6.76-6.97 (m, 1H), 6.57-6.66 (m, 1H), 6.13-6.28 (m, 1H), 5.76-5.82 (m, 1H), 4.80-5.14 (m, 1H), 4.23-4.49 (m, 2H), 3.97-4.22 (m, 1H), 3.60-3.83 (m, 2H), 2.65-2.77 (m, 2H), 1.91-1.97 (m, 3H), 1.29-1.37 (m, 3H), 1.05-1.12 (m, 3H), 0.90-1.00 (m, 3H). |
| 58-7-2 | 611.0 | $^1$H NMR (400 MHz, DMSO-d$_6$)) δ ppm 10.41-10.67 (m, 1H), 8.29-8.43 (m, 2H), 7.16-7.26 (m, 1H), 7.06-7.13 (m, 1H), 6.78-6.96 (m, 1H), 6.58-6.66 (m, 1H), 6.14-6.30 (m, 1H), 5.73-5.83 (m, 2H), 4.87-5.00 (m, 1H), 4.24-4.47 (m, 2H), 3.97-4.22 (m, 1H), 3.60-3.81 (m, 2H), 2.64-2.77 (m, 1H), 1.89-1.99 (m, 3H), 1.32-1.39 (m, 3H), 1.03-1.11 (m, 3H), 0.92-0.98 (m, 3H). |
| 58-8 | 576.2 | $^1$H NMR (400 MHz, DMSO-d$_6$) δ ppm 8.38-8.43 (m, 1H), 7.44-7.63 (m, 2H), 7.17-7.25 (m, 1H), 7.08-7.16 (m, 1H), 6.57-6.68 (m, 1H), 6.35-6.41 (m, 1H), 6.14-6.27 (m, 1H), 5.71-5.81 (m, 1H), 5.38-5.50 (m, 2H), 4.85-5.03 (m, 1H), 4.25-4.46 (m, 2H), 3.98-4.22 (m, 1H), 3.61-3.85 (m, 2H), 2.65-2.79 (m, 2H), 1.88-1.98 (m, 3H), 1.28-1.37 (m, 3H), 1.05-1.15 (m, 3H), 0.90-0.98 (m, 3H). |
| 58-8-1 | 576.2 | $^1$H NMR (400 MHz, DMSO-d$_6$) δ ppm 8.37-8.43 (m, 1H), 8.26-8.36 (m, 1H), 7.16-7.23 (m, 1H), 7.08-7.15 (m, 1H), 6.81-6.94 (m, 1H), 6.58-6.68 (m, 1H), 6.33-6.41 (m, 1H), 6.15-6.27 (m, 1H), 5.77-5.82 (m, 1H), 5.39-5.49 (m, 2H), 4.85-4.98 (m, 1H), 4.36-4.48 (m, 1H), 4.23-4.36 (m, 2H), 3.98-4.21 (m, 1H), 3.60-3.81 (m, 2H), 2.64-2.76 (m, 1H), 1.89-1.97 (m, 3H), 1.31-1.39 (m, 3H), 1.03-1.12 (m, 3H), 0.92-0.99 (m, 3H). |
| 58-8-2 | 576.2 | $^1$H NMR (400 MHz, DMSO-d$_6$) δ ppm 8.37-8.44 (m, 1H), 8.25-8.37 (m, 1H), 7.17-7.23 (m, 1H), 7.06-7.15 (m, 1H), 6.80-6.95 (m, 1H), 6.58-6.67 (m, 1H), 6.33-6.39 (m, 1H), 6.15-6.26 (m, 1H), 5.76-5.82 (m, 1H), 5.39-5.47 (m, 2H), 4.88-5.01 (m, 1H), 4.37-4.48 (m, 1H), 4.23-4.35 (m, 2H), 3.97-4.22 (m, 1H), 3.62-3.82 (m, 2H), 2.62-2.79 (m, 1H), 1.87-1.98 (m, 3H), 1.28-1.38 (m, 3H), 1.03-1.13 (m, 3H), 0.90-0.99 (m, 3H). |
| 58-9 | 577.2 | $^1$H NMR (400 MHz, DMSO-d$_6$) δ ppm 10.09-10.26 (m, 1H), 8.35-8.43 (m, 1H), 8.21-8.38 (m, 1H), 7.22-7.30 (m, 1H), 7.15-7.22 (m, 1H), 6.91-6.96 (m, 1H), 6.81-6.91 (m, 2H), 6.16-6.26 (m, 1H), 5.74-5.80 (m, 1H), 4.83-5.05 (m, 1H), 4.23-4.49 (m, 2H), 3.97-4.21 (m, 1H), 3.62-3.82 (m, 2H), 2.64-2.81 (m, 2H), 1.86-1.96 (m, 3H), 1.29-1.39 (m, 3H), 1.05-1.12 (m, 3H), 0.86-1.01 (m, 3H). |
| 58-9-1 | 577.2 | $^1$H NMR (400 MHz, DMSO-d$_6$) δ ppm 10.04-10.34 (m, 1H), 8.18-8.50 (m, 2H), 7.06-7.44 (m, 2H), 6.77-7.00 (m, 3H), 6.07-6.32 (m, 1H), 5.65-5.92 (m, 2H), 4.82-4.96 (m, 1H), 4.22-4.48 (m, 2H), 3.97-4.22 (m, 1H), 3.61-3.78 (m, 2H), 2.65-2.82 (m, 1H), 1.84-1.96 (m, 3H), 1.32-1.42 (m, 3H), 1.07-1.12 (m, 3H), 0.86-1.01 (m, 3H). |
| 58-9-2 | 577.2 | $^1$H NMR (400 MHz, DMSO-d$_6$) δ ppm 10.03-10.25 (m, 1H), 8.21-8.44 (m, 2H), 7.10-7.35 (m, 2H), 6.79-6.98 (m, 3H), |

TABLE 88-continued

| | Analytical Data | |
|---|---|---|
| Ex. # | LRMS: m/z (ESI, +ve ion): (M + H)+ | NMR |
| | | 6.12-6.29 (m, 1H), 5.64-5.87 (m, 1H), 4.89-5.07 (m, 1H), 4.21-4.47 (m, 2H), 3.96-4.21 (m, 1H), 3.59-3.85 (m, 2H), 2.62-2.82 (m, 2H), 1.81-1.96 (m, 3H), 1.29-1.35 (m, 3H), 1.05-1.12 (m, 3H), 0.87-0.99 (m, 3H). |
| 58-10 | 563.2 | $^1$H NMR (400 MHz, DMSO-$d_6$) δ ppm 8.42-8.48 (m, 1H), 8.30-8.41 (m, 1H), 7.38-7.47 (m, 1H), 7.27-7.37 (m, 1H), 7.19-7.26 (m, 2H), 6.79-6.95 (m, 1H), 6.15-6.27 (m, 1H), 5.73-5.82 (m, 1H), 4.87-5.00 (m, 1H), 4.25-4.50 (m, 2H), 3.98-4.24 (m, 2H), 3.60-3.83 (m, 2H), 2.65-2.79 (m, 1H), 1.89-2.00 (m, 3H), 1.27-1.40 (m, 3H), 1.04-1.13 (m, 3H), 0.91-1.00 (m, 3H). |
| 58-10-1 | 563.2 | $^1$H NMR (400 MHz, DMSO-$d_6$) δ ppm 8.42-8.48 (m, 1H), 8.28-8.40 (m, 1H), 7.37-7.47 (m, 1H), 7.28-7.37 (m, 1H), 7.18-7.28 (m, 2H), 6.78-6.95 (m, 1H), 6.15-6.28 (m, 1H), 5.76-5.82 (m, 1H), 4.86-5.00 (m, 1H), 4.25-4.46 (m, 2H), 3.99-4.22 (m, 1H), 3.59-3.84 (m, 2H), 3.41-3.56 (m, 1H), 2.65-2.80 (m, 1H), 1.89-1.99 (m, 3H), 1.31-1.38 (m, 3H), 1.06-1.10 (m, 3H), 0.91-1.00 (m, 3H). |
| 58-10-2 | 563.2 | $^1$H NMR (400 MHz, DMSO-$d_6$) δ ppm 8.42-8.48 (m, 1H), 8.31-8.42 (m, 1H), 7.37-7.47 (m, 1H), 7.28-7.36 (m, 1H), 7.20-7.27 (m, 2H), 6.80-6.97 (m, 1H), 6.15-6.28 (m, 1H), 5.74-5.81 (m, 1H), 4.89-5.00 (m, 1H), 4.24-4.49 (m, 2H), 3.98-4.22 (m, 1H), 3.58-3.83 (m, 2H), 3.42-3.57 (m, 1H), 2.65-2.79 (m, 1H), 1.90-2.01 (m, 3H), 1.28-1.38 (m, 3H), 1.03-1.10 (m, 3H), 0.91-0.99 (m, 3H). |
| 58-11 | 562.2 | $^1$H NMR (400 MHz, DMSO-$d_6$) δ ppm 10.00-10.36 (m, 1H), 8.77-9.05 (m, 1H), 8.20-8.52 (m, 1H), 7.23-7.34 (m, 1H), 6.65-6.78 (m, 2H), 6.15-6.26 (m, 1H), 5.72-5.81 (m, 2H), 4.88-5.04 (m, 1H), 4.24-4.48 (m, 2H), 3.92-4.22 (m, 2H), 3.66-3.87 (m, 2H), 2.72-2.85 (m, 1H), 2.07-2.16 (m, 3H), 1.30-1.41 (m, 3H), 1.07-1.14 (m, 3H), 0.90-1.00 (m, 3H). |
| 58-11-1 | 562.2 | $^1$H NMR (400 MHz, DMSO-$d_6$) δ ppm 10.16-10.39 (m, 1H), 8.92-9.01 (m, 1H), 8.22-8.39 (m, 1H), 7.23-7.37 (m, 1H), 6.79-6.94 (m, 1H), 6.62-6.79 (m, 2H), 6.15-6.28 (m, 1H), 5.77-5.81 (m, 1H), 4.87-5.00 (m, 1H), 4.24-4.46 (m, 3H), 3.95-4.22 (m, 1H), 3.60-3.82 (m, 2H), 2.71-2.84 (m, 1H), 2.08-2.15 (m, 3H), 1.34-1.41 (m, 3H), 1.08-1.13 (m, 3H), 0.92-0.99 (m, 3H). |
| 58-11-2 | 562.2 | $^1$H NMR (400 MHz, DMSO-$d_6$) δ ppm 10.18-10.37 (m, 1H), 8.92-9.02 (m, 1H), 8.28-8.40 (m, 1H), 7.22-7.34 (m, 1H), 6.79-6.95 (m, 1H), 6.63-6.78 (m, 2H), 6.14-6.27 (m, 1H), 5.77-5.83 (m, 1H), 4.92-5.05 (m, 1H), 4.24-4.47 (m, 3H), 3.99-4.22 (m, 1H), 3.71-3.85 (m, 1H), 3.59-3.71 (m, 1H), 2.72-2.83 (m, 1H), 2.06-2.15 (m, 3H), 1.31-1.38 (m, 3H), 1.07-1.13 (m, 3H), 0.91-0.98 (m, 3H). |
| 58-12 | 546.2 | $^1$H NMR (400 MHz, DMSO-$d_6$) δ ppm 8.99-9.04 (m, 1H), 8.31-8.46 (m, 1H), 7.54-7.61 (m, 1H), 7.25-7.39 (m, 3H), 6.79-6.96 (m, 1H), 6.16-6.30 (m, 1H), 5.76-5.81 (m, 1H), 4.90-5.06 (m, 1H), 4.26-4.50 (m, 2H), 3.98-4.24 (m, 1H), 3.59-3.86 (m, 2H), 3.42-3.58 (m, 1H), |

TABLE 88-continued

Analytical Data

| Ex. # | LRMS: m/z (ESI, +ve ion): (M + H)+ | NMR |
|---|---|---|
| | | 2.73-2.88 (m, 1H), 2.12-2.20 (m, 3H), 1.31-1.40 (m, 3H), 1.06-1.14 (m, 3H), 0.92-1.00 (m, 3H). |
| 58-13 | 558.0 | $^1$H NMR (400 MHz, DMSO-d$_6$) δ ppm 10.20 (br d, J = 1.7 Hz, 1H), 8.18-8.35 (m, 1H), 7.23-7.31 (m, 1H), 7.14-7.19 (m, 1H), 7.10-7.13 (m, 1H), 6.79-6.93 (m, 2H), 6.66-6.75 (m, 2H), 6.15-6.24 (m, 1H), 5.73-5.78 (m, 1H), 4.75-4.97 (m, 1H), 3.96-4.48 (m, 3H), 3.42-3.78 (m, 2H), 2.92-3.23 (m, 1H), 1.91 (s, 3H), 1.42-1.54 (m, 1H), 1.28-1.35 (m, 3H), 0.56-0.67 (m, 1H), 0.42-0.54 (m, 2H), 0.37 (br dd, J = 8.5, 3.5 Hz, 1H). |
| 58-13-1 | 558.0 | $^1$H NMR (400 MHz, DMSO-d$_6$) δ ppm 10.21 (br s, 1H), 8.23-8.34 (m, 1H), 7.24-7.32 (m, 1H), 7.15-7.20 (m, 1H), 7.10-7.14 (m, 1H), 6.79-6.94 (m, 2H), 6.66-6.75 (m, 2H), 6.16-6.25 (m, 1H), 5.77 (dd, J = 10.0, 2.7 Hz, 1H), 4.84-4.96 (m, 1H), 3.98-4.48 (m, 3H), 3.40-3.77 (m, 2H), 2.99-3.22 (m, 1H), 1.92 (s, 3H), 1.42-1.54 (m, 1H), 1.31 (br d, J = 6.2 Hz, 3H), 0.57-0.67 (m, 1H), 0.43-0.56 (m, 2H), 0.32-0.40 (m, 1H). |
| 58-13-2 | 558.0 | $^1$H NMR (400 MHz, DMSO-d$_6$) δ ppm 10.20 (br s, 1H), 8.19-8.29 (m, 1H), 7.23-7.31 (m, 1H), 7.16 (d, J = 7.5 Hz, 1H), 7.09-7.13 (m, 1H), 6.77-6.92 (m, 2H), 6.65-6.75 (m, 2H), 6.10-6.27 (m, 1H), 5.74-5.78 (m, 1H), 4.79-4.89 (m, 1H), 4.00-4.48 (m, 3H), 3.45-3.73 (m, 2H), 3.17 (d, J = 4.8 Hz, 1H), 1.91 (s, 3H), 1.42-1.52 (m, 1H), 1.33 (d, J = 6.6 Hz, 3H), 0.57-0.66 (m, 1H), 0.42-0.56 (m, 2H), 0.32-0.41 (m, 1H). |
| 58-14 | 542.2 | $^1$H NMR (400 MHz, DMSO-d$_6$) δ ppm 8.22-8.37 (m, 1H), 7.48-7.63 (m, 1H), 7.27-7.39 (m, 3H), 7.18-7.24 (m, 1H), 7.11-7.16 (m, 1H), 6.79-6.94 (m, 2H), 6.14-6.26 (m, 1H), 5.74-5.79 (m, 1H), 4.89 (br d, J = 5.4 Hz, 1H), 4.23-4.47 (m, 2H), 3.97-4.20 (m, 1H), 3.38-3.77 (m, 2H), 3.01-3.28 (m, 1H), 1.92-1.99 (m, 3H), 1.44 (br dd, J = 6.6, 3.7 Hz, 1H), 1.32 (br d, J = 6.6 Hz, 3H), 0.61-0.69 (m, 1H), 0.49-0.59 (m, 2H), 0.33-0.45 (m, 1H). |
| 58-15 | 561.0 | $^1$H NMR (400 MHz, DMSO-d$_6$) δ ppm 10.21 (br s, 1H), 8.36 (d, J = 5.2 Hz, 1H), 8.30 (br d, J = 10.0 Hz, 1H), 7.20-7.35 (m, 2H), 6.85 (br s, 1H), 6.61-6.78 (m, 2H), 6.21 (br d, J = 16.8 Hz, 1H), 5.70-5.83 (m, 1H), 4.80-5.01 (m, 1H), 4.23-4.50 (m, 2H), 3.96-4.20 (m, 1H), 3.42-3.80 (m, 2H), 3.06-3.28 (m, 1H), 2.55-2.73 (m, 1H), 2.06 (s, 3H), 1.34 (t, J = 6.8 Hz, 3H), 1.08 (d, J = 6.8 Hz, 3H), 0.94 (d, J = 6.8 Hz, 3H). |
| 58-15-1 | 561.0 | $^1$H NMR (400 MHz, DMSO-d$_6$) δ ppm 10.21 (br s, 1H), 8.35 (d, J = 5.2 Hz, 1H), 8.24-8.33 (m, 1H), 7.20-7.33 (m, 2H), 6.78-6.95 (m, 1H), 6.62-6.76 (m, 2H), 6.14-6.27 (m, 1H), 5.76 (dd, J = 10.5, 2.2 Hz, 1H), 4.83-5.01 (m, 1H), 4.21-4.46 (m, 2H), 3.96-4.19 (m, 1H), 3.41-3.80 (m, 2H), 3.03-3.26 (m, 1H), 2.54-2.65 (m, 1H), 2.06 (s, 3H), 1.32 (d, J = 6.6 Hz, 3H), 1.07 (d, J = 6.6 Hz, 3H), 0.93 (d, J = 6.8 Hz, 3H). |
| 58-15-2 | 561.0 | $^1$H NMR (400 MHz, DMSO-d$_6$) δ ppm 10.20 (br s, 1H), 8.35 (d, J = 5.0 Hz, 1H), 8.23-8.33 (m, 1H), 7.19-7.35 (m, 2H), 6.79-6.95 (m, 1H), 6.64-6.78 (m, 2H), |

TABLE 88-continued

Analytical Data

| Ex. # | LRMS: m/z (ESI, +ve ion): (M + H)⁺ | NMR |
|---|---|---|
| | | 6.21 (br d, J = 16.2 Hz, 1H), 5.76 (br d, J = 10.4 Hz, 1H), 4.90 (br s, 1H), 4.24-4.46 (m, 2H), 3.98-4.18 (m, 1H), 3.46-3.78 (m, 2H), 3.08-3.26 (m, 1H), 2.55-2.64 (m, 1H), 2.05 (s, 3H), 1.34 (br d, J = 6.6 Hz, 3H), 1.07 (br d, J = 6.6 Hz, 3H), 0.93 (br d, J = 6.8 Hz, 3H). |
| 58-16 | 545.0 | $^1$H NMR (400 MHz, DMSO-$d_6$) δ ppm 8.40 (d, J = 5.2 Hz, 1H), 8.31-8.38 (m, 1H), 7.50-7.59 (m, 1H), 7.22-7.37 (m, 4H), 6.80-6.92 (m, 1H), 6.21 (br d, J = 16.4 Hz, 1H), 5.77 (dd, J = 10.4, 2.3 Hz, 1H), 4.87-5.01 (m, 1H), 4.24-4.46 (m, 2H), 3.98-4.19 (m, 1H), 3.40-3.81 (m, 2H), 3.03-3.27 (m, 1H), 2.56-2.72 (m, 1H), 2.09 (s, 3H), 1.33 (d, J = 6.6 Hz, 3H), 1.08 (d, J = 6.8 Hz, 3H), 0.95 (dd, J = 6.8, 2.3 Hz, 3H). |
| 58-16-1 | 545.0 | $^1$H NMR (400 MHz, DMSO-$d_6$) δ ppm 8.40 (d, J = 5.2 Hz, 1H), 8.32-8.39 (m, 1H), 7.51-7.59 (m, 1H), 7.23-7.38 (m, 4H), 6.80-6.94 (m, 1H), 6.21 (br d, J = 17.0 Hz, 1H), 5.77 (dd, J = 10.5, 2.2 Hz, 1H), 4.94 (br d, J = 1.0 Hz, 1H), 4.24-4.47 (m, 2H), 3.97-4.20 (m, 1H), 3.41-3.78 (m, 2H), 3.06-3.29 (m, 1H), 2.55-2.71 (m, 1H), 2.10 (s, 3H), 1.34 (d, J = 6.6 Hz, 3H), 1.08 (d, J = 6.8 Hz, 3H), 0.95 (d, J = 6.8 Hz, 3H). |
| 58-16-2 | 545.0 | $^1$H NMR (400 MHz, DMSO-$d_6$) δ ppm 8.40 (d, J = 5.2 Hz, 1H), 8.29-8.38 (m, 1H), 7.50-7.59 (m, 1H), 7.20-7.39 (m, 4H), 6.80-6.94 (m, 1H), 6.21 (br d, J = 16.8 Hz, 1H), 5.76 (dd, J = 10.9, 1.8 Hz, 1H), 4.93 (br s, 1H), 4.24-4.45 (m, 2H), 3.99-4.18 (m, 1H), 3.41-3.79 (m, 2H), 3.05-3.28 (m, 1H), 2.53-2.71 (m, 1H), 2.09 (s, 3H), 1.33 (d, J = 6.6 Hz, 3H), 1.08 (d, J = 6.8 Hz, 3H), 0.96 (d, J = 6.8 Hz, 3H). |
| 58-17 | 544.2 | $^1$H NMR (400 MHz, DMSO-$d_6$) δ ppm 8.19-8.39 (m, 1H), 7.49-7.61 (m, 2H), 7.33 (td, J = 5.55, 8.19 Hz, 2H), 7.22-7.29 (m, 3H), 7.01 (d, J = 7.88 Hz, 1H), 6.77-6.94 (m, 1H), 6.20 (br d, J = 16.79 Hz, 1H), 5.72-5.80 (m, 1H), 4.76-4.96 (m, 1H), 3.95-4.50 (m, 3H), 3.41-3.72 (m, 2H), 2.88-3.21 (m, 1H), 1.21-1.37 (m, 3H), 1.14 (s, 9H). $^{19}$F NMR (376 MHz, DMSO-$d_6$) δ −114.88 (d, J = 7.80 Hz, 1F), −129.18 (br d, J = 6.94 Hz, 1F). |
| 58-17-1 | 544.2 | $^1$H NMR (400 MHz, DMSO-$d_6$) δ ppm 8.34 (br d, J = 8.71 Hz, 1H), 7.49-7.61 (m, 2H), 7.30-7.37 (m, 2H), 7.22-7.29 (m, 3H), 7.01 (d, J = 7.67 Hz, 1H), 6.79-6.93 (m, 1H), 6.14-6.26 (m, 1H), 5.72-5.79 (m, 1H), 4.83-4.94 (m, 1H), 4.26-4.51 (m, 1H), 3.97-4.23 (m, 2H), 3.60-3.73 (m, 1H), 3.36 (br d, J = 4.35 Hz, 1H), 2.89-3.13 (m, 1H), 1.24 (br s, 3H), 1.14 (s, 9H). $^{19}$F NMR (376 MHz, DMSO-$d_6$) δ −113.52 (d, J = 33.81 Hz, 1F), −131.85−−127.68 (m, 1F). |
| 58-17-2 | 544.2 | $^1$H NMR (400 MHz, DMSO-$d_6$) δ 8.20-8.32 (m, 1H), 7.50-7.62 (m, 2H), 7.30-7.38 (m, 2H), 7.22-7.29 (m, 3H), 6.97-7.04 (m, 1H), 6.78-6.93 (m, 1H), 6.20 (br d, J = 16.59 Hz, 1H), 5.76 (dd, J = 1.97, 10.47 Hz, 1H), 4.82 (br s, 1H), 4.21-4.44 (m, 2H), 3.95-4.18 (m, 1H), 3.44-3.71 (m, 2H), 3.17 (br d, J = 5.39 Hz, 1H), 1.34 (br d, J = 6.43 Hz, 3H), 1.14 (s, 9H). $^{19}$F |

TABLE 88-continued

Analytical Data

| Ex. # | LRMS: m/z (ESI, +ve ion): (M + H)+ | NMR |
|---|---|---|
| | | NMR (376 MHz, DMSO-d$_6$) δ ppm −113.53 (d, J = 32.95 Hz, 1F), −130.02 (d, J = 33.81 Hz, 1F). |
| 58-18 | 560.1 | $^1$H NMR (400 MHz, CDCl$_3$) δ ppm 9.49 (1 H, br s) 7.91 (1 H, br d, J = 8.50 Hz) 7.46 (1 H, t, J = 7.67 Hz) 7.36-7.41 (1 H, m) 7.25-7.32 (2 H, m) 6.57-6.73 (3 H, m) 6.43 (1 H, br d, J = 16.17 Hz) 5.83 (1 H, br d, J = 10.16 Hz) 2.48-5.23 (7 H, m) 1.96-2.08 (3 H, m) 1.45-1.63 (3 H, m) 1.18-1.26 (3 H, m) 0.99-1.06 (3 H, m). |
| 58-18-1 | 560.0 | $^1$H NMR (400 MHz, CDCl$_3$) δ ppm 9.44 (1 H, br s) 7.87 (1 H, d, J = 9.33 Hz) 7.41 (1 H, t, J = 7.46 Hz) 7.34 (1 H, d, J = 7.67 Hz) 7.20-7.28 (2 H, m) 6.52-6.69 (3 H, m) 6.38 (1 H, d, J = 16.59 Hz) 5.79 (1 H, d, J = 10.37 Hz) 2.98-5.11 (7 H, m) 2.50-2.69 (1 H, m) 1.90-2.03 (3 H, m) 1.42-1.59 (3 H, m) 1.18 (3 H, d, J = 6.22 Hz) 0.99 (3 H, d, J = 6.01 Hz). |
| 58-18-2 | 560.2 | $^1$H NMR (400 MHz, CDCl$_3$) δ ppm 9.39 (1 H, br s) 7.81 (1 H, d, J = 9.33 Hz) 7.35 (1 H, t, J = 7.46 Hz) 7.28 (1 H, d, J = 7.56 Hz) 7.13-7.23 (2 H, m) 6.44-6.63 (3 H, m) 6.32 (1 H, d, J = 16.59 Hz) 5.73 (1 H, d, J = 9.95 Hz) 2.88-5.15 (7 H, m) 2.39-2.60 (1 H, m) 1.93 (3 H, br s) 1.30-1.51 (3 H, m) 1.08-1.15 (3 H, m) 0.86-0.97 (3 H, m). |
| 58-19 | 559.1 | $^1$H NMR (400 MHz, DMSO-d$_6$) δ ppm 10.23 (s, 1 H), 8.28-8.33 (m, 2 H), 7.28 (q, J = 8.09 Hz, 1 H), 6.84-6.90 (m, 1 H), 6.81 (br dd, J = 5.2, 2.3 Hz, 1 H), 6.74 (d, J = 8.5 Hz, 1 H), 6.70 (t, J = 8.9 Hz, 1 H), 6.20 (br d, J = 17.0 Hz, 1 H), 5.76 (dd, J = 10.5, 2.0 Hz, 1 H), 4.83-4.98 (m, 1 H), 4.20-4.44 (m, 2 H), 3.60-3.79 (m, 3 H), 3.01-3.23 (m, 1 H), 2.08 (s, 3 H), 1.45-1.57 (m, 1 H), 1.33 (dd, J = 11.6, 6.6 Hz, 3 H), 0.48-0.93 (m, 4 H). |
| 58-19-1 | 558.8 | $^1$H NMR (400 MHz, DMSO-d$_6$) δ ppm 10.24 (s, 1 H), 8.31 (br t, J = 9.3 Hz, 1 H), 8.27 (d, J = 5.2 Hz, 1 H), 7.21-7.35 (m, 1 H), 6.84-6.94 (m, 1 H), 6.82 (d, J = 5.2 Hz, 1 H), 6.75 (d, J = 8.3 Hz, 1 H), 6.70 (t, J = 8.9 Hz, 1 H), 6.21 (br d, J = 16.6 Hz, 1 H), 5.77 (dd, J = 10.2, 3.3 Hz, 1 H), 4.89-4.99 (m, 1 H), 4.10-4.45 (m, 2 H), 3.60-3.79 (m, 3 H), 3.01-3.23 (m, 1 H), 2.09 (s, 3 H), 1.48-1.58 (m, 2 H), 1.32 (d, J = 6.6 Hz, 3 H), 0.21-1.09 (m, 4 H). |
| 58-19-2 | 558.8 | $^1$H NMR (400 MHz, DMSO-d$_6$) δ ppm 10.24 (s, 1 H), 8.31 (br t, J = 9.3 Hz, 1 H), 8.27 (d, J = 5.2 Hz, 1 H), 7.21-7.35 (m, 1 H), 6.84-6.94 (m, 1 H), 6.82 (d, J = 5.2 Hz, 1 H), 6.75 (d, J = 8.3 Hz, 1 H), 6.70 (t, J = 8.9 Hz, 1 H), 6.21 (br d, J = 16.6 Hz, 1 H), 5.77 (dd, J = 10.2, 3.3 Hz, 1 H), 4.89-4.99 (m, 1 H), 4.11-4.45 (m, 2 H), 3.60-3.79 (m, 3 H), 3.01-3.23 (m, 1 H), 2.08 (s, 3 H), 1.49-1.55 (m, 1 H), 1.35 (d, J = 6.6 Hz, 3 H), 0.49-0.91 (m, 4 H). |
| 58-20 | 542.9 | $^1$H NMR (400 MHz, DMSO-d$_6$) δ ppm 8.35 (d, J = 10.4 Hz, 1 H), 8.30 (d, J = 5.2 Hz, 1 H), 7.53-7.61 (m, 1 H), 7.28-7.38 (m, 3 H), 6.81-6.94 (m, 2 H), 6.21 (br d, J = 17.0 Hz, 1 H), 5.77 (dd, J = 10.7, 2.2 Hz, 1 H), 4.93 (br s, 1 H), 4.02-4.46 (m, 3 H), 3.45-3.77 (m, 2 H), 3.19-3.29 (m, 1 H), 2.13 (s, 3 H), 1.46-1.52 |

TABLE 88-continued

Analytical Data

| Ex. # | LRMS: m/z (ESI, +ve ion): $(M + H)^+$ | NMR |
|---|---|---|
| | | (m, 1 H), 1.34 (dd, J = 6.6, 3.9 Hz, 3 H), 0.57-0.88 (m, 4 H). |
| 58-20-1 | 542.9 | $^1$H NMR (400 MHz, DMSO-d$_6$) δ ppm 8.31 (br t, J = 9.3 Hz, 1 H), 8.27 (d, J = 5.2 Hz, 1 H), 7.51-7.62 (m, 1 H), 7.27-7.40 (m, 3 H), 6.84-6.94 (m, 1 H), 6.82 (d, J = 5.2 Hz, 1 H), 6.21 (br d, J = 16.6 Hz, 1 H), 5.77 (dd, J = 10.2, 3.3 Hz, 1 H), 4.89-4.99 (m, 1 H), 3.98-4.45 (m, 3 H), 3.61-3.80 (m, 2 H), 3.29 (m, 1 H), 2.09 (s, 3 H), 1.44-1.44 (m, 1 H), 1.32 (d, J = 6.6 Hz, 3 H), 0.21-1.09 (m, 4 H) |
| 58-20-2 | 542.9 | $^1$H NMR (400 MHz, DMSO-d$_6$) δ ppm 8.35 (d, J = 10.4 Hz, 1 H), 8.30 (d, J = 5.2 Hz, 1 H), 7.50-7.61 (m, 1 H), 7.29-7.39 (m, 3 H), 6.86-6.91 (m, 1 H), 6.83 (d, J = 5.2 Hz, 1 H), 6.21 (br d, J = 15.8 Hz, 1 H), 5.76 (dd, J = 10.2, 3.1 Hz, 1 H), 4.93 (br s, 1 H), 3.95-4.47 (m, 3 H), 3.58-3.79 (m, 2 H), 3.19-3.29 (m, 1 H), 2.13 (s, 3 H), 1.43-1.58 (m, 1 H), 1.33 (d, J = 6.84 Hz, 3 H), 0.56-0.91 (m, 4 H) |
| 58-21 | 485.1 | $^1$H NMR (400 MHz, DMSO-d$_6$) δ ppm 8.48 (d, J = 4.8 Hz, 1 H), 8.34-8.44 (m, 1 H), 7.26 (d, J = 5.0 Hz, 1 H), 6.79-6.92 (m, 1 H), 6.20 (br d, J = 17.0 Hz, 1 H), 5.71-5.80 (m, 1 H), 4.87 (br s, 1 H), 3.97-4.43 (m, 3 H), 3.38-3.76 (m, 2 H), 3.01-3.27 (m, 1 H), 2.57-2.65 (m, 1 H), 1.94 (s, 3 H), 1.26-1.33 (m, 3 H), 1.06 (d, J = 6.6 Hz, 3 H), 1.00 (dd, J = 6.6, 1.5 Hz, 3 H). $^{19}$F NMR (376 MHz, DMSO-d$_6$) δ ppm −128.39 (d, J = 13.9 Hz, 1 F). |
| 58-22 | 546.2 | $^1$H NMR (400 MHz, DMSO-d$_6$) δ ppm 9.05 (1 H, s), 8.33-8.43 (1 H, m), 7.53-7.61 (1 H, m), 7.34-7.40 (1 H, m), 7.25-7.33 (2 H, m), 6.81-6.94 (1 H, m), 6.16-6.27 (1 H, m), 5.75-5.81 (1 H, m), 4.91-5.02 (1 H, m), 4.26-4.44 (2 H, m), 4.00-4.22 (1 H, m), 3.58-3.81 (2 H, m), 3.40-3.56 (1 H, m), 2.37-2.48 (4 H, m), 1.35 (3 H, d, J = 6.6 Hz), 1.07 (6 H, td, J = 7.4, 1.6 Hz). $^{19}$F NMR (376 MHz, DMSO-d$_6$) δ ppm −113.95 (1 F, s), −114.03 (1 F, s), −128.78 (1 F, s), −128.86 (1 F, s). |
| 58-23 | 562.2 | $^1$H NMR (400 MHz, DMSO-d$_6$) δ ppm 10.22-10.27 (1 H, m), 9.01 (1 H, s), 8.27-8.37 (1 H, m), 7.25-7.33 (1 H, m), 6.80-6.93 (1 H, m), 6.75 (1 H, d, J = 8.3 Hz), 6.70 (1 H, t, J = 8.9 Hz), 6.22 (1 H, br d, J = 16.6 Hz), 5.74-5.81 (1 H, m), 4.95 (1 H, br dd, J = 3.5, 2.3 Hz), 4.25-4.46 (3 H, m), 4.00-4.22 (1 H, m), 3.61-3.75 (1 H, m), 3.45-3.55 (1 H, m), 2.32-2.47 (4 H, m), 1.35 (3 H, d, J = 6.6 Hz), 1.02-1.10 (6 H, m). $^{19}$F NMR (376 MHz, DMSO-d$_6$) δ ppm −115.75 (1 F, s), −115.77 (1 F, s), −127.96 (1 F, s), −127.98 (1 F, s). |
| 59-1 | 612.1 | $^1$H NMR (400 MHz, CDCl$_3$) δ ppm 9.35-9.39 (1 H, m) 7.79-7.89 (1 H, m) 7.72 (1 H, br d, J = 7.26 Hz) 7.53-7.64 (2 H, m) 7.19-7.31 (2 H, m) 6.55-6.73 (3 H, m) 6.39-6.45 (1 H, m) 5.83 (1 H, br d, J = 10.37 Hz) 2.85-5.31 (7 H, m) 1.51-1.68 (3 H, m) 1.23-1.33 (1 H, m) 1.14-1.06 (1 H, m) 0.99-1.06 (1 H, m) 0.86-0.93 (1 H, m). |
| 59-1-1 | 612.2 | $^1$H NMR (400 MHz, CDCl$_3$) δ ppm 9.34 (1 H, s) 7.85 (1 H, d, J = 8.70 Hz) 7.71 (1 H, d, J = 7.70 Hz) 7.51-7.62 (2 H, m) 7.15-7.30 (2 H, m) 6.51-6.71 (3 H, m) |

TABLE 88-continued

Analytical Data

| Ex. # | LRMS: m/z (ESI, +ve ion): (M + H)+ | NMR |
|---|---|---|
| | | 6.40 (1 H, d, J = 16.79 Hz) 5.81 (1 H, d, J = 10.60 Hz) 2.82-5.32 (7 H, m) 1.37 (3 H, br d, J = 6.63 Hz) 1.17-1.32 (1 H, m) 0.96-1.12 (1 H, m) 0.84-0.90 (1 H, m). |
| 59-1-2 | 612.2 | $^1$H NMR (400 MHz, CDCl$_3$) δ ppm 9.38 (1 H, s) 7.81 (1 H, d, J = 9.10 Hz) 7.72 (1 H, d, J = 7.50 Hz) 7.53-7.64 (2 H, m) 7.18-7.33 (2 H, m) 6.52-6.73 (3 H, m) 6.42 (1 H, d, J = 16.79 Hz) 5.82 (1 H, d, J = 10.20 Hz) 3.01-4.89 (7 H, m) 1.49-1.69 (3 H, m) 1.20-1.34 (1 H, m) 0.98-1.14 (2 H, m) 0.86-0.93 (1 H, m). |
| 59-2 | 564.0 | $^1$H NMR (400 MHz, CDCl$_3$) δ ppm 9.40 (1 H, br s) 7.86 (1 H, br d, J = 9.33 Hz) 7.48 (1 H, q, J = 7.33 Hz) 7.26-7.32 (2 H, m) 7.11 (1 H, br t, J = 8.50 Hz) 6.52-6.70 (3 H, m) 6.39 (1 H, br d, J = 16.80 Hz) 5.79 (1 H, br d, J = 10.16 Hz) 2.96-5.19 (7 H, m) 2.62-2.83 (1 H, m) 1.41-1.63 (3 H, m) 1.18-1.32 (3 H, m) 0.99-1.08 (3 H, m). |
| 59-2-1 | 563.9 | $^1$H NMR (400 MHz, CDCl$_3$) δ ppm 9.42 (1 H, s) 7.89 (1 H, d, J = 9.33 Hz) 7.51 (1 H, td, J = 8.14, 5.91 Hz) 7.25-7.35 (2 H, m) 7.14 (1 H, t, J = 8.60 Hz) 6.54-6.74 (3 H, m) 6.38-6.46 (1 H, m) 5.82 (1 H, dd, J = 10.47, 1.55 Hz) 3.01-5.13 (7 H, m) 2.71-2.84 (1 H, m) 1.46-1.64 (3 H, m) 1.26 (3 H, d, J = 6.84 Hz) 1.07 (3 H, d, J = 6.84 Hz). |
| 59-2-2 | 563.9 | $^1$H NMR (400 MHz, CDCl$_3$) δ ppm 9.43 (1 H, s) 7.90 (1 H, d, J = 9.54 Hz) 7.51 (1 H, td, J = 8.09, 5.80 Hz) 7.25-7.34 (2 H, m) 7.14 (1 H, t, J = 8.40 Hz) 6.54-6.74 (3 H, m) 6.42 (1 H, dd, J = 16.79, 1.45 Hz) 5.82 (1 H, dd, J = 10.47, 1.76 Hz) 3.00-5.22 (7 H, m) 2.65-2.83 (1 H, m) 1.45-1.64 (3 H, m) 1.26 (3 H, d, J = 6.84 Hz) 1.06 (3 H, d, J = 6.63 Hz) |
| 59-3 | 548.2 | $^1$H NMR (400 MHz, CDCl$_3$) δ ppm 7.76 (1 H, d, J = 8.10 Hz) 7.32-7.44 (2 H, m) 7.25-7.32 (1 H, m) 7.19 (1 H, d, J = 7.90 Hz) 7.06-7.16 (2 H, m) 7.01 (1 H, t, J = 8.60 Hz) 6.50-6.67 (1 H, m) 6.38 (1 H, d, J = 16.20 Hz) 5.78 (1 H, d, J = 10.40 Hz) 2.96-5.15 (7 H, m) 2.62-2.84 (1 H, m) 1.37-1.62 (3 H, m) 1.17-1.27 (3 H, m) 0.95-1.05 (3 H, m). |
| 59-3-1 | 548.3 | $^1$H NMR (400 MHz, CHLOROFORM-d) δ ppm 7.76 (1 H, d, J = 8.90 Hz) 7.32-7.43 (2 H, m) 7.29 (1 H, t, J = 6.90 Hz) 7.19 (1 H, d, J = 8.10 Hz) 7.06-7.16 (2 H, m) 7.01 (1 H, t, J = 8.70 Hz) 6.51-6.66 (1 H, m) 6.37 (1 H, d, J = 16.59 Hz) 5.78 (1 H, d, J = 10.40 Hz) 2.99-5.08 (7 H, m) 2.66-2.82 (1 H, m) 1.41-1.66 (3 H, m) 1.22 (3 H, d, J = 6.80 Hz) 1.00 (3 H, d, J = 6.60 Hz) |
| 59-3-2 | 548.2 | $^1$H NMR (400 MHz, CHLOROFORM-d) δ ppm 7.76 (1 H, d, J = 8.50 Hz) 7.32-7.44 (2 H, m) 7.29 (1 H, t, J = 7.50 Hz) 7.19 (1 H, d, J = 7.70 Hz) 7.06-7.16 (2 H, m) 7.01 (1 H, t, J = 8.60 Hz) 6.50-6.68 (1 H, m) 6.38 (1 H, d, J = 16.60 Hz) 5.78 (1 H, d, J = 10.40 Hz) 2.96-5.15 (7 H, m) 2.61-2.81 (1 H, m) 1.39-1.52 (3 H, m) 1.23 (3 H, d, J = 6.80 Hz) 1.00 (3 H, d, J = 6.20 Hz) |
| 59-4 | 586.3 | $^1$H NMR (400 MHz, CDCl$_3$) δ ppm 9.10 (1 H, s) 8.86 (1 H, s) 7.91 (1 H, d, J = 9.30 Hz) 7.26-7.34 (1 H, m) 6.50-6.77 (3 H, m) 6.40 (1 H, d, J = 16.79 Hz) 5.81 (1 H, d, J = 9.70 Hz) 2.95-5.22 (7 H, m) |

TABLE 88-continued

Analytical Data

| Ex. # | LRMS: m/z (ESI, +ve ion): (M + H)+ | NMR |
|---|---|---|
| | | 1.43-1.65 (5 H, m) 1.13-1.31 (4 H, m) 0.92-1.03 (2 H, m) 0.74-0.87 (2 H, m). |
| 59-5 | 570.2 | $^1$H NMR (400 MHz, CDCl$_3$) δ ppm 8.86 (1 H, s) 7.89 (1 H, d, J = 8.70 Hz) 7.48-7.56 (1 H, m) 7.45 (1 H, br t, J = 7.05 Hz) 7.16-7.29 (2 H, m) 6.58-6.74 (1 H, m) 6.46 (1 H, d, J = 16.59 Hz) 5.87 (1 H, d, J = 10.20 Hz) 3.03-5.28 (7 H, m) 1.47-1.75 (5 H, m) 1.17-1.35 (4 H, m) 0.95-1.09 (2 H, m) 0.81-0.93 (2 H, m). |
| 59-6 | 545.9 | $^1$H NMR (400 MHz, DMSO-d$_6$) δ ppm 0.70-0.90 (m, 3 H) 0.92-1.06 (m, 1 H) 1.25-1.50 (m, 3 H) 1.79 (br s, 1 H) 2.99-3.28 (m, 1 H) 3.37-3.90 (m, 2 H) 4.02-4.50 (m, 3 H) 4.81-5.10 (m, 1 H) 5.75-5.80 (m, 1 H) 6.21 (br d, J = 17.00 Hz, 1 H) 6.64-6.78 (m, 2 H) 6.78-6.96 (m, 1 H) 7.18-7.36 (m, 1 H) 8.18-8.35 (m, 1 H) 8.38 (d, J = 2.28 Hz, 1 H) 8.51 (d, J = 2.28 Hz, 1 H) 10.19 (s, 1 H). |
| 60-1 | 544.8 | $^1$H NMR (400 MHz, CDCl$_3$) δ ppm 8.42 (dd, J = 4.6, 1.5 Hz, 1 H) 8.04 (d, J = 1.7 Hz, 1 H) 7.46 (ddd, J = 7.6, 4.2, 1.5 Hz, 1 H) 7.35-7.43 (m, 1 H) 7.28 (dd, J = 7.7, 4.8 Hz, 1 H) 7.19-7.25 (m, 1 H) 7.12-7.17 (m, 1 H) 7.09 (t, J = 9.2 Hz, 1 H) 6.51-6.72 (m, 1 H) 6.35-6.45 (m, 1 H) 5.80 (dd, J = 10.6, 1.7 Hz, 1 H) 4.17-5.25 (m, 3 H) 3.49-4.09 (m, 3 H) 2.91-3.34 (m, 1 H) 1.40-1.60 (m, 3 H) 1.29-1.35 (m, 1 H) 0.75-0.85 (m, 2 H) 0.64-0.74 (m, 1 H) 0.46-0.55 (m, 1 H). $^{19}$F NMR (377 MHz, CDCl$_3$) δ ppm −111.91 (s, 1 F). |
| 60-2 | 476.0 | $^1$H NMR (400 MHz, CDCl$_3$) δ ppm 7.99 (s, 1H), 6.52-6.66 (m, 1H), 6.29-6.43 (m, 1H), 5.79 (dd, J = 1.45, 10.57 Hz, 1H), 4.66 (s, 2H), 3.74-3.98 (m, 8H), 1.15 (br s, 2H), 0.98-1.10 (m, 2H). $^{19}$F NMR (376 MHz, CDCl$_3$) δ ppm −69.26 (s, 1F). |
| 60-3 | 552.0 | $^1$H NMR (400 MHz, CDCl$_3$) δ ppm 8.11 (s, 1H), 7.32-7.43 (m, 2H), 6.91 (d, J = 8.29 Hz, 1H), 6.80 (t, J = 8.91 Hz, 1H), 6.60 (dd, J = 10.37, 16.79 Hz, 1H), 6.40 (dd, J = 1.45, 16.79 Hz, 1H), 5.81 (d, J = 10.57 Hz, 1H), 3.76-4.06 (m, 8H), 1.21-1.32 (m, 2H), 0.95-1.13 (m, 2H). $^{19}$F NMR (376 MHz, CDCl$_3$) δ ppm −69.33 (s, 3F), −109.46 (s, 1F). |
| 60-4 | 536.2 | $^1$H NMR (400 MHz, CDCl$_3$) δ ppm 8.05 (s, 1H), 7.48-7.59 (m, 2H), 7.30-7.38 (m, 1H), 7.13-7.24 (m, 1H), 6.55-6.65 (m, 1H), 6.39 (dd, J = 1.76, 16.69 Hz, 1H), 5.81 (dd, J = 1.87, 10.57 Hz, 1H), 4.75 (s, 2H), 3.77-4.04 (m, 8H), 1.09 (br s, 2H), 0.94-1.02 (m, 2H). $^{19}$F NMR (376 MHz, CDCl$_3$) δ ppm −69.24 (s, 3F), −112.37 (s, 1F). |
| 60-5 | 500.1 | $^1$H NMR (400 MHz, CDCl$_3$) δ ppm 8.06 (s, 1H), 7.37 (dt, J = 6.53, 8.34 Hz, 1H), 6.90 (d, J = 8.29 Hz, 1H), 6.75-6.83 (m, 1H), 6.60 (dd, J = 10.57, 16.79 Hz, 1H), 6.39 (dd, J = 1.66, 16.79 Hz, 1H), 5.80 (dd, J = 1.87, 10.57 Hz, 1H), 4.27 (br s, 2H), 3.72-4.05 (m, 8H), 0.98 (s, 9H). $^{19}$F NMR (376 MHz, CDCl$_3$) δ −108.77--107.70 (m, 1F). |
| 60-6 | 484.3 | $^1$H NMR (400 MHz, CDCl$_3$) δ ppm 8.02 (s, 1H), 7.46-7.57 (m, 2H), 7.30-7.35 (m, 1H), 7.18-7.25 (m, 1H), 6.61 (dd, J = 10.37, 16.79 Hz, 1H), 6.39 (dd, J = 1.87, 16.79 Hz, 1H), 5.80 (dd, J = 1.76, |

TABLE 88-continued

| Ex. # | LRMS: m/z (ESI, +ve ion): (M + H)+ | NMR |
|---|---|---|
| | | 10.47 Hz, 1H), 4.37 (s, 2H), 3.78-4.02 (m, 8H), 0.98 (s, 9H). ¹⁹F NMR (376 MHz, CDCl₃) δ ppm −112.57 (s, 1F). |
| 60-7 | 521.2 | ¹H NMR (400 MHz, CDCl₃) δ ppm 8.38 (d, J = 4.15 Hz, 1H), 8.03 (s, 1H), 7.50 (dt, J = 1.76, 7.72 Hz, 1H), 7.21 (dt, J = 6.53, 8.24 Hz, 1H), 7.08 (dd, J = 4.98, 6.84 Hz, 1H), 6.94 (dt, J = 1.76, 8.34 Hz, 1H), 6.79 (d, J = 7.88 Hz, 1H), 6.71 (dd, J = 1.97, 7.98 Hz, 1H), 6.53-6.65 (m, 2H), 6.38 (dd, J = 1.76, 16.69 Hz, 1H), 5.79 (dd, J = 1.87, 10.57 Hz, 1H), 5.28 (s, 2H), 3.75-3.99 (m, 8H). ¹⁹F NMR (376 MHz, CDCl₃) δ −110.32 (s, 1F). |
| 60-8 | 562.0 | ¹H NMR (400 MHz, MeOH-d₄) δ ppm 8.54 (d, J = 2.5 Hz, 1 H) 8.44-8.52 (m, 1 H) 8.38 (d, 4 = 2.5 Hz, 1 H) 7.26 (td, J = 8.3, 6.7 Hz, 1 H) 6.81-6.96 (m, 1 H) 6.70 (d, J = 8.3 Hz, 1 H) 6.64 (t, 4 = 8.7 Hz, 1 H) 6.36 (br d, 4 = 16.6 Hz, 1 H) 5.88 (dd, J = 10.7, 2.0 Hz, 1 H) 5.02-5.27 (m, 1 H) 4.56-4.67 (m, 1 H) 4.49 (br d, J = 13.5 Hz, 1 H) 4.09-4.31 (m, 1 H) 3.54-4.02 (m, 2 H) 3.14-3.47 (m, 1 H) 1.88 (br s, 1 H) 1.48-1.62 (m, 3 H) 1.12-1.21 (m, 1 H) 0.94-1.07 (m, 2 H) 0.85-0.94 (m, 1 H). ¹⁹F NMR (377 MHz, MeOH-d₄) δ −116.65 (br s, 1F) −116.88 (br s, 1 F). |
| 60-9 | 552.0 | ¹H NMR (400 MHz, CDCl₃) δ ppm 7.91 (1 H, s) 7.30 (1 H, td, J = 8.24. 6.53 Hz) 6.83 (1 H, d, J = 8.29 Hz) 6.71 (1 H, t, J = 9.02 Hz) 6.43-6.62 (1 H, m) 6.33 (1 H, d, J = 16.59 Hz) 5.73 (1 H, d, J = 10.37 Hz) 2.64-5.09 (8 H, m) 2.36-2.48 (1 H, m) 1.99-2.15 (1 H, m) 1.95-1.97 (1 H, m) 1.85-1.94 (1 H, m) 1.15-1.66 (11 H, m). |
| 60-10 | 546.0 | ¹H NMR (400 MHz, CDCl₃) δ ppm 8.45 (1 H, d, J = 2.28 Hz) 8.33 (1 H, dd, J = 2.28, 1.24 Hz) 8.06 (1 H, d, J = 3.32 Hz) 7.39-7.46 (1 H, m) 7.23-7.28 (1 H, m) 7.08-7.19 (2 H, m) 6.53-6.69 (1 H, m) 6.42 (1 H, dd, J = 16.79, 1.66 Hz) 5.82 (1 H, dd, J = 10.57, 1.66 Hz) 2.89-5.31 (7 H, m) 1.69-1.84 (1 H, m) 1.39-1.68 (3 H, m) 1.19-1.26 (1 H, m) 0.82-1.11 (3 H, m). |
| 60-11 | 586.2 | ¹H NMR (400 MHz, CDCl₃) δ ppm 8.76 (1 H, s) 8.09 (1 H, s) 7.39-7.47 (1 H, m) 7.24-7.30 (1 H, m) 7.07-7.21 (2 H, m) 6.51-6.67 (1 H, m) 6.39 (1 H, d, J = 16.79 Hz) 5.80 (1 H, d, J = 10.37 Hz) 2.95-5.24 (7 H, m) 1.41-1.67 (5 H, m) 1.16-1.28 (2 H, m) 1.06-1.16 (2 H, m) 0.88-1.01 (2 H, m) 0.76-0.87 (2 H, m). |
| 60-12 | 458.0 | ¹H NMR (400 MHz, DMSO-d₆) δ ppm 8.43 (br dd, J = 12.3, 5.1 Hz, 1 H), 7.27-7.41 (m, 3 H), 7.18 (dd, J = 7.3, 3.1 Hz, 1 H), 6.77-6.93 (m, 1 H), 6.20 (br d, J = 16.0 Hz, 1 H), 5.72-5.79 (m, 1 H), 4.86 (br d, J = 31.3 Hz, 1 H), 4.07-4.43 (m, 3 H), 3.33-3.83 (m, 2 H), 2.95-3.26 (m, 1 H), 1.95 (d, J = 7.0 Hz, 3 H), 1.29 (t, J = 6.5 Hz, 3 H). |
| 60-13 | 496.0 | ¹H NMR (400 MHz, DMSO-d₆) δ ppm 8.21 (br dd, J = 12.1, 5.3 Hz, 1 H), 7.25-7.41 (m, 3 H), 7.16 (d, J = 7.3 Hz, 1 H), 6.75-6.93 (m, 1 H), 6.19 (br d, J = 16.4 Hz, 1 H), 5.71-5.80 (m, 1 H), 4.78 (br d, J = 34.0 Hz, 1 H), 3.94-4.44 (m, 3 H), 3.90 (t, J = 6.7 Hz, 2 H), 3.33-3.76 (m, 2 H), 2.92-3.25 (m, 1 H), 1.94 (d, J = 3.1 Hz, 3 H), 1.37 (quin, J = 7.3 Hz, 2 H), |

TABLE 88-continued

| | Analytical Data | |
|---|---|---|
| Ex. # | LRMS: m/z (ESI, +ve ion): (M + H)⁺ | NMR |
| | | 1.23-1.31 (m, 3 H), 1.07 (dq, J = 14.9, 7.4 Hz, 2 H), 0.75 (t, J = 7.5 Hz, 3 H). |
| 60-14 | 518.0 | ¹H NMR (400 MHz, DMSO-d₆) δ ppm 8.33-8.45 (m, 1 H), 7.47-7.55 (m, 1 H), 7.21-7.36 (m, 6 H), 7.15-7.21 (m, 1 H), 6.78-6.92 (m, 1 H), 6.21 (br d, J = 16.2 Hz, 1 H), 5.72-5.79 (m, 1 H), 4.78-5.04 (m, 1 H), 3.97-4.46 (m, 3 H), 3.35-3.87 (m, 2 H), 2.96-3.27 (m, 1 H), 1.96 (d, J = 2.3 Hz, 3 H), 1.33 (dd, J = 14.9, 6.6 Hz, 3 H). ¹⁹F NMR (376 MHz, DMSO-d₆) δ ppm -113.56 (br d, J = 30.3 Hz, 1 F). |
| 60-15 | 533.9 | ¹H NMR (400 MHz, DMSO-d₆) δ ppm 10.13 (br s, 1 H), 8.37 (br d, J = 27.2 Hz, 1 H), 7.08-7.38 (m, 5 H), 6.77-6.93 (m, 1 H), 6.60-6.75 (m, 2 H), 6.21 (br d, J = 16.2 Hz, 1 H), 5.71-5.80 (m, 1 H), 4.69-5.08 (m, 1 H), 3.54-4.48 (m, 5 H), 2.92-3.22 (m, 1 H), 1.91 (br d, J = 4.8 Hz, 3 H), 1.33 (br dd, J = 26.2, 5.9 Hz, 3 H). ¹⁹F NMR (376 MHz, DMSO-d₆) δ ppm -115.65 (br dd, J = 277.9, 19.5 Hz, 1 F). |
| 60-16 | 479.9 | ¹H NMR (400 MHz, DMSO-d₆) δ ppm 8.50 (br d, J = 5.0 Hz, 1 H), 7.55-7.67 (m, 1 H), 7.34 (t, J = 8.5 Hz, 2 H), 6.75-6.91 (m, 1 H), 6.20 (br d, J = 16.2 Hz, 1 H), 5.76 (dd, J = 10.4, 2.3 Hz, 1 H), 4.95 (br s, 1 H), 4.19-4.40 (m, 2 H), 3.96-4.16 (m, 1 H), 3.79 (br d, J = 12.0 Hz, 1 H), 3.36-3.65 (m, 1 H), 3.00-3.26 (m, 1 H), 1.31 (d, J = 6.6 Hz, 3 H). ¹⁹F NMR (376 MHz, DMSO-d₆) δ ppm -118.67--118.03 (m, 2 F) |
| 60-17 | 556.0 | ¹H NMR (400 MHz, DMSO-d₆) δ ppm 10.18 (br s, 1 H), 8.43 (br d, J = 9.5 Hz, 1 H), 7.45-7.54 (m, 1 H), 7.18-7.30 (m, 3 H), 6.78-6.92 (m, 1 H), 6.64-6.76 (m, 2 H), 6.21 (br d, J = 16.2 Hz, 1 H), 5.73-5.80 (m, 1 H), 4.98 (br d, J = 42.5 Hz, 1 H), 4.21-4.46 (m, 2 H), 4.08 (br dd, J = 40.8, 12.6 Hz, 1 H), 3.68-3.93 (m, 1 H), 3.38-3.67 (m, 1 H), 3.00-3.28 (m, 1 H), 1.34 (br dd, J = 13.0, 6.3 Hz, 3 H). ¹⁹F NMR (376 MHz, DMSO-d₆) δ ppm -115.91--115.54 (m, 1 F), -119.13--118.13 (m, 2 F). |
| 60-18 | 541.0 | ¹H NMR (400 MHz, DMSO-d₆) δ ppm 8.28 (br s, 1 H), 7.49-7.58 (m, 1 H), 7.29 (dt, J = 10.0, 2.3 Hz, 1 H), 7.20 (td, J = 8.5, 2.1 Hz, 1 H), 7.13 (dd, J = 8.2, 1.8 Hz, 1 H), 6.83 (br d, J = 10.2 Hz, 1 H), 6.18 (br d, J = 17.0 Hz, 1 H), 5.71-5.77 (m, 1 H), 4.61-4.74 (m, 1 H), 4.35 (ddd, J = 11.6, 7.7, 4.4 Hz, 1 H), 3.47-4.26 (m, 4 H), 2.59-3.17 (m, 4 H), 2.33-2.45 (m, 3 H), 2.07 (s, 3 H), 1.96 (br t, J = 12.2 Hz, 1 H), 1.50-1.57 (m, 2 H), 1.22 (br d, J = 6.6 Hz, 3 H). ¹⁹F NMR (376 MHz, DMSO-d₆) δ ppm -111.23 (s, 1 F). |
| 60-19 | 576.2 | ¹H NMR (400 MHz, CDCl₃) δ ppm 8.03 (s, 1H), 7.28-7.55 (m, 3H), 7.03-7.21 (m, 3H), 6.99 (d, J = 7.88 Hz, 1H), 6.81 (d, J = 7.05 Hz, 1H), 6.46-6.71 (m, 1H), 6.28-6.44 (m, 1H), 5.69-5.85 (m, 1H), 3.72-5.23 (m, 6H), 3.63-3.70 (m, 3H), 2.52-3.40 (m, 3H), 1.39-1.61 (m, 3H), 1.17-1.22 (m, 3H), 0.99-1.07 (m, 3H). ¹⁹F NMR (376 MHz, CDCl₃) δ -112.38 (s, 1F). |
| 60-20 | 571.2 | ¹H NMR (400 MHz, CDCl₃) δ ppm 8.09 (d, J = 3.32 Hz, 1H), 7.66 (dd, J = 1.24, 7.88 Hz, 1H), 7.59 (d, J = 7.46 Hz, 1H), |

TABLE 88-continued

Analytical Data

| Ex. # | LRMS: m/z (ESI, +ve ion): (M + H)+ | NMR |
|---|---|---|
| | | 7.48 (t, J = 15.50 Hz, 1H), 7.37-7.44 (m, 1H), 7.19-7.25 (m, 1H), 7.15 (t, J = 14.70 Hz, 1H), 7.09 (t, J = 18.20 Hz, 1H), 6.51-6.73 (m, 1H), 6.40 (dd, J = 1.66, 16.79 Hz, 1H), 5.81 (dd, J = 1.66, 10.37 Hz, 1H), 4.82-5.21 (m, 1H), 4.22-4.81 (m, 2H), 3.53-4.09 (m, 3H), 2.95-3.40 (m, 1H), 2.64-2.86 (m, 1H), 1.54 (d, J = 14.72 Hz, 3H), 1.19-1.29 (m, 3H), 0.99-1.05 (m, 3H). $^{19}$F NMR (376 MHz, CDCl$_3$) δ ppm −112.29 (s, 1F). |
| 60-20-1 | 571.2 | $^1$H NMR (400 MHz, DMSO-d$_6$) δ 8.56 (br s, 1H), 7.79-7.85 (m, 2H), 7.59 (t, J = 16.00 Hz, 1H), 7.48-7.55 (m, 1H), 7.25-7.37 (m, 2H), 7.19-7.25 (m, 1H), 6.78-6.97 (m, 1H), 6.22 (d, J = 16.38 Hz, 1H), 5.77 (dd, J = 2.28, 10.37 Hz, 1H), 4.98-5.18 (m, 1H), 4.23-4.47 (m, 2H), 3.99-4.22 (m, 1H), 3.79-3.96 (m, 1H), 3.39-3.72 (m, 1H), 3.04-3.28 (m, 1H), 2.70-2.81 (m, 1H), 1.34 (d, J = 6.84 Hz, 3H), 1.11 (d, J = 6.84 Hz, 3H), 0.98 (d, J = 6.84 Hz, 3H). $^{19}$F NMR (376 MHz, DMSO-d$_6$) δ −113.69 (s, 1F). |
| 60-20-2 | 571.3 | $^1$H NMR (400 MHz, DMSO-d$_6$) δ 8.51 (d, J = 6.84 Hz, 1H), 7.78-7.85 (m, 2H), 7.58 (t, J = 15.30 Hz, 1H), 7.49-7.55 (m, 1H), 7.26-7.36 (m, 2H), 7.18-7.25 (m, 1H), 6.79-6.95 (m, 1H), 6.15-6.28 (m, 1H), 5.77 (dd, J = 2.28, 9.95 Hz, 1H), 4.87-5.02 (m, 1H), 4.25-4.48 (m, 2H), 4.00-4.23 (m, 1H), 3.43-3.82 (m, 2H), 3.08-3.28 (m, 1H), 2.70-2.80 (m, 1H), 1.36 (d, J = 6.63 Hz, 3H), 1.11 (d, J = 6.84 Hz, 3H), 0.99 (d, J = 6.63 Hz, 3H). $^{19}$F NMR (376 MHz, DMSO-d$_6$) δ −113.70 (s, 1F). |
| 60-21 | 538.7 | $^1$H NMR (400 MHz, DMSO-d$_6$) δ ppm 9.04 (s, 1 H), 8.40 (br s, 1 H), 7.48-7.65 (m, 1 H), 7.23-7.39 (m, 3 H), 6.68-6.97 (m, 1 H), 6.21 (br d, J = 16.4 Hz, 1 H), 5.76 (dd, J = 10.2, 1.9 Hz, 1 H), 4.87-5.00 (m, 1 H), 4.09-4.45 (m, 3 H), 3.77 (br d, J = 3.1 Hz, 1 H), 3.55-3.65 (m, 1 H), 3.02-3.27 (m, 1 H), 2.40 (q, J = 7.3 Hz, 2 H), 1.33 (br t, J = 7.4 Hz, 3 H), 1.06 (t, J = 7.5 Hz, 3 H) |
| 60-22 | 554.8 | $^1$H NMR (400 MHz, DMSO-d$_6$) δ ppm 10.14 (br s, 1 H), 9.01 (s, 1 H), 8.38 (br s, 1 H), 7.28 (q, J = 8.3 Hz, 1 H), 6.79-6.92 (m, 1 H), 6.75 (d, J = 8.3 Hz, 1 H), 6.71 (t, J = 8.8 Hz, 1 H), 6.21 (br d, J = 16.8 Hz, 1 H), 5.77 (dd, J = 10.2, 2.1 Hz, 1 H), 4.92 (br d, J = 5.2 Hz, 1 H), 4.10-4.46 (m, 2 H), 4.02 (q, J = 7.1 Hz, 2 H), 3.54-3.87 (m, 2 H), 3.04-3.28 (m, 1 H), 2.27-2.42 (m, 1 H), 1.34 (br d, J = 6.4 Hz, 3 H), 1.05 (t, J = 7.5 Hz, 3 H). |
| 60-23 | 548.2 | $^1$H NMR (400 MHz, DMSO-d$_6$) δ ppm 8.47 (s, 1 H), 7.19-7.34 (m, 2 H), 7.03-7.19 (m, 2 H), 6.88-6.97 (m, 2 H), 6.83 (dd, J = 16.6, 10.4 Hz, 1 H), 6.69-6.78 (m, 2 H), 6.19 (dd, J = 16.7, 2.4 Hz, 1 H), 5.67-5.84 (m, 1 H), 3.65-3.99 (m, 8 H), 2.40-2.45 (m, 1 H), 0.95-1.04 (m, 3 H), 0.69-0.79 (m, 3 H) |
| 60-24 | 548.2 | $^1$H NMR (400 MHz, DMSO-d$_6$) δ ppm 10.06 (br s, 1 H), 8.47 (s, 1 H), 7.37-7.44 (m, 1 H), 7.30-7.36 (m, 1 H), 7.17-7.27 (m, 2 H), 7.07 (br d, J = 7.7 Hz, 1 H), 6.84 (dd, J = 16.7, 10.5 Hz, 1 H), 6.61-6.74 (m, 2 H), 6.20 (dd, J = 16.7, 2.4 Hz, 1 H), 5.73-5.82 (m, 1 H), 3.70-4.13 |

TABLE 88-continued

Analytical Data

| Ex. # | LRMS: m/z (ESI, +ve ion): (M + H)+ | NMR |
|---|---|---|
| 60-24-1 | 548.2 | (m, 9 H), 1.02-1.11 (m, 3 H), 0.97 (d, J = 6.8 Hz, 3 H). <br> $^1$H NMR (400 MHz, DMSO-d$_6$) δ ppm 10.04 (br s, 1 H), 8.46 (s, 1 H), 7.36-7.43 (m, 1 H), 7.29-7.35 (m, 1 H), 7.16-7.27 (m, 2 H), 7.07 (br d, J = 7.9 Hz, 1 H), 6.83 (dd, J = 16.8, 10.4 Hz, 1 H), 6.69 (d, J = 8.3 Hz, 1 H), 6.64 (br t, J = 8.7 Hz, 1 H), 6.19 (dd, J = 16.7, 2.4 Hz, 1 H), 5.71-5.79 (m, 1 H), 3.90-4.10 (m, 4 H), 3.68-3.89 (m, 4 H), 2.53-2.59 (m, 1 H), 1.06 (d, J = 6.8 Hz, 3 H), 0.96 (d, J = 6.8 Hz, 3 H). $^{19}$F NMR (376 MHz, DMSO-d$_6$) δ ppm −115.36 (br s, 1 F). |
| 60-24-2 | 548.2 | $^1$H NMR (400 MHz, DMSO-d$_6$) δ ppm 10.00 (br s, 1 H), 8.46 (s, 1 H), 7.36-7.44 (m, 1 H), 7.28-7.35 (m, 1 H), 7.18-7.26 (m, 2 H), 7.07 (br d, J = 7.7 Hz, 1 H), 6.83 (dd, J = 16.7, 10.5 Hz, 1 H), 6.59-6.75 (m, 2 H), 6.19 (dd, J = 16.7, 2.4 Hz, 1 H), 5.72-5.80 (m, 1 H), 3.90-4.06 (m, 4 H), 3.70-3.89 (m, 4 H), 2.53-2.60 (m, 1 H), 1.06 (d, J = 6.8 Hz, 3 H), 0.96 (d, J = 6.8 Hz, 3 H). $^{19}$F NMR (376 MHz, DMSO-d$_6$) δ ppm −115.34 (1 F, br s). |
| 60-25 | 587.2 (M + Na) | $^1$H NMR (400 MHz, DMSO-d$_6$) δ ppm 8.25-8.42 (m, 1 H), 6.70-6.93 (m, 1 H), 6.18 (br d, J = 15.8 Hz, 1 H), 5.74 (dd, J = 10.4, 2.1 Hz, 1 H), 4.75 (br d, J = 1.2 Hz, 1 H), 4.16-4.43 (m, 1 H), 3.81-4.13 (m, 8 H), 3.44-3.76 (m, 2 H), 2.89-3.21 (m, 1 H), 1.34-1.44 (m, 14 H), 1.24 (br d, J = 6.6 Hz, 3 H). |
| 60-26 | 636.0 | $^1$H NMR (400 MHz, DMSO-d$_6$) δ ppm 8.32-8.48 (m, 1 H), 7.65-7.77 (m, 1 H), 7.56 (d, J = 8.9 Hz, 1 H), 7.37-7.43 (m, 1 H), 7.33 (t, J = 7.4 Hz, 1 H), 7.20-7.27 (m, 1 H), 7.09 (d, J = 7.9 Hz, 1 H), 6.93-7.01 (m, 1 H), 6.73 (d, J = 2.9 Hz, 1 H), 6.14-6.28 (m, 1 H), 5.72-5.81 (m, 1 H), 4.75-5.03 (m, 1 H), 4.22-4.45 (m, 2 H), 4.10-4.22 (m, 2 H), 4.03 (q, J = 7.1 Hz, 1 H), 3.70 (s, 3 H), 3.60-3.65 (m, 1 H), 2.54-2.60 (m, 1 H), 1.31-1.37 (m, 3 H), 1.08 (d, J = 7.0 Hz, 3 H), 0.96-1.03 (m, 3 H). |
| 60-27 | 564.0 | $^1$H NMR (400 MHz, DMSO-d$_6$) δ ppm 1.15-1.26 (m, 3 H) 1.27-1.40 (m, 3 H) 2.99-3.29 (m, 1 H) 3.36-5.02 (m, 8 H) 5.75-5.81 (m, 1 H) 6.21 (br d, J = 16.59 Hz, 1 H) 6.60-6.74 (m, 2 H) 6.78-6.93 (m, 1 H) 7.07 (br dd, J = 6.95, 4.87 Hz, 1 H) 7.19-7.33 (m, 2 H) 7.37 (br t, J = 7.36 Hz, 1 H) 7.56-7.63 (m, 1 H) 8.31-8.46 (m, 1 H) 9.71-10.48 (m, 1 H). |
| 60-28 | 547.0 | $^1$H NMR (400 MHz, DMSO-d$_6$) δ ppm 1.01 (d, J = 6.84 Hz, 3 H) 1.12 (d, J = 6.84 Hz, 3 H) 1.29-1.40 (m, 3 H) 2.56-2.69 (m, 1 H) 2.97-3.28 (m, 1 H) 3.41-4.44 (m, 5 H) 4.79-5.17 (m, 1 H) 5.74-5.79 (m, 1 H) 6.21 (br d, J = 15.55 Hz, 1 H) 6.75-6.97 (m, 1 H) 7.15-7.21 (m, 1 H) 7.22-7.33 (m, 2 H) 7.42 (dd, J = 7.77, 4.66 Hz, 1 H) 7.46-7.56 (m, 1 H) 7.91 (dd, J = 7.88, 1.66 Hz, 1 H) 8.32-8.51 (m, 2 H). |
| 60-29 | 602.2 | $^1$H NMR (400 MHz, CHLOROFORM-d) δ ppm 8.85 (1 H, s) 8.18 (1 H, s) 8.07 (1 H, br s) 7.26-7.34 (1 H, m) 6.54-6.80 (3 H, m) 6.42 (1 H, d, J = 16.59 Hz) 5.83 (1 H, d, J = 10.20 Hz) 2.99-5.27 (7 H, m) 1.43-1.75 (5 H, m) 1.16-1.31 (4 H, m) 0.95-1.06 (2 H, m) 0.79-0.90 (2 H, m) |

TABLE 88-continued

Analytical Data

| Ex. # | LRMS: m/z (ESI, +ve ion): (M + H)+ | NMR |
|---|---|---|
| 60-30 | 560.2 | $^1$H NMR (400 MHz, CHLOROFORM-d) δ ppm 8.87 (1 H, s) 8.12 (1 H, s) 7.41-7.50 (1 H, m) 7.10-7.28 (3 H, m) 6.53-6.70 (1 H, m) 6.42 (1 H, d, J = 16.20 Hz) 5.83 (1 H, d, J = 10.20 Hz) 3.00-5.24 (7 H, m) 2.29 (3 H, br s) 1.38-1.82 (4 H, m) 1.22-1.30 (1 H, m) 1.11-1.21 (1 H, m) 0.95-1.06 (1 H, m) 0.81-0.91 (1 H, m) |
| 60-30-1 | 560.2 | $^1$H NMR (400 MHz, CHLOROFORM-d) δ ppm 8.86 (1 H, s) 8.12 (1 H, s) 7.42-7.49 (1 H, m) 7.09-7.28 (3 H, m) 6.53-6.70 (1 H, m) 6.39-6.46 (1 H, m) 5.83 (1 H, dd, J = 10.37, 1.66 Hz) 3.00-5.23 (7 H, m) 2.28 (3 H, br s) 1.42-1.69 (4 H, m) 1.21-1.30 (1 H, m) 1.10-1.19 (1 H, m) 0.93-1.03 (1 H, m) 0.80-0.90 (1 H, m) |
| 60-30-2 | 560.2 | $^1$H NMR (400 MHz, CHLOROFORM-d) δ ppm 8.86 (1 H, s) 8.12 (1 H, s) 7.41-7.49 (1 H, m) 7.09-7.28 (3 H, m) 6.52-6.72 (1 H, m) 6.42 (1 H, d, J = 16.59 Hz) 5.83 (1 H, d, J = 10.60 Hz) 2.99-5.26 (7 H, m) 2.27 (3 H, br s) 1.42-1.77 (4 H, m) 1.21-1.30 (1 H, m) 1.10-1.19 (1 H, m) 0.93-1.04 (1 H, m) 0.80-0.91 (1 H, m) |
| 60-31 | 512.2 | $^1$H NMR (400 MHz, CDCl$_3$) δ ppm 8.01 (d, J = 2.49 Hz, 1H), 7.44-7.58 (m, 2H), 7.29-7.39 (m, 1H), 7.20-7.26 (m, 1H), 6.61 (dd, J = 10.57, 16.79 Hz, 1H), 6.33-6.43 (m, 1H), 5.79 (d, J = 10.57 Hz, 1H), 4.66-5.15 (m, 1H), 3.90 (br d, J = 4.77 Hz, 8H), 2.62-2.78 (m, 2H), 1.06 (dd, J = 6.74, 10.88 Hz, 6H), 0.83 (d, J = 6.84 Hz, 6H). |
| 60-32 | 534.2 | $^1$H NMR (400 MHz, CDCl$_3$) δ ppm 8.06 (s, 1H), 7.55-7.65 (m, 2H), 7.36 (d, J = 8.50 Hz, 1H), 6.52-6.68 (m, 1H), 6.36-6.44 (m, 1H), 5.79 (dd, J = 1.76, 10.47 Hz, 1H), 5.28 (br d, J = 16.38 Hz, 1H), 4.71 (br s, 1H), 4.30-4.59 (m, 1H), 3.93-4.07 (m, 1H), 3.84 (br d, J = 12.65 Hz, 1H), 3.60-3.75 (m, 1H), 3.57 (br s, 1H), 3.43 (s, 1H), 2.95-3.31 (m, 1H), 2.29 (s, 3H), 2.15-2.26 (m, 2H), 1.74-1.86 (m, 2H), 1.37-1.57 (m, 3H), 0.79 (t, J = 7.46 Hz, 6H). |
| 60-33 | 552.2 | $^1$H NMR (400 MHz, CDCl$_3$) δ ppm 7.90-7.96 (m, 1H), 7.45-7.53 (m, 2H), 7.26-7.32 (m, 1H), 7.16-7.22 (m, 1H), 6.49-6.65 (m, 1H), 6.32-6.41 (m, 1H), 5.73-5.80 (m, 1H), 4.57-4.83 (m, 3H), 4.35-4.51 (m, 1H), 3.97-4.25 (m, 1H), 3.76-3.97 (m, 1H), 3.46-3.74 (m, 2H), 2.90-3.28 (m, 1H), 1.35-1.50 (m, 3H), 1.17 (s, 6H). $^{19}$F NMR (376 MHz, CDCl$_3$) δ ppm −77.27 (s, 3F), −112.45 (s, 1F). |
| 60-34 | 588.2 | $^1$H NMR (400 MHz, CDCl$_3$) δ ppm 8.05 (s, 1H), 7.51-7.66 (m, 2H), 7.37 (d, J = 8.50 Hz, 1H), 6.52-6.69 (m, 1H), 6.36-6.46 (m, 1H), 5.81 (dd, J = 1.55, 10.47 Hz, 1H), 4.95-5.22 (m, 1H), 4.70-4.80 (m, 1H), 4.65 (br d, J = 1.24 Hz, 2H), 4.42-4.58 (m, 1H), 3.97-4.35 (m, 1H), 3.69-3.93 (m, 1H), 3.47-3.83 (m, 2H), 3.12 (br s, 1H), 2.27 (s, 3H), 1.38-1.58 (m, 3H), 1.15 (br d, J = 4.77 Hz, 6H). $^{19}$F NMR (376 MHz, CDCl$_3$) δ ppm −77.14 (s, 3F) |
| 60-35 | 452.1 | $^1$H NMR (400 MHz, CDCl$_3$) δ ppm 7.96 (d, J = 1.45 Hz, 1H), 6.58 (dd, J = 10.47, 16.69 Hz, 1H), 6.39 (s, 1H), 5.75-5.82 (m, 1H), 4.76-4.89 (m, 1H), 3.84 (br s, |

TABLE 88-continued

| | Analytical Data | |
|---|---|---|
| Ex. # | LRMS: m/z (ESI, +ve ion): (M + H)+ | NMR |
| | | 8H), 2.66-2.77 (m, 2H), 1.04-1.12 (m, 6H), 0.80 (dd, J = 6.84, 10.99 Hz, 6H). |
| 61-1 | 486.2 | $^1$H NMR (400 MHz, DMSO-d$_6$) δ ppm 8.33-8.55 (m, 1 H), 7.37-7.59 (m, 2 H), 7.30 (t, J = 7.6 Hz, 1 H), 7.13 (dd, J = 7.6, 3.2 Hz, 1 H), 6.75-6.97 (m, 1 H), 6.21 (br d, J = 16.8 Hz, 1 H), 5.76 (dd, J = 10.3, 2.2 Hz, 1 H), 4.74-5.05 (m, 1 H), 3.92-4.45 (m, 3 H), 3.28-3.87 (m, 3 H), 2.92-3.26 (m, 1 H), 1.22-1.30 (m, 3 H), 1.08 (br d, J = 6.8 Hz, 3 H), 1.03 (br d, J = 6.8 Hz, 3 H). |
| 61-1-2 | 486.2 | $^1$H NMR (400 MHz, DMSO-d$_6$) δ ppm 8.40 (br d, J = 6.0 Hz, 1 H), 7.46-7.52 (m, 1 H), 7.38-7.46 (m, 1 H), 7.29 (td, J = 7.5, 1.5 Hz, 1 H), 7.08-7.15 (m, 1 H), 6.77-6.93 (m, 1 H), 6.20 (br d, J = 17.0 Hz, 1 H), 5.70-5.81 (m, 1 H), 4.82 (br s, 1 H), 4.20-4.42 (m, 2 H), 3.94-4.17 (m, 1 H), 3.45-3.75 (m, 2 H), 3.01-3.24 (m, 1 H), 2.52 (br s, 1 H), 1.31 (d, J = 6.6 Hz, 3 H), 1.05-1.10 (m, 3 H), 0.99-1.05 (m, 3 H). |
| 61-2-1 | 501.2 | $^1$H NMR (400 MHz, DMSO-d$_6$) δ ppm 8.39-8.57 (m, 2 H), 7.28 (d, J = 4.8 Hz, 1 H), 6.75-6.95 (m, 1 H), 6.20 (br d, J = 16.6 Hz, 1 H), 5.71-5.83 (m, 1 H), 4.89 (br s, 1 H), 4.21-4.43 (m, 2 H), 3.97-4.17 (m, 1 H), 3.56-3.80 (m, 2 H), 3.04-3.28 (m, 1 H), 2.59-2.74 (m, 1 H), 1.95 (s, 3 H), 1.31 (d, J = 6.6 Hz, 3 H), 1.07 (d, J = 6.8 Hz, 3 H), 1.02 (d, J = 6.6 Hz, 3 H). |
| 61-2-2 | 501.2 | $^1$H NMR (400 MHz, DMSO-d$_6$) δ ppm 8.50 (d, J = 4.8 Hz, 2 H), 7.30 (d, J = 4.8 Hz, 1 H), 6.77-6.94 (m, 1 H), 6.20 (br d, J = 16.0 Hz, 1 H), 5.76 (dd, J = 10.5, 2.4 Hz, 1 H), 4.92 (br s, 1 H), 3.96-4.44 (m, 3 H), 3.54-3.85 (m, 2 H), 3.00-3.24 (m, 1 H), 2.59-2.70 (m, 1 H), 1.97 (s, 3 H), 1.30 (br d, J = 6.6 Hz, 3 H), 1.07 (d, J = 6.6 Hz, 3 H), 1.02 (d, J = 6.6 Hz, 3 H). |
| 62-1 | 544.8 | $^1$H NMR (400 MHz, CDCl$_3$) δ ppm 7.84 (1 H, s) 7.34-7.57 (4 H, m) 7.12-7.25 (4 H, m) 6.58-6.75 (1 H, m) 6.55 (1 H, s) 6.43 (1 H, dd, J = 16.79, 1.24 Hz) 5.83 (1 H, dd, J = 10.47, 0.94 Hz) 2.61-5.22 (9 H, m) 1.43-1.61 (3 H, m) 1.26 (3 H, d, J = 6.63 Hz) 1.11 (3 H, d, J = 6.84 Hz). |
| 62-1-1 | 545.0 | $^1$H NMR (400 MHz, CDCl$_3$) δ ppm 7.83 (1 H, s) 7.33-7.55 (4 H, m) 7.11-7.23 (4 H, m) 6.56-6.73 (1 H, m) 6.54 (1 H, s) 6.42 (1 H, dd, J = 16.79, 1.45 Hz) 5.82 (1 H, d, J = 10.78 Hz) 2.55-5.03 (8 H, m) 1.45-1.60 (3 H, m) 1.24 (3 H, d, J = 6.63 Hz) 1.09 (3 H, d, J = 6.84 Hz). |
| 62-1-2 | 545.0 | $^1$H NMR (400 MHz, CDCl$_3$) δ ppm 7.80 (1 H, br s) 7.30-7.50 (4 H, m) 7.09-7.19 (4 H, m) 6.54-6.70 (1 H, m) 6.51 (1 H, s) 6.40 (1 H, dd, J = 16.79, 1.45 Hz) 5.80 (1 H, dd, J = 10.60, 1.20 Hz) 2.56-5.16 (8 H, m) 1.41-1.53 (3 H, m) 1.22 (3 H, d, J = 6.63 Hz) 1.07 (3 H, d, J = 6.84 Hz). |
| 62-2 | 595.2 | $^1$H NMR (500 MHz, DMSO-d$_6$) δ ppm 7.96-8.01 (1 H, m) 7.80 (1 H, dd, J = 7.85, 3.05 Hz) 7.72 (1 H, q, J = 7.27 Hz) 7.61-7.67 (1 H, m) 7.48-7.52 (1 H, m) 7.40-7.45 (1 H, m) 7.29-7.35 (1 H, m) 7.24-7.29 (1 H, m) 7.10-7.18 (1 H, |

TABLE 88-continued

| | Analytical Data | |
|---|---|---|
| Ex. # | LRMS: m/z (ESI, +ve ion): (M + H)+ | NMR |
| | | m) 6.81-6.93 (1 H, m) 6.17-6.24 (2 H, m) 5.76 (1 H, dd, J = 10.38, 2.21 Hz) 2.48-4.91 (9 H, m) 1.30-1.36 (3 H, m) 1.07-1.11 (3 H, m) 0.93-0.99 (3 H, m). |
| 62-3 | 560.0 | $^1$H NMR (400 MHz, DMSO-$d_6$) δ ppm 10.10 (1 H, br s) 8.56 (1 H, br s) 8.44 (1 H, br d, J = 11.61 Hz) 7.98 (1 H, d, J = 11.20 Hz) 7.36 (1 H, d, J = 4.56 Hz) 7.23 (1 H, q, J = 7.74 Hz) 6.78-6.95 (1 H, m) 6.62-6.77 (2 H, m) 6.28-6.34 (1 H, m) 6.14-6.26 (1 H, m) 5.76 (1 H, dd, J = 10.37, 2.28 Hz) 2.95-4.96 (7 H, m) 1.46-1.62 (1 H, m) 1.29-1.40 (3 H, m) 0.43-0.95 (4 H, m). |
| 63-1 | 560.3 | $^1$H NMR (400 MHz, DMSO-$d_6$) δ ppm 10.16 (s, 1H), 8.40 (d, J = 9.33 Hz, 1H), 7.18-7.32 (m, 3H), 7.10 (dd, J = 2.18, 6.53 Hz, 1H), 6.63-6.87 (m, 3H), 6.18 (br d, J = 17.21 Hz, 1H), 5.70-5.76 (m, 1H), 4.47-4.77 (m, 1H), 4.33-4.45 (m, 1H), 3.96-4.21 (m, 2H), 3.58-3.89 (m, 3H), 2.66-2.68 (m, 1H), 1.82 (s, 3H), 1.06 (d, J = 6.84 Hz, 3H), 0.92 (d, J = 6.84 Hz, 3H), 0.83-0.89 (m, 3H). $^{19}$F NMR (376 MHz, DMSO-$d_6$) δ ppm −115.53 (br d, J = 6.07 Hz, 1F), −128.92 (br d, J = 5.20 Hz, 1F). |
| 63-2 | 560.2 | $^1$H NMR (400 MHz, DMSO-$d_6$) δ ppm 10.15 (s, 1H), 8.39 (d, J = 9.12 Hz, 1H), 7.17-7.31 (m, 3H), 7.11 (dd, J = 1.76, 6.53 Hz, 1H), 6.62-6.89 (m, 3H), 6.18 (br d, J = 15.34 Hz, 1H), 5.73 (br d, J = 1.66 Hz, 1H), 4.45-4.79 (m, 1H), 4.37 (br dd, J = 4.46, 9.02 Hz, 1H), 3.94-4.25 (m, 2H), 3.54-3.86 (m, 3H), 2.56 (m, 1H), 1.88 (s, 3H), 1.04 (d, J = 6.84 Hz, 3H), 0.91 (d, J = 6.84 Hz, 3H), 0.86 (br t, J = 6.84 Hz, 3H). $^{19}$F NMR (376 MHz, DMSO-$d_6$) δ ppm −115.37 (d, J = 6.07 Hz, 1F), −129.05 (br d, J = 6.07 Hz, 1F). |
| 63-3 | 574.3 | $^1$H NMR (400 MHz, DMSO-$d_6$) δ ppm 8.32 (br d, J = 8.91 Hz, 1H), 7.18-7.28 (m, 3H), 7.12 (dd, J = 2.38, 6.32 Hz, 1H), 6.86 (dd, J = 10.37, 16.79 Hz, 1H), 6.51-6.73 (m, 2H), 6.20 (dd, J = 2.28, 16.59 Hz, 1H), 5.75 (d, J = 2.28 Hz, 1H), 4.30 (br d, J = 1.87 Hz, 2H), 4.07 (br d, J = 12.02 Hz, 1H), 3.82-3.96 (m, 1H), 3.59-3.78 (m, 2H), 2.46 (m, 2H), 1.86 (s, 3H), 1.23 (br d, J = 6.01 Hz, 6H), 1.05 (d, J = 6.84 Hz, 3H), 0.94 (d, J = 6.84 Hz, 3H). $^{19}$F NMR (376 MHz, DMSO-$d_6$) δ ppm −115.92--115.32 (m, 1F), −128.53--127.59 (m, 1F). |
| 63-4 | 574.3 | $^1$H NMR (400 MHz, DMSO-$d_6$) δ ppm 9.98-10.32 (m, 1H), 8.23 (br d, J = 8.50 Hz, 1H), 7.18-7.32 (m, 3H), 7.11 (dd, J = 2.38, 6.53 Hz, 1H), 6.58-7.00 (m, 3H), 6.21 (br d, J = 16.38 Hz, 1H), 5.68-5.82 (m, 1H), 3.54-3.97 (m, 4H), 3.47-3.52 (m, 1H), 1.99 (s, 2H), 1.84 (s, 3H), 1.53-1.60 (m, 6H), 1.06 (d, J = 6.84 Hz, 3H), 0.93 (d, J = 6.84 Hz, 3H). $^{19}$F NMR (376 MHz, DMSO-$d_6$) δ ppm −115.96--115.22 (m, 1F), −129.12--128.34 (m, 1F). |
| 63-5 | 558.2 | $^1$H NMR (400 MHz, DMSO-$d_6$) δ ppm 10.16 (s, 1H), 8.10 (d, J = 9.12 Hz, 1H), 7.16-7.33 (m, 3H), 7.09 (dd, J = 2.38, 6.12 Hz, 1H), 6.61-6.77 (m, 2H), 6.27-6.43 (m, 1H), 6.13 (dd, J = 1.97, 16.90 Hz, 1H), 5.70 (dd, J = 1.97, 10.26 Hz, 1H), 4.96-5.22 (m, 2H), 4.49 (br s, 4H), 4.21 (br s, 2H), 2.56 (m, 1H), 1.85 (s, 3H), 1.05 (d, J = 6.63 Hz, 3H), 0.91 (d, |

TABLE 88-continued

Analytical Data

| Ex. # | LRMS: m/z (ESI, +ve ion): (M + H)⁺ | NMR |
|---|---|---|
| | | J = 6.84 Hz, 3H). ¹⁹F NMR (376 MHz, DMSO-d₆) δ −115.75 (d, J = 5.20 Hz, 1F), −128.98 (d, J = 5.20 Hz, 1F). |
| 64-1 | 560.0 | ¹H NMR (400 MHz, DMSO-d₆) δ ppm 8.44 (br s, 1 H), 7.46-7.55 (m, 1 H), 7.07-7.35 (m, 6 H), 6.86 (dt, J = 16.1, 10.7 Hz, 1 H), 6.21 (br d, J = 16.6 Hz, 1 H), 5.72-5.81 (m, 1 H), 4.93 (br s, 1 H), 3.95-4.47 (m, 3 H), 3.40-3.84 (m, 2 H), 3.02-3.30 (m, 1 H), 2.52-2.59 (m, 1 H), 1.89 (s, 3 H), 1.33 (d, J = 6.6 Hz, 3 H), 1.06 (d, J = 6.8 Hz, 3 H), 0.94 (d, J = 6.8 Hz, 3 H). ¹⁹F NMR (376 MHz, DMSO-d₆) δ ppm −113.97 (s, 1 F). |
| 64-2 | 594.2 | ¹H NMR (400 MHz, DMSO-d₆) δ ppm 10.29 (br s, 1H), 8.37 (br s, 1H), 7.30-7.21 (m, 2H), 7.13 (dd, J = 2.1, 6.6 Hz, 1H), 7.01 (m, 1H), 6.92-6.79 (m, 2H), 6.21 (m, 1H), 5.80-5.72 (m, 1H), 4.90 (m, 1H), 4.46-3.95 (m, 3H), 3.82-3.38 (m, 2H), 3.27-2.97 (m, 2H), 1.88 (s, 3H), 1.32 (d, J = 6.6 Hz, 3H), 1.06 (d, J = 6.8 Hz, 3H), 0.96 (d, J = 6.8 Hz, 3H); ¹⁹F NMR (376 MHz, DMSO-d₆) δ ppm −134.51 (br d, J = 23.4 Hz, 1F), −150.84 (br d, J = 23.4 Hz, 1F). |
| 64-3 | 576.0 | ¹H NMR (400 MHz, DMSO-d₆) δ ppm 9.95 (s, 1H), 8.37 (br s, 1H), 7.17-7.28 (m, 3H), 7.12 (dd, J = 6.3, 2.4 Hz, 1H), 6.76-6.90 (m, 3H), 6.20 (br dd, J = 17.1, 4.5 Hz, 1H), 5.76 (dd, J = 10.4, 2.3 Hz, 1H), 4.91 (br d, J = 4.4 Hz, 1H), 3.97-4.48 (m, 3H), 3.40-3.83 (m, 2H), 3.03-3.28 (m, 1H), 2.52-2.59 (m, 1H), 1.88 (s, 3H), 1.32 (d, J = 6.6 Hz, 3H), 1.06 (d, J = 6.8 Hz, 3H), 0.96 (d, J = 6.8 Hz, 3H). |
| 65-1 | 577.0 | ¹H NMR (400 MHz, DMSO-d₆) δ ppm 8.29-8.42 (m, 2H), 7.49 (m, 1H), 7.20 (m, 1H), 6.79-6.92 (m, 1H), 6.53 (m, 1H), 6.31 (m, 2H), 6.20 (m, 1H), 5.76 4.89 (br s, 1H), 4.30 (m, 2H), 3.93-4.19 (m, 1H), 3.44-3.76 (m, 2H), 3.17 (m, 1H), 2.68-2.73 (m, 1H),, 1.85-1.93 (m, 3H), 1.34 (br d, J = 6.4 Hz, 3H), 1.06 (br d, J = 6.2 Hz, 3H), 0.95 ppm (m, 3H). ¹⁹F NMR (377 MHz, DMSO-d₆) δ ppm −131.55 ppm (s, 1F). |
| 65-2 | 561.0 | ¹H NMR (400 MHz, DMSO-d₆) δ ppm 8.40 (d, J = 4.8 Hz, 1H), 8.35-8.28 (m, 1H), 7.40 (t, J = 9.2 Hz, 1H), 7.19 (d, J = 5.0 Hz, 1H), 6.91-6.81 (m, 1H), 6.55 (dd, J = 3.1, 8.9 Hz, 1H), 6.29-6.13 (m, 1H), 5.99 (s, 2H), 5.79-5.74 (m, 1H), 4.91 (m, 1H), 4.48-3.92 (m, 3H), 3.68 (m, 1H), 3.17 (m, 1H), 3.22-3.14 (m, 1H), 2.34-2.31 (m, 1H), 1.91 (s, 3H), 1.33 (d, J = 6.6 Hz, 3H), 1.06 (d, J = 6.6 Hz, 3H), 0.96 (d, J = 6.4 Hz, 3H); ¹⁹F NMR (376 MHz, DMSO-d₆): δ ppm −131.10 (s, 1F), −142.18 ppm (s, 1F). |
| 65-3 | 579.5 | 1H NMR (400 MHz, DMSO-d6) δ ppm 10.85 (br s, 1H), 8.40 (d, J = 4.8 Hz, 1H), 8.28 (m, 1H), 7.19 (d, J = 4.8 Hz, 1H), 6.79-6.93 (m, 1H), 6.62-6.76 (m, 1H), 6.51 (m, 1H), 6.21 (m, 1H), 5.74-5.79 (m, 1H), 4.89 (br s, 1H), 4.31 (m, 2H), 3.93-4.19 (m, 1H), 3.52-3.81 (m, 2H), 2.67 (m, 1H), 2.33 (m, 1H), 1.90 (s, 3H), 1.35 (d, J = 6.6 Hz, 3H), 1.08 (d, J = 6.6 Hz, 3H), 0.94 ppm (d, J = 6.6 Hz, 3H): ¹⁹F NMR (376 MHz, DMSO-d₆) δ ppm −107.51(s, 1F), −112.54 (s, 1F), −128.54 (s, 1F). |
| 66-1 | 549.2 | ¹H NMR (400 MHz, DMSO-d₆) δ ppm 7.98 (br d, J = 4.6 Hz, 1 H), 7.27-7.38 (m, |

TABLE 88-continued

Analytical Data

| Ex. # | LRMS: m/z (ESI, +ve ion): (M + H)+ | NMR |
|---|---|---|
| | | 1 H), 7.15-7.23 (m, 2 H), 6.76-6.91 (m, 1 H), 6.11-6.25 (m, 1 H), 5.69-5.81 (m, 1 H), 4.67-4.84 (m, 1 H), 4.38 (br d, J = 12.2 Hz, 1 H), 4.13 (br d, J = 13.1 Hz, 1 H), 3.79-4.01 (m, 2 H), 3.48-3.64 (m, 2 H), 3.23-3.29 (m, 4 H), 3.02 (br d, J = 2.3 Hz, 1 H), 2.13-2.34 (m, 4 H), 1.39-1.54 (m, 2 H), 1.13-1.29 (m, 6 H), 0.92-1.05 (m, 6 H). |
| 66-2 | 557.2 | $^1$H NMR (400 MHz, DMSO-d$_6$) δ ppm 8.05 (s, 1H), 7.33 (t, J = 8.0 Hz, 1H), 7.20 (m, 2H), 6.90-6.79 (m, 1H), 6.19 (m, 1H), 5.75 (dd, J = 4.0, 8.0 Hz, 1H), 4.71 (br m, 1H), 4.42-4.21 (m, 5H), 4.14-3.93 (m, 2H), 2.24-2.12 (m, 4H), 1.24 (m, 3H), 0.97 (t, J = 4.0 Hz, 6H). |
| 66-3 | 537.2 | $^1$H NMR (400 MHz, DMSO-d$_6$) δ ppm 7.89 (s, 1H), 7.30 (t, J = 4.0 Hz, 1H), 7.18 (d, J = 8.0 Hz, 2H), 6.92-6.76 (m, 1H), 6.23-6.13 (m, 1H), 5.74 (dd, J = 4.0, 8.0 Hz, 1H), 5.58 (d, J = 4.0 Hz, 1H), 4.68 (br m, 1H), 4.48-4.31 (m, 2H), 4.27-3.87 (m, 5H), 3.77-3.39 (m, 4H), 2.26-2.10 (m, 4H), 1.24 (m, 3H), 0.98 (t, J = 4.0 Hz, 6H). |
| 66-4 | 539.2 | $^1$H NMR (400 MHz, DMSO-d$_6$) δ ppm 7.96 (s, 1H), 7.31 (t, J = 4.0 Hz, 1H), 7.19 (d, J = 8.0 Hz, 2H), 6.90-6.78 (m, 1H), 6.21-6.13 (m, 1H), 5.75 (dd, J = 4.0, 8.0 Hz, 1H), 5.29 (d, J = 56 Hz, 1H), 4.69 (m, 1H), 4.42-3.85 (m, 8H), 3.66-3.49 (m, 2H), 2.25-2.12 (m, 4H), 1.23 (m, 3H), 0.97 (t, J = 4.0, 8.0 Hz, 6H). |
| 66-5 | 549.2 | $^1$H NMR (400 MHz, DMSO-d$_6$) δ ppm 7.92 (s, 1H), 730 (t, J = 4.0, 8.0 Hz, 1H), 7.19 (d, J = 8.0 Hz, 2H), 6.92-6.77 (m, 1H), 6.25-6.13 (m, 1H), 5.74 (dd, J = 4.0, 8.0 Hz, 1H), 4.75 (m, 1H), 4.00 (m, 2H), 3.65-3.50 (m, 2H), 3.26-3.15 (m, 2H), 3.02-2.91 (m, 2H), 2.30-2.06 (m, 7H), 1.89-1.80 (m, 1H), 1.39-1.33 (m, 1H), 1.20 (m, 3H), 1.05-0.87 (m, 9H). |
| 66-6 | 553.2 | $^1$H NMR (400 MHz, DMSO-d$_6$) δ ppm 7.92 (m, 1H), 7.32 (t, J = 8.0 Hz, 1H), 7.20 (d, J = 8.0 Hz, 2H), 6.92-6.76 (m, 1H), 6.23-6.13 (m, 1H), 5.74 (dd, J = 4.0 Hz, 8.0 Hz, 1H), 5.24 (d, J = 56.0 Hz, 1H), 4.62 (br m, 1H), 4.42-3.93 (m, 3H), 3.63-3.38 (m, 6H), 3.18-3.02 (m, 1H), 2.31-2.04 (m, 6H), 1.31 (d, J = 8.0 Hz, 3H), 0.99 (t. J = 8.0 Hz, 3H), 0.94 (t, J = 8.0 Hz, 3H). |
| 66-7 | 553.2 | $^1$H NMR (400 MHz, DMSO-d$_6$) δ ppm 8.00 (m, 1H), 7.32 (t, J = 8.0 Hz, 1H), 7.20 (d, J = 8.0 Hz, 2H), 6.92-6.76 (m, 1H), 6.23-6.13 (m, 1H), 5.74 (dd, J = 4.0 Hz, 8.0 Hz, 1H), 5.24 (d, J = 56 Hz, 1H), 4.81 (br m, 1H), 4.42-3.93 (m, 3H), 3.63-3.38 (m, 6H), 2.98-2.85 (m, 1H), 2.31-2.04 (m, 6H), 1.19 (m, 3H), 0.99 (t, J = 8.0 Hz, 3H), 0.94 (t, J = 8.0 Hz, 3H). |
| 66-8 | 551.2 | $^1$H NMR (400 MHz, DMSO-d$_6$) δ ppm 7.93 (m, 1H), 7.31 (t, J = 8.0 Hz, 1H), 7.19 (d, J = 8.0 Hz, 2H), 6.91-6.76 (m, 1H), 6.25-6.12 (m, 1H), 5.74 (dd, J = 4.0, 8.0 Hz, 1H), 4.88 (d, J = 4.0 Hz, 1H), 4.77 (m, 1H), 4.18 (m, 2H), 3.99 (m, 2H), 3.45 (m, 1H), 3.47-3.38 (br m, 2H), 3.22 (br m, 2H), 2.33-2.11 (m, 6H), 1.84-1.63 (br m, 2H), 1.19 (m, 3H), 1.06-0.89 (m, 6H). |
| 66-9 | 565.2 | $^1$H NMR (400 MHz, DMSO-d$_6$) δ ppm 7.85 (m, 1H), 7.29 (m, 1H), 7.18 (m, |

TABLE 88-continued

Analytical Data

| Ex. # | LRMS: m/z (ESI, +ve ion): $(M + H)^+$ | NMR |
|---|---|---|
| | | 2H), 6.35 (m, 1H), 6.20 (m, 1H), 5.74 (d, J = 8.0 Hz, 1H), 4.59 (m, 1H), 4.26 (m, 2H), 3.76 (m, 2H), 3.61 (m, 2H), 3.07 (m, 2H), 2.38 (br m, 2H), 2.35-2.06 (m, 5H), 1.35 (br m, 2H), 1.64 (br m, 2H), 3.31 (m, 3H), 1.06-0.94 (m, 6H). |
| 66-10 | 549.2 | $^1$H NMR (400 MHz, DMSO-d$_6$) δ ppm 7.89 (m, 1H), 7.30 (t, J = 8.0 Hz, 1H), 7.19 (d, J = 8.0 Hz, 2H), 6.86 (m, 1H), 6.19 (m, 1H), 5.74 (dd, J = 4.0, 8.0 Hz, 1H), 4.69 (m, 1H), 4.43-4.20 (m, 1H), 4.13 (m, 1H), 3.99 (m, 1H), 3.55 (m, 3H), 3.23 (m, 2H), 2.97 (m, 2H), 2.29-2.05 (m, 5H), 1.84 (m, 1H), 1.33 (m, 1H), 1.33-1.17 (m, 3H), 1.03-0.8 (m, 9H). |
| 66-11 | 563.2 | $^1$H NMR (400 MHz, DMSO-d$_6$) δ ppm 7.90 (m, 1H), 7.31 (t, J = 8.0 Hz, 1H), 7.18 (d, J = 8.0 Hz, 2H), 6.85 (m, 1H), 6.19 (m, 1H), 5.75 (dd, J = 4.0, 8.0 Hz, 1H), 4.71 (m, 1H), 4.43-4.20 (m, 1H), 4.14 (m, 1H), 3.98 (m, 1H), 3.66-3.36 (m, 4H), 2.95 (m, 2H), 2.30-2.06 (m, 4H), 1.90 (m, 2H), 1.42-1.17 (m, 7H), 1.04-0.92 (m, 6H), 0.80 (t, J = 8.0 Hz, 3H). |
| 66-12 | 591.2 | $^1$H NMR (400 MHz, DMSO-d$_6$) δ ppm 7.90 (m, 1H), 7.29 (t, J = 8.0 Hz, 1H), 7.19 (d, J = 8.0 Hz, 2H), 6.83 (m, 1H), 6.18 (m, 1H), 5.74 (dd, J = 4.0, 8.0 Hz, 1H), 4.70 (m, 1H), 4.45-4.19 (m, 1H), 4.16 (m, 1H), 3.97 (m, 1H), 3.69-3.35 (m, 6H), 2.91 (m, 1H), 2.28-1.99 (m, 6H), 1.88 (m, 1H), 1.49-0.80 (m, 18H). |
| 66-13 | 565.2 | $^1$H NMR (400 MHz, DMSO-d$_6$) δ ppm 7.94 (m, 1H), 7.31 (t, J = 4.0, 8.0 Hz, 1H), 7.19 (d, J = 8.0 Hz, 2H), 6.86 (m, 1H), 6.17 (m, 1H), 5.74 (dd, J = 4.0, 8.0 Hz, 1H), 4.76 (m, 1H), 3.99 (m, 2H), 3.86 (m, 2H), 3.60 (m, 2H), 3.44-3.34 (m, 4 H), 3.13 (s, 3H), 2.26-2.10 (m, 5H), 1.91 (m, 1H), 1.79 (m, 1H), 1.20 (m, 3H), 1.03-0.93 (m, 6H). |
| 66-14 | 571.2 | $^1$H NMR (400 MHz, DMSO-d$_6$) δ ppm 8.46 (m, 0.5H), 8.01 (m, 0.5H), 7.34 (m, 1H), 7.22 (m, 2H), 6.85 (m, 1H), 6.19 (m, 1H), 5.75 (m, 1H), 4.79 (m, 1H), 4.43-3.94 (m, 4H), 3.74 (m, 2H), 3.66-3.37 (m, 3H), 3.26-3.00 (m, 1H), 2.41-2.26 (m, 2H), 2.26-2.13 (m, 4H), 1.33-1.24 (m, 3H), 1.02-0.91 (m, 6H). |
| 66-15 | 579.3 | $^1$H NMR (400 MHz, DMSO-d$_6$) δ ppm 8.05 (m, 1H), 7.32 (m, 1H), 7.22 (m, 2H), 6.86 (m, 1H), 6.20 (m, 1H), 5.76 (dd, J = 4.0, 8.0 Hz, 1H), 4.78 (m, 1H), 4.48-3.96 (m, 3H), 3.88-3.55 (m, 6H), 3.22 (m, 2H), 3.01 (m, 2H), 2.37-2.09 (m, 4H), 1.33-1.10 (m, 5H), 1.05-0.92 (m, 6H), 0.72 (m, 3H). |
| 66-16 | 579.2 | $^1$H NMR (400 MHz, DMSO-d$_6$) δ ppm 8.06 (m, 1H), 7.34 (m, 1H), 7.22 (m, 2H), 6.85 (m, 1H), 6.20 (m, 1H), 5.76 (m, 1H), 4.78 (m, 1H), 4.46-3.91 (m, 4H), 3.80-3.50 (m, 4H), 3.19 (m, 4H), 2.36-2.10 (m, 4H), 1.26 (m, 3H), 1.05-0.77 (m, 12H). |
| 66-17 | 605.2 | $^1$H NMR (400 MHz, DMSO-d$_6$) δ ppm 8.00 (m, 1H), 7.32 (t, J = 8.0 Hz, 1H), 7.19 (d, J = 8.0 Hz, 2H), 6.83 (m, 1H), 6.18 (m, 1H), 5.74 (dd, J = 4.0, 8.0 Hz, 1H), 4.76 (m, 1H), 4.46-3.92 (m, 4H), 3.57 (m, 2H), 3.47-3.34 (m, 4H), 3.27-3.20 (m, 3H), 2.34-2.11 (m, 6H), 1.50 |

TABLE 88-continued

| | Analytical Data | |
|---|---|---|
| Ex. # | LRMS: m/z (ESI, +ve ion): (M + H)+ | NMR |
| | | (m, 3H), 1.32-1.15 (m, 5H), 1.06-0.94 (m, 6H). |
| 66-18 | 593.4 | $^1$H NMR (400 MHz, DMSO-d$_6$) δ ppm 8.03 (m, 1H), 7.30 (m, 1H), 7.19 (m, 2H), 6.83 (m, 1H), 6.118 (m, 1H), 5.74 (dd, J = 4.0, 8.0 Hz, 1H), 4.76 (m, 1H), 4.45-3.94 (m, 3H), 3.92-3.49 (m, 5H), 3.26 (m, 1H), 2.98-2.81 (m, 4H), 2.85-2.11 (m, 4H), 1.39 (m, 1H), 1.27 (m, 3H), 0.96 (m, 6H), 0.76 (d, J = 8.0 Hz, 3H), 0.63 (m, 3H). |
| 66-19 | 579.2 | $^1$H NMR (400 MHz, DMSO-d$_6$) δ ppm 8.00 (m, 1H), 7.33 (m, 1H), 7.22 (m, 2H), 6.84 (m, 1H), 6.19 (m, 1H), 5.75 (d, J = 8.0 Hz, 1H), 4.76 (m, 1H), 4.45-3.90 (m, 3H), 3.58 (m, 1H), 3.44-3.33 (m, 5H), 3.22-3.13 (m, 3H), 2.30-2.12 (m, 4H), 1.25 (m, 3H), 1.05-0.92 (m, 6H), 0.87 (s, 6H). |
| 66-20 | 591.4 | $^1$H NMR (400 MHz, DMSO-d$_6$) δ ppm 7.89 (m, 1H), 7.30 (t, J = 8.0 Hz, 1H), 7.18 (d, J = 8.0 Hz, 2H), 6.85 (m, 1H), 6.18 (m, 1H), 5.75 (dd, J = 4.0, 8.0 Hz, 1H), 4.71 (br s, 1H), 3.38 (m, 0.5H), 4.24 (m, 0.5H), 4.13-3.97 (m, 2H), 3.54 (m, 2H), 3.17 (m, 1H), 3.09-2.98 (m, 3H), 2.23-2.11 (m, 4H), 1.56 (t, J = 8.0 Hz, 1H), 1.26-1.14 (m, 8H), 0.96 (m, 6H), 0.69 (t, J = 8.0 Hz, 6H). |
| 66-21 | 591.4 | $^1$H NMR (400 MHz, DMSO-d$_6$) δ ppm 7.85 (m, 1H), 7.29 (m, 1H), 7.18 (m, 2H), 6.84 (m, 1H), 6.18 (m, 1H), 5.74 (dd, J = 4.0, 8.0 Hz, 1H), 4.78-4.52 (m, 1H), 4.20 (m, 1H), 3.98 (m, 1H), 3.60 (m, 2H), 3.12 (m, 2H, 2.96 (m, 1H), 2.32-2.10 (m, 4H), 1.96-1.75 (m, 2H), 1.43 (m, 1H), 1.24 (m, 1H), 1.17 (m, 1H), 1.03-0.97 (m, 3H), 0.96-0.91 (m, 3H), 0.88 (m, 1H), 0.83 (s, 3H), 0.77 (s, 9H). |
| 66-22 | 565.2 | $^1$H NMR (400 MHz, DMSO-d$_6$) δ ppm 7.88 (m, 1H), 7.31 (t, J = 8.0 Hz, 1H), 7.19 (m, 2H), 6.85 (m, 1H), 6.18 (m, 1H), 5.74 (dd, J = 4.0, 8.0 Hz, 1H), 4.63 (br m, 1H), 4.45-3.92 (m, 3H), 3.85 (s, 1H), 3.57-3.40 (m, 5H), 3.12 (s, 3H), 3.06 (m, 2H), 2.27-2.06 (m, 4H), 1.88 (m, 1H), 1.79 (m, 1H), 1.28 (d, J = 8.0 Hz, 3H), 0.99 (t, J = 8.0 Hz, 3H), 0.94 (t, J = 8.0 Hz, 3H). |
| 66-23 | 560.2 | $^1$H NMR (400 MHz, DMSO-d$_6$) δ ppm 8.46 (m, 1H), 7.36 (t, J = 8.0 Hz, 1H), 7.24 (d, J = 8.0 Hz, 2H), 6.84 (m, 1H), 6.19 (m, 1H), 5.74 (dd, J = 4.0, 8.0 Hz, 1H), 4.87 (m, 1H), 4.43-3.97 (m, 4H), 3.84-3.57 (m, 3H), 3.26-3.04 (m, 1H), 2.77-2.11 (m, 6H), 1.29 (d, J = 8.0 Hz, 3H), 0.99 (t, J = 8.0 Hz, 6H). |
| 66-24 | 565.2 | $^1$H NMR (400 MHz, DMSO-d$_6$) δ ppm 7.98 (m, 1H), 7.31 (t, J = 8.0 Hz, 1H), 7.19 (d, J = 8.0 Hz, 2H), 6.85 (m, 1H), 6.19 (m, 1H), 5.74 (dd, J = 4.0, 8.0 Hz, 1H), 4.75 (m, 2H), 4.39 (m, 0.5H), 4.26 (m, 0.5H), 4.11 (m, 1.5H), 3.99 (m, 0.5H), 3.75 (m, 1H), 3.56 (m, 1.5H), 3.17 (m, 0.5H), 3.01 (m, 0.5H), 2.86 (m, 1H), 2.75 (m, 1H), 2.23-2.11 (m, 4H), 1.71 (m, 1H), 1.42 (m, 1H), 1.25 (m, 4H), 1.13 (m, 1H), 0.95 (m, 6H). |
| 66-25 | 591.4 | $^1$H NMR (400 MHz, DMSO-d$_6$) δ ppm 8.02 (m, 1H), 7.34 (t, J = 8.0 Hz, 1H), 7.22 (d, J = 8.0 Hz, 2H), 6.87 (m, 1H), 6.19 (m, 1H), 5.76 (dd, J = 4.0, 8.0 Hz, 1H), 4.77 (m, 1H), 4.39 (m, 0.5H), 4.26 (m, 0.5H), 4.21-3.96 (m, 2H), 3.79 (m, |

TABLE 88-continued

Analytical Data

| Ex. # | LRMS: m/z (ESI, +ve ion): (M + H)+ | NMR |
|---|---|---|
| | | 2H), 3.71-3.42 (m, 3H), 3.22-2.96 (m, 4H), 2.68 (m, 1H), 2.28-2.06 (m, 4H), 1.34-1.20 (m, 3H), 0.96 (m, 6H), 0.61 (m, 1H), 0.37 (m, 1H), 0.28 (m, 1H), 0.11 (m, 1H), −0.12 (m, 1H). |
| 66-26 | 608.2 | $^1$H NMR (400 MHz, DMSO-$d_6$) δ ppm 8.03 (m, 1H), 7.32 (t, J = 8.0 Hz, 1H), 7.20 (m, 2H), 6.84 (m, 1H), 6.19 (m, 1H), 5.75 (dd, J = 4.0, 8.0 Hz, 1H), 4.77 (m, 1H), 4.37 (m, 0.5H), 4.26 (m, 0.5H), 4.12 (m, 1.5H), 4.00 (m, 0.5H), 3.82-3.52 (m, 6H), 3.31-3.16 (m, 2H), 3.06 (m, 0.5H), 3.05 (m, 1H), 2.59-2.54 (m, 1H), 2.19-2.13 (m, 5H), 2.07 (s, 6H), 1.97 (m, 1H), 1.26 (m, 3H), 0.97 (m, 6H). |
| 66-27 | 579-2 | $^1$H NMR (400 MHz, DMSO-$d_6$) δ ppm 7.98 (m, 1H), 7.31 (t, J = 8.0 Hz, 1H), 7.19 (m, 2H), 6.84 (m, 1H), 6.18 (m, 1H), 5.74 (dd, J = 4.0, 8.0 Hz, 1H), 4.76 (m, 1H), 4.40 (m, 1.5H), 4.25 (m, 0.5H), 4.12 (m, 1.5H), 3.99 (m, 0.5H), 3.84 (m, 1H), 3.72 (m, 1H), 3.56 (m, 1H), 3.19 (m, 0.5H), 3.04 (m, 2.5H), 2.73 (m, 1H), 2.61 (m, 1.5H), 2.24-2.11 (m, 4H), 1.59 (m, 1H), 1.36 (m, 2H), 1.25 (m, 3.5H), 1.14 (m, 2.5H), 0.95 (m, 6H). |
| 66-28 | 563.4 | $^1$H NMR (400 MHz, DMSO-$d_6$) δ ppm 7.94 (m, 1H), 7.32 (t, J = 8.0 Hz, 1H), 7.20 (m, 2H), 6.85 (m, 1H), 6.19 (m, 1H), 5.76 (dd, J = 4.0, 8.0 Hz, 1H), 4.71 (br s, 1H), 4.37 (m, 0.5 H), 4.20 (m, 0.5H), 4.17 (m, 1H), 4.11 (m, 0.5H), 3.96 (m, 1.5H), 3.60-3.49 (m, 2.5H), 3.15 (m, 0.5 H), 3.07 (m, 0.5H), 2.82 (m, 1H), 2.24 (m, 1H), 2.20-2.08 (m, 4H), 1.59 (m, 1H), 1.44 (m, 1H), 1.29 (m, 4H), 1.16 (m, 1H), 1.03-0.96 (m, 4H), 0.93 (t, J = 8.0 Hz, 3H), 0.57 (d, J = 4.0 Hz, 3H). |
| 66-29 | 577.4 | $^1$H NMR (400 MHz, DMSO-$d_6$) δ ppm 7.97 (m, 1H), 7.31 (t, J = 8.0 Hz, 1H), 7.19 (m, 2H), 6.85 (m, 1H), 6.19 (m, 1H), 5.74 (dd, J = 4.0, 8.0 Hz, 1H), 4.76 (br s, 1H), 4.38, (m, 0.5H), 4.25 (m, 0.5H), 4.12 (m, 1.5H), 3.99 (m, 0.5H), 3.57 (m, 1.5H), 3.40 (m, 0.5H), 3.28 (m, 4H), 3.18 (m, 0.5H), 3.02 (m, 0.5H), 2.21-2.15 (m, 4H), 1.25 (m, 3H), 1.08 (m, 4H), 0.95 (m, 6H), 0.83 (s, 6H). |
| 66-30 | 565.4 | $^1$H NMR (400 MHz, DMSO-$d_6$) δ ppm 8.08 (m, 1H), 7.32 (m, 1H), 7.21 (m, 2H), 6.86 (m, 1H), 6.19 (m, 1H), 5.75 (dd, J = 4.0, 8.0 Hz, 1H), 4.84 (br s, 1H), 4.38 (m, 0.5H), 4.27 (m, 0.5H), 4.12 (m, 0.5H), 4.02 (m, 1.5H), 3.78 (m, 1H), 3.63 (m, 1.5H), 3.56 (m, 1H), 3.46-3.40 (m, 2.5H), 3.22 (m, 2H), 3.10 (m, 1H), 2.96 (m, 0.5H), 2.28-2.08 (m, 4H), 1.22 (m, 3H), 1.02-0.88 (m, 9H). |
| 66-31 | 563.4 | $^1$H NMR (400 MHz, DMSO-$d_6$) δ 7.92 (br d, 1H), 7.31 (t, J = 8.0 Hz, 1H), 7.19 (m, 2H), 6.85 (m, 1H), 6.19 (t, J = 8.0 Hz, 1H), 5.75 (dd, J = 4.0, 8.0 Hz, 1H), 4.63 (br s, 1H), 4.52 (s, 1H), 4.37 (br d, 0.5H), 4.21 (m, 1.5H), 4.11 (br d, 0.5H), 4.05 (br s, 1H), 3.96 (br d, 0.5 H), 3.76 (br d, 1H), 3.53 (m, 0.5H), 3.50-3.44 (m, 1.5H), 3.38 (d, J = 8.0 Hz, 1H), 3.30 (d, J = 8.0 Hz, 1H), 3.12 (m, 1H), 2.27-2.08 (m, 4H), 1.74 (d, J = 8.0 Hz, 1H), 1.66 (d, J = 8.0 Hz, 1H), 1.30 (d, J = 8.0 Hz, 3H), 1.00 (t, J = 4.0 Hz, 3H), 0.94 (t, J = 4.0 Hz, 3H). |

TABLE 88-continued

Analytical Data

| Ex. # | LRMS: m/z (ESI, +ve ion): $(M + H)^+$ | NMR |
|---|---|---|
| 66-32 | 563.2 | $^1$H NMR (400 MHz, DMSO-d$_6$) δ ppm 8.02 (br d, 1H), 7.31 (t, J = 8.0 Hz, 1H), 7.20 (d, J = 8.0 Hz, 1H), 7.18 (d, J = 8.0 Hz, 1H), 6.86 (m, 1H), 6.19 (t, J = 8.0 Hz, 1H), 5.75 (dd, J = 4.0, 8.0 Hz, 1H), 4.83 (br s, 1H), 4.52 (s, 1H), 4.39 (br d, 0.5H), 4.27 (br d, 0.5H), 4.13 (br d, 0.5H), 4.02 (m, 2.5H), 3.77 (br d, 1H), 3.63 (m, 1.5H), 3.38 (d, J = 4.0 Hz, 1H), 3.29 (d, J = 4.0 Hz, 1H), 3.24 (br d, 0.5H), 2.92 (m, 0.5H), 2.27-2.10 (m, 4H), 1.75 (d, J = 4.0 Hz, 1H), 1.66 (d, J = 4.0 Hz, 1H), 1.19 (m, 3H), 0.99 (t, J = 4.0 Hz, 3H), 0.95 (t, J = 4.0 Hz, 3H). |
| 66-33 | 565.4 | $^1$H NMR (400 MHz, DMSO-d$_6$) δ ppm 8.00 (br d, 1H), 7.32 (m, 1H), 7.25-7.19 (m, 2H), 6.85 (m, 1H), 6.19 (br t, 1H), 5.76 (dd, J = 4.0, 8.0 Hz, 1H), 4.70 (br s, 1H), 4.37 (br d, 0.5H), 4.22 (m, 1.5H), 4.11 (br d, 0.5H), 3.98 (br d, 0.5H), 3.78 (m, 1H), 3.56 (m, 1.5H), 3.43 (m, 2.5H), 3.23 (m, 1H), 3.14-3.06 (1.5H), 2.27-2.08 (m, 4H), 1.29 (d, J = 8.0 Hz, 3H), 1.05-0.97 (m, 6H), 0.93 (t, J = 8.0 Hz, 3H). |
| 67-1 | 547.0 | $^1$H NMR (400 MHz, CD$_2$Cl$_2$) δ ppm 1.03 (d, J = 6.8 Hz, 3 H), 1.17 (d, J = 6.8 Hz, 3 H), 1.48 (br d, J = 5.2 Hz, 3 H), 2.63 (br s, 1 H), 2.93-3.15 (m, 1 H), 3.18-3.35 (m, 1 H), 3.45-3.82 (m, 3 H), 3.84-3.95 (m, 0.5 H) 4.00-4.12 (m, 0.5 H) 4.18-4.30 (m, 1 H), 4.32-4.51 (m, 1 H), 4.60-4.74 (m, 1 H), 4.84 (br s, 0.5 H), 4.91-5.06 (m, 1 H), 5.77 (dd, J = 10.5, 2.0 Hz, 1 H), 6.32 (dd, J = 16.7, 2.0 Hz, 1 H), 6.56-6.70 (m, 1 H), 7.08 (br d, J = 7.7 Hz, 1 H), 7.17 (t, J = 5.4 Hz, 1 H), 7.29 (td, J = 7.3, 2.0 Hz, 1 H), 7.37-7.47 (m, 2 H), 8.12 (s, 1 H), 8.44 (d, J = 4.6 Hz, 1 H), 8.51 (s, 1 H). $^{19}$F NMR (376 MHz, CD$_2$Cl$_2$) δ ppm −127.69 (s, 1 F). |
| 67-2 | 599.9 | $^1$H NMR (400 MHz, DMSO-d$_6$) δ ppm 0.89 (d, J = 6.8 Hz, 3 H), 1.09 (d, J = 6.6 Hz, 3 H), 1.32 (d, J = 6.6 Hz, 3 H), 2.58-2.71 (m, 1 H), 3.01-3.15 (m, 0.5 H), 3.26 (br d, J = 13.4 Hz, 0.5 H), 3.36 (s, 3 H), 3.44-3.47 (m, 0.5 H), 3.58-3.70 (m, 0.5 H), 3.72-3.86 (m, 1 H), 4.00-4.07 (m, 0.5 H), 4.11-4.19 (m, 0.5 H), 4.20-4.34 (m, 1.5 H), 4.40 (br d, J = 12.9 Hz, 0.5 H), 4.93 (br s, 1 H), 5.73-5.80 (m, 1 H), 6.21 (br d, J = 16.6 Hz, 1 H), 6.79-6.94 (m, 1 H), 7.17 (d, J = 7.7 Hz, 1 H), 7.27-7.32 (m, 1 H), 7.33 (s, 1 H), 7.40-7.46 (m, 1 H), 7.46-7.51 (m, 1 H), 8.44-8.49 (m, 1 H); $^{19}$F NMR (376 MHz, DMSO-d$_6$) δ ppm −60.52 (s, 1 F). |
| 67-3 | 545.9 | $^1$H NMR (400 MHz, DMSO-d$_6$) δ ppm 0.87-0.92 (m, 3 H), 1.09 (d, J = 6.8 Hz, 3 H), 1.29-1.38 (m, 3 H), 1.85 (s, 3 H), 2.56-2.71 (m, 1 H), 2.99-3.16 (m, 0.5 H), 3.18-3.29 (m, 0.5 H), 3.38 (s, 3 H), 3.57-3.69 (m, 0.5 H), 3.70-3.88 (m, 1 H), 4.00-4.06 (m, 1 H), 4.10-4.19 (m, 0.5 H), 4.27 (br t, J = 13.2 Hz, 1.5 H), 4.40 (br d, J = 14.1 Hz, 0.5 H), 4.83-5.04 (m, 1 H), 5.72-5.81 (m, 1 H), 6.19 (br s, 0.5 H), 6.23 (br s, 0.5 H), 6.78-6.95 (m, 1 H), 7.13 (d, J = 7.9 Hz, 1 H), 7.23-7.29 (m, 2 H), 7.35-7.40 (m, 1 H), 7.41-7.46 (m, 1 H), 8.36-8.48 (m, 1 H). |

TABLE 88-continued

Analytical Data

| Ex. # | LRMS: m/z (ESI, +ve ion): (M + H)+ | NMR |
|---|---|---|
| 67-4-1 | 533.9 | $^1$H NMR (400 MHz, DMSO-d$_6$) δ ppm 0.98 (d, J = 7.1 Hz, 3 H), 1.09 (d, J = 6.8 Hz, 3 H), 1.33 (d, J = 6.8 Hz, 3 H), 2.53-2.61 (m, 1 H), 3.02-3.14 (m, 0.5 H), 3.17-3.26 (m, 0.5 H), 3.40-3.54 (m, 0.5 H), 3.58-3.77 (m, 1.5 H), 3.95-4.07 (m, 0.5 H), 4.09-4.20 (m, 0.5 H), 4.24-4.33 (m, 1 H), 4.34-4.45 (m, 0.5 H), 4.85 (br s, 1 H), 5.71-5.81 (m, 1 H), 6.21 (br d, J = 15.8 Hz, 1 H), 6.78-6.94 (m, 1 H), 7.08-7.18 (m, 2 H), 7.27-7.35 (m, 1 H), 7.42-7.49 (m, 1 H), 7.49-7.55 (m, 1 H), 7.72-7.79 (m, 1 H), 7.97-8.04 (m, 1 H), 8.29-8.34 (m, 1 H). |
| 67-4-2 | 533.9 | $^1$H NMR (400 MHz, DMSO-d$_6$) δ ppm 0.97 (d, J = 6.8 Hz, 3 H), 1.09 (d, J = 6.6 Hz, 3 H), 1.31 (br d, J = 6.6 Hz, 3 H), 2.52-2.60 (m, 1 H), 2.98-3.11 (m, 0.5 H), 3.18-3.26 (m, 0.5 H), 3.36-3.47 (m, 0.5 H), 3.57-3.66 (m, 0.5 H), 3.69-3.82 (m, 1 H), 3.97-4.08 (m, 0.5 H), 4.10-4.23 (m, 1.5 H), 4.29 (br d, J = 12.9 Hz, 0.5 H), 4.39 (br d, J = 12.9 Hz, 0.5 H), 4.93 (br s, 1 H), 5.72-5.80 (m, 1 H), 6.21 (br d, J = 17.0 Hz, 1 H), 6.78-6.93 (m, 1 H), 7.09-7.18 (m, 2 H), 7.28-7.35 (m, 1 H), 7.42-7.48 (m, 1 H), 7.49-7.56 (m, 1 H), 7.75 (d, J = 4.8 Hz, 1 H), 8.00 (d, J = 3.1 Hz, 1 H), 8.33 (br s, 1 H). |
| 68-1 | 575.9 | $^1$H NMR (400 MHz, DMSO-d$_6$) δ ppm 0.88-0.97 (m, 3 H), 1.06 (d, J = 6.6 Hz, 3 H), 1.32 (br dd, J = 14.4, 6.5 Hz, 3 H), 1.85 (br s, 3 H), 2.55-2.60 (m, 1 H), 3.04-3.21 (m, 0.5 H), 3.42-3.58 (m, 0.5 H), 3.59-3.81 (m, 1.5 H), 4.00-4.06 (m, 0.5 H), 4.08-4.19 (m, 0.5 H), 4.20-4.35 (m, 1.5 H), 4.41 (br d, J = 11.0 Hz, 0.5 H), 4.80-5.01 (m, 1 H), 5.71-5.83 (m, 1 H), 6.21 (br d, J = 16.4 Hz, 1 H), 6.79-6.89 (m, 2 H), 6.92 (d, J = 8.1 Hz, 1 H), 7.06-7.14 (m, 1 H), 7.17-7.29 (m, 3 H), 8.16-8.38 (m, 1 H), 10.12-10.14 (m, 1 H). $^{19}$F NMR (376 MHz, DMSO-d$_6$) δ ppm −130.05−−129.96 (m, 1 F). |
| 68-1-1 | 575.9 | $^1$H NMR (400 MHz, DMSO-d$_6$) δ ppm 0.92 (br dd, J = 17.3, 6.7 Hz, 3 H), 1.06 (br d, J = 6.8 Hz, 3 H), 1.34 (br d, J = 6.4 Hz, 3 H), 1.84 (br d, J = 4.2 Hz, 3 H), 2.53-2.62 (m, 1 H), 3.10-3.21 (m, 0.5 H), 346-3.57 (m, 0.5 H), 3.58-3.73 (m, 1.5 H), 3.96-4.07 (m, 0.5 H), 4.09-4.19 (m, 0.5 H), 4.20-4.34 (m, 1.5 H), 4.35-4.44 (m, 0.5 H), 4.77-4.96 (m, 1 H), 5.70-5.80 (m, 1 H), 6.20 (br d, J = 15.8 Hz, 1 H), 6.77-6.96 (m, 3 H), 7.04-7.14 (m, 1 H), 7.18-7.32 (m, 3 H), 8.15-8.39 (m, 1 H), 10.14 (br s, 1 H). $^{19}$F NMR (376 MHz, DMSO-d$_6$) δ ppm −130.02−−129.93 (m, 1 F). |
| 68-1-2 | 575.9 | $^1$H NMR (400 MHz, DMSO-d$_6$) δ ppm 0.84-0.97 (m, 3 H), 1.06 (br d, J = 4.8 Hz, 3 H), 1.30 (br d, J = 3.3 Hz, 3 H), 1.85 (br s, 3 H), 3.00-3.17 (m, 0.5 H), 3.42-3.56 (m, 0.5 H), 3.60-3.82 (m, 1.5 H), 3.94-4.08 (m, 0.5 H), 4.10-4.33 (m, 2 H), 4.36-4.52 (m, 0.5 H), 4.92 (br s, 1 H), 5.76 (br d, J = 8.9 Hz, 1 H), 6.06-6.34 (m, 1 H), 6.74-6.98 |

TABLE 88-continued

Analytical Data

| Ex. # | LRMS: m/z (ESI, +ve ion): (M + H)+ | NMR |
|---|---|---|
| | | (m, 3 H), 7.01-7.14 (m, 1 H), 7.21 (br s, 3 H), 8.30 (br s, 1 H), 10.15 (br s, 1 H). $^{19}$F NMR (376 MHz, DMSO-d$_6$) δ ppm −130.04 (s, 1 F). |
| 68-2 | 580.0 | $^1$H NMR (400 MHz, DMSO-d$_6$) δ ppm 0.85 (br d, J = 6.8 Hz, 3 H), 1.05 (br d, J = 6.6 Hz, 3 H), 1.35 (br dd, J = 16.5, 6.5 Hz, 3 H), 1.90 (br d, J = 4.2 Hz, 3 H), 2.08 (s, 3 H), 2.55-2.64 (m, 1 H), 3.03-3.16 (m, 0.5 H), 3.44-3.61 (m, 0.5 H), 3.62-3.73 (m, 1 H), 3.74-3.84 (m, 0.5 H), 3.99-4.10 (m, 0.5 H), 4.12-4.23 (m, 0.5 H), 4.25-4.36 (m, 1 H), 4.37-4.48 (m, 1 H), 4.91 (br s, 0.5 H), 4.99 (br s, 0.5 H), 5.72-5.82 (m, 1 H), 6.22 (br d, J = 15.8 Hz, 1 H), 6.82-6.95 (m, 1 H), 7.10 (br d, J = 6.8 Hz, 1 H), 7.14-7.21 (m, 2 H), 7.22-7.28 (m, 1 H), 7.45-7.62 (m, 2 H), 8.26-8.45 (m, 1 H), 13.10 (s, 1 H). $^{19}$F NMR (376 MHz, DMSO-d$_6$) δ ppm −129.03 (s, 1 F). |
| 68-2-1 | 580.0 | $^1$H NMR (400 MHz, DMSO-d$_6$) δ ppm 0.85 (d, J = 6.8 Hz, 3 H), 1.05 (d, J = 6.8 Hz, 3 H), 1.33 (br d, J = 6.6 Hz, 3 H), 1.90 (s, 3 H), 2.08 (s, 3 H), 2.57-2.61 (m, 1 H), 3.00-3.18 (m, 0.5 H), 3.43-3.55 (m, 0.5 H), 3.64-3.72 (m, 0.5 H), 3.78 (br t, J = 12.1 Hz, 1 H), 4.05 (br d, J = 14.7 Hz, 0.5 H), 4.17 (br d, J = 12.4 Hz, 0.5 H), 4.25-4.37 (m, 1.5 H), 4.44 (br d, J = 12.4 Hz, 0.5 H), 4.98 (br s, 1 H), 5.71-5.81 (m, 1 H), 6.22 (br d, J = 16.2 Hz, 1 H), 6.81-6.95 (m, 1 H), 7.10 (dd, J = 7.0, 1.6 Hz, 1 H), 7.14-7.21 (m, 2 H), 7.21-7.28 (m, 1 H), 7.47-7.57 (m, 2 H), 8.35-8.39 (m, 1 H), 13.10 (s, 1 H). $^{19}$F NMR (376 MHz, DMSO-d$_6$) δ ppm −129.05 (s, 1 F). |
| 68-2-2 | 580.0 | $^1$H NMR (400 MHz, DMSO-d$_6$) δ ppm 0.85 (d, J = 6.6 Hz, 3 H), 1.05 (d, J = 6.6 Hz, 3 H), 1.37 (d, J = 6.6 Hz, 3 H), 1.89 (s, 3 H), 2.08 (s, 3 H), 2.55-2.64 (m, 1 H), 3.19 (br t, J = 10.9 Hz, 0.5 H), 3.49-3.60 (m, 0.5 H), 3.61-3.76 (m, 1.5 H), 4.04 (br d, J = 13.3 Hz, 0.5 H), 4.12-4.21 (m, 0.5 H), 4.30 (br d, J = 13.3 Hz, 0.5 H), 4.34-4.46 (m, 1.5 H), 4.91 (br s, 1 H), 5.74-5.82 (m, 1 H), 6.21 (br d, J = 16.2 Hz, 1 H), 6.88 (dt, J = 16.4, 11.3 Hz, 1 H), 7.10 (dd, J = 7.0, 1.4 Hz, 1 H), 7.14-7.21 (m, 2 H), 7.22-7.28 (m, 1 H), 7.51 (br d, J = 8.7 Hz, 2 H), 8.27-8.40 (m, 1 H), 13.10 (s, 1 H). $^{19}$F NMR (376 MHz, DMSO-d$_6$) δ ppm −129.01 (s, 1 F). |
| 69-1 | 535.3 | $^1$H NMR (400 MHz, DMSO-d$_6$) δ ppm 7.85-8.03 (m, 1 H), 7.42-7.50 (m, 1 H), 7.34-7.42 (m, 1 H), 7.26 (t, J = 7.5 Hz, 1 H), 7.05 (d, J = 7.7 Hz, 1 H), 6.74-6.92 (m, 1 H), 6.19 (br dd, J = 17.5, 4.5 Hz, 1 H), 5.71-5.78 (m, 1 H), 4.68-4.84 (m, 1 H), 4.21-4.45 (m, 1 H), 3.93-4.19 (m, 2 H), 3.35-3.66 (m, 2 H), 3.25 (br s, 4 H), 2.89-3.19 (m, 1 H), 2.45-2.48 (m, 1 H), 1.34 (br d, J = 3.9 Hz, 3 H), 1.20-1.29 (m, 6 H), 1.08 (d, J = 6.8 Hz, 3 H), 0.98 (br d, J = 6.8 Hz, 3 H). |
| 69-1-1 | 535.3 | $^1$H NMR (400 MHz, DMSO-d$_6$) δ ppm 7.94 (br s, 1 H), 7.41-7.48 (m, 1 H), 7.33-7.41 (m, 1 H), 7.26 (td, J = 7.6, 1.5 Hz, 1 H), 7.05 (d, J = 7.7 Hz, 1 H), 6.74-6.94 (m, 1 H), 6.19 (br dd, J = 16.0, 5.0 Hz, 1 H), 5.67-5.80 (m, 1 H), 4.74 (br d, J = 3.3 Hz, 1 H), 4.21-4.43 (m, 1 H), 3.92- |

TABLE 88-continued

Analytical Data

| Ex. # | LRMS: m/z (ESI, +ve ion): (M + H)+ | NMR |
|---|---|---|
| | | 4.18 (m, 2 H), 3.35-3.64 (m, 2 H), 3.19-3.29 (m, 4 H), 2.96-3.18 (m, 1 H), 2.53-2.60 (m, 1 H), 1.44-1.55 (m, 2 H), 1.31-1.39 (m, 4 H), 1.27 (d, J = 6.6 Hz, 3 H), 1.08 (d, J = 6.8 Hz, 3 H), 0.98 (d, J = 6.8 Hz, 3 H). |
| 69-1-2 | 535.3 | $^1$H NMR (400 MHz, DMSO-d$_6$) δ ppm 7.96 (br s, 1 H), 7.41-7.48 (m, 1 H), 7.34-7.41 (m, 1 H), 7.26 (td, J = 7.5, 1.5 Hz, 1 H), 7.05 (d, J = 7.5 Hz, 1 H), 6.77-6.92 (m, 1 H), 6.19 (br dd, J = 16.1, 5.7 Hz, 1 H), 5.69-5.80 (m, 1 H), 4.72-4.84 (m, 1 H), 4.20-4.45 (m, 1 H), 3.93-4.15 (m, 2 H), 3.57 (br d, J = 12.9 Hz, 1 H), 3.33-3.42 (m, 1 H), 3.25 (br s, 4 H), 2.88-3.19 (m, 1 H), 2.51-2.56 (m, 1 H), 1.43-1.52 (m, 2 H), 1.31-1.41 (m, 4 H), 1.25 (br d, J = 6.6 Hz, 3 H), 1.08 (d, J = 6.8 Hz, 3 H), 0.98 (d, J = 6.8 Hz, 3 H). |
| 69-2 | 507.2 | $^1$H NMR (400 MHz, DMSO-d$_6$) δ ppm 7.83 (br s, 1 H), 7.32-7.47 (m, 2 H), 7.18-7.30 (m, 1 H), 7.00 (br d, J = 7.5 Hz, 1 H), 6.76-6.92 (m, 1 H), 6.11-6.26 (m, 1 H), 5.69-5.80 (m, 1 H), 4.58-4.77 (m, 1 H), 4.18-4.45 (m, 1 H), 3.79-4.16 (m, 6 H), 3.44-3.68 (m, 2 H), 2.90-3.23 (m, 1 H), 2.52-2.56 (m, 1 H), 2.05-2.21 (m, 2 H), 1.24 (m, 3H), 1.04-1.11 (m, 3 H), 0.96-1.04 (m, 3 H). |
| 69-3 | 521.2 | $^1$H NMR (400 MHz, DMSO-d$_6$) δ ppm 7.88 (br d, J = 7.5 Hz, 1 H), 7.42-7.47 (m, 1 H), 7.35-7.41 (m, 1 H), 7.26 (t, J = 7.5 Hz, 1 H), 7.03 (d, J = 7.7 Hz, 1 H), 6.74-6.95 (m, 1 H), 6.15-6.25 (m, 1 H), 5.75 (dd, J = 10.4, 2.5 Hz, 1 H), 4.64-4.80 (m, 1 H), 4.22-4.45 (m, 1 H), 3.94-4.18 (m, 2 H), 3.47-3.66 (m, 2 H), 3.33-3.42 (m, 2 H), 2.93-3.22 (m, 1 H), 2.53-2.59 (m, 1 H), 1.65-1.79 (m, 4 H), 1.26 (br t, J = 6.9 Hz, 5 H), 1.09 (d, J = 6.8 Hz, 3 H), 1.00 (dd, J = 6.8, 1.2 Hz, 3 H). |
| 69-4 | 495.2 | $^1$H NMR (400 MHz, DMSO-d$_6$) δ ppm 7.92 (br d, J = 5.6 Hz, 1 H), 7.42-7.49 (m, 1 H), 7.34-7.42 (m, 1 H), 7.22-7.30 (m, 1 H), 7.04 (d, J = 7.9 Hz, 1 H), 6.73-6.95 (m, 1 H), 6.12-6.26 (m, 1 H), 5.70-5.79 (m, 1 H), 4.67-4.82 (m, 1 H), 4.21-4.45 (m, 1 H), 3.93-4.17 (m, 2 H), 3.34-3.66 (m, 2 H), 2.91-3.23 (m, 1 H), 2.83 (s, 6 H), 2.52-2.60 (m, 1 H), 1.26 (br t, J = 6.7 Hz, 3 H), 1.08 (d, J = 6.8 Hz, 3 H), 0.99 (dd, J = 6.8, 2.3 Hz, 3 H). |
| 69-5 | 549.2 | $^1$H NMR (400 MHz, DMSO-d$_6$) δ ppm 7.86-8.01 (m, 1 H), 7.41-7.48 (m, 1 H), 7.34-7.41 (m, 1 H), 7.22-7.30 (m, 1 H), 6.98-7.11 (m, 1 H), 6.77-6.91 (m, 1 H), 6.19 (br d, J = 16.6 Hz, 1 H), 5.71-5.79 (m, 1 H), 4.61-4.91 (m, 1 H), 3.93-4.43 (m, 4 H), 3.40-3.71 (m, 3 H), 3.07-3.25 (m, 1 H), 2.81-2.98 (m, 1 H), 2.56-2.69 (m, 1 H), 1.17-1.61 (m, 9 H), 1.06-1.12 (m, 3 H), 0.90-1.05 (m, 6 H). |
| 69-6 | 523.3 | $^1$H NMR (400 MHz, DMSO-d$_6$) δ ppm 7.93 (br s, 1 H), 7.34-7.49 (m, 2 H), 7.26 (t, J = 7.5 Hz, 1 H), 7.05 (d, J = 7.5 Hz, 1 H), 6.72-6.93 (m, 1 H), 6.12-6.26 (m, 1 H), 5.67-5.83 (m, 1 H), 4.67-4.83 (m, 1 H), 4.20-4.46 (m, 1 H), 4.07-4.18 (m, 1 H), 3.32-3.56 (m, 4 H), 2.88-3.24 (m, 1 H), 2.69 (s, 3 H), 2.53-2.61 (m, 1 H), 1.23-1.31 (m, 3 H), 1.08 (d, J = 6.8 Hz, 3 H), 0.98 (d, J = 6.8 Hz, 3 |

TABLE 88-continued

| Ex. # | LRMS: m/z (ESI, +ve ion): (M + H)⁺ | NMR |
|---|---|---|
| | | Analytical Data |
| | | H), 0.92 (dd, J = 6.6, 4.6 Hz, 3 H), 0.86 (t, J = 6.5 Hz, 3 H). |
| 69-7 | 525.2 | 1H NMR (400 MHz, DMSO-d$_6$) δ ppm 7.90 (br d, J = 6.6 Hz, 1 H), 7.40-7.47 (m, 1 H), 7.33-7.40 (m, 1 H), 7.26 (t, J = 7.6 Hz, 1 H), 7.03 (d, J = 7.7 Hz, 1 H), 6.74-6.93 (m, 1 H), 6.19 (br dd, J = 16.5, 5.3 Hz, 1 H), 5.71-5.79 (m, 1 H), 4.64-4.84 (m, 1 H), 4.48-4.57 (m, 1 H), 4.21-4.43 (m, 1 H), 3.92-4.19 (m, 2 H), 3.47-3.65 (m, 2 H), 3.33-3.45 (m, 2 H), 2.97-3.29 (m, 2 H), 2.92 (s, 3 H), 2.53-2.60 (m, 1 H), 1.19-1.32 (m, 3 H), 1.08 (d, J = 6.8 Hz, 3 H), 0.99 (br d, J = 6.6 Hz, 3 H). |
| 70-1 | 578.2 | $^1$H NMR (400 MHz, DMSO-d$_6$) δ ppm 8.39 (br d, J = 19.7 Hz, 1 H), 7.46 (d, J = 8.9 Hz, 1 H), 7.37-7.43 (m, 1 H), 7.30-7.37 (m, 1 H), 7.23 (t, J = 7.5 Hz, 1 H), 7.06-7.12 (m, 1 H), 6.78-6.93 (m, 1 H), 6.49 (d, J = 8.9 Hz, 1 H), 6.27 (br d, J = 1.5 Hz, 2 H), 6.15-6.24 (m, 1 H), 5.76 (dd, J = 10.4, 2.3 Hz, 1 H), 4.74-5.04 (m, 1 H), 3.96-4.47 (m, 3 H), 3.36-3.87 (m, 2 H), 3.00-3.26 (m, 1 H), 2.52-2.60 (m, 1 H), 1.32 (br dd, J = 16.5, 6.5 Hz, 3 H), 1.06 (d, J = 6.8 Hz, 3 H), 0.98 (d, J = 6.8 Hz, 3 H). |
| 70-2 | 594.2 | $^1$H NMR (400 MHz, DMSO-d$_6$) δ ppm 8.44 (br d, J = 10.2 Hz, 1 H), 7.54 (br d, J = 8.5 Hz, 1 H), 7.40 (br t, J = 7.5 Hz, 1 H), 7.27-7.34 (m, 1 H), 7.24 (br t, J = 7.4 Hz, 1 H), 6.94-7.20 (m, 4 H), 6.80-6.94 (m, 1 H), 6.68 (s, 1 H), 6.22 (br d, J = 16.4 Hz, 1 H), 6.00 (br s, 2 H), 5.72-5.82 (m, 1 H), 4.83-5.04 (m, 1 H), 4.01-4.51 (m, 3 H), 3.56-3.88 (m, 2 H), 3.01-3.19 (m, 1 H), 2.55-2.65 (m, 1 H), 1.30-1.41 (m, 3 H), 1.06 (br d, J = 6.6 Hz, 3 H), 0.90 (br d, J = 5.2 Hz, 3 H). |
| 70-3 | 592.2 | $^1$H NMR (400 MHz, DMSO-d$_6$) δ ppm 8.42 (br s, 1 H), 7.46 (d, J = 8.7 Hz, 1 H), 7.17-7.28 (m, 2 H), 7.11 (dd, J = 6.6, 1.9 Hz, 1 H), 6.72-6.93 (m, 1 H), 6.49 (d, J = 8.9 Hz, 1 H), 6.28 (s, 2 H), 6.20 (br d, J = 16.4 Hz, 1 H), 5.70-5.81 (m, 1 H), 4.87 (br s, 1 H), 4.21-4.44 (m, 2 H), 3.94-4.18 (m, 1 H), 3.41-3.81 (m, 2 H), 3.00-3.26 (m, 1 H), 2.53-2.58 (m, 1 H), 1.85 (s, 3 H), 1.32 (d, J = 6.6 Hz, 3 H), 1.05 (d, J = 6.8 Hz, 3 H), 0.95 (d, J = 6.8 Hz, 3 H). |
| 70-4 | 576.2 | $^1$H NMR (400 MHz, DMSO-d$_6$) δ ppm 8.42 (br s, 1 H), 7.38 (t, J = 9.0 Hz, 1 H), 7.19-7.29 (m, 2 H), 7.11 (dd, J = 6.5, 1.8 Hz, 1 H), 6.70-6.98 (m, 1 H), 6.50 (dd, J = 9.0, 3.2 Hz, 1 H), 6.20 (br dd, J = 16.9, 4.7 Hz, 1 H), 5.86-6.10 (br s, 2 H), 5.69-5.79 (m, 1 H), 4.91 (br s, 1 H), 4.05-4.45 (m, 3 H), 3.61-3.83 (m, 2 H), 2.98-3.32 (m, 1 H), 2.39-2.47 (m, 1 H), 1.86 (s, 3 H), 1.31 (br d, J = 6.6 Hz, 3 H), 1.04 (d, J = 6.8 Hz, 3 H), 0.94 (d, J = 6.8 Hz, 3 H). $^{19}$F NMR (376 MHz, DMSO-d$_6$) δ ppm −142.96 (1 F, s). |
| 71-1 | 576.2 | $^1$H NMR (400 MHz, DMSO-d$_6$) δ ppm 8.31 (br d, J = 7.3 Hz, 1 H), 7.48 (d, J = 8.9 Hz, 1 H), 7.18-7.32 (m, 2 H), 7.12 (dd, J = 6.8, 1.7 Hz, 1 H), 6.76-6.96 (m, 1 H), 6.52 (d, J = 8.9 Hz, 1 H), 6.12-6.42 (m, 3 H), 5.72-5.85 (m, 1 H), 4.88 (br s, 1 H), 4.20-4.47 (m, 2 H), 3.92-4.18 (m, 1 H), 3.60-3.78 (m, 2 H), 3.12-3.29 (m, 1 H), 2.54-2.61 (m, 1 H), 1.85 (d, J = 3.9 |

TABLE 88-continued

Analytical Data

| Ex. # | LRMS: m/z (ESI, +ve ion): (M + H)+ | NMR |
|---|---|---|
| | | Hz, 3 H), 1.31 (br t, J = 6.5 Hz, 3 H), 1.05 (d, J = 6.6 Hz, 3 H), 0.94 (dd, J = 6.7, 3.2 Hz, 3 H). $^{19}$F NMR (376 MHz, DMSO-d$_6$) δ ppm −132.10 (br s, 1 F). |
| 71-1-1 | 576.2 | $^1$H NMR (400 MHz, DMSO-d$_6$) δ ppm 8.19-8.41 (m, 1 H), 7.48 (d, J = 8.9 Hz, 1 H), 7.17-7.33 (m, 2 H), 7.12 (dd, J = 6.7, 1.8 Hz, 1 H), 6.73-6.98 (m, 1 H), 6.52 (d, J = 8.9 Hz, 1 H), 6.31 (s, 2 H), 6.20 (br d, J = 16.6 Hz, 1 H), 5.69-5.84 (m, 1 H), 4.86 (br s, 1 H), 3.94-4.46 (m, 3 H), 3.42-3.73 (m, 2 H), 3.02-3.28 (m, 1 H), 1.85 (s, 3 H), 1.32 (d, J = 6.6 Hz, 3 H), 1.04 (dd, J = 6.4, 5.2 Hz, 4 H), 0.94 (d, J = 6.8 Hz, 3 H). $^{19}$F NMR (376 MHz, DMSO-d$_6$) δ ppm −132.10 (br s, 1 F). |
| 71-1-2 | 576.2 | $^1$H NMR (400 MHz, DMSO-d$_6$) δ ppm 8.32 (br t, J = 9.0 Hz, 1 H), 7.48 (d, J = 8.9 Hz, 1 H), 7.19-7.30 (m, 2 H), 7.12 (dd, J = 6.8, 1.7 Hz, 1 H), 6.75-6.95 (m, 1 H), 6.52 (d, J = 8.9 Hz, 1 H), 6.31 (s, 2 H), 6.20 (br d, J = 16.0 Hz, 1 H), 5.70-5.81 (m, 1 H), 4.89 (br d, J = 2.9 Hz, 1 H), 3.95-4.49 (m, 3 H), 3.41-3.74 (m, 2 H), 3.04-3.27 (m, 1 H), 1.86 (s, 3 H), 1.30 (br d, J = 6.4 Hz, 3 H), 1.04 (dd, J = 6.4, 3.9 Hz, 4 H), 0.94 (d, J = 6.8 Hz, 3 H) $^{19}$F NMR (376 MHz, DMSO-d$_6$) δ ppm −132.10 (br s, 1 F). |
| 71-2 | 592.3 | $^1$H NMR (400 MHz, DMSO-d$_6$) δ ppm 8.44 (br d, J = 10.2 Hz, 1 H), 7.54 (br d, J = 8.5 Hz, 1 H), 7.40 (br t, J = 7.5 Hz, 1 H), 7.27-7.34 (m, 1 H), 7.24 (br t, J = 7.4 Hz, 1 H), 6.94-7.20 (m, 4 H), 6.80-6.94 (m, 1 H), 6.68 (s, 1 H), 6.22 (br d, J = 16.4 Hz, 1 H), 6.00 (br s, 2 H), 5.72-5.82 (m, 1 H), 4.83-5.04 (m, 1 H), 4.01-4.51 (m, 3 H), 3.56-3.88 (m, 2 H), 3.01-3.19 (m, 1 H), 2.55-2.65 (m, 1 H), 1.30-1.41 (m, 3 H), 1.06 (br d, J = 6.6 Hz, 3 H), 0.90 (br d, J = 5.2 Hz, 3 H) $^{19}$F NMR (376 MHz, DMSO-d$_6$) δ ppm −131.07 (br s, 1 F). |
| 71-2-1 | 592.3 | $^1$H NMR (400 MHz, DMSO-d$_6$) δ ppm 8.38 (br t, J = 8.9 Hz, 1 H), 7.55 (d, J = 8.3 Hz, 1 H), 7.37-7.44 (m, 1 H), 7.33 (d, J = 8.5 Hz, 1 H), 7.14-7.21 (m, 2 H), 7.05-7.11 (m, 1 H), 6.91-6.99 (m, 1 H), 6.82-6.91 (m, 1 H), 6.72 (s, 1 H), 6.21 (br d, J = 16.0 Hz, 1 H), 6.04 (s, 2 H), 5.70-5.83 (m, 1 H), 4.87-5.02 (m, 1 H), 3.99-4.49 (m, 3 H), 3.40-3.85 (m, 2 H), 3.01-3.22 (m, 1 H), 2.56-2.64 (m, 1 H), 1.91 (s, 3 H), 1.33 (br d, J = 6.6 Hz, 3 H), 1.04 (dd, J = 6.2, 5.4 Hz, 3 H), 0.92 (d, J = 6.8 Hz, 3 H). $^{19}$F NMR (376 MHz, DMSO-d$_6$) δ ppm −131.07 (br s, 1 F). |
| 71-2-2 | 592.3 | $^1$H NMR (400 MHz, DMSO-d$_6$) δ ppm 8.36 (br t, J = 9.5 Hz, 1 H), 7.56 (d, J = 8.5 Hz, 1 H), 7.37-7.45 (m, 1 H), 7.34 (d, J = 8.5 Hz, 1 H), 7.14-7.21 (m, 2 H), 7.07-7.11 (m, 1 H), 6.92-7.01 (m, 1 H), 6.81-6.91 (m, 1 H), 6.73 (s, 1 H), 6.22 (br d, J = 16.0 Hz, 1 H), 6.05 (s, 2 H), 5.73-5.82 (m, 1 H), 4.90 (br s, 1 H), 3.96-4.51 (m, 3 H), 3.45-3.78 (m, 2 H), 3.12-3.25 (m, 1 H), 2.57-2.63 (m, 1 H), 1.90 (s, 3 H), 1.36 (d, J = 6.6 Hz, 3 H), 1.06 (d, J = 6.8 Hz, 3 H), 0.93 (d, J = 6.8 Hz, 3 H) $^{19}$F NMR (376 MHz, DMSO-d$_6$) δ ppm −131.09 (br s, 1 F). |
| 72-1 | 561.0 | $^1$H NMR (400 MHz, DMSO-d$_6$) δ ppm 0.96 (d, J = 6.8 Hz, 3 H), 1.08 (d, J = 6.8 Hz, 3 H), 1.33 (d, J = 6.8 Hz, 3 H), 1.94 |

TABLE 88-continued

Analytical Data

| Ex. # | LRMS: m/z (ESI, +ve ion): (M + H)+ | NMR |
|---|---|---|
| | | (s, 3 H), 2.68-2.78 (m, 1 H), 3.04-3.20 (m, 0.5 H), 3.22-3.29 (m, 0.5 H), 3.44-3.56 (m, 0.5 H), 3.60-3.80 (m, 1.5 H), 3.97-4.09 (m, 0.5 H), 4.11-4.19 (m, 0.5 H), 4.29 (br d, J = 13.5 Hz, 1.5 H), 4.40 (br d, J = 12.7 Hz, 0.5 H), 4.91 (br s, 1 H), 5.71-5.81 (m, 1 H), 6.21 (br d, J = 16.4 Hz, 1 H), 6.80-6.94 (m, 2 H), 7.09 (dd, J = 9.4, 3.2 Hz, 1 H), 7.18 (td, J = 8.5, 3.1 Hz, 1 H), 7.26 (d, J = 5.0 Hz, 1 H), 8.26-8.38 (m, 1 H), 8.48 (d, J = 5.0 Hz, 1 H), 10.35 (s, 1 H). $^{19}$F NMR (376 MHz, DMSO-$d_6$) δ ppm −126.02 (s, 1 F), −125.16 (s, 1 F). |
| 72-2 | 578.9 | $^1$H NMR (400 MHz, DMSO-$d_6$) δ ppm 0.96 (d, J = 6.6 Hz, 3 H), 1.08 (d, J = 6.6 Hz, 3 H), 1.33 (d, J = 6.6 Hz, 3 H), 1.94 (s, 3 H), 2.72 (dt, J = 13.1, 6.6 Hz, 1 H), 3.06-3.19 (m, 0.5 H), 3.44-3.56 (m, 0.5 H), 3.60-3.79 (m, 1.5 H), 4.10-4.20 (m, 0.5 H), 4.28 (br d, J = 13.9 Hz, 1.5 H), 4.40 (br d, J = 13.5 Hz, 0.5 H), 4.91 (br s, 1 H), 5.73-5.80 (m, 1 H), 6.14-6.28 (m, 1 H), 6.79-6.99 (m, 2 H), 7.26 (d, J = 5.0 Hz, 1 H), 7.34 (dd, J = 11.5, 9.2 Hz, 1 H), 8.26-8.39 (m, 1 H), 8.48 (d, J = 4.8 Hz, 1 H), 10.90 (br s, 1 H). $^{19}$F NMR (376 MHz, DMSO-$d_6$) δ ppm −132.0 (d, J = 22.6 Hz, 1F), −149.69 (d, J = 22.6 Hz, 1F), −126.32 (s, 1 F). |
| 72-3 | 561.0 | $^1$H NMR (400 MHz, DMSO-$d_6$) δ ppm 0.96 (d, J = 6.6 Hz, 3 H), 1.08 (d, J = 6.6 Hz, 3 H), 1.34 (d, J = 6.6 Hz, 3 H), 1.95 (s, 3 H), 2.73 (sept, J = 6.6 Hz, 1 H), 3.07-3.20 (m, 0.5 H), 3.44-3.55 (m, 0.5 H), 3.61-3.79 (m, 1.5 H), 4.15 (br d, J = 12.9 Hz, 0.5 H), 4.30 (br d, J = 13.7 Hz, 1.5 H), 4.40 (br d, J = 13.3 Hz, 0.5 H), 4.92 (br s, 1 H), 5.67-5.84 (m, 1 H), 6.21 (br d, J = 16.4 Hz, 1 H), 6.77-6.96 (m, 2 H), 7.17-7.36 (m, 3 H), 8.33 (br t, J = 11.0 Hz, 1 H), 8.48 (d, J = 5.0 Hz, 1 H), 10.7 (s, 1 H). $^{19}$F NMR (376 MHz, DMSO-$d_6$) δ ppm −134.98 (s, 1 F), −126.12 (s, 1 F). |
| 72-4 | 557.0 | $^1$H NMR (400 MHz, DMSO-$d_6$) δ ppm 1.07 (br d, J = 6.4 Hz, 3 H), 1.36 (d, J = 6.6 Hz, 3 H), 1.81 (br s, 3 H), 1.90 (br s, 3 H), 2.68-2.84 (m, 1 H), 3.10-3.27 (m, 1 H), 3.45-3.59 (m, 0.5 H), 3.61-3.76 (m, 1.5 H), 4.02 (br d, J = 13.5 Hz, 0.5 H), 4.08-4.21 (m, 0.5 H), 4.22-4.50 (m, 2 H), 4.88 (br s, 1 H), 5.72-5.82 (m, 1 H), 6.21 (br d, J = 16.4 Hz, 1 H), 6.65 (br d, J = 7.5 Hz, 1 H), 6.70 (d, J = 8.1 Hz, 1 H), 6.78-6.94 (m, 1 H), 7.09 (t, J = 7.9 Hz, 1 H), 7.18 (br s, 1 H), 8.13-8.31 (m, 1 H), 8.38 (d, J = 4.8 Hz, 1 H), 9.55 (br s, 1 H). $^{19}$F NMR (376 MHz, DMSO-$d_6$) δ ppm −128.74 (s, 1 F), −128.11 (s, 1 F). |
| 72-5 | 560.9 | $^1$H NMR (400 MHz, DMSO-$d_6$) δ ppm 0.95 (d, J = 6.6 Hz, 3 H), 1.07 (d, J = 6.6 Hz, 3 H), 1.33 (d, J = 6.8 Hz, 3 H), 1.93 (s, 3 H), 2.71 (sept, J = 6.6 Hz, 1 H), 3.12 (br t, J = 11.0 Hz, 0.5 H), 3.21-3.30 (m, 0.5 H), 3.42-3.54 (m, 0.5 H), 3.59-3.79 (m, 1.5 H), 3.95-4.07 (m, 0.5 H), 4.14 (br d, J = 12.7 Hz, 0.5 H), 4.31 (br d, J = 13.3 Hz, 1.5 H), 4.40 (br d, J = 12.9 Hz, 0.5 H), 4.92 (br s, 1 H), 5.70-5.82 (m, 1 H), 6.21 (br d, J = 16.6 Hz, 1 H), 6.55-6.65 (m, 1 H), 6.78-6.92 (m, |

TABLE 88-continued

Analytical Data

| Ex. # | LRMS: m/z (ESI, +ve ion): $(M + H)^+$ | NMR |
|---|---|---|
| | | 1 H), 6.98-7.11 (m, 2 H), 7.21 (d, J = 5.0 Hz, 1 H), 8.25-8.37 (m, 1 H), 8.43 (d, J = 5.0 Hz, 1 H), 10.16 (s, 1 H). $^{19}$F NMR (376 MHz, DMSO-$d_6$) δ ppm −137.72 (d, J = 30.1 Hz, 1 F), −129.00 (d, J = 30.1 Hz, 1 F). |
| 72-6 | 593.0 | $^1$H NMR (400 MHz, DMSO-$d_6$) δ ppm 0.97 (d, J = 6.63 Hz, 3 H) 1.09 (d, J = 6.84 Hz, 3 H) 1.33 (d, J = 6.63 Hz, 3 H) 1.94 (s, 3 H) 2.68-2.77 (m, 1 H) 3.05-3.17 (m, 1 H) 3.22-3.28 (m, 1 H) 3.41-3.54 (m, 1 H) 3.65 (s, 3 H) 3.68-3.77 (m, 1 H) 3.97-4.08 (m, 1H) 4.10-4.19 (m, 1 H) 4.22-4.34 (m, 1 H) 4.36-4.46 (m, 1 H) 4.93 (br d, J = 4.15 Hz, 1 H) 5.72-5.81 (m, 1 H) 6.14-6.28 (m, 1 H) 6.80-6.87 (m, 1 H) 6.90 (dd, J = 9.43, 6.53 Hz, 1 H) 7.24 (d, J = 4.98 Hz, 1 H) 7.42-7.52 (m, 1 H) 8.30-8.39 (m, 1 H) 8.45 (d, J = 4.77 Hz, 1 H). $^{19}$F NMR (376 MHz, DMSO-$d_6$) δ ppm −128.5 (d, 1 F, J = 41 Hz), −127.0 (s, 1 F), −118.7 (d, 1 F, J = 41 Hz). |
| 72-7 | 578.9 | $^1$H NMR (400 MHz, DMSO-$d_6$) δ ppm 0.95 (d, J = 6.84 Hz, 3 H) 1.08 (d, J = 6.84 Hz, 3 H) 1.33 (d, J = 6.63 Hz, 3 H) 1.93 (s, 3 H) 2.68-2.76 (m, 1 H) 3.05-3.18 (m, 1 H) 3.21-3.29 (m, 1 H) 3.43-3.54 (m, 1 H) 3.58-3.78 (m, 2 H) 3.96-4.06 (m, 1 H) 4.10-4.19 (m, 1 H) 4.24-4.34 (m, 1 H) 4.35-4.45 (m, 1 H) 4.90 (br s, 1 H) 5.72-5.81 (m, 1 H) 6.21 (br d, J = 17.00 Hz, 1 H) 6.79 (dd, J = 9.33, 7.05 Hz, 1 H) 6.83-6.93 (m, 1 H) 7.22 (d, J = 4.98 Hz, 1 H) 7.33 (t, J = 10.47 Hz, 1 H) 8.25-8.37 (m, 1 H) 8.44 (d, J = 4.98 Hz, 1 H) 9.87-10.51 (m, 1 H). $^{19}$F NMR (376 MHz, DMSO-$d_6$) δ ppm −129.2 (d, 1 F, J = 30 Hz), −128.05 (s, 1 F), −122.35 (br s, 1 F). |
| 72-8 | 578.9 | $^1$H NMR (400 MHz, DMSO-$d_6$) δ ppm 0.93 (d, J = 6.63 Hz, 3 H) 1.07 (d, J = 6.63 Hz, 3 H) 1.35 (d, J = 6.63 Hz, 3 H) 1.90 (s, 3 H) 2.65-2.78 (m, 1 H) 3.07-3.20 (m, 1 H) 3.25 (br s, 1 H) 3.44-3.57 (m, 1 H) 3.59-3.76 (m, 1 H) 4.02 (br d, J = 13.06 Hz, 1 H) 4.14 (br d, J = 12.02 Hz, 1 H) 4.20-4.35 (m, 1 H) 4.40 (br d, J = 12.44 Hz, 1 H) 4.90 (br s, 1 H) 5.71-5.84 (m, 1 H) 6.21 (br d, J = 16.59 Hz, 1 H) 6.62-6.74 (m, 1 H) 6.86 (dt, J = 16.17, 10.37 Hz, 1 H) 7.19 (d, J = 4.77 Hz, 1 H) 7.34 (q, J = 9.54 Hz, 1 H) 8.24-8.35 (m, 1 H) 8.40 (d, J = 4.98 Hz, 1 H) 10.21 (br s, 1 H). $^{19}$F NMR (376 MHz, DMSO-$d_6$) δ ppm −150.6 (d, 1 F, J = 26 Hz), −140.2 (d, 1 F, J = 26 Hz), −128.7 (s, 1F). |
| 72-9 | 578.9 | $^1$H NMR (400 MHz, DMSO-$d_6$) δ ppm 0.92 (d, J = 6.63 Hz, 3 H) 1.07 (d, J = 6.63 Hz, 3 H) 1.35 (d, J = 6.63 Hz, 3 H) 1.90 (s, 3 H) 2.68-2.77 (m, 1 H) 3.08-3.20 (m, 1 H) 3.21-3.29 (m, 1 H) 3.45-3.57 (m, 1 H) 3.59-3.77 (m, 2 H) 4.02 (br d, J = 13.48 Hz, 1 H) 4.14 (br d, J = 11.61 Hz, 1 H) 4.21-4.35 (m, 1 H) 4.40 (br d, J = 12.65 Hz, 1 H) 4.90 (br s, 1 H) 5.70-5.81 (m, 2 H) 6.20 (br d, J = 15.96 Hz, 1 H) 6.71 (br s, 1 H) 6.79-6.94 (m, 1 H) 7.18 (d, J = 4.98 Hz, 1 H) 7.23-7.38 (m, 1 H) 8.24-8.35 (m, 1 H) 8.39 (d, J = 4.77 Hz, 1 H) 10.46 (br s, 1 H). $^{19}$F NMR (376 MHz, DMSO-$d_6$) δ ppm −128.87 (s, 1 F) −120.19 (s, 1 F) −120.15 (s, 1 F). |

TABLE 88-continued

Analytical Data

| Ex. # | LRMS: m/z (ESI, +ve ion): (M + H)+ | NMR |
|---|---|---|
| 72-10 | 575.2 | ¹H NMR (500 MHz, DMSO-d₆) δ ppm 0.93 (d, J = 6.62 Hz, 3 H) 1.07 (d, J = 6.75 Hz, 3 H) 1.34 (d, J = 6.62 Hz, 3 H) 1.91 (s, 3 H) 2.11 (s, 3 H) 2.66-2.77 (m, 1 H) 3.17 (d, J = 4.41 Hz, 3 H) 3.27 (br dd, J = 12.65, 1.75 Hz, 1 H) 3.65 (br d, J = 14.14 Hz, 1 H) 3.68-3.76 (m, 1 H) 4.04 (br d, J = 13.75 Hz, 1 H) 4.08-4.20 (m, 1 H) 4.23-4.34 (m, 1 H) 4.41 (br d, J = 12.85 Hz, 1 H) 4.89 (br s, 1 H) 5.77 (br d, J = 10.64 Hz, 1 H) 6.21 (br dd, J = 16.28, 9.28 Hz, 1 H) 6.66 (t, J = 8.82 Hz, 1 H) 6.87 (td, J = 16.15, 10.38 Hz, 1 H) 7.14-7.23 (m, 2 H) 8.31 (br dd, J = 17.32, 9.15 Hz, 1 H) 8.39 (d, J = 4.80 Hz, 1 H) 9.12 (s, 1 H). ¹⁹F NMR (376 MHz, DMSO-d₆) δ ppm −118.32 (s, 1 F) −118.29 (s, 1 F). |
| 72-11 | 560.2 | ¹H NMR (400 MHz, DMSO-d₆) δ ppm 8.44 (d, J = 5.0 Hz, 1 H), 8.23-8.38 (m, 1 H), 7.22 (d, J = 5.0 Hz, 1 H), 7.04-7.15 (m, 1 H), 6.77-6.94 (m, 1 H), 6.48 (d, J = 8.3 Hz, 1 H), 6.37 (dd, J = 9.7, 8.7 Hz, 1 H), 6.21 (br d, J = 16.0 Hz, 1 H), 5.71-5.82 (m, 1 H), 5.35 (s, 2 H), 4.89 (br s, 1 H), 4.09-4.48 (m, 3 H), 3.40-3.79 (m, 2 H), 3.07-3.27 (m, 1 H), 2.68-2.85 (m, 1 H), 1.93 (s, 3 H), 1.34 (d, J = 6.8 Hz, 3 H), 1.07 (d, J = 6.6 Hz, 3 H), 0.94 (d, J = 6.6 Hz, 3 H). ¹⁹F NMR (376 MHz, DMSO-d₆) δ ppm −114.17 (br d, J = 30.3 Hz, 1 F), −127.18 (br d, J = 30.3 Hz, 1 F) |
| 72-12 | 499.1 | ¹H NMR (400 MHz, DMSO-d₆) δ ppm 8.44-8.57 (m, 2 H), 7.31 (d, J = 5.0 Hz, 1 H), 6.85 (dd, J = 16.6, 10.4 Hz, 1 H), 6.20 (dd, J = 16.7, 2.4 Hz, 1 H), 5.71-5.80 (m, 1 H), 4.35 (br s, 2 H), 4.03-4.14 (m, 1 H), 3.87 (br d, J = 12.4 Hz, 1 H), 3.62-3.79 (m, 2 H), 2.58-2.73 (m, 1 H), 1.95 (s, 3 H), 1.24 (d, J = 6.4 Hz, 6 H), 1.07 (d, J = 6.8 Hz, 3 H), 1.03 (d, J = 6.6 Hz, 3 H). ¹⁹F NMR (376 MHz, DMSO-d₆) δ ppm −127.43 (s, 1 F) |
| 72-13 | 574.2 | ¹H NMR (400 MHz, DMSO-d₆) δ ppm 8.44 (br d, J = 4.4 Hz, 1 H), 8.37 (br d, J = 9.3 Hz, 1 H), 7.18-7.28 (m, 1 H), 7.06-7.15 (m, 1 H), 6.86 (br dd, J = 16.5, 10.3 Hz, 1 H), 6.47 (br d, J = 8.5 Hz, 1 H), 6.36 (br t, J = 8.9 Hz, 1 H), 6.21 (br d, J = 16.6 Hz, 1 H), 5.77 (br d, J = 10.4 Hz, 1 H), 5.35 (br s, 2 H), 4.41 (br s, 2 H), 4.02-4.15 (m, 1 H), 3.83-3.95 (m, 1 H), 3.73 (br d, J = 10.2 Hz, 2 H), 2.64-2.74 (m, 1 H), 1.94 (s, 3 H), 1.29 (br d, J = 5.8 Hz, 6 H), 1.06 (br d, J = 6.2 Hz, 3 H), 0.95 (br d, J = 6.2 Hz, 3 H). ¹⁹F NMR (376 MHz, DMSO-d₆) δ ppm −114.63 (br d, J = 26.0 Hz, 1 F), −126.70 (br d, J = 26.9 Hz, 1 F) |
| 72-14 | 559.3 | ¹H NMR (400 MHz, DMSO-d₆) δ ppm 8.48 (d, J = 4.8 Hz, 1 H), 8.43 (d, J = 9.7 Hz, 1 H), 7.50-7.62 (m, 1 H), 7.23-7.41 (m, 4 H), 6.85 (dd, J = 16.6, 10.4 Hz, 1 H), 6.21 (dd, J = 16.6, 2.3 Hz, 1 H), 5.73-5.81 (m, 1 H), 4.45 (br d, J = 3.7 Hz, 2 H), 4.08 (br d, J = 11.0 Hz, 1 H), 3.82-3.93 (m, 1 H), 3.75 (br t, J = 12.4 Hz, 2 H), 2.74 (dt, J = 13.5, 6.5 Hz, 1 H), 1.97 (s, 3 H), 1.30 (d, J = 6.4 Hz, 6 H), 1.09 (d, J = 6.8 Hz, 3 H), 0.99 (d, J = 6.8 Hz, 3 H). ¹⁹F NMR (376 MHz, DMSO-d₆) δ ppm −113.94 (d, J = 31.2 Hz, 1 F), −128.28 (br d, J = 31.2 Hz, 1 F) |
| 73-1 | 576.2 | ¹H NMR (400 MHz, DMSO-d₆) δ ppm 8.33-8.47 (m, 2 H), 7.18 (d, J = 4.8 Hz, 1 |

TABLE 88-continued

Analytical Data

| Ex. # | LRMS: m/z (ESI, +ve ion): (M + H)+ | NMR |
|---|---|---|
| | | H), 7.05 (q, J = 7.9 Hz, 1 H), 6.78-6.99 (m, 1 H), 6.44 (d, J = 8.3 Hz, 1 H), 6.32 (t, J = 9.0 Hz, 1 H), 6.21 (br d, J = 17.4 Hz, 1 H), 5.69-5.84 (m, 1 H), 5.06-5.16 (m, 2 H), 4.91 (br d, J = 3.3 Hz, 1 H), 3.96-4.47 (m, 3 H), 3.40-3.86 (m, 2 H), 2.99-3.26 (m, 1 H), 2.60-2.90 (m, 1 H), 1.81-2.02 (m, 3 H), 1.35 (br d, J = 6.4 Hz, 3 H), 1.03-1.12 (m, 3 H), 0.88 (d, J = 6.6 Hz, 3 H). $^{19}$F NMR (376 MHz, DMSO-$d_6$) δ ppm −115.50 (br d, J = 11.3 Hz), −115.73 (br d, J = 12.1 Hz). |
| 73-2 | 579.2 | $^1$H NMR (400 MHz, DMSO-$d_6$) δ ppm 8.44-8.53 (m, 1 H), 8.40 (d, J = 5.0 Hz, 1 H), 7.39 (td, J = 6.4, 1.6 Hz, 2 H), 7.20 (d, J = 5.0 Hz, 1 H), 7.02-7.12 (m, 1 H), 6.79-6.93 (m, 1 H), 6.21 (br d, J = 16.6 Hz, 1 H), 5.73-5.80 (m, 1 H), 4.94 (br s, 1 H), 4.25-4.44 (m, 2 H), 3.99-4.22 (m, 1 H), 3.39-3.84 (m, 2 H), 3.05-3.24 (m, 1 H), 2.64-2.76 (m, 1 H), 1.94 (s, 3 H), 1.34 (d, J = 6.6 Hz, 3 H), 1.07 (d, J = 6.8 Hz, 3 H), 0.94 (d, J = 6.6 Hz, 3 H). $^{19}$F NMR (376 MHz, DMSO-$d_6$) δ ppm −118.15 (d, J = 18.2 Hz, 1 F), −119.63 (br d, J = 17.3 Hz, 1 F). |
| 73-3 | 575.2 | $^1$H NMR (400 MHz, DMSO-$d_6$) δ ppm 8.45 (br d, J = 4.6 Hz, 1 H), 8.40 (d, J = 4.8 Hz, 1 H), 7.26-7.36 (m, 1 H), 7.12-7.23 (m, 2 H), 6.98 (dd, J = 6.8, 1.7 Hz, 1 H), 6.74-6.93 (m, 1 H), 6.09-6.32 (m, 1 H), 5.70-5.85 (m, 1 H), 4.95 (br s, 1 H), 3.96-4.48 (m, 3 H), 3.39-3.90 (m, 2 H), 3.03-3.26 (m, 1 H), 2.62-2.78 (m, 1 H), 2.24 (s, 3 H), 1.94 (s, 3 H), 1.34 (d, J = 6.6 Hz, 3 H), 1.07 (d, J = 6.6 Hz, 3 H), 0.97 (d, J = 6.6 Hz, 3 H). $^{19}$F NMR (376 MHz, DMSO-$d_6$) δ ppm −119.16 (s, 1 F). |
| 73-4 | 595.1 | $^1$H NMR (400 MHz, DMSO-$d_6$) δ ppm 8.45-8.52 (m, 1 H), 8.41 (d, J = 5.0 Hz, 1 H), 7.59 (ddd, J = 8.9, 4.4, 2.7 Hz, 1 H), 7.39 (t, J = 9.2 Hz, 1 H), 7.28 (dd, J = 6.0, 2.7 Hz, 1 H), 7.20 (d, J = 5.0 Hz, 1 H), 6.79-6.94 (m, 1 H), 6.21 (br d, J = 16.6 Hz, 1 H), 5.72-5.82 (m, 1 H), 4.95 (br s, 1 H), 4.02-4.43 (m, 3 H), 3.47-3.85 (m, 2 H), 3.01-3.18 (m, 1 H), 2.64-2.77 (m, 1 H), 1.94 (s, 3 H), 1.34 (d, J = 6.8 Hz, 3 H), 1.06 (d, J = 6.8 Hz, 4 H), 0.96 (d, J = 6.8 Hz, 3 H). $^{19}$F NMR (376 MHz, DMSO-$d_6$) δ ppm −116.18 (1 F, br s). |
| 73-5 | 586.1 | $^1$H NMR (400 MHz, DMSO-$d_6$) δ ppm 8.51 (br d, J = 5.6 Hz, 1 H), 8.40 (d, J = 4.8 Hz, 1 H), 8.06 (ddd, J = 8.7, 4.8, 2.3 Hz, 1 H), 7.80 (dd, J = 6.4, 2.1 Hz, 1 H), 7.60 (t, J = 9.1 Hz, 1 H), 7.20 (d, J = 5.0 Hz, 1 H), 6.76-6.94 (m, 1 H), 6.11-6.30 (m, 1 H), 5.68-5.83 (m, 1 H), 4.94 (br s, 1 H), 4.01-4.43 (m, 3 H), 3.52-3.85 (m, 2 H), 3.05-3.19 (m, 1 H), 2.63-2.75 (m, 1 H), 1.95 (s, 3 H), 1.34 (d, J = 6.6 Hz, 3 H), 1.06 (d, J = 7.0 Hz, 3 H), 0.94 (d, J = 6.6 Hz, 3 H). $^{19}$F NMR (376 MHz, DMSO-$d_6$) δ ppm −104.97 (1 F, br s). |
| 73-6 | 591.2 | $^1$H NMR (400 MHz, DMSO-$d_6$) δ ppm 8.45 (br d, J = 5.2 Hz, 1 H), 8.41 (d, J = 4.8 Hz, 1 H), 7.15-7.27 (m, 2 H), 7.05 (dt, J = 9.0, 3.6 Hz, 1 H), 6.79-6.95 (m, 1 H), 6.68 (dd, J = 5.6, 3.3 Hz, 1 H), 6.21 (br d, J = 16.8 Hz, 1 H), 5.71-5.82 (m, 1 H), 4.95 (br s, 1 H), 4.00-4.47 (m, 3 H), 3.70-3.87 (m, 1 H), 3.67 (s, 3 H), 3.40- |

TABLE 88-continued

Analytical Data

| Ex. # | LRMS: m/z (ESI, +ve ion): $(M + H)^+$ | NMR |
|---|---|---|
| | | 3.65 (m, 1 H), 3.02-3.16 (m, 1 H), 2.65-2.73 (m, 1 H), 1.94 (s, 3 H), 1.34 (d, J = 6.8 Hz, 3 H), 1.07 (d, J = 6.6 Hz, 3 H), 0.96 (d, J = 6.6 Hz, 3 H). $^{19}$F NMR (376 MHz, DMSO-d$_6$) δ ppm −124.46 (br s, 1 F). |
| 73-7 | 645.2 | $^1$H NMR (400 MHz, DMSO-d$_6$) δ ppm 8.46-8.55 (m, 1 H), 8.41 (d, J = 5.0 Hz, 1 H), 7.54-7.62 (m, 1 H), 7.45-7.53 (m, 1 H), 7.21-7.28 (m, 1 H), 7.20 (d, J = 4.8 Hz, 1 H), 6.80-6.93 (m, 1 H), 6.22 (br d, J = 16.6 Hz, 1 H), 5.73-5.81 (m, 1 H), 4.89-5.05 (m, 1 H), 4.04-4.46 (m, 3 H), 3.49-3.88 (m, 2 H), 3.21-3.30 (m, 1 H), 2.66-2.77 (m, 1 H), 1.95 (s, 3 H), 1.35 (d, J = 6.8 Hz, 3 H), 1.07 (d, J = 7.0 Hz, 3 H), 0.95 (d, J = 6.6 Hz, 3 H). $^{19}$F NMR (376 MHz, DMSO-d$_6$) δ ppm −57.46 (3F, s), −114.63 (1 F, br s). |
| 73-8 | 629.0 | $^1$H NMR (400 MHz, DMSO-d$_6$) δ ppm 8.51 (br d, J = 4.6 Hz, 1 H), 8.40 (d, J = 4.8 Hz, 1 H), 7.90-7.99 (m, 1 H), 7.54-7.67 (m, 2 H), 7.19 (d, J = 5.0 Hz, 1 H), 6.78-6.94 (m, 1 H), 6.14-6.27 (m, 1 H), 5.72-5.83 (m, 1 H), 4.96 (br s, 1 H), 4.24-4.46 (m, 2 H), 3.99-4.22 (m, 1 H), 3.41-3.89 (m, 2 H), 3.03-3.25 (m, 1 H), 2.64-2.80 (m, 1 H), 1.94 (s, 3 H), 1.34 (d, J = 6.6 Hz, 3 H), 1.07 (d, J = 6.8 Hz, 3 H), 0.97 (d, J = 6.6 Hz, 3 H). $^{19}$F NMR (376 MHz, DMSO-d$_6$) δ ppm −60.76 (s, 3 F), −107.44 (s, 1 F) |
| 73-9 | 601.2 | $^1$H NMR (400 MHz, DMSO-d$_6$) δ ppm 8.35-8.48 (m, 2 H), 7.07-7.29 (m, 3 H), 6.75-6.93 (m, 2 H), 6.21 (br d, J = 16.6 Hz, 1 H), 5.70-5.83 (m, 1 H), 4.87-5.06 (m, 1 H), 4.11-4.47 (m, 3 H), 3.51-3.85 (m, 2 H), 3.01-3.13 (m, 1 H), 2.61-2.78 (m, 1 H), 1.94 (s, 3 H), 1.82-1.90 (m, 1 H), 1.33 (d, J = 6.6 Hz, 3 H), 1.05-1.10 (m, 3 H), 0.97 (d, J = 6.6 Hz, 3 H), 0.93 (dd, J = 8.5, 2.1 Hz, 2 H), 0.50 (tt, J = 4.8, 2.3 Hz, 2 H). $^{19}$F NMR (376 MHz, DMSO-d$_6$) δ ppm −118.31 (s, 1 F) |
| 73-10 | 644.2 | $^1$H NMR (400 MHz, DMSO-d$_6$) δ ppm 8.47 (br d, J = 3.9 Hz, 1 H), 8.38 (d, J = 4.8 Hz, 1 H), 7.94 (ddd, J = 8.6, 4.9, 2.3 Hz, 1 H), 7.71 (dd, J = 7.0, 2.1 Hz, 1 H), 7.27-7.43 (m, 2 H), 7.18 (d, J = 5.0 Hz, 1 H), 6.74-6.93 (m, 1 H), 6.21 (br d, J = 16.8 Hz, 1 H), 5.69-5.84 (m, 1 H), 4.95 (br s, 1 H), 4.00-4.46 (m, 3 H), 3.48-3.88 (m, 2 H), 3.01-3.21 (m, 1 H), 2.81 (td, J = 7.4, 3.7 Hz, 1 H), 2.63-2.74 (m, 1 H), 1.94 (s, 3 H), 1.34 (d, J = 6.8 Hz, 3 H), 1.06 (d, J = 7.0 Hz, 3 H), 0.97 (d, J = 6.6 Hz, 3 H), 0.63-0.73 (m, 2 H), 0.48-0.59 (m, 2 H). $^{19}$F NMR (376 MHz, DMSO-d$_6$) δ ppm −111.07 (s, 1 F) |
| 73-11 | 515.2 | $^1$H NMR (400 MHz, DMSO-d$_6$) δ ppm 8.46-8.57 (m, 1 H), 8.35 (s, 1 H), 7.32 (br s, 1 H), 6.89 (br dd, J = 16.5, 10.7 Hz, 1 H), 6.24 (br d, J = 16.8 Hz, 1 H), 5.79 (br d, J = 10.0 Hz, 1 H), 4.99 (br s, 1 H), 4.90 (br s, 1 H), 4.30 (br d, J = 12.9 Hz, 1 H), 4.05 (br d, J = 13.7 Hz, 1 H), 3.49-3.67 (m, 1 H), 3.16 (br t, J = 12.0 Hz, 1 H), 2.65 (br d, J = 8.9 Hz, 1 H), 1.97 (br s, 3 H), 1.21-1.51 (m, 6 H), 1.07 (br d, J = 6.4 Hz, 3 H), 1.02 (br d, J = 6.4 Hz, 3 H) |
| 73-12 | 590.2 | $^1$H NMR (400 MHz, DMSO-d$_6$) δ ppm 8.40 (d, J = 4.8 Hz, 1 H), 8.34 (s, 1 H), |

TABLE 88-continued

Analytical Data

| Ex. # | LRMS: m/z (ESI, +ve ion): (M + H)+ | NMR |
|---|---|---|
| | | 7.19 (d, J = 5.0 Hz, 1 H), 7.01-7.13 (m, 1 H), 6.91 (br dd, J = 16.6, 10.4 Hz, 1 H), 6.45 (br d, J = 8.3 Hz, 1 H), 6.33 (t, J = 8.9 Hz, 1 H), 6.26 (dd, J = 16.6, 2.3 Hz, 1 H), 5.78-5.84 (m, 1 H), 5.07-5.16 (m, 2 H), 4.88-5.07 (m, 2 H), 4.33 (br d, J = 12.4 Hz, 1 H), 4.00-4.15 (m, 1 H), 3.53-3.69 (m, 1 H), 3.12-3.25 (m, 1 H), 2.65-2.90 (m, 1 H), 1.80-2.06 (m, 3 H), 1.48 (br dd, J = 10.3, 7.2 Hz, 6 H), 1.04-1.13 (m, 3 H), 0.86-1.03 (m, 3 H). $^{19}$F NMR (376 MHz, DMSO-$d_6$) δ ppm −115.87−−115.33 (m, 1 F) |
| 73-13 | 591.2 | $^1$H NMR (400 MHz, DMSO-$d_6$) δ ppm 10.11 (br d, J = 1.2 Hz, 1 H), 8.39 (d, J = 4.8 Hz, 1 H), 8.34 (s, 1 H), 7.16-7.31 (m, 2 H), 6.89 (dd, J = 16.6, 10.4 Hz, 1 H), 6.62-6.75 (m, 2 H), 6.25 (dd, J = 16.7, 2.2 Hz, 1 H), 5.75-5.84 (m, 1 H), 4.93-5.12 (m, 2 H), 4.31 (br d, J = 12.6 Hz, 1 H), 4.01-4.13 (m, 1 H), 3.53-3.66 (m, 2 H), 2.64-2.81 (m, 1 H), 1.92 (br s, 3 H), 1.40-1.54 (m, 6 H), 1.08 (br d, J = 6.6 Hz, 3 H), 0.94 (br d, J = 6.4 Hz, 3 H). $^{19}$F NMR (376 MHz, DMSO-$d_6$) δ ppm −115.96 (br d, J = 261.8 Hz, 1 F) |
| 73-14 | 515.2 | $_1$H NMR (400 MHz, DMSO-$d_6$) δ ppm 8.58 (s, 1 H), 8.53 (d, J = 5.0 Hz, 1 H), 7.34 (br d, J = 4.4 Hz, 1 H), 6.84 (dd, J = 16.6, 10.4 Hz, 1 H), 6.20 (dd, J = 16.8, 2.3 Hz, 1 H), 5.72-5.80 (m, 1 H), 4.39 (br s, 2 H), 4.01-4.11 (m, 1 H), 3.80-3.90 (m, 1 H), 3.73 (br d, J = 13.9 Hz, 2 H), 2.62-2.75 (m, 1 H), 1.97 (s, 3 H), 1.26 (d, J = 6.4 Hz, 6 H), 1.06 (dd, J = 13.9, 6.6 Hz, 6 H) |
| 73-15 | 590.2 | $^1$H NMR (400 MHz, DMSO-$d_6$) δ ppm 8.40 (d, J = 4.8 Hz, 1 H), 8.34 (s, 1 H), 7.19 (d, J = 5.0 Hz, 1 H), 7.01-7.13 (m, 1 H), 6.91 (br dd, J = 16.6, 10.4 Hz, 1 H), 6.45 (br d, J = 8.3 Hz, 1 H), 6.33 (t, J = 8.9 Hz, 1 H), 6.26 (dd, J = 16.6, 2.3 Hz, 1 H), 5.78-5.84 (m, 1 H), 5.07-5.16 (m, 2 H), 4.88-5.07 (m, 2 H), 4.33 (br d, J = 12.4 Hz, 1 H), 4.00-4.15 (m, 1 H), 3.53-3.69 (m, 1 H), 3.12-3.25 (m, 1 H), 2.65-2.90 (m, 1 H), 1.80-2.06 (m, 3 H), 1.48 (br dd, J = 10.3, 7.2 Hz, 6 H), 1.04-1.13 (m, 3 H), 0.86-1.03 (m, 3 H). $^{19}$F NMR (376 MHz, DMSO-$d_6$) δ ppm −116.15−−115.77 (m, 1 F) |
| 73-16 | 591.2 | $^1$H NMR (400 MHz, DMSO-$d_6$) δ ppm 10.10 (br d, J = 7.0 Hz, 1 H), 8.50 (br s, 1 H), 8.39 (d, J = 4.8 Hz, 1 H), 7.15-7.31 (m, 2 H), 6.84 (br dd, J = 16.7, 10.5 Hz, 1 H), 6.62-6.76 (m, 2 H), 6.21 (dd, J = 16.7, 2.2 Hz, 1 H), 5.77 (dd, J = 10.5, 2.2 Hz, 1 H), 4.37-4.56 (m, 2 H), 4.01-4.14 (m, 1 H), 3.67-3.92 (m, 3 H), 2.63-2.74 (m, 1 H), 1.90 (br s, 3 H), 1.31 (br d, J = 4.4 Hz, 6 H), 1.06 (d, J = 6.6 Hz, 3 H), 0.94 (br d, J = 6.4 Hz, 3 H). $^{19}$F NMR (376 MHz, DMSO-$d_6$) δ ppm −115.96 (br d, J = 183.8 Hz, 1 F) |
| 73-17 | 515.2 | $^1$H NMR (400 MHz, DMSO-$d_6$) δ ppm 8.55 (s, 1 H), 8.51 (d, J = 5.0 Hz, 1 H), 7.31 (d, J = 4.8 Hz, 1 H), 6.82 (dd, J = 16.7, 10.5 Hz, 1 H), 6.20 (dd, J = 16.7, 2.4 Hz, 1 H), 5.72-5.79 (m, 1 H), 4.43 (br s, 2 H), 4.02 (q, J = 7.2 Hz, 2 H), 3.76-3.86 (m, 2 H), 2.58-2.73 (m, 1 H), 1.96 (s, 3 H), 1.28 (d, J = 6.4 Hz, 6 H), 1.04 (dd, J = 14.5, 6.6 Hz, 6 H) |

TABLE 88-continued

Analytical Data

| Ex. # | LRMS: m/z (ESI, +ve ion): (M + H)+ | NMR |
|---|---|---|
| 73-18 | 590.2 | $^1$H NMR (400 MHz, DMSO-d$_6$) δ ppm 8.53 (br s, 1 H), 8.40 (br s, 1 H), 7.21 (br s, 1 H), 7.05 (br d, J = 5.8 Hz, 1 H), 6.79-6.95 (m, 1 H), 6.44 (br s, 1 H), 6.31 (br s, 1 H), 6.21 (br d, J = 16.4 Hz, 1 H), 5.77 (br d, J = 9.3 Hz, 1 H), 5.15 (br d, J = 6.4 Hz, 2 H), 4.35 (br s, 2 H), 4.01-4.18 (m, 1 H), 3.90 (br d, J = 8.3 Hz, 1 H), 3.74 (br d, J = 3.3 Hz, 2 H), 2.62-2.84 (m, 1 H), 1.81-2.07 (m, 3 H), 1.26 (br d, J = 4.6 Hz, 6 H), 0.84-1.13 (m, 6 H). $^{19}$F NMR (376 MHz, DMSO-d$_6$) δ ppm −116.18−−115.91 (1 F, m) |
| 73-19 | 591.2 | $^1$H NMR (400 MHz, DMSO-d$_6$) δ ppm 10.11 (br s, 1 H), 8.52 (s, 1 H), 8.39 (d, J = 4.8 Hz, 1 H), 7.16-7.32 (m, 2 H), 6.85 (br dd, J = 16.5, 10.5 Hz, 1 H), 6.62-6.75 (m, 2 H), 6.21 (dd, J = 16.7, 1.8 Hz, 1 H), 5.70-5.81 (m, 1 H), 4.40 (br d, J = 1.5 Hz, 2 H), 4.07 (br d, J = 12.0 Hz, 1 H), 3.80-3.93 (m, 1 H), 3.76 (br dd, J = 12.2, 1.2 Hz, 2 H), 2.61-2.72 (m, 1 H), 1.93 (br s, 3 H), 1.28 (br d, J = 5.6 Hz, 6 H), 1.06 (br d, J = 6.6 Hz, 3 H), 0.93 (br d, J = 6.4 Hz, 3 H). $^{19}$F NMR (376 MHz, DMSO-d$_6$) δ ppm −115.97 (br d, J = 207.2 Hz, 1 F) |
| 74-1 | 526.0 | $^1$H NMR (400 MHz, DMSO-d$_6$) δ ppm 8.15 (s, 1 H), 7.42-7.49 (m, 1 H), 7.39 (dd, J = 7.5, 1.0 Hz, 1 H), 7.32 (dt, J = 7.3, 1.0 Hz, 1 H), 7.19-7.29 (m, 3 H), 7.15 (dt, J = 7.7, 1.4 Hz, 1 H), 7.08 (d, J = 7.7 Hz, 1 H), 6.77-6.97 (m, 1 H), 6.20 (dd, J = 17.0, 5.0 Hz, 1 H), 5.76 (dd, J = 10.2, 2.1 Hz, 1 H), 4.81 (br s, 1 H), 4.10-4.55 (m, 3 H), 3.45-3.81 (m, 2 H), 2.52-2.56 (m, 1 H), 1.35 (d, J = 6.6 Hz, 3 H), 1.21-1.33 (m, 4 H), 1.06 (d, J = 6.8 Hz, 3 H), 0.94-0.98 (m, 3 H). |
| 74-1-1 | 526.0 | $^1$H NMR (400 MHz, DMSO-d$_6$) δ ppm 8.16 (br s, 1 H), 7.42-7.50 (m, 1 H), 7.40 (dd, J = 7.7, 0.8, Hz, 1 H), 7.19-7.35 (m, 4 H), 7.16 (dt, J = 7.5, 1.4 Hz, 1 H), 7.09 (d, J = 7.5 Hz, 1 H), 6.79-6.94 (m, 1 H), 6.21 (dd, J = 16.4, 5.2 Hz, 1 H), 5.76 (dd, J = 10.5, 2.2 Hz, 1 H), 4.82 (br s, 1 H), 3.91-4.53 (m, 3 H), 3.61 (br d, J = 12.6 Hz, 2 H), 3.07-3.24 (m, 1 H), 2.19 (s, 3 H), 1.36 (d, J = 6.6 Hz, 3 H), 1.07 (d, J = 6.8 Hz, 3 H), 0.96 (d, J = 6.8 Hz, 3 H). |
| 74-1-2 | 526.0 | $^1$H NMR (400 MHz, DMSO-d$_6$) δ ppm 8.20 (br s, 1 H), 7.37-7.56 (m, 2 H), 7.13-7.35 (m, 5 H), 7.09 (br d, J = 7.7 Hz, 1 H), 6.80-6.97 (m, 1 H), 6.21 (br d, J = 15.3 Hz, 1 H), 5.76 (br d, J = 10.4 Hz, 1 H), 4.97 (br s, 1 H), 3.85-4.56 (m, 4 H), 3.40-3.83 (m, 2 H), 2.98-3.10 (m, 1 H), 2.18 (br s, 3 H), 1.31 (br d, J = 5.8 Hz, 3 H), 1.07 (br d, J = 6.4 Hz, 3 H), 0.97 (br d, J = 6.4 Hz, 3 H). |
| 74-2 | 541.1 | $^1$H NMR (400 MHz, DMSO-d$_6$) δ 8.38 (d, J = 4.5 Hz, 1 H), 8.25 (br s, 1 H), 7.40-7.53 (m, 1 H), 7.22-7.32 (m, 2 H), 7.14-7.20 (m, 2 H), 6.75-6.99 (m, 1 H), 6.21 (dd, J = 16.2, 5.0 Hz, 1 H), 5.77 (dd, J = 9.9, 2.7 Hz, 1 H), 4.94 (br s, 1 H), 3.94-4.59 (m, 3 H), 3.58-3.82 (m, 2 H), 3.02-3.18 (m, 1 H), 2.59-2.79 (m, 1 H), 2.21 (s, 3 H), 1.92 (s, 3 H), 1.34 (d, J = 6.0 Hz, 3 H), 1.07 (d, J = 6.6 Hz, 3 H), 0.93 (dd, J = 6.6, 2.3 Hz, 3 H) |
| 74-2-1 | 541.1 | $^1$H NMR (400 MHz, DMSO-d$_6$) δ 8.38 (d, J = 5.0 Hz, 1 H), 8.25 (br s, 1 H), 7.41-7.55 (m, 1 H), 7.22-7.32 (m, 2 H), 7.14- |

TABLE 88-continued

Analytical Data

| Ex. # | LRMS: m/z (ESI, +ve ion): (M + H)+ | NMR |
|---|---|---|
| | | 7.20 (m, 2 H), 6.81-6.94 (m, 1 H), 6.21 (dd, J = 15.6, 6.4 Hz, 1 H), 5.77 (dd, J = 10.4, 2.5 Hz, 1 H), 4.94 (br d, J = 4.2 Hz, 1 H), 3.94-4.56 (m, 3 H), 3.42-3.80 (m, 2 H), 3.06-3.28 (m, 1 H), 2.68 (quin, J = 6.5 Hz, 1 H), 2.21 (s, 3 H), 1.92 (s, 3 H), 1.35 (d, J = 6.6 Hz, 3 H), 1.07 (d, J = 6.84 Hz, 3 H), 0.94 (d, J = 6.63 Hz, 3 H) |
| 74-2-2 | 541.1 | $^1$H NMR (400 MHz, DMSO-d$_6$) δ 8.38 (br d, J = 4.8 Hz, 1 H), 8.25 (br s, 1 H), 7.41-7.55 (m, 1 H), 7.22-7.35 (m, 2 H), 7.10-7.22 (m, 2 H), 6.88 (q, J = 13.5 Hz, 1 H), 6.01-6.40 (m, 1 H), 5.77 (br d, J = 11.0 Hz, 1 H), 4.94 (br d, J = 1.04 Hz, 1 H), 3.94-4.52 (m, 3 H), 3.61-3.80 (m, 2 H), 3.18-3.28 (m, 1 H), 2.60-2.73 (m, 1 H), 2.21 (s, 3 H), 1.92 (s, 3 H), 1.34 (br d, J = 6.4 Hz, 3 H), 1.07 (br d, J = 6.6 Hz, 3 H), 0.93 (br d, J = 6.4 Hz, 3 H) |
| 74-3 | 557.2 | $^1$H NMR (400 MHz, DMSO-d$_6$) δ 9.99 (s, 1 H), 8.41 (br d, J = 5.0 Hz, 1 H), 8.21 (t, J = 4.2 Hz, 1 H), 7.16-7.32 (m, 2 H), 6.80-6.94 (m, 1 H), 6.72 (d, J = 8.3 Hz, 1 H), 6.65 (t, J = 8.8 Hz, 1 H), 6.21 (br dd, J = 16.4, 5.6 Hz, 1 H), 5.77 (dd, J = 10.4, 2.3 Hz, 1 H), 4.87-5.01 (m, 1 H), 4.11-4.61 (m, 3 H), 3.17-3.83 (m, 3 H), 2.69-2.78 (m, 1 H), 2.14 (s, 3 H), 1.92 (s, 3 H), 1.34 (dd, J = 8.8, 6.7 Hz, 3 H), 1.10 (d, J = 6.6 Hz, 3 H), 0.95 (br d, J = 6.6 Hz, 3 H) |
| 74-3-1 | 557.0 | $^1$H NMR (400 MHz, DMSO-d$_6$) δ 9.98 (br s, 1 H), 8.36 (d, J = 4.5 Hz, 1 H), 8.20 (br s, 1 H), 7.14-7.25 (m, 2 H), 6.77-6.98 (m, 1 H), 6.71 (d, J = 8.3 Hz, 1 H), 6.65 (t, J = 8.8 Hz, 1 H), 6.21 (br dd, J = 16.6, 6.0 Hz, 1 H), 5.77 (dd, J = 10.2, 2.7 Hz, 1 H), 4.91 (br s, 1 H), 3.94-4.52 (m, 4 H), 3.60-3.79 (m, 2 H), 2.59-2.80 (m, 1 H), 2.14 (s, 3 H), 1.88 (s, 3 H), 1.35 (d, J = 6.63 Hz, 3 H), 1.07 (d, J = 6.6 Hz, 3 H), 0.92 (d, J = 6.6 Hz, 3 H) |
| 74-3-2 | 557.0 | $^1$H NMR (400 MHz, DMSO-d$_6$) δ 9.99 (br s, 1 H), 8.36 (d, J = 5.0 Hz, 1 H), 8.21 (br s, 1 H), 7.12-7.26 (m, 2 H), 6.79-6.96 (m, 1 H), 6.71 (d, J = 8.3 Hz, 1 H), 6.65 (t, J = 8.7 Hz, 1 H), 6.16-6.25 (m, 1 H), 4.88-5.04 (m, 1 H), 3.93-4.51 (m, 4 H), 3.59-3.79 (m, 3 H), 2.56-2.75 (m, 1 H), 2.14 (s, 3 H), 1.89 (s, 3 H), 1.33 (d, J = 6.6 Hz, 3H), 1.07 (d, J = 6.6 Hz, 3 H), 0.92 (d, J = 6.6 Hz, 3 H) |
| 75-1 | 575.0 | $^1$H NMR (400 MHz, DMSO-d$_6$) δ ppm 10.20 (br s, 1H), 8.38 (d, J = 5.0 Hz, 1H), 8.15 (d, J = 9.5 Hz, 1H), 7.22-7.30 (m, 1H), 7.18 (d, J = 4.8 Hz, 1H), 6.89 (dd, J = 16.7, 10.5 Hz, 1H), 6.73 (d, J = 7.8 Hz, 1H), 6.68 (m, 1H), 6.25 (dd, J = 16.7, 2.4 Hz, 1H), 5.75-5.83 (m, 1H), 5.00 (br s, 2H), 4.30 (m, 1H), 4.03 (m, 1H), 3.60 (m, 1H), 3.21 (br s, 1H), 2.68-2.76 (m, 1H), 1.90 (br s, 3H), 1.47 (m, 3H), 1.45 (m, 3H), 1.07 (d, J = 6.6 Hz, 3H), 0.93 ppm (d, J = 6.6 Hz, 3H). $^{19}$F NMR (376 MHz, DMSO-d$_6$) δ ppm −115.68 (br s, 1F), −128.58 (br s, 1F) |
| 75-2 | 561.2 | $^1$H NMR (400 MHz, DMSO-d$_6$) δ ppm 10.18 (d, J = 1.45 Hz, 1H), 8.33-8.48 (m, 2H), 7.23-7.33 (m, 1H), 7.18 (d, J = 4.98 Hz, 1H), 6.63-6.88 (m, 3H), 6.18 (br d, J = 16.38 Hz, 1H), 5.73(m, 1H), 3.58-4.72 (m, 7H), 2.57-2.70 (m, 1H), 1.93 (s, 3H), 1.29 (m, 3H), 1.06 (d, J = 6.63 Hz, 3H), |

TABLE 88-continued

Analytical Data

| Ex. # | LRMS: m/z (ESI, +ve ion): (M + H)+ | NMR |
|---|---|---|
| | | 0.91 (d, J = 6.63 Hz, 3H). $^{19}$F NMR (376 MHz, DMSO-d$_6$) δ ppm −115.58 (d, J = 5.20 Hz, 1F), −128.63 (br d, J = 5.20 Hz, 1F). |
| 75-3 | 575.3 | $^1$H NMR (400 MHz, DMSO-d$_6$) δ ppm 10.19 (s, 1H), 8.33-8.42 (m, 2H), 7.16-7.33 (m, 2H), 6.85 (dd, J = 10.37, 16.59 Hz, 1H), 6.64-6.75 (m, 2H), 6.21 (dd, J = 2.28, 16.79 Hz, 1H), 5.76 (dd, J = 2.28, 10.37 Hz, 1H), 4.42 (br d, J = 3.73 Hz, 2H), 3.98-4.14 m, 1H), 3.66-3.93 (m, 3H), 2.63-2.72 (m, 1H), 1.91 (s, 3H), 1.29 (d, J = 6.22 Hz, 6H), 1.06 (d, J = 6.84 Hz, 3H), 0.94 (d, J = 6.63 Hz, 3H). $^{19}$F NMR (376 MHz, DMSO-d$_6$) δ ppm −115.51 (d, J = 5.20 Hz, 1F), −128.17 (d, J = 5.20 Hz, 1F). |
| 75-4 | 547.3 | $^1$H NMR (400 MHz, DMSO-d$_6$) δ ppm 10.20 (d, J = 1.24 Hz, 1H), 8.37-8.43 (m, 2H), 7.24-7.33 (m, 1H), 7.19 (d, J = 4.98 Hz, 1H), 6.84 (dd, J = 10.37, 16.79 Hz, 1H), 6.65-6.75 (m, 2H), 6.19 (dd, J = 2.38, 16.69 Hz, 1H), 5.72-5.81 (m, 1H), 4.01 (br d, J = 4.98 Hz, 4H), 3.74-3.93 (m, 4H), 2.68-2.76 (m, 1H), 1.90 (s, 3H), 1.07 (d, J = 6.63 Hz, 3H), 0.93 (d, J = 6.63 Hz, 3H). $^{19}$F NMR (376 MHz, DMSO-d$_6$) δ ppm −115.67 (d, J = 5.20 Hz, 1F), −128.65 (d, J = 5.20 Hz, 1F). |
| 75-5 | 561.2 | $^1$H NMR (400 MHz, DMSO-d$_6$) δ ppm 10.20 (br s, 1H), 8.24-8.46 (m, 2H), 7.13-7.34 (m, 2H), 6.78-6.97 (m, 1H), 6.60-6.77 (m, 2H), 6.11-6.28 (m, 1H), 5.76 (br d, J = 10.37 Hz, 1H), 4.95 (br s, 1H), 3.96-4.49 (m, 3H), 3.59-3.82 (m, 2H), 3.15 (m, 1H), 2.70 (br d, J = 13.89 Hz, 1H), 1.91 (br s, 3H), 1.32 (br d, J = 5.80 Hz, 3H), 1.07 (br d, J = 5.80 Hz, 3H), 0.93 (br d, J = 6.01 Hz, 3H). $^{19}$F NMR (377 MHz, DMSO-d$_6$) δ ppm −115.65 (br s, 1F), −128.62 (br s, 1F). |
| 75-6 | 533.2 | $^1$H NMR (DMSO-d$_6$) δ: 10.13-10.30 (m, 1H), 8.93 (br d, J = 6.4 Hz, 1H), 8.38 (d, J = 4.8 Hz, 1H), 8.19 (d, J = 9.1 Hz, 1H), 7.11-7.35 (m, 2H), 6.62-6.78 (m, 2H), 6.11-6.36 (m, 2H), 5.70 (dd, J = 9.7, 2.3 Hz, 1H), 5.05-5.34 (m, 1H), 4.52-4.86 (m, 3H), 4.08-4.39 (m, 1H), 1.90 (s, 3H), 1.07 (d, J = 6.6 Hz, 3H), 0.92 (d, J = 6.6 Hz, 3H). $^{19}$F NMR (376 MHz, DMSO-d$_6$) δ −115.88 (br s, 1F), −128.49--128.00 (m, 1F). |
| 75-7 | 559.2 | $^1$H NMR (DMSO-d$_6$) δ: 10.18 (br s, 1H), 8.38 (d, J = 5 0 Hz, 1H), 8.06-8.30 (m, 3H), 7.11-7.33 (m, 2H), 6.62-6.83 (m, 3H), 6.11-6.25 (m, 1H), 5.64-5.79 (m, 1H), 5.17-5.38 (m, 1H), 4.84-5.11 (m, 1H), 4.50-4.75 (m, 1H), 4.24-4.46 (m, 1H), 4.10-4.22 (m, 1H), 1.90 (s, 3H), 1.23 (s, 1H), 1.05-1.12 (m, 1H), 1.07 (br d, J = 6.6 Hz, 3H), 0.92 (d, J = 6.8 Hz, 3H). $^{19}$F NMR (376 MHz, DMSO-d$_6$) δ −115.93 (br s, 1F), −128.62--128.26 (m, 1F). |
| 75-8 | 574.1 | $^1$H NMR (400 MHz, CHLOROFORM-d) δ = 8.55 (d, J = 5.0 Hz, 1H), 7.95 (d, J = 9.7 Hz, 1H), 7.17-7.09 (m, 2H), 6.70-6.62 (m, 1H), 6.51-6.43 (m, 2H), 6.38 (d, J = 8.1 Hz, 1H), 5.84 (dd, J = 1.9, 10.4 Hz, 1H), 5.51-5.19 (m, 1H), 5.05-4.77 (m, 1H), 4.58 (m, 1H), 4.43 (br s, 2H), 3.91 (m, 1H), 3.67 (m, 1H), 3.20 (m, 1H), 2.93-2.69 (m, 1H), 2.06 (m, 3H), 1.77-1.59 (m, 6H), 1.33-1.26 (m, 3H), |

TABLE 88-continued

Analytical Data

| Ex. # | LRMS: m/z (ESI, +ve ion): (M + H)⁺ | NMR |
|---|---|---|
| | | 1.12-1.02 (m, 3H); ¹⁹F NMR (376 MHz, CHLOROFORM-d) δ = −111.06 (br d, J = 55.5 Hz, 1F), −121.33-−124.45 (m, 1F) |
| 75-9-1 | 597.0 | ¹H NMR (400 MHz, DMSO-d₆) δ = 10.22 (br s, 1H), 8.45-8.38 (m, 2H), 7.31-7.18 (m, 2H), 6.83 (br dd, J = 10.7, 16.7 Hz, 1H), 6.75-6.54 (m, 2H), 6.19 (dd, J = 2.2, 16.7 Hz, 1H), 5.80-5.74 (m, 1H), 5.20 (m, 1H), 4.77-4.11 (m, 3H), 3.89 (br t, J = 11.1 Hz, 1H), 3.31 (s, 2H), 2.63-2.53 (m, 1H), 1.95 (s, 3H), 1.06 (d, J = 6.6 Hz, 3H), 0.91 (d, J = 6.6 Hz, 3H); ¹⁹F NMR (376 MHz, DMSO-d₆) δ = −115.58 (br s, 1F), −124.14 (br s, 2F), −128.19 (br s, 1F) |
| 75-9-2 | 597.0 | ¹H NMR (400 MHz, DMSO-d₆) δ = 10.22 (s, 1H), 8.49-8.35 (m, 2H), 7.32-7.22 (m, 1H), 7.19 (d, J = 4.8 Hz, 1H), 6.84 (br dd, J = 10.8, 15.8 Hz, 1H), 6.76-6.32 (m, 2H), 6.19 (dd, J = 2.2. 16.7 Hz, 1H), 5.82-5.71 (m, 1H), 5.22 (m, 1H), 4.85-4.09 (m, 3H), 4.01-3.66 (m, 1H), 3.51-3.37 (m, 1H), 3.31 (s, 2H), 2.81 (m, 1H), 2.60-2.52 (m, 1H), 1.86 (s, 3H), 1.08 (d, J = 6.6 Hz, 3H), 0.95 (d, J = 6.8 Hz, 3H); ¹⁹F NMR (376 MHz, DMSO-d₆) δ = −115.79 (br d, J = 5.2 Hz, 1F), −123.57-−124.92 (m, 2F), −128.02 (br d, J = 5.2 Hz, 1F) |
| 76-1 | 532.8 | 1H NMR (400 MHz, DMSO-d6) δ ppm 0.88-0.97 (m, 3 H) 1.02-1.10 (m, 3 H) 1.88-1.96 (m, 3 H) 2.65-2.76 (m, 1 H) 4.05-4.19 (m, 1 H) 4.23-4.41 (m, 2 H) 4.61-4.74 (m, 1 H) 4.94-5.08 (m, 1 H) 5.67-5.77 (m, 1 H) 6.10-6.22 (m, 1 H) 6.33-6.49 (m, 1 H) 7.15-7.35 (m, 4 H) 7.45-7.56 (m, 1 H) 8.34-8.43 (m, 1 H) 8.96-9.05 (m, 1 H) 9.24-9.36 (m, 1 H) 19F NMR (376 MHz, DMSO-d6) δ ppm −117.37-−110.35 (m, 1 F) |
| 76-2 | 546.8 | 1H NMR (400 MHz, DMSO-d6) δ ppm 0.89-0.99 (m, 3 H) 1.03-1.13 (m, 3 H) 1.95-2.11 (m, 3 H) 2.80-2.94 (m, 1 H) 2.95-3.11 (m, 3 H) 3.66-3.89 (m, 3 H) 3.95-4.16 (m, 1 H) 4.34-4.93 (m, 1 H) 5.65-5.80 (m, 1 H) 6.10-6.26 (m, 1 H) 6.68-6.93 (m, 1 H) 7.15-7.35 (m, 4 H) 7.40-7.55 (m, 1 H) 8.34-8.46 (m, 1 H) 8.50-8.65 (m, 1 H) 19F NMR (376 MHz, DMSO-d6) δ ppm −114.67 (br d, J = 17.34 Hz, 1 F) |
| 77-1 | 484.3 | ¹H NMR (400 MHz, CHLOROFORM-d) δ 7.38-7.49 (m, 1H), 7.27 (br s, 2H), 7.10-7.25 (m, 5H), 6.88 (s, 1H), 6.63 (dd, J = 10.57, 16.79 Hz, 1H), 6.36 (dd, J = 1.66, 16.79 Hz, 1H), 5.73-5.82 (m, 1H), 3.72-3.98 (m, 8H), 2.26 (s, 3H), 2.21 (s, 3H). ¹⁹F NMR (376 MHz, CHLOROFORM-d) δ −112.90 (s, 1F). |
| 77-2 | 498.2 | ¹H NMR (400 MHz, CHLOROFORM-d) δ 7.36-7.50 (m, 1H), 7.08-7.24 (m, 7H), 6.83-6.90 (m, 1H), 6.48-6.74 (m, 1H), 6.37 (d, J = 16.79 Hz, 1H), 5.76 (br d, J = 9.74 Hz, 1H), 4.67 (br dd, J = 2.18, 10.47 Hz, 1H), 4.34-4.56 (m, 1H), 3.89-4.29 (m, 1H), 3.60-3.86 (m, 2H), 3.43-3.58 (m, 1H), 3.06-3.35 (m, 1H), 2.18-2.28 (m, 6H), 1.37-1.45 (m, 3H). ¹⁹F NMR (376 MHz, CHLOROFORM-d) −112.95 (br s, 1F). |
| 78-1 | 561.2 | ¹H NMR (400 MHz, DMSO-d₆) δ ppm 8.60 (s, 1 H), 8.39 (d, J = 4.8 Hz, 1 H), 7.46-7.55 (m, 1 H), 7.14-7.34 (m, 4 |

TABLE 88-continued

Analytical Data

| Ex. # | LRMS: m/z (ESI, +ve ion): (M + H)+ | NMR |
|---|---|---|
| | | H), 6.81 (dd, J = 16.6, 10.4 Hz, 1 H), 6.19 (br d, J = 16.6 Hz, 1 H), 5.69-5.79 (m, 1 H), 4.48-4.79 (m, 1 H), 4.41 (br dd, J = 8.6, 5.1 Hz, 1 H), 4.22 (br dd, J = 13.6, 2.6 Hz, 1 H), 3.94-4.13 (m, 1 H), 3.50-3.93 (m, 3 H), 2.64 (spt, J = 6.7 Hz, 1 H), 1.96 (s, 3 H), 1.29 (br s, 3 H), 1.06 (d, J = 6.6 Hz, 3 H), 0.95 (d, J = 6.6 Hz, 3 H) $^{19}$F NMR (376 MHz, DMSO-d$_6$) δ ppm −113.98 (s, 1 F). |
| 78-2 | 587.0 | $^1$H NMR (400 MHz, CHLOROFORM-d) δ 8.50 (d, J = 4.98 Hz, 1H), 8.17 (s, 1H), 7.37-7.46 (m, 1H), 7.07-7.21 (m, 4H), 6.63 (dd, J = 10.57, 16.79 Hz, 1H), 6.42 (dd, J = 1.87, 16.79 Hz, 1H), 5.79-5.87 (m, 1H), 5.02 (br s, 1H), 4.81-4.94 (m, 1H), 4.60 (br t, J = 14.72 Hz, 1H), 4.36 (br s, 1H), 3.72-3.82 (m, 1H), 3.55-3.66 (m, 1H), 2.64-2.81 (m, 1H), 1.92-2.31 (m, 8H), 1.66-1.86 (m, 1H), 1.23 (d, J = 6.84 Hz, 3H), 1.07 (d, J = 6.84 Hz, 3H). $^{19}$F NMR (377 MHz, CHLOROFORM-d) δ −112.55 (d, J = 3.47 Hz, 1F). |
| 78-3 | 596.8 | $^1$H NMR (400 MHz, CDCl$_3$) δ 8.42-8.50 (m, 1 H) 8.20 (s, 1 H) 7.39 (br d, J = 6.6 Hz, 1 H) 7.13 (br d, J = 4.6 Hz, 2 H) 7.02-7.11 (m, 2 H) 6.52-6.67 (m, 1 H) 6.38 (br d, J = 16.8 Hz, 1 H) 5.97-6.33 (m, 1 H) 5.81 (br d, J = 10.4 Hz, 1 H) 4.17-5.45 (m, 4 H) 3.97 (br d, J = 0.8 Hz, 1 H) 2.93-3.58 (m, 1 H) 2.53-2.83 (m, 1 H) 1.95-2.06 (m, 3 H) 1.17-1.21 (m, 3 H) 1.04 (br t, J = 6.7 Hz, 3 H). $^{19}$F NMR (377 MHz, CDCl$_3$) δ −112.42 (br s, 1 F) −112.65 (s, 1 F) −124.87-−122.20 (m, 1 F) −126.67-−125.16 (m, 1 F). |
| 78-3-1 | 596.8 | $^1$H NMR (400 MHz, CDCl$_3$) δ 8.59 (d, J = 4.8 Hz, 1 H) 8.28 (s, 1 H) 7.48-7.56 (m, 1 H) 7.16-7.28 (m, 4 H) 6.67-6.78 (m, 1 H) 6.51 (dd, J = 16.7, 1.8 Hz, 1 H) 6.10-6.43 (m, 1 H) 5.94 (dd, J = 10.6, 1.7 Hz, 1 H) 4.45-5.58 (m, 2 H) 3.75-4.45 (m, 3 H) 3.10-3.56 (m, 1 H) 2.88 (sept, J = 7.1 Hz, 1 H) 2.09 (s, 3 H) 1.32 (d, J = 6.8 Hz, 3 H) 1.15 (d, J = 6.6 Hz, 3 H). $^{19}$F NMR (376 MHz, CDCl$_3$) δ −112.56 (s, 1 F) −126.92-−122.32 (m, 1 F). |
| 78-3-2 | 596.8 | $^1$H NMR (400 MHz, CDCl$_3$) δ 8.50 (d, J = 5.0 Hz, 1 H) 8.19 (s, 1 H) 7.37-7.46 (m, 1 H) 7.05-7.21 (m, 4 H) 6.58-6.69 (m, 1 H) 6.42 (dd, J = 16.8, 1.7 Hz, 1 H) 6.00-6.35 (m, 1 H) 5.84 (dd, J = 10.5, 1.8 Hz, 1 H) 3.65-5.47 (m, 6 H) 2.93-3.65 (m, 1 H) 2.62 (quin, J = 6.7 Hz, 1 H) 2.07 (s, 3 H) 1.22 (d, J = 6.6 Hz, 3 H) 1.07 (d, J = 6.8 Hz, 3 H). $^{19}$F NMR (376 MHz, CDCl$_3$) δ −112.34 (br s, 1 F) −126.82-−121.91 (m, 1 F). |
| 78-4 | 572.8 | $^1$H NMR (400 MHz, CDCl$_3$) δ 8.45-8.51 (m, 1 H) 8.11-8.41 (m, 1 H) 7.41 (br d, J = 6.4 Hz, 1 H) 7.15 (br d, J = 5.2 Hz, 2 H) 7.05-7.13 (m, 2 H) 6.45-6.76 (m, 1 H) 6.34-6.43 (m, 1 H) 5.80 (br s, 1 H) 3.79-4.30 (m, 6 H) 2.64-2.76 (m, 1 H) 2.02 (s, 3 H) 1.45 (br s, 2 H) 1.20-1.24 (m, 3 H) 1.10 (br s, 2 H) 1.06 (br d, J = 6.6 Hz, 3 H). $^{19}$F NMR (377 MHz, CDCl$_3$) δ −112.59 (br s, 1 F). |
| 78-5 | 578.9 | $^1$H NMR (400 MHz, CDCl$_3$) δ 8.50 (br d, J = 4.4 Hz, 1 H) 8.08-8.39 (m, 1 H) 7.42 (br d, J = 6.4 Hz, 1 H) 7.17 (br s, 2 H) 7.04-7.14 (m, 2 H) 6.62 (br dd, J = 16.7, 10.3 Hz, 1 H) 6.35-6.46 (m, 1 H) 5.84 (br d, J = 10.6 Hz, 1 H) 5.02-5.42 |

TABLE 88-continued

| | Analytical Data | |
|---|---|---|
| Ex. # | LRMS: m/z (ESI, +ve ion): (M + H)+ | NMR |
| | | (m, 1 H) 4.61-4.94 (m, 2 H) 4.17-4.61 (m, 2 H) 3.55-3.93 (m, 2 H) 3.01-3.39 (m, 1 H) 2.61-2.85 (m, 1 H) 2.04 (br d, J = 4.4 Hz, 3 H) 1.19-1.25 (m, 3 H), 1.01-1.10 (m, 3 H). $^{19}$F NMR (377 MHz, CDCl$_3$) δ -112.58 (br s, 1 F) -224.51--223.92 (m, 1 F) -226.83--226.19 (m, 1 F). |
| 78-6 | 576.8 | $^1$H NMR (400 MHz, CDCl$_3$) δ 8.60 (s, 1 H), 8.51 (br s, 1 H), 7.40 (br s, 1 H), 7.03-7.18 (m, 4 H) 6.46-6.61 (m, 1 H) 6.26 (br d, J = 16.6 Hz, 1 H) 5.68 (br d, J = 10.6 Hz, 1 H) 4.38-4.57 (m, 1 H) 4.22 (br s, 2 H) 3.75-4.01 (m, 1 H) 2.93-3.26 (m, 3 H) 2.65-2.88 (m, 3 H), 2.08 (s, 3 H) 1.20 (br d, J = 6.2 Hz, 3 H) 1.05-1.12 (m, 3 H). $^{19}$F NMR (377 MHz, CDCl$_3$) δ -112.95 (br s, 1 F). |
| 78-7 | 574.8 | $^1$H NMR (400 MHz, CDCl$_3$) δ 8.48 (d, J = 5.0 Hz, 1 H) 8.22 (s, 1 H), 7.37-7.45 (m, 1 H) 7.04-7.19 (m, 4 H) 6.61-6.71 (m, 1 H) 6.46 (dd, J = 16.6, 1.9 Hz, 1 H) 5.84 (dd, J = 10.5, 1.8 Hz, 1 H), 5.30-5.45 (m, 1 H) 4.88 (br s, 1 H) 4.52-5.63 (m, 1 H) 3.91 (br d, J = 12.9 Hz, 1 H) 3.56-3.80 (m, 1 H) 3.20 (br d, J = 11.4 Hz, 1 H) 2.57-2.83 (m, 1 H), 1.98-2.08 (m, 3 H) 1.54-1.72 (m, 6 H) 1.23 (d, J = 6.8 Hz, 3 H) 1.06 (d, J = 6.6 Hz, 3 H), $^{19}$F NMR (376 MHz, CDCl$_3$) δ -112.57 (br d, J = 52.9 Hz, 1 F). |
| 78-8 | 574.8 | $^1$H NMR (400 MHz, CDCl$_3$) δ 8.49 (d, J = 4.8 Hz, 1 H) 8.23 (s, 1 H), 7.37-7.45 (m, 1 H) 7.05-7.20 (m, 4 H) 6.63 (dd, J = 16.7, 10.5 Hz, 1 H) 6.41 (dd, J = 16.8, 1.7 Hz, 1 H) 5.77-5.84 (m, 1 H) 4.30-4.40 (m, 2 H), 3.79-4.08 (m, 3 H) 3.62-3.79 (m, 1 H) 2.69 (spt, J = 6.8 Hz, 1 H) 2.02 (s, 3 H) 1.41 (br s, 6 H) 1.22 (d, J = 6.6 Hz, 3 H) 1.09 (d, J = 6.6 Hz, 3 H). $^{19}$F NMR (376 MHz, CDCl$_3$) δ -112.63 (s, 1 F). |
| 78-9 | 614.8 | $^1$H NMR (400 MHz, CDCl$_3$) δ 8.51 (br d, J = 1.9 Hz, 1 H) 8.19 (s, 1 H) 7.43 (br d, J = 4.1 Hz, 1 H) 7.06-7.23 (m, 4 H) 6.54-6.68 (m, 1 H) 6.35-6.46 (m, 1 H) 5.94 (br s, 1 H) 5.85 (br d, J = 10.6 Hz, 1 H) 4.36-5.23 (m, 2 H) 3.76-3.92 (m, 1 H) 3.41 (br d, J = 6.4 Hz, 1 H) 2.88-3.04 (m, 1 H) 2.49-2.88 (m, 1 H) 1.95-2.13 (m, 3 H) 1.18-1.27 (m, 3 H) 1.08 (br t, J = 7.6 Hz, 3 H). $^{19}$F NMR (377 MHz, CDCl$_3$-d) δ -69.92 (br d, J = 49.4 Hz, 1 F) -70.55--70.06 (m, 1 F) -112.28 (br s, 1 F) -112.61 (s, 1 F). |
| 78-9-1 | 614.9 | $^1$H NMR (400 MHz, CDCl$_3$) δ 8.51 (br d, J = 4.1 Hz, 1 H) 8.18 (s, 1 H) 7.43 (br d, J = 6.6 Hz, 1 H) 7.06-7.20 (m, 4 H) 6.55-6.67 (m, 1 H) 6.34-6.46 (m, 1 H) 5.88-6.09 (m, 1 H) 5.85 (br d, J = 10.2 Hz, 1 H) 4.37-5.23 (m, 2 H) 4.07-4.25 (m, 2 H) 2.90-3.93 (m, 2 H) 2.76-2.90 (m, 1 H) 1.98 (s, 3 H) 1.24 (br d, J = 6.6 Hz, 3 H) 1.07 (br d, J = 6.4 Hz, 3 H). $^{19}$F NMR (377 MHz, CDCl$_3$) δ -70.58--69.70 (m, 1 F) -112.60 (s, 1 F). |
| 78-9-2 | 614.9 | $^1$H NMR (400 MHz, CDCl$_3$) δ 8.48-8.55 (m, 1 H) 8.18 (s, 1 H) 7.43 (br d, J = 5.8 Hz, 1 H) 7.06-7.21 (m, 4 H) 6.55-6.68 (m, 1 H) 6.36-6.47 (m, 1 H) 5.87-6.01 (m, 1 H) 5.84 (br d, J = 10.4 Hz, 1 H) 2.73-5.25 (m, 5 H) 2.49-2.62 (m, 1 H) 2.10 (s, 3 H) 1.22 (br d, J = 6.4 Hz, 3 H) 1.09 (br d, J = 6.4 Hz, 3 H). $^{19}$F NMR |

TABLE 88-continued

Analytical Data

| Ex. # | LRMS: m/z (ESI, +ve ion): (M + H)+ | NMR |
|---|---|---|
| | | (377 MHz, CDCl$_3$) δ −70.50–−69.70 (m, 1 F) −112.26 (br s, 1 F). |
| 78-10 | 558.8 | $^1$H NMR (400 MHz, CDCl$_3$) δ 8.43-8.53 (m, 1 H) 8.30 (s, 1 H) 7.40 (br d, J = 6.8 Hz, 1 H) 7.02-7.19 (m, 4 H) 6.39-6.49 (m, 1 H) 6.26-6.37 (m, 1 H) 5.77 (br d, J = 10.2 Hz, 1 H) 5.68 (br s, 1 H) 5.23 (br s, 1 H) 4.27 (br d, J = 8.9 Hz, 1 H) 4.14 (br d, J = 8.1 Hz, 1 H) 3.99 (br d, J = 9.5 Hz, 1 H) 3.77 (br d, J = 9.7 Hz, 1 H) 2.66 (quin, J = 6.4 Hz, 1 H) 2.03-2.22 (m, 2 H) 2.07 (s, 3 H) 1.22 (br d, J = 6.4 Hz, 3 H) 1.03 (br d, J = 6.2 Hz, 3 H). $^{19}$F NMR (377 MHz, CDCl$_3$) δ −112.56 (s, 1 F). |
| 78-11 | 558.8 | $^1$H NMR (400 MHz, CDCl$_3$) δ 8.45-8.53 (m, 1 H) 8.30 (s, 1 H) 7.40 (br d, J = 6.4 Hz, 1 H) 7.03-7.18 (m, 4 H) 6.42-6.50 (m, 1 H) 6.27-6.39 (m, 1 H) 5.79 (br d, J = 10.0 Hz, 1 H) 5.68 (br s, 1 H) 5.24 (br s, 1 H) 4.27 (br d, J = 8.9 Hz, 1 H) 4.15 (br d, J = 9.3 Hz, 1 H) 4.00 (br d, J = 9.5 Hz, 1 H) 3.78 (br d, J = 10.0 Hz, 1 H) 2.75-2.88 (m, 1 H) 2.03-2.23 (m, 2 H) 2.00 (s, 3 H) 1.23 (br d, J = 6.4 Hz, 3 H) 1.06 (br d, J = 6.6 Hz, 3 H). $^{19}$F NMR (377 MHz, CDCl$_3$) δ −112.77 (s, 1 F) −112.81 (s, 1 F). |
| 78-12 | 521.0 | $^1$H NMR (400 MHz, CDCl$_3$) δ 9.08 (br s, 1 H) 8.40 (s, 1 H) 8.38 (d, J = 5.0 Hz, 1 H) 7.80 (br t, J = 5.6 Hz, 1 H) 7.26-7.35 (m, 1 H) 6.93-7.08 (m, 4 H) 6.22-6.31 (m, 1 H) 6.06-6.15 (m, 1 H) 5.55-5.62 (m, 1 H) 3.78-3.84 (m, 2 H) 2.69 (spt, J = 6.7 Hz, 1 H) 1.95 (s, 3 H) 1.16 (t, J = 7.0 Hz, 2 H) 1.13 (d, J = 6.6 Hz, 3 H) 0.97 (d, J = 6.8 Hz, 3 H). $^{19}$F NMR (376 MHz, CDCl$_3$) δ −113.13 (s, 1 F). |
| 78-13 | 573.0 | $^1$H NMR (400 MHz, CDCl$_3$) δ 8.48-8.56 (m, 1 H) 8.18 (s, 1 H) 7.41 (br d, J = 6.8 Hz, 1 H) 7.05-7.22 (m, 4 H) 6.55-6.65 (m, 1 H) 6.35-6.45 (m, 1 H) 5.81 (br d, J = 10.4 Hz, 1 H) 5.22 (br s, 1 H) 5.03 (br s, 1 H) 4.71 (br d, J = 12.9 Hz, 1 H) 3.94 (br d, J = 11.6 Hz, 1 H) 3.74-3.82 (m, 1 H) 3.28 (br d, J = 13.1 Hz, 1 H) 2.73 (br d, J = 2.5 Hz, 1 H) 2.18 (br s, 2 H) 2.04 (br s, 3 H) 1.79-2.02 (m, 2 H) 1.23 (br d, J = 6.8 Hz, 3 H) 1.06 (br d, J = 6.4 Hz, 3 H). $^{19}$F NMR (377 MHz, CDCl$_3$) δ −112.65 (br d, J = 18.2 Hz, 1 F). |
| 78-14 | 576.8 | $^1$H NMR (400 MHz, CDCl$_3$) δ 8.44 (d, J = 5.0 Hz, 1 H) 8.03 (s, 1 H) 7.31-7.39 (m, 1 H) 7.00-7.12 (m, 4 H) 6.52-6.65 (m, 1 H) 6.44-6.52 (m, 1 H) 6.26-6.40 (m, 1 H) 5.79 (dd, J = 10.6, 1.7 Hz, 1 H) 3.98-5.14 (m, 4 H) 3.63-3.80 (m, 1 H) 3.14 (br s, 2 H) 2.93 (dquin, J = 13.5, 6.9, 6.9, 6.9, 6.9 Hz, 1 H) 2.81 (br d, J = 9.5 Hz, 1 H) 2.56-2.68 (m, 1 H) 2.04 (s, 3 H) 1.22 (d, J = 6.8 Hz, 3 H) 1.06 (d, J = 6.8 Hz, 3 H). $^{19}$F NMR (376 MHz, CDCl$_3$) δ −113.36–−113.68 (m, 1 F). |
| 78-15 | 546.8 | $^1$H NMR (400 MHz, CDCl$_3$) δ 8.45-8.55 (m, 1 H) 8.17 (s, 1 H) 7.42 (br d, J = 7.0 Hz, 1 H) 7.05-7.21 (m, 4 H) 6.63 (br dd, J = 16.8, 10.6 Hz, 1 H) 6.41 (br d, J = 16.8 Hz, 1 H) 5.82 (br d, J = 10.4 Hz, 1 H) 4.08 (br s, 4 H) 3.77-4.02 (m, 4 H) 2.65-2.80 (m, 1 H) 2.04 (s, 3 H) 1.23 |

TABLE 88-continued

Analytical Data

| Ex. # | LRMS: m/z (ESI, +ve ion): (M + H)+ | NMR |
|---|---|---|
| | | (br d, J = 6.6 Hz, 3 H) 1.07 (br d, J = 6.4 Hz, 3 H). $^{19}$F NMR (377 MHz, CDCl$_3$) δ −112.57 (s, 1 F). |
| 78-16 | 574.8 | $^1$H NMR (400 MHz, CDCl$_3$) δ 8.46-8.55 (m, 1 H) 8.24 (s, 1 H) 7.42 (br d, J = 7.0 Hz, 1 H) 7.06-7.23 (m, 4 H) 6.63 (br dd, J = 16.6, 10.6 Hz, 1 H) 6.41 (br d, J = 16.8 Hz, 1 H) 5.81 (br d, J = 10.4 Hz, 1 H) 4.35 (br s, 2 H) 3.96 (br s, 3 H) 3.69 (br s, 1 H) 2.68 (sept, 6.5 Hz, 1 H) 2.04 (s, 3 H) 1.41 (br s, 6 H) 1.22 (br d, J = 6.4 Hz, 3 H) 1.06 (br d, J = 6.4 Hz, 3 H). $^{19}$F NMR (377 MHz, CDCl$_3$) δ −112.70 (s, 1 F). |
| 78-17 | 559.1 | $^1$H NMR (400 MHz, CDCl$_3$) δ 8.46 (d, J = 4.1 Hz, 1 H) 8.02 (d, J = 1.5 Hz, 1 H) 7.36-7.44 (m, 1 H) 7.03-7.17 (m, 4 H) 6.55-6.64 (m, 1 H) 6.40-6.50 (m, 1 H) 5.80 (ddd, J = 10.2, 4.6, 2.1 Hz, 1 H) 5.17-5.26 (m, 1 H) 5.06-5.12 (m, 1 H) 4.64-4.77 (m, 1 H) 4.14-4.26 (m, 1 H) 4.00-4.08 (m, 1 H) 3.73-3.90 (m, 1 H), 3.06-3.15 (m, 1 H), 2.62-2.81 (m, 1 H) 2.02 (d, J = 14.3 Hz, 3 H) 1.87 (d, J = 9.3 Hz, 1 H) 1.20 (dd, J = 6.6, 3.1 Hz, 3 H) 1.05 (dd, J = 17.2, 6.6 Hz, 3 H). $^{19}$F NMR (376 MHz, CDCl$_3$) δ −112.54 (s, 1 F) −112.74 (s, 1 F). |
| 78-18 | 573.0 | $^1$H NMR (400 MHz, CDCl$_3$) δ 8.48 (d, J = 5.0 Hz, 1 H) 8.35 (s, 1 H) 7.37-7.45 (m, 1 H) 7.03-7.17 (m, 4 H) 6.39-6.61 (m, 2 H) 5.78-5.88 (m, 1 H) 5.49-5.53 (m, 1 H) 5.05-5.10 (m, 1 H) 4.34-4.42 (m, 1 H) 4.14-4.25 (m, 2 H) 3.73-3.80 (m, 1 H) 2.68-2.82 (m, 1 H) 2.26-2.46 (m, 1 H) 2.12-2.26 (m, 1 H), 2.03-2.10 (m, 2 H) 2.02 (s, 3 H) 1.22 (d, J = 6.6 Hz, 3 H) 1.05 (d, J = 6.8 Hz, 3 H). $^{19}$F NMR (376 MHz, CDCl$_3$) δ −112.65 (s, 1 F). |
| 79-1 | 534.1 | $^1$H NMR (400 MHz, DMSO-d$_6$) δ ppm 8.83 (s, 1 H), 8.43 (d, J = 4.8 Hz, 1 H), 7.47-7.64 (m, 1 H), 7.18-7.39 (m, 4 H), 6.32-6.51 (m, 1 H), 6.16 (dd, J = 17.0, 2.1 Hz, 1 H), 5.62-5.84 (m, 2 H), 4.70-4.85 (m, 1 H), 4.54 (td, J = 10.4, 3.2 Hz, 1 H), 4.44 (br dd, J = 11.2, 6.8 Hz, 1 H), 4.23-4.37 (m, 1 H), 2.76 (dt, J = 13.4, 6.8 Hz, 1 H), 1.96 (s, 3 H), 1.07 (d, J = 6.8 Hz, 3 H), 0.94 (d, J = 6.6 Hz, 3 H). $^{19}$F NMR (376 MHz, DMSO-d$_6$) δ ppm −114.69 (d, J = 4.3 Hz, 1 F) |
| 79-2 | 548.2 | $^1$H NMR (400 MHz, DMSO-d$_6$) δ ppm 8.70 (d, J = 6.8 Hz, 1 H), 8.42 (d, J = 4.8 Hz, 1 H), 7.45-7.60 (m, 1 H), 7.24-7.38 (m, 2 H), 7.16-7.24 (m, 2 H), 6.53-6.77 (m, 1 H), 6.12-6.26 (m, 1 H), 5.82-5.96 (m, 1 H), 5.65-5.76 (m, 1 H), 3.97-4.11 (m, 1 H), 3.65-3.95 (m, 3 H), 2.75 (dq, J = 13.2, 6.6 Hz, 1 H), 2.20-2.44 (m, 2 H), 1.96 (s, 3 H), 1.06 (d, J = 6.8 Hz, 3 H), 0.93 (d, J = 6.8 Hz, 3 H). $^{19}$F NMR (376 MHz, DMSO-d$_6$) δ ppm −114.73 (d, J = 10.4 Hz, 1 F) |
| 79-3 | 562.1 | $^1$H NMR (400 MHz, DMSO-d$_6$) δ ppm 8.24-8.49 (m, 2 H), 7.43-7.62 (m, 1 H), 7.13-7.38 (m, 4 H), 6.67-7.03 (m, 1 H), 6.12 (br d, J = 16.4 Hz, 1 H), 5.52-5.79 (m, 1 H), 5.44 (br s, 1 H), 4.14-4.32 (m, 1 H), 3.43-3.92 (m, 2 H), 3.06 (br t, J = 11.6 Hz, 1 H), 2.62-2.81 (m, 1 H), 1.99-2.23 (m, 2 H), 1.96 (s, 3 H), 1.79-1.91 (m, 1 H), 1.52-1.70 (m, 1 H), 1.07 (d, J = 6.8 Hz, 3 H), 0.94 (d, J = 6.6 |

TABLE 88-continued

Analytical Data

| Ex. # | LRMS: m/z (ESI, +ve ion): (M + H)+ | NMR |
|---|---|---|
| 79-4 | 562.1 | Hz, 3 H). $^{19}$F NMR (376 MHz, DMSO-d$_6$) δ ppm −114.73 (1 F, br d, J = 31.2 Hz) $^{1}$H NMR (400 MHz, DMSO-d$_6$) δ ppm 8.75 (s, 1 H), 8.42 (d, J = 5.0 Hz, 1 H), 7.46-7.57 (m, 1 H), 7.19-7.36 (m, 4 H), 6.89 (dd, J = 16.7, 10.5 Hz, 1 H), 6.14 (dd, J = 16.7, 2.4 Hz, 1 H), 5.71 (dd, J = 10.5, 2.4 Hz, 1 H), 5.66 (dt, J = 6.6, 3.2 Hz, 1 H), 3.81-4.00 (m, 2 H), 3.63-3.79 (m, 2 H), 2.75 (dt, J = 13.3, 6.7 Hz, 1 H), 2.04 (br d, J = 9.1 Hz, 2 H), 1.96 (s, 3 H), 1.84-1.94 (m, 2 H), 1.06 (d, J = 6.6 Hz, 3 H), 0.94 (d, J = 6.6 Hz, 3 H). $^{19}$F NMR (376 MHz, DMSO-d$_6$) δ ppm −114.69 (s, 1 F) |
| 79-5 | 562.1 | $^{1}$H NMR (400 MHz, DMSO-d$_6$) δ ppm 8.46 (br d, J = 4.6 Hz, 1 H), 8.28-8.43 (m, 1 H), 7.52 (br d, J = 5.6 Hz, 1 H), 7.22-7.37 (m, 3 H), 6.85-6.98 (m, 1 H), 6.72-6.85 (m, 1 H), 6.09 (br d, J = 16.8 Hz, 1 H), 5.53-5.74 (m, 1 H), 5.44 (br s, 1 H), 4.14-4.30 (m, 2 H), 3.43-3.59 (m, 1 H), 3.01-3.20 (m, 1 H), 2.74-2.90 (m, 1 H), 2.02-2.19 (m, 2 H), 1.98 (br d, J = 9.3 Hz, 3 H), 1.53-1.83 (m, 2 H), 1.08 (br d, J = 6.4 Hz, 3 H), 0.94 (br d, J = 6.4 Hz, 3 H). $^{19}$F NMR (376 MHz, DMSO-d$_6$) δ ppm −114.77 (d, J = 10.4 Hz, 1 F) |
| 80-1 | 617.2 | $^{1}$H NMR (400 MHz, DMSO-d$_6$) δ ppm 0.92 (dd, J = 6.84, 2.70 Hz, 3 H) 1.05 (d, J = 6.84 Hz, 3 H) 1.30-1.38 (m, 3 H) 1.75 (s, 2 H) 1.87 (s, 3 H) 2.14 (s, 6 H) 3.35 (s, 2 H) 3.64 (br d, J = 13.48 Hz, 1 H) 3.68-3.83 (m, 1 H) 3.95-4.07 (m, 1 H) 4.10-4.52 (m, 2 H) 4.93 (br s, 1 H) 5.72-5.81 (m, 1 H) 6.14-6.28 (m, 1 H) 6.54-6.72 (m, 1 H) 6.78-6.94 (m, 1 H) 7.02 (s, 1 H) 7.11 (s, 1 H) 7.15-7.35 (m, 4 H) 7.44-7.57 (m, 1 H) 8.43 (br s, 1 H). $^{19}$F NMR (376 MHz, DMSO-d$_6$) δ ppm −113.53 (s, 1 F) −113.51 (s, 1 F). |
| 80-1-1 | 617.2 | $^{1}$H NMR (400 MHz, DMSO-d$_6$) δ ppm 0.86 (t, J = 6.84 Hz, 3 H) 0.92 (d, J = 6.84 Hz, 3 H) 1.05 (d, J = 6.84 Hz, 3 H) 1.25 (br s, 4 H) 1.32 (d, J = 6.63 Hz, 3 H) 1.87 (s, 3 H) 2.14 (s, 6 H) 3.03-3.16 (m, 1 H) 3.35 (s, 2 H) 3.41-3.55 (m, 1 H) 3.57-3.67 (m, 1 H) 3.69-3.83 (m, 1 H) 4.03 (br d, J = 13.48 Hz, 1 H) 4.09-4.20 (m, 1 H) 4.27 (br d, J = 13.06 Hz, 1 H) 4.35-4.47 (m, 1 H) 4.93 (br s, 1 H) 5.75-5.80 (m, 1 H) 6.21 (br d, J = 16.79 Hz, 1 H) 6.77-6.95 (m, 1 H) 7.02 (s, 1 H) 7.11 (s, 1 H) 7.15-7.21 (m, 1 H) 7.21-7.26 (m, 1 H) 7.26-7.32 (m, 1 H) 7.45-7.57 (m, 1 H) 8.43 (br s, 1 H). $^{19}$F NMR (376 MHz, DMSO-d$_6$) δ ppm −113.51 (s, 1 F). |
| 80-1-2 | 617.2 | $^{1}$H NMR (400 MHz, DMSO-d$_6$) δ ppm 0.86 (br t, J = 6.74 Hz, 4 H) 0.92 (d, J = 6.84 Hz, 3 H) 1.05 (d, J = 6.63 Hz, 3 H) 1.22-1.28 (m, 5 H) 1.33 (br d, J = 6.63 Hz, 3 H) 1.77-1.93 (m, 3 H) 2.03-2.24 (m, 6 H) 3.01-3.16 (m, 1 H) 3.35 (s, 2 H) 3.42-3.54 (m, 1 H) 3.58-3.68 (m, 1 H) 3.68-3.83 (m, 1 H) 3.95-4.07 (m, 1 H) 4.10-4.20 (m, 1 H) 4.22-4.35 (m, 1 H) 4.35-4.50 (m, 1 H) 4.92 (br s, 1 H) 5.75-5.83 (m, 1 H) 6.11-6.26 (m, 1 H) 6.78-6.94 (m, 1 H) 7.03 (s, 1 H) 7.11 (s, 1 H) 7.14-7.21 (m, 1 H) 7.21 7.26 (m, 1 H) 7.26-7.33 (m, 1 H) 7.43-7.55 (m, 1 H) 8.42 (br d, J = 4.77 Hz, 1 H). $^{19}$F NMR (376 MHz, DMSO-d$_6$) δ ppm −113.53 (s, 1 F). |

TABLE 88-continued

Analytical Data

| Ex. # | LRMS: m/z (ESI, +ve ion): $(M + H)^+$ | NMR |
|---|---|---|
| 80-2 | 590.0 | $^1$H NMR (DMSO-$d_6$) δ: 8.43 (br d, J = 4.6 Hz, 1H), 7.47-7.55 (m, 1H), 7.24-7.34 (m, 2H), 7.18-7.23 (m, 1H), 7.16 (s, 1H), 7.05 (s, 1H), 6.80-6.93 (m, 1H), 6.20 (br dd, J = 16.6, 3.3 Hz, 1H), 5.71-5.79 (m, 1H), 5.14 (t, J = 15 8 Hz, 1H), 4.92 (br s, 1H), 4.46 (d, J = 5.8 Hz, 2H), 4.23-4.43 (m, 2H), 3.98-4.19 (m, 1H), 3.41-3.80 (m, 2H), 3.04-3.26 (m, 1H), 2.52-2.59 (m, 1H), 1.87 (s, 3H), 1.33 (d, J = 6.8 Hz, 3H), 1.05 (d, J = 6.8 Hz, 3H), 0.94 (dd, J = 6.8, 2.9 Hz, 3H) $^{19}$F NMR (DMSO-$d_6$) δ: −114.27 (d, J = 12.1 Hz, 1F) |
| 80-2-1 | 590.0 | $^1$H NMR (DMSO-$d_6$) δ: 8.42 (br d, J = 5.0 Hz, 1H), 7.45-7.54 (m, 1H), 7.24-7.33 (m, 2H), 7.17-7.23 (m, 1H), 7.15 (s, 1H), 7.05 (s, 1H), 6.79-6.93 (m, 1H), 6.20 (br d, J = 17.2 Hz, 1H), 5.70-5.78 (m, 1H), 5.14 (br s, 1H), 4.91 (br s, 1H), 4.46 (br d, J = 3.5 Hz, 2H), 4.23-4.44 (m, 2H), 4.05-4.19 (m, 1H), 3.68-3.80 (m, 1H), 3.42-3.67 (m, 1H), 3.05-3.25 (m, 1H), 2.52-2.58 (m, 1H), 1.87 (s, 3H), 1.32 (d, J = 6.6 Hz, 3H), 1.05 (d, J = 6.8 Hz, 3H), 0.93 (d, J = 6.8 Hz, 3H). $^{19}$F NMR (DMSO-$d_6$) δ: −114.29 (s, 1F) |
| 80-2-2 | 590.0 | $^1$H NMR (DMSO-$d_6$) δ: 8.44 (br s, 1H) 7.47-7.55 (m, 1H), 7.24-7.35 (m, 2H), 7.18-7.24 (m, 1H), 7.16 (s, 1H), 7.05 (s, 1H), 6.79-6.92 (m, 1H), 6.21 (br d, J = 16.6 Hz, 1H), 5.70-5.80 (m, 1H), 5.14 (t, J = 5.8 Hz, 1H), 4.92 (br s, 1H), 4.46 (d, J = 5.8 Hz, 2H), 4.23-4.43 (m, 2H), 3.99-4.19 (m, 1H), 3.41-3.81 (m, 2H), 3.05-3.26 (m, 1H), 2.56 (br s, 1H), 1.87 (s, 3H), 1.33 (d, J = 6.6 Hz, 3H), 1.05 (d, J = 6.8 Hz, 3H), 0.94 (d, J = 6.8 Hz, 3H) $^{19}$F NMR (DMSO-$d_6$) δ: −114.26 (s, 1F) |
| 81-1 | 544.1/546.1 | $^1$H NMR (400 MHz, METHANOL-$d_4$) δ ppm 7.74 (1 H, br d, J = 8.1 Hz), 7.45-7.52 (1 H, m), 7.39 (1 H, td, J = 7.8, 1.7 Hz), 7.30-7.36 (3 H, m), 7.23-7.30 (2 H, m), 7.16 (1 H, br dd, J = 8.2, 1.8 Hz), 6.80-6.90 (1 H, m), 6.25-6.32 (1 H, m), 5.79-5.85 (1 H, m), 3.87-3.96 (4 H, m), 3.79-3.87 (4 H, m), 2.25 (3 H, s), 2.19 (3 H, br s). |
| 81-2 | 512.2 | $^1$H NMR (400 MHz, DMSO-$d_6$) δ ppm 7.50-7.58 (1 H, m), 7.42-7.46 (1 H, m), 7.36-7.41 (2 H, m), 7.29-7.36 (2 H, m), 7.24 (1 H, t, J = 7.5 Hz), 7.06 (1 H, d, J = 7.7 Hz), 6.83-6.92 (2 H, m), 6.19 (1 H, dd, J = 16.7, 2.4 Hz), 5.75 (1 H, dd, J = 10.4, 2.3 Hz), 3.82-3.89 (8 H, m), 2.71-2.80 (1 H, m), 2.27 (3 H, s), 1.15 (3 H, d, J = 6.8 Hz), 1.03 (3 H, d, J = 6.8 Hz). $^{19}$F NMR (376 MHz, DMSO-$d_6$) δ ppm −74.46 (1 F, s), −114.61 (1 F, s) as mono-TFA salt. |
| 81-3 | 526.1 | $^1$H NMR (400 MHz, DMSO-$d_6$) δ ppm 7.50-7.59 (1 H, m), 7.40-7.46 (1 H, m), 7.29-7.40 (4 H, m), 7.24 (1 H, t, J = 7.3 Hz), 7.06 (1 H, d, J = 7.5 Hz), 6.82-6.93 (2 H, m), 6.15-6.26 (1 H, m), 5.76 (1 H, dd, J = 10.4, 2.3 Hz), 4.39-4.67 (2 H, m), 4.23-4.38 (1 H, m), 3.99-4.22 (2 H, m), 3.14-3.28 (1 H, m), 3.01-3.13 (1 H, m), 2.76 (1 H, br dd, J = 14.6, 6.9 Hz), 2.28 (3 H, d, J = 3.3 Hz), 1.30-1.40 (3 H, m), 1.12-1.19 (3 H, m), 1.03 (3 H, d, J = 6.8 Hz). $^{19}$F NMR (376 MHz, DMSO-$d_6$) δ ppm −74.47 (1 F, s), −114.57 (1 F, s), −114.65 (1 F, s) as mono-TFA salt. |

TABLE 88-continued

Analytical Data

| Ex. # | LRMS: m/z (ESI, +ve ion): $(M + H)^+$ | NMR |
|---|---|---|
| 82-1 | 597.2 | $^1$H NMR (DMSO-$d_6$) δ: 12.95-13.29 (m, 1H), 8.48 (br d, J = 6.0 Hz, 1H), 8.30 (dd, J = 11.2, 5.0 Hz, 1H), 7.40-7.52 (m, 2H), 7.23 (dd, J = 8.6, 2.2 Hz, 1H), 7.08-7.18 (m, 1H), 6.81-6.95 (m, 1H), 6.22 (br d, J = 16.0 Hz, 1H), 5.74-5.81 (m, 1H), 4.88-5.03 (m, 1H), 4.05-4.47 (m, 3H), 3.50-3.86 (m, 2H), 3.10-3.24 (m, 1H), 2.71-2.86 (m, 1H), 1.86-2.09 (m, 6H), 1.38 (dd, J = 6.6, 2.1 Hz, 3H), 1.06 (dd, J = 6.6, 3.5 Hz, 3H), 0.76-0.94 (m, 3H) |
| 82-2 | 601.0 | $^1$H NMR (DMSO-$d_6$) δ: 13.37 (s, 1H), 8.49 (br d, J = 6.2 Hz, 1H), 8.31 (d, J = 4.8 Hz, 1H), 7.66 (dd, J = 8.9, 3.7 Hz, 1H), 7.49 (s, 1H), 7.32 (t, J = 9.5 Hz, 1H), 7.17 (d, J = 5.0 Hz, 1H), 6.76-6.93 (m, 1H), 6.20 (br dd, J = 16.6, 5.4 Hz, 1H), 5.74-5.81 (m, 1H), 4.94 (br s, 1H), 3.89-4.44 (m, 5H), 3.11-3.39 (m, 1H), 2.66-2.82 (m, 1H), 1.96 (br s, 3H), 1.37 (d, J = 6.6 Hz, 3H), 1.04 (d, J = 6.6 Hz, 3H), 0.83-0.87 (m, 3H) |
| 83-1 | 577.2 | $^1$H NMR (400 MHz, DMSO-$d_6$) δ ppm 9.70 (s, 1 H), 8.40-8.48 (m, 1 H), 8.08 (s, 1 H), 7.48-7.56 (m, 1 H), 7.25-7.36 (m, 2 H), 7.17-7.24 (m, 1 H), 6.78-6.93 (m, 1 H), 6.15-6.28 (m, 1 H), 5.74-5.78 (m, 1 H), 4.93 (br s, 1 H), 4.23-4.45 (m, 2 H), 3.98-4.20 (m, 1 H), 3.42-3.83 (m, 2 H), 3.04-3.28 (m, 1 H), 2.54-2.60 (m, 1 H), 1.75 (s, 3 H), 1.34 (d, J = 6.6 Hz, 3 H), 1.01 (d, J = 6.8 Hz, 3 H), 0.90 (d, J = 6.8 Hz, 3 H) $^{19}$F NMR (376 MHz, DMSO-$d_6$) δ ppm −114.11 (s, 1 F) |
| 83-2 | 577.2 | $^1$H NMR (400 MHz, DMSO-$d_6$) δ ppm 9.71 (s, 1 H), 8.45 (br s, 1 H), 8.08 (s, 1 H), 7.48-7.56 (m, 1 H), 7.26-7.34 (m, 2 H), 7.18-7.24 (m, 1 H), 6.79-6.93 (m, 1 H), 6.15-6.26 (m, 1 H), 5.74-5.78 (m, 1 H), 4.95 (br s, 1 H), 4.23-4.46 (m, 2 H), 4.09 (br dd, J = 43.8, 13.4 Hz, 1 H), 3.38-3.86 (m, 2 H), 3.03-3.27 (m, 1 H), 2.55 (br d, J = 6.6 Hz, 1 H), 1.75 (s, 3 H), 1.33 (d, J = 6.6 Hz, 3 H), 1.01 (d, J = 6.6 Hz, 3 H), 0.90 (d, J = 6.8 Hz, 3 H) $^{19}$F NMR (376 MHz, DMSO-$d_6$) δ ppm −114.08 (s, 1 F) |
| 84-1 | 577.2 | $^1$H NMR (400 MHz, DMSO-$d_6$) δ ppm 8.53 (d, J = 4.8 Hz, 1 H), 8.44 (br d, J = 5.8 Hz, 1 H), 7.47-7.55 (m, 1 H), 7.39 (d, J = 5.0 Hz, 1 H), 7.24-7.34 (m, 2 H), 7.17-7.23 (m, 1 H), 6.79-6.94 (m, 1 H), 6.21 (br d, J = 15.8 Hz, 1 H), 5.74-5.79 (m, 1 H), 5.32 (t, J = 5.6 Hz, 1 H), 4.92 (br s, 1 H), 4.34 (br d, J = 13.9 Hz, 2 H), 4.26 (br dd, J = 16.0, 5.4 Hz, 1 H), 4.05-4.20 (m, 2 H), 3.42-3.84 (m, 2 H), 3.06-3.28 (m, 1 H), 2.63-2.74 (m, 1 H), 1.35 (d, J = 6.6 Hz, 3 H), 1.07 (d, J = 6.8 Hz, 3 H), 0.95 (d, J = 6.8 Hz, 3 H) $^{19}$F NMR (376 MHz, DMSO-$d_6$) δ ppm −113.72 (s, 1 F) |
| 84-2 | 577.2 | $^1$H NMR (400 MHz, DMSO-$d_6$) δ ppm 8.53 (d, J = 4.8 Hz, 1 H), 8.46 (br s, 1 H), 7.47-7.55 (m, 1 H), 7.39 (d, J = 5.0 Hz, 1 H), 7.24-7.34 (m, 2 H), 7.17-7.23 (m, 1 H), 6.79-6.93 (m, 1 H), 6.21 (br d, J = 16.2 Hz, 1 H), 5.74-5.80 (m, 1 H), 5.32 (t, J = 5.8 Hz, 1 H), 4.97 (br s, 1 H), 4.21-4.45 (m, 3 H), 4.00-4.20 (m, 2 H), 3.40-3.87 (m, 2 H), 3.03-3.29 (m, |

TABLE 88-continued

Analytical Data

| Ex. # | LRMS: m/z (ESI, +ve ion): (M + H)+ | NMR |
|---|---|---|
| | | 1 H), 2.66 (dt, J = 12.6, 6.5 Hz, 1 H), 1.33 (d, J = 6.8 Hz, 3 H), 1.07 (d, J = 6.8 Hz, 3 H), 0.96 (d, J = 6.6 Hz, 3 H) $^{19}$F NMR (376 MHz, DMSO-d$_6$) δ ppm −113.72 (s, 1 F) |
| 85-1 | 545.2 | $^1$H NMR (CHLOROFORM-d) δ: 8.40-8.48 (m, 1H), 7.36-7.44 (m, 3H), 7.27-7.31 (m, 1H), 7.06-7.24 (m, 3H), 6.95-7.03 (m, 1H), 6.60-6.72 (m, 1H), 6.29-6.44 (m, 1H), 5.75-5.84 (m, 1H), 4.47-4.60 (m, 1H), 4.26-4.42 (m, 1H), 3.86-4.10 (m, 4H), 3.57-3.71 (m, 4H), 2.39-2.53 (m, 1H), 1.04-1.08 (m, 3H), 0.98-1.03 (m, 3H). |
| 85-2 | 559.2 | $^1$H NMR (CHLOROFORM-d) δ: 8.46-8.52 (m, 1H), 7.34-7.45 (m, 3H), 7.27-7.31 (m, 1H), 7.07-7.24 (m, 3H), 6.99-7.06 (m, 1H), 6.56-6.75 (m, 1H), 6.30-6.43 (m, 1H), 5.75-5.85 (m, 1H), 4.50-4.60 (m, 1H), 4.27-4.38 (m, 1H), 4.09-4.29 (m, 2H), 3.88-4.08 (m, 1H), 3.50-3.86 (m, 4H), 2.34-2.46 (m, 1H), 1.22-1.31 (m, 4H), 0.95-1.09 (m, 6H). |
| 85-3 | 527.2 | $^1$H NMR (DMSO-d$_6$) δ: 8.61-8.77 (m, 1H), 7.54-7.66 (m, 1H), 7.34-7.48 (m, 3H), 7.28-7.36 (m, 1H), 7.21-7.27 (m, 1H), 7.12-7.18 (m, 1H), 6.89-7.03 (m, 2H), 6.18-6.28 (m, 1H), 5.77-5.85 (m, 1H), 3.82-4.01 (m, 4H), 3.48-3.61 (m, 4H), 2.23-2.36 (m, 3H), 1.36-1.49 (m, 1H), 0.60-0.76 (m, 3H), 0.49-0.60 (m, 1H) |
| 85-4 | 543.2 | $^1$H NMR (DMSO-d$_6$) δ: 8.58-8.67 (m, 1H), 7.47-7.58 (m, 1H), 7.37-7.43 (m, 1H), 7.26-7.36 (m, 4H), 7.16-7.26 (m, 1H), 7.03-7.11 (m, 1H), 6.82-6.97 (m, 1H), 6.13-6.27 (m, 1H), 5.64-5.81 (m, 1H), 4.10-4.26 (m, 2H), 4.00-4.10 (m, 1H), 3.85-4.00 (m, 1H), 3.69-3.85 (m, 1H), 2.20-2.26 (m, 3H), 1.95-2.07 (m, 1H), 1.43-1.57 (m, 1H), 0.92-1.06 (m, 7H), 0.82-0.89 (m, 3H) |
| 85-5 | 529.2 | $^1$H NMR (DMSO-d$_6$) δ: 8.54-8.75 (m, 1H), 7.46-7.59 (m, 1H), 7.37-7.42 (m, 1H), 7.27-7.36 (m, 4H), 7.17-7.23 (m, 1H), 7.00-7.09 (m, 1H), 6.82-6.94 (m, 1H), 6.10-6.23 (m, 1H), 5.66-5.81 (m, 1H), 3.79-3.99 (m, 4H), 3.41-3.59 (m, 4H), 2.37-2.47 (m, 1H), 2.19-2.26 (m, 3H), 1.00-1.03 (m, 3H), 0.95-0.99 (m, 3H) |
| 85-6 | 485.0 | $^1$H NMR (DMSO-d$_6$) δ: 13.08-13.40 (m, 1H), 8.65-8.71 (m, 1H), 7.60-7.69 (m, 1H), 7.53-7.60 (m, 1H), 7.39-7.46 (m, 2H), 6.82-6.92 (m, 1H), 6.13-6.23 (m, 1H), 5.70-5.78 (m, 1H), 4.57-4.63 (m, 2H), 3.77-3.90 (m, 4H), 3.56-3.65 (m, 4H), 3.33-3.34 (m, 3H) |
| 85-7 | 559.2 | $^1$H NMR (CHLOROFORM-d) δ: 8.29-8.53 (m, 1H), 7.35-7.43 (m, 3H), 7.27-7.31 (m, 1H), 7.05-7.18 (m, 4H), 6.60-6.72 (m, 1H), 6.29-6.42 (m, 1H), 5.72-5.84 (m, 1H), 4.24-4.41 (m, 2H), 3.86-4.09 (m, 4H), 3.59-3.76 (m, 4H), 3.30-3.40 (m, 3H), 2.41-2.57 (m, 1H), 0.95-1.08 (m, 6H) |
| 86-1 | 586.2 | $^1$H NMR (CHLOROFORM-d) δ: 8.37-8.49 (m, 1H), 7.35-7.45 (m, 3H), 7.19-7.23 (m, 1H), 7.02-7.19 (m, 4H), 6.56-6.79 (m, 1H), 6.31-6.44 (m, 1H), 5.71-5.81 (m, 1H), 4.07-4.41 (m, 2H), 3.47-3.83 (m, 5H), 2.66-3.07 (m, 2H), 2.15-2.52 (m, 4H), 1.20-1.29 (m, 6H), 1.04-1.11 (m, 3H), 0.92-1.03 (m, 3H) |

TABLE 88-continued

Analytical Data

| Ex. # | LRMS: m/z (ESI, +ve ion): (M + H)+ | NMR |
|---|---|---|
| 86-2 | 572.2 | $^1$H NMR (CHLOROFORM-d) δ: 8.38-8.45 (m, 1H), 7.35-7.43 (m, 3H), 7.23-7.25 (m, 1H), 7.18-7.24 (m, 1H), 7.11-7.17 (m, 1H), 7.01-7.10 (m, 2H), 6.62-6.74 (m, 1H), 6.29-6.41 (m, 1H), 5.72-5.80 (m, 1H), 3.87-4.06 (m, 4H), 3.53-3.83 (m, 6H), 2.37-2.63 (m, 7H), 1.03-1.12 (m, 3H), 0.93-1.00 (m, 3H) |
| 87-1 | 604.3 | $^1$H NMR (400 MHz, CHLOROFORM-d) δ ppm 9.15 (s, 1H), 8.27 (s, 1H), 7.39-7.47 (m, 1H), 7.05-7.23 (m, 3H), 6.63 (dd, J = 10.37, 16.79 Hz, 1H), 6.42 (dd, J = 1.76, 16.69 Hz, 1H), 5.82 (dd, J = 1.87, 10.57 Hz, 1H), 4.38-4.50 (m, 2H), 3.99 (br d, J = 10.37 Hz, 2H), 3.92 (br s, 1H), 3.66-3.84 (m, 1H), 2.68 (tt, J = 6.71, 13.09 Hz, 2H), 1.46 (br d, J = 6.01 Hz, 6H), 1.24 (dd, J = 2.70, 6.63 Hz, 6H), 1.05 (t, J = 7.15 Hz, 6H). $^{19}$F NMR (376 MHz, CHLOROFORM-d) δ ppm −113.37 (s, 1F) |
| 87-2 | 604.3 | $^1$H NMR (400 MHz, CHLOROFORM-d) δ ppm 9.15 (s, 1H), 8.26 (s, 1H), 7.40-7.47 (m, 1H), 7.09-7.19 (m, 3H), 6.67 (dd, J = 10.47, 16.69 Hz, 1H), 6.48 (dd, J = 1.76, 16.69 Hz, 1H), 5.86 (dd, J = 1.76, 10.47 Hz, 1H), 5.39 (br s, 1H), 4.84-5.02 (m, 1H), 4.60 (br d, J = 12.23 Hz, 1H), 3.93 (br d, J = 11.61 Hz, 1H), 3.61-3.76 (m, 1H), 3.21 (br d, J = 11.40 Hz, 1H), 2.61-2.84 (m, 2H), 1.70 (br s, 3H), 1.60 (br s, 3H), 1.26 (d, J = 6.84 Hz, 6H), 1.04 (br d, J = 6.01 Hz, 6H). $^{19}$F NMR (376 MHz, CHLOROFORM-d) δ ppm −113.28 (s, 1F) |
| 87-3 | 604.2 | $^1$H NMR (400 MHz, CHLOROFORM-d) δ ppm 9.13 (s, 1H), 8.27 (s, 1H), 7.38-7.47 (m, 1H), 7.08-7.19 (m, 3H), 6.63 (dd, J = 10.47, 16.69 Hz, 1H), 6.41 (dd, J = 1.66, 16.79 Hz, 1H), 5.82 (dd, J = 1.76, 10.47 Hz, 1H), 4.38-4.49 (m, 2H), 3.61-4.07 (m, 4H), 2.67 (tt, J = 6.63, 12.85 Hz, 2H), 1.45 (br d, J = 6.01 Hz, 6H), 1.23 (dd, J = 2.80, 6.74 Hz, 6H), 1.04 (t, J = 7.05 Hz, 6H). $^{19}$F NMR (376 MHz, CHLOROFORM-d) δ ppm −113.37 (s, 1F) |
| 87-4 | 615.4 | 1H NMR (500 MHz, DMSO-d6) δ ppm 8.39 (br d, J = 7.14 Hz, 1 H) 8.19-8.22 (m, 1 H) 7.87 (br d, J = 8.82 Hz, 1 H) 7.51-7.54 (m, 3 H) 7.39-7.41 (m, 1 H) 7.20 (d, J = 7.91 Hz, 1 H) 5.65 (br s, 1 H) 4.98 (br s, 1 H) 4.72 (br d, J = 6.62 Hz, 1 H) 4.24-4.29 (m, 2 H) 4.05-4.09 (m, 2 H) 1.84-1.85 (m, 2 H) 0.84-1.44 (m, 15 H) |
| 87-5 | 605.4 | $^1$H NMR (500 MHz, DMSO-d$_6$) δ ppm 9.09 (s, 1 H) 8.42 (br d, J = 10.51 Hz, 1 H) 7.04 (t, J = 7.47 Hz, 1 H) 6.88 (td, J = 16.32, 10.44 Hz, 1 H) 6.39 (d, J = 11.66 Hz, 1 H) 6.34 (t, J = 8.36 Hz, 1 H) 6.21 (br dd, J = 16.67, 7.98 Hz, 1 H) 5.75-5.79 (m, 1 H) 5.39 (s, 2 H) 4.96 (br s, 1 H) 4.27-4.44 (m, 2 H) 4.01-4.21 (m, 1 H) 3.62-3.86 (m, 1 H) 2.68-2.76 (m, 2 H) 1.33 (d, J = 6.75 Hz, 3 H) 1.07 (d, J = 6.62 Hz, 6 H) 0.93 (d, J = 6.62 Hz, 6 H) |
| 88 | 531-2 | $^1$H NMR (400 MHz, CDCl$_3$) δ ppm 7.87 (1 H, s) 7.33-7.54 (4 H, m) 7.10-7.22 (4 H, m) 6.65 (1 H, dd, J = 16.79, 10.57 Hz) 6.53 (1 H, s) 6.40 (1 H, dd, J = 16.79, |

TABLE 88-continued

Analytical Data

| Ex. # | LRMS: m/z (ESI, +ve ion): (M + H)⁺ | NMR |
|---|---|---|
| | | 1.66 Hz) 5.81 (1 H, dd, J = 10.57, 1.87 Hz) 3.80-4.09 (8 H, m) 2.68 (1 H, spt, J = 6.84 Hz) 1.24 (3 H, d, J = 6.84 Hz) 1.09 (3 H, d, J = 6.84 Hz). |
| 88-1 | 531.0 | ¹H NMR (400 MHz, CDCl₃) δ ppm 7.86 (1 H, s) 7.30-7.51 (4 H, m) 7.08-7.19 (4 H, m) 6.63 (1 H, dd, J = 16.79, 10.37 Hz) 6.51 (1 H, s) 6.39 (1 H, dd, J = 16.79, 1.87 Hz) 5.80 (1 H, dd, J = 10.57, 1.87 Hz) 3.80-4.06 (8 H, m) 2.66 (1 H, spt, J = 6.84 Hz) 1.22 (3 H, d, J = 6.84 Hz) 1.07 (3 H, d, J = 6.84 Hz). |
| 88-2 | 531.0 | ¹H NMR (400 MHz, CDCl₃) δ ppm 7.86 (1 H, s) 7.43-7.52 (2 H, m) 7.30-7.42 (2 H, m) 7.08-7.19 (4 H, m) 6.63 (1 H, dd, J = 16.79, 10.57 Hz) 6.52 (1 H, s) 6.39 (1 H, dd, J = 16.79, 1.87 Hz) 5.80 (1 H, dd, J = 10.57, 1.87 Hz) 3.80-4.06 (8 H, m) 2.66 (1 H, spt, J = 6.80 Hz) 1.22 (3 H, d, J = 6.84 Hz) 1.07 (3 H, d, J = 6.84 Hz). |
| 89 | 499.3 | ¹H NMR (400 MHz, CDCl₃) δ ppm 8.15-8.59 (m, 1H), 7.64 (s, 1H), 7.42 (s, 1H), 7.19-7.32 (m, 1H), 6.93 (d, J = 8.29 Hz, 1H), 6.71 (t, J = 8.60 Hz, 1H), 6.53 (br d, J = 10.57 Hz, 1H), 6.30-6.38 (m, 1H), 5.76 (d, J = 11.61 Hz, 1H), 3.58-4.00 (m, 10H), 0.93 (s, 9H). ¹⁹F NMR (376 MHz, CDCl₃) δ ppm −113.66 (s, 1F). |
| 90-1 | 575.2 | ¹H NMR (400 MHz, MeOH-d₄) δ ppm 7.76-7.91 (m, 1H) 7.32-7.50 (m, 3 H) 7.08-7.31 (m, 3 H) 6.70-6.86 (m, 1 H) 6.55-6.70 (m, 2 H) 6.25 (br d, J = 16.79 Hz, 1 H) 5.77 (br d, J = 10.57 Hz, 1 H) 4.54 (br s, 1 H) 4.17-4.34 (m, 1 H) 3.92-4.17 (m, 2 H) 3.44-3.72 (m, 3 H) 2.50-2.63 (m, 1 H) 1.18-1.32 (m, 6 H) 1.03-1.16 (m, 6 H). |
| 90-2 | 575.2 | ¹H NMR (400 MHz, MeOH-d₄) δ ppm 7.77-7.81 (m, 2 H) 7.30-7.39 (m, 2 H) 7.06-7.21 (m, 3 H) 6.64-6.81 (m, 1 H) 6.56-6.61 (m, 1 H) 6.53 (t, J = 8.45 Hz, 1 H) 6.19 (br dd, J = 16.69, 4.25 Hz, 1 H) 5.71 (d, J = 12.02 Hz, 1 H) 4.47 (s, 1 H) 4.33 (br d, J = 10.99 Hz, 1 H) 4.10-4.25 (m, 1 H) 3.79-4.04 (m, 1 H) 3.61 (br d, J = 9.33 Hz, 1 H) 3.45 (br s, 1 H) 3.06 (br d, J = 11.82 Hz, 1 H) 2.47-2.56 (m, 1 H) 1.26-1.39 (m, 6 H) 0.99-1.09 (m, 6 H). |
| 91 | 535.2 | ¹H NMR (400 MHz, DMSO-d₆) δ ppm 7.92-8.07 (m, 1H), 7.52 (s, 2H), 7.21-7.39 (m, 3H), 7.04 (s, 1H), 6.76-6.93 (m, 1H), 6.21 (br d, J = 10.57 Hz, 2H), 5.72-5.82 (m, 1H), 4.73-5.09 (m, 1H), 3.56-4.49 (m, 7H), 1.30-1.42 (m, 6H), 1.17-1.26 (m, 3H). ¹⁹F NMR (376 MHz, DMSO-d₆) δ ppm −115.10-−114.52 (m, 1F). |
| 92 | 604.0 | ¹H NMR (400 MHz, DMSO-d₆) δ ppm 10.10 (br s, 1 H), 8.03 (d, J = 1.2 Hz, 1 H), 7.50-7.56 (m, 1 H), 7.45 (t, J = 7.5 Hz, 1 H), 7.30-7.37 (m, 1 H), 7.13-7.25 (m, 2 H), 6.59-6.76 (m, 4 H), 6.23 (d, J = 13.9 Hz, 1 H), 3.65-4.07 (m, 8 H), 3.06 (d, J = 5.2 Hz, 2 H), 2.50-2.59 (m, 1 H), 2.17 (s, 6 H), 0.94-1.12 (m, 6 H). |
| 93 | 571.1 | ¹H NMR (400 MHz, CDCl₃) δ ppm 1.43-1.69 (m, 3 H) 2.95-3.45 (m, 1 H) 3.48-4.15 (m, 3 H) 4.25-4.87 (m, 2 H) 4.88-5.29 (m, 1 H) 5.87 (d, J = 10.78 Hz, 1 H) 6.42-6.50 (m, 2 H) 6.59-6.79 (m, 1 H) 7.14-7.29 (m, 3 H) 7.42-7.51 (m, 2 H) 7.69 (dd, J = 15.34, 7.88 Hz, 1 H) 7.79-7.90 (m, 2 H) 7.94 (d, J = 8.09 Hz, 1 H). |

TABLE 88-continued

Analytical Data

| Ex. # | LRMS: m/z (ESI, +ve ion): (M + H)⁺ | NMR |
|---|---|---|
| | | 19F NMR (376 MHz, CDCl₃) δ ppm −61.42 (s, 1F), −75.99 (s, 1F), −113.64 (s, 1F). |
| 94 | 506.1 | ¹H NMR (400 MHz, CDCl₃) δ ppm 7.89 (s, 1 H), 7.36-7.43 (m, 1 H), 7.24 (d, J = 7.7 Hz, 2 H), 6.53-6.74 (m, 1 H), 6.42 (dd, J = 1.1, 16.9 Hz, 1 H), 5.82 (dd, J = 1.8, 10.5 Hz, 1 H), 4.97-5.15 (m, 1 H), 4.64-4.83 (m, 1 H), 4.38-4.58 (m, 1 H), 3.96-4.32 (m, 1 H), 3.45-3.91 (m, 3 H), 2.94-3.34 (m, 1 H), 2.08-2.49 (m, 4 H), 1.40-1.53 (m, 3 H), 1.01-1.16 (m, 6 H), 0.93 (br dd, J = 3.3, 7.7 Hz, 2 H), 0.53-0.68 (m, 2 H). |
| 95 | 512.3 | ¹H NMR (400 MHz, CDCl₃) δ ppm 7.54-7.63 (m, 1 H), 7.30-7.38 (m, 1 H), 7.20 (d, J = 7.5 Hz, 2 H), 6.50-6.72 (m, 1 H), 6.38 (br d, J = 17.0 Hz, 1 H), 5.78 (dd, J = 1.7, 10.4 Hz, 1 H), 4.95-5.10 (m, 1 H), 4.57-4.76 (m, 1 H), 4.35-4.54 (m, 1 H), 4.19 (td, J = 1.9, 12.0 Hz, 1 H), 3.57-4.02 (m, 2 H), 2.91-3.55 (m, 1 H), 2.40 (dt, J = 4.0, 8.1 Hz, 1 H), 2.08-2.36 (m, 4 H), 2.00-2.07 (m, 1 H), 0.96-1.09 (m, 10 H), 0.83 (br dd, J = 3.2, 7.8 Hz, 3 H), 0.55-0.68 (m, 4 H). |
| 96 | 590.3 | ¹H NMR (400 MHz, DMSO-d₆) δ ppm 8.49-8.59 (m, 1H), 7.43-7.57 (m, 1H), 7.11-7.33 (m, 6H), 6.74-6.91 (m, 1H), 6.17 (br d, J = 16.17 Hz, 1H), 5.74-5.82 (m, 1H), 5.18-5.36 (m, 1H), 4.16-4.79 (m, 7H), 2.11-2.27 (m, 4H), 0.89-1.01 (m, 6H). |
| 97 | 544.8 | ¹H NMR (400 MHz, MeOH-d₄) δ ppm 8.41 (br s, 1H), 7.60 (dd, J = 6.5, 2.2 Hz, 1H), 7.48-7.57 (m, 3H), 7.35-7.41 (m, 1H), 7.20 (d, J = 7.5 Hz, 1H), 6.86-7.02 (m, 1H), 6.48 (t, J = 6.7 Hz, 1H), 6.36-6.43 (m, 1H), 5.92 (dd, J = 10.7, 1.8 Hz, 1H), 5.04-5.20 (m, 1H), 4.45-4.73 (m, 2H), 4.12-4.36 (m, 1H), 3-56-3.99 (m, 2H), 3.18-3.34 (m, 1H), 2.65-2.80 (m, 1H), 1.56 (d, J = 6.6 Hz, 3H), 1.27 (d, J = 6.8 Hz, 3H), 1.13 (d, J = 6.8 Hz, 3H). |
| 98 | 570.8 | ¹H NMR (400 MHz, MeOH-d₄) δ ppm 8.47-8.68 (m, 1H), 7.66-7.73 (m, 2H), 7.55-7.62 (m, 1H), 7.40-7.50 (m, 2H), 7.27-7.36 (m, 1H), 7.11-7.24 (m, 1H), 6.83-6.97 (m, 1H), 6.37 (br d, J = 15.5 Hz, 1H), 5.89 (dd, J = 10.6, 1.9 Hz, 1H), 5.11 (br d, J = 6.6 Hz, 1H), 4.44-4.66 (m, 2H), 4.11-4.31 (m, 1H), 3.61-4.00 (m, 2H), 3.39-3.58 (m, 1H), 2.60-2.87 (m, 1H), 1.51-1.60 (m, 3H), 1.23 (d, J = 6.8 Hz, 3H), 0.94-1.03 (m, 3H). |
| 98-1 | 570.8 | ¹H NMR (400 MHz, MeOH-d₄) δ ppm 8.58 (br s, 1H), 7.68-7.73 (m, 2H), 7.59 (ddd, J = 9.3, 5.9, 3.8 Hz, 1H), 7.41-7.51 (m, 2H), 7.28-7.37 (m, 1H), 7.10-7.25 (m, 1H), 6.83-6.98 (m, 1H), 6.38 (br d, J = 15.8 Hz, 1H), 5.89 (dd, J = 10.6, 1.9 Hz, 1H), 5.12 (br d, J = 3.7 Hz, 1H), 4.44-4.65 (m, 2H), 4.10-4.31 (m, 1H), 3.87-3.99 (m, 1H), 3.41-3.85 (m, 2H), 2.65-2.84 (m, 1H), 1.57 (br d, J = 6.4 Hz, 3H), 1.24 (d, J = 6.8 Hz, 3H), 0.94-1.02 (m, 3H). |
| 98-2 | 570.8 | ¹H NMR (400 MHz, MeOH-d₄) δ ppm 8.63 (br s, 1H), 7.72-7.76 (m, 2H), 7.59-7.66 (m, 1H), 7.44-7.54 (m, 2H), 7.31-7.41 (m, 1H), 7.15-7.28 (m, 1H), 6.87-7.01 (m, 1H), 6.38-6.45 (m, 1H), 5.93 (dd, J = 10.6, 1.9 Hz, 1H), 5.13-5.27 (m, 1H), 4.48-4.70 (m, 2H), 4.15-4.36 (m, |

TABLE 88-continued

Analytical Data

| Ex. # | LRMS: m/z (ESI, +ve ion): (M + H)+ | NMR |
|---|---|---|
| | | 1H), 3.45-4.06 (m, 3H), 2.63-2.89 (m, 1H), 1.58 (d, J = 6.8 Hz, 3H), 1.27 (d, J = 6.8 Hz, 3H), 1.00-1.06 (m, 3H). |
| 99 | 548.0 | $^1$H NMR (400 MHz, CDCl$_3$) δ ppm 9.16 (d, J = 1.2 Hz, 1 H) 8.94 (s, 1 H) 8.13 (s, 1 H) 7.46-7.53 (m, 1 H) 7.20-7.28 (m, 2 H) 7.17 (t, J = 9.2 Hz, 1 H) 6.58-6.78 (m, 1 H) 6.43-6.52 (m, 1 H) 5.89 (dd, J = 10.5, 1.8 Hz, 1 H) 4.26-5.33 (m, 3 H) 3.88-4.16 (m, 1 H) 3.55-3.85 (m, 2 H) 3.00-3.44 (m, 1 H) 2.78-2.97 (m, 1 H) 1.51-1.63 (m, 3 H) 1.37-1.42 (m, 3 H) 1.21 (d, J = 6.8 Hz, 3 H). $^{19}$F NMR (377 MHz, CDCl$_3$) δ −112.43 (br d, J = 25.1 Hz, 1 F). |
| 100 | 520.1 | $^1$H NMR (400 MHz, DMSO-d$_6$) δ ppm 10.07 (br s, 1H), 8.35-8.38 (m, 1H), 8.31-8.40 (m, 1H), 7.43 (t, J = 15.10 Hz, 2H), 7.34 (dd, J = 7.05, 14.72 Hz, 1H), 7.20-7.29 (m, 3H), 6.79-6.93 (m, 1H), 6.72 (d, J = 8.29 Hz, 1H), 6.67 (t, J = 17.60 Hz, 1H), 6.15-6.27 (m, 1H), 5.77 (dd, J = 2.28, 10.16 Hz, 1H), 4.81-4.95 (m, 1H), 4.27-4.45 (m, 1H), 3.97-4.27 (m, 2H), 3.57-3.80 (m, 2H), 3.34-3.53 (m, 1H), 1.34 (d, J = 6.84 Hz, 3H). $^{19}$F NMR (376 MHz, DMSO-d$_6$) δ ppm −113.43 (s, 1F), −113.44 (s, 1F), −114.38 (s, 1F), −115.34 (s, 1F), −115.35 (s, 1F). |
| 101 | 561.2 | $^1$H NMR (400 MHz, CDCl$_3$) δ ppm 8.60 (dd, J = 1.45, 4.77 Hz, 1H), 8.07 (d, J = 4.15 Hz, 1H), 7.51 (d, J = 8.09 Hz, 1H), 7.37-7.45 (m, 1H), 7.23-7.28 (m, 1H), 7.13-7.22 (m, 2H), 7.06-7.13 (m, 1H), 6.52-6.72 (m, 1H), 6.41 (dd, J = 1.87, 17.00 Hz, 1H), 5.81 (dd, J = 1.45, 10.37 Hz, 1H), 4.25-5.16 (m, 3H), 3.51-4.08 (m, 3H), 2.95-3.35 (m, 1H), 2.36-2.47 (m, 2H), 2.08-2.24 (m, 1H), 1.39-1.61 (m, 3H), 0.82 (dd, J = 2.07, 6.63 Hz, 3H), 0.77 (d, J = 6.63 Hz, 3H). $^{19}$F NMR (376 MHz, CDCl$_3$) δ ppm −112.21 (s, 1F). |
| 102 | 540.0 | $^1$H NMR (400 MHz, DMSO-d$_6$) δ ppm 8.22 (s, 1 H), 7.41-7.53 (m, 1 H), 7.19-7.31 (m, 4 H), 7.16 (td, J = 7.5, 1.7 Hz, 1 H), 7.11 (dd, J = 6.1, 2.6 Hz, 1 H), 6.81-6.95 (m, 1 H), 6.21 (dd, J = 16.1, 7.1, 1 H), 5.78 (dd, J = 10.2, 2.3 Hz, 1 H), 4.87-4.93 (m, 1 H), 3.94-4.55 (m, 3 H), 3.57-3.70 (m, 2 H), 2.49-2.53 (m, 1 H), 2.19 (s, 3 H), 1.87 (s, 3 H), 1.33 (d, J = 6.6 Hz, 3 H), 1.25 (br s, 1 H), 1.06 (d, J = 6.8 Hz, 3 H), 0.93 (dd, J = 6.6, 3.7 Hz, 3 H). |
| 102-1 | 539.9 | $^1$H NMR (400 MHz, DMSO-d$_6$) δ ppm 8.22 (br s, 1 H), 7.39-7.55 (m, 1 H), 7.06-7.33 (m, 6 H), 6.77-6.96 (m, 1 H), 6.13-6.29 (m, 1 H), 5.76 (br d, J = 10.6 Hz, 1 H), 4.90 (br s, 1 H), 3.97-4.55 (m, 4 H), 3.55-3.74 (m, 2 H), 3.22-3.25 (m, 1 H), 2.19 (s, 3 H), 1.86 (s, 3 H), 1.33 (br d, J = 6.4 Hz, 3 H), 1.05 (br d, J = 6.4 Hz, 3 H), 0.92 (br d, J = 6.6 Hz, 3 H). |
| 102-2 | 539.9 | $^1$H NMR (400 MHz, DMSO-d$_6$) δ ppm 8.22 (br s, 1 H), 7.40-7.53 (m, 1 H), 7.03-7.33 (m, 6 H), 6.80-6.97 (m, 1 H), 6.21 (br d, J = 16.4 Hz, 1 H), 5.76 (br d, J = 10.6 Hz, 1 H), 4.91 (br s, 1 H), 3.94-4.51 (m, 4 H), 3.59-3.75 (m, 2 H), 3.21-3.35 (m, 1 H), 2.19 (s, 3 H), 1.86 (s, 3 |

TABLE 88-continued

Analytical Data

| Ex. # | LRMS: m/z (ESI, +ve ion): (M + H)+ | NMR |
|---|---|---|
| | | H), 1.32 (br d, J = 6.4 Hz, 3 H), 1.05 (br d, J = 6.6 Hz, 3 H), 0.93 (br d, J = 6.4 Hz, 3 H). |
| 103 | 559.3 | $^1$H NMR (400 MHz, CDCl$_3$) δ ppm 7.83 (br s, 1H), 7.34-7.42 (m, 2H), 7.26-7.28 (m, 3H), 7.07-7.20 (m, 3H), 6.52-6.73 (m, 1H), 6.45-6.48 (m, 1H), 6.39 (dd, J = 1.66, 16.79 Hz, 1H), 5.79 (dd, J = 1.87, 10.57 Hz, 1H), 4.78-5.13 (m, 1H), 4.21-4.77 (m, 2H), 3.51-4.09 (m, 3H), 2.95-3.36 (m, 1H), 2.34-2.48 (m, 2H), 2.19-2.33 (m, 2H), 1.48 (d, J = 9.33 Hz, 3H), 1.06-1.15 (m, 6H). $^{19}$F NMR (377 MHz, CDCl$_3$) δ ppm −113.93 (s, 1F). |
| 104 | 546.2 | $^1$H NMR (400 MHz, CDCl$_3$) δ ppm 8.54-8.61 (m, 1H), 7.96 (dd, J = 1.87, 7.67 Hz, 1H), 7.87 (s, 1H), 7.50 (dd, J = 4.77, 7.88 Hz, 1H), 7.42-7.47 (m, 1H), 7.21-7.28 (m, 2H), 7.18 (t, J = 18.00 Hz, 1H), 6.57-6.77 (m, 1H), 6.41-6.51 (m, 2H), 5.88 (d, J = 10.57 Hz, 1H), 4.86-5.24 (m, 1H), 4.36-4.85 (m, 2H), 3.30-3.98 (m, 3H), 2.97-3.27 (m, 1H), 2.80-2.94 (m, 1H), 1.45-1.69 (m, 3H), 1.37 (d, J = 6.84 Hz, 3H), 1.16 (d, J = 6.84 Hz, 3H). $^{19}$F NMR (376 MHz, CDCl$_3$) δ ppm −113.78 (s, 1F). |
| 105 | 552.2 | $^1$H NMR (400 MHz, CDCl$_3$) δ ppm 7.84 (s, 1H), 7.26-7.37 (m, 2H), 7.08-7.18 (m, 2H), 6.71 (d, J = 8.29 Hz, 1H), 6.54-6.67 (m, 2H), 6.51 (d, J = 3130.75 Hz, 1H), 6.38 (d, J = 16.38 Hz, 1H), 5.79 (d, J = 10.37 Hz, 1H), 4.72-5.14 (m, 1H), 4.17-4.71 (m, 2H), 3.76-4.02 (m, 1H), 3.44-3.75 (m, 2H), 2.92-3.30 (m, 1H), 2.44-2.71 (m, 1H), 1.90-2.01 (m, 3H), 1.35-1.54 (m, 3H), 1.20-1.28 (m, 2H), 1.14 (dd, J = 6.84, 11.61 Hz, 3H), 0.97-1.05 (m, 3H). $^{19}$F NMR (376 MHz, CDCl$_3$) δ ppm −114.04−−113.40 (m, 1F). |
| 106 | 575.2 | $^1$H NMR (400 MHz, CDCl$_3$) δ ppm 7.84 (s, 1H), 7.26-7.37 (m, 2H), 7.08-7.18 (m, 2H), 6.71 (d, J = 8.29 Hz, 1H), 6.54-6.67 (m, 2H), 6.51 (d, J = 3130.75 Hz, 1H), 6.38 (d, J = 16.38 Hz, 1H), 5.79 (d, J = 10.37 Hz, 1H), 4.72-5.14 (m, 1H), 4.17-4.71 (m, 2H), 3.76-4.02 (m, 1H), 3.44-3.75 (m, 2H), 2.92-3.30 (m, 1H), 2.44-2.71 (m, 1H), 1.90-2.01 (m, 3H), 1.35-1.54 (m, 3H), 1.20-1.28 (m, 2H), 1.14 (dd, J = 6.84, 11.61 Hz, 3H), 0.97-1.05 (m, 3H). $^{19}$F NMR (376 MHz, CDCl$_3$) δ ppm −114.04−−113.40 (m, 1F). |
| 107 | 542.2 | $^1$H NMR (400 MHz, DMSO-d$_6$) δ 11.67 (br. s., 1H) 8.48 (m, 1H) 7.75 (d, J = 8.0 Hz, 1H) 7.41 (t, J = 8.0 Hz, 1H) 7.29 (m, 3H) 6.85 (m, 1H) 6.76 (m, 1H) 6.62 (d, J = 8.0 Hz, 1H) 6.20 (br m, 1H) 5.76 (m, 1H) 4.87 (br. m., 1H) 4.42 (br. m., 0.5H) 4.30 (br. m., 2H) 4.16 (br. m., 0.5H) 3.64 (br. m., 2H) 3.48 (br. m., 0.5H) 3.13 (br. m., 0.5H) 2.23 (m, 4H) 1.34 (d, J = 8.0 Hz, 3H) 0.98 (m, 6H). |
| 108 | 541.1 | $^1$H NMR (400 MHz, DMSO-d$_6$) δ ppm 7.48-7.63 (m, 2 H), 7.41 (dt, J = 7.9, 2.1 Hz, 1 H), 7.19-7.37 (m, 4 H), 7.10 (dt, J = 7.7, 1.0 Hz, 1 H), 6.80-6.95 (m, 1 H), 6.21 (br d, J = 16.8 Hz, 1 H), 5.76 (dd, J = 11.0, 1.4 Hz, 1 H), 5.04-5.46 (m, 1 H), 3.86-5.07 (m, 2 H), 3.59-3.76 (m, 3 H), 3.57-3.58 (m, 2 H), 2.61-2.75 (m, 2 H), 1.29-1.45 (m, 3 H), 1.21 (t, J = 7.4 Hz, 3 H), 1.02-1.12 (m, 3 H), 0.96 (d, J = 6.8 Hz, 3 H). |

TABLE 88-continued

Analytical Data

| Ex. # | LRMS: m/z (ESI, +ve ion): $(M + H)^+$ | NMR |
|---|---|---|
| 109 | 542.9 | $^1$H NMR (400 MHz, DMSO-d$_6$) δ 7.47-7.55 (m, 1 H), 7.43 (dt, J = 7.9, 1.3 Hz, 1 H), 7.36 (tt, J = 7.5, 1.4 Hz, 1 H), 7.25-7.32 (m, 3 H), 7.23 (dd, J = 7.0, 1.4 Hz, 1 H), 7.11 (td, J = 7.8, 1.0 Hz, 1 H), 6.79-6.97 (m, 1 H), 6.21 (br d, J = 16.8 Hz, 1 H), 5.76 (dd, J = 10.5, 2.0 Hz, 1 H), 4.00-4.53 (m, 3 H), 3.96 (s, 3 H), 3.37-3.83, m, 2 H), 2.56-2.74 (m, 2 H), 1.21-1.51 (m, 4 H), 1.10 (t, J = 6.3 Hz, 3 H), 0.98 (d, J = 5.8 Hz, 3 H). |
| 110 | 545.9 | $^1$H NMR (400 MHz, CDCl$_3$) δ ppm 7.25-7.51 (m, 4H), 7.05-7.18 (m, 4H), 6.78 (s, 1H), 6.58 (br d, J = 9.95 Hz, 1H), 6.32-6.39 (m, 1H), 5.83-6.31 (m, 1H), 5.74 (br d, J = 10.16 Hz, 1H), 4.84-5.67 (m, 1H), 4.58 (br s, 1H), 3.01-4.07 (m, 4H), 2.56-2.80 (m, 1H), 1.45 (br, 3H), 1.19 (d, J = 6.84 Hz, 3H), 1.03 (d, J = 6.84 Hz, 3H). $^{19}$F NMR (376 MHz, CDCl$_3$) δ ppm −113.73 (br d, J = 10.41 Hz, 1F). |
| 110-1 | 545.9 | $^1$H NMR (400 MHz, CDCl$_3$) δ ppm 7.32-7.55 (m, 4H), 7.11-7.23 (m, 4H), 6.83 (s, 1H), 6.57-6.70 (m, 1H), 6.40 (br d, J = 16.59 Hz, 1H), 6.00 (br s, 1H), 5.79 (br d, J = 10.57 Hz, 1H), 4.99-5.74 (m, 1H), 4.21-4.68 (m, 1H), 3.28 (br s, 4H), 2.65-2.76 (m, 1H), 1.35-1.68 (m, 2H), 1.24 (d, J = 6.84 Hz, 3H), 1.08 (d, J = 6.84 Hz, 3H). $^{19}$F NMR (376 MHz, CDCl$_3$) δ ppm −113.72 (br s, 1F). |
| 110-2 | 545.9 | $^1$H NMR (400 MHz, CDCl$_3$) δ ppm 7.32-7.55 (m, 4H), 7.09-7.23 (m, 4H), 6.83 (s, 1H), 6.56-6.70 (m, 1H), 6.40 (br d, J = 15.96 Hz, 1H), 6.05 (br s, 1H), 5.79 (br d, J = 10.37 Hz, 1H), 4.91-5.48 (m, 1H), 4.65 (br d, J = 11.82 Hz, 1H), 3.11-4.12 (m, 4H), 2.76 (td, J = 6.76, 13.63 Hz, 1H), 1.50 (br s, 3H), 1.24 (d, J = 6.84 Hz, 3H), 1.08 (d, J = 6.84 Hz, 3H). $^{19}$F NMR (376 MHz, CDCl$_3$) δ ppm −113.75 (br s, 1F). |
| 111 | 561.8 | $^1$H NMR (400 MHz, DMSO-d$_6$) δ ppm 8.41 (d, J = 4.8 Hz, 1 H), 7.50-7.66 (m, 1 H), 7.26-7.42 (m, 3 H), 7.20 (d, J = 4.8 Hz, 1 H), 6.89 (br dd, J = 16.6, 10.8 Hz, 1 H), 6.22 (br d, J = 17.2 Hz, 1 H), 5.76 (dd, J = 10.2, 1.9 Hz, 1 H), 4.15-4.40 (m, 2 H), 3.65-3.75 (m, 2 H), 3.50-3.61 (m, 2 H), 2.75-2.91 (m, 1 H), 1.95-2.01 (m, 3 H), 1.21-1.54 (m, 4 H), 1.07 (t, J = 5.9 Hz, 3 H), 0.96 (dd, J = 6.6, 4.2 Hz, 3 H) |
| 111-1 | 562.1 | $^1$H NMR (400 MHz, DMSO-d$_6$) δ ppm 8.41 (d, J = 4.8 Hz, 1 H), 7.49-7.66 (m, 1 H), 7.28-7.40 (m, 3 H), 7.20 (d, J = 5.0 Hz, 1 H), 6.89 (br dd, J = 16.4, 10.2 Hz, 1 H), 6.22 (dd, J = 17.0, 1.4 Hz, 1 H), 5.76 (dd, J = 10.4, 1.1 Hz, 1 H), 4.71-5.63 (m, 1 H), 3.48-4.44 (m, 6 H), 2.85 (quin, J = 6.2 Hz, 1 H), 1.97 (s, 3 H), 1.28-1.49 (m, 3 H), 1.08 (d, J = 6.63 Hz, 3 H), 0.95 (d, J = 6.6 Hz, 3 H). |
| 111-2 | 562.1 | $^1$H NMR (400 MHz, DMSO-d$_6$) δ ppm 8.41 (d, J = 5.0 Hz, 1 H), 7.51-7.67 (m, 1 H), 7.29-7.40 (m, 3 H), 7.20 (d, J = 5.0 Hz, 1 H), 6.89 (br dd, J = 16.3, 10.5 Hz, 1 H), 6.22 (br d, J = 16.8 Hz, 1 H), 5.76 (dd, J = 9.9, 1.7 Hz, 1 H), 4.71-5.57 (m, 1 H), 3.44-4.41 (m, 6 H), 2.73-2.90 (m, 1 H), 1.99 (s, 3 H), 1.23-1.45 (m, 3 H), 1.07 (d, J = 6.6 Hz, 3 H), 0.96 (d, J = 6.6 Hz, 3 H). |
| 112 | 500.0 | $^1$H NMR (400 MHz, DMSO-d$_6$) δ ppm 0.99 (d, J = 6.8 Hz, 3 H), 1.05 (d, J = |

TABLE 88-continued

Analytical Data

| Ex. # | LRMS: m/z (ESI, +ve ion): (M + H)+ | NMR |
|---|---|---|
| | | 6.8 Hz, 3 H), 1.28 (br d, J = 6.6 Hz, 3 H), 1.89 (s, 3 H), 2.43 (sept, J = 6.8 Hz, 1 H), 2.95-3.11 (m, 0.5 H), 3.19-3.27 (m, 0.5 H), 3.37-3.43 (m, 0.5 H), 3.57-3.66 (m, 0.5 H), 3.67-3.81 (m, 1 H), 3.96-4.07 (m, 0.5 H), 4.08-4.23 (m, 1.5 H), 4.24-4.31 (m, 0.5 H), 4.33-4.43 (m, 0.5 H), 4.90 (br s, 1 H), 5.71-5.79 (m, 1 H), 6.20 (br d, J = 16.6 Hz, 1 H), 6.78-6.93 (m, 1 H), 7.18 (dd, J = 7.2, 1.4 Hz, 1 H), 7.26-7.38 (m, 2 H), 8.47 (br s, 1 H). |
| 113 | 576.2 | $^1$H NMR (400 MHz, DMSO-d$_6$) δ ppm 0.97 (br d, J = 6.8 Hz, 3 H), 1.07 (br d, J = 6.6 Hz, 3 H), 1.31 (br d, J = 6.4 Hz, 3 H), 1.88 (s, 3 H), 2.53-2.58 (m, 1H), 3.02-3.18 (m, 1 H), 3.23-3.28 (m, 0.5 H), 3-40-3.54 (m, 0.5 H), 3.61-3.79 (m, 1.5 H), 4.01-4.05 (m, 0.5 H), 4.10-4.19 (m, 0.5 H), 4.20-4.33 (m, 1.5 H), 4.41 (br d, J = 12.9 Hz, 0.5 H), 4.89 (br s, 1 H), 5.71-5.82 (m, 1 H), 6.21 (br d, J = 15.8 Hz, 1 H), 6.78-6.98 (m, 2 H), 7.19 (br d, J = 6.6 Hz, 1 H), 7.26-7.47 (m, 4 H), 8.28-8.33 (m, 1 H), 10.69 (s, 1 H). $^{19}$F NMR (376 MHz, DMSO-d$_6$) δ ppm −126.44 (s, 1 F). |
| 114 | 576.2 | $^1$H NMR (400 MHz, DMSO-d$_6$) δ ppm 0.96 (d, J = 6.8 Hz, 3 H), 1.06 (d, J = 6.8 Hz, 3 H), 1.32 (d, J = 6.6 Hz, 3 H), 1.89 (s, 3 H), 2.52-2.59 (m, 1 H), 3.04-3.16 (m, 0.5 H), 3.22-3.30 (m, 0.5 H), 3.41-3.54 (m, 0.5 H), 3.58-3.77 (m, 1.5 H), 4.03 (br d, J = 13.3 Hz, 0.5 H), 4.11-4.20 (m, 0.5 H), 4.27 (br d, J = 13.1 Hz, 1.5 H), 4.35-4.47 (m, 0.5 H), 4.89 (br s, 1 H), 5.70-5.82 (m, 1 H), 6.21 (br d, J = 16.2 Hz, 1 H), 6.76-6.94 (m, 2 H), 7.19 (dd, J = 7.0, 1.4 Hz, 1 H), 7.26-7.42 (m, 4 H), 8.22-8.41 (m, 1 H), 10.69 (br s, 1 H). $^{19}$F NMR (376 MHz, DMSO-d$_6$) δ ppm −126.45 (s, 1 F). |
| 115 | 549.2 | $^1$H NMR (400 MHz, DMSO-d$_6$) δ ppm 7.85-8.04 (m, 1 H), 7.35-7.49 (m, 2 H), 7.22-7.33 (m, 1 H), 6.96-7.12 (m, 1 H), 6.75-6.94 (m, 1 H), 6.19 (br dd, J = 16.6, 5.8 Hz, 1 H), 5.67-5.82 (m, 1 H), 4.60-4.95 (m, 1 H), 3.87-4.46 (m, 4 H), 3.40-3.77 (m, 3 H), 3.02-3.21 (m, 1 H), 2.80-2.97 (m, 1 H), 2.56-2.74 (m, 1 H), 1.19-1.62 (m, 9 H), 1.05-1.14 (m, 3 H), 0.88-1.05 (m, 6 H). |
| 116 | 575.2 | $^1$H NMR (400 MHz, CDCl$_3$) δ ppm 7.84 (s, 1H), 7.35-7.47 (m, 2H), 7.30 (d, J = 7.67 Hz, 2H), 7.19 (dd, J = 7.05, 14.72 Hz, 1H), 7.09-7.16 (m, 2H), 6.54-6.82 (m, 1H), 6.50-6.53 (m, 1H), 6.41 (d, J = 16.59 Hz, 1H), 5.81 (dd, J = 2.07, 10.78 Hz, 1H), 4.83-5.30 (m, 1H), 4.54-4.81 (m, 1H), 4.29-4.53 (m, 1H), 3.57-4.16 (m, 3H), 2.96-3.36 (m, 1H), 2.41-2.54 (m, 2H), 2.10-2.31 (m, 2H), 1.51 (d, J = 17.41 Hz, 3H), 1.11-1.19 (m, 6H). $^{19}$F NMR (376 MHz, CDCl$_3$) δ ppm −113.90 (s, 1F). |
| 117 | 620.3 | $^1$H NMR (400 MHz, DMSO-d$_6$) δ ppm 7.94 (1 H, br t, J = 5.2 Hz), 6.93-7.03 (2 H, m), 6.78-6.93 (2 H, m), 6.14-6.26 (1 H, m), 5.72-5.80 (1 H, m), 4.66-4.84 (1 H, m), 4.31-4.42 (1 H, m), 4.19-4.28 (2 H, m), 3.94-4.19 (2 H, m), 3.65-3.72 (2 H, m), 3.47-3.64 (2 H, m), 3.24-3.30 (3 H, m), 2.94-3.09 (2 H, m), 2.41-2.48 (1 H, m), 1.44-1.57 (2 H, |

TABLE 88-continued

Analytical Data

| Ex. # | LRMS: m/z (ESI, +ve ion): (M + H)+ | NMR |
|---|---|---|
| | | m), 1.39 (4 H, br d, J = 4.6 Hz), 1.22-1.30 (3 H, m), 1.08 (3 H, d, J = 6.8 Hz), 0.98 (3 H, br d, J = 6.6 Hz) |
| 118 | 545.2 | $^1$H NMR (400 MHz, DMSO-d$_6$) δ ppm 8.14-8.25 (1 H, m), 8.10 (1 H, s), 7.38-7.59 (1 H, m), 7.20-7.35 (2 H, m), 7.09-7.20 (3 H, m), 6.75-6.93 (1 H, m), 6.06-6.20 (1 H, m), 5.63-5.74 (1 H, m), 4.36-4.69 (1 H, m), 4.03-4.35 (1 H, m), 2.56-2.66 (2 H, m), 2.23-2.36 (4 H, m), 2.19 (1 H, dt, J = 14.1, 7.1 Hz), 1.86-2.09 (2 H, m), 1.44-1.68 (2 H, m), 0.87-1.06 (6 H, m). $^{19}$F NMR (376 MHz, DMSO-d$_6$) δ ppm −114.37 (1 F, s), −114.45 (1 F, s), −114.50 (1 F, s). |
| 119 | 444.1 | $^1$H NMR (400 MHz, DMSO-d$_6$) δ ppm 11.52 (1 H, s), 10.17 (1 H, s), 8.26 (1 H, br s), 7.23-7.41 (1 H, m), 6.69-6.90 (3 H, m), 6.19 (1 H, br d, J = 15.8 Hz), 5.70-5.78 (1 H, m), 4.77 (1 H, br s), 4.35 (1 H, br d, J = 11.6 Hz), 4.24 (1 H, br d, J = 13.3 Hz), 4.02-4.19 (2 H, m), 3.97 (1 H, br d, J = 13.5 Hz), 3.52-3.71 (1 H, m), 1.28 (3 H, br d, J = 6.6 Hz). $^{19}$F NMR (376 MHz, DMSO-d$_6$) δ ppm −115.41 (1 F, s). |
| 120 | 463.3 | $^1$H NMR (400 MHz, DMSO-d$_6$) δ ppm 8.31 (1 H, d, J = 7.8 Hz), 8.13 (1 H, td, J = 7.9, 1.7 Hz), 7.72 (1 H, dd, J = 8.2, 2.0 Hz), 7.49-7.61 (1 H, m), 7.36-7.46 (2 H, m), 6.78-6.95 (1 H, m), 6.06-6.23 (2 H, m), 5.72 (1 H, d, J = 2.1 Hz), 4.49 (1 H, br d, J = 11.0 Hz), 4.41 (1 H, br s), 4.28 (1 H, br d, J = 10.2 Hz), 3.91-4.14 (1 H, m), 3.82 (2 H, br d, J = 10.4 Hz), 3.52-3.68 (1 H, m), 3.29-3.33 (1 H, m), 2.85-3.02 (1 H, m), 0.92 (9 H, s). $^{19}$F NMR (376 MHz, DMSO-d6) δ ppm −114.14 (1 F, s), −115.54 (1 F, s) |
| 121 | 497.2 | $^1$H NMR (400 MHz, MeOH-d$_4$) δ ppm 8.35 (1 H, s), 7.48-7.65 (2 H, m), 7.32-7.42 (1 H, m), 7.27 (1 H, br t, J = 9.2 Hz), 6.86 (1 H, br d, J = 10.4 Hz), 6.24-6.40 (2 H, m), 5.75-5.93 (1 H, m), 4.46 (1 H, br s), 4.39 (1 H, br d, J = 9.7 Hz), 4.32 (1 H, br d, J = 12.0 Hz), 4.02-4.19 (1 H, m), 3.98 (1 H, br d, J = 10.0 Hz), 3.86 (1 H, br s), 3.64-3.82 (1 H, m), 3.40-3.60 (1 H, m), 3.02 (1 H, br d, J = 12.0 Hz), 1.07 (3 H, br d, J = 5.8 Hz), 0.93 (9 H, s). $^{19}$F NMR (376 MHz, MeOH-d$_4$) δ ppm −115.68 (1 F, s). |
| 122 | 483.2 | $^1$H NMR (400 MHz, DMSO-d$_6$) δ ppm 8.25 (1 H, s), 7.57-7.66 (1 H, m), 7.54 (1 H, td, J = 7.5, 2.0 Hz), 7.36-7.45 (2 H, m), 6.86 (1 H, dd, J = 16.7, 10.5 Hz), 6.09-6.25 (2 H, m), 5.71-5.79 (1 H, m), 4.28 (2 H, s), 3.76-3.91 (4 H, m), 3.15 (4 H, br s), 0.88 (9 H, s). $^{19}$F NMR (376 MHz, DMSO-d$_6$) δ ppm −114.11 (1 F, s). |
| 123 | 449.2 | $^1$H NMR (400 MHz, DMSO-d6) δ ppm 6 8.30 (1 H, d, J = 8.3 Hz), 8.10-8.19 (1 H, m), 7.71-7.79 (1 H, m), 7.52-7.61 (1 H, m), 7.32-7.48 (2 H, m), 6.81-6.93 (1 H, m), 6.11-6.22 (1 H, m), 6.05-6.11 (1 H, m), 5.68-5.81 (1 H, m), 4.44 (2 H, br s), 3.82 (4 H, br s), 3.06-3.20 (4 H, m), 0.88-0.95 (9 H, s). $^{19}$F NMR (376 MHz, DMSO-d$_6$) δ ppm −115.48 (1 F, s). |
| 124 | 480.2 | $^1$H NMR (400 MHz, DMSO-d$_6$) δ ppm 8.28 (1 H, s), 7.59-7.66 (1 H, m), 7.50-7.56 (1 H, m), 7.36-7.46 (2 H, m), 6.76-7.01 (1 H, m), 6.68 (1 H, s), 6.13-6.24 (1 H, m), 5.99-6.11 (1 H, m), 5.74 (1 H, br d, J = 10.2 Hz), 4.19-4.44 (6 H, m), |

TABLE 88-continued

Analytical Data

| Ex. # | LRMS: m/z (ESI, +ve ion): (M + H)+ | NMR |
|---|---|---|
| | | 3.80-3.92 (2 H, m), 0.90 (9 H, s). $^{19}$F NMR (376 MHz, DMSO-d$_6$) δ ppm −114.23 (1 F, s). |
| 125 | 482.2 | $^1$H NMR (400 MHz, DMSO-d$_6$) δ ppm 8.68 (1 H, s), 7.57-7.65 (1 H, m), 7.53 (1 H, td, J = 7.5, 1.9 Hz), 7.36-7.44 (2 H, m), 6.85 (1 H, dd, J = 16.8, 10.6 Hz), 6.64 (1 H, s), 6.12 (1 H, dd, J = 16.7, 2.4 Hz), 5.69 (1 H, dd, J = 10.5, 2.4 Hz), 4.58-4.68 (1 H, m), 4.27-4.36 (2 H, m), 4.15-4.27 (1 H, m), 3.46-3.57 (1 H, m), 2.84-2.96 (1 H, m), 2.42 (1 H, br s), 1.93 (2 H, br d, J = 12.4 Hz), 1.49-1.68 (2 H, m), 0.88 (9 H, s). $^{19}$F NMR (376 MHz, DMSO-d$_6$) δ ppm −114.30 (1 F, s). |
| 126 | 545.2 | $^1$H NMR (400 MHz, DMSO-d$_6$) δ ppm 8.33 (1 H, d, J = 5.0 Hz), 7.45-7.51 (1 H, m), 7.40-7.45 (1 H, m), 7.35 (1 H, t, J = 7.6 Hz), 7.14-7.32 (4 H, m), 7.05-7.14 (1 H, m), 6.88 (1 H, br s), 6.28 (1 H, d, J = 14.5 Hz), 6.14-6.24 (1 H, m), 5.73-5.78 (1 H, m), 4.32 (1 H, br d, J = 12.4 Hz), 3.97-4.16 (1 H, m), 3.89 (2 H, br d, J = 18.9 Hz), 3.60-3.75 (1 H, m), 3.00 (1 H, br d, J = 8.7 Hz), 2.37-2.44 (1 H, m), 2.08 (1 H, s), 0.99-1.09 (6 H, m), 0.96 (3 H, t, J = 7.3 Hz). $^{19}$F NMR (376 MHz, DMSO-d$_6$) δ ppm −114.06 (1 F, s), −114.17 (1 F, s), −114.20 (1 F, s). |
| 127 | 511.2 | . $^1$H NMR (400 MHz, DMSO-d$_6$) δ ppm 8.37 (1 H, dd, J = 8.3, 3.3 Hz), 7.75 (1 H, d, J = 7.9 Hz), 7.50-7.53 (1 H, m), 7.39-7.49 (3 H, m), 7.26-7.35 (2 H, m), 7.13-7.19 (1 H, m), 7.07-7.13 (1 H, m), 6.82-6.97 (1 H, m), 6.14-6.24 (2 H, m), 5.72-5.79 (1 H, m), 4.29-4.41 (1 H, m), 4.03-4.16 (1 H, m), 3.82-4.01 (3 H, m), 3.59 (1 H, br d, J = 8.5 Hz), 3.01-3.09 (1 H, m), 1.08 (3 H, t, J = 7.4 Hz), 1.02 (3 H, br d, J = 3.3 Hz), 0.95 (2 H, d, J = 6.8 Hz), 0.91 (2 H, d, J = 6.8 Hz). $^{19}$F NMR (376 MHz, DMSO-d$_6$) δ ppm −115.14 (1 F, s), −115.16 (1 F, s), −115.18 (1 F, s). |
| 128 | 541.0 and 543.0 | $^1$H NMR (400 MHz, CDCl$_3$) δ ppm 7.92 (d, J = 7.67 Hz, 1H), 7.76-7.84 (m, 2H), 7.69 (t, J = 15.10 Hz, 1H), 7.36 (d, J = 7.46 Hz, 1H), 6.68-6.71 (m, 1H), 6.59 (dd, J = 10.57, 17.00 Hz, 1H), 6.38 (dd, J = 1.87, 16.79 Hz, 1H), 5.79 (dd, J = 1.87, 10.37 Hz, 1H), 3.74-4.08 (m, 8H). $^{19}$F NMR (376 MHz, CDCl$_3$) δ −61.44 (s, 3F). |
| 129 | 577.0 | $^1$H NMR (400 MHz, DMSO-d$_6$) δ ppm 10.11 (br s, 1 H), 8.56 (s, 1 H), 8.37 (d, J = 4.8 Hz, 1 H), 7.23 (q, J = 8.1 Hz, 1 H), 7.17 (d, J = 4.8 Hz, 1 H), 6.81 (dd, J = 16.7, 10.5 Hz, 1 H), 6.70 (d, J = 8.3 Hz, 1 H), 6.66 (br t, J = 8.8 Hz, 1 H), 6.19 (br d, J = 16.8 Hz, 1 H), 5.71-5.78 (m, 1 H), 4.46-4.78 (m, 1 H), 4.39 (br dd, J = 8.1, 4.8 Hz, 1 H), 4.22 (br d, J = 8.9 Hz, 1 H), 3.96-4.14 (m, 1 H), 3.56-3.92 (m, 3 H), 2.57-2.71 (m, 1 H), 1.93 (br s, 3 H), 1.30 (br s, 3 H), 1.06 (d, J = 6.6 Hz, 3 H), 0.92 (br d, J = 6.4 Hz, 3 H) $^{19}$F NMR (376 MHz, DMSO-d$_6$) δ ppm −115.87 (br d, J = 284.4 Hz, 1 F) |
| 130 | 515.0 | $^1$H NMR (400 MHz, DMSO-d$_6$) δ 8.71 (s, 1 H), 8.23 (s, 1 H), 7.48-7.61 (m, 1 H), 7.28-7.42 (m, 5 H), 7.20 (td, J = 7.5, 1.7 Hz, 1 H), 7.16 (dd, J = 7.1, 1.0 Hz, 1 H), 6.89 (dd, J = 16.7, 10.5 Hz, 1 H), 6.18 (dd, J = 16.7, 2.4 Hz, 1 H), 5.75 (dd, J = 10.4, 2.9 Hz, 1 H), 3.87 (br s, 4 H), 3.52 (br s, |

TABLE 88-continued

Analytical Data

| Ex. # | LRMS: m/z (ESI, +ve ion): (M + H)+ | NMR |
|---|---|---|
| | | 4 H), 2.59 (quin, J = 6.8 Hz, 1 H), 1.03 (d, J = 6.8 Hz, 3 H), 0.98 (d, J = 6.8 Hz, 3 H) |
| 131 | 469.0 | $^1$H NMR (DMSO-d$_6$) δ: 8.58-8.65 (m, 1H), 7.58-7.68 (m, 1H), 7.51-7.60 (m, 1H), 7.36-7.46 (m, 2H), 6.78-6.92 (m, 1H), 6.10-6.24 (m, 1H), 5.69-5.79 (m, 1H), 3.75-3.89 (m, 7H), 3.55-3.65 (m, 4H), 2.46-2.48 (m, 3H) |
| 132 | 590.2 | $^1$H NMR (400 MHz, CHLOROFORM-d) δ 8.05 (s, 1H), 8.01 (br s, 1H), 7.63 (d, J = 7.88 Hz, 1H), 7.45 (t, J = 15.80 Hz, 1H), 7.33-7.40 (m, 1H), 7.02-7.18 (m, 3H), 6.47-6.83 (m, 1H), 6.32-6.44 (m, 1H), 5.79 (d, J = 9.54 Hz, 1H), 2.94-5.17 (m, 7H), 2.73-2.92 (m, 1H), 2.09 (s, 1H), 1.37-1.58 (m, 3H), 1.18-1.25 (m, 3H), 1.05 (d, J = 5.80 Hz, 3H). $^{19}$F NMR (376 MHz, CHLOROFORM-d) δ −112.26 (s, 1F) |
| 133 | 581.8 | $^1$H NMR (400 MHz, CDCl$_3$) δ 8.93 (s, 1 H) 8.12 (s, 1 H) 7.41-7.19 (m, 1 H) 7.15-7.25 (m, 2 H) 7.12 (br t, J = 9.3 Hz, 1 H) 6.52-6.71 (m, 1 H) 6.36-6.46 (m, 1 H) 5.82 (br d, J = 11.0 Hz, 1 H) 4.25-5.29 (m, 3 H) 3.53-4.08 (m, 3 H) 2.75-3.37 (m, 2 H) 1.46-1.60 (m, 3 H) 1.28 (br d, J = 6.2 Hz, 3 H) 1.09 (br d, J = 6.4 Hz, 3 H). $^{19}$F NMR (377 MHz, CDCl$_3$) δ −112.3−−112.6 (m, 1 F). |
| 134 | 531.0 | $^1$H NMR (400 MHz, CDCl$_3$) δ ppm 8.35 (br s, 1 H) 7.33-7.43 (m, 2 H) 7.04-7.25 (m, 6 H) 6.58-6.72 (m, 1 H) 6.39 (dd, J = 16.79, 1.45 Hz, 1 H) 5.77 (dd, J = 10.57, 1.66 Hz, 1 H) 4.00-4.42 (m, 2 H) 3.92-3.98 (m, 3 H) 3.60 (br s, 5 H) 2.07 (d, J = 10.37 Hz, 3 H) 1.29 (br t, J = 5.08 Hz, 3 H). $^{19}$F NMR (376 MHz, DMSO-d$_6$) δ −113.0 (s, 1F). m/z (ESI, +ve) 531.0 (M + H)+. |
| 135 | 559.1 | $^1$H NMR (400 MHz, DMSO-d$_6$) δ 8.86 (s, 1H), 8.37 (d, J = 4.98 Hz, 1H), 7.47-7.53 (m, 1H), 7.15-7.32 (m, 4H), 6.52 (dd, J = 10.16, 17.00 Hz, 1H), 6.18 (dd, J = 2.07, 17.00 Hz, 1H), 5.70-5.76 (m, 1H), 4.86 (br s, 1H), 4.54 (br s, 1H), 4.37 (br d, J = 12.44 Hz, 4H), 2.63-2.76 (m, 2H), 1.91 (s, 3H), 1.72 (d, J = 8.91 Hz, 1H), 1.05 (d, J = 6.63 Hz, 3H), 0.91 (d, J = 6.63 Hz, 3H). $^{19}$F NMR (376 MHz, DMSO-d$_6$) δ −114.25 (s, 1F). |
| 136 | 576.0 | 1H NMR (DMSO-d$_6$) δ: 8.40 (br s, 1H), 7.48-7.60 (m, 1H), 7.22-7.36 (m, 3H), 6.78-6.93 (m, 1H), 6.15-6.25 (m, 2H), 5-70-5.84 (m, 3H), 4.79-5.03 (m, 1H), 4.22-4.49 (m, 2H), 3.96-4.19 (m, 1H), 3.40-3.83 (m, 2H), 3.01-3.29 (m, 2H), 1.73 (s, 3H), 1.29-1.35 (m, 3H), 0.99 (d, J = 6.8 Hz, 3H), 0.86-0.89 (m, 3H) |
| 137 | 577.1 | 1H NMR (DMSO-d6) δ: 11.18-11.46 (m, 1H), 8.41 (br d, J = 3.1 Hz, 1H), 7.55 (br s, 1H), 7.33 (br d, J = 4.8 Hz, 3H), 6.56-6.96 (m, 1H), 6.02-6.28 (m, 2H), 5.76 (br d, J = 9.1 Hz, 1H), 4.76-5.06 (m, 1H), 4.07-4.49 (m, 3H), 3.48-4.06 (m, 3H), 2.87-3.14 (m, 1H), 1.69 (br s, 3H), 1.33 (br d, J = 5.8 Hz, 3H), 1.07 (br s, 3H), 0.94 (br s, 3H). 19F NMR (376 MHz, DMSO-d6) δ −114.09 (s, 1F) |
| 138 | 572.3 | $^1$H NMR (400 MHz, CHLOROFORM-d) δ ppm 8.49 (1 H, s) 7.40-7.52 (2 H, m) 7.12-7.32 (5 H, m) 6.63-6.79 (1 H, m) 6.45 (1 H, d, J = 16.79 Hz) 5.83 (1 H, d, |

TABLE 88-continued

Analytical Data

| Ex. # | LRMS: m/z (ESI, +ve ion): (M + H)+ | NMR |
|---|---|---|
| | | J = 10.40 Hz) 3.56-4.48 (7 H, m) 2.21-2.35 (2 H, m) 1.38 (3 H, br s) 1.11-1.20 (6 H, m) 0.96-1.02 (6 H, m) |
| 139 | 604.6 | $^1$H NMR (400 MHz, DMSO-d$_6$) δ ppm 0.85 (br d, J = 6.01 Hz, 6 H) 1.00 (br d, J = 6.01 Hz, 6 H) 1.33 (br d, J = 6.01 Hz, 3 H) 3.01-3.26 (m, 2 H) 3.42-3.85 (m, 3 H) 3.98-4.47 (m, 3 H) 4.94 (br s, 1 H) 5.76 (br d, J = 10.16 Hz, 1 H) 6.21 (br d, J = 1.00 Hz, 1 H) 6.48 (br s, 2 H) 6.77-6.96 (m, 1 H) 7.18-7.26 (m, 1 H) 7.27-7.41 (m, 2 H) 7.49-7.59 (m, 1 H) 8.43 (br s, 1 H) |
| 140 | 591.2 | $^1$H NMR (400 MHz, DMSO-d$_6$) δ ppm 0.81-0.90 (m, 4 H), 1.01 (d, J = 6.63 Hz, 2 H), 1.32 (br d, J = 6.63 Hz, 3 H), 2.54 (br d, J = 7.05 Hz, 1 H) 2.84 (s, 5 H) 3.00-3.13 (m, 1 H) 3.24 (br s, 1 H) 3.42-3.49 (m, 1 H) 3.56-3.68 (m, 1 H), 3.68-3.85 (m, 1 H) 4.10-4.20 (m, 1 H), 4.21-4.46 (m, 2 H) 4.94 (br s, 1 H) 5.70-5.82 (m, 1 H) 6.18 (br s, 1 H) 6.22 (br s, 1 H) 6.76-6.94 (m, 1 H), 7.23-7.38 (m, 3 H), 7.51-7.61 (m, 1 H) 8.43 (s, 1 H) 8.48 (br s, 1 H). $^{19}$F NMR (376 MHz, DMSO-d$_6$) δ ppm −113.72 (s, 1 F). |
| 140-1 | 591.0 | $^1$H NMR (400 MHz, DMSO-d$_6$) δ ppm 0.86 (d, J = 5.18 Hz, 3 H) 1.02 (d, J = 6.63 Hz, 3 H) 1.32 (d, J = 6.63 Hz, 3 H), 2.84 (s, 6 H) 3.23 (br s, 1 H) 3.64 (br d, J = 14.10 Hz, 1 H) 3.74 (br d, J = 8.29 Hz, 1 H) 4.03 (br d, J = 13.06 Hz, 1 H) 4.09-4.19 (m, 1 H) 4.23-4.46 (m, 2 H), 4.93 (br s, 1 H) 5.78 (br d, J = 2.28 Hz, 1 H) 6.20 (br d, J = 16.59 Hz, 1 H) 6.78-6.94 (m, 1 H) 7.20-7.30 (m, 1 H) 7.31-7.40 (m, 2 H) 7.49-7.61 (m, 1 H), 8.43 (s, 1 H) 8.48 (br s, 1 H). $^{19}$F NMR (376 MHz, DMSO-d$_6$) δ ppm −113.72 (s, 1 F). |
| 140-2 | 591.0 | $^1$H NMR (400 MHz, DMSO-d$_6$) δ ppm 0.85-0.89 (m, 4 H) 1.02 (d, J = 6.63 Hz, 3 H), 1.32 (d, J = 6.63 Hz, 3 H) 2.84 (s, 6 H) 3.22 (br dd, J = 11.51, 1.55 Hz, 1 H) 3.61 (br d, J = 12.85 Hz, 1 H) 3.69-3.84 (m, 1 H) 3.96-4.06 (m, 1 H) 4.10-4.18 (m, 1 H), 4.22-4.43 (m, 2 H) 4.95 (br d, J = 1.87 Hz, 1 H) 5.78 (br d, J = 2.28 Hz, 1 H) 6.20 (br d, J = 16.17 Hz, 1 H) 6.79-6.92 (m, 1 H) 7.22-7.30 (m, 1 H) 7.30-7.39 (m, 2 H) 7.50-7.60 (m, 1 H) 8.43 (s, 1 H) 8.47 (br d, J = 5.60 Hz, 1 H). $^{19}$F NMR (376 MHz, DMSO-d$_6$) δ ppm −113.73 (s, 1 F). |
| 141 | 604.0 | $^1$H NMR (DMSO-d$_6$) δ: 12.68-13.20 (m, 1H), 8.46 (br d, J = 4.6 Hz, 1H), 7.66-7.81 (m, 2H), 7.47-7.53 (m, 1H), 7.18-7.32 (m, 3H), 6.77-6.94 (m, 1H), 6.21 (br d, J = 16.8 Hz, 1H), 5.70-5.82 (m, 1H), 4.95 (br s, 1H), 4.11-4.47 (m, 3H), 4.03 (q, J = 7.0 Hz, 1H), 3.43-3.84 (m, 2H), 3.04-3.19 (m, 1H), 2.55-2.64 (m, 1H), 1.95 (s, 3H), 1.34 (d, J = 6.6 Hz, 3H), 1.08 (d, J = 6.8 Hz, 3H), 0.96 (dd, J = 6.7, 2.0 Hz, 3H). $^{19}$F NMR (DMSO-d$_6$) δ: −114.11 (d, J = 11.3 Hz, 1F) |
| 142-1 | 589.3 | $^1$H NMR (400 MHz, DMSO-d$_6$) δ 8.38 (d, J = 6.22 Hz, 1H), 7.45-7.58 (m, 4H), 7.41 (t, J = 13.70 Hz, 1H), 7.19-7.32 (m, 3H), 7.03 (s, 1H), 6.78-6.94 (m, 1H), 6.21 (dd, J = 6.43, 16.59 Hz, 1H), 5.76 (d, J = 10.37 Hz, 1H), 4.76-4.90 (m, 1H), 4.26-4.49 (m, 1H), 3.98-4.25 (m, 2H), 3.38-3.76 (m, 2H), 2.99-3.30 (m, 1H), 2.64-2.79 (m, 1H), 1.30 (d, J = 6.63 Hz, |

TABLE 88-continued

Analytical Data

| Ex. # | LRMS: m/z (ESI, +ve ion): (M + H)⁺ | NMR |
|---|---|---|
| | | 3H), 0.96-1.16 (m, 6H). ¹⁹F NMR (376 MHz, DMSO-d₆) δ −113.26 (s, 1F). |
| 142-2 | 589.3 | ¹H NMR (400 MHz, DMSO-d₆) δ 8.29-8.37 (m, 1H), 7.38-7.49 (m, 4H), 7.34 (dd, J = 7.88, 15.34 Hz, 1H), 7.10-7.25 (m, 3H), 6.95 (br s, 1H), 6.71-6.86 (m, 1H), 6.14 (d, J = 15.34 Hz, 1H), 5.69 (dd, J = 2.07, 10.37 Hz, 1H), 4.79-4.94 (m, 1H), 3.90-4.40 (m, 3H), 3.28-3.78 (m, 2H), 2.92-3.19 (m, 1H), 2.62-2.74 (m, 1H), 1.23 (d, J = 6.43 Hz, 3H), 1.02 (d, J = 6.84 Hz, 3H), 0.91 (d, J = 7.05 Hz, 3H). ¹⁹F NMR (376 MHz, DMSO-d₆) δ −113.21 (s, 1F). |
| 143 | 542.2 | . ¹H NMR (400 MHz, DMSO-d₆) δ 8.41 (d, J = 4.8 Hz, 1 H), 7.47-7.60 (m, 1 H), 7.26-7.38 (m, 3 H), 7.20 (d, J = 5.0 Hz, 1 H), 6.81-6.95 (m, 1 H), 6.21 (br d, J = 16.8 Hz, 1 H), 5.76 (dd, J = 10.6, 1.9 Hz, 1 H), 4.61-5.43 (m, 1 H), 3.49-4.47 (m, 4 H), 2.68-2.88 (m, 1 H), 2.45 (d, J = 0.6 Hz, 3 H), 1.95 (br d, J = 14.5 Hz, 3 H), 1.34-1.56 (m, 2H), 1.22-1.51 (m, 3 H), 1.07 (t, J = 6.1 Hz, 3 H), 0.94 (dd, J = 6.8, 1.4 Hz, 3 H) |
| 143-1 | 542.2 | ¹H NMR (400 MHz, DMSO-d₆) δ 8.40 (d, J = 4.8 Hz, 1 H), 7.46-7.63 (m, 1 H), 7.26-7.38 (m, 3 H), 7.19 (d, J = 4.8 Hz, 1 H), 6.81-6.95 (m, 1 H), 6.21 (d, J = 17.0 Hz, 1 H), 5.50-6.10 (m, 2 H), 3.47-5.45 (m, 6 H), 2.66 2.77 (m, 1 H), 2.45 (s, 3 H), 1.97 (s, 3 H), 1.27-1.49 (m, 3 H), 1.07 (br d, J = 6.6 Hz, 3 H), 0.94 (br d, J = 6.6 Hz, 3 H) |
| 143-2 | 542.2 | ¹H NMR (400 MHz, DMSO-d₆) 8.41 (d, J = 4.8 Hz, 1 H), 7.47-7.62 (m, 1 H), 7.28-7.39 (m, 3 H), 7.21 (d, J = 5.0 Hz, 1 H), 6.81-6.95 (m, 1 H), 6.21 (br d, J = 16.4 Hz, 1 H), 5.70-6.10 (m, 2 H), 3.64-5.48 (m, 6 H), 2.74-2.89 (m, 1 H), 2.45 (s, 3 H), 1.94 (s, 3 H), 1.20-1.51 (m, 3 H), 1.08 (d, J = 6.8 Hz, 3 H), 0.94 (d, J = 6.6 Hz, 3 H) |
| 144 | 538.2 | ¹H NMR (DMSO-d₆) δ: 8.52-8.71 (m, 1H), 7.57-7.67 (m, 1H), 7.48-7.56 (m, 1H), 7.35-7.45 (m, 2H), 6.82-6.92 (m, 1H), 6.12-6.22 (m, 1H), 5.71-5.75 (m, 1H), 3.77-3.91 (m, 4H), 3.48-3.53 (m, 5H), 2.44-2.46 (m, 4H), 1.45-1.53 (m, 3H), 1.34-1.42 (m, 3H), 1.02-1.09 (m, 3H), 0.88-0.97 (m, 3H) |
| 145 | 618.3 | ¹H NMR (400 MHz, DMSO-d₆) δ ppm: 10.20 (br s, 1H), 8.39 (d, J = 4.98 Hz, 1H), 8.24-8.33 (m, 1H), 7.23-7.31 (m, 1H), 7.19 (d, J = 4.98 Hz, 1H), 6.62-6.76 (m, 4H), 4.91 (br s, 1H), 4.21-4.44 (m, 2H), 3.90-4.19 (m, 1H), 3.43-3.79 (m, 2H), 3.13-3.27 (m, 1H), 3.09 (br d, J = 4.56 Hz, 2H), 2.67-2.76 (m, 1H), 2.19 (s, 6H), 1.90 (s, 3H), 1.35 (d, J = 6.63 Hz, 3H), 1.08 (d, J = 6.63 Hz, 3H), 0.94 (d, J = 6.63 Hz, 3H). ¹⁹F NMR (376 MHz, DMSO-d₆) δ ppm: −115.63 (s, 1F), −128.63 (s, 1F) |
| 146 | 540.0 | ¹H NMR (CHLOROFORM-d) δ: 8.43-8.47 (m, 1H), 7.39-7.48 (m, 3H), 7.27-7.33 (m, 1H), 7.06-7.21 (m, 4H), 6.59-6.73 (m, 1H), 6.30-6.44 (m, 1H), 5.74-5.84 (m, 1H), 3.83-4.06 (m, 4H), 3.62-3.71 (m, 4H), 2.41-2.55 (m, 1H), 1.11-1.16 (m, 3H), 1.03-1.08 (m, 3H) |
| 147 | 558.2 | ¹H NMR (CHLOROFORM-d) δ: 8.44-8.49 (m, 1H), 7.37-7.47 (m, 2H), 7.32-7.35 (m, 2H), 7.27-7.32 (m, 1H), 7.14- |

TABLE 88-continued

| Ex. # | LRMS: m/z (ESI, +ve ion): (M + H)⁺ | NMR |
|---|---|---|
| | | 7.19 (m, 3H), 7.07-7.13 (m, 1H), 6.97-7.01 (m, 1H), 6.59-6.72 (m, 1H), 6.33-6.43 (m, 1H), 5.76-5.85 (m, 1H), 3.86-4.10 (m, 4H), 3.53-3.67 (m, 4H), 2.40-2.52 (m, 1H), 1.08-1.11 (m, 3H), 0.96-1.01 (m, 3H) |
| 148 | 565.2 | ¹H NMR (CHLOROFORM-d) δ: 8.42-8.51 (m, 1H), 7.37-7.45 (m, 3H), 7.27-7.31 (m, 1H), 7.19-7.25 (m, 1H), 7.05-7.19 (m, 3H), 6.58-6.74 (m, 1H), 6.17-6.53 (m, 2H), 5.71-5.84 (m, 1H), 3.85-4.06 (m, 4H), 3.59-3.75 (m, 4H), 2.41-2.53 (m, 1H), 0.99-1.07 (m, 6H) |
| 149 | 552.2 | ¹H NMR (CHLOROFORM-d) δ: 8.36-8.42 (m, 1H), 7.45-7.59 (m, 2H), 7.27-7.30 (m, 1H), 7.14-7.24 (m, 1H), 6.57-6.72 (m, 1H), 6.33-6.43 (m, 1H), 5.74-5.84 (m, 1H), 4.89-4.97 (m, 1H), 4.67-4.75 (m, 1H), 4.43-4.54 (m, 1H), 3.75-4.08 (m, 5H), 3.63-3.76 (m, 5H), 1.51-1.62 (m, 2H), 1.42-1.49 (m, 2H), 1.21-1.26 (m, 3H), 0.85-0.92 (m, 3H) |
| 150 | 441.2 | ¹H NMR (DMSO-d₆) δ: 8.58-8.63 (m, 1H), 7.58-7.70 (m, 2H), 7.49-7.55 (m, 1H), 7.38-7.46 (m, 2H), 6.78-6.96 (m, 1H), 6.13-6.25 (m, 1H), 5.70-5.80 (m, 1H), 5.47-5.56 (m, 1H), 4.55-4.69 (m, 2H), 4.08-4.23 (m, 2H), 3.72-4.08 (m, 3H), 3.56-3.69 (m, 1H), 3.45-3.55 (m, 1H), 1.03-1.11 (m, 3H) |
| 151 | 577.2 | ¹H NMR (400 MHz, DMSO-d₆) δ ppm 8.48 (br d, J = 4.6 Hz, 1 H), 8.12 (d, J = 6.6 Hz, 1 H), 7.50-7.57 (m, 1 H), 7.22-7.36 (m, 4 H), 6.79-6.93 (m, 1 H), 6.21 (br d, J = 16.8 Hz, 1 H), 5.73-5.80 (m, 1 H), 4.97 (br s, 1 H), 4.24-4.45 (m, 2 H), 3.99-4.20 (m, 1 H), 3.40-3.87 (m, 2 H), 3.05-3.29 (m, 1 H), 2.85-3.04 (m, 1 H), 1.87 (s, 3 H), 1.34 (d, J = 6.6 Hz, 3 H), 1.22 (br d, J = 6.6 Hz, 3 H), 1.12 (d, J = 6.8 Hz, 3 H) ¹⁹F NMR (376 MHz, DMSO-d₆) δ ppm −114.03 (s, 1 F) |
| 152 | 604.0 | ¹H NMR (400 MHz, DMSO-d₆) δ ppm 8.48 (d, J = 5.0 Hz, 1 H), 8.46 (br s, 1 H), 7.45-7.54 (m, 1 H), 7.22-7.34 (m, 3 H), 7.16 (td, J = 7.4, 1.6 Hz, 1 H), 6.79-6.93 (m, 1 H), 6.21 (br d, J = 16.2 Hz, 1 H), 5.73-5.80 (m, 1 H), 4.95 (br s, 1 H), 4.23-4.47 (m, 2 H), 3.99-4.21 (m, 1 H), 3.41-3.83 (m, 3 H), 2.98-3.08 (m, 2 H), 2.74 (dt, J = 13.3, 6.6 Hz, 1 H), 1.91 (s, 6 H), 1.34 (br d, J = 6.6 Hz, 3 H), 1.08 (d, J = 6.6 Hz, 3 H), 0.96 (d, J = 6.6 Hz, 3 H) ¹⁹F NMR (376 MHz, DMSO-d₆) δ ppm −114.42 (s, 1 F) |
| 153 | 515.9 | ¹H NMR (400 MHz, DMSO-d₆) δ 8.35 (d, J = 7.9 Hz, 1 H), 7.44-7.56 (m, 1 H), 7.19-7.37 (m, 6 H), 7.12-7.18 (m, 1 H), 6.82-6.96 (m, 1 H), 6.19 (dd, J = 16.4, 6.4 Hz, 1 H), 5.74 (dd, J = 10.6, 2.1 Hz, 1 H), 5.44 (br d, J = 4.6 Hz, 2 H), 3.57-4.24 (m, 5 H), 3.32-3.53 (m, 2 H), 1.99 (d, J = 16.6 Hz, 3 H), 1.12 (br d, J = 4.8 Hz, 3 H) |
| 154 | 518.9 | ¹H NMR (400 MHz, CDCl₃) δ 8.38 (s, 1 H), 7.35-7.50 (m, 2 H), 7.27-7.32 (m, 4 H), 7.20 (td, J = 7.7, 0.8 Hz, 1 H), 7.12 (t, J = 9.1 Hz, 1 H), 6.52-6.77 (m, 1 H), 6.38 (dd, J = 16.9, 1.76 Hz, 1 H), 5.78 (dd, J = 10.6, 1.7 Hz, 1 H), 4.19-4.58 (m, 2 H), 3.42-4.08 (m, 5 H), 2.12 (d, J = 13.5 Hz, 3 H), 1.32 (br t, J = 5.5 Hz, 3 H). |

TABLE 88-continued

Analytical Data

| Ex. # | LRMS: m/z (ESI, +ve ion): (M + H)+ | NMR |
|---|---|---|
| 155 | 561.2 | ¹H NMR (400 MHz, CDCl₃) δ 8.05 (s, 1H), 7.34-7.45 (m, 1H), 7.04-7.25 (m, 4H), 6.84 (d, J = 7.67 Hz, 1H), 6.71 (d, J = 7.88 Hz, 1H), 6.51-6.66 (m, 1H), 6.40 (d, J = 15.55 Hz, 1H), 5.80 (d, J = 12.02 Hz, 1H), 4.19-5.22 (m, 3H), 3.47-4.07 (m, 3H), 2.92-3.34 (m, 1H), 2.34-2.77 (m, 3H), 1.51 (d, J = 24.26 Hz, 3H), 1.13 (d, J = 6.84 Hz, 3H), 0.98 (dd, J = 1.87, 6.43 Hz, 3H). ¹⁹F NMR (376 MHz, CDCl₃) δ −111.78 (s, 1F). |
| 155-1 | 561.2 | 561.2 (M + H)⁺. ¹H NMR (400 MHz, DMSO-d₆) δ 8.38 (s, 1H), 7.48-7.58 (m, 1H), 7.25-7.37 (m, 2H), 7.17-7.25 (m, 1H), 6.99 (dd, J = 7.88, 15.76 Hz, 1H), 6.80-6.93 (m, 1H), 6.53 (d, J = 3.32 Hz, 1H), 6.51 (d, J = 3.94 Hz, 1H), 6.22 (d, J = 16.79 Hz, 1H), 5.77 (dd, J = 2.07, 10.16 Hz, 1H), 4.97 (br s, 1H), 4.89 (br s, 2H), 4.23-4.48 (m, 1H), 3.97-4.22 (m, 2H), 3.73-3.91 (m, 1H), 3.34-3.69 (m, 1H), 2.96-3.30 (m, 1H), 2.30 (q, J = 25.70 Hz, 1H), 1.32 (d, J = 6.22 Hz, 3H), 1.02 (d, J = 7.05 Hz, 3H), 0.91 (d, J = 6.43 Hz, 3H). ¹⁹F NMR (376 MHz, DMSO-d₆) δ −113.44 (s, 1F). |
| 155-2 | 561.2 | ¹H NMR (400 MHz, DMSO-d₆) δ 8.30 (d, J = 7.26 Hz, 1H), 7.48-7.57 (m, 1H), 7.26-7.36 (m, 2H), 7.19-7.25 (m, 1H), 6.99 (dd, J = 7.88, 15.55 Hz, 1H), 6.78-6.95 (m, 1H), 6.55 (d, J = 0.83 Hz, 1H), 6.51 (d, J = 1.24 Hz, 1H), 6.15-6.27 (m, 1H), 5.77 (dd, J = 2.07, 10.16 Hz, 1H), 4.89 (br s, 2H), 4.75 (br s, 1H), 4.25-4.51 (m, 2H), 3.99-4.23 (m, 1H), 3.43-3.69 (m, 2H), 3.06-3.26 (m, 1H), 2.33 (q, J = 26.50 Hz, 1H), 1.38 (d, J = 6.43 Hz, 3H), 1.02 (d, J = 6.84 Hz, 3H), 0.91 (d, J = 6.84 Hz, 3H). ¹⁹F NMR (376 MHz, DMSO-d₆) δ −113.33 (s, 1F). |
| 156 | 618.0 | ¹H NMR (400 MHz, DMSO-d₆) δ 8.46 (br s, 1H), 7.71-7.83 (m, 2H), 7.50 (br d, J = 6.2 Hz, 1H), 7.24-7.34 (m, 2H), 7.16-7.23 (m, 1H), 6.79-6.92 (m, 1H), 6.21 (br d, J = 16.8 Hz, 1H), 5.76 (br d, J = 10.6 Hz, 1H), 4.95 (br s, 1H), 4.24-4.46 (m, 2H), 3.99-4.21 (m, 1H), 3.85 (s, 3H), 3.77 (br d, J = 9.1 Hz, 1H), 3.43-3.69 (m, 1H), 3.04-3.25 (m, 1H), 2.61 (br d, J = 5.8 Hz, 1H), 1.96 (br s, 3H), 1.34 (br d, J = 6.4 Hz, 3H), 1.08 (br d, J = 6.4 Hz, 3H), 0.96 (br d, J = 6.4 Hz, 3H). ¹⁹F NMR (DMSO-d₆) δ −114.16 (br d, J = 11.3 Hz, 1F) |
| 157 | 512.4 | ¹H NMR (400 MHz, CHLOROFORM-d) δ 7.44-7.50 (m, 2H), 7.28-7.36 (m, 1H), 7.22 (t, J = 7.88 Hz, 2H), 7.10-7.16 (m, 1H), 6.86 (t, J = 7.26 Hz, 1H), 6.68 (br d, J = 7.67 Hz, 2H), 6.35 (br t, J = 15.96 Hz, 1H), 5.75 (br t, J = 10.26 Hz, 1H), 4.85-5.02 (m, 1H), 4.19-4.44 (m, 1H), 3.89-4.05 (m, 1H), 3.75-3.89 (m, 1H), 3.49-3.74 (m, 4H), 3.30-3.46 (m, 1H), 3.03-3.28 (m, 1H), 2.80-2.93 (m, 1H), 2.54-2.80 (m, 2H), 1.77 (td, J = 6.63, 13.27 Hz, 1H), 1.17-1.31 (m, 12H) |

For compounds in Table 89, the following assay conditions were employed:

Coupled Nucleotide Exchange Assay:

Purified GDP-bound KRAS protein (aa 1-169), containing both G12C and C118A amino acid substitutions and an N-terminal His-tag. was pre-incubated in assay buffer (25 mM HEPES pH 7.4, 10 mM MgCl₂, and 0.01% Triton X-100) with a compound dose-response titration for either 5 min or 2 hours (see Table 15). Following compound pre-incubation. purified SOS protein (aa 564-1049) and GTP (Roche 10106399001) were added to the assay wells and incubated for an additional 30 min (for 5 min compound pre-incubation) or 1 hour (for 2 hour compound pre-incubation). To determine the extent of inhibition of SOS-mediated nucleotide exchange, purified GST-tagged cRAF (aa 1-149), nickel chelate AlphaLISA acceptor beads (PerkinElmer AL108R), and AlphaScreen glutathione donor beads (PerkinElmer 6765302) were added to the assay wells and incubated for 10 minutes. The assay plates were then read on a PerkinElmer EnVision Multilabel Reader, using AlphaScreen® technology, and data were analyzed using a 4-parameter logistic model to calculate $IC_{50}$ values.

Phospho-ERK1/2 MSD Assay:

MIA PaCa-2 (ATCC® CRL-1420™) and A549 (ATCC® CCL-185™) cells were cultured in RPMI 1640 Medium (ThermoFisher Scientific 11875093) containing 10% fetal bovine serum (ThermoFisher Scientific 16000044) and 1× penicillin-streptomycin-glutamine (ThermoFisher Scientific 10378016). Sixteen hours prior to compound treatment, MIA PaCa-2 or A549 cells were seeded in 96-well cell culture plates at a density of 25,000 cells/well and incubated at 37° C., 5% $CO_2$. A compound dose-response titration was diluted in growth media, added to appropriate wells of a cell culture plate, and then incubated at 37° C., 5% $CO_2$ for 2 or 4 hours (see Table 15). Following compound treatment, cells were stimulated with 10 ng/mL EGF (Roche 11376454001) for 10 min, washed with ice-cold Dulbecco's phosphate-buffered saline, no $Ca^{2+}$ or $Mg^{2+}$ (ThermoFisher Scientific 14190144), and then lysed in RIPA buffer (50 mM Tris-HCl pH 7.5, 1% Igepal, 0.5% sodium deoxycholate, 150 mM NaCl, and 0.5% sodium dodecyl sulfate) containing protease inhibitors (Roche 4693132001) and phosphatase inhibitors (Roche 4906837001). Phosphorylation of ERK1/2 in compound-treated lysates was assayed using Phospho-ERK1/2 Whole Cell Lysate kits (Meso Scale Discovery K151DWD) according to the manufacturer's protocol. Assay plates were read on a Meso Scale Discovery Sector Imager 6000, and data were analyzed using a 4-parameter logistic model to calculate $IC_{50}$ values.

TABLE 89

Biochemical and cellular activity of compounds

| Ex. # | Coupled exchange IC50 (5 min \| 2 h; μM) | p-ERK IC50 (2 h \| 4 h; MIA PaCa-2, μM) | p-ERK IC50 (2 h \| 4 h; A549, μM) |
|---|---|---|---|
| 8-8 | 0.653 \| 0.117 | 0.327 \| 0.143 | nda \| 100 |
| 9-17 | nda \| 0.289 | nda \| 1.11 | nda \| 74.4 |
| 9-17-1 | nda \| 0.607 | nda \| 2.18 | nda \| 75.8 |
| 9-17-2 | 1.66 \| 0.163 | 1.06 \| 0.859 | 10 \| 100 |
| 54-1 | 0.225 \| nda | 0.109 \| nda | 10 \| nda |
| 54-2 | nda \| 0.167 | 66.6 \| 55.6 | 100 \| 100 |
| 54-3 | nda \| 0.781 | nda \| 8.58 | nda \| 100 |
| 54-4 | nda \| 0.218 | 2.25 \| nda | 48.9 \| nda |
| 54-5 | 0.445 \| nda | 0.554 \| nda | 10 \| nda |
| 54-6 | 0.306 \| nda | 0.528 \| nda | 10 \| nda |
| 54-7 | 1.75 \| nda | nda | nda |
| 54-8 | nda \| 250 | nda | nda |
| 54-9 | 0.147 \| nda | 0.086 \| nda | 10 \| nda |
| 54-9-1 | 0.302 \| nda | 0.076 \| nda | 10 \| nda |
| 54-9-2 | 0.046 \| nda | 0.034 \| nda | 10 \| nda |
| 54-10 | 0.185 \| nda | 0.182 \| nda | 10 \| nda |
| 54-10-1 | 1.21 \| nda | nda | nda |
| 54-10-2 | 0.071 \| nda | 0.06 \| nda | nda |
| 54-11 | 0.069 \| nda | 0.063 \| nda | 10 \| nda |
| 54-11-1 | 0.049 \| nda | 0.054 \| nda | nda |
| 54-11-2 | 0.343 \| nda | 0.174 \| nda | nda |
| 54-12 | 0.289 \| nda | 0.162 \| nda | 10 \| nda |
| 54-12-1 | 0.13 \| nda | 0.078 \| nda | nda |
| 54-12-2 | 0.949 \| nda | 0.689 \| nda | nda |
| 54-13 | 0.811 \| nda | 2.56 \| nda | 10 \| nda |
| 54-14 | 12.4 \| nda | nda | nda |
| 54-15 | 0.564 \| nda | 0.347 \| nda | nda |
| 54-16 | 0.149 \| nda | 0.149 \| nda | nda |
| 54-17 | 0.085 \| nda | 0.504 \| nda | nda |
| 54-17-1 | 0.299 \| nda | 0.413 \| nda | nda |
| 54-17-2 | 0.023 \| nda | 0.065 \| nda | nda |
| 54-18 | 0.087 \| nda | 0.081 \| nda | nda |
| 54-18-1 | 0.044 \| nda | 0.036 \| nda | nda |
| 54-18-2 | 0.729 \| nda | 0.643 \| nda | nda |
| 54-19 | 12.2 \| nda | nda | nda |
| 54-20 | 2.26 \| nda | nda | nda |
| 54-21 | 1.67 \| nda | 2.48 \| nda | nda |
| 54-22 | 0.347 \| 0.097 | 0.245 \| nda | 33.3 \| nda |
| 54-23 | 0.103 \| nda | 0.122 \| nda | 10 \| nda |
| 54-24 | 0.797 \| nda | 0.942 \| nda | 10 \| nda |
| 54-25 | 0.164 \| nda | 0.218 \| nda | nda |
| 54-26 | 0.105 \| nda | 0.22 \| nda | nda |
| 54-27 | 0.03 \| nda | 0.011 \| nda | nda |
| 54-27-1 | 0.021 \| nda | 0.011 \| nda | nda |
| 54-27-2 | 0.198 \| nda | 0.115 \| nda | nda |
| 54-28 | 0.19 \| nda | 0.245 \| nda | nda |
| 54-29 | 0.406 \| nda | 0.717 \| nda | nda |
| 54-30 | 0.824 \| nda | 0.453 \| nda | 10 \| nda |
| 54-31 | 0.395 \| nda | 0.237 \| nda | 10 \| nda |
| 54-32 | 1.963 \| nda | 0.796 \| nda | 10 \| nda |
| 54-33 | 0.176 \| nda | 0.215 \| nda | 10 \| nda |
| 54-34 | 0.325 \| nda | 0.097 \| nda | nda |
| 54-35 | 0.582 \| nda | 0.383 \| nda | nda |
| 54-36 | 0.149 \| nda | 0.158 \| nda | nda |
| 54-37 | 0.304 \| nda | 0.227 \| nda | nda |
| 54-38 | 0.651 \| nda | 0.297 \| nda | nda |
| 54-39 | 32.1 \| nda | nda | nda |
| 54-40 | 21.3 \| nda | nda | nda |
| 54-41 | 0.724 \| nda | 2.895 \| nda | 10 \| nda |
| 54-42 | 0.79 \| nda | 0.322 \| nda | nda |
| 54-43 | 0.426 \| nda | 0.251 \| nda | nda |
| 54-43-1 | 4.85 \| nda | nda | nda |
| 54-43-2 | 0.173 \| nda | 0.146 \| nda | nda |
| 54-44 | 3.9 \| nda | nda | nda |
| 54-45 | 132 \| nda | nda | nda |
| 54-46 | 7.24 \| nda | nda | nda |
| 54-47 | 10.7 \| nda | nda | nda |
| 54-48 | 0.779 \| nda | 2.38 \| nda | 10 \| nda |
| 54-49 | 5.65 \| nda | nda | nda |
| 54-50 | 88.8 \| nda | nda | nda |
| 54-51 | 0.265 \| nda | 0.204 \| nda | nda |
| 54-51-1 | 0.108 \| nda | 0.263 \| nda | nda |
| 54-51-2 | 1.84 \| nda | \| nda | nda |
| 54-52 | 0.445 \| nda | 0.666 \| nda | nda |
| 54-53 | 0.193 \| nda | 0.593 \| nda | nda |
| 54-54 | 0.377 \| nda | 0.36 \| nda | nda |
| 54-55 | 0.133 \| nda | 0.578 \| nda | nda |
| 54-56 | 1.42 \| nda | nda | nda |
| 54-56-1 | 2.49 \| nda | nda | nda |
| 54-56-2 | 1.24 \| nda | nda | nda |
| 54-57 | 0.083 \| nda | 0.053 \| nda | 10 \| nda |
| 54-58 | 3.44 \| nda | nda | nda |
| 54-59 | 0.22 \| nda | 0.712 \| nda | 10 \| nda |
| 54-60 | 0.216 \| 0.093 | 0.145 \| 0.091 | 10 \| 11.1 |
| 54-61 | nda \| 0.379 | nda \| 1.37 | nda \| 11.1 |
| 54-62 | 0.808 \| 0.172 | 0.407 \| 0.223 | 10 \| 100 |
| 54-63 | 0.845 \| 0.164 | 0.291 \| 0.136 | nda \| 33.3 |
| 54-64 | nda \| 7.97 | nda | nda |
| 54-65 | 0.253 \| 0.054 | 0.14 \| 0.133 | 10 \| 100 |
| 54-66 | nda \| 0.104 | 0.1 \| 0.122 | 10 \| 100 |
| 54-67 | nda \| 0.175 | 10 \| nda | 10 \| nda |
| 54-68 | 4.65 \| nda | nda | nda |
| 54-69 | 0.306 \| nda | 0.199 \| nda | 10 \| nda |
| 54-70 | 0.057 \| nda | 0.088 \| nda | nda |
| 54-71 | 0.174 \| nda | 0.164 \| nda | nda |
| 54-71-1 | 0.053 \| nda | 0.127 \| nda | nda |
| 54-71-2 | 0.108 \| nda | 0.179 \| nda | nda |
| 54-72 | 0.108 \| nda | 0.183 \| nda | nda |

TABLE 89-continued

Biochemical and cellular activity of compounds

| Ex. # | Coupled exchange IC50 (5 min \| 2 h; µM) | p-ERK IC50 (2 h \| 4 h; MIA PaCa-2, µM) | p-ERK IC50 (2 h \| 4 h; A549, µM) |
|---|---|---|---|
| 54-73 | 0.062 \| nda | 0.064 \| nda | nda |
| 54-73-1 | 0.025 \| nda | 0.038 \| nda | nda |
| 54-73-2 | 0.368 \| nda | 0.927 \| nda | nda |
| 54-74 | 0.582 \| nda | 0.926 \| nda | nda |
| 54-75 | 1.08 \| nda | nda | nda |
| 54-75-1 | 0.419 \| nda | 0.853 \| nda | nda |
| 54-75-2 | 10.6 \| nda | nda | nda |
| 54-76 | 5.48 \| nda | nda | nda |
| 54-77 | 0.218 \| nda | 0.158 \| nda | nda |
| 54-77-1 | 2.71 \| nda | nda | nda |
| 54-77-2 | 0.136 \| nda | 0.176 \| nda | nda |
| 54-78 | 0.326 \| nda | 0.171 \| nda | nda |
| 54-78-1 | 7.26 \| nda | nda | nda |
| 54-78-2 | 0.212 \| nda | 0.311 \| nda | nda |
| 54-79 | 0.072 \| nda | 0.098 \| nda | nda |
| 54-80 | nda \| 1.99 | nda \| 5.64 | nda \| 100 |
| 54-82 | nda \| 2.6 | nda | nda |
| 54-84 | nda \| 0.11 | 0.054 \| 0.084 | 100 \| 100 |
| 54-84-1 | nda \| 0.26 | 0.744 \| nda | 100 \| nda |
| 54-84-2 | nda \| 0.066 | 0.056 \| nda | 100 \| nda |
| 54-85 | nda \| 0.107 | 0.16 \| nda | 100 \| nda |
| 54-85-1 | 3.4 \| nda | 1.51 \| nda | nda |
| 54-85-2 | 0.078 \| nda | 0.079 \| nda | nda |
| 54-86 | 0.102 \| 0.128 | 0.09 \| nda | 33.3 \| nda |
| 54-86-1 | nda \| 0.273 | 0.67 \| nda | 10 \| nda |
| 54-86-2 | 0.067 \| 0.035 | 0.066 \| nda | 10 \| nda |
| 54-87 | 0.109 \| nda | 0.066 \| nda | 10 \| nda |
| 54-88 | 0.139 \| nda | 0.101 \| nda | 10 \| nda |
| 54-88-1 | 0.077 \| nda | 0.084 \| nda | nda |
| 54-88-2 | 1.36 \| nda | nda | nda |
| 54-89 | 0.271 \| nda | 0.212 \| nda | nda |
| 54-90 | 0.105 \| nda | 0.121 \| nda | nda |
| 54-90-1 | 0.047 \| nda | 0.063 \| nda | nda |
| 54-90-2 | 0.633 \| nda | 0.568 \| nda | nda |
| 54-91 | 0.033 \| nda | 0.039 \| nda | nda |
| 54-91-1 | 0.021 \| nda | 0.033 \| nda | nda |
| 54-91-2 | 0.181 \| nda | 0.509 \| nda | nda |
| 54-92 | 1.27 \| nda | nda | nda |
| 54-93 | 1.43 \| nda | nda | nda |
| 54-94 | 1.19 \| nda | nda | nda |
| 54-95 | 0.756 \| nda | 0.821 \| nda | nda |
| 54-96 | 0.676 \| nda | 0.363 \| nda | nda |
| 54-97 | 0.128 \| nda | 0.256 \| nda | nda |
| 54-97-1 | 0.971 \| nda | 1.02 \| nda | nda |
| 54-97-2 | 0.044 \| nda | 0.141 \| nda | nda |
| 54-98 | 5.45 \| nda | nda | nda |
| 54-99 | 0.153 \| nda | 0.294 \| nda | nda |
| 54-99-1 | 1.52 \| nda | nda | nda |
| 54-99-2 | 0.094 \| nda | 0.174 \| nda | nda |
| 54-100 | 2.51 \| nda | nda | nda |
| 54-101 | 0.162 \| nda | 0.157 \| nda | nda |
| 54-102 | 0.161 \| nda | 0.176 \| nda | nda |
| 54-103 | 0.136 \| nda | 0.173 \| nda | nda |
| 54-103-1 | 0.073 \| nda | 0.093 \| nda | nda |
| 54-103-2 | 1.48 \| nda | nda | nda |
| 54-104 | 0.09 \| nda | 0.07 \| nda | nda |
| 54-104-1 | 0.743 \| nda | nda | nda |
| 54-104-2 | 0.035 \| nda | 0.21 \| nda | nda |
| 54-105 | 0.07 \| nda | 0.089 \| nda | nda |
| 54-106 | 0.51 \| nda | nda | nda |
| 54-107 | 0.159 \| nda | 0.099 \| nda | nda |
| 54-107-1 | 0.731 \| nda | nda | nda |
| 54-107-2 | 0.067 \| nda | 0.048 \| nda | nda |
| 54-108 | 0.434 \| nda | 3.77 \| nda | nda |
| 54-109 | 0.355 \| nda | nda | nda |
| 54-110 | 0.404 \| nda | 0.408 \| nda | nda |
| 54-110-1 | 7.71 \| nda | nda | nda |
| 54-110-2 | 0.194 \| nda | 0.119 \| nda | nda |
| 54-111 | 0.417 \| nda | 0.791 \| nda | nda |
| 54-112 | 0.084 \| nda | 0.222 \| nda | nda |
| 54-112-1 | 0.075 \| nda | 0.125 \| nda | nda |
| 54-112-2 | 5.02 \| nda | nda | nda |
| 55-1 | 0.124 \| nda | 0.226 \| nda | nda |
| 55-2 | 0.021 \| nda | 0.025 \| nda | nda |
| 55-3 | 0.966 \| nda | 0.918 \| nda | nda |
| 55-4 | 0.057 \| nda | 0.08 \| nda | nda |
| 55-4-1 | 0.023 \| nda | 0.037 \| nda | nda |
| 55-4-2 | 0.642 \| nda | nda | nda |
| 55-5 | 0.045 \| nda | 0.031 \| nda | nda |
| 55-6 | 0.318 \| nda | 0.317 \| nda | nda |
| 55-7 | 0.806 \| nda | nda | nda |
| 55-7-1 | 0.863 \| nda | nda | nda |
| 55-7-2 | 0.325 \| nda | 0.587 \| nda | nda |
| 55-8 | 0.127 \| nda | 0.025 \| nda | nda |
| 55-8-1 | 0.04 \| nda | 0.045 \| nda | nda |
| 55-8-2 | 0.27 \| nda | 0.16 \| nda | nda |
| 55-9 | 0.24 \| nda | 0.214 \| nda | nda |
| 55-9-1 | 0.804 \| nda | 1.35 \| nda | nda |
| 55-9-2 | 0.158 \| nda | 0.298 \| nda | nda |
| 55-10 | 0.123 \| nda | 0.156 \| nda | nda |
| 55-10-1 | 0.065 \| nda | 0.082 \| nda | nda |
| 55-10-2 | 0.266 \| nda | 0.344 \| nda | nda |
| 55-11 | 0.309 \| nda | 0.235 \| nda | nda |
| 55-12 | 0.583 \| nda | 0.775 \| nda | nda |
| 55-13 | 0.191 \| nda | 0.179 \| nda | nda |
| 55-13-1 | 0.722 \| nda | nda | nda |
| 55-13-2 | 0.02 \| nda | 0.055 \| nda | 10 \| nda |
| 55-14 | 0.086 \| nda | 0.134 \| nda | nda |
| 55-14-1 | 0.407 \| nda | 1.09 \| nda | nda |
| 55-14-2 | 0.03 \| nda | 0.038 \| nda | nda |
| 55-15 | 0.055 \| nda | 0.092 \| nda | nda |
| 55-15-1 | 0.169 \| nda | 0.206 \| nda | nda |
| 55-15-2 | 0.061 \| nda | 0.076 \| nda | nda |
| 55-16 | 0.154 \| nda | 0.199 \| nda | nda |
| 55-16-1 | 1.05 \| nda | nda | nda |
| 55-16-2 | 0.039 \| nda | 0.123 \| nda | 10 \| nda |
| 55-17 | 0.18 \| nda | 0.123 \| nda | nda |
| 55-18 | 0.067 \| nda | 0.083 \| nda | nda |
| 55-19 | 0.22 \| nda | 0.191 \| nda | nda |
| 55-20 | 0.695 \| nda | 2.67 \| nda | nda |
| 55-21 | 0.444 \| nda | 10 \| nda | nda |
| 55-22 | 0.653 \| nda | 0.303 \| nda | nda |
| 55-23 | 0.208 \| nda | 0.26 \| nda | nda |
| 55-23-1 | 18.55 \| nda | nda | nda |
| 55-23-2 | 0.062 \| nda | 0.077 \| nda | 10 \| nda |
| 55-24 | 0.113 \| nda | 0.074 \| nda | nda |
| 55-25 | 2.29 \| nda | nda | nda |
| 55-26 | 0.091 \| nda | 0.215 \| nda | nda |
| 55-26-1 | 36.9 \| nda | nda | nda |
| 55-26-2 | 0.031 \| nda | 0.124 \| nda | nda |
| 55-27 | nda | nda | nda |
| 55-28 | 12.9 \| nda | nda | nda |
| 55-29 | 7.19 \| nda | nda | nda |
| 55-30 | 1.95 \| nda | 1.61 \| nda | 10 \| nda |
| 55-31 | 0.098 \| nda | 0.079 \| nda | nda |
| 55-32 | 3.07 \| nda | nda | nda |
| 55-33 | 45.8 \| nda | nda | nda |
| 55-34 | 20.8 \| nda | nda | nda |
| 55-35 | 0.225 \| nda | 0.252 \| nda | nda |
| 55-36 | 38.6 \| nda | nda | nda |
| 55-37 | 0.03 \| nda | 0.057 \| nda | nda |
| 55-38 | 0.377 \| nda | nda | nda |
| 55-38-1 | 0.534 \| nda | nda | nda |
| 55-38-2 | 0.133 \| nda | 0.108 \| nda | nda |
| 55-39 | 0.292 \| nda | 0.271 \| nda | nda |
| 55-39-1 | 1.795 \| nda | nda | nda |
| 55-39-2 | 0.121 \| nda | 0.111 \| nda | nda |
| 55-40 | 0.1 \| nda | 0.149 \| nda | nda |
| 55-40-1 | 1.02 \| nda | nda | nda |
| 55-40-2 | 0.078 \| nda | 0.081 \| nda | nda |
| 55-41 | 0.292 \| nda | 0.908 \| nda | nda |
| 55-42 | 0.351 \| nda | nda | nda |
| 55-43 | 0.073 \| nda | 0.07 \| nda | nda |
| 55-43-1 | 2.87 \| nda | nda | nda |
| 55-43-2 | 0.022 \| nda | 0.032 \| nda | nda |
| 56-1 | 0.149 \| nda | 0.359 \| nda | nda |
| 56-1-1 | 5.29 \| nda | nda | nda |
| 56-1-2 | 0.068 \| nda | 0.145 \| nda | nda |

TABLE 89-continued

Biochemical and cellular activity of compounds

| Ex. # | Coupled exchange IC50 (5 min \| 2 h; μM) | p-ERK IC50 (2 h \| 4 h; MIA PaCa-2, μM) | p-ERK IC50 (2 h \| 4 h; A549, μM) |
|---|---|---|---|
| 56-2 | 0.061 \| nda | 0.052 \| nda | nda |
| 56-3 | 3.85 \| nda | nda | nda |
| 56-4 | 5.32 \| nda | nda | nda |
| 56-5 | 0.433 \| nda | 0.74 \| nda | nda |
| 56-5-1 | 0.154 \| nda | 0.188 \| nda | nda |
| 56-5-2 | 0.668 \| nda | 0.823 \| nda | nda |
| 56-6 | 0.125 \| nda | 0.084 \| nda | nda |
| 56-7 | 0.11 \| nda | 0.069 \| nda | nda |
| 56-7-1 | 0.079 \| nda | 0.029 \| nda | nda |
| 56-7-2 | 0.676 \| nda | 0.134 \| nda | nda |
| 56-8 | 1.56 \| nda | nda | nda |
| 56-9 | 0.269 \| nda | 0.16 \| nda | nda |
| 56-10 | 0.332 \| nda | 0.26 \| nda | nda |
| 57-1 | 0.835 \| nda | 0.171 \| nda | nda |
| 57-1-1 | 0.524 \| nda | 0.63 \| nda | nda |
| 57-1-2 | 2.47 \| nda | nda | nda |
| 57-2 | 0.74 \| nda | 0.3 \| nda | nda |
| 57-3 | 0.664 \| nda | 0.241 \| nda | nda |
| 57-4 | 0.1 \| nda | 0.061 \| nda | nda |
| 57-5 | 0.221 \| nda | 0.107 \| nda | nda |
| 57-6 | 1.67 \| nda | nda | nda |
| 57-6-1 | 3.163 \| nda | 2.09 \| nda | nda |
| 57-6-2 | 0.208 \| nda | 0.099 \| nda | 10 \| nda |
| 57-7 | 0.991 \| nda | 0.45 \| nda | 10 \| nda |
| 57-7-1 | 8.89 \| nda | nda | nda |
| 57-7-2 | 0.384 \| nda | 0.236 \| nda | 10 \| nda |
| 57-8-1 | 125 \| nda | nda | nda |
| 57-8-2 | 0.514 \| nda | 0.166 \| nda | nda |
| 57-9 | 0.752 \| nda | 0.239 \| nda | nda |
| 57-10 | 0.452 \| nda | 0.105 \| nda | nda |
| 57-11 | 0.24 \| nda | 0.265 \| nda | nda |
| 57-12 | 0.472 \| nda | 0.539 \| nda | nda |
| 57-13-1 | 1.46 \| nda | nda | nda |
| 57-13-2 | 8.13 \| nda | nda | nda |
| 57-14-1 | 0.288 \| nda | 0.348 \| nda | nda |
| 57-14-2 | 1.8 \| nda | nda | nda |
| 57-15-1 | 0.089 \| nda | 0.104 \| nda | nda |
| 57-15-2 | 0.841 \| nda | 0.984 \| nda | nda |
| 57-16 | 3.79 \| nda | nda | nda |
| 57-16-1 | 1.76 \| nda | nda | nda |
| 57-16-2 | 7.56 \| nda | nda | nda |
| 57-17 | 0.574 \| nda | 1.44 \| nda | nda |
| 57-17-1 | 0.316 \| nda | 0.3 \| nda | nda |
| 57-17-2 | 3.9 \| nda | nda | nda |
| 57-18 | 1.73 \| nda | nda | nda |
| 58-1 | 0.661 \| nda | 0.696 \| nda | nda |
| 58-1-1 | 5.95 \| nda | nda | nda |
| 58-1-2 | 0.572 \| nda | 0.57 \| nda | nda |
| 58-2 | 0.754 \| nda | 0.556 \| nda | nda |
| 58-2-1 | 0.487 \| nda | 0.399 \| nda | nda |
| 58-2-2 | 1.96 \| nda | nda | nda |
| 58-3 | 0.261 \| nda | 0.181 \| nda | nda |
| 58-3-1 | 0.097 \| nda | 0.144 \| nda | nda |
| 58-3-2 | 0.485 \| nda | 0.867 \| nda | nda |
| 58-4 | 0.395 \| nda | 0.183 \| nda | nda |
| 58-4-1 | 0.212 \| nda | 0.114 \| nda | nda |
| 58-4-2 | 4.82 \| nda | nda | nda |
| 58-5 | 0.484 \| nda | 1.99 \| nda | nda |
| 58-5-1 | 5.6 \| nda | nda | nda |
| 58-5-2 | 0.216 \| nda | 0.743 \| nda | nda |
| 58-6 | 0.623 \| nda | 0.842 \| nda | nda |
| 58-6-1 | 8.63 \| nda | nda | nda |
| 58-6-2 | 0.236 \| nda | 0.367 \| nda | nda |
| 58-7 | 0.072 \| nda | 1.99 \| nda | nda |
| 58-7-1 | 0.335 \| nda | 1.84 \| nda | nda |
| 58-7-2 | 0.041 \| nda | 0.515 \| nda | nda |
| 58-8 | 0.393 \| nda | 0.437 \| nda | nda |
| 58-8-1 | 0.213 \| nda | 0.18 \| nda | nda |
| 58-8-2 | 2.02 \| nda | nda | nda |
| 58-9 | 0.095 \| nda | 0.22 \| nda | nda |
| 58-9-1 | 0.046 \| nda | 0.047 \| nda | nda |
| 58-9-2 | 0.349 \| nda | 0.326 \| nda | nda |
| 58-10 | 0.445 \| nda | 0.433 \| nda | nda |
| 58-10-1 | 0.264 \| nda | 0.257 \| nda | nda |
| 58-10-2 | 6.31 \| nda | nda | nda |
| 58-11 | 0.473 \| nda | 0.742 \| nda | nda |
| 58-11-1 | 0.098 \| nda | 0.128 \| nda | nda |
| 58-11-2 | 1.815 \| nda | nda | nda |
| 58-12 | 0.953 \| nda | 0.508 \| nda | nda |
| 58-13 | 0.809 \| nda | 0.263 \| nda | nda |
| 58-13-1 | 1.56 \| nda | nda | nda |
| 58-13-2 | 0.26 \| nda | 0.371 \| nda | nda |
| 58-14 | 2.45 \| nda | nda | nda |
| 58-15 | 0.191 \| nda | 0.365 \| nda | nda |
| 58-15-1 | 2.13 \| nda | nda | nda |
| 58-15-2 | 0.097 \| nda | 0.142 \| nda | nda |
| 58-16 | 0.553 \| nda | 0.556 \| nda | nda |
| 58-16-1 | 11.6 \| nda | nda | nda |
| 58-16-2 | 0.315 \| nda | 0.317 \| nda | nda |
| 58-17 | 1.68 \| nda | nda | nda |
| 58-17-1 | 33.2 \| nda | nda | nda |
| 58-17-2 | 0.849 \| nda | 0.672 \| nda | nda |
| 58-18 | 0.358 \| nda | 0.272 \| nda | nda |
| 58-18-1 | 0.124 \| nda | 0.09 \| nda | nda |
| 58-18-2 | 1.31 \| nda | 0.715 \| nda | nda |
| 58-19 | 0.44 \| nda | 0.957 \| nda | nda |
| 58-19-1 | 4.06 \| nda | nda | nda |
| 58-19-2 | 0.226 \| nda | 0.525 \| nda | nda |
| 58-20 | 1.96 \| nda | nda | nda |
| 58-20-1 | 16.2 \| nda | nda | nda |
| 58-20-2 | 0.807 \| nda | 0.41 \| nda | nda |
| 58-21 | 17.5 \| nda | nda | nda |
| 58-22 | 2.71 \| nda | nda | nda |
| 58-23 | 0.732 \| nda | 0.894 \| nda | nda |
| 59-1 | 2.98 \| nda | nda | nda |
| 59-1-1 | 11.8 \| nda | nda | nda |
| 59-1-2 | 1.1 \| nda | nda | nda |
| 59-2 | 0.257 \| nda | 0.737 \| nda | nda |
| 59-2-1 | 0.112 \| nda | 0.137 \| nda | nda |
| 59-2-2 | 7.49 \| nda | nda | nda |
| 59-3 | 0.521 \| nda | 0.619 \| nda | nda |
| 59-3-1 | 0.128 \| nda | 0.343 \| nda | nda |
| 59-3-2 | 33 \| nda | nda | nda |
| 59-4 | 0.133 \| nda | 0.163 \| nda | nda |
| 59-5 | 0.501 \| nda | nda | nda |
| 59-6 | 0.932 \| nda | 0.659 \| nda | nda |
| 60-1 | 0.422 \| nda | 0.204 \| nda | nda |
| 60-2 | nda \| 7.62 | nda | nda |
| 60-3 | 1.02 \| 0.101 | 0.657 \| 0.552 | 100 \| 65 |
| 60-4 | nda \| 0.207 | nda \| 2.25 | nda |
| 60-5 | 0.589 \| 0.102 | 0.492 \| 0.447 | 52.4 \| 60.5 |
| 60-6 | 1.85 \| 0.161 | nda \| 1.04 | nda \| 67.7 |
| 60-7 | nda \| 26.9 | nda | nda |
| 60-8 | 0.173 \| nda | 0.072 \| nda | 10 \| nda |
| 60-9 | 0.484 \| nda | 1.6 \| nda | nda |
| 60-10 | 0.328 \| nda | 0.156 \| nda | nda |
| 60-11 | 0.08 \| nda | 0.063 \| nda | 10 \| nda |
| 60-12 | 22.2 \| nda | nda | nda |
| 60-13 | 85 \| nda | nda | nda |
| 60-14 | 2.24 \| nda | 0.946 \| nda | 10 \| nda |
| 60-15 | 0.686 \| nda | 0.492 \| nda | 10 \| nda |
| 60-16 | 46.1 \| nda | nda | nda |
| 60-17 | 5.74 \| nda | nda | nda |
| 60-18 | 250 \| nda | nda | nda |
| 60-19 | 0.137 \| nda | 0.156 \| nda | nda |
| 60-20 | 0.053 \| nda | 0.062 \| nda | nda |
| 60-20-1 | 10.2 \| nda | nda | nda |
| 60-20-2 | 0.024 \| nda | 0.033 \| nda | nda |
| 60-21 | 0.35 \| nda | 0.334 \| nda | nda |
| 60-22 | 0.159 \| nda | 0.433 \| nda | nda |
| 60-23 | nda \| 3.45 | nda \| 4.49 | nda \| 37.9 |
| 60-24-1 | 0.115 \| 0.056 | 0.069 \| 0.065 | 100 \| 100 |
| 60-24-2 | 1.03 \| 0.193 | 0.704 \| 0.976 | 100 \| 33.3 |
| 60-25 | 25.5 \| nda | nda | nda |
| 60-26 | 0.809 \| nda | 0.387 \| nda | 10 \| nda |
| 60-27 | 1.3 \| nda | nda | nda |
| 60-28 | 0.101 \| nda | 0.045 \| nda | nda |
| 60-29 | 0.034 \| nda | 0.036 \| nda | nda |

TABLE 89-continued

Biochemical and cellular activity of compounds

| Ex. # | Coupled exchange IC50 (5 min \| 2 h; μM) | p-ERK IC50 (2 h \| 4 h; MIA PaCa-2, μM) | p-ERK IC50 (2 h \| 4 h; A549, μM) |
|---|---|---|---|
| 60-30 | 0.218 \| nda | 0.2 \| nda | nda |
| 60-30-1 | 1.26 \| nda | nda | nda |
| 60-30-2 | 0.108 \| nda | 0.081 \| nda | nda |
| 60-31 | 0.919 \| 0.115 | 1 \| 0.71 | 40.9 \| 86.6 |
| 60-32 | 0.392 \| 0.157 | 0.221 \| 0.213 | 87.4 \| 63.9 |
| 60-33 | 1.24 \| 0.139 | 1.697 \| nda | 100 \| nda |
| 60-34 | 0.478 \| nda | 0.508 \| nda | 10 \| nda |
| 60-35 | nda \| 1.95 | nda \| 10.7 | nda \| 46.2 |
| 61-1 | nda \| 0.776 | 2.48 \| 0.992 | 100 \| 11.1 |
| 61-1-1 | 2.94 \| nda | nda | nda |
| 61-1-2 | 20.6 \| nda | nda | nda |
| 61-2-1 | 8.24 \| nda | nda | nda |
| 61-2-2 | 2.37 \| nda | nda | nda |
| 62-1 | 0.073 \| 0.108 | 0.116 \| nda | 100 \| nda |
| 62-1-1 | 0.468 \| nda | 0.431 \| nda | 10 \| nda |
| 62-1-2 | 0.031 \| nda | 0.047 \| nda | 10 \| nda |
| 62-2 | nda \| 0.129 | 0.442 \| nda | 10 \| nda |
| 62-3 | 0.147 \| nda | 0.845 \| nda | 10 \| nda |
| 63-1 | 2.15 \| nda | nda | nda |
| 63-2 | 0.311 \| nda | 0.609 \| nda | nda |
| 63-3 | 0.059 \| nda | 0.108 \| nda | nda |
| 63-4 | 1.15 \| nda | nda | nda |
| 63-5 | 182 \| nda | nda | nda |
| 64-1 | 0.044 \| nda | 0.076 \| nda | nda |
| 64-2 | 0.151 \| nda | 0.258 \| nda | nda |
| 64-3 | 0.189 \| nda | 0.219 \| nda | nda |
| 65-1 | 0.606 \| nda | 1.52 \| nda | nda |
| 65-2 | 1.31 \| nda | nda | nda |
| 65-3 | 0.096 \| nda | 0.1 \| nda | nda |
| 66-1 | nda \| 1.05 | nda | nda |
| 66-2 | nda \| 1.42 | nda | nda |
| 66-3 | nda \| 10.3 | nda | nda |
| 66-4 | nda \| 1.87 | nda | nda |
| 66-5 | 21.2 \| nda | nda | nda |
| 66-6 | 14.9 \| nda | nda | nda |
| 66-7 | 88 \| nda | nda | nda |
| 66-8 | 100 \| nda | nda | nda |
| 66-9 | 99.5 \| nda | nda | nda |
| 66-10 | 26.4 \| nda | nda | nda |
| 66-11 | 29 \| nda | nda | nda |
| 66-12 | 65 \| nda | nda | nda |
| 66-13 | 133 \| nda | nda | nda |
| 66-14 | 5.51 \| nda | nda | nda |
| 66-15 | 89.7 \| nda | nda | nda |
| 66-16 | 250 \| nda | nda | nda |
| 66-17 | 75.5 \| nda | nda | nda |
| 66-18 | 76.7 \| nda | nda | nda |
| 66-19 | 250 \| nda | nda | nda |
| 66-20 | 28.2 \| nda | nda | nda |
| 66-21 | 33 \| nda | nda | nda |
| 66-22 | 40.7 \| nda | nda | nda |
| 66-23 | 160 \| nda | nda | nda |
| 66-24 | 250 \| nda | nda | nda |
| 66-25 | 95 \| nda | nda | nda |
| 66-26 | 250 \| nda | nda | nda |
| 66-27 | 186 \| nda | nda | nda |
| 66-28 | 16.6 \| nda | nda | nda |
| 66-29 | 25.3 \| nda | nda | nda |
| 66-30 | 16.05 \| nda | nda | nda |
| 66-31 | 84.25 \| nda | nda | nda |
| 66-32 | 123 \| nda | nda | nda |
| 66-33 | 15.9 \| nda | nda | nda |
| 67-1 | 3.51 \| nda | nda | nda |
| 67-2 | 6.45 \| nda | nda | nda |
| 67-3 | 2.87 \| nda | nda | nda |
| 67-4-1 | 7.34 \| nda | nda | nda |
| 67-4-2 | 1.91 \| nda | nda | nda |
| 68-1 | 0.111 \| nda | 0.214 \| nda | nda |
| 68-1-1 | 0.084 \| nda | 0.128 \| nda | nda |
| 68-1-2 | 0.613 \| nda | 0.735 \| nda | nda |
| 68-2 | 0.947 \| nda | 0.999 \| nda | nda |
| 68-2-1 | 5.29 \| nda | nda | nda |
| 68-2-2 | 0.31 \| nda | 0.607 \| nda | nda |
| 69-1 | nda \| 0.231 | nda \| 1.86 | nda \| 64.8 |
| 69-1-1 | 44.1 \| nda | nda | nda |
| 69-1-2 | 0.604 \| nda | 1.02 \| nda | 10 \| nda |
| 69-2 | nda \| 0.511 | 1.31 \| nda | 33.3 \| nda |
| 69-3 | nda \| 0.758 | 1.7 \| nda | nda |
| 69-4 | nda \| 1.38 | nda | nda |
| 69-5 | 5.64 \| nda | nda | nda |
| 69-6 | 13.7 \| nda | nda | nda |
| 69-7 | 48.5 \| nda | nda | nda |
| 70-1 | 0.225 \| nda | 0.225 \| nda | nda |
| 70-2 | 0.184 \| nda | 0.213 \| nda | nda |
| 70-3 | 0.125 \| nda | 0.206 \| nda | nda |
| 70-4 | 0.398 \| nda | 0.28 \| nda | nda |
| 71-1 | 1.12 \| nda | nda | nda |
| 71-1-1 | 0.49 \| nda | 0.725 \| nda | nda |
| 71-1-2 | 4.89 \| nda | nda | nda |
| 71-2 | 2.17 \| nda | nda | nda |
| 71-2-1 | 8.7 \| nda | nda | nda |
| 71-2-2 | 1.06 \| nda | nda | nda |
| 72-1 | 1.17 \| nda | nda | nda |
| 72-2 | 0.534 \| nda | 0.595 \| nda | nda |
| 72-3 | 3.29 \| nda | nda | nda |
| 72-4 | 0.08 \| nda | 0.115 \| nda | nda |
| 72-5 | 2.91 \| nda | nda | nda |
| 72-6 | 0.315 \| nda | 0.564 \| nda | nda |
| 72-7 | 0.262 \| nda | 2.24 \| nda | nda |
| 72-8 | 0.042 \| nda | 0.091 \| nda | nda |
| 72-9 | 0.191 \| nda | 0.554 \| nda | nda |
| 72-10 | 0.158 \| nda | 0.15 \| nda | nda |
| 72-11 | 0.039 \| nda | 0.044 \| nda | nda |
| 72-12 | 4.51 \| nda | nda | nda |
| 72-13 | 0.021 \| nda | 0.012 \| nda | nda |
| 72-14 | 0.081 \| nda | 0.055 \| nda | nda |
| 73-1 | 0.012 \| nda | 0.014 \| nda | 10 \| nda |
| 73-2 | 0.067 \| nda | 0.101 \| nda | nda |
| 73-3 | 0.031 \| nda | 0.04 \| nda | nda |
| 73-4 | 0.047 \| nda | 0.062 \| nda | nda |
| 73-5 | 0.184 \| nda | 0.228 \| nda | nda |
| 73-6 | 0.059 \| nda | 0.104 \| nda | nda |
| 73-7 | 0.241 \| nda | 0.375 \| nda | nda |
| 73-8 | 0.236 \| nda | 0.653 \| nda | nda |
| 73-9 | 0.06 \| nda | 0.281 \| nda | nda |
| 73-10 | 0.385 \| nda | 0.544 \| nda | nda |
| 73-11 | 0.625 \| nda | nda | nda |
| 73-12 | 0.01 \| nda | 0.01 \| nda | nda |
| 73-13 | 0.023 \| nda | 0.017 \| nda | nda |
| 73-14 | 0.711 \| nda | nda | nda |
| 73-15 | 0.015 \| nda | 0.004 \| nda | nda |
| 73-16 | 0.019 \| nda | 0.007 \| nda | nda |
| 73-17 | 250 \| nda | nda | nda |
| 73-18 | 5.54 \| nda | nda | nda |
| 73-19 | 7.55 \| nda | nda | nda |
| 74-1 | 0.951 \| nda | 0.621 \| nda | nda |
| 74-1-1 | 2.16 \| nda | nda | nda |
| 74-1-2 | 0.118 \| nda | 0.152 \| nda | nda |
| 74-2 | 0.228 \| nda | 0.3 \| nda | nda |
| 74-2-1 | 0.26 \| nda | 0.136 \| nda | nda |
| 74-2-2 | 2.325 \| nda | 1.04 \| nda | nda |
| 74-3 | 0.136 \| nda | 0.347 \| nda | nda |
| 74-3-1 | 0.05 \| nda | 0.103 \| nda | nda |
| 74-3-2 | 1.12 \| nda | nda | nda |
| 75-1 | 0.048 \| nda | 0.049 \| nda | 10 \| nda |
| 75-2 | 0.493 \| nda | 0.306 \| nda | nda |
| 75-3 | 0.029 \| nda | 0.027 \| nda | 10 \| nda |
| 75-4 | 0.552 \| nda | 0.543 \| nda | nda |
| 75-5 | 2.03 \| nda | nda | nda |
| 75-6 | 85 \| nda | nda | nda |
| 75-7 | 250 \| nda | nda | nda |
| 75-8 | 0.023 \| nda | 0.038 \| nda | nda |
| 75-9-1 | 1.87 \| nda | nda | nda |
| 75-9-2 | 0.136 \| nda | 0.113 \| nda | nda |
| 76-1 | 117 \| nda | nda | nda |
| 76-2 | 20.1 \| nda | nda | nda |
| 77-1 | 169 \| nda | nda | nda |
| 77-2 | 77.7 \| nda | nda | nda |

TABLE 89-continued

Biochemical and cellular activity of compounds

| Ex. # | Coupled exchange IC50 (5 min \| 2 h; µM) | p-ERK IC50 (2 h \| 4 h; MIA PaCa-2, µM) | p-ERK IC50 (2 h \| 4 h; A549, µM) |
|---|---|---|---|
| 78-1 | 0.213 \| nda | 0.049 \| nda | nda |
| 78-2 | 0.436 \| nda | 0.376 \| nda | nda |
| 78-3 | 0.141 \| nda | 0.246 \| nda | nda |
| 78-3-1 | 1.19 \| nda | nda | nda |
| 78-3-2 | 0.094 \| nda | 0.08 \| nda | nda |
| 78-4 | 30.3 \| nda | nda | nda |
| 78-5 | 0.349 \| nda | 2.61 \| nda | nda |
| 78-6 | 119 \| nda | nda | nda |
| 78-7 | 0.034 \| nda | 0.023 \| nda | nda |
| 78-8 | 0.026 \| nda | 0.01 \| nda | nda |
| 78-9 | 0.515 \| nda | 0.348 \| nda | nda |
| 78-9-1 | 1.26 \| nda | nda | nda |
| 78-9-2 | 0.423 \| nda | nda | nda |
| 78-10 | 120 \| nda | nda | nda |
| 78-11 | 250 \| nda | nda | nda |
| 78-12 | 15.4 \| nda | nda | nda |
| 78-13 | 2.22 \| nda | nda | nda |
| 78-14 | 0.133 \| nda | 0.081 \| nda | nda |
| 78-15 | 0.124 \| nda | 0.061 \| nda | nda |
| 78-16 | 16.6 \| nda | nda | nda |
| 78-17 | 26 \| nda | nda | nda |
| 78-18 | 250 \| nda | nda | nda |
| 79-1 | 3.29 \| nda | nda | nda |
| 79-2 | 28.6 \| nda | nda | nda |
| 79-3 | 184 \| nda | nda | nda |
| 79-4 | 180 \| nda | nda | nda |
| 79-5 | 250 \| nda | nda | nda |
| 80-1 | 0.08 \| nda | 0.052 \| nda | nda |
| 80-1-1 | 0.044 \| nda | 0.029 \| nda | nda |
| 80-1-2 | 0.556 \| nda | 0.236 \| nda | nda |
| 80-2 | 0.11 \| nda | 0.097 \| nda | nda |
| 80-2-1 | 0.824 \| nda | nda | nda |
| 80-2-2 | 0.048 \| nda | 0.047 \| nda | nda |
| 81-1 | 172 \| nda | nda | nda |
| 81-2 | 14.1 \| nda | nda | nda |
| 81-3 | 2.87 \| nda | nda | nda |
| 82-1 | 0.077 \| nda | 0.106 \| nda | nda |
| 82-2 | 0.096 \| nda | 0.239 \| nda | nda |
| 83-1 | 0.548 \| nda | nda | nda |
| 83-2 | 0.035 \| nda | 0.084 \| nda | nda |
| 84-1 | 2.71 \| nda | nda | nda |
| 84-2 | 0.058 \| nda | 0.043 \| nda | nda |
| 85-1 | 6.34 \| nda | nda | nda |
| 85-2 | 114 \| nda | nda | nda |
| 85-3 | 161 \| nda | 10 \| nda | nda |
| 85-4 | 250 \| nda | 10 \| nda | nda |
| 85-5 | 250 \| nda | nda | nda |
| 85-6 | 250 \| nda | nda | nda |
| 85-7 | 250 \| nda | nda | nda |
| 86-1 | 3.95 \| nda | 4.3 \| nda | nda |
| 86-2 | 6.6 \| nda | nda | nda |
| 87-1 | 0.034 \| nda | 0.011 \| nda | nda |
| 87-2 | 0.035 \| nda | 0.033 \| nda | nda |
| 87-3 | 17.3 \| nda | nda | nda |
| 87-4 | 0.254 \| nda | 0.262 \| | nda |
| 87-5 | 0.251 \| nda | 0.181 \| nda | nda |
| 88 | nda \| 0.135 | 0.232 \| 0.243 | nda \| 89.4 |
| 88-1 | 0.088 \| nda | 0.08 \| nda | 10 \| nda |
| 88-2 | 1.41 \| nda | 1.65 \| nda | 10 \| nda |
| 89 | nda \| 0.229 | 0.687 \| 0.294 | 10 \| 11.1 |
| 90-1 | nda \| 0.328 | nda \| 0.221 | nda \| 33.3 |
| 90-2 | 0.151 \| 0.175 | nda \| 0.111 | nda \| 33.3 |
| 91 | 0.2 \| nda | 0.312 \| nda | 10 \| nda |
| 92 | nda \| 0.123 | nda \| 1.55 | nda \| 108 |
| 93 | 1.59 \| nda | nda | nda |
| 94 | 0.781 \| 0.112 | 1.51 \| nda | 10 \| nda |
| 95 | nda \| 1.7 | nda | nda |
| 96 | 4.85 \| nda | nda | nda |
| 97 | 39 \| nda | nda | nda |
| 98 | 0.27 \| nda | 0.207 \| nda | nda |
| 98-1 | 0.193 \| nda | 0.155 \| nda | nda |
| 98-2 | 3.38 \| nda | nda | nda |
| 99 | 0.237 \| nda | 0.072 \| nda | nda |
| 100 | 3.45 \| nda | nda | nda |
| 101 | 0.147 \| nda | 0.148 \| nda | nda |
| 102 | 0.421 \| nda | 0.667 \| nda | nda |
| 102-1 | 3.45 \| nda | nda | nda |
| 102-2 | 0.182 \| nda | 0.211 \| nda | nda |
| 103 | 0.099 \| nda | 0.178 \| nda | nda |
| 104 | 0.062 \| nda | 0.078 \| nda | nda |
| 105 | 0.051 \| nda | 0.065 \| nda | nda |
| 106 | 0.074 \| nda | 0.105 \| nda | nda |
| 107 | nda \| 3.14 | nda | nda |
| 108 | 1 \| nda | nda | nda |
| 109 | 1.32 \| nda | nda | nda |
| 110 | 0.166 \| nda | 0.426 \| nda | nda |
| 110-1 | 3.22 \| nda | nda | nda |
| 110-2 | 0.071 \| nda | 0.247 \| nda | nda |
| 111 | 0.174 \| nda | 0.195 \| nda | nda |
| 111-1 | 0.076 \| nda | 0.102 \| nda | 10 \| nda |
| 111-2 | 0.86 \| nda | nda | nda |
| 112 | 2.45 \| nda | nda | nda |
| 113 | 1.02 \| nda | nda | nda |
| 114 | 6.435 \| nda | nda | nda |
| 115 | 2.92 \| nda | nda | nda |
| 116 | 0.232 \| nda | 0.543 \| nda | nda |
| 117 | nda \| 0.916 | 4.88 \| nda | 10 \| nda |
| 118 | 133 \| nda | nda | nda |
| 119 | 10.8 \| nda | nda | nda |
| 120 | 71.1 \| nda | nda | nda |
| 121 | 14.2 \| nda | nda | nda |
| 122 | 5.29 \| nda | nda | nda |
| 123 | 38.6 \| nda | nda | nda |
| 124 | 6.22 \| nda | nda | nda |
| 125 | 35.4 \| nda | nda | nda |
| 126 | 2.05 \| nda | 1.72 \| nda | nda |
| 127 | 27.2 \| nda | nda | nda |
| 128 | nda \| 18 | nda | nda |
| 129 | 0.045 \| nda | 0.095 \| nda | nda |
| 130 | 250 \| nda | nda | nda |
| 131 | 250 \| nda | nda | nda |
| 132 | 0.107 \| nda | 10 \| nda | nda |
| 133 | 0.119 \| nda | 0.198 \| nda | nda |
| 134 | 1.95 \| nda | nda | nda |
| 135 | 3.32 \| nda | nda | nda |
| 136 | 0.135 \| nda | 0.121 \| nda | nda |
| 137 | 0.5 \| nda | 1.79 \| nda | nda |
| 138 | 1.75 \| nda | 1.59 \| nda | nda |
| 139 | 0.117 \| nda | 0.025 \| nda | nda |
| 140 | 0.09 \| nda | 0.096 \| nda | nda |
| 140-1 | 0.073 \| nda | 0.047 \| nda | nda |
| 140-2 | 0.677 \| nda | nda | nda |
| 141 | 0.393 \| nda | 5.2 \| nda | nda |
| 142-1 | 23.9 \| nda | nda | nda |
| 142-2 | 0.029 \| nda | 0.029 \| nda | nda |
| 143 | 0.497 \| nda | nda | nda |
| 143-1 | 2.72 \| nda | 3.54 \| nda | nda |
| 143-2 | 2.43 \| nda | 0.397 \| nda | nda |
| 144 | 8.31 \| nda | nda | nda |
| 145 | 0.952 \| nda | 3.92 \| nda | nda |
| 146 | 38.7 \| nda | nda | nda |
| 147 | 13.6 \| nda | nda | nda |
| 148 | 250 \| nda | nda | nda |
| 149 | 20.6 \| nda | nda | nda |
| 150 | 250 \| nda | 3.33 \| nda | nda |
| 151 | 0.065 \| nda | 0.237 \| nda | nda |
| 152 | 0.084 \| nda | 0.021 \| nda | nda |
| 153 | 250 \| nda | nda | nda |
| 154 | 250 \| nda | nda | nda |
| 155 | 0.108 \| nda | 0.103 \| nda | nda |
| 155-1 | 0.038 \| nda | 0.043 \| nda | nda |
| 155-2 | 13.5 \| nda | nda | nda |
| 156 | 0.057 \| nda | 0.08 \| nda | nda |
| 157 | 132 | nda | nda |

"nda" = no data available

The present invention is described in connection with preferred embodiments. However, it should be appreciated US 11,090,304 B2
that the invention is not limited to the disclosed embodiments. It is understood that, given the description of the embodiments of the invention herein, various modifications can be made by a person skilled in the art. Such modifications are encompassed by the claims below.
What is claimed:
1. A compound having a structure selected from:
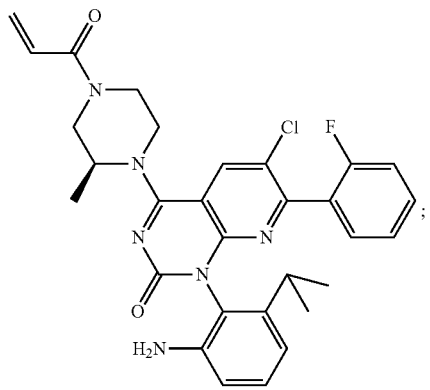
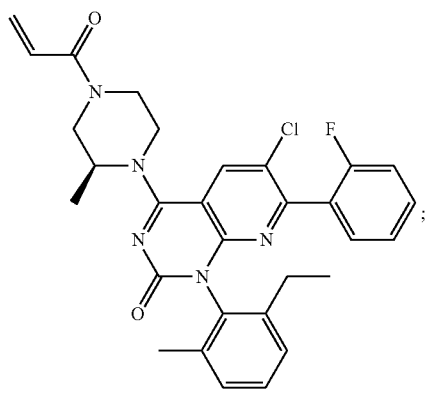
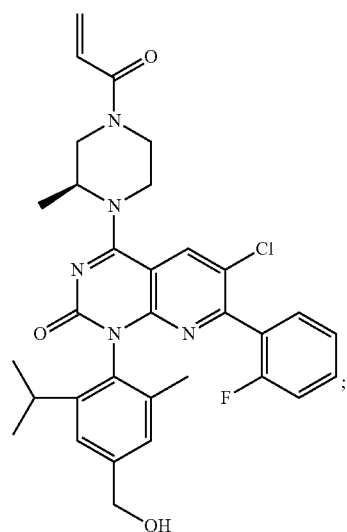
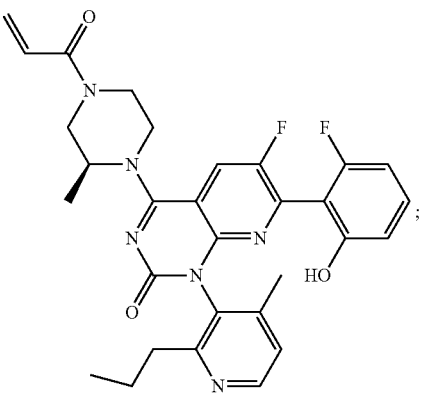
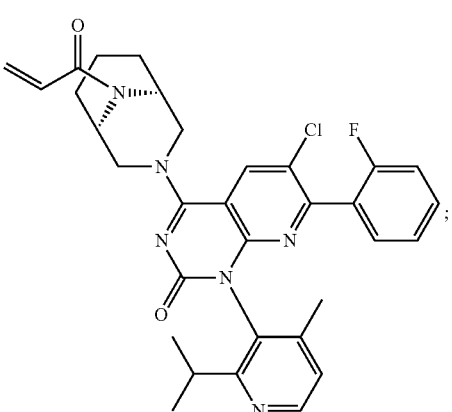
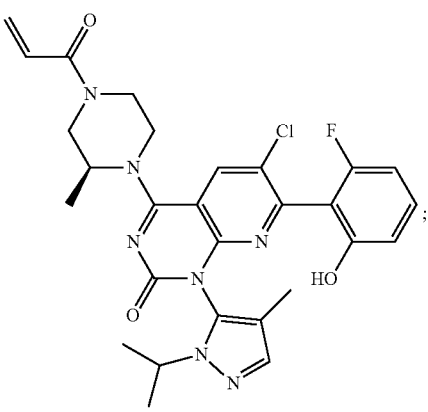
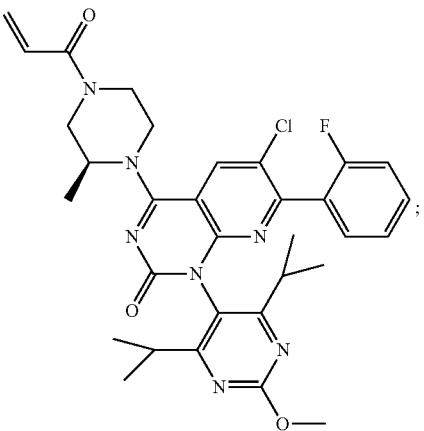

1147
-continued
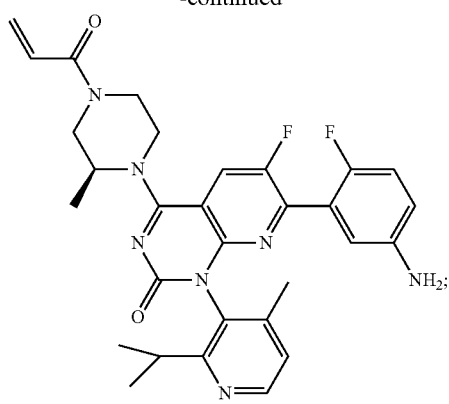
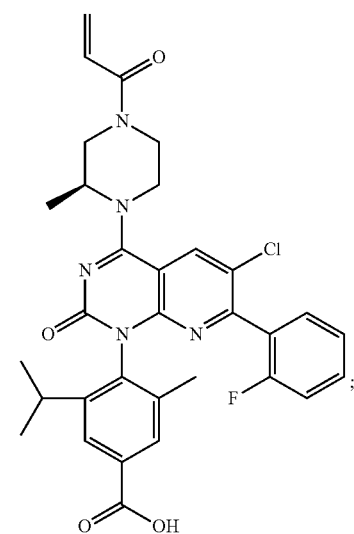
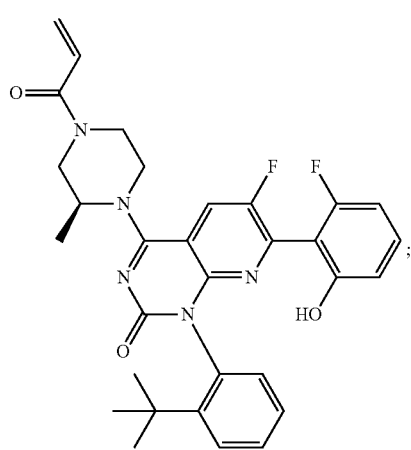
1148
-continued
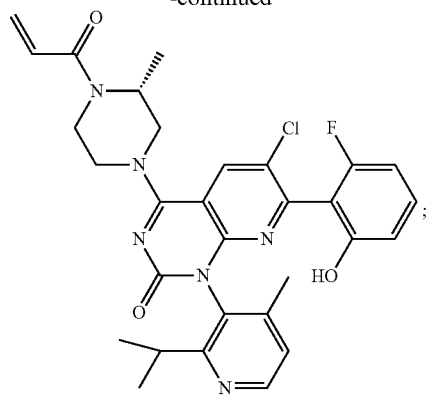
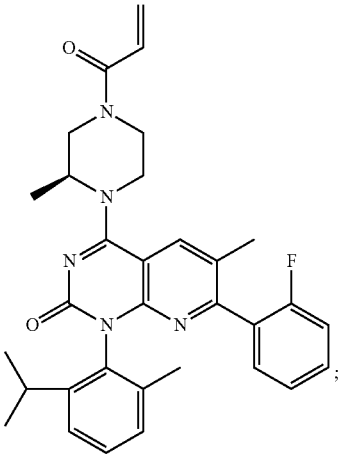
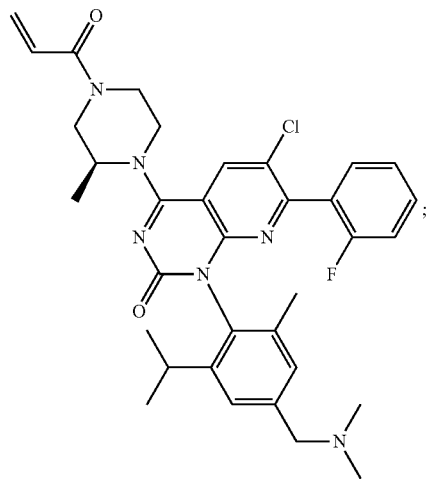
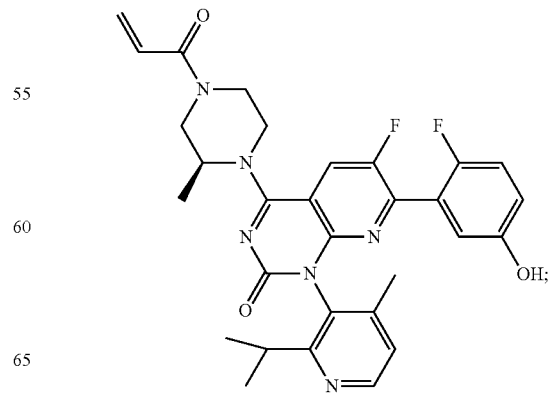

1149
-continued
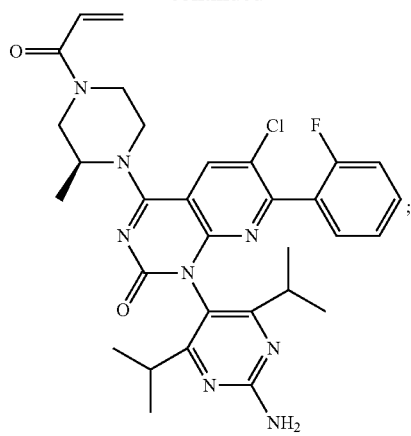
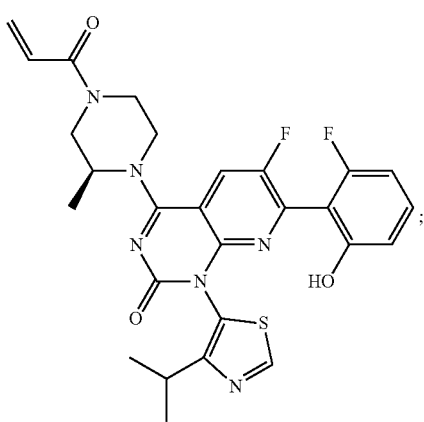
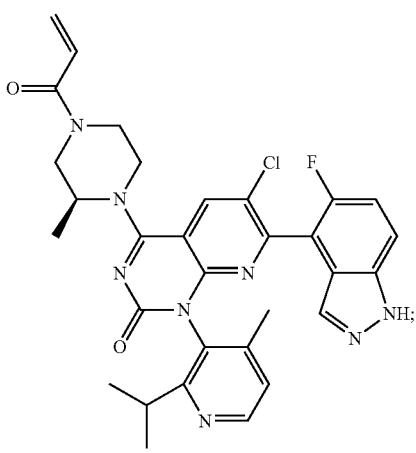
1150
-continued
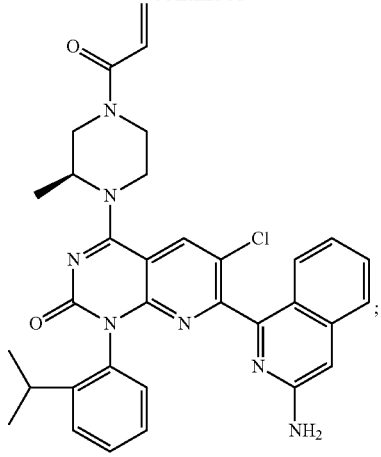
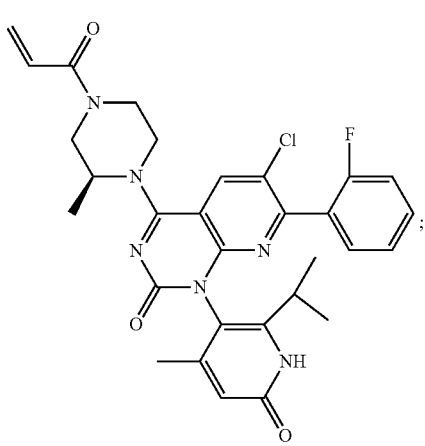
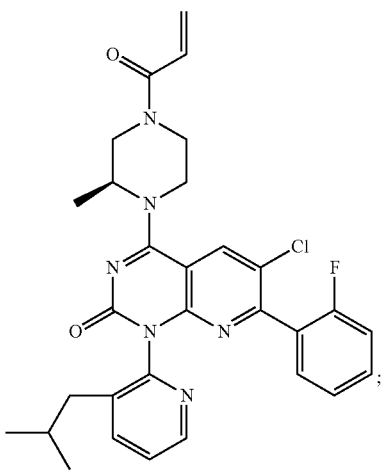

1151
-continued
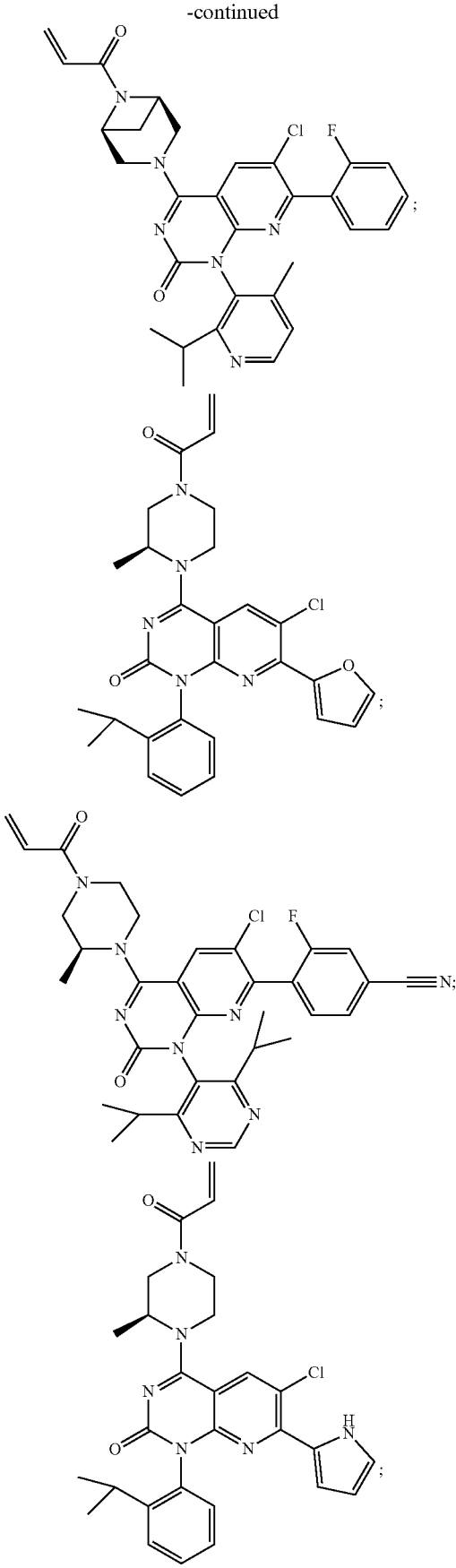
1152
-continued
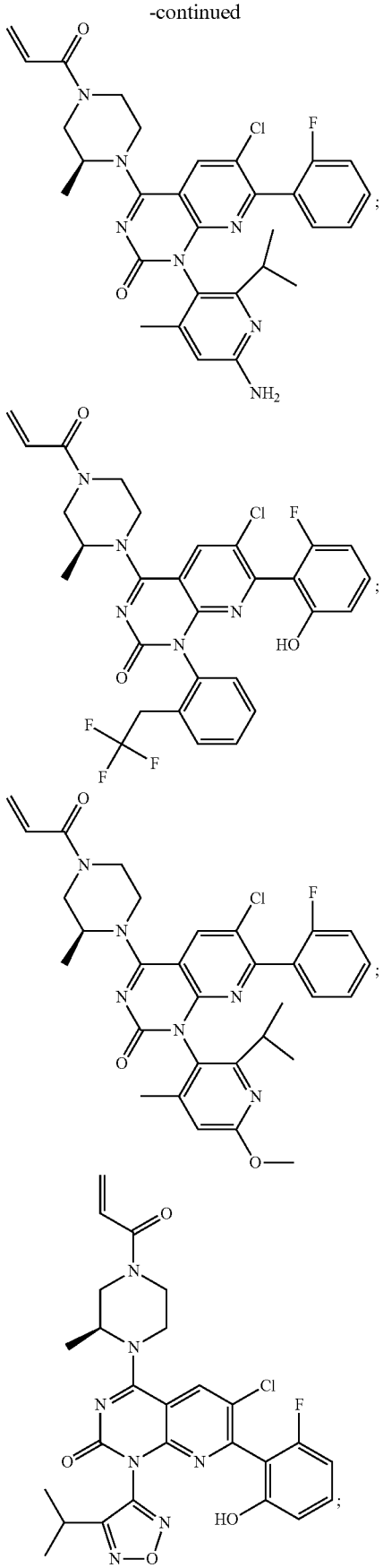

1153
-continued
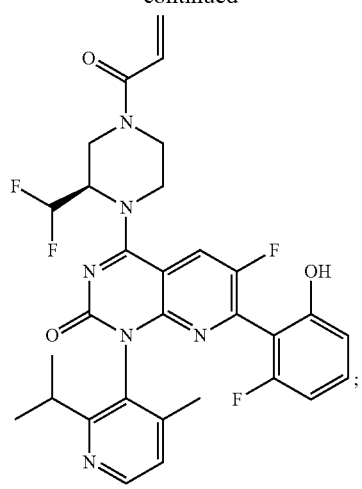
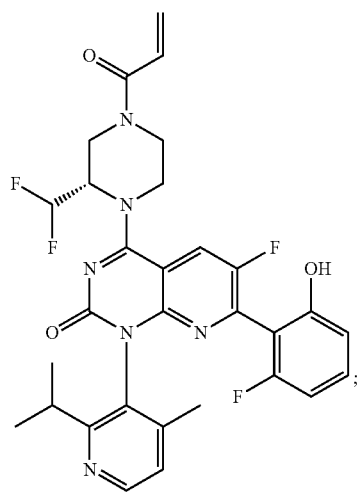
1154
-continued
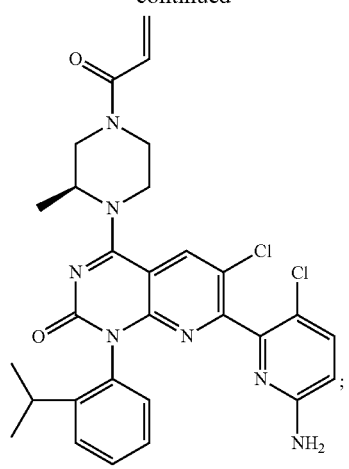
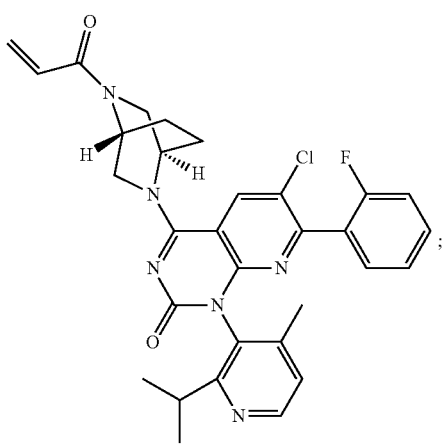
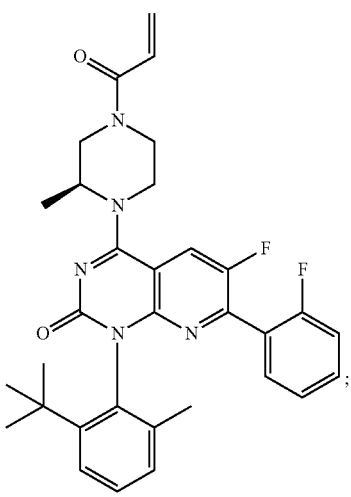

1155
-continued
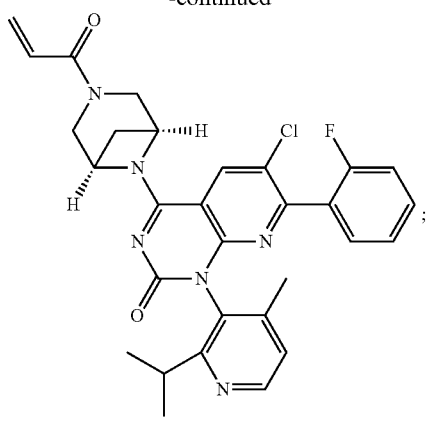
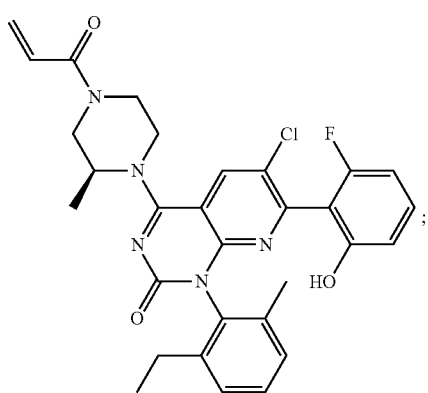
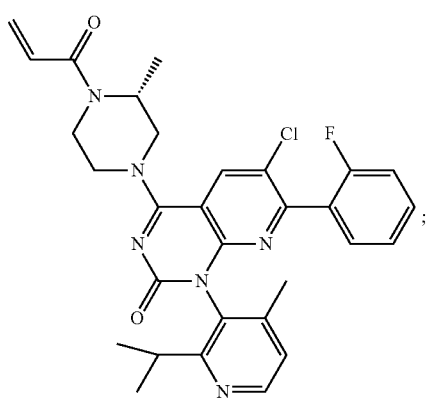
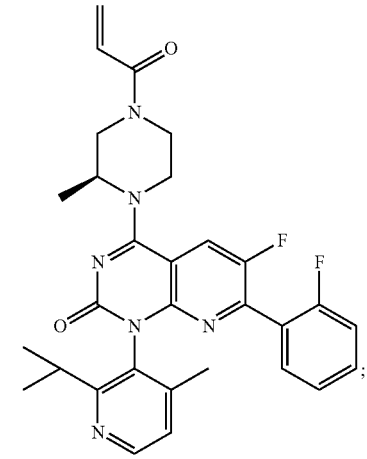
1156
-continued
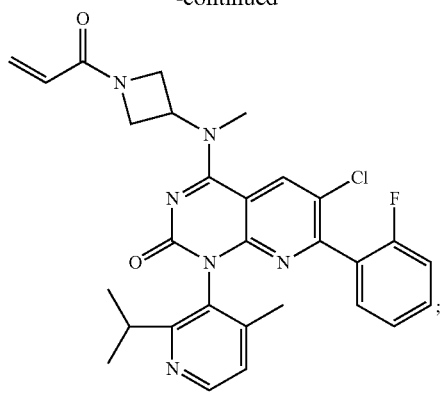
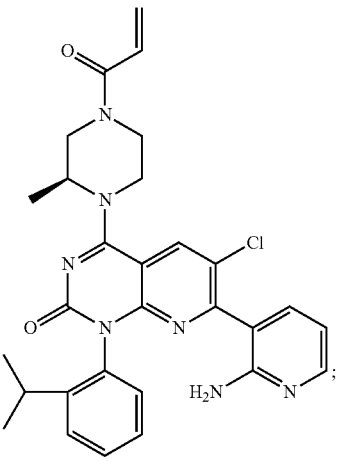
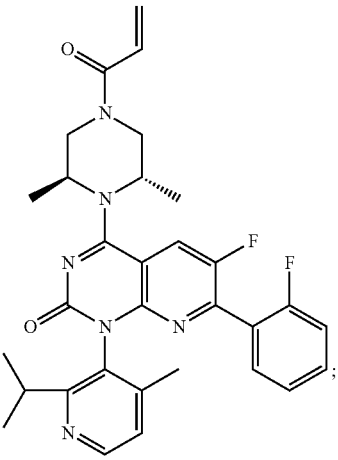

1157
-continued
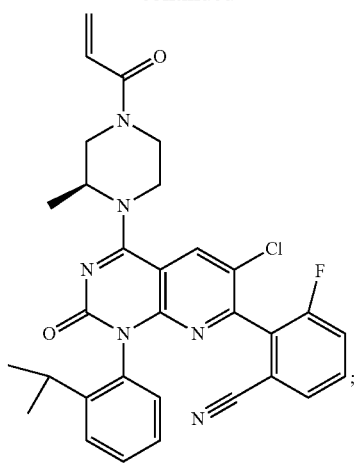
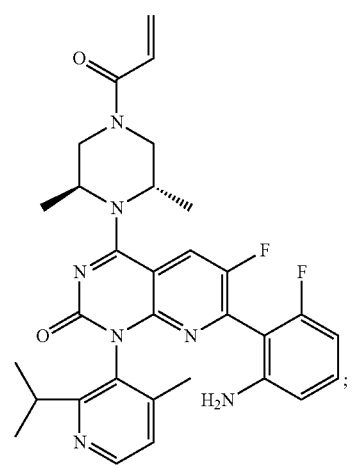
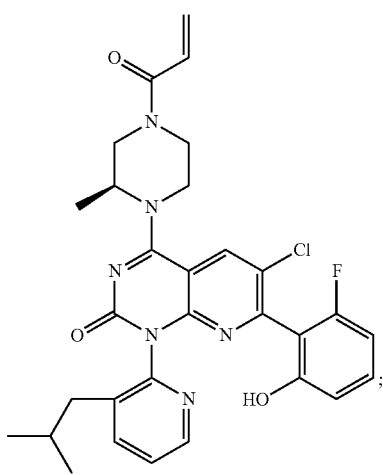
1158
-continued
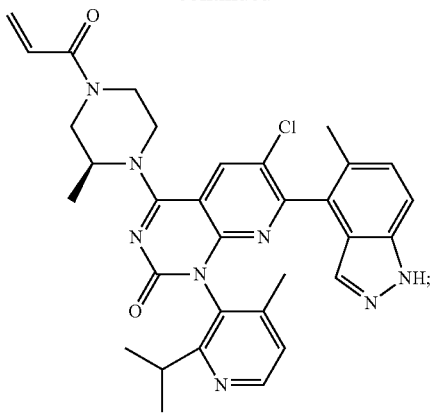
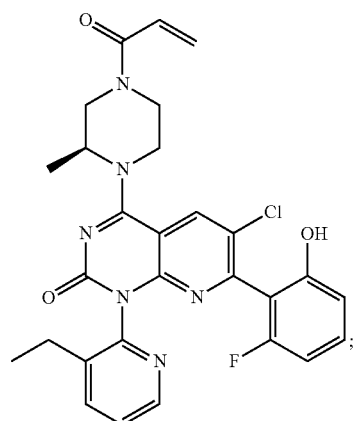
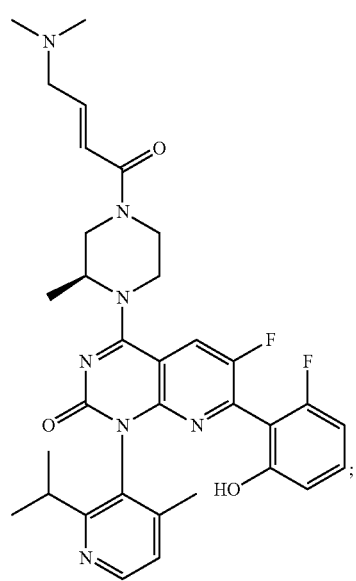

1159
-continued
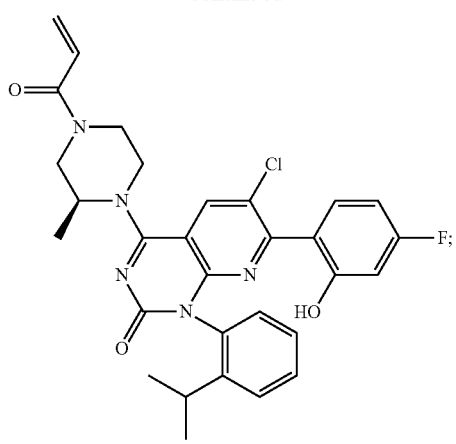
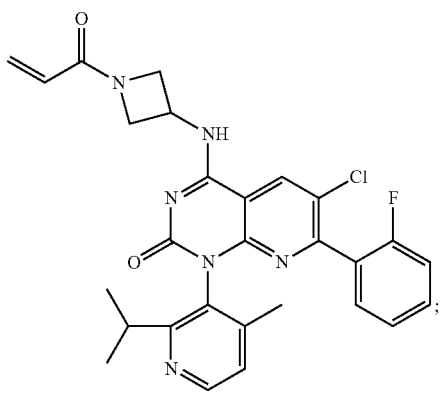
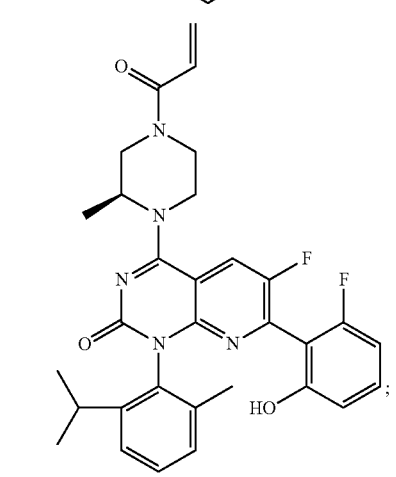
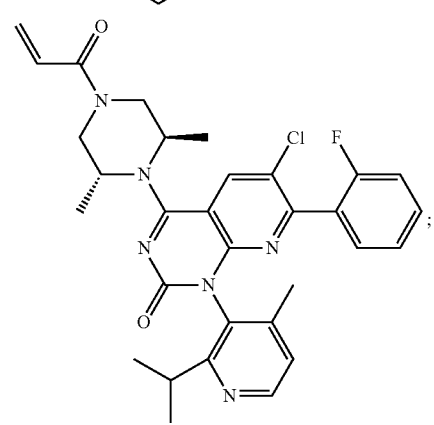
1160
-continued
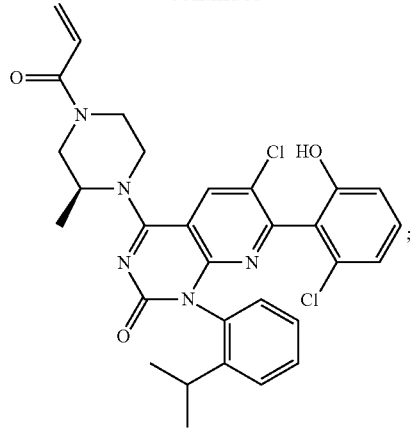
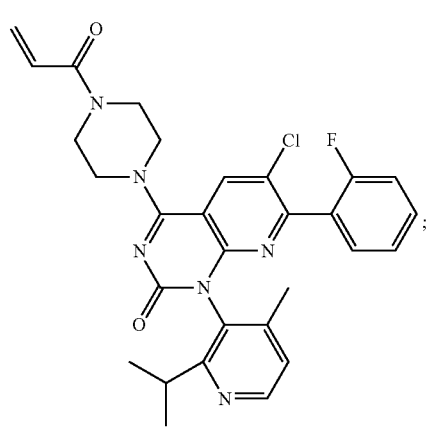
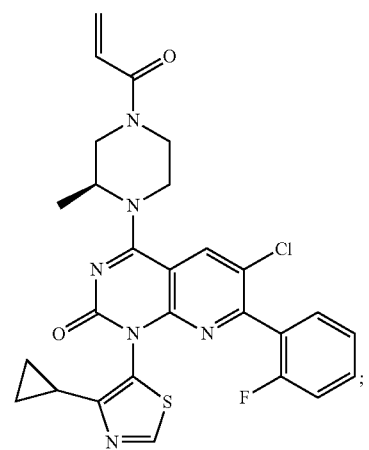

1161
-continued
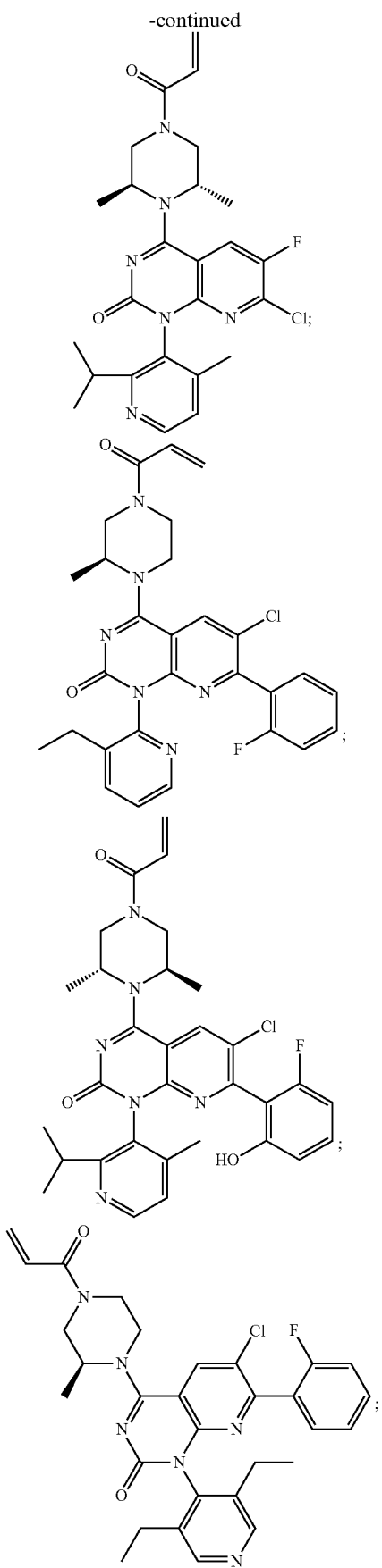
1162
-continued
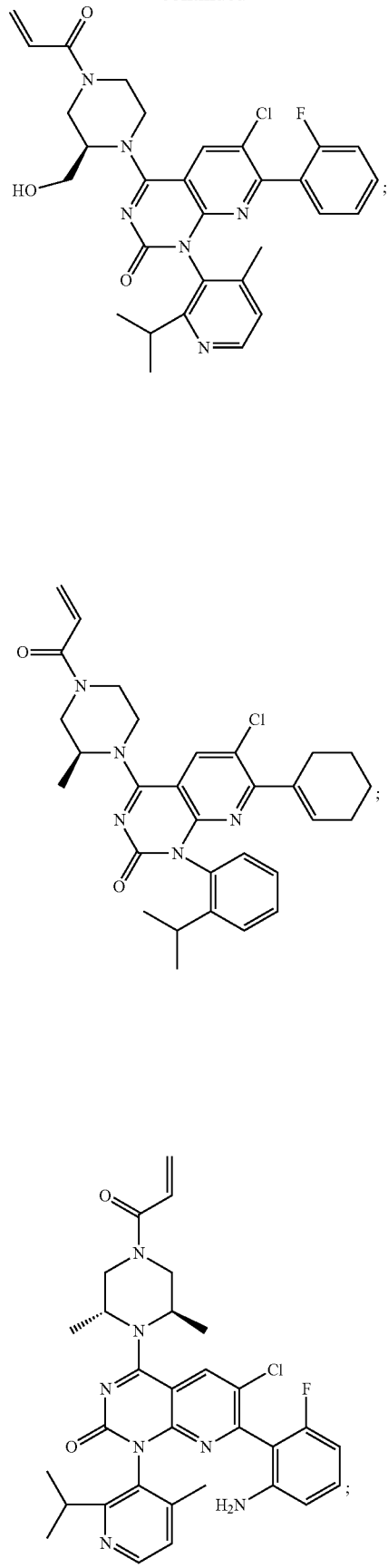

1163
-continued
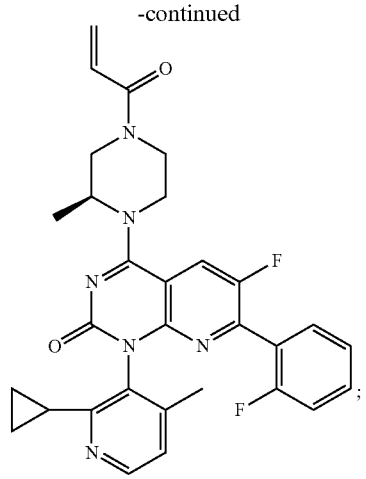
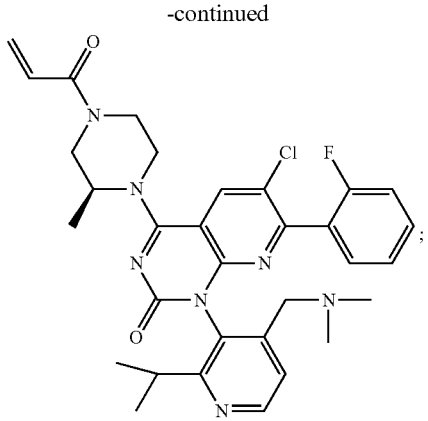
1164
-continued
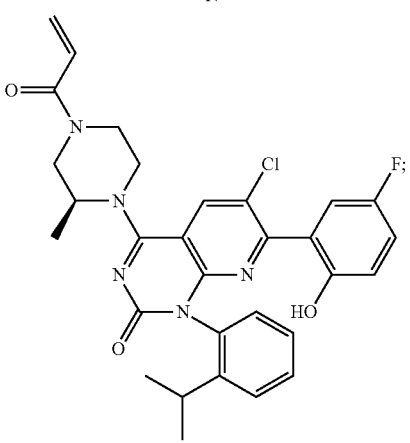
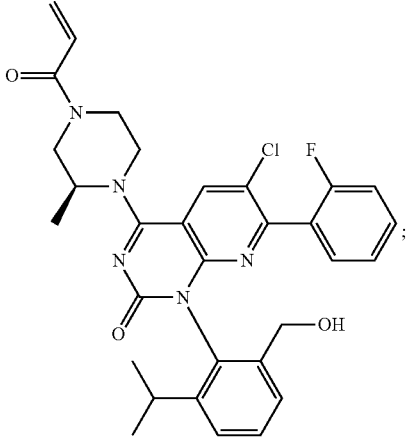
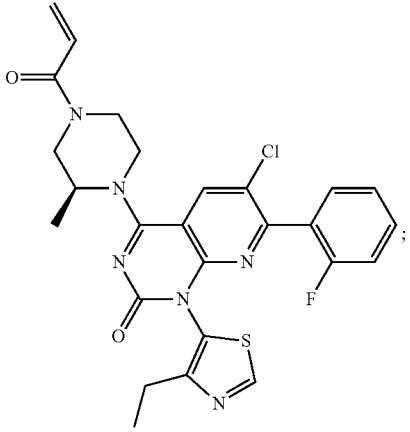

1165
-continued
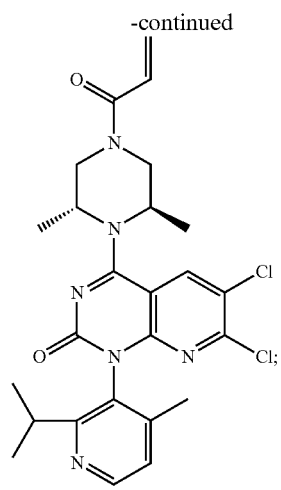
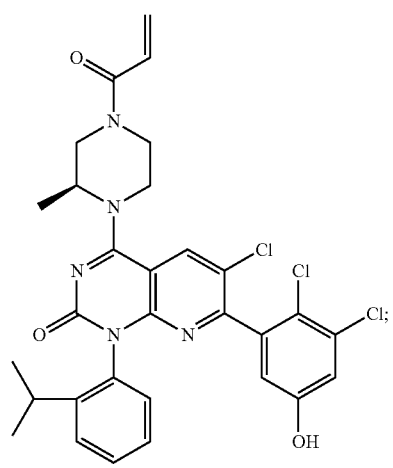
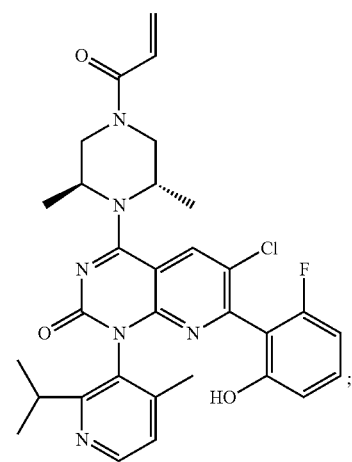
1166
-continued
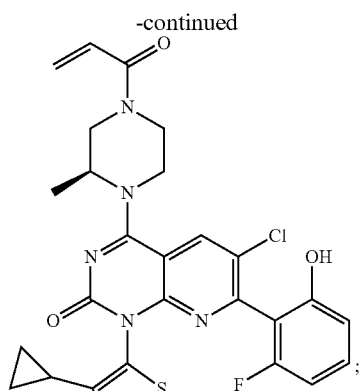
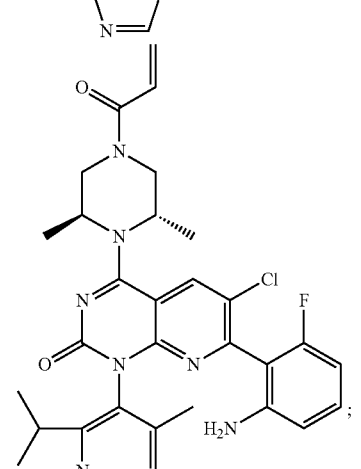
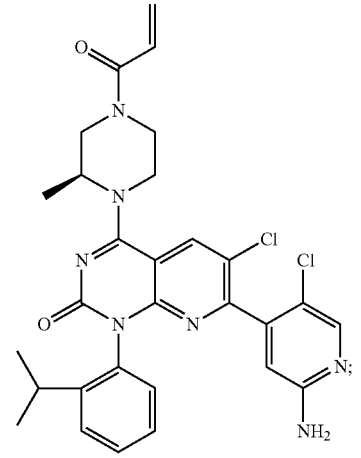
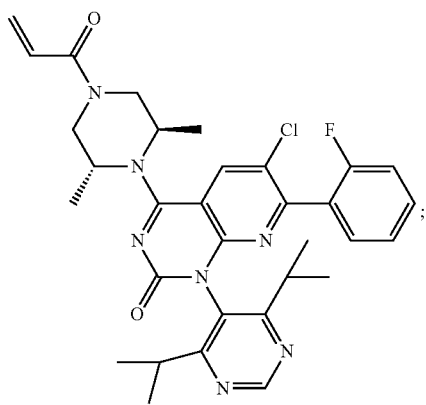

1167
-continued
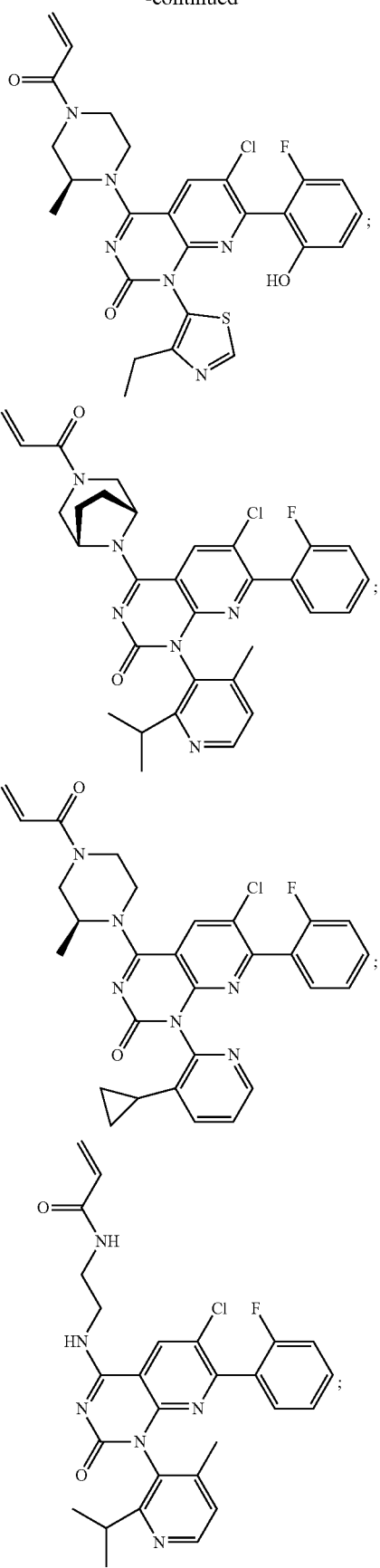
1168
-continued
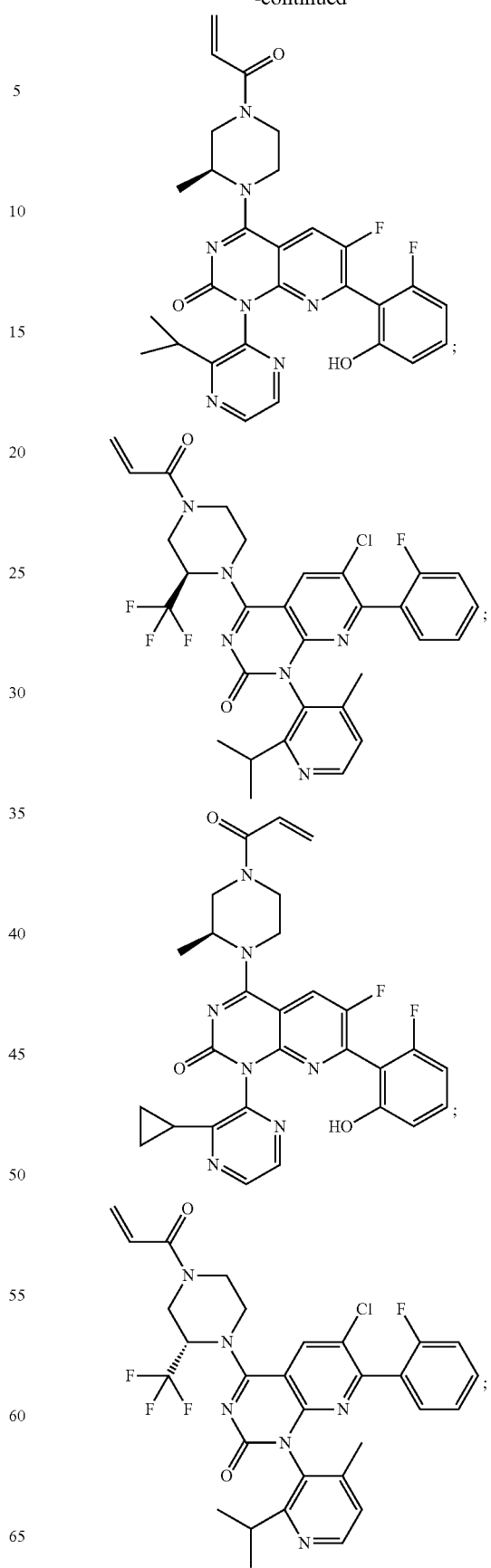

1169
-continued
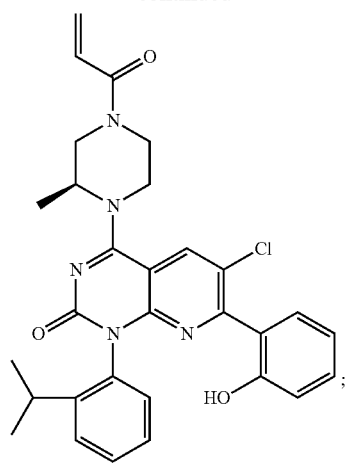
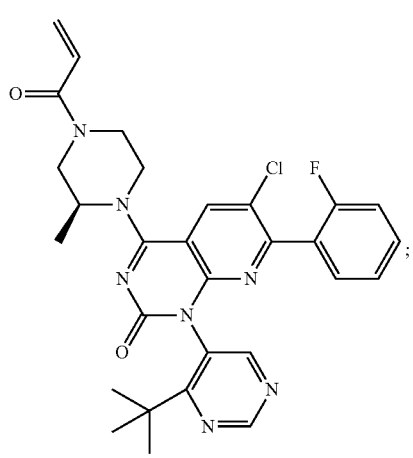
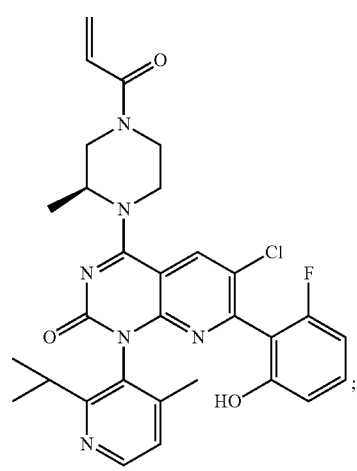
1170
-continued
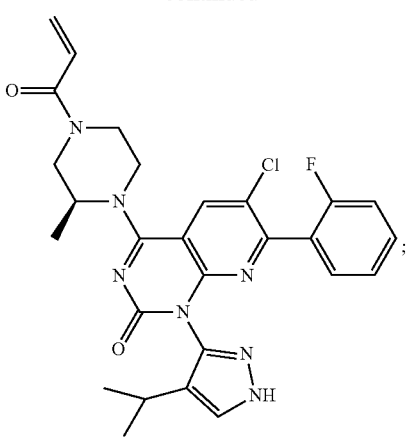
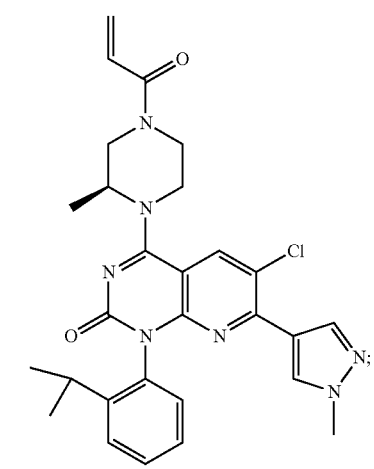
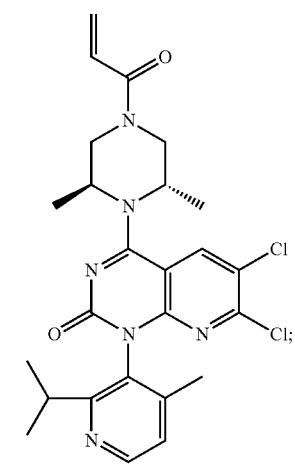

1171
-continued
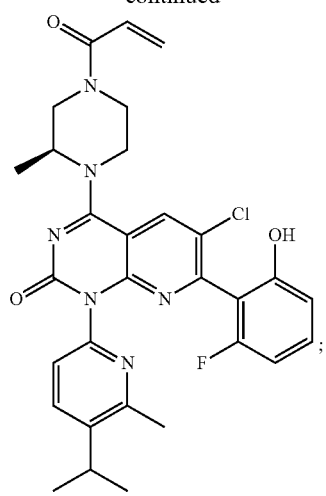
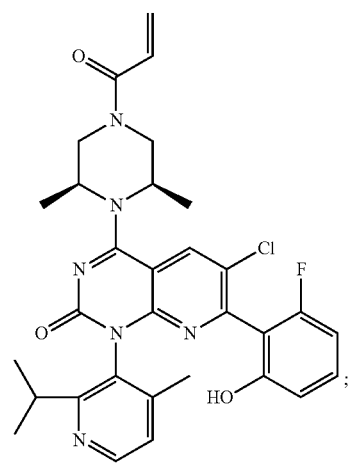
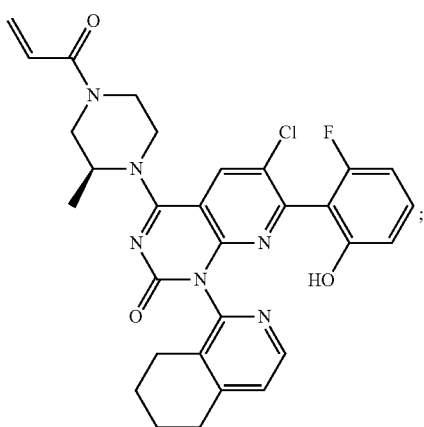
1172
-continued
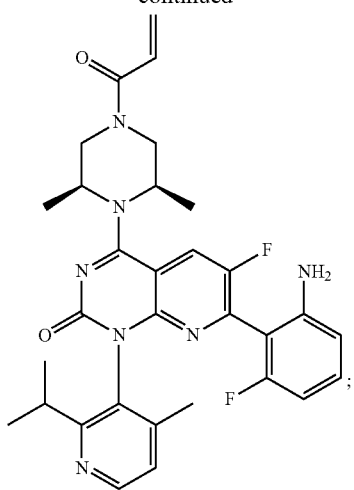
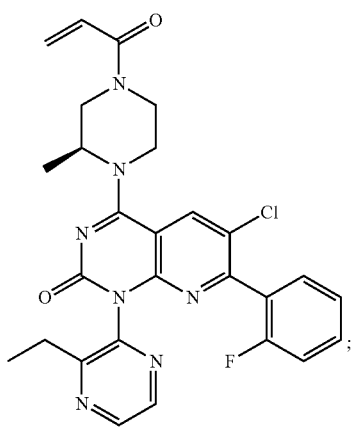
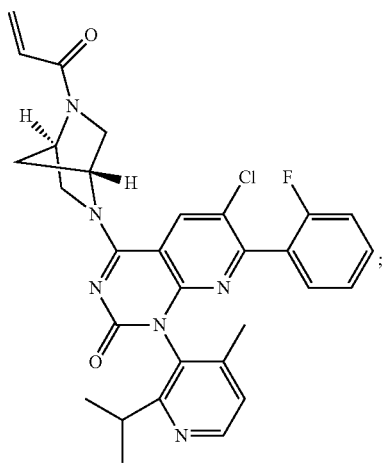

1173
-continued
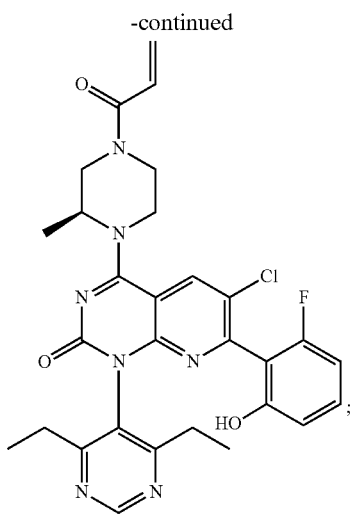
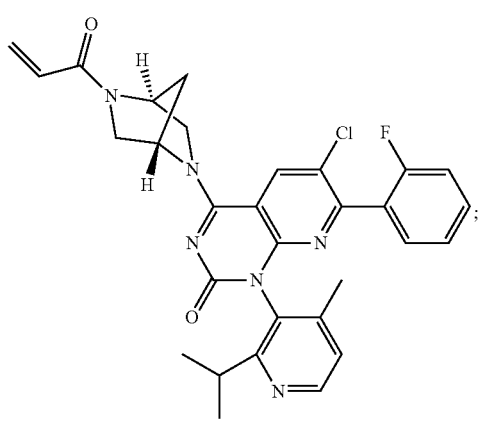
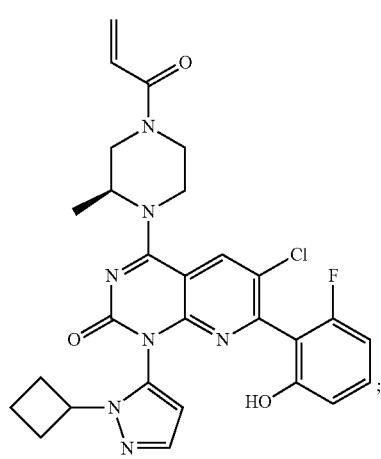
1174
-continued
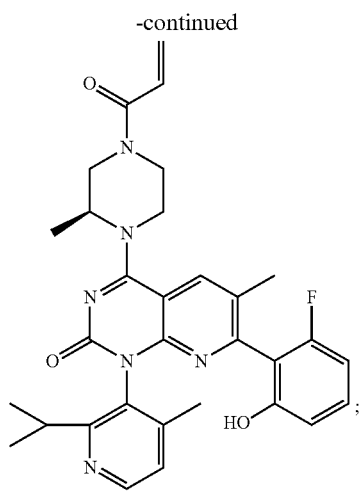
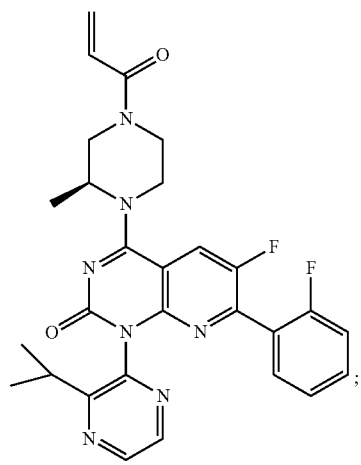
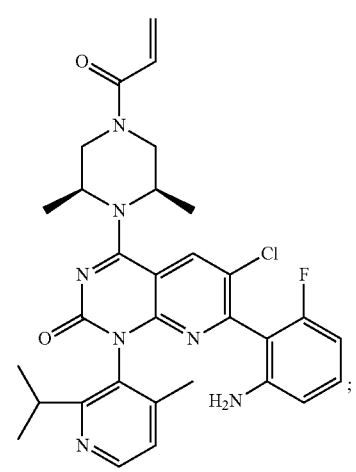

1175
-continued
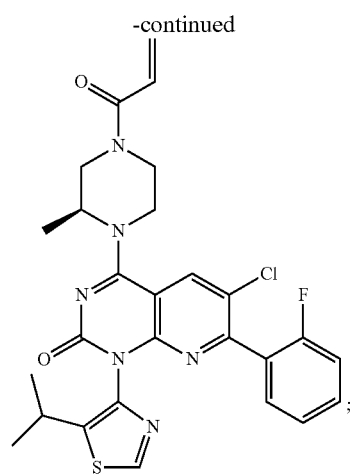
1176
-continued
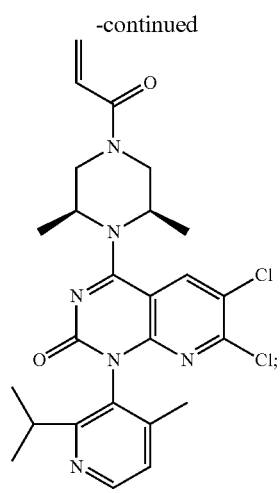
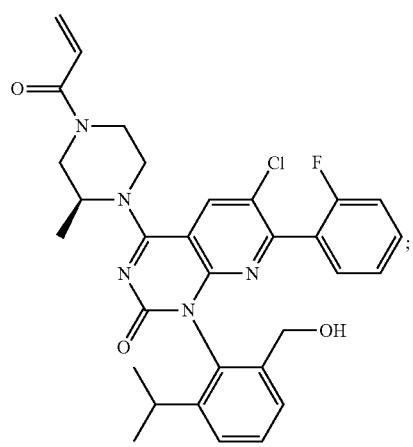
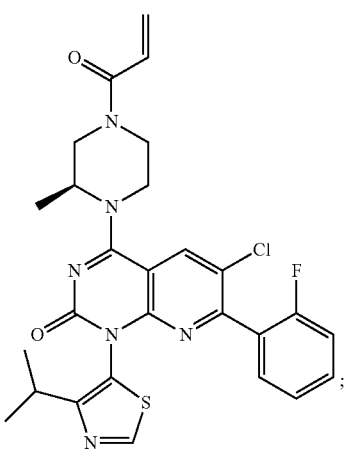
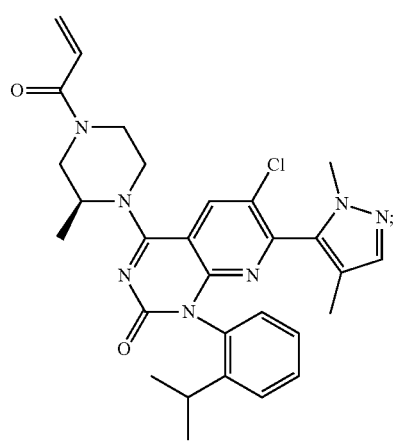
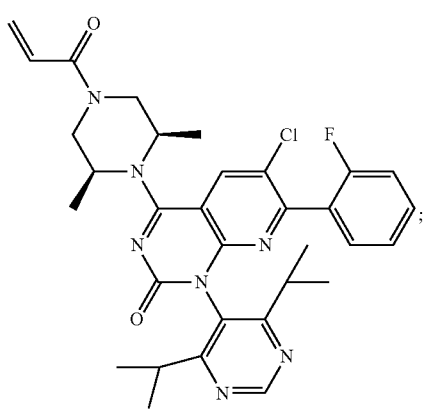

1177
-continued
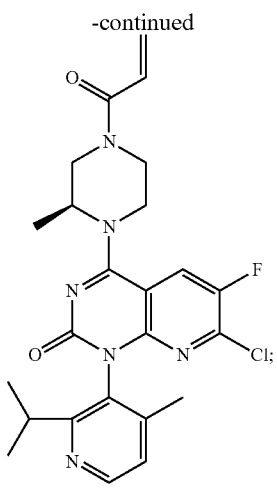
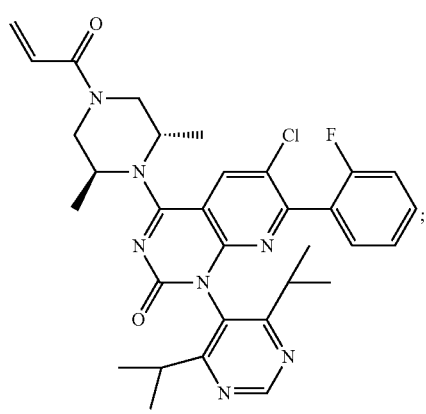
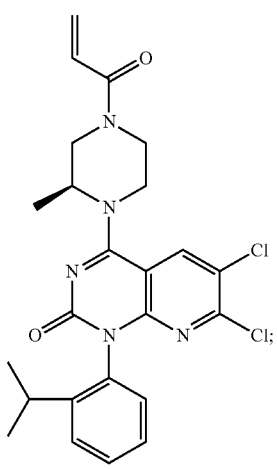
1178
-continued
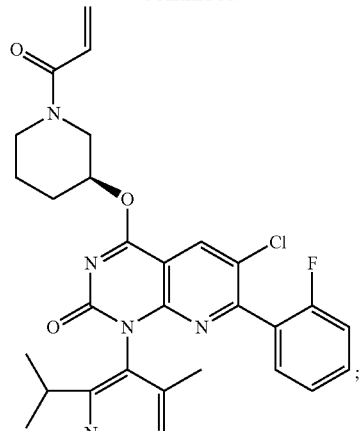
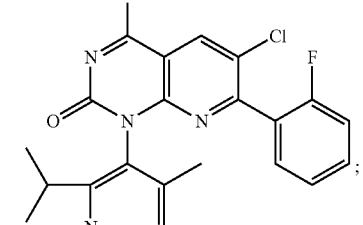

1179
-continued
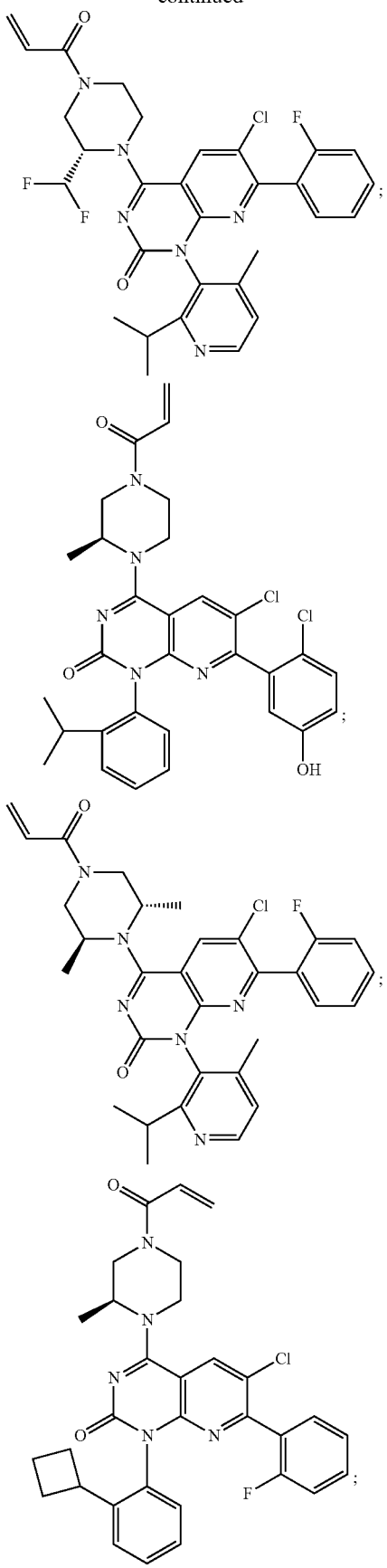
1180
-continued
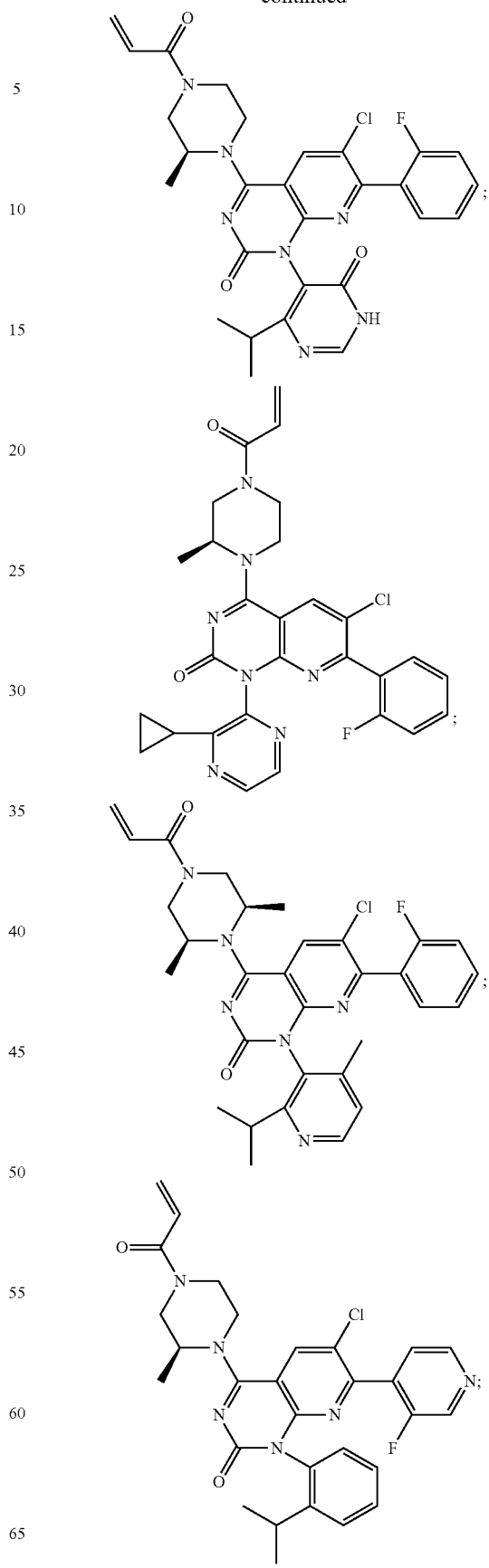

1181
-continued
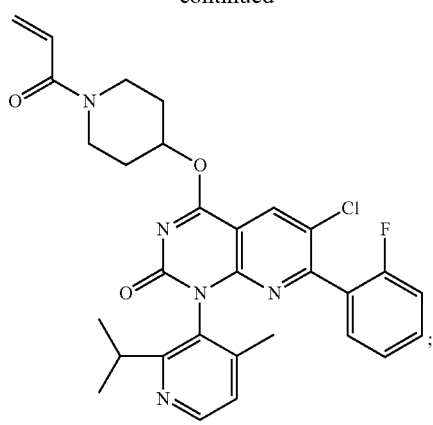
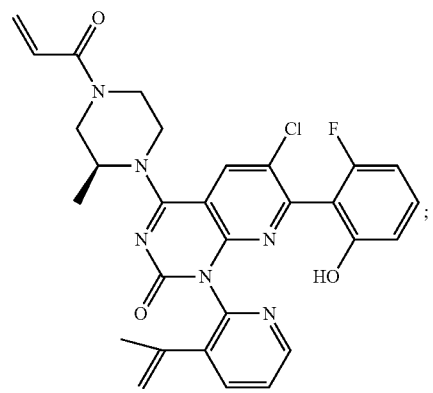
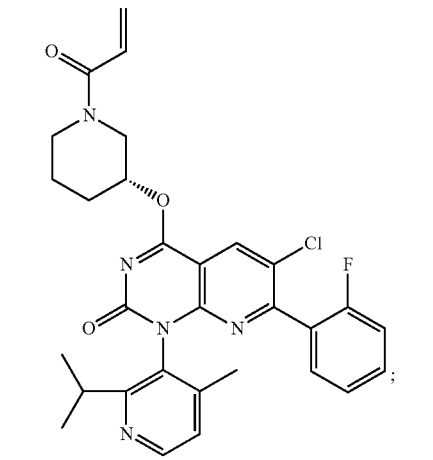
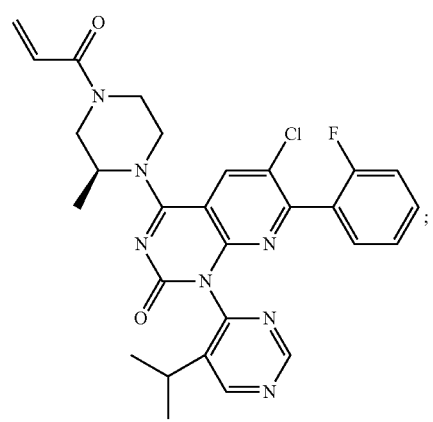
1182
-continued
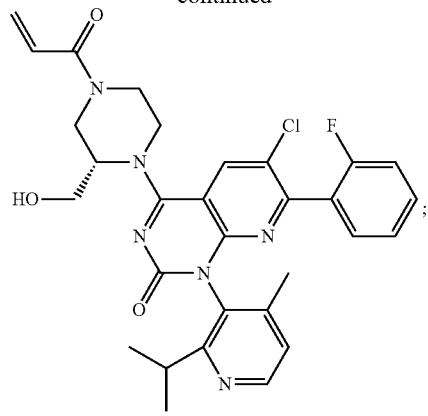
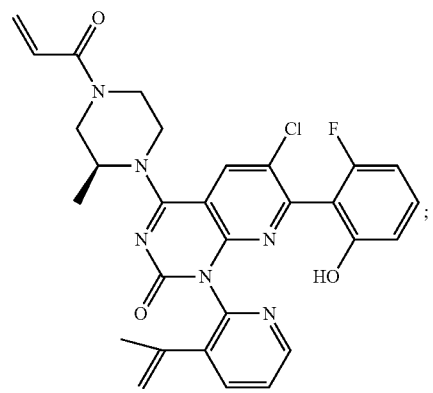
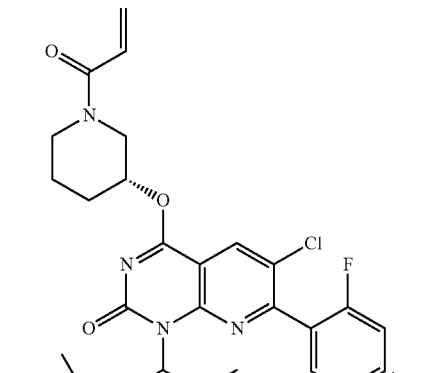

1183
-continued
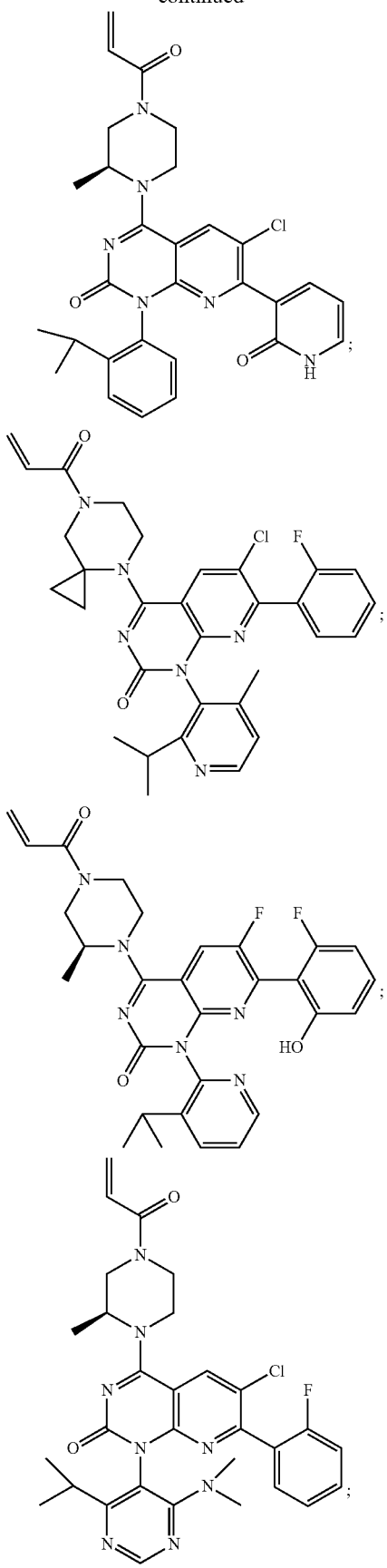
1184
-continued
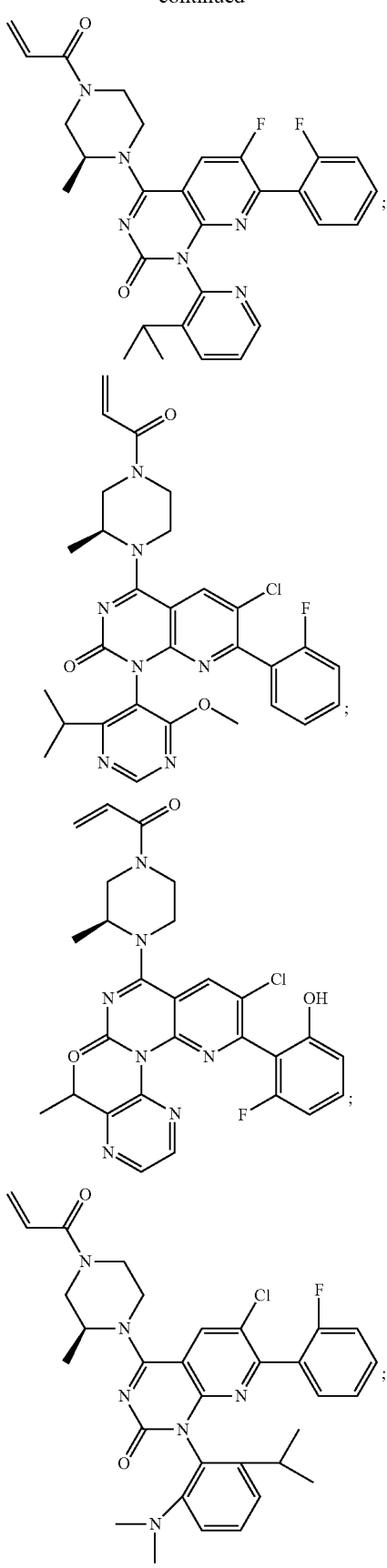

1185
-continued
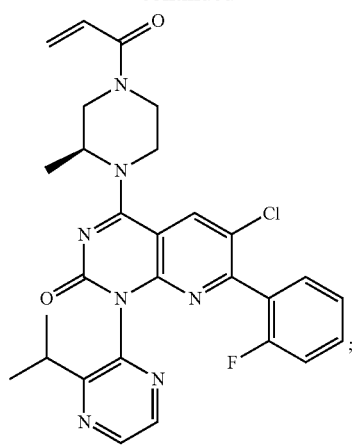
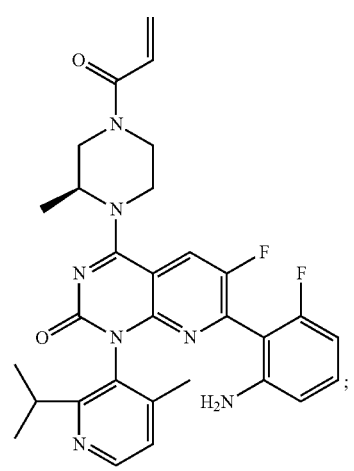
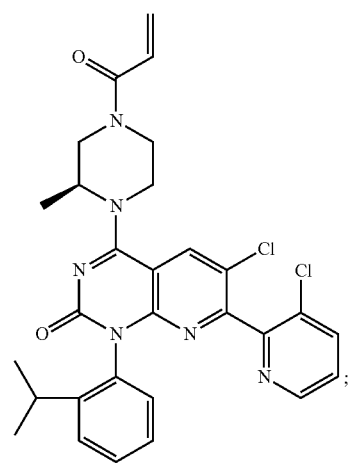
1186
-continued
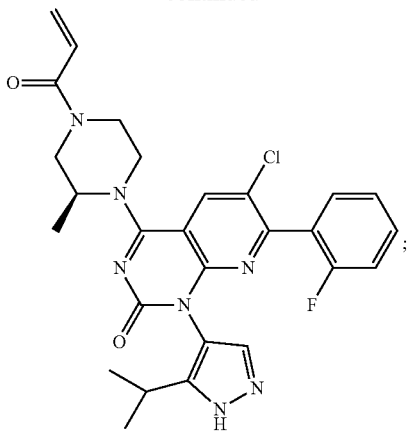
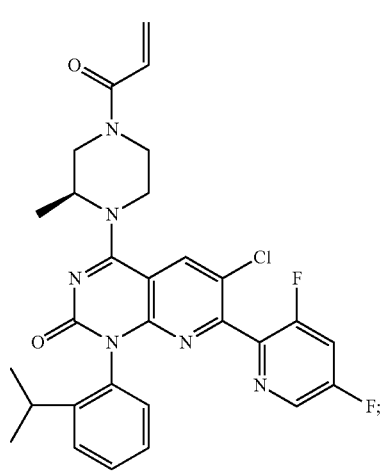
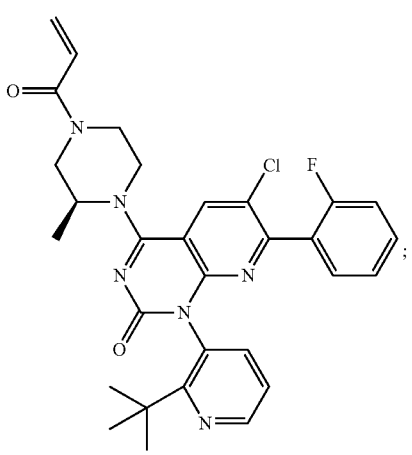

1187
-continued
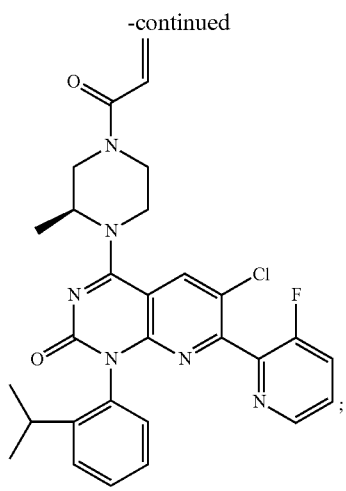
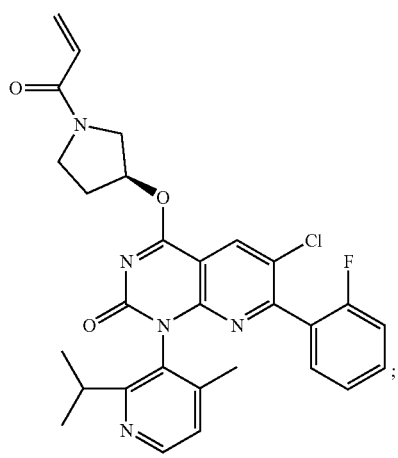
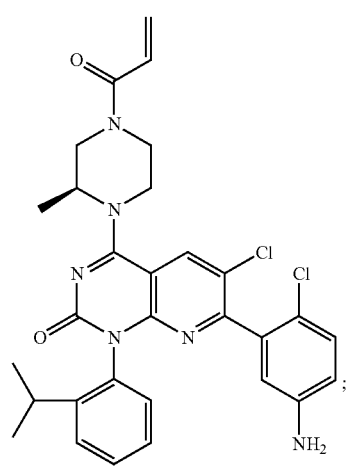
1188
-continued
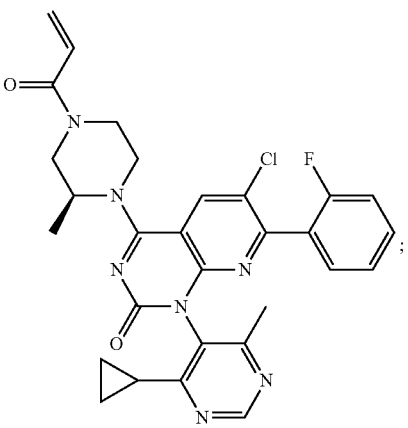
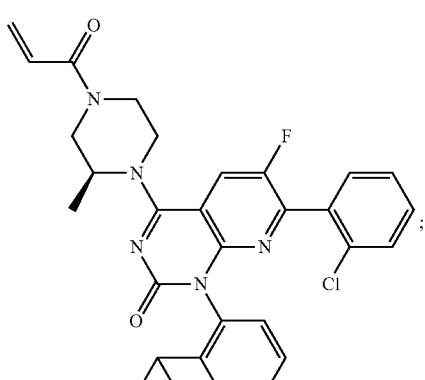
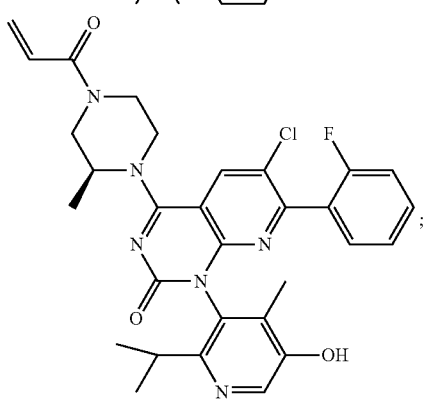
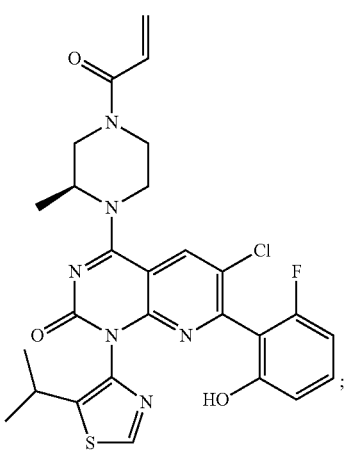

1189
-continued
1190
-continued
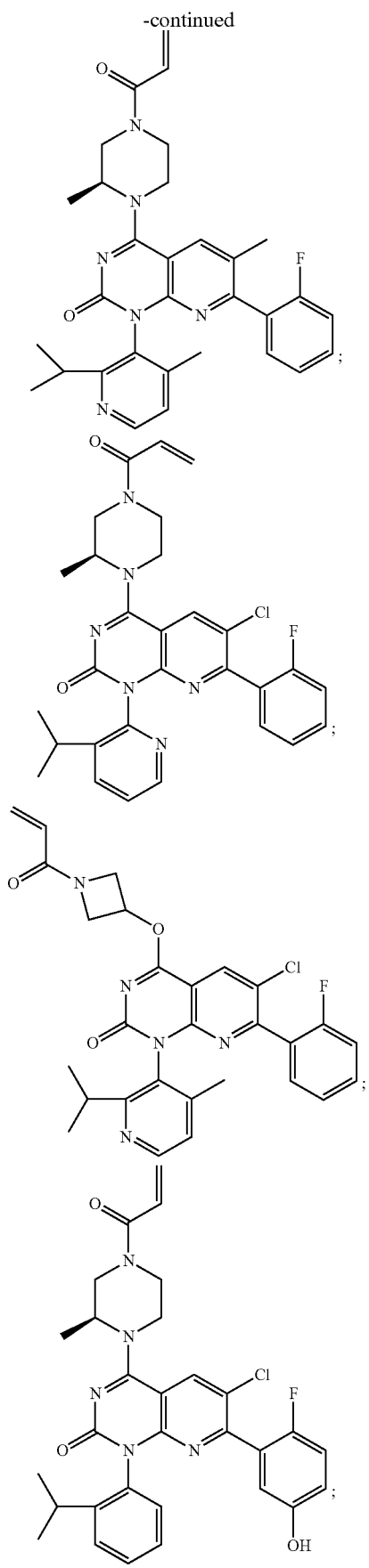
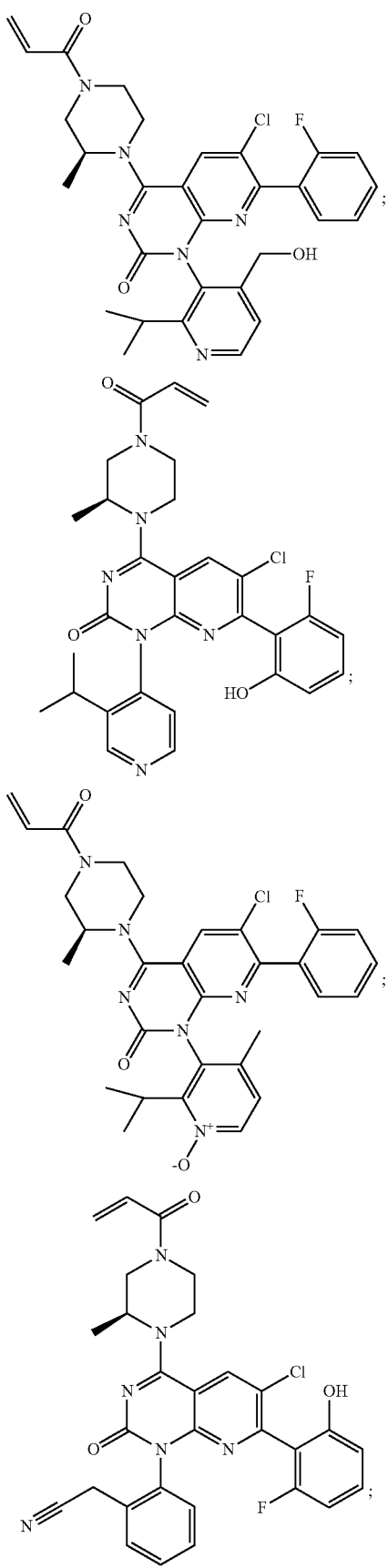

1191
-continued
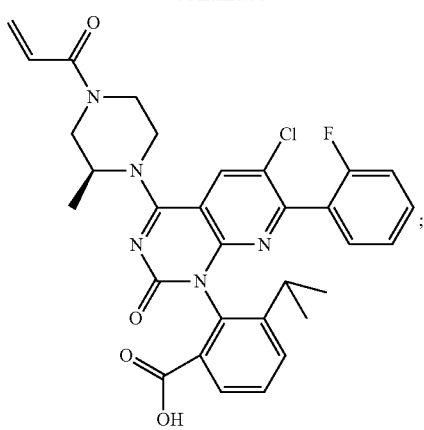
1192
-continued
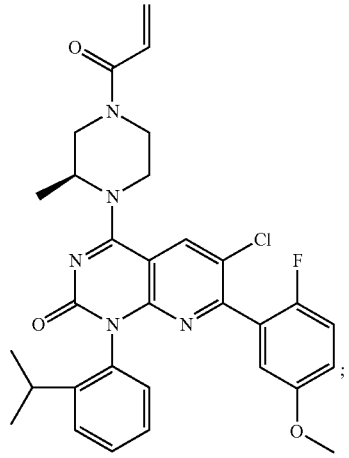
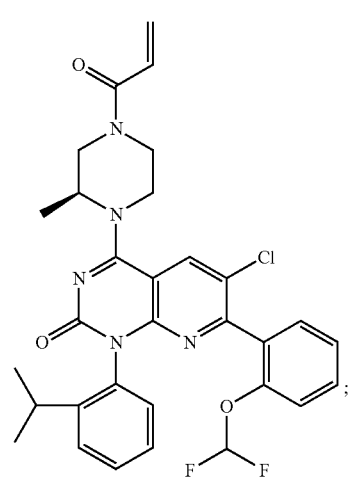
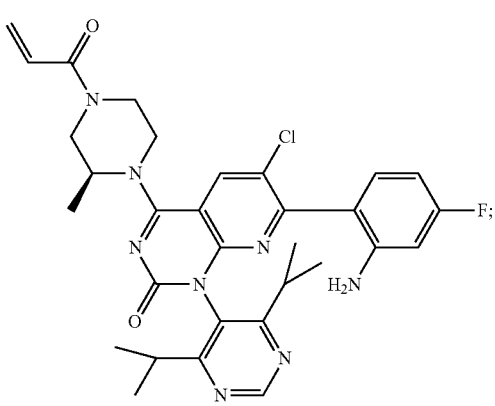
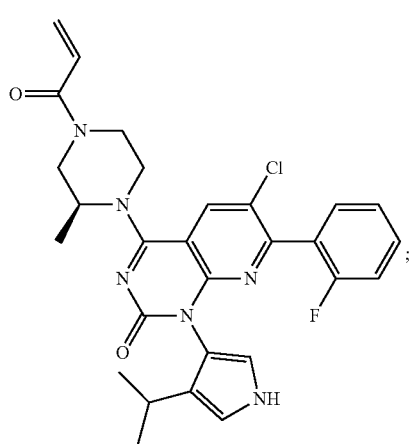
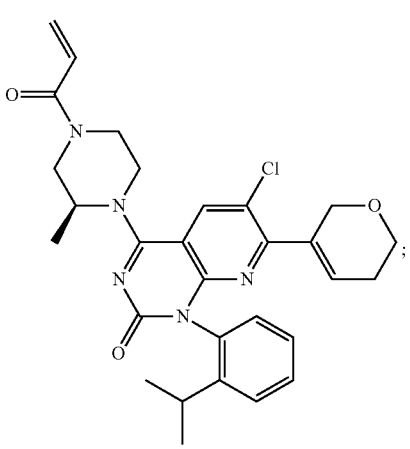

1193
-continued
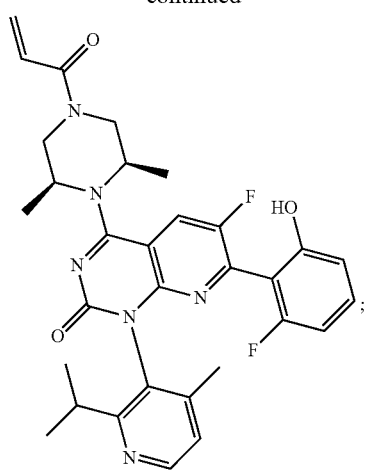
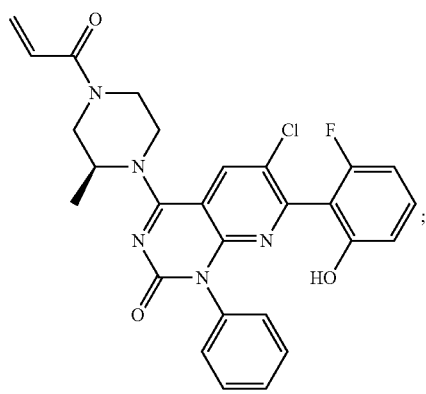
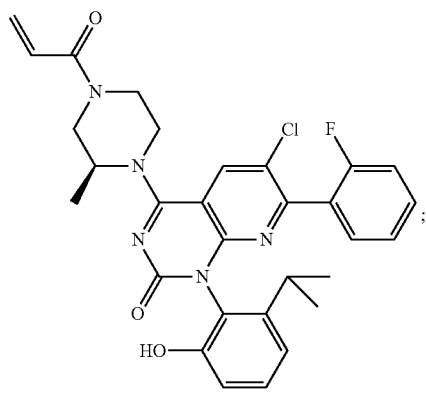
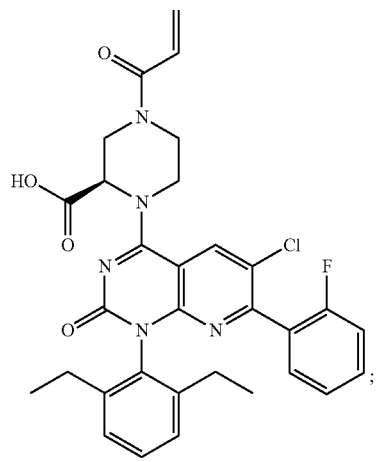
1194
-continued
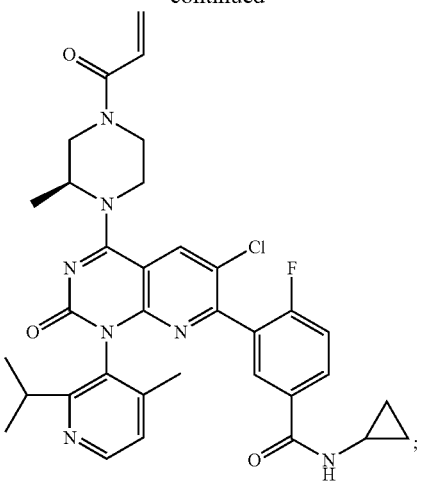
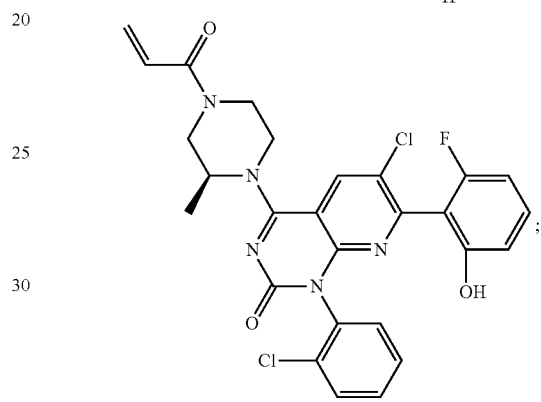
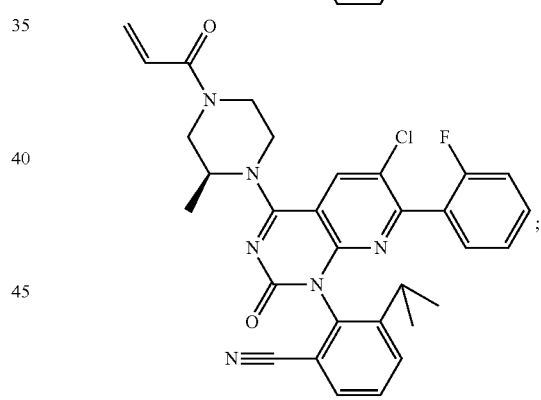
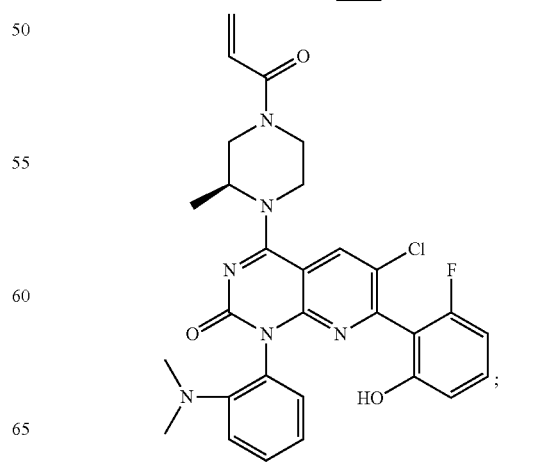

1195
-continued
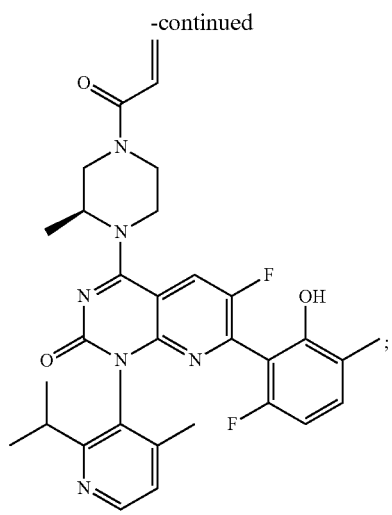
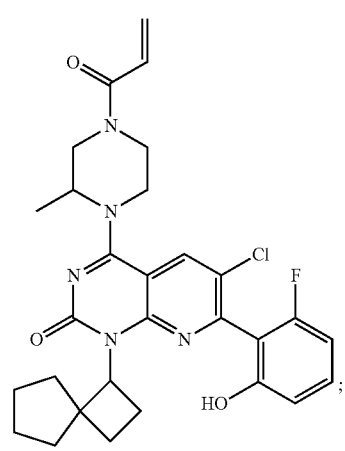
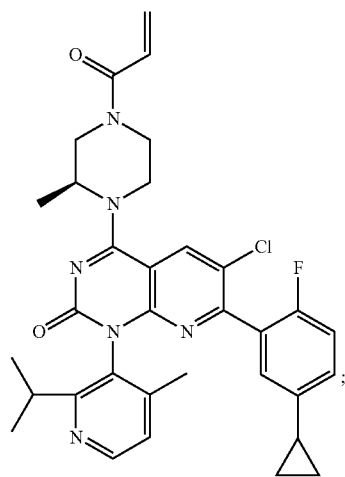
1196
-continued
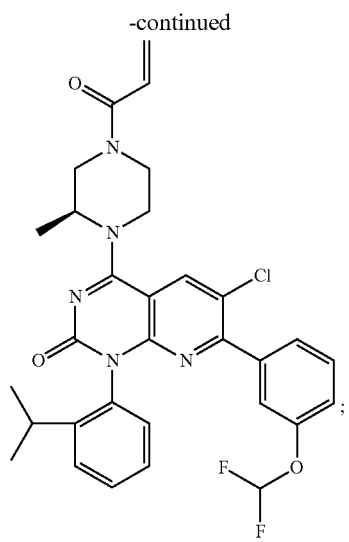
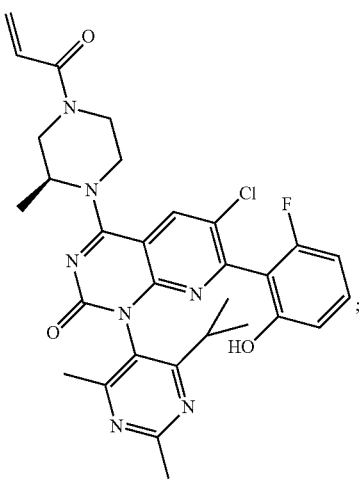
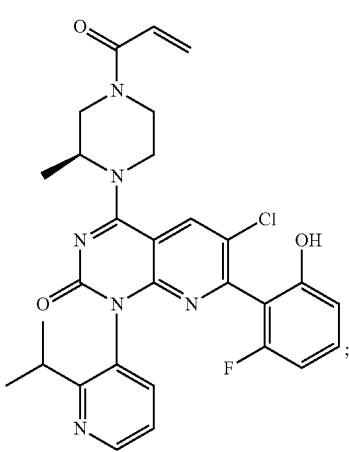

1197
-continued
1198
-continued
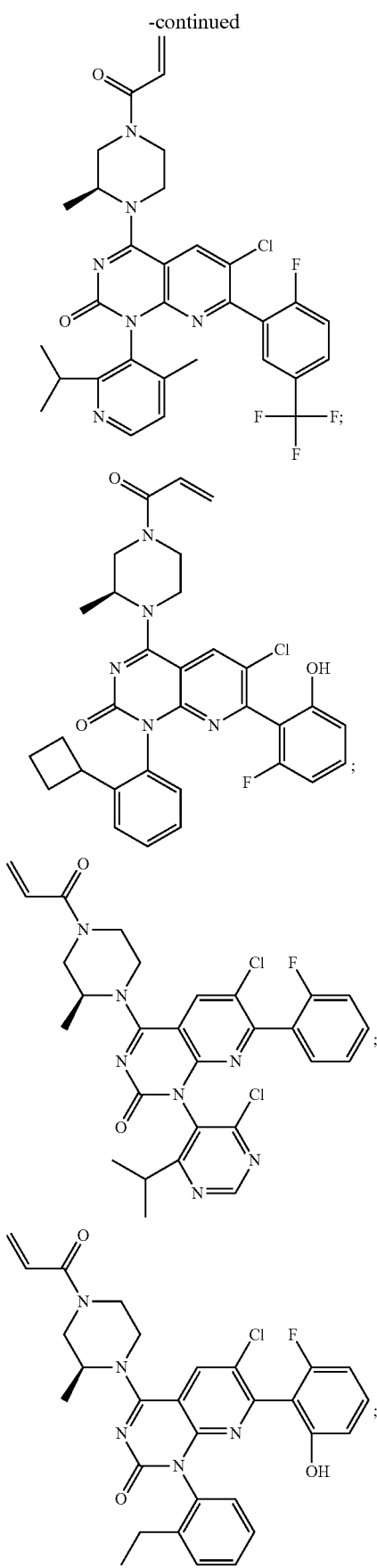
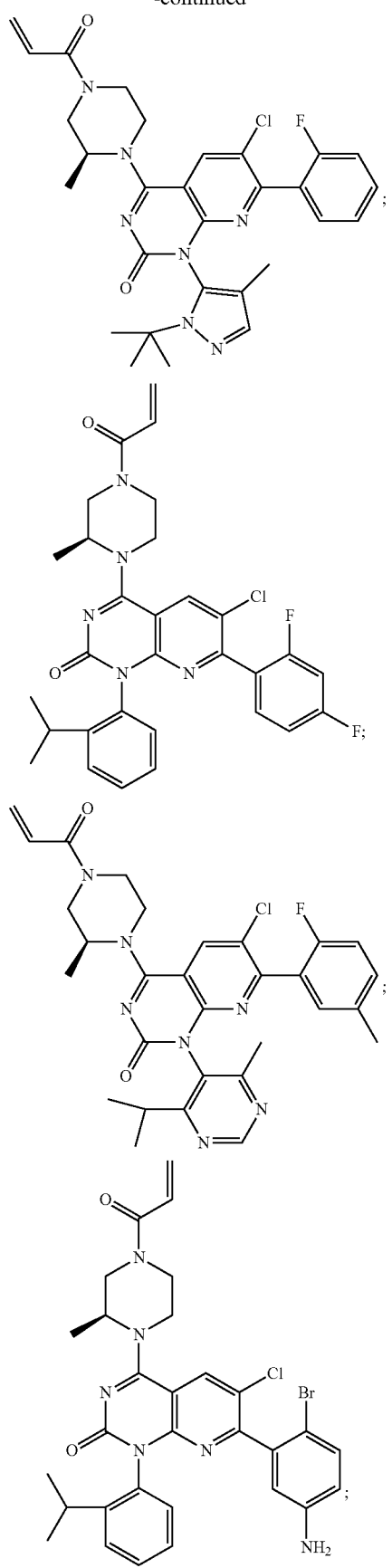

1199
-continued
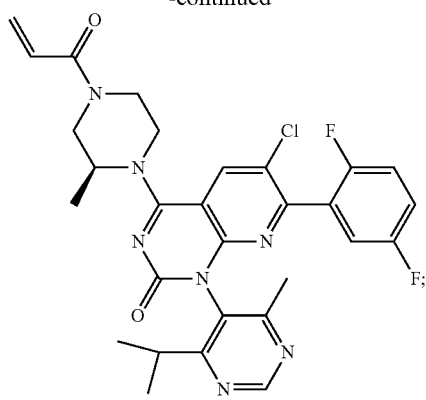
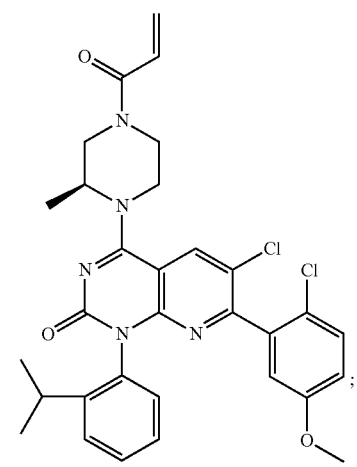
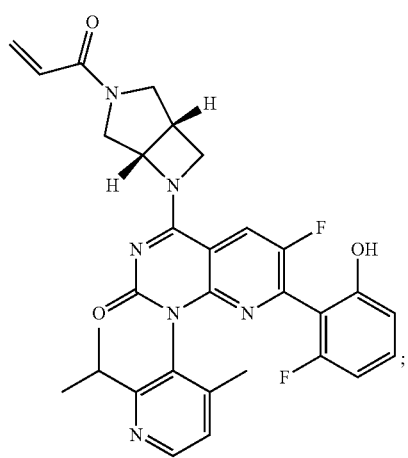
1200
-continued
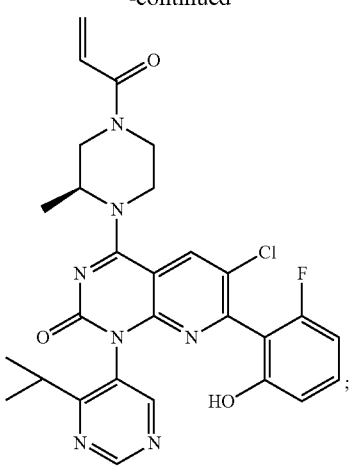
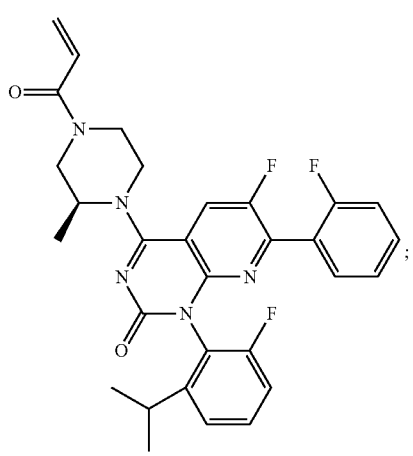
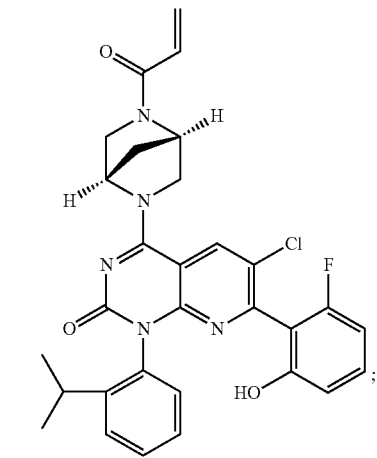

1201
-continued
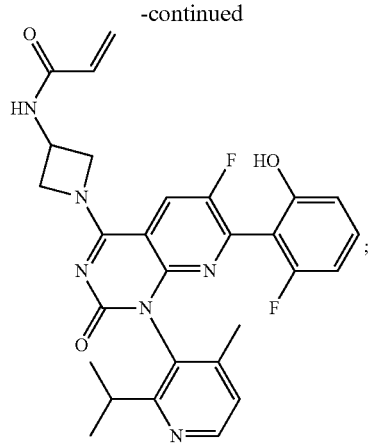
;
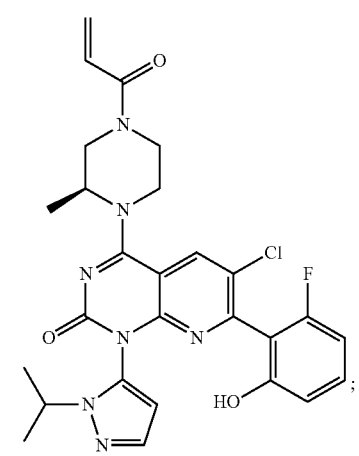
;
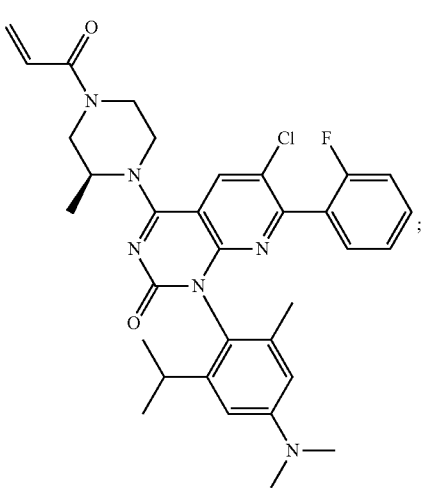
;
1202
-continued
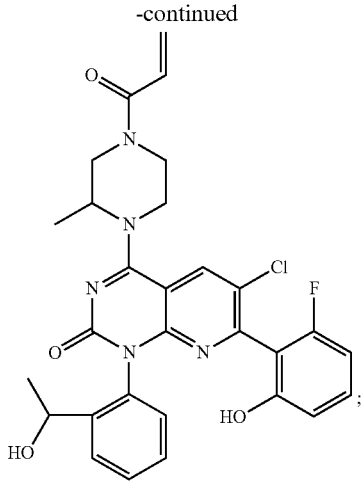
;
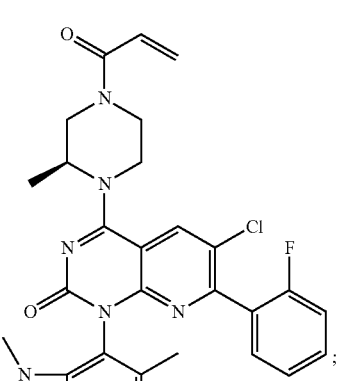
;
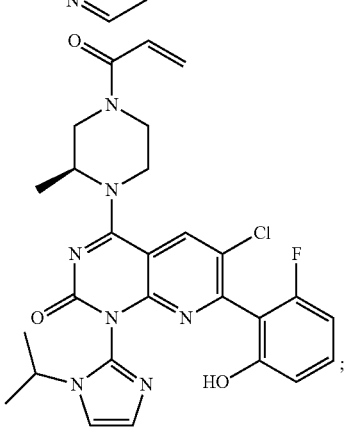
;
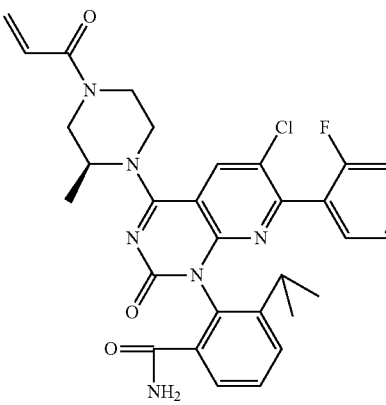
;

1203
-continued
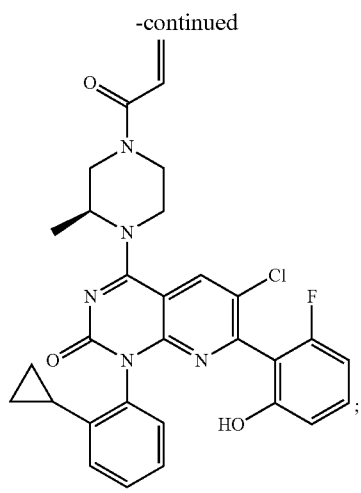
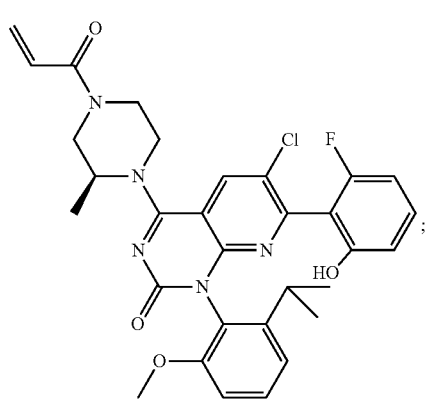
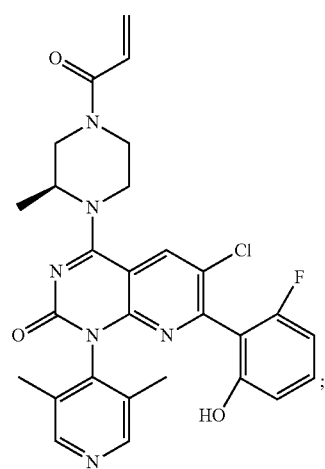
1204
-continued
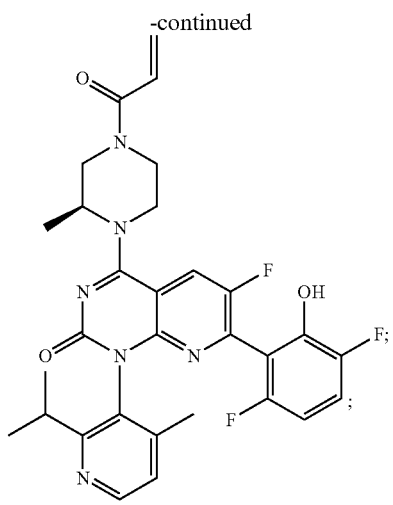
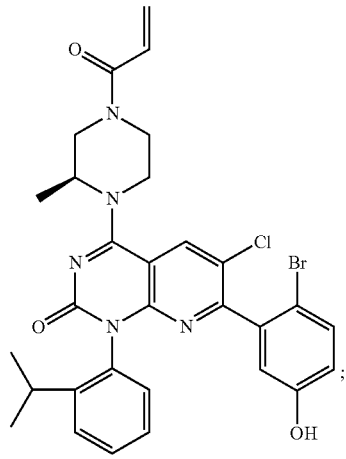
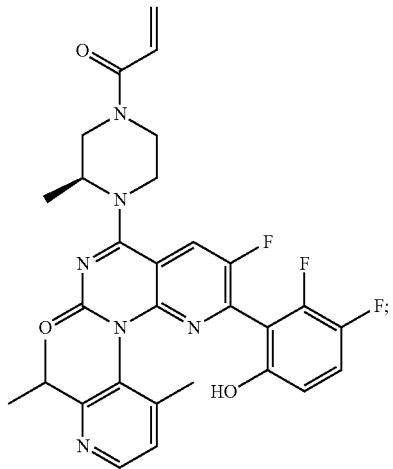

1205
-continued
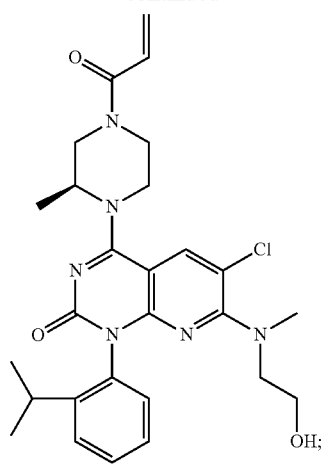
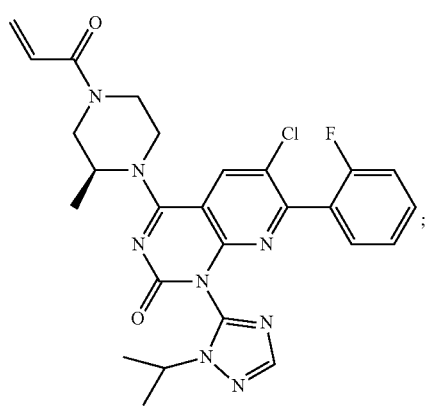
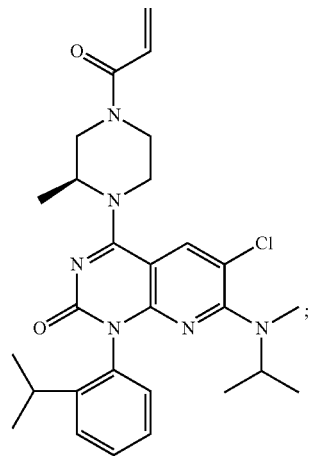
1206
-continued
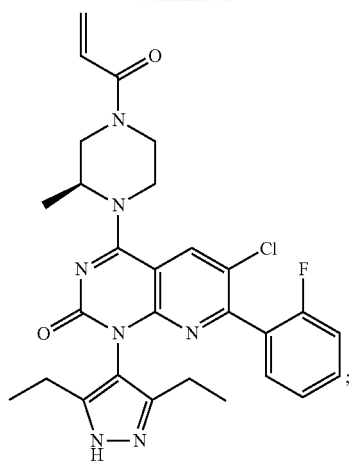
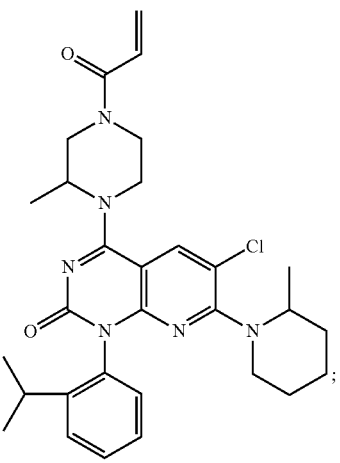
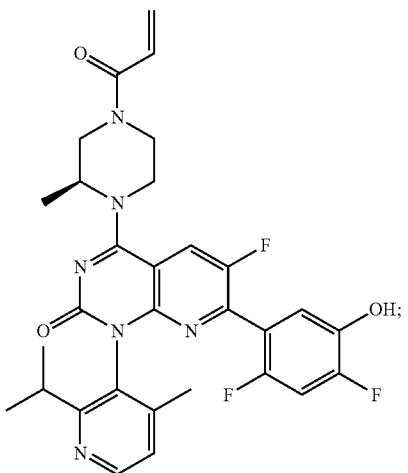

1207
-continued
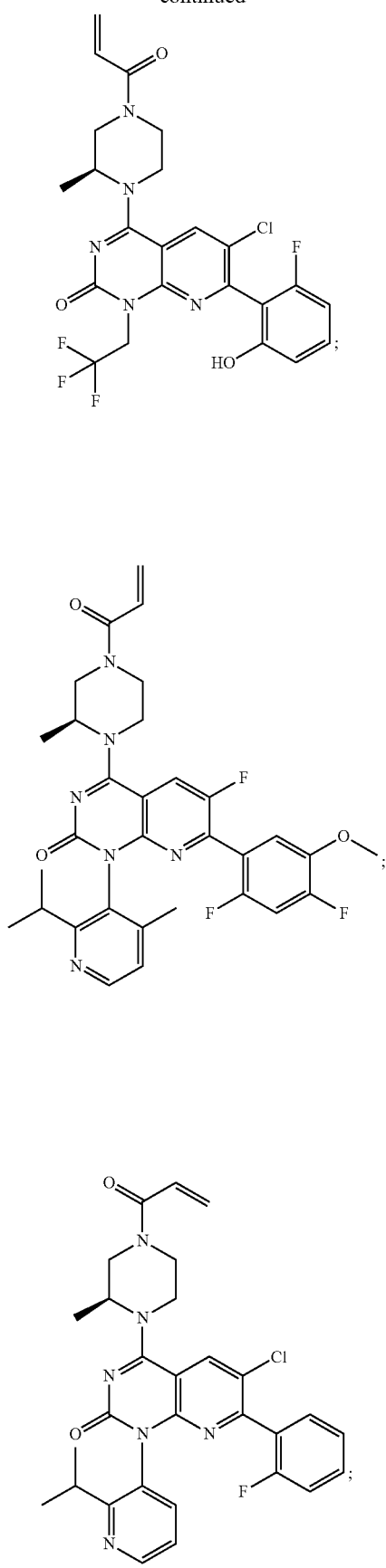
1208
-continued
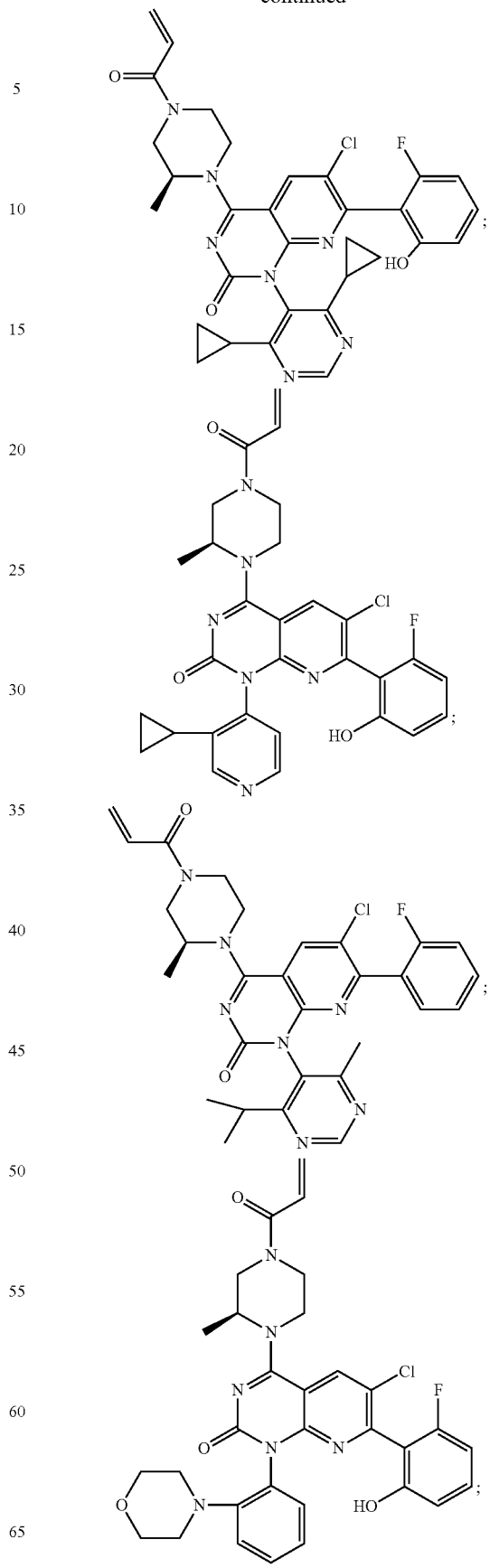

1209
-continued
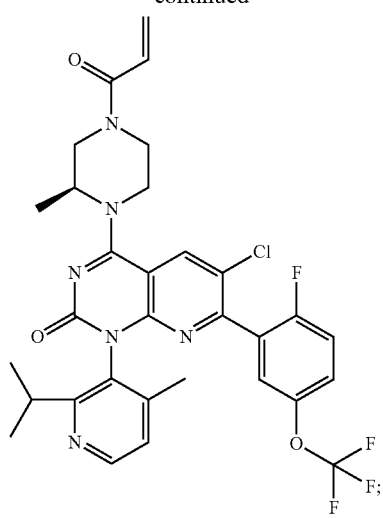
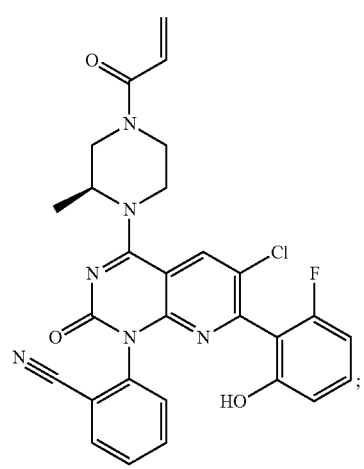
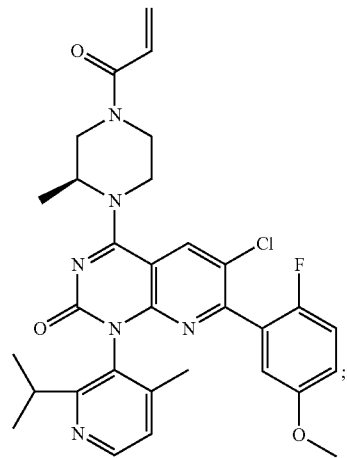
1210
-continued
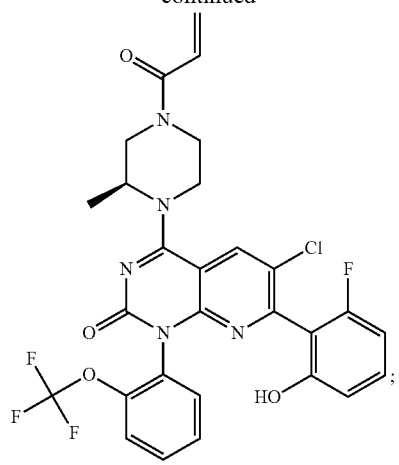
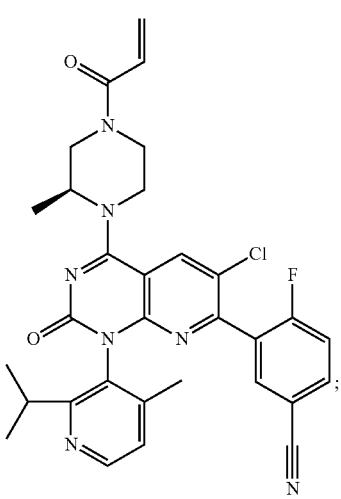
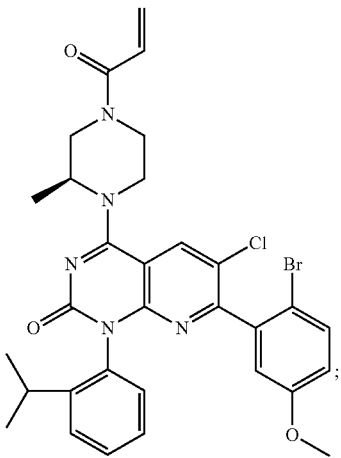

1211
-continued
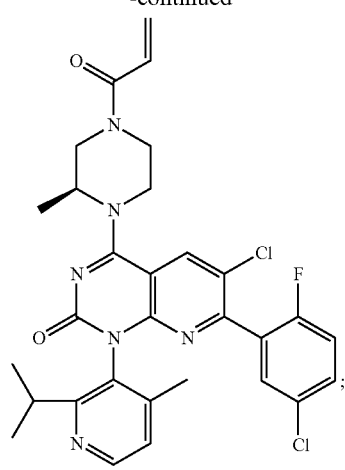
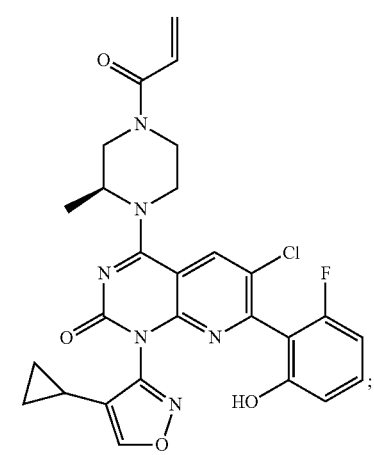
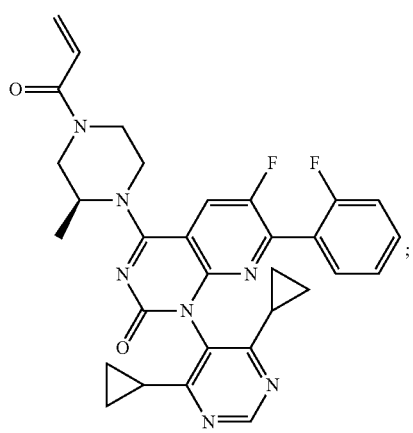
1212
-continued
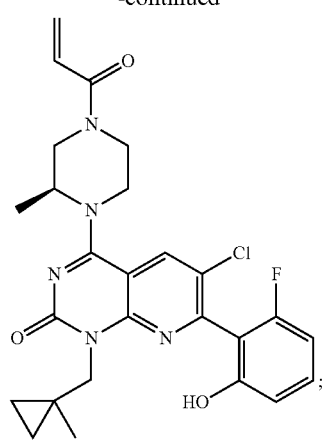
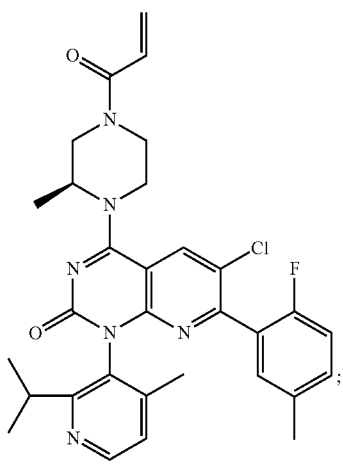
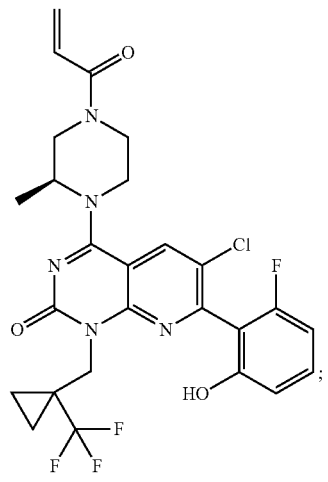

1213
-continued
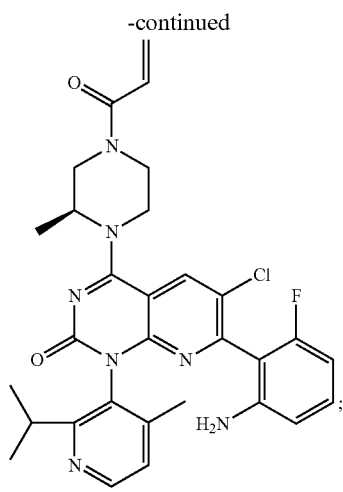
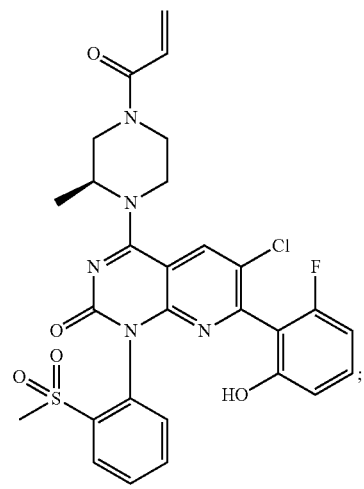
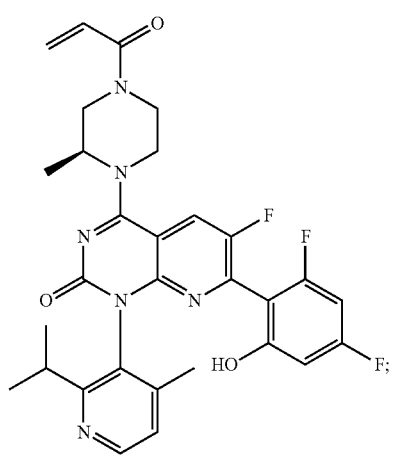
1214
-continued
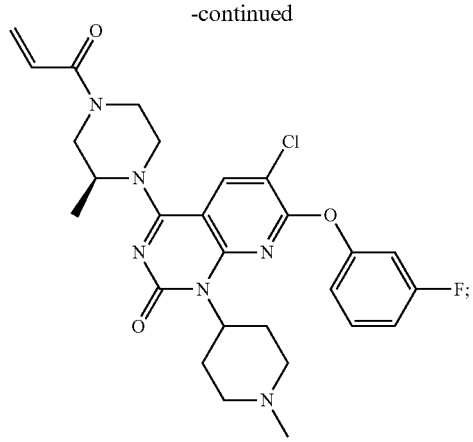
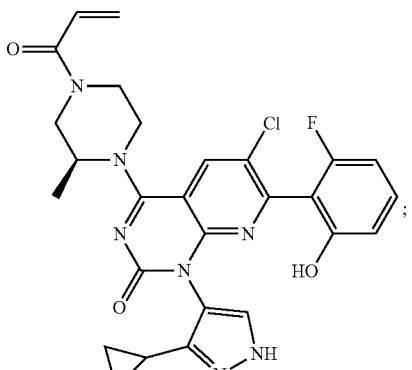
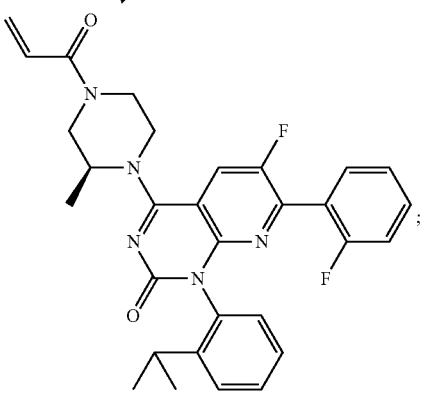

1215
-continued
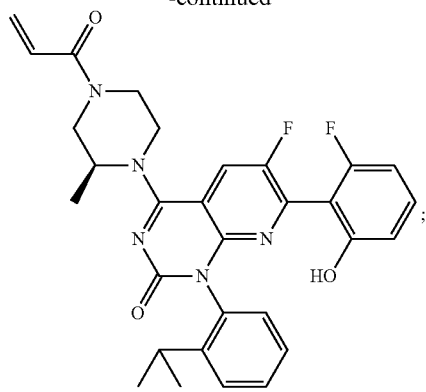
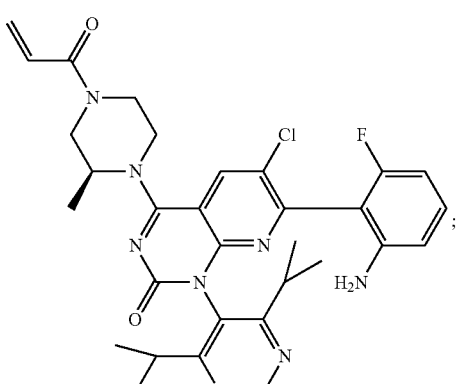
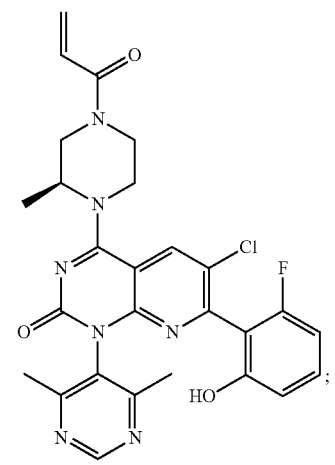
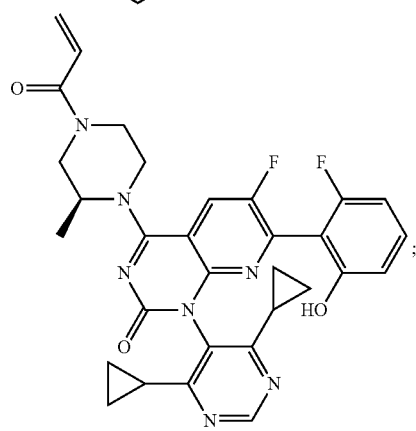
1216
-continued
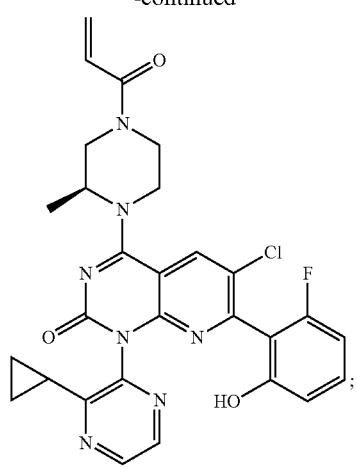
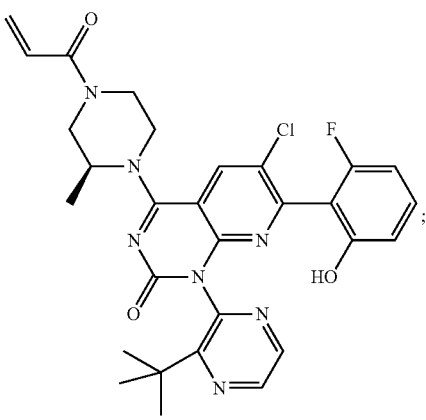
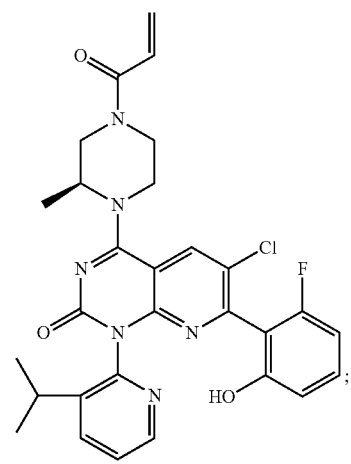

1217
-continued
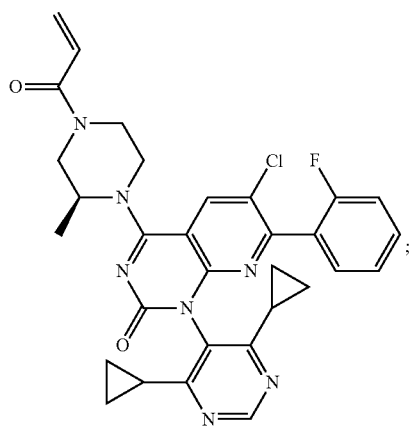
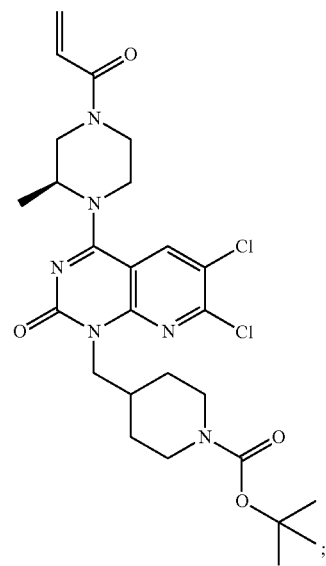
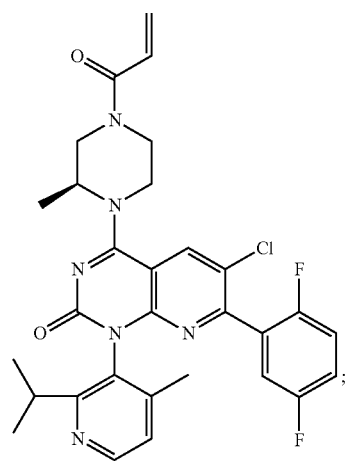
1218
-continued
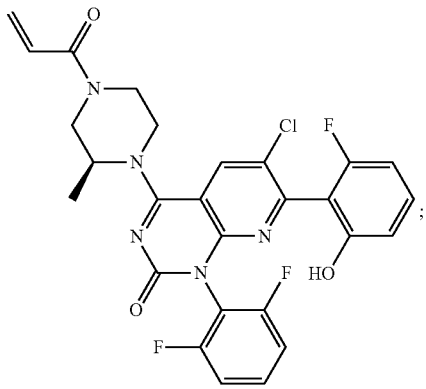
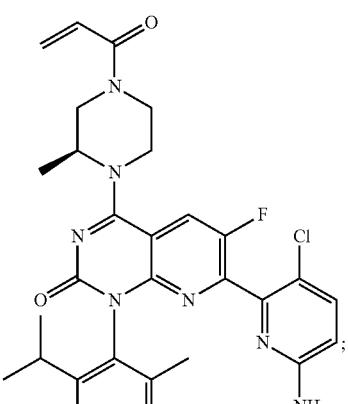
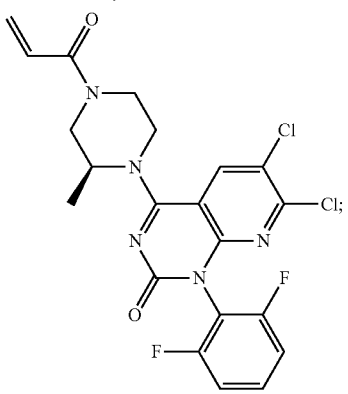
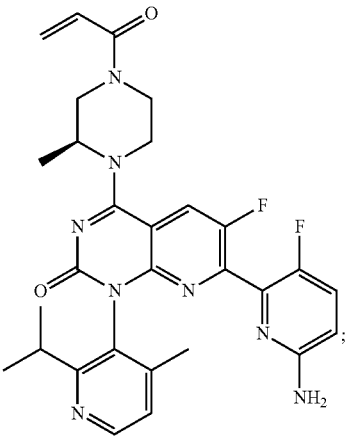

1219
-continued
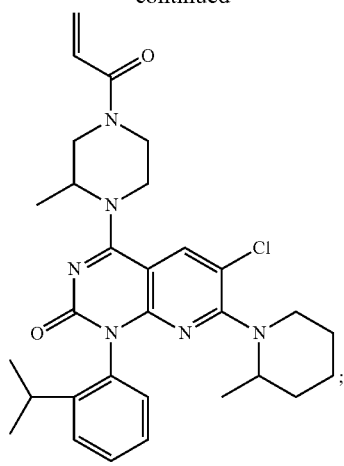
1220
-continued
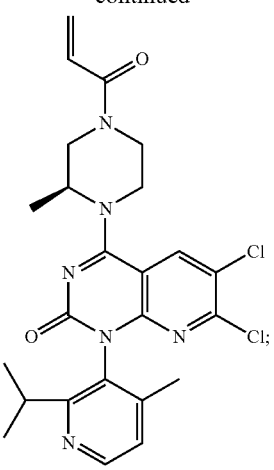
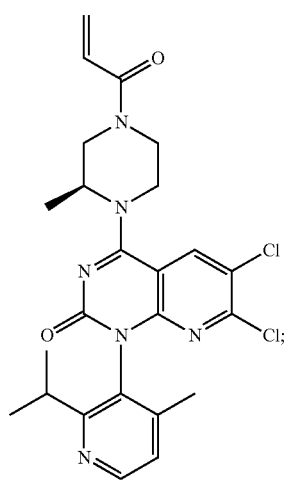
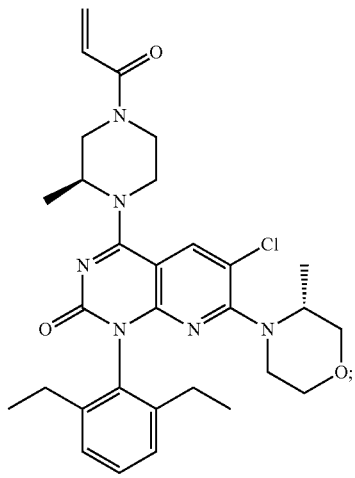
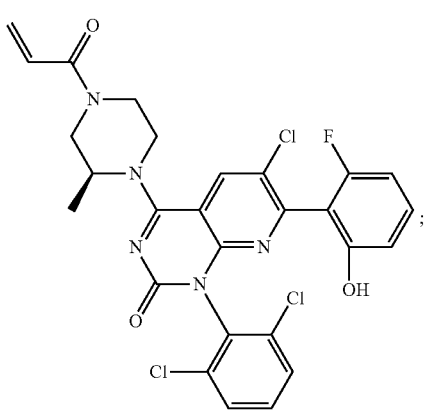
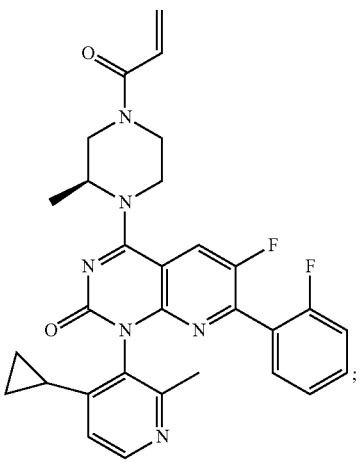

1221
-continued
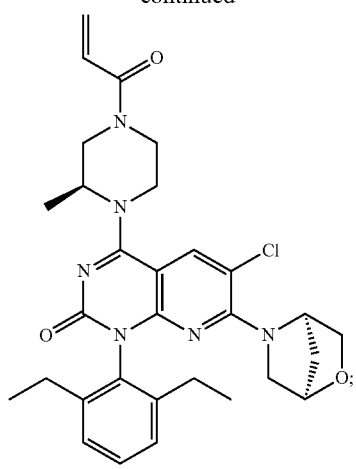
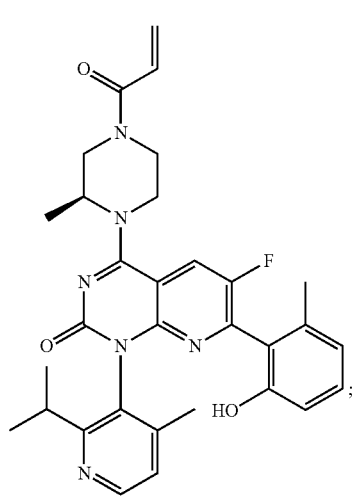
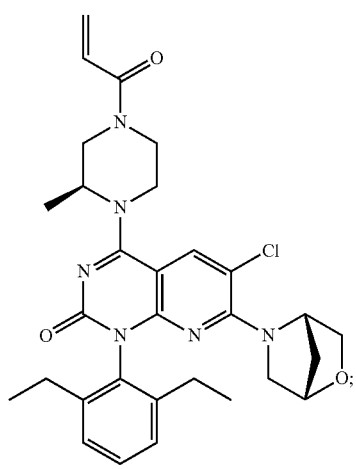
1222
-continued
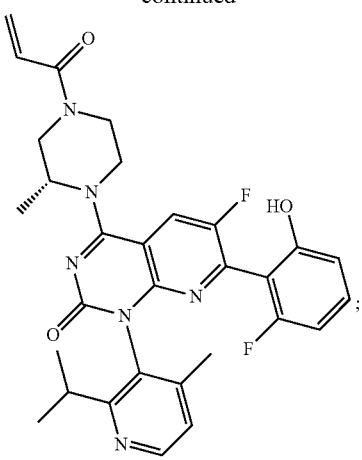
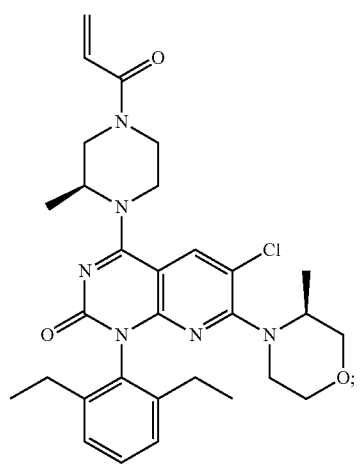
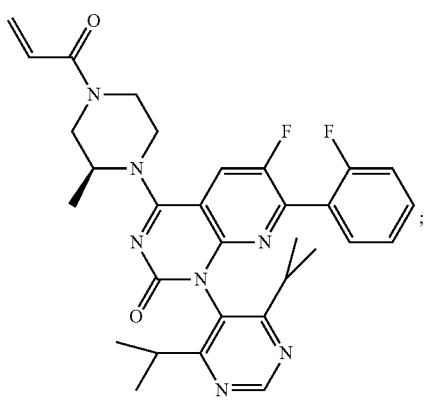

1223
-continued
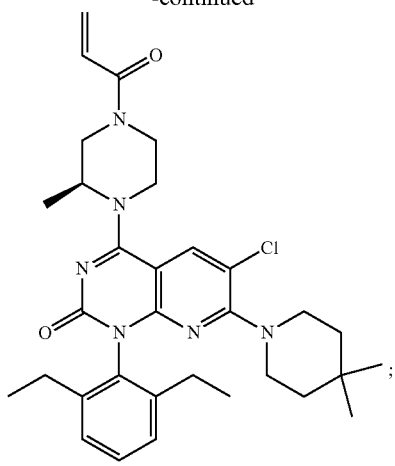
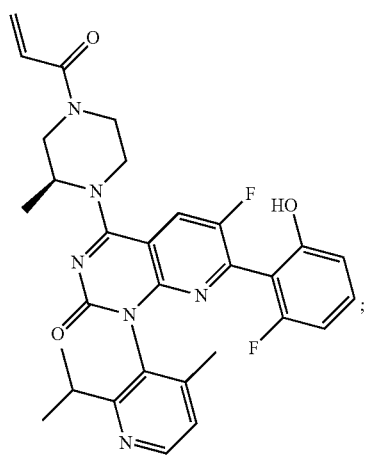
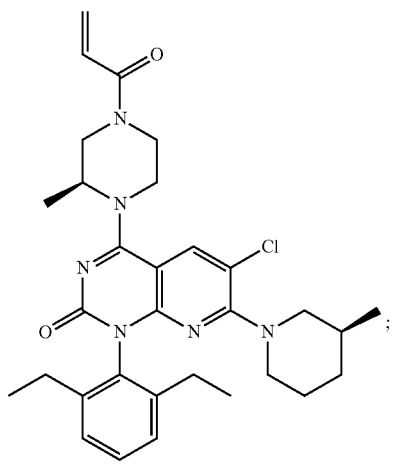
1224
-continued
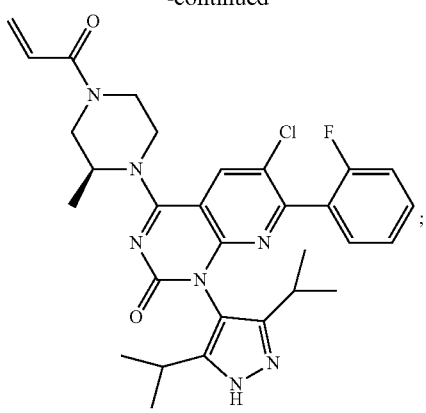
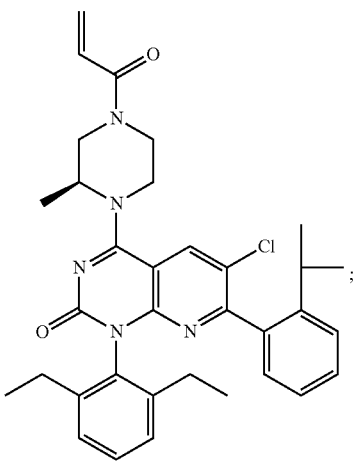
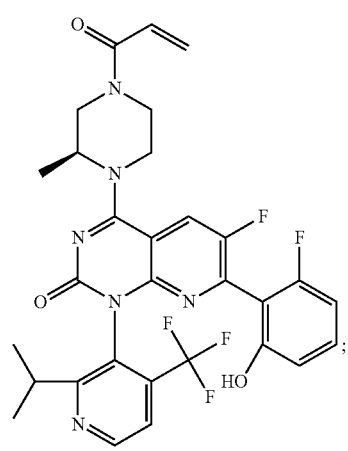

1225
-continued
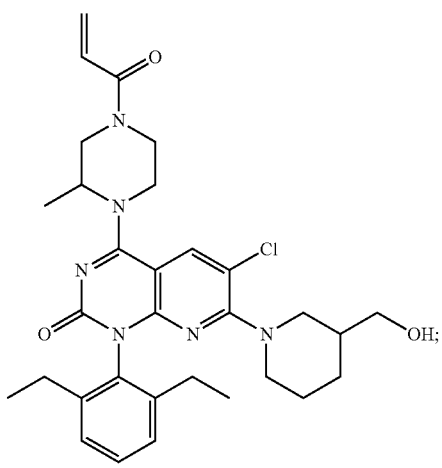
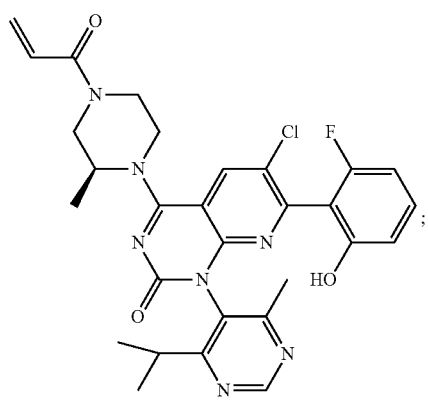
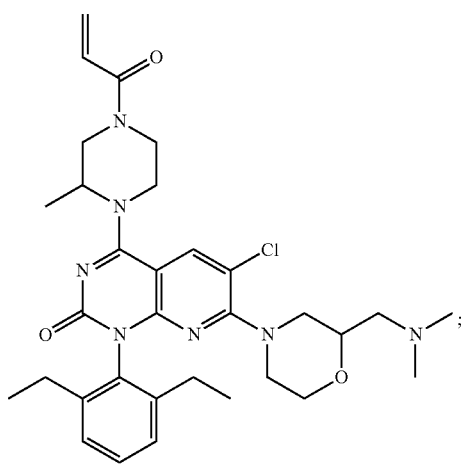
1226
-continued
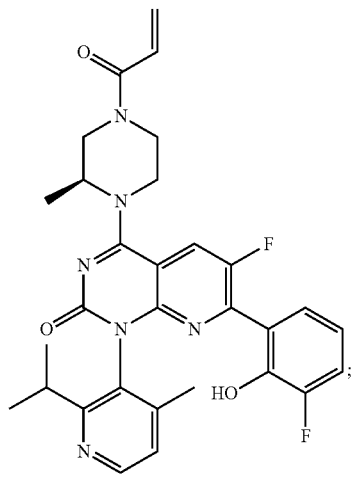
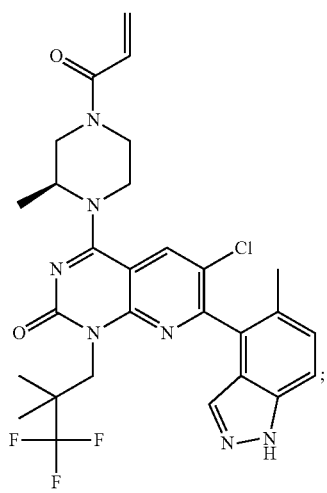
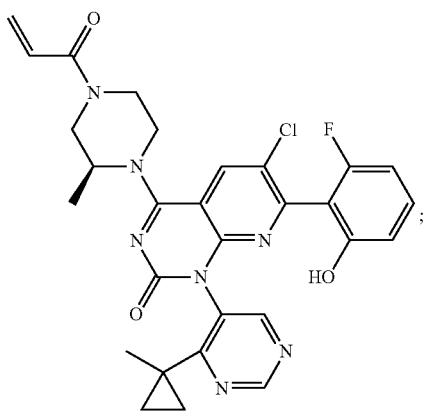

1227
-continued
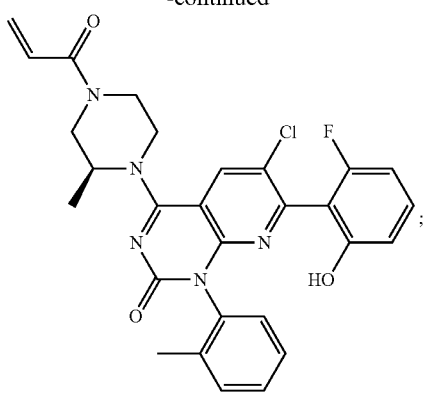
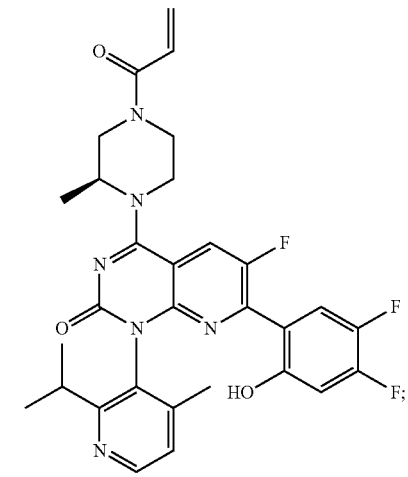
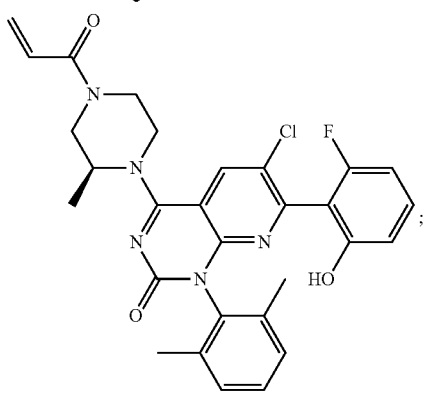
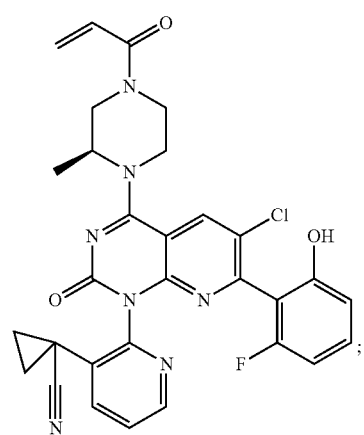
1228
-continued
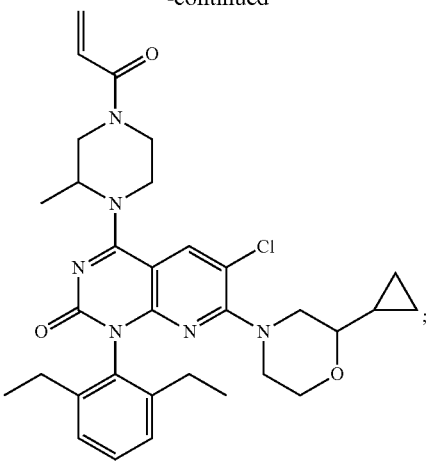
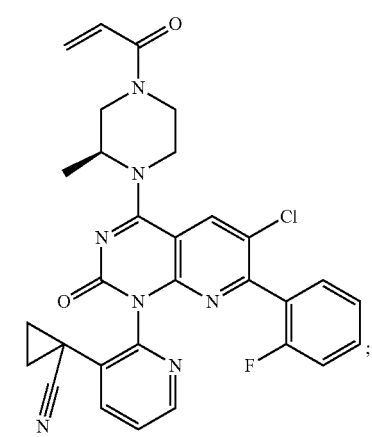
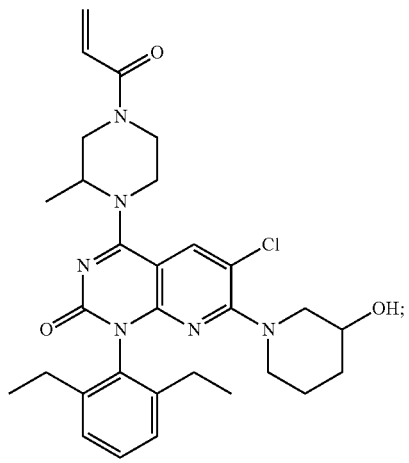

1229
-continued
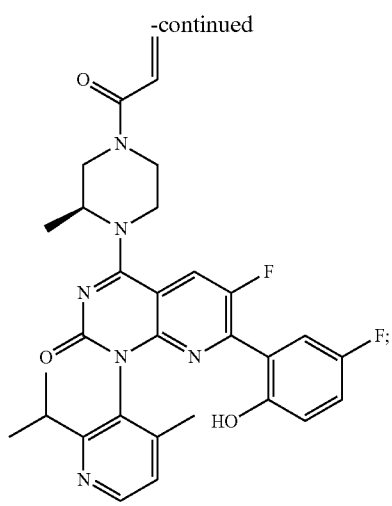
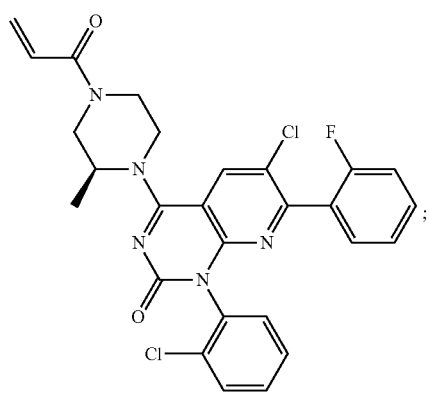
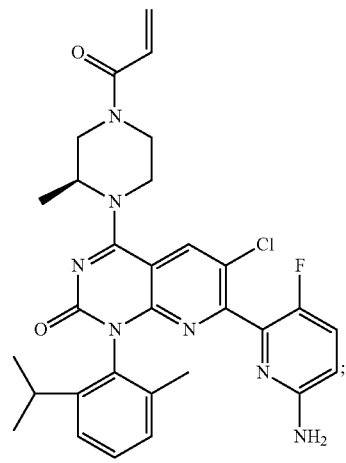
1230
-continued
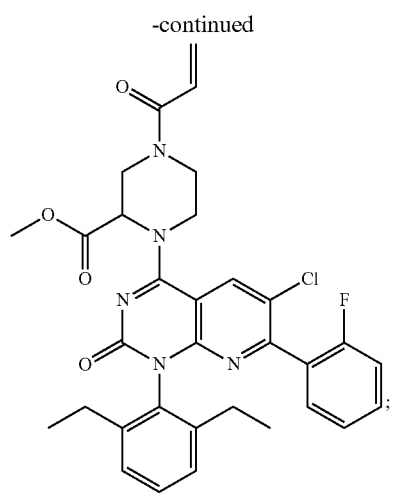
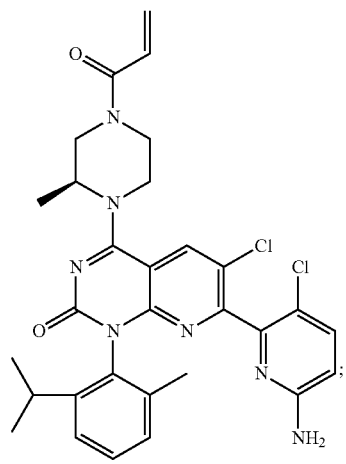
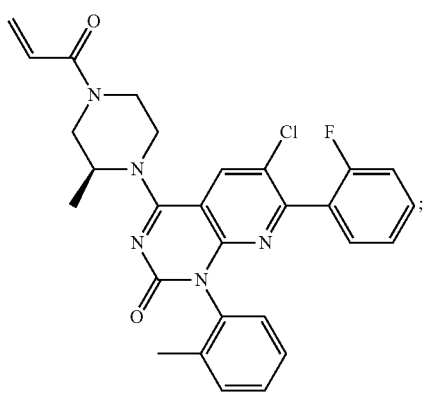

1231
-continued
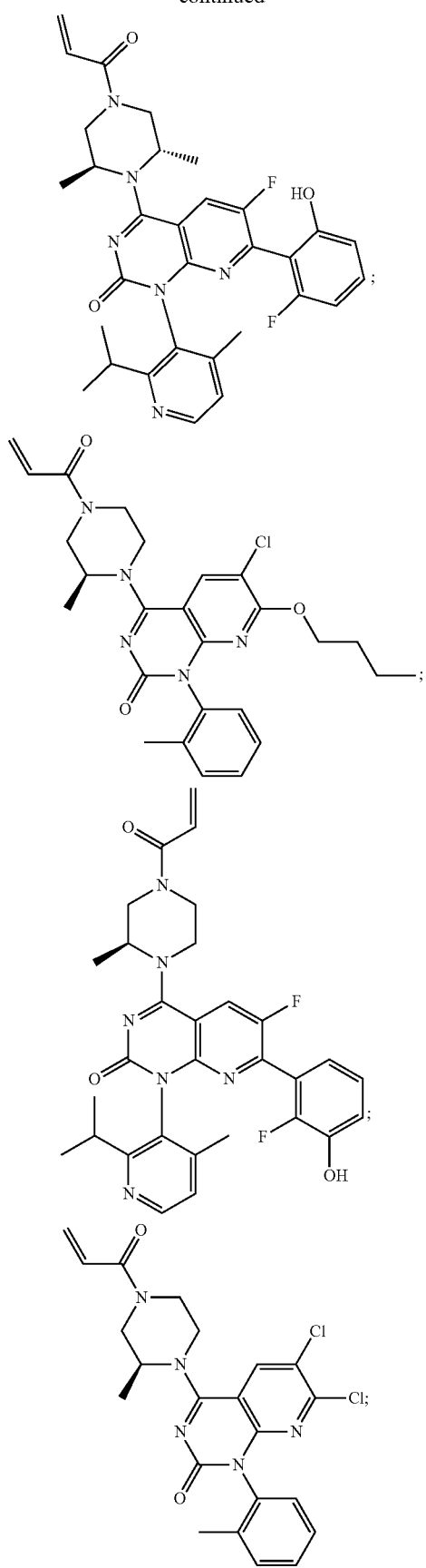
1232
-continued
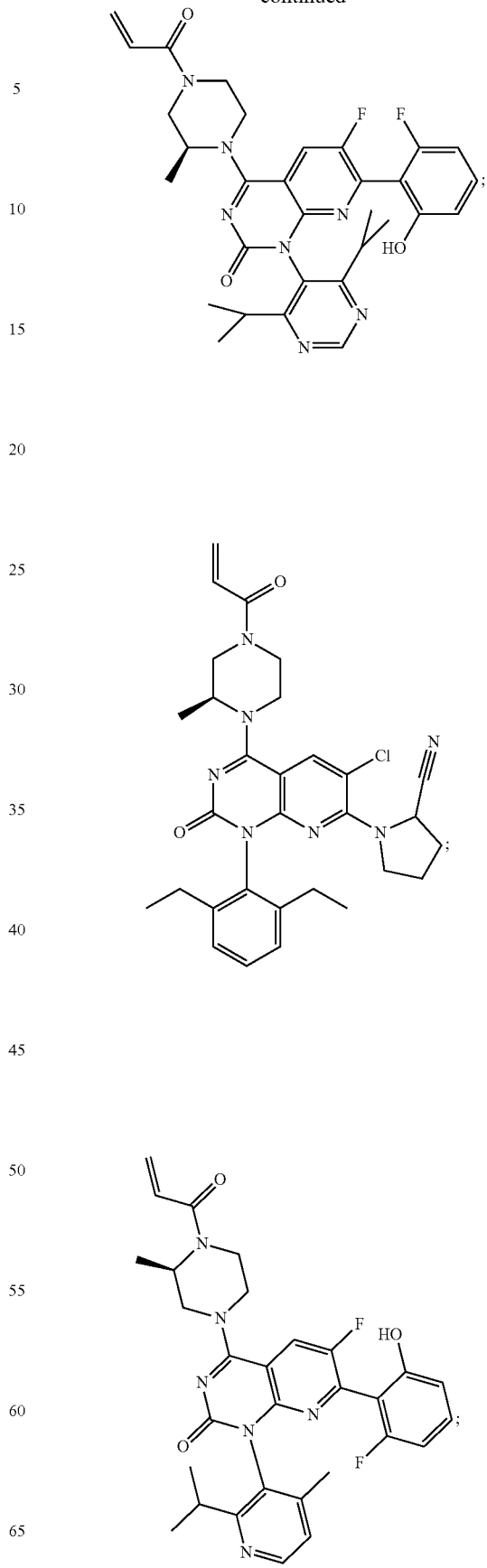

1233
-continued
1234
-continued
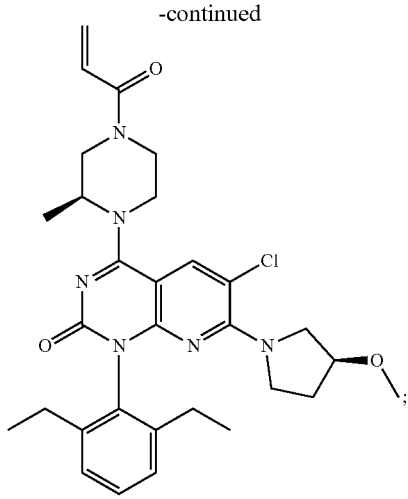
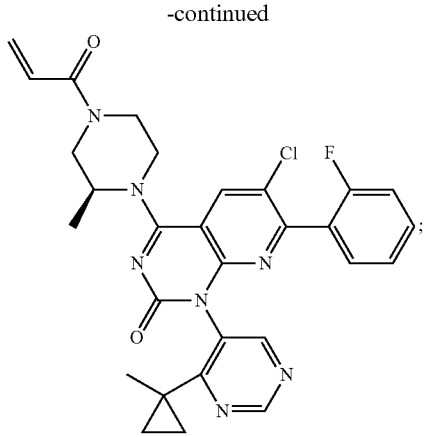
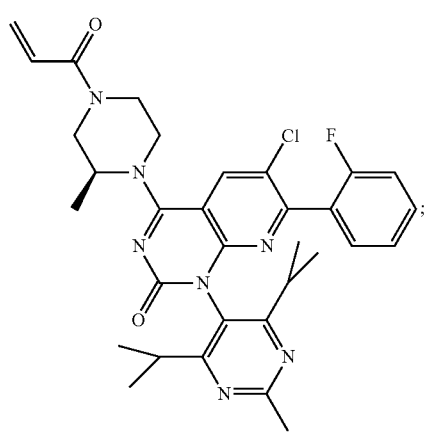
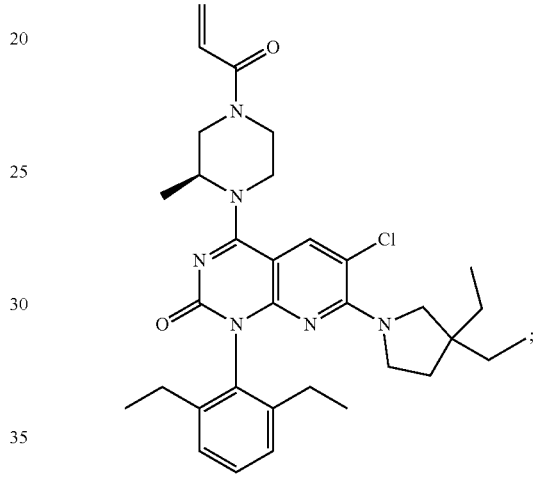
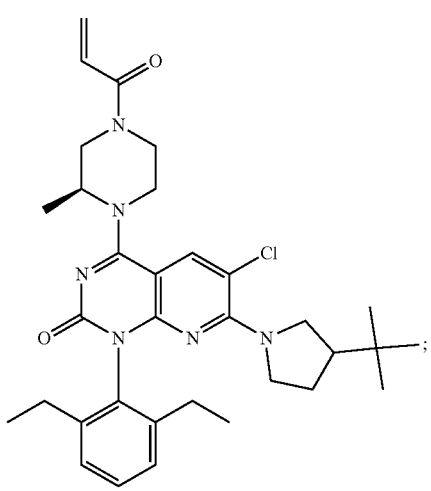
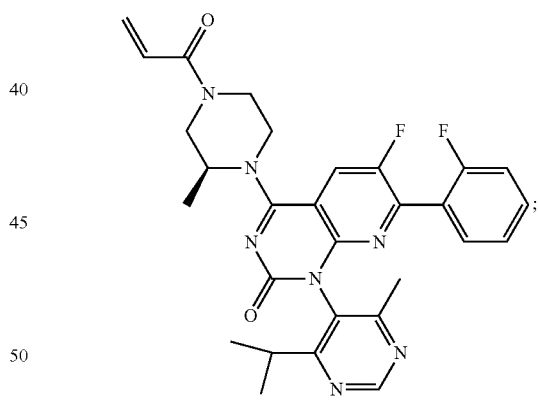
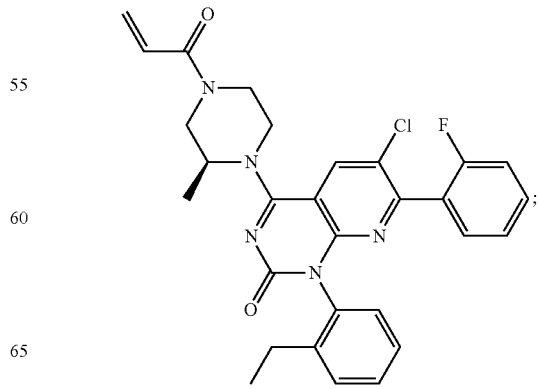

1235
-continued
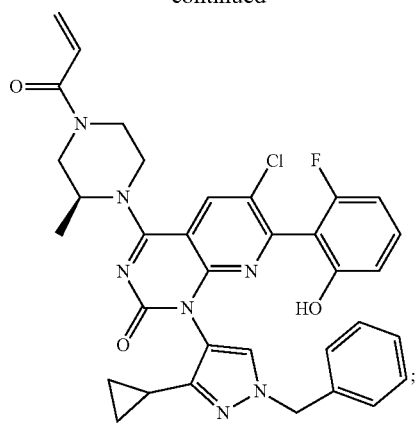
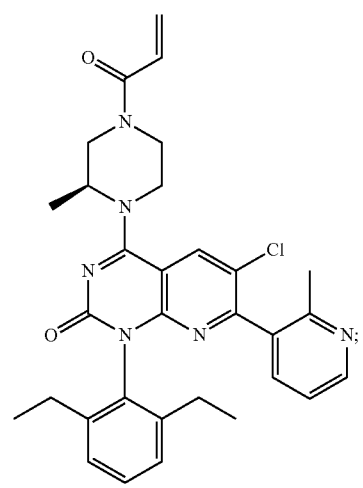
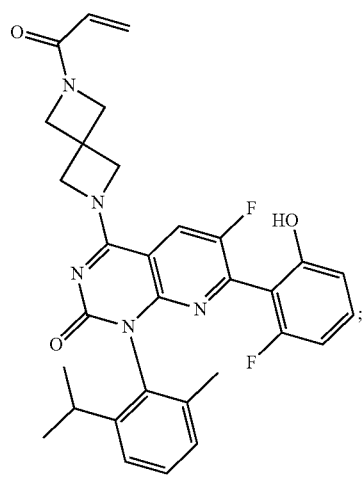
1236
-continued
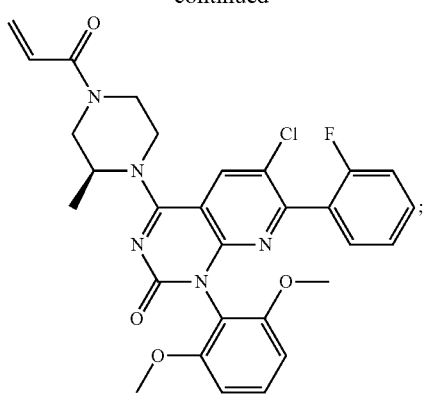
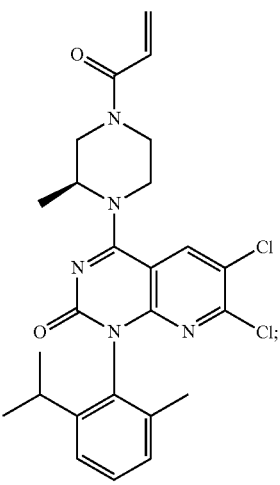
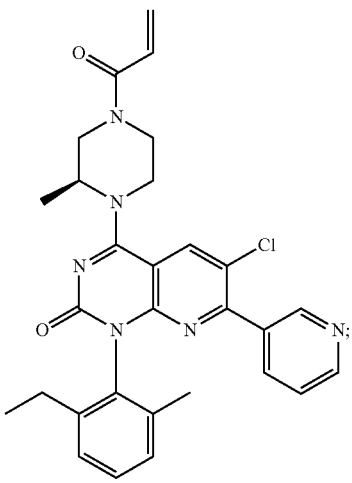

1237
-continued
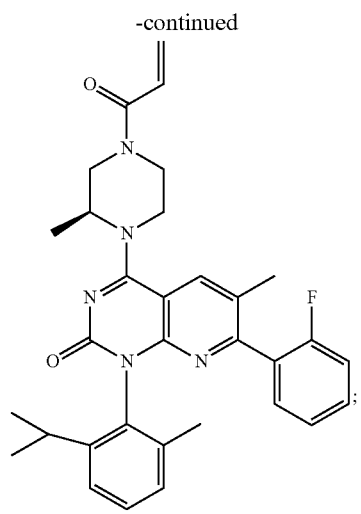
1238
-continued
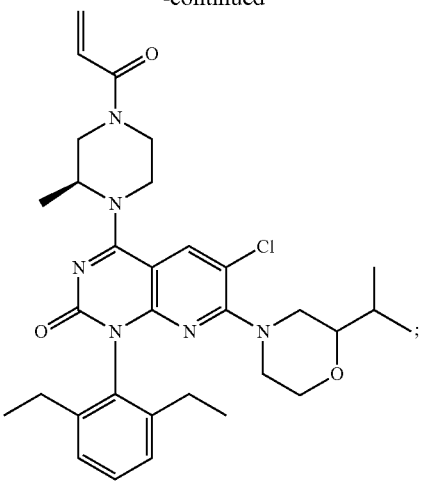
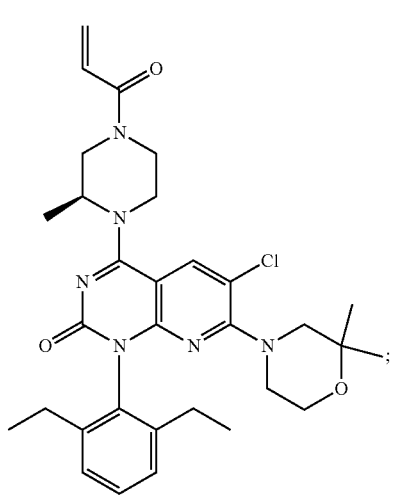
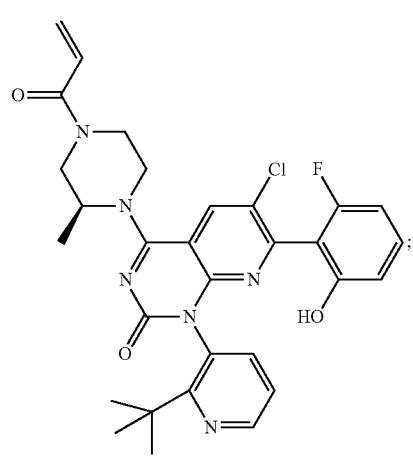
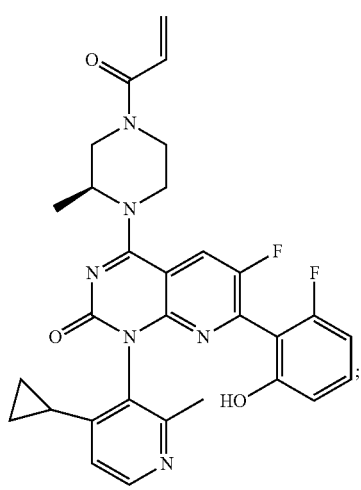
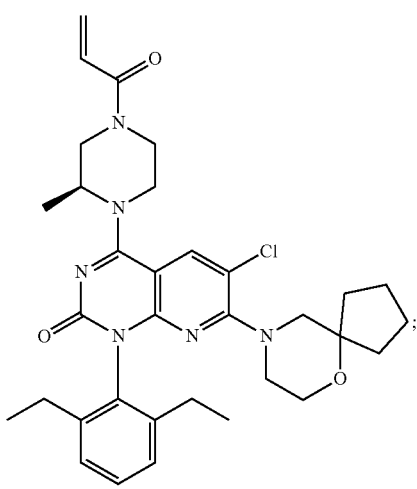

1239
-continued
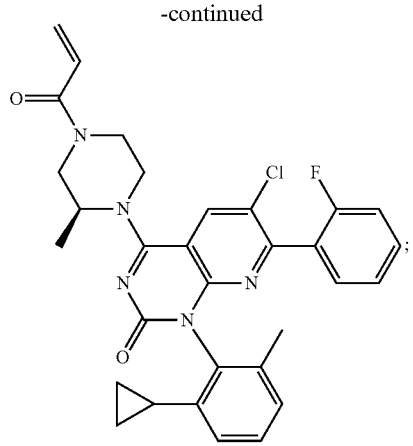
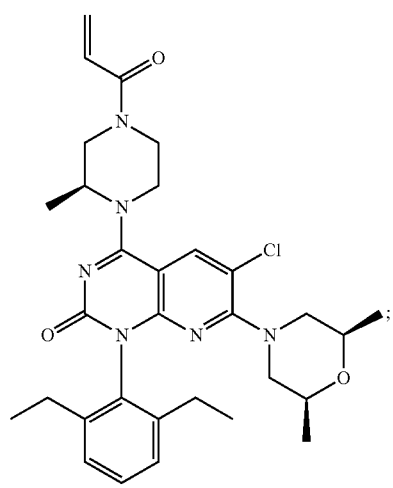
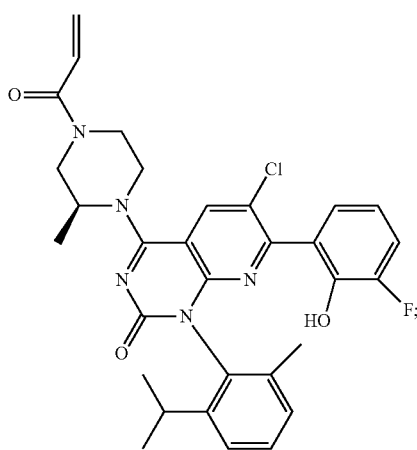
1240
-continued
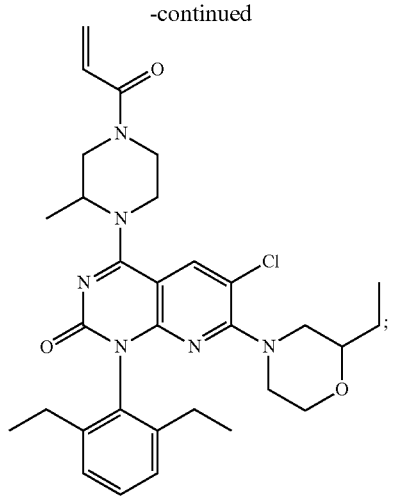
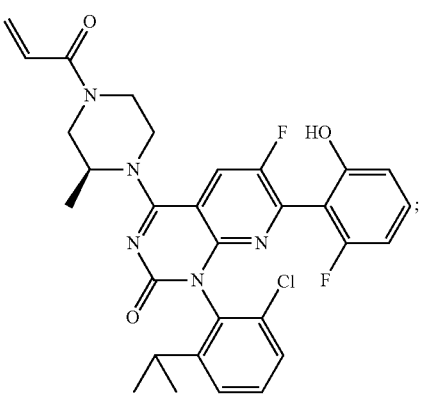
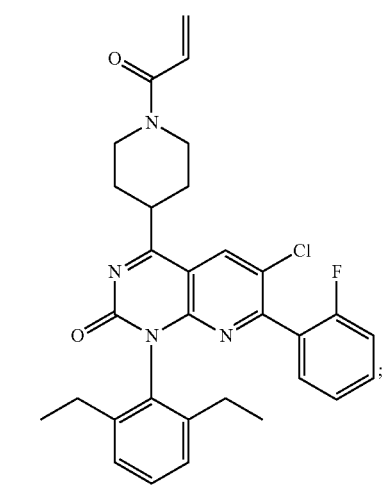

1241
-continued
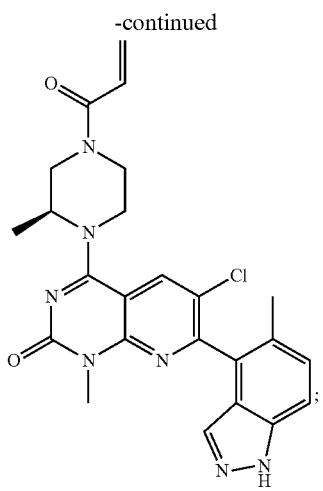
1242
-continued
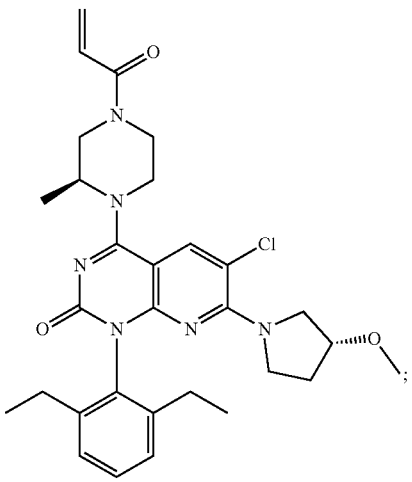
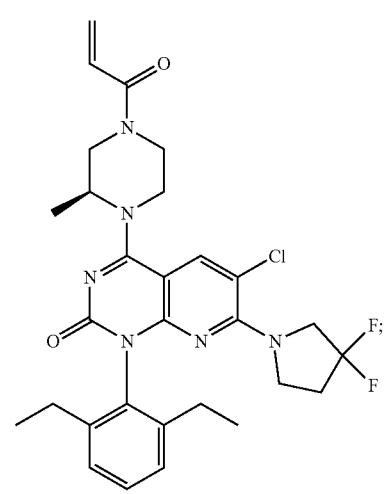
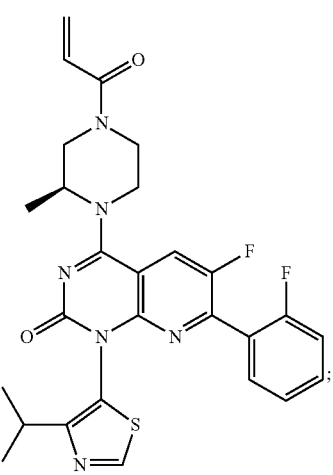
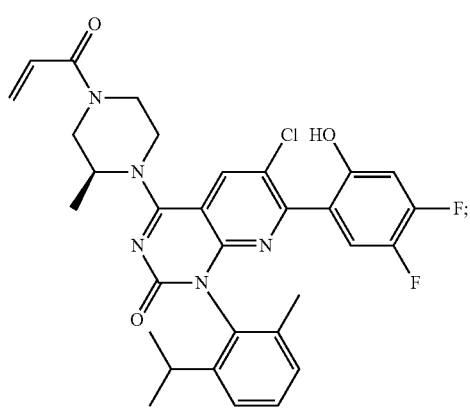
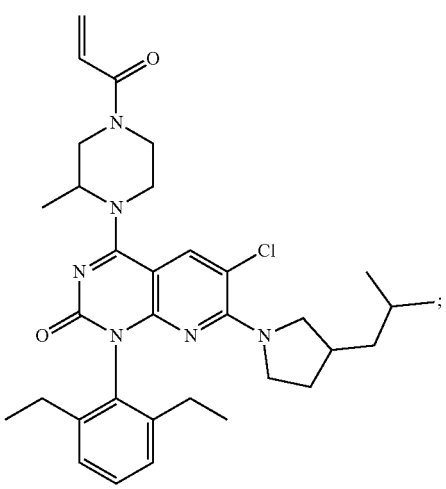

1243
-continued
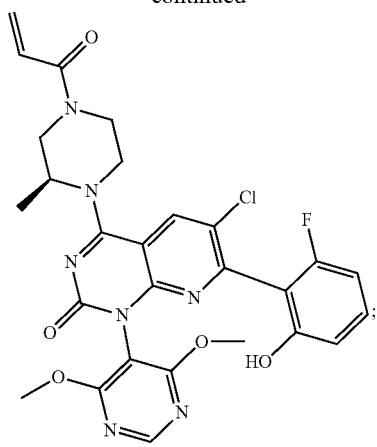
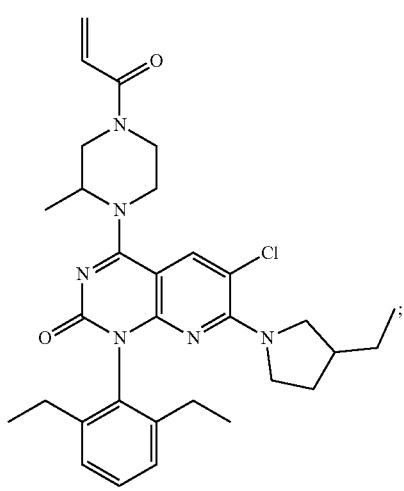
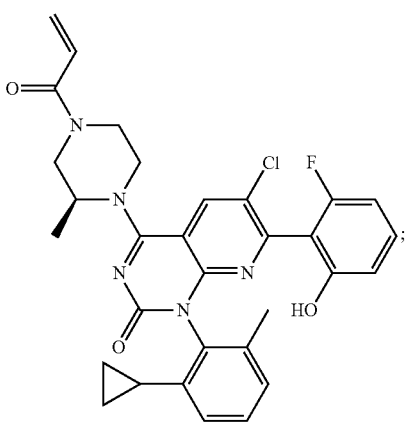
1244
-continued
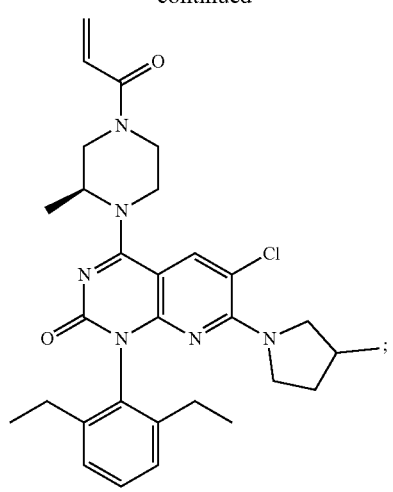
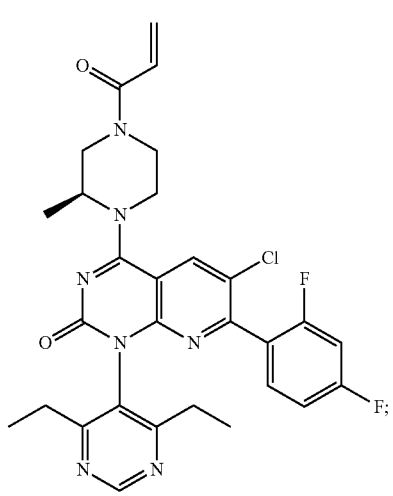
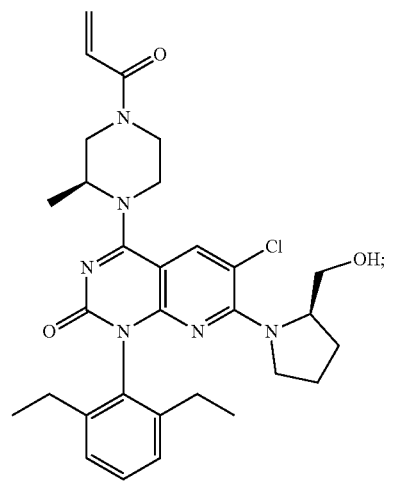

1245
-continued
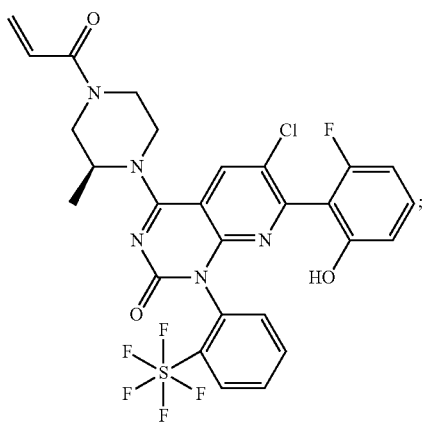
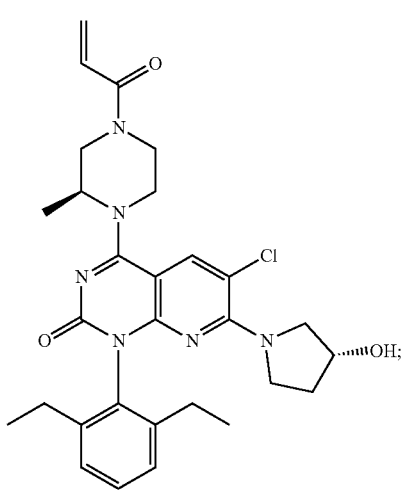
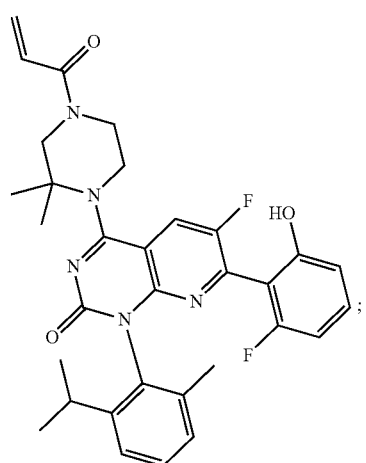
1246
-continued
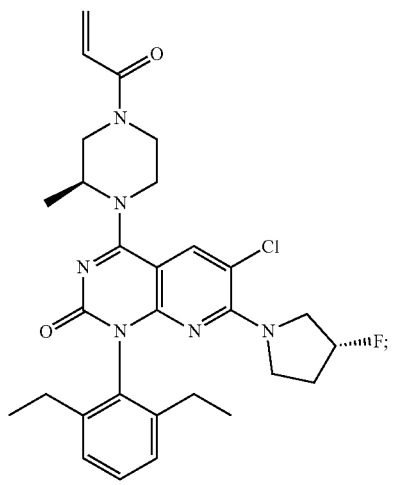
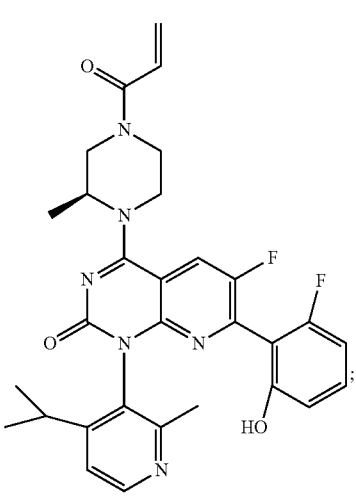
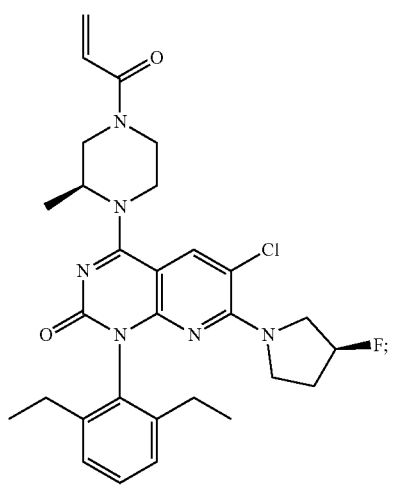

1247
-continued
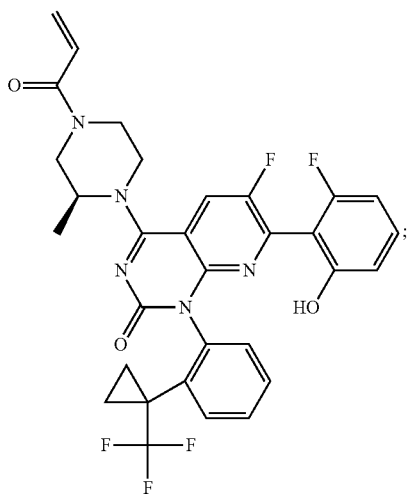
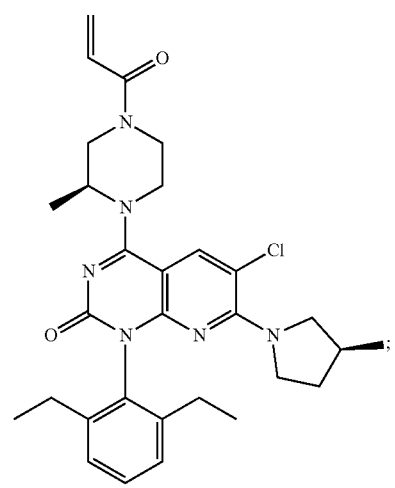
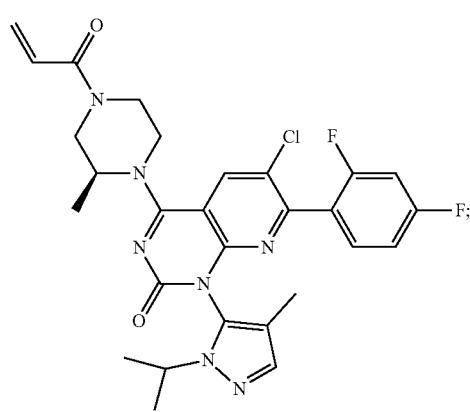
1248
-continued
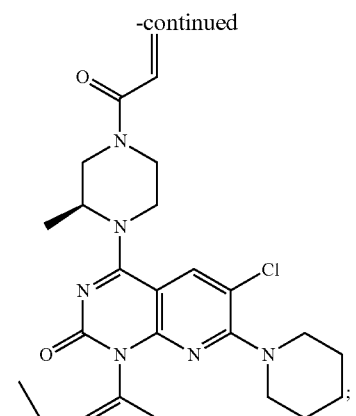
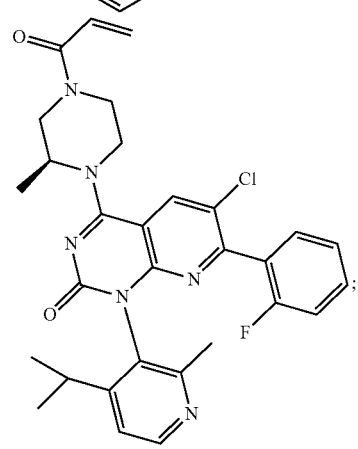
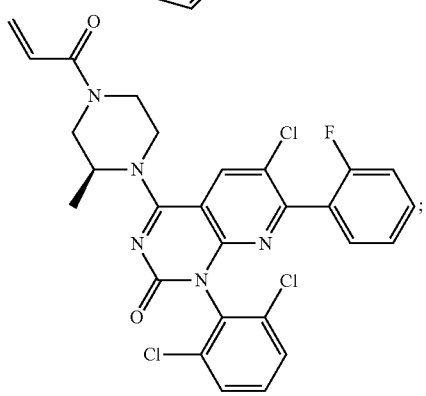
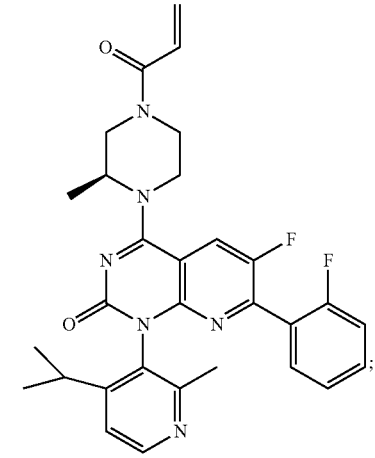

1249
-continued
1250
-continued
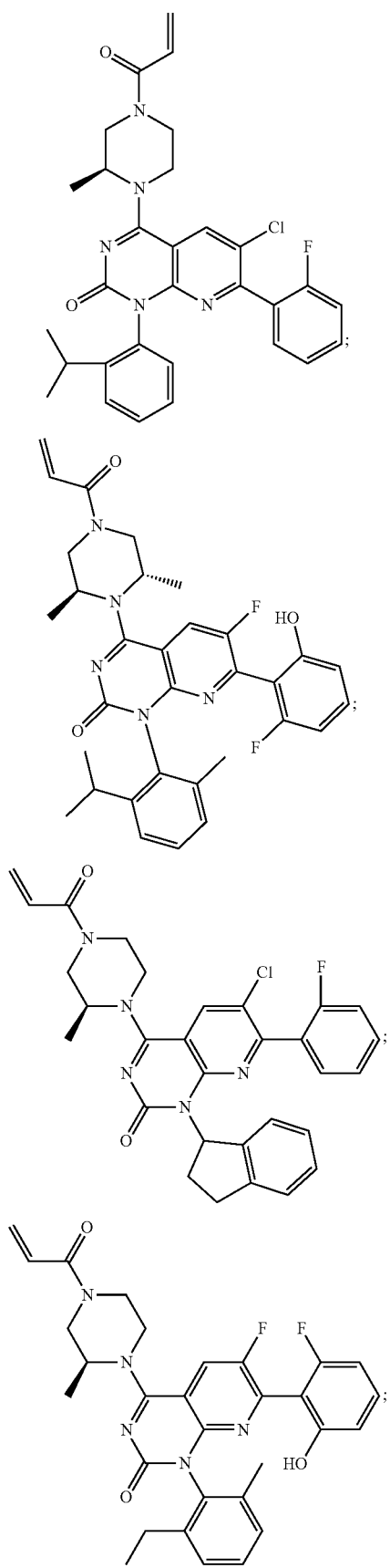
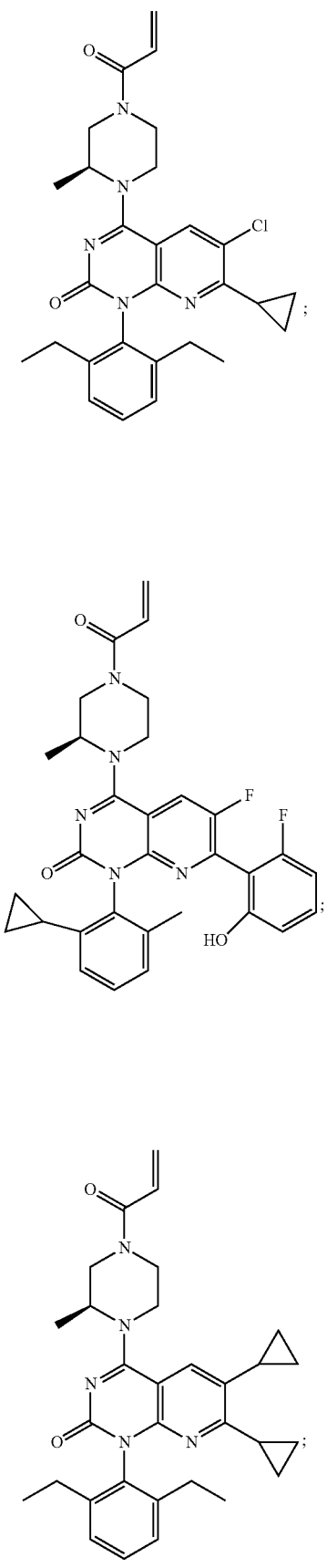

-continued
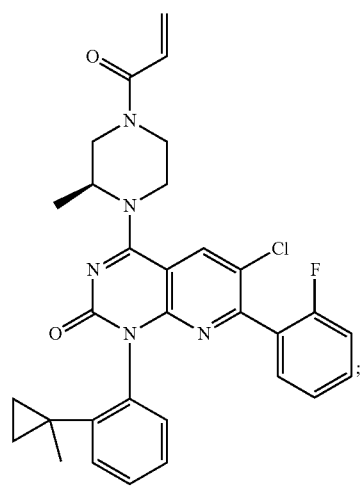
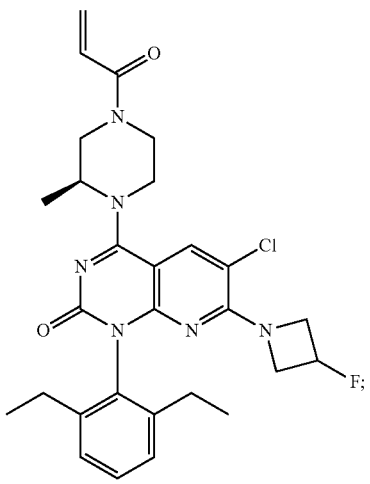
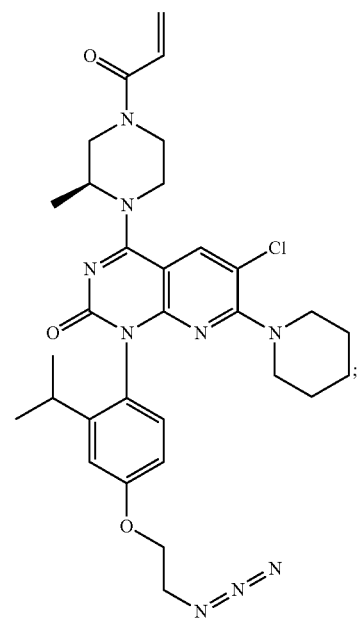
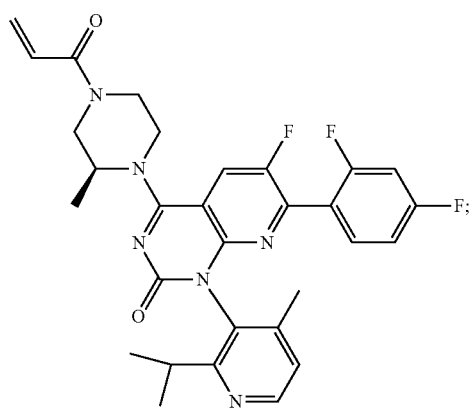
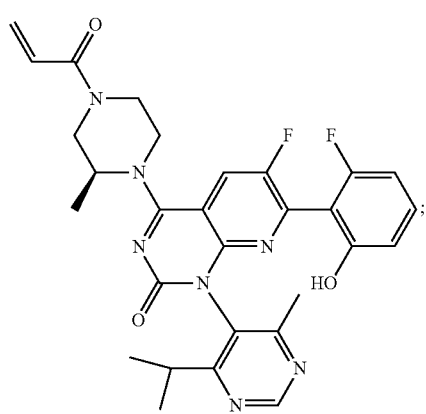
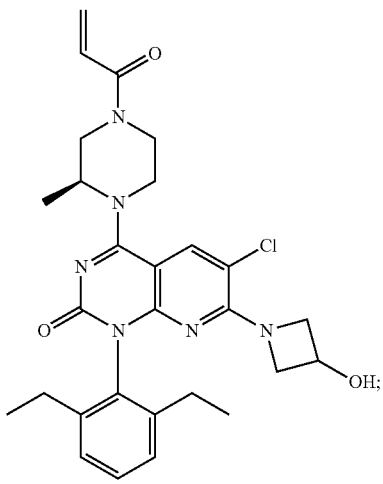

1253
-continued
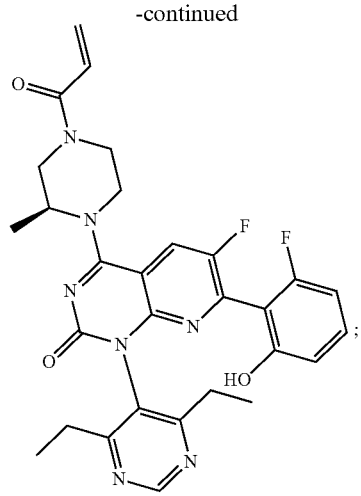
1254
-continued
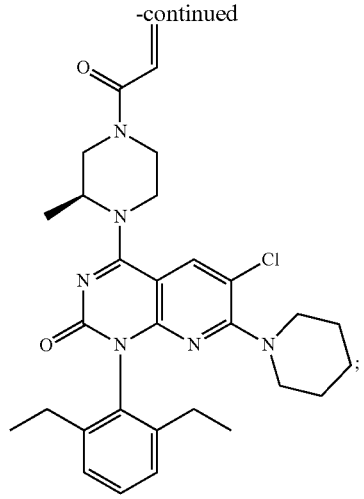
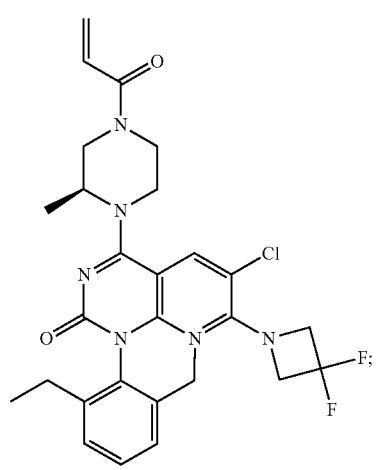
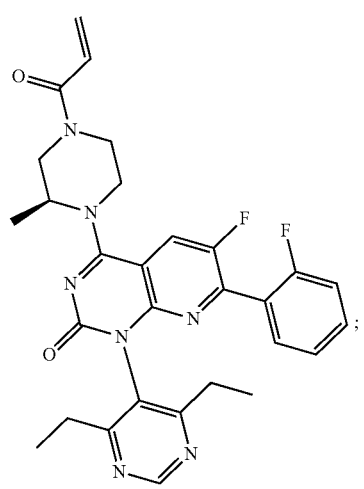
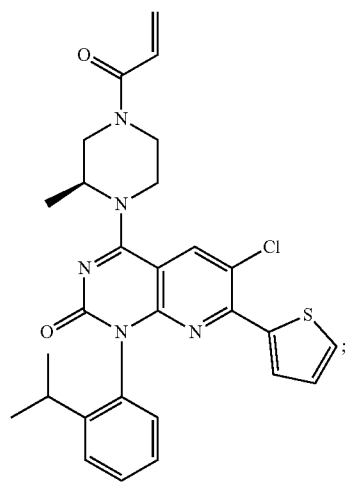
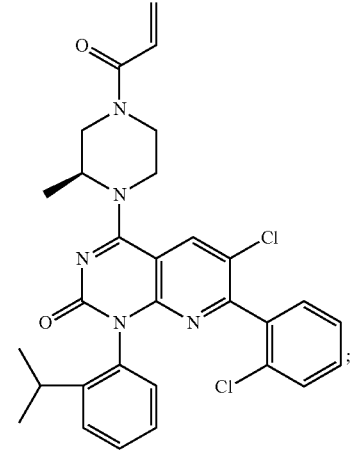

1255
-continued
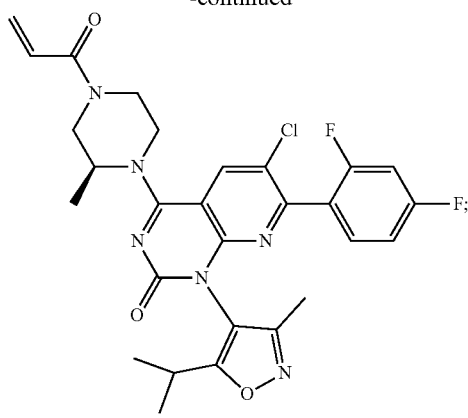
1256
-continued
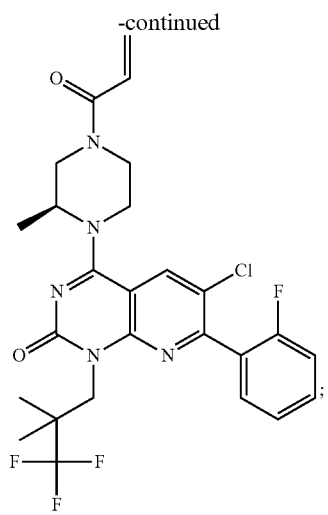
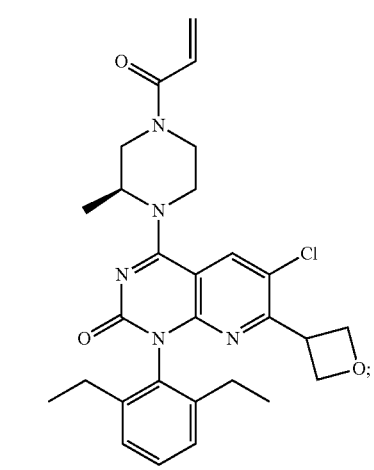
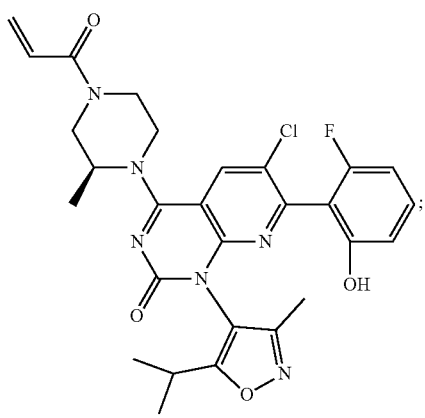
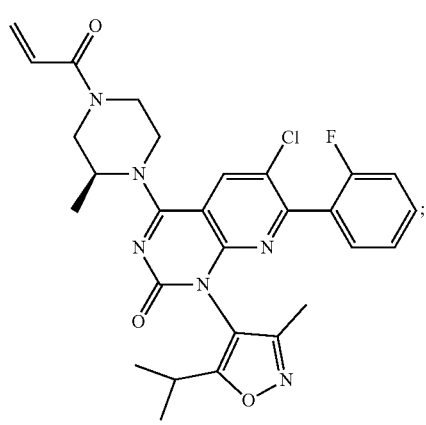
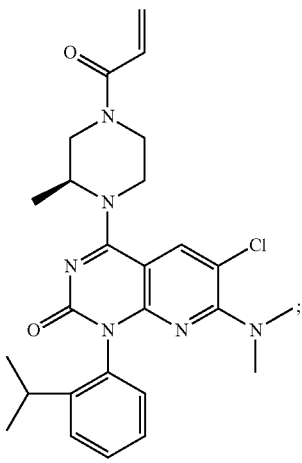

1257
-continued
1258
-continued
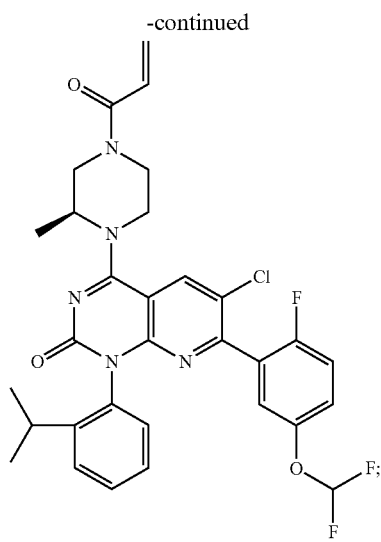
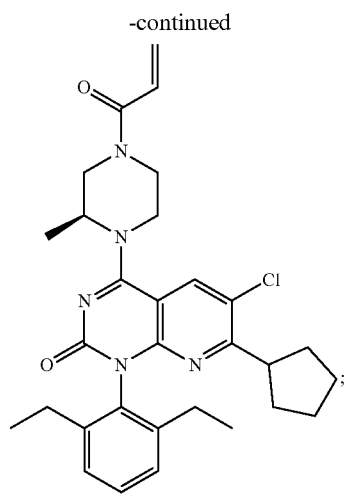
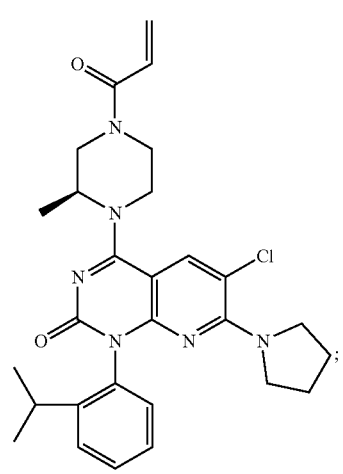
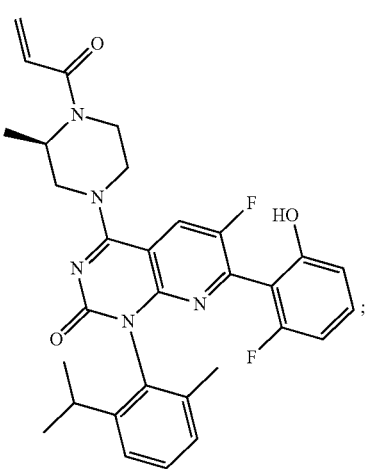
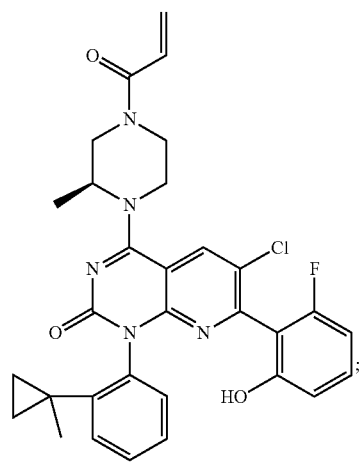
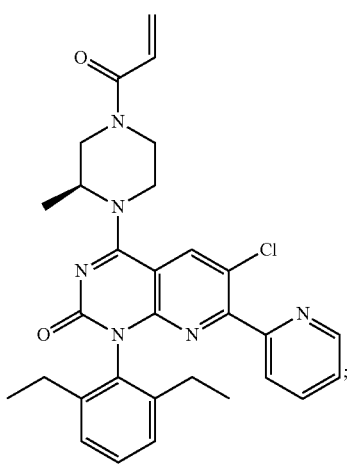

1259
-continued
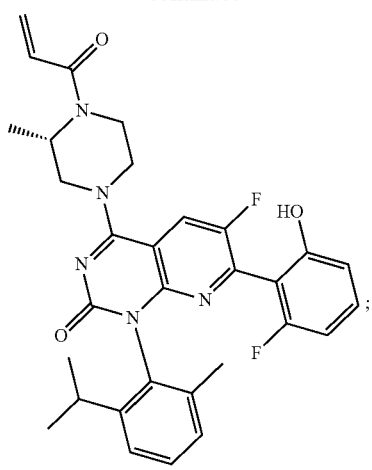
1260
-continued
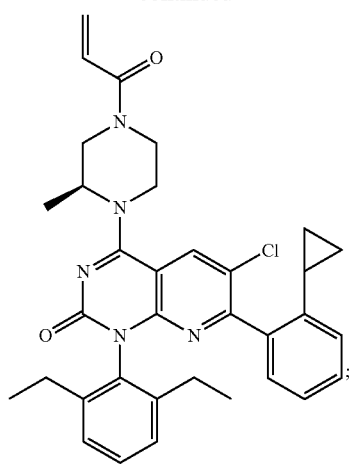
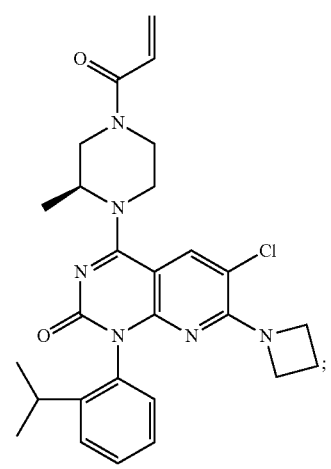
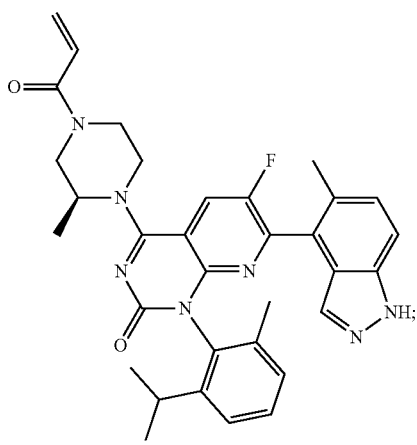
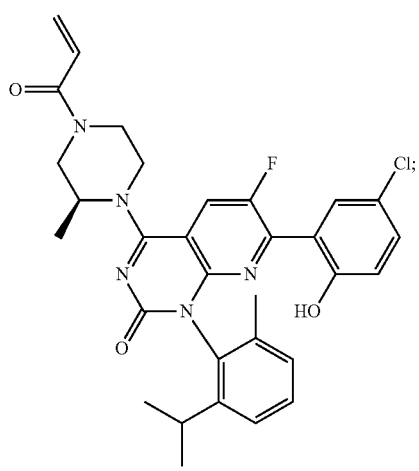
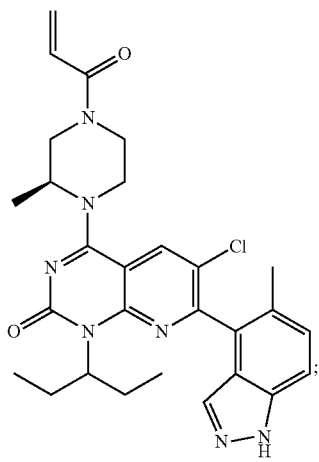

1261
-continued
1262
-continued
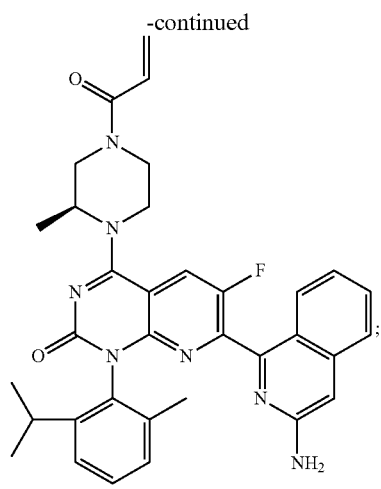
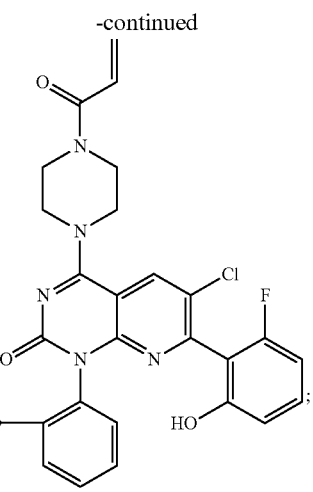

1263
-continued
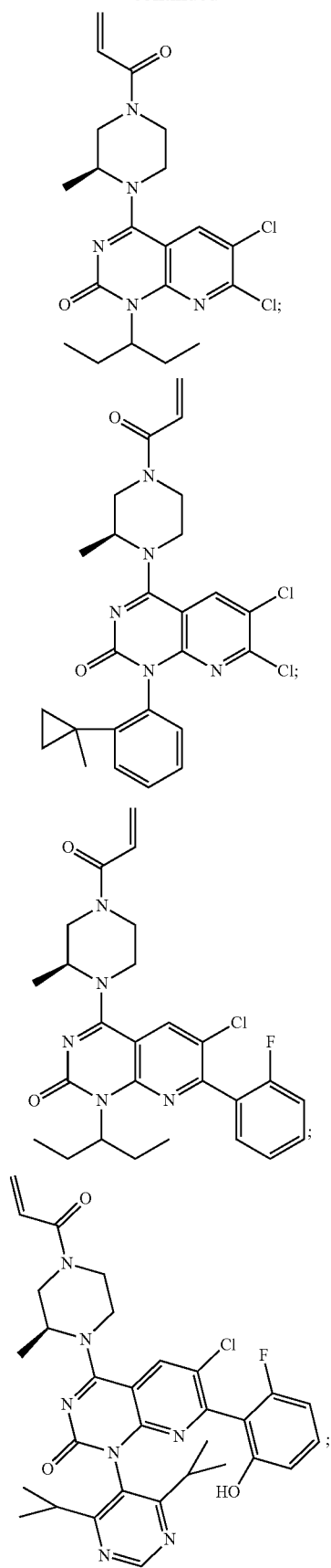
1264
-continued
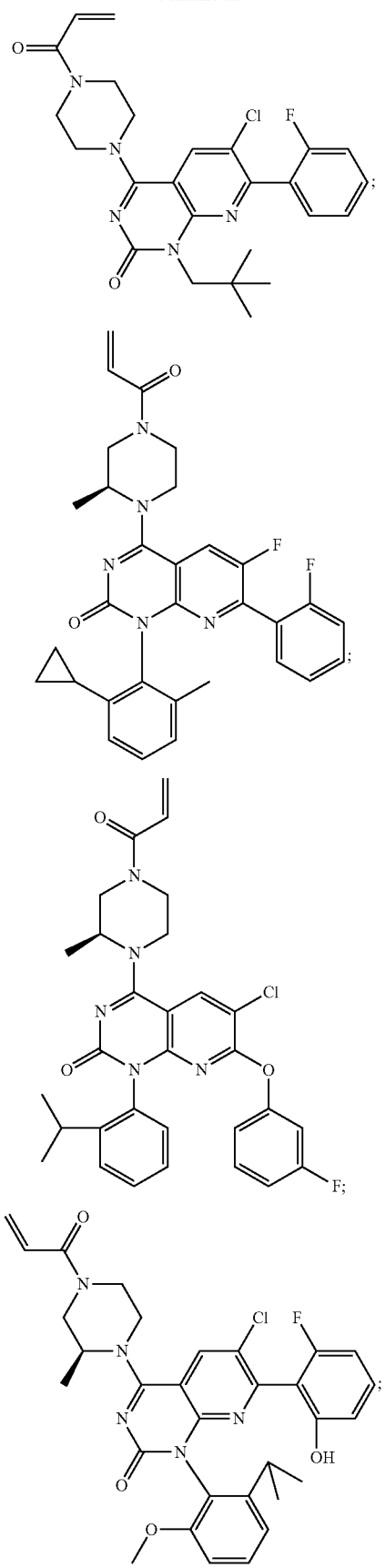

1265
-continued
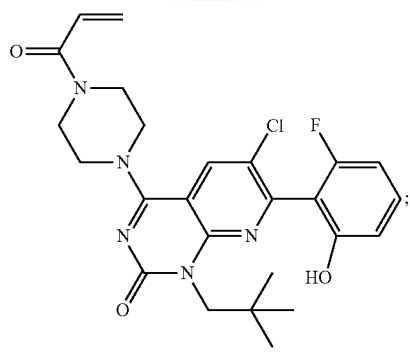
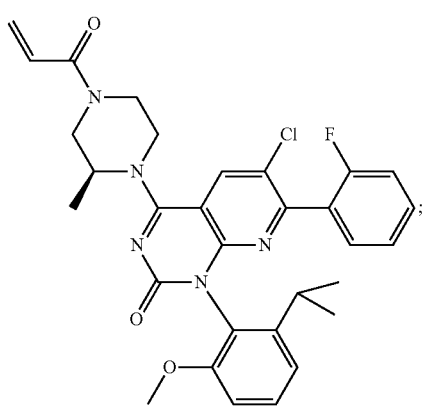
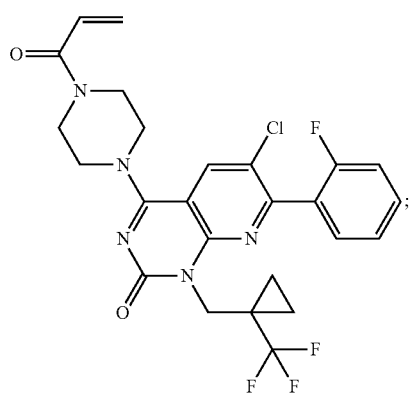
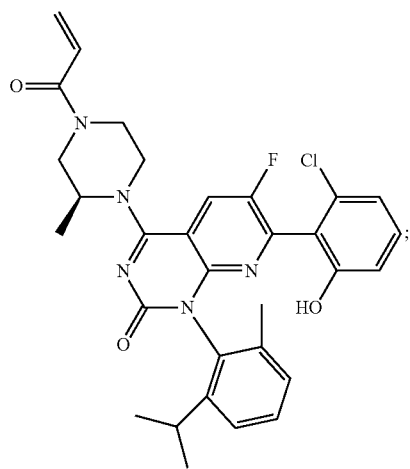
1266
-continued
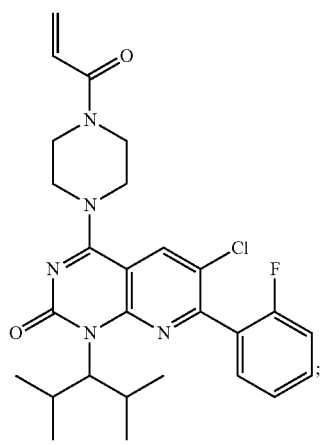
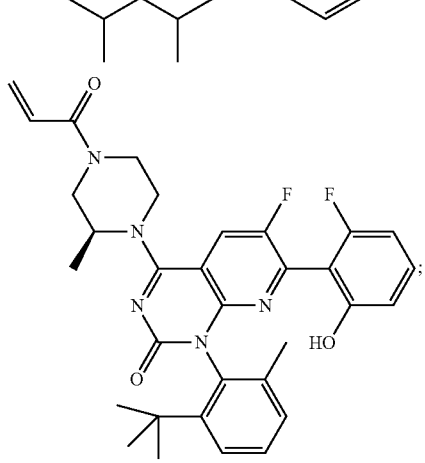
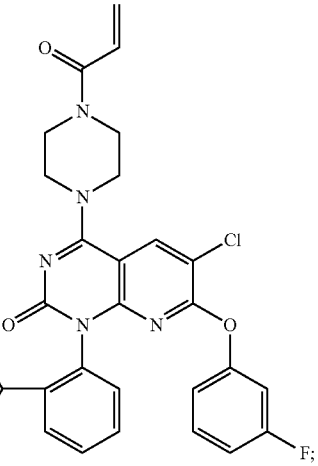
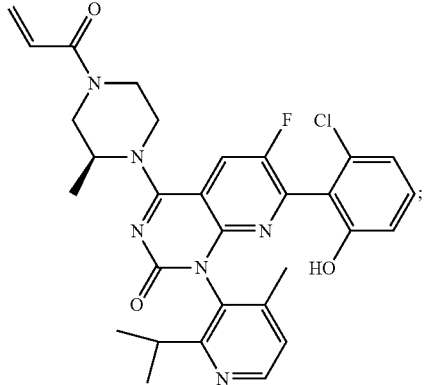

1267
-continued
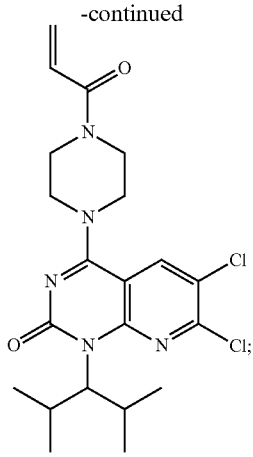
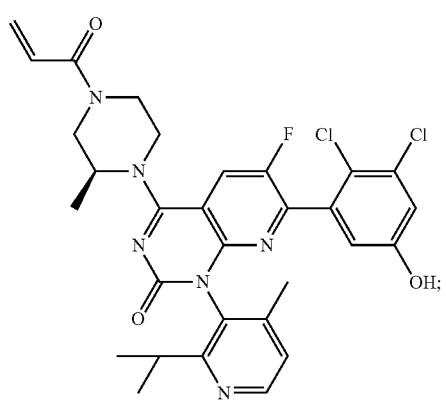
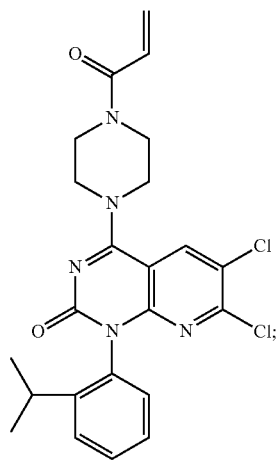
1268
-continued
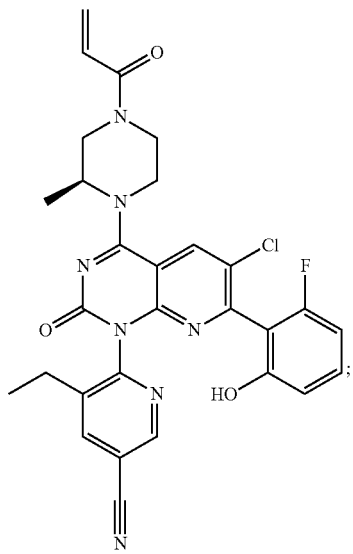
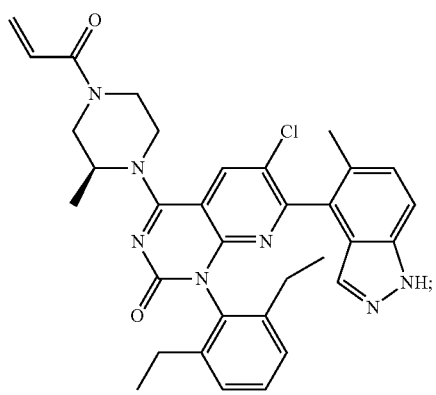
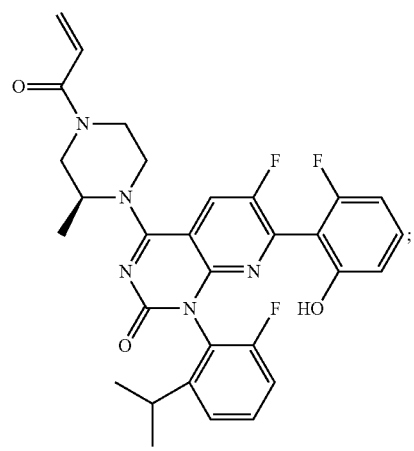

1269
-continued
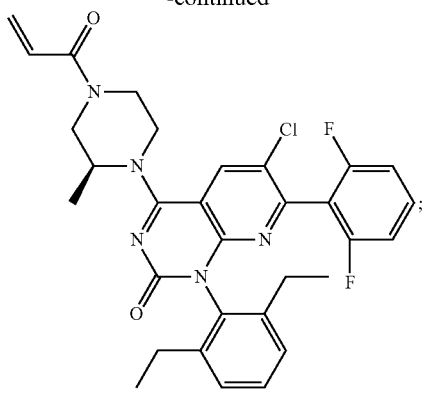
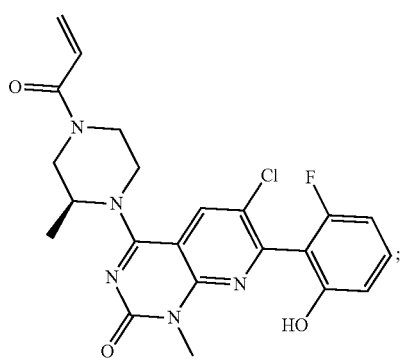
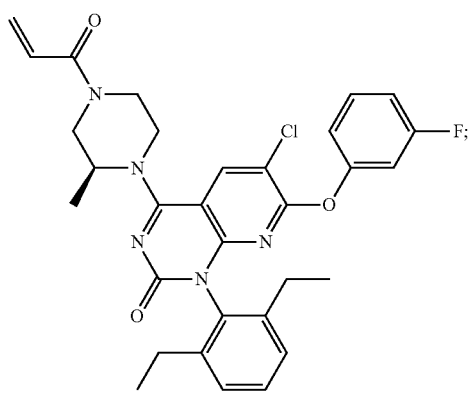
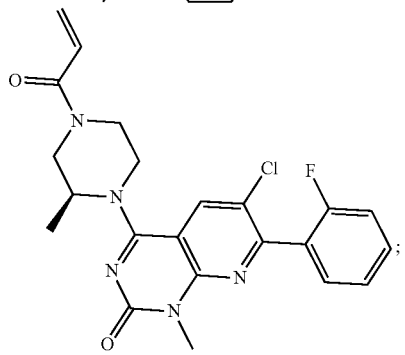
1270
-continued
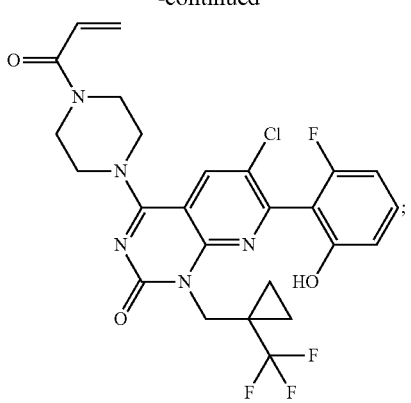
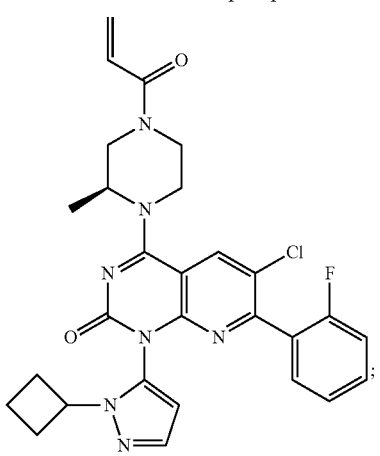
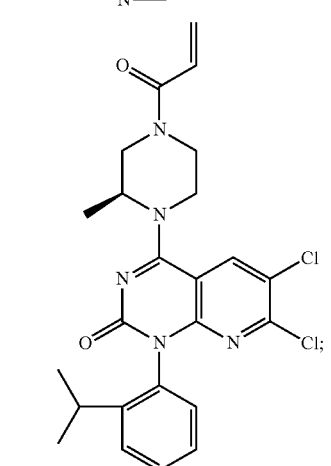
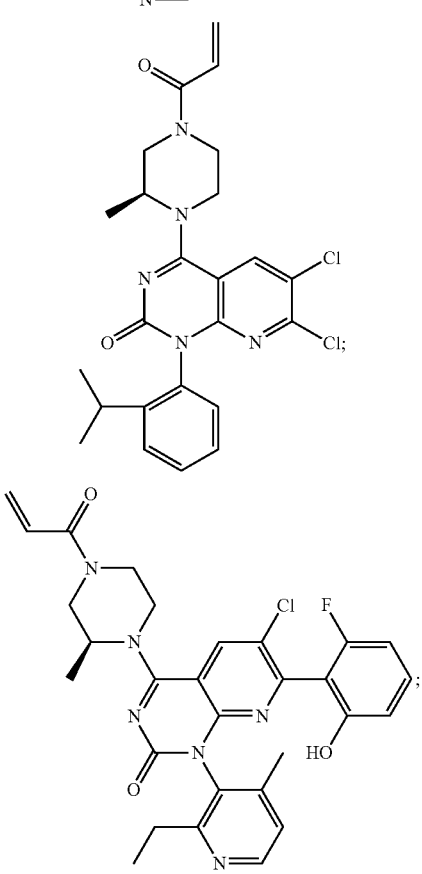

1271
-continued
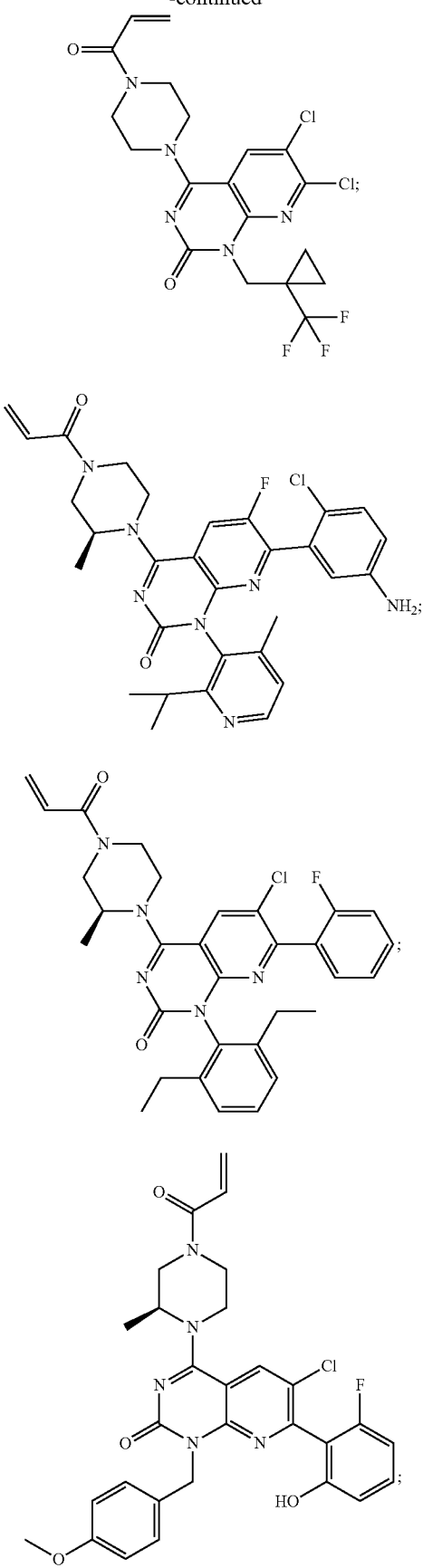
1272
-continued
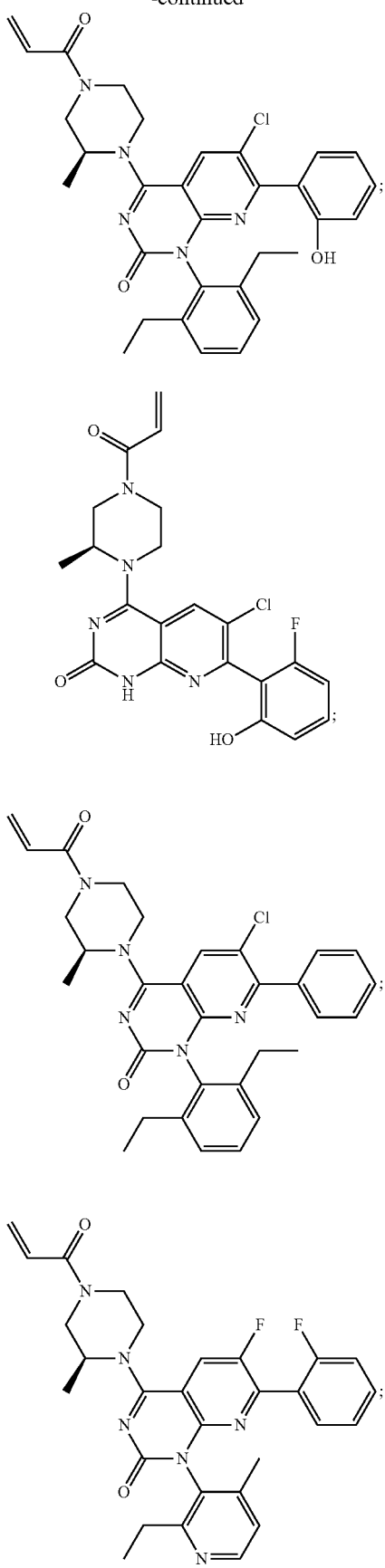

1273
-continued
1274
-continued
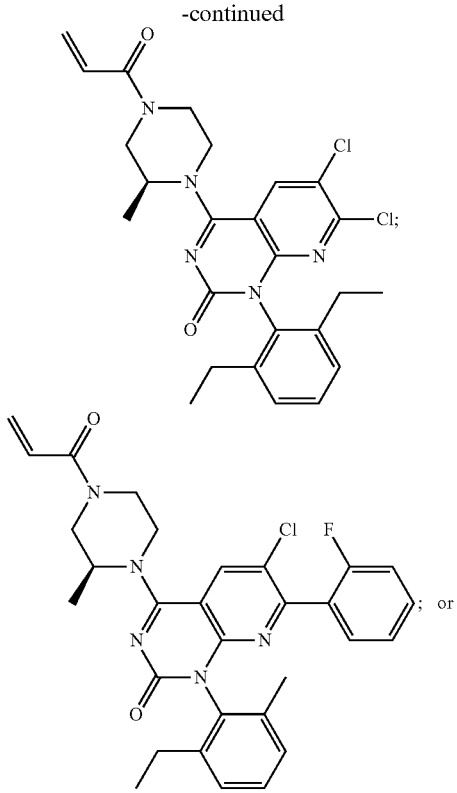
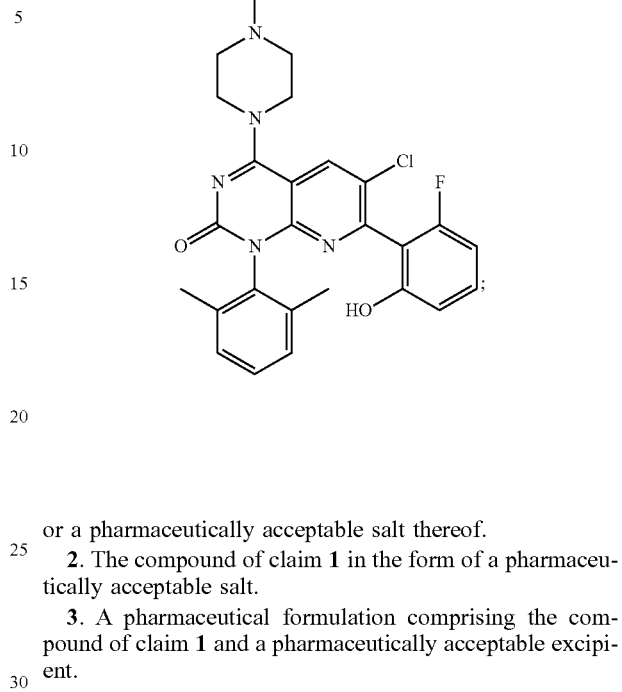
or a pharmaceutically acceptable salt thereof.
2. The compound of claim 1 in the form of a pharmaceutically acceptable salt.
3. A pharmaceutical formulation comprising the compound of claim 1 and a pharmaceutically acceptable excipient.
* * * * *